(12) United States Patent
Mandal et al.

(10) Patent No.: US 9,708,336 B2
(45) Date of Patent: Jul. 18, 2017

(54) METALLO-BETA-LACTAMASE INHIBITORS

(71) Applicant: Merck Sharp & Dohme Corp., Rahway, NJ (US)

(72) Inventors: Mihir Mandal, Westfield, NJ (US); Haifeng Tang, Metuchen, NJ (US); Li Xiao, Cranbury, NJ (US); Jing Su, Scotch Plains, NJ (US); Guoqing Li, Belle Mead, NJ (US); Shu-Wei Yang, Edison, NJ (US); Weidong Pan, Hillsborough, NJ (US); Haiqun Tang, Belle Mead, NJ (US); Reynalda DeJesus, East Brunswick, NJ (US); Jacqueline Hicks, Scotch Plains, NJ (US); Matthew Lombardo, Flemington, NJ (US); Hong Chu, Livingston, NJ (US); William Hagmann, Westfield, NJ (US); Alex Pasternak, Princeton, NJ (US); Xin Gu, Scotch Plains, NJ (US); Jinlong Jiang, Scotch Plains, NJ (US); Shuzhi Dong, Plainsboro, NJ (US); Fa-Xiang Ding, Staten Island, NY (US); Clare London, Chatham, NJ (US); Dipshikha Biswas, Woodbridge, NJ (US); Katherine Young, Metuchen, NJ (US); David N. Hunter, Scotch Plains, NJ (US); Zhiqiang Zhao, Scotch Plains, NJ (US); Dexi Yang, Livingston, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/110,431

(22) PCT Filed: Jan. 16, 2015

(86) PCT No.: PCT/US2015/011735
§ 371 (c)(1),
(2) Date: Jul. 8, 2016

(87) PCT Pub. No.: WO2015/112441
PCT Pub. Date: Jul. 30, 2015

(65) Prior Publication Data
US 2016/0333021 A1  Nov. 17, 2016

Related U.S. Application Data

(60) Provisional application No. 61/930,310, filed on Jan. 22, 2014.

(51) Int. Cl.
*C07D 491/048* (2006.01)
*A61K 31/437* (2006.01)
(Continued)

(52) U.S. Cl.
CPC ........ *C07D 491/048* (2013.01); *A61K 31/197* (2013.01); *A61K 31/407* (2013.01); *A61K 31/41* (2013.01); *A61K 31/4155* (2013.01); *A61K 31/4178* (2013.01); *A61K 31/4192* (2013.01); *A61K 31/422* (2013.01); *A61K 31/427* (2013.01); *A61K 31/4245* (2013.01); *A61K 31/437* (2013.01); *A61K 31/4439* (2013.01); *A61K 31/454* (2013.01); *A61K 31/496* (2013.01); *A61K 31/497* (2013.01); *A61K 31/501* (2013.01); *A61K 31/506* (2013.01); *A61K 31/5025* (2013.01); *A61K 31/5377* (2013.01); *A61K 31/541* (2013.01); *A61K 31/55* (2013.01); *A61K 45/06* (2013.01); *C07D 257/04* (2013.01); *C07D 401/04* (2013.01);
(Continued)

(58) Field of Classification Search
None
See application file for complete search history.

(56) References Cited

U.S. PATENT DOCUMENTS 4,746,353 A  5/1988 Levitt
4,786,311 A  11/1988 Levitt
(Continued)

FOREIGN PATENT DOCUMENTS

CN  1095549  11/1994
EP  204513  12/1986
(Continued)

OTHER PUBLICATIONS

Anderson, The pandemic of antibiotic resistance, Nature Medicine, 1999, 147-149, 5(2).
(Continued)

*Primary Examiner* — Brian J Davis
(74) *Attorney, Agent, or Firm* — Alysia A. Finnegan; Gloria M. Fuentes

(57) ABSTRACT

The present invention relates to compounds of formula (I) that are metallo-β-lactamase inhibitors, the synthesis of such compounds, and the use of such compounds for use with β-lactam antibiotics for overcoming resistance.

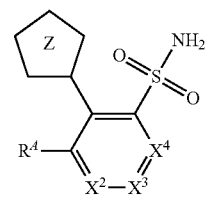

26 Claims, No Drawings

(51) Int. Cl.

| | | |
|---|---|---|
| A61K 31/4439 | (2006.01) | |
| A61K 31/454 | (2006.01) | |
| A61K 31/496 | (2006.01) | |
| A61K 31/497 | (2006.01) | |
| A61K 31/501 | (2006.01) | |
| A61K 31/5025 | (2006.01) | |
| A61K 31/506 | (2006.01) | |
| A61K 31/5377 | (2006.01) | |
| A61K 31/541 | (2006.01) | |
| A61K 31/55 | (2006.01) | |
| A61K 45/06 | (2006.01) | |
| C07D 401/04 | (2006.01) | |
| C07D 409/10 | (2006.01) | |
| C07D 487/04 | (2006.01) | |
| C07D 471/10 | (2006.01) | |
| C07D 471/04 | (2006.01) | |
| C07D 451/04 | (2006.01) | |
| C07D 417/14 | (2006.01) | |
| C07D 417/10 | (2006.01) | |
| C07D 413/10 | (2006.01) | |
| C07D 401/14 | (2006.01) | |
| C07D 405/12 | (2006.01) | |
| C07D 405/10 | (2006.01) | |
| C07D 403/10 | (2006.01) | |
| C07D 401/10 | (2006.01) | |
| C07D 413/14 | (2006.01) | |
| C07D 405/14 | (2006.01) | |
| A61K 31/41 | (2006.01) | |
| C07D 257/04 | (2006.01) | |
| A61K 31/197 | (2006.01) | |
| A61K 31/407 | (2006.01) | |
| A61K 31/4155 | (2006.01) | |
| A61K 31/4178 | (2006.01) | |
| A61K 31/4192 | (2006.01) | |
| A61K 31/422 | (2006.01) | |
| A61K 31/4245 | (2006.01) | |
| A61K 31/427 | (2006.01) | |

(52) U.S. Cl.
CPC .......... *C07D 401/10* (2013.01); *C07D 401/14* (2013.01); *C07D 403/10* (2013.01); *C07D 405/10* (2013.01); *C07D 405/12* (2013.01); *C07D 405/14* (2013.01); *C07D 409/10* (2013.01); *C07D 413/10* (2013.01); *C07D 413/14* (2013.01); *C07D 417/10* (2013.01); *C07D 417/14* (2013.01); *C07D 451/04* (2013.01); *C07D 471/04* (2013.01); *C07D 471/10* (2013.01); *C07D 487/04* (2013.01)

(56) References Cited

U.S. PATENT DOCUMENTS

| | | | |
|---|---|---|---|
| 4,838,925 | A | 6/1989 | Tseng |
| 5,510,343 | A | 4/1996 | Charnas et al. |
| 5,698,577 | A | 12/1997 | Hubschwerlen et al. |
| 6,472,406 | B1 | 10/2002 | Besterman et al. |
| 2003/0199541 | A1 | 10/2003 | Lampilas et al. |
| 2004/0157826 | A1 | 8/2004 | Lampilas et al. |

FOREIGN PATENT DOCUMENTS

| | | |
|---|---|---|
| EP | 244166 | 11/1987 |
| WO | WO2008039420 | 4/2008 |
| WO | WO2013103760 | 7/2013 |

OTHER PUBLICATIONS

Bush et al., Tackling antibiotic resistance, Nature Reviews in Microbiology, 2011, 894-896, 9.
Cohen, Epidemiology of Drug Resistance: Implications for a Post-Antimicrobial Era, Science, 1992, 1050-1055, 257.
Coulton et al., 6 Beta-Lactamases: Targets for Drug Design, Progress in Medicinal Chemistry, 1994, 297-349, 31.
Dudley, Bacterial Resistance Mechanisms to Beta-Lactam Antibiotics: Assessment of Management Strategies, Pharmacotherapy, 1995, 9S-14S, 15.
English language abstract for CN1095549, published Nov. 30, 1994.
Fast et al., Metallo-β-lactamase: inhibitors and reporter substrates, Biochimica et Biophysica Acta—Proteins and Proteomics, 2013, 1648-1659, 1834(8).
Green et al., Inhibition of bacterial peptide deformylase by biaryl acid analogs, Archives of Biochemistry and Biophysics, 2000, 355-358, 375(2).
Hanaki et al., TOC-39, a Novel Parenteral Broad-Spectrum Cephalosporin with Excellent Activity against Methicillin-Resistant *Staphylococcus aureus*, Antimicrobial Agents and Chemotherapy, 1995, 1120-1126, 30.
Heinze-Krauss et al., Structure-Based Design of β-Lactamase Inhibitors. 1. Synthesis and Evaluation of Bridged Monobactams, J. Med. Chem., 1998, 3961-3971, 41.
Levy et al, Antibacterial resistance worldwide: causes, challenges and responses, Nature Medicine, 2004, S122-S129, 10.
Livermore, Bacterial resistance: origins, epidemiology, and impact, Clinical Infectious Diseases, 2003, S11-S23, 36.
Livermore, Potentiation of beta-lactams against Pseudomonas aeruginosa strains by Ro 48-1256, a bridged monobactam inhibitor of AmpC beta-lactamases, J. Med. Chem., 1997, 335-343, 40.
Neu, The Crisis in Antibiotic Resistance, Science, 1992, 1064-1073, 257.
Oelschlaeger et al., Evolving carbapenemases: can medicinal chemists advance one step ahead of the coming storm?, J. Med. Chem., 2010, 3013-3027, 53.
Olsen et al., Docking and scoring of metallo-beta-lactamases inhibitors, Journal of Computer-Aided Molecular Design, 2004, 287-302, 18(4).
Payne et al., Comparative Activities of Clavulanic Acid, Sulbactam, and Tazobactam against Clinically Important beta-Lactamases, Antimicrobial Agents and Chemotherapy, 1994, 767-772, 38.
Poole, Resistance to beta-lactam antibiotics, Cell. Mol. Life Sci., 2004, 2200-2223, 61.
Pubchem AGN-PC-000MU7, pp. 1-12, Create Date: Feb. 9, 2007; p. 3; [retrieved on Mar. 18, 2015). Retrieved from the Internet: <URL: http://pubchem.ncbi.nlm.nih.gov/compound/14179831#section=Top>.
Pubchem AGN-PC-0154U2, CID 68886301, pp. 1-10, Create Date: Nov. 30, 2012; p. 3; [retrieved on Mar. 18, 2015). Retrieved from the Internet:<URL: http://pubchem.ncbi.nlm.nih.gov/compound/68886301 ? from=summary#section=Top>.
Pubchem AGN-PC-018CXL, pp. 1-10, Create Date: Nov. 30, 2012; p. 3; [retrieved on Mar. 18, 2015). Retrieved from the Internet:<URL: http://pubchem.ncbi.nlm.nih.gov/compound/69052709?from=summary#section=Top>.
Roberts et al., Hospital and societal costs of antimicrobial-resistant infections in a Chicago teaching hospital: implications for antibiotic stewardship, Clinical Infectious Diseases, 2009, 1175-1184, 49.
Shen et al., Inhibitor Discovery of Full-Length New Delhi Metallo-b-Lactamase-1 (NDM-1), PLOS One, 2013, 1-7, 8 (5) e62955.
Toney et al., Antibiotic sensitization using biphenyl tetrazoles as potent inhibitors of Bacteroides fragilis metallo-beta-lactamase, Chemistry & Biology, 1998, 185-196, 5(4).
Toney et al., Structure-activity relationships of biphenyl tetrazoles as metallo-beta-lactamase inhibitors, Bioorganic & Medicinal Chemistry Letters, 1999, 2741-2746, 18(9).

METALLO-BETA-LACTAMASE INHIBITORS

CROSS-REFERENCE TO RELATED APPLICATIONS

This application is a §371 National Phase Application of International Application No. PCT/US2015/011735, filed Jan. 16, 2015, which claims the benefit of U.S. Application No. 61/930,310, filed Jan. 22, 2014, now expired.

FIELD OF THE INVENTION

This invention relates to novel metallo-β-lactamase inhibitors and their uses. A preferred use of the metallo-β-lactamase inhibitors is for reducing bacterial beta-lactam antibiotic resistance.

BACKGROUND OF THE INVENTION

Bacterial antibiotic resistance has become one of the most serious threats to modern health care. Infections caused by resistant bacteria frequently result in longer hospital stays, higher mortality and increased cost of treatment. See, e.g., Cohen, *Science* 1992, 257:1051-1055. The need for new antibiotics will continue to escalate because bacteria have a remarkable ability to develop resistance to new agents rendering them quickly ineffective. See, e.g., Neu, *Science* 1992, 257: 1064-1073. The spread of antibiotic resistance has been referred to as a pandemic and that a solution to the growing public health threat will require an interdisciplinary approach. See, e.g., Anderson, *Nature America* 1999, 5: 147-149. See also Bush et al., *Nature Reviews in Microbiology* 2011, 9: 894-896; Levy and Marshall, *Nature Medicine* 2004, 10: S122-S129; Livermore, *Clinical Infectious Diseases* 2003, 36: S11-S23; and Roberts et al. *Clinical Infectious Diseases* 2009, 49: 1175-1184.

The present crisis has prompted various efforts to elucidate the mechanisms responsible for bacterial resistance. The widespread use of penicillins and cephalosporins has resulted in the emergence of β-lactamases, a family of bacterial enzymes that catalyze the hydrolysis of the β-lactam ring common to numerous presently used antibiotics. See, Coulton et al., *Progress in Medicinal Chemistry* 1994, 31: 297-349. This family of bacterial β-lactamases is further divided into four sub-families: A, C, and D which have a serine at the active site that catalyzes the hydrolysis of β-lactam antibiotics and a B family β-lactamases which are zinc metalloenzymes. Resistance mediated by β-lactamases is a critical aspect at the core of the development of bacterial antibiotic resistance. See, Dudley, *Pharmacotherapy* 1995, 15: 9S-14S. Clavulanic acid, which is a metabolite of *Streptomyces clavuligerus*, and two semi-synthetic inhibitors, sulbactam and tazobactam, are currently available semi-synthetic or natural product β-lactamase inhibitors. Synthetic β-lactamase inhibitors have also been described. See, U.S. Pat. Nos. 5,698,577; 5,510,343; 6,472,406; Hubschwerlen et al., *J. Med. Chem.* 1998, 41: 3961; and Livermore et al., *J. Med. Chem.* 1997, 40: 335-343. Poole, *Cell. Mol. Life Sci.* 2004, 61: 2200-2223 provides a review of the resistance of bacterial pathogens to β-lactam antibiotics and approaches for overcoming resistance. For a review of inhibitors of metallo β-lactamases, see Fast and Sutton, *Biochimica et Biophysica Acta—Proteins and Proteomics* 2013, 1834(8): 1648-1659.

U.S. Patent Application Publication No. US 2003/0199541 A1 discloses certain azabicyclic compounds including certain 7-oxo-6-diazabicyclic[3.2.1]octane-2-carboxamides and their use as anti-bacterial agents. U.S. Patent Application Publication No. US 2004/0157826 A1 discloses heterobicyclic compounds including certain diazepine carboxamide and diazepine carboxylate derivatives and their use as anti-bacterials and β-lactamase inhibitors. International Patent Application Publication No. WO 2008/039420 A2 discloses 7-oxo-2,6-diazabicyclo[3.2.0]heptane-6-sulfooxy-2-carboxamides and their use as β-lactamase inhibitors.

Zheng et al., in PLOS One 2013, 8(5), e62955, discloses substituted 2,5-bis-tetrazolylmethyl-thiophenes and their use as β-lactamse inhibitors. Chinese Patent Application Publication No. CN103130686 A discloses N,N'-diarylureas and their use as inhibitors of metallo β-lactamases. Chinese Patent Application Publication No. CN103191091 A discloses substituted arylsulfonamides and their use as inhibitors of metallo β-lactamases.

U.S. Pat. Nos. 4,786,311; 4,746,353; 4,838,925; European Patent Application Publication Nos. EP204513A2, EP244166A2, and Chinese Patent Application Publication No. CN1095549A disclose substituted 2-(1H-tetrazol-5-yl) benzenesulfonamides and their use as herbicides.

SUMMARY OF THE INVENTION

The present invention is directed to certain substituted 1H- and 2H-tetrazol-5-yl sulfonamide compounds which are metallo-β-lactamase inhibitors. The compounds, and their pharmaceutically acceptable salts, are useful, for example, in combination with β-lactam antibiotics for the treatment of bacterial infections, particularly antibiotic-resistant bacterial infections. More particularly, the present invention includes compounds of Formula I:

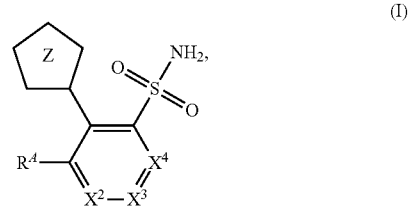

or a pharmaceutically acceptable salt thereof,
wherein:
$X^2$ is N or $CR^B$;
$X^3$ is N or $CR^C$;
$X^4$ is N or $CR^D$;
wherein no more than 2 of $X^2$, $X^3$, and $X^4$ are N;
Z is tetrazolyl, wherein Z is linked to the six membered ring (containing $X^2$-$X^4$) through a carbon to carbon bond;
$R^A$ is H, $C_1$-$C_6$ alkyl, —$(CH_2)_{0-3}$—$C_3$-$C_8$ cycloalkyl, —$C_3$-$C_6$ cycloalkenyl, —$CF_3$, $C_1$-$C_6$ alkoxy, —$COOR^a$, —CN, —$NR^aR^b$, —$(CH_2)_{0-3}$HetA, —$(CH_2)_{0-3}$-AryA, —$(CH_2)_{0-1}$—O-AryA, —$NR^a(CH_2)_{0-2}$—$C_3$-$C_8$ cycloalkyl, —$NR^a(CH_2)_{1-2}$-phenyl, —C≡C-pyridinyl, —C≡C—$CH_2$-HetC, or —C≡C—$CH_2$—O-HetC; wherein the $R^A$ $C_1$-$C_6$ alkyl or any $R^A$ $C_3$-$C_8$ cycloalkyl is optionally substituted with 1, 2, or 3 substituents independently selected from $C_1$-$C_6$ alkoxy, $C_3$-$C_7$ cycloalkyl, —OH, F, —$CF_3$, —CN, —$(CH_2)_{0-3}NR^aR^b$, —C(=NH)$NH_2$, —$CONR^aR^b$, —$(CH_2)_{0-1}$NHC(=NH)$NH_2$; —$NHCONR^aR^b$, —NHCO-diaminoC$_2$alkyl, —NH$(CH_2)_{0-1}$—$C_3$-$C_6$cycloalkyl; —NHSO$_2$—$C_1$-$C_6$ alkyl, —SO$_2$—$C_1$-$C_6$alkyl, —SO$_2$—$C_3$-$C_6$cycloalkyl, —SO$_2NR^aR^b$, AryB, —NH(CH$_2$)$_{0-1}$-AryB, HetB, and —NH(CHR$^a$)$_{0-1}$-HetB, and wherein any C$_3$-C$_6$cycloalkyl is optionally substituted with —(CH$_2$)$_{0-2}$NH$_2$, wherein —C$_3$-C$_6$ cycloalkenyl is optionally substituted with cyano; and the pyridinyl is optionally substituted with 1 or 2 substituents independently selected from —CH$_2$OH and —NH$_2$;

R$^B$ is H, C$_1$-C$_6$ alkyl, —OH, C$_1$-C$_6$ alkoxy, —CN, F, Cl, Br, or —NR$^a$R$^b$, wherein the R$^B$ C$_1$-C$_6$ alkyl can optionally be substituted with 1, 2 or 3 substituents selected from —OH, —F, —NR$^a$R$^b$, —CF$_3$, C$_1$-C$_6$ alkoxy, and —CONR$^a$R$^b$;

or R$^A$ and R$^B$ together with the atom(s) to which they are attached form a 5-7 membered fused ring containing 0, 1, or 2 heteroatoms independently selected from N, O and S, wherein N is optionally substituted with R$^d$;

R$^C$ is H, C$_1$-C$_6$ alkyl, F, Cl, —CF$_3$, —COOCH$_3$, —C(O)NH$_2$, or AryC;

R$^D$ is H, C$_1$-C$_6$ alkyl, C$_1$-C$_6$ hydroxyalkyl, —(CH$_2$)$_{0-2}$C$_3$-C$_6$ cycloalkyl, —C$_3$-C$_6$ cycloalkenyl, —(CH$_2$)$_2$C(O)OH, —CF$_3$, F, Cl, Br, —(CH$_2$)$_{0-1}$AryA, or —(CH$_2$)$_{0-2}$HetA, wherein the R$^D$ C$_1$-C$_6$ alkyl or R$^D$ C$_3$-C$_6$ cycloalkyl is optionally substituted with 1, 2, or 3 substituents independently selected from C$_3$-C$_6$ cycloalkyl, —OH, F, —CN, —(CH$_2$)$_{0-3}$NR$^a$R$^b$, —CF$_3$, —(CH$_2$)$_{0-2}$HetB, —(CH$_2$)$_{0-2}$AryB, —(CH$_2$)$_{0-1}$NHC(=NH)NH$_2$; —SO$_2$—C$_1$-C$_6$alkyl, —SO$_2$—C$_3$-C$_6$cycloalkyl, —SO$_2$NR$^a$R$^b$, C$_1$-C$_6$ alkoxy, and —(CH$_2$)$_{0-4}$CONR$^a$R$^b$, and wherein the —C$_3$-C$_6$ cycloalkenyl is optionally substituted with cyano;

wherein when R$^A$, R$^B$, R$^C$ and R$^D$ are all present, then 1, 2 or 3 of R$^A$, R$^B$, R$^C$ and R$^D$ are H;

wherein when 1 or 2 of X$^2$, X$^3$, X$^4$ are N, then at least one of R$^A$, R$^B$, R$^C$, and R$^D$, if present, is not H;

AryA is an aromatic ring system selected from:
1) a 5-6 membered monocyclic ring with 0, 1, 2 or 3 heteroatom ring atoms independently selected from N, O and S, optionally substituted with 1, 2 or 3 substituents independently selected from:
   a) —C$_1$-C$_6$ alkyl,
   b) —C$_2$-C$_6$diaminoalkyl;
   c) —C$_1$-C$_6$ hydroxyalkyl,
   d) —C$_1$-C$_6$ dihydroxyalkyl,
   e) —C$_3$-C$_6$ cycloalkyl optionally substituted with 1 or 2 substituents selected from —OH and —NR$^a$R$^b$,
   f) —C$_3$-C$_6$ cycloalkenyl optionally substituted with —CN,
   g) —(CH$_2$)$_{0-6}$NR$^a$R$^b$,
   h) —CH(OH)R$^e$,
   i) —CH$_2$OR$^a$,
   j) —(CH$_2$)$_{0-2}$C(O)NR$^a$R$^b$,
   k) —CH$_2$NR$^a$—C$_2$-C$_4$alkyl-NR$^a$R$^b$,
   l) —C(=NH)NHR$^b$;
   m) —CH$_2$NHCH(=NH);
   n) —CH$_2$NHCH$_2$C(O)NR$^a$R$^b$,
   o) —(CH$_2$)$_{0-2}$C(O)OR$^a$,
   p) —CH$_2$NR$^a$—C$_1$-C$_3$alkyl-C(O)OR$^a$,
   q) —CH$_2$NH—CH[C(OH)CH$_3$][C(O)OR$^a$],
   r) —CH$_2$NR$^a$—C$_1$-C$_6$ hydroxyalkyl,
   s) —(CH$_2$)$_{0-2}$SO$_2$—C$_1$-C$_6$ alkyl,
   t) —NR$^a$SO$_2$—C$_3$-C$_6$ cycloalkyl,
   u) —NR$^a$SO$_2$—C$_1$-C$_6$ alkyl,
   v) —NR$^a$SO$_2$—NR$^a$R$^b$,
   w) —CH$_2$NHC(=NH)NHR$^b$;
   x) —NHC(=NH)NH$_2$;
   y) —OR$^a$,
   z) —O(CH$_2$)$_{0-6}$NR$^a$R$^b$;
   aa) —O—C$_1$-C$_6$ hydroxyalkyl,
   bb) —(CH$_2$)$_{0-1}$SO$_2$(CH$_2$)$_{0-2}$NR$^a$R$^b$,
   cc) —SO$_2$(CH$_2$)$_{0-2}$OH,
   dd) —CN,
   ee) halogen,
   ff) —CF$_3$,
   gg) —CH$_2$NR$^a$(CH$_2$)$_{0-1}$—C$_3$-C$_6$cycloalkyl optionally substituted with —OH, NR$^a$R$^b$ or 2 F,
   hh) —(CH$_2$)$_{0-1}$-AryB,
   ii) —CH$_2$NR$^a$—C$_1$-C$_3$alkyl-AryB,
   jj) —CH$_2$NR$^a$—CH(COOH)CH$_2$-AryB,
   kk) —C$_0$-C$_2$alkyl-HetB,
   ll) —CH(OH)-HetB,
   mm) —(CH$_2$)$_{0-1}$NR$^a$(CH$_2$)$_{0-2}$-HetB,
   nn) —C(=NH)NH-HetB;
   oo) —O(CH$_2$)$_{0-2}$-HetB,
   pp) —C(O)-HetB, and
   qq) —C(O)NR$^a$(CH$_2$)$_{0-2}$-HetB; or
2) a 9- or 10-membered bicyclic ring with 1, 2, 3 or 4 heteroatom ring atoms selected from N, O and S, wherein an N atom is optionally in the form of a quaternary amine and wherein the ring is optionally substituted with 1, 2 or 3 substituents independently selected from C$_1$-C$_6$ alkyl, C$_3$-C$_6$ cycloalkyl, C$_1$-C$_6$ alkoxy, C$_1$-C$_6$ hydroxyalkyl, C$_1$-C$_6$aminoalkyl, —CF$_3$, —C(=NH)NH$_2$, —COOR$^a$, —(CH$_2$)$_{0-1}$C(O)NR$^a$R$^b$, —CN, —(CH$_2$)$_{0-3}$NR$^a$R$^b$, —NHCH$_2$CH$_2$N(CH$_3$)$_2$, —NH—C$_3$-C$_6$ cycloalkyl, —NHC(=NH)NH$_2$, —NH-HetB, —OR$^a$, —SO$_2$—C$_1$-C$_6$ alkyl, —SO$_2$-phenyl, halogen, and oxo, wherein the C$_3$-C$_6$ cycloalkyl is optionally substituted with —NH$_2$;

AryB is
1) a 5-6 membered monocyclic aromatic ring with 0, 1, 2, 3, or 4 ring atoms selected from N, O and S, optionally substituted with 1 or 2 substituents selected from C$_1$-C$_6$ alkyl, —CH$_2$NH$_2$, —CONH$_2$, —CH$_2$OH, —NH$_2$, —OH, —CH(OH)R$^e$, halogen, —CF$_3$, and pyrrolidinyl; or
2) a 9- or 10-membered bicyclic ring with 1, 2 or 3 N ring atoms optionally substituted with 1 or 2 substituents selected from C$_1$-C$_6$ alkyl, C$_1$-C$_6$hydroxyalkyl, C$_1$-C$_6$aminoalkyl, —CONH$_2$, —NH$_2$, —OH, —CH(OH)R$^e$, halogen, —CF$_3$, piperidinyl, pyrrolidinyl, and oxo;

AryC is
1) phenyl optionally substituted with —CONH$_2$;
2) a 5-6 membered monocyclic aromatic ring with 1 or 2 N ring atoms, optionally substituted with —CH$_3$ or —OH; or
3) a 9-membered bicyclic ring with 1 N ring atom optionally substituted with oxo;

AryD is a 5-membered monocyclic aromatic ring with 2 N ring atoms, optionally substituted with —CH$_3$;

HetA is
1) a 4-6-membered saturated or monounsaturated monocyclic ring with 1 or 2 heteroatom ring atoms independently selected from N, O and S, wherein an N atom is optionally in the form of a quaternary amine and wherein the ring is optionally substituted with 1 or 2 substituents independently selected from
   a) C$_1$-C$_6$ alkyl,
   b) —C$_1$-C$_6$ hydroxyalkyl,
   c) C$_3$-C$_6$cycloalkyl optionally substituted with —NH$_2$,
   d) —C(O)—C$_3$-C$_6$cycloalkyl optionally substituted with phenyl,
   e) —(CH$_2$)$_{0-4}$NR$^a$R$^b$,
   f) —C(=NH)NH$_2$;
   g) —(CH$_2$)$_{0-1}$C(O)NR$^a$R$^b$, h) —(CH$_2$)$_{0-2}$C(O)OR$^a$,
i) —(CH$_2$)$_{0-2}$SO$_2$—C$_1$-C$_6$ alkyl,
j) —CN,
k) —NHC(=NH)NH$_2$;
l) —OR$^a$,
m) F,
n) —CF$_3$,
o) —(CH$_2$)$_{0-1}$-AryB,
p) —O-AryB,
q) —C$_0$-C$_2$ alkyl-HetB, and
r) oxo; or 2) a 6-11-membered bicyclic ring with 1 to 3 heteroatom ring atoms selected from N and O, optionally substituted with —CH$_2$OH, —C(=NH)NH$_2$; —CH$_2$C$_3$-C$_6$cycloalkyl, —C(=O), —NH$_2$, or oxo, wherein the rings in the bicyclic ring are bridged, fused or spirocyclic, and wherein the C$_3$-C$_6$cycloalkyl is optionally substituted with —NH$_2$;

HetB is
1) a 4-7 membered saturated or monounsaturated monocyclic ring with 1 or 2 heteroatom ring atoms independently selected from N, O and S, wherein an N atom is optionally in the form of a quaternary amine and wherein the ring is optionally substituted with 1, 2 or 3 substituents independently selected from —CF$_3$, F, C$_1$-C$_6$ alkyl, C$_1$-C$_6$ hydroxyalkyl, C$_2$-C$_6$ aminoalkyl, C$_1$-C$_6$ haloalkyl, —CH$_2$CH$_2$N$^+$(CH$_3$)$_3$; —(CH$_2$)$_{0-1}$C$_3$-C$_6$ cycloalkyl, —OH, C$_1$-C$_6$ alkoxy, —C(O)OR$^a$, —C(O)NH$_2$, —CH(=NH), —C(=NH)NH$_2$, —CN, —C(OH)(CH$_3$)$_2$, —CH(OH)(CH$_3$), —(CH$_2$)$_{0-2}$NR$^a$R$^b$, —CH$_2$CHR$^f$—(CH$_2$)$_{0-2}$—NHR$^g$, —CH$_2$-AryD, —(CH$_2$)$_{0-2}$-HetD, oxo, and —SO$_2$—C$_1$-C$_6$ alkyl, wherein the cycloalkyl is optionally substituted with —(CH$_2$)$_{0-2}$NHR$^a$; or 2) a 7-11-membered bicyclic ring with 1 or 2 N ring atoms optionally substituted with methyl, wherein the bicyclic ring is bridged, fused or spirocyclic;

HetC is a 5-6 membered saturated monocyclic ring with 1 or 2 heteroatom ring atoms independently selected from N, O and S, optionally substituted with 1 or 2 oxo substituents;

HetD is
1) a 4-6 membered saturated monocyclic ring with 1 or 2 heteroatom ring atoms independently selected from N and O;
2) 7-9 membered bicyclic ring with 1 N heteroatom ring atom, wherein the bicyclic ring is bridged or spirocyclic;

R$^a$ is H or C$_1$-C$_6$ alkyl;
R$^b$ is H, —OH, C$_1$-C$_6$ alkyl, C$_1$-C$_6$ alkoxy, C$_2$-C$_6$ hydroxyalkyl, C$_2$-C$_6$ aminoalkyl, C$_2$-C$_6$ dihydroxyalkyl, C$_2$-C$_6$ diaminoalkyl, dimethylaminoC$_2$-C$_6$alkyl, C$_2$-C$_6$ hydroxyaminoalkyl, —(CH$_2$)$_{0-1}$—C$_3$-C$_6$ cycloalkyl, —C(O)C$_1$-C$_6$ alkyl, or —CH$_2$C(O)NHOH; or R$^a$ and R$^b$ together with the atom(s) to which they are attached form a 3-7 membered cycloheteroalkyl ring with 0, 1 or 2 additional heteroatom ring atoms independently selected from N, O and S, wherein N is optionally substituted with R$^d$;

R$^d$ is H, C$_1$-C$_6$ alkyl, C$_3$-C$_6$ cycloalkyl, —C(O)—C$_1$-C$_6$ alkyl, —C(O)-AryC, —SO$_2$—C$_1$-C$_6$ alkyl, or —SO$_2$-AryC;

R$^e$ is C$_1$-C$_6$ alkyl, —CF$_3$ or —CHF$_2$;
R$^f$ is C$_1$-C$_6$ alkyl, —CH$_2$OH, —(CH$_2$)$_{1-4}$NH$_2$, —(CH$_2$)$_{1-3}$CONH$_2$, —CH$_2$-imidazole, or benzyl; and
R$^g$ is H or C$_1$-C$_6$ alkyl; or
R$^f$ and R$^g$ together with the atom(s) to which they are attached form a 4-6 membered cycloheteroalkyl ring with 0, 1 or 2 additional heteroatom ring atoms independently selected from N, O and S. In one aspect, a N ring atom on HetB can be substituted with 2 methyl groups to afford a positively charged quaternary amine.

Compounds of Formula I inhibit metallo-β-lactamases and can synergize the antibacterial effects of β-lactam antibiotics (e.g., imipenem, ceftazidime and piperacillin) against microorganisms normally resistant to β-lactam antibiotics as a result of the presence of the metallo-β-lactamases. The compounds of the present invention are effective against metallo-β-lactamases and their combination with a β-lactam antibiotic, such as imipenem, ceftazidine or piperacillin, can provide for effective treatment of bacterial infections caused by metallo-β-lactamase producing microorganisms. Accordingly, in certain embodiments, the present invention includes combinations of a compound of Formula I with a β-lactam antibiotic suitable for use against metallo-β-lactamase producing bacteria such as *Pseudomonas* spp. and *Klebsiella* spp. The invention also includes compositions comprising a compound of Formula I or its pharmaceutically acceptable salt, and a pharmaceutically acceptable carrier. The invention further includes methods for treating bacterial infections and inhibiting bacterial growth by use of a compound of Formula I or its salt or a combination or composition containing the compound or its salt.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I, wherein the compounds are metallo-β-lactamase inhibitors suitable for use in combination with β-lactam antibiotics and class A, C, and D β-lactamase inhibitors for the treatment of bacterial infections.

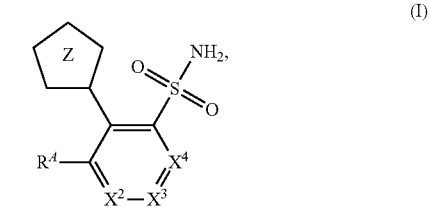

(I)

In a first embodiment of the invention, the compound is a compound of formula (I), or a pharmaceutically acceptable salt thereof, wherein:

R$^A$ is H, C$_1$-C$_6$ alkyl, —(CH$_2$)$_{0-2}$—C$_3$-C$_8$ cycloalkyl, —CF$_3$, C$_1$-C$_6$ alkoxy, —COOR$^a$, —CN, —NR$^a$R$^b$, HetA, —(CH$_2$)$_{0-2}$-AryA, —(CH$_2$)$_{0-1}$—O-AryA, —NR$^a$(CH$_2$)$_{1-2}$—C$_3$-C$_8$ cycloalkyl, —NR$^a$(CH$_2$)$_{1-2}$-phenyl, —C≡C-pyridinyl, or —C≡C—CH$_2$-HetC; wherein the R$^A$ C$_1$-C$_6$ alkyl or any R$^A$ C$_3$-C$_8$ cycloalkyl is optionally substituted with —OH, —(CH$_2$)$_{0-2}$NR$^a$R$^b$, —NHSO$_2$—C$_1$-C$_6$ alkyl, AryB, or HetB;

R$^B$ is H, C$_1$-C$_6$ alkyl, —OH, C$_1$-C$_6$ alkoxy, —CN, F, or —NR$^a$R$^b$;

or R$^A$ and R$^B$ together with the atom(s) to which they are attached form a 5-6 membered fused aromatic ring containing 0, 1, or 2 heteroatoms independently selected from N, O and S, wherein N is optionally substituted with R$^d$;

$R^C$ is H, $C_1$-$C_6$ alkyl, F, Cl, —COOCH$_3$, —C(O)NH$_2$, or AryC;

$R^D$ is H, $C_1$-$C_6$ alkyl, —(CH$_2$)$_{0-1}$C$_3$-C$_6$ cycloalkyl, —CH$_2$-phenyl, —CH$_2$-azetidinyl, —(CH$_2$)$_{1-2}$-piperidinyl, or —CH$_2$-pyrrolidinyl, —CF$_3$, —CN, Cl, or Br, wherein the cycloalkyl is optionally substituted with —(CH$_2$)$_{0-1}$NH$_2$ and the piperidinyl is optionally substituted with fluoro;

AryA is an aromatic ring system selected from:
1) a 5-6 membered monocyclic ring with 0, 1, 2 or 3 heteroatom ring atoms independently selected from N, O and S, optionally substituted with 1 or 2 substituents independently selected from:
   a) —C$_1$-C$_6$ alkyl,
   b) —C$_1$-C$_6$ hydroxyalkyl,
   c) —C$_3$-C$_6$ cycloalkyl optionally substituted with —OH,
   d) —C$_3$-C$_6$ cycloalkenyl optionally substituted with —CN,
   e) —(CH$_2$)$_{0-6}$NR$^a$R$^b$,
   f) —CH$_2$NHCH=NH;
   g) —CH(OH)R$^e$,
   h) —CH$_2$OR$^a$,
   i) —(CH$_2$)$_{0-1}$C(O)NR$^a$R$^b$,
   j) —CH$_2$NR$^a$—C$_3$-C$_4$alkyl-NR$^a$R$^b$,
   k) —CH$_2$NHCH$_2$C(O)NR$^a$R$^b$,
   l) —(CH$_2$)$_{0-2}$C(O)OR$^a$,
   m) —CH$_2$NR$^a$—C$_1$-C$_3$alkyl-C(O)OR$^a$,
   n) —CH$_2$NH—CH[C(OH)CH$_3$][C(O)OR$^a$],
   o) —CH$_2$NR$^a$—C$_1$-C$_6$ hydroxyalkyl,
   p) —(CH$_2$)$_{0-2}$SO$_2$—C$_1$-C$_6$ alkyl,
   q) —NR$^a$SO$_2$—C$_1$-C$_6$ alkyl,
   r) —OR$^a$,
   s) —O(CH$_2$)$_{0-6}$NR$^a$R$^b$;
   t) —O—C$_1$-C$_6$ hydroxyalkyl,
   u) —SO$_2$NR$^a$R$^b$,
   v) —CN,
   w) halogen,
   x) —CH$_2$NR$^a$(CH$_2$)$_{0-1}$—C$_3$-C$_6$cycloalkyl optionally substituted with —OH, NR$^a$R$^b$ or 2F,
   y) —(CH$_2$)$_{0-1}$-AryB,
   z) —CH$_2$NR$^a$—C$_1$-C$_3$alkyl-AryB,
   aa) —CH$_2$NR$^a$—CH(COOH)CH$_2$-AryB,
   bb) —C$_0$-C$_2$alkyl-HetB,
   cc) —(CH$_2$)$_{0-1}$NR$^a$(CH$_2$)$_{0-2}$-HetB,
   dd) —O(CH$_2$)$_{0-2}$-HetB,
   ee) —C(O)-HetB, and
   ff) —C(O)NR$^a$(CH$_2$)$_{0-2}$-HetB; or
2) a 9- or 10-membered bicyclic ring with 1, 2 or 3 heteroatom ring atoms selected from N, O and S, optionally substituted with 1 or 2 substituents independently selected from C$_1$-C$_6$ alkyl, C$_1$-C$_6$ alkoxy, —NH$_2$, C$_1$-C$_6$ aminoalkyl, —CF$_3$, —COOR$^a$, —CONH$_2$, —SO$_2$—C$_1$-C$_6$ alkyl, —SO$_2$-phenyl, —CN, Cl, and oxo;

AryB is
1) a 5-6 membered monocyclic aromatic ring with 0, 1, 2, 3, or 4 ring atoms selected from N, O and S, optionally substituted with C$_1$-C$_6$ alkyl, —CH$_2$NH$_2$, —NH$_2$, —CH(OH)R$^e$, or pyrrolindinyl; or
2) a 9-membered bicyclic ring with 2 or 3 N ring atoms optionally substituted with —CH$_3$;

AryC is
1) phenyl optionally substituted with —C(=O)NH$_2$;
2) a 5-6 membered monocyclic aromatic ring with 1 or 2 N ring atoms, optionally substituted with —CH$_3$ or —OH; or
3) a 9-membered bicyclic ring with 1 N ring atom optionally substituted with oxo;

HetA is
1) a 6-membered monounsaturated monocyclic ring with 1 heteroatom ring atoms independently selected from N, O and S, optionally substituted with 1 or 2 substituents independently selected from C$_1$-C$_6$ alkyl, —CN, and oxo;
2) a 6-membered saturated monocyclic ring with 1 N ring atom, optionally substituted with 1 substituent selected from
   a) —C$_1$-C$_6$ hydroxyalkyl,
   b) —C(O)—C$_3$-C$_6$cycloalkyl,
   c) —(CH$_2$)$_{1-2}$NR$^a$R$^b$,
   d) —(CH$_2$)$_{0-1}$C(O)NR$^a$R$^b$,
   e) —(CH$_2$)$_{0-2}$C(O)OR$^a$,
   f) —(CH$_2$)$_{0-2}$SO$_2$—C$_1$-C$_6$ alkyl,
   g) —OH,
   h) —(CH$_2$)$_{0-1}$-AryB,
   i) —O-AryB, and
   j) —C$_0$-C$_2$ alkyl-HetB; or
3) a 10-11-membered spirocyclic ring with 2 or 3 N ring atoms optionally substituted with oxo;

HetB is
1) a 4-6 membered saturated or monounsaturated monocyclic ring with 1 or 2 heteroatom ring atoms independently selected from N, O and S, optionally substituted with 1, 2 or 3 substituents independently selected from —CF$_3$, F, C$_1$-C$_6$ alkyl, C$_1$-C$_6$ hydroxyalkyl, C$_3$-C$_6$ cycloalkyl, —OH, C$_1$-C$_6$ alkoxy, —C(O)OR$^a$, —C(O)NH$_2$, —C(=NH$_2$)NH$_2$, —CN, —C(OH)(CH$_3$)$_2$, —CH(OH)(CH$_3$); —NH$_2$, —N(CH$_3$)$_2$, and oxo; or
2) 8-methyl-8-azabicyclo[3.2.1]octane with the point of attachment being the 3-position of the bridged bicycle;

HetC is a 5-6 membered saturated monocyclic ring with 1 or 2 heteroatom ring atoms independently selected from N, O and S, optionally substituted with 1 or 2 oxo substituents;

$R^a$ is H or C$_1$-C$_6$ alkyl;

$R^b$ is H, —OH, C$_1$-C$_6$ alkyl, C$_1$-C$_6$ alkoxy, C$_1$-C$_6$ hydroxyalkyl, C$_1$-C$_6$ dihydroxyalkyl, C$_3$-C$_6$ cycloalkyl, —C(O) C$_1$-C$_6$ alkyl, —CH$_2$C(O)NHOH, or C$_1$-C$_6$ aminoalkyl; or $R^a$ and $R^b$ together with the atom(s) to which they are attached form a 3-7 membered cycloheteroalkyl ring with 0, 1 or 2 additional heteroatom ring atoms independently selected from N, O and S, wherein N is optionally substituted with R$^d$;

$R^e$ is —C$_1$-C$_6$ alkyl, —CF$_3$ or —CHF$_2$; and the other groups are as provided in the general formula I above.

In a second embodiment of the invention, the compound is a compound of formula I, or a pharmaceutically acceptable salt thereof, wherein $R^A$ is C$_1$-C$_6$ alkyl, —(CH$_2$)$_{0-2}$—C$_3$-C$_8$ cycloalkyl, —CF$_3$, C$_1$-C$_6$ alkoxy, —COOR$^a$, —CN, —NR$^a$R$^b$, HetA, —(CH$_2$)$_{0-2}$-AryA, —CH$_2$—O-AryA, —NR$^a$(CH$_2$)$_{1-2}$—C$_3$-C$_8$ cycloalkyl, —NR$^a$(CH$_2$)$_{1-2}$-phenyl, —C≡C-pyridinyl, or —C≡C—CH$_2$-HetC; wherein the $R^A$ cycloalkyl is optionally substituted with —OH, —(CH$_2$)$_{0-2}$NH$_2$, —NHSO$_2$—C$_1$-C$_6$ alkyl or HetB, and the other groups are as provided in the general formula I above, or as in the first embodiment.

In a third embodiment of the invention, the compound is a compound of Formula I, or a pharmaceutically acceptable salt thereof, wherein Formula I is

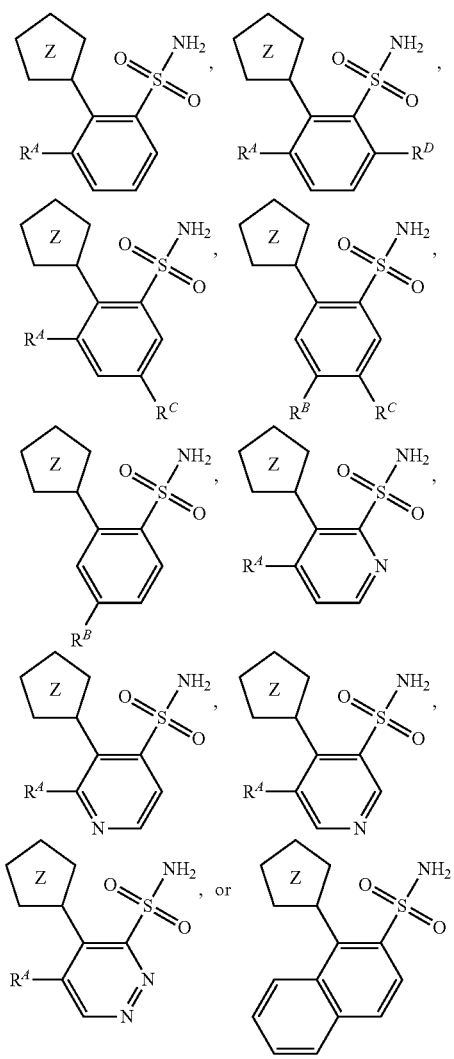

wherein

R$^A$ is C$_1$-C$_6$ alkyl, —(CH$_2$)$_{0-2}$—C$_3$-C$_8$ cycloalkyl, —CF$_3$; C$_1$-C$_6$ alkoxy, —COOR$^a$, —CN, —NR$^a$R$^b$, HetA, —(CH$_2$)$_{0-2}$-AryA, —CH$_2$—O-AryA, —NR$^a$(CH$_2$)$_{1-2}$—C$_3$-C$_8$ cycloalkyl, —NR$^a$(CH$_2$)$_{1-2}$-phenyl, —C≡C-pyridinyl, or —C≡C—CH$_2$-HetC; wherein the R$^A$ cycloalkyl is optionally substituted with —(CH$_2$)$_{0-1}$NR$^a$R$^b$, AryB, or —OH;

R$^B$ is C$_1$-C$_6$ alkyl, —OH, C$_1$-C$_6$ alkoxy, —CN, F, or —NR$^a$R$^b$,

R$^C$ is C$_1$-C$_6$ alkyl, Cl, —COOCH$_3$, —C(O)NH$_2$, or AryC; and

R$^D$ is C$_1$-C$_6$ alkyl, —(CH$_2$)$_{0-1}$C$_3$-C$_8$ cycloalkyl, —CH$_2$-phenyl, —CH$_2$-azetidinyl, —(CH$_2$)$_{1-2}$-piperidinyl, or —CH$_2$-pyrrolidinyl, —CF$_3$, Cl, or Br, wherein the cycloalkyl is optionally substituted with —(CH$_2$)$_{0-1}$NH$_2$ and the piperidinyl is optionally substituted with fluoro; and the other groups are as provided in the general formula I above, or as in the first or second embodiment.

In a fourth embodiment of the invention, the compound is a compound of formula I, or a pharmaceutically acceptable salt thereof, wherein AryA is 1) phenyl optionally substituted with:
   a) —C$_1$-C$_6$ alkyl,
   b) —C$_1$-C$_2$ hydroxyalkyl,
   c) —(CH$_2$)$_{1-3}$NR$^a$R$^b$,
   d) —CH$_2$NHCH=NH;
   e) —CH$_2$NHC(=NH)NH$_2$;
   f) —CH(OH)R$^e$,
   g) —CH$_2$OR$^a$,
   h) —CH$_2$NR$^a$—C$_1$-C$_6$ hydroxyalkyl,
   i) —(CH$_2$)$_{0-1}$C(O)NR$^a$R$^b$,
   j) —C(O)OR$^a$,
   k) —NHSO$_2$—C$_1$-C$_6$ alkyl,
   l) —OR$^a$,
   m) —OCH(CH$_3$)CH$_2$OH,
   n) —SO$_2$—C$_1$-C$_6$ alkyl,
   o) —SO$_2$NR$^a$R$^b$,
   p) halogen,
   q) —CN,
   r) —CH$_2$NR$^a$(CH$_2$)$_{0-1}$—C$_3$-C$_6$cycloalkyl optionally substituted with —OH, NR$^a$R$^b$ or 2 F,
   s) AryB,
   t) —CH$_2$NR$^a$—C$_3$-C$_4$alkyl-NR$^a$R$^b$,
   u) —CH$_2$NHCH$_2$C(O)NR$^a$R$^b$,
   v) —CH$_2$NR$^a$—C$_1$-C$_3$alkyl-C(O)OR$^a$,
   w) —CH$_2$NH—CH[C(OH)CH$_3$][C(O)OR$^a$],
   x) —CH$_2$NR$^a$—C$_1$-C$_3$alkyl-AryB,
   y) —CH$_2$NR$^a$—CH(COOH)CH$_2$-AryB,
   z) —C$_0$-C$_2$ alkyl-HetB,
   aa) —C(O)-HetB,
   bb) —(CH$_2$)$_{0-1}$NR$^a$(CH$_2$)$_{0-2}$-HetB,
   cc) —C(O)NR$^a$(CH$_2$)$_{0-2}$-HetB, or
   dd) —O(CH2)$_{0-2}$-HetB; or 2) dihydroindenyl substituted with —NH$_2$ or —NHC(=NH)NH$_2$; and the other groups are as provided in the general formula I above, or as in any of the first through third embodiments.

In a fifth embodiment of the invention, the compound is a compound of formula I, or a pharmaceutically acceptable salt thereof, wherein AryA is an aromatic ring system selected from:

a) a 5-6 membered monocyclic ring with 1 or 2 heteroatom ring atoms independently selected from N, O and S, optionally substituted with 1 or 2 substituents selected from C$_1$-C$_6$ alkyl; C$_1$-C$_6$ hydroxyalkyl; C$_1$-C$_6$ alkoxy; C$_1$-C$_6$ aminoalkyl; C$_3$-C$_6$ hydroxycycloalkyl; —CH$_2$CH$_2$C(O)OCH$_2$CH$_3$; —CN; —(CH$_2$)$_{0-2}$SO$_2$CH$_3$; —NR$^a$R$^b$, —N(R$^a$)SO$_2$CH$_3$; —OH; —O(CH$_2$)$_{0-6}$NR$^a$R$^b$; dioxolanyl substituted with —CF$_3$; halogen; —(CH$_2$)$_{0-1}$-AryB; —C$_0$-C$_2$alkyl-HetB; and —(CH$_2$)$_{0-1}$NR$^a$(CH$_2$)$_{0-2}$-HetB; or b) a 9- or 10-membered bicyclic ring with 1, 2 or 3 heteroatom ring atoms selected from N, S and O, optionally substituted with 1 or 2 substituents independently selected from C$_1$-C$_6$ alkyl, C$_1$-C$_6$ alkoxy, —NR$^a$R$^b$, C$_1$-C$_6$ aminoalkyl, —CF$_3$, —C(=NH)NH$_2$, —COOR$^a$, —CONH$_2$, —SO$_2$—C$_1$-C$_6$ alkyl, —SO$_2$-phenyl, —CN, Cl, and oxo; and the other groups are as provided in the general formula I above, or as in any of the first through third embodiments.

In a sixth embodiment of the invention, the compound is a compound of formula I, or a pharmaceutically acceptable salt thereof, wherein AryA is an aromatic ring system selected from:

a) a monocyclic ring selected from furanyl, imidazolyl, morpholinyl, pyrazinyl, pyrazolyl, pyridazinyl, pyridinyl; pyrimidinyl, thiazolyl, and thiophenyl, wherein the monocyclic ring is optionally substituted with 1 or 2 substituents selected from C$_1$-C$_6$ alkyl; C$_1$-C$_6$ hydroxyalkyl; C$_1$-C$_6$ alkoxy; C$_1$-C$_6$ aminoalkyl; C$_3$-C$_6$ hydroxycycloalkyl; —CH$_2$CH$_2$C(O)OCH$_2$CH$_3$;

—CN; —(CH$_2$)$_{0-2}$SO$_2$CH$_3$; —NR$^a$R$^b$, —N(R$^a$)SO$_2$CH$_3$; —OH; —O(CH$_2$)$_{0-6}$NR$^a$R$^b$; dioxolanyl substituted with —CF$_3$; halogen; —(CH$_2$)$_{0-1}$-AryB; —C$_0$-C$_2$alkyl-HetB; and —(CH$_2$)$_{0-1}$NR$^a$(CH$_2$)$_{0-2}$-HetB; or b) a bicyclic ring selected from 1H-benzo[d]imidazolyl, benzodiimidazolyl, benzooxadiazolyl, benzo[d]thiazolyl, benzothiophenyl, benzotriazolyl, dihydrobenzimidazol, dihydrobenzodioxinyl, dihydrobenzooxazinyl, dihydrochromenyl, dihydroisoindolyl, dihydroindolyl, dihydroquinazolinyl, furopyridinyl, imidazopyridinyl, indazolyl, indolinyl, indolyl, isoindolinyl, isoquinolinyl, naphthyridinyl, pyrazolopyrazinyl, pyrazolopyridinyl, pyrrolopyrazinyl, pyrroloppyridinyl, quinolinyl, tetrahydroimidazopyridinyl, tetrahydropyrazolopyridinyl, tetrahydroquinolinyl, and triazolopyridinyl; wherein the bicyclic ring is optionally substituted with 1 or 2 substituents independently selected from C$_1$-C$_6$ alkyl, C$_1$-C$_6$ alkoxy, —NR$^a$R$^b$, C$_1$-C$_6$ aminoalkyl, —CF$_3$, —COOR$^a$, —CONH$_2$, —SO$_2$—C$_1$-C$_6$ alkyl, —SO$_2$-phenyl, —CN, Cl, and oxo; and the other groups are as provided in the general formula I above, or as in any of the first through third embodiments.

In a seventh embodiment of the invention, HetB is azabicyclo[3.2.1]octyl, azetidinyl, 1,1-dimethylazetidin-1-ium, 1,1-dimethylpiperidin-1-ium, dioxolanyl, morpholinyl, oxoimidazolidinyl, oxazolidinyl, oxopiperazinyl, oxopiperidinyl, oxopyrrolidinyl, oxazolidinyl, piperidinyl, piperazinyl, pyrazolyl, pyrrolidinyl, tetrahydrofuranyl, tetrahydropyranyl, or thiazolidinyl; wherein HetB is optionally substituted with 1, 2 or 3 substituents independently selected from —CF$_3$, F, C$_1$-C$_6$ alkyl, —C$_1$-C$_6$ hydroxyalkyl, C$_3$-C$_6$ cycloalkyl, —OH, C$_1$-C$_6$ alkoxy, —C(O)OR$^a$, —C(O)NH$_2$, —CH(=NH), —C(=NH$_2$)NH$_2$, —CN, —C(OH)(CH$_3$)$_2$, —CH(OH)(CH$_3$), —NH$_2$, —N(CH$_3$)$_2$, —(CH$_2$)-azetidinyl, and oxo; or HetC is dioxidothiomorpholinyl, morpholinyl, piperidinyl, or pyrrolidin-1-yl; and the other groups are as provided in the general formula I above, or as in any of the first through sixth embodiments.

In an eighth embodiment of the invention, the compound is a compound of a formula below, or a pharmaceutically acceptable salt thereof,

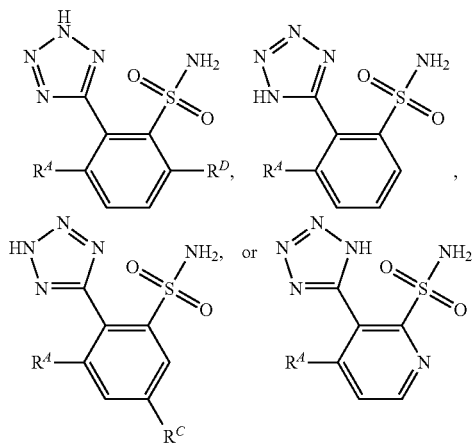

wherein
R$^A$ is
1) —(CH$_2$)$_{0-2}$AryA optionally substituted with
 a) —C$_1$-C$_6$ alkyl,
 b) —C$_1$-C$_2$ hydroxyalkyl,
 c) —(CH$_2$)$_{0-3}$NR$^a$R$^b$,
 d) —C(=NH)NH$_2$
 e) —CH$_2$NHCH=NH;
 f) —CH$_2$NHC(=NH)NH$_2$;
 g) —(CH$_2$)$_{0-1}$C(O)NR$^a$R$^b$,
 h) —NHC(=NH)NH$_2$;
 i) —NHSO$_2$—C$_1$-C$_6$ alkyl,
 j) —OH,
 k) —SO$_2$NR$^a$R$^b$, or
 l) HetB, or
2) —(CH$_2$)$_{0-2}$ C$_3$-C$_6$-cycloalkyl, wherein the C$_3$-C$_6$ cycloalkyl optionally substituted with —OH or —(CH$_2$)$_{0-2}$NR$^a$R$^b$;

HetB is
1) a 4-6 membered saturated or monounsaturated monocyclic ring with 1 N ring atom, optionally substituted with 1 or 2 substituents selected from —CH(=NH), —C(=NH)NH$_2$, —NH$_2$, and —OH; or
2) a 4-6 membered saturated monocyclic ring with 1 N ring atom, in the form of a quarternary amine, wherein the N ring atom is substituted with 2 methyl groups;

R$^C$ is Cl;
R$^D$ is C$_1$-C$_6$ alkyl, C$_3$-C$_6$ cycloalkyl, —CF$_3$, Cl, Br, —CH$_2$-cyclohexyl-(CH$_2$)$_{0-1}$NH$_2$, —CH$_2$-azetidinyl, —(CH$_2$)$_{1-2}$-piperidinyl, or —CH$_2$-pyrrolidinyl, wherein the piperidinyl is optionally substituted with fluoro;
R$^a$ is H or CH$_3$;
R$^b$ is H or CH$_3$; and the other groups are as provided in the general formula I above, or as in the first embodiment.

In a ninth embodiment of the invention; the compound is a compound of a formula in the eighth embodiment; or a pharmaceutical salt thereof; wherein AryA is phenyl substituted with 1) —CH$_3$, 2) —CH$_2$CH$_2$CH$_3$, 3) —CH$_2$OH, 4) —CH$_2$NH$_2$, 5) —CH$_2$NHCH=NH, 6) —CH$_2$NHC(=NH)NH$_2$, 7) —CH$_2$CH$_2$NH$_2$, 8) —CH$_2$CH$_2$CH$_2$NH$_2$, 9) —C(O)NH$_2$, 10) —(CH$_2$)C(O)NH$_2$, 11) —NHSO$_2$CH$_3$, 12) —SO$_2$NH$_2$, 13) —SO$_2$NHCH$_3$, 14) dimethylazetidinium, 15) azetidinyl optionally substituted with —C(=NH)NH$_2$ or —OH, 16) piperidinyl optionally substituted with 1 or 2 substituents selected from —NH$_2$, 17) —C(=NH)NH$_2$, 18) —CH(=NH), 19) —CH-azetidinyl, or 20) pyrrolidinyl optionally substituted with —OH or 2,5-dihydro-1H-pyrrolyl, and the other groups are as provided in the eighth embodiment.

In a tenth embodiment of the invention, the compound is a compound of a formula in the eighth embodiment, or a pharmaceutical salt thereof, wherein AryA is pyridinyl substituted with —NH$_2$, and the other groups are as provided in the eighth embodiment.

In an eleventh embodiment of the invention, the compound is a compound of a formula in the eighth embodiment, or a pharmaceutical salt thereof, wherein AryA is benzodimidazolyl substituted with —NH$_2$; benzothiophenyl; benzothiazolyl substituted with —NH$_2$ or —C(=NH)NH$_2$; dihydrobenzimidazol; dihydroindenyl substituted with —NH$_2$ or —NHC(=NH)NH$_2$; dihydroisoindolyl substituted with oxo; imidazopyridinyl; indazolyl optionally substituted with —NH$_2$; isoindolinyl optionally substituted with —CH(=NH)NH$_2$; pyrazolopyridinyl; pyrrolopyrazinyl; pyrrolopyridinyl; quinolinyl optionally substituted with —CH$_2$NH$_2$; or tetrahydroimidazopyridinyl; and the other groups are as provided in the eighth embodiment.

In another embodiment of the invention, the compound of the invention is selected from the exemplary species depicted in Examples 1-840 shown below, and pharmaceutically acceptable salts thereof.

In another embodiment of the invention, the compound of the invention is selected from the exemplary species depicted in Examples 131, 132, 134, 168, 178, 180, 181, 198, 259, 260, 264, 265, 267, 268, 269, 270, 271, 272, 273, 274, 275, 276, 284, 285, 286, 298, 312, 315, 423, 425, 433, 434, 435, 436, 437, 438, 439, 440, 441, 442, 443, 446, 447, 455, 456, 457, 460, 463, 464, 468, 469, 474, 481, 482, 494, 499, 544, 545, 551, 574, 590, 596, 597, 610, 612, 671, 783, and 820 shown below, and pharmaceutically acceptable salts thereof.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) The pharmaceutical composition of (a), further comprising an effective amount of a β-lactam antibiotic.

(c) The pharmaceutical composition of (b), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(d) The pharmaceutical composition of (b), wherein the β-lactam antibiotic is imipenem.

(e) The pharmaceutical composition of (b), wherein the β-lactam antibiotic is ceftazidime.

(f) The pharmaceutical composition of (b), wherein the β-lactam antibiotic is piperacillin.

(g) The pharmaceutical composition of (a), further comprising effective amounts of a β-lactam antibiotic and a renal dehydropeptidase (DHP) inhibitor.

(h) The pharmaceutical composition of (g), wherein the β-lactam antibiotic is imipenem, and the DHP inhibitor is cilastatin or a pharmaceutically acceptable salt thereof.

(i) A combination of effective amounts of a compound of Formula I as defined above, or a pharmaceutically acceptable salt thereof, and a β-lactam antibiotic.

(j) The combination of (i), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

(k) The combination of (i), wherein the β-lactam antibiotic is imipenem.

(l) The combination of (i), wherein the β-lactam antibiotic is ceftazidime.

(m) The combination of (i), wherein the β-lactam antibiotic is piperacillin.

(n) A combination of effective amounts of a compound of Formula I as defined above, or a pharmaceutically acceptable salt thereof, a β-lactam antibiotic and a DHP inhibitor.

(o) The combination of (n), wherein the β-lactam antibiotic is imipenem, and the DHP inhibitor is cilastatin or a pharmaceutically acceptable salt thereof.

(p) A method for treating a bacterial infection which comprises administering to a subject in need of such treatment a therapeutically effective amount of a compound of Formula I, or a pharmaceutically acceptable salt thereof, optionally in combination with an effective amount of a β-lactam antibiotic.

(q) A method for treating a bacterial infection which comprises administering to a subject in need of such treatment a therapeutically effective amount of a compound of Formula I, or a pharmaceutically acceptable salt thereof, in combination with effective amounts of a β-lactam antibiotic and a DHP inhibitor.

(r) A method for treating a bacterial infection which comprises administering to a subject in need of such treatment a therapeutically effective amount of the composition of (a), (b), (c), (d), (e), (f), (g) or (h).

(s) A method for treating a bacterial infection which comprises administering to a subject in need of such treatment a therapeutically effective amount of the combination of (i), (j), (k), (l), (m), (n) or (o).

(t) A method of treating a bacterial infection as set forth in (p), (q), (r), or (s), wherein the bacterial infection is due to *Pseudomonas* spp., *Klebsiella* spp., *Enterobacter* spp., *Escherichi* spp.a, *Morganella* spp., *Citrobacter* spp., *Serratia*, spp. or *Acintetobacter* spp.

The present invention also includes a compound of Formula I, or a pharmaceutically acceptable salt thereof, (i) for use in, (ii) for use as a medicament for, or (iii) for use in the preparation (or manufacture) of a medicament for, inhibiting beta-lactamase activity or treating bacterial infection. In these uses, the compounds of the present invention can optionally be employed in combination with one or more β-lactam antibiotics and/or one or more DHP inhibitors.

Additional embodiments of the invention include the pharmaceutical compositions, combinations and methods set forth in (a)-(t) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (t) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

The term "metallo-β-lactamase inhibitor" refers to a compound which is capable of inhibiting metallo-β-lactamase activity. As used herein, inhibiting metallo-β-lactamase activity means inhibiting the activity of a class B metallo-β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include a metallo-β-lactamases of *Escherichia coli* (such as New Delhi Metallo-b-lactamase, NDM), *Serratia marcescens* (such as IMP), and *Klebsiella* spp. (such as Verona integron-encoded metallo-β-lactamase, VIM)). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation off 1%, 2%, 3%, 4%, 5%, 10%, or 20%.

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Definitions:

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aminoalkyl" means saturated carbon chains which may be linear or branched or combinations thereof which are substituted with one amino group which may be terminal ($-NH_2$) or internal ($-NH-$).

"Hydroxyalkyl" means saturated carbon chains which may be linear or branched or combinations thereof which are substituted with one hydroxyl ($-OH$) group.

"Diaminoalkyl" means saturated carbon chains which may be linear or branched or combinations thereof which are substituted with two amino ($-NH_2$) groups.

"Dihydroxyalkyl" means saturated carbon chains which may be linear or branched or combinations thereof which are substituted with two hydroxyl ($-OH$) groups.

"Hydroxyaminoalkyl" means saturated carbon chains which may be linear or branched or combinations thereof which are substituted with one hydroxyl ($-OH$) group and one amino ($-NH_2$) group.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Aromatic ring system" means monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quarternary amine.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, 1,2,3,4-tetrahydronaphthyl and the like. In one embodiment of the present invention, cycloalkyl is selected from: cyclopropane, cyclobutane, cyclopentane and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" or "heterocycloalkyl" means a saturated or partly unsaturated non-aromatic monocyclic, bicyclic or bridged carbocyclic ring or ring system containing at least one ring heteroatom selected from N, S (including SO and $SO_2$) and O. The cycloheteroalkyl ring may be substituted on the ring carbons and/or the ring nitrogen(s). Examples of cycloheteroalkyl include tetrahydrofuran, piperazine, piperidine, morpholine, oxetane, tetrahydropyran, indolinyl, isoindolinyl, azabicyclooctane, hexahydrofuro[3,2-b]furan, and 2,3,3a,5,6,6a-hexahydrofuro[3,2-b]furan. Where the ring or ring system contains one or more N atoms, the N can be in the form of quarternary amine.

"Heteroaryl" means monocyclic, bicyclic or tricyclic ring or ring system containing 3-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quarternary amine Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like.

"Halogen" includes fluorine, chlorine, bromine and iodine.

Where any amine is present in the compound, the N atom may be optionally in the form of a quaternary amine having an appropriate additional substitution.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The compounds of the present invention may have one or more asymmetric centers. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the compound and, in certain embodiments, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof).

As set forth above, the present invention includes pharmaceutical compositions comprising a compound of Formula I of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, or a pharmaceutically acceptable salt thereof, optionally in combination with a β-lactam antibiotic and/or a DHP inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to inhibit β-lactamase and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, $21^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 microgram/mL, and in additional embodiment at least about 10 micrograms/mL, and at least about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula I is typically co-administered with a β-lactam antibiotic.

Compounds of the invention can be employed for the treatment, prophylaxis or inhibition of bacterial growth or infections due to bacteria that are resistant to β-lactam antibiotics. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with antibiotic agents for the treatment of infections caused by Class B-β-lactamase producing strains, in addition to those infections which are subsumed within the antibacterial spectrum of the antibiotic agent. Examples of class B-metallo-β-lactamase producing bacteria are *Pseudomonas aeruginosa*, *Pseudomonas putida*, *Enterobacter cloacae*, *Klebsiella pneumoniae*, *Klebsiella oxytoca*, *Escherichia coli*, *Serratia marcescens*, *Enterobacter aerogenes*, *Enterobacter asburiae*, *Citrobacter freundii*, *Proteus mirabilis*, *Morganella morganii*, *Providencia rettgeri*, and *Acinetobacter baumannii*.

It is generally advantageous to use a compound of Formula I in admixture or conjunction with a carbapenem, penicillin, cephalosporin, or other β-lactam antibiotic, or a prodrug thereof. It is advantageous to use a compound of Formula I in combination with one or more β-lactam antibiotics because of the class B β-lactamase inhibitory properties of the compounds. It is also advantageous to use a compound of Formula I in combination with one or more Class A, C, and D β-lactamase inhibitors to further limit β-lactam susceptibility. As already noted, the compound of Formula I and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class B-β-lactamases.

When the compounds of Formula I are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent Inhibitors of DHP and their use with carbapenems are disclosed in, e.g., U.S. Pat. Nos. 4,539,208; 4,616,038; 4,880,793; and 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, ertapenem, meropenem, biapenem, (4R, 5S, 6S)-3-[3S, 5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S, 5R, 6S)-2-(4-(2-(((carbamoylmethyl)-1,4-diazoniabicyclo[2.2.2]oct-1-yl)-ethyl(1,8-naphthosultam)methyl)-6-(1(R)-hydroxyethyl]-1-methylcarbapen-2-em-3-carboxylate chloride, BMS181139 ([4R-[4α,5β,6β(R*)]]-4-[2-[(aminoiminomethyl)amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4α,5β,6β(R*)]]-6-(1-hydroxyethyl)-3-[[5-[1-hydroxy-3-(methylamino)propyl]-3-pyrrolidinyl]thio]-4-methyl-7-oxo-1-azabicyclo[3.2.0] hept-2-ene-2-carboxylic acid monohydrochloride), E1010 ((1R, 5S, 6S)-6-[1(R)-hydroxymethyl]-2-[2(S)-[1(R)-hydroxy-1-[pyrrolidin-3(R)-yl]methyl]pyrrolidin-4(S)-ylsulfanyl]-1-methyl-1-carba-2-penem-3-carboxylic acid hydrochloride) and S4661 ((1R,5S,6S)-2-[(3 S,5S)-5-(sulfamoylaminomethyl) pyrrolidin-3-yl]thio-6-[(1R)-1-hydroxyethyl]-1-methylcarbapen-2-em-3-carboxylic acid), (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

β-Lactam antibiotics other than penicillins and cephalosporins that may be co-administered with compounds of the present invention include aztreonam, latamoxef (MOXALACTAM), and other known β-lactam antibiotics such as carbapenems like imipenem, ertapenem, meropenem or (4R, 5S, 6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, ertapenem, meropenem and (4R, 5S, 6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone and ceftazidime, which are optionally used in the form of their pharmaceutically acceptable salts, for example their sodium salts.

When co-administered with a β-lactam antibiotic, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: acac=acetylacetonate; ACN=acetonitrile; AIBN=2,2-azobisisobutyronitrile; BISPIN=4,4,4',4',5,5,5',5'-octamethyl-2,2'-bi(1,3,2-dioxaborolane); BLI=β-lactamase inhibitor; Bn=benzyl; BOC (or Boc)=tert-butyloxycarbonyl; Boc anhydride=Boc$_2$O=di-tert-butyl dicarbonate; BOC-ON=2-(tert-butoxycarbonyloxyamino)-2-phenyl acetonitrile; BOC-OSN=N-tert-butoxycarbonyloxy)succinimide; BOP=benzotriazol-1-yloxy)tris(dimethylamino)phosphonium hexafluorophosphate; BSA=bovine serum albumin; CBZ (or Cbz)=carbobenzoxy (alternatively, benzyloxycarbonyl); CH$_3$CN=acetonitrile; COD=cyclooctadieneyl; DBU=1,8-diazabicyclo[5.4.0]undec-7-ene; DCC=dicyclohexyl carbodiimide; DCE=1,2-dichloroethane; DCM=dichloromethane; DIBAL-H=diisobutylaluminum hydride; DIPEA=diisopropylethylamine (or Hunig's base); DMA=dimethylacetamide; DMAC=N,N-dimethylacetamide; DMAP=4-dimethylaminopyridine or N,N-dimethylaminopyridine; DME=1,2-dimethoxyethane; DMF=N,N-dimethylformamide; DMSO=dimethyl sulfoxide; EDC=1-ethyl-3-(3-dimethylaminopropyl) carbodiimide; DSC=differential scanning calorimetry; EA=EtOAc=ethyl acetate; Et=ethyl; EtOH=ethanol; hex=hexane; HMDS=hexamethyldisilazide; HOBT=1-hydroxy benzotriazole; HOPO=2-hydroxypyridine-N-oxide; HPLC=high-performance liquid chromatography; IPA=isopropyl alcohol; IPAc=isopropyl acetate; i-Pr=isopropyl; LC/MS=liquid chromatography/mass spectrometry; mCPBA=meta-chloroperoxybenzoic acid; Me=methyl; MeCN=acetonitrile; MHBII=Mueller Hinton Broth type II; MIC=minimum inhibitory concentration; MPLC=medium pressure liquid chromatography; MSA=methanesulfonic acid; NMO=N-methylmorpholine-N-oxide; NMP=N-methyl pyrrolidinone; PCy3 Pd G2=Chloro[(tricyclohexylphosphine)-2-(2'-aminobiphenyl)]palladium(II); Pd(dppf)Cl2.DCM=[1,1'-Bis(diphenylphosphino)ferrocene]dichloropalladium(II), complex with dichloromethane; PE=petroleum ether; PG=protective group; Ph=phenyl; Pd(DTBPF)Cl$_2$=[1,1'-Bis(di-tert-butylphosphino)ferrocene]dichloropalladium(II); RT=rt=room temperature; SEM-Cl=2-(Trimethylsilyl)ethoxymethyl chloride; SFC=supercritical fluid chromatography; SiliaMetS® DMT (Si-DMT) is the silica bound equivalent of 2,4,6-trimercaptotriazine (trithiocyanuric acid). It is a versatile metal scavenger for a variety of metals including Cd, Co, Ni, Pd, Pt, Rh, and Ru under a wide range of conditions and the preferred metal scavenger for ruthenium catalysts; SPhos-Pd-G2=2nd Generation SPhos Precatalyst, Chloro(2-dicyclohexylphosphino-2',6'-dimethoxy-1,1'-biphenyl)[2-(2'-amino-1,1'-biphenyl)]palladium(II); SM=starting material; TBAF=tetrabutylammonium fluoride; TEA=triethylamine; TFA=trifluoroacetic acid; TFE=2,2,2-trifluoroethaonol; THF=tetrahydrofuran; TLC=thin layer chromatography; TNS-N$_3$=azidotrimethylsilane; TPAP=Tetrapropylammonium perruthenate; TSB=trypticase soy broth; TsOH=p-toluenesulfonic acid; XPhos-Pd-2G or XPHOS Pd G2 precatalyst=Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst; XRPD=X-ray powder diffraction.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

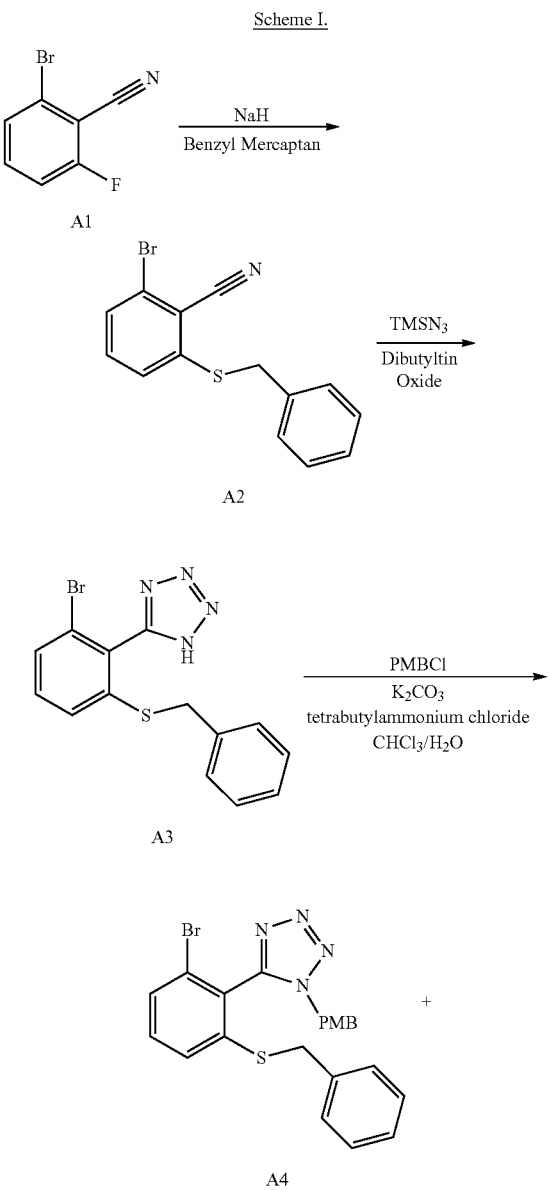

Scheme I.

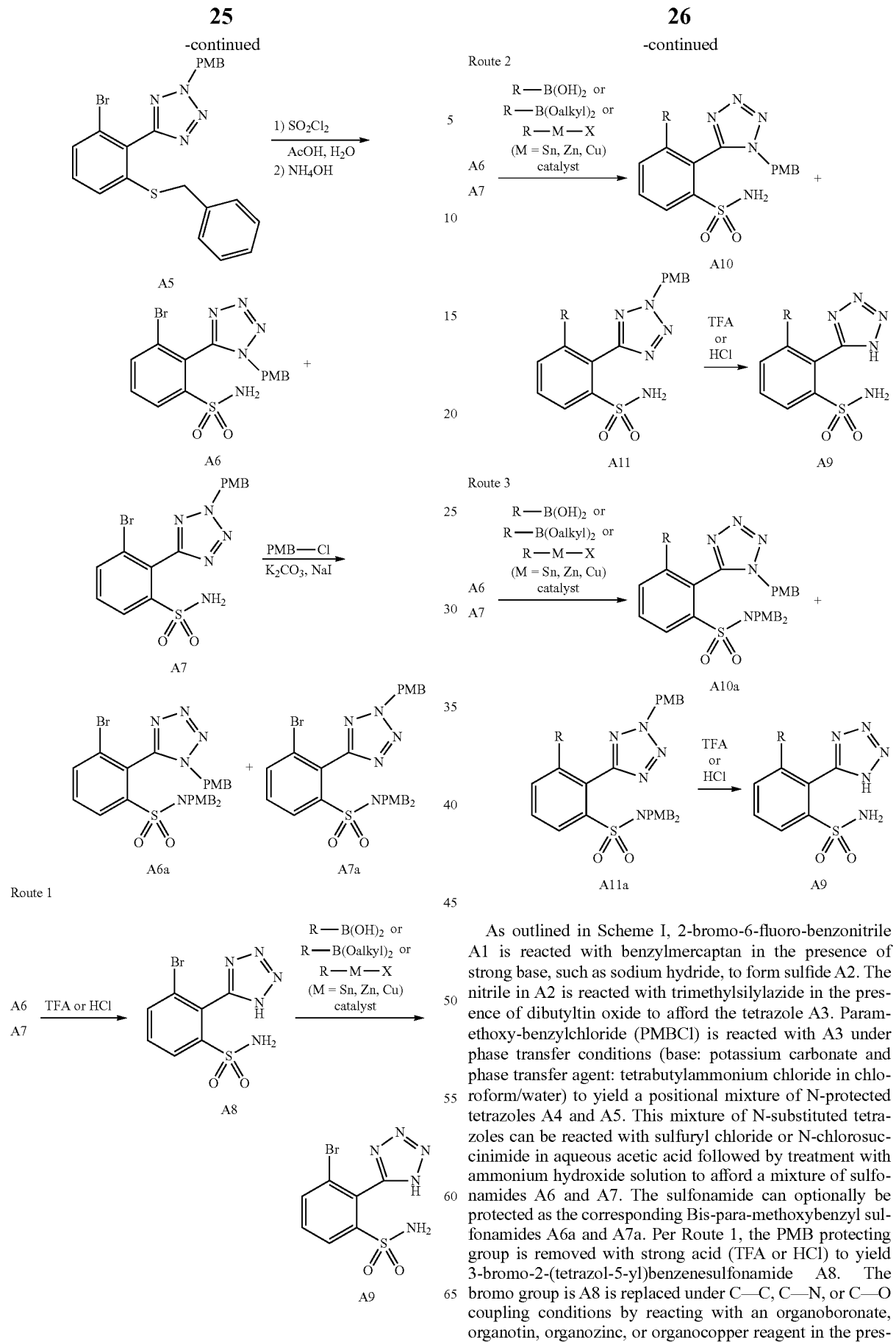

As outlined in Scheme I, 2-bromo-6-fluoro-benzonitrile A1 is reacted with benzylmercaptan in the presence of strong base, such as sodium hydride, to form sulfide A2. The nitrile in A2 is reacted with trimethylsilylazide in the presence of dibutyltin oxide to afford the tetrazole A3. Param-ethoxy-benzylchloride (PMBCl) is reacted with A3 under phase transfer conditions (base: potassium carbonate and phase transfer agent: tetrabutylammonium chloride in chloroform/water) to yield a positional mixture of N-protected tetrazoles A4 and A5. This mixture of N-substituted tetrazoles can be reacted with sulfuryl chloride or N-chlorosuccinimide in aqueous acetic acid followed by treatment with ammonium hydroxide solution to afford a mixture of sulfonamides A6 and A7. The sulfonamide can optionally be protected as the corresponding Bis-para-methoxybenzyl sulfonamides A6a and A7a. Per Route 1, the PMB protecting group is removed with strong acid (TFA or HCl) to yield 3-bromo-2-(tetrazol-5-yl)benzenesulfonamide A8. The bromo group is A8 is replaced under C—C, C—N, or C—O coupling conditions by reacting with an organoboronate, organotin, organozinc, or organocopper reagent in the presence of a catalyst, usually a palladium catalyst, to afford the 3-substituted 2-(tetrazol-5-yl)benzenesulfonamide A9. Alternatively, according to Route 2 the order of the last two steps may be switched; the mixture of bromo sulfonamides A6 and A7 is subjected to C—C, C—N, or C—O coupling conditions by reacting with an organoboronate, organotin, organozinc, or organocopper reagent in the presence of a catalyst, usually a palladium catalyst, to afford the coupled PMB protected tetrazole isomers A10 and A11. Final PMB protective group removal under acidic conditions such as by using TFA in the presence of a carbocation scavenger, such as anisole or triethylsilane, provides target compounds A9. When the organoboronate, organotin, organozinc, or organocopper reagent contains an acid labile protecting group (like tert-butoxycarbonyl) concurrent removal of this protecting group occurs in the final acidic removal of the PMB groups. This can be done in one step, or in stepwise fashion by treatment with TFA at room temperature to remove a group such as tert-butoxycarbonyl, then heating with TFA and anisole or thioanisole to remove the PMB group. Similarly, according to Route 3, the Bis-para-methoxybenzyl sulfonamides A6a and A7a may be employed as in Route 2, sometimes providing improved coupling yields compared to A6 and A7. Other positional isomers may be available starting with other bromo isomers of A1. Moreover, the bromo sulfonamides, including PMB protected tetrazole positional isomers may be separated by chromatography and each individual isomer may be used in place of the isomer mixture with similar results. The R group in A10, A11, A10a, A11a or A9 may be further modified. For example, when the R group contains an amine functional group, reductive alkylation reactions with aldehydes or ketones will provide amine containing examples. Alternatively, when the R group contains an amine functional group it may be converted to amide, sulfonamide, or urea containing analogs by, for example, coupling with acids, sulfonyl chlorides, or isocyanates, respectively. Or when the R group contains an aldehyde or ketone group, reductive amination with amines will also provide substituted amine containing examples.

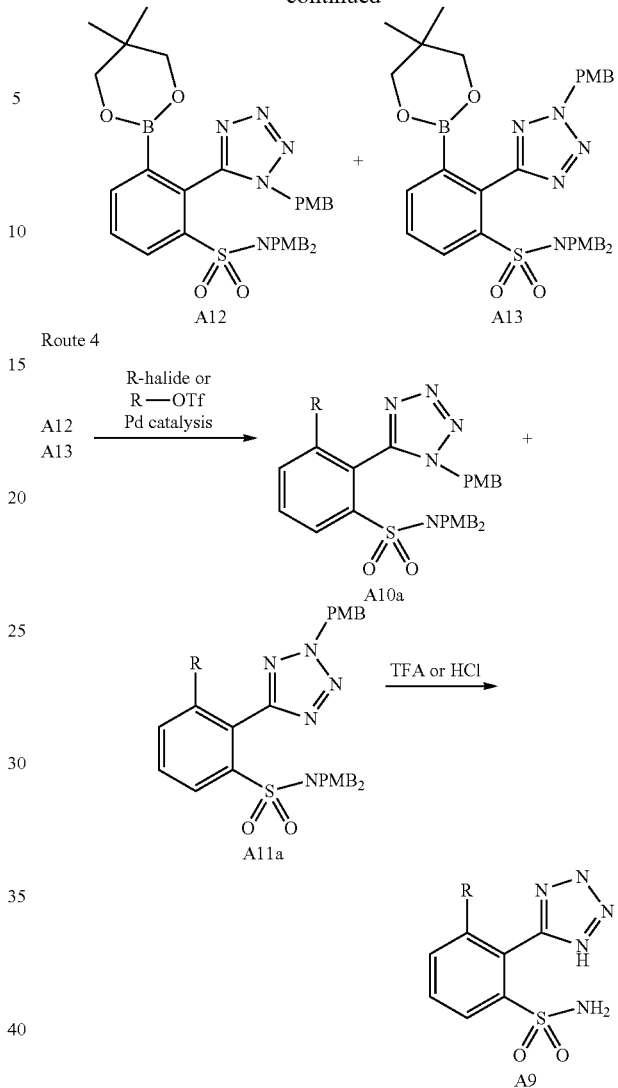

According to Scheme 2 analogs A9 may also be prepared from boronic acid or boronic ester precursors. Intermediates A6a and A7a may be converted to the corresponding boronic acids and boronic esters in a number of ways, for example, by coupling with 5,5,5',5'-tetramethyl-2,2'-bi(1,3,2-dioxaborinane) or other similar reagents using palladium catalysis. This affords the boronic esters A12 and A13 or their corresponding boronic acids. The boronic esters or boronic acids may be coupled with halide or triflate reagents according to Route 4 to provide A10a and A11a, which can be deprotected as previously described in Scheme 1.

Scheme II:

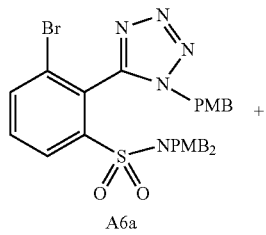

A6a

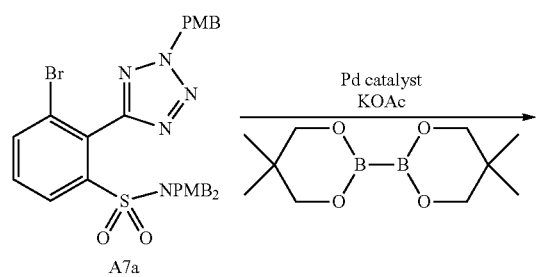

A7a

Scheme III:

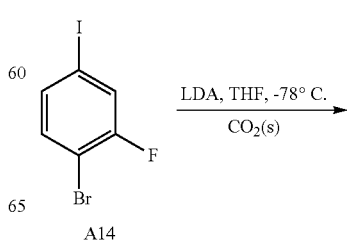

A14

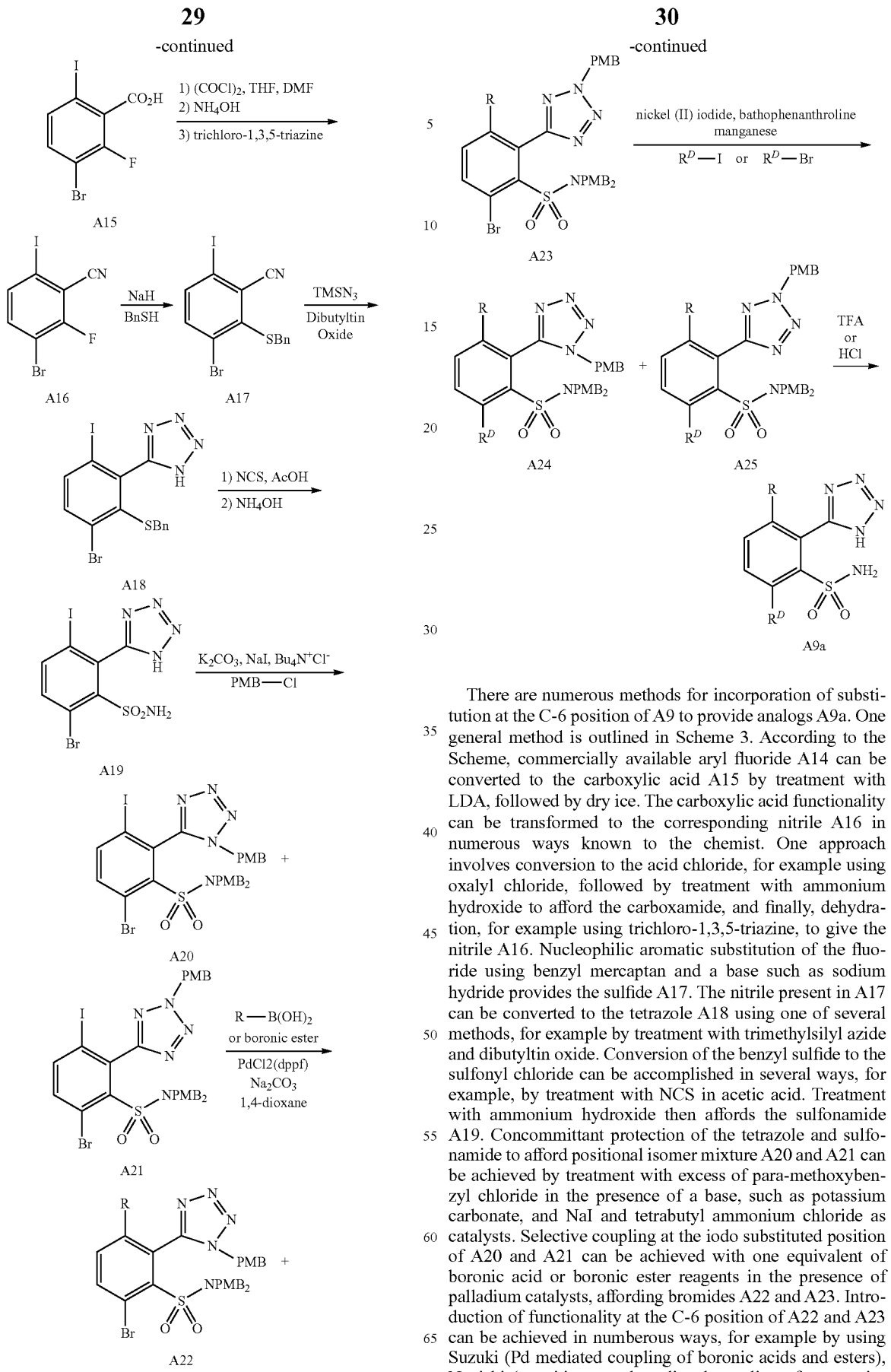

There are numerous methods for incorporation of substitution at the C-6 position of A9 to provide analogs A9a. One general method is outlined in Scheme 3. According to the Scheme, commercially available aryl fluoride A14 can be converted to the carboxylic acid A15 by treatment with LDA, followed by dry ice. The carboxylic acid functionality can be transformed to the corresponding nitrile A16 in numerous ways known to the chemist. One approach involves conversion to the acid chloride, for example using oxalyl chloride, followed by treatment with ammonium hydroxide to afford the carboxamide, and finally, dehydration, for example using trichloro-1,3,5-triazine, to give the nitrile A16. Nucleophilic aromatic substitution of the fluoride using benzyl mercaptan and a base such as sodium hydride provides the sulfide A17. The nitrile present in A17 can be converted to the tetrazole A18 using one of several methods, for example by treatment with trimethylsilyl azide and dibutyltin oxide. Conversion of the benzyl sulfide to the sulfonyl chloride can be accomplished in several ways, for example, by treatment with NCS in acetic acid. Treatment with ammonium hydroxide then affords the sulfonamide A19. Concommittant protection of the tetrazole and sulfonamide to afford positional isomer mixture A20 and A21 can be achieved by treatment with excess of para-methoxybenzyl chloride in the presence of a base, such as potassium carbonate, and NaI and tetrabutyl ammonium chloride as catalysts. Selective coupling at the iodo substituted position of A20 and A21 can be achieved with one equivalent of boronic acid or boronic ester reagents in the presence of palladium catalysts, affording bromides A22 and A23. Introduction of functionality at the C-6 position of A22 and A23 can be achieved in numerous ways, for example by using Suzuki (Pd mediated coupling of boronic acids and esters), Negishi (transition metal mediated coupling of organozincates), or Sonogashira coupling (palladium mediated coupling of alkynes) conditions. One generally useful method for introduction of alkyl substitution is shown in Scheme 3, wherein reductive Nickel coupling of A22 and A23 with alkyl iodides or bromides is accomplished to afford A24 and A25 using nickel(II) iodide, bathophenanthroline and manganese (Biswas, Soumik; Weix, Daniel J. *J. Am. Chem. Soc.* 2013, 135, 16192-16197). Removal of the para-methoxybenzyl protective groups is achieved under acidic conditions as described in Scheme 1 to provide analogs A9a.

REFERENCE EXAMPLE 1

3-Bromo-2-(1-(4-methoxybenzyl)(1H-tetrazol-5-yl)) benzenesulfonamide and 3-bromo-2-(2-(4-methoxybenzyl)(1H-tetrazol-5-yl))benzenesulfonamide

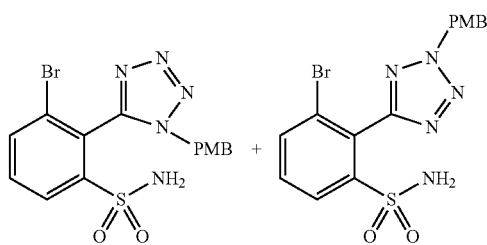

Step A: 2-(Benzylthio)-6-bromobenzonitrile

To a mixture of 2-bromo-6-fluorobenzonitrile (10 g, 50.0 mmol) and benzyl mercaptan (5.87 mL, 50.0 mmol) in 1,4-dioxane (100 mL) was added NaH (2.40 g, 60.0 mmol) at 0° C., and the resulting solution was slowly warmed to room temperature and stirred for 2 hr, then it was heated at 60° C. for 1.5 hr. The mixture was cooled to rt, diluted with ethyl acetate (20 mL), washed with 1N hydrochloric acid (20 mL) followed by addition of brine. The organic layer was dried over MgSO$_4$, filtered and was evaporated under reduced pressure to provide 2-(benzylthio)-6-bromobenzonitrile.

Step B: 5-(2-(Benzylthio)-6-bromophenyl)-1H-tetrazole

To a solution of 2-(benzylthio)-6-bromobenzonitrile, 10.5 g, 34.5 mmol) and dibutyltin oxide (1.72 g, 6.90 mmol) in toluene (75 mL) was added TMS-N$_3$ (9.16 mL, 69.0 mmol), and resulting mixture was heated at 105° C. for 12 hr. The reaction mixture was cooled to rt, filtered, and the precipitate was collected. The filtrate was concentrated and diluted with sat. Na$_2$CO$_3$ (30 mL), 2N NaOH (5 mL) and subsequently transferred to a separatory funnel, and washed with ethyl acetate (100 mL). The aqueous layer was acidified by 6N HCl to pH~1, and the white precipitate was collected by filtration. The combined solids were dried under vacuum to afford 5-(2-(benzylthio)-6-bromophenyl)-1H-tetrazole, which was used in the next step without further purification.

Step C: 5-(2-(Benzylthio)-6-bromophenyl)-1-(4-methoxybenzyl)-1H-tetrazole and 5-(2-(benzylthio)-6-bromophenyl)-2-(4-methoxybenzyl)-1H-tetrazole To a solution of 5-(2-(benzylthio)-6-bromophenyl)-1H-tetrazole in a mixture of chloroform and water (6 mL and 8 mL, respectively) were added potassium carbonate (1.544 g, 11.17 mmol), tetrabutylammonium chloride (0.311 g, 1.12 mmol) followed by a solution of 1-(chloromethyl)-4-methoxybenzene (1.14 mL, 8.38 mmol) in 2 mL of CHCl$_3$ at 15° C. The resulting mixture was slowly warm to rt, and heated at 50° C. for 3 hr. The reaction mixture was cooled to rt, and transferred to a sep. funnel. The organic layer was separated, dried over MgSO$_4$, filtered and purified using 5 to 80% ethyl acetate in hexanes to provide a mixture of 5-(2-(benzylthio)-6-bromophenyl)-1-(4-methoxybenzyl)-1H-tetrazole and 5-(2-(benzylthio)-6-bromophenyl)-2-(4-methoxybenzyl)-1H-tetrazole.

Step D: 3-Bromo-2-(1-(4-methoxybenzyl)-1H-tetrazol-5-yl) benzenesulfonamide and 3-bromo-2-(2-(4-methoxybenzyl)-1H-tetrazol-5-yl)benzenesulfonamide To a solution of the mixture of 5-(2-(benzylthio)-6-bromophenyl)-1-(4-methoxybenzyl)-1H-tetrazole and 5-(2-(benzylthio)-6-bromophenyl)-2-(4-methoxybenzyl)-1H-tetrazole in DCM (40 mL) was added water (0.251 mL, 13.9 mmol) followed by acetic acid (0.796 ml, 13.91 mmol). The resulting mixture was cooled to 0° C., then a solution of sulfuryl chloride (1.131 mL, 13.91 mmol) in DCM (2 mL) was slowly added. The reaction mixture was slowly warmed to rt, and stirred for 4 hr, and then evaporated to dryness. To this residue was added THF (5 mL) and then a mixture of aqueous ammonium hydroxide and THF (20 mL each) at 0° C. The reaction mixture was slowly warmed to rt and stirred for 1.5 hr. The resulting solution was diluted with ethyl acetate (100 mL), washed with water (50 mL) and brine (50 mL). The organic layer was dried over MgSO$_4$, filtered and purified by column chromatography on silica gel eluted with 10 to 90% ethyl acetate in hexanes to provide mixture of 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide.

The isomer mixture 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide may be separated to single isomers employing SFC (35% MeOH/CO$_2$ on DEAP column, flow rate 70 mL/min). The individual isomers or the mixture may be used as intermediates in the below examples with similar results.

REFERENCE EXAMPLE 2

4-Bromo-3-(2-(4-methoxybenzyl)-2H-tetrazol-5-yl) pyridine-2-sulfonamide and 4-Bromo-3-(1-(4-methoxybenzyl)-1H-tetrazol-5-yl)pyridine-2-sulfonamide

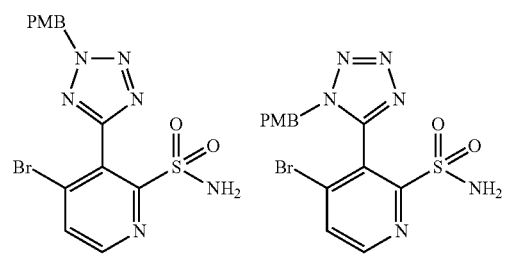

Step A: 4-Amino-2-((2-(trimethylsilyl)ethyl)thio)nicotinonitrile

A mixture of 2-chloro-3-iodopyridin-4-amine (5000 mg, 20 mmol) and copper(i) cyanide (2800 mg, 31 mmol) in DMF (15 ml) was heated to 135° C. for 30 minutes in a microwave reactor. LC showed complete reaction. The dark brown suspension was poured into 200 mL of DCM to ppt the copper salt. The suspension was filtered through a pad of celite. The filtrate was washed with ammonium hydroxide, dried over sodium sulfate, and concentrated down on a rotavapor. LC/MS [M+H]+: 154.

To the resulting DMSO solution was added 2-(trimethylsilyl)ethanethiol (4200 mg, 31 mmol) and potassium carbonate (5400 mg, 39 mmol). The mixture was purged three times was nitrogen, and heated to 50° C. overnight. LC showed the reaction was very clean. The reaction was diluted with water, and extracted with EtOAc. The extraction was dried over sodium sulfate, filtered and concentrated, and the resulting yellow oil was used in the next step without further purification. LC/MS [M+H]+: 252.

Step B: 4-Bromo-2-((2-(trimethylsilyl)ethyl)thio)nicotinonitrile

To a solution of 4-amino-2-((2-(trimethylsilyl)ethyl)thio)nicotinonitrile (4.9 g, 19 mmol) in acetonitrile (100 mL) was added copper(II) bromide (8.7 g, 39 mmol) and tert-butyl nitrite (4.0 g, 39 mmol). The reaction was allowed to stir at 0° C. then warmed up naturally as the ice bath melted and reached room temperature, and then stirred at room temperature over the weekend. LC showed formation of the desired product. The reaction was diluted with EtOAc, washed with NH4OH and brine, and separated. The crude solution was dried over sodium sulfate, filtered and concentrated to give a brown oil. The oil was loaded onto a 80G ISCO column, and separated by MPLC with hexane and EtOAc. The product eluted at about 8% EtOAc. It was a waxy solid. LC/MS [M-CN]: 288.

Step C: 4-Bromo-2-((2-(trimethylsilyl)ethyl)sulfonyl)nicotinonitrile

To a solution of 4-bromo-2-((2-(trimethylsilyl)ethyl)thio)nicotinonitrile (3.0 g, 9.5 mmol) in DCM (50 ml) was added m-CPBA (7.0 g, 28 mmol) at 0° C. The mixture was allowed to stir for 16 hr. LC showed a clean reaction. Excess m-CPBA was quenched with Na2S2O3, and the crude material was extracted with DCM. The DCM solution was dried over sodium sulfate, filtered and concentrated. The residue was adsorbed onto silica gel, and purified by MPLC with a 80G ISCO column with hexane and EtOAc. LC/MS [M+H]+: 349.

Step D: 4-Bromo-3-(2-(4-methoxybenzyl)-2H-tetrazol-5-yl)-2-((2-(trimethylsilyl)ethyl)sulfonyl)pyridine and 4-bromo-3-(1-(4-methoxybenzyl)-1H-tetrazol-5-yl)-2-((2-(trimethylsilyl)ethyl)sulfonyl)pyridine A mixture of 4-bromo-2-((2-(trimethylsilyl)ethyl)sulfonyl)nicotinonitrile (2.5 g, 7.2 mmol), azidotrimethylsilane (1.66 g, 14.4 mmol), and dibutylstannanone (0.54 g, 2.2 mmol) in toluene (50 mL) was heated to 115° C. for 24 hours. LC showed a complete reaction. LC/MS [M+H]+: 392. The solvent was removed, and the dark residue was dissolved in acetonitrile (50 mL). To the solution was added Hunig's base (2.9 g, 22 mmol) and 1-(chloromethyl)-4-methoxybenzene (2.3 g, 14.4 mmol). The mixture was allowed to stir for 72 hours. LC showed a complete reaction. The reaction was diluted with EtOAc, washed with water, and the separated organic layer was dried over sodium sulfate, filtered, and concentrated. The resulting dark residue was loaded onto an 80G ISCO column, and purified by MPLC with hexane and EtOAc. LC/MS [M+H]+: 512.

Step E: 4-Bromo-3-(2-(4-methoxybenzyl)-2H-tetrazol-5-yl)pyridine-2-sulfonamide and 4-bromo-3-(1-(4-methoxybenzyl)-1H-tetrazol-5-yl)pyridine-2-sulfonamide To a solution of a mixture of 4-bromo-3-(2-(4-methoxybenzyl)-2H-tetrazol-5-yl)-2-((2-(trimethylsilyl)ethyl)sulfonyl)pyridine and 4-bromo-3-(1-(4-methoxybenzyl)-1H-tetrazol-5-yl)pyridine-2-sulfonamide (2.5 g, 4.9 mmol) in THF (10 mL) was added TBAF (20 mL, 20 mmol), and the mixture was allowed to stir at 50° C. for 16 hours. LC showed disappearance of all starting material. The reaction was cooled, and to the reaction was added sodium acetate (4.0 g, 49 mmol) in 10 mL water and (aminooxy)sulfonic acid (5.5 g, 49 mmol). The mixture was allowed to stir at RT for 24 hours. LC showed a good reaction. It was diluted with water, extracted with DCM twice. The extractions were combined, dried over sodium sulfate, and concentrated. The residue was loaded onto a 80G silica column, and purified by MPLC with DCM and MeOH system to afford a mixture of 4-bromo-3-(2-(4-methoxybenzyl)-2H-tetrazol-5-yl)pyridine-2-sulfonamide and 4-bromo-3-(1-(4-methoxybenzyl)-1H-tetrazol-5-yl)pyridine-2-sulfonamide. LC/MS [M+H]+: 427.

REFERENCE EXAMPLE 3

2-((Benzyloxy)methyl)-5-(tributylstannyl)-2H-tetrazole

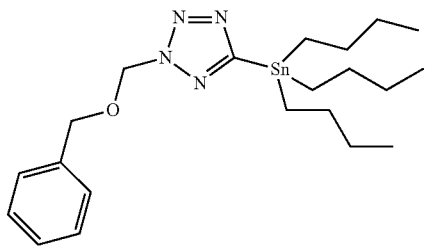 [SMILES: CCC[CH2][Sn]([CH2]CCC)([CH2]CCC)[c]1nnn(COCc2ccccc2)n1]

Step A: 2-((Benzyloxy)methyl)-2H-tetrazole

[1H]-tetrazole (1 g, 14.27 mmol) and K2CO3 (2.96 g, 21.41 mmol) were dissolved in DMF (15 ml) and cooled to 0° C., then ((chloromethoxy)methyl)benzene (2.382 ml, 17.13 mmol) was added. The reaction was stirred for 30 mins before warming up to RT and stirred for 16 hrs. The reaction was poured into water and extracted with ether. The ether layer was washed with water, brine, dried over sodium sulfate and concentrated. The residue was absorbed onto silica gel and purified by MPLC with ETOAc and hexane to yield a colorless oil. $^1$H-NMR (500 MHz, CDCl3) δ ppm 8.62 (s,1H), 7.42-7.36 (m,5H), 6.00 (s, 2H), 4.70 (s, 2H).

Step B: 2-((Benzyloxy)methyl)-5-(tributylstannyl)-2H-tetrazole 2-((Benzyloxy)methyl)-2H-tetrazole (1.0 g, 5.26 mmol) and TMEDA (1.603 ml, 10.62 mmol) were dissolved in ethyl ether (15 mL) and cooled to −78° C., then n-BuLi (2.313 mL, 5.78 mmol) was added. The reaction was stirred for 0.5 hr, then cannulated to a solution of tributyltin chloride (1.426 ml, 5.26 mmol) in ether (15 ml) at −78° C. After stirring for 45 mins, the reaction was quenched with saturated NH4Cl solution and extracted with ether. The organic layer was washed with brine, dried over Na2SO4, and concentrated. The residue was absorbed onto silica gel and purified by MPLC with 0-15% ETOAc/hexane to yield an oil. $^1$H-NMR (500 MHz, CDCl3) δ ppm 7.40-7.33 (m,5H), 6.01(s, 2H), 4.68 (s, 2H), 1.67-1.61 (m,6H), 1.42-1.33 (m, 6H), 1.30-1.26 (m, 6H), 0.92 (t, J=7.25 Hz, 9H).

REFERENCE EXAMPLE 4 tert-Butyl (3-(4-(4,4,5,5-tetramethyl-1,3,2-dioxaborolan-2-yl)phenyl)propyl)carbamate

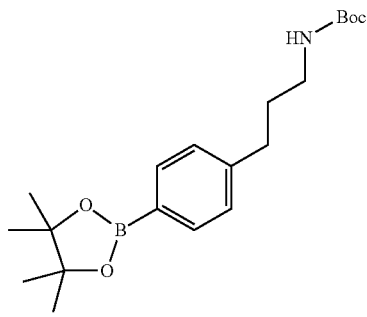 [SMILES: CC(C)(C)OC(=O)NCCCc1ccc(B2OC(C)(C)C(C)(C)O2)cc1]

Step A: tert-Butyl (3-(4-chlorophenyl)propyl)carbamate

A 40 mL reaction vial was charged with 3-(4-chlorophenyl)propan-1-amine (150 mg, 0.884 mmol), BOC-Anhydride (0.226 ml, 0.973 mmol), DMF (3 mL) and triethylamine (0.370 mL, 2.65 mmol). The reaction was allowed to stir at room temp for 30 minutes. The reaction was diluted with ethyl acetate and washed with water three times. The organic layer was extracted out and concentrated. The residue was purified by normal phase ISCO on a 12 g column eluted with 0% to 100% ethyl acetate in hexane. The pure fractions were concentrated to afford tert-butyl (3-(4-chlorophenyl)propyl)carbamate. LC-MS: calculated for $C_{14}H_{20}ClNO_2$ 269.12 observed m/e: 214.21 (M-t-butyl)$^+$.

Step B: tert-Butyl (3-(4-(4,4,5,5-tetramethyl-1,3,2-dioxaborolan-2-yl)phenyl)propyl)carbamate A 40 mL reaction vial was charged with tert-butyl (3-(4-chlorophenyl)propyl)carbamate (182 mg, 0.675 mmol)), potassium acetate (199 mg, 2.024 mmol) and 4,4,4',4',5,5,5',5'-octamethyl-2,2'-bi(1,3,2-dioxaborolane) (343 mg, 1.349 mmol)) and 2nd generation x-phos precatalyst (53.1 mg, 0.067 mmol). The vial was capped via a red sure seal, and the vial was degassed via vacuum/nitrogen flushes three times (line with needle from manifold). Then, dioxane (6 ml) was syringed in, and again, the vial was degassed via vacuum/nitrogen flushes (3 times). After stirring at room temp for 10 minutes, the vial was heated at 80° C. via an oil bath for 18 hr. The excess catalyst was filtered off, and the solution was concentrated. The residue was purified by normal phase ISCO on a 24 g column eluted with 0% to 100% ethyl acetate in hexane. The pure fractions were concentrated to afford tert-butyl (3-(4-(4,4,5,5-tetramethyl-1,3,2-dioxaborolan-2-yl)phenyl)propyl)carbamate. LC-MS: calculated for $C_{20}H_{32}BNO_4$ 361.283 observed m/e: 384.48 (M+Na)$^+$. $^1$H NMR δ (ppm) (MeOH): 7.63 (d, 2H), 7.18 (d, 2H), 3.03 (t, 2H), 2.62 (t, 2H), 1.72-1.79 (m, 2H), 1.42 (s,9H), 1.32 (s, 12H).

The following Reference Examples 5-7 were prepared by the method described in Reference Example 4 substituting the appropriate amine starting material:

| Reference Example No. | Structure | HPLC-mass spectrum m/e |
|---|---|---|
| 5 | 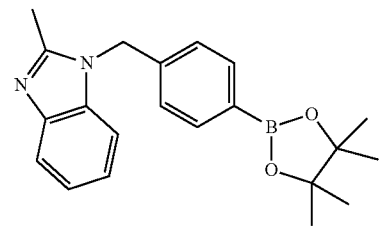 [SMILES: Cc1nc2ccccc2n1Cc1ccc(B2OC(C)(C)C(C)(C)O2)cc1] | Observed: 349 (M + H)$^+$ |
| 6 | 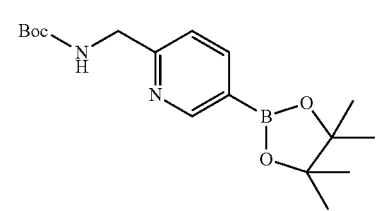 [SMILES: CC(C)(C)OC(=O)NCc1ccc(B2OC(C)(C)C(C)(C)O2)cn1] | Observed: 253 (Boronic acid observed) |
| 7 | 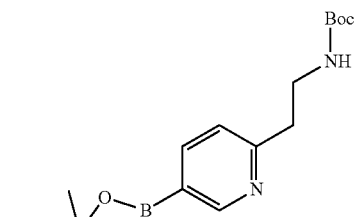 | Observed: 267 (Boronic acid observed) |

REFERENCE EXAMPLE 8

3-bromo-N,N-bis(4-methoxybenzyl)-2-(1-(4-methoxybenzyl)-1H-tetrazol-5-yl)benzenesulfonamide and 3-bromo-N,N-bis(4-methoxybenzyl)-2-(2-(4-methoxybenzyl)-2H-tetrazol-5-yl) benzenesulfonamide

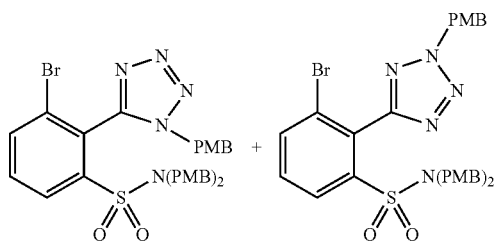

To a mixture of 3-Bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide isomers (3.00 g, 7.07 mmol), 1-(chloromethyl)-4-methoxybenzene (2.436 g, 15.56 mmol), in butanone at room temperature, was added potassium carbonate (3.91 g, 28.3 mmol) and sodium iodide (2.332 g, 15.56 mmol). The reaction mixture was stirred overnight under $N_2$ at 80° C. LC-MS showed completion of the reaction. The reaction was filtered and the cake was washed with EtOAc. The filtrates were evaporated, and the crude product was purified by column chromatography (EtOAc/hexanes 0-100%) to afford the title compounds. LC/MS [M+H]+: 664, 666.

REFERENCE EXAMPLE 9

3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide

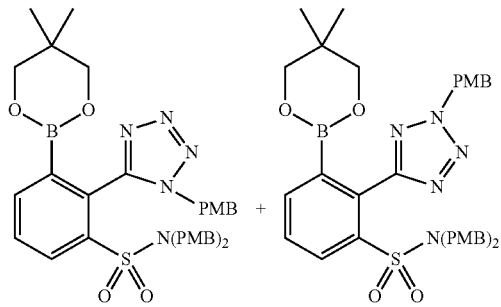

To a reaction vessel was added an isomeric mixture of 3-bromo-N,N-bis(4-methoxybenzyl)-2-(1-(4-methoxybenzyl)-1H-tetrazol-5-yl)benzenesulfonamide and 3-bromo-N,N-bis(4-methoxybenzyl)-2-(2-(4-methoxybenzyl)-2H-tetrazol-5-yl)benzenesulfonamide (3.23 g, 4.86 mmol), 5,5,5',5'-tetramethyl-2,2'-bi(1,3,2-dioxaborinane) (3.29 g, 14.6 mmol), PCy3 Pd G2 (0.287 g, 0.486 mmol), and potassium acetate (1.431 g, 14.58 mmol). Then anhydrous acetonitrile (new bottle, 25 mL) was added to this flask. Nitrogen was bubbled through this mixture for 10 min, then the mixture was heated at 85° C. for 24 hr. The mixture was cooled to room temperature. 1 M NaOH was added to the reaction mixture. The mixture was extracted with EtOAc. The organic phase was concentrated under reduced pressure. The residue was purified by column chromatography on silica gel, eluting with 0-80% hexane/EtOAc to give the product, which was contaminated by about ⅓ of de-Br side product.

REFERENCE EXAMPLE 10

5-chloro-2-(1-(4-methoxybenzyl)-1H-tetrazol-5-yl)-4'-methyl-[1,1'-biphenyl]-3-sulfonamide and 5-chloro-2-(2-(4-methoxybenzyl)-2H-tetrazol-5-yl)-4'-methyl-[1,1'-biphenyl]-3-sulfonamide

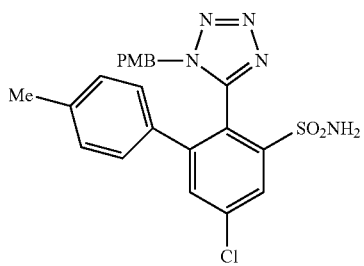

-continued

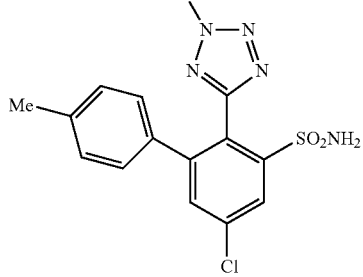

Step A: (3-bromo-4-(1-(4-methoxybenzyl)-1H-tetrazol-5-yl)-5-sulfamoylphenyl)boronic acid and (3-bromo-4-(2-(4-methoxybenzyl)-2H-tetrazol-5-yl)-5-sulfamoylphenyl)boronic acid (1,5-cyclooctadiene)(methoxy)iridium(I) dimer (0.312 g, 0.471 mmol) and BISPIN (4.79 g, 18.9 mmol) were dissolved in 3 mL THF and added to a 15 mL pressure tube containing a 2 mL THF solution of 3,4,7,8-tetramethyl-1,10-phenanthroline (0.223 g, 0.943 mmol). Finally, a 1 mL THF solution containing an isomeric mixture of 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide (4.00 g, 9.43 mmol) was added to the pressure tube via pipette and the reaction vessel was sealed and heated in an oil bath at 80° C. for 16 hr. The reaction mixture was concentrated under reduced pressure. The crude product was purified by reverse phase HPLC, eluting with 10% to 100% MeCN in water.

Step B: 3-bromo-5-chloro-2-(1-(4-methoxybenzyl)-1H-tetrazol-5-yl)benzenesulfonamide and 3-bromo-5-chloro-2-(2-(4-methoxybenzyl)-2H-tetrazol-5-yl)benzenesulfonamide To a solution of (3-bromo-4-(1-(4-methoxybenzyl)-1H-tetrazol-5-yl)-5-sulfamoylphenyl)boronic acid and (3-bromo-4-(2-(4-methoxybenzyl)-2H-tetrazol-5-yl)-5-sulfamoylphenyl)boronic acid (2.7 g, 5.8 mmol) in MeCN (57.7 mL) was added N-chloro succinimide (0.770 g, 5.77 mmol) and copper (I) chloride (0.571 g, 5.77 mmol). The reaction mixture was heated at 65° C. for 6 hr. The reaction mixture was diluted with water and extracted twice with ethyl acetate. The combined organic layers were washed with brine, dried over anhydrous Na2SO4, filtered, and concentrated. The crude product was purified by MPLC (ISCO 120 g column, eluting with 0% to 100% EtOAc in hexane gradient.

Step C: 5-chloro-2-(1-(4-methoxybenzyl)-1H-tetrazol-5-yl)-4'-methyl-[1,1'-biphenyl]-3-sulfonamide and 5-chloro-2-(2-(4-methoxybenzyl)-2H-tetrazol-5-yl)-4'-methyl-[1,1'-biphenyl]-3-sulfonamide A 40 dram reaction vial was charged with p-tolylboronic acid (0.363 g, 2.67 mmol) and the isomer mixture 3-bromo-5-chloro-2-(1-(4-methoxybenzyl)-1H-tetrazol-5-yl)benzenesulfonamide and 3-bromo-5-chloro-2-(2-(4-methoxybenzyl)-2H-tetrazol-5-yl)benzenesulfonamide (1.36 g, 2.96 mmol). EtOH (29.6 mL) and 1 M potassium phosphate (8.89 mL, 8.89 mmol) were added and the reaction mixture was sparged with N2 for 10 min. To this mixture was added 1,1'-Bis(di-tert-butylphosphino)ferrocene palladium dichloride (0.193 g, 0.296 mmol) and then the reaction mixture was heated to 80° C. for 1 hr in a microwave apparatus. The reaction mixture was diluted with water and extracted with ethyl acetate. The organic phase was washed with brine, dried over anhydrous Na2SO4, filtered, and concentrated. The crude residue was purified by MPLC (ISCO 80 g column, eluted with 0% to 100% EtOAc in Hexane gradient) to afford the title compounds (isomer mixture). LC/MS (M+H)$^+$=470.3, 472.3 (3:1 ratio).

REFERENCE EXAMPLE 11 tert-butyl 3-hydroxy-3-(4-(4,4,5,5-tetramethyl-1,3,2-dioxaborolan-2-yl)phenyl)azetidine-1-carboxylate

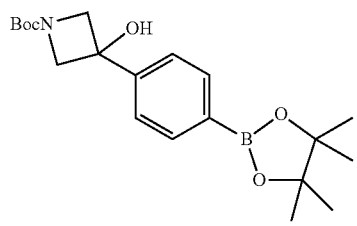 [SMILES: CC(C)(C)OC(=O)N1CC(O)(c2ccc(B3OC(C)(C)C(C)(C)O3)cc2)C1]

Step A: tert-butyl 3-(4-bromophenyl)-3-hydroxyazetidine-1-carboxylate

To a solution of 1,4-dibromobenzene (5.37 g, 22.8 mmol) in THF (15 mL) at −78° C. under N$_2$ was added N-butyl lithium (7.01 mL, 17.5 mmol) dropwise. The reaction mixture was stirred for 40 minutes. Then the resulting mixture was added to a pre-cooled −78° C. solution of 1-Boc-3-azetidinone (3.00 g, 17.5 mmol) in 20 mL THF. The mixture was stirred at −78° C. for 20 minutes and was warmed up to rt by removing the dry-ice acetone bath. Aqueous NH$_4$Cl was added and the mixture was extracted with EtOAc four times. The combined organic layers were dried over anhydrous Na$_2$SO$_4$, filtered, and concentrated to give a viscous residue. To the residue was added ether, followed by hexane. Collection of the resulting white solid by filtration to remove the organic solvents gave the title compound.

Step B: tert-butyl 3-hydroxy-3-(4-(4,4,5,5-tetramethyl-1,3,2-dioxaborolan-2-yl)phenyl)azetidine-1-carboxylate A dried round bottom flask was charged with tert-butyl 3-(4-bromophenyl)-3-hydroxyazetidine-1-carboxylate (1.00 g, 3.05 mmol), potassium acetate (0.897 g, 9.14 mmol), 1,1'-Bis(diphenylphosphino)ferrocene-palladium(II)dichloride dichloromethane complex (0.124 g, 0.152 mmol) and Bis(pinacolato)diboron (1.16 g, 4.57 mmol). DMSO (8 mL) was added and the reaction mixture was degassed with N$_2$, three times. The mixture was heated at 80° C. for 90 minutes. The reaction mixture was allowed to cool to room temperature (over about 90 minutes). The reaction mixture was diluted with water and extracted with EtOAc. The organic layer was dried over anhydrous Na$_2$SO$_4$, filtered, and concentrated under reduced pressure. The crude material was dissovled in DCM and purified by MPLC chromatography, RediSep Column: Silica 24 g, to give desired compound. LC/MS [M+H]$^+$=376.

REFERENCE EXAMPLE 12 tert-butyl 4-(4-(4,4,5,5-tetramethyl-1,3,2-dioxaborolan-2-yl)phenoxy)piperidine-1-carboxylate

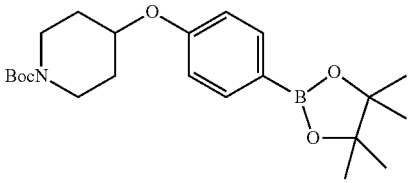 [SMILES: CC(C)(C)OC(=O)N1CCC(Oc2ccc(B3OC(C)(C)C(C)(C)O3)cc2)CC1]

In a reaction vessel, tert-butyl 4-(4-bromophenoxy)piperidine-1-carboxylate and Bis(pinacolato)diboron (285 mg, 1.12 mmol) were combined, followed by addition of potassium acetate (110 mg, 1.123 mmol) and XPHOS PD G2 (22 mg, 0.028 mmol). This mixture was then evacuated and backfilled with N$_2$ (3 times). Then dry, degassed dioxane (2807 μl) was added to this flask. This mixture was then heated at 110° C. for 12 hr. The mixture was cooled, water was added and the mixture was extracted with EtOAc twice. The combined organic fractions were washed with brine, dried (anhydrous Na$_2$SO$_4$), filtered and the solvent was evaporated under reduced pressure. The residue was purified by column chromatography on silica gel, eluting with hexane/EtOAc (0-100% gradient) to give the title compound. LC/MS [M+H]$^+$=404.

REFERENCE EXAMPLE 13

6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide

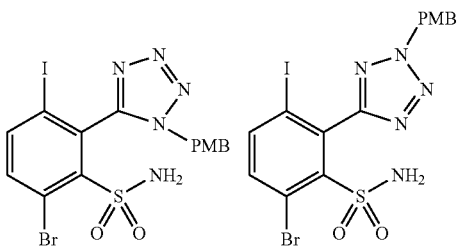

Step A: 3-bromo-2-fluoro-6-iodobenzoic acid

Into a 2000-mL 3-necked round-bottom flask purged and maintained with an inert atmosphere of nitrogen was placed a solution of (i-Pr)$_2$NH (40.4 g, 400.00 mmol, 1.20 equiv) in tetrahydrofuran (400 mL). This was followed by the addition of n-butyl lithium (146 mL, 1.10 equiv) dropwise with stirring at −20° C. over 30 min. To this was added a solution of 1-bromo-2-fluoro-4-iodobenzene (100 g, 332.34 mmol, 1.00 equiv) in tetrahydrofuran (600 mL) dropwise with stirring at −78° C. The resulting solution was stirred for 90 min at −78° C. The reaction mixture was then poured into 1.5 L of dry ice. The resulting mixture was concentrated under vacuum. The residue was diluted with 2000 mL of aq. sodium hydroxide (4 M), then washed with 2×800 mL of ether. The aq. solution was adjusted to pH 2 with HCl (2 M), then extracted with 3×800 mL of ethyl acetate. The organic layers were combined, washed with 3×500 mL of water, dried and concentrated under vacuum to afford the title compound.

Step B: 3-bromo-2-fluoro-6-iodobenzoyl chloride

Into a 3000-mL round-bottom flask was placed 3-bromo-2-fluoro-6-iodobenzoic acid (235 g, 681.35 mmol, 1.00 equiv) and thionyl chloride (1175 mL). The resulting solution was stirred for 2 hr at 80° C. in an oil bath. The resulting mixture was cooled and concentrated under vacuum to afford the title compound.

Step C: 3-bromo-2-fluoro-6-iodobenzamide

Into a 10000-mL 4-necked round-bottom flask was placed a solution of $NH_4OH$ (840 g) in tetrahydrofuran (2000 mL). This was followed by the addition of a solution of 3-bromo-2-fluoro-6-iodobenzoyl chloride (223 g, 614 mmol, 1.00 equiv) in tetrahydrofuran (2460 mL) dropwise with stirring at 0° C. The resulting solution was stirred for 60 min at room temperature. The resulting mixture was concentrated under vacuum. The solids were collected by filtration to afford the title compound.

Step D: 3-bromo-2-fluoro-6-iodobenzonitrile

Into a 10000-mL 4-necked round-bottom flask was placed a solution of 3-bromo-2-fluoro-6-iodobenzamide (223 g, 648 mmol, 1.00 equiv) in N,N-dimethylformamide (4460 mL), trichloro-1,3,5-triazine (840 g, 4.56 mol, 7.00 equiv). The resulting solution was stirred overnight at room temperature. The reaction mixture was poured into 10 L of aq. sodium bicarbonate. The solids were collected by filtration to afford the title compound.

Step E: 2-(benzylsulfanyl)-3-bromo-6-iodobenzonitrile

Into a 5000-mL 4-necked round-bottom flask purged and maintained with an inert atmosphere of nitrogen was placed a solution of sodium hydride (14.8 g, 617 mmol, 1.20 equiv) in 1,4-dioxane (1000 mL). This was followed by the addition of a solution of phenylmethanethiol (38.1 g, 306.76 mmol, 1.00 equiv) in 1,4-dioxane (100 mL) dropwise with stirring at 0° C. over 20 min. To this was added a solution of 3-bromo-2-fluoro-6-iodobenzonitrile (100 g, 306.84 mmol, 1.00 equiv) in 1,4-dioxane (400 mL) dropwise with stirring at 0° C. The resulting solution was stirred for 60 min at room temperature and for an additional 60 min at 60° C. The reaction was then quenched by the addition of 750 mL of HCl (1 M). The resulting solution was diluted with 3 L of water, then extracted with 3×1 L of ethyl acetate. The organic layers were combined, dried and concentrated under vacuum. The residue was applied onto a silica gel column and eluted with ethyl acetate/petroleum ether (1:4) to afford the title compound.

Step F: 5-[2-(benzylsulfanyl)-3-bromo-6-iodophenyl]-1H-1,2,3,4-tetrazole

Into a 3000-mL 4-necked round-bottom flask was placed a solution of 2-(benzylsulfanyl)-3-bromo-6-iodobenzonitrile (54.0 g, 126 mmol, 1.00 equiv) in toluene (750 mL), $TMSN_3$ (43.4 g, 3.00 equiv) and dibutyltin oxide (6.3 g, 0.20 equiv). The resulting solution was stirred for 48 hr at 105° C. in an oil bath. The reaction mixture was cooled to r.t. The resulting solution was diluted with 3 L of aq. sodium hydroxide, then extracted with ethyl acetate. The aqueous layer was adjusted to pH 3 with HCl (2 M), then extracted with 2×1 L of ethyl acetate. The organic layers were combined, washed with 2×1 L of water, dried over anhydrous sodium sulfate and concentrated under vacuum to provide the title compound.

Step G: 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole Into a 3000-mL 3-necked round-bottom flask purged and maintained with an inert atmosphere of nitrogen was placed a solution of 5-[2-(benzylsulfanyl)-3-bromo-6-iodophenyl]-1H-1,2,3,4-tetrazole (84.4 g, 178 mmol, 1.00 equiv) in chloroform (700 mL), a solution of potassium carbonate (49.0 g, 355 mmol, 2.00 equiv) in water (520 mL), and tetrabutylammonium chloride (10.2 g, 0.20 equiv). This was followed by the addition of para-methoxybenzyl chloride (42.2 g, 1.50 equiv) dropwise with stirring at 15° C. The resulting solution was stirred for 180 min at 50° C. in an oil bath. The reaction mixture was cooled to r.t. The resulting solution was diluted with 200 mL of water, then extracted with 2×200 mL of dichloromethane. The organic layers were combined, dried over sodium sulfate and concentrated under vacuum. The residue was applied onto a silica gel column and eluted with ethyl acetate/petroleum ether (1:2). This resulted in the title compound as a mixture of two isomers.

Step H: 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl chloride Into a 2000-mL 4-necked round-bottom flask purged and maintained with an inert atmosphere of nitrogen was placed mixture of 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole (50.0 g, 84.3 mmol, 1.00 equiv, 60%), dichloromethane (750 mL), AcOH (12.7 g, 211 mmol, 2.50 equivalents), and water (3.8 g, 2.5 equiv). This was followed by the addition of $SO_2Cl_2$ (28.3 g, 2.50 equivalents) dropwise with stirring at 0° C. The resulting solution was stirred for 60 min at room temperature. The resulting mixture was concentrated under vacuum to afford the title compound isomer mixture.

Step I: 6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide Into a 2000-mL 4-necked round-bottom flask purged and maintained with an inert atmosphere of nitrogen was placed a solution of 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl chloride (isomer mixture, 50.0 g, 52.7 mmol, 1.00 equiv, 60%) in tetrahydrofuran (300 mL) and a solution of $NH_4OH$ (200 mL) in tetrahydrofuran (200 mL). The resulting solution was stirred for 60 min at room temperature. The resulting solution was extracted with 3×150 mL of ethyl acetate. The organic layers were combined, dried over anhydrous sodium sulfate and concentrated under vacuum. The crude product was purified with Flash-Prep-HPLC under the following conditions: Column, C18 silica gel; mobile phase, $H_2O$: MeCN=25 increasing to H2O:MeCN=55 within 30 min; Detector, UV 210 nm, to afford the title compound.

H-NMR (DMSO-d6, 300MHz, ppm): δ 3.727-3.748 (3H, d), 5.001-5.068 (0.78H, m), 5.428-5.477 (0.75H, m), 5.941 (0.5H, m), 6.823-6.958 (2H, m), 7.148-7.363 (2H, m), 7.732-7.864 (1.6H, m), 7.993-8.117 (3H, m).

REFERENCE EXAMPLE 14 tert-butyl 3-(4-(4,4,5,5-tetramethyl-1,3,2-dioxaborolan-2-yl)phenyl)pyrrolidine-1-carboxylate

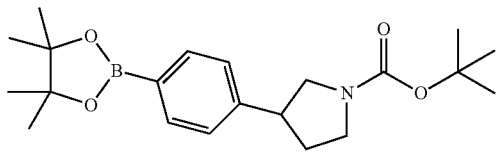 [SMILES: CC(C)(C)OC(=O)N1CCC(c2ccc(B3OC(C)(C)C(C)(C)O3)cc2)C1]

Step A: tert-butyl 3-(4-chlorophenyl)pyrrolidine-1-carboxylate

In 50 ml RB flask, Boc-Anhydride (0.792 mL, 3.41 mmol) was added to 3-(4-chlorophenyl)pyrrolidine, HCl (500 mg, 2.27 mmol) and TEA (0.48 ml, 3.4 mmol) in DCM (20 mL) then stirred at RT overnight. The reaction was poured into 1N HCl and extracted with more DCM (20 ml). The DCM was dried over $Na_2SO_4$, filtered and concentrated. The residue was purified by MPLC ISCO Combi-flash on ISCO Redi-Sep 40 g column, eluting with 0-50% EtOAc/hexane to give the title compound. LC-MS [M+1]$^+$: 282.

Step B: tert-butyl 3-(4-(4,4,5,5-tetramethyl-1,3,2-dioxaborolan-2-yl)phenyl)pyrrolidine-1-carboxylate To a 25 mL microwave vial was added tert-butyl 3-(4-chlorophenyl)pyrrolidine-1-carboxylate (270 mg, 0.95 mmol), potassium acetate (280 mg, 2.8 mmol), 4,4,4',4',5,5,5',5'-octamethyl-2,2'-bi(1,3,2-dioxaborolane) (480 mg, 1.9 mmol), 2nd generation XPHOS precatalyst (149 mg, 0.19 mmol) and dioxane (5 ml). The vial was capped and degassed via vacuum/nitrogen flushes (3 times). After stirring at room temp for 10 minutes, the vial was microwaved at 70° C. for 3 hrs. The reaction was filtered and concentrated. The residue was purified by MPLC ISCO Combi-flash on ISCO Redi-Sep 40 g column, eluting with 0-50% EtOAc/hexane to give a colorless solid. LC-MS [M+1]$^+$: 374.

REFERENCE EXAMPLE 15 tert-butyl 4-(4-(4,4,5,5-tetramethyl-1,3,2-dioxaborolan-2-yl)phenyl)piperidine-1-carboxylate

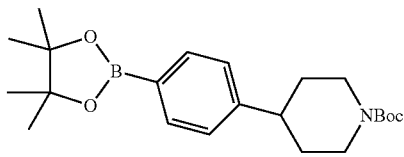 [SMILES: CC(C)(C)OC(=O)N1CCC(c2ccc(B3OC(C)(C)C(C)(C)O3)cc2)CC1]

Step A: tert-butyl 4-(4-bromophenyl)-4-hydroxypiperidine-1-carboxylate

A solution of 1,4-dibromobenzene (35.5 g, 150 mmol) in THF (250 mL) at −78° C. was treated with n-BuLi (2.5 M, 60 mL, 150 mmol) and stirred for 1 hr, followed by N-Boc-4-piperidone (10.0 g, 50 mmol) in THF (20 mL). After 1 hr the cooling bath was removed and the reaction mixture was stirred for 16 hr at 20° C. The mixture was diluted with saturated aqueous $NH_4Cl$, extracted with ethyl acetate, and the combined organic layers were washed with 0.1 N HCl, brine, dried over anhydrous $Na_2SO_4$ and concentrated to get the crude product, which was purified by silica gel (PE: EA=10:1) to obtain the title compound. $^1$H NMR (300 MHz, CDCl3) δ: 7.48 (d, J1=6.9 Hz, J2=1.8 Hz, 2H), 7.34 (d, J1=6.9 Hz, J2=1.8 Hz, 2H), 4.02 (brs, 2H), 3.21 (brt, J=12.3 Hz, 2H), 1.91 (m, 2H), 1.61-1.71 (m, 3H), 1.47 (s, 9H).

Step B: 4-(4-bromophenyl)-1,2,3,6-tetrahydropyridine

The mixture of tert-butyl 4-(4-bromophenyl)-4-hydroxypiperidine-1-carboxylate (2.0 g, 14 mmol) in acetic acid (1 mL) and concentrated HCl (10 mL) was heated at 100° C. for 16 hr. The reaction mixture was cooled down and washed with EA. The aqueous layer was basified by saturated $NaHCO_3$ solution and the solid $K_2CO_3$ to pH 8. Then the mixture was extracted with EA, dried and concentrated to obtain the title compound. $^1$H NMR (300 MHz, CDCl3) δ: 7.44 (d, J=8.7 Hz, 2H), 7.24 (d, J=9.0 Hz, 2H), 6.12 (s, 1H), 4.70 (brs, 1H), 3.51 (d, J=3.0 Hz, 2H), 3.10 (t, J=5.7 Hz, 2H), 2.42 (t, J=1.5 Hz, 2H).

Step C: tert-butyl 4-(4-bromophenyl)-5,6-dihydropyridine-1(2H)-carboxylate

An ice-cooled mixture of 4-(4-bromophenyl)-1,2,3,6-tetrahydropyridine (1.3 g, 5.46 mmol) in 1,4-dioxane (4 mL) and 1N NaOH (6 mL) was were added a solution of $Boc_2O$ (1.2 g, 5.46 mmol) in 1,4-dioxane (4 mL) and the mixture was stirred for 2 hr at room temperature and concentrated to remove the dioxane, extracted with EA. The combined organic layer was washed with 0.1 N HCl, water and brine, dried over anhydrous $Na_2SO_4$, concentrated to obtain the title compound. $^1$H NMR (300 MHz, CDCl3) δ: 7.43 (d, J=8.7 Hz, 2H), 7.23 (d, J=8.4 Hz, 2H), 6.04 (brs, 1H), 4.06-4.10 (m, 2H), 3.62 (m, 2H), 2.49 (m, 2H), 1.48 (s, 9H).

Step D: tert-butyl 4-(4-(4,4,5,5-tetramethyl-1,3,2-dioxaborolan-2-yl)phenyl)-5,6-dihydropyridine-1(2H)-carboxylate To the solution of tert-butyl 4-(4-bromophenyl)-5,6-dihydropyridine-1(2H)-carboxylate (1.4 g, 4.1 mmol) in DMSO (30 mL) was added bis(pinacolato)-diboron (1.6 g, 6.2 mmol), $Pd(PPh_3)_2Cl_2$ (0.35 g) and KOAc (1.2 g, 12.3 mmol). The reaction mixture was heated at 100° C. for 16 hr under $N_2$. The reaction mixture was cooled down and filtered, diluted with water (400 mL), and extracted with DCM (200 mL×3). The combined organic phases were washed with water, brine, dried and concentrated. The crude product was purified by silica gel to obtain the title compound. $^1$H NMR (300 MHz, CDCl3) δ: 7.78 (d, J=8.4 Hz, 2H), 7.37 (d, J=8.4 Hz, 2H), 6.10 (s, 1H), 4.08 (s, 2H), 3.63 (m, 2H), 2.54 (m, 2H), 1.50 (s, 9H), 1.36 (s, 12H).

Step E: tert-butyl 4-(4-(4,4,5,5-tetramethyl-1,3,2-dioxaborolan-2-yl)phenyl)piperidine-1-carboxylate To the solution of tert-butyl 4-(4-(4,4,5,5-tetramethyl-1,3,2-dioxaborolan-2-yl)phenyl)-5,6-dihydropyridine-1(2H)-carboxylate (6.0 g, 15.6 mmol) in methanol (150 mL) was added Pd/C (10%, 0.6 g). The reaction mixture was stirred at room temperature under hydrogen gas for 16 hr. The Pd/C was filtered off and the filtrate was concentrated to obtain the title compound. $^1$H NMR (300 MHz, CDCl3) δ: 7.75 (d, J=7.2 Hz, 2H), 7.21 (d, J=6.9 Hz, 2H), 4.25 (s, 2H), 2.61-2.82 (m, 3H), 1.60-1.83 (m, 4H), 1.47 (s, 9H), 1.33 (s, 12H).

REFERENCE EXAMPLE 16

2-(2-(4-methoxybenzyl)-2H-tetrazol-5-yl)-3-(piperidin-4-yl)benzenesulfonamide and 2-(1-(4-methoxybenzyl)-1H-tetrazol-5-yl)-3-(piperidin-4-yl)benzenesulfonamide

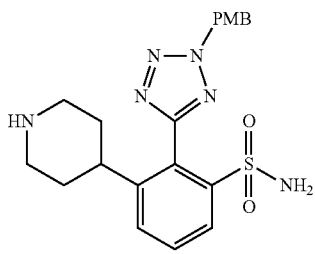

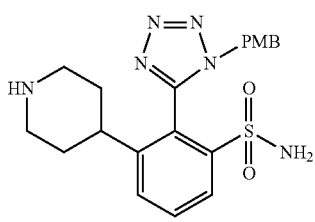

Step A: tert-butyl 4-(2-(2-(4-methoxybenzyl)-2H-tetrazol-5-yl)-3-sulfamoylphenyl)piperidine-1-carboxylate and tert-butyl 4-(2-(1-(4-methoxybenzyl)-1H-tetrazol-5-yl)-3-sulfamoylphenyl)piperidine-1-carboxylate To a mixture of 3-Bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (60 mg, 0.141 mmol), tert-butyl 4-iodopiperidine-1-carboxylate (88 mg, 0.283 mmol), pyridine (0.057 mL, 0.707 mmol), nickel chloride dimethoxyethane adduct (6.21 mg, 0.028 mmol), zinc (55.5 mg, 0.849 mmol), and ligand A 2,2':6', 2"-terpyridine (19.79 mg, 0.085 mmol) (or ligand B 4,4',4"-tri-tert-butyl-2,2':6',2"-terpyridine) in a $N_2$ filled microwave reaction vial was added DMA (1 mL). The vial was capped, and the reaction was heated to 100° C. for 1 hr in a microwave. The excess catalyst was filtered off and the solution was concentrated. The residue was purified by reverse phase HPLC column (acetonitrile/water/0.05% TFA system) eluted with 20% to 70% MeCN in water. The pure fractions were concentrated to afford the product. LC-MS: calculated for C, 25; H, 32; N, 6; O, 5; S, 528.62; observed m/e: 529.45 $(M+H)^+$.

Step B: 2-(2-(4-methoxybenzyl)-2H-tetrazol-5-yl)-3-(piperidin-4-yl)benzenesulfonamide and 2-(1-(4-methoxybenzyl)-1H-tetrazol-5-yl)-3-(piperidin-4-yl)benzenesulfonamide The product from Step A was dissolved in $CH_2Cl_2$ (1 mL) and TFA (1 mL). The reaction was stirred at room temperature for 20 min, then was concentrated to give crude TFA salt which was used for the next step without any purification.

REFERENCE EXAMPLE 17 tert-butyl 5-(4,4,5,5-tetramethyl-1,3,2-dioxaborolan-2-yl)isoindoline-2-carboxylate

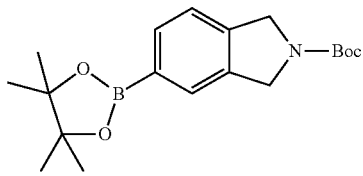 [SMILES: CC(C)(C)OC(=O)N1Cc2ccc(B3OC(C)(C)C(C)(C)O3)cc2C1]

Commercially available tert-butyl 5-bromoisoindoline-2-carboxylate (i.e., Matric Scientific, catalog #74109) (20 g, 0.0671 mol), 4,4,4',4',5,5,5',5'-octamethyl-2,2'-bi(1,3,2-dioxaborolane) (17 g, 0.0671 mol), KAc (8.5 g, 0.087 mol) and $PdCl_2dppf$ (1.8 g, 0.00221 mol) in 200 mL 1,4-dioxane was heated to 80° C. overnight. The mixture was cooled, water was added, the mixture was extracted with EA, dried and concentrated. The residue was purified by chromatography on silica gel to afford the title compound. $^1$HNMR (300 MHz, DMSO) δ: 1.2-1.3 (s, 12H), 1.4-1.5 (s, 9H), 4.5-4.6 (s, 4H), 7.2-7.3(m,1H), 7.5-7.6 (M,2H); LC-MS: m/z=246 $(M+1-100)^+$.

REFERENCE EXAMPLE 18

2-(2-(4-Methoxybenzyl)-2H-tetrazol-5-yl)-3-(4-oxocyclohexyl)benzenesulfonamide

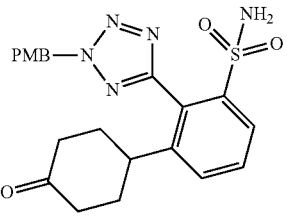

Step A: 2-(2-(4-Methoxybenzyl)-2H-tetrazol-5-yl)-3-(1,4-dioxaspiro[4.5]dec-7-en-8-yl)benzenesulfonamide 4,4,5,5-Tetramethyl-2-(1,4-dioxaspiro[4.5]dec-7-en-8-yl)-1,3,2-dioxaborolane (3.76 g, 14.1 mmol), 3-bromo-2-(2-(4-methoxybenzyl)-2H-tetrazol-5-yl)benzenesulfonamide (5.00 g, 11.8 mmol), $Na_2CO_3$ (2.498 g, 23.57 mmol), and PdCl2(dppf) (0.862 g, 1.18 mmol) were placed in a reaction vessel, and 1,4-dioxane (58.9 mL) and water (19.64 mL) were added). $N_2$ was bubbled through the mixture for 20 min. The reaction vessel was sealed and the mixture heated at 95° C. overnight. The reaction mixture was diluted with EtOAc and washed with water. The organic layer was separated, concentrated and the resulting residue was purified by column chromatography (0-90% EtOAc/Hexane) to give the title compound. LC-MS 484 (M+1).

Step B: 2-(2-(4-Methoxybenzyl)-2H-tetrazol-5-yl)-3-(1,4-dioxaspiro[4.5]decan-8-yl)benzenesulfonamide A flask was charged with 2-(2-(4-Methoxybenzyl)-2H-tetrazol-5-yl)-3-(1,4-dioxaspiro[4.5]dec-8-en-8-yl)benzenesulfonamide (4.00 g, 8.27 mmol), dissolved in MeOH (40 mL) and DCM (40 mL). Palladium hydroxide on carbon (2846 mg, 4.05 mmol) was added under $N_2$. The reaction was stirred under an atmosphere of H$_2$ for 3 hr. The reaction mixture was filtered through a pad of celite and the filtrate was concentrated to give the title compound.

LC-MS 486 (M+1)$^+$.

Step C: 2-(2-(4-Methoxybenzyl)-2H-tetrazol-5-yl)-3-(4-oxocyclohexyl)benzenesulfonamide 2-(2-(4-Methoxybenzyl)-2H-tetrazol-5-yl)-3-(1,4-dioxaspiro[4.5]decan-8-yl)benzenesulfonamide (3.56 g, 7.33 mmol) was dissolved in THF (70 mL) and treated with 2N HCl (5 mL). The reaction mixture was stirred at rt for 4 hr. LC-MS showed that the reaction was not completed yet. An additional amount of 2N HCl (10 mL) was added and stirred at rt overnight. The reaction mixture was diluted with EtOAc and washed with saturated NaHCO$_3$ aqueous solution. The organic layer was separated and washed with brine, dried (Na$_2$SO$_4$), filtered and concentrated. The residue was purified by column chromatography (0-100% EtOAc/Hexane) to give the title compound.

REFERENCE EXAMPLE 19

(4-iodopiperidin-1-yl)(1-phenylcyclopropyl)methanone

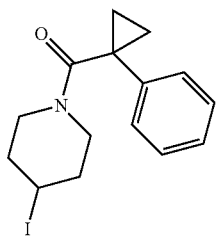 [SMILES: O=C(N1CCC(I)CC1)C1(c2ccccc2)CC1]

Step A: 4-iodopiperidine, TFA Salt

To a solution of tert-butyl 4-iodopiperidine-1-carboxylate (3.02 g, 9.72 mmol) in CH$_2$Cl$_2$ (10 mL) was added TFA (10 mL). The reaction was stirred at room temperature for 30 min, then was concentrated to give crude TFA salt which was used for the next step without any purification.

Step B: (4-iodopiperidin-1-yl)(1-phenylcyclopropyl)methanone

To 4-iodopiperidine, TFA salt from Step A in CH$_2$Cl$_2$ (14 mL) was added 1-phenylcyclopropanecarboxylic acid (1.928 g, 11.66 mmol), HATU (4.806 g, 12.64 mmol) and DIEA (3.40 mL, 38.88 mmol). The mixture was stirred at room temperature for 30 min and the solvent was concentrated. The residue was purified by normal phase ISCO on a 120 g column eluting with 0% to 50% ethyl acetate in hexane. The pure fractions were concentrated to afford product. LC-MS: calculated for C, 15; H, 18; INO, 355.21; observed m/e: 355.94 (M+H)$^+$.

REFERENCE EXAMPLE 20

5-(piperidin-4-yl)-1,3,4-thiadiazol-2-amine

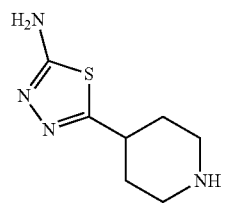

Into a 2000-mL round-bottom flask, was placed piperidine-4-carboxylic acid (50 g, 387 mmol, 1.00 equiv), aminothiourea (70.5 g, 774 mmol, 2.00 equiv), and hydrogen chloride (750 mL, 2.00 equiv, 10 M). The reaction mixture was heated to reflux overnight in an oil bath, and then concentrated under vacuum. The residue was diluted with 100 mL of water at 0° C. The pH of the solution was adjusted to 10-11 with saturated NaOH. The resulting mixture was stirred for 30 min. The solid was collected by filtration. The filter cake was washed with 2×200 mL of ice/water. The crude product was purified by re-crystallization from 200 mL of ethanol. LC/MS (ES, m/z): 185 [M+1]$^+$; H-NMR (CDCl3, ppm): δ 5.136 (s, 2H), 3.111 (m, 3H), 2.783 (m, 2H), 2.088 (m, 2H), 1.708 (m, 2H).

REFERENCE EXAMPLE 21

3-(piperidin-4-yl)pyridine dihydrochloride

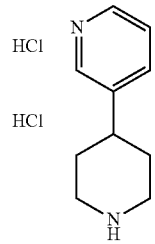 [SMILES: Cl ; Cl ; c1cncc(C2CCNCC2)c1]

Step A: trifluoro-N-phenyl-N-(trifluoromethylsulfonyl)methanesulfonamide

A solution of aniline (80 g, 0.86 mol) and NEt$_3$ (191 g, 1.89 mol) in dry CH$_2$Cl$_2$ (2 L) was added Tf$_2$O (507 g, 1.8 mol) dropwise at 78° C., maintained at this temperature for about 1 hr, then warmed to room temperature and allowed to stir overnight. The CH$_2$Cl$_2$ was removed under reduced pressure and the residue was washed by C$_2$H$_5$OH/CH$_3$OH=5:1 (500 mL×3) to obtain the title compound.

Step B: 1-(tert-butoxycarbonyl)-1,2,3,6-tetrahydropyridin-4-yltrifluoromethanesulfonate Di-iso-propylamine (6.06 g, 0.06 mol) dissolved in dry THF (100 mL), cooled to 78° C. under N$_2$, n-BuLi (24 mL, 0.06 mol) was added dropwise, and the reaction mixture was stirred at 78° C. for 1 hr. tert-butyl 4-oxopiperidine-1-carboxylate (10 g, 0.05 mol) in 50 mL THF was added dropwise at 78° C., then trifluoro-N-phenyl-N-(trifluoromethylsulfonyl)methanesulfonamide (19.8 g, 0.055 mol) in 50 mL THF was added dropwise at 78° C. and maintained at this temperature for about 1 hr after which it was allowed to be warmed to room temperature overnight. The reaction mixture was quenched with NH₄Cl (aq) with vigorously stirred. The aqueous was extracted with EtOAc (100 mL×3) and the combined organic extracts was dried, concentrated in vacuum and the residue was purified on silica gel (PE: EA=10:1) to give the product.

Step C: tert-butyl 5,6-dihydro-4-(pyridin-3-yl)pyridine-1(2H)-carboxylate 3-pyridylboronic acid (8.9 g, 0.072 mol), 1-(tert-butoxycarbonyl)-1,2,3,6-tetrahydropyridin-4-yltrifluoromethanesulfonate (20 g, 0.06 mol) and K₂CO₃ (24.8 g, 0.18) was dissolved in toluene (500 mL) and water (80 mL). The mixture was degassed and Pd (PPh₃)₄ (3.5 g, 3 mmol) was added in. The mixture was then heated to reflux for 2 hr with vigorous stirring. The reaction was cooled to room temperature and concentrated under reduced pressure. The residue was partitioned between DCM and saturated NaHCO₃; the aqueous was extracted with DCM (20 mL×3) and the combined organic extracts were dried. The solvent was removed under reduced pressure and the residue was purified on silica gel (PE:EA=5:1) to obtain product. LC-MS: m/e=261 (M+H)⁺.

Step D: tert-butyl 4-(pyridin-3-yl)piperidine-1-carboxylate tert-butyl 5,6-dihydro-4-(pyridin-3-yl)pyridine-1(2H)-carboxylate (51 g, 196 mmol) was dissolved in methanol (1000 mL), and Pd(OH)2 (9.5 g, 9.8 mmol, 15%) was added in. The mixture was stirred under H₂ (0.35 Mpa) at room temperature for 8 hr. After evaporation of the solvent, the residue was purified by column chromatography on silica gel (PE:EA=2:1) to give the product. LC-MS: m/e=261 (M+H)⁺.

Step E: 3-(piperidin-4-yl)pyridine dihydrochloride tert-butyl 4-(pyridin-3-yl)piperidine-1-carboxylate (12 g, 45.8 mmol) was dissolved in the dioxane (100 mL) then HCl gas was introduced. White precipitates was collected and recrystallized to afford the product. LC-MS: m/e=163 (M+H)⁺; 1HNMR (DMSO, 300 MHz): δ 9.5 (s, 2H), 8.84 (s, 2H), 8.5 (m, 1H), 8.1 (m, 1H), 3.37 (m, 2H), 3.33 (m, 1H), 3.19 (s, 1H), 2.5 (m, 4H).

REFERENCE EXAMPLE 22

2-(piperidin-3-yl)pyridine hydrochloride

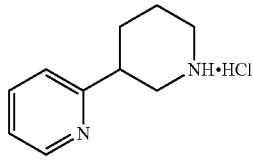

Step A: methyl 2-(pyridin-2-yl)acetate

To a stirred solution of 2-(pyridin-2-yl)acetic acid (245 g, 1.41 mol) in methanol (2.5 L) was added thionyl chloride (206 mL, 2.83 mol) drop wise over a period of 45 min at 0° C. The resulting reaction mixture was allowed to come to room temperature and stirred for 16 hr. After completion of the reaction (TLC), the reaction mixture was concentrated under reduced pressure to get the crude compound. The crude compound was dissolved in ethyl acetate (2.5 L) and washed with saturated sodium carbonate solution. The organic layer was dried over sodium sulphate and concentrated under reduced pressure to afford the crude title compound.

Step B: methyl 4-cyano-2-(pyridin-2-yl)butanoate

To a stirred solution of methyl 2-(pyridin-2-yl)acetate (190 g, 1.260 mol) in 1,4-dioxane (1.9 L) was added Triton-B (Benzyl Trimethyl ammonium hydroxide) (46 mL, 0.252 mol) at room temperature and stirred for 10 min. Acrylonitrile (49.7 mL, 0.760 mol) was dissolved in 1,4-dioxane (0.9 L) and was added drop wise over period of 30 minutes. The resulting reaction mixture was stirred for 16 hr at room temperature. The reaction progress was monitored by TLC. After completion of the reaction (TLC), the reaction mixture was concentrated under reduced pressure to afford the crude title compound. Purification by column chromatography was by using (100-200 silica gels) using 15% ethyl acetate and pet. ether as the eluent afforded pure compound.

Step C: 3-(pyridin-2-yl)piperidin-2-one

To a stirred solution of methyl 4-cyano-2-(pyridin-2-yl)butanoate (60 g, 0.292 mol) in methanol (600 mL) was added Raney Ni (30 g) and Aq ammonia (10 mL) at room temperature. The resulting reaction mixture was hydrogenated in a par shaker vessel at 60 psi for 16 hr. The reaction progress was monitored by TLC. After completion of reaction (TLC), the reaction mixture was filtered through celite bed and the bed was washed with methanol (600 mL) and the filtrate was concentrated under reduced pressure to afford the crude compound (50 g). Purification: The crude compound was triturated with diethyl ether (2×100 mL) and to afford pure compound.

Step D: tert-butyl 3-(pyridin-2-yl)piperidine-1-carboxylate

To a stirred solution of 3-(pyridin-2-yl)piperidin-2-one (60 g, 0.340 mol) in THF (430 mL) was added sodium borohydride (38.5 g, 1.019 mol) and BF₃ Et₂O (86 mL, 0.686 mol) at 0° C. The resulting reaction mixture was allowed to come to room temperature and stirred for 16 hr. The reaction progress was monitored by TLC. After completion of the reaction (TLC), the reaction mixture was quenched with conc. HCl (175 mL) and heated to 90° C. for 1 hr and then cooled to 0° C. The reaction mixture was basified with 10 N NaOH solution (200 mL) and BOC anhydride (93.34 mL, 0.406 mol) was added and the reaction stirred for 1 hr. After completion of reaction (TLC), the reaction mixture was diluted with water (1 L) and extracted into ethyl acetate (2×1 L). The organic layer was dried over sodium sulphate and concentrated under reduced pressure to obtain the crude compound (80 g). Purification: Crude was obtained which was purified by column chromatography by using (100-200 silica gels) using 10% ethyl acetate and pet ether as the eluent to afford pure compound.

Step E: 2-(piperidin-3-yl)pyridine hydrochloride

To a stirred solution of tert-butyl 3-(pyridin-2-yl)piperidine-1-carboxylate (80 g, 0.306 mol) in dioxane (80 mL) was added HCl in 1,4-dioxane (500 mL, 3 M solution) drop wise over a period of 15 minutes at 0° C. The resulting reaction mixture was allowed to come to room temperature and stirred for 16 hr. After completion of the reaction (TLC), the reaction mixture was concentrated under reduced pressure to afford the crude compound. Purification: The crude compound was washed with diethyl ether (2×250 mL) and dried under vacuum to afford the title compound. LC-MS: 99.56%, (m/z=163.1, [M+H]⁺).

REFERENCE EXAMPLE 23

3-(piperidin-4-yl)-5,6,7,8-tetrahydroimidazo[1,2-a]pyridine hydrochloride

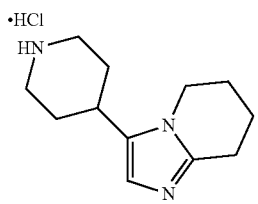 [SMILES: Cl ; c1nc2n(c1C1CCNCC1)CCCC2]

Step A: tert-butyl 4-(2-ethoxy-2-oxoethylidene)piperidine-1-carboxylate

To a stirred suspension of sodium hydride (60.2 g, 2.509 mol) in tetrahydrofuran (2.0 L) was added diethyl ethoxymethylphosphonate (309.1 g, 1.380 mol) drop wise under nitrogen atmosphere at 0° C. and stirred for 1 h. Tert-butyl 4-oxopiperidine-1-carboxylate (250 g, 1.254 mol) in tetrahydrofuran (2.0 L) was added drop wise to above reaction mixture at 0° C. and stirred at same temperature for 1 hr. After the completion of reaction (TLC), reaction mixture was quenched in ice cold water (1.0 L) and extracted with ethyl acetate (2×1.5 L). The combined organic layer was washed with brine (500 mL) and dried over sodium sulfate. The solvent was evaporated under reduced pressure to afford title compound.

Step B: tert-butyl 4-(2-ethoxy-2-oxoethyl)piperidine-1-carboxylate

To a stirred solution of tert-butyl 4-(2-ethoxy-2-oxoethylidene)piperidine-1-carboxylate (120 g, 0.446 mol) in methanol (1.0 L), 10% Pd/C (45 g) was added portion wise under nitrogen atmosphere at room temperature. The reaction mixture was hydrogenated under hydrogen atmosphere at 60 psi for 2 hr. The reaction progress was monitored by TLC method [(silica gel plate 60 F254 from Merck), 25% ethyl acetate in pet ether, using 254 nm UV light to visualize the spots]. Rf values of starting material and product were 0.4 and 0.35 respectively. After the completion of the reaction (TLC), the reaction mixture was filtered through celite bed and washed the bed with excess methanol. Filtrate was concentrated under reduced pressure to afford title compound.

Step C: tert-butyl 4-(1-bromo-2-ethoxy-2-oxoethyl)piperidine-1-carboxylate

To a stirred solution of LiHMDS (389.5 g, 2.029 mol) in tetrahydrofuran (2.0 L) was added tert-butyl 4-(2-ethoxy-2-oxoethyl)piperidine-1-carboxylate (250 g, 0.922 mol) in tetrahydrofuran (200 mL) drop wise under nitrogen atmosphere at −78° C. over a period of 1 hr. Trimethylsilyl chloride (314.5 g, 2.894 mol) was added drop wise to the above reaction mixture at −78° C. over a period of 2 hr and followed by drop wise addition of bromine (186 g, 1.162 mol) at the same temperature over a period of 45 minutes. After the completion of the reaction (TLC), the reaction mixture was quenched in saturated sodium bicarbonate solution (1.0 L) and extracted with ethyl acetate (2×1.5 L). The combined organic layer was washed with brine (500 mL) and dried over sodium sulfate. The solvent was evaporated under reduced pressure to afford title compound.

Step D: tert-butyl 4-(1-bromo-2-hydroxyethyl)piperidine-1-carboxylate

To a stirred solution of tert-butyl 4-(1-bromo-2-ethoxy-2-oxoethyl)piperidine-1-carboxylate (250 g, 0.716 mol) in tetrahydrofuran (2.5 L) was added sodium borohydride (136.1 g, 3.581 mol) portion wise at 0° C. Methanol (600 mL) was added drop wise to above reaction mixture at 0° C. The reaction mixture was allowed to stir at room temperature for 16 hr. After the completion of reaction (TLC), the reaction mixture was concentrated under reduced pressure to afford the residue. The residue was diluted with water (1.0 L) and extracted with ethyl acetate (2×1.5 L). The combined organic layer was washed with brine (500 mL) and dried over sodium sulfate. The solvent was evaporated under reduced pressure to afford the crude compound. The crude compound was adsorbed on 500 g of 100-200 silica gel, which was loaded over a pre-packed column with silica gel [200 mm×120 cm width and height of column, loaded with 3.0 kg of 100-200 silica gel]. Elution started with 20% ethyl acetate/pet. ether and finished with 30% ethyl acetate/pet. ether to afford the title compound.

Step E: tert-butyl 4-(1-bromo-2-oxoethyl)piperidine-1-carboxylate

To a stirred solution of tert-butyl 4-(1-bromo-2-hydroxyethyl)piperidine-1-carboxylate (200 g, 0.653 mol) in dichloromethane (2.0 L) was added Dess-martin periodinane (304.8 g, 0.718 mol) at 0° C. The resulting reaction mixture was allowed to stir at room temperature for 16 hr. After the completion of the reaction (TLC), the reaction mixture was quenched in saturated sodium bicarbonate solution (1.0 L) and extracted with dichloromethane (2×1.5 L). The combined organic layer was washed with brine (500 mL) and dried over sodium sulfate. The solvent was evaporated under reduced pressure to afford the title compound.

Step F: tert-butyl 4-(imidazo[1,2-a]pyridin-3-yl)piperidine-1-carboxylate

To a stirred solution of tert-butyl 4-(1-bromo-2-oxoethyl)piperidine-1-carboxylate (175 g, 0.571 mol) in ethanol (1.5 L) was added 2-amino pyridine (75.26 g, 0.8 mol) at room temperature. The resulting reaction mixture was refluxed for 16 hr. After completion of the reaction (TLC), the reaction mixture was evaporated under reduced pressure to afford the crude title compound. The crude compound was adsorbed on 400 g of 100-200 silica gel, which was loaded over a pre-packed column with silica gel [120 mm×90 cm width and height of column, loaded with 2.5 kg of 100-200 silica gel]. Elution started with 1% methanol/dichloromethane and finished with 3% ethyl methanol/dichloromethane to afford the pure title compound.

Step G: tert-butyl 4-(5,6,7,8-tetrahydroimidazo[1,2-a]pyridin-3-yl)piperidine-1-carboxylate To a stirred solution of tert-butyl 4-(imidazo[1,2-a]pyridin-3-yl)piperidine-1-carboxylate (60 g, 0.199 mol) in acetic acid (600 mL) was added 10% Pd/C (20 g) portion wise under nitrogen atmosphere at room temperature. The reaction mixture was hydrogenated under hydrogen atmosphere at 40 psi for 6 hr. After completion of the reaction (TLC), the reaction mixture was filtered through celite bed and the bed was washed with methanol. Filtrate was evaporated under reduced pressure to afford crude compound. The crude product was washed with 10% methyl tertiary butyl ether in pet. ether (500 mL) and dried under vacuum to afford the title compound.

Step H: 3-(piperidin-4-yl)-5,6,7,8-tetrahydroimidazo[1,2-a]pyridine hydrochloride To a stirred solution of tert-butyl 4-(5,6,7,8-tetrahydroimidazo[1,2-a]pyridin-3-yl)piperidine-1-carboxylate (50 g, 0.164 mol) in 1,4-dioxane (500 mL) was added drop wise HCl in 1,4-dioxane solution (500 mL, 3M solution) over a period of 45 minutes at 0° C. The resulting reaction mixture was allowed to stir at room temperature for 16 hr. The reaction mixture was concentrated under reduced pressure to afford the crude compound. Purification: The above crude compound was washed with MTBE (2×100 mL) and dried under vacuum to afford the title compound. LC/MS: 98.85%, (m/z=206.0 [(M−HCl)+H]⁺.

REFERENCE EXAMPLE 24

3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl)benzenesulfonamide

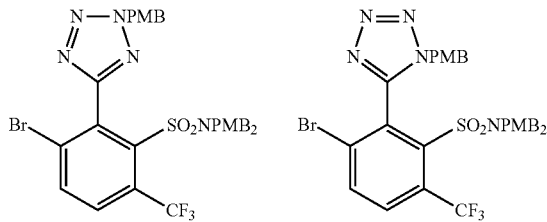

Step A: 6-bromo-2-fluoro-3-(trifluoromethyl)benzoic acid

Into a 10000-mL 4-necked round-bottom flask purged and maintained with an inert atmosphere of nitrogen, was placed tetrahydrofuran (5000 mL), NH(i-Pr)₂ (249 g, 1.20 equiv). This was followed by the addition of n-BuLi (905 mL, 1.10 equiv) dropwise with stirring in 30 min at −70° C. The resulting solution was stirred for 0.5 hr at −30° C. To this was added 4-bromo-2-fluoro-1-(trifluoromethyl)benzene (500 g, 2.06 mol, 1.00 equiv) dropwise with stirring at −78° C. in 2 hr. The resulting solution was stirred for 2 hr at −78° C. The reaction was then poured into 1000 g of CO₂(s) at −70° C. The pH value of the solution was adjusted to 3 with hydrogen chloride (2N) (1.5 mol/L). The resulting solution was extracted with 3×2000 mL of ethyl acetate and the organic layers combined and dried over anhydrous sodium sulfate and concentrated under vacuum. This resulted in 301 g (50%) of 6-bromo-2-fluoro-3-(trifluoromethyl)benzoic acid as a white solid.

Step B: 6-bromo-2-fluoro-3-(trifluoromethyl)benzoyl chloride

Into a 10000-mL 4-necked round-bottom flask purged and maintained with an inert atmosphere of nitrogen, was placed 6-bromo-2-fluoro-3-(trifluoromethyl)benzoic acid (560 g, 1.95 mol, 1.00 equiv), tetrahydrofuran (5600 mL), COCl₂ (374 g), N,N-dimethylformamide (2 g). The resulting solution was stirred for 12 hr at 25° C. The resulting mixture was concentrated under vacuum to afford crude 6-bromo-2-fluoro-3-(trifluoromethyl)benzoyl chloride.

Step C: 6-bromo-2-fluoro-3-(trifluoromethyl)benzamide

Into a 10000-mL 4-necked round-bottom flask, was placed NH₄OH (837 mL), tetrahydrofuran (4000 mL). This was followed by the addition of 6-bromo-2-fluoro-3-(trifluoromethyl)benzoyl chloride (600 g, 1.96 mol, 1.00 equiv) dropwise with stirring at 0° C. The resulting solution was stirred for 2 hr at 0° C. The resulting solution was concentrated under vacuum to afford 6-bromo-2-fluoro-3-(trifluoromethyl)benzamide.

Step D: 6-bromo-2-fluoro-3-(trifluoromethyl)benzonitrile

Into a 10000-mL 4-necked round-bottom flask, was placed 6-bromo-2-fluoro-3-(trifluoromethyl)benzamide (400 g, 1.40 mol, 1.00 equiv), trichloro-1,3,5-triazine (1807 g, 9.80 mol, 7.00 equiv), N,N-dimethylformamide (4000 mL). The resulting solution was stirred for 12 hr at 25° C. The reaction was then quenched by pouring into 10000 mL of water/ice. The solids were collected by filtration and dried in an oven under reduced pressure to afford the title compound.

Step E: 2-(benzylsulfanyl)-6-bromo-3-(trifluoromethyl)benzonitrile

Into a 10000-mL 4-necked round-bottom flask purged and maintained with an inert atmosphere of nitrogen, was placed 6-bromo-2-fluoro-3-(trifluoromethyl)benzonitrile (300 g, 1.12 mol, 1.00 equiv), 1,4-dioxane (3000 mL). To the above was added sodium hydride (138 g, 5.75 mol, 1.20 equiv) at 0° C. This was followed by the addition of BnSH (138 g) dropwise with stirring at 0° C. The resulting solution was stirred for 2 hr at 25° C. The reaction was then quenched by pouring into 1000 mL of water/ice. The resulting solution was extracted with 3×1000 mL of ethyl acetate and the organic layers combined and concentrated under vacuum to afford the title compound.

Step F: 5-[2-(benzylsulfanyl)-6-bromo-3-(trifluoromethyl)phenyl]-1H-1,2,3,4-tetrazole Into a 3000-mL 4-necked round-bottom flask purged and maintained with an inert atmosphere of nitrogen, was placed 2-(benzylsulfanyl)-6-bromo-3-(trifluoromethyl)benzonitrile (100 g, 269 mmol, 1.00 equiv), toluene (1000 mL), azidotrimethylsilane (77.5 g, 673 mmol, 2.50 equiv), Bu₂SnSO₂ (13.4 g). The resulting solution was stirred for 48 hr at 100° C. The resulting mixture was concentrated under vacuum providing the title compound.

Step G: 3-bromo-2-(1H-1,2,3,4-tetrazol-5-yl)-6-(trifluoromethyl)benzene-1-sulfonyl chloride Into a 3000-mL 4-necked round-bottom flask purged and maintained with an inert atmosphere of nitrogen, was placed 5-[2-(benzylsulfanyl)-6-bromo-3-(trifluoromethyl)phenyl]-1H-1,2,3,4-tetrazole (240 g, 577.99 mmol, 1.00 equiv), AcOH (200 mL), water (200 mL). To the above was added NCS (160 g) in portions at RT. The resulting solution was stirred for 12 hr at 25° C. The resulting mixture was concentrated under vacuum to afford the title compound.

Step H: 3-bromo-2-(1H-1,2,3,4-tetrazol-5-yl)-6-(trifluoromethyl)benzene-1-sulfonamide Into a 5000-mL 4-necked round-bottom flask, was placed 3-bromo-2-(1H-1,2,3,4-tetrazol-5-yl)-6-(trifluoromethyl)benzene-1-sulfonyl chloride (200 g, 511 mmol, 1.00 equiv), NH₄OH (1200 mL), tetrahydrofuran (2000 mL). The resulting solution was stirred for 1 hr at 25° C. The resulting mixture was concentrated under vacuum to furnish the title compound.

Step I: 3-bromo-N,N-bis[(4-methoxyphenyl)methyl]-2-[1-[(4-methoxyphenyl)methyl]-1H-1,2,3,4-tetrazol-5-yl]-6-(trifluoromethyl)benzene-1-sulfonamide, and 3-bromo-N,N-bis[(4-methoxyphenyl)methyl]-2-[2-[(4-methoxyphenyl)methyl]-2H-1,2,3,4-tetrazol-5-yl]-6-(trifluoromethyl)benzene-1-sulfonamide Into a 10000-mL 4-necked round-bottom flask purged and maintained with an inert atmosphere of nitrogen, was placed 3-bromo-2-(1H-1,2,3,4-tetrazol-5-yl)-6-(trifluoromethyl)benzene-1-sulfonamide (230 g, 618.08 mmol, 1.00 equiv), potassium carbonate (276 g, 2.00 mol, 3.23 equiv), NaI (18.4 g), Bu₄NCl (34.0 g, 122 mmol, 0.20 equiv), chloroform (3800 mL, 1.00 equiv), 1-(chloromethyl)-4-methoxybenzene (380 g, 2.43 mol, 3.93 equiv), water (2550 mL).

The resulting solution was stirred for 12 hr at 55° C. The aqueous phase was extracted with 2×1000 mL of DCM. The mixture was dried over anhydrous sodium sulfate and concentrated under vacuum. The residue was applied onto a silica gel column with ethyl acetate/hexane (1:10). Purification afforded 3-bromo-N,N-bis[(4-methoxyphenyl)methyl]-2-[1-[(4-methoxyphenyl)methyl]-1H-1,2,3,4-tetrazol-5-yl]-6-(trifluoromethyl)benzene-1-sulfonamide, and 3-bromo-N,N-bis[(4-methoxyphenyl)methyl]-2-[2-[(4-methoxyphenyl)methyl]-2H-1,2,3,4-tetrazol-5-yl]-6-(trifluoromethyl)benzene-1-sulfonamide.

LC-MS: (ES, m/z): 732 [M+H]+.

H-NMR: (CDCl3, 300 Hz, ppm): δ 3.763 (9H, s), 3.820-3.872 (2H, d, J=15.6), 4.402-4.454 (2H, d, J=15.6), 5.154-5.203 (1H, d, J=14.7), 5.560-5.609 (1H,d, J=14.7), 6.702-6.763 (6H, m), 6.912-6.941 (4H, m), 7.109-7.138 (2H, m), 7.839-7.854 (2H, m).

REFERENCE EXAMPLE 25

(3-[bis[(4-methoxyphenyl)methyl]sulfamoyl]-2-[1-[(4-methoxyphenyl)methyl]-1H-1,2,3,4-tetrazol-5-yl]-4-(trifluoromethyl)phenyl)boronic acid and (3-[bis[(4-methoxyphenyl)methyl]sulfamoyl]-2-[2-[(4-methoxyphenyl)methyl]-2H-1,2,3,4-tetrazol-5-yl]-4-(trifluoromethyl)phenyl)boronic acid

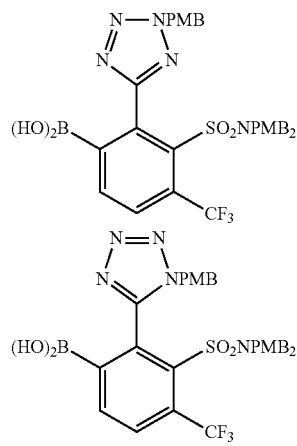

Into a 1 L 4-necked round-bottom flask purged and maintained with an inert atmosphere of nitrogen, was placed a mixture of 3-bromo-N,N-bis[(4-methoxyphenyl)methyl]-2-[1-[(4-methoxyphenyl)methyl]-1H-1,2,3,4-tetrazol-5-yl]-6-(trifluoromethyl)benzene-1-sulfonamide and 3-bromo-N,N-bis[(4-methoxyphenyl)methyl]-2-[2-[(4-methoxyphenyl)methyl]-2H-1,2,3,4-tetrazol-5-yl]-6-(trifluoromethyl)benzene-1-sulfonamide (REFERENCE EXAMPLE 24, 120 g, 163.81 mmol, 1.00 equiv), 1,4-dioxane (360 mL), 2-(5,5-dimethyl-1,3,2-dioxaborinan-2-yl)-5,5-dimethyl-1,3,2-dioxaborinane (111 g, 491 mmol, 3.00 equiv), KOAc (80.3 g, 818 mmol, 5.00 equiv), 2-2-[chloro(triphenyl-^5-phosphanylidene)palladio]phenylaniline (9.4 g, 16.42 mmol, 0.10 equiv). The resulting solution was stirred for 6 hr at 60° C. The resulting solution was diluted with 500 mL of CH3CN. The solids were filtered out. The filtrate was concentrated under vacuum. The crude product was purified by Flash-Prep-HPLC with the following conditions (CombiFlash-1): Column, C18 silica gel; mobile phase, CH3CN/H2O=1:2 increasing to CH3CN/H2O=2:1 within 25 min, and then CH3CN/H2O=2:1 within 25 min, and then CH3CN/H2O=1:0 within 10 min; Detector, UV 210 nm. This afforded (3-[bis[(4-methoxyphenyl)methyl]sulfamoyl]-2-[1-[(4-methoxyphenyl)methyl]-1H-1,2,3,4-tetrazol-5-yl]-4-(trifluoromethyl)phenyl)boronic acid and (3-[bis[(4-methoxyphenyl)methyl]sulfamoyl]-2-[2-[(4-methoxyphenyl)methyl]-2H-1,2,3,4-tetrazol-5-yl]-4-(trifluoromethyl)phenyl)boronic acid.

LC-MS: (ES, m/z): 698 [M+H]+

H-NMR: (300 MHz, DMSO, ppm): δ 3.616-3.860 (11H, m), 3.860 (0.855H, s), 4.459-4.511 (1.492H, m),5.172 (1.335H, s), 5.877 (0.403H, s), 6.733-6.827 (10H, m), 7.199-7.306 (2 H, m), 8.456 (1.2H, m).

REFERENCE EXAMPLE 26

2-(1-(4-methoxybenzyl)-1H-tetrazol-5-yl)-4'-(piperidin-4-yl)-[1,1'-biphenyl]-3-sulfonamide and 2-(2-(4-methoxybenzyl)-2H-tetrazol-5-yl)-4'-(piperidin-4-yl)-[1,1'-biphenyl]-3-sulfonamide

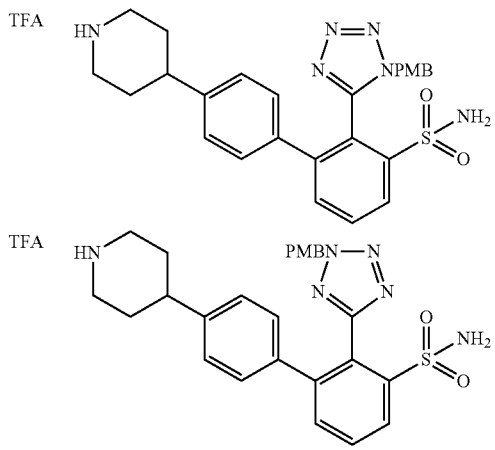

Step A: tert-butyl 4-(2'-(1-(4-methoxybenzyl)-1H-tetrazol-5-yl)-3'-sulfamoyl-[1,1'-biphenyl]-4-yl)piperidine-1-carboxylate and tert-butyl 4-(2'-(2-(4-methoxybenzyl)-2H-tetrazol-5-yl)-3'-sulfamoyl-[1,1'-biphenyl]-4-yl)piperidine-1-carboxylate tert-Butyl 4-(4-(4,4,5,5-tetramethyl-1,3,2-dioxaborolan-2-yl)phenyl)piperidine-1-carboxylate (3.29 g, 8.49 mmol), 3-bromo-2-(1-(4-methoxybenzyl)-1H-tetrazol-5-yl)benzenesulfonamide (and the PMB tetrazole isomer, 3 g, 7.07 mmol), Na2CO3 (1.499 g, 14.14 mmol), PdCl2(dppf) (0.517 g, 0.707 mmol) was placed in a reaction vessel, and to this was added 1,4-Dioxane (35.4 mL) and water (11.8 mL). N2 was bubbled through the mixture for 20 min. The mixture was then heated at 95° C. overnight. The reaction mixture was diluted with EtOAc and washed with water. The organic layer was concentrated and the crude product was purified by column chromatography (0% EtOAc/hexane to 100% EtOAc/Hexane gradient) to give the product. LC/MS (M+H)+: 605.5.

Step B: 2-(1-(4-methoxybenzyl)-1H-tetrazol-5-yl)-4'-(piperidin-4-yl)-[1,1'-biphenyl]-3-sulfonamide and 2-(2-(4-methoxybenzyl)-2H-tetrazol-5-yl)-4'-(piperidin-4-yl)-[1,1'-biphenyl]-3-sulfonamide tert-Butyl 4-(2'-(1-(4-methoxybenzyl)-1H-tetrazol-5-yl)-3'-sulfamoyl-[1,1'-biphenyl]-4-yl)piperidine-1-carboxylate and tert-butyl 4-(2'-(2-(4-methoxybenzyl)-2H-tetrazol-5-yl)-3'-sulfamoyl-[1,1'-biphenyl]-4-yl)piperidine-1-carboxylate (2.95 g, 4.88 mmol) was dissolved in DCM (20 mL) and then treated with TFA (10 mL). The reaction mixture was stirred at RT for 2 hr. The mixture was concentrated and co-evaporated with DCM and toluene to afford the title compound as a mixture of two isomers.

REFERENCE EXAMPLE 27

3-(2-bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide

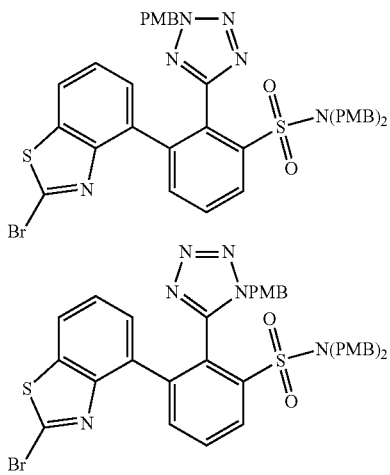

Step A: 3-(2-aminobenzo[d]thiazol-4-yl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-N,N-bis(4-methoxybenzyl)-2-(2-(4-methoxybenzyl)-2H-tetrazol-5-yl)benzenesulfonamide 4-Bromobenzo[d]thiazol-2-amine (600 mg, 2.62 mmol), a mixture of (3-(N,N-bis(4-methoxybenzyl)sulfamoyl)-2-(1-(4-methoxybenzyl)-1H-tetrazol-5-yl)phenyl)boronic acid and (3-(N,N-bis(4-methoxybenzyl)sulfamoyl)-2-(2-(4-methoxybenzyl)-2H-tetrazol-5-yl)phenyl)boronic acid (2473 mg, 3.93 mmol), 2nd Generation Xphos Precatalyst (309 mg, 0.393 mmol), Cs$_2$CO$_3$ (2560 mg, 7.86 mmol) was placed in a reaction vessel, and 1,4-Dioxane (1.40E+04 μl) and Water (3492 μl) were added. N$_2$ was bubbled through the mixture for 20 min. The mixture was then heated at 85° C. for 20 hr. The crude product was directly loaded onto a silica gel column and purified by column chromatography (100% EtOAc to 20% MeOH/EtOAc gradient). LC/MS (M+H)$^+$: 734.

Step B: 3-(2-bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide The isomer mixture from Step A (1.56 g, 2.126 mmol) was added portionwise to a solution of Copper(II) Bromide (0.570 g, 2.55 mmol) and Tert-Butyl Nitrite (0.351 g, 3.40 mmol) in Acetonitrile (7.87 mL) at rt under N$_2$. The mixture was stirred for 30 min. The mixture was diluted with 1N HCl solution and extracted with EtOAc. After concentration of the organic extract, the crude product was purified by column chromatography (100% hexane to 50% EtOAc/Hexane gradient) to give the title compound. LC/MS (M+H)$^+$: 797, 799.

REFERENCE EXAMPLE 28

3-(6-bromopyridin-3-yl)-N,N-bis(4-methoxybenzyl)-2-(2-(4-methoxybenzyl)-2H-tetrazol-5-yl)benzenesulfonamide and 3-(6-bromopyridin-3-yl)-N,N-bis(4-methoxybenzyl)-2-(1-(4-methoxybenzyl)-1H-tetrazol-5-yl)benzenesulfonamide

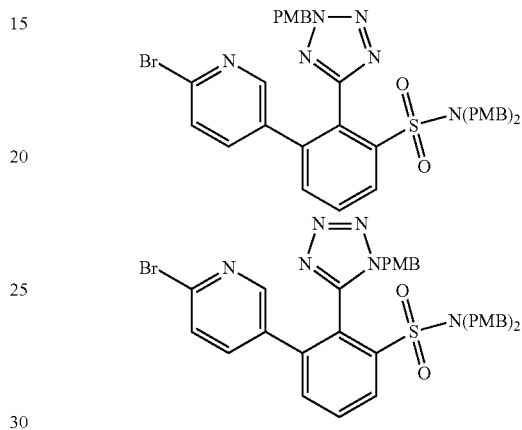

Step A: 3-(6-aminopyridin-3-yl)-N,N-bis(4-methoxybenzyl)-2-(2-(4-methoxybenzyl)-2H-tetrazol-5-yl)benzenesulfonamide and 3-(6-aminopyridin-3-yl)-N,N-bis(4-methoxybenzyl)-2-(1-(4-methoxybenzyl)-1H-tetrazol-5-yl)benzenesulfonamide To a mixture of 5-(4,4,5,5-tetramethyl-1,3,2-dioxaborolan-2-yl)pyridin-2-amine (6.64 g, 30.2 mmol), and a mixture of 3-bromo-N,N-bis(4-methoxybenzyl)-2-(1-(4-methoxybenzyl)-1H-tetrazol-5-yl)benzenesulfonamide and 3-bromo-N,N-bis(4-methoxybenzyl)-2-(2-(4-methoxybenzyl)-2H-tetrazol-5-yl)benzenesulfonamide (10.0 g, 15.1 mmol) and Na$_2$CO$_3$ (4.80 g, 45.2 mmol) in 1,4,-dioxane (100 mL) and water (25 mL) was added Pd(dppf)Cl$_2$ (0.17 g, 0.15 mmol) and the mixture was stirred at 80° C. overnight. The resulting mixture was filtered, the filtrate was concentrated in vacuo, the residue was diluted with water and extracted with EtOAc (100 mL×3), the combined organic phase was dried over anhydrous sodium sulfate, filtered and the filtrate was concentrated in vacuo, the residue was purified with column purification procedure (PE: EA=1:1) to give the title compound. MS (ESI): m/z (M+H)+ 678.2

Step B: 3-(6-bromopyridin-3-yl)-N,N-bis(4-methoxybenzyl)-2-(2-(4-methoxybenzyl)-2H-tetrazol-5-yl)benzenesulfonamide and 3-(6-bromopyridin-3-yl)-N,N-bis(4-methoxybenzyl)-2-(1-(4-methoxybenzyl)-1H-tetrazol-5-yl)benzenesulfonamide To a solution of 3-(6-aminopyridin-3-yl)-N,N-bis(4-methoxybenzyl)-2-(2-(4-methoxybenzyl)-2H-tetrazol-5-yl)benzenesulfonamide and 3-(6-aminopyridin-3-yl)-N,N-bis(4-methoxybenzyl)-2-(1-(4-methoxybenzyl)-1H-tetrazol-5-yl)benzenesulfonamide (5.0 g, 7.5 mmol) and benzyltrimethylammonium bromide (7.72 g, 33.7 mmol) in dibromomethane (75 mL) was added tert-butylnitrite (7.72 g, 75.0 mmol) at room temperature. The mixture was stirred at room temperature overnight. The resulting mixture was concentrated in vacuo, the residue was diluted with water and extracted with DCM (50 mL*3), the combined organic phase was dried over anhydrous sodium sulfate, filtered and the filtrate was concentrated in vacuo, the residue was purified with column purification procedure (PE: EA=30:1) to give the title compound. $^1$HNMR HL00386-012-1 (CDCl$_3$, 400MHz): δ 8.15 (d, J=7.6 Hz, 1H), 7.68-7.69 (m, 2H), 7.49 (d, J=8.0 Hz, 1H), 6.97-7.14 (m, 6H), 6.65-6.74 (m, 8H), 5.46 (d, J=15.2 Hz, 1H), 4.90 (d, J=15.2 Hz, 1H), 4.15 (d, J=15.2 Hz, 2H), 3.96 (d, J=15.2 Hz, 2H), 3.74-3.81 (m, 9H). MS (ESI): m/z (M+H)+741.1, 743.1.

REFERENCE EXAMPLE 29

6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide

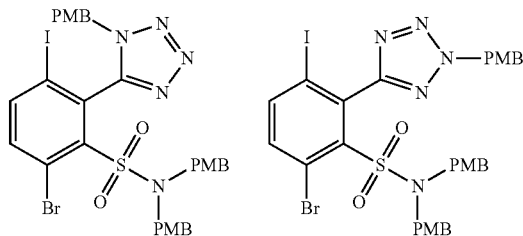

Step A: 3-bromo-2-fluoro-6-iodobenzoic acid

Into a 5000-mL 4-necked round-bottom flask purged and maintained with an inert atmosphere of nitrogen, was placed bis(propan-2-yl)amine (121.2 g, 1.20 mol, 1.20 equiv), tetrahydrofuran (1000 mL). This was followed by the addition of butyllithium (440 mL, 1.10 equiv, 2.5 N) dropwise with stirring at −78° C. in 20 min. 60 min later, to this was added a solution of 1-bromo-2-fluoro-4-iodobenzene (300 g, 997 mmol, 1.00 equiv) in tetrahydrofuran (2000 mL) dropwise with stirring at −78° C. in 30 min. The resulting solution was stirred for 2 hr at −78° C. in a liquid nitrogen bath. The reaction progress was monitored by LCMS. The reaction was then quenched by pouring into 5000 g of dry ice. After stirring for 2 hours, the resulting mixture was concentrated under vacuum. The residue was dissolved in 3000 mL of 4N sodium hydroxide. The resulting solution was extracted with 2×1000 mL of ether and the aqueous layers combined. The pH value of the solution was adjusted to 2-3 with hydrogen chloride (1 mmol/L). The resulting solution was extracted with 4×1000 mL of ethyl acetate and the organic layers combined and dried over anhydrous sodium sulfate and concentrated under vacuum. The crude product was purified by re-crystallization from Hexane.

Step B: 3-bromo-2-fluoro-6-iodobenzoyl

Into a 5000-mL 3-necked round-bottom flask purged and maintained with an inert atmosphere of nitrogen, was placed 3-bromo-2-fluoro-6-iodobenzoic acid (273 g, 791.52 mmol, 1.00 equiv), tetrahydrofuran (2730 mL), N,N-dimethylformamide (27.3 mL). This was followed by the addition of (COCl)$_2$ (110.9 g, 1.10 equiv) dropwise with stirring at 20° C. in 20 min. The resulting solution was stirred for 1 hr at room temperature. The reaction progress was monitored by LCMS. The resulting mixture was concentrated under vacuum.

Step C: 3-bromo-2-fluoro-6-iodobenzamide

Into a 5000-mL 4-necked round-bottom flask purged and maintained with an inert atmosphere of nitrogen, was placed NH$_4$OH (1200 g). This was followed by the addition of a solution of 3-bromo-2-fluoro-6-iodobenzoyl chloride (280 g, 771 mmol, 1.00 equiv) in tetrahydrofuran (2800 mL) dropwise with stirring at 0° C. in 30 min. The resulting solution was stirred for 1 hr at room temperature. The reaction progress was monitored by LCMS. The resulting mixture was concentrated under vacuum. The solids were collected by filtration, washed with H$_2$O to afford the title compound.

Step D: 3-bromo-2-fluoro-6-iodobenzonitrile

Into a 10000-mL 4-necked round-bottom flask purged and maintained with an inert atmosphere of nitrogen, was placed 3-bromo-2-fluoro-6-iodobenzamide (270 g, 785.07 mmol, 1.00 equiv), N,N-dimethylformamide (5400 mL). This was followed by the addition of trichloro-1,3,5-triazine (1014 g, 5.50 mol, 7.00 equiv), in portions at 0° C. The resulting solution was stirred for 2 hr at room temperature. The reaction progress was monitored by LCMS. The reaction was then quenched by the addition of 15000 mL of sodium bicarbonate aq. The solids were collected by filtration to afford the title compound.

Step E: 2-(benzylsulfanyl)-3-bromo-6-iodobenzonitrile

Into a 5000-mL 4-necked round-bottom flask purged and maintained with an inert atmosphere of nitrogen, was placed sodium hydride (34 g, 852 mmol, 1.20 equiv, 60%), 1,4-dioxane (700 mL). This was followed by the addition of a solution of phenylmethanethiol (88.7 g, 714.15 mmol, 1.00 equiv) in 1,4-dioxane (950 mL) dropwise with stirring at 10° C. in 15 min. 30 min later, to this was added a solution of 3-bromo-2-fluoro-6-iodobenzonitrile (230 g, 705.73 mmol, 1.00 equiv) in 1,4-dioxane (1800 mL) dropwise with stirring at 10° C. The resulting solution was stirred for 2 hr at room temperature. The reaction progress was monitored by LCMS. The reaction was then quenched by pouring into 5000 mL of water/ice. The resulting solution was extracted with 5×1000 mL of ethyl acetate and the organic layers combined. The resulting mixture was washed with 2×1000 mL of water and 2×1000 mL of sodium bicarbonate and 2×1000 mL of sodium chloride. The mixture was dried over anhydrous sodium sulfate and concentrated under vacuum. The crude product was purified by re-crystallization from ether to afford the title compound.

Step F: 5-[2-(benzylsulfanyl)-3-bromo-6-iodophenyl]-1H-1,2,3,4-tetrazole

Into a 2000-mL 4-necked round-bottom flask, was placed 2-(benzylsulfanyl)-3-bromo-6-iodobenzonitrile (66 g, 153.45 mmol, 1.00 equiv), toluene (660 mL), azidotrimethylsilane (44.2 g, 383.65 mmol, 2.50 equiv), dibutylstannanone (7.7 g, 30.93 mmol, 0.20 equiv). The resulting solution was stirred for 48 hr at 105° C. in an oil bath. The reaction progress was monitored by LCMS. The reaction mixture was cooled to room temperature. The resulting mixture was concentrated under vacuum. The residue was purified by silica gel column with tetrahydrofuran:PE (100:1) to afford the title compound.

Step G: 6-bromo-3-iodo-2-(1H-1,2,3,4-tetrazol-5-yl)benzene-1-sulfonyl chloride

Into a 2000-mL 3-necked round-bottom flask purged and maintained with an inert atmosphere of nitrogen, was placed 5-[2-(benzylsulfanyl)-3-bromo-6-iodophenyl]-1H-1,2,3,4-tetrazole (115.6 g, 244.33 mmol, 1.00 equiv), acetic acid (1156 mL), water (115.6 mL), NCS (81.74 g, 612.15 mmol, 2.50 equiv). The resulting solution was stirred overnight at room temperature in an ice/salt bath. The reaction progress was monitored by LCMS. The resulting mixture was concentrated under vacuum to afford the title compound.

Step H: 6-bromo-3-iodo-2-(1H-1,2,3,4-tetrazol-5-yl)benzene-1-sulfonamide

Into a 3000-mL 4-necked round-bottom flask purged and maintained with an inert atmosphere of nitrogen, was placed NH$_4$OH (1180 mL), tetrahydrofuran (290 mL). This was followed by the addition of a solution of 6-bromo-3-iodo-2-(1H-1,2,3,4-tetrazol-5-yl)benzene-1-sulfonyl chloride (118 g, 262.54 mmol, 1.00 equiv) in tetrahydrofuran (300 mL) dropwise with stirring at 0° C. The resulting solution was stirred for 2 hr at 0-25° C. in an ice/salt bath (slowly warming to RT). The reaction progress was monitored by LCMS. The resulting mixture was concentrated under vacuum. The resulting solution was diluted with 500 mL of ether. After stirring for 30 min, the solids were collected by filtration to afford the title compound.

Step I: 6-bromo-3-iodo-N,N-bis[(4-methoxyphenyl)methyl]-2-[1-[(4-methoxyphenyl)methyl]-1H-1,2,3,4-tetrazol-5-yl]benzene-1-sulfonamide and 6-bromo-3-iodo-N,N-bis[(4-methoxyphenyl)methyl]-2-[2-[(4-methoxyphenyl)methyl]-2H-1,2,3,4-tetrazol-5-yl]benzene-1-sulfonamide Into a 3000-mL 4-necked round-bottom flask purged and maintained with an inert atmosphere of nitrogen, was placed 6-bromo-3-iodo-2-(1H-1,2,3,4-tetrazol-5-yl)benzene-1-sulfonamide (105 g, 244.17 mmol, 1.00 equiv), chloroform (1050 mL), potassium carbonate (168.9 g, 1.22 mol, 5.00 equiv), water (525 mL), NaI (11 g, 0.30 equiv), tetrabutyl(chloro)amine (20.4 g, 73.40 mmol, 0.30 equiv), 1-(chloromethyl)-4-methoxybenzene (230 g, 1.47 mol, 6.00 equiv). The resulting solution was stirred overnight at 50° C. in an oil bath. The reaction progress was monitored by LCMS. The reaction mixture was cooled to room temperature. The resulting solution was extracted with 2×1000 mL of dichloromethane and the organic layers combined and dried over anhydrous sodium sulfate and concentrated under vacuum to afford the title compounds.

LC-MS: (ES, m/z): 790 [M+H]$^+$

H-NMR: (300 MHz, CDCl$_3$, ppm): δ 7.956-7.928 (m, 0.5H), 7.852-7.824 (m, 1H), 7.656-7.612 (m, 1.5H), 7.323-7.282 (m, 1.5H), 7.195-7.224 (m, 2H), 6.944-6.908 (m, 6H), 6.822-6.760 (m, 9H), 5.791 (m, 1H), 5.570-5.521 (m, 1H), 5.149-5.100 (m, 1H), 4.769-4.718 (m, 2H), 4.232-4.221 (m, 2H), 3.900-3.848 (m, 2H), 3.789-3.742 (m, 14H).

REFERENCE EXAMPLE 30 tert-butyl 4-(2-iodoethyl)piperidine-1-carboxylate

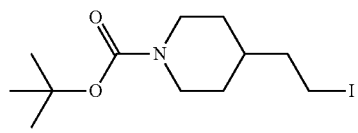 [SMILES: CC(C)(C)OC(=O)N1CCC(CCI)CC1]

Step A: tert-butyl 4-(2-hydroxyethyl)piperidine-1-carboxylate

To a stirred solution of 1-(tert-butoxycarbonyl)piperidine-4-carboxylic acid (2.00 g, 8.72 mmol) in THF (20 mL), a solution of borane (1 M) in THF (8.72 mL) was added dropwise at 0° C. The resulting mixture was stirred for 6 hr at ambient temperature and then quenched with water (20 mL), extracted with EtOAc (2×40 mL). The combined organic layers were washed with brine (2×30 mL), dried over anhydrous Na$_2$SO$_4$ and concentrated under reduced pressure to afford tert-butyl 4-(hydroxymethyl)piperidine-1-carboxylate which was used in the next step directly. LCMS (ESI) calc'd for C$_{12}$H$_{23}$NO$_3$ [M+H]$^+$: 230, found 230.

Step B: tert-butyl 4-(2-iodoethyl)piperidine-1-carboxylate

To a stirred mixture of tert-butyl 4-(hydroxymethyl)piperidine-1-carboxylate (1.80 g, 8.36 mmol), triphenylphosphine (2.63 g, 10.0 mmol) and 1H-imidazole (0.68 g, 10.03 mmol) in THF (30 mL) was added dropwise a solution of I$_2$ (2.55 g, 10.03 mmol) in THF (10 mL) at 0° C. The resulting mixture was stirred 12 hr at ambient temperature and then quenched with water (50 mL), extracted with EtOAc (3×50 mL). The combined organic layers were washed with Na$_2$SO$_3$ (aq.) (2×50 mL), dried over anhydrous Na$_2$SO$_4$ and concentrated under vacuum. The residue was purified by silica gel chromatography, eluted with EtOAc/PE (1/5). The combined organic fractions were concentrated under reduced pressure to afford tert-butyl 4-(iodomethyl)piperidine-1-carboxylate: LCMS (ESI) calc'd for: C$_{11}$H$_{20}$INO$_2$ [M+H]$^+$: 326. found 326; $^1$H NMR (400 MHz, CDCl$_3$): δ 4.10-4.07 (m, 2H), 3.23-3.19 (m, 2H), 2.73-2.66 (m, 2H), 1.80-1.75 (m, 2H), 1.67-1.58 (m, 3H), 1.57 (s, 9H), 1.15-1.08 (m, 2H).

REFERENCE EXAMPLES 31A, 31B (R)-tert-butyl 3-amino-3-(4-bromophenyl)pyrrolidine-1-carboxylate and (S)-tert-butyl 3-amino-3-(4-bromophenyl)pyrrolidine-1-carboxylate

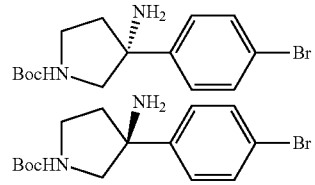

Step A: Synthesis of tert-butyl 3-(4-bromophenyl)-3-hydroxypyrrolidine-1-carboxylate To a stirred solution of 1-bromo-4-iodobenzene (20.00 g, 70.70 mmol) in THF (320 mL) was added dropwise n-butyllithium (30 mL, 75 mmol, 2.5 M in THF) at −78° C. After the resulting mixture was stirred at −78° C. for 1 hr, a solution of tert-butyl 3-oxopyrrolidine-1-carboxylate (19.64 g, 0.11 mol) in THF (20 mL) was added dropwise. The resulting mixture was stirred at −78° C. for 2 hr and then it was quenched with water (50 mL), diluted with water (200 mL) and extracted with EtOAc (3×200 mL). The combined organic layers were washed with brine (3×100 mL), dried over anhydrous Na$_2$SO$_4$ and concentrated under vacuum. The residue was purified by silica gel column chromatography, eluted with EtOAc/PE (1/1) to afford tert-butyl 3-(4-bromophenyl)-3-hydroxypyrrolidine-1-carboxylate: LCMS (ESI) calc'd for C$_{15}$H$_{20}$BrNO$_3$ [M-56]$^+$: 268, 270 (1:1), found: 268, 270 (1:1). $^1$H NMR (300 MHz, DMSO-d$_6$): δ 7.52 (d, J=6.6 Hz, 2H), 7.46 (d, J=6.6 Hz, 2H), 3.62-3.39 (m, 3H), 2.25-2.01 (m, 3H), 1.42 (s, 9H).

Step B: Synthesis of tert-butyl 3-(4-bromophenyl)-3-(2-chloroacetamido)pyrrolidine-1-carboxylate To a stirred mixture of tert-butyl 3-(4-bromophenyl)-3-hydroxypyrrolidine-1-carboxylate (5.00 g, 14.61 mmol) in 2-chloroacetonitrile (55 g, 0.73 mmol) was added dropwise sulfuric acid (3 mL, 14.61 mmol) at 0° C. The resulting mixture was stirred for 1 hr at ambient temperature and then concentrated under vacuum. The residue was added to the ice/water and the pH of the solution was adjusted to 8 with saturated $Na_2CO_3$. Methanol (10 mL) and di-tert-butyl dicarbonate (4.78 g, 21.92 mmol) were added to the mixture. The resulting mixture was stirred for 1 hr and then extracted with EtOAc (3×100 mL). The combined organic phases were dried over anhydrous $Na_2SO_4$, concentrated under vacuum. The residue was purified by silica gel column chromatography, eluted with EtOAc/PE (1/2) to afford 1.50 g (25%) of tert-butyl 3-(4-bromophenyl)-3-(2-chloroacetamido) pyrrolidine-1-carboxylate as a yellow solid: LCMS (ESI) calc'd for $C_{17}H_{22}BrClN_2O_3$ [M-56]$^+$: 363, found: 363.

Step C: Synthesis of (R)-tert-butyl 3-amino-3-(4-bromophenyl)pyrrolidine-1-carboxylate and (S)-tert-butyl 3-amino-3-(4-bromophenyl)pyrrolidine-1-carboxylate To a stirred mixture of tert-butyl 3-(4-bromophenyl)-3-(2-chloroacetamido) pyrrolidine-1-carboxylate (1.50 g, 3.59 mmol) in EtOH (10 mL) were added thiourea (2.73 g, 35.90 mmol), acetic acid (0.43 g, 7.18 mmol) at ambient temperature. The resulting mixture was stirred at 120° C. for 6 hr and then concentrated under vacuum. The residue was diluted with DCM (20 mL). The solids were filtered out and the filtrate was concentrated. The residue was purified by silica gel column chromatography, eluted with EtOAC/PE (5/1) to afford 0.30 g (25%) of tert-butyl 3-amino-3-(4-bromophenyl)pyrrolidine-1-carboxylate as a brown oil. The product was purified by Chiral-Prep-HPLC with the following conditions: Column, Chiralpak IA, 2×25 cm, 5 µm; Mobile phase: Hex and ethanol (hold 40.0% ethanol in 30 min); Detector: UV 254/220 nm. The collected fractions were concentrated to afford (R)-tert-butyl 3-amino-3-(4-bromophenyl)pyrrolidine-1-carboxylate (faster eluting, stereochemistry arbitrarily assigned): LCMS (ESI) calc'd for $C_{15}H_{21}BrN_2O_2$ [M+H]$^+$: 341, 343 (1:1), found: 341, 343 (1:1). $^1H$ NMR (300 MHz, $CDCl_3$): δ 7.50 (d, J=8.7 Hz, 2H), 7.33 (d, J=8.4 Hz, 2H), 3.85-7.51 (m, 4H), 2.28-2.25 (br, 2H), 1.46 (s, 9H) and (S)-tert-butyl 3-amino-3-(4-bromophenyl)pyrrolidine-1-carboxylate as a yellow solid (slower eluting, stereochemistry arbitrarily assigned): LCMS (ESI) calc'd for $C_{15}H_{21}BrN_2O_2$ [M+H]$^+$: 341, 343 (1:1), found: 341, 343 (1:1). $^1H$ NMR (300 MHz, $CDCl_3$): δ 7.49 (d, J=6.4 Hz, 2H), 7.32 (d, J=7.8 Hz, 2H), 3.78-3.52 (m, 4H), 2.26-2.21 (m, 2H), 1.46 (s, 9H).

REFERENCE EXAMPLE 32 tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)azetidine-1-carboxylate

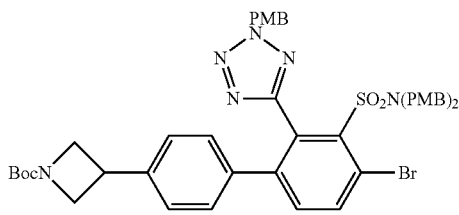

Step A: Synthesis of tert-butyl 3-(4-bromophenyl)azetidine-1-carboxylate

To a stirred solution of (4-bromophenyl)boronic acid (2.13 g, 10.60 mmol) in 2-Propanol (20 mL) was added tert-butyl-3-iodoazetidine-1-carboxylate (2.00 g, 7.06 mmol) at ambient temperature. To the mixture was added (1S,2S)-2-aminocyclohexanol (0.08 g, 0.71 mmol), nickel (II) iodide (0.22 g, 0.71 mmol) and sodium bis(trimethylsilyl)amide (7.06 mL, 1.0 mol/L) under nitrogen. After the resulting mixture was stirred for 30 min at ambient temperature, it was irradiated with microwave radiation at 80° C. for 1 hr. The reaction was quenched with water (25 mL), extracted with EtOAc (3×150 mL). The combined organic layers were washed with brine (2×100 mL), dried over anhydrous $Na_2SO_4$ and concentrated under vacuum. The residue was purified by silica gel chromatography, eluted with EtOAc/PE (1/10) to afford the title compound: LCMS (ESI) calc'd for $C_{14}H_{18}BrNO_2$ [M+H]$^+$: 312, 314 (1:1), found 312, 314 (1:1).

Step B: Synthesis of tert-butyl 3-(4-(4,4,5,5-tetramethyl-1,3,2-dioxaborolan-2-yl)phenyl)azetidine-1-carboxylate To a stirred mixture of 4,4,4',4',5,5,5',5'-octamethyl-2,2'-bi(1,3,2-dioxaborolane) (3.40 g, 13.45 mmol) and potassium acetate (3.30 g, 33.60 mmol) in DMF (35 mL) were added tert-butyl-3-(4-bromophenyl)azetidine-1-carboxylate (3.50 g, 11.20 mmol) and Pd(dppf)$Cl_2$ adduct $CH_2Cl_2$ (0.92 g, 1.12 mmol) at ambient temperature under nitrogen. The resulting mixture was degassed for two times under nitrogen and then stirred at 110° C. for 16 hr. The reaction was quenched with water (25 mL) and extracted with EtOAc (2×150 mL). The combined organic layers were washed with brine (2×100 mL), dried over anhydrous $Na_2SO_4$ and concentrated under vacuum. The residue was purified by silica gel chromatography, eluted with EtOAc/PE (1/10) to afford the title compound: LCMS (ESI) calc'd for $C_{20}H_{30}NO_4$ [M+H]$^+$: 360, found 360.

Step C: Synthesis of tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)azetidine-1-carboxylate A degassed solution of 6-bromo-3-iodo-N,N-bis-(4-methoxybenzyl)-2-(1-(4-methoxybenzyl)-1H-tetrazol-5-yl)benzenesulfonamide (1.60 g, 3.20 mmol), tert-butyl 3-(4-(4,4,5,5-tetramethyl-1,3,2-dioxaborolan-2-yl)phenyl)azetidine-1-carboxylate (1.30 g, 3.50 mmol), $Na_2CO_3$ (1.00 g, 9.50 mmol) and Pd(PPh$_3$)$_4$ (0.37 g, 0.32 mmol) in 1,4-dioxane (50 mL) and water (5 mL) was stirred at 80° C. for 16 hr under nitrogen. The resulting mixture was cooled down to ambient temperature and filtered. The filtrate was concentrated under vacuum. The residue was purified by silica gel chromatography, eluted with EtOAC/PE (1/2) to afford the title compound: LCMS (ESI) calc'd for $C_{45}H_{47}N_6O_7S$ [M+H]$^+$: 895, 897 (1:1), found 895, 897 (1:1). $^1H$ NMR (400 MHz, $CDCl_3$): δ 8.08-8.00 (m, 1H), 7.43 (d, J=8.4 Hz, 2H), 7.07 (d, J=8.0 Hz, 1H), 7.02 (d, J=8.8 Hz, 3H), 6.88-6.80 (m, 9H), 6.79-6.71 (m, 2H), 5.19-5.15 (m, 1H), 4.92-4.88 (m, 1H), 4.82 (d, J=9.2 Hz, 1H), 4.34-4.30 (m, 2H), 4.14-4.10 (m, 1H), 3.99-3.91 (m, 2H), 3.89-3.80 (m, 2H), 3.78 (s, 9H), 3.70-3.60 (m, 1H), 1.49 (s, 9H).

REFERENCE EXAMPLE 33 tert-butyl ((1r,4r)-4-(iodomethyl)cyclohexyl)methylcarbamate

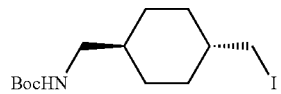 [SMILES: CC(C)(C)OC(=O)NC[C@H]1CC[C@H](CI)CC1]

Step A: Synthesis of tert-butyl ((1r,4r)-4-(hydroxymethyl)cyclohexyl)methylcarbamate Borane (7.77 mL, 15.5 mmol) was added dropwise to a stirred solution of (1r,4r)-4-(((tert-butoxycarbonyl)amino)methyl)cyclohexanecarboxylic acid (2.0 g, 7.77 mmol) in THF (20 ml) at 0° C. After the reaction mixture was stirred for 6 hr at ambient temperature, it was quenched with water (20 mL) and extracted with EtOAc (2×40 mL). The combined organic layers were washed brine (2×30 mL), dried over anhydrous $Na_2SO_4$ and concentrated under vacuum to afford the title compound: $^1$H NMR (400 MHz, $CDCl_3$) δ 4.60-4.50 (brs, 1H), 3.46 (d, J=6.4 Hz, 2H), 3.01-2.98 (m, 2H), 1.90-1.82 (m, 4H), 1.81-1.80 (m, 1H), 1.46 (brs, 9H), 1.45-1.42 (m, 2H), 1.02-0.97(m, 4H).

Step B: Synthesis of tert-butyl ((1r,4r)-4-(iodomethyl)cyclohexyl)methylcarbamate $I_2$ (2.253 g, 8.88 mmol) in 10 ml THF was added dropwise to a stirred mixture of tert-butyl (((1r,4r)-4-(hydroxymethyl)cyclohexyl)methyl)carbamate (1.8 g, 7.40 mmol), triphenylphosphine (2.328 g, 8.88 mmol) and 1H-imidazole (0.604 g, 8.88 mmol) in THF (30 ml) at 0° C. The reaction mixture was stirred 12 hr at ambient temperature and then quenched with water (50 mL) and extracted with EtOAc (3×50 mL). The combined organic layers were washed with $Na_2SO_3$ (aq.) (2×50 mL), dried over anhydrous $Na_2SO_4$ and concentrated under vacuum. The residue was purified by silica gel chromatography, eluted with EtOAc/PE (1/5) to give the title compound: $^1$H NMR (400 MHz, $CDCl_3$) δ 4.70-4.60 (m, 1H), 3.10 (dd, J=6.4 Hz, 2H), 2.99 (dd, J=6.4 Hz, 2H), 1.94-1.92 (m, 2H), 1.80-1.78 (m, 2H), 1.45 (brs, 9H), 1.42-1.39 (m, 2H), 1.04-0.97 (m,4H).

REFERENCE EXAMPLE 34 tert-butyl (4-(iodomethyl)cyclohexyl)methylcarbamate

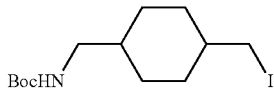 [SMILES: CC(C)(C)OC(=O)NCC1CCC(CI)CC1]

Step A: Synthesis of tert-butyl (4-(iodomethyl)cyclohexyl)methylcarbamate

Borane (7.77 mL, 15.5 mmol) was added dropwise to a stirred solution of 4-(((tert-butoxycarbonyl)amino)methyl)cyclohexanecarboxylic acid (2.0 g, 7.77 mmol) in THF (20 ml) at 0° C. To the reaction mixture was stirred for 6 hr at ambient temperature and then quenched with water (20 mL) and extracted with EtOAc (2×40 mL). The combined organic layers were washed brine (2×30 mL), dried over anhydrous $Na_2SO_4$ and concentrated under vacuum to afford the title compound: $^1$H NMR (400 MHz, $CDCl_3$) δ 4.70-4.60 (brs, 1H), 3.47 (dd, J=6.0 Hz, 2H), 3.01-2.98 (m, 2H), 1.90-1.80 (m, 4H), 1.71-1.69 (m, 1H), 1.46 (brs, 9H), 1.43-1.40 (m, 2H), 1.02-0.97 (m, 4H).

Step B: Synthesis of tert-butyl (4-(iodomethyl)cyclohexyl)methylcarbamate $I_2$ (2.253 g, 8.88 mmol) in 10 ml THF was added dropwise to a stirred mixture of tert-butyl (((1r,4r)-4-(hydroxymethyl)cyclohexyl)methyl)carbamate (1.8 g, 7.40 mmol), triphenylphosphine (2.328 g, 8.88 mmol) and 1H-imidazole (0.604 g, 8.88 mmol) in THF (30 ml) at 0° C. The reaction mixture was stirred 12 hr at ambient temperature and then quenched with water (50 mL) and extracted with EtOAc (3×50 mL). The combined organic layers were washed with $Na_2SO_3$ (aq.) (2×50 mL), dried over anhydrous $Na_2SO_4$ and concentrated under vacuum. The residue was purified by silica gel chromatography, eluted with EtOAc/PE (1/5) to give the title compound: $^1$H NMR (400 MHz, $CDCl_3$) δ 4.70-4.60 (brs, 1H), 3.10 (dd, J=6.4 Hz, 2H), 2.99 (dd, J=6.4 Hz, 2H), 1.94-1.92 (m, 2H), 1.80-1.78 (m, 2H), 1.45 (brs, 9H), 1.42-1.40 (m, 2H), 1.04-0.97 (m, 4H).

REFERENCE EXAMPLE 35 tert-butyl (1s,4s)-4-(iodomethyl)cyclohexylcarbamate

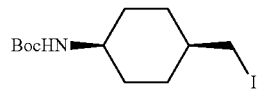 [SMILES: CC(C)(C)OC(=O)N[C@H]1CC[C@@H](CI)CC1]

Step A: Synthesis of tert-butyl (1s,4s)-4-(hydroxymethyl)cyclohexylcarbamate

Borane (8.22 mL, 16.4 mmol) was added dropwise to a stirred solution of (1s,4s)-4-((tert-butoxycarbonyl)amino)cyclohexanecarboxylic acid (2.0 g, 8.22 mmol) in THF (20 ml) at 0° C. After the reaction mixture was stirred for 6 hr at room temperature, it was quenched with water (20 mL) and extracted with EtOAc (2×40 mL). The combined organic layers were washed brine (2×30 mL), dried over anhydrous $Na_2SO_4$ and concentrated under vacuum to afford the title compound which was used in the next step directly.

Step B: Synthesis of tert-butyl (1s,4s)-4-(iodomethyl)cyclohexylcarbamate $I_2$ (2.125 g, 8.37 mmol) in 10 ml THF) was added dropwise to a stirred mixture of tert-butyl ((1s,4s)-4-(hydroxymethyl)cyclohexyl)carbamate (1.6 g, 6.98 mmol), triphenylphosphine (2.196 g, 8.37 mmol) and 1H-imidazole (0.570 g, 8.37 mmol) in THF (30 ml) at 0° C. The resulting mixture was stirred 12 hr at ambient temperature and then quenched with water (50 mL) and extracted with ethyl acacate (3×50 mL). The combined organic layers was washed with $Na_2SO_3$ (aq.) (2×50 mL), dried over anhydrous $Na_2SO_4$ and concentrated under vacuum. The residue was purified by silica gel chromatography, eluted with EtOAc/PE (1/5) to the title compound: $^1$H NMR (400 MHz, $CDCl_3$) δ 4.70-4.60 (brs, 1H), 3.80-3.70 (brs, 1H), 3.40-3.30 (m, 1H), 3.16 (dd, J=6.0 Hz, 1H), 1.98-1.80 (m, 1H), 1.80-1.70 (m, 2H), 1.60-1.50 (m, 4H), 1.47 (brs, 9H), 1.34-1.30 (m, 2H).

REFERENCE EXAMPLE 36 tert-butyl 4-(2-iodoethyl)cyclohexylcarbamate

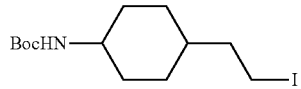 [SMILES: CC(C)(C)OC(=O)NC1CCC(CCI)CC1]

Step A: Synthesis of tert-butyl 4-(2-hydroxyethyl)cyclohexylcarbamate

Borane (7.77 mL, 15.5 mmol) was added dropwise to a stirred solution of 2-(4-((tert-butoxycarbonyl)amino)cyclohexyl)acetic acid (2.0 g, 7.8 mmol) in THF (20 mL) at 0° C.

The resulting mixture was stirred for 6 hr at room temperature and then quenched with water (20 mL) and extracted with EtOAC (2×40 mL). The combined organic layers was washed brine (2×30 mL), dried over anhydrous sodium sulfate and filtered. The filtrate was concentrated under vacuum to afford the title compound, which was used in the next step directly.

Step B: Synthesis of tert-butyl (4-(2-iodoethyl)cyclohexyl) carbamate $I_2$ (2.128 g, 8.38 mmol)(in 10 ml THF) was added dropwise to a stirred mixture of tert-butyl (4-(2-hydroxyethyl)cyclohexyl)carbamate (1.7 g, 6.99 mmol), triphenylphosphine (2.199 g, 8.38 mmol) and 1H-imidazole (0.571 g, 8.38 mmol) in THF (30 ml) at 0° C. The reaction mixture was stirred 12 hr at ambient temperature and then quenched with water (50 mL) and extracted with ethyl acetate (3×50 mL). The combined organic layers were washed with $Na_2SO_3$ (aq.) (2×50 mL), dried over anhydrous sodium sulfate and concentrated under vacuum. The residue was purified by silica gel chromatography, eluted with EtOAc/petroleum ether (1/5) to give the title compound: $^1$H NMR (400 MHz, $CDCl_3$) δ 4.40-4.30 (brs, 1H), 3.40-3.30 (brs, 1H), 3.24-3.20 (m, 2H), 2.08-1.95 (m, 2H), 1.84-1.73 (m, 4H), 1.70-1.1.60 (m, 2H), 1.47 (brs, 9H), 1.40-1.30 (m, 1H), 1.10-0.90 (m, 2H).

REFERENCE EXAMPLE 37

N,N-bis(4-methoxybenzyl)-2-(1-(4-methoxybenzyl)-1H-tetrazol-5-yl)-3-(4-oxocyclohexyl)-6-(trifluoromethyl)benzenesulfonamide

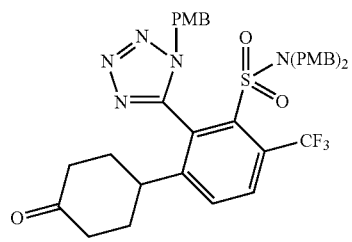

Step A: 4'-hydroxy-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide The title compound was prepared by coupling of 3-bromo-N,N-bis(4-methoxybenzyl)-2-(1-(4-methoxybenzyl)-1H-tetrazol-5-yl)-6-(trifluoromethyl)benzenesulfonamide and 4-(4,4,5,5-tetramethyl-1,3,2-dioxaborolan-2-yl)cyclohex-3-en-1-ol in an analogous fashion as shown in step A of REFERENCE EXAMPLE 18. LC/MS: Cal'd mass: 749.25; Observed mass 750.62 (M+H)+.

Step B: 3-(4-hydroxycyclohexyl)-N,N-bis(4-methoxybenzyl)-2-(1-(4-methoxybenzyl)-1H-tetrazol-5-yl)-6-(trifluoromethyl)benzenesulfonamide 4'-hydroxy-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide (2.45 g, 3.27 mmol) was stirred with palladium hydroxide on carbon (2.29 g, 3.27 mmol) under $H_2$ (balloon) overnight. The reaction mixture was filtered and concentrated to give the title compound. LC/MS: Cal'd mass: 751.27; Observed mass 752.59 (M+H)+.

Step C: N,N-bis(4-methoxybenzyl)-2-(1-(4-methoxybenzyl)-1H-tetrazol-5-yl)-3-(4-oxocyclohexyl)-6-(trifluoromethyl)benzenesulfonamide To a solution of 3-(4-hydroxycyclohexyl)-N,N-bis(4-methoxybenzyl)-2-(1-(4-methoxybenzyl)-1H-tetrazol-5-yl)-6-(trifluoromethyl)benzenesulfonamide (200 mg, 0.266 mmol) in $CH_2Cl_2$ (2660 μl), was added NMO (46.7 mg, 0.399 mmol) and 4A molecular sieves (160 mg). Stirred at rt under $N_2$ for 0.5 hr, then added TPAP (9.35 mg, 0.027 mmol). The mixture was stirred at rt under $N_2$ for 1.5 hr. LC-MS showed the completion of the reaction. Filtered and filtrates were concentrated and purified by column chromatography (100% hexane to 70% EtOAc/Hexane) to give the title compound. LC/MS: Cal'd mass: 749.25; Observed mass 750.57 (M+H)+.

REFERENCE EXAMPLE 38

3-(2-(6-Amino-5-(methoxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide and 3-(2-(6-amino-5-(methoxymethyl)pyridin-3-yl)ethyl)-N,N-bis(4-methoxybenzyl)-2-(1-(4-methoxybenzyl)-1H-tetrazol-5-yl)-6-(trifluoromethyl)benzenesulfonamide

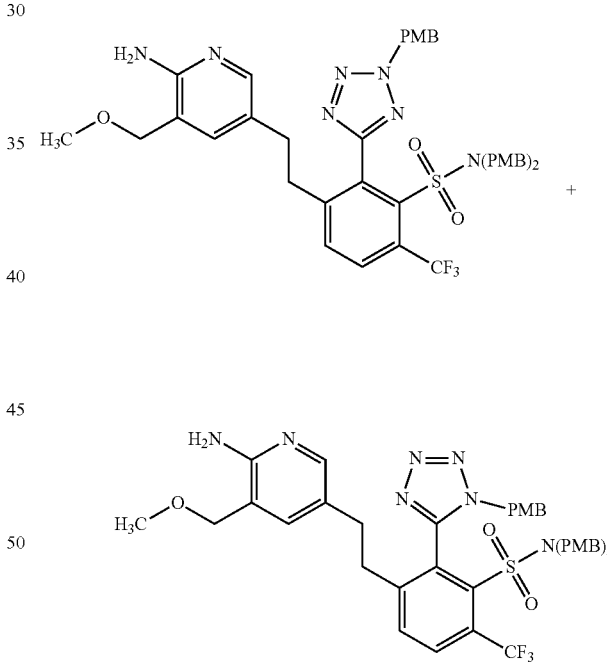

3-((6-Amino-5-(hydroxymethyl)pyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)-6-(trifluoromethyl)benzenesulfonamide (100 mg, 0.124 mmol) was taken into Ethanol (1244 μl) and iodomethane (46.7 μl, 0.746 mmol) was added and stirred for 16 hr under a nitrogen atmosphere. The solution was filtered and concentrated under reduced pressure and used without further purification. LC/MS [M+H]+: 818.55.

REFERENCE EXAMPLE 39

3-(2-(5-Amino-6-(aminomethyl)pyridin-3-yl)ethyl)-N,N-bis(4-methoxybenzyl)-2-(1-(4-methoxybenzyl)-1H-tetrazol-5-yl)-6-(trifluoromethyl)benzenesulfonamide and 3-(2-(5-amino-6-(aminomethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide

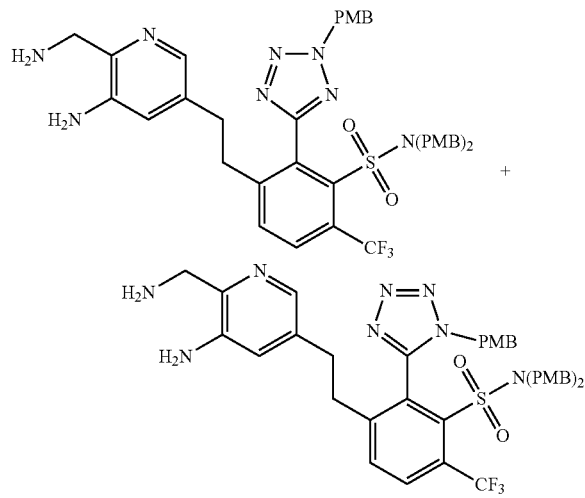

Step A: 3-((6-Cyano-5-nitropyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-cyano-5-nitropyridin-3-yl)ethynyl)-N,N-bis(4-methoxybenzyl)-2-(1-(4-methoxybenzyl)-1H-tetrazol-5-yl)-6-(trifluoromethyl)benzenesulfonamide To a solution of 3-ethynyl-N,N-bis(4-methoxybenzyl)-2-(2-(4-methoxybenzyl)-2H-tetrazol-5-yl)-6-(trifluoromethyl)benzenesulfonamide and 3-ethynyl-N,N-bis(4-methoxybenzyl)-2-(1-(4-methoxybenzyl)-1H-tetrazol-5-yl)-6-(trifluoromethyl)benzenesulfonamide (200 mg, 0.295 mmol) and 5-bromo-3-nitropicolinonitrile (100 mg, 0.439 mmol) was treated following the procedure from 3-((6-Amino-5-(hydroxymethyl)pyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)-6-(trifluoromethyl)benzenesulfonamide above using Pd(PPh$_3$)$_4$, TEA, and CuI in THF and stirring for 4 hr at 80° C. LC/MS [M+H]$^+$: 825.61.

Step B: 3-(2-(5-Amino-6-(aminomethyl)pyridin-3-yl)ethyl)-N,N-bis(4-methoxybenzyl)-2-(1-(4-methoxybenzyl)-1H-tetrazol-5-yl)-6-(trifluoromethyl)benzenesulfonamide and 3-(2-(5-amino-6-(aminomethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide A mixture of 3-((6-cyano-5-nitropyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-cyano-5-nitropyridin-3-yl)ethynyl)-N,N-bis(4-methoxybenzyl)-2-(1-(4-methoxybenzyl)-1H-tetrazol-5-yl)-6-(trifluoromethyl)benzenesulfonamide (243 mg, 0.295 mmol) and platinum(IV) oxide (0.475 mmol) in AcOH (5 mL) was stirred under a hydrogen atmosphere for 16 hr. The solution was filtered through celite and then concentrated and the title compounds and used without further purification. LC/MS [M+H]$^+$: 803.

REFERENCE EXAMPLE 40

5-(3-(N,N-Bis(4-methoxybenzyl)sulfamoyl)-2-(1-(4-methoxybenzyl)-1H-tetrazol-5-yl)-4-(trifluoromethyl)phenyl)quinoline 1-oxide and 5-(3-(N,N-bis(4-methoxybenzyl)sulfamoyl)-2-(2-(4-methoxybenzyl)-2H-tetrazol-5-yl)-4-(trifluoromethyl)phenyl)quinoline 1-oxide

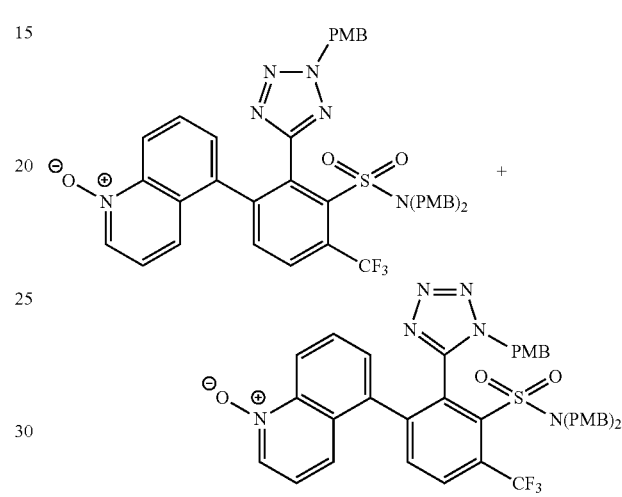

N,N-Bis(4-methoxybenzyl)-2-(1-(4-methoxybenzyl)-1H-tetrazol-5-yl)-3-(quinolin-5-yl)-6-(trifluoromethyl)benzenesulfonamide and N,N-bis(4-methoxybenzyl)-2-(2-(4-methoxybenzyl)-2H-tetrazol-5-yl)-3-(quinolin-5-yl)-6-(trifluoromethyl)benzenesulfonamide (300 mg, 0.384 mmol) was dissolved in dichloromethane (10 mL) and mCPBA (172 mg, 0.768 mmol) was added and stirred for 3 hr. The solution was diluted with EtOAc (50 mL) and washed with 1N NaOH (10 mL), dried over MgSO$_4$, and concentrated under reduced pressure. Purified by silica gel chromatography to isolate the title compounds. LC/MS [M+H]$^+$: 797.33.

REFERENCE EXAMPLE 41

3-(Isoquinolin-5-yl)-N,N-bis(4-methoxybenzyl)-2-(1-(4-methoxybenzyl)-1H-tetrazol-5-yl)-6-(trifluoromethyl)benzenesulfonamide and 3-(isoquinolin-5-yl)-N,N-bis(4-methoxybenzyl)-2-(2-(4-methoxybenzyl)-2H-tetrazol-5-yl)-6-(trifluoromethyl)benzenesulfonamide

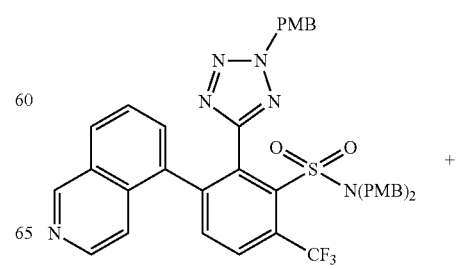

-continued

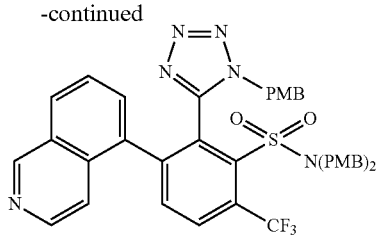

A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl) benzenesulfonamide (1000 mg, 1.365 mmol) and isoquinolin-5-ylboronic acid (283 mg, 1.638 mmol), Na$_2$CO$_3$ (723 mg, 6.83 mmol) and PdCl$_2$(dppf)-CH$_2$Cl$_2$Adduct (111 mg, 0.137 mmol). The vial was sealed, degassed, and filled with Dioxane (4095 µL) and Water (1365 µL). The resulting mixture was heated at 175° C. for 15 min in the microwave. The solution was filtered and concentrated and loaded onto a Teledyne ISCO gold silica 120 g column. Fractions containing product were combined and concentrated. LC/MS [M+H]$^+$: 781.42.

REFERENCE EXAMPLE 42

5-(3-(N,N-Bis(4-methoxybenzyl)sulfamoyl)-2-(1-(4-methoxybenzyl)-1H-tetrazol-5-yl)-4-(trifluoromethyl)phenyl)isoquinoline 2-oxide and 5-(3-(N,N-bis(4-methoxybenzyl)sulfamoyl)-2-(2-(4-methoxybenzyl)-2H-tetrazol-5-yl)-4-(trifluoromethyl)phenyl)isoquinoline 2-oxide

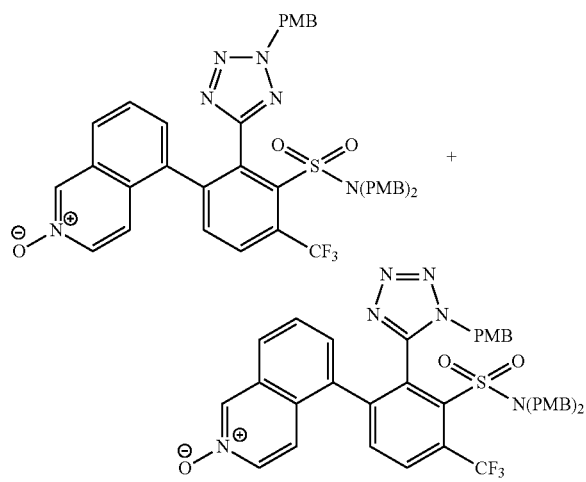

3-(Isoquinolin-5-yl)-N,N-bis(4-methoxybenzyl)-2-(1-(4-methoxybenzyl)-1H-tetrazol-5-yl)-6-(trifluoromethyl)benzenesulfonamide and 3-(isoquinolin-5-yl)-N,N-bis(4-methoxybenzyl)-2-(2-(4-methoxybenzyl)-2H-tetrazol-5-yl)-6-(trifluoromethyl)benzenesulfonamide (120 mg, 0.154 mmol) was dissolved in CH$_2$Cl$_2$ (2 mL) and mCPBA (68.9 mg, 0.307 mmol) was added and stirred for 3 hr. The solution was diluted with EtOAc (50 mL) and washed with 1N NaOH (10 mL), dried (MgSO$_4$), and concentrated under reduced pressure. LC/MS [M+H]$^+$: 797.42.

REFERENCE EXAMPLE 43

N,N-Bis(4-methoxybenzyl)-2-(2-(4-methoxybenzyl)-2H-tetrazol-5-yl)-3-(1,2,3,4-tetrahydroisoquinolin-5-yl)-6-(trifluoromethyl)benzenesulfonamide and N,N-bis(4-methoxybenzyl)-2-(1-(4-methoxybenzyl)-1H-tetrazol-5-yl)-3-(1,2,3,4-tetrahydroisoquinolin-5-yl)-6-(trifluoromethyl)benzenesulfonamide

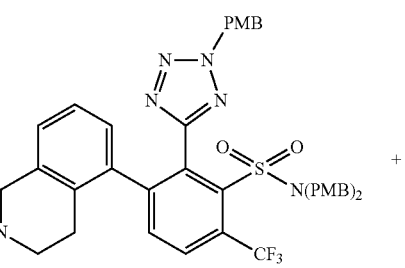

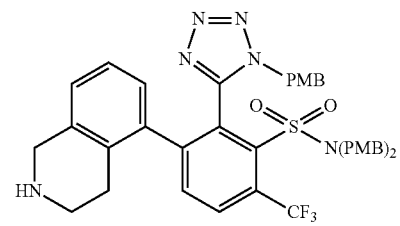

3-(Isoquinolin-5-yl)-N,N-bis(4-methoxybenzyl)-2-(1-(4-methoxybenzyl)-1H-tetrazol-5-yl)-6-(trifluoromethyl)benzenesulfonamide and 3-(isoquinolin-5-yl)-N,N-bis(4-methoxybenzyl)-2-(2-(4-methoxybenzyl)-2H-tetrazol-5-yl)-6-(trifluoromethyl) benzenesulfonamide (370 mg, 0.413 mmol) and platinum(IV) oxide (46.9 mg, 0.207 mmol) in AcOH (20 mL) was stirred under 50 psi of hydrogen for 16 hr. The catalyst was filtered off and the filtrate was concentrated and used without further purification to isolate the title compounds. LC/MS [M+H]$^+$: 785.57.

REFERENCE EXAMPLE 44

N,N-Bis(4-methoxybenzyl)-2-(1-(4-methoxybenzyl)-1H-tetrazol-5-yl)-3-(1,2,3,4-tetrahydroquinolin-5-yl)-6-(trifluoromethyl)benzenesulfonamide and N,N-bis(4-methoxybenzyl)-2-(2-(4-methoxybenzyl)-2H-tetrazol-5-yl)-3-(1,2,3,4-tetrahydroquinolin-5-yl)-6-(trifluoromethyl)benzenesulfonamide

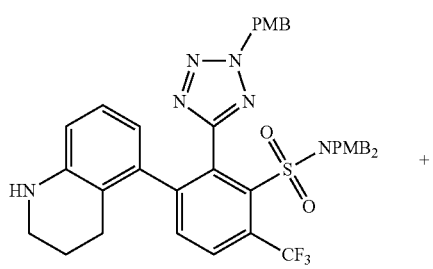

-continued

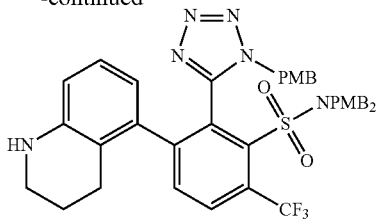

To a solution of N,N-bis(4-methoxybenzyl)-2-(1-(4-methoxybenzyl)-1H-tetrazol-5-yl)-3-(quinolin-5-yl)-6-(trifluoromethyl)benzenesulfonamide and N,N-bis(4-methoxybenzyl)-2-(2-(4-methoxybenzyl)-2H-tetrazol-5-yl)-3-(quinolin-5-yl)-6-(trifluoromethyl) benzenesulfonamide (100 mg, 0.112 mmol) was combined with platinum(IV) oxide in AcOH under 50 psi of hydrogen according to the immediately preceding Reference Example 43 to yield N,N-bis(4-methoxybenzyl)-2-(1-(4-methoxybenzyl)-1H-tetrazol-5-yl)-3-(1,2,3,4-tetrahydroquinolin-5-yl)-6-(trifluoromethyl)benzenesulfonamide and N,N-bis(4-methoxybenzyl)-2-(2-(4-methoxybenzyl)-2H-tetrazol-5-yl)-3-(1,2,3,4-tetrahydroquinolin-5-yl)-6-(trifluoromethyl) benzenesulfonamide.

REFERENCE EXAMPLE 45

N,N-Bis(4-methoxybenzyl)-2-(1-(4-methoxybenzyl)-1H-tetrazol-5-yl)-3-(5,6,7,8-tetrahydroquinolin-5-yl)benzenesulfonamide and N,N-bis(4-methoxybenzyl)-2-(2-(4-methoxybenzyl)-2H-tetrazol-5-yl)-3-(5,6,7,8-tetrahydroquinolin-5-yl)benzenesulfonamide

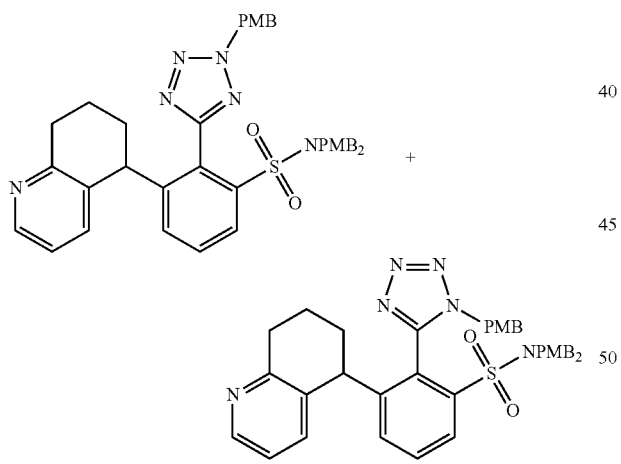

Step A: 3-(7,8-Dihydroquinolin-5-yl)-N,N-bis(4-methoxybenzyl)-2-(1-(4-methoxybenzyl)-1H-tetrazol-5-yl)benzenesulfonamide and 3-(7,8-dihydroquinolin-5-yl)-N,N-bis(4-methoxybenzyl)-2-(2-(4-methoxybenzyl)-2H-tetrazol-5-yl)benzenesulfonamide To a mixture of (3-(N,N-bis(4-methoxybenzyl)sulfamoyl)-2-(1-(4-methoxybenzyl)-1H-tetrazol-5-yl)phenyl)boronic acid and (3-(N,N-bis(4-methoxybenzyl)sulfamoyl)-2-(2-(4-methoxybenzyl)-2H-tetrazol-5-yl)phenyl)boronic acid (1.5 g, 2.383 mmol) and 7,8-dihydroquinolin-5-yl trifluoromethanesulfonate (0.998 g, 3.57 mmol), a solution of 7,8-dihydroquinolin-5-yltrifluoromethanesulfonate (0.998 g, 3.57 mmol), 1,1'-bis(di-tert-butylphosphino) ferrocene palladium dichloride (0.078 g, 0.119 mmol), (3-(N,N-bis(4-methoxybenzyl)sulfamoyl)-2-(1-(4-methoxybenzyl)-1H-tetrazol-5-yl)phenyl)boronic acid (1.5 g, 2.4 mmol) and Potassium Carbonate (9.53 mmol) in THF (50 mL) was stirred at rt for two days. The mixture was diluted with EtOAc, washed with brine, dried over MgSO$_4$, and concentrated. The residue was purified by ISCO column (0-50% EtOAc in hexane). LC/MS [M+H]$^+$: 715.65.

Step B: N,N-Bis(4-methoxybenzyl)-2-(1-(4-methoxybenzyl)-1H-tetrazol-5-yl)-3-(5,6,7,8-tetrahydroquinolin-5-yl)benzenesulfonamide and N,N-bis(4-methoxybenzyl)-2-(2-(4-methoxybenzyl)-2H-tetrazol-5-yl)-3-(5,6,7,8-tetrahydroquinolin-5-yl)benzenesulfonamide A solution of 3-(7,8-dihydroquinolin-5-yl)-N,N-bis(4-methoxybenzyl)-2-(1-(4-methoxybenzyl)-1H-tetrazol-5-yl)benzenesulfonamide and 3-(7,8-dihydroquinolin-5-yl)-N,N-bis(4-methoxybenzyl)-2-(2-(4-methoxybenzyl)-2H-tetrazol-5-yl)benzenesulfonamide (120 mg, 0.168 mmol) in a mixture solvent of DCM (20 mL) and MeOH (20 mL) was hydrogenated under H$_2$ atmosphere of a balloon at rt overnight. The catalyst was filtered off through a celite pad. The filtration was concentrated. LC/MS [M+H]$^+$: 717.70.

REFERENCE EXAMPLE 46

5-(3-(N,N-Bis(4-methoxybenzyl)sulfamoyl)-2-(2-(4-methoxybenzyl)-2H-tetrazol-5-yl)-4-(trifluoromethyl)phenyl)-2,2-dimethyl-1,2,3,4-tetrahydroisoquinolin-2-ium and 5-(3-(N,N-bis(4-methoxybenzyl)sulfamoyl)-2-(1-(4-methoxybenzyl)-1H-tetrazol-5-yl)-4-(trifluoromethyl)phenyl)-2,2-dimethyl-1,2,3,4-tetrahydroisoquinolin-2-ium

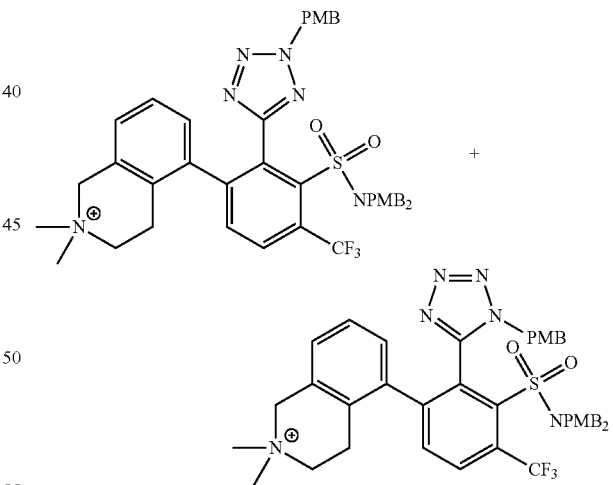

N,N-bis(4-methoxybenzyl)-2-(2-(4-methoxybenzyl)-2H-tetrazol-5-yl)-3-(1,2,3,4-tetrahydroisoquinolin-5-yl)-6-(trifluoromethyl)benzenesulfonamide and N,N-bis(4-methoxybenzyl)-2-(1-(4-methoxybenzyl)-1H-tetrazol-5-yl)-3-(1,2,3,4-tetrahydroisoquinolin-5-yl)-6-(trifluoromethyl) benzenesulfonamide (100 mg, 0.127 mmol) in Ethanol (1274 μL) was treated with Iodomethane (7.17 μl, 0.115 mmol) and K$_2$CO$_3$ (38.7 mg, 0.280 mmol) and stirred overnight at room temperature. The reaction mixture was filtered and concentrated under reduced pressure. LC/MS [M+H]$^+$: 813.48.

REFERENCE EXAMPLE 47

N,N-Bis(4-methoxybenzyl)-2-(1-(4-methoxybenzyl)-1H-tetrazol-5-yl)-3-(3-oxo-2,3-dihydrobenzofuran-7-yl)benzenesulfonamide and N,N-bis(4-methoxybenzyl)-2-(2-(4-methoxybenzyl)-2H-tetrazol-5-yl)-3-(3-oxo-2,3-dihydrobenzofuran-7-yl)benzenesulfonamide

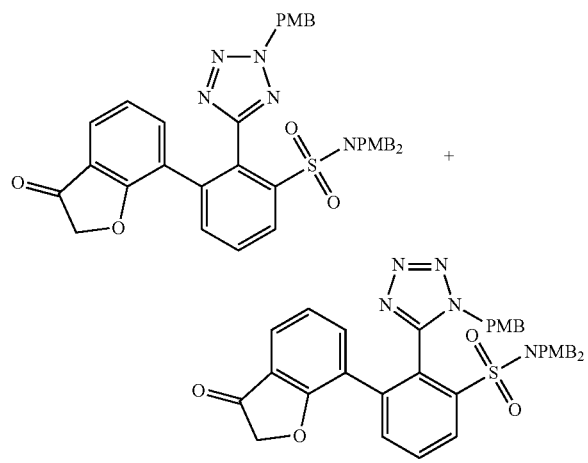

A mixture of N,N-bis(4-methoxybenzyl)-2-(1-(4-methoxybenzyl)-1H-tetrazol-5-yl)-3-(4,4,5,5-tetramethyl-1,3,2-dioxaborolan-2-yl)benzenesulfonamide and N,N-bis(4-methoxybenzyl)-2-(2-(4-methoxybenzyl)-2H-tetrazol-5-yl)-3-(4,4,5,5-tetramethyl-1,3,2-dioxaborolan-2-yl)benzenesulfonamide (1200 mg, 1.686 mmol) with 7-bromobenzofuran-3(2H)-one (395 mg, 1.855 mmol), $Na_2CO_3$ (894 mg, 8.43 mmol) and Pd $dppf_2$ $CH_2Cl_2$ adduct (catalytic) was sealed in a microwave vial, degassed, and filled with Dioxane (4216 µL) and Water (1405 µL). Then the mixture was heated at 120° C. for 40 min, concentrated and purified by MPLC. LC/MS $[M+H]^+$: 718.36.

REFERENCE EXAMPLE 48

3-(3-Hydroxy-2,3-dihydrobenzofuran-7-yl)-N,N-bis(4-methoxybenzyl)-2-(1-(4-methoxybenzyl)-1H-tetrazol-5-yl)benzenesulfonamide and 3-(3-hydroxy-2,3-dihydrobenzofuran-7-yl)-N,N-bis(4-methoxybenzyl)-2-(2-(4-methoxybenzyl)-2H-tetrazol-5-yl)benzenesulfonamide

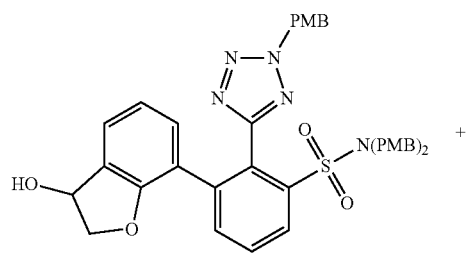

+

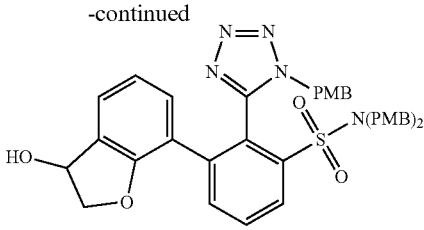

To a mixture of N,N-bis(4-methoxybenzyl)-2-(1-(4-methoxybenzyl)-1H-tetrazol-5-yl)-3-(3-oxo-2,3-dihydrobenzofuran-7-yl)benzenesulfonamide and N,N-bis(4-methoxybenzyl)-2-(2-(4-methoxybenzyl)-2H-tetrazol-5-yl)-3-(3-oxo-2,3-dihydrobenzofuran-7-yl)benzenesulfonamide (1000 mg, 1.393 mmol) was dissolved in THF (4644 µL) and sodium borohydride (105 mg, 2.79 mmol) was added to the solution and the reaction was stirred under nitrogen for 16 hr. Water (10 mL) was added slowly to the reaction mixture. The aqueous was extracted with EtOAc (3×30 mL). Organic was dried and concentrated and used without further purification to yield title compounds. LC/MS $[M+H]^+$: 720.42.

REFERENCE EXAMPLE 49

3-(5,6-Diaminopyridin-3-yl)-N,N-bis(4-methoxybenzyl)-2-(1-(4-methoxybenzyl)-1H-tetrazol-5-yl)benzenesulfonamide and 3-(5,6-diaminopyridin-3-yl)-N,N-bis(4-methoxybenzyl)-2-(2-(4-methoxybenzyl)-2H-tetrazol-5-yl)benzenesulfonamide Step A: 3-(6-Amino-5-nitropyridin-3-yl)-N,N-bis(4-methoxybenzyl)-2-(1-(4-methoxybenzyl)-1H-tetrazol-5-yl)benzenesulfonamide and 3-(6-amino-5-nitropyridin-3-yl)-N,N-bis(4-methoxybenzyl)-2-(2-(4-methoxybenzyl)-2H-tetrazol-5-yl)benzenesulfonamide To a mixture of N,N-bis(4-methoxybenzyl)-2-(1-(4-methoxybenzyl)-1H-tetrazol-5-yl)-3-(4,4,5,5-tetramethyl-1,3,2-dioxaborolan-2-yl)benzenesulfonamide and N,N-bis(4-methoxybenzyl)-2-(2-(4-methoxybenzyl)-2H-tetrazol-5-yl)-3-(4,4,5,5-tetramethyl-1,3,2-dioxaborolan-2-yl)benzenesulfonamide (300 mg, 0.422 mmol) and 5-iodo-3-nitro-pyridin-2-amine (134 mg, 0.506 mmol) was added $Na_2CO_3$ (223 mg, 2.108 mmol) and $PdCl_2$(dppf)-$CH_2Cl_2$ Adduct (34.4 mg, 0.042 mmol). The vial was sealed, degassed, and filled with Dioxane (3162 μL) and Water (1054 μL). Then the sample was microwaved at 120° C. for 40 minutes. The solution was filtered through celite and the material was taken into EtOAc (20 mL) and washed with water (10 mL), brine (10 mL), and dried (MgSO$_4$). LC/MS [M+H]$^+$: 723.50.

Step B: 3-(5,6-Diaminopyridin-3-yl)-N,N-bis(4-methoxybenzyl)-2-(1-(4-methoxybenzyl)-1H-tetrazol-5-yl)benzenesulfonamide and 3-(5,6-diaminopyridin-3-yl)-N,N-bis(4-methoxybenzyl)-2-(2-(4-methoxybenzyl)-2H-tetrazol-5-yl) benzenesulfonamide 3-(6-Amino-5-nitropyridin-3-yl)-N,N-bis(4-methoxybenzyl)-2-(1-(4-methoxybenzyl)-1H-tetrazol-5-yl)benzenesulfonamide and 3-(6-amino-5-nitropyridin-3-yl)-N,N-bis(4-methoxybenzyl)-2-(2-(4-methoxybenzyl)-2H-tetrazol-5-yl) benzenesulfonamide (305 mg, 0.422 mmol) was dissolved in ethyl acetate (5 mL) and Pd—C (13.5 mg, 0.127 mmol) was introduced into the system as well as HCl (4M, 0.5 mL) in dioxanes. The system was degassed three times then a balloon of hydrogen was added. The solution was stirred 4 hr and then filtered through celite. The resulting solution was concentrated to isolate the title compounds. LC/MS [M+H]$^+$: 693.47.

REFERENCE EXAMPLE 50

3-(2-(4-Guanidinocyclohexyl)ethyl)-N,N-bis(4-methoxybenzyl)-2-(1-(4-methoxybenzyl)-1H-tetrazol-5-yl)-6-(trifluoromethyl)benzenesulfonamide and 3-(2-(4-guanidinocyclohexyl)ethyl)-N,N-bis(4-methoxybenzyl)-2-(2-(4-methoxybenzyl)-2H-tetrazol-5-yl)-6-(trifluoromethyl)benzenesulfonamide

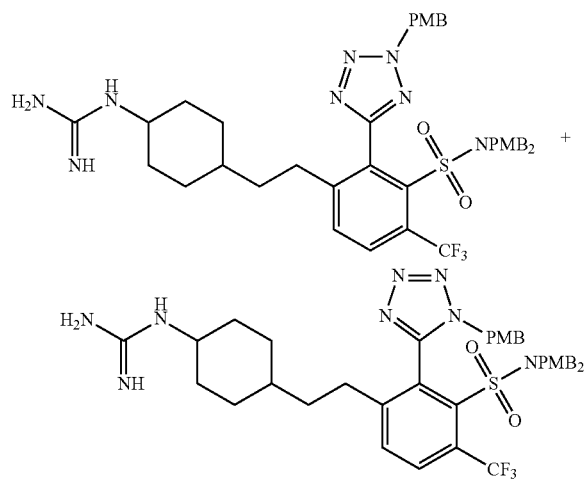

Step A: 4-((tert-Butoxycarbonyl)amino)cyclohex-1-en-1-yl trifluoromethanesulfonate tert-Butyl (4-oxocyclohexyl)carbamate (5.00 g, 23.4 mmol) was dissolved in tetrahydrofuran (234 ml) at −78° C. Lithium bis(trimethylsilyl)amide (58.6 mL, 58.6 mmol) was added and stirred for 15 min before the addition of 2-[N,N-bis(trifluoromethanesulfonyl)amino]-5-chloropyridine (11.1 g, 28.1 mmol) suspended in 30 mL THF in a dry ice/acetone bath. Upon addition of the material, the solution went from an opaque suspension to a clear yellow solution. The solution was stirred for 30 min. Water (100 mL) was added to quench the reaction. The solution was then concentrated under reduced pressure. After the concentration, hexanes (300 mL) was added causing a precipitate to form and was filtered off. The solid was advanced to the next step.

Step B: tert-Butyl (4-((3-(N,N-bis(4-methoxybenzyl)sulfamoyl)-2-(1-(4-methoxybenzyl)-1H-tetrazol-5-yl)-4-(trifluoromethyl)phenyl)ethynyl)cyclohex-3-en-1-yl)carbamate and tert-butyl (4-((3-(N,N-bis(4-methoxybenzyl)sulfamoyl)-2-(2-(4-methoxybenzyl)-2H-tetrazol-5-yl)-4-(trifluoromethyl)phenyl)ethynyl)cyclohex-3-en-1-yl)carbamate To a solution of 3-ethynyl-N,N-bis(4-methoxybenzyl)-2-(2-(4-methoxybenzyl)-2H-tetrazol-5-yl)-6-(trifluoromethyl)benzenesulfonamide and 3-ethynyl-N,N-bis(4-methoxybenzyl)-2-(1-(4-methoxybenzyl)-1H-tetrazol-5-yl)-6-(trifluoromethyl)benzenesulfonamide (400 mg, 0.590 mmol) was added 4-((tert-butoxycarbonyl)amino)cyclohex-1-en-1-yl trifluoromethanesulfonate (306 mg, 0.885 mmol), Pd tetrakis (136 mg, 0.118 mmol)), triethylamine (165 μl, 1.180 mmol)) and copper(I) iodide (11.24 mg, 0.059 mmol) in Dioxane (1.18E+04 μL) and the resulting mixture was stirred for overnight at 80° C. under nitrogen atmosphere. Additional reagents added in the same amount as before with the exception of 3 equiv ethynyl-TMS. The reaction was quenched by brine, extracted with ethyl acetate (3×30 mL). The combined organic layers were washed with brine (1×30 mL), dried over anhydrous Na$_2$SO$_4$, filtered and concentrated under reduced pressure to give a residue, which was purified by a silica gel column, eluting with EtOAc:Hex (0-100%) to afford the title compounds. LC/MS [M+H]$^+$: 873.65.

Step C: tert-Butyl (4-(3-(N,N-bis(4-methoxybenzyl)sulfamoyl)-2-(1-(4-methoxybenzyl)-1H-tetrazol-5-yl)-4-(trifluoromethyl)phenethyl)cyclohexyl)carbamate and tert-butyl (4-(3-(N,N-bis(4-methoxybenzyl)sulfamoyl)-2-(2-(4-methoxybenzyl)-2H-tetrazol-5-yl)-4-(trifluoromethyl) phenethyl)cyclohexyl)carbamate To a solution of tert-butyl (4-((3-(N,N-bis(4-methoxybenzyl)sulfamoyl)-2-(1-(4-methoxybenzyl)-1H-tetrazol-5-yl)-4-(trifluoromethyl)phenyl)ethynyl)cyclohex-3-en-1-yl)carbamate and tert-butyl (4-((3-(N,N-bis(4-methoxybenzyl) sulfamoyl)-2-(2-(4-methoxybenzyl)-2H-tetrazol-5-yl)-4-(trifluoromethyl)phenyl)ethynyl)cyclohex-3-en-1-yl) carbamate (278 mg, 0.318 mmol) in Acetic Acid (10 mL) was added platinum (IV) oxide (36.2 mg, 0.159 mmol). The solution was degassed and Hydrogen was introduced into the system. When the reaction had proceeded to completion by HPLC-MS the mixture was filtered and concentrated to afford the title compounds. LC/MS [M+H]$^+$: 880.2.

Step D: 3-(2-(4-Aminocyclohexyl)ethyl)-N,N-bis(4-methoxybenzyl)-2-(1-(4-methoxybenzyl)-1H-tetrazol-5-yl)-6-(trifluoromethyl)benzenesulfonamide and 3-(2-(4-aminocyclohexyl)ethyl)-N,N-bis(4-methoxybenzyl)-2-(2-(4-methoxybenzyl)-2H-tetrazol-5-yl)-6-(trifluoromethyl) benzenesulfonamide To a solution tert-butyl (4-(3-(N,N-bis(4-methoxybenzyl) sulfamoyl)-2-(1-(4-methoxybenzyl)-1H-tetrazol-5-yl)-4-(trifluoromethyl)phenethyl)cyclohexyl)carbamate and tert-butyl (4-(3-(N,N-bis(4-methoxybenzyl)sulfamoyl)-2-(2-(4-methoxybenzyl)-2H-tetrazol-5-yl)-4-(trifluoromethyl) phenethyl)cyclohexyl)carbamate (280 mg, 0.319 mmol) was added TFA (0.245 mL, 3.19 mmol) at 0° C. The solution was slowly warmed to room temperature. After 3 hr, the reaction was at completion for the title compound. The solution was concentrated and toluene (3×25 mL) was added and concentrated to isolate the title compounds. LC/MS [M+H]$^+$: 779.76.

Step E: 3-(2-(4-Guanidinocyclohexyl)ethyl)-N,N-bis(4-methoxybenzyl)-2-(1-(4-methoxybenzyl)-1H-tetrazol-5-yl)-

6-(trifluoromethyl)benzenesulfonamide and 3-(2-(4-guanidinocyclohexyl)ethyl)-N,N-bis(4-methoxybenzyl)-2-(2-(4-methoxybenzyl)-2H-tetrazol-5-yl)-6-(trifluoromethyl)benzenesulfonamide 3-(2-(4-Aminocyclohexyl)ethyl)-N,N-bis(4-methoxybenzyl)-2-(1-(4-methoxybenzyl)-1H-tetrazol-5-yl)-6-(trifluoromethyl)benzenesulfonamide and 3-(2-(4-aminocyclohexyl)ethyl)-N,N-bis(4-methoxybenzyl)-2-(2-(4-methoxybenzyl)-2H-tetrazol-5-yl)-6-(trifluoromethyl)benzenesulfonamide (140 mg, 0.180 mmol) in DMF (3595 μL) was treated with 1H-pyrazole-1-carboxamidine hydrochloride (42.2 mg, 0.288 mmol) and DIEA (157 μL, 0.899 mmol). The solution was stirred at room temperature under a nitrogen atmosphere for 16 hr. The material was added to EtOAc (50 mL) and washed with brine (2×15 mL) and dried with magnesium sulfate. The solution was filtered and concentrated to isolate the title compound and used in the next step without further purification. [M+H]$^+$: 821.83.

REFERENCE EXAMPLE 51

N,N-Bis(4-methoxybenzyl)-2-(1-(4-methoxybenzyl)-1H-tetrazol-5-yl)-3-(1-oxoisoindolin-4-yl)-6-(trifluoromethyl)benzenesulfonamide and N,N-bis(4-methoxybenzyl)-2-(2-(4-methoxybenzyl)-2H-tetrazol-5-yl)-3-(1-oxoisoindolin-4-yl)-6-(trifluoromethyl)benzenesulfonamide

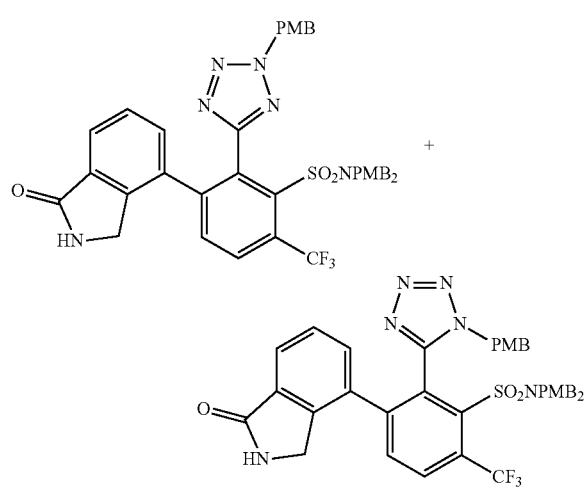

A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl)benzenesulfonamide (300 mg, 0.410 mmol) and 4-(4,4,5,5-tetramethyl-1,3,2-dioxaborolan-2-yl)isoindolin-1-one (170 mg, 0.655 mmol) and Toluene (3723 μL):EtOH (372 μL) and 4-(4,4,5,5-tetramethyl-1,3,2-dioxaborolan-2-yl)isoindolin-1-one (170 mg, 0.655 mmol) was added. The solution was degassed and Pd(Ph$_3$P)$_4$ (47.3 mg, 0.041 mmol), Lithium Chloride (1.736 mg, 0.041 mmol) and lastly Pd(Ph$_3$P)$_4$ (47.3 mg, 0.041 mmol) was added. The solution was degassed for another 20 min. and then was heated to 70° C. overnight. EtOAc (60 mL) was added to the mixture and then it was washed with water (30 mL), brine (30 mL), dried (MgSO$_4$) and concentrated under reduced pressure. LC/MS [M+H]$^+$: 785.75.

REFERENCE EXAMPLE 52

8-Amino-4-(3-(N,N-bis(4-methoxybenzyl)sulfamoyl)-2-(1-(4-methoxybenzyl)-1H-tetrazol-5-yl)-4-(trifluoromethyl)phenyl)quinoline-2-carboxylic acid and 8-amino-4-(3-(N,N-bis(4-methoxybenzyl)sulfamoyl)-2-(2-(4-methoxybenzyl)-2H-tetrazol-5-yl)-4-(trifluoromethyl)phenyl)quinoline-2-carboxylic acid

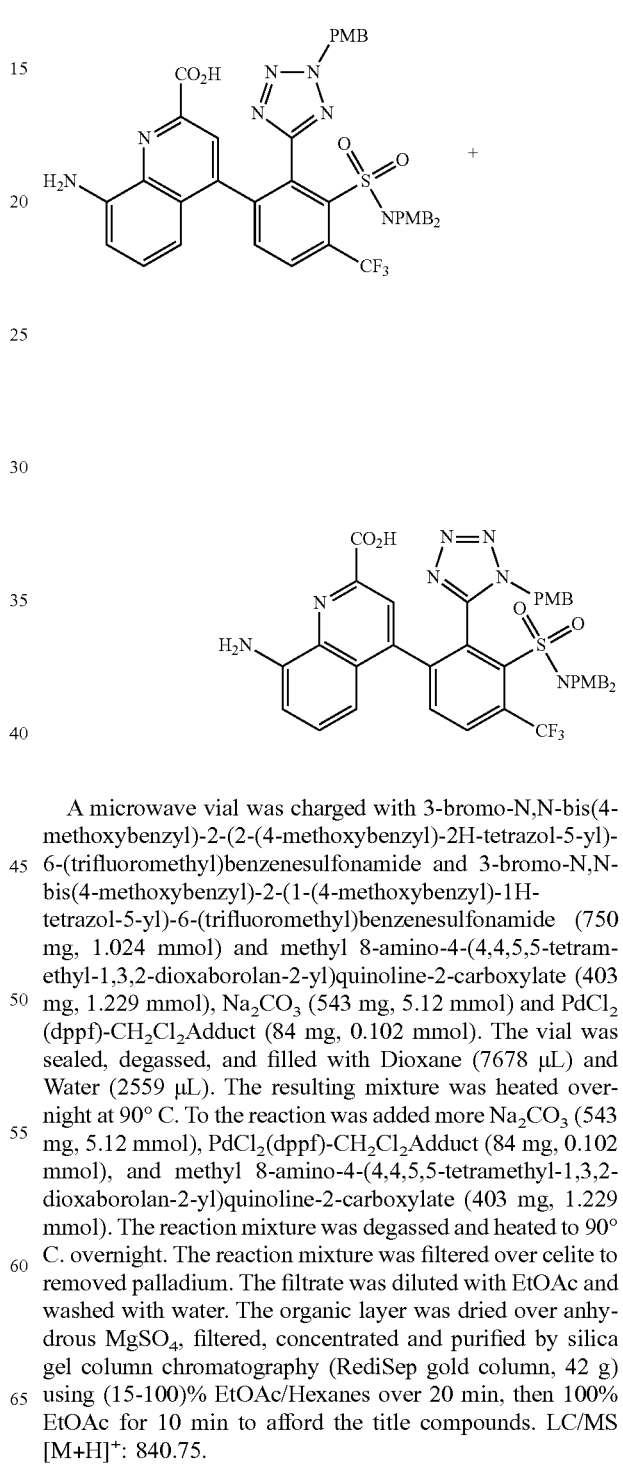

A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl)benzenesulfonamide (750 mg, 1.024 mmol) and methyl 8-amino-4-(4,4,5,5-tetramethyl-1,3,2-dioxaborolan-2-yl)quinoline-2-carboxylate (403 mg, 1.229 mmol), Na$_2$CO$_3$ (543 mg, 5.12 mmol) and PdCl$_2$(dppf)-CH$_2$Cl$_2$Adduct (84 mg, 0.102 mmol). The vial was sealed, degassed, and filled with Dioxane (7678 μL) and Water (2559 μL). The resulting mixture was heated overnight at 90° C. To the reaction was added more Na$_2$CO$_3$ (543 mg, 5.12 mmol), PdCl$_2$(dppf)-CH$_2$Cl$_2$Adduct (84 mg, 0.102 mmol), and methyl 8-amino-4-(4,4,5,5-tetramethyl-1,3,2-dioxaborolan-2-yl)quinoline-2-carboxylate (403 mg, 1.229 mmol). The reaction mixture was degassed and heated to 90° C. overnight. The reaction mixture was filtered over celite to removed palladium. The filtrate was diluted with EtOAc and washed with water. The organic layer was dried over anhydrous MgSO$_4$, filtered, concentrated and purified by silica gel column chromatography (RediSep gold column, 42 g) using (15-100)% EtOAc/Hexanes over 20 min, then 100% EtOAc for 10 min to afford the title compounds. LC/MS [M+H]$^+$: 840.75.

REFERENCE EXAMPLE 53

5-(3-(N,N-Bis(4-methoxybenzyl)sulfamoyl)-2-(1-(4-methoxybenzyl)-1H-tetrazol-5-yl)-4-(trifluoromethyl)phenyl)-N,N-bis(4-methoxybenzyl)picolinamide and 5-(3-(N,N-bis(4-methoxybenzyl)sulfamoyl)-2-(2-(4-methoxybenzyl)-2H-tetrazol-5-yl)-4-(trifluoromethyl)phenyl)-N,N-bis(4-methoxybenzyl)picolinamide

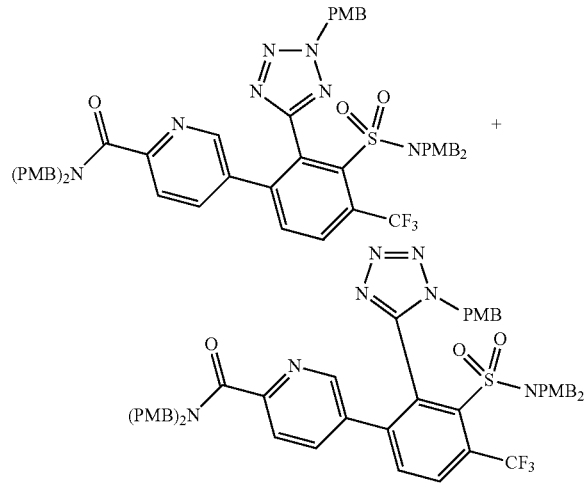

Step A: 5-(3-(N,N-Bis(4-methoxybenzyl)sulfamoyl)-2-(1-(4-methoxybenzyl)-1H-tetrazol-5-yl)-4-(trifluoromethyl)phenyl)picolinic acid and 5-(3-(N,N-bis(4-methoxybenzyl)sulfamoyl)-2-(2-(4-methoxybenzyl)-2H-tetrazol-5-yl)-4-(trifluoromethyl)phenyl)picolinic acid A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl) benzenesulfonamide (500 mg, 0.683 mmol) and ethyl 5-(4,4,5,5-tetramethyl-1,3,2-dioxaborolan-2-yl)picolinate (300 mg, 1.083 mmol), $Na_2CO_3$ (362 mg, 3.41 mmol) and PdCl2(dppf)-CH2Cl2Adduct (55.7 mg, 0.068 mmol). The vial was sealed, degassed, and filled with Dioxane (2048 µL) and Water (683 µL). The resulting mixture was heated overnight at 90° C. The reaction mixture was filtered over celite to removed palladium. The filtrate was diluted with EtOAc and washed with water. The organic layer was dried over anhydrous $MgSO_4$, filtered, concentrated and purified by silica gel column chromatography (RediSep gold column, 80 g) using (15-100)% EtOAc/Hexanes over 20 min, then 100% EtOAc for 10 min. LC/MS $[M+H]^+$: 775.72.

Step B: 5-(3-(N,N-Bis(4-methoxybenzyl)sulfamoyl)-2-(1-(4-methoxybenzyl)-1H-tetrazol-5-yl)-4-(trifluoromethyl)phenyl)-N,N-bis(4-methoxybenzyl)picolinamide and 5-(3-(N,N-bis(4-methoxybenzyl)sulfamoyl)-2-(2-(4-methoxybenzyl)-2H-tetrazol-5-yl)-4-(trifluoromethyl)phenyl)-N,N-bis(4-methoxybenzyl)picolinamide 5-(3-(N,N-bis(4-methoxybenzyl)sulfamoyl)-2-(1-(4-methoxybenzyl)-1H-tetrazol-5-yl)-4-(trifluoromethyl)phenyl)picolinic acid and 5-(3-(N,N-bis(4-methoxybenzyl)sulfamoyl)-2-(2-(4-methoxybenzyl)-2H-tetrazol-5-yl)-4-(trifluoromethyl)phenyl)picolinic acid (22.4 mg, 0.029 mmol) was dissolved in DMF (1 mL) and EDC (19.40 mg, 0.101 mmol), 1-hydroxy-7-azabenzotriazole (3.94 mg, 0.029 mmol), and DIPEA (0.025 mL, 0.145 mmol) were added. The solution was stirred for 5 minutes before the addition of bis(4-methoxybenzyl)amine (18.60 mg, 0.072 mmol). The solution was stirred at for 16 hr. The solution is added to EtOAc (20 mL) and washed with water (3×5 mL) and brine (2×5 mL). Then the organic is dried, concentrated and purified by silica gel chromatography to isolate the title compounds. LC/MS $[M+H]^+$: 1014.94.

REFERENCE EXAMPLE 54

7-(3-(N,N-Bis(4-methoxybenzyl)sulfamoyl)-2-(1-(4-methoxybenzyl)-1H-tetrazol-5-yl)-4-(trifluoromethyl)phenyl)-N,N-bis(4-methoxybenzyl)-1H-indole-2-carboxamide and 7-(3-(N,N-bis(4-methoxybenzyl)sulfamoyl)-2-(2-(4-methoxybenzyl)-2H-tetrazol-5-yl)-4-(trifluoromethyl)phenyl)-N,N-bis(4-methoxybenzyl)-1H-indole-2-carboxamide

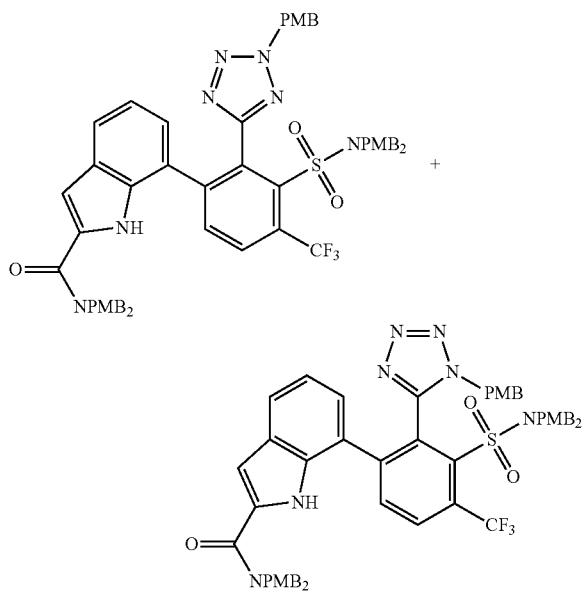

Step A: Ethyl 7-(3-(N,N-bis(4-methoxybenzyl)sulfamoyl)-2-(1-(4-methoxybenzyl)-1H-tetrazol-5-yl)-4-(trifluoromethyl)phenyl)-1H-indole-2-carboxylate and ethyl 7-(3-(N,N-bis(4-methoxybenzyl)sulfamoyl)-2-(2-(4-methoxybenzyl)-2H-tetrazol-5-yl)-4-(trifluoromethyl)phenyl)-1H-indole-2-carboxylate A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl) benzenesulfonamide (500 mg, 0.683 mmol) and ethyl 7-(4,4,5,5-tetramethyl-1,3,2-dioxaborolan-2-yl)-1H-indole-2-carboxylate (300 mg, 0.952 mmol), [1,1'-Bis(Diphenylphosphino) Ferrocene]Dichloropalladium(Ii) (49.9 mg, 0.068 mmol) and sodium carbonate (2.05 mmol) in Toluene (5688 µL) and Ethanol (1138 µL) and was heated at 90° C. for 17 hr. The mixture was filtered through a celite pad. The filtrate was concentrated, and the residue was purified by MPLC (0-100% EtOAc in Hexane). LC/MS $[M+H]^+$: 841.76.

Step B: 7-(3-(N,N-Bis(4-methoxybenzyl)sulfamoyl)-2-(1-(4-methoxybenzyl)-1H-tetrazol-5-yl)-4-(trifluoromethyl)phenyl)-1H-indole-2-carboxylic acid and 7-(3-(N,N-bis(4-methoxybenzyl)sulfamoyl)-2-(2-(4-methoxybenzyl)-2H-tetrazol-5-yl)-4-(trifluoromethyl)phenyl)-1H-indole-2-carboxylic acid Ethyl 7-(3-(N,N-bis(4-methoxybenzyl)sulfamoyl)-2-(1-(4-methoxybenzyl)-1H-tetrazol-5-yl)-4-(trifluoromethyl)phenyl)-1H-indole-2-carboxylate and ethyl 7-(3-(N,N-bis(4-methoxybenzyl)sulfamo3yl)-2-(2-(4-methoxybenzyl)-2H-tetrazol-5-yl)-4-(trifluoromethyl)phenyl)-1H-indole-2-carboxylate (187 mg, 0.222 mmol) was dissolved in dioxane (2224 µL):water (2224 µL) and LiOH (53.3 mg, 2.224 mmol) was added to the system and stirred for 16 hr. The solution was added to EtOAc (50 mL) and washed with brine (3×15 mL) and concentrated. The title compounds were used without further purification. LC/MS [M+H]$^+$: 813.68.

Step C: 7-(3-(N,N-Bis(4-methoxybenzyl)sulfamoyl)-2-(1-(4-methoxybenzyl)-1H-tetrazol-5-yl)-4-(trifluoromethyl)phenyl)-N,N-bis(4-methoxybenzyl)-1H-indole-2-carboxamide and 7-(3-(N,N-bis(4-methoxybenzyl)sulfamoyl)-2-(2-(4-methoxybenzyl)-2H-tetrazol-5-yl)-4-(trifluoromethyl)phenyl)-N,N-bis(4-methoxybenzyl)-1H-indole-2-carboxamide 7-(3-(N,N-Bis(4-methoxybenzyl)sulfamoyl)-2-(1-(4-methoxybenzyl)-1H-tetrazol-5-yl)-4-(trifluoromethyl)phenyl)-1H-indole-2-carboxylic acid and 7-(3-(N,N-bis(4-methoxybenzyl)sulfamoyl)-2-(2-(4-methoxybenzyl)-2H-tetrazol-5-yl)-4-(trifluoromethyl)phenyl)-1H-indole-2-carboxylic acid (90 mg, 0.111 mmol) was dissolved in DMF (1 mL) and EDC (53.1 mg, 0.277 mmol), 1-Hydroxy-7-Azabenzotriazole (1.507 mg, 0.011 mmol), and Hunig's Base (0.077 mL, 0.443 mmol) were added. This was stirred for 5 mins before the addition of Bis(4-Methoxybenzyl) Amine (85 mg, 0.332 mmol). The solution was stirred overnight. An additional equiv of amine, EDC, and Hunig's base was added and the mixture was stirred over the weekend. The reaction mixture was diluted with EtOAc (40 mL) and extracted with water (2×20 mL) brine (2×20 mL) dried (MgSO$_4$) and concentrated. Used crude in next step. LC/MS [M+H]$^+$: 1052.96.

REFERENCE EXAMPLE 55

6-Cyclopropyl-N,N-bis(4-methoxybenzyl)-2-(1-(4-methoxybenzyl)-1H-tetrazol-5-yl)-3-(quinolin-5-yl)benzenesulfonamide and 6-cyclopropyl-N,N-bis(4-methoxybenzyl)-2-(2-(4-methoxybenzyl)-2H-tetrazol-5-yl)-3-(quinolin-5-yl)benzenesulfonamide

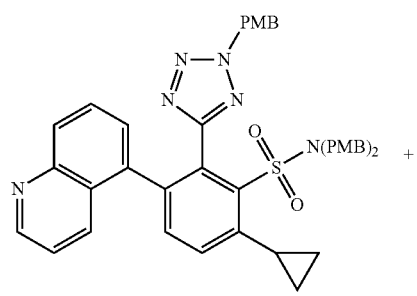

+

-continued

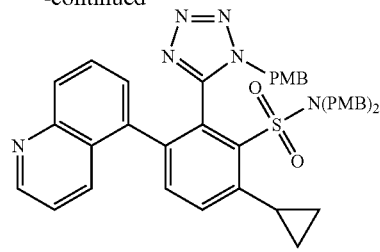

A mixture of N,N-bis(4-methoxybenzyl)-2-(2-(4-methoxybenzyl)-2H-tetrazol-5-yl)-3-(quinolin-5-yl)-6-(trifluoromethyl)benzenesulfonamide and 6-bromo-N,N-bis(4-methoxybenzyl)-2-(1-(4-methoxybenzyl)-1H-tetrazol-5-yl)-3-(quinolin-5-yl)benzenesulfonamide (described above, 200 mg, 0.253 mmol), 2-cyclopropyl-4,4,5,5-tetramethyl-1,3,2-dioxaborolane (63.7 mg, 0.379 mmol) and PdCl$_2$(dppf)-CH$_2$Cl$_2$Adduct (20.63 mg, 0.025 mmol) was sealed in a microwave vial, degassed, and filled with Dioxane (758 µL) and Water (253 µL). The resulting mixture was heated overnight at 90° C. The reaction mixture was filtered over celite to remove the palladium. The filtrate was diluted with MeOH and loaded onto 3×SCX (20 g) ion exchange columns. The material was washed with MeOH. Next, the columns were washed with 1N NH$_3$ in MeOH until the red band on the cartridge was fully eluted to afford the title compound after removal of the volatiles. LC/MS [M+H]$^+$: 753.47.

REFERENCE EXAMPLE 56

6-(2-Hydroxyethyl)-N,N-bis(4-methoxybenzyl)-2-(1-(4-methoxybenzyl)-1H-tetrazol-5-yl)-3-(quinolin-5-yl)benzenesulfonamide and 6-(2-hydroxyethyl)-N,N-bis(4-methoxybenzyl)-2-(2-(4-methoxybenzyl)-2H-tetrazol-5-yl)-3-(quinolin-5-yl)benzenesulfonamide

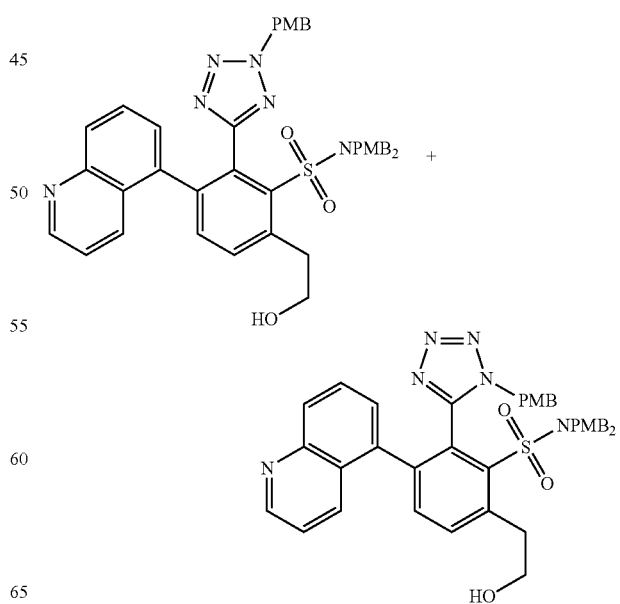

Step A: tert-Butyl 2-(2-(N,N-bis(4-methoxybenzyl)sulfamoyl)-3-(1-(4-methoxybenzyl)tetrazolidin-5-yl)-4-(quinolin-5-yl)phenyl)acetate and tert-butyl 2-(2-(N,N-bis(4-methoxybenzyl)sulfamoyl)-3-(2-(4-methoxybenzyl)-2H-tetrazol-5-yl)-4-(quinolin-5-yl)phenyl)acetate N,N-Bis(4-methoxybenzyl)-2-(2-(4-methoxybenzyl)-2H-tetrazol-5-yl)-3-(quinolin-5-yl)-6-(trifluoromethyl)benzenesulfonamide and 6-bromo-N,N-bis(4-methoxybenzyl)-2-(1-(4-methoxybenzyl)-1H-tetrazol-5-yl)-3-(quinolin-5-yl)benzenesulfonamide (100 mg, 0.126 mmol) and second generation SPHOS (9.10 mg, 0.013 mmol) was placed in a microwave tube, and added anhydrous THF (421 μl). The tube was sealed and nitrogen was used to degas for 10 min. (2-(tert-butoxy)-2-oxoethyl)zinc(II) chloride (1010 μl, 0.505 mmol) was then added to the solution and the resulting mixture was heated at 50° C. for 16 hr. The reaction was quenched with a saturated NH₄Cl solution. The reaction mixture was extracted with EtOAc (60 mL). Organic washed with brine (15 mL), dried (Na₂SO₄), filtered and concentrated. The reaction mixture was purified by silica gel chromatography to isolate the title compounds. LC/MS [M+H]⁺: 827.46.

Step B: 6-(2-Hydroxyethyl)-N,N-bis(4-methoxybenzyl)-2-(1-(4-methoxybenzyl)-1H-tetrazol-5-yl)-3-(quinolin-5-yl)benzenesulfonamide and 6-(2-hydroxyethyl)-N,N-bis(4-methoxybenzyl)-2-(2-(4-methoxybenzyl)-2H-tetrazol-5-yl)-3-(quinolin-5-yl)benzenesulfonamide tert-Butyl 2-(2-(N,N-bis(4-methoxybenzyl)sulfamoyl)-3-(1-(4-methoxybenzyl)tetrazolidin-5-yl)-4-(quinolin-5-yl)phenyl)acetate and tert-butyl 2-(2-(N,N-bis(4-methoxybenzyl)sulfamoyl)-3-(2-(4-methoxybenzyl)-2H-tetrazol-5-yl)-4-(quinolin-5-yl)phenyl)acetate (522 mg, 0.631 mmol) was dissolved in tetrahydrofuran (6312 μL) at 0° C. where upon lithium aluminum hydride 1 M in diethyl ether (947 μL, 1.894 mmol) was added to the solution. The solution stirred for 16 hr and was cooled to 0° C. and the reaction was quenched with water (100 μL, 5.55 mmol) and NaOH (1578 μL, 3.16 mmol)). The resulting solution was stirred for 30 minutes where a white suspension formed. The suspension was filtered. The solution was concentrated and the oil was purified by silica MPLC to isolate the title compounds. LC/MS [M+H]⁺: 757.46.

REFERENCE EXAMPLE 57

3-(2-Aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide

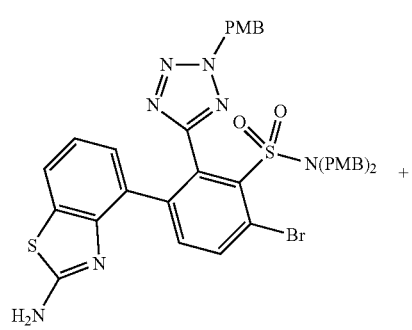

+

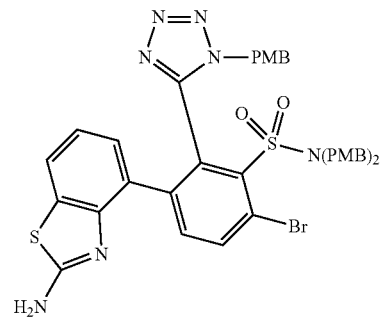

Step A: (2-Aminobenzo[d]thiazol-4-yl)boronic acid

In the reaction vessel 4-bromobenzo[d]thiazol-2-amine (10 g, 43.6 mmol) and bispinacolatodiboron (33.3 g, 131 mmol) were combined, followed by potassium acetate (12.85 g, 131 mmol) and PCy3 Pd G2 (2.58 g, 4.36 mmol). Then dry dioxane (400 ml) was added to this flask. This mixture was degassed and then heated at 80° C. for 72 hr. The solution was filtered, and the filtrate was concentrated under reduced pressure. The residue was dissolved in EtOAc (400 mL), and extracted with 2N HCl (2×150 ml). The aqueous was concentrated under reduced pressure. The crude material was dissolved in 3:1 CHCl3:i-PrOH, dried over MgSO₄. The MgSO₄ was filtered off and the filtrate was concentrated. The material was used without further purification. LC/MS [M+H]⁺: 195

Step B: 3-(2-Aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide Starting with a solution of 6-bromo-3-iodo-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)tetrazolidin-5-yl)benzenesulfonamide (7.3 g, 9.24 mmol) and (2-aminobenzo[d]thiazol-4-yl)boronic acid (1.971 g, 10.16 mmol) the title compounds were prepared in an analogous fashion as described for 6-Bromo-N,N-bis(4-methoxybenzyl)-2-(1-(4-methoxybenzyl)-1H-tetrazol-5-yl)-3-(quinolin-5-yl)benzenesulfonamide and 6-bromo-N,N-bis(4-methoxybenzyl)-2-(2-(4-methoxybenzyl)-2H-tetrazol-5-yl)-3-(quinolin-5-yl)benzenesulfonamide. LC/MS [M+H]⁺: 812, 814.

REFERENCE EXAMPLE 58

3-(2-Aminobenzo[d]thiazol-4-yl)-6-(2-hydroxyethyl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-(2-hydroxyethyl)-N,N-bis(4-methoxybenzyl)-2-(2-(4-methoxybenzyl)-2H-tetrazol-5-yl)benzenesulfonamide

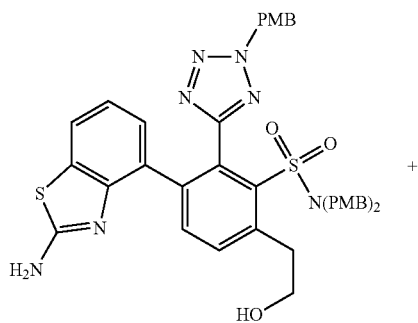

+

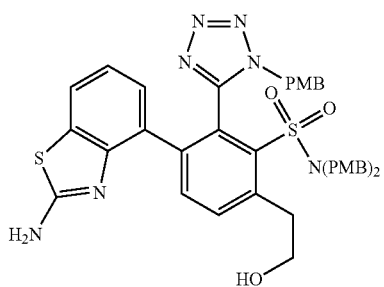

Step A: tert-Butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate To 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide (2.6 g, 3.2 mmol) was dissolved in DCM (16 mL). Then DMAP (0.039 g, 0.320 mmol) was added to the system followed by the addition of BOC-Anhydride (1.63 mL, 7.04 mmol). The solution was stirred for 16 hr. The resulting solution was taken into EtOAc (100 mL) and washed with brine (30 mL), dried over magnesium sulfate and concentrated to isolate the title compounds. LC/MS [M+H]$^+$: 1012, 1014.

Step B: tert-Butyl 2-(2-(N,N-bis(4-methoxybenzyl)sulfamoyl)-4-(2-(((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-(((tert-butoxycarbonyl)amino)benzo[d]thiazol-4-yl)-3-(2-(4-methoxybenzyl)-2H-tetrazol-5-yl)phenyl)acetate To a solution of tert-Butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate (1.3 g, 1.3 mmol) and 2nd Gen SPHOS (0.185 g, 0.257 mmol) was placed in a microwave tube, and anhydrous THF (4.3 mL) was added. The tube was sealed and N$_2$ was bubbled through for 10 min. (2-(tert-butoxy)-2-oxoethyl)zinc(II) chloride (12.8 mL, 6.42 mmol) was then added. The resulting mixture was heated at 60° C. for overnight. A mixture of di boc, mono boc, and no boc material was identified by LC-MS. LC/MS [M+H]$^+$: 948.81.

Step C: tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate To a solution of tert-butyl 2-(2-(N,N-bis(4-methoxybenzyl)sulfamoyl)-4-(2-(((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-(((tert-butoxycarbonyl)amino)benzo[d]thiazol-4-yl)-3-(2-(4-methoxybenzyl)-2H-tetrazol-5-yl)phenyl)acetate (900 mg, 0.949 mmol was dissolved in DCM (9493 µL) and TFA (293 µL, 3.80 mmol) was added to the system. The reaction was stirred for 16 hr. The solution was concentrated to yield the title compound and used without further purification. LC/MS [M+H]$^+$: 848.85.

Step D: 3-(2-Aminobenzo[d]thiazol-4-yl)-6-(2-hydroxyethyl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-(2-hydroxyethyl)-N,N-bis(4-methoxybenzyl)-2-(2-(4-methoxybenzyl)-2H-tetrazol-5-yl)benzenesulfonamide tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate (717 mg, 0.846 mmol) was dissolved in Tetrahydrofuran (8455 µL) at 0° C. where LAH 1 M in diethyl ether (1268 µL, 2.54 mmol) was added to the solution. The solution stirred overnight. The solution was cooled to 0° C. and the reaction was quenched with Water (15.23 µL, 0.846 mmol) and Sodium Hydroxide (5.92 mmol)). The resulting solution was stirred for 30 mins where a white suspension formed. The suspension was filtered. The solution was concentrated and the oil was loaded onto a teledyne isco silica 24 g column eluting with EtOAC: Ethanol (3:1): Hexanes from 10-70% over 20 min. LC/MS [M+H]$^+$: 778.66.

REFERENCE EXAMPLE 59

6-(1-Fluoro-2-hydroxyethyl)-N,N-bis(4-methoxybenzyl)-2-(1-(4-methoxybenzyl)-1H-tetrazol-5-yl)-3-(2-((4-methoxybenzyl)amino)benzo[d]thiazol-4-yl)benzenesulfonamide and 6-(1-fluoro-2-hydroxyethyl)-N,N-bis(4-methoxybenzyl)-2-(2-(4-methoxybenzyl)-2H-tetrazol-5-yl)-3-(2-((4-methoxybenzyl)amino)benzo[d]thiazol-4-yl)benzenesulfonamide

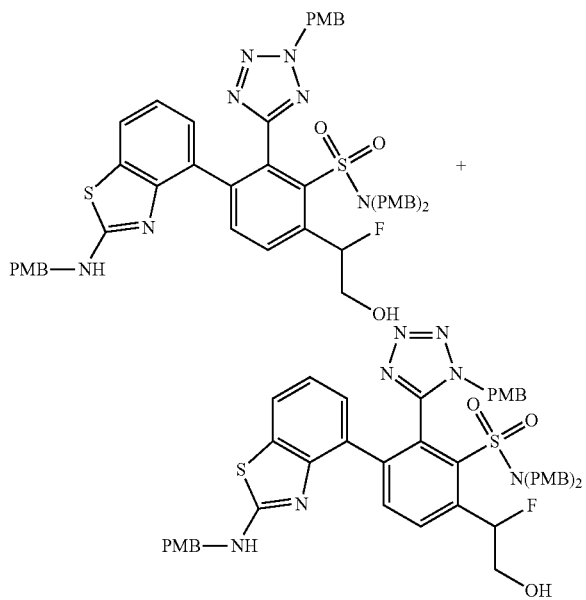

Step A: 3-(2-(Bis(4-methoxybenzyl)amino)benzo[d]thiazol-4-yl)-6-bromo-N,N-bis(4-methoxybenzyl)-2-(1-(4-methoxybenzyl)-1H-tetrazol-5-yl)benzenesulfonamide and 3-(2-(bis(4-methoxybenzyl)amino)benzo[d]thiazol-4-yl)-6-bromo-N,N-bis(4-methoxybenzyl)-2-(2-(4-methoxybenzyl)-2H-tetrazol-5-yl)benzenesulfonamide 3-(2-Aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide (1.6 g, 1.97 mmol) was dissolved into 2-butanone (9.84 mL). This was followed by the addition of 4-methoxybenzyl chloride (0.587 mL, 4.33 mmol), NaI (0.649 g, 4.33 mmol), and $K_2CO_3$ (1.088 g, 7.87 mmol). The reaction was heated to 80° C. under an atmosphere of nitrogen for 16 hr. The solution was filtered to remove the inorganics. The resulting solution was taken into to EtOAc (60 mL) and washed with water (2×20 mL), brine (20 mL), dried ($MgSO_4$), and concentrated under reduced pressure resulting in an oil. The oil was loaded onto a silica column to yield the title compound. LC/MS $[M+H]^+$: 1054.92.

Step B: tert-Butyl 2-(4-(2-(bis(4-methoxybenzyl)amino)benzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-(bis(4-methoxybenzyl)amino)benzo[d]thiazol-4-yl)-2-(N,N-bis(4-methoxybenzyl)sulfamoyl)-3-(2-(4-methoxybenzyl)-2H-tetrazol-5-yl)phenyl)acetate To a solution of 3-(2-(bis(4-methoxybenzyl)amino)benzo[d]thiazol-4-yl)-6-bromo-N,N-bis(4-methoxybenzyl)-2-(1-(4-methoxybenzyl)-1H-tetrazol-5-yl)benzenesulfonamide and 3-(2-(bis(4-methoxybenzyl)amino)benzo[d]thiazol-4-yl)-6-bromo-N,N-bis(4-methoxybenzyl)-2-(2-(4-methoxybenzyl)-2H-tetrazol-5-yl)benzenesulfonamide and (2-(tert-butoxy)-2-oxoethyl)zinc(II) chloride (6852 µl, 3.43 mmol) were reacted in an analogous fashion to that described for tert-Butyl 2-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)acetate to isolate the title compounds. LC/MS $[M+H]^+$: 1089.04.

Step C: tert-Butyl 2-(2-(N,N-bis(4-methoxybenzyl)sulfamoyl)-3-(1-(4-methoxybenzyl)-1H-tetrazol-5-yl)-4-(2-((4-methoxybenzyl)amino)benzo[d]thiazol-4-yl)phenyl)-2-fluoroacetate and tert-butyl 2-(2-(N,N-bis(4-methoxybenzyl)sulfamoyl)-3-(2-(4-methoxybenzyl)-2H-tetrazol-5-yl)-4-(2-((4-methoxybenzyl)amino)benzo[d]thiazol-4-yl)phenyl)-2-fluoroacetate To a solution of tert-butyl 2-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)acetate (655 mg, 0.602 mmol) was dissolved in THF (10 mL) and chilled to –78° C. and 2 M LDA (1.204 mL, 2.407 mmol) was added to the system. After an hour N-fluorobenzenesulfonimide (569 mg, 1.806 mmol) was added and the mixture was stirred under a nitrogen atmosphere for 16 hr. Upon completion, the solution was poured into brine (20 mL) and EtOAc (3×30 mL) was used to extract the aqueous. The organic was dried and purified on silica to isolate the title compounds. LC/MS $[M+H]^+$: 986.88.

Step D: 6-(1-Fluoro-2-hydroxyethyl)-N,N-bis(4-methoxybenzyl)-2-(1-(4-methoxybenzyl)-1H-tetrazol-5-yl)-3-(2-((4-methoxybenzyl)amino)benzo[d]thiazol-4-yl)benzenesulfonamide and 6-(1-fluoro-2-hydroxyethyl)-N,N-bis(4-methoxybenzyl)-2-(2-(4-methoxybenzyl)-2H-tetrazol-5-yl)-3-(2-((4-methoxybenzyl)amino)benzo[d]thiazol-4-yl)benzenesulfonamide To a solution of tert-butyl 2-(2-(N,N-bis(4-methoxybenzyl)sulfamoyl)-3-(1-(4-methoxybenzyl)-1H-tetrazol-5-yl)-4-(2-((4-methoxybenzyl)amino)benzo[d]thiazol-4-yl)phenyl)-2-fluoroacetate and tert-butyl 2-(2-(N,N-bis(4-methoxybenzyl)sulfamoyl)-3-(2-(4-methoxybenzyl)-2H-tetrazol-5-yl)-4-(2-((4-methoxybenzyl)amino)benzo[d]thiazol-4-yl)phenyl)-2-fluoroacetate (131 mg, 0.133 mmol) was treated in an analogous fashion as described for 3-(2-Aminobenzo[d]thiazol-4-yl)-6-(2-hydroxyethyl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-(2-hydroxyethyl)-N,N-bis(4-methoxybenzyl)-2-(2-(4-methoxybenzyl)-2H-tetrazol-5-yl)benzenesulfonamide to isolate the title compounds. LC/MS $[M+H]^+$: 916.79.

REFERENCE EXAMPLE 60

3-(2-Aminobenzo[d]thiazol-4-yl)-6-(3-hydroxypropyl)-2-(1-(4-methoxybenzyl)-1H-tetrazol-5-yl)benzenesulfonamide and 3-(2-aminobenzo[d]thiazol-4-yl)-6-(3-hydroxypropyl)-2-(2-(4-methoxybenzyl)-2H-tetrazol-5-yl)benzenesulfonamide

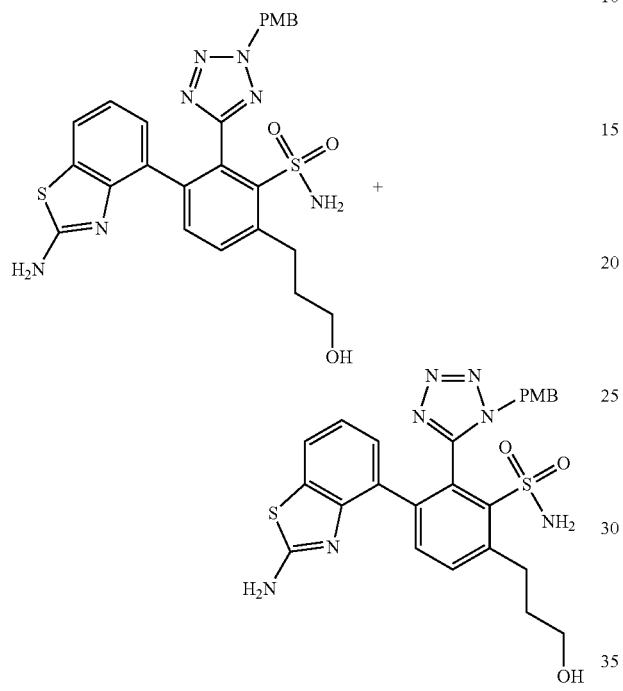

Step A: Ethyl 3-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)propanoate and ethyl 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoate To a solution of tert-butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate, (1000 mg, 0.987 mmol) and (3-ethoxy-3-oxopropyl)zinc(II) bromide (9872 µl, 4.94 mmol) were reacted in an analogous fashion to that described for tert-Butyl 2-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)acetate to afford the title compounds. LC/MS [M+H]$^+$: 934.9.

Step B: Ethyl 3-(4-(2-aminobenzo[d]thiazol-4-yl)-3-(1-(4-methoxybenzyl)-1H-tetrazol-5-yl)-2-sulfamoylphenyl)propanoate and ethyl 3-(4-(2-aminobenzo[d]thiazol-4-yl)-3-(2-(4-methoxybenzyl)-2H-tetrazol-5-yl)-2-sulfamoylphenyl)propanoate To a solution from ethyl 3-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)propanoate and ethyl 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoate (1021 mg, 0.987 mmol) was dissolved in DCM (20 mL) and TFA (1.521 mL, 19.74 mmol) was added to the system. The solution was stirred for 16 hr. The solution was concentrated and used without further purification to isolate the title compounds. LC/MS [M+H]$^+$: 594.50.

Step C: 3-(2-Aminobenzo[d]thiazol-4-yl)-6-(3-hydroxypropyl)-2-(1-(4-methoxybenzyl)-1H-tetrazol-5-yl)benzenesulfonamide and 3-(2-aminobenzo[d]thiazol-4-yl)-6-(3-hydroxypropyl)-2-(2-(4-methoxybenzyl)-2H-tetrazol-5-yl)benzenesulfonamide To a solution of ethyl 3-(4-(2-aminobenzo[d]thiazol-4-yl)-3-(1-(4-methoxybenzyl)-1H-tetrazol-5-yl)-2-sulfamoylphenyl)propanoate and ethyl 3-(4-(2-aminobenzo[d]thiazol-4-yl)-3-(2-(4-methoxybenzyl)-2H-tetrazol-5-yl)-2-sulfamoylphenyl)propanoate (586 mg, 0.987 mmol) was treated in an analogous fashion as described for 3-(2-Aminobenzo[d]thiazol-4-yl)-6-(2-hydroxyethyl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-(2-hydroxyethyl)-N,N-bis(4-methoxybenzyl)-2-(2-(4-methoxybenzyl)-2H-tetrazol-5-yl)benzenesulfonamide to isolate the title compounds. LC/MS [M+H]$^+$: 552.58.

REFERENCE EXAMPLE 61

3-(2-Aminobenzo[d]thiazol-4-yl)-6-(5-hydroxypentyl)-2-(1-(4-methoxybenzyl)-1H-tetrazol-5-yl)benzenesulfonamide and 3-(2-aminobenzo[d]thiazol-4-yl)-6-(5-hydroxypentyl)-2-(2-(4-methoxybenzyl)-2H-tetrazol-5-yl)benzenesulfonamide

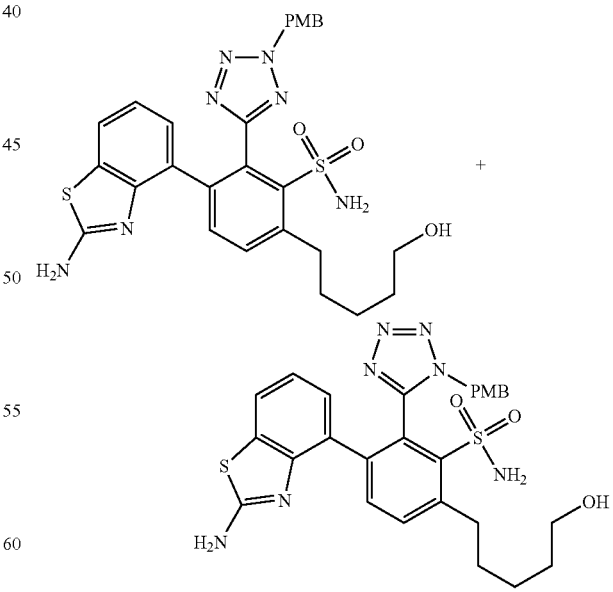

Step A: Ethyl 5-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)pentanoate and ethyl 5-(2-(N,N-bis(4-methoxybenzyl)sulfamoyl)-4-(2-

((tert-butoxycarbonyl)amino)benzo[d]thiazol-4-yl)-3-(2-(4-methoxybenzyl)-2H-tetrazol-5-yl)phenyl)pentanoate To a solution of tert-butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate (1000 mg, 0.987 mmol) and (5-ethoxy-5-oxopentyl)zinc(II) bromide (9872 µl, 4.94 mmol) were reacted in an analogous fashion to that described for tert-Butyl 2-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)acetate to afford the title compounds. LC/MS [M+H]+: 962.89.

Step B: Ethyl 5-(4-(2-aminobenzo[d]thiazol-4-yl)-3-(1-(4-methoxybenzyl)-1H-tetrazol-5-yl)-2-sulfamoylphenyl)pentanoate and ethyl 5-(4-(2-aminobenzo[d]thiazol-4-yl)-3-(2-(4-methoxybenzyl)-2H-tetrazol-5-yl)-2-sulfamoylphenyl)pentanoate To a solution of ethyl 5-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)pentanoate and ethyl 5-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)pentanoate (597 mg, 0.620 mmol) was treated in an analogous fashion as described for the synthesis of tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate to isolate title compounds. LC/MS [M+H]+: 742.64.

Step C: 3-(2-Aminobenzo[d]thiazol-4-yl)-6-(5-hydroxypentyl)-2-(1-(4-methoxybenzyl)-1H-tetrazol-5-yl)benzenesulfonamide and 3-(2-aminobenzo[d]thiazol-4-yl)-6-(5-hydroxypentyl)-2-(2-(4-methoxybenzyl)-2H-tetrazol-5-yl)benzenesulfonamide To a solution of ethyl 5-(4-(2-aminobenzo[d]thiazol-4-yl)-3-(1-(4-methoxybenzyl)-1H-tetrazol-5-yl)-2-sulfamoylphenyl)pentanoate and ethyl 5-(4-(2-aminobenzo[d]thiazol-4-yl)-3-(2-(4-methoxybenzyl)-2H-tetrazol-5-yl)-2-sulfamoylphenyl)pentanoate (460 mg, 0.620 mmol) was treated in an analogous fashion as described for 3-(2-Aminobenzo[d]thiazol-4-yl)-6-(2-hydroxyethyl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-(2-hydroxyethyl)-N,N-bis(4-methoxybenzyl)-2-(2-(4-methoxybenzyl)-2H-tetrazol-5-yl)benzenesulfonamide to isolate the title compounds. LC/MS [M+H]+: 580.52.

REFERENCE EXAMPLE 62

3-(2-Aminobenzo[d]thiazol-4-yl)-6-(cyclobutylmethyl)-N-(4-methoxybenzyl)-2-(1-(4-methoxybenzyl)-1H-tetrazol-5-yl)benzenesulfonamide and 3-(2-aminobenzo[d]thiazol-4-yl)-6-(cyclobutylmethyl)-N-(4-methoxybenzyl)-2-(2-(4-methoxybenzyl)-2H-tetrazol-5-yl)benzenesulfonamide

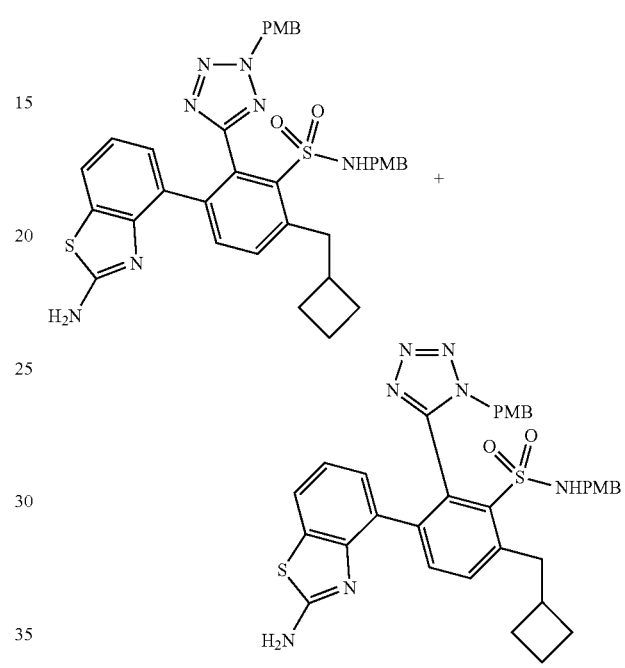

Step A: tert-Butyl (4-(3-(N,N-bis(4-methoxybenzyl)sulfamoyl)-4-(cyclobutylmethyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(cyclobutylmethyl)-2-(2-(4-methoxybenzyl)-2H-tetrazol-5-yl)phenyl)benzo[d]thiazol-2-yl)carbamate To a solution of tert-butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate (200 mg, 0.197 mmol) and 0.5 M (cyclobutylmethyl)zinc(II) chloride (1974 µl, 0.987 mmol) in diethyl ether were reacted in an analogous fashion to that described for tert-Butyl 2-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)acetate and tert-butyl 2-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)acetate to afford the title compounds. LC/MS [M+H]+: 902.86.

Step B: 3-(2-Aminobenzo[d]thiazol-4-yl)-6-(cyclobutylmethyl)-N-(4-methoxybenzyl)-2-(1-(4-methoxybenzyl)-1H-tetrazol-5-yl)benzenesulfonamide and 3-(2-aminobenzo[d]thiazol-4-yl)-6-(cyclobutylmethyl)-N-(4-methoxybenzyl)-2-(2-(4-methoxybenzyl)-2H-tetrazol-5-yl)benzenesulfonamide To a solution of tert-butyl (4-(3-(N,N-bis(4-methoxybenzyl)sulfamoyl)-4-(cyclobutylmethyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(cyclobutylmethyl)-2-(2-(4-methoxybenzyl)-2H-tetrazol-5-yl)phenyl)benzo[d]thiazol-2-yl)carbamate (170 mg, 0.188 mmol) was treated in an analogous fashion to that described for the synthesis of tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate to afford the title compounds. LC/MS [M+H]$^+$: 682.63.

REFERENCE EXAMPLE 63

3-(2-Aminobenzo[d]thiazol-4-yl)-6-(2-aminothiazol-5-yl)-2-(1-(4-methoxybenzyl)-1H-tetrazol-5-yl)benzenesulfonamide and 3-(2-aminobenzo[d]thiazol-4-yl)-6-(2-aminothiazol-5-yl)-2-(2-(4-methoxybenzyl)-2H-tetrazol-5-yl)benzenesulfonamide

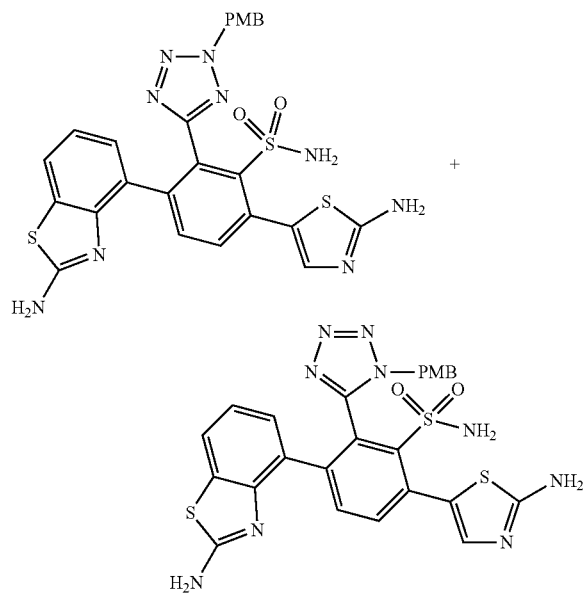

Step A: tert-Butyl (4-(3-(N,N-bis(4-methoxybenzyl)sulfamoyl)-4-(2-((tert-butoxycarbonyl)amino)thiazol-5-yl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(2-((tert-butoxycarbonyl)amino)thiazol-5-yl)-2-(2-(4-methoxybenzyl)-2H-tetrazol-5-yl)phenyl)benzo[d]thiazol-2-yl)carbamate To a solution of tert-butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate (327 mg, 0.323 mmol) and tert-butyl (5-(4,4,5,5-tetramethyl-1,3,2-dioxaborolan-2-yl)thiazol-2-yl)carbamate (211 mg, 0.646 mmol) was treated as described for the synthesis of 6-Bromo-N,N-bis(4-methoxybenzyl)-2-(1-(4-methoxybenzyl)-1H-tetrazol-5-yl)-3-(quinolin-5-yl)benzenesulfonamide compound with 6-bromo-N,N-bis(4-methoxybenzyl)-2-(2-(4-methoxybenzyl)-2H-tetrazol-5-yl)-3-(quinolin-5-yl)benzenesulfonamide to afford the title compound. LC/MS [M+H]$^+$: 1032.92.

Step B: 3-(2-Aminobenzo[d]thiazol-4-yl)-6-(2-aminothiazol-5-yl)-2-(1-(4-methoxybenzyl)-1H-tetrazol-5-yl)benzenesulfonamide and 3-(2-aminobenzo[d]thiazol-4-yl)-6-(2-aminothiazol-5-yl)-2-(2-(4-methoxybenzyl)-2H-tetrazol-5-yl)benzenesulfonamide To a solution of tert-butyl (4-(3-(N,N-bis(4-methoxybenzyl)sulfamoyl)-4-(2-((tert-butoxycarbonyl)amino)thiazol-5-yl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(2-((tert-butoxycarbonyl)amino)thiazol-5-yl)-2-(2-(4-methoxybenzyl)-2H-tetrazol-5-yl)phenyl)benzo[d]thiazol-2-yl)carbamate (120 mg, 0.116 mmol) was treated in an analogous fashion to that described for the synthesis of tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate to afford the title compounds. LC/MS [M+H]$^+$: 592.47.

REFERENCE EXAMPLE 64

3-(2-Aminobenzo[d]thiazol-4-yl)-2-(1-(4-methoxybenzyl)-1H-tetrazol-5-yl)-6-neopentylbenzenesulfonamide and 3-(2-aminobenzo[d]thiazol-4-yl)-2-(2-(4-methoxybenzyl)-2H-tetrazol-5-yl)-6-neopentylbenzenesulfonamide

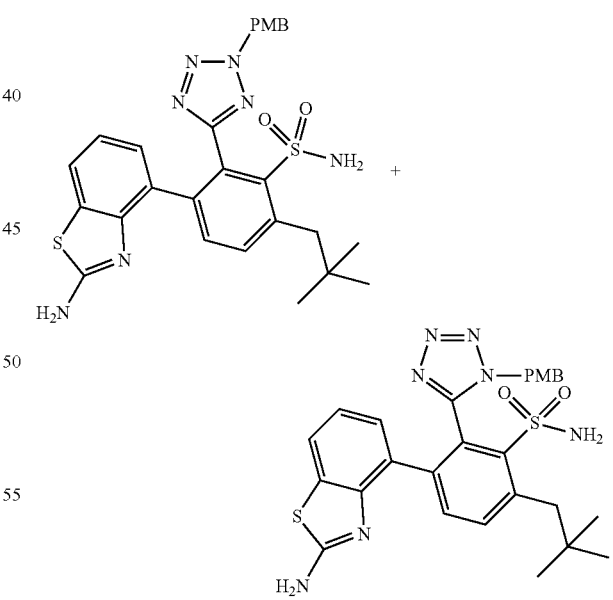

The title compounds were prepared in an analogous fashion to that described for 3-(2-Aminobenzo[d]thiazol-4-yl)-6-(cyclobutylmethyl)-N-(4-methoxybenzyl)-2-(1-(4-methoxybenzyl)-1H-tetrazol-5-yl)benzenesulfonamide and 3-(2-aminobenzo[d]thiazol-4-yl)-6-(cyclobutylmethyl)-N-(4-methoxybenzyl)-2-(2-(4-methoxybenzyl)-2H-tetrazol-5-yl)benzenesulfonamide Starting from tert-butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate and 0.5 M Neopentylzinc Bromide (2369 µl, 1.185 mmol). LC/MS [M+H]+: 564.57.

REFERENCE EXAMPLE 65

3-(4-(2-Aminobenzo[d]thiazol-4-yl)-3-(1-(4-methoxybenzyl)-1H-tetrazol-5-yl)-2-sulfamoylphenyl)propanoic acid and 3-(4-(2-aminobenzo[d]thiazol-4-yl)-3-(2-(4-methoxybenzyl)-2H-tetrazol-5-yl)-2-sulfamoylphenyl)propanoic acid

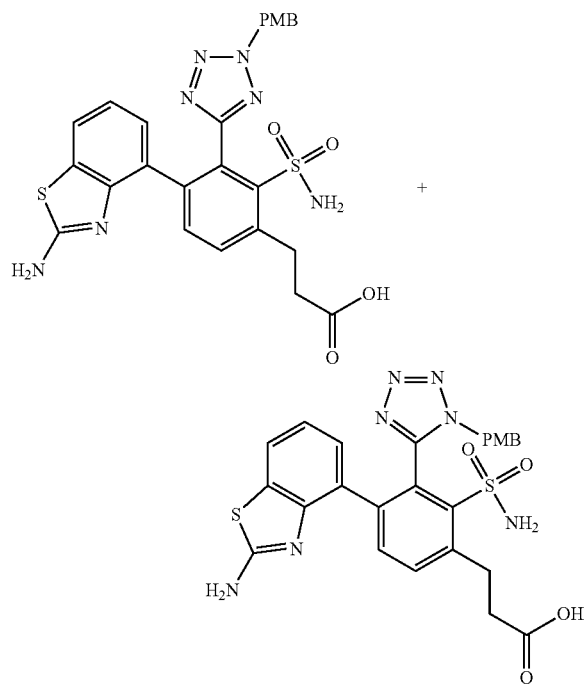

Step A: 3-(2-(N,N-Bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)propanoic acid and 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoic acid To a solution of ethyl 3-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)propanoate and ethyl 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoate (220 mg, 0.236 mmol) was dissolved in dioxane (2355 µl):water (2355 µl) and LiOH (28.2 mg, 1.178 mmol) was added to the system. The solution was stirred for 16 hr. The solution was then added to EtOAc (60 mL) and washed with brine (2×20 mL). The organic was dried and used without further purification to isolate the title compounds. LC/MS [M+H]+: 906.91

Step B: 3-(4-(2-Aminobenzo[d]thiazol-4-yl)-3-(1-(4-methoxybenzyl)-1H-tetrazol-5-yl)-2-sulfamoylphenyl)propanoic acid and 3-(4-(2-aminobenzo[d]thiazol-4-yl)-3-(2-(4-methoxybenzyl)-2H-tetrazol-5-yl)-2-sulfamoylphenyl)propanoic acid To a solution of 3-(2-(N,N-Bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)propanoic acid and 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoic acid (100 mg, 0.110 mmol) was treated in the same fashion as described for the synthesis of tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate to afford the title compounds. LC/MS [M+H]+: 566.44.

REFERENCE EXAMPLE 66

3-(4-(2-Aminobenzo[d]thiazol-4-yl)-3-(1-(4-methoxybenzyl)-1H-tetrazol-5-yl)-2-sulfamoylphenyl)-N-(4-methoxybenzyl)propanamide and 3-(4-(2-aminobenzo[d]thiazol-4-yl)-3-(2-(4-methoxybenzyl)-2H-tetrazol-5-yl)-2-sulfamoylphenyl)-N-(4-methoxybenzyl)propanamide

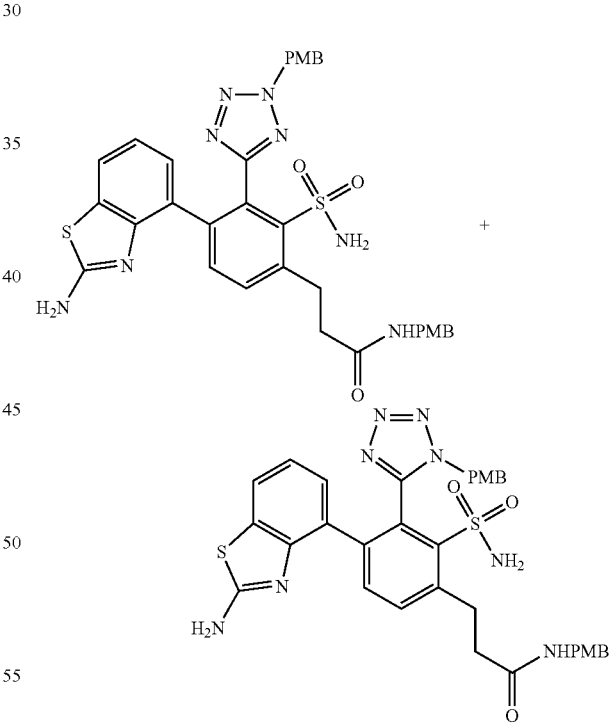

Step A: tert-Butyl (4-(4-(3-(bis(4-methoxybenzyl)amino)-3-oxopropyl)-3-(N,N-bis(4-methoxybenzyl)sulfamoyl)-2-(1-(4-methoxybenzyl)-1H-tetrazol-5-yl)phenyl)benzo[d]thiazol-2-yl)carbamate and tert-butyl (4-(4-(3-(bis(4-methoxybenzyl)amino)-3-oxopropyl)-3-(N,N-bis(4-methoxybenzyl)sulfamoyl)-2-(2-(4-methoxybenzyl)-2H-tetrazol-5-yl)phenyl)benzo[d]thiazol-2-yl)carbamate To a solution of 3-(2-(N,N-bis(4-methoxybenzyl)sulfamoyl)-4-(2-((tert-butoxycarbonyl)amino)benzo[d]thiazol-4- yl)-3-(1-(4-methoxybenzyl)-1H-tetrazol-5-yl)phenyl)propanoic acid and 3-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)propanoic acid (100 mg, 0.110 mmol) was dissolved in DMF (3 mL) and EDC (52.9 mg, 0.276 mmol), HOAT (1.502 mg, 0.011 mmol), and DIPEA (0.077 mL, 0.441 mmol) was added. This was stirred for 5 minutes before the addition of bis(4-methoxybenzyl)amine (85 mg, 0.331 mmol). The solution was stirred under an atmosphere of nitrogen for 16 hr. The solution was diluted with EtOAc (40 mL) and extracted with water (2×20 mL), brine (2×20 mL), dried (MgSO$_4$) and concentrated. The reaction mixture was used without further purification to isolate the title compounds. LC/MS [M+H]$^+$: 1146.24.

Step B: 3-(4-(2-Aminobenzo[d]thiazol-4-yl)-3-(1-(4-methoxybenzyl)-1H-tetrazol-5-yl)-2-sulfamoylphenyl)-N-(4-methoxybenzyl)propanamide and 3-(4-(2-aminobenzo[d]thiazol-4-yl)-3-(2-(4-methoxybenzyl)-2H-tetrazol-5-yl)-2-sulfamoylphenyl)-N-(4-methoxybenzyl)propanamide To a solution of tert-butyl (4-(4-(3-(bis(4-methoxybenzyl)amino)-3-oxopropyl)-3-(N,N-bis(4-methoxybenzyl)sulfamoyl)-2-(1-(4-methoxybenzyl)-1H-tetrazol-5-yl)phenyl)benzo[d]thiazol-2-yl)carbamate compound with tert-butyl (4-(4-(3-(bis(4-methoxybenzyl)amino)-3-oxopropyl)-3-(N,N-bis(4-methoxybenzyl)sulfamoyl)-2-(2-(4-methoxybenzyl)-2H-tetrazol-5-yl)phenyl)benzo[d]thiazol-2-yl)carbamate (126 mg, 0.110 mmol) was treated in the same fashion as described for the synthesis of tert-Butyl 2-(4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)acetate and tert-butyl 2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)acetate to afford the title compounds. LC/MS [M+H]$^+$: 685.63.

REFERENCE EXAMPLE 67 tert-Butyl (4-(3-(N,N-bis(4-methoxybenzyl)sulfamoyl)-4-ethynyl-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-ethynyl-2-(2-(4-methoxybenzyl)-2H-tetrazol-5-yl)phenyl)benzo[d]thiazol-2-yl)carbamate

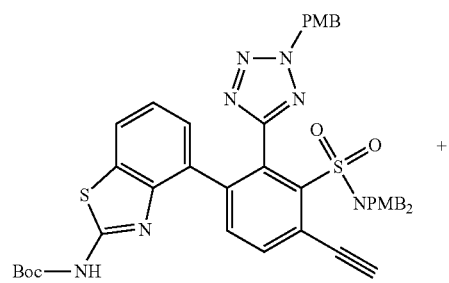

+

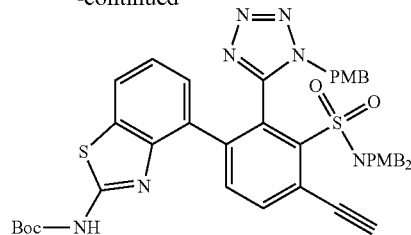

Step A: 3-(2-Aminobenzo[d]thiazol-4-yl)-N,N-bis(4-methoxybenzyl)-2-(1-(4-methoxybenzyl)-1H-tetrazol-5-yl)-6-((trimethylsilyl)ethynyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-((trimethylsilyl)ethynyl)benzenesulfonamide To a solution of 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-bromo-N,N-bis(4-methoxybenzyl)-2-(2-(4-methoxybenzyl)-2H-tetrazol-5-yl)benzenesulfonamide (3.5 g, 4.31 mmol) was treated as in the synthesis of N,N-bis(4-methoxybenzyl)-2-(2-(4-methoxybenzyl)-2H-tetrazol-5-yl)-3-((trimethylsilyl)ethynyl)benzenesulfonamide and N,N-bis(4-methoxybenzyl)-2-(1-(4-methoxybenzyl)-1H-tetrazol-5-yl)-3-((trimethylsilyl)ethynyl)benzenesulfonamide to afford the title compounds. LC/MS [M+H]$^+$: 830.72.

Step B: 3-(2-Aminobenzo[d]thiazol-4-yl)-6-ethynyl-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-ethynyl-N,N-bis(4-methoxybenzyl)-2-(2-(4-methoxybenzyl)-2H-tetrazol-5-yl)benzenesulfonamide To a solution of 3-(2-aminobenzo[d]thiazol-4-yl)-N,N-bis(4-methoxybenzyl)-2-(1-(4-methoxybenzyl)-1H-tetrazol-5-yl)-6-((trimethylsilyl)ethynyl)benzenesulfonamide and 3-(2-aminobenzo[d]thiazol-4-yl)-N,N-bis(4-methoxybenzyl)-2-(2-(4-methoxybenzyl)-2H-tetrazol-5-yl)-6-((trimethylsilyl)ethynyl)benzenesulfonamide (3.1 g, 3.73 mmol) in THF was stirred with TBAF (2 equivalents) at room temperature for 1 hr. The mixture was diluted with ether (100 mL), washed with brine (3×25 mL), dried over MgSO$_4$ and concentrated to give the title compound.

Step C: tert-Butyl (4-(3-(N,N-bis(4-methoxybenzyl)sulfamoyl)-4-ethynyl-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-ethynyl-2-(2-(4-methoxybenzyl)-2H-tetrazol-5-yl)phenyl)benzo[d]thiazol-2-yl)carbamate To a solution of 3-(2-aminobenzo[d]thiazol-4-yl)-6-ethynyl-N,N-bis(4-methoxybenzyl)-2-(1-(4-methoxybenzyl)-1H-tetrazol-5-yl)benzenesulfonamide and 3-(2-aminobenzo[d]thiazol-4-yl)-6-ethynyl-N,N-bis(4-methoxybenzyl)-2-(2-(4-methoxybenzyl)-2H-tetrazol-5-yl)benzenesulfonamide was treated as in the synthesis of tert-Butyl N-[4-[3-[bis[(4-methoxyphenyl)methyl]sulfamoyl]-4-bromo-2-[2-[(4-methoxyphenyl)methyl]tetrazol-5-yl]phenyl]-1,3-benzothiazol-2-yl]-N-tert-butoxycarbonyl-carbamate and tert-butyl N-[4-[3-[bis[(4-methoxyphenyl)methyl]sulfamoyl]-4-bromo-2-[1-[(4-methoxyphenyl)methyl]tetrazol-5-yl]phenyl]-1,3-benzothiazol-2-yl]-N-tert-butoxycarbonyl-carbamate to provide the title compounds. LC/MS [M+H]$^+$: 858.71.

REFERENCE EXAMPLE 68 tert-Butyl 4-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenethyl)piperidine-1-carboxylate and tert-butyl 4-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenethyl)piperidine-1-carboxylate

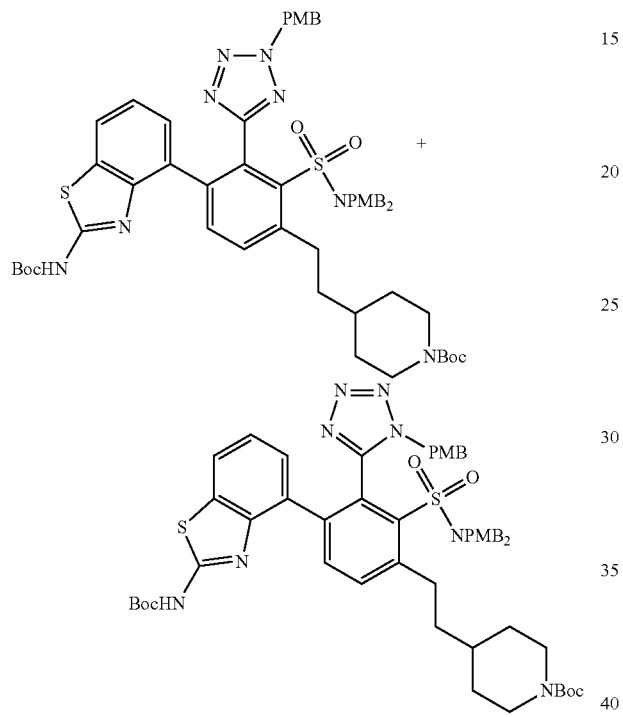

Step A: tert-Butyl 4-((2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)ethynyl)-3,6-dihydropyridine-1(2H)-carboxylate and tert-butyl 4-((2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)ethynyl)-3,6-dihydropyridine-1(2H)-carboxylate To a solution of tert-butyl (4-(3-(N,N-bis(4-methoxybenzyl)sulfamoyl)-4-ethynyl-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-ethynyl-2-(2-(4-methoxybenzyl)-2H-tetrazol-5-yl)phenyl)benzo[d]thiazol-2-yl)carbamate (0.4 g, 0.466 mmol) and tert-butyl 4-bromo-5,6-dihydropyridine-1(2H)-carboxylate (0.183 g, 0.699 mmol) was treated as in the synthesis of 3-((6-Amino-5-(hydroxymethyl)pyridin-3-yl)ethynyl)-N,N-bis(4-methoxybenzyl)-2-(2-(4-methoxybenzyl)-2H-tetrazol-5-yl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)benzenesulfonamide to provide the title compounds. LC/MS [M+H]⁺: 1039.96.

Step B: tert-Butyl 4-(2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenethyl)piperidine-1-carboxylate and tert-butyl 4-(2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenethyl)piperidine-1-carboxylate To a solution of tert-butyl 4-((2-(N,N-bis(4-methoxybenzyl)sulfamoyl)-4-(2-((tert-butoxycarbonyl)amino)benzo[d]thiazol-4-yl)-3-(1-(4-methoxybenzyl)-1H-tetrazol-5-yl)phenyl)ethynyl)-3,6-dihydropyridine-1(2H)-carboxylate and tert-butyl 4-((2-(N,N-bis(4-methoxybenzyl)sulfamoyl)-4-(2-((tert-butoxycarbonyl)amino)benzo[d]thiazol-4-yl)-3-(2-(4-methoxybenzyl)-2H-tetrazol-5-yl)phenyl)ethynyl)-3,6-dihydropyridine-1(2H)-carboxylate (0.090 g, 0.087 mmol) are treated as in the synthesis of 3-(2-(6-Amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide and 3-(2-(6-amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide to isolate the title compounds.

REFERENCE EXAMPLE 69 tert-Butyl (4-(3-(N,N-bis(4-methoxybenzyl)sulfamoyl)-4-(2-(4-((tert-butoxycarbonyl)amino)cyclohexyl)ethyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(2-(4-((tert-butoxycarbonyl)amino)cyclohexyl)ethyl)-2-(2-(4-methoxybenzyl)-2H-tetrazol-5-yl)phenyl)benzo[d]thiazol-2-yl)carbamate

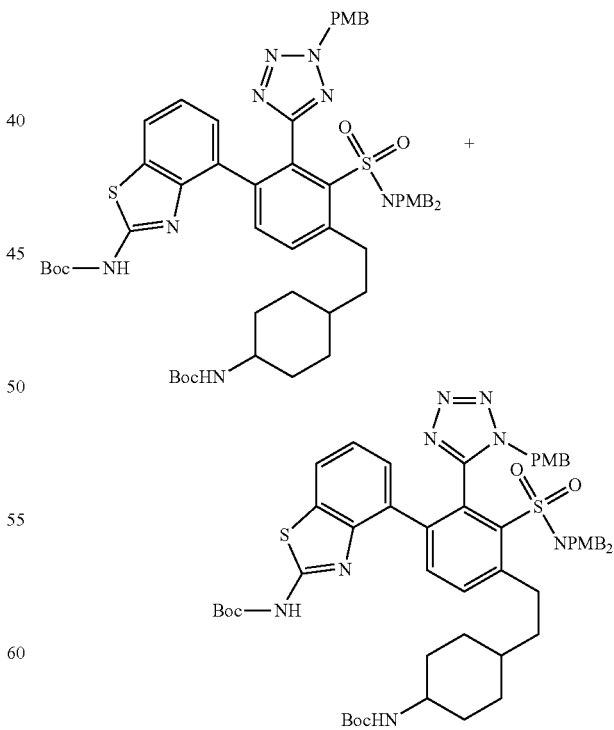

Step A: tert-Butyl (4-(3-(N,N-bis(4-methoxybenzyl)sulfamoyl)-4-((4-((tert-butoxycarbonyl)amino)cyclohex-1-en-1-yl)ethynyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-((4-((tert-butoxycarbonyl)amino)cyclohex-1-en-1-yl)ethynyl)-2-(2-(4-methoxybenzyl)-2H-tetrazol-5-yl)phenyl)benzo[d]thiazol-2-yl)carbamate To a solution of tert-butyl (4-(3-(N,N-bis(4-methoxybenzyl)sulfamoyl)-4-ethynyl-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-ethynyl-2-(2-(4-methoxybenzyl)-2H-tetrazol-5-yl)phenyl)benzo[d]thiazol-2-yl)carbamate (0.2 g, 0.233 mmol) was added 4-((tert-butoxycarbonyl)amino)cyclohex-1-en-1-yl trifluoromethanesulfonate (0.121 g, 0.350 mmol) and was treated as in the synthesis of 3-((6-Amino-5-(hydroxymethyl)pyridin-3-yl)ethynyl)-N,N-bis(4-methoxybenzyl)-2-(2-(4-methoxybenzyl)-2H-tetrazol-5-yl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)benzenesulfonamide to provide the title compounds. LC/MS [M+H]$^+$: 1054.05.

Step B: tert-Butyl (4-(3-(N,N-bis(4-methoxybenzyl)sulfamoyl)-4-(2-(4-((tert-butoxycarbonyl)amino)cyclohexyl)ethyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-(2-(4-((tert-butoxycarbonyl)amino)cyclohexyl)ethyl)-2-(2-(4-methoxybenzyl)-2H-tetrazol-5-yl)phenyl)benzo[d]thiazol-2-yl)carbamate A solution of tert-butyl (4-(3-(N,N-bis(4-methoxybenzyl)sulfamoyl)-4-((4-((tert-butoxycarbonyl)amino)cyclohex-1-en-1-yl)ethynyl)-2-(1-(4-methoxybenzyl)-1H-tetrazol-5-yl)phenyl)benzo[d]thiazol-2-yl)carbamate and tert-butyl (4-(3-(N,N-bis(4-methoxybenzyl)sulfamoyl)-4-((4-((tert-butoxycarbonyl)amino)cyclohex-1-en-1-yl)ethynyl)-2-(2-(4-methoxybenzyl)-2H-tetrazol-5-yl)phenyl)benzo[d]thiazol-2-yl)carbamate (0.090 g, 0.085 mmol) was treated as in the synthesis of 3-(2-(6-Amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide and 3-(2-(6-amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide to isolate the title compounds. LC/MS [M+H]$^+$: 1060.03.

REFERENCE EXAMPLE 70

3,6-Bis(5-hydroxypentyl)-N,N-bis(4-methoxybenzyl)-2-(1-(4-methoxybenzyl)-1H-tetrazol-5-yl)benzenesulfonamide and 3,6-bis(5-hydroxypentyl)-N,N-bis(4-methoxybenzyl)-2-(2-(4-methoxybenzyl)-2H-tetrazol-5-yl)benzenesulfonamide

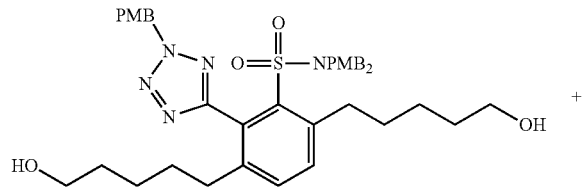

+

-continued

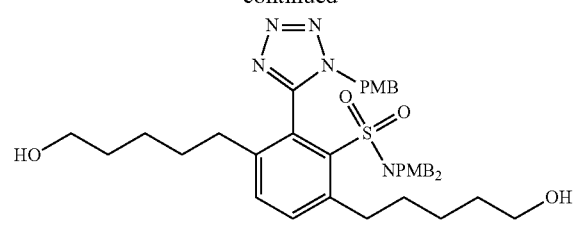

Step A: Diethyl 5,5'-(2-(N,N-bis(4-methoxybenzyl)sulfamoyl)-3-(1-(4-methoxybenzyl)-1H-tetrazol-5-yl)-1,4-phenylene)dipentanoate and diethyl 5,5'-(2-(N,N-bis(4-methoxybenzyl)sulfamoyl)-3-(2-(4-methoxybenzyl)-2H-tetrazol-5-yl)-1,4-phenylene)dipentanoate To a solution of 6-bromo-3-iodo-N,N-bis(4-methoxybenzyl)-2-(2-(4-methoxybenzyl)-2H-tetrazol-5-yl)benzenesulfonamide and 6-bromo-3-iodo-N,N-bis(4-methoxybenzyl)-2-(1-(4-methoxybenzyl)-1H-tetrazol-5-yl)benzenesulfonamide was added 0.5 M 5-ethoxy-oxopentylzinc bromide (1.27E+04 µl, 6.33 mmol) and treated in an analogous fashion as in the synthesis of tert-Butyl 2-(2-(N,N-bis(4-methoxybenzyl)sulfamoyl)-3-(1-(4-methoxybenzyl)tetrazolidin-5-yl)-4-(quinolin-5-yl)phenyl)acetate and tert-butyl 2-(2-(N,N-bis(4-methoxybenzyl)sulfamoyl)-3-(2-(4-methoxybenzyl)-2H-tetrazol-5-yl)-4-(quinolin-5-yl)phenyl)acetate to provide the title compounds. LC/MS [M+H]$^+$: 842.75.

Step B: 3,6-Bis(5-hydroxypentyl)-N,N-bis(4-methoxybenzyl)-2-(1-(4-methoxybenzyl)-1H-tetrazol-5-yl)benzenesulfonamide and 3,6-bis(5-hydroxypentyl)-N,N-bis(4-methoxybenzyl)-2-(2-(4-methoxybenzyl)-2H-tetrazol-5-yl)benzenesulfonamide To the solution of diethyl 5,5'-(2-(N,N-bis(4-methoxybenzyl)sulfamoyl)-3-(1-(4-methoxybenzyl)-1H-tetrazol-5-yl)-1,4-phenylene)dipentanoate and diethyl 5,5'-(2-(N,N-bis(4-methoxybenzyl)sulfamoyl)-3-(2-(4-methoxybenzyl)-2H-tetrazol-5-yl)-1,4-phenylene)dipentanoate (210 mg, 0.249 mmol) in THF (10 mL) was added DIBAL-H (2.494 mL, 2.494 mmol). The solution was stirred for 2 hr and the reaction was quenched with HCl (1.871 mL, 3.74 mmol) and then concentrated under reduced pressure to yield the title compound. LC/MS [M+H]$^+$: 758.7

REFERENCE EXAMPLE 71

3,6-Bis(6-hydroxyhexyl)-N,N-bis(4-methoxybenzyl)-2-(1-(4-methoxybenzyl)-1H-tetrazol-5-yl)benzenesulfonamide and 3,6-bis(6-hydroxyhexyl)-N,N-bis(4-methoxybenzyl)-2-(2-(4-methoxybenzyl)-2H-tetrazol-5-yl)benzenesulfonamide

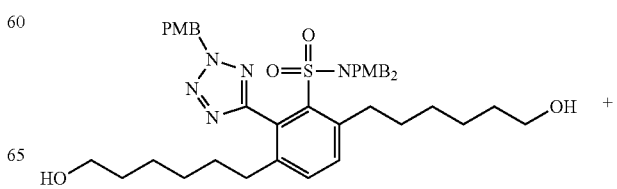

+

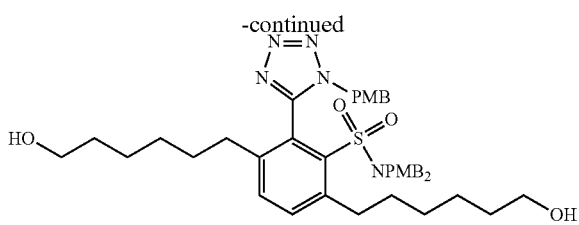

Step A: Di-tert-butyl 6,6'-(2-(N,N-bis(4-methoxybenzyl)sulfamoyl)-3-(1-(4-methoxybenzyl)-1H-tetrazol-5-yl)-1,4-phenylene)dihexanoate and di-tert-butyl 6,6'-(2-(N,N-bis(4-methoxybenzyl)sulfamoyl)-3-(2-(4-methoxybenzyl)-2H-tetrazol-5-yl)-1,4-phenylene)dihexanoate To a solution of 6-bromo-3-iodo-N,N-bis(4-methoxybenzyl)-2-(2-(4-methoxybenzyl)-2H-tetrazol-5-yl)benzenesulfonamide and 6-bromo-3-iodo-N,N-bis(4-methoxybenzyl)-2-(1-(4-methoxybenzyl)-1H-tetrazol-5-yl)benzenesulfonamide (500 mg, 0.670 mmol) was added 0.5 M (6-(tert-butoxy)-6-oxohexyl)zinc(II) bromide (13.400 mL, 6.70 mmol) in diethyl ether and was treated in an analogous fashion as in the synthesis of tert-Butyl 2-(2-(N,N-bis(4-methoxybenzyl)sulfamoyl)-3-(1-(4-methoxybenzyl)tetrazolidin-5-yl)-4-(quinolin-5-yl)phenyl)acetate and tert-butyl 2-(2-(N,N-bis(4-methoxybenzyl)sulfamoyl)-3-(2-(4-methoxybenzyl)-2H-tetrazol-5-yl)-4-(quinolin-5-yl)phenyl)acetate to provide the title compounds. LC/MS [M+H]⁺: 927.03.

Step B: 3,6-Bis(6-hydroxyhexyl)-N,N-bis(4-methoxybenzyl)-2-(1-(4-methoxybenzyl)-1H-tetrazol-5-yl)benzenesulfonamide and 3,6-bis(6-hydroxyhexyl)-N,N-bis(4-methoxybenzyl)-2-(2-(4-methoxybenzyl)-2H-tetrazol-5-yl)benzenesulfonamide To a solution of di-tert-butyl 6,6'-(2-(N,N-bis(4-methoxybenzyl)sulfamoyl)-3-(1-(4-methoxybenzyl)-1H-tetrazol-5-yl)-1,4-phenylene)dihexanoate and di-tert-butyl 6,6'-(2-(N,N-bis(4-methoxybenzyl)sulfamoyl)-3-(2-(4-methoxybenzyl)-2H-tetrazol-5-yl)-1,4-phenylene)dihexanoate (412 mg, 0.445 mmol) was treated in the same fashion as in the synthesis of 6-(2-Hydroxyethyl)-N,N-bis(4-methoxybenzyl)-2-(1-(4-methoxybenzyl)-1H-tetrazol-5-yl)-3-(quinolin-5-yl)benzenesulfonamide and 6-(2-hydroxyethyl)-N,N-bis(4-methoxybenzyl)-2-(2-(4-methoxybenzyl)-2H-tetrazol-5-yl)-3-(quinolin-5-yl)benzenesulfonamide to provide the title compound. LC/MS [M+H]⁺: 786.83.

EXAMPLE 1

4'-Methyl-2-(1H-tetrazol-5-yl)-[1,1'-biphenyl]-3-sulfonamide

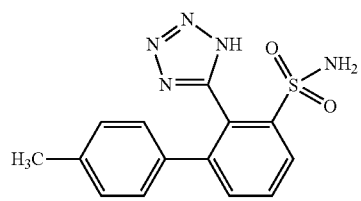 [SMILES: Cc1ccc(-c2cccc(S(N)(=O)=O)c2-c2nnn[nH]2)cc1]

To a solution of 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide (250 mg, 0.589 mmol) in a mixture of DME (4 mL) and water (1 mL) was added bis(tri-tert-butylphosphine)palladium(0) (30.1 mg, 0.059 mmol), p-tolylboronic acid (96 mg, 0.707 mmol) and Na₂CO₃ (74.9 mg, 0.707 mmol) at rt. The resulting mixture was degassed and heated at 97° C. for 12 hr. The reaction mixture was cooled to rt, diluted with ethyl acetate (20 mL), washed with 1N HCl (10 mL) followed by brine (10 mL). The organic layer was dried over MgSO₄, filtered and concentrated to dryness to give crude products which were taken to the next step without further purification. To this crude product was added anisole (0.102 mL, 0.932 mmol) followed by TFA (3 mL) and the resulting mixture was stirred at room temperature for 12 hr. The reaction mixture was concentrated to dryness and purified by reverse phase C18 column using 0 to 90% water (0.05% TFA) in acetonitrile (0.05% TFA). LC/MS (M+Na)⁺: 338.2.

EXAMPLES 2-18

Parallel Synthesis of 4'-Substituted 2-(1H-tetrazol-5-yl)-[1,1'-biphenyl]-3-sulfonamides

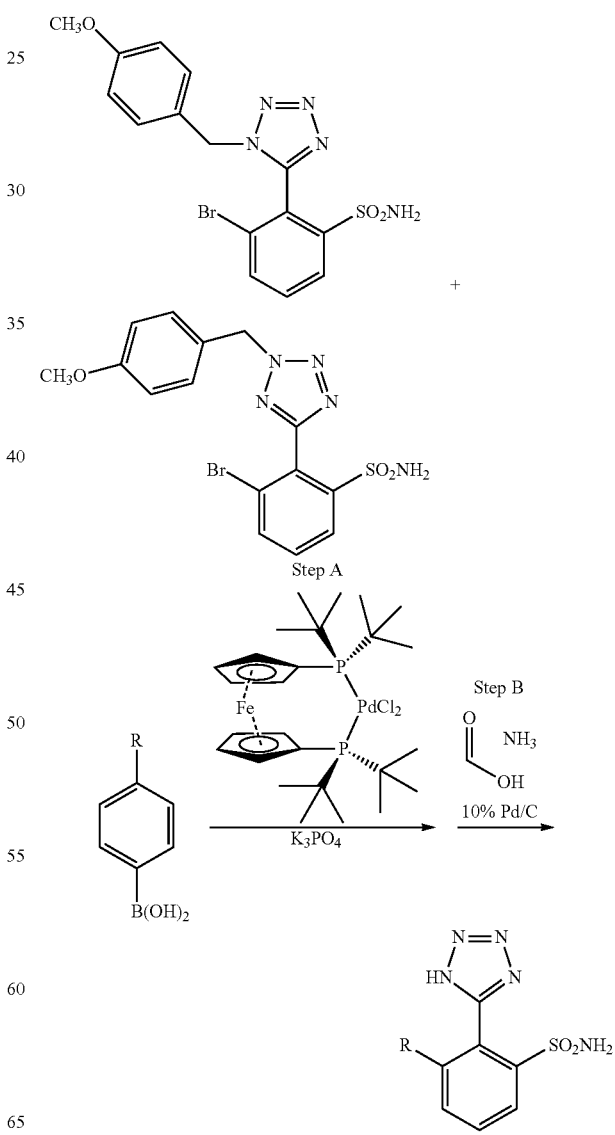

Step A: Palladium Catalyzed C—C Coupling of Arylbromide and Boronic Acids or Boronic Esters (Such as Pinacol Esters)

Into 2 dram vials were added substituted boronic acid or esters (commercially available, known from the literature, or prepared as described herein) and 1,1'-bis(di-tert-butylphosphino) ferrocene palladium chloride (2.480 mg, 3.80 µmol) and 254 µL of 1 N degassed aq. $K_3PO_4$ solution. In a glove box under a dry nitrogen atmosphere, 1.5 mL of a solution of the mixture of isomers 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide from Reference Example 1 (25 mg, 0.063 mmol) in EtOH were added into each vial. The vials were capped and heated at 70° C. with stirring for 20 hr. After the vials were cooled to room temperature, the solvent was removed in a GeneVac. Into each residue was added 600 µL of $H_2O$ and 2 mL of EtOAc. The organic layers were transferred into 2 dram vials. The organic solvent was removed in GeneVac to afford the crude intermediates which were deprotected without further purification in the subsequent step.

Step B: Removal of the p-methoxybenzyl (PMB) Protecting Group by Hydrogenation

The residues from Step A were dissolved in 1.5 mL of EtOH. Into each vial was added 20 mg of 10% Pd/C and 250 mg of ammonium formate (250.0 mg, 3.96 mmol). The vials were sealed and heated at 55° C. under stirring. The pressure was released periodically by unscrewing the cap. After 5 hr, the reactions were monitored by UPLC. The reaction only partially proceeded. Another aliquot of ammonium formate (250.0 mg, 3.96 mmol) was added and the vial heated at 55° C. for another 5 hrs. The mixtures were cooled to room temperature and filtered through filters. The filtrates were concentrated in a GeneVac. The residues were dissolved in DMSO. Each crude mixture was filtered into a 96-well tray and purified with HPLC to afford Examples 2-18.

| Ex. No. | Structure | Name | Calc'd MW [M + H]+ | LC/MS m/e [M + H]+ |
|---|---|---|---|---|
| 2 | 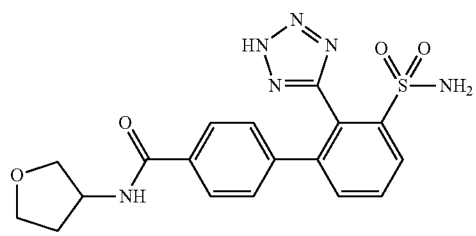 [SMILES: NS(=O)(=O)c1cccc(-c2ccc(C(=O)NC3CCOC3)cc2)c1-c1nn[nH]n1] | 3'-sulfamoyl-N-(tetrahydrofuran-3-yl)-2'-(2H-tetrazol-5-yl)biphenyl-4-carboxamide | 415.1 | 415.1 |
| 3 | 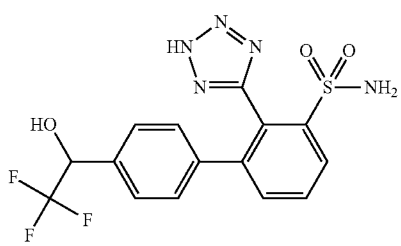 [SMILES: NS(=O)(=O)c1cccc(-c2ccc(C(O)C(F)(F)F)cc2)c1-c1nn[nH]n1] | 2(2H-tetrazol-5-yl)4'-(2,2,2-trifluoro-1-hydroxyethyl)biphenyl-3-sulfonamide | 400.1 | 400.1 |
| 4 | 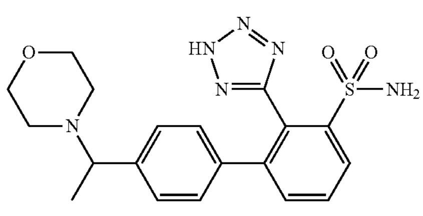 [SMILES: CC(c1ccc(-c2cccc(S(N)(=O)=O)c2-c2nn[nH]n2)cc1)N1CCOCC1] | 4'-(1-morpholin-4-ylethyl)-2-(2H-tetrazol-5-yl)biphenyl-3-sulfonamide | 415.2 | 415.2 |
| 5 | 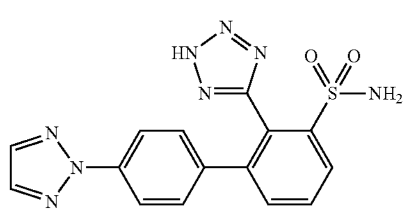 [SMILES: NS(=O)(=O)c1cccc(-c2ccc(-n3nccn3)cc2)c1-c1nn[nH]n1] | 2-(2H-tetrazol-5-yl)-4'-(2H-1,2,3-triazol-2-yl)biphenyl-3-sulfonamide | 369.1 | 369.1 |

-continued

| Ex. No. | Structure | Name | Calc'd MW [M + H]+ | LC/MS m/e [M + H]+ |
|---|---|---|---|---|
| 6 | 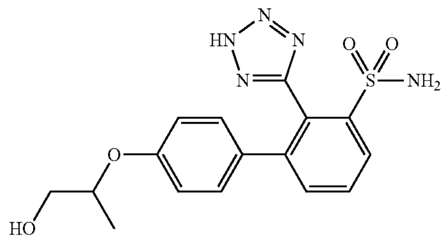 [SMILES: CC(CO)Oc1ccc(-c2cccc(S(N)(=O)=O)c2-c2nn[nH]n2)cc1] | 4'-(2-hydroxy-1-methylethoxy)-2-(2H-tetrazol-5-yl)biphenyl-3-sulfonamide | 376.1 | 376.1 |
| 7 | 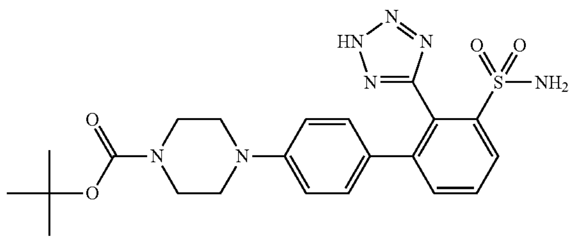 [SMILES: CC(C)(C)OC(=O)N1CCN(c2ccc(-c3cccc(S(N)(=O)=O)c3-c3nn[nH]n3)cc2)CC1] | tert-butyl 4-[3'-sulfamoyl-2'-(2H-tetrazol-5-yl)biphenyl-4-yl]piperazine-1-carboxylate | 486.2 | 486.2 |
| 8 | 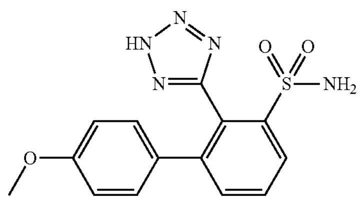 [SMILES: COc1ccc(-c2cccc(S(N)(=O)=O)c2-c2nn[nH]n2)cc1] | 4'-methoxy-2-(2H-tetrazol-5-yl)biphenyl-3-sulfonamide | 332.1 | 332.1 |
| 9 | 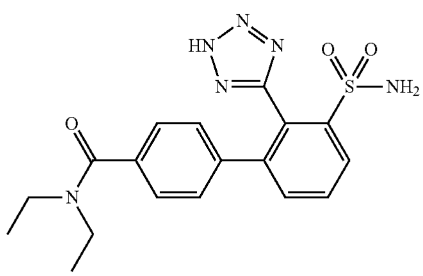 [SMILES: CCN(CC)C(=O)c1ccc(-c2cccc(S(N)(=O)=O)c2-c2nn[nH]n2)cc1] | N,N-diethyl-3'-sulfamoyl-2'-(2H-tetrazol-5-yl)biphenyl-4-carboxamide | 401.1 | 401.1 |
| 10 | 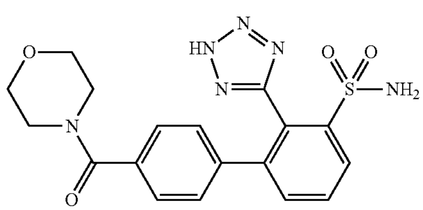 [SMILES: NS(=O)(=O)c1cccc(-c2ccc(C(=O)N3CCOCC3)cc2)c1-c1nn[nH]n1] | 4'-(morpholin-4-ylcarbonyl)-2-(2H-tetrazol-5-yl)biphenyl-3-sulfonamide | 415.1 | 415.1 |
| 11 | 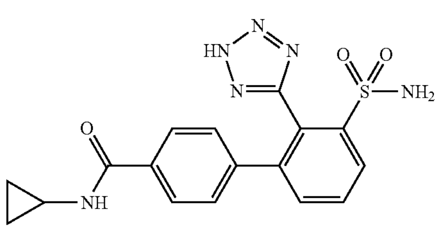 [SMILES: NS(=O)(=O)c1cccc(-c2ccc(C(=O)NC3CC3)cc2)c1-c1nn[nH]n1] | N-cyclopropyl-3'-sulfamoyl-2'-(2H-tetrazol-5-yl)biphenyl-4-carboxamide | 385.1 | 385.1 |

-continued

| Ex. No. | Structure | Name | Calc'd MW [M + H]+ | LC/MS m/e [M + H]+ |
|---|---|---|---|---|
| 12 | 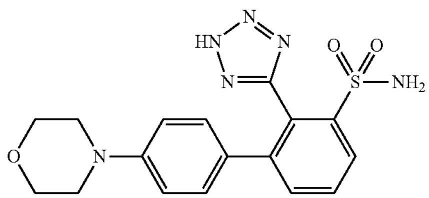 [SMILES: NS(=O)(=O)c1cccc(-c2ccc(N3CCOCC3)cc2)c1-c1nn[nH]n1] | 4'-(morpholin-4-yl-2-(2H-tetrazol-5-yl)biphenyl-3-sulfonamide | 387.1 | 387.1 |
| 13 | 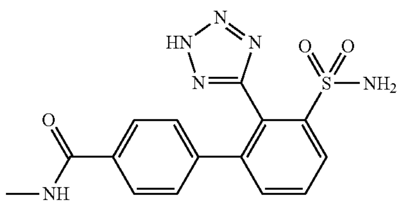 [SMILES: CNC(=O)c1ccc(-c2cccc(S(N)(=O)=O)c2-c2nn[nH]n2)cc1] | N-methyl-3'-sulfamoyl-2'-(2H-tetrazol-5-yl)biphenyl-4-carboxamide | 359.1 | 359.1 |
| 14 | 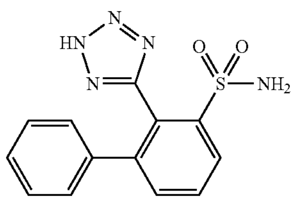 [SMILES: NS(=O)(=O)c1cccc(-c2ccccc2)c1-c1nn[nH]n1] | 2-(2H-tetrazol-5-yl)biphenyl-3-sulfonamide | 302.1 | 302.1 |
| 15 | 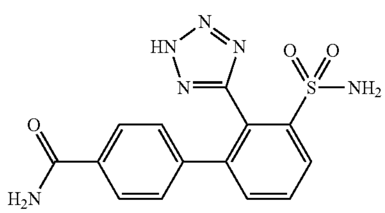 [SMILES: NC(=O)c1ccc(-c2cccc(S(N)(=O)=O)c2-c2nn[nH]n2)cc1] | 3'-sulfamoyl-2'-(2H-tetrazol-5-yl)biphenyl-4-carboxamide | 345.1 | 345.1 |
| 16 | 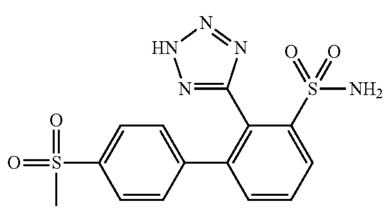 [SMILES: CS(=O)(=O)c1ccc(-c2cccc(S(N)(=O)=O)c2-c2nn[nH]n2)cc1] | 4'-(methylsulfonyl)-2-(2H-tetrazol-5-yl)biphenyl-3-sulfonamide | 380.0 | 380.0 |
| 17 | 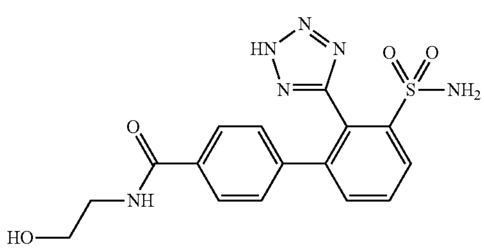 [SMILES: NS(=O)(=O)c1cccc(-c2ccc(C(=O)NCCO)cc2)c1-c1nn[nH]n1] | N-(2-hydroxyethyl)-3'-sulfamoyl-2'-(2H-tetrazol-5-yl)biphenyl-4-carboxamide | 389.1 | 389.1 |
| 18 | 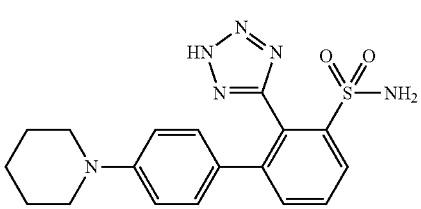 [SMILES: NS(=O)(=O)c1cccc(-c2ccc(N3CCCCC3)cc2)c1-c1nn[nH]n1] | 4'-piperidin-1-yl-2-(2H-tetrazol-5-yl)biphenyl-3-sulfonamide | 385.1 | 385.1 |

EXAMPLES 19-30

Parallel Synthesis of 3-Substituted 2-(1H-tetrazol-5-yl)benzenesulfonamides

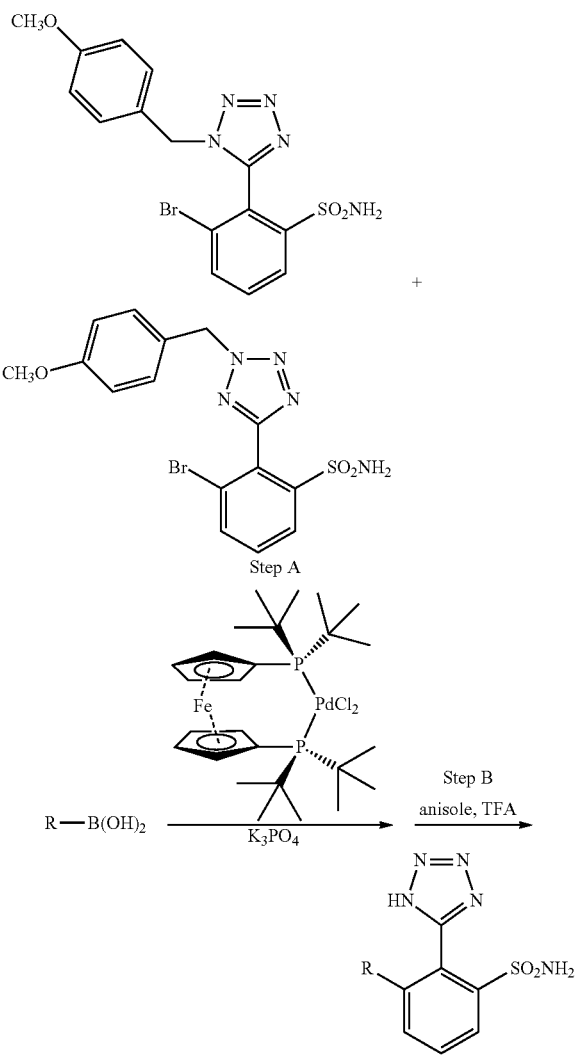

Step A: Palladium Catalyzed C—C Coupling of Arylbromide and Boronic Acids or Boronic Esters (Such as Pinacol Esters)

Into 2 dram vials were added substituted boronic acids or esters (commercially available, or prepared as described herein, 0.071 mmol) and 1,1'-bis(di-tert-butylphosphino) ferrocene palladium chloride (3.07 mg, 4.7 μmol) and 189 μL of 1 N degassed aq. $K_3PO_4$ solution. In glove box, 1.3 mL of solution of the mixture of isomeric 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide from Reference Example 1 (20 mg, 0.047 mmol) in EtOH were added into each vial. The vials were capped and heated at 70° C. with stirring for 20 hr (overnight). After the vials were cooled down to room temperature, the solvent was removed in GeneVac. Into each residue was added 600 μL of $H_2O$ and 2 mL of EtOAc. The organic layers were transferred into 2 dram vials. The organic solvent was removed in GeneVac to afford the crude intermediates.

Step B: Removal of the p-methoxybenzyl (PMB) Protecting Group Under Acidic Conditions Into each vial was added a solution of anisole (21 mg) in TFA (600 μL). The vials were heated at 45° C. for 16 hr. The solvent was removed in a GeneVac. The residues were dissolved in 1.3 mL of DMSO. Each crude mixture was filtered into a 96-well tray and purified by HPLC to afford the following Examples. Boronic acids and boronic esters were obtained from commercial sources, are known in the literature, or were prepared as described herein. Note that in some instances the boronic acid used in Step A contains an amine group. In these cases, the reagent is typically obtained with a tert-butoxycarbonyl protective group on the amine moiety, which is concurrently removed under the final PMB deprotection step (Step B) with TFA and anisole.

| Ex. No. | Structure | Name | Calc'd Mass $[M + H]^+$ | LC/MS m/e $[M + H]^+$ |
|---|---|---|---|---|
| 19 | 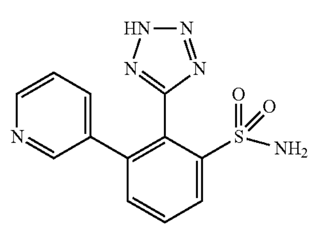 [SMILES: NS(=O)(=O)c1cccc(-c2cccnc2)c1-c1nn[nH]n1] | 3-pyridin-3-yl-2-(2H-tetrazol-5-yl)benzenesulfonamide | 303.3 | ND |

-continued

| Ex. No. | Structure | Name | Calc'd Mass [M + H]+ | LC/MS m/e [M + H]+ |
|---|---|---|---|---|
| 20 | 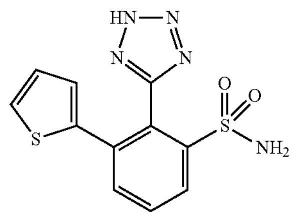 [SMILES: NS(=O)(=O)c1cccc(-c2cccs2)c1-c1nn[nH]n1] | 2-(2H-tetrazol-5-yl)-3-thiophen-2-ylbenzenesulfonamide | 308.4 | 308.0 |
| 21 | 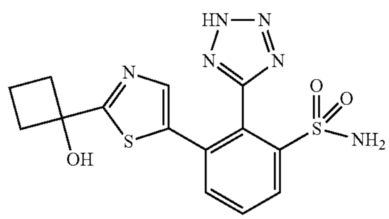 [SMILES: NS(=O)(=O)c1cccc(-c2cnc(C3(O)CCC3)s2)c1-c1nn[nH]n1] | 3-[2-(1-hydroxycyclobutyl)-1,3-thiazol-5-yl]-2-(2H-tetrazol-5-yl)benzenesulfonamide | 379.4 | 379.1 |
| 22 | 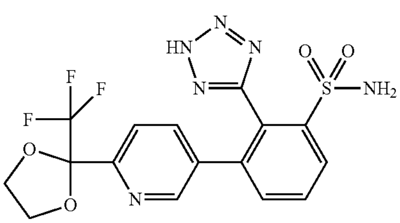 [SMILES: NS(=O)(=O)c1cccc(-c2ccc(C3(C(F)(F)F)OCCO3)nc2)c1-c1nn[nH]n1] | 2-(2H-tetrazol-5-yl)-3-{6-[2-(trifluoromethyl)-1,3-dioxolan-2-yl]pyridin-3-yl}benzenesulfonamide | 443.4 | 443.0 |
| 23 | 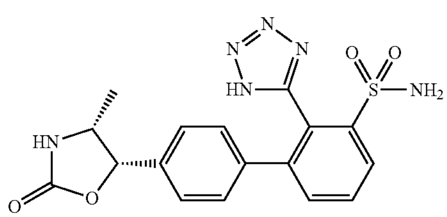 [SMILES: C[C@H]1NC(=O)O[C@H]1c1ccc(-c2cccc(S(N)(=O)=O)c2-c2nnn[nH]2)cc1] | 4'-[(4R,5S)-4-methyl-2-oxo-1,3-oxazolidin-5-yl]-2-(1H-tetrazol-5-yl)biphenyl-3-sulfonamide | 401.4 | 401.1 |
| 24 | 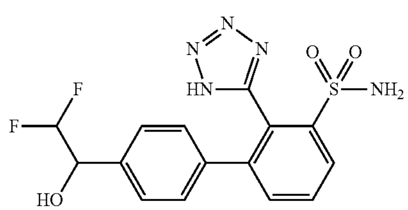 [SMILES: NS(=O)(=O)c1cccc(-c2ccc(C(O)C(F)F)cc2)c1-c1nnn[nH]1] | 4'-(2,2-difluoro-1-hydroxyethyl)-2-(1H-tetrazol-5-yl)biphenyl-3-sulfonamide | 382.4 | 382.1 |
| 25 | 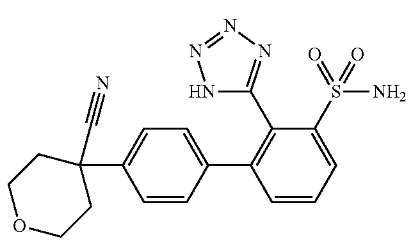 [SMILES: N#CC1(c2ccc(-c3cccc(S(N)(=O)=O)c3-c3nnn[nH]3)cc2)CCOCC1] | 4'-(4-cyanotetrahydro-2H-pyran-4-yl)-2-(1H-tetrazol-5-yl)biphenyl-3-sulfonamide | 411.5 | 411.1 |
| 26 | 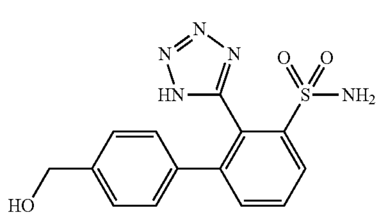 [SMILES: NS(=O)(=O)c1cccc(-c2ccc(CO)cc2)c1-c1nnn[nH]1] | 4'-(hydroxymethyl)-2-(1H-tetrazol-5-yl)biphenyl-3-sulfonamide | 332.4 | 332.1 |

-continued

| Ex. No. | Structure | Name | Calc'd Mass [M + H]+ | LC/MS m/e [M + H]+ |
|---|---|---|---|---|
| 27 | 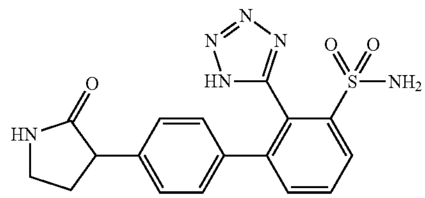 [SMILES: NS(=O)(=O)c1cccc(-c2ccc(C3CCNC3=O)cc2)c1-c1nnn[nH]1] | 4'-(2-oxopyrrolidin-3-yl)-2-(1H-tetrazol-5-yl)biphenyl-3-sulfonamide | 385.4 | 385.1 |
| 28 | 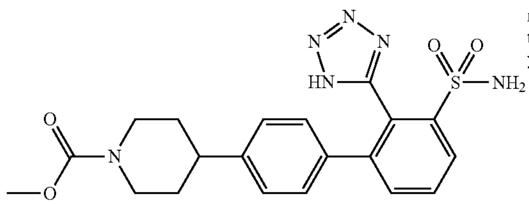 [SMILES: COC(=O)N1CCC(c2ccc(-c3cccc(S(N)(=O)=O)c3-c3nnn[nH]3)cc2)CC1] | methyl 4-[3'-sulfamoyl-2'-(1H-tetrazol-5-yl)biphenyl-4-yl]piperidine-1-carboxylate | 443.5 | 443.1 |
| 29 | 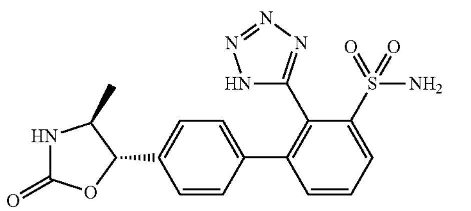 | 4'-[(4S,5S)-4-methyl-2-oxo-1,3-oxazolidin-5-yl]-2-(1H-tetrazol-5-yl)biphenyl-3-sulfonamide | 401.4 | 401.1 |
| 30 | 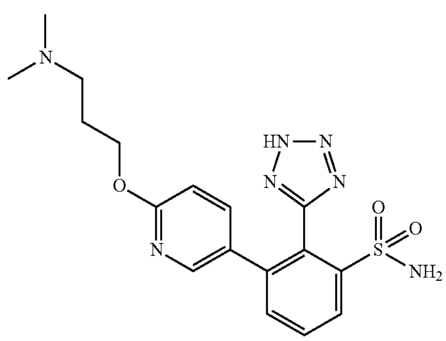 [SMILES: CN(C)CCCOc1ccc(-c2cccc(S(N)(=O)=O)c2-c2nn[nH]n2)cn1] | 3-(6-(3-(dimethylamino)propoxy)pyridin-3-yl)-2-(2H-tetrazol-5-yl)benzenesulfonamide | 404 | 404 |

EXAMPLE 31

4'-piperidin-4-yl-2-(1H-tetrazol-5-yl)biphenyl-3-sulfonamide, hydrochloride salt

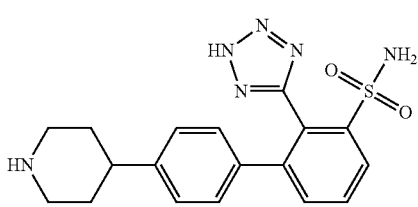 [SMILES: NS(=O)(=O)c1cccc(-c2ccc(C3CCNCC3)cc2)c1-c1nn[nH]n1]

Step A: tert-butyl 4-(2'-(2-(4-methoxybenzyl)-2H-tetrazol-5-yl)-3'-sulfamoyl-[1,1'-biphenyl]-4-yl)piperidine-1-carboxylate and tert-butyl 4-(2'-(1-(4-methoxybenzyl)-1H-tetrazol-5-yl)-3'-sulfamoyl-[1,1'-biphenyl]-4-yl)piperidine-1-carboxylate To the isomer mixture 3-Bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (200 mg, 0.471 mmol), tert-butyl 4-(4-(4,4,5,5-tetramethyl-1,3,2-dioxaborolan-2-yl)phenyl)piperidine-1-carboxylate (274 mg, 0.707 mmol), 1,1'-Bis(di-tert-butylphosphino)ferrocene palladium dichloride (46.1 mg, 0.071 mmol) and ethanol (5 mL) was added aqueous potassium phosphate (1.414 mL, 1.414 mmol). The closed vial was evacuated by vacuum and flushed with $N_2$ three times, and then stirred at 90° C. overnight. The solution was filtered and partitioned between $H_2O$ and EtOAc. The organic layer was separated from aqueous, dried over $Na_2SO_4$, filtered, and evaporated to dryness. The crude product as an isomer mixture was used directly in the next reaction. LC/MS [M+H]+ 605.6.

Step B: 4'-piperidin-4-yl-2-(1H-tetrazol-5-yl)biphenyl-3-sulfonamide, hydrochloride salt TFA (3631 μL, 47.1 mmol) was added into a mixture of tert-butyl 4-(2'-(2-(4-methoxybenzyl)-2H-tetrazol-5-yl)-3'-sulfamoyl-[1,1'-biphenyl]-4-yl)piperidine-1-carboxylate and tert-butyl 4-(2'-(1-(4-methoxybenzyl)-1H-tetrazol-5-yl)-3'-sulfamoyl-[1,1'-biphenyl]-4-yl)piperidine-1-carboxylate (285 mg, 0.471 mmol) and thioanisole (1115 μL, 9.43 mmol). The mixture was stirred at RT overnight. The reaction mixture was heated to 45° C. for ~4 hr to drive to completion, then was stirred at RT overnight. The reaction mixture was concentrated, then triturated with hexane. The hexane was removed. The residue was evaporated, and purified by reverse phase HPLC. To a sample of 19 mg of the purified product was added water (5 mL). To this stirred suspension was added HCl (1N, ~450 uL) dropwise, during which the solids dissolved and the solution turned clear. The solution was freeze-dried using a lyophilizer to obtain the HCl salt. LC/MS [M+H]+ 385.

EXAMPLE 32

4-(3'-Sulfamoyl-2'-(2H-tetrazol-5-yl)-[1,1'-biphenyl]-4-yl)piperidine-1-carboximidamide

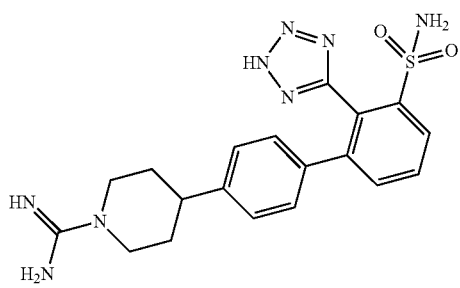 [SMILES: N=C(N)N1CCC(c2ccc(-c3cccc(S(N)(=O)=O)c3-c3nn[nH]n3)cc2)CC1]

Step A: 4-(2'-(2-(4-Methoxybenzyl)-2H-tetrazol-5-yl)-3'-sulfamoyl-[1,1'-biphenyl]-4-yl)piperidine-1-carboximidamide 4-(2'-(2-(4-Methoxybenzyl)-2H-tetrazol-5-yl)-3'-sulfamoyl-[1,1'-biphenyl]-4-yl)piperidine-1-carboximidamide 2,2,2-trifluoroacetate (0.384 g, 0.62 mmol) in THF (6.20 mL) was treated with 1H-pyrazole-1-carboxamidine hydrochloride (0.273 g, 1.86 mmol) and DIEA (1.08 mL, 6.20 mmol). The reaction mixture was stirred at rt under N₂ overnight. The mixture was concentrated and purified by reverse phase HPLC (0-55% CH3CN/water with 0.1% FA). The correct fractions were combined and concentrated to give the crude title compound, which was used directly in the next step. LC-MS 547 (M+1)+;

Step B: 4-(3'-Sulfamoyl-2'-(2H-tetrazol-5-yl)-[1,1'-biphenyl]-4-yl)piperidine-1-carboximidamide 4-(2'-(2-(4-methoxybenzyl)-2H-tetrazol-5-yl)-3'-sulfamoyl-[1,1'-biphenyl]-4-yl)piperidine-1-carboximidamide (339 mg, 0.62 mmol) was treated with TFA at 80° C. for 3 hr. The reaction mixture was concentrated and the crude product was purified by reverse phase HPLC (5-55% CH₃CN/water with 0.1% FA). The correct fractions were combined, concentrated and converted to HCl salt and then lypholized. LC-MS 427 (M+1)+.

EXAMPLE 33

1,1-dimethyl-4-(3'-sulfamoyl-2'-(1H-tetrazol-5-yl)-[1,1'-biphenyl]-4-yl)piperidin-1-ium 2,2,2-trifluoroacetate

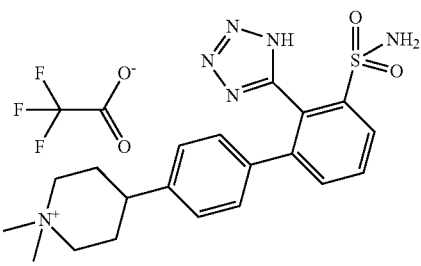 [SMILES: C[N+]1(C)CCC(c2ccc(-c3cccc(S(N)(=O)=O)c3-c3nnn[nH]3)cc2)CC1 ; O=C([O-])C(F)(F)F]

Step A: 4-(4-Bromophenyl)-1,1-dimethylpiperidin-1-ium

In acetone (20 mL), 4-(4-bromophenyl)-1-methylpiperidine (500 mg, 1.967 mmol) was dissolved, and MeI (160 µL, 2.56 mmol) was added dropwise. The mixture was stirred at rt for 2.5 hr. LC-MS showed the reaction was complete. The mixture was filtered and the solid was washed with acetone and collected.

Step B: 4-(3'-(N,N-bis(4-methoxybenzyl)sulfamoyl)-2'-(2-(4-methoxybenzyl)-2H-tetrazol-5-yl)[1,1'-biphenyl]-4-yl)-1,1-dimethylpiperidin-1-ium 4-(4-Bromophenyl)-1,1-dimethylpiperidin-1-ium (93 mg, 0.344 mmol), 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide (200 mg, 0.287 mmol), Na₂CO₃ (60.8 mg, 0.573 mmol), and PdCl₂(dppf) (20.98 mg, 0.029 mmol) was placed in a reaction vessel, to which 1,4-dioxane (1433 µL) and water (478 µL) was added. N₂ was bubbled through for 20 min. The reaction mixture was heated at 95° C. overnight. The reaction mixture was diluted with EtOAc and filtered. The filtrates were concentrated and the residue was purified by Gilson (30-100% CH₃CN/water with 0.05% TFA) to give the title compound. LC-MS 773 (M)+;

Step C: 1,1-dimethyl-4-(3'-sulfamoyl-2'-(1H-tetrazol-5-yl)-[1,1'-biphenyl]-4-yl)piperidin-1-ium 4-(3'-(N,N-bis(4-methoxybenzyl)sulfamoyl)-2'-(2-(4-methoxybenzyl)-2H-tetrazol-5-yl)-[1,1'-biphenyl]-4-yl)-1,1-dimethylpiperidin-1-ium (30 mg, 0.039 mmol) was heated in TFA for 2 hr. The mixture was concentrated and purified with Gilson (2-40% CH₃CN/water with 0.1% TFA). The correct fractions were combined, concentrated and lypholized. LC-MS 413 (M)+.

EXAMPLES 34-49

Parallel Synthesis of 3-Substituted 2-(1H-tetrazol-5-yl)benzenesulfonamides

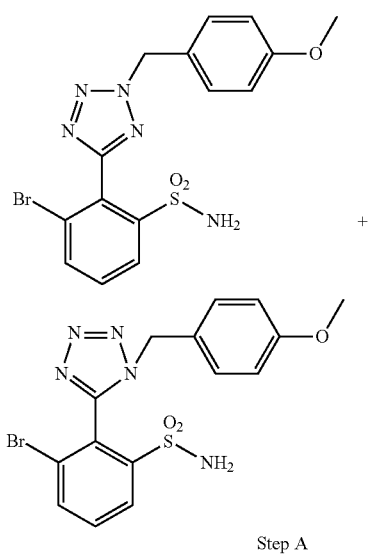

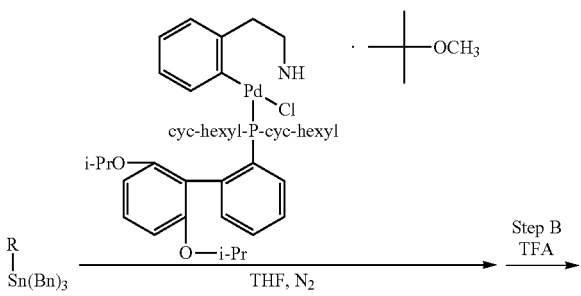

Step A

Step B
TFA

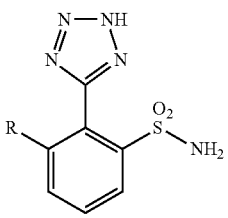

Step A: Palladium Catalyzed C—C Coupling of Arylbromides and Substituted Tin Reagents A mixture of 3-bromo-2-(1-(4-methoxybenzyl)-2H-tetrazol-5-yl)benzenesulfonamide and 3-bromo-2-(2-(4-methoxybenzyl)-2H-tetrazol-5-yl)benzenesulfonamide from Reference Example 1 (15 mg, 0.035 mmol), substituted tin reagents (0.07 mmol), and (RuPhos)palladium (II) phenthylamine chloride catalyst (2.5 mg, 0.0035 mmol) were mixed into a 1-dram vial. Under dry nitrogen atmosphere, THF (300 μl) was added into the vial and the reaction was agitated at 75° C. for 16 hours. The solvent was removed under reduced pressure to afford the intermediates.

Step B: Removal of the p-methoxybenzyl (PMB) Protecting Group Under Acidic Conditions TFA (545 μl, 7.07 mmol) was added to each vial. The vials were heated to 65° C. for 16 hours. LC/MS showed formation of the desired products. Solvent was removed under reduced pressure. To each vial, 1 mL DMSO was added and filtered into a 96-well plate. The crude products were purified by HPLC to afford Examples 35-50.

| Ex. No. | Structure | Name | Calc'd Mass [M + H]+ | LC/MS m/e [M + H]+ |
|---|---|---|---|---|
| 34 | 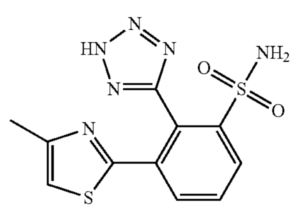 [SMILES: Cc1csc(-c2cccc(S(N)(=O)=O)c2-c2nn[nH]n2)n1] | 3-(4-methyl-1,3-thiazol-2-yl)-2-(2H-tetrazol-5-yl)benzenesulfonamide | 323.0 | 323.0 |
| 35 | 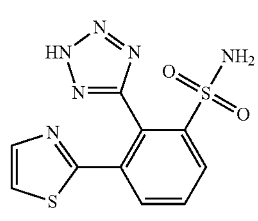 [SMILES: NS(=O)(=O)c1cccc(-c2nccs2)c1-c1nn[nH]n1] | 2-(2H-tetrazol-5-yl)-3-(1,3-thiazol-2-yl)benzenesulfonamide | 309.0 | 309.0 |

-continued

| Ex. No. | Structure | Name | Calc'd Mass [M + H]+ | LC/MS m/e [M + H]+ |
|---|---|---|---|---|
| 36 | 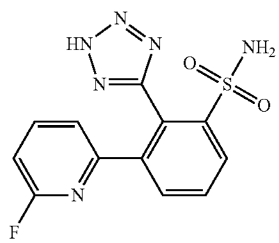 [SMILES: NS(=O)(=O)c1cccc(-c2cccc(F)n2)c1-c1nn[nH]n1] | 3-(6-fluoropyridin-2-yl)-2-(2H-tetrazol-5-yl)benzenesulfonamide | 321.0 | 321.1 |
| 37 | 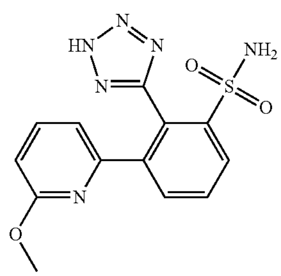 [SMILES: COc1cccc(-c2cccc(S(N)(=O)=O)c2-c2nn[nH]n2)n1] | 3-(6-methoxypyridin-2-yl)-2-(2H-tetrazol-5-yl)benzenesulfonamide | 333.0 | 333.1 |
| 38 | 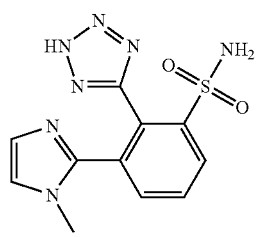 [SMILES: Cn1ccnc1-c1cccc(S(N)(=O)=O)c1-c1nn[nH]n1] | 3-(1-methyl-1H-imidazol-2-yl)-2-(2H-tetrazol-5-yl)benzenesulfonamide | 306.0 | 306.1 |
| 39 | 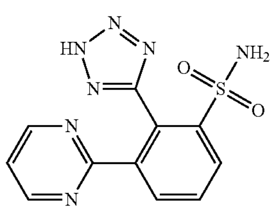 [SMILES: NS(=O)(=O)c1cccc(-c2ncccn2)c1-c1nn[nH]n1] | 3-pyrimidin-2-yl-2-(2H-tetrazol-5-yl)benzenesulfonamide | 304.0 | 304.1 |
| 40 | 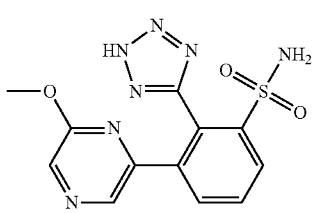 [SMILES: COc1cncc(-c2cccc(S(N)(=O)=O)c2-c2nn[nH]n2)n1] | 3-(6-methoxypyrazin-2-yl)-2-(2H-tetrazol-5-yl)benzenesulfonamide | 334.0 | 334.1 |
| 41 | 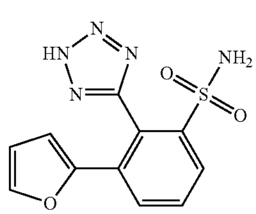 | 3-furan-2-yl-2-(2H-tetrazol-5-yl)benzenesulfonamide | 292.0 | 292.0 |

-continued

| Ex. No. | Structure | Name | Calc'd Mass [M + H]+ | LC/MS m/e [M + H]+ |
|---|---|---|---|---|
| 42 | 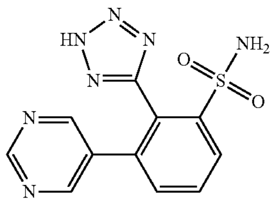 [SMILES: NS(=O)(=O)c1cccc(-c2cncnc2)c1-c1nn[nH]n1] | 3-pyrimidin-5-yl-2-(2H-tetrazol-5-yl)benzenesulfonamide | 304.0 | 304.1 |
| 43 | 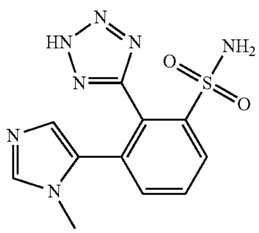 [SMILES: Cn1cncc1-c1cccc(S(N)(=O)=O)c1-c1nn[nH]n1] | 3-(1-methyl-1H-imidazol-5-yl)-2-(2H-tetrazol-5-yl)benzenesulfonamide | 306.0 | 306.1 |
| 44 | 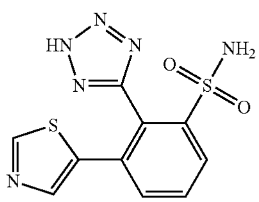 [SMILES: NS(=O)(=O)c1cccc(-c2cncs2)c1-c1nn[nH]n1] | 2-(2H-tetrazol-5-yl)-3-(1,3-thiazol-5-yl)benzenesulfonamide | 309.0 | 309.0 |
| 45 | 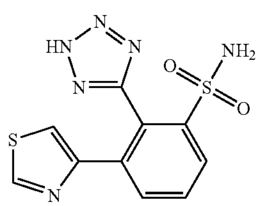 [SMILES: NS(=O)(=O)c1cccc(-c2cscn2)c1-c1nn[nH]n1] | 2-(2H-tetrazol-5-yl)-3-(1,3-thiazol-4-yl)benzenesulfonamide | 309.0 | 309.0 |
| 46 | 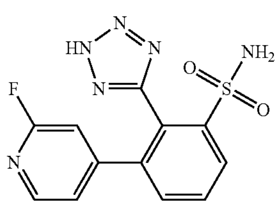 [SMILES: NS(=O)(=O)c1cccc(-c2ccnc(F)c2)c1-c1nn[nH]n1] | 3-(2-fluoropyridin-4-yl)-2-(2H-tetrazol-5-yl)benzenesulfonamide | 321.0 | 321.1 |
| 47 | 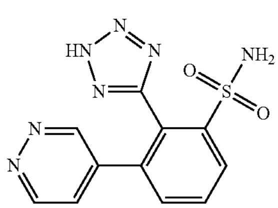 [SMILES: NS(=O)(=O)c1cccc(-c2ccnnc2)c1-c1nn[nH]n1] | 3-pyridazin-4-yl-2-(2H-tetrazol-5-yl)benzenesulfonamide | 304.0 | 304.1 |
| 48 | 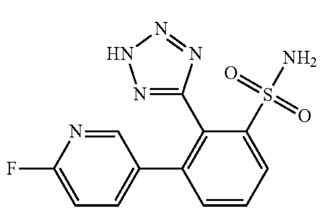 [SMILES: NS(=O)(=O)c1cccc(-c2ccc(F)nc2)c1-c1nn[nH]n1] | 3-(6-fluoropyridin-3-yl)-2-(2H-tetrazol-5-yl)benzenesulfonamide | 321.0 | 321.1 |

-continued

| Ex. No. | Structure | Name | Calc'd Mass [M + H]+ | LC/MS m/e [M + H]+ |
|---|---|---|---|---|
| 49 | 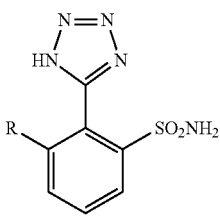 | 3-(1-methyl-1H-pyrazol-5-yl)-2-(2H-tetrazol-5-yl)benzenesulfonamide | 306.0 | 306.1 |

EXAMPLES 50-110

Parallel Synthesis of 3-Substituted 2-(1H-tetrazol-5-yl)benzenesulfonamides

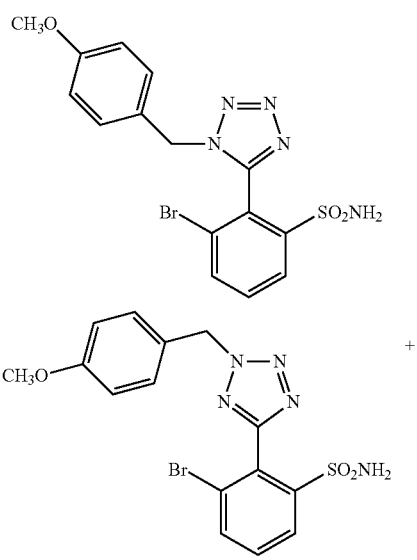

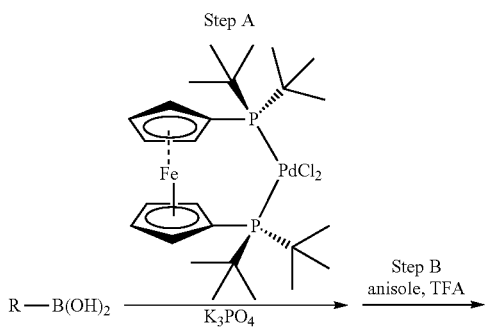

Step A: Palladium Catalyzed C—C Coupling of Arylbromide and Boronic Acids or Boronic Esters (Such as Pinacol Esters)

A mixture of 3-bromo-2-(1-(4-methoxybenzyl)-2H-tetrazol-5-yl)benzenesulfonamide and 3-bromo-2-(2-(4-methoxybenzyl)-2H-tetrazol-5-yl)benzenesulfonamide from Reference Example 1 (30 mg, 0.071 mmol), substituted boronic acids or esters (0.142 mmol), potassium phosphate (0.212 mL 1N solution, 0.212 mmol), 1,1'-bis(di-tert-butylphosphino) ferrocene palladium chloride (4.61 mg, 7.07 μmol) were mixed into a 1-dram vial, and under dry nitrogen atmosphere, EtOH (1 mL) was added into the vial under $N_2$ and the reaction was agitated at 70-75° C. for 16 hours. Crude LC/MS showed formation of the desired intermediate. Solvent was removed under reduced pressure. To each vial, 1.5 mL DCM was added along with 0.4 mL water, with shaking for 15 min. The organic layer was collected and solvent was removed under reduced pressure.

Step B: Removal of the p-methoxybenzyl (PMB) Protecting Group Under Acidic Conditions To each vial from Step A, TFA (0.545 mL, 7.07 mmol), anisole (7.72 μl, 0.071 mmol) was added and agitated at 60° C. for 12 hours. Crude LC/MS showed formation of the desired products. The solvent were removed under reduced pressure. To each vial, 1 mL DMSO was added and filtered into a 96-well plate. These crude materials were purified by HPLC to afford Examples 51-110.

| Ex. No. | Structure | Name | Calc'd Mass [M + H]+ | LC/MS m/e [M + H]+ |
|---|---|---|---|---|
| 50 | 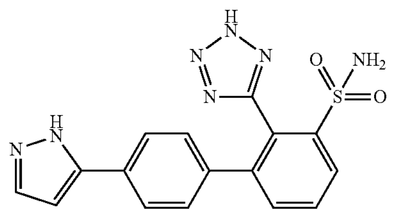 [SMILES: NS(=O)(=O)c1cccc(-c2ccc(-c3ccn[nH]3)cc2)c1-c1nn[nH]n1] | 4'-(1H-pyrazol-5-yl)-2-(2H-tetrazol-5-yl)biphenyl-3-sulfonamide | 368.0 | 368 |
| 51 | 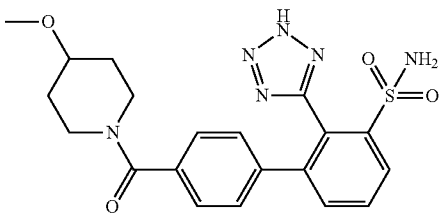 [SMILES: COC1CCN(C(=O)c2ccc(-c3cccc(S(N)(=O)=O)c3-c3nn[nH]n3)cc2)CC1] | 4'-[(4-methoxypiperidin-1-yl)carbonyl]-2-(2H-tetrazol-5-yl)biphenyl-3-sulfonamide | 443.0 | 443.1 |
| 52 | 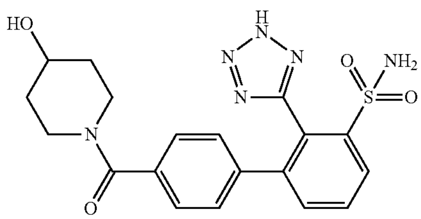 [SMILES: NS(=O)(=O)c1cccc(-c2ccc(C(=O)N3CCC(O)CC3)cc2)c1-c1nn[nH]n1] | 4'-[(4-hydroxypiperidin-1-yl)carbonyl]-2-(2H-tetrazol-5-yl)biphenyl-3-sulfonamide | 429.0 | 429.1 |
| 53 | 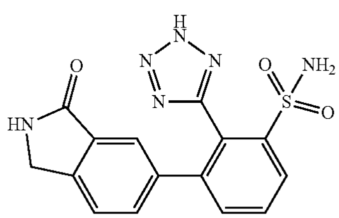 [SMILES: NS(=O)(=O)c1cccc(-c2ccc3c(c2)C(=O)NC3)c1-c1nn[nH]n1] | 3-(3-oxo-2,3-dihydro-1H-isoindol-5-yl)-2-(2H-tetrazol-5-yl)benzenesulfonamide | 357.0 | 357.1 |
| 54 | 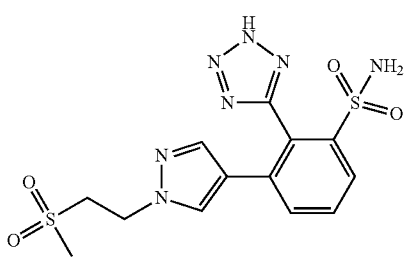 [SMILES: CS(=O)(=O)CCn1cc(-c2cccc(S(N)(=O)=O)c2-c2nn[nH]n2)cn1] | 3-{1-[2-(methylsulfonyl)ethyl]-1H-pyrazol-4-yl}-2-(2H-tetrazol-5-yl)benzenesulfonamide | 398.0 | 398.1 |
| 55 | 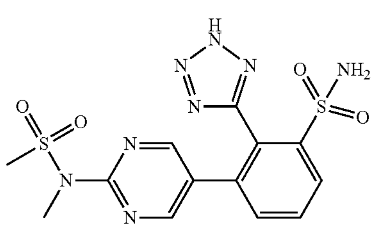 [SMILES: CN(c1ncc(-c2cccc(S(N)(=O)=O)c2-c2nn[nH]n2)cn1)S(C)(=O)=O] | 3-{2-[methyl(methylsulfonyl)amino]pyrimidin-5-yl}-2-(2H-tetrazol-5-yl)benzenesulfonamide | 411.0 | 411.1 |

| Ex. No. | Structure | Name | Calc'd Mass [M + H]⁺ | LC/MS m/e [M + H]⁺ |
|---|---|---|---|---|
| 56 | 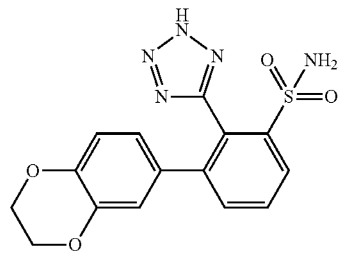 [SMILES: NS(=O)(=O)c1cccc(-c2ccc3c(c2)OCCO3)c1-c1nn[nH]n1] | 3-(2,3-dihydro-1,4-benzodioxin-6-yl)-2-(2H-tetrazol-5-yl)benzenesulfonamide | 360.0 | 360.1 |
| 57 | 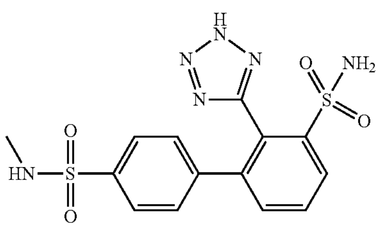 [SMILES: CNS(=O)(=O)c1ccc(-c2cccc(S(N)(=O)=O)c2-c2nn[nH]n2)cc1] | N~4~'-methyl-2-(2H-tetrazol-5-yl)biphenyl-3,4'-disulfonamide | 395.0 | 395.1 |
| 58 | 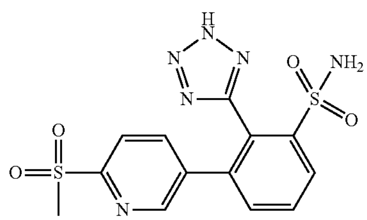 [SMILES: CS(=O)(=O)c1ccc(-c2cccc(S(N)(=O)=O)c2-c2nn[nH]n2)cn1] | 3-[6-(methylsulfonyl)pyridin-3-yl]-2-(2H-tetrazol-5-yl)benzenesulfonamide | 381.0 | 381.1 |
| 59 | 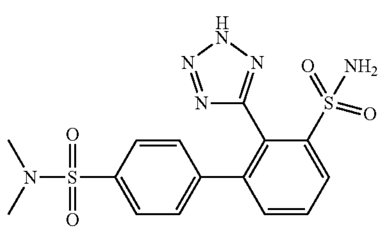 [SMILES: CN(C)S(=O)(=O)c1ccc(-c2cccc(S(N)(=O)=O)c2-c2nn[nH]n2)cc1] | N~4~',N~4~'-dimethyl-2-(2H-tetrazol-5-yl)biphenyl-3,4'-disulfonamide | 409.0 | 409.1 |
| 60 | 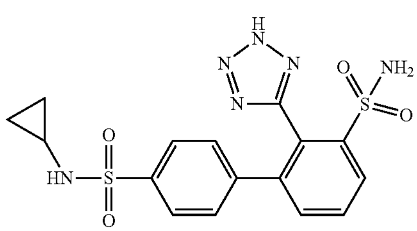 [SMILES: NS(=O)(=O)c1cccc(-c2ccc(S(=O)(=O)NC3CC3)cc2)c1-c1nn[nH]n1] | N~4~'-cyclopropyl-2-(2H-tetrazol-5-yl)biphenyl-3,4'-disulfonamide | 421.0 | 421.1 |
| 61 | 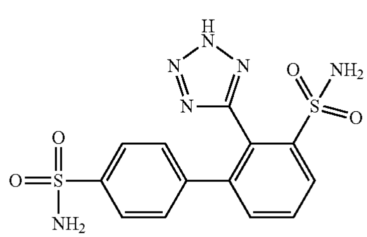 [SMILES: NS(=O)(=O)c1ccc(-c2cccc(S(N)(=O)=O)c2-c2nn[nH]n2)cc1] | 2-(2H-tetrazol-5-yl)biphenyl-3,4'-disulfonamide | 381.0 | 381.0 |

-continued

| Ex. No. | Structure | Name | Calc'd Mass [M + H]+ | LC/MS m/e [M + H]+ |
|---|---|---|---|---|
| 62 | 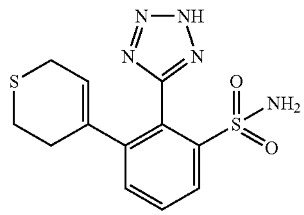 [SMILES: NS(=O)(=O)c1cccc(C2=CCSCC2)c1-c1nn[nH]n1] | 3-(3,6-dihydro-2H-thiopyran-4-yl)-2-(2H-tetrazol-5-yl)benzenesulfonamide | 324.0 | 324.1 |
| 63 | 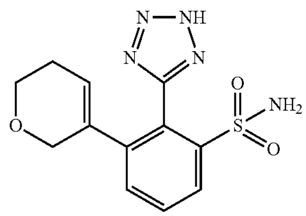 [SMILES: NS(=O)(=O)c1cccc(C2=CCCOC2)c1-c1nn[nH]n1] | 3-(5,6-dihydro-2H-pyran-3-yl)-2-(2H-tetrazol-5-yl)benzenesulfonamide | 308.0 | 308.1 |
| 64 | 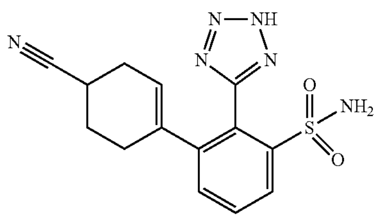 [SMILES: N#CC1CC=C(c2cccc(S(N)(=O)=O)c2-c2nn[nH]n2)CC1] | 3-(4-cyanocyclohex-1-en-1-yl)-2-(2H-tetrazol-5-yl)benzenesulfonamide | 331.0 | 331.1 |
| 65 | 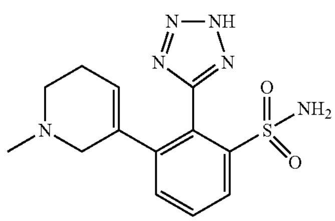 [SMILES: CN1CCC=C(c2cccc(S(N)(=O)=O)c2-c2nn[nH]n2)C1] | 3-(1-methyl-1,2,5,6-tetrahydropyridin-3-yl)-2-(2H-tetrazol-5-yl)benzenesulfonamide | 321.0 | 321.1 |
| 66 | 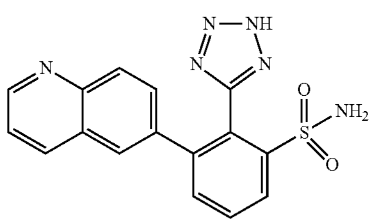 [SMILES: NS(=O)(=O)c1cccc(-c2ccc3ncccc3c2)c1-c1nn[nH]n1] | 3-quinolin-6-yl-2-(2H-tetrazol-5-yl)benzenesulfonamide | 353.0 | 353.1 |
| 67 | 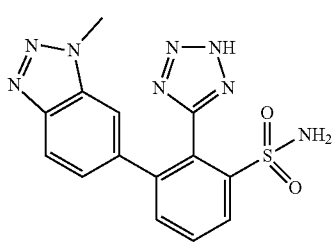 [SMILES: Cn1nnc2ccc(-c3cccc(S(N)(=O)=O)c3-c3nn[nH]n3)cc21] | 3-(1-methyl-1H-benzotriazol-6-yl)-2-(2H-tetrazol-5-yl)benzenesulfonamide | 357.0 | 357.1 |
| 68 | 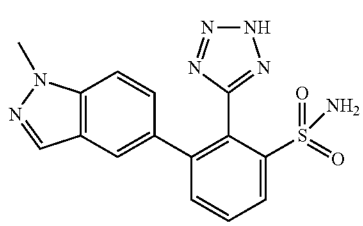 [SMILES: Cn1ncc2cc(-c3cccc(S(N)(=O)=O)c3-c3nn[nH]n3)ccc21] | 3-(1-methyl-1H-indazol-5-yl)-2-(2H-tetrazol-5-yl)benzenesulfonamide | 356.0 | 356.1 |

-continued

| Ex. No. | Structure | Name | Calc'd Mass [M + H]⁺ | LC/MS m/e [M + H]⁺ |
|---|---|---|---|---|
| 69 | 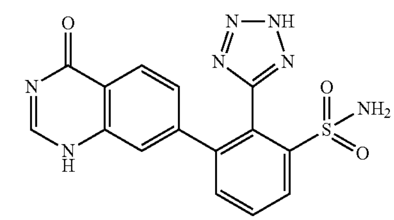 [SMILES: NS(=O)(=O)c1cccc(-c2ccc3c(=O)nc[nH]c3c2)c1-c1nn[nH]n1] | 3-(4-oxo-1,4-dihydroquinazolin-7-yl)-2-(2H-tetrazol-5-yl)benzenesulfonamide | 370.0 | 370 |
| 70 | 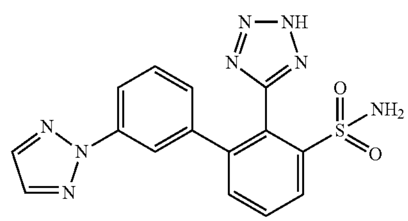 [SMILES: NS(=O)(=O)c1cccc(-c2cccc(-n3nccn3)c2)c1-c1nn[nH]n1] | 2-(2H-tetrazol-5-yl)-3'-(2H-1,2,3-triazol-2-yl)biphenyl-3-sulfonamide | 369.0 | 369.1 |
| 71 | 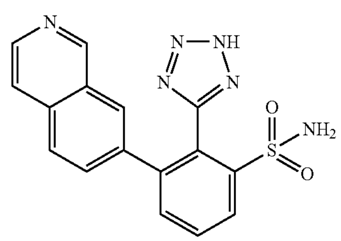 [SMILES: NS(=O)(=O)c1cccc(-c2ccc3ccncc3c2)c1-c1nn[nH]n1] | 3-isoquinolin-7-yl-2-(2H-tetrazol-5-yl)benzenesulfonamide | 353.0 | ND |
| 72 | 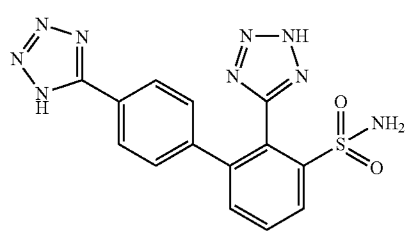 [SMILES: NS(=O)(=O)c1cccc(-c2ccc(-c3nnn[nH]3)cc2)c1-c1nn[nH]n1] | 4'-(1H-tetrazol-5-yl)-2-(2H-tetrazol-5-yl)biphenyl-3-sulfonamide | 370.0 | 370.1 |
| 73 | 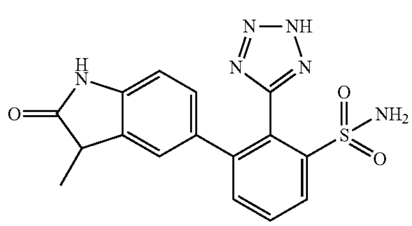 [SMILES: CC1C(=O)Nc2ccc(-c3cccc(S(N)(=O)=O)c3-c3nn[nH]n3)cc21] | 3-(3-methyl-2-oxo-2,3-dihydro-1H-indol-5-yl)-2-(2H-tetrazol-5-yl)benzenesulfonamide | 371.0 | 371.1 |
| 74 | 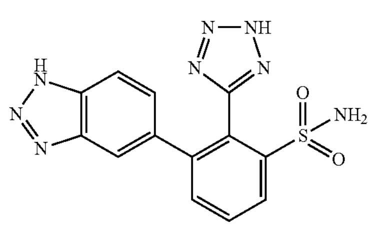 [SMILES: NS(=O)(=O)c1cccc(-c2ccc3[nH]nnc3c2)c1-c1nn[nH]n1] | 3-(1H-benzotriazol-5-yl)-2-(2H-tetrazol-5-yl)benzenesulfonamide | 343.0 | 343.1 |

-continued

| Ex. No. | Structure | Name | Calc'd Mass [M + H]+ | LC/MS m/e [M + H]+ |
|---|---|---|---|---|
| 75 | 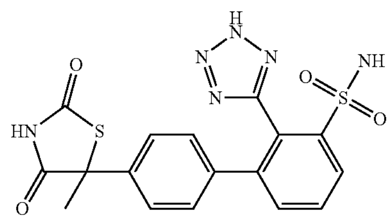 [SMILES: CC1(c2ccc(-c3cccc(S(N)(=O)=O)c3-c3nn[nH]n3)cc2)SC(=O)NC1=O] | 4'-(5-methyl-2,4-dioxo-1,3-thiazolidin-5-yl)-2-(2H-tetrazol-5-yl)biphenyl-3-sulfonamide | 431.0 | 431.1 |
| 76 | 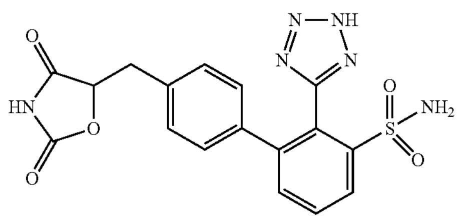 [SMILES: NS(=O)(=O)c1cccc(-c2ccc(CC3OC(=O)NC3=O)cc2)c1-c1nn[nH]n1] | 4'-[(2,4-dioxo-1,3-oxazolidin-5-yl)methyl]-2-(2H-tetrazol-5-yl)biphenyl-3-sulfonamide | 415.0 | 415.1 |
| 77 | 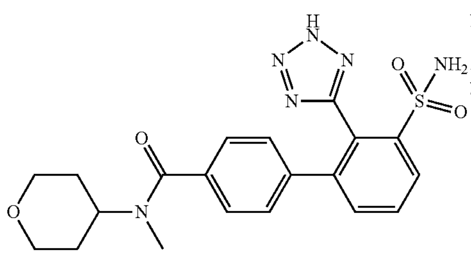 [SMILES: CN(C(=O)c1ccc(-c2cccc(S(N)(=O)=O)c2-c2nn[nH]n2)cc1)C1CCOCC1] | N-methyl-3'-sulfamoyl-N-(tetrahydro-2H-pyran-4-yl)-2'-(2H-tetrazol-5-yl)biphenyl-4-carboxamide | 443.0 | 443.1 |
| 78 | 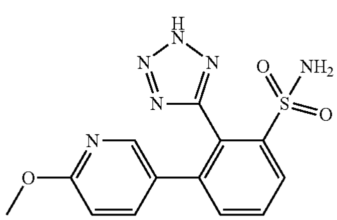 [SMILES: COc1ccc(-c2cccc(S(N)(=O)=O)c2-c2nn[nH]n2)cn1] | 3-(6-methoxypyridin-3-yl)-2-(2H-tetrazol-5-yl)benzenesulfonamide | 333.0 | 333.1 |
| 79 | 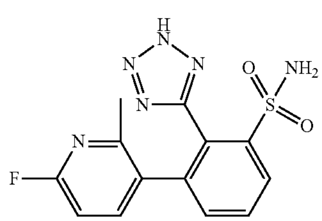 [SMILES: Cc1nc(F)ccc1-c1cccc(S(N)(=O)=O)c1-c1nn[nH]n1] | 3-(6-fluoro-2-methylpyridin-3-yl)-2-(2H-tetrazol-5-yl)benzenesulfonamide | 335.0 | 335.1 |
| 80 | 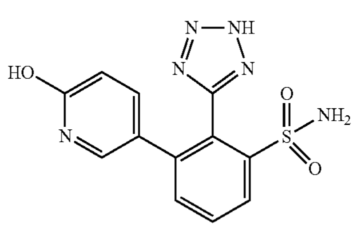 [SMILES: NS(=O)(=O)c1cccc(-c2ccc(O)nc2)c1-c1nn[nH]n1] | 3-(6-hydroxypyridin-3-yl)-2-(2H-tetrazol-5-yl)benzenesulfonamide | 319.0 | 319.1 |

-continued

| Ex. No. | Structure | Name | Calc'd Mass [M + H]+ | LC/MS m/e [M + H]+ |
|---|---|---|---|---|
| 81 | 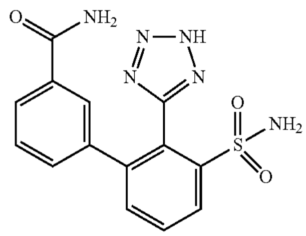 [SMILES: NC(=O)c1cccc(-c2cccc(S(N)(=O)=O)c2-c2nn[nH]n2)c1] | 3'-sulfamoyl-2'-(2H-tetrazol-5-yl)biphenyl-3-carboxamide | 345.0 | 345.1 |
| 82 | 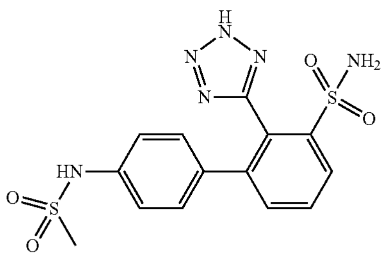 [SMILES: CS(=O)(=O)Nc1ccc(-c2cccc(S(N)(=O)=O)c2-c2nn[nH]n2)cc1] | 4'-[(methylsulfonyl)amino]-2-(2H-tetrazol-5-yl)biphenyl-3-sulfonamide | 395.0 | 395.1 |
| 83 | 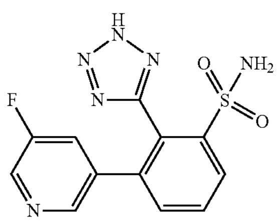 [SMILES: NS(=O)(=O)c1cccc(-c2cncc(F)c2)c1-c1nn[nH]n1] | 3-(5-fluoropyridin-3-yl)-2-(2H-tetrazol-5-yl)benzenesulfonamide | 321.0 | 321.1 |
| 84 | 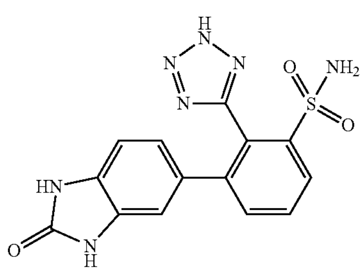 [SMILES: NS(=O)(=O)c1cccc(-c2ccc3[nH]c(=O)[nH]c3c2)c1-c1nn[nH]n1] | 3-(2-oxo-2,3-dihydro-1H-benzimidazol-5-yl)-2-(2H-tetrazol-5-yl)benzenesulfonamide | 358.0 | 358.1 |
| 85 | 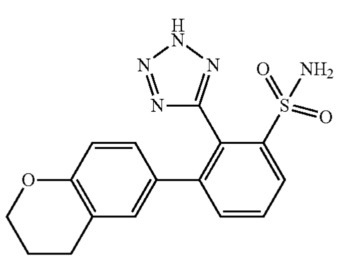 [SMILES: NS(=O)(=O)c1cccc(-c2ccc3c(c2)CCCO3)c1-c1nn[nH]n1] | 3-(3,4-dihydro-2H-chromen-6-yl)-2-(2H-tetrazol-5-yl)benzenesulfonamide | 358.0 | 358.1 |
| 86 | 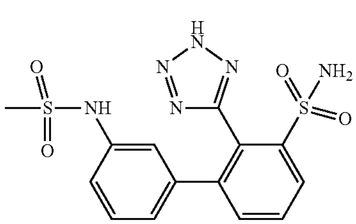 [SMILES: CS(=O)(=O)Nc1cccc(-c2cccc(S(N)(=O)=O)c2-c2nn[nH]n2)c1] | 3'-[(methylsulfonyl)amino]-2-(2H-tetrazol-5-yl)biphenyl-3-sulfonamide | 395.0 | 395.1 |

-continued

| Ex. No. | Structure | Name | Calc'd Mass [M + H]⁺ | LC/MS m/e [M + H]⁺ |
|---|---|---|---|---|
| 87 | 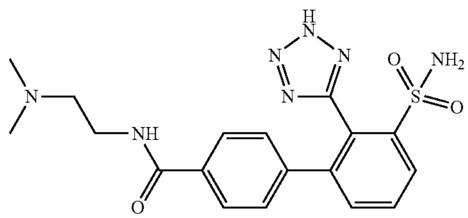 [SMILES: CN(C)CCNC(=O)c1ccc(-c2cccc(S(N)(=O)=O)c2-c2nn[nH]n2)cc1] | N-[2-(dimethylamino)ethyl]-3'-sulfamoyl-2'-(2H-tetrazol-5-yl)biphenyl-4-carboxamide | 416.0 | 416.1 |
| 88 | 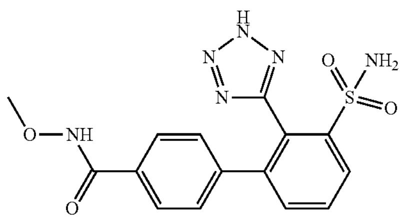 [SMILES: CONC(=O)c1ccc(-c2cccc(S(N)(=O)=O)c2-c2nn[nH]n2)cc1] | N-methoxy-3'-sulfamoyl-2'-(2H-tetrazol-5-yl)biphenyl-4-carboxamide | 375.0 | 375.1 |
| 89 | 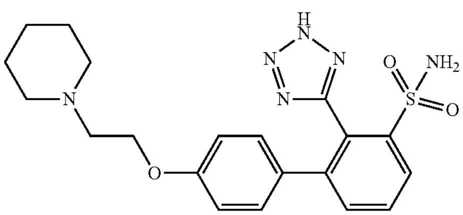 [SMILES: NS(=O)(=O)c1cccc(-c2ccc(OCCN3CCCCC3)cc2)c1-c1nn[nH]n1] | 4'-(2-piperidin-1-ylethoxy)-2-(2H-tetrazol-5-yl)biphen-3-sulfonamide | 429.0 | 429.2 |
| 90 | 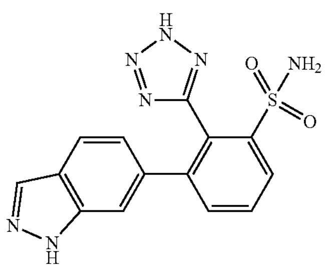 [SMILES: NS(=O)(=O)c1cccc(-c2ccc3cn[nH]c3c2)c1-c1nn[nH]n1] | 3-(1H-indazol-6-yl)-2-(2H-tetrazol-5-yl)benzenesulfonamide | 342.0 | 342.1 |
| 91 | 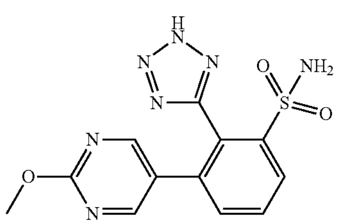 [SMILES: COc1ncc(-c2cccc(S(N)(=O)=O)c2-c2nn[nH]n2)cn1] | 3-(2-methoxypyrimidin-5-yl)-2-(2H-tetrazol-5-yl)benzenesulfonamide | 334.0 | 334.1 |
| 92 | 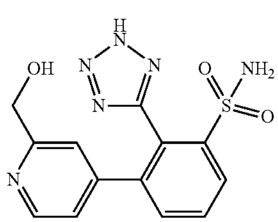 [SMILES: NS(=O)(=O)c1cccc(-c2ccnc(CO)c2)c1-c1nn[nH]n1] | 3-[2-(hydroxymethyl)pyridin-4-yl]-2-(2H-tetrazol-5-yl)benzenesulfonamide | 333.0 | 333.1 |

| Ex. No. | Structure | Name | Calc'd Mass [M + H]⁺ | LC/MS m/e [M + H]⁺ |
|---|---|---|---|---|
| 93 | 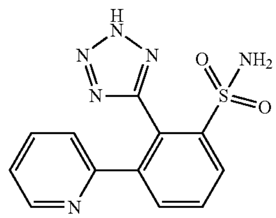 [SMILES: NS(=O)(=O)c1cccc(-c2ccccn2)c1-c1nn[nH]n1] | 3-pyridin-2-yl-2-(2H-tetrazol-5-yl)benzenesulfonamide | 303.0 | 303.1 |
| 94 | 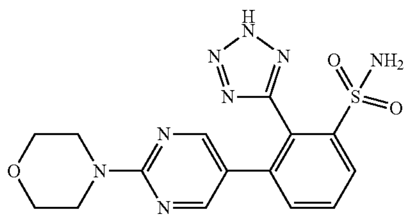 [SMILES: NS(=O)(=O)c1cccc(-c2cnc(N3CCOCC3)nc2)c1-c1nn[nH]n1] | 3-(2-morpholin-4-ylpyrimidin-5-yl)-2-(2H-tetrazol-5-yl)benzenesulfonamide | 389.0 | 389.1 |
| 95 | 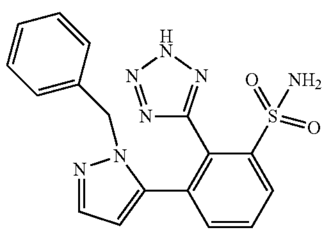 [SMILES: NS(=O)(=O)c1cccc(-c2ccnn2Cc2ccccc2)c1-c1nn[nH]n1] | 3-(1-benzyl-1H-pyrazol-5-yl)-2-(2H-tetrazol-5-yl)benzenesulfonamide | 382.0 | 382.1 |
| 96 | 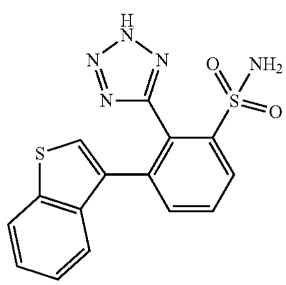 [SMILES: NS(=O)(=O)c1cccc(-c2csc3ccccc23)c1-c1nn[nH]n1] | 3-(1-benzothiophen-3-yl)-2-(2H-tetrazol-5-yl)benzenesulfonamide | 358.0 | 358.0 |
| 97 | 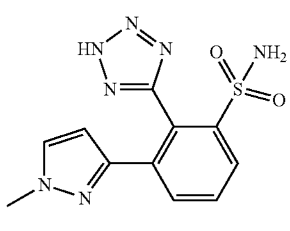 [SMILES: Cn1ccc(-c2cccc(S(N)(=O)=O)c2-c2nn[nH]n2)n1] | 3-(1-methyl-1H-pyrazol-3-yl)-2-(2H-tetrazol-5-yl)benzenesulfonamide | 306.0 | 306.1 |
| 98 | 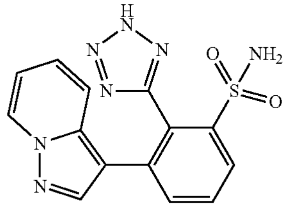 [SMILES: NS(=O)(=O)c1cccc(-c2cnn3ccccc23)c1-c1nn[nH]n1] | 3-pyrazolo[1,5-a]pyridin-3-yl-2-(2H-tetrazol-5-yl)benzenesulfonamide | 342.0 | 342.1 |

-continued

| Ex. No. | Structure | Name | Calc'd Mass [M + H]+ | LC/MS m/e [M + H]+ |
|---|---|---|---|---|
| 99 | 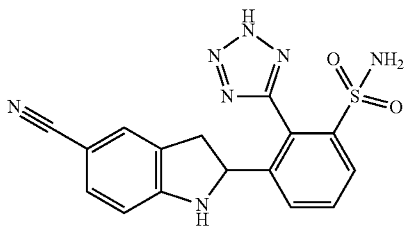 [SMILES: N#Cc1ccc2c(c1)CC(c1cccc(S(N)(=O)=O)c1-c1nn[nH]n1)N2] | 3-(5-cyano-1H-indol-2-yl)-2-(2H-tetrazol-5-yl)benzenesulfonamide | 366.0 | 366.1 |
| 100 | 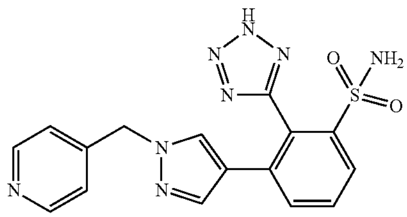 [SMILES: NS(=O)(=O)c1cccc(-c2cnn(Cc3ccncc3)c2)c1-c1nn[nH]n1] | 3-[1-(pyridin-4-ylmethyl)-1H-pyrazol-4-yl]-2-(2H-tetrazol-5-yl)benzenesulfonamide | 383.0 | 383.1 |
| 101 | 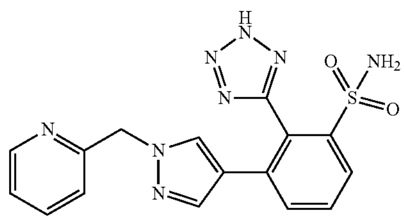 [SMILES: NS(=O)(=O)c1cccc(-c2cnn(Cc3ccccn3)c2)c1-c1nn[nH]n1] | 3-[1-(pyridin-2-ylmethyl)-1H-pyrazol-4-yl]-2-(2H-tetrazol-5-yl)benzenesulfonamide | 383.0 | 383.1 |
| 102 | 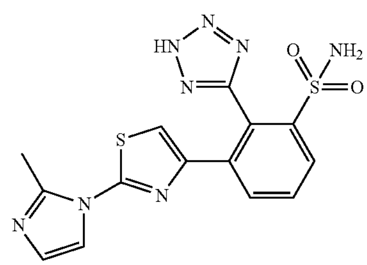 [SMILES: Cc1nccn1-c1nc(-c2cccc(S(N)(=O)=O)c2-c2nn[nH]n2)cs1] | 3-[2-(2-methyl-1H-imidazol-1-yl)-1,3-thiazol-4-yl]-2-(2H-tetrazol-5-yl)benzenesulfonamide | 389.0 | 389.1 |
| 103 | 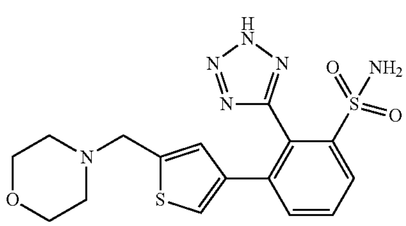 [SMILES: NS(=O)(=O)c1cccc(-c2csc(CN3CCOCC3)c2)c1-c1nn[nH]n1] | 3-[5-(morpholin-4-ylmethyl)thiophen-3-yl]-2-(2H-tetrazol-5-yl)benzenesulfonamide | 407.0 | 407.1 |
| 104 | 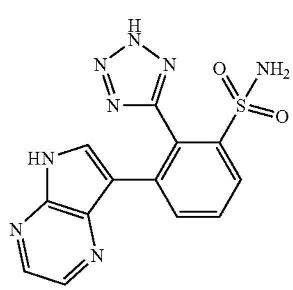 [SMILES: NS(=O)(=O)c1cccc(-c2c[nH]c3nccnc23)c1-c1nn[nH]n1] | 3-(5H-pyrrolo[2,3-b]pyrazin-7-yl)-2-(2H-tetrazol-5-yl)benzenesulfonamide | 343.0 | 343.1 |

-continued

| Ex. No. | Structure | Name | Calc'd Mass [M + H]+ | LC/MS m/e [M + H]+ |
|---|---|---|---|---|
| 105 | 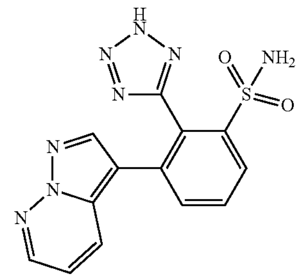 [SMILES: NS(=O)(=O)c1cccc(-c2cnn3ncccc23)c1-c1nn[nH]n1] | 3-pyrazolo[1,5-b]pyridazin-3-yl-2-(2H-tetrazol-5-yl)benzenesulfonamide | 343.0 | 343.1 |
| 106 | 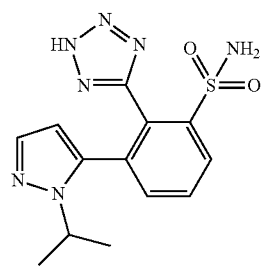 [SMILES: CC(C)n1nccc1-c1cccc(S(N)(=O)=O)c1-c1nn[nH]n1] | 3-[1-(1-methylethyl)-1H-pyrazol-5-yl]-2-(2H-tetrazol-5-yl)benzenesulfonamide | 334.0 | 334.1 |
| 107 | 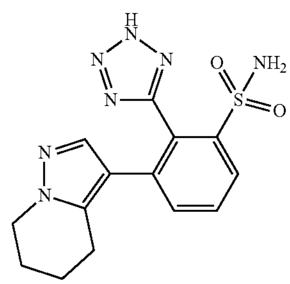 [SMILES: NS(=O)(=O)c1cccc(-c2cnn3c2CCCC3)c1-c1nn[nH]n1] | 3-(4,5,6,7-tetrahydropyrazolo[1,5-a]pyridin-3-yl)-2-(2H-tetrazol-5-yl)benzenesulfonamide | 346.0 | 346.1 |
| 108 | 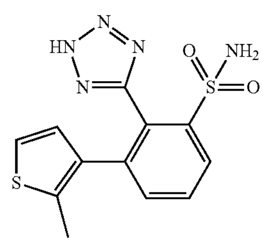 [SMILES: Cc1sccc1-c1cccc(S(N)(=O)=O)c1-c1nn[nH]n1] | 3-(2-methylthiophen-3-yl)-2-(2H-tetrazol-5-yl)benzenesulfonamide | 322.0 | 322.0 |
| 109 | 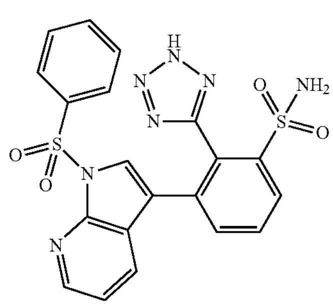 [SMILES: NS(=O)(=O)c1cccc(-c2cn(S(=O)(=O)c3ccccc3)c3ncccc23)c1-c1nn[nH]n1] | 3-[1-(phensulfonyl)-1H-pyrrolo[2,3-b]pyridin-3-yl]-2-(2H-tetrazol-5-yl)benzenesulfonamide | 482.0 | 482.1 |

-continued

| Ex. No. | Structure | Name | Calc'd Mass [M + H]+ | LC/MS m/e [M + H]+ |
|---|---|---|---|---|
| 110 | 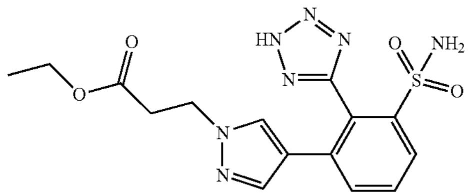 [SMILES: CCOC(=O)CCn1cc(-c2cccc(S(N)(=O)=O)c2-c2nn[nH]n2)cn1] | ethyl 3-{4-[3-sulfamoyl-2-(2H-tetrazol-5-yl)phenyl]-1H-pyrazol-1-yl}propanoate | 392.0 | 392.1 |

EXAMPLES 111-130

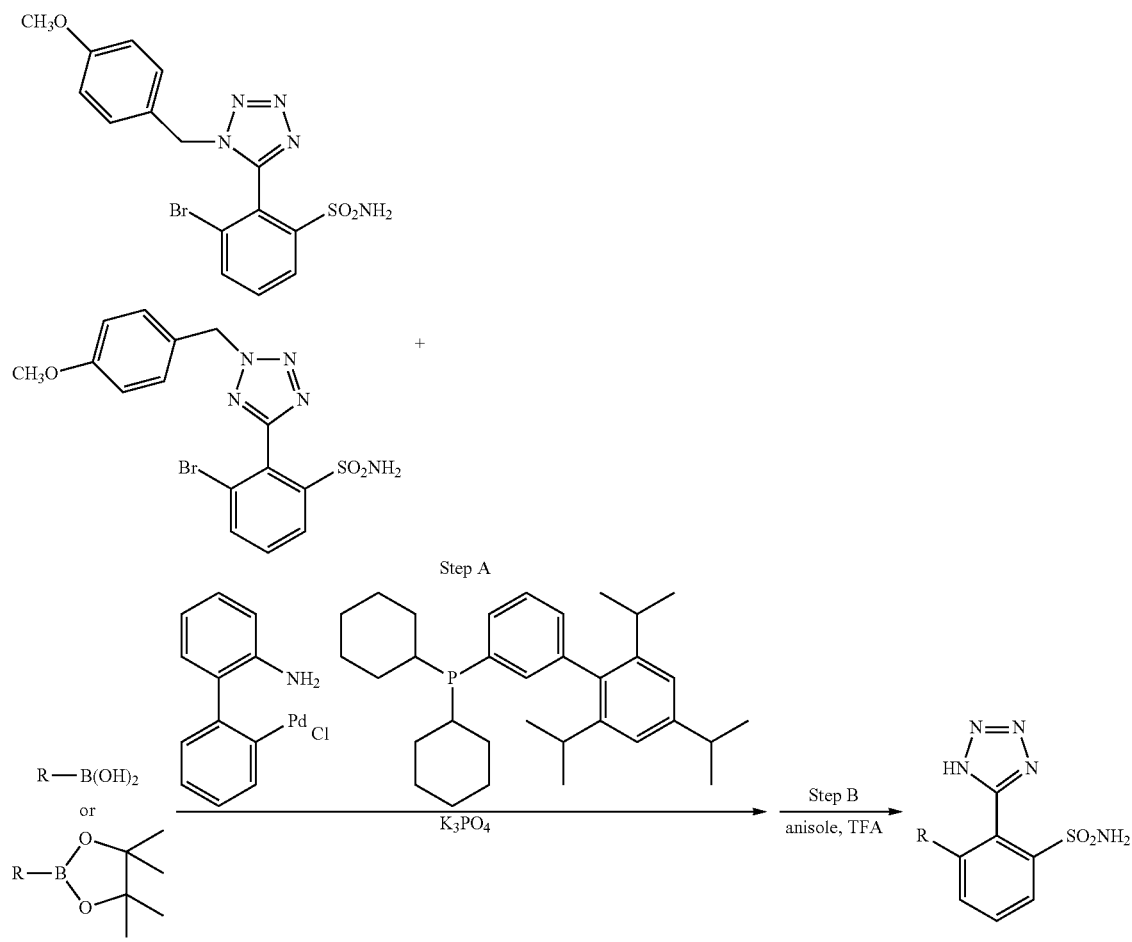

Step A: Palladium Catalyzed C—C Coupling of Arylbromide and Boronic Acids or Boronic Esters (Such as Pinacol Esters)

A mixture of 3-bromo-2-(1-(4-methoxybenzyl)-2H-tetrazol-5-yl)benzenesulfonamide and 3-bromo-2-(2-(4-methoxybenzyl)-2H-tetrazol-5-yl)benzenesulfonamide from Reference Example 1 (30 mg, 0.071 mmol), commercially available or known boronic acids (0.071 mmol) and XPhos-Pd-2G precatalyst (2.23 mg, 2.83 μmol) were weighed into a 1 dram vial and taken into the glove box. THF (1 mL) and 1 M potassium phosphate (0.25 mL, 0.250 mmol) were added and the mixture was stirred at 65° C. for 4 days. The organic solvents were removed under reduced pressure.

Step B: Removal of the p-methoxybenzyl (PMB) Protecting Group Under Acidic Conditions To remove the PMB protecting group, TFA (1 mL) and anisole (0.031 mL, 0.283 mmol) were added to the intermediates from Step A and the mixtures were stirred at 65° C.

for 3 hours. The mixtures were allowed to cool and concentrated under reduced pressure. To each vial, 1 mL DMSO was added and the mixtures were filtered into a 96-well plate. These crude materials and others prepared in the same way were purified by mass directed reverse phase HPLC to afford Examples 111-130.

| Ex. No. | Structure | Name | Calc'd Mass [M + H]+ | LC/MS m/e [M + H]+ |
|---|---|---|---|---|
| 111 | 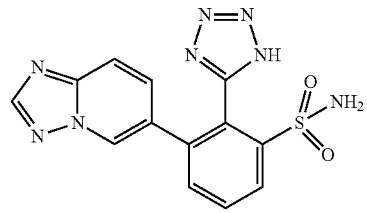 [SMILES: NS(=O)(=O)c1cccc(-c2ccc3ncnn3c2)c1-c1nnn[nH]1] | 3-([1,2,4]triazolo[1,5-a]pyridin-6-yl)-2-(1H-tetrazol-5-yl)benzenesulfonamide | 343 | 343 |
| 112 | 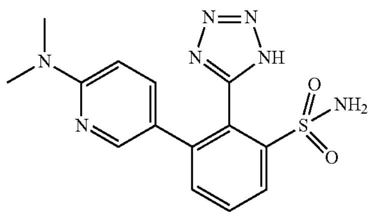 [SMILES: CN(C)c1ccc(-c2cccc(S(N)(=O)=O)c2-c2nnn[nH]2)cn1] | 3-(6-(dimethylamino)pyridin-3-yl)-2-(1H-tetrazol-5-yl)benzenesulfonamide | 346 | 346 |
| 113 | 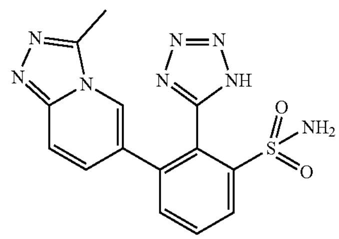 [SMILES: Cc1nnc2ccc(-c3cccc(S(N)(=O)=O)c3-c3nnn[nH]3)cn12] | 3-(3-methyl-[1,2,4]triazolo[4,3-a]pyridin-6-yl)-2-(1H-tetrazol-5-yl)benzenesulfonamide | 357 | 357 |
| 114 | 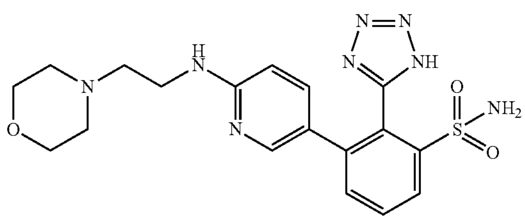 [SMILES: NS(=O)(=O)c1cccc(-c2ccc(NCCN3CCOCC3)nc2)c1-c1nnn[nH]1] | 3-(6-((2-morpholinoethyl)amino)pyridin-3-yl)-2-(1H-tetrazol-5-yl)benzenesulfonamide | 431 | 431 |
| 115 | 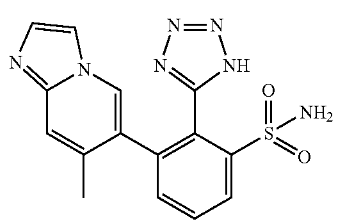 [SMILES: Cc1cc2nccn2cc1-c1cccc(S(N)(=O)=O)c1-c1nnn[nH]1] | 3-(7-methylimidazo[1,2-a]pyridin-6-yl)-2-(1H-tetrazol-5-yl)benzenesulfonamide | 356 | 356 |
| 116 | 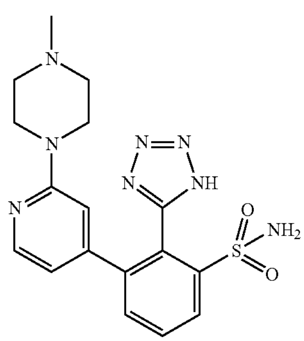 [SMILES: CN1CCN(c2cc(-c3cccc(S(N)(=O)=O)c3-c3nnn[nH]3)ccn2)CC1] | 3-(2-(4-methylpiperazin-1-yl)pyridin-4-yl)-2-(1H-tetrazol-5-yl)benzenesulfonamide | 401 | 401 |

-continued

| Ex. No. | Structure | Name | Calc'd Mass [M + H]+ | LC/MS m/e [M + H]+ |
|---|---|---|---|---|
| 117 | 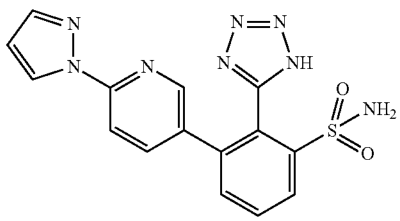 [SMILES: NS(=O)(=O)c1cccc(-c2ccc(-n3cccn3)nc2)c1-c1nnn[nH]1] | 3-(6-(1H-pyrazol-1-yl)pyridin-3-yl)-2-(1H-tetrazol-5-yl)benzenesulfonamide | 369 | 369 |
| 118 | 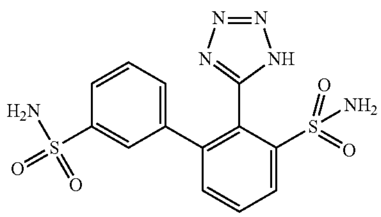 [SMILES: NS(=O)(=O)c1cccc(-c2cccc(S(N)(=O)=O)c2-c2nnn[nH]2)c1] | 2-(1H-tetrazol-5-yl)-[1,1'-biphenyl]-3,3'-disulfonamide | 381 | 381 |
| 119 | 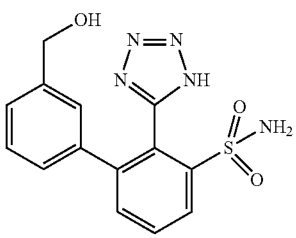 [SMILES: NS(=O)(=O)c1cccc(-c2cccc(CO)c2)c1-c1nnn[nH]1] | 3'-(hydroxymethyl)-2-(1H-tetrazol-5-yl)-[1,1'-biphenyl]-3-sulfonamide | 332 | 332 |
| 120 | 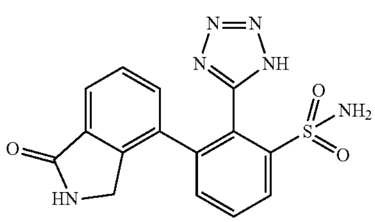 [SMILES: NS(=O)(=O)c1cccc(-c2cccc3c2CNC3=O)c1-c1nnn[nH]1] | 3-(1-oxoisoindolin-4-yl)-2-(1H-tetrazol-5-yl)benzenesulfonamide | 357 | 357 |
| 121 | 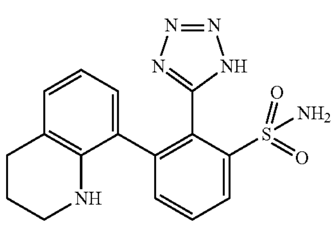 [SMILES: NS(=O)(=O)c1cccc(-c2cccc3c2NCCC3)c1-c1nnn[nH]1] | 3-(1,2,3,4-tetrahydroquinolin-8-yl)-2-(1H-tetrazol-5-yl)benzenesulfonamide | 357 | 357 |
| 122 | 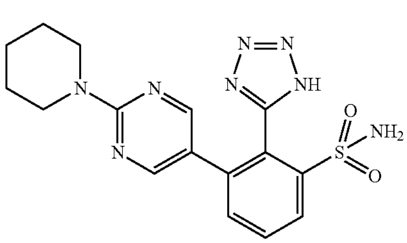 [SMILES: NS(=O)(=O)c1cccc(-c2cnc(N3CCCCC3)nc2)c1-c1nnn[nH]1] | 3-(2-(piperidin-1-yl)pyrimidin-5-yl)-2-(1H-tetrazol-5-yl)benzenesulfonamide | 387 | 387 |

-continued

| Ex. No. | Structure | Name | Calc'd Mass [M + H]+ | LC/MS m/e [M + H]+ |
|---|---|---|---|---|
| 123 | 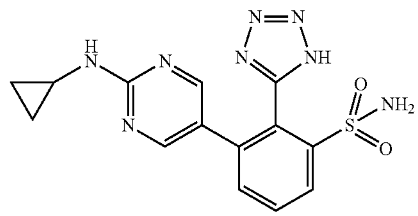 [SMILES: NS(=O)(=O)c1cccc(-c2cnc(NC3CC3)nc2)c1-c1nnn[nH]1] | 3-(2-(cyclopropylamino)pyrimidin-5-yl)-2-(1H-tetrazol-5-yl)benzenesulfonamide | 359 | 359 |
| 124 | 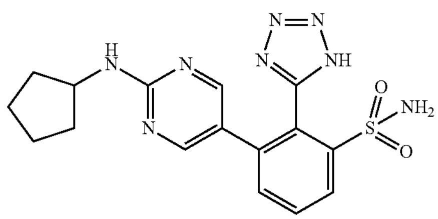 [SMILES: NS(=O)(=O)c1cccc(-c2cnc(NC3CCCC3)nc2)c1-c1nnn[nH]1] | 3-(2-(cyclopentylamino)pyrimidin-5-yl)-2-(1H-tetrazol-5-yl)benzenesulfonamide | 387 | 387 |
| 125 | 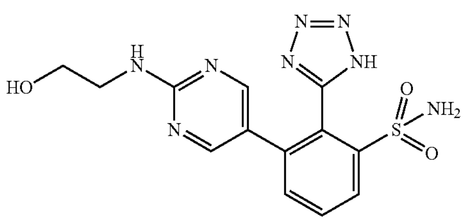 [SMILES: NS(=O)(=O)c1cccc(-c2cnc(NCCO)nc2)c1-c1nnn[nH]1] | 3-(2-((2-hydroxyethyl)amino)pyrimidin-5-yl)-2-(1H-tetrazol-5-yl)benzenesulfonamide | 363 | 363 |
| 126 | 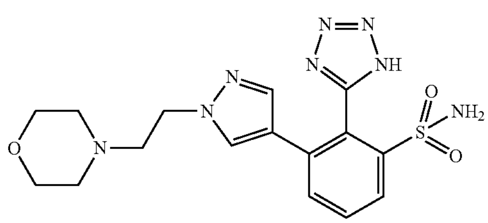 [SMILES: NS(=O)(=O)c1cccc(-c2cnn(CCN3CCOCC3)c2)c1-c1nnn[nH]1] | 3-(1-(2-morpholinoethyl)-1H-pyrazol-4-yl)-2-(1H-tetrazol-5-yl)benzenesulfonamide | 405 | 405 |
| 127 | 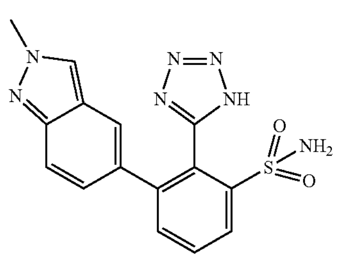 [SMILES: Cn1cc2cc(-c3cccc(S(N)(=O)=O)c3-c3nnn[nH]3)ccc2n1] | 3-(2-methyl-2H-indazol-5-yl)-2-(1H-tetrazol-5-yl)benzenesulfonamide | 356 | 356 |
| 128 | 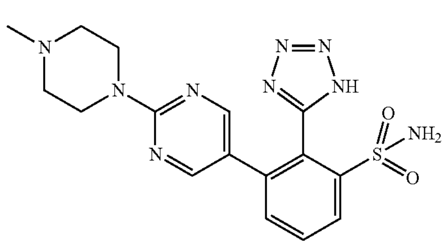 [SMILES: CN1CCN(c2ncc(-c3cccc(S(N)(=O)=O)c3-c3nnn[nH]3)cn2)CC1] | 3-(2-(4-methylpiperazin-1-yl)pyrimidin-5-yl)-2-(1H-tetrazol-5-yl)benzenesulfonamide | 402 | 402 |

| Ex. No. | Structure | Name | Calc'd Mass [M + H]⁺ | LC/MS m/e [M + H]⁺ |
|---|---|---|---|---|
| 129 | 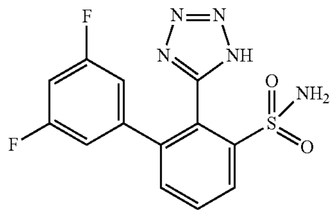 [SMILES: NS(=O)(=O)c1cccc(-c2cc(F)cc(F)c2)c1-c1nnn[nH]1] | 3',5'-difluoro-2-(1H-tetrazol-5-yl)-[1,1'-biphenyl]-3-sulfonamide | 338 | 338 |
| 130 | 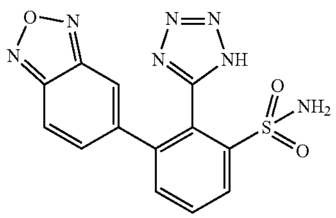 [SMILES: NS(=O)(=O)c1cccc(-c2ccc3nonc3c2)c1-c1nnn[nH]1] | 3-(benzo[c][1,2,5]oxadiazol-5-yl)-2-(1H-tetrazol-5-yl)benzenesulfonamide | 344 | 344 |

EXAMPLES 131-139

Parallel Synthesis of 3-Substituted 2-(1H-tetrazol-5-yl)benzenesulfonamides

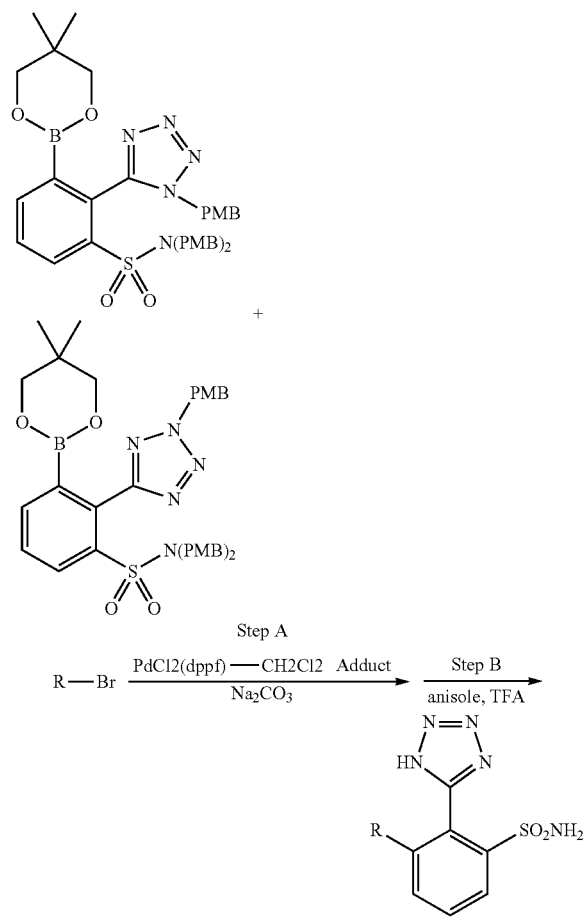

Step A: Palladium Catalyzed C—C Coupling of Arylboronic Ester with Bromides

An isomeric mixture of 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl) benzenesulfonamide, Reference Example 9, (30 mg, 0.043 mmol), were combined with commercially available or known aryl or heteroaryl bromides (0.065 mmol), sodium carbonate (9.12 mg, 0.086 mmol) and PdCl₂(dppf)-CH₂Cl₂ adduct (5.27 mg, 6.45 μmol) in a 1 dram vial and taken into the glove box. Acetonitrile (1 mL) and water (0.1 mL) were added and the mixture stirred at 95° C. for 18 hours. The mixtures were allowed to cool and the solvent was removed under reduced pressure. 1 mL DCM and 1 mL saturated ammonium chloride were added and the mixtures stirred for 5 minutes. The aqeuous layer was removed by pipette and the remaining organic phases were concentrated under reduced pressure.

Step B: Removal of the p-methoxybenzyl (PMB) Protecting Group Under Acidic Conditions To each vial from Step A was added TFA (1 mL) and anisole (0.019 mL, 0.172 mmol) and the mixtures were stirred at 50° C. for 3 hours. The vials were allowed to cool and the volatile organics were removed under reduced pressure. DMSO (1 mL) was added and the mixtures were filtered through a 96 well 0.4 micron filter plate. These crude materials and others made in the same way were purified by HPLC to afford Examples 131-139.

| Ex. No. | Structure | Name | Calc'd Mass [M + H]+ | LC/MS m/e [M + H]+ |
|---|---|---|---|---|
| 131 | 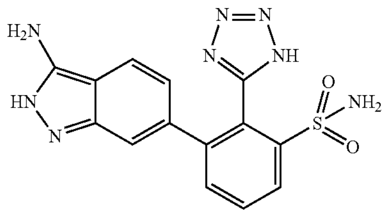 [SMILES: Nc1[nH]nc2cc(-c3cccc(S(N)(=O)=O)c3-c3nnn[nH]3)ccc12] | 3-(3-amino-2H-indazol-6-yl)-2-(1H-tetrazol-5-yl)benzenesulfonamide | 357 | 357 |
| 132 | 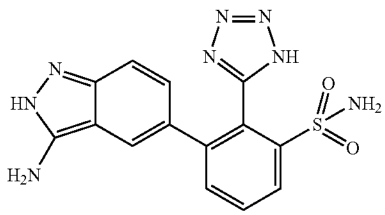 [SMILES: Nc1[nH]nc2ccc(-c3cccc(S(N)(=O)=O)c3-c3nnn[nH]3)cc12] | 3-(3-amino-2H-indazol-5-yl)-2-(1H-tetrazol-5-yl)benzenesulfonamide | 357 | 357 |
| 133 | 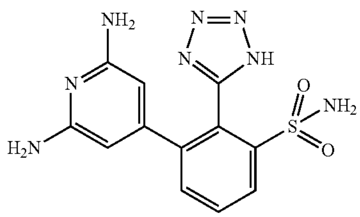 [SMILES: Nc1cc(-c2cccc(S(N)(=O)=O)c2-c2nnn[nH]2)cc(N)n1] | 3-(2,6-diaminopyridin-4-yl)-2-(1H-tetrazol-5-yl)benzenesulfonamide | 333 | 333 |
| 134 | 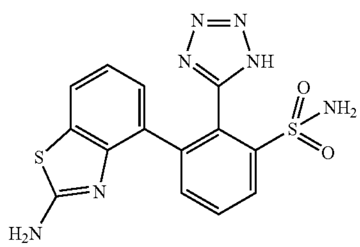 [SMILES: Nc1nc2c(-c3cccc(S(N)(=O)=O)c3-c3nnn[nH]3)cccc2s1] | 3-(2-aminobenzo[d]thiazol-4-yl)-2-(1H-tetrazol-5-yl)benzenesulfonamide | 374 | 374 |
| 135 | 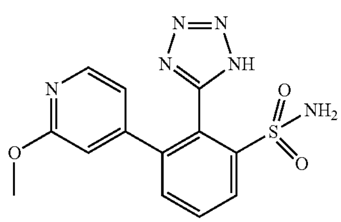 [SMILES: COc1cc(-c2cccc(S(N)(=O)=O)c2-c2nnn[nH]2)ccn1] | 3-(2-methoxypyridin-4-yl)-2-(1H-tetrazol-5-yl)benzenesulfonamide | 333 | 333 |
| 136 | 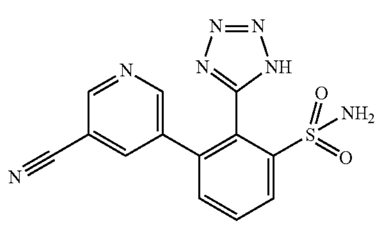 [SMILES: N#Cc1cncc(-c2cccc(S(N)(=O)=O)c2-c2nnn[nH]2)c1] | 3-(5-cyanopyridin-3-yl)-2-(1H-tetrazol-5-yl)benzenesulfonamide | 328 | 328 |
| 137 | 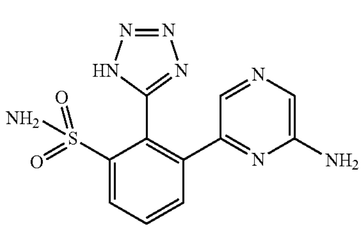 [SMILES: Nc1cncc(-c2cccc(S(N)(=O)=O)c2-c2nnn[nH]2)n1] | 3-(6-aminopyrazin-2-yl)-2-(1H-tetrazol-5-yl)benzenesulfonamide | 319 | 319 |

-continued

| Ex. No. | Structure | Name | Calc'd Mass [M + H]+ | LC/MS m/e [M + H]+ |
|---|---|---|---|---|
| 138 | 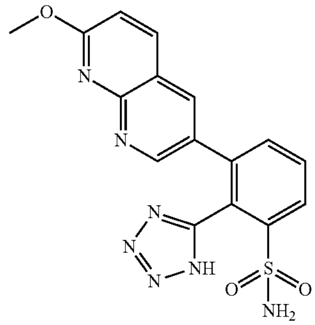 [SMILES: COc1ccc2cc(-c3cccc(S(N)(=O)=O)c3-c3nnn[nH]3)cnc2n1] | 3-(7-methoxy-1,8-naphthyridin-3-yl)-2-(1H-tetrazol-5-yl)benzenesulfonamide | 384 | 384 |
| 139 | 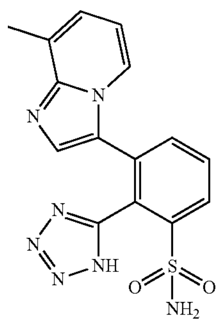 [SMILES: Cc1cccn2c(-c3cccc(S(N)(=O)=O)c3-c3nnn[nH]3)cnc12] | 3-(8-methylimidazo[1,2-a]pyridin-3-yl)-2-(1H-tetrazol-5-yl)benzenesulfonamide | 356 | 356 |

EXAMPLES 140-144

Parallel Synthesis of 3-Substituted 2-(1H-tetrazol-5-yl)benzenesulfonamides

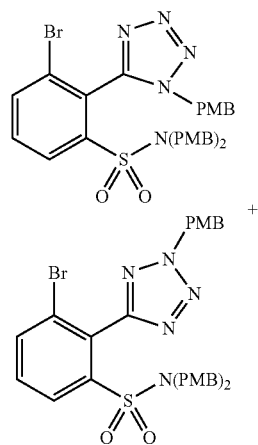

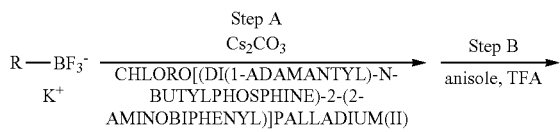

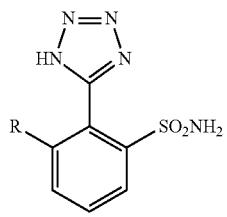

Step A: Palladium Catalyzed C—C Coupling of Alkyl, Vinyl and Aryl-BF$_3^-$ Salts with 3-bromo-N,N-bis(4-methoxybenzyl)-2-(1-(4-methoxybenzyl)-1H-tetrazol-5-yl)benzenesulfonamide and 3-bromo-N,N-bis(4-methoxybenzyl)-2-(2-(4-methoxybenzyl)-2H-tetrazol-5-yl)benzenesulfonamide 3-Bromo-N,N-bis(4-methoxybenzyl)-2-(1-(4-methoxybenzyl)-1H-tetrazol-5-yl)benzenesulfonamide and 3-bromo-N,N-bis(4-methoxybenzyl)-2-(2-(4-methoxybenzyl)-2H-tetrazol-5-yl)benzenesulfonamide (40 mg, 0.060 mmol), cesium carbonate (58.8 mg, 0.181 mmol), commercially available alkyl, vinyl and aryl-BF$_3^-$ salts (0.060 mmol) and chloro[(di(1-adamantyl)-N-butylphosphine)-2-(2-aminobiphenyl)]palladium(II) (4.02 mg, 6.02 μmol) were weighed into a 1 dram vial and taken into the glove box. Toluene (1 mL) and water (0.1 mL) were added and the mixtures were stirred at 110° C. for 18 hours. The mixtures were allowed to cool and the organics were removed under reduced pressure.

Step B: Removal of the p-methoxybenzyl (PMB) Protecting Group Under Acidic Conditions To remove the PMB protecting groups TFA (1 mL) and anisole (0.026 mL, 0.241 mmol) were added and the mixtures were stirred at 55° C. for 3 hours. The mixtures were allowed to cool and concentrated under reduced pressure. DMSO (1 mL) was added and the mixtures were filtered through a (96 well) 0.4 micron filter plate. These crude materials and others made in the same way were purified by HPLC to afford Examples 140-144.

| Ex. No. | Structure | Name | Calc'd Mass [M + H]+ | LC/MS m/e [M + H]+ |
|---|---|---|---|---|
| 140 | 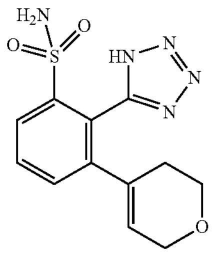 [SMILES: NS(=O)(=O)c1cccc(C2=CCOCC2)c1-c1nnn[nH]1] | 3-(3,6-dihydro-2H-pyran-4-yl)-2-(1H-tetrazol-5-yl)benzenesulfonamide | 308 | 308 |
| 141 | 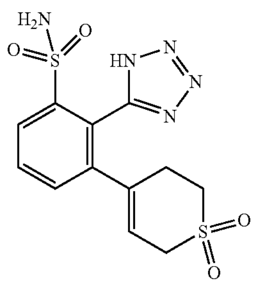 [SMILES: NS(=O)(=O)c1cccc(C2=CCS(=O)(=O)CC2)c1-c1nnn[nH]1] | 3-(1,1-dioxido-3,6-dihydro-2H-thiopyran-4-yl)-2-(1H-tetrazol-5-yl)benzenesulfonamide | 356 | 356 |
| 142 | 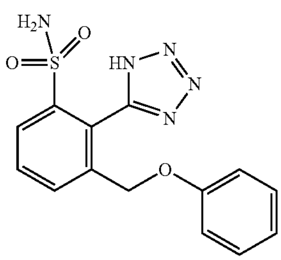 [SMILES: NS(=O)(=O)c1cccc(COc2ccccc2)c1-c1nnn[nH]1] | 3-(phenoxymethyl)-2-(1H-tetrazol-5-yl)benzenesulfonamide | 332 | 332 |
| 143 | 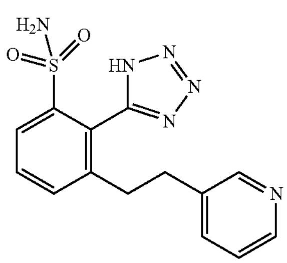 [SMILES: NS(=O)(=O)c1cccc(CCc2cccnc2)c1-c1nnn[nH]1] | 3-(2-pyridin-3-ylethyl)-2-(1H-tetrazol-5-yl)benzenesulfonamide | 331 | 331 |
| 144 | 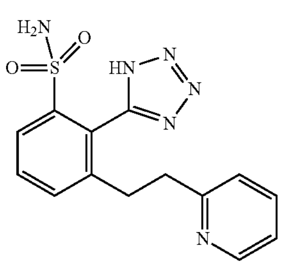 [SMILES: NS(=O)(=O)c1cccc(CCc2ccccn2)c1-c1nnn[nH]1] | 3-(2-pyridin-2-ylethyl)-2-(1H-tetrazol-5-yl)benzenesulfonamide | 331 | 331 |

EXAMPLES 145-148

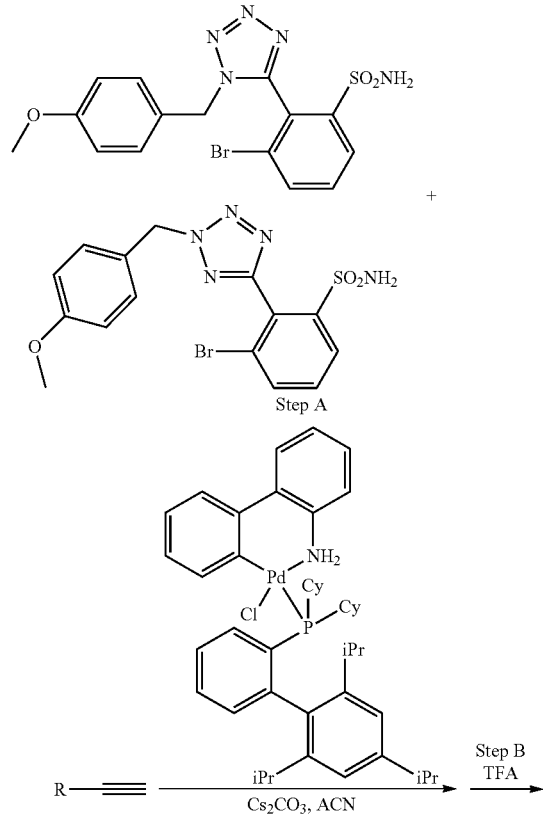

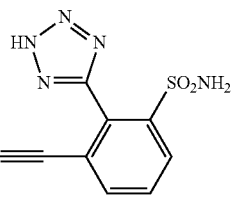

Step A: Palladium Catalyzed C—C Coupling of Arylbromide with Substituted Acetylenes In the reaction vessel, a mixture of isomeric 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide from Reference Example 1 (30 mg, 0.071 mmol) and alkynes were combined, followed by cesium carbonate (69.1 mg, 0.212 mmol), and XPhos-Pd-2G precatalyst (5.56 mg, 7.07 μmol). This mixture was then evacuated and backfilled with N₂ (3 times). Then dry, degassed acetonitrile (700 μl) was added to this flask. This mixture was stirred at 90° C. for 16 hours. Crude LC/MS showed formation of the desired intermediates.

Step B: Removal of the p-methoxybenzyl (PMB) Protecting Group Under Acidic Conditions To each vial, TFA (0.7 mL) was added and agitated at 65° C. for 16 hours. The solvent was removed and to each vial, siliaMetS DMT (Vendor: Silicycle, Cat. No.: R79030B) resin (40 mg) was added followed by addition of 1.1 mL of DMSO with shaking for 12 hours. The crude was filtered into a 96-well plate and purified by HPLC to yield Examples 145-148.

| Ex. No. | Structure | Name | Calc'd Mass [M + H]⁺ | LC/MS m/e [M + H]⁺ |
|---|---|---|---|---|
| 145 | 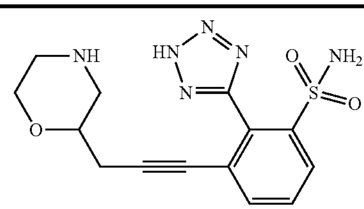 | 3-(3-morpholin-2-ylprop-1-yn-1-yl)-2-(2H-tetrazol-5-yl)benzenesulfonamide | 349.0 | 349.1 |
| 146 | 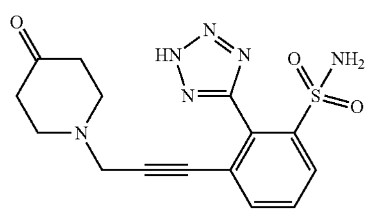 [SMILES: NS(=O)(=O)c1cccc(C#CCN2CCC(=O)CC2)c1-c1nn[nH]n1] | 3-[3-(4-oxopiperidin-1-yl)prop-1-yn-1-yl]-2-(2H-tetrazol-5-yl)benzenesulfonamide | 361.0 | 361.1 |
| 147 | 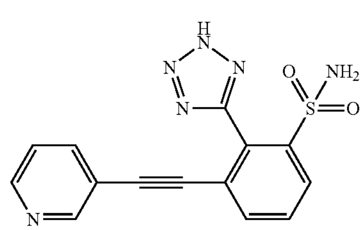 [SMILES: NS(=O)(=O)c1cccc(C#Cc2cccnc2)c1-c1nn[nH]n1] | 3-(pyridin-3-ylethynyl)-2-(2H-tetrazol-5-yl)benzenesulfonamide | 327.0 | 327.1 |

| Ex. No. | Structure | Name | Calc'd Mass [M + H]+ | LC/MS m/e [M + H]+ |
|---------|-----------|------|----------------------|---------------------|
| 148 | 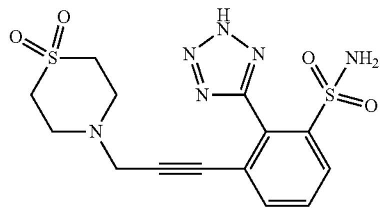 [SMILES: NS(=O)(=O)c1cccc(C#CCN2CCS(=O)(=O)CC2)c1-c1nn[nH]n1] | 3-[3-(1,1-dioxidothiomorpholin-4-yl)prop-1-yn-1-yl]-2-(2H-tetrazol-5-yl)benzenesulfonamide | 397.0 | 397.1 |

EXAMPLES 149-166

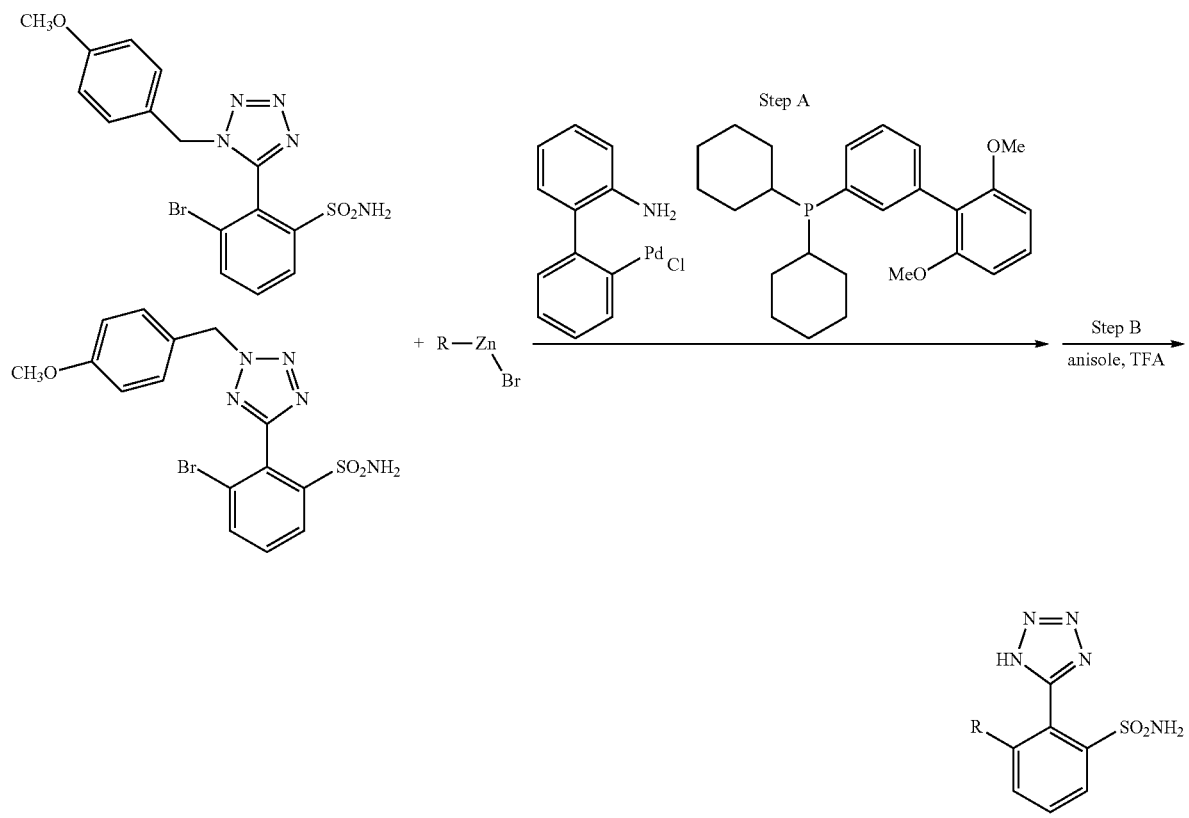

Step A: Palladium Catalyzed C—C Coupling of Alkyl, Aryl or Heteroaryl Zinc Bromides To a 40 mL vial was added 1040 mg of a mixture of isomeric 3-bromo-2-(1-(4-methoxybenzyl)-1H-tetrazol-5-yl)benzenesulfonamide and 3-bromo-2-(2-(4-methoxybenzyl)-1H-tetrazol-5-yl)benzenesulfonamide from Reference Example 1 (enough for 13 reactions each having 80 mg, 0.189 mmol) and 136 mg of SPhos-Pd-G2 precatalyst (enough for 13 reactions each having (5.44 mg, 7.54 µmol)). The vial was taken into the glove box. Then 3.64 mL of THF was added. 0.26 mL of this solution was added to each of 13×1 dram vials. Commercially available alkyl, aryl or heteroaryl zinc bromides were added to the vials which were then stirred at 55° C. for 18 hours. The mixtures were allowed to cool and then 1 mL of saturated ammonium chloride solution and 1 mL of DCM were added. The mixtures were stirred for 20 minutes. The layers were separated and the organic phases were concentrated under reduced pressure.

Step B: Removal of the p-methoxybenzyl (PMB) Protecting Group Under Acidic Conditions The intermediates from Step A were treated with anisole (0.082 mL, 0.754 mmol) and TFA (0.5 mL). The mixtures were stirred uncapped for 2 hours at 65° C. The mixtures were allowed to cool and the volatile organics were removed under reduced pressure. 1 mL DMSO was added to each vial and the mixtures filtered through a (96 well) 0.4 micron filter plate. These crude materials (and others prepared in the same fashion) were purified by mass directed reverse phase HPLC to afford Examples 149-166.

| Ex. No. | Structure | Name | Calc'd Mass [M + H]+ | LC/MS m/e [M + H]+ |
|---|---|---|---|---|
| 149 | 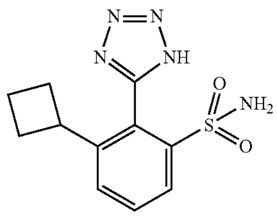 [SMILES: NS(=O)(=O)c1cccc(C2CCC2)c1-c1nnn[nH]1] | 3-cyclobutyl-2-(1H-tetrazol-5-yl)benzenesulfonamide | 280 | 280 |
| 150 | 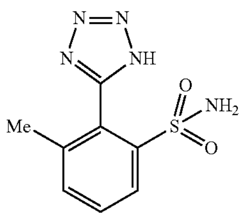 [SMILES: Cc1cccc(S(N)(=O)=O)c1-c1nnn[nH]1] | 3-methyl-2-(1H-tetrazol-5-yl)benzenesulfonamide | 240 | 240 |
| 151 | 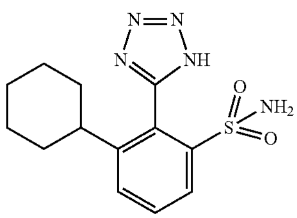 [SMILES: NS(=O)(=O)c1cccc(C2CCCCC2)c1-c1nnn[nH]1] | 3-cyclohexyl-2-(1H-tetrazol-5-yl)benzenesulfonamide | 308 | 308 |
| 152 | 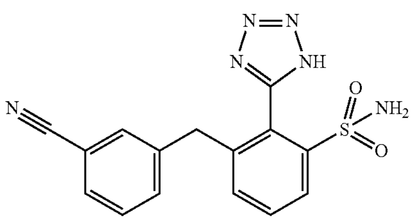 [SMILES: N#Cc1cccc(Cc2cccc(S(N)(=O)=O)c2-c2nnn[nH]2)c1] | 3-(3-cyanobenzyl)-2-(1H-tetrazol-5-yl)benzenesulfonamide | 341 | 341 |
| 153 | 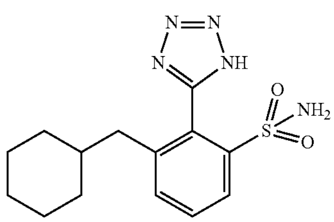 [SMILES: NS(=O)(=O)c1cccc(CC2CCCCC2)c1-c1nnn[nH]1] | 3-(cyclohexylmethyl)-2-(1H-tetrazol-5-yl)benzenesulfonamide | 322 | 322 |
| 154 | 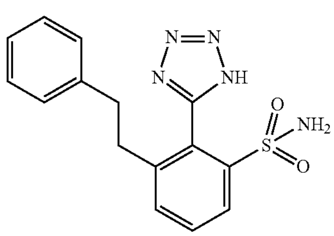 [SMILES: NS(=O)(=O)c1cccc(CCc2ccccc2)c1-c1nnn[nH]1] | 3-phenethyl-2-(1H-tetrazol-5-yl)benzenesulfonamide | 330 | 330 |
| 155 | 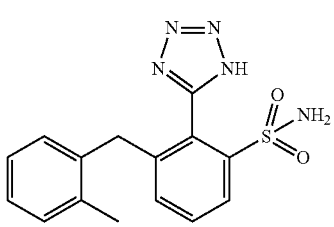 [SMILES: Cc1ccccc1Cc1cccc(S(N)(=O)=O)c1-c1nnn[nH]1] | 3-(2-methylbenzyl)-2-(1H-tetrazol-5-yl)benzenesulfonamide | 330 | 330 |

-continued

| Ex. No. | Structure | Name | Calc'd Mass [M + H]+ | LC/MS m/e [M + H]+ |
|---|---|---|---|---|
| 156 | 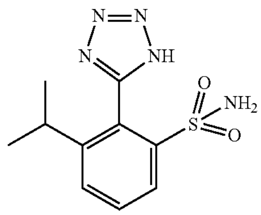 [SMILES: CC(C)c1cccc(S(N)(=O)=O)c1-c1nnn[nH]1] | 3-isopropyl-2-(1H-tetrazol-5-yl)benzenesulfonamide | 268 | 268 |
| 157 | 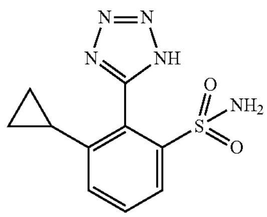 [SMILES: NS(=O)(=O)c1cccc(C2CC2)c1-c1nnn[nH]1] | 3-cyclopropyl-2-(1H-tetrazol-5-yl)benzenesulfonamide | 266 | 266 |
| 158 | 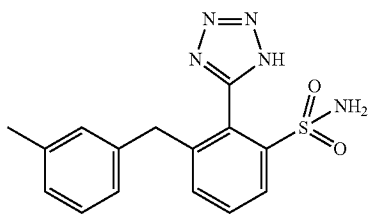 [SMILES: Cc1cccc(Cc2cccc(S(N)(=O)=O)c2-c2nnn[nH]2)c1] | 3-(3-methylbenzyl)-2-(1H-tetrazol-5-yl)benzenesulfonamide | 330 | 330 |
| 159 | 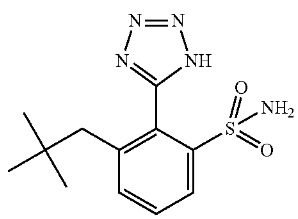 [SMILES: CC(C)(C)Cc1cccc(S(N)(=O)=O)c1-c1nnn[nH]1] | 3-neopentyl-2-(1H-tetrazol-5-yl)benzenesulfonamide | 296 | 296 |
| 160 | 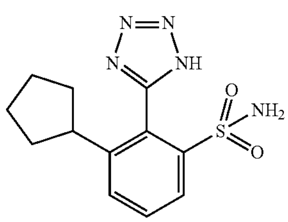 [SMILES: NS(=O)(=O)c1cccc(C2CCCC2)c1-c1nnn[nH]1] | 3-cyclopentyl-2-(1H-tetrazol-5-yl)benzenesulfonamide | 294 | 294 |
| 161 | 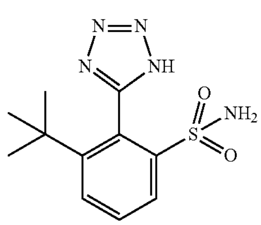 [SMILES: CC(C)(C)c1cccc(S(N)(=O)=O)c1-c1nnn[nH]1] | 3-(tert-butyl)-2-(1H-tetrazol-5-yl)benzenesulfonamide | 282 | 282 |
| 162 | 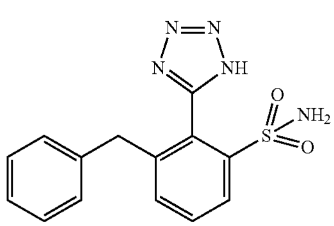 [SMILES: NS(=O)(=O)c1cccc(Cc2ccccc2)c1-c1nnn[nH]1] | 3-benzyl-2-(1H-tetrazol-5-yl)benzenesulfonamide | 316 | 316 |

| Ex. No. | Structure | Name | Calc'd Mass [M + H]+ | LC/MS m/e [M + H]+ |
|---|---|---|---|---|
| 163 | 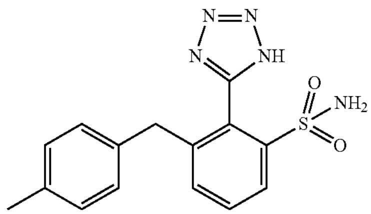 [SMILES: Cc1ccc(Cc2cccc(S(N)(=O)=O)c2-c2nnn[nH]2)cc1] | 3-(4-methylbenzyl)-2-(1H-tetrazol-5-yl)benzenesulfonamide | 330 | 330 |
| 164 | 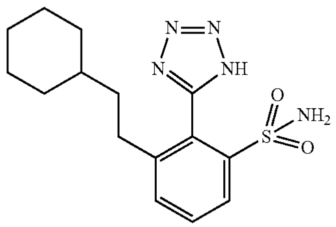 [SMILES: NS(=O)(=O)c1cccc(CCC2CCCCC2)c1-c1nnn[nH]1] | 3-(2-cyclohexylethyl)-2-(1H-tetrazol-5-yl)benzenesulfonamide | 336 | 336 |
| 165 | 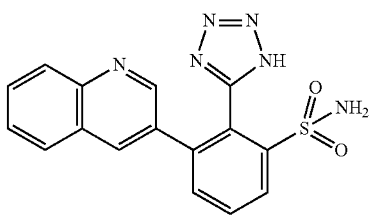 [SMILES: NS(=O)(=O)c1cccc(-c2cnc3ccccc3c2)c1-c1nnn[nH]1] | 3-(quinolin-3-yl)-2-(1H-tetrazol-5-yl)benzenesulfonamide | 353 | 353 |
| 166 | 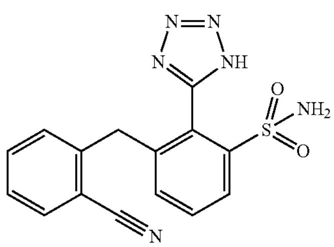 [SMILES: N#Cc1ccccc1Cc1cccc(S(N)(=O)=O)c1-c1nnn[nH]1] | 3-(2-cyanobenzyl)-2-(1H-tetrazol-5-yl)benzenesulfonamide | 341 | 341 |

EXAMPLE 167

3-isobutyl-2-(2H-tetrazol-5-yl)benzenesulfonamide

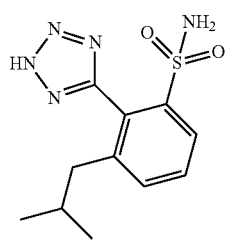 [SMILES: CC(C)Cc1cccc(S(N)(=O)=O)c1-c1nn[nH]n1]

Step A: 3-Isobutyl-2-(2-(4-methoxybenzyl)-2H-tetrazol-5-yl)benzenesulfonamide

3-Bromo-2-(1-(4-methoxybenzyl)-1H-tetrazol-5-yl)benzenesulfonamide (200 mg, 0.471 mmol) and 2nd generation SPHOS precatalyst (34.0 mg, 0.0470 mmol) was placed in a microwave tube, to which anhydrous THF (471 μL) was added. The tube was sealed and $N_2$ was bubbled through for 10 min. Isobutyl zinc(II) bromide (3771 μL, 1.886 mmol) was then added. The resulting mixture was heated at 50° C. for 3 hr. After being cooled to rt, the reaction was quenched with a saturated $NH_4Cl$ solution. The resulting mixture was extracted with EtOAC, and the organic layers were separated, washed with brine, dried ($Na_2SO_4$), filtered and concentrated. The crude product was purified by column chromatography (0-80% EtOAc/Hexane) to give the title compound. LC-MS 402 (M+1)+.

Step B: 3-Isobutyl-2-(2H-tetrazol-5-yl)benzenesulfonamide

3-Isobutyl-2-(2-(4-methoxybenzyl)-2H-tetrazol-5-yl)benzenesulfonamide (50 mg, 0.125 mmol) was heated at 80° C. in TFA (2 mL). The reaction mixture was concentrated and the residue was purified with Gilson 5-65% $CH_3CN$/water with 0.1% FA. The correct fractions were combined, concentrated and lypholized to give the title compound. LC-MS 282 (M+1)+.

EXAMPLE 168

3-(4-Aminocyclohexyl)-2-(2H-tetrazol-5-yl)benzenesulfonamide

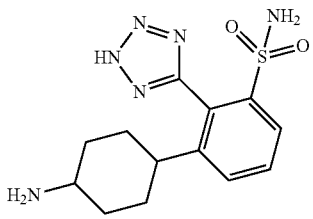 [SMILES: NC1CCC(c2cccc(S(N)(=O)=O)c2-c2nn[nH]n2)CC1]

Step A: 3-(4-Aminocyclohexyl)-2-(2-(4-methoxybenzyl)-2H-tetrazol-5-yl)benzenesulfonamide To a microwave tube was added 2-(2-(4-Methoxybenzyl)-2H-tetrazol-5-yl)-3-(4-oxocyclohexyl)benzenesulfonamide (400 mg, 0.906 mmol), NaCNBH$_4$ (159 mg, 2.54 mmol), ammonium acetate (908 mg, 11.8 mmol), magnesium sulfate (600 mg, 4.98 mmol) and MeOH (6 mL). The tube was sealed and heated at 80° C. overnight. The reaction mixture was cooled and filtered, and the filtration cake was washed with MeOH. The filtrates were concentrated and partitioned between EtOAc and a small amount of water. The EtOAc layer was washed with brine, dried (Na$_2$SO$_4$), filtered and concentrated to give the title compound. LC-MS 443 (M+1)$^+$.

Step B: 3-(4-Aminocyclohexyl)-2-(2H-tetrazol-5-yl)benzenesulfonamide 3-(4-Aminocyclohexyl)-2-(2-(4-methoxybenzyl)-2H-tetrazol-5-yl)benzenesulfonamide (100 mg, 0.226 mmol) was heated in TFA for 2 h at 80° C. The mixture was concentrated and the residue was purified with Gilson (2-40% CH$_3$CN/water with 0.1% TFA). The product was concentrated and lypholized from CH$_3$CN/water. LC-MS 323 (M+1)$^+$.

EXAMPLE 169

3-(4-(methylsulfonamido)cyclohexyl)-2-(2H-tetrazol-5-yl)benzenesulfonamide

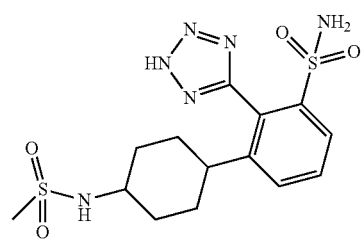 [SMILES: CS(=O)(=O)NC1CCC(c2cccc(S(N)(=O)=O)c2-c2nn[nH]n2)CC1]

Step A: 2-(2-(4-Methoxybenzyl)-2H-tetrazol-5-yl)-3-(4-(methylsulfonamido)cyclohexyl)benzenesulfonamide 3-(4-Aminocyclohexyl)-2-(2-(4-methoxybenzyl)-2H-tetrazol-5-yl)benzenesulfonamide (140 mg, 0.316 mmol) was dissolved in DCM (1.6 mL), cooled to −78° C. and treated with TEA (132 μL, 0.949 mmol), followed by dropwise addition of methanesulfonyl chloride (29.4 μL, 0.380 mmol) in DCM (0.5 mL). The mixture was stirred at this temperature for 40 min. LC-MS showed most of the starting material was consumed and the desired product was the major product. The reaction was quenched by adding water (2 mL). The mixture was allowed to warm up to rt and extracted with DCM. The organics were washed with sat. NaHCO$_3$ solution, concentrated and the residue was purified by column chromatography (0-100% EtOAC/hexane) to give the title compound. LC-MS 521 (M+1)$^+$.

Step B: 3-(4-(Methylsulfonamido)cyclohexyl)-2-(2H-tetrazol-5-yl)benzenesulfonamide 2-(2-(4-Methoxybenzyl)-2H-tetrazol-5-yl)-3-(4-(methylsulfonamido)cyclohexyl)benzenesulfonamide (81 mg, 0.16 mmol) was heated in TFA (2 mL) in the presence of anisole (85 μl, 0.778 mmol) at 60° C. overnight. The reaction mixture was concentrated and purified with Gilson (2-40% CH$_3$CN/water with 0.1% TFA) to give the title compound.

EXAMPLE 170

3-(4-(piperazin-1-yl)cyclohexyl)-2-(2H-tetrazol-5-yl)benzenesulfonamide

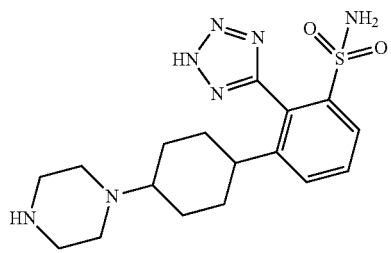 [SMILES: NS(=O)(=O)c1cccc(C2CCC(N3CCNCC3)CC2)c1-c1nn[nH]n1]

Step A: 2-(2-(4-Methoxybenzyl)-2H-tetrazol-5-yl)-3-(4-(piperazin-1-yl)cyclohexyl)benzenesulfonamide To a solution of 2-(2-(4-Methoxybenzyl)-2H-tetrazol-5-yl)-3-(4-oxocyclohexyl)benzenesulfonamide (150 mg, 0.340 mmol) and tert-butyl piperazine-1-carboxylate (69.6 mg, 0.374 mmol) in THF (1.1 mL) was added titanium(IV) isopropoxide (151 μL, 0.510 mmol). The mixture was stirred at rt under N$_2$ overnight. Sodium cyanoborohydride (64.1 mg, 1.02 mmol) was added in one portion and stirring was continued for 2 hr. The reaction was quenched with water and extracted with EtOAc. Purification by column chromatography (0-90% EtOAc/Hexane) gave the title compound. LC-MS 612 (M+1)$^+$.

Step B: 3-(4-(Piperazin-1-yl)cyclohexyl)-2-(2H-tetrazol-5-yl)benzenesulfonamide tert-Butyl 2-(2-(4-Methoxybenzyl)-2H-tetrazol-5-yl)-3-(4-(piperazin-1-yl)cyclohexyl)benzenesulfonamide (60 mg, 0.098 mmol) was treated with TFA (1 mL) in DCM (1 mL). After the reaction was stirred at rt for 1 hr, LC-MS indicated that the Boc protecting was removed. The reaction mixture was concentrated and co-evaporated with toluene 3 times. The resulting residue was taken up in TFA (2 mL) and heated at 80° C. for 1.5 hr, and then concentrated to remove the excess of TFA. The crude product was purified with gilson (1-40% CH3CN/water with 0.1% TFA), and lypholized to give the title compound. LC-MS 392 (M+1)$^+$.

EXAMPLE 171

3-(4-hydroxycyclohexyl)-2-(2H-tetrazol-5-yl)benzenesulfonamide

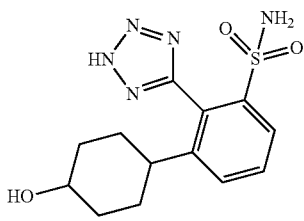 [SMILES: NS(=O)(=O)c1cccc(C2CCC(O)CC2)c1-c1nn[nH]n1]

Step A: 3-(4-Hydroxycyclohexyl)-2-(2-(4-methoxybenzyl)-2H-tetrazol-5-yl)benzenesulfonamide 2-(2-(4-Methoxybenzyl)-2H-tetrazol-5-yl)-3-(4-oxocyclohexyl)benzenesulfonamide (500 mg, 1.132 mmol) was suspended in MeOH (10 mL). Under $N_2$ and at 0° C. $NaBH_4$ (42.8 mg, 1.132 mmol) was added. The mixture was stirred at 0° C. for 2 hr, and then quenched with $NH_4Cl$ aqueous solution. The mixture was filtered and the filtrates were concentrated to remove MeOH. The residue was partitioned between EtOAc and water. The organic phase was separated, washed with brine, dried ($Na_2SO_4$) and concentrated to give the title compound. LC-MS 444 (M+1)$^+$.

Step B: 3-(4-Hydroxycyclohexyl)-2-(2H-tetrazol-5-yl)benzenesulfonamide 3-(4-Hydroxycyclohexyl)-2-(2-(4-methoxybenzyl)-2H-tetrazol-5-yl)benzenesulfonamide (100 mg, 0.225 mmol) was heated in TFA (2 mL) for 2 hr at 80° C. The reaction mixture was then concentrated to remove the excess of TFA. The residue was dissolved in THF (2 mL) and treated with saturated $Na_2CO_3$ aqueous solution (2 mL). After being stirred at rt for 2 hr, the reaction mixture was extracted with EtOAc. The organic layers were combined, dried ($Na_2SO4$) and concentrated. The residue was purified with Gilson (2-35% $CH_3CN$/water with 0.1% TFA) and the desired fractions were combined, lypholized (freezed without concentration) to give the title compound. LC-MS 324 (M+1)$^+$.

EXAMPLE 172

3-(1-(methylsulfonyl)piperidin-4-yl)-2-(2H-tetrazol-5-yl)benzenesulfonamide

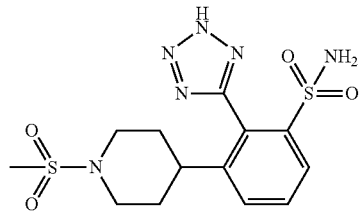 [SMILES: CS(=O)(=O)N1CCC(c2cccc(S(N)(=O)=O)c2-c2nn[nH]n2)CC1]

ethyl 4-(3-sulfamoyl-2-(2H-tetrazol-5-yl)phenyl)piperidine-1-carboxylate

To a 1-dram vial with methanesulfonyl chloride (5.35 mg, 0.047 mmol) was added isomer mixture 2-(2-(4-methoxybenzyl)-2H-tetrazol-5-yl)-3-(piperidin-4-yl)benzenesulfonamide and 2-(3-(4-methoxybenzyl)-2H-tetrazol-5-yl)-3-(piperidin-4-yl)benzenesulfonamide (20 mg, 0.047 mmol) in DMF (1.5 mL) followed by DIEA (0.033 mL, 0.187 mmol). The vial was agitated for 16 hr at 25° C. The solvent was removed and residue was dissolved in 1 mL TFA and agitated at 65° C. for 12 hours. The solvent was removed and 1.5 mL DMSO was added, and the mixture was filtered and purified by reverse phase HPLC. LC/MS [M+H]$^+$ 387.

EXAMPLE 173

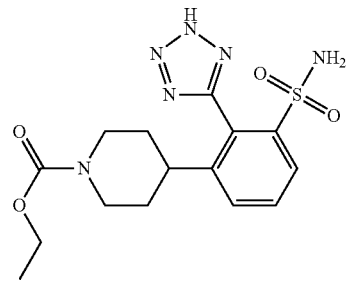 [SMILES: CCOC(=O)N1CCC(c2cccc(S(N)(=O)=O)c2-c2nn[nH]n2)CC1]

To a 1-dram vial with isomer mixture 2-(2-(4-methoxybenzyl)-2H-tetrazol-5-yl)-3-(piperidin-4-yl)benzenesulfonamide and 2-(3-(4-methoxybenzyl)-2H-tetrazol-5-yl)-3-(piperidin-4-yl)benzenesulfonamide (Reference Example 16, 20 mg, 0.047 mmol) was added ethyl chloroformate (15.2 mg, 0.140 mmol) in DMF (1.5 mL) followed by addition of DIEA (0.033 mL, 0.187 mmol). The vial was agitated for 16 hr at 25° C. The solvent was removed and residue was dissolved in 1 mL TFA and agitated at 65° C. for 12 hours. The solvent was removed and 1.5 mL DMSO was added. The mixture was filtered and purified by reverse phase HPLC. LC/MS [M+H]$^+$ 381.

EXAMPLE 174

N-ethyl-4-(3-sulfamoyl-2-(2H-tetrazol-5-yl)phenyl)piperidine-1-carboxamide

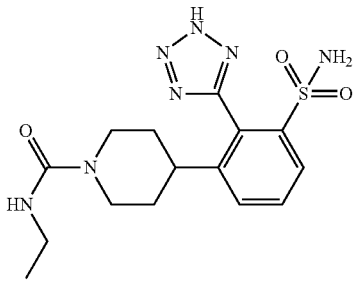 [SMILES: CCNC(=O)N1CCC(c2cccc(S(N)(=O)=O)c2-c2nn[nH]n2)CC1]

To a 1-drum vial with an isomer mixture of 2-(2-(4-methoxybenzyl)-2H-tetrazol-5-yl)-3-(piperidin-4-yl)benzenesulfonamide and 2-(3-(4-methoxybenzyl)-2H-tetrazol-5-yl)-3-(piperidin-4-yl)benzenesulfonamide (20 mg, 0.047 mmol) was added isocyanatoethane (3.32 mg, 0.047 mmol) in DMF (1.5 mL) followed by addition of DIEA (0.033 mL, 0.187 mmol). The vial was agitated for 16 hr at 25° C. The crude intermediate material was purified by reverse phase HPLC. The solvent was removed and residue was dissolved in 1 mL TFA and agitated at 65° C. for 12 hours. The solvent was removed and 1.5 mL DMSO was added. The mixture was filtered and purified by reverse phase HPLC. LC/MS [M+H]+ 380.

EXAMPLE 175

3-(piperidin-3-yl)-2-(2H-tetrazol-5-yl)benzenesulfonamide

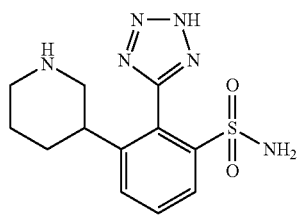 [SMILES: NS(=O)(=O)c1cccc(C2CCCNC2)c1-c1nn[nH]n1]

Step A: To a mixture of 3-bromo-2-(2-(4-methoxybenzyl)-2H-tetrazol-5-yl)benzenesulfonamide (1.00 g, 2.36 mmol), tert-butyl 3-iodopiperidine-1-carboxylate (1.47 g, 4.71 mmol), pyridine (0.953 mL, 11.8 mmol), nickel chloride dimethoxyethane adduct (0.104 g, 0.471 mmol), zinc (0.925 g, 14.1 mmol), and ligand A 2,2':6',2''-terpyridine (0.330 g, 1.414 mmol) (or ligand B 4,4',4''-tri-tert-butyl-2,2':6',2''-terpyridine) in an N$_2$ filled microwave reaction vial was added DMA (8 mL). The vial was capped, and the reaction was heated to 100° C. for 2 hr in a microwave. The excess catalyst was filtered off and the solution was concentrated. The crude material was used for the next step.

Step B: The crude from Step A was dissolved in CH$_2$Cl$_2$ (4 mL) and TFA (2 mL). The reaction was stirred at room temperature for 20 min; the resulting suspension was filtered, washed with small amount of MeOH. Then the solution was passed through Varian Bond Elut SCX ion exchange cartridge, washed with MeOH to get rid of most of the impurities from the previous step, and the desired product was eluted from the cartridge with 2 M NH$_4$OH/MeOH, and concentrated to get 2-(2-(4-methoxybenzyl)-2H-tetrazol-5-yl)-3-(piperidin-3-yl)benzenesulfonamide. LC-MS: calculated for C$_{20}$H$_{24}$N$_6$O$_3$S 428.51 observed m/e: 429.41 (M+H)+.

Step C: 10 mg of the product from Step B was dissolved in 1 mL of TFA, and was heated to 65° C. for 16 hr. The reaction was concentrated and purified by reverse phase HPLC column (acetonitrile/water/0.05% TFA system) eluted with 2% to 30% MeCN in water. The pure fractions were concentrated to afford product. LC-MS: calculated for C12H16N6O2S 308.36 observed m/e: 309.30 (M+H)+; 1H NMR δ (ppm) (CD3OD): 8.08-8.12 (d, 1H), 7.75-7.85 (m, 2H), 3.35-3.30 (m, 2H) 3.17 (t, 1H), 2.8-2.9 (m, 2H), 1.8-1.9 (m, 2H), 1.6-1.7 (m, 2H).

EXAMPLE 176

3-(1-(1-phenylcyclopropanecarbonyl)piperidin-4-yl)-2-(2H-tetrazol-5-yl)benzenesulfonamide

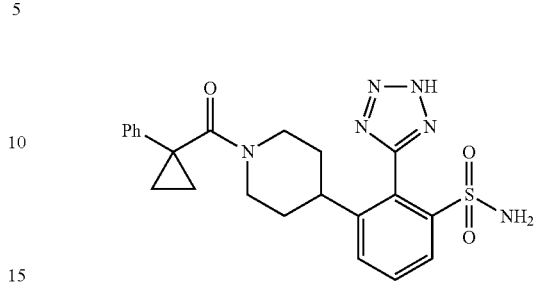

The title compound was prepared using Reference Example 19, 3-bromo-2-(2-(4-methoxybenzyl)-2H-tetrazol-5-yl)benzenesulfonamide and Ligand B (see below) in an analogous fashion to 3-(piperidin-3-yl)-2-(2H-tetrazol-5-yl)benzenesulfonamide. LC/MS [M+H]+ 453.34.

Ligand B

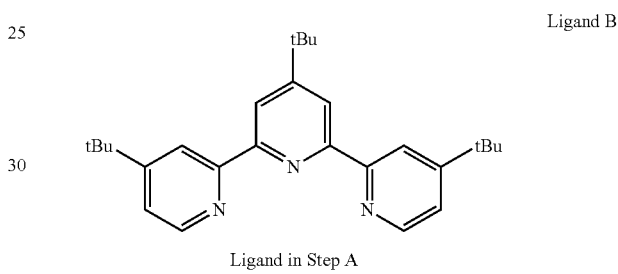

Ligand in Step A

EXAMPLE 177

3-(1-(cyclopropanecarbonyl)piperidin-3-yl)-2-(2H-tetrazol-5-yl)benzenesulfonamide

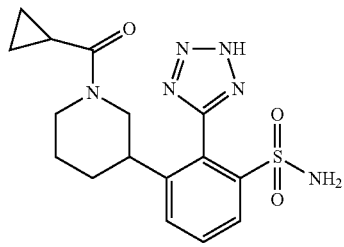 [SMILES: NS(=O)(=O)c1cccc(C2CCCN(C(=O)C3CC3)C2)c1-c1nn[nH]n1]

Step A: To a solution of 2-(2-(4-methoxybenzyl)-2H-tetrazol-5-yl)-3-(piperidin-3-yl)benzenesulfonamide (20 mg, 0.047 mmol) in 1 mL of CH$_2$Cl$_2$ was added cyclopropanecarbonyl chloride (7.32 mg, 0.070 mmol) and TEA (0.065 mL, 0.467 mmol), stirred at rt for 1 hr. The reaction solution was concentrated and purified by reverse phase HPLC column (acetonitrile/water/0.05% TFA system) and eluted with 10% to 60% MeCN in water. The pure fractions were concentrated to afford the desired product. LC-MS: calculated for C$_{24}$H$_{28}$N$_6$O$_4$S 496.58 observed m/e: 497.47 (M+H)+;

Step B: The resulting product from Step A was dissolved in 1 mL of TFA, and was heated to 65° C. for 16 hr. The reaction was concentrated and purified by reverse phase HPLC column (acetonitrile/water/0.05% TFA system) and eluted with 2% to 30% MeCN in water. The pure fractions were concentrated to afford product. LC-MS: calculated for C16H20N6O3S 376.43 observed m/e: 377.39 (M+H)+; 1H NMR δ (ppm) (CD3OD): 8.17-8.19 (d, 1H), 7.73-7.75 (m, 2H), 4.65-4.68 (m, 1H), 4.30-4.34 (m, 1H), 2.89-2.92 (m, 1H), 2.39-2.43 (m, 1H), 2.22-2.26 (m, 1H), 1.92-1.95 (m, 1H), 1.81-1.86 (m, 1H), 1.77-1.81 (m, 2H), 1.45-1.49 (m, 1H), 0.84-0.89 (m, 2H), 0.82-0.84 (m, 2H).

EXAMPLE 178

3-(5,6,7,8-tetrahydroimidazo[1,5-a]pyridin-7-yl)-2-(2H-tetrazol-5-yl)benzenesulfonamide

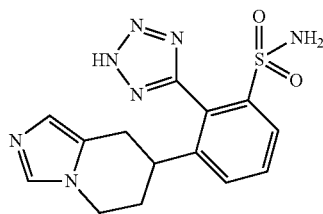 [SMILES: NS(=O)(=O)c1cccc(C2CCn3cncc3C2)c1-c1nn[nH]n1]

Step A: 2-(2-(4-Methoxybenzyl)-2H-tetrazol-5-yl)-3-(5,6,7,8-tetrahydroimidazo[1,5-a]pyridin-7-yl)benzenesulfonamide 3-(Imidazo[1,5-a]pyridin-7-yl)-2-(2-(4-methoxybenzyl)-2H-tetrazol-5-yl)benzenesulfonamide (121 mg, 0.262 mmol) was dissolved in MeOH (2.6 mL), to which was added 2 drops of conc. HCl, then Pd—C (120 mg). The reaction head space was vacuumed and filled with H2 two times. The mixture was stirred at rt under H2 for 48 hr. LC-MS showed the conversion was complete. The reaction mixture was filtered and the filtrates were concentrated to give the title compound, which was used directly in the next step.

Step B: 3-(5,6,7,8-Tetrahydroimidazo[1,5-a]pyridin-7-yl)-2-(2H-tetrazol-5-yl)benzenesulfonamide 2-(1-(4-Methoxybenzyl)-1H-tetrazol-5-yl)-3-(5,6,7,8-tetrahydroimidazo[1,5-a]pyridin-7-yl)benzenesulfonamide (122 mg, 0.262 mmol) was heated in TFA (3 mL) at 80° C. for 2 hr. LC-MS showed the reaction was completed. The mixture was then concentrated and the residue was purified with Gilson (5%-40% CH3CN/water with 0.1% FA). The correct fractions were combined, concentrated and lypholized to give the title compound. LC-MS 346 (M+1)+.

EXAMPLE 179

2-(2H-tetrazol-5-yl)-3-(p-tolyloxy)benzenesulfonamide

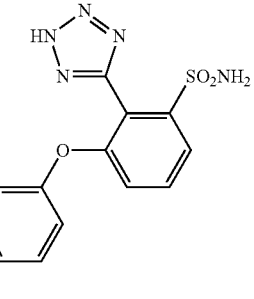

Step A: 2-(p-tolyloxy)-6-((2-(trimethylsilyl)ethyl)thio)benzonitrile

To a solution of 2-fluoro-6-(p-tolyloxy)benzonitrile (0.5 g, 2.2 mmol) and potassium carbonate (0.608 g, 4.40 mmol) in DMF (30 mL) was added 2-(trimethylsilyl)ethanethiol (0.355 g, 2.64 mmol) and the resulting mixture was stirred at room temperature overnight. The reaction mixture was filtered. The filtrate was diluted with EtOAc, and washed with water and brine. The organic layer was dried over anhydrous MgSO4, filtered, and concentrated. The residue was purified by silica gel column chromatography using 0-30% EtOAc/Hexanes as mobile phase to afford the title compound. LC-MS (IE, m/z): 342.18 [M+1]+.

Step B: 2-(p-tolyloxy)-6-((2-(trimethylsilyl)ethyl)sulfonyl)benzonitrile

To a solution of 2-(p-tolyloxy)-6-((2-(trimethylsilyl)ethyl)thio)benzonitrile (0.44 g, 1.288 mmol) in DCM (8.6 mL) at 0° C. was added mCPBA (0.778 g, 4.51 mmol) and the mixture was stirred at room temperature overnight. Sat. Na2S2O3 was added to the mixture and stirred for 10 min, followed by sat. NaHCO3. After separation of layers, aqueous layer was extracted with DCM. The combined organic layer was dried over anhydrous Na2SO4, filtered and concentrated to get the title compound. LC-MS (IE, m/z): 374.26 [M+1]+.

Step C: 5-(2-(p-tolyloxy)-6-((2-(trimethylsilyl)ethyl)sulfonyl)phenyl)-2H-tetrazole To a solution of 2-(p-tolyloxy)-6-((2-(trimethylsilyl)ethyl)sulfonyl)benzonitrile (200 mg, 0.535 mmol) in toluene (4.5 mL) was added azidotrimethyltin (551 mg, 2.68 mmol) and the resulting mixture was heated overnight at 100° C. Solid precipitate was filtered, and washed with hexanes. The filtrate was purified by silica gel column chromatography using 0-10% MeOH/DCM (containing 0.2% AcOH additive) as solvent system to afford the title compound. LC-MS (IE, m/z): 417.19 [M+1]+.

Step D: 2-(2H-tetrazol-5-yl)-3-(p-tolyloxy)benzenesulfonamide

To a solution of 5-(2-(p-tolyloxy)-6-((2-(trimethylsilyl)ethyl)sulfonyl)phenyl)-1H-tetrazole (120 mg, 0.288 mmol) in THF (5761 μL) was added TBAF in THF (1440 μl, 1.440 mmol). The resulting solution was degassed with N2, stirred at 40° C. for 2 hr, and checked by LCMS for completion of the first step conversion. Then sodium acetate (236 mg, 2.88 mmol) in 2.5 mL water was added, followed by addition of hydroxylamine-O-sulfonic acid (326 mg, 2.88 mmol). The resulting solution was stirred at rt overnight. The mixture was partitioned between EtOAc (50 mL) and saturated NaHCO₃. The organic phase was washed with NaHCO₃ twice, dried over Na₂SO₄, and concentrated. The residue was purified by silica gel column chromatography using 0-10% MeOH/DCM and 0.5% AcOH as mobile phase to give the title compound. LC-MS (IE, m/z): 332.34 [M+1]+.

EXAMPLE 180

4'-(pyrrolidin-3-yl)-2-(1H-tetrazol-5-yl)-[1,1'-biphenyl]-3-sulfonamide

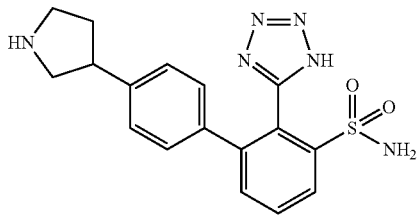 [SMILES: NS(=O)(=O)c1cccc(-c2ccc(C3CCNC3)cc2)c1-c1nnn[nH]1]

Step A: tert-butyl 3-(2'-(1-(4-methoxybenzyl)-1H-tetrazol-5-yl)-3'-sulfamoyl-[1,1'-biphenyl]-4-yl)pyrrolidine-1-carboxylate In a 25 mL microwave tube, 3-bromo-2-(1-(4-methoxybenzyl)-1H-tetrazol-5-yl)benzenesulfonamide (300 mg, 0.71 mmol), tert-butyl 3-(4-(4,4,5,5-tetramethyl-1,3,2-dioxaborolan-2-yl)phenyl)pyrrolidine-1-carboxylate (Reference Example 14, 530 mg, 1.41 mmol), 1,1'-bis(diphenylphosphino)ferrocene-palladium(II)dichloride dichloromethane complex (115 mg, 0.14 mmol) and K₂CO₃ (390 mg, 2.83 mmol) were dissolved in a mixture of EtOH:water (10:1.4 ml) then degassed and sealed under nitrogen. The mixture was microwaved for 2 hr at 120° C. The reaction was cooled, filtered and concentrated then the residue was purified by MPLC ISCO Combi-flash on ISCO Redi-Sep 40 g column, eluting with 5% MeOH:CH₂Cl₂. LC-MS [M+H]+: 591.

Step B: 4'-(pyrrolidin-3-yl)-2-(1H-tetrazol-5-yl)-[1,1'-biphenyl]-3-sulfonamide

In a 50 mL round bottomed flask under N₂, tert-butyl 3-(2'-(1-(4-methoxybenzyl)-1H-tetrazol-5-yl)-3'-sulfamoyl-[1,1'-biphenyl]-4-yl)pyrrolidine-1-carboxylate (200 mg, 0.34 mmol) was stirred in DCM:TFA (6 mL) for 0.5 hour. The reaction was concentrated and the residue was taken up with DCM then washed with sat'd NaHCO₃, brine, dried over Na₂SO₄, filtered and concentrated to give 2-(1-(4-methoxybenzyl)-1H-tetrazol-5-yl)-4'-(pyrrolidin-3-yl)-[1,1'-biphenyl]-3-sulfonamide. LC-MS [M+H]+: 491.

Step C: 4'-(pyrrolidin-3-yl)-2-(1H-tetrazol-5-yl)-[1,1'-biphenyl]-3-sulfonamide 2-(1-(4-methoxybenzyl)-1H-tetrazol-5-yl)-4'-(pyrrolidin-3-yl)-[1,1'-biphenyl]-3-sulfonamide was redissolved in thioanisole (3 ml):TFA (3 mL) and heated to 65° C. overnight. LC-MS showed some starting material was present. The reaction was heated at 80° C. for another 2 hr. The reaction was concentrated and the residue was purified by reverse phase HPLC with ACN and water buffered with 0.05% TFA to afford 4'-(pyrrolidin-3-yl)-2-(1H-tetrazol-5-yl)-[1,1'-biphenyl]-3-sulfonamide. LC-MS [M+1]+: 371.3.

EXAMPLE 181

4-(4-(Hydroxymethyl)phenyl)-3-(1H-tetrazol-5-yl)pyridine-2-sulfonamide

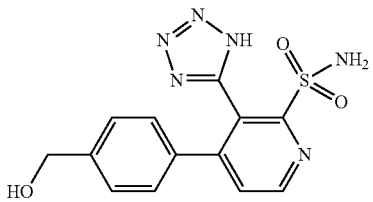 [SMILES: NS(=O)(=O)c1nccc(-c2ccc(CO)cc2)c1-c1nnn[nH]1]

Step A: 2-Chloro-4-(4-(hydroxymethyl)phenyl)nicotinonitrile

To a 100 mL RB flask charged with (4-bromophenyl)methanol (1000 mg, 5.4 mmol), 2-chloro-4-(4,4,5,5-tetramethyl-1,3,2-dioxaborolan-2-yl)nicotinonitrile (2100 mg, 8.02 mmol), and a stir bar was added Pd(DTBPF)Cl₂ (523 mg, 0.802 mmol), K₃PO₄ (1.0 M, 10.7 ml, 10.7 mmol), and EtOH (50 ml). The mixture was purged three times with nitrogen, and heated to 60° C. for 18 hours. LC showed good reaction. The reaction was diluted with EtOAc, washed with water, and separated. The crude solution was dried over sodium sulfate, filtered and concentrated. The resulting residue was adsorbed onto silica gel, and purified by MPLC with hexane and EtOAc. 2-Chloro-4-(4-(hydroxymethyl)phenyl)nicotinonitrile was isolated as a white solid. LC/MS [M+H]+: 245.

Step B: 4-(4-(Hydroxymethyl)phenyl)-2-((2-(trimethylsilyl)ethyl)thio)nicotinonitrile To a flask charged with 2-chloro-4-(4-(hydroxymethyl)phenyl)nicotinonitrile (400 mg, 1.64 mmol) and a stir bar was added 2-(trimethylsilyl)ethanethiol (329 mg, 2.45 mmol), K₂CO₃ (452 mg, 3.27 mmol), and DMF (20 ml). The mixture was heated to 50° C. for 16 hours. LC showed complete and clean reaction. The reaction was diluted with EtOAc, washed with water and brine, and separated. The crude solution was dried over sodium sulfate, filtered and concentrated to give 4-(4-(hydroxymethyl)phenyl)-2-((2-(trimethylsilyl)ethyl)thio)nicotinonitrile as a light yellow solid which was used in the next step without further purification. LC/MS [M+H]+: 343.

Step C: 4-(4-(Hydroxymethyl)phenyl)-2-((2-(trimethylsilyl)ethyl)sulfonyl)nicotinonitrile To a solution of 4-(4-(hydroxymethyl)phenyl)-2-((2-(trimethylsilyl)ethyl)thio)nicotinonitrile (560 mg, 1.64 mmol) in DCM was added m-CPBA (1100 mg, 4.90 mmol). The mixture was allowed to stir for 72 hours. LC showed good reaction. The reaction was diluted with DCM, and quenched with Na₂S₂O₃. The DCM layer was separated, dried over sodium sulfate, and concentrated. The resulting oil was adsorbed onto silica gel, and purified by MPLC with hexanes and EtOAc. The product was a white solid. LC/MS [M+H]+: 375.

Step D: (4-(3-(1H-Tetrazol-5-yl)-2-((2-(trimethylsilyl)ethyl)sulfonyl)pyridin-4-yl)phenyl)methanol To a flask charged with 4-(4-(hydroxymethyl)phenyl)-2-((2-(trimethylsilyl)ethyl)sulfonyl)nicotinonitrile (240 mg, 0.64 mmol) and a stir bar was added dibutyltin oxide (48 mg, 0.19 mmol), azidotrimethylsilane (220 mg, 1.9 mmol), and toluene (5 ml). The mixture was heated to 100° C. for 16 hours. LC/MS suggested little starting material was left, and the reaction was fairly clean. The solvent was removed under vacuum, and the brown residue was used in the next step without further purification. LC/MS [M+H]+: 418.0.

Step E: 4-(4-(Hydroxymethyl)phenyl)-3-(1H-tetrazol-5-yl)pyridine-2-sulfonamide

To a 100 mL RB flask charged with (4-(3-(2H-tetrazol-5-yl)-2-((2-(trimethylsilyl)ethyl)sulfonyl)pyridin-4-yl)phenyl)methanol (200 mg, 0.48 mmol) and a stir bar was added THF (10 ml) and TBAF (1.4 ml, 1.4 mmol). The mixture was allowed to stir at 55° C. for 24 hours. LC showed all starting material was gone. The reaction was cooled, and added aq. sodium acetate (390 mg, 4.8 mmol) in 5 mL of water and hydroxylamine-O-sulfonic acid (540 mg, 4.8 mmol). The mixture was allowed to age for 24 hours at RT. LC/MS showed formation of the desired product. THF was removed on a rotavapor, and the resulting aqueous solution was filtered. The solution was purified on a C18 reverse phase HPLC. The product eluted at about 20% ceric ammonium nitrate and was isolated as a light yellow solid. LC/MS [M+H]+: 333.2.

EXAMPLE 182

Methyl 4-(2-sulfamoyl-3-(1H-tetrazol-5-yl)pyridin-4-yl)benzoate

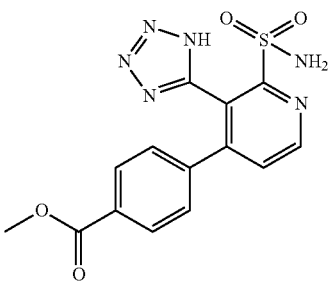 [SMILES: COC(=O)c1ccc(-c2ccnc(S(N)(=O)=O)c2-c2nnn[nH]2)cc1]

Step A: Methyl 4-(2-chloro-3-cyanopyridin-4-yl)benzoate

To a 100 RB flask was added methyl 4-bromobenzoate (1000 mg, 4.6 mmol), 2-chloro-4-(4,4,5,5-tetramethyl-1,3,2-dioxaborolan-2-yl)nicotinonitrile (1230 mg, 4.6 mmol), Pd(DTBPF)Cl$_2$ (300 mg, 0.46 mmol), K$_3$PO$_4$ (1.0 M, 9.30 ml, 9.30 mmol), EtOH (20 ml), and a stir bar. The mixture was sealed with a condenser, and purged three times with nitrogen. It was then heated to 60° C. for 5 hours. TLC and LC showed very good reaction. The reaction was diluted with EtOAc, washed with water and brine, dried over sodium sulfate, filtered and concentrated to give a brown oil. The oil was dissolved in DCM (30 mL) and adsorbed onto silica gel, and purified by MPLC with hexanes and EtOAc. Methyl 4-(2-chloro-3-cyanopyridin-4-yl)benzoate eluted at about 40% EtOAc and was isolated as a white solid. LC/MS [M+H]+: 273.

Step B: Methyl 4-(3-cyano-2-((2-(trimethylsilyl)ethyl)thio)pyridin-4-yl)benzoate A mixture of methyl 4-(2-chloro-3-cyanopyridin-4-yl)benzoate (600 mg, 2.2 mmol), 2-(trimethylsilyl)-ethanethiol (380 mg, 2.9 mmol), and K$_2$CO$_3$ (460 mg, 3.3 mmol) in DMF (10 ml) was allowed to stir at RT overnight. TLC and LC showed a clean reaction. The reaction was diluted with EtOAc (50 mL), washed with water and brine, and separated. The crude solution was dried over sodium sulfate, filtered and concentrated to give methyl 4-(3-cyano-2-((2-(trimethylsilyl)ethyl)thio)pyridin-4-yl)benzoate as a yellow oil. The material was used in the next step without purification. LC/MS [M+H]+: 371.

Step C: Methyl 4-(3-cyano-2-((2-(trimethylsilyl)ethyl)sulfonyl)pyridin-4-yl)benzoate To a solution of methyl 4-(3-cyano-2-((2-(trimethylsilyl)ethyl)thio)pyridin-4-yl)benzoate (800 mg, 2.16 mmol) in CH$_2$Cl$_2$ (40 mL) was added m-CPBA (1452 mg, 6.48 mmol). The reaction was allowed to stir at RT for 2 hours. The reaction was quenched with aq Na$_2$S$_2$O$_3$ solution. The mixture was stirred for 1 hour, diluted with DCM, and separated. The solution was dried over sodium sulfate, filtered and concentrated to give a sticky oil, which was then injected onto a 40G ISCO column and purified by MPLC with hexanes and EtOAc gradient system. LC/MS [M+H]+: 403.

Step D: methyl 4-(3-(1H-tetrazol-5-yl)-2-((2-(trimethylsilyl)ethyl)sulfonyl)pyridin-4-yl)benzoate To a solution of methyl 4-(3-cyano-2-((2-(trimethylsilyl)ethyl)sulfonyl)pyridin-4-yl)benzoate (800 mg, 2.0 mmol) in toluene (10 mL) was added dibutyltin oxide (99 mg, 0.40 mmol) and azidotrimethylsilane (460 mg, 4.0 mmol). The mixture was allowed to reflux for 16 hours. LC showed complete and clean reaction. The solvent was removed under reduced pressure, and the residue was dissolved in DCM and injected onto a 40G ISCO column. The product was purified by MPLC eluted with a DCM and MeOH gradient. Methyl 4-(3-(1H-tetrazol-5-yl)-2-((2-(trimethylsilyl)ethyl)thio)pyridin-4-yl)benzoate eluted at about 4% MeOH. LC/MS [M+H]+: 446.

Step E: Methyl 4-(2-sulfamoyl-3-(1H-tetrazol-5-yl)pyridin-4-yl)benzoate

To a THF solution of methyl 4-(3-(1H-tetrazol-5-yl)-2-((2-(trimethylsilyl)ethyl)sulfonyl)pyridin-4-yl)benzoate (100 mg, 0.22 mmol) was added TBAF (0.45 ml, 0.45 mmol) and CsF (170 mg, 1.12 mmol). The mixture was allowed to stir at 60° C. for 3 hours. At that point, LC showed most of the starting material was gone. The reaction was cooled, and added an aq. solution of sodium acetate (180 mg, 2.2 mmol), followed by addition of hydroxylamine-O-sulfonic acid (250 mg, 2.2 mmol). The mixture was allowed to stir at RT for 16 hours. LC showed good and clean reaction. The reaction was filtered and purified by HPLC eluted with a gradient of ACN and water containing 0.05% TFA. LC/MS [M+H]+: 360.9.

EXAMPLE 183

4-(2-Sulfamoyl-3-(1H-tetrazol-5-yl)pyridin-4-yl)benzamide and 4-(2-Sulfamoyl-3-(1H-tetrazol-5-yl)pyridin-4-yl)benzoic acid

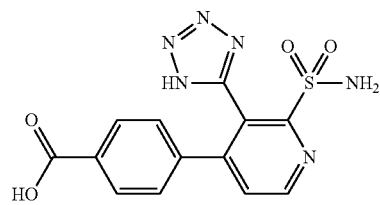 [SMILES: NS(=O)(=O)c1nccc(-c2ccc(C(=O)O)cc2)c1-c1nnn[nH]1]

Step A: 4-(3-(1H-Tetrazol-5-yl)-2-((2-(trimethylsilyl)ethyl)sulfonyl)pyridin-4-yl)benzoic acid To a 20 mL microwave tube charged with methyl 4-(3-(1H-tetrazol-5-yl)-2-((2-(trimethylsilyl)ethyl)sulfonyl)pyridin-4-yl)benzoate from Example 182, Steps A-D (100 mg, 0.224 mmol) and a stir bar was added ammonium hydroxide (5 ml, 36 mmol) and MeOH (1 ml). The tube was sealed and heated to 140° C. for 30 minutes. LC/MS showed formation of both the amide and acid in about 1:1 ratio. The reaction was transferred into a RB flask, and the volatiles were removed under reduced pressure. The resulting foam was used directly in the next step. LC/MS [M+H]$^+$: 431, 432.

Step B: 4-(2-Sulfamoyl-3-(1H-tetrazol-5-yl)pyridin-4-yl) benzoic acid

To a solution of a crude mixture of 4-(3-(1H-tetrazol-5-yl)-2-((2-(trimethylsilyl)ethyl)sulfonyl)pyridin-4-yl)benzamide and 4-(3-(1H-tetrazol-5-yl)-2-((2-(trimethylsilyl)ethyl)sulfonyl)pyridin-4-yl)benzoic acid in THF (5 mL) was added cesium fluoride (176 mg, 1.2 mmol) and TBAF (0.46 mL, 0.46 mmol). The mixture was heated to 60° C. for 2 hours. Most of the starting material was still there, so another 10 eq. of TBAF was added to the reaction, and the reaction was allowed to reflux overnight. LC/MS suggested complete consumption of the starting materials at that point. The reaction was cooled to rt, and an aq. solution of sodium acetate (190 mg, 2.3 mmol) was added, followed by addition of (aminooxy)sulfonic acid (260 mg, 2.3 mmol). The reaction was allowed to stir at rt. LC/MS showed formation of the desired products within 1 hour. The reaction was allowed to age overnight, the solvent removed in vacuo and the residue purified by reverse phase HPLC eluted with water and acetonitrile containing 0.05% TFA to afford the amide and 4-(2-sulfamoyl-3-(1H-tetrazol-5-yl)pyridin-4-yl)benzoic acid. LC/MS [M+H]$^+$: 346.9.

EXAMPLE 184

4-(2-Sulfamoyl-3-(1H-tetrazol-5-yl)pyridin-4-yl)benzamide

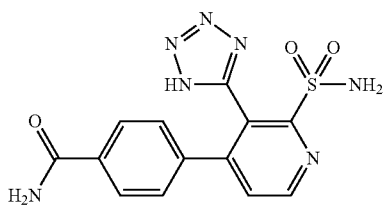 [SMILES: NC(=O)c1ccc(-c2ccnc(S(N)(=O)=O)c2-c2nnn[nH]2)cc1]

To a solution of 4-(2-sulfamoyl-3-(1H-tetrazol-5-yl)pyridin-4-yl)benzoic acid from Example 183 (29 mg, 0.084 mmol), N,N-diisopropylethylamine (0.12 ml, 0.67 mmol) and HATU (47.8 mg, 0.13 mmol) in DMF (5 ml) was added ammonium chloride (134 mg, 2.51 mmol). The reaction mixture was stirred under a dry nitrogen atmosphere at room temperature for 16 hours. The reaction mixture was concentrated under vacuum and purified by reverse phase HPLC eluted with ACN and H$_2$O containing 0.05% TFA to afford 4-(2-sulfamoyl-3-(1H-tetrazol-5-yl)pyridin-4-yl)benzamide. LC/MS [M+H]$^+$: 346.1.

EXAMPLE 185

N-Cyclopropyl-4-(2-sulfamoyl-3-(1H-tetrazol-5-yl)pyridin-4-yl)benzamide

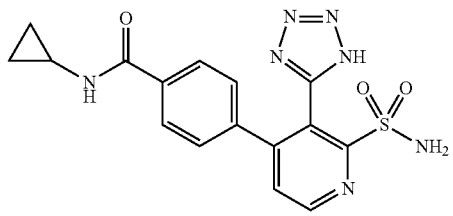 [SMILES: NS(=O)(=O)c1nccc(-c2ccc(C(=O)NC3CC3)cc2)c1-c1nnn[nH]1]

N-cyclopropyl-4-(2-sulfamoyl-3-(1H-tetrazol-5-yl)pyridin-4-yl)benzamide was prepared by the method described in Example 184 substituting cyclopropylamine HCl for ammonium chloride. LC/MS [M+H]$^+$: 386.1.

EXAMPLE 186

4-(2-Sulfamoyl-3-(1H-tetrazol-5-yl)pyridin-4-yl)-N-(tetrahydro-2H-pyran-4-yl)benzamide

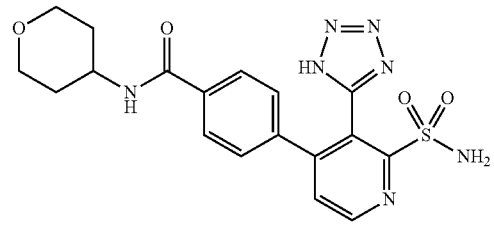 [SMILES: NS(=O)(=O)c1nccc(-c2ccc(C(=O)NC3CCOCC3)cc2)c1-c1nnn[nH]1]

4-(2-sulfamoyl-3-(1H-tetrazol-5-yl)pyridin-4-yl)-N-(tetrahydro-2H-pyran-4-yl)benzamide was prepared by the method described in Example 184 substituting 4-aminotetrahydro-2H-pyran HCl for ammonium chloride. LC/MS [M+H]$^+$: 430.1.

EXAMPLE 187

4-(4-(Tetrahydro-2H-pyran-4-yl)phenyl)-3-(1H-tetrazol-5-yl)pyridine-2-sulfonamide

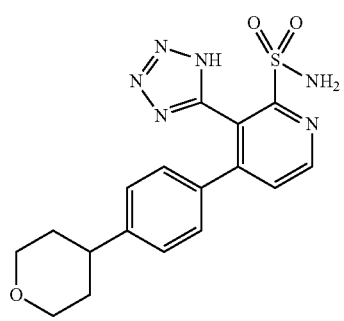 [SMILES: NS(=O)(=O)c1nccc(-c2ccc(C3CCOCC3)cc2)c1-c1nnn[nH]1]

Step A: 4-(4-(Tetrahydro-2H-pyran-4-yl)phenyl)-2-((2-(trimethylsilyl)ethyl)sulfonyl)nicotinonitrile To a 5 mL microwave tube charged with a stir bar was added 4-bromo-2-((2-(trimethylsilyl)ethyl)sulfonyl)nicotinonitrile (45 mg, 0.13 mmol), (4-(tetrahydro-2H-pyran-4-yl)phenyl)boronic acid (40 mg, 0.19 mmol), Pd(DTBPF)Cl$_2$ (17 mg, 0.026 mmol), K$_3$PO$_4$ (1 M, 0.39 mL), and EtOH (1.5 mL). The mixture was sealed, purged with nitrogen, and then heated to 60° C. for 1 hour. LC showed complete and clean reaction. The reaction was diluted with EtOAc, washed with brine, and separated. The crude solution was dried over sodium sulfate, and concentrated. The residue was adsorbed onto silica gel, and purified by MPLC with eluted with hexane and EtOAc on a 24G ISCO column. 4-(4-(Tetrahydro-2H-pyran-4-yl)phenyl)-2-((2-(trimethylsilyl)ethyl)sulfonyl)nicotinonitrile was isolated as a white solid. LC/MS [M+H]$^+$: 429.

Step B: 4-(4-(Tetrahydro-2H-pyran-4-yl)phenyl)-3-(1H-tetrazol-5-yl)-2-((2-(trimethylsilyl)ethyl)sulfonyl)pyridine To a 20 mL microwave tube charged with 4-(4-(tetrahydro-2H-pyran-4-yl)phenyl)-2-((2-(trimethylsilyl)ethyl)sulfonyl)nicotinonitrile (50 mg, 0.12 mmol) and a stir bar was added azidotrimethylsilane (40 mg, 0.35 mmol), dibutylstannanone (8.7 mg, 0.035 mmol), and toluene (2 ml). The mixture was sealed and heated to 115° C. for 16 hours. LC showed complete reaction. The solvent was removed under vacuum, and the residue was dissolved in DCM and loaded onto a 24G ISCO column. The product was eluted with hexane and EtOAc with a gradient of MeOH and eluted at about 10% MeOH. LC/MS [M+H]$^+$: 472.

Step C: 4-(4-(Tetrahydro-2H-pyran-4-yl)phenyl)-3-(1H-tetrazol-5-yl)pyridine-2-sulfonamide To a solution of 4-(4-(tetrahydro-2H-pyran-4-yl)phenyl)-3-(2H-tetrazol-5-yl)-2-((2-(trimethylsilyl)ethyl)sulfonyl)pyridine (20 mg, 0.042 mmol) in THF (1 mL) was added TBAF (0.21 mL, 0.21 mmol). The mixture was heated to 65° C. for 1 hour. LC showed all starting material was gone. The reaction was cooled, and aq. NaOAc (35 mg, 0.42 mmol) and hydroxylamine-O-sulfonic acid (48 mg, 0.42 mmol) was added. The mixture was allowed to stir at rt for 16 hours. LC showed formation of the desired product. The product was isolated by HPLC eluted with ACN and water (containing 0.05% TFA). LC showed the product contained some TBAF, so it was passed through a negative ion-exchange resin column with water. 4-(4-(Tetrahydro-2H-pyran-4-yl)phenyl)-3-(1H-tetrazol-5-yl)pyridine-2-sulfonamide was isolated. LC/MS [M+H]$^+$: 387.1.

EXAMPLE 188

2-(4-(Hydroxymethyl)phenyl)-3-(1H-tetrazol-5-yl)pyridine-4-sulfonamide

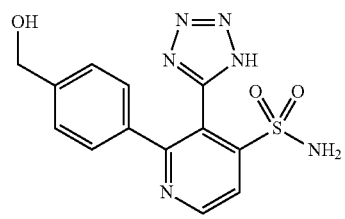 [SMILES: NS(=O)(=O)c1ccnc(-c2ccc(CO)cc2)c1-c1nnn[nH]1]

Step A: 2-Chloro-4-((2-(trimethylsilyl)ethyl)thio)nicotinonitrile

To a solution of 2-chloro-4-iodonicotinonitrile (2.0 g, 7.6 mmol) and K$_2$CO$_3$ (1.57 g, 11.34 mmol) in DMF (7 mL) was added 2-(trimethylsilyl)ethanethiol (1.21 mL, 7.56 mmol) under dry N$_2$ atmosphere at room temperature. The mixture was stirred at the room temperature for 16 hours. The crude UPLC did not show the desired peak but the TLC indicated complete consumption of starting material. The reaction mixture was concentrated under vacuo. The crude was adsorbed onto silica gel, and loaded onto silica gel column and eluted with hexane and ethyl acetate to give 2-chloro-4-((2-(trimethylsilyl)ethyl)thio)nicotinonitrile. LC/MS [M+H]$^+$: 271.

Step B: 2-Chloro-4-((2-(trimethylsilyl)ethyl)sulfonyl)nicotinonitrile

To a solution of 2-chloro-4-((2-(trimethylsilyl)ethyl)thio)nicotinonitrile (900 mg, 3.32 mmol) in DCM (20 mL) was added mCPBA (2.0, 11.63 mmol) under dry N$_2$ atmosphere at room temperature. The mixture was stirred for 16 hours at room temperature. The TLC in 20:80 EtOAc:Hex indicated complete consumption of starting material. To that mixture, sat. Na$_2$S$_2$O$_3$ was added and stirred for 15 minutes and then sat. NaHCO$_3$ was added and stirred for another 15 minutes. The organic was extracted with DCM (3x), dried over Na$_2$SO$_4$, filtered and concentrated to give 2-chloro-4-((2-(trimethylsilyl)ethyl)sulfonyl)nicotinonitrile which was used without purification. LC/MS [M+H]$^+$: 302.

Step C: 2-(4-(Hydroxymethyl)phenyl)-4-((2-(trimethylsilyl)ethyl)sulfonyl)nicotinonitrile A solution of 2-chloro-4-((2-(trimethylsilyl)ethyl)sulfonyl)nicotinonitrile (300 mg, 0.99 mmol) (4-(hydroxymethyl)phenyl)boronic acid (527 mg, 3.47 mmol), aminobiphenyl palladium chloride precatalyst (XPhos-Pd-G2; 78 mg, 0.10 mmol) and potassium phosphate tribasic (735 mg, 3.46 mmol) dissolved in 3 mL of water was purged with dry N$_2$. The mixture was heated at 60° C. for 16 hours. The crude UPLC showed the desired peak at 1.28 ppm, 375 m/e. The reaction mixture was filtered through a packed celite pad and washed with EtOAc. The filtrate was concentrated in vacuo to dryness. The crude material was adsorbed onto silica gel and purified by MPLC eluted with hexane and ethyl acetate to give 2-(4-(hydroxymethyl)phenyl)-4-((2-(trimethylsilyl)ethyl)sulfonyl)nicotinonitrile. LC/MS [M+H]$^+$: 375.

Step D: (4-(3-(1H-Tetrazol-5-yl)-4-((2-(trimethylsilyl)ethyl)sulfonyl)pyridin-2-yl)phenyl)methanol A solution of 2-(4-(hydroxymethyl)phenyl)-4-((2-(trimethylsilyl)ethyl)sulfonyl)nicotinonitrile (100 mg, 0.27 mmol) and azidotrimethyltin (275 mg, 1.34 mmol) in THF (4 mL) was purged several times with dry nitrogen. The mixture was heated in a microwave at 140° C. for 30 minutes. The crude UPLC indicated a desired peak at 1.18 ppm, 418 m/z. Very small amount of starting material still remained at 1.29 ppm, 375 m/z. The mixture was concentrated in vacuo. The crude was purified by silica gel column eluted with hexane and ethyl acetate as solvent to give (4-(3-(1H-tetrazol-5-yl)-4-((2-(trimethylsilyl)ethyl)sulfonyl)pyridin-2-yl)phenyl)methanol. LC/MS [M+H]$^+$: 418.

Step E: 2-(4-(Hydroxymethyl)phenyl)-3-(1H-tetrazol-5-yl)pyridine-4-sulfonamide

A solution of (4-(3-(1H-tetrazol-5-yl)-4-((2-(trimethylsilyl)ethyl)sulfonyl)pyridin-2-yl)phenyl)methanol (20 mg, 0.048 mmol) and tetrabutylammonium fluoride (0.144 ml, 0.144 mmol) in THF (3 ml) was heated at 70° C. for 3 hours. The sulfinic acid peak was observed at 0.79 ppm, 317 m/z. Sodium acetate (19.65 mg, 0.239 mmol) dissolved in water (0.112 ml, 6.23 mmol) and hydroxylamine-o-sulfonic acid (27.1 mg, 0.239 mmol) were added and stirred at 70° C. for 16 hours. The reaction mixture was filtered and concentrated. The crude product was purified by HPLC and eluted with a gradient of ACN and H$_2$O buffered with 0.05 TFA. After removing the solvent in vacuo, the compound was dissolved in H$_2$O/acetone and eluted via a packed resin column (Dowex 50wx8, 100-200 mesh, ion-exchange resin) which was activated with 1N NaOH and neutralized to pH~7 with H₂O. The eluted water was concentrated and dried under lyophilizer to give 2-(4-(hydroxymethyl)phenyl)-3-(1H-tetrazol-5-yl)pyridine-4-sulfonamide. LC/MS [M+H]⁺: 333.1.

EXAMPLE 189

5-(4-(Hydroxymethyl)phenyl)-4-(1H-tetrazol-5-yl)pyridine-3-sulfonamide

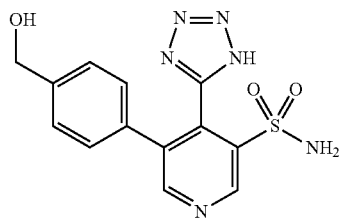 [SMILES: NS(=O)(=O)c1cncc(-c2ccc(CO)cc2)c1-c1nnn[nH]1]

Step A: 3-Chloro-5-(4-(hydroxymethyl)phenyl)isonicotinonitrile

A solution of 3,5-dichloro-4-pyridinecarbonitrile (2.27 g, 13.12 mmol), 4-(hydroxymethyl)phenylboronic acid (1.99 g, 13.12 mmol), potassium phosphate tribasic (19.68 ml, 19.68 mmol) dissolved in water (17 mL) and XPhos (1.032 g, 1.312 mmol) in THF (100 ml) was flashed with N₂. The mixture was heated at 60° C. under dry N₂ for 4 hours. The reaction mixture was allowed to stir for a total of 24 hours. The reaction mixture was filtered and concentrated under vacuum. The crude product was purified on a silica gel column, RediSep Column, eluted with hexane and ethyl acetate to afford 3-chloro-5-(4-(hydroxymethyl)phenyl)isonicotinonitrile. LC/MS [M+H]⁺: 245.

Step B: 3-(4-(Hydroxymethyl)phenyl)-5-((2-(trimethylsilyl)ethyl)thio)isonicotinonitrile To a solution of 3-chloro-5-(4-(hydroxymethyl)phenyl)isonicotinonitrile (1.1 g, 4.50 mmol) and potassium carbonate (0.746 g, 5.39 mmol) in DMF (25 mL) was added 2-(trimethylsilyl)ethanethiol (1.1 mL, 6.87 mmol) at room temperature under N₂. The reaction mixture was stirred for 3 hours. The crude UPLC indicated starting material still remained. The mixture was allowed to stir for a total of 24 hours. The crude UPLC indicated complete consumption of starting material. The reaction was diluted with EtOAc and washed with H₂O. The organic layer was concentrated under vacuum and purified on a silica gel column eluted with hexane and ethyl acetate to give 3-(4-(hydroxymethyl)phenyl)-5-((2-(trimethylsilyl)ethyl)thio)isonicotinonitrile. LC/MS [M+H]⁺: 343.

Step C: 3-(4-(Hydroxymethyl)phenyl)-5-((2-(trimethylsilyl)ethyl)sulfonyl)isonicotinonitrile A solution of 3-(4-(hydroxymethyl)phenyl)-5-((2-(trimethylsilyl)ethyl)thio)isonicotinonitrile (1.4 g, 4.09 mmol) and mCPBA (2.47 g, 14.31 mmol) in DCM (40 ml) was stirred at room temperature under N₂ for 16 hours. The TLC indicated complete consumption of starting material. To a reaction mixture, sat. Na₂S₂O₃ was added and stirred for 15 minutes and then sat. NaHCO₃ was added and stirred for another 15 more minutes. The organic layer was extracted with DCM (4×), dried over Na₂SO₄, filtered and concentrated. The crude was purified on a silica gel column eluted with hexane and ethyl acetate to afford 3-(4-(hydroxymethyl)phenyl)-5-((2-(trimethylsilyl)ethyl)sulfonyl)isonicotinonitrile. LC/MS [M+H]⁺: 375.

Step D: (4-(4-(1H-Tetrazol-5-yl)-5-((2-(trimethylsilyl)ethyl)sulfonyl)pyridin-3-yl)phenyl)methanol A solution of 3-(4-(hydroxymethyl)phenyl)-5-((2-(trimethylsilyl)ethyl)sulfonyl)isonicotinonitrile (200 mg, 0.53 mmol) and azidotrimethyltin (550 mg, 2.67 mmol) in THF (4 ml) was microwaved at 140° C. for 30 minutes. The crude reaction mixture was injected directly onto a HPLC and eluted with a gradient of ACN and H₂O buffered with 0.05% TFA to afford (4-(4-(1H-tetrazol-5-yl)-5-((2-(trimethylsilyl)ethyl)sulfonyl)pyridin-3-yl)phenyl)methanol. LC/MS [M+H]⁺: 418.

Step E: 5-(4-(Hydroxymethyl)phenyl)-4-(1H-tetrazol-5-yl)pyridine-3-sulfonamide

A solution of (4-(4-(1H-tetrazol-5-yl)-5-((2-(trimethylsilyl)ethyl)sulfonyl)pyridin-3-yl)phenyl)methanol (180 mg, 0.43 mmol) and tetrabutylammonium fluoride (1.29 ml, 1.29 mmol) in THF (5 ml) was heated at 68° C. for 2 hours. The mixture was allowed to stir for total of 17 hours. A solution of sodium acetate (177 mg, 2.16 mmol) in water (1.01 mL, 56.0 mmol) and hydroxylamine-o-sulfonic acid (244 mg, 2.16 mmol) were added sequentially, and the mixture was stirred for 2 more hours. The reaction mixture was injected directly into HPLC and was eluted with a gradient of ACN and H₂O buffering with 0.05% TFA. The ¹H-NMR showed strong peaks of tetrabutyl ammonium salt. The compound was dissolved in H₂O and a minimum amount of acetone was added. The crude solution was placed on a packed resin column (Dowex 50wx8, 100-200 mesh, ion-exchange resin) which was activated with 1N NaOH and neutralized to pH-7 with H₂O to give 5-(4-(hydroxymethyl)phenyl)-4-(1H-tetrazol-5-yl)pyridine-3-sulfonamide. LC/MS [M+H]⁺: 333.1.

EXAMPLE 190

3-(1H-Tetrazol-5-yl)-4-(p-tolyl)pyridine-2-sulfonamide

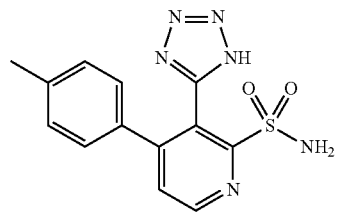 [SMILES: Cc1ccc(-c2ccnc(S(N)(=O)=O)c2-c2nnn[nH]2)cc1]

Step A: 2-Chloro-4-(p-tolyl)nicotinonitrile

A microwave vial containing 2-chloro-3-cyanopyridine-4-boronic acid pinacol ester (2 g, 7.56 mmol), 4-bromotoluene (1.94 g, 11.34 mmol), freshly prepared aqueous 1 M of potassium phosphate tribasic (11.34 ml, 11.34 mmol) and 1,1'-bis(di-tert-butylphosphino)ferrocene palladium dichloride (0.49 g, 0.76 mmol) in EtOH (40 ml) was purged with N₂ (3×). The mixture was stirred at 55° C. for 12 hours. The crude UPLC indicated the desired product. The reaction mixture was diluted with EtOAc and washed with H₂O and brine. The organic was dried over Na₂SO₄, filtered and concentrated under vacuum. The crude was purified by Silica gel column with hexane and ethyl acetate to give the desired compound. LC/MS [M+H]⁺: 229.

Step B: 4-(p-Tolyl)-2-((2-(trimethylsilyl)ethyl)thio)nicotinonitrile

To a solution of 2-chloro-4-(p-tolyl)nicotinonitrile (907 mg, 3.97 mmol) and potassium carbonate (1.1 g, 7.93 mmol) in DMF (10 mL) was added 2-(trimethylsilyl)ethanethiol (0.57 ml, 3.57 mmol) at room temperature under dry $N_2$. The mixture was stirred for 60 hours. The reaction mixture was poured into a separatory funnel containing $H_2O$ and the organic layer was extracted with EtOAc (3×). The combined extracts were dried over $Na_2SO_4$, filtered and the solution was evaporated to dryness under reduced pressure. The crude 1H-NMR showed 4-(p-tolyl)-2-((2-(trimethylsilyl)ethyl)thio)nicotinonitrile with small amount of impurities so the crude product was used without further purification in the next step. LC/MS [M+H]⁺: 327.

Step C: 4-(p-Tolyl)-2-((2-(trimethylsilyl)ethyl)sulfonyl)nicotinonitrile

To a solution of 4-(p-tolyl)-2-((2-(trimethylsilyl)ethyl)thio)nicotinonitrile (2.3 g crude, 7.04 mmol) in DCM (40 mL) was added mCPBA (4.25 g, 24.7 mmol) at 0° C. The reaction was slowly brought to room temperature and stirred for 1½ hours. To the reaction mixture, sat. $Na_2SO_3$ was added and stirred for 20 minutes and then sat. $NaHCO_3$ was added. After stirring for 20 minutes, the organic layer was extracted with DCM (3×), dried over $NaSO_4$, filtered and concentrated. The crude product was used in the next step without further purification. LC/MS [M+H]⁺: 359.

Step D: 3-(1H-Tetrazol-5-yl)-4-(p-tolyl)-2-((2-(trimethylsilyl)ethyl)sulfonyl)pyridine A solution of 4-(p-tolyl)-2-((2-(trimethylsilyl)ethyl)sulfonyl)nicotinonitrile (1.0 g, 2.79 mmol) and tributyltin azide (1.53 ml, 5.58 mmol) in THF (25 ml) was refluxed overnight. The crude UPLC showed a very small amount of the desired product. The reaction mixture was transferred into a microwave vial and it was microwaved at 140° C. for 4 hours. The reaction mixture was concentrated under vacuum. The crude reaction was dissolved in DMSO and purified by HPLC eluted with a gradient of ACN and $H_2O$ buffered with 0.05% TFA to give 3-(1H-tetrazol-5-yl)-4-(p-tolyl)-2-((2-(trimethylsilyl)ethyl)sulfonyl)pyridine. LC/MS [M+H]⁺: 403.

Step E: 3-(1H-Tetrazol-5-yl)-4-(p-tolyl)pyridine-2-sulfonamide

To a solution of 3-(1H-tetrazol-5-yl)-4-(p-tolyl)-2-((2-(trimethylsilyl)ethyl)sulfonyl)pyridine (400 mg, 1.0 mmol) in THF (10 ml) was added tetrabutylammonium fluoride (2.99 ml, 2.99 mmol). The mixture was refluxed for 1 hr and cooled to room temperature. A solution of sodium acetate (409 mg, 4.98 mmol) in water (2.33 ml, 129 mmol) and aminooxysulfonic acid (563 mg, 4.98 mmol) were added sequentially, and the mixture was stirred for 2 hours. The crude UPLC indicated starting material mostly remained. Another 3 eq. of tetrabutylammonium fluoride (3.0 mL) was added and reaction was allowed to stir overnight. The crude UPLC indicated that most of starting material was consumed. The reaction was evaporated under vacuum and the crude was dissolved in $H_2O$ and purified by HPLC eluted with a gradient of ACN and $H_2O$ buffered with 0.05% TFA. The ¹H-NMR showed a large amount of tBu-ammonium salt. The organic layer was eluted via a column cartridge containing activated Dowex 50Wx8 100-200 mesh, Ion-exchange resin charged with 1N NaOH and then neutralized with water. The water was removed under vacuum and dried under lyophilizer to give 3-(1H-tetrazol-5-yl)-4-(p-tolyl)pyridine-2-sulfonamide as a white solid compound. LC/MS [M+H]⁺: 317.2.

EXAMPLE 191

(±)-4-(4-(cis-4-Methyl-2-oxooxazolidin-5-yl)phenyl)-3-(1H-tetrazol-5-yl)pyridine-2-sulfonamide

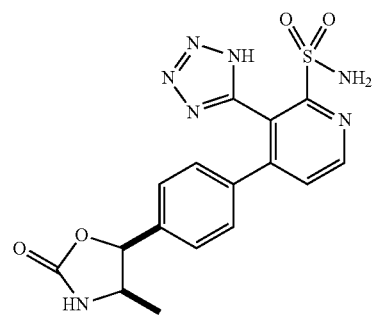

Step A: General Method Via Pd-Coupling from Br-Intermediate

A solution of the mixture of 4-bromo-3-(2-(4-methoxybenzyl)-2H-tetrazol-5-yl)pyridine-2-sulfonamide and 4-bromo-3-(1-(4-methoxybenzyl)-1H-tetrazol-5-yl)pyridine-2-sulfonamide from Reference Example 2 (60 mg, 0.14 mmol), (±)-cis-4-methyl-5-(4-(4,4,5,5-tetramethyl-1,3,2-dioxaborolan-2-yl)phenyl)oxazolidin-2-one (64 mg, 0.21 mmol), Pd(DTBPF)Cl₂ (9.2 mg, 0.014 mmol), and K₃PO₄ (1 M, 0.42 mL, 0.42 mmol) in EtOH (2 mL) was heated to 70° C. for 24 hours. LC showed formation of the desired product, along with a small amount of starting material left. The reaction was cooled, and extracted three times with EtOAc. The extractions were combined, and concentrated. The residue was dissolved in anisole (0.1 mL) and TFA (1 mL), and the solution was heated to 45° C. for 16 hours. LC showed good reaction. The solvents were removed, and the residue was purified by reverse phase HPLC with ACN and water with (0.05% TFA). LC/MS [M+H]⁺: 402.2.

EXAMPLES 192-198

The following Examples 192-198 were prepared according to the general procedure described above for Example 191, using boronic acids or boronic esters that are commercially available, known, or prepared as described herein. Note that in some instances the boronic acid or boronic ester contains an amine group. In these cases, the amine moiety is typically protected with a tert-butoxycarbonyl group, which is concurrently removed under the final PMB deprotection step (Step B) with TFA and anisole. Alternatively, a Boc protected amine may be de-protected by treatment with TFA at room temperature, followed by deprotection of the PMB group with heating as described.

| Ex. No. | Structure | Name | Calc'd Mass [M + H]+ | LC/MS m/e [M + H]+ |
|---|---|---|---|---|
| 192 | 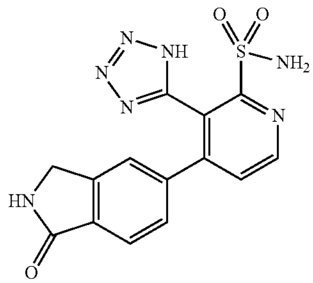 [SMILES: NS(=O)(=O)c1nccc(-c2ccc3c(c2)CNC3=O)c1-c1nnn[nH]1] | 4-(1-oxoisoindolin-5-yl)-3-(1H-tetrazol-5-yl)pyridine-2-sulfonamide | 357.1 | 358.1 |
| 193 | 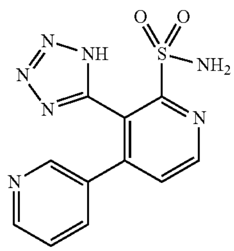 [SMILES: NS(=O)(=O)c1nccc(-c2cccnc2)c1-c1nnn[nH]1] | 3'-(1H-tetrazol-5-yl)-[3,4'-bipyridine]-2'-sulfonamide | 304.1 | 304.2 |
| 194 | 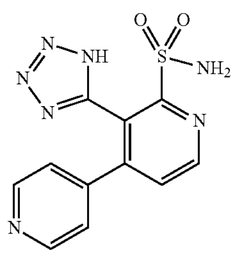 [SMILES: NS(=O)(=O)c1nccc(-c2ccncc2)c1-c1nnn[nH]1] | 3-(1H-tetrazol-5-yl)-[4,4'-bipyridine]-2-sulfonamide | 304.1 | 304.3 |
| 195 | 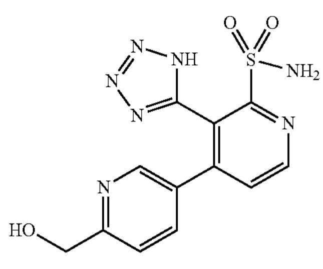 [SMILES: NS(=O)(=O)c1nccc(-c2ccc(CO)nc2)c1-c1nnn[nH]1] | 6-(hydroxymethyl)-3'-(1H-tetrazol-5-yl)-[3,4'-bipyridine]-2'-sulfonamide | 334.1 | 334.3 |
| 196 | 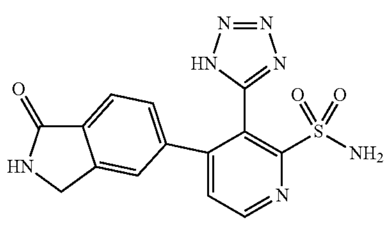 [SMILES: NS(=O)(=O)c1nccc(-c2ccc3c(c2)CNC3=O)c1-c1nnn[nH]1] | 4-(1-oxoisoindolin-5-yl)-3-(1H-tetrazol-5-yl)pyridine-2-sulfonamide | 358.1 | 358.1 |
| 197 | 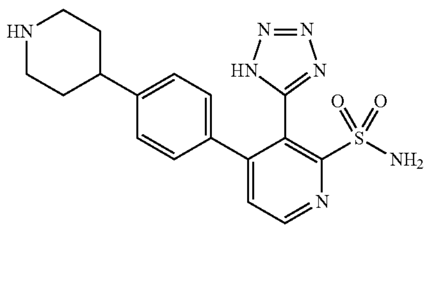 [SMILES: NS(=O)(=O)c1nccc(-c2ccc(C3CCNCC3)cc2)c1-c1nnn[nH]1] | 4-(4-(piperidin-4-yl)phenyl)-3-(1H-tetrazol-5-yl)pyridine-2-sulfonamide | 386.1 | 386.3 |

-continued

| Ex. No. | Structure | Name | Calc'd Mass [M + H]+ | LC/MS m/e [M + H]+ |
|---|---|---|---|---|
| 198 | 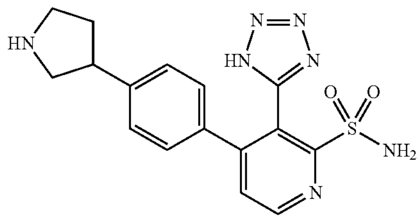 [SMILES: NS(=O)(=O)c1nccc(-c2ccc(C3CCNC3)cc2)c1-c1nnn[nH]1] | 4-(4-(pyrrolidin-3-yl)phenyl)-3-(1H-tetrazol-5-yl)pyridine-2-sulfonamide | 372.1 | 372.3 |

EXAMPLES 199-215

Parallel Synthesis of 4-Substituted 3-(1H-tetrazol-5-yl)pyridine-2-sulfonamides

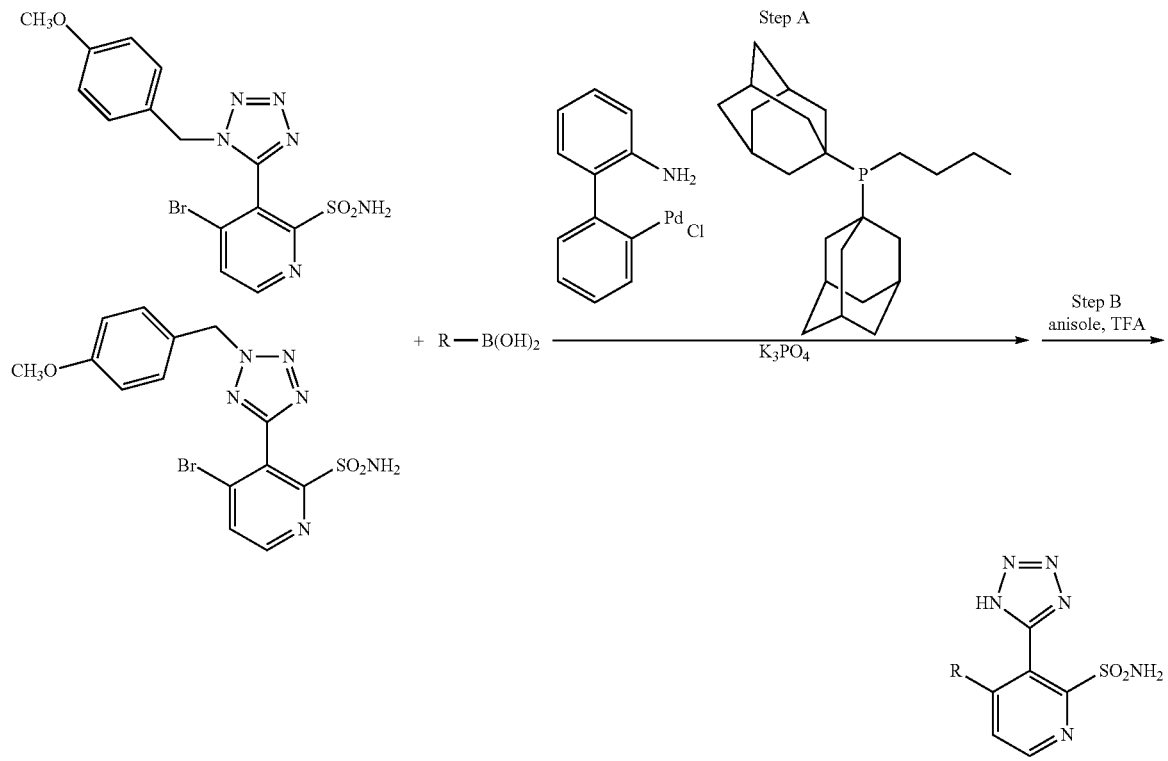

Step A: Palladium Catalyzed C—C Coupling of Pyridyl Bromide and Boronic Acids or Boronic Esters Such as Pinicol Esters Boronic acids or esters (commercially available, known, or prepared as described herein, 0.235 mmol) and Chloro[(di(1-adamantyl)-N-butylphosphine)-2-(2-aminobiphenyl)]palladium(II) (7.86 mg, 0.012 mmol) were added into a microwave vial and under $N_2$. Then a mixture of 4-Bromo-3-(2-(4-methoxybenzyl)-2H-tetrazol-5-yl)pyridine-2-sulfonamide and 4-Bromo-3-(1-(4-methoxybenzyl)-1H-tetrazol-5-yl)pyridine-2-sulfonamide (50 mg, 0.118 mmol) in THF (1 mL) was added into the vial under $N_2$ followed by 1.0 M potassium phosphate (0.470 mL, 0.470 mmol) and the reaction was agitated at 110° C. for 16 hours. Solvent was removed under reduced pressure. To each vial, 1.5 mL DCM was added along with 0.4 mL water, with shaking for 15 min. The organic layer was collected and solvent was removed under reduced pressure.

Step B: Removal of the p-methoxybenzyl (PMB) Protecting Group Under Acidic Conditions To each vial from Step A, TFA (0.545 mL, 7.07 mmol), anisole (7.72 µL, 0.071 mmol) was added and agitated at 60° C. for 12 hours. LC/MS showed formation of the desired products. The solvent were removed under reduced pressure. To each vial, 1 mL DMSO was added followed by addition of SiliaMetS® DMT to remove the Pd catalyst. The mixtures were shaken for 6 hours and filtered into a 96-well plate. These crude materials were purified by HPLC to afford Examples 199-215.

| Ex. No. | Structure | Name | Calc'd Mass [M + H]+ | LC/MS m/e [M + H]+ |
|---|---|---|---|---|
| 199 | 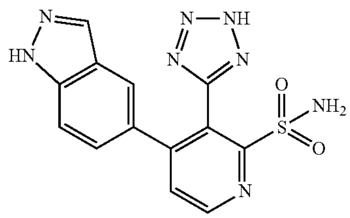 [SMILES: NS(=O)(=O)c1nccc(-c2ccc3[nH]ncc3c2)c1-c1nn[nH]n1] | 4-(1H-indazol-5-yl)-3-(2H-tetrazol-5-yl)pyridine-2 sulfonamide | 343 | 343 |
| 200 | 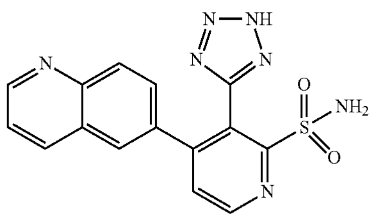 [SMILES: NS(=O)(=O)c1nccc(-c2ccc3ncccc3c2)c1-c1nn[nH]n1] | 4-(quinolin-6-yl)-3-(2H-tetrazol-5-yl)pyridine-2-sulfonamide | 354 | 354 |
| 201 | 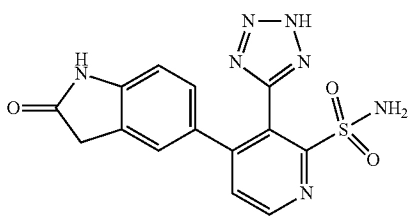 [SMILES: NS(=O)(=O)c1nccc(-c2ccc3c(c2)CC(=O)N3)c1-c1nn[nH]n1] | 4-(2-oxoindolin-5-yl)-3-(2H-tetrazol-5-yl)pyridine-2-sulfonamide | 358 | 358 |
| 202 | 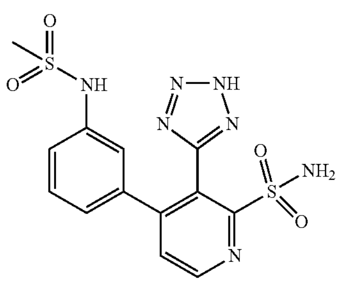 [SMILES: CS(=O)(=O)Nc1cccc(-c2ccnc(S(N)(=O)=O)c2-c2nn[nH]n2)c1] | 4-(3-(methylsulfonamido)phenyl)-3-(2H-tetrazol-5-yl)pyridine-2-sulfonamide | 396 | 396 |
| 203 | 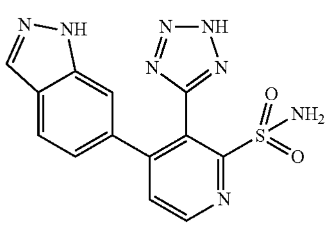 [SMILES: NS(=O)(=O)c1nccc(-c2ccc3cn[nH]c3c2)c1-c1nn[nH]n1] | 4-(1H-indazol-6-yl)-3-(2H-tetrazol-5-yl)pyridine-2-sulfonamide | 343 | 343 |
| 204 | 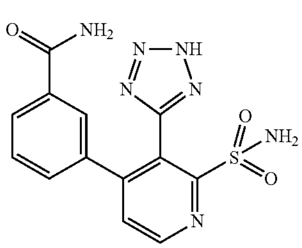 [SMILES: NC(=O)c1cccc(-c2ccnc(S(N)(=O)=O)c2-c2nn[nH]n2)c1] | 3-(2-sulfamoyl-3-(2H-tetrazol-5-yl)pyridin-4-yl)benzamide | 346 | 346 |

-continued

| Ex. No. | Structure | Name | Calc'd Mass [M + H]⁺ | LC/MS m/e [M + H]⁺ |
|---|---|---|---|---|
| 205 | 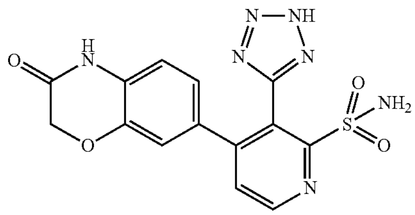 [SMILES: NS(=O)(=O)c1nccc(-c2ccc3c(c2)OCC(=O)N3)c1-c1nn[nH]n1] | 4-(3-oxo-3,4-dihydro-2H-benzo[b][1,4]oxazin-7-yl)-3-(2H-tetrazol-5-yl)pyridine-2-sulfonamide | 374 | 374 |
| 206 | 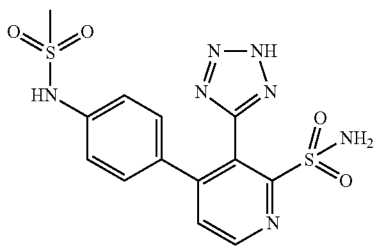 [SMILES: CS(=O)(=O)Nc1ccc(-c2ccnc(S(N)(=O)=O)c2-c2nn[nH]n2)cc1] | 4-(4-(methylsulfonamido)phenyl)-3-(2H-tetrazol-5-yl)pyridine-2-sulfonamide | 396 | 396 |
| 207 | 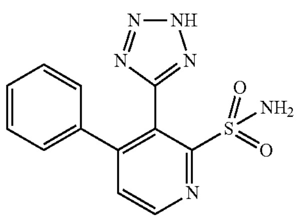 [SMILES: NS(=O)(=O)c1nccc(-c2ccccc2)c1-c1nn[nH]n1] | 4-phenyl-3-(2H-tetrazol-5-yl)pyridine-2-sulfonamide | 303 | 303 |
| 208 | 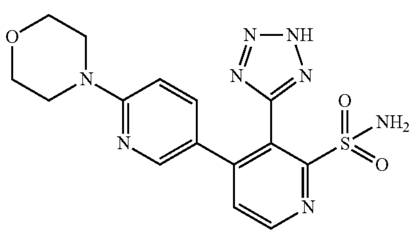 [SMILES: NS(=O)(=O)c1nccc(-c2ccc(N3CCOCC3)nc2)c1-c1nn[nH]n1] | 6-morpholino-3'-(2H-tetrazol-5-yl)-[3,4'-bipyridine]-2'-sulfonamide | 389 | 389 |
| 209 | 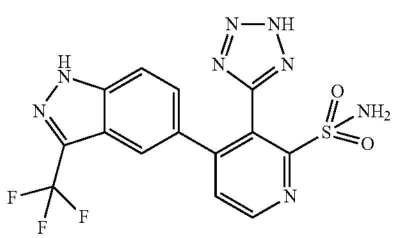 [SMILES: NS(=O)(=O)c1nccc(-c2ccc3[nH]nc(C(F)(F)F)c3c2)c1-c1nn[nH]n1] | 3-(2H-tetrazol-5-yl)-4-(3-(trifluoromethyl)-1H-indazol-5-yl)pyridine-2-sulfonamide | 411 | 411 |
| 210 | 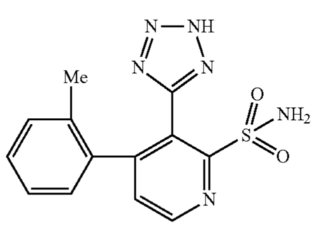 [SMILES: Cc1ccccc1-c1ccnc(S(N)(=O)=O)c1-c1nn[nH]n1] | 3-(2H-tetrazol-5-yl)-4-(o-tolyl)pyridine-2-sulfonamide | 317 | 317 |

-continued

| Ex. No. | Structure | Name | Calc'd Mass [M + H]+ | LC/MS m/e [M + H]+ |
|---|---|---|---|---|
| 211 | 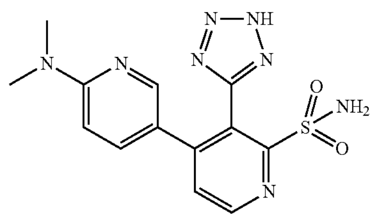 [SMILES: CN(C)c1ccc(-c2ccnc(S(N)(=O)=O)c2-c2nn[nH]n2)cn1] | 6-(dimethylamino)-3'-(2H-tetrazol-5-yl)-[3,4'-bipyridine]-2'-sulfonamide | 347 | 347 |
| 212 | 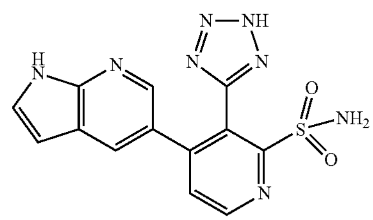 [SMILES: NS(=O)(=O)c1nccc(-c2cnc3[nH]ccc3c2)c1-c1nn[nH]n1] | 4-(1H-pyrrolo[2,3-b]pyridin-5-yl)-3-(2H-tetrazol-5-yl)pyridine-2-sulfonamide | 343 | 343 |
| 213 | 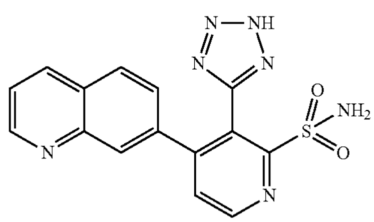 [SMILES: NS(=O)(=O)c1nccc(-c2ccc3cccnc3c2)c1-c1nn[nH]n1] | 4-(quinolin-7-yl)-3-(2H-tetrazol-5-yl)pyridine-2-sulfonamide | 354 | 354 |
| 214 | 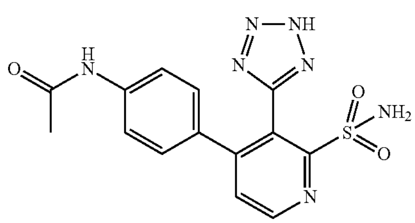 [SMILES: CC(=O)Nc1ccc(-c2ccnc(S(N)(=O)=O)c2-c2nn[nH]n2)cc1] | N-(4-(2-sulfamoyl-3-(2H-tetrazol-5-yl)pyridin-4-yl)phenyl)acetamide | 360 | 360 |
| 215 | 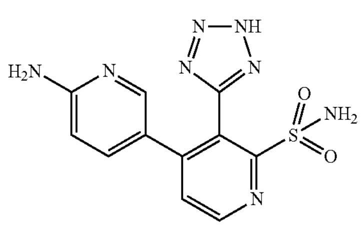 [SMILES: Nc1ccc(-c2ccnc(S(N)(=O)=O)c2-c2nn[nH]n2)cn1] | 6-amino-3'-(2H-tetrazol-5-yl)-[3,4'-bipyridine]-2'-sulfonamide | 319 | 319 |

EXAMPLES 216-244

Parallel Synthesis of Aminopyridinyl Examples

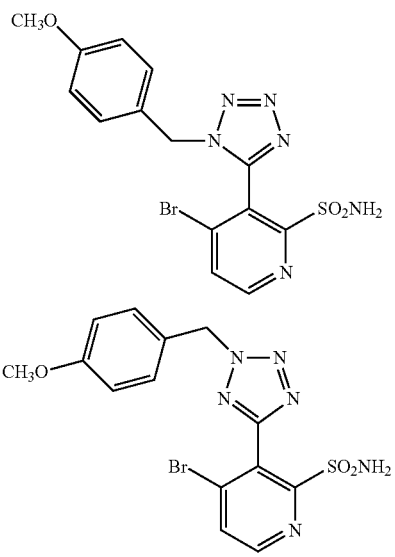

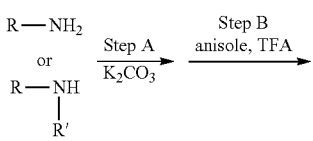

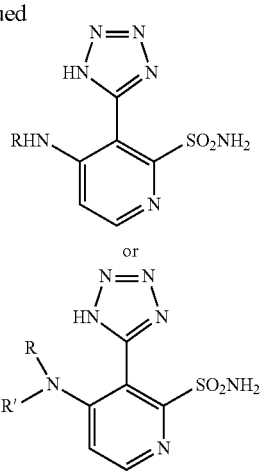

Step A: Coupling of Commercially Available or Known Amines with 4-Bromo-3-(2-(4-methoxybenzyl)-2H-tetrazol-5-yl)pyridine-2-sulfonamide and 4-Bromo-3-(1-(4-methoxybenzyl)-1H-tetrazol-5-yl)pyridine-2-sulfonamide A mixture of 4-Bromo-3-(2-(4-methoxybenzyl)-2H-tetrazol-5-yl)pyridine-2-sulfonamide and 4-Bromo-3-(1-(4-methoxybenzyl)-1H-tetrazol-5-yl)pyridine-2-sulfonamide (30 mg, 0.071 mmol) was combined with potassium carbonate (58.5 mg, 0.423 mmol) and commercially available or known primary or secondary amines (0.071 mmol) in a microwave vial with DMF (1 mL). The mixture was stirred at 150° C. for 1 hour. The mixtures were concentrated under reduced pressure.

Step B: Removal of the PMB Protective Group Under Acidic Conditions

To the intermediates produced in Step A was added TFA (0.5 mL) and Anisole (0.031 mL, 0.282 mmol) and the mixtures were stirred at 65° C. for 3 hours. The mixtures were allowed to cool and were then concentrated under reduced pressure. DMSO (1 mL) was added to each vial and the mixtures were filtered through a (96 well) 0.4 micron filter plate. Purification by mass directed reverse phase HPLC afforded Examples 216-244.

| Ex. No. | Structure | Name | Calc'd Mass [M + H]+ | LC/MS m/e [M + H]+ |
|---|---|---|---|---|
| 216 | 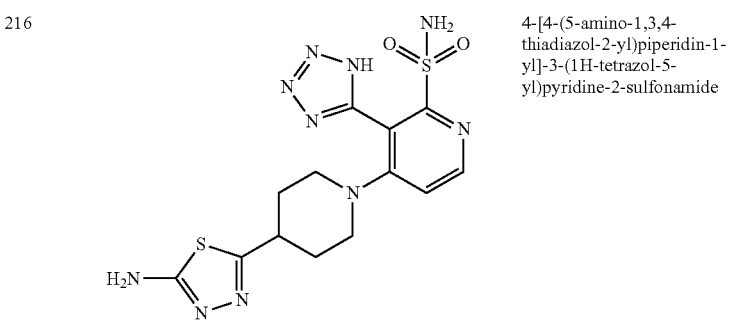 | 4-[4-(5-amino-1,3,4-thiadiazol-2-yl)piperidin-1-yl]-3-(1H-tetrazol-5-yl)pyridine-2-sulfonamide | 409 | 409 |

-continued

| Ex. No. | Structure | Name | Calc'd Mass [M + H]+ | LC/MS m/e [M + H]+ |
|---|---|---|---|---|
| 217 | 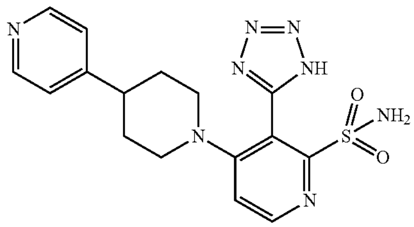 [SMILES: NS(=O)(=O)c1nccc(N2CCC(c3ccncc3)CC2)c1-c1nnn[nH]1] | 4-(4-pyridin-4-ylpiperidin-1-yl)-3-(1H-tetrazol-5-yl)pyridine-2-sulfonamide | 387 | 387 |
| 218 | 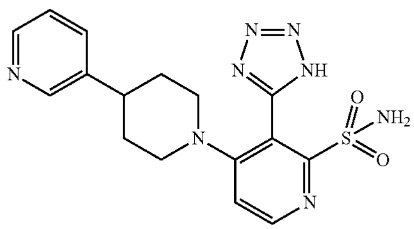 [SMILES: NS(=O)(=O)c1nccc(N2CCC(c3cccnc3)CC2)c1-c1nnn[nH]1] | 4-(4-pyridin-3-ylpiperidin-1-yl)-3-(1H-tetrazol-5-yl)pyridine-2-sulfonamide | 387 | 387 |
| 219 | 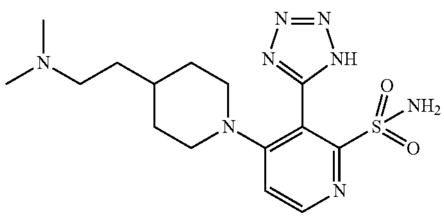 [SMILES: CN(C)CCC1CCN(c2ccnc(S(N)(=O)=O)c2-c2nnn[nH]2)CC1] | 4-{4-[2-(dimethylamino)ethyl]piperidin-1-yl}-3-(1H-tetrazol-5-yl)pyridine-2-sulfonamide | 381 | 381 |
| 220 | 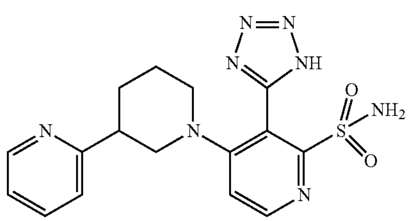 [SMILES: NS(=O)(=O)c1nccc(N2CCCC(c3ccccn3)C2)c1-c1nnn[nH]1] | 4-(3-pyridin-2-ylpiperidin-1-yl)-3-(1H-tetrazol-5-yl)pyridine-2-sulfonamide | 387 | 387 |
| 221 | 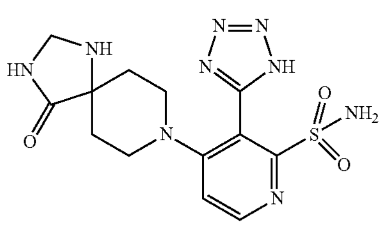 [SMILES: NS(=O)(=O)c1nccc(N2CCC3(CC2)NCNC3=O)c1-c1nnn[nH]1] | 4-(4-oxo-1,3,8-triazaspiro[4.5]dec-8-yl)-3-(1H-tetrazol-5-yl)pyridine-2-sulfonamide | 380 | 380 |
| 222 | 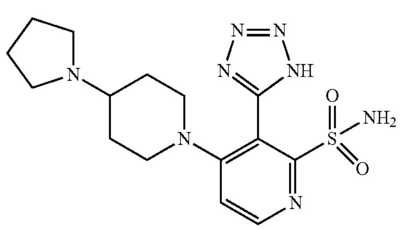 [SMILES: NS(=O)(=O)c1nccc(N2CCC(N3CCCC3)CC2)c1-c1nnn[nH]1] | 4-(4-pyrrolidin-1-ylpiperidin-1-yl)-3-(1H-tetrazol-5-yl)pyridine-2-sulfonamide | 379 | 379 |

-continued

| Ex. No. | Structure | Name | Calc'd Mass [M + H]+ | LC/MS m/e [M + H]+ |
|---|---|---|---|---|
| 223 | 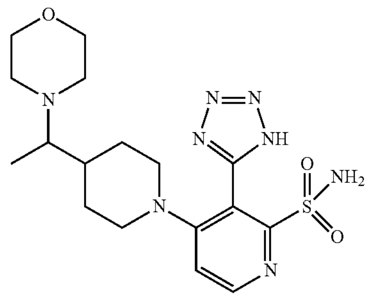 [SMILES: CC(C1CCN(c2ccnc(S(N)(=O)=O)c2-c2nnn[nH]2)CC1)N1CCOCC1] | 4-[4-(1-morpholin-4-ylethyl)piperidin-1-yl]-3-(1H-tetrazol-5-yl)pyridine-2-sulfonamide | 423 | 423 |
| 224 | 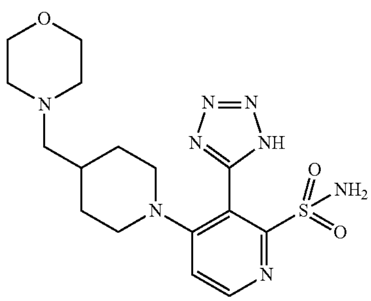 [SMILES: NS(=O)(=O)c1nccc(N2CCC(CN3CCOCC3)CC2)c1-c1nnn[nH]1] | 4-[4-(morpholin-4-ylmethyl)piperidin-1-yl]-3-(1H-tetrazol-5-yl)pyridine-2-sulfonamide | 409 | 409 |
| 225 | 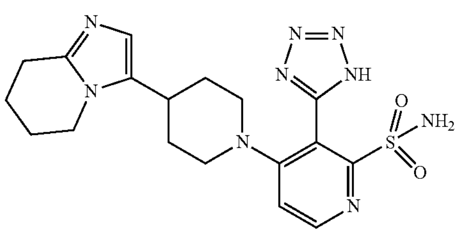 [SMILES: NS(=O)(=O)c1nccc(N2CCC(c3cnc4n3CCCC4)CC2)c1-c1nnn[nH]1] | 4-[4-(5,6,7,8-tetrahydroimidazo[1,2-a]pyridin-3-yl)piperidin-1-yl]-3-(1H-tetrazol-5-yl)pyridine-2-sulfonamide | 430 | 430 |
| 226 | 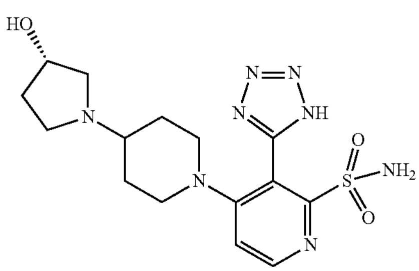 [SMILES: NS(=O)(=O)c1nccc(N2CCC(N3CC[C@H](O)C3)CC2)c1-c1nnn[nH]1] | 4-{4-[(3S)-3-hydroxypyrrolidin-1-yl]piperidin-1-yl}-3-(1H-tetrazol-5-yl)pyridine-2-sulfonamide | 395 | 395 |
| 227 | 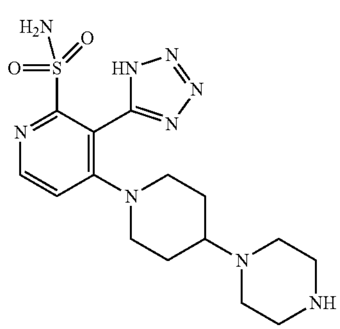 [SMILES: NS(=O)(=O)c1nccc(N2CCC(N3CCNCC3)CC2)c1-c1nnn[nH]1] | 4-(4-piperazin-1-ylpiperidin-1-yl)-3-(1H-tetrazol-5-yl)pyridine-2-sulfonamide | 394 | 394 |

| Ex. No. | Structure | Name | Calc'd Mass [M + H]⁺ | LC/MS m/e [M + H]⁺ |
|---|---|---|---|---|
| 228 | 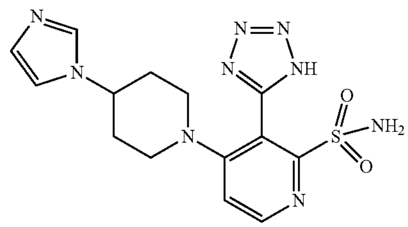 [SMILES: NS(=O)(=O)c1nccc(N2CCC(n3ccnc3)CC2)c1-c1nnn[nH]1] | 4-[4-(1H-imidazol-1-yl)piperidin-1-yl]-3-(1H-tetrazol-5-yl)pyridine-2-sulfonamide | 376 | 376 |
| 229 | 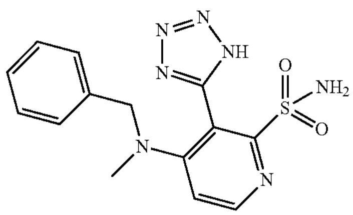 [SMILES: CN(Cc1ccccc1)c1ccnc(S(N)(=O)=O)c1-c1nnn[nH]1] | 4-[benzyl(methyl)amino]-3-(1H-tetrazol-5-yl)pyridine-2-sulfonamide | 346 | 346 |
| 230 | 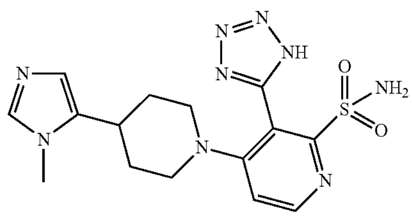 [SMILES: Cn1cncc1C1CCN(c2ccnc(S(N)(=O)=O)c2-c2nnn[nH]2)CC1] | 4-[4-(1-methyl-1H-imidazol-5-yl)piperidin-1-yl]-3-(1H-tetrazol-5-yl)pyridine-2-sulfonamide | 390 | 390 |
| 231 | 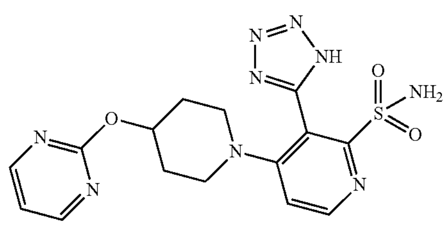 [SMILES: NS(=O)(=O)c1nccc(N2CCC(Oc3ncccn3)CC2)c1-c1nnn[nH]1] | 4-[4-(pyrimidin-2-yloxy)piperidin-1-yl]-3-(1H-tetrazol-5-yl)pyridine-2-sulfonamide | 404 | 404 |
| 232 | 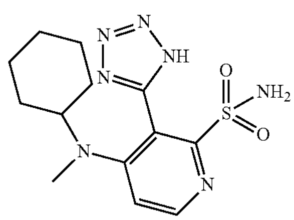 [SMILES: CN(c1ccnc(S(N)(=O)=O)c1-c1nnn[nH]1)C1CCCCC1] | 4-[cyclohexyl(methyl)amino]-3-(1H-tetrazol-5-yl)pyridine-2-sulfonamide | 338 | 338 |
| 233 | 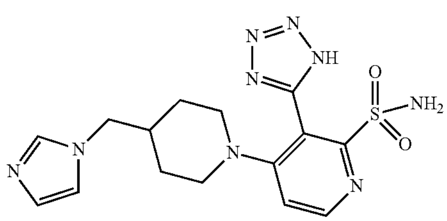 [SMILES: NS(=O)(=O)c1nccc(N2CCC(Cn3ccnc3)CC2)c1-c1nnn[nH]1] | 4-[4-(1H-imidazol-1-ylmethyl)piperidin-1-yl]-3-(1H-tetrazol-5-yl)pyridine-2-sulfonamide | 390 | 390 |
| 234 | 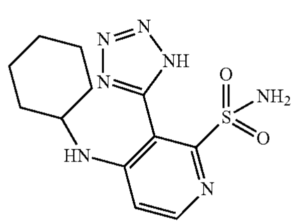 [SMILES: NS(=O)(=O)c1nccc(NC2CCCCC2)c1-c1nnn[nH]1] | 4-(cyclohexylamino)-3-(1H-tetrazol-5-yl)pyridine-2-sulfonamide | 324 | 324 |

-continued

| Ex. No. | Structure | Name | Calc'd Mass [M + H]⁺ | LC/MS m/e [M + H]⁺ |
|---|---|---|---|---|
| 235 | 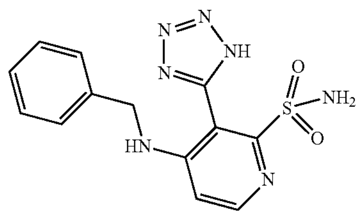 [SMILES: NS(=O)(=O)c1nccc(NCc2ccccc2)c1-c1nnn[nH]1] | 4-(benzylamino)-3-(1H-tetrazol-5-yl)pyridine-2-sulfonamide | 332 | 332 |
| 236 | 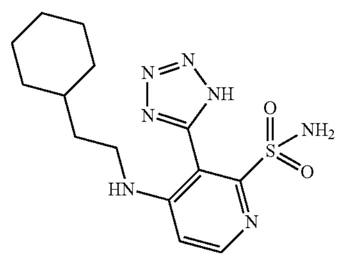 [SMILES: NS(=O)(=O)c1nccc(NCCC2CCCCC2)c1-c1nnn[nH]1] | 4-[(2-cyclohexylethyl)amino]-3-(1H-tetrazol-5-yl)pyridine-2-sulfonamide | 352 | 352 |
| 237 | 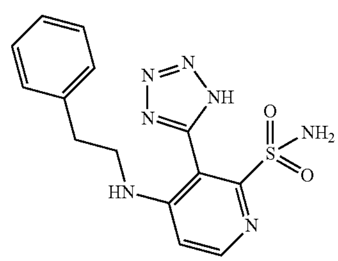 [SMILES: NS(=O)(=O)c1nccc(NCCc2ccccc2)c1-c1nnn[nH]1] | 4-[(2-phenylethyl)amino]-3-(1H-tetrazol-5-yl)pyridine-2-sulfonamide | 346 | 346 |
| 238 | 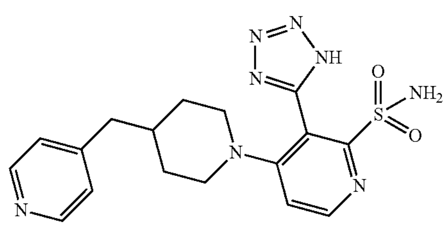 [SMILES: NS(=O)(=O)c1nccc(N2CCC(Cc3ccncc3)CC2)c1-c1nnn[nH]1] | 4-[4-(pyridin-4-ylmethyl)piperidin-1-yl]-3-(1H-tetrazol-5-yl)pyridine-2-sulfonamide | 401 | 401 |
| 239 | 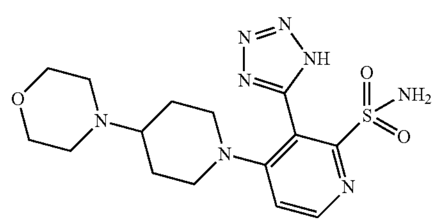 [SMILES: NS(=O)(=O)c1nccc(N2CCC(N3CCOCC3)CC2)c1-c1nnn[nH]1] | 4-(4-morpholin-4-ylpiperidin-1-yl)-3-(1H-tetrazol-5-yl)pyridine-2-sulfonamide | 395 | 395 |
| 240 | 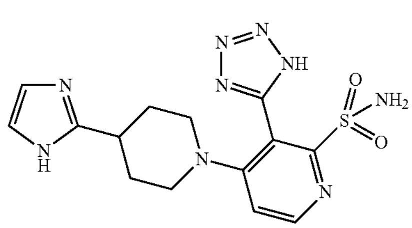 [SMILES: NS(=O)(=O)c1nccc(N2CCC(c3ncc[nH]3)CC2)c1-c1nnn[nH]1] | 4-[4-(1H-imidazol-2-yl)piperidin-1-yl]-3-(1H-tetrazol-5-yl)pyridine-2-sulfonamide | 376 | 376 |

| Ex. No. | Structure | Name | Calc'd Mass [M + H]+ | LC/MS m/e [M + H]+ |
|---|---|---|---|---|
| 241 | 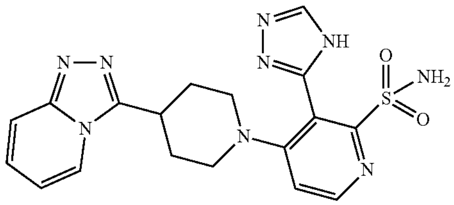 [SMILES: NS(=O)(=O)c1nccc(N2CCC(c3nnc4ccccn34)CC2)c1-c1nnc[nH]1] | 3-(1H-tetrazol-5-yl)-4-(4-[1,2,4]triazolo[4,3-a]pyridin-3-ylpiperidin-1-yl)pyridine-2-sulfonamide | 427 | 427 |
| 242 | 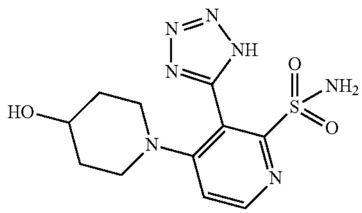 [SMILES: NS(=O)(=O)c1nccc(N2CCC(O)CC2)c1-c1nnn[nH]1] | 4-(4-hydroxypiperidin-1-yl)-3-(1H-tetrazol-5-yl)pyridine-2-sulfonamide | 326 | 326 |
| 243 | 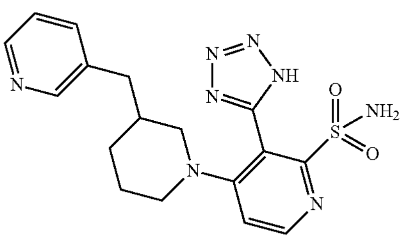 [SMILES: NS(=O)(=O)c1nccc(N2CCCC(Cc3cccnc3)C2)c1-c1nnn[nH]1] | 4-[3-(pyridin-3-ylmethyl)piperidin-1-yl]-3-(1H-tetrazol-5-yl)pyridine-2-sulfonamide | 401 | 401 |
| 244 | 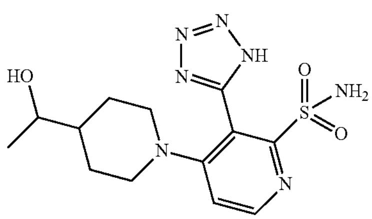 [SMILES: CC(O)C1CCN(c2ccnc(S(N)(=O)=O)c2-c2nnn[nH]2)CC1] | 4-[4-(1-hydroxyethyl)piperidin-1-yl]-3-(1H-tetrazol-5-yl)pyridine-2-sulfonamide | 354 | 354 |

EXAMPLE 245

4-(3,9-diazaspiro[5.5]undecan-3-yl)-3-(2H-tetrazol-5-yl)pyridine-2-sulfonamide

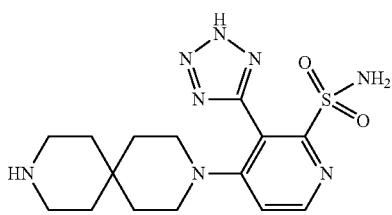 [SMILES: NS(=O)(=O)c1nccc(N2CCC3(CCNCC3)CC2)c1-c1nn[nH]n1]

Step A: tert-butyl 9-(3-(2-(4-methoxybenzyl)-2H-tetrazol-5-yl)-2-sulfamoylpyridin-4-yl)-3,9-diazaspiro[5.5]undecane-3-carboxylate and tert-butyl 9-(3-(1-(4-methoxybenzyl)-1H-tetrazol-5-yl)-2-sulfamoylpyridin-4-yl)-3,9-diazaspiro[5.5]undecane-3-carboxylate The mixture of tert-butyl 3,9-diazaspiro[5.5]undecane-3-carboxylate hydrochloride (29.3 mg, 0.101 mmol), 4-Bromo-3-(2-(4-methoxybenzyl)-2H-tetrazol-5-yl)pyridine-2-sulfonamide and 4-Bromo-3-(1-(4-methoxybenzyl)-1H-tetrazol-5-yl)pyridine-2-sulfonamide (33 mg, 0.078 mmol), and K₂CO₃ (42.9 mg, 0.310 mmol) in DMF (1 mL) was heated at 140° C. overnight. The mixture was partitioned between EtOAc (50 mL) and sat. NaHCO₃, the organic phase was washed with NaHCO₃ twice, dried over Na₂SO₄, concentrated and the residue was purified on preparative TLC (1000MU) using 10% MeOH/DCM as developing solvents to give the residue which was then further purified on preparative TLC (1000MU) using EtOAc as developing solvent to the title compound.

Step B: 4-(3,9-diazaspiro[5.5]undecan-3-yl)-3-(2H-tetrazol-5-yl)pyridine-2-sulfonamide To the solution of tert-butyl 9-(3-(2-(4-methoxybenzyl)-2H-tetrazol-5-yl)-2-sulfamoylpyridin-4-yl)-3,9-diazaspiro[5.5]undecane-3-carboxylate and tert-butyl 9-(3-(1-(4-methoxybenzyl)-1H-tetrazol-5-yl)-2-sulfamoylpyridin-4-yl)-3,9-diazaspiro[5.5]undecane-3-carboxylate (37 mg, 0.062 mmol) in CH₂Cl₂ (2 mL) was added TFA (2 mL, 26.0 mmol), and the resulting solution was stirred at rt for 1 hr, and then was concentrated; to the resulting residue was added triisopropylsilane (98 mg, 0.62 mmol) and TFA (2 mL, 26.0 mmol). The solution was then transferred to a sealed tube and heated at 80° C. for 1 hr. After removing the volatiles, the residue was dissolved in acetonitrile/water and purified by reverse phase HPLC using 5-40% acetonitrile (0.1% formic acid) over 10 min to give the title compound. LC/MS [M+H]+ 379.

EXAMPLE 246

4-(1H-benzo[d]imidazol-1-yl)-3-(2H-tetrazol-5-yl)pyridine-2-sulfonamide

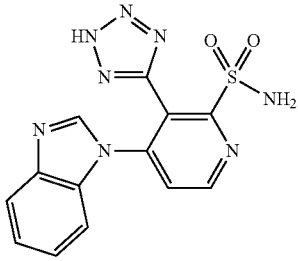 [SMILES: NS(=O)(=O)c1nccc(-n2cnc3ccccc32)c1-c1nn[nH]n1]

Step A: 1-(3-(2-(4-methoxybenzyl)-2H-tetrazol-5-yl)-2-((2-(trimethylsilyl)ethyl)sulfonyl)pyridin-4-yl)-1H-benzo[d]imidazole To a microwave vial was charged 4-bromo-3-(1-(4-methoxybenzyl)-1H-tetrazol-5-yl)-2-((2-(trimethylsilyl)ethyl)sulfonyl)pyridine (300 mg, 0.588 mmol), 1H-benzo[d]imidazole (83 mg, 0.705 mmol), Pd2(dba)3 (53.8 mg, 0.059 mmol), Xantphos (68.0 mg, 0.118 mmol), and potassium carbonate (244 mg, 1.76 mmol). The vial was sealed, degassed, and filled with dioxane (2938 µl). The reaction mixture was heated at 90° C. overnight, and was diluted with water, and extracted with EtOAc. The organic layer was washed with brine, dried, and evaporated to give the crude product, which was purified by silica gel column chromatography (0-10% MeOH/DCM) to give the title compound. LC-MS (IE, m/z): 548.7 [M+1]+.

Step B: 4-(1H-benzo[d]imidazol-1-yl)-3-(2-(4-methoxybenzyl)-2H-tetrazol-5-yl)pyridine-2-sulfonamide In a glove box to the solution of 1-(3-(2-(4-methoxybenzyl)-2H-tetrazol-5-yl)-2-((2-(trimethylsilyl)ethyl)sulfonyl)pyridin-4-yl)-1H-benzo[d]imidazole (150 mg, 0.274 mmol) in THF (5.5 mL) was added TBAF (1.4 mL, 1 M in THF, 1.4 mmol). The resulting solution was stirred at rt for 2 hr, and checked by LCMS for completion of the first step conversion. Sodium acetate (225 mg, 2.74 mmol) in 2 mL of water was then added followed by addition of hydroxylamine-O-sulfonic acid (310 mg, 2.74 mmol). The resulting solution was stirred at rt overnight in the glove box. The mixture was partitioned between EtOAc (50 mL) and sat. NaHCO3. The organic phase was washed with NaHCO3 twice, and dried over Na2SO4, concentrated and the residue was purified by silica gel chromatography using 10% MeOH/DCM as mobile phase to afford the title compound.

LC-MS (IE, m/z): 463.28 [M+1]+.

Step C: 4-(1H-benzo[d]imidazol-1-yl)-3-(2H-tetrazol-5-yl)pyridine-2-sulfonamide

To a solution of 4-(1H-benzo[d]imidazol-1-yl)-3-(2-(4-methoxybenzyl)-2H-tetrazol-5-yl)pyridine-2-sulfonamide (100 mg, 0.216 mmol) in DCM (3 mL) was added thioanisole (0.512 ml, 4.32 mmol) and TFA (1.666 mL, 21.62 mmol). The resulting solution was heated at 80° C. for 1.5 hr. After removing the volatile, the residue was purified by reverse phase HPLC using DMSO to load sample and 5-40% acetonitrile/water (0.1% formic acid additive) as mobile phase to afford the title compound. LC-MS (IE, m/z): 343.22 [M+1]+.

EXAMPLE 247

3-(Imidazo[1,5-a]pyridin-7-yl)-2-(2H-tetrazol-5-yl)benzenesulfonamide

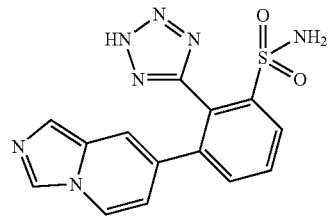 [SMILES: NS(=O)(=O)c1cccc(-c2ccn3cncc3c2)c1-c1nn[nH]n1]

Step A: 3-(Imidazo[1,5-a]pyridin-7-yl)-2-(2-(4-methoxybenzyl)-2H-tetrazol-5-yl)benzenesulfonamide In a reaction vessel, 7-bromoimidazo[1,5-a]pyridine (200 mg, 1.02 mmol) and bispinacolatodiboron (773 mg, 3.05 mmol) were combined, followed by potassium acetate (299 mg, 3.05 mmol) and PCy3 Pd G2 (59.9 mg, 0.102 mmol). Then dry dioxane (5 mL) was added to this flask. This mixture was degassed and then heated at 80° C. for 12 hr. The reaction was cooled to rt, then to the reaction was added 3-bromo-2-(2-(4-methoxybenzyl)-2H-tetrazol-5-yl)benzenesulfonamide (431 mg, 1.02 mmol), PdCl2(dppf)-CH2Cl2adduct (83 mg, 0.102 mmol), and K2CO3 (842 mg, 6.09 mmol) dissolved in 1.2 ml of water. N2 was bubbled through for 10 min. The mixture was then heated at 85° C. overnight. The mixture was cooled, diluted with EtOAc, and washed with water. The combined organic fractions were separated and the solvent was evaporated under reduced pressure. The residue was purified by column chromatography on silica gel (80 g), eluting with 0-5% MeOH/EtOAc to give the title compound. LC-MS 462 (M+1)+.

Step B: 3-(Imidazo[1,5-a]pyridin-7-yl)-2-(2H-tetrazol-5-yl)benzenesulfonamide 3-(Imidazo[1,5-a]pyridin-7-yl)-2-(2-(4-methoxybenzyl)-2H-tetrazol-5-yl)benzenesulfonamide was heated at 80° C. in TFA for 3 hr. The mixture was then cooled and concentrated to remove the excess of TFA. The residue was dissolved in CH3CN/H2O/MeOH and purified by reverse phase HPLC, eluting with 5-40% CH3CN/H2O with 0.1% formic acid. The correct fractions were combined, concentrated and lypholized. LC-MS 342 (M+1)+.

EXAMPLE 248

3-(5-Methylpyrazin-2-yl)-2-(2H-tetrazol-5-yl)benzenesulfonamide

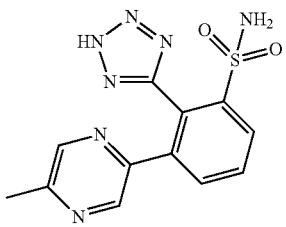 [SMILES: Cc1cnc(-c2cccc(S(N)(=O)=O)c2-c2nn[nH]n2)cn1]

Step A: N,N-bis(4-Methoxybenzyl)-2-(2-(4-methoxybenzyl)-2H-tetrazol-5-yl)-3-(5-methylpyrazin-2-yl)benzenesulfonamide To a reaction vessel, was added 3-bromo-N,N-bis(4-methoxybenzyl)-2-(2-(4-methoxybenzyl)-2H-tetrazol-5-yl)benzenesulfonamide (200 mg, 0.301 mmol), 5,5,5',5'-tetramethyl-2,2'-bi(1,3,2-dioxaborinane) (204 mg, 0.903 mmol), PCy3 Pd G2 (17.8 mg, 0.030 mmol), and potassium acetate (89 mg, 0.90 mmol). Then amhydrous $CH_3CN$ (1.5 mL) was added to this flask. The mixture was sealed and degassed for 10 min. This mixture was then heated at 85° C. for 24 hr. LC-MS analysis indicated the formation of the desired boronic ester. After cooling to rt, to this reaction mixture, was added 2-bromo-5-methylpyrazine (78 mg, 0.451 mmol), $PdCl_2(dppf)$ (22.02 mg, 0.030 mmol), and $Na_2CO_3$ (63.8 mg, 0.602 mmol) dissolved in water (0.4 mL). The reaction mixture was degassed for 10 min and heated at 95° C. overnight. The mixture was cooled, water was added and the mixture was extracted with EtOAc. The combined organic fractions were washed with brine, dried ($Na_2SO_4$), filtered and the solvent was evaporated under reduced pressure. The residue was purified by column chromatography on silica gel, eluting with EtOAc/Hexanes (0-100%) to give the title compound. LC-MS 678 $(M+1)^+$.

Step B: 3-(5-Methylpyrazin-2-yl)-2-(2H-tetrazol-5-yl)benzenesulfonamide

N,N-bis(4-methoxybenzyl)-2-(1-(4-methoxybenzyl)-1H-tetrazol-5-yl)-3-(5-methylpyrazin-2-yl)benzenesulfonamide (78 mg, 0.12 mmol) was treated with TFA (2 mL) and Anisole (12.57 µL, 0.115 mmol). After heating at 60° C. for 3 hr, LC-MS analysis showed completion of the reaction. The reaction mixture was concentrated and the residue was purified by reverse phase HPLC (5-60% $CH_3CN$/water with 0.1% TFA). The correct fractions were combined, concentrated, and lypholized to give the title compound. LC-MS 318 $(M+1)^+$.

EXAMPLE 249

4'-(5-(Aminomethyl)-1,2,4-oxadiazol-3-yl)-2-(2H-tetrazol-5-yl)-[1,1'-biphenyl]-3-sulfonamide

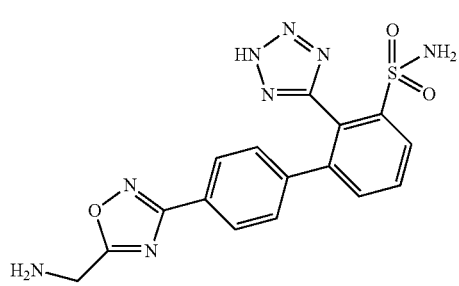 [SMILES: NCc1nc(-c2ccc(-c3cccc(S(N)(=O)=O)c3-c3nn[nH]n3)cc2)no1]

Step A: 4'-Cyano-2-(2-(4-methoxybenzyl)-2H-tetrazol-5-yl)-[1,1'-biphenyl]-3-sulfonamide To a reaction vessel was added 3-bromo-2-(2-(4-methoxybenzyl)-2H-tetrazol-5-yl)benzenesulfonamide (2.00 g, 4.71 mmol), 4-(4,4,5,5-tetramethyl-1,3,2-dioxaborolan-2-yl)benzonitrile (1.296 g, 5.66 mmol), $PdCl_2(dppf)$ (0.345 g, 0.471 mmol), and $Na_2CO_3$ (0.999 g, 9.43 mmol) followed by 1,4-dioxane (23.57 mL) and water (7.86 mL). The mixture was degassed for 10 min and then heated at 90° C. overnight. After cooled to rt, the mixture was filtered through a pad of celite. The filtrates were concentrated and the residue was purified by column chromatography (0-70% EtOAc/Hexane) to give the title compound. LC-MS 447 $(M+1)^+$;

Step B: N-Hydroxy-2'-(2-(4-methoxybenzyl)-2H-tetrazol-5-yl)-3'-sulfamoyl-[1,1'-biphenyl]-4-carboximidamide 4'-Cyano-2-(2-(4-methoxybenzyl)-2H-tetrazol-5-yl)-[1,1'-biphenyl]-3-sulfonamide (3 g, 6.72 mmol) and hydroxylamine (8.24 mL, 134 mmol) in EtOH (20 mL) was heated at 80° C. overnight. The mixture was cooled and the excess solvents and reagent were removed under the reduced pressure to give the title compound, which was used directly in the next step. LC-MS 480 $(M+1)^+$.

Step C: tert-butyl ((3-(2'-(2-(4-methoxybenzyl)-2H-tetrazol-5-yl)-3'-sulfamoyl-[1,1'-biphenyl]-4-yl)-1,2,4-oxadiazol-5-yl)methyl)carbamate 2-((tert-Butoxycarbonyl)amino)acetic acid (65.8 mg, 0.375 mmol) in $CH_2Cl_2$ (3.1 mL) was treated with di($^1$H-imidazol-1-yl)methanone (60.9 mg, 0.375 mmol). The mixture was stirred at rt under $N_2$ for 30 min before N-hydroxy-2'-(2-(4-methoxybenzyl)-2H-tetrazol-5-yl)-3'-sulfamoyl-[1,1'-biphenyl]-4-carboximidamide (150 mg, 0.313 mmol) was added. The resulting mixture was stirred at rt under $N_2$ overnight and then concentrated. The residue was heated at 110° C. in toluene for 8 hr. LC-MS showed the desired mass. The mixture was concentrated and the residue was purified by column chromatography to give the title compound. LC-MS 619 $(M+1)^+$.

Step D: 4'-(5-(Aminomethyl)-1,2,4-oxadiazol-3-yl)-2-(2H-tetrazol-5-yl)-[1,1'-biphenyl]-3-sulfonamide tert-butyl ((3-(2'-(2-(4-methoxybenzyl)-2H-tetrazol-5-yl)-3'-sulfamoyl-[1,1'-biphenyl]-4-yl)-1,2,4-oxadiazol-5-yl)methyl)carbamate (129 mg, 0.209 mmol) was treated with TFA at rt until LC-MS indicated the Boc group was removed. The reaction was concentrated under the reduced pressure and co-evaporated with toluene 3 times. Then the resulting residue was heated in TFA at 80° C. for 3 hr before the reaction mixture was cooled and concentrated. The crude product was purified by Gilson (5%-40% ACN/water with 0.1% TFA). The correct fractions were combined, concentrated, converted to HCl salt and lypholized to give the title compound. LC-MS 399 $(M+1)^+$.

EXAMPLE 250

4'-(5-(pyrrolidin-3-yl)-1,2,4-oxadiazol-3-yl)-2-(2H-tetrazol-5-yl)-[1,1'-biphenyl]-3-sulfonamide

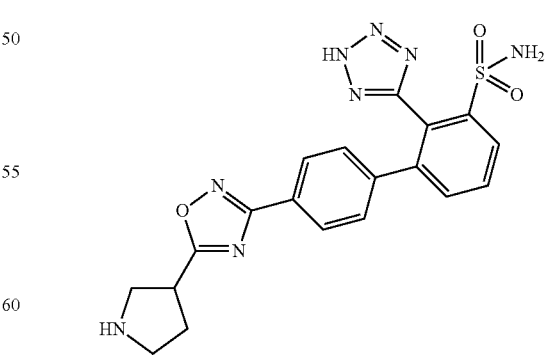

The title compound was prepared in a similar fashion to the synthesis of 4'-(5-(Aminomethyl)-1,2,4-oxadiazol-3-yl)-2-(2H-tetrazol-5-yl)-[1,1'-biphenyl]-3-sulfonamide from 1-Boc-pyrrolidine-3-carboxylic acid and N-hydroxy-2'-(2-

(4-methoxybenzyl)-2H-tetrazol-5-yl)-3'-sulfamoyl-[1,1'-biphenyl]-4-carboximidamide. LC-MS 439 (M+1)+.

EXAMPLE 251

(S)-4'-(5-(1-hydroxyethyl)-1,2,4-oxadiazol-3-yl)-2-(2H-tetrazol-5-yl)-[1,1'-biphenyl]-3-sulfonamide

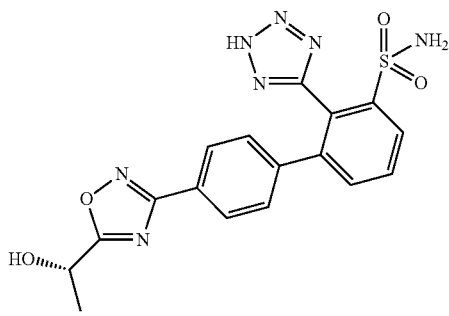 [SMILES: C[C@H](O)c1nc(-c2ccc(-c3cccc(S(N)(=O)=O)c3-c3nn[nH]n3)cc2)no1]

Step A: (S)-4'-(5-(1-hydroxyethyl)-1,2,4-oxadiazol-3-yl)-2-(2-(4-methoxybenzyl)-2H-tetrazol-5-yl)-[1,1'-biphenyl]-3-sulfonamide L-(+)-lactic acid (28.2 mg, 0.313 mmol) was combined with EDC (90 mg, 0.469 mmol), HOBt (86 mg, 0.563 mmol), and N-hydroxy-2'-(1-(4-methoxybenzyl)-1H-tetrazol-5-yl)-3'-sulfamoyl-[1,1'-biphenyl]-4-carboximidamide (150 mg, 0.313 mmol), then DCM (1.6 mL) was added and then TEA (131 µl, 0.938 mmol). The mixture was stirred at rt for 16 hr. After being diluted with EtOAc, the reaction mixture was washed with water, sat. NaHCO₃ solution and brine, dried (Na₂SO₄) and concentrated to give an oil, which was dissolved in pyridine (1.5 mL) and heated at 80° C. overnight. The reaction mixture was concentrated and the residue was purified with column chromatography to give the title compound. LC-MS 534 (M+1)+.

Step B: (S)-4'-(5-(1-hydroxyethyl)-1,2,4-oxadiazol-3-yl)-2-(2H-tetrazol-5-yl)-[1,1'-biphenyl]-3-sulfonamide (S)-4'-(5-(1-hydroxyethyl)-1,2,4-oxadiazol-3-yl)-2-(2-(4-methoxybenzyl)-2H-tetrazol-5-yl)-[1,1'-biphenyl]-3-sulfonamide (100 mg, 0.187 mmol) was heated in TFA for 3 hr before it was concentrated. The crude product was purified by reverse phase HPLC (5-60% acetonitrile/water with 0.1% FA) and the correct fractions were combined, concentrated and lypholized to give the title compound. LC-MS 414 (M+1)+.

EXAMPLE 252

4,5-Dimethyl-2-(2H-tetrazol-5-yl)benzenesulfonamide

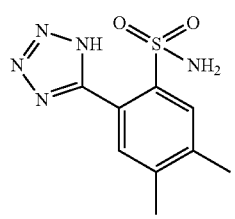 [SMILES: Cc1cc(-c2nnn[nH]2)c(S(N)(=O)=O)cc1C]

Step A: 2-(2-((Benzyloxy)methyl)-2H-tetrazol-5-yl)-4,5-dimethylbenzenesulfonamide A mixture of 2-((benzyloxy)methyl)-5-(tributylstannyl)-2H-tetrazole (109 mg, 0.227 mmol), 2-bromo-4,5-dimethylbenzenesulfonamide (50 mg, 0.189 mmol), tetrakis(triphenylphosphine)palladium(0) (10.94 mg, 9.46 µmol) and copper(I) iodide (3.61 mg, 0.019 mmol) in toluene (1 ml) was refluxed at 110° C. for 4 hr. The reaction was filtered through celite and concentrated then purified by mass directed reverse phase HPLC with ACN and water with 0.05% TFA. LC/MS [M+H]+:374.

Step B: 4,5-Dimethyl-2-(2H-tetrazol-5-yl)benzenesulfonamide

A mixture of 2-(2-((benzyloxy)methyl)-2H-tetrazol-5-yl)-4,5-dimethylbenzenesulfonamide (16 mg, 0.043 mmol) and HCl (14 µl, 0.084 mmol) in methanol (1 ml) was heated at 65° C. for 2 hr. LC/MS showed incomplete hydrolysis of BOM group. Another 0.3 ml of 6N HCl was added and heating continued for another 3 hr. The reaction was concentrated and purified by mass directed reverse phase hplc with ACN and water with 0.05% TFA. LC/MS [M+H]+: 254.1.

EXAMPLE 253

4-Methoxy-2-(2H-tetrazol-5-yl)benzenesulfonamide

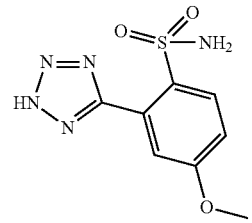 [SMILES: COc1ccc(S(N)(=O)=O)c(-c2nn[nH]n2)c1]

Step A: 2-(2-((Benzyloxy)methyl)-2H-tetrazol-yl)-4-methoxybenzenesulfonamide 2-((Benzyloxy)methyl)-5-(tributylstannyl)-2H-tetrazole from Reference Example 3 (180 mg, 0.376 mmol), 2-bromo-4-methoxybenzenesulfonamide (50 mg, 0.188 mmol) and chloro(2-dicyclohexylphosphino-2',6'-di-i-propoxy-1,1'-biphenyl)[2-(2-aminoethylphenyl)]palladium(II) methyl-t-butylether adduct (15.35 mg, 0.019 mmol) were dissolved in THF (376 µl) and heated to 80° C. overnight. The reaction was filtered and concentrated and the residue was purified by mass directed reverse phase HPLC with ACN and water with 0.05% TFA. LC/MS [M+H]+:376.

Step B: 4-Methoxy-2-(2H-tetrazol-5-yl)benzenesulfonamide 2-(2-((Benzyloxy)methyl)-2H-tetrazol-5-yl)-4-methoxybenzenesulfonamide (20 mg, 0.053 mmol) was dissolved in MeOH (1 ml) then HCl (0.018 ml, 0.107 mmol) was added and the reaction heated to 65° C. The reaction was monitored with LC/MS until no starting material was left. The reaction was concentrated and the residue was purified by reverse phase hplc with ACN and water with 0.05% TFA. LC/MS [M+H]+:256.2.

EXAMPLE 254

4-Hydroxy-2-(2H-tetrazol-yl)benzenesulfonamide

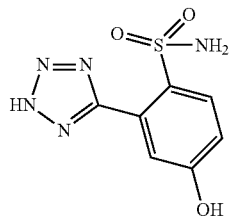 [SMILES: NS(=O)(=O)c1ccc(O)cc1-c1nn[nH]n1]

4-Methoxy-2-(2H-tetrazol-5-yl)benzenesulfonamide from Example 148 (6.6 mg, 0.026 mmol) was dissolved in DCM (5 ml) then cooled to 0° C. and BBr$_3$ (0.259 mL, 1 M, 0.259 mmol) was added. The reaction was then warmed up to RT and stirred for 18 hr. The reaction was quenched with water and concentrated. The residue purified by reverse phase HPLC with ACN and water with 0.05% TFA to afford 4-hydroxy-2-(2H-tetrazol-yl)benzenesulfonamide. LC/MS [M+H]$^+$:242.1.

EXAMPLE 255

Methyl 3-sulfamoyl-4-(2H-tetrazol-5-yl)benzoate

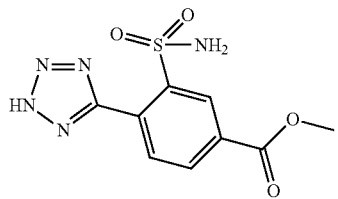 [SMILES: COC(=O)c1ccc(-c2nn[nH]n2)c(S(N)(=O)=O)c1]

Step A: Methyl 4-(2-((benzyloxy)methyl)-2H-tetrazol-5-yl)-3-sulfamoylbenzoate 2-((Benzyloxy)methyl)-5-(tributylstannyl)-2H-tetrazole from Reference Example 3 (384 mg, 0.801 mmol), methyl 4-chloro-3-sulfamoylbenzoate (100 mg, 0.401 mmol) and chloro(2-dicyclohexylphosphino-2',6'-di-i-propoxy-1,1'-biphenyl)[2-(2-aminoethylphenyl)]palladium(ii) methyl-t-butylether adduct (32.7 mg, 0.040 mmol) in THF (0.8 mL) was heated at 80° C. overnight. The reaction was filtered and concentrated. The residue was absorbed onto silica gel and purified by MPLC with 5% methanol in methylene chloride. LC/MS [M+H]$^+$:404.

Step B: Methyl 3-sulfamoyl-4-(2H-tetrazol-5-yl)benzoate

Methyl 4-(2-((benzyloxy)methyl)-2H-tetrazol-5-yl)-3-sulfamoylbenzoate (149 mg, 0.369 mmol) was dissolved in MeOH (2 ml) then HCl (0.185 ml, 0.739 mmol) was added and the reaction was heated to 65° C. overnight. The reaction was concentrated and the residue purified by reverse phase HPLC with ACN and water with 0.05% TFA to afford the title compound. $^1$H-NMR (500 MHz, CD3OD) δ ppm 8.81 (s, 1H), 8.38 (d, J=8 Hz, 1H), 7.93 (d, J=8 Hz, 1H) 4.01 (s, 3H); LC/MS [M+H]$^+$:284.1.

EXAMPLE 256

2-(1H-Tetrazol-5-yl)-3-(trifluoromethyl)benzenesulfonamide

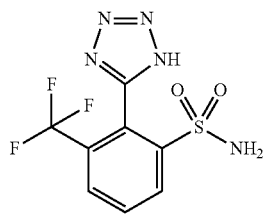 [SMILES: NS(=O)(=O)c1cccc(C(F)(F)F)c1-c1nnn[nH]1]

Step A: 2-(Trifluoromethyl)-6-((2-(trimethylsilyl)ethyl)thio)benzonitrile

To a solution of 2-fluoro-6-(trifluoromethyl)benzonitrile (1.0 g, 5.29 mmol) and K$_2$CO$_3$ (1.46 g, 10.58 mmol) in DMF (5 mL) was added 2-(trimethylsilyl)ethanethiol (1.01 ml, 6.35 mmol). The mixture was stirred at room temperature for 4 hours. The TLC indicated complete consumption of starting material. The mixture was filtered and evaporated to dryness in vacuo. The crude was adsorbed onto silica gel, and purified by hexane and ethyl acetate to afford the desired compound. LC/MS [M+H]$^+$:304.

Step B: 2-(Trifluoromethyl)-6-((2-(trimethylsilyl)ethyl)sulfonyl)benzonitrile

To a solution of 2-(trifluoromethyl)-6-((2-(trimethylsilyl)ethyl)thio)benzonitrile (400 mg, 1.32 mmol) in DCM (10 ml) was added mCPBA (796 mg, 4.61 mmol). The mixture was stirred at room temperature for 3 hours. The TLC indicated complete consumption of starting material. Sat. Na$_2$S$_2$O$_3$ was added to the mixture and stirred for 10 minutes, then sat. NaHCO$_3$ was added. The organic was extracted with DCM (3×), dried over Na$_2$SO$_4$, filtered and concentrated. The crude 2-(trifluoromethyl)-6-((2-(trimethylsilyl)ethyl)sulfonyl)benzonitrile was used without further purification in the next step. $^1$H-NMR (CDCl$_3$): δ 0.098 (s, 9H), 0.98-1.01 ppm (m, 2H), 3.41-3.44 ppm (m, 2H), 8.0 (dd, J=7.8 Hz, 1H), 8.13 (d, J=7.8 Hz, 1H), 8.45 (d, J=7.8 Hz, 1H).

Step C: 5-(2-(Trifluoromethyl)-6-((2-(trimethylsilyl)ethyl)sulfonyl)phenyl)-1H-tetrazole A solution of 2-(trifluoromethyl)-6-((2-(trimethylsilyl)ethyl)sulfonyl)benzonitrile (350 mg, 1.04 mmol), azidotrimethylsilane (0.28 ml, 2.09 mmol) and dibutyltin oxide (78 mg, 0.31 mmol) was heated at 110° C. overnight. The crude was concentrated and purified by HPLC with ACN and H$_2$O with buffering with 0.05 TFA to give the desired compound. LC/MS [M+H]$^+$:379.

Step D: 2-(1H-Tetrazol-5-yl)-3-(trifluoromethyl)benzenesulfonamide

A solution of 5-(2-(trifluoromethyl)-6-((2-(trimethylsilyl)ethyl)sulfonyl)phenyl)-1H-tetrazole (301 mg, 0.80 mmol) and tetrabutylammonium fluoride (7.95 ml, 7.95 mmol) in THF (8 ml) was heated at 60° C. for 16 hr. To that reaction mixture, sodium acetate (652 mg, 7.95 mmol) dissolved in water (3.73 ml, 207 mmol) followed by hydroxylamine-o-sulfonic acid (899 mg, 7.95 mmol) were added and stirred overnight. The reaction mixture was concentrated under vacuum and purified by HPLC with ACN and H$_2$O buffered with 0.05% TFA to give the desired compound. LC/MS [M+H]$^+$:294.2.

EXAMPLE 257

3-Methoxy-2-(1H-tetrazol-5-yl)benzenesulfonamide

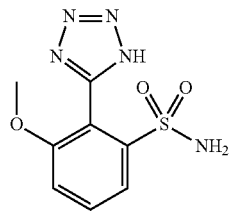 [SMILES: COc1cccc(S(N)(=O)=O)c1-c1nnn[nH]1]

Step A: 2-Methoxy-6-((2-(trimethylsilyl)ethyl)thio)benzonitrile

To a solution of 2-fluoro-6-methoxybenzonitrile (1.0 g, 6.62 mmol) and potassium carbonate (1.83 g, 13.23 mmol) in DMF (5 ml) was added 2-(trimethylsilyl)ethanethiol (1.27 ml, 7.94 mmol). The mixture was stirred at room temperature for 4 hours. The TLC indicated complete consumption of starting material. The mixture was filtered and the filtrate was concentrated under vacuum. The crude was adsorbed onto silica gel, and purified by silica gel column with hexane and ethyl acetate to give 2-methoxy-6-((2-(trimethylsilyl)ethyl)thio)benzonitrile. LC/MS [M+H]$^+$:266.

Step B: 2-Methoxy-6-((2-(trimethylsilyl)ethyl)sulfonyl)benzonitrile

A solution of 2-methoxy-6-((2-(trimethylsilyl)ethyl)thio) benzonitrile (200 mg, 0.75 mmol) and mCPBA (455 mg, 2.64 mmol) in DCM (5 ml) was stirred at room temperature for 2 hr. The TLC indicated complete consumption of starting material. Sat. Na$_2$S$_2$O$_3$ was added to the mixture and stirred for 10 minutes and then sat. NaHCO$_3$ was added. After stirring for another 10 minutes, organic was extracted with DCM (3×), dried over Na$_2$SO$_4$, filtered and the filtrate was concentrated to dryness in vacuo. The crude 2-methoxy-6-((2-(trimethylsilyl)ethyl)sulfonyl)benzonitrile was taken as is for the next step. LC/MS [M+H]$^+$:298.

Step C: 5-(2-Methoxy-6-((2-(trimethylsilyl)ethyl)sulfonyl)phenyl)-1H-tetrazole

A solution of 2-methoxy-6-((2-(trimethylsilyl)ethyl)sulfonyl)benzonitrile (120 mg, 0.40 mmol), azidotrimethylsilane (0.11 ml, 0.81 mmol) and dibutyltin oxide (50.2 mg, 0.20 mmol) in toluene (5 ml) was heated at 110° C. for 2 days. The reaction mixture was concentrated under vacuum. The crude was dissolved in DMSO and purified by HPLC with ACN and H$_2$O buffering with 0.05% TFA to give the desired compound. LC/MS [M+H]$^+$:341.

Step D: 3-Methoxy-2-(1H-tetrazol-5-yl)benzenesulfonamide

A solution of 5-(2-methoxy-6-((2-(trimethylsilyl)ethyl) sulfonyl)phenyl)-1H-tetrazole (103 mg, 0.30 mmol) and tetrabutylammonium fluoride (3.03 ml, 3.03 mmol) was heated at 60° C. overnight. The crude reaction mixture was concentrated and dissolved in DMF and purified by HPLC with ACN and H$_2$O buffered with 0.05% TFA to afford 3-methoxy-2-(1H-tetrazol-5-yl)benzenesulfonamide. LC/MS [M+H]$^+$:256.1.

EXAMPLE 258

3-(6-(Hydroxymethyl)pyridin-3-yl)-2-(1H-tetrazol-5-yl)benzenesulfonamide

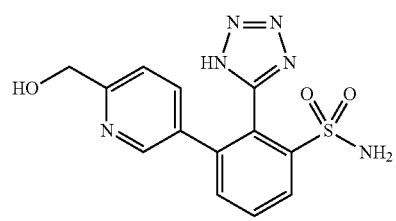 [SMILES: NS(=O)(=O)c1cccc(-c2ccc(CO)nc2)c1-c1nnn[nH]1]

Step A: 3-(6-(Hydroxymethyl)pyridin-3-yl)-2-(1-(4-methoxybenzyl)-1H-tetrazol-5-yl)benzenesulfonamide and 2-(1-(3-chloro-4-methoxybenzyl)-1H-tetrazol-5-yl)-3-(6-(hydroxymethyl)pyridin-3-yl)benzenesulfonamide A solution of mixture of 3-bromo-2-(1-(4-methoxybenzyl)-1H-tetrazol-5-yl)benzenesulfonamide (600 mg, 1.41 mmol) and 3-bromo-2-(1-(3-chloro-4-methoxybenzyl)-1H-tetrazol-5-yl)benzenesulfonamide, potassium phosphate tribasic (4.24 ml, 4.24 mmol), 1,1'-bis(di-tert-butylphosphino)ferrocene palladium dichloride (184 mg, 0.28 mmol) and 6-(hydroxymethyl)pyridine-3-boronic acid (281 mg, 1.84 mmol) in ethanol (3 mL) was purged with N$_2$. The mixture was heated at 95° C. for 16 hours. The mixture was filtered and concentrated under vacuum. The crude residue was adsorbed onto silica gel, and purified by column chromatograph on silica gel with hexane and ethyl acetate to give a mixture of 3-(6-(hydroxymethyl)pyridin-3-yl)-2-(1-(4-methoxybenzyl)-1H-tetrazol-5-yl)benzenesulfonamide and 2-(1-(3-chloro-4-methoxybenzyl)-1H-tetrazol-5-yl)-3-(6-(hydroxymethyl)pyridin-3-yl)benzenesulfonamide. LC/MS [M+H]$^+$:453.

Step B: 3-(6-(Hydroxymethyl)pyridin-3-yl)-2-(1H-tetrazol-5-yl)benzenesulfonamide A solution of a mixture 3-(6-(hydroxymethyl)pyridin-3-yl)-2-(1-(4-methoxybenzyl)-1H-tetrazol-5-yl)benzenesulfonamide (140 mg, 0.31 mmol) and 2-(1-(3-chloro-4-methoxybenzyl)-1H-tetrazol-5-yl)-3-(6-(hydroxymethyl) pyridin-3-yl)benzenesulfonamide, trifluoroacetic acid (3.9 mL, 51.1 mmol) and anisole (67.6 µL, 0.62 mmol) was heated at room temperature for 5 hours. The crude UPLC indicated only starting material remained. The temperature was increased to 40° C. and stirred for 16 hours. A small desired peak was observed on crude UPLC. The temperature was increased to 80° C. and stirred for another 6 hours. The crude UPLC indicated most of the starting material was consumed. The reaction mixture was filtered and removal of the solvent furnished a residue that was purified by Reverse HPLC with ACN and H$_2$O containing 0.16% formic acid to give 3-(6-(hydroxymethyl)pyridin-3-yl)-2-(1H-tetrazol-5-yl)benzenesulfonamide. LC/MS [M+H]$^+$:333.1.

EXAMPLE 259

4-Bromo-4'-(piperidin-4-yl)-2-(1H-tetrazol-5-yl)-[1,1'-biphenyl]-3-sulfonamide

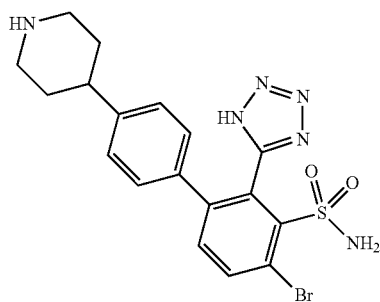 [SMILES: NS(=O)(=O)c1c(Br)ccc(-c2ccc(C3CCNCC3)cc2)c1-c1nnn[nH]1]

Step A: tert-Butyl 4-(4'-bromo-2'-cyano-3'-fluoro-[1,1'-biphenyl]-4-yl)piperidine-1-carboxylate 40 mL reaction vials were charged with 3-bromo-2-fluoro-6-iodobenzonitrile (4.2 g, 12.89 mmol), tert-butyl 4-(4-(4,4,5,5-tetramethyl-1,3,2-dioxaborolan-2-yl)phenyl)piperidine-1-carboxylate (4.99 g, 12.89 mmol), potassium carbonate (5.34 g, 38.7 mmol) and 1,1'-Bis(di-tert-butylphosphino)ferrocene palladium (2.105 g, 2.58 mmol). The vials were capped via a red sure seal pressure release cap, and the vials were degassed via vacuum/nitrogen flushes three times (via line with needle through manifold). Then, dioxane (8 mL) was added via syringe to each vial. Again, the vials were degassed via vacuum/nitrogen flushes three times (via line with needle through manifold). After stirring at room temp for 10 minutes, the vials were heated at 70° C. via an oil bath for 18 hr. Contents from the vials were then combined. After diluting with ethyl acetate, the organic solvent was filtered to remove excess catalyst, and the solvent was concentrated. The residue was purified by normal phase ISCO on a 120 g column eluted with 0% to 100% ethyl acetate in hexane. The pure fractions were concentrated to afford tert-butyl 4-(4'-bromo-2'-cyano-3'-fluoro-[1,1'-biphenyl]-4-yl)piperidine-1-carboxylate (1.44 g, 24.3%). LC-MS: calculated for $C_{23}H_{24}BrFN_2O_2$ 458.1; observed m/e (M+H)$^+$: 459.4.

Step B: tert-Butyl 4-(4'-bromo-2'-cyano-3'-((2-(trimethylsilyl)ethyl)thio)-[1,1'-biphenyl]-4-yl)piperidine-1-carboxylate To a round bottom containing tert-butyl 4-(4'-bromo-2'-cyano-3'-fluoro-[1,1'-biphenyl]-4-yl)piperidine-1-carboxylate (1.41 g, 3.07 mmol) was added potassium carbonate (0.636 g, 4.60 mmol), followed by a solution of 2-(trimethylsilyl)ethanethiol (0.309 g, 2.302 mmol) in DMF (15 ml). The reaction stirred at room temp for 7 hr. The reaction was diluted with ethyl acetate and washed with water and brine (3 times). The organic was extracted out and concentrated. The residue was purified by normal phase ISCO on a 40 g column eluted with 0% to 30% ethyl acetate in hexane. The pure fractions were concentrated to afford tert-butyl 4-(4'-bromo-2'-cyano-3'-((2-(trimethylsilyl)ethyl)thio)-[1,1'-biphenyl]-4-yl)piperidine-1-carboxylate (540 mg, 29.1%). LC-MS: calculated for $C_{28}H_{37}BrN_2O_2SSi$ 572.2 observed m/e (M+H)$^+$: 573.5.

Step C: tert-Butyl 4-(4'-bromo-2'-cyano-3'-((2-(trimethylsilyl)ethyl)sulfonyl)-[1,1'-biphenyl]-4-yl)piperidine-1-carboxylate To a round bottom flask containing tert-butyl 4-(4'-bromo-2'-cyano-3'-((2-(trimethylsilyl)ethyl)thio)-[1,1'-biphenyl]-4-yl)piperidine-1-carboxylate (540 mg, 0.941 mmol) was added DCM (20 mL), followed by mCPBA (487 mg, 2.82 mmol). The reaction needed 7 hours to complete. The reaction was quenched with $Na_2S_2O_3$ (saturated aqueous solution) and diluted with ethyl acetate. The organic layer was extracted out and concentrated. The residue was purified by normal phase ISCO on a 40 g column eluted with 0% to 100% ethyl acetate in hexane. The pure fractions were concentrated to afford tert-butyl 4-(4'-bromo-2'-cyano-3'-((2-(trimethylsilyl)ethyl)sulfonyl)-[1,1'-biphenyl]-4-yl)piperidine-1-carboxylate (418 mg, 73.3%). LC-MS: calculated for $C_{28}H_{37}BrN_2O_4SSi$ 606.1; observed m/e (M+H)$^+$: 607.4.

Step D: tert-Butyl 4-(4'-bromo-2'-(1H-tetrazol-5-yl)-3'-((2-(trimethylsilyl)ethyl)sulfonyl)-[1,1'-biphenyl]-4-yl)piperidine-1-carboxylate A 40 mL reaction vial was charged with tert-butyl 4-(4'-bromo-2'-cyano-3'-((2-(trimethylsilyl)ethyl)sulfonyl)-[1,1'-biphenyl]-4-yl)piperidine-1-carboxylate (15 mg, 0.025 mmol), azidotrimethyltin (25.5 mg, 0.124 mmol) and toluene (2 mL). The vial was capped via a red sure seal cap, and the vial was heated at 100° C. via an oil bath for 10 hr. The crude was dissolved in acetonitrile (1.5 mL) and washed with hexane to remove the tin impurity. Purification by reverse phase HPLC column (acetonitrile/water/0.05% TFA system) eluted with 10% to 100% MeCN in water. The solution was concentrated to afford tert-butyl 4-(4'-bromo-2'-(1H-tetrazol-5-yl)-3'-((2-(trimethylsilyl)ethyl)sulfonyl)-[1,1'-biphenyl]-4-yl)piperidine-1-carboxylate (7 mg, 43.6%). LC-MS: calculated for $C_{28}H_{38}BrN_5O_4SSi$ 647.2; observed m/e (M+H)$^+$: 648.4.

Step E: 4-Bromo-4'-(piperidin-4-yl)-2-(1H-tetrazol-5-yl)-[1,1'-biphenyl]-3-sulfonamide To a 40 mL reaction vial containing tert-butyl 4-(4'-bromo-2'-(1H-tetrazol-5-yl)-3'-((2-(trimethylsilyl)ethyl)sulfonyl)-[1,1'-biphenyl]-4-yl)piperidine-1-carboxylate (10 mg, 0.015 mmol) was added THF (500 µL) and TBAF (0.077 mL, 0.077 mmol). The vial was capped, and the reaction was heated at 40° C. via an oil bath for 6 hr. LCMS showed a good profile. Then, a solution of sodium acetate (25.3 mg, 0.308 mmol) in water (500 µL) was added to the reaction, which was then followed by addition of hydroxylamine-o-sulfonic acid (34.9 mg, 0.308 mmol). The vial was capped, and the reaction stirred at room temp for 3 hr. The reaction was concentrated. To the vial was added DCM (1000 µL), followed by a mixture of TFA (1 mL, 12.98 mmol) and anisole (0.034 mL, 0.308 mmol). The reaction was allowed to stir at room temp for 1 hr and then concentrated. The crude was dissolved in a 1 mL:1 mL acetonitrile:water mix, and the solution was acidified with 0.5 mL TFA. Purification by reverse phase HPLC column (acetonitrile/water/0.05% TFA system) eluted with 0% to 20% MeCN in water. The solution was concentrated to afford 4-bromo-4'-(piperidin-4-yl)-2-(1H-tetrazol-5-yl)-[1,1'-biphenyl]-3-sulfonamide as the TFA salt (5 mg, 56.3%). LC-MS: calculated for $C_{18}H_{19}BrN_6O_2S$ 464.1 observed m/e (M+H)$^+$: 465.3. $^1$H NMR δ (ppm) (MeOH): 8.13 (d, 1H), 7.49 (d, 1H), 7.145 (d, 2H), 7.01 (d, 2H), 3.42-3.49 (m, 2H), 3.04-3.15 (m, 2H), 2.81-2.90 (m, 1H), 1.96-2.04 (m, 2H), 1.76-1.83 (m, 2H).

EXAMPLE 260

4'-(Piperidin-4-yl)-4-propyl-2-(1H-tetrazol-5-yl)-[1,1'-biphenyl]-3-sulfonamide

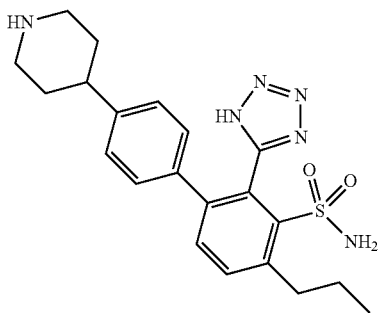 [SMILES: CCCc1ccc(-c2ccc(C3CCNCC3)cc2)c(-c2nnn[nH]2)c1S(N)(=O)=O]

Step A: tert-Butyl 4-(2'-cyano-4'-propyl-3'-((2-(trimethylsilyl)ethyl)sulfonyl)-[1,1'-biphenyl]-4-yl)piperidine-1-carboxylate A 40 mL reaction vial was charged with 4-bromo-4'-(piperidin-4-yl)-2-(1H-tetrazol-5-yl)-[1,1'-biphenyl]-3-sulfonamide (100 mg, 0.165 mmol), and Chloro(2-dicyclohexylphosphino-2',6'-diisopropoxy-1,1'-biphenyl)[2-(2'-amino-1,1'-biphenyl)]palladium(II) [Aldrich] (51.3 mg, 0.066 mmol). The vial was capped via a red sure seal and degassed three times with vacuum/nitrogen (line with needle connected to manifold). Then, DMA (2 mL), THF (1 mL) and propylzinc(II) bromide (0.991 ml, 0.495 mmol) were added via syringe. Again, the vial was degassed three times with vacuum/nitrogen (line with needle connected to manifold). After stirring at room temp for 10 minutes, the reaction was allowed to stir at 80° C. via an oil bath for 5 hr. The reaction was diluted with ethyl acetate and quenched with NH$_4$Cl (sat. aq.). The organic layer was extracted out and concentrated. The residue was purified by normal phase ISCO on a 24 g column eluted with 0% to 100% ethyl acetate in hexane. The pure fractions were concentrated to afford product (24 mg, 25.6%). LC-MS: calculated for $C_{31}H_{44}N_2O_4SSi$ 568.8; observed m/e (M+H)$^+$: 569.6.

Step B: tert-Butyl 4-(4'-propyl-2'-(1H-tetrazol-5-yl)-3'-((2-(trimethylsilyl)ethyl)sulfonyl)-[1,1'-biphenyl]-4-yl)piperidine-1-carboxylate To a 40 mL reaction vial containing tert-butyl 4-(2'-cyano-4'-propyl-3'-((2-(trimethylsilyl)ethyl)sulfonyl)-[1,1'-biphenyl]-4-yl)piperidine-1-carboxylate (24 mg, 0.042 mmol) was added azidotrimethyltin (43.4 mg, 0.211 mmol) and toluene (1.5 mL). The vial was capped via a red sure seal cap, and the vial was heated at 100° C. via an oil bath for 10 hr to completion of the reaction. The crude was dissolved in acetonitrile (1.5 mL), washed with hexane to remove the tin. The acetonitrile layer was extracted and diluted with water (1.5 mL). The reaction was purified by reverse phase HPLC column (acetonitrile/water/0.05% TFA system) and eluted with 0% to 100% MeCN in water. The solution was concentrated to afford tert-butyl 4-(4'-propyl-2'-(1H-tetrazol-5-yl)-3'-((2-(trimethylsilyl)ethyl)sulfonyl)-[1,1'-biphenyl]-4-yl)piperidine-1-carboxylate (15 mg, 58.1%). LC-MS: calculated for $C_{31}H_{45}N_5O_4SSi$ 611.871 observed m/e: 612.65 (M+H)$^+$.

Step C: 4'-(Piperidin-4-yl)-4-propyl-2-(1H-tetrazol-5-yl)-[1,1'-biphenyl]-3-sulfonamide To a vial containing tert-butyl 4-(4'-propyl-2'-(1H-tetrazol-5-yl)-3'-((2-(trimethylsilyl)ethyl)sulfonyl)-[1,1'-biphenyl]-4-yl)piperidine-1-carboxylate (15 mg, 0.025 mmol) was added THF (2 mL) and TBAF (0.074 mL, 0.074 mmol). The vial was capped, and the reaction was heated at 40° C. via an oil bath for 2 hr. Then, a solution of sodium acetate (40.2 mg, 0.490 mmol) in water (2 mL) was added, followed by addition of hydroxylamine-o-sulfonic acid (55.4 mg, 0.490 mmol). The reaction was stirred at room temp overnight, and was then concentrated. Purification by reverse phase HPLC column (acetonitrile/water/0.05% TFA system) eluted with 0% to 100% MeCN in water. The major fraction was concentrated to afford tert-butyl 4-(4'-propyl-3'-sulfamoyl-2'-(1H-tetrazol-5-yl)-[1,1'-biphenyl]-4-yl)piperidine-1-carboxylate (3.5 mg, 27.1%). LC-MS: calculated for $C_{21}H_{26}N_6O_2S$ 526.535 observed m/e (M+H)$^+$: 527.5 (Rt 1.34/2 min)

Step D: 4'-(piperidin-4-yl)-4-propyl-2-(1H-tetrazol-5-yl)-[1,1'-biphenyl]-3-sulfonamide To a vial containing tert-butyl 4-(4'-propyl-3'-sulfamoyl-2'-(1H-tetrazol-5-yl)-[1,1'-biphenyl]-4-yl)piperidine-1-carboxylate (3.5 mg, 6.65 μmol) was added DCM (1000 μL), followed by a mixture of TFA (1 mL, 12.98 mmol) and anisole (0.015 mL, 0.133 mmol). The reaction was allowed to stir at room temp for 2 hr and then concentrated. The reaction was purified by reverse phase HPLC column (acetonitrile/water/0.05% TFA system) and eluted with 0% to 20% MeCN in water. The solution was concentrated to afford 4'-(piperidin-4-yl)-4-propyl-2-(1H-tetrazol-5-yl)-[1,1'-biphenyl]-3-sulfonamide as the TFA salt (2.7 mg, 75%). LC-MS: calculated for $C_{21}H_{26}N_6O_2S$: 426; observed m/e (M+H)$^+$: 427.4; $^1$H NMR δ (ppm) (MeOH): 7.74 (d, 1H), 7.60 (d, 1H), 7.175 (d, 2H), 7.03 (d, 2H), 3.46-3.52 (m, 2H), 3.17-3.28 (m, 2H), 3.10-3.14 (m, 2H), 2.84-2.92 (m, 1H), 2.02-2.08 (m, 2H), 1.77-1.90 (m, 4H), 1.10 (t, 3H).

EXAMPLES 261-262

The following Examples 261-262 were prepared according to the general procedure described in Example 260 above:

| Ex. No. | Structure | Name | Calc'd. Mass (M + H)$^+$ | LC/MS m/e (M + H)$^+$ |
|---|---|---|---|---|
| 261 | 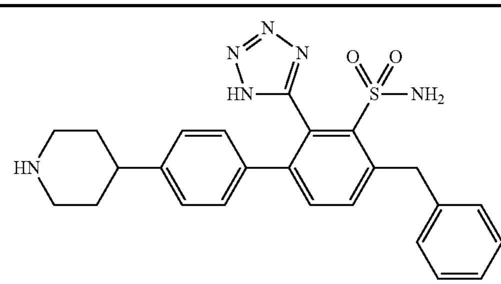 | 4-benzyl-4'-(piperidin-4-yl)-2-(1H-tetrazol-5-yl)-[1,1'-biphenyl]-3-sulfonamide, 2,2,2-trifluoroacetate salt | 475.2 | 475.4 |

| Ex. No. | Structure | Name | Calc'd. Mass (M + H)+ | LC/MS m/e (M + H)+: |
|---|---|---|---|---|
| 262 | 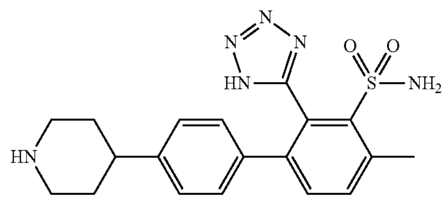 [SMILES: Cc1ccc(-c2ccc(C3CCNCC3)cc2)c(-c2nnn[nH]2)c1S(N)(=O)=O] | 4-methyl-4'-(piperidin-4-yl)-2-(1H-tetrazol-5-yl)-[1,1'-biphenyl]-3-sulfonamide, 2,2,2-trifluoroacetate salt | 399.2 | 399.4 |

EXAMPLE 263

4-chloro-4'-methyl-2-(2H-tetrazol-5-yl)-[1,1'-biphenyl]-3-sulfonamide

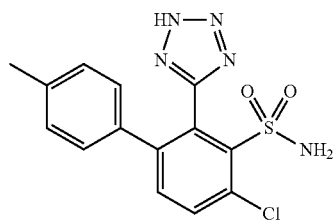 [SMILES: Cc1ccc(-c2ccc(Cl)c(S(N)(=O)=O)c2-c2nn[nH]n2)cc1]

Step A: 3-chloro-6-iodo-2-((2-(trimethylsilyl)ethyl)thio)benzonitrile

To a solution of 3-chloro-2-fluoro-6-iodobenzonitrile (0.500 g, 1.78 mmol) and $K_2CO_3$ (0.491 g, 3.55 mmol) in DMF (3 mL) was added 2-(trimethylsilyl)ethanethiol (0.341 mL, 2.13 mmol), and the resulting mixture was stirred at room temperature overnight. The reaction mixture was filtered, the filtrate was diluted with EtOAc and washed with water (twice) and then with brine. The organic layer was dried over anhydrous $MgSO_4$, filtered, concentrated and purified by silica gel column chromatography using (0-15)% EtOAc/Hexanes as mobile phase to afford the title compound.

Step B: 3-chloro-6-iodo-2-((2-(trimethylsilyl)ethyl)sulfonyl)benzonitrile

To a solution of 3-chloro-6-iodo-2-((2-(trimethylsilyl)ethyl)thio)benzonitrile (0.43 g, 1.1 mmol) in DCM (7.24 mL) at 0° C. was added 3-chloroperoxybenzoic acid (0.656 g, 3.80 mmol) and the mixture was stirred at room temperature overnight. Saturated $Na_2S_2O_3$ was added to the mixture and it was stirred for 10 min. Then saturated $NaHCO_3$ was added. After separation of layers, the aqueous layer was extracted with DCM (3×), the combined organic layers were dried over anhydrous $Na_2SO_4$, filtered, and concentrated to get the title compound.

Step C: 4-chloro-4'-methyl-3-((2-(trimethylsilyl)ethyl)sulfonyl)-[1,1'-biphenyl]-2-carbonitrile 3-Chloro-6-iodo-2-((2-(trimethylsilyl)ethyl)sulfonyl)benzonitrile (300 mg, 0.701 mmol), p-tolylboronic acid (95 mg, 0.70 mmol), $Na_2CO_3$ (149 mg, 1.40 mmol) and $PdCl_2(dppf)$-$CH_2Cl_2$ adduct (57.3 mg, 0.070 mmol) were combined in dioxane (4.5 mL) and water (1.5 mL) in a microwave vial. The mixture was degassed with nitrogen and the resulting mixture was heated overnight at 90° C. The reaction mixture was filtered over celite to removed palladium. The filtrate was diluted with EtOAc and washed with water. The organic layer was dried over anhydrous $MgSO_4$, filtered, concentrated and purified by silica gel column chromatography (RediSep gold column, 40 g) using (0-25)% EtOAc/Hexanes gradient as the mobile phase to afford the title compound.

Step D: 5-(4-chloro-4'-methyl-3-((2-(trimethylsilyl)ethyl)sulfonyl)-[1,1'-biphenyl]-2-yl)-2H-tetrazole To a solution of 4-chloro-4'-methyl-3-((2-(trimethylsilyl)ethyl)sulfonyl)-[1,1'-biphenyl]-2-carbonitrile (157 mg, 0.401 mmol) in toluene (3 mL) in a microwave vial was added azidotrimethyltin (412 mg, 2.00 mmol) and the resulting mixture was heated overnight at 100° C. The precipitated solid was filtered and washed with hexanes. Purification of the solid was by silica gel column chromatography (24 g RediSep gold column) using (40-100)% EtOAc/Hexanes gradient (containing 1 ml AcOH per 500 mL of solvent) to afford the title compound. LC/MS [M+H]+ 435, 437.

Step E: 4-chloro-4'-methyl-2-(2H-tetrazol-5-yl)-[1,1'-biphenyl]-3-sulfonamide

To a solution of 5-(4-chloro-4'-methyl-3-((2-(trimethylsilyl)ethyl)sulfonyl)-[1,1'-biphenyl]-2-yl)-2H-tetrazole (115 mg, 0.264 mmol) in THF (4.5 mL) was added TBAF in THF (1.322 mL, 1.322 mmol) and the resulting solution was stirred at 40° C. for 2 hr. Sodium acetate (217 mg, 2.64 mmol) in 2 mL of water was added followed by addition of hydroxylamine-O-sulfonic acid (299 mg, 2.64 mmol) and the resulting solution was stirred at rt overnight. The mixture was partitioned between EtOAc (50 mL) and saturated $NaHCO_3$, the organic phase was washed with $NaHCO_3$ twice, dried over anhydrous $Na_2SO_4$, concentrated, and the residue was purified by silica gel column chromatography (RediSep gold, 24 g column), eluting with 2.5% MeOH/DCM (containing 0.2 mL of acetic acid per 100 mL of solvent) to give the title compound. LC/MS [M+H]+ 350.

EXAMPLE 264

3-(6-aminopyridin-3-yl)-6-bromo-2-(2H-tetrazol-5-yl)benzenesulfonamide

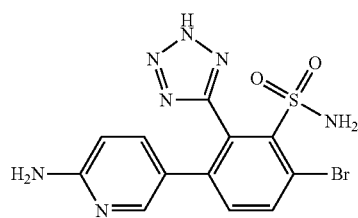 [SMILES: Nc1ccc(-c2ccc(Br)c(S(N)(=O)=O)c2-c2nn[nH]n2)cn1]

Step A: 3-(6-aminopyridin-3-yl)-6-bromo-2-(2-(4-methoxybenzyl)-2H-tetrazol-5-yl)benzenesulfonamide A microwave vial was charged with 6-bromo-3-iodo-2-(2-(4-methoxybenzyl)-2H-tetrazol-5-yl)benzenesulfonamide (1.0 g, 1.8 mmol), (6-aminopyridin-3-yl)boronic acid hydrochloride (0.697 g, 4.00 mmol), Na$_2$CO$_3$ (0.578 g, 5.45 mmol) and PdCl$_2$(dppf)-CH$_2$Cl$_2$ adduct (0.223 g, 0.273 mmol). The vial was sealed, degassed, and filled with dioxane (9.09 mL) and water (3.03 mL). The resulting mixture was heated overnight at 90° C. The reaction mixture was filtered over celite to remove palladium. The filtrate was diluted with EtOAc and washed with water. The organic layer was dried over anhydrous MgSO$_4$, filtered, and concentrated. The crude mixture was purified by silica gel column chromatography using 0-10% MeOH/DCM as mobile phase to afford the title compound. LC-MS (IE, m/z): 518.3 [M+2]$^+$.

Step B: 3-(6-aminopyridin-3-yl)-6-bromo-2-(2H-tetrazol-5-yl)benzenesulfonamide

To a solution of 3-(6-aminopyridin-3-yl)-6-bromo-2-(2-(4-methoxybenzyl)-2H-tetrazol-5-yl)benzenesulfonamide (430 mg, 0.833 mmol) in DCM (4.2 mL) was added anisole (0.9 mL, 8.33 mmol) and TFA (6.4 mL, 83 mmol) at rt. The resulting mixture was heated at 80° C. for 1 hr. After removing the volatile the residue was purified by reverse phase HPLC using DMSO to load sample and 5-45% acetonitrile/water (0.1% formic acid as additive) as mobile phase to afford the title compound. LC-MS (IE, m/z): 397.99 [M+2]$^+$.

EXAMPLE 265

3-(6-aminopyridin-3-yl)-2-(2H-tetrazol-5-yl)-6-(trifluoromethyl)benzenesulfonamide

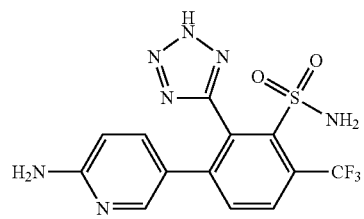 [SMILES: Nc1ccc(-c2ccc(C(F)(F)F)c(S(N)(=O)=O)c2-c2nn[nH]n2)cn1]

Step A: 3-(6-aminopyridin-3-yl)-2-(2-(4-methoxybenzyl)-2H-tetrazol-5-yl)-6-(trifluoromethyl)benzenesulfonamide To a microwave vial was added (1,10-phenanthroline)(trifluoromethyl)copper(I) (242 mg, 0.775 mmol), 3-(6-aminopyridin-3-yl)-6-bromo-2-(2-(4-methoxybenzyl)-2H-tetrazol-5-yl)benzenesulfonamide (Step A, 200 mg, 0.387 mmol) and copper(I) iodide (148 mg, 0.775 mmol). The vial was sealed, flushed with N$_2$, and DMF (2.6 mL) was added. This resulting mixture was then heated at 80° C. overnight. The reaction mixture was cooled, filtered through celite, and rinsed with EtOAc. The filtrate was evaporated and the residue was purified by silica gel chromatograph, eluting with 0-10% MeOH/DCM to give the title compound. LC-MS (IE, m/z): 506.4 [M+1]$^+$.

Step B: 3-(6-aminopyridin-3-yl)-2-(2H-tetrazol-5-yl)-6-(trifluoromethyl)benzenesulfonamide To a solution of 3-(6-aminopyridin-3-yl)-2-(2-(4-methoxybenzyl)-2H-tetrazol-5-yl)-6-(trifluoromethyl)benzenesulfonamide (200 mg, 0.396 mmol) in DCM (2.0 mL) was added TFA (3.0 mL, 39.6 mmol) and anisole (0.43 mL, 3.96 mmol). The resulting mixture was heated at 80° C. for 1 hr. After removing the volatile the residue was purified by reverse phase HPLC using DMSO to load sample and 5-60% acetonitrile/water (0.1% formic acid as additive) as mobile phase to afford the title compound. LC-MS (IE, m/z): 386.23 [M+1]$^+$.

EXAMPLES 266-274

The following compounds were prepared in an analogous fashion to Examples 264 (3-(6-aminopyridin-3-yl)-6-bromo-2-(2H-tetrazol-5-yl)benzenesulfonamide) and 265 (3-(6-aminopyridin-3-yl)-2-(2H-tetrazol-5-yl)-6-(trifluoromethyl)benzenesulfonamide) starting from 6-bromo-3-iodo-2-(2-(4-methoxybenzyl)-2H-tetrazol-5-yl)benzenesulfonamide (Reference Example 13) and the corresponding boronic acids or esters (commercially available, known, or prepared as described herein) listed below.

| Ex. No. | Intermediates | Structure/Name | Characterization LC/MS |
|---|---|---|---|
| 266 | quinolin-4-yl boronic acid | 6-bromo-3-(quinolin-4-yl)-2-(2H-tetrazol-5-yl)benzenesulfonamide | [M + 2]$^+$: 433.02 |

-continued

| Ex. No. | Intermediates | Structure/Name | Characterization LC/MS |
|---|---|---|---|
| 267 | p-tolylboronic acid | 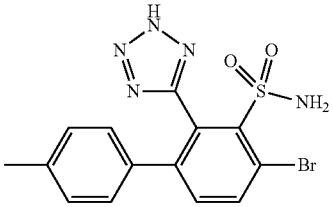 [SMILES: Cc1ccc(-c2ccc(Br)c(S(N)(=O)=O)c2-c2nn[nH]n2)cc1]<br>4-bromo-4'-methyl-2-(2H-tetrazol-5-yl)-[1,1'-biphenyl]-3-sulfonamide | [M + 2]$^+$: 396.12 |
| 268 | p-tolylboronic acid | 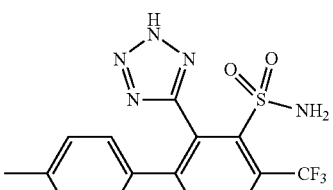<br>4'-methyl-2-(2H-tetrazol-5-yl)-4-(trifluoromethyl)-[1,1'-biphenyl]-3-sulfonamide | [M + 1]$^+$: 384.10 |
| 269 | (4-(1-(tert-butoxycarbonyl)piperidin-4-yl)phenyl)boronic acid | 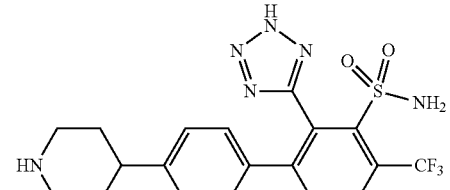<br>4'-(piperidin-4-yl)-2-(2H-tetrazol-5-yl)-4-(trifluoromethyl)-[1,1'-biphenyl]-3-sulfonamide | [M + 1]+: 453.38 |
| 270 | (4-(methylsulfonamido)phenyl)boronic acid | 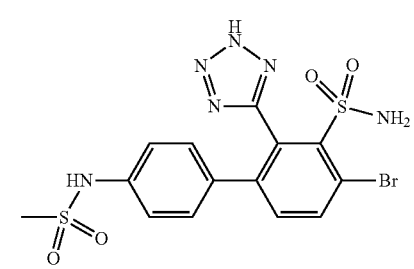 [SMILES: CS(=O)(=O)Nc1ccc(-c2ccc(Br)c(S(N)(=O)=O)c2-c2nn[nH]n2)cc1]<br>4-bromo-4'-(methylsulfonamido)-2-(2H-tetrazol-5-yl)-[1,1'-biphenyl]-3-sulfonamide | [M + 2]$^+$: 475.25 |
| 271 | (4-(((tert-butoxycarbonyl)amino)methyl)phenyl)boronic acid | 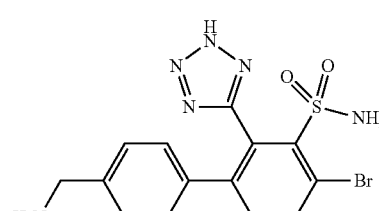<br>4'-(aminomethyl)-4-bromo-2-(2H-tetrazol-5-yl)-[1,1'-biphenyl]-3-sulfonamide | [M + 2]$^+$: 411.58 |

| Ex. No. | Intermediates | Structure/Name | Characterization LC/MS |
|---|---|---|---|
| 272 | tert-butyl 5-(4,4,5,5-tetramethyl-1,3,2-dioxaborolan-2-yl)isoindoline-2-carboxylate | 6-bromo-3-(isoindolin-5-yl)-2-(2H-tetrazol-5-yl)benzenesulfonamide | [M + 2]⁺: 423.03 |
| 273 | quinolin-4-yl boronic acid | 3-(quinolin-4-yl)-2-(2H-tetrazol-5-yl)-6-(trifluoromethyl)benzenesulfonamide | [M + 1]⁺: 421.06 |
| 274 | (4-(methylsulfonamido)phenyl)boronic acid | 4'-(methylsulfonamido)-2-(2H-tetrazol-5-yl)-4-(trifluoromethyl)-[1,1'-biphenyl]-3-sulfonamide | [M + 1]⁺: 463.07 |

EXAMPLE 275

6-cyclopropyl-3-(quinolin-4-yl)-2-(2H-tetrazol-5-yl)benzenesulfonamide

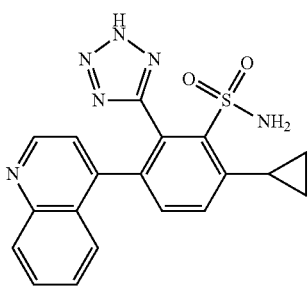 [SMILES: NS(=O)(=O)c1c(C2CC2)ccc(-c2ccnc3ccccc23)c1-c1nn[nH]n1]

Step A: 6-bromo-3-iodo-N,N-bis(4-methoxybenzyl)-2-(2-(4-methoxybenzyl)-2H-tetrazol-5-yl)benzenesulfonamide To a mixture of 6-bromo-3-iodo-2-(1-(4-methoxybenzyl)-1H-tetrazol-5-yl)benzenesulfonamide (Reference Example 13) 3200 mg, 5.82 mmol), 1-(chloromethyl)-4-methoxybenzene (2004 mg, 12.80 mmol) in 2-butanone (29 mL) at rt, 1-(chloromethyl)-4-methoxybenzene (2004 mg, 12.80 mmol) was added, followed by potassium carbonate (3215 mg, 23.27 mmol) and sodium iodide (1918 mg, 12.80 mmol). The reaction was stirred under nitrogen overnight at 80° C. and monitored by LCMS. The reaction mixture was then filtered, and rinsed by EtOAc. The combined organic layer was evaporated, and the crude product was purified by silica gel column chromatography with EtOAc/Hex (0-100%) as eluent to give the title compound. LC-MS (IE, m/z): 792.6 [M+2]⁺.

Step B: 6-bromo-N,N-bis(4-methoxybenzyl)-2-(2-(4-methoxybenzyl)-2H-tetrazol-5-yl)-3-(quinolin-4-yl)benzenesulfonamide A microwave vial was charged with 6-bromo-3-iodo-N,N-bis(4-methoxybenzyl)-2-(2-(4-methoxybenzyl)-2H-tetrazol-5-yl)benzenesulfonamide (1.00 g, 1.27 mmol), quinolin-4-ylboronic acid (0.481 g, 2.78 mmol), PdCl₂(dppf)-CH₂Cl₂ adduct (0.103 g, 0.127 mmol) and sodium carbonate (0.402 g, 3.80 mmol). The vial was sealed, degassed, and filled with dioxane (6.33 mL) and water (2.11 mL). The resulting mixture was heated overnight at 90° C. The reaction mixture was filtered over celite to removed palladium. The filtrate was diluted with EtOAc and washed with water. The organic layer was dried over anhydrous MgSO₄, filtered, concentrated and purified by silica gel column chromatography using 15-60% EtOAc/Hexanes as mobile phase to afford the title compound. LC-MS (IE, m/z): 793.60[M+2]⁺.

Step C: 6-cyclopropyl-N,N-bis(4-methoxybenzyl)-2-(2-(4-methoxybenzyl)-2H-tetrazol-5-yl)-3-(quinolin-4-yl)benzenesulfonamide A microwave vial was charged with 6-bromo-N,N-bis(4-methoxybenzyl)-2-(2-(4-methoxybenzyl)-2H-tetrazol-5-yl)-3-(quinolin-4-yl)benzenesulfonamide (0.228 g, 0.288 mmol), and chloro(2-dicyclohexylphosphino-2',6'-dimethoxy-1,1'-biphenyl)[2-(2-aminoethylphenyl)]palladium(II)-methyl-t-butyl ether adduct (0.022 g, 0.029 mmol). The vial was sealed, degassed, and filled with THF (2.88 mL) and cyclopropylzinc(II) bromide (1.728 mL, 0.5 M in THF, 0.864 mmol). The resulting mixture was heated overnight at 60° C. The reaction mixture was filtered over celite to removed palladium. The filtrate was concentrated and purified by silica gel column chromatography using 0-100% EtOAc/Hexanes as mobile phase to afford the title compound. LC-MS (IE, m/z): 753.2 [M+1]⁺.

Step D: 6-cyclopropyl-3-(quinolin-4-yl)-2-(2H-tetrazol-5-yl)benzenesulfonamide

To a solution of 6-cyclopropyl-N,N-bis(4-methoxybenzyl)-2-(2-(4-methoxybenzyl)-2H-tetrazol-5-yl)-3-(quinolin-4-yl)benzenesulfonamide (100 mg, 0.133 mmol) in DCM (2.6 mL) was added TFA (1.0 mL, 13.28 mmol) and anisole (0.29 μL, 2.66 mmol). The resulting mixture was heated at 80° C. for 1 hr. After removing the volatile the residue was purified by reverse phase HPLC using DMSO to load sample and 5-70% acetonitrile/water (0.1% formic acid as additive) as mobile phase to afford the title compound. LC-MS (IE, m/z): 393.18 [M+1]⁺.

EXAMPLE 276

4-chloro-4'-(piperidin-4-yl)-2-(2H-tetrazol-5-yl)-[1,1'-biphenyl]-3-sulfonamide

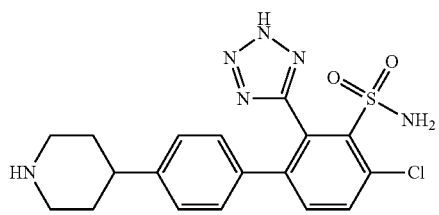 [SMILES: NS(=O)(=O)c1c(Cl)ccc(-c2ccc(C3CCNCC3)cc2)c1-c1nn[nH]n1]

Step A: 3-chloro-6-iodo-2-((2-(trimethylsilyl)ethyl)thio)benzonitrile

To a solution of 3-chloro-2-fluoro-6-iodobenzonitrile (2.00 g, 7.11 mmol) and potassium carbonate (1.964 g, 14.21 mmol) in DMF (12 mL) was added 2-(trimethylsilyl) ethanethiol (1.25 mL, 7.82 mmol), and the resulting mixture was stirred at room temperature overnight. The reaction mixture was filtered. The filtrate was diluted with EtOAc, washed with water and brine. The organic layer was dried over MgSO₄, filtered, and concentrated. The residue was purified by silica gel column chromatography using 0-15% EtOAc/Hexanes as mobile phase to afford the title compound. ¹H NMR (500 MHz, CDCl₃), δ 7.76 (d, J=8.5 Hz, 1H), 7.31 (d, J=8.5 Hz, 1H), 3.08-3.04 (m, 2H), 0.88-0.84 (m, 2H), 0.00 (s, 9H).

Step B: 3-chloro-6-iodo-2-((2-(trimethylsilyl)ethyl)sulfonyl)benzonitrile

To a solution of 3-chloro-6-iodo-2-((2-(trimethylsilyl)ethyl)thio)benzonitrile (0.88 g, 2.2 mmol) in DCM (14.82 mL) at 0° C., was added mCPBA (1.34 g, 7.78 mmol), and the mixture was stirred at room temperature overnight. Saturated Na₂S₂O₃ solution was added to the mixture to quench the reaction, and saturated NaHCO₃ was then added. After separation of layers, the aqueous layer was extracted with DCM. The combined organic layer was dried over anhydrous Na₂SO₄, filtered and concentrated to get the title compound. ¹H NMR (500 MHz, CDCl₃), δ 8.10 (d, J=8.6 Hz, 1H), 7.40 (d, J=8.6 Hz, 1H), 3.36-3.32 (m, 2H), 0.96-0.92 (m, 2H), 0.00 (s, 9H).

Step C: tert-butyl 4-(4'-chloro-2'-cyano-3'-((2-(trimethylsilyl)ethyl)sulfonyl)-[1,1'-biphenyl]-4-yl)piperidine-1-carboxylate 3-Chloro-6-iodo-2-((2-(trimethylsilyl)ethyl)sulfonyl)benzonitrile (160 mg, 0.374 mmol), (4-(1-(tert-butoxycarbonyl)piperidin-4-yl)phenyl)boronic acid (114 mg, 0.374 mmol), sodium carbonate (79 mg, 0.748 mmol) and PdCl₂(dppf)·CH₂Cl₂ adduct (30.5 mg, 0.037 mmol) were combined in dioxane (4.5 mL) and water (1.5 mL) in a microwave vial. The vial was sealed, degassed, and the resulting mixture was heated overnight at 90° C. The reaction mixture was filtered over celite to removed palladium. The filtrate was diluted with EtOAc and washed with water. The organic layer was dried over anhydrous MgSO₄, filtered, and concentrated. The residue was purified by silica gel column chromatography using 0-25% EtOAc/Hexanes as mobile phase to afford the title compound. LC-MS (IE, m/z): 561.35 [M]⁺.

Step D: tert-butyl 4-(4'-chloro-2'-(2H-tetrazol-5-yl)-3'-((2-(trimethylsilyl)ethyl)sulfonyl)-[1,1'-biphenyl]-4-yl)piperidine-1-carboxylate To a solution of tert-butyl 4-(4'-chloro-2'-cyano-3'-((2-(trimethylsilyl)ethyl)sulfonyl)-[1,1'-biphenyl]-4-yl)piperidine-1-carboxylate (290 mg, 0.517 mmol) in toluene (4.3 mL) in a microwave vial was added azidotrimethyltin (532 mg, 2.58 mmol) and the resulting mixture was heated overnight at 100° C. Solid precipitate was filtered, and washed with hexanes. The filtrate was concentrated, and purified by silica gel column chromatography using 40-100% EtOAc/Hexanes (containing 0.2% AcOH as additive) as solvent system to afford the title compound. LC-MS (IE, m/z): 604.37 [M]⁺.

Step E: tert-butyl 4-(4'-chloro-3'-sulfamoyl-2'-(2H-tetrazol-5-yl)-[1,1'-biphenyl]-4-yl)piperidine-1-carboxylate To a solution of tert-butyl 4-(4'-chloro-2'-(1H-tetrazol-5-yl)-3'-((2-(trimethylsilyl)ethyl)sulfonyl)-[1,1'-biphenyl]-4-yl)piperidine-1-carboxylate (200 mg, 0.331 mmol) in THF (6.6 mL) was added TBAF in THF (1.66 mL, 1M in THF, 1.66 mmol). The resulting solution was bubbled with N₂, stirred at 40° C. for 2 hr, and checked by LCMS for completion of the first step conversion. Then sodium acetate (272 mg, 3.31 mmol) in 2.5 mL water was added, followed by addition of hydroxylamine-O-sulfonic acid (374 mg, 3.31 mmol). The resulting solution was stirred at rt overnight. The mixture was partitioned between EtOAc (50 mL) and sat. NaHCO₃. The organic phase was washed with NaHCO₃, dried over Na₂SO₄, and concentrated. The residue was purified by silica gel column chromatography using 0-15% MeOH/DCM (containing 0.2% AcOH as additive) as mobile phase to give the title compound. LC-MS (IE, m/z): 519.46 [M]⁺.

Step F: 4-chloro-4'-(piperidin-4-yl)-2-(2H-tetrazol-5-yl)-[1,1'-biphenyl]-3-sulfonamide To a solution of tert-butyl 4-(4'-chloro-3'-sulfamoyl-2'-(2H-tetrazol-5-yl)-[1,1'-biphenyl]-4-yl)piperidine-1-carboxylate (70 mg, 0.135 mmol) in DCM (2.7 mL) was added anisole (0.6 mL, 5.39 mmol) and TFA (1.0 mL, 13.49 mmol) at rt. The resulting mixture was stirred at rt for 1 hr. After removing the volatile the residue was purified by reverse phase HPLC using DMSO to load sample and 5-40% acetonitrile/water (0.1% formic acid as additive) as mobile phase to afford the title compound. LC-MS (IE, m/z): 419.14 [M]+.

EXAMPLE 277

5-(4-Bromophenyl)-4-(2H-tetrazol-5-yl)pyridazine-3-sulfonamide

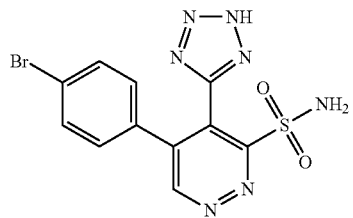 [SMILES: NS(=O)(=O)c1nncc(-c2ccc(Br)cc2)c1-c1nn[nH]n1]

Step A: 5-(4-Bromophenyl)-3-hydroxypyridazine-4-carbonitrile 2-(4-Bromophenyl)-2-oxoacetaldehyde (10.7 g, 50.2 mmol) and cyanoacetohydrazide (4.98 g, 50.2 mmol) were dissolved in EtOH (67.0 mL) and stirred overnight at rt. The reaction was filtered and concentrated to afford 5-(4-bromophenyl)-3-hydroxypyridazine-4-carbonitrile. LC-MS: calculated for $C_{11}H_6BrN_3O$ 275.0; observed m/e (M+H)+: 275.9.

Step B: 5-(4-Bromophenyl)-3-chloropyridazine-4-carbonitrile 5-(4-Bromophenyl)-3-hydroxypyridazine-4-carbonitrile (1.00 g, 3.62 mmol) was dissolved in dioxane (36.2 mL) and $POCl_3$ (0.405 mL, 4.35 mmol) was added. The reaction was heated to reflux overnight. The solution was poured into water at 0° C. and 5-(4-bromophenyl)-3-chloropyridazine-4-carbonitrile was collected as a solid. LC-MS: calculated for $C_{11}H_5BrClN_3$ 292.9; observed m/e (M+H)+: 294.0.

Step C: 5-(4-Bromophenyl)-3-((2-(trimethylsilyl)ethyl)thio)pyridazine-4-carbonitrile 5-(4-Bromophenyl)-3-chloropyridazine-4-carbonitrile (2.50 g, 8.49 mmol) was dissolved in DMF (42.4 mL). $K_2CO_3$ (2.346 g, 16.98 mmol) and 2-(trimethylsilyl)ethanethiol (1.03 g, 7.64 mmol) were added and the reaction was stirred overnight at rt. The reaction was diluted with EtOAc and water. The organic phase was washed with water (×2) and brine, then dried over anhydrous $Na_2SO_4$, filtered, and concentrated. The residue was purified by MPLC on a 40 g silica column eluting with 0% to 35% EtOAc in Hexane to afford 5-(4-bromophenyl)-3-((2-(trimethylsilyl)ethyl)thio)pyridazine-4-carbonitrile. LC-MS: calculated for $C_{16}H_{18}BrN_3SSi$ 393.0; observed m/e (M+H)+: 394.2. $^1$H NMR δ (ppm) (MeOH): 9.09 (s, 1H), 7.67 (d, 2H), 7.57 (d, 2H), 3.42-3.37 (m, 2H), 1.04-0.99 (m, 2H), 0.00 (s, 9H).

Step E: 5-(4-Bromophenyl)-3-((2-(trimethylsilyl)ethyl)sulfonyl)pyridazine-4-carbonitrile 5-(4-Bromophenyl)-3-((2-(trimethylsilyl)ethyl)thio)pyridazine-4-carbonitrile (85 mg, 0.217 mmol) was dissolved in DCM (2.17 mL). mCPBA (97 mg, 0.43 mmol) was added and the reaction was stirred overnight at rt. The reaction was diluted with EtOAc and sat. $Na_2S_2O_3$. The aqueous phase was extracted with EtOAc (×2) and the combined extracts were washed with brine, dried over $Na_2SO_4$, filtered, and concentrated. The residue was purified by MPLC on a 40 g silica column eluted with 0% to 40% EtOAc in Hexane to give 5-(4-bromophenyl)-3-((2-(trimethylsilyl)ethyl)sulfonyl)pyridazine-4-carbonitrile. LC-MS: calculated for $C_{16}H_{18}BrN_3O_2SSi$ 423.0; observed m/e (M+H)+: 424.2.

Step F: 5-(4-Bromophenyl)-4-(2H-tetrazol-5-yl)-3-((2-(trimethylsilyl)ethyl)sulfonyl)pyridazine 5-(4-Bromophenyl)-3-((2-(trimethylsilyl)ethyl)sulfonyl)pyridazine-4-carbonitrile (60 mg, 0.141 mmol) was dissolved in toluene (1414 μL). Dibutyltin oxide (10.6 mg, 0.042 mmol) and azidotrimethylsilane (56.3 μl, 0.424 mmol) were added and the reaction was heated to 100° C. for 5 hr. The reaction mixture was concentrated and partitioned between hexane/acetonitrile. The MeCN layer was collected and dilute with water, then purified by reverse phase HPLC on a C18 column eluted with 10% to 100% MeCN in water. The combined fractions were concentrated to provide 5-(4-bromophenyl)-4-(2H-tetrazol-5-yl)-3-((2-(trimethylsilyl)ethyl)sulfonyl)pyridazine as a white solid. LC-MS: calculated for $C_{16}H_{19}BrN_6O_2SSi$ 468.0; observed m/e (M+H)+: 469.26.

Step G: 5-(4-Bromophenyl)-4-(2H-tetrazol-5-yl)pyridazine-3-sulfonamide 5-(4-Bromophenyl)-4-(2H-tetrazol-5-yl)-3-((2-(trimethylsilyl)ethyl)sulfonyl)pyridazine (10 mg, 0.021 mmol) was dissolved in THF (500 μL). TBAF (64.2 μL, 0.064 mmol) was added and the reaction heated to 55° C. overnight. Sodium acetate (17.6 mg, 0.214 mmol) in water (500 μL) and hydroxylamine-O-sulfonic acid (24.2 mg, 0.214 mmol) were added and the reaction was stirred at rt overnight. The crude reaction mixture was concentrated and purified by reverse phase HPLC on a C18 column eluted with 0% to 80% MeCN in water. A significant amount of TBAF was determined to be present by NMR. The oil was dissolved in TFA (1 mL) then repurified by reverse phase HPLC on a C18 column eluted with 0% to 80% MeCN in water. The combined fractions were lyophilized to provide 5-(4-bromophenyl)-4-(2H-tetrazol-5-yl)pyridazine-3-sulfonamide. LC-MS: calculated for $C_{11}H_8BrN_7O_2S$ 383.0 observed m/e (M+H)+: 384.11. $^1$H NMR δ (ppm) (MeOH): 9.55 (s, 1H), 7.51 (d, 2H), 7.11 (d, 2H).

EXAMPLE 278

3-(5-chloro-2-(methylsulfonyl)-1H-benzo[d]imidazol-6-yl)-2-(2H-tetrazol-5-yl)benzenesulfonamide

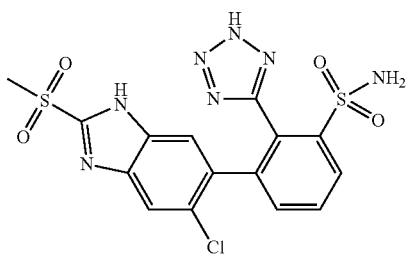 [SMILES: CS(=O)(=O)c1nc2cc(Cl)c(-c3cccc(S(N)(=O)=O)c3-c3nn[nH]n3)cc2[nH]1]

Step A: 6-chloro-5-iodo-2-(methylsulfonyl)-1-((2-(trimethylsilyl)ethoxy)methyl)-1H-benzo[d]imidazole To a suspension of 6-chloro-5-iodo-2-(methylsulfonyl)-1H-benzo[d]imidazole (5.042 g, 14.14 mmol) in DCM (100 mL) at 0° C. was added TEA (2.96 mL, 21.21 mmol), and SEM-Cl (2.76 mL, 15.55 mmol) dropwise. The resulting solution was stirred from 0° C. for 1 hr. The reaction mixture was partitioned between water (200 mL) and DCM (100 mL), the aqueous phase was extracted with DCM (200 mL), and the combined organic phase was dried over anhydrous Na$_2$SO$_4$, concentrated and the residue was purified on silica gel column using EtOAc/hexane as eluting solvents to give the title compound. LC/MS: (M+1)$^+$: 487.17.

Step B: 6-chloro-2-(methylsulfonyl)-5-(4,4,5,5-tetramethyl-1,3,2-dioxaborolan-2-yl)-1-((2-(trimethylsilyl)ethoxy)methyl)-1H-benzo[d]imidazole A mixture of potassium acetate (4.02 g, 40.9 mmol), bis(pinacolato)diboron (4.16 g, 16.4 mmol), and 6-chloro-5-iodo-2-(methylsulfonyl)-1-((2-(trimethylsilyl)ethoxy)methyl)-1H-benzo[d]imidazole (6.64 g, 13.6 mmol) in dioxane (100 mL) was degassed with N$_2$ for 1 hr before addition of PdCl$_2$(dppf)-CH$_2$Cl$_2$ adduct (0.557 g, 0.682 mmol). The resulting mixture was heated at 100° C. overnight. After filtration through celite, the filtrate was concentrated and the residue was partitioned between DCM (200 mL) and water (200 mL), the aqueous phase was extracted with DCM (200 mL) and the combined organic phase was dried over Na$_2$SO$_4$, concentrated and the residue was purified on silica gel column using EtOAc/hexane as eluting solvents to give the title compound. LC/MS: (M+1)$^+$: 487.37

Step C: 3-(5-chloro-2-(methylsulfonyl)-1-((2-(trimethylsilyl)ethoxy)methyl)-1H-benzo[d]imidazol-6-yl)-2-(2-(4-methoxybenzyl)-2H-tetrazol-5-yl)benzenesulfonamide To a mixture of 6-chloro-2-(methylsulfonyl)-5-(4,4,5,5-tetramethyl-1,3,2-dioxaborolan-2-yl)-1-((2-(trimethylsilyl)ethoxy)methyl)-1H-benzo[d]imidazole (1.149 g, 2.359 mmol) and 3-bromo-2-(2-(4-methoxybenzyl)-2H-tetrazol-5-yl)benzenesulfonamide (0.77 g, 1.8 mmol) in dioxane (10 mL) was added Na$_2$CO$_3$ (2.72 mL, 5.44 mmol) and PdCl$_2$(dppf)-CH$_2$Cl$_2$ adduct (0.148 g, 0.182 mmol). After being flushed with N$_2$, the mixture was heated in microwave at 140° C. for 30 min. After filtration through celite, the filtrate was concentrated and the residue was purified on silica gel column using EtOAc/hexane as eluting solvents to give the title compound. LC/MS: (M+1)$^+$:704.36.

Step D: 3-(5-chloro-2-(methylsulfonyl)-1H-benzo[d]imidazol-6-yl)-2-(2H-tetrazol-5-yl)benzenesulfonamide To a mixture of 3-(5-chloro-2-(methylsulfonyl)-1-((2-(trimethylsilyl)ethoxy)methyl)-1H-benzo[d]imidazol-6-yl)-2-(2-(4-methoxybenzyl)-2H-tetrazol-5-yl)benzenesulfonamide (70 mg, 0.099 mmol) and triisopropylsilane (157 mg, 0.994 mmol) was added trifluoroacetic acid (2 mL, 26.0 mmol). The resulting solution was heated at 80° C. for 3 hr. After removing the volatile materials the residue was purified by reverse phase HPLC using acetonitrile (0.05% TFA)/water (0.05% TFA) as mobile phase to give the title compound. LC/MS: (M+1)$^+$: 454.25.

EXAMPLE 279

3-(5-chloro-2-methoxy-1H-benzo[d]imidazol-6-yl)-2-(2H-tetrazol-5-yl)benzenesulfonamide

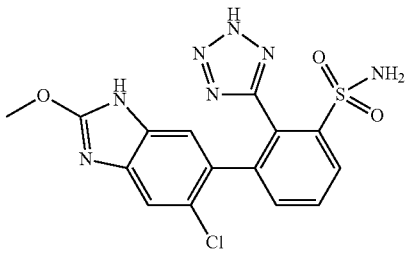 [SMILES: COc1nc2cc(Cl)c(-c3cccc(S(N)(=O)=O)c3-c3nn[nH]n3)cc2[nH]1]

Step A: 3-(5-chloro-2-methoxy-1-((2-(trimethylsilyl)ethoxy)methyl)-1H-benzo[d]imidazol-6-yl)-2-(2-(4-methoxybenzyl)-2H-tetrazol-5-yl)benzenesulfonamide 3-(5-chloro-2-(methylsulfonyl)-1-((2-(trimethylsilyl)ethoxy)methyl)-1H-benzo[d]imidazol-6-yl)-2-(2-(4-methoxybenzyl)-2H-tetrazol-5-yl)benzenesulfonamide (described above, 70 mg, 0.099 mmol) in 7 N ammonia/MeOH (2 mL) was heated at 80° C. for 2 hr. After concentration the residue was purified by preparative TLC using EtOAc/hexane as developing solvents to give the title compound. LC/MS: (M+1)$^+$: 656.63.

Step B: 3-(5-chloro-2-methoxy-1H-benzo[d]imidazol-6-yl)-2-(2H-tetrazol-5-yl)benzenesulfonamide The solution of 3-(5-chloro-2-methoxy-1-((2-(trimethylsilyl)ethoxy)methyl)-1H-benzo[d]imidazol-6-yl)-2-(2-(4-methoxybenzyl)-2H-tetrazol-5-yl)benzenesulfonamide (65 mg, 0.099 mmol) and triisopropylsilane (100 mg, 0.631 mmol) in trifluoroacetic acid (2 mL) was heated at 80° C. for 0.5 hr. After removing the volatile materials the residue was purified on reverse phase HPLC using acetonitrile (0.05% TFA)/water (0.05% TFA) as mobile phase to give the title compound. LC/MS: (M+1)$^+$: 406.41.

EXAMPLE 280

3-(1-(aminomethyl)isoquinolin-6-yl)-2-(2H-tetrazol-5-yl)benzenesulfonamide

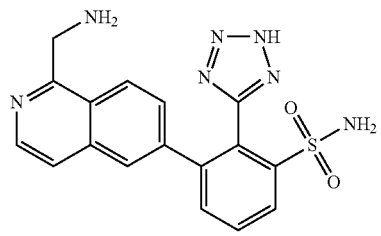 [SMILES: NCc1nccc2cc(-c3cccc(S(N)(=O)=O)c3-c3nn[nH]n3)ccc12]

Step A: (1-cyanoisoquinolin-6-yl)boronic acid

A mixture of 4,4,4',4',5,5,5',5'-octamethyl-2,2'-bi(1,3,2-dioxaborolane) (2.83 g, 11.2 mmol), 6-bromoisoquinoline-1-carbonitrile (2.00 g, 8.58 mmol), and potassium acetate (2.53 g, 25.7 mmol) in dioxane (20 mL) was degassed for 30 min before addition of PdCl$_2$(dppf)-CH$_2$Cl$_2$ adduct (0.701 g, 0.858 mmol). The resulting mixture was heated at 100° C. overnight. After cooling to rt the mixture was filtered through celite, the filtrate was concentrated and the residue was partitioned between 0.1N NaOH (200 mL) and DCM (200 mL). The alkaline phase was extracted with DCM twice. The alkaline phase was then acidified by 2N HCl to pH 5 and extracted with 30% isopropanol/DCM three times. The combined isopropanol/DCM phase was dried over $Na_2SO_4$, concentrated to give (1-cyanoisoquinolin-6-yl)boronic acid. LC/MS: $(M+1)^+$: 199.10.

Step B: 3-(1-cyanoisoquinolin-6-yl)-2-(2-(4-methoxybenzyl)-2H-tetrazol-5-yl)benzenesulfonamide A mixture of 3-bromo-2-(2-(4-methoxybenzyl)-2H-tetrazol-5-yl)benzenesulfonamide (2.97 g, 7.00 mmol), (1-cyanoisoquinolin-6-yl)boronic acid (1.66 g, 8.40 mmol), and aqueous $Na_2CO_3$ (10.50 mL, 21.00 mmol) in dioxane (40 mL) was bubbled with $N_2$ for 1 hr before addition of $PdCl_2$(dppf)-$CH_2Cl_2$ adduct (0.572 g, 0.700 mmol). The mixture was heated at 90° C. overnight. After cooling to rt the mixture was filtered through celite, the filtrate was concentrated and the residue was purified on silica gel column using EtOAc/hexane as eluting solvents to give the title compound. LC/MS: $(M+1)^+$: 498.65.

Step C: 3-(1-(aminomethyl)isoquinolin-6-yl)-2-(2-(4-methoxybenzyl)-2H-tetrazol-5-yl)benzenesulfonamide To a solution of 3-(1-cyanoisoquinolin-6-yl)-2-(2-(4-methoxybenzyl)-2H-tetrazol-5-yl)benzenesulfonamide (1.58 g, 3.18 mmol) in toluene (20 mL) and $CH_2Cl_2$ (40 mL) at −78° C. was added DIBAL-H in THF (15.88 mL, 15.88 mmol) dropwise. The resulting solution was stirred at −78° C. for 2 hr, and quenched by addition of MeOH (5 mL) dropwise, followed by addition of 20 mL of saturated $Na_2SO_4$ solution; the mixture was then stirred at rt for 0.5 hr. The mixture was filtered and the filtrate was concentrated and the residue was purified on reverse phase HPLC using acetonitrile (0.1% formic acid)/water (0.1% formic acid) as mobile phase to give the title compound. LC/MS: $(M+1)^+$: 502.57.

Step D: 3-(1-(aminomethyl)isoquinolin-6-yl)-2-(2H-tetrazol-5-yl)benzenesulfonamide To a solution of 3-(1-(aminomethyl)isoquinolin-6-yl)-2-(2-(4-methoxybenzyl)-2H-tetrazol-5-yl)benzenesulfonamide (45 mg, 0.090 mmol) in trifluoroacetic acid (3 mL) was added anisole (0.078 mL, 0.718 mmol), and the resulting solution was heated at 80° C. for 2 hr. After removing the volatile materials the residue was purified on reverse phase HPLC using acetonitrile (0.1% TFA)/water (0.1% formic acid) as mobile phase to give 3-(1-(aminomethyl)isoquinolin-6-yl)-2-(2H-tetrazol-5-yl)benzenesulfonamide. LC/MS: $(M+1)^+$: 382.45.

EXAMPLE 281

6-(3-sulfamoyl-2-(2H-tetrazol-5-yl)phenyl)isoquinoline-1-carboxamide

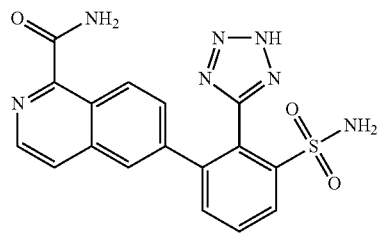 [SMILES: NC(=O)c1nccc2cc(-c3cccc(S(N)(=O)=O)c3-c3nn[nH]n3)ccc12]

Step A: 6-(2-(2-(4-methoxybenzyl)-2H-tetrazol-5-yl)-3-sulfamoylphenyl)isoquinoline-1-carboxamide The solution of 3-(1-cyanoisoquinolin-6-yl)-2-(2-(4-methoxybenzyl)-2H-tetrazol-5-yl)benzenesulfonamide (76 mg, 0.15 mmol) and cerium(IV) oxide (131 mg, 0.764 mmol) in dioxane (1 mL) and water (1 mL) was heated at 100° C. for 2 days. After filtration the filtrate was concentrated and the residue was purified on reverse phase HPLC using acetonitrile (0.1% TFA)/water (0.1% formic acid) as mobile phase to give the title compound. LC/MS: $(M+1)^+$: 516.59.

Step B: 6-(3-sulfamoyl-2-(2H-tetrazol-5-yl)phenyl)isoquinoline-1-carboxamide

The solution of 6-(2-(2-(4-methoxybenzyl)-2H-tetrazol-5-yl)-3-sulfamoylphenyl)isoquinoline-1-carboxamide (34 mg, 0.066 mmol) and triisopropylsilane (41.8 mg, 0.264 mmol) in TFA (3 mL, 38.9 mmol) was heated at 80° C. for 1 hr. After concentration the residue was purified by reverse phase HPLC using 5-40% acetonitrile (0.1% formic acid) gradient over 10 min to give the title compound. LC/MS: $(M+1)^+$: 396.45.

EXAMPLE 282

4'-(3-amino-4-hydroxypiperidin-4-yl)-2-(2H-tetrazol-5-yl)-[1,1'-biphenyl]-3-sulfonamide dihydrochloride (trans, racemate)

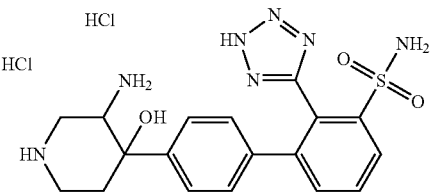 [SMILES: Cl ; NC1CNCCC1(O)c1ccc(-c2cccc(S(N)(=O)=O)c2-c2nn[nH]n2)cc1 ; Cl]

Step A: tert-butyl 4-(4-chlorophenyl)-5,6-dihydropyridine-1 (2H)-carboxylate

The mixture of tert-butyl 4-(((trifluoromethyl)sulfonyl)oxy)-5,6-dihydropyridine-1(2H)-carboxylate (5.00 g, 15.09 mmol), (4-chlorophenyl)boronic acid (2.360 g, 15.09 mmol) and aqueous $Na_2CO_3$ (22.64 mL, 45.3 mmol) in dioxane (100 mL) was degassed by $N_2$ for 1 hr before addition of $PdCl_2$(dppf) (0.552 g, 0.755 mmol). The resulting mixture was heated at 100° C. overnight. After filtration through celite, the filtrate was concentrated and the residue was purified on silica gel column using EtOAc/hexane as eluting solvents to give the title compound. LC/MS: $(M-56+1)^+$: 238.12 (100%); 240.08 (30%).

Step B: tert-butyl 6-(4-chlorophenyl)-7-oxa-3-azabicyclo[4.1.0]heptane-3-carboxylate To the solution of tert-butyl 4-(4-chlorophenyl)-5,6-dihydropyridine-1(2H)-carboxylate (2.15 g, 7.32 mmol) in DCM (100 mL) at 0° C. was added mCPBA (2.53 g, 11.0 mmol) and the resulting solution was stirred from 0° C. to rt overnight. The mixture was partitioned between DCM and 10% $K_2CO_3$/water, the organic phase was washed with 10% $K_2CO_3$/water, dried over $Na_2SO_4$, concentrated, and the residue was purified on silica gel column using EtOAC/hexane as eluting solvents to give the title compound. LC/MS: $(M-56+1)^+$: 254.18 (100%), 256.15 (30%).

Step C: tert-butyl 3-azido-4-(4-chlorophenyl)-4-hydroxypiperidine-1-carboxylate (trans, racemate)

To the solution of tert-butyl 6-(4-chlorophenyl)-7-oxa-3-azabicyclo[4.1.0]heptane-3-carboxylate (1.59 g, 5.13 mmol) in DMSO (20 mL) was added sodium azide (1.67 g, 25.7 mmol) and the resulting mixture was heated at 100° C. under N₂ overnight. After cooling to rt the mixture was partitioned between EtOAc and water, the organic phase was washed with water, brine, dried over Na₂SO₄, concentrated, and the residue was purified on silica gel column using EtOAc/hexane as eluting solvents to give the title compound (trans, racemate). LC/MS: (M+1)⁺: 353.30 (100%), 355.08 (30%).
Step D: tert-butyl 3-amino-4-(4-chlorophenyl)-4-hydroxypiperidine-1-carboxylate (trans, racemate)

To the solution of tert-butyl 3-azido-4-(4-chlorophenyl)-4-hydroxypiperidine-1-carboxylate (trans, racemate, 0.74 g, 2.1 mmol) in THF (20 mL) was added LiAlH₄ (5.03 mL, 5.03 mmol) at 0° C., the resulting solution was stirred at 0° C. for 4 hr. The reaction was quenched with water, the mixture was treated with Na₂SO₄, filtered and washed with DCM; the filtrate was concentrated to give crude title compound (trans, racemate). LC/MS: (M+1)⁺: 327.27 (100%), 329.22 (30%).
Step E: tert-butyl 3-((tert-butoxycarbonyl)amino)-4-(4-chlorophenyl)-4-hydroxypiperidine-1-carboxylate (trans, racemate)

To the solution of tert-butyl 3-amino-4-(4-chlorophenyl)-4-hydroxypiperidine-1-carboxylate (trans, racemate, 700 mg, 2.14 mmol) and Boc₂O (0.597 mL, 2.57 mmol) in DCM (20 mL) was added triethylamine (0.597 mL, 4.28 mmol). The resulting solution was stirred at rt overnight. After concentration the residue was purified by preparative TLC using EtOAc/hexane as developing solvents to give the title compound (trans, racemate). LC/MS: (M+1)⁺: 427.38 (100%), 429.31 (30%).
Step F: tert-butyl 3-((tert-butoxycarbonyl)amino)-4-hydroxy-4-(4-(4,4,5,5-tetramethyl-1,3,2-dioxaborolan-2-yl)phenyl)piperidine-1-carboxylate (trans, racemate)

The mixture of potassium acetate (252 mg, 2.57 mmol), tert-butyl 3-((tert-butoxy carbonyl)amino)-4-(4-chlorophenyl)-4-hydroxypiperidine-1-carboxylate (trans, racemate, 366 mg, 0.857 mmol), and bis(pinacolato)diboron (435 mg, 1.72 mmol) in dioxane (10 mL) was degassed with N₂ by vacuum/N₂ three times before addition of 2nd generation xphos precatalyst (135 mg, 0.171 mmol). The resulting mixture was further degassed by vacuum/N₂ three times and heated at 70° C. overnight under N₂. After filtration through celite, the filtrate was concentrated and the residue was purified on silica gel column using EtOAc/hexane as eluting solvents to give the title compound (trans, racemate). LC/MS: (M+1)⁺: 519.47.
Step G: tert-butyl 3-((tert-butoxycarbonyl)amino)-4-hydroxy-4-(2'-(2-(4-methoxybenzyl)-2H-tetrazol-5-yl)-3'-sulfamoyl-[1,1'-biphenyl]-4-yl)piperidine-1-carboxylate (trans, racemate)

A mixture of tert-butyl 3-((tert-butoxycarbonyl)amino)-4-hydroxy-4-(4-(4,4,5,5-tetramethyl-1,3,2-dioxaborolan-2-yl)phenyl)piperidine-1-carboxylate (trans, racemate, 690 mg, 1.331 mmol), 3-bromo-2-(2-(4-methoxybenzyl)-2H-tetrazol-5-yl)benzenesulfonamide (1129 mg, 2.66 mmol), and K₂CO₃ (552 mg, 3.99 mmol) in dioxane (7 mL) and water (2 mL) was degassed by vacuum/N₂ three times before addition of PdCl₂(dppf) (195 mg, 0.266 mmol). The resulting mixture was further degassed by vacuum/N₂ three times, then heated at 90° C. for 2 days. After filtration through celite, the filtrate was concentrated and the residue was purified on silica gel column using EtOAc/hexane as eluting solvents to give the residue which was further purified on reverse phase HPLC using acetonitrile (0.1% formic acid)/water (0.1% formic acid) as mobile phase to give the title compound (trans, racemate). LC/MS: (M+1)⁺: 736.86.

Step H: 4'-(3-amino-4-hydroxypiperidin-4-yl)-2-(2-(4-methoxybenzyl)-2H-tetrazol-5-yl)-[1,1'-biphenyl]-3-sulfonamide (trans, racemate)

To a solution of tert-butyl 3-((tert-butoxycarbonyl)amino)-4-hydroxy-4-(2'-(2-(4-methoxybenzyl)-2H-tetrazol-5-yl)-3'-sulfamoyl-[1,1'-biphenyl]-4-yl)piperidine-1-carboxylate (trans, racemate) (215 mg, 0.292 mmol) in DCM (2 mL) was added trifluoroacetic acid (2 mL, 26.0 mmol) and the resulting solution was stirred at rt for 1 hr. After concentration the residue was purified on reverse phase HPLC using acetonitrile (0.1% formic acid)/water (0.1% formic acid) as mobile phase to give the title compound (trans, racemate). LC/MS: (M+1)⁺: 536.44.
Step I: 4'-(3-amino-4-hydroxypiperidin-4-yl)-2-(2H-tetrazol-5-yl)-[1,1'-biphenyl]-3-sulfonamide dihydrochloride (trans, racemate)

To a solution of 4'-(3-amino-4-hydroxypiperidin-4-yl)-2-(2-(4-methoxybenzyl)-2H-tetrazol-5-yl)-[1,1'-biphenyl]-3-sulfonamide (trans, racemate, 126 mg, 0.235 mmol) in trifluoroacetic acid (3 mL, 38.9 mmol) was added anisole (0.103 mL, 0.941 mmol), and the resulting solution was heated at 80° C. for 1 hr. After concentration, the residue was purified on reverse phase HPLC using acetonitrile (0.1% formic acid)/water (0.1% formic acid) as mobile phase to give the residue which was dissolved in MeOH (10 mL) and treated with HCl (1.25 M in ethanol) (0.226 mL, 0.282 mmol) at 0° C.; the resulting solution was stirred at 0° C. for 10 min before concentration. The residue was lyophilized from acetonitrile/water to give 4'-(3-amino-4-hydroxypiperidin-4-yl)-2-(2H-tetrazol-5-yl)-[1,1'-biphenyl]-3-sulfonamide dihydrochloride (trans, racemate). LC/MS: (M+1)⁺: 416.29.

EXAMPLE 283

4'-(4-aminopiperidin-4-yl)-2-(2H-tetrazol-5-yl)-[1,1'-biphenyl]-3-sulfonamide dihydrochloride

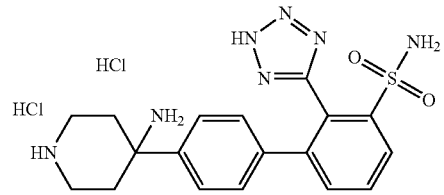 [SMILES: Cl ; NC1(c2ccc(-c3cccc(S(N)(=O)=O)c3-c3nn[nH]n3)cc2)CCNCC1 ; Cl]

Step A: tert-butyl 4-(4-chlorophenyl)-4-hydroxypiperidine-1-carboxylate

To a solution of tert-butyl 4-oxopiperidine-1-carboxylate (2.06 g, 10.3 mmol) in THF (20 mL) was added lanthanum trichloride lithium chloride complex in THF (17.23 mL, 10.34 mmol) and the resulting solution was stirred at rt for 1 hr. The solution was cooled to 0° C. and was treated with 4-chlorophenylmagnesium bromide (12.41 mL, 12.41 mmol) dropwise. The resulting solution was stirred at rt for 2 hr. The reaction was quenched with saturated NH₄Cl solution, and partitioned between EtOAc/brine. The organic phase was dried over Na₂SO₄, concentrated, and the residue was purified on silica gel column using EtOAc/hexane as eluting solvents to give the title compound. LC/MS: (M+1)⁺: 312.23 (100%), 314.21 (30%).
Step B: 4-(4-chlorophenyl)piperidin-4-ol To the solution of tert-butyl 4-(4-chlorophenyl)-4-hydroxypiperidine-1-carboxylate (2.83 g, 9.08 mmol) in CH₂Cl₂ (20 mL) was added trifluoroacetic acid (7.0 mL, 91 mmol) and the resulting solution was stirred at rt for 2 hr. The reaction solution was concentrated to give 4-(4-chlorophenyl)piperidin-4-ol. LC/MS: (M+1)⁺: 212.16 (100%), 214.11 (30%).

Step C: benzyl 4-(4-chlorophenyl)-4-hydroxypiperidine-1-carboxylate

To the solution of 4-(4-chlorophenyl)piperidin-4-ol (1.92 g, 9.08 mmol) in CH₂Cl₂ (30 mL) was added triethylamine (5.06 mL, 36.3 mmol) and Cbz-Cl (1.30 mL, 9.08 mmol) at 0° C.; the resulting solution was stirred at 0° C. for 1 hr. The reaction was quenched by addition of water, the mixture was partitioned between DCM and saturated NaHCO₃, the aqueous phase was extracted with DCM three times, the combined organic phases were dried over Na₂SO₄, concentrated and the residue was purified on silica gel column using EtOAc/hexane as eluting solvents to give the title compound. LC/MS: (M+1)⁺: 346.24 (100%), 348.23 (30%).

Step D: tert-butyl 4-(2-chloroacetamido)-4-(4-chlorophenyl)piperidine-1-carboxylate To a solution of benzyl 4-(4-chlorophenyl)-4-hydroxypiperidine-1-carboxylate (2.23 g, 6.45 mmol) in chloroacetonitrile (20 mL, 315 mmol) at 0° C. was added H₂SO₄ (5.16 mL, 97 mmol) and the resulting solution was stirred at rt for 2 hr. The reaction mixture was poured into ice water/K₂CO₃, the aqueous phase was extracted with DCM three times, the organic phase was dried over Na₂SO₄, concentrated and the residue was suspended in DCM (100 mL) and saturated NaHCO₃ (100 mL). To this solution was added Boc₂O (1.50 mL, 6.45 mmol) in DCM (10 mL), and the resulting mixture was stirred at rt overnight. The mixture was extracted with DCM three times, the combined organic phase was dried over Na₂SO₄, concentrated and the residue was purified by silica gel column chromatography using EtOAc/hexane as eluting solvents to give the title compound. LC/MS: (M+1)⁺: 331.38 (100%), 333.38 (70%).

Step E: tert-butyl 4-amino-4-(4-chlorophenyl)piperidine-1-carboxylate

To a solution of tert-butyl 4-(2-chloroacetamido)-4-(4-chlorophenyl)piperidine-1-carboxylate (0.715 g, 1.85 mmol) in ethanol (20 mL) was added thiourea (1.405 g, 18.46 mmol). The resulting mixture was heated at 120° C. for 2.5 hr. After filtration the filtrate was concentrated and the residue was suspended in DCM (100 mL) and filtered. The filtrate was concentrated to give the title compound. LC/MS: (M+1)⁺: 311.20 (100%), 313.18 (30%).

Step F: tert-butyl 4-((tert-butoxycarbonyl)amino)-4-(4-chlorophenyl)piperidine-1-carboxylate To the solution of tert-butyl 4-amino-4-(4-chlorophenyl)piperidine-1-carboxylate (574 mg, 1.85 mmol) in CH₂Cl₂ (20 mL) was added Boc₂O (0.515 mL, 2.22 mmol) in DCM (5 mL) and triethylamine (0.515 mL, 3.69 mmol). The resulting solution was stirred at rt over the weekend. Additional Boc₂O (0.515 mL, 2.22 mmol) and triethylamine (0.25 mL) were added and the resulting mixture was heated at reflux for 1 hr. After concentration, the residue was purified on silica gel column using EtOAc/hexane as eluting solvents to give the title compound. LC/MS: (M+1)⁺: 411.29 (100%), 413.27 (30%).

Step G: tert-butyl 4-((tert-butoxycarbonyl)amino)-4-(4-(4,4,5,5-tetramethyl-1,3,2-dioxaborolan-2-yl)phenyl)piperidine-1-carboxylate The mixture of potassium acetate (221 mg, 2.249 mmol), tert-butyl 4-((tert-butoxycarbonyl)amino)-4-(4-chlorophenyl)piperidine-1-carboxylate (308 mg, 0.750 mmol), and bis(pinacolato)diboron (381 mg, 1.50 mmol) in dioxane (10 mL) was degassed with N₂ by vacuum/N₂ three times before addition of 2nd generation xphos precatalyst (118 mg, 0.150 mmol). The resulting mixture was further degassed by vacuum/N₂ three times and heated at 70° C. overnight under N₂. After filtration through celite, the filtrate was concentrated and the residue was purified on reverse phase HPLC using acetonitrile (0.1% formic)/water (0.1% formic acid) to give tert-butyl 4-((tert-butoxycarbonyl)amino)-4-(4-(4,4,5,5-tetramethyl-1,3,2-dioxaborolan-2-yl)phenyl)piperidine-1-carboxylate. LC/MS: (M+1)⁺: 503.44.

Step H: tert-butyl 4-((tert-butoxycarbonyl)amino)-4-(2'-(2-(4-methoxybenzyl)-2H-tetrazol-5-yl)-3'-sulfamoyl-[1,1'-biphenyl]-4-yl)piperidine-1-carboxylate The mixture of tert-butyl 4-((tert-butoxycarbonyl)amino)-4-(4-(4,4,5,5-tetramethyl-1,3,2-dioxaborolan-2-yl)phenyl)piperidine-1-carboxylate (242 mg, 0.482 mmol), 3-bromo-2-(2-(4-methoxybenzyl)-2H-tetrazol-5-yl)benzenesulfonamide (286 mg, 0.674 mmol), and K₂CO₃ (200 mg, 1.45 mmol) in dioxane (7 mL) and water (2 mL) was degassed by vacuum/N₂ three times before addition of PdCl₂(dppf) (70.5 mg, 0.096 mmol). The resulting mixture was further degassed by vacuum/N₂ three times, then heated at 90° C. for 2 days. After filtration through celite, the filtrate was concentrated and the residue was purified on silica gel column using EtOAc/hexane as eluting solvents to give the title compound. LC/MS: (M+1)⁺: 720.44.

Step I: 4'-(4-aminopiperidin-4-yl)-2-(2-(4-methoxybenzyl)-2H-tetrazol-5-yl)-[1,1'-biphenyl]-3-sulfonamide To the solution of tert-butyl 4-((tert-butoxycarbonyl)amino)-4-(2'-(2-(4-methoxybenzyl)-2H-tetrazol-5-yl)-3'-sulfamoyl-[1,1'-biphenyl]-4-yl)piperidine-1-carboxylate (125 mg, 0.174 mmol) in DCM (2 mL) was added trifluoroacetic acid (2 mL, 26.0 mmol) and the resulting solution was stirred at rt for 1 hr. After concentration the residue was purified by reverse phase HPLC using acetonitrile (0.1% formic acid)/water (0.1% formic acid) to give the title compound. LC/MS: (M+1)⁺: 520.60.

Step J: 4'-(4-aminopiperidin-4-yl)-2-(2H-tetrazol-5-yl)-[1,1'-biphenyl]-3-sulfonamide dihydrochloride To the solution of 4'-(4-aminopiperidin-4-yl)-2-(2-(4-methoxybenzyl)-2H-tetrazol-5-yl)-[1,1'-biphenyl]-3-sulfonamide (70 mg, 0.135 mmol) in trifluoroacetic acid (2 mL, 26.0 mmol) was added anisole (0.059 mL, 0.539 mmol), and the resulting solution was heated at 80° C. for 1 hr. After concentration, the residue was purified on reverse phase HPLC using acetonitrile (0.1% formic acid)/water (0.1% formic acid) as mobile phase to give the pure product which was dissolved in MeOH (10 mL) and treated with HCl in ethanol (1.25 N) (0.216 mL, 0.269 mmol); after concentration, the residue was lyophilized from acetonitrile/water to give 4'-(4-aminopiperidin-4-yl)-2-(2H-tetrazol-5-yl)-[1,1'-biphenyl]-3-sulfonamide dihydrochloride. LC/MS: (M+1)⁺: 400.22.

EXAMPLES 284 and 285

4'-(3-hydroxypyrrolidin-3-yl)-2-(2H-tetrazol-5-yl)-[1,1'-biphenyl]-3-sulfonamide and 4'-(2,5-dihydro-1H-pyrrol-3-yl)-2-(2H-tetrazol-5-yl)-[1,1'-biphenyl]-3-sulfonamide

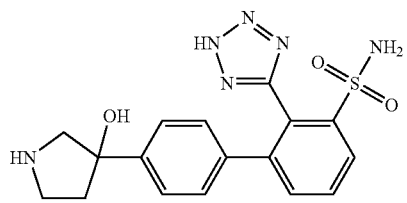

-continued

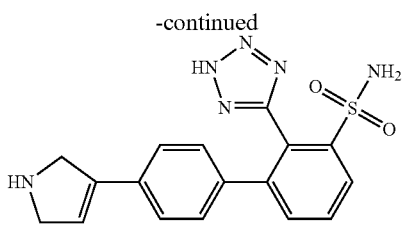

Step A: tert-butyl 3-(4-chlorophenyl)-3-hydroxypyrrolidine-1-carboxylate

To a solution of tert-butyl 3-oxopyrrolidine-1-carboxylate (4.86 g, 26.2 mmol) in THF (40 mL) was added lanthanum trichloride lithium chloride complex in THF (43.7 mL, 26.2 mmol) and the resulting solution was stirred at rt for 1 hr. The solution was cooled to 0° C. and was treated with 4-chlorophenylmagnesium bromide (31.5 mL, 31.5 mmol) dropwise. The resulting solution was stirred at rt for 2 hr. The reaction was quenched by sat. NH$_4$Cl solution, and partitioned between EtOAc/brine. The organic phase was dried over Na$_2$SO$_4$, concentrated, and the residue was purified on silica gel column using EtOAc/hexane as eluting solvents to give the title compound. LC/MS: (M+1)$^+$: 298 (100%), 300 (30%).

Step B: tert-butyl 3-hydroxy-3-(4-(4,4,5,5-tetramethyl-1,3,2-dioxaborolan-2-yl)phenyl)pyrrolidine-1-carboxylate A mixture of potassium acetate (513 mg, 5.23 mmol), tert-butyl 3-(4-chlorophenyl)-3-hydroxypyrrolidine-1-carboxylate (519 mg, 1.74 mmol), and bis(pinacolato)diboron (885 mg, 3.49 mmol) in dioxane (10 mL) was degassed with N$_2$ by vacuum/N$_2$ three times before addition of 2nd generation xphos precatalyst (274 mg, 0.349 mmol). The resulting mixture was further degassed by vacuum/N$_2$ three times and heated at 70° C. overnight under N$_2$. After filtration through celite, the filtrate was concentrated and the residue was purified on silica gel column using EtOAc/hexane as eluting solvents to give the title compound. LC/MS: (M+1)$^+$: 390.52.

Step C: tert-butyl 3-hydroxy-3-(2'-(2-(4-methoxybenzyl)-2H-tetrazol-5-yl)-3'-sulfamoyl-[1,1'-biphenyl]-4-yl)pyrrolidine-1-carboxylate The mixture of tert-butyl 3-hydroxy-3-(4-(4,4,5,5-tetramethyl-1,3,2-dioxaborolan-2-yl)phenyl)pyrrolidine-1-carboxylate (0.568 g, 1.46 mmol), 3-bromo-2-(2-(4-methoxybenzyl)-2H-tetrazol-5-yl)benzenesulfonamide (0.619 g, 1.46 mmol), and Na$_2$CO$_3$ (2.2 mL, 4.38 mmol) in dioxane (10 mL) was degassed by vacuum/N$_2$ three times before addition of PdCl$_2$(dppf) (0.214 g, 0.292 mmol). The resulting mixture was further degassed by vacuum/N$_2$ three times, then heated at 90° C. for 2 days. After filtration through celite, the filtrate was concentrated and the residue was purified on silica gel column using EtOAc/hexane as eluting solvents to give the title compound. LC/MS: (M+1)$^+$: 607.29.

Step D: 4'-(3-hydroxypyrrolidin-3-yl)-2-(2-(4-methoxybenzyl)-2H-tetrazol-5-yl)-[1,1'-biphenyl]-3-sulfonamide 2,2,2-trifluoroacetate To a solution of tert-butyl 3-hydroxy-3-(2'-(2-(4-methoxybenzyl)-2H-tetrazol-5-yl)-3'-sulfamoyl-[1,1'-biphenyl]-4-yl)pyrrolidine-1-carboxylate (330 mg, 0.544 mmol) in DCM (3 mL) was added trifluoroacetic acid (3 mL, 38.9 mmol). The resulting solution was stirred at rt for 1 hr then the reaction solution was concentrated to give the title compound. LC/MS: (M+1)+: 507.25.

Step E: 4'-(3-hydroxypyrrolidin-3-yl)-2-(2H-tetrazol-5-yl)-[1,1'-biphenyl]-3-sulfonamide and 4'-(2,5-dihydro-1H-pyrrol-3-yl)-2-(2H-tetrazol-5-yl)-[1,1'-biphenyl]-3-sulfonamide To a solution of 4'-(3-hydroxypyrrolidin-3-yl)-2-(2-(4-methoxybenzyl)-2H-tetrazol-5-yl)-[1,1'-biphenyl]-3-sulfonamide 2,2,2-trifluoroacetate (200 mg, 0.322 mmol) in trifluoroacetic acid (2 mL) was added anisole (0.141 mL, 1.29 mmol) and the resulting solution was heated at 80° C. for 0.5 hr. After concentration, the residue was purified on reverse phase HPLC using acetonitrile (0.1% formic acid)/water (0.1% formic acid) as mobile phase to give 4'-(3-hydroxypyrrolidin-3-yl)-2-(2H-tetrazol-5-yl)-[1,1'-biphenyl]-3-sulfonamide. LC/MS: (M+1)$^+$: 387.15, and 4'-(2,5-dihydro-1H-pyrrol-3-yl)-2-(2H-tetrazol-5-yl)-[1,1'-biphenyl]-3-sulfonamide. LC/MS: (M+1)$^+$: 369.15.

EXAMPLE 286

3-(2-(aminomethyl)quinolin-6-yl)-2-(2H-tetrazol-5-yl)benzenesulfonamide

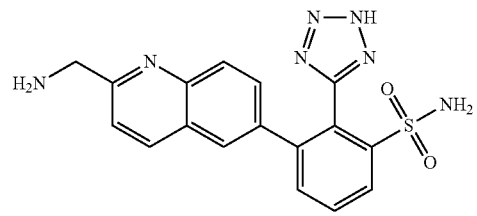 [SMILES: NCc1ccc2cc(-c3cccc(S(N)(=O)=O)c3-c3nn[nH]n3)ccc2n1]

Step A: (2-cyanoquinolin-6-yl)boronic acid

A mixture of 4,4,4',4',5,5,5',5'-octamethyl-2,2'-bi(1,3,2-dioxaborolane) (2.86 g, 11.3 mmol), 6-bromoquinoline-2-carbonitrile (2.02 g, 8.67 mmol), and potassium acetate (2.55 g, 26.0 mmol) in dioxane (20 mL) was degassed for 30 min before addition of PdCl$_2$(dppf)-CH$_2$Cl$_2$ adduct (0.708 g, 0.867 mmol). The resulting mixture was heated at 100° C. overnight. After cooling to rt the mixture was filtered through celite, the filtrate was concentrated, and the residue was partitioned between 0.1N NaOH (200 mL) and DCM (200 mL). The alkaline phase was extracted with DCM twice. The alkaline phase was then acidified by 2N HCl to pH 5, extracted with 30% isopropanol/DCM (3×150 mL). The combined isopropanol/DCM phases were dried over Na$_2$SO$_4$, concentrated to give (2-cyanoquinolin-6-yl)boronic acid as a crude product which was used in next step directly without further purification. LC/MS: (M+1)$^+$: 199.11.

Step B: 3-(2-cyanoquinolin-6-yl)-2-(2-(4-methoxybenzyl)-2H-tetrazol-5-yl)benzenesulfonamide The mixture of 3-bromo-2-(2-(4-methoxybenzyl)-2H-tetrazol-5-yl)benzenesulfonamide (1.73 g, 4.07 mmol), (2-cyanoquinolin-6-yl)boronic acid (1.68 g, 5.09 mmol), and Na$_2$CO$_3$ (7.64 mL, 15.3 mmol) in dioxane (40 mL) was bubbled with N$_2$ for 1 hr before addition of PdCl$_2$(dppf)-CH$_2$Cl$_2$ adduct (0.416 g, 0.509 mmol). The mixture was heated at 90° C. overnight. After cooled to rt the mixture was filtered through celite, the filtrate was concentrated and the residue was purified by silica gel column using EtOAc/hexane as eluting solvents to give the title compound. LC/MS: (M+1)$^+$: 498.25.

Step C: 3-(2-(aminomethyl)quinolin-6-yl)-2-(2-(4-methoxybenzyl)-2H-tetrazol-5-yl)benzenesulfonamide To the solution of 3-(2-cyanoquinolin-6-yl)-2-(2-(4-methoxybenzyl)-2H-tetrazol-5-yl)benzenesulfonamide (0.43 g, 0.864 mmol) in CH$_2$Cl$_2$ (20 mL) and MeOH (20 mL) was added Boc$_2$O (0.221 mL, 0.951 mmol) and Raney nickel (0.074 g, 0.864 mmol). The resulting mixture was subjected to hydrogenation at 50 psi at rt overnight. After filtration through celite under N$_2$, the filtrate was concentrated and the residue was dissolved in DCM (5 mL) and the resulting solution was treated with trifluoroacetic acid (5 mL) at rt for 1 hr. The reaction solution was concentrated to give 3-(2-(aminomethyl)quinolin-6-yl)-2-(2-(4-methoxybenzyl)-2H-tetrazol-5-yl)benzenesulfonamide. LC/MS: (M+1)$^+$: 502.18.

Step D: 3-(2-(aminomethyl)quinolin-6-yl)-2-(2H-tetrazol-5-yl)benzenesulfonamide

To the solution of 3-(2-(aminomethyl)quinolin-6-yl)-2-(2-(4-methoxybenzyl)-2H-tetrazol-5-yl)benzenesulfonamide (227 mg, 0.453 mmol) in trifluoroacetic acid (2 mL, 26.0 mmol) was added anisole (0.198 mL, 1.81 mmol), and the resulting solution was heated at 80° C. for 1 hr. After concentration, the residue was purified on reverse phase HPLC using acetonitrile (0.1% formic acid)/water (0.1% formic acid) as mobile phase to give 3-(2-(aminomethyl)quinolin-6-yl)-2-(2H-tetrazol-5-yl)benzenesulfonamide. LC/MS: (M+1)$^+$: 382.20.

EXAMPLE 287

6-(3-sulfamoyl-2-(2H-tetrazol-5-yl)phenyl)quinoline-2-carboxylic acid

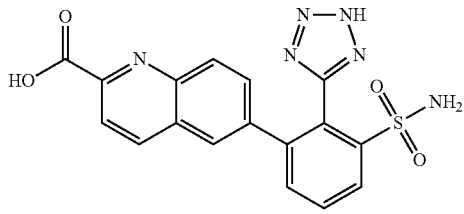 [SMILES: NS(=O)(=O)c1cccc(-c2ccc3nc(C(=O)O)ccc3c2)c1-c1nn[nH]n1]

Step A: 6-(2-(2-(4-methoxybenzyl)-2H-tetrazol-5-yl)-3-sulfamoylphenyl)quinoline-2-carboxylic acid and 6-(2-(2-(4-methoxybenzyl)-2H-tetrazol-5-yl)-3-sulfamoylphenyl)quinoline-2-carboxamide The solution of 3-(2-cyanoquinolin-6-yl)-2-(2-(4-methoxybenzyl)-2H-tetrazol-5-yl)benzenesulfonamide (90 mg, 0.181 mmol) in dioxane (2 mL) and water (2 mL) was added H$_2$O$_2$ (0.032 ml, 0.362 mmol) and NaOH (1N, 0.362 mL, 0.362 mmol). The resulting mixture was heated at 70° C. overnight. After acidified to pH 4, the mixture was extracted with 30% isopropanol/CHCl$_3$ three times, the combined organic phase was dried over Na$_2$SO$_4$, concentrated and the residue was purified on reverse phase HPLC using acetonitrile (0.1% formic acid)/water (0.1% formic acid) to give the title compound. LC/MS: (M+1)$^+$: 517.20, and 6-(2-(2-(4-methoxybenzyl)-2H-tetrazol-5-yl)-3-sulfamoylphenyl)quinoline-2-carboxamide. LC/MS: (M+1)$^+$: 516.21.

Step B: 6-(3-sulfamoyl-2-(2H-tetrazol-5-yl)phenyl)quinoline-2-carboxylic acid

To the solution of 6-(2-(2-(4-methoxybenzyl)-2H-tetrazol-5-yl)-3-sulfamoylphenyl)quinoline-2-carboxylic acid (20 mg, 0.039 mmol) in trifluoroacetic acid (3 mL, 38.9 mmol) was added anisole (0.017 mL, 0.155 mmol), the resulting solution was heated 80° C. for 1 hr. After concentration, the residue was purified on reverse phase HPLC using acetonitrile (0.1% formic acid)/water (0.1% formic acid) to give 6-(3-sulfamoyl-2-(2H-tetrazol-5-yl)phenyl)quinoline-2-carboxylic acid. LC/MS: (M+1)$^+$: 397.13.

EXAMPLE 288

6-(3-sulfamoyl-2-(2H-tetrazol-5-yl)phenyl)quinoline-2-carboxamide

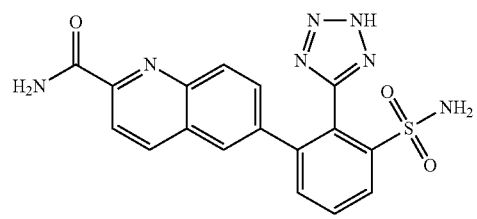 [SMILES: NC(=O)c1ccc2cc(-c3cccc(S(N)(=O)=O)c3-c3nn[nH]n3)ccc2n1]

To a solution of 6-(2-(2-(4-methoxybenzyl)-2H-tetrazol-5-yl)-3-sulfamoylphenyl)quinoline-2-carboxamide (22 mg, 0.043 mmol) in trifluoroacetic acid (3 mL, 38.9 mmol) was added anisole (0.019 mL, 0.171 mmol) and the resulting solution was heated 80° C. for 1 hr. After concentration, the residue was purified on reverse phase HPLC using acetonitrile (0.1% formic acid)/water (0.1% formic acid) over 1 min to give 6-(3-sulfamoyl-2-(2H-tetrazol-5-yl)phenyl)quinoline-2-carboxamide. LC/MS: (M+1)$^+$:396.15.

EXAMPLE 289

5-Chloro-3-(3-oxo-2,3-dihydro-1H-isoindol-5-yl)-2-(2H-tetrazol-5-yl)benzenesulfonamide

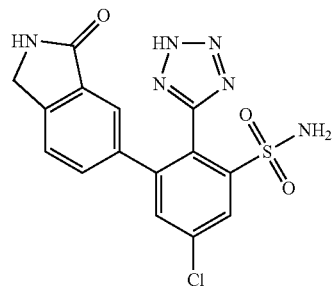 [SMILES: NS(=O)(=O)c1cc(Cl)cc(-c2ccc3c(c2)C(=O)NC3)c1-c1nn[nH]n1]

Step A: (3-Bromo-4-(2-(4-methoxybenzyl)-2H-tetrazol-5-yl)-5-sulfamoylphenyl)boronic acid (1,5-Cyclooctadiene)(methoxy)iridium(i) dimer (39.1 mg, 0.059 mmol) and bis(pinacolato)diboron (449 mg, 1.768 mmol) were dissolved in 3 mL THF and added to a 15 mL pressure tube containing a 2 mL THF solution of 3,4,7,8-tetramethyl-1,10-phenanthroline (27.8 mg, 0.118 mmol). Finally, a 1 mL THF solution containing 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (500 mg, 1.178 mmol) was added to the pressure tube via pipette and the reaction vessel was sealed and heated in an oil bath at 80° C. for 16 hr. The reaction was dark red. The reaction mixture was concentrated and purified by reverse phase HPLC with C-18 column, eluted with 10% to 100% MeCN in water with 0.05% TFA. The solution was lyopholized to provide (3-bromo-4-(2-(4-methoxybenzyl)-2H-tetrazol-5-yl)-5-sulfamoylphenyl)boronic acid. LC-MS: calculated for $C_{15}H_{15}BBrN_5O_5S$ 469.0 observed m/e (M+H)$^+$: 470.2.

Step B: 3-Bromo-5-chloro-2-(2-(4-methoxybenzyl)-2H-tetrazol-5-yl)benzenesulfonamide (3-Bromo-4-(2-(4-methoxybenzyl)-2H-tetrazol-5-yl)-5-sulfamoylphenyl)boronic acid (2.7 g, 5.77 mmol) was dissolved in ACN (57.7 ml), to which was added NCS (0.770 g, 5.77 mmol) and copper(I) chloride (0.571 g, 5.77 mmol), and then heated to 65° C. for 6 hr. The reaction was diluted with water and EtOAc. The aqueous phase was extracted with EtOAc (×2) and the combined extracts were washed with brine, dried over $Na_2SO_4$, filtered, and concentrated. The residue was purified by MPLC on a 120 g silica column eluted with 0% to 100% EtOAc in Hexane. The major UV active material was collected (only major PMB regioisomer) to provide the target compound. LC-MS: calculated for $C_{15}H_{13}BrClN_5O_3S$ 457.0 observed m/e (M+H)$^+$: 457.9; $^1$H NMR δ (ppm) (MeOH): 8.15 (s, 1H), 8.01 (s, 1H), 7.12 (d, 2H), 6.77 (d, 2H), 5.53 (d, 1H), 5.27 (d, 1H), 3.75 (s, 3H).

Step C: 5-Chloro-2-(2-(4-methoxybenzyl)-2H-tetrazol-5-yl)-3-(3-oxoisoindolin-5-yl)benzenesulfonamide A reaction vial was charged with 6-(4,4,5,5-tetramethyl-1,3,2-dioxaborolan-2-yl)isoindolin-1-one (73.2 mg, 0.283 mmol) and 3-bromo-5-chloro-2-(2-(4-methoxybenzyl)-2H-tetrazol-5-yl)benzenesulfonamide (144 mg, 0.314 mmol). EtOH (3139 µl) and potassium phosphate tribasic (942 µl, 0.942 mmol) were added and the reaction mixture was sparged with $N_2$ for 10 min. 1,1'-bis(di-tert-butylphosphino)ferrocene palladium dichloride (20.46 mg, 0.031 mmol) was added and the reaction was heated to 100° C. for 1 hr in a microwave. The crude reaction mixture was diluted with EtOAc and water. The aqueous phase was extracted with EtOAc (×2) and the combined organic extracts were washed with brine, dried over $Na_2SO_4$, filtered, and concentrated. The residue was purified by reverse phase HPLC on a C18 column eluted with 5% to 90% MeCN in water with 0.05% TFA. The solution was concentrated to provide 5-chloro-2-(2-(4-methoxybenzyl)-2H-tetrazol-5-yl)-3-(3-oxoisoindolin-5-yl)benzenesulfonamide. LC-MS: calculated for $C_{23}H_{19}ClN_6O_4S$ 510.09; observed m/e (M+H)$^+$: 511.3.

Step D: 5-Chloro-3-(3-oxo-2,3-dihydro-1H-isoindol-5-yl)-2-(2H-tetrazol-5-yl)benzenesulfonamide 5-chloro-2-(2-(4-methoxybenzyl)-2H-tetrazol-5-yl)-3-(3-oxoisoindolin-5-yl)benzenesulfonamide (45 mg, 0.088 mmol) was dissolved in TFA (1120 µl, 14.53 mmol) and Anisole (28.9 µl, 0.264 mmol) was added. The reaction was heated to 45° C. overnight then concentrated in vacuo. The residue was purified by reverse phase HPLC on a $C_{18}$ column and eluted with 0% to 70% MeCN in water with 0.05% TFA. The solution was lyopholized to provide 5-chloro-3-(3-oxo-2,3-dihydro-1H-isoindol-5-yl)-2-(2H-tetrazol-5-yl)benzenesulfonamide. LC-MS: calculated for $C_{15}H_{11}ClN_6O_3S$ 390.03 observed m/e: 391.26 (M+H)$^+$; $^1$H NMR δ (ppm) (MeOH): 8.15 (s, 1H), 7.79 (s, 1H), 7.49 (s, 1H), 7.40 (d, 1H), 7.19 (d, 1H), 4.36 (s, 3H).

EXAMPLE 290

4'-Methyl-5-(1-oxoisoindolin-5-yl)-2-(2H-tetrazol-5-yl)-[1,1'-biphenyl]-3-sulfonamide

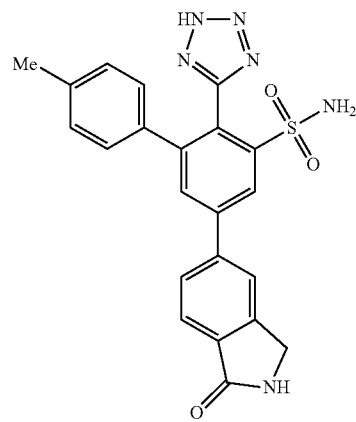 [SMILES: Cc1ccc(-c2cc(-c3ccc4c(c3)CNC4=O)cc(S(N)(=O)=O)c2-c2nn[nH]n2)cc1]

Step A: 2-(2-(4-Methoxybenzyl)-2H-tetrazol-5-yl)-4'-methyl-[1,1'-biphenyl]-3-sulfonamide A reaction flask was charged with 4,4,5,5-tetramethyl-2-(p-tolyl)-1,3,2-dioxaborolane (1928 mg, 8.84 mmol) and a mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (3000 mg, 7.07 mmol). EtOH (23.6 mL) and potassium phosphate tribasic (21.21 ml, 21.21 mmol) were added and the reaction mixture was sparged with $N_2$ for 10 min. 1,1'-bis(di-tert-butylphosphino)ferrocene palladium dichloride (461 mg, 0.707 mmol) was added and the reaction heated to 100° C. for 18 hr. The crude reaction mixture was diluted with water and EtOAc. The organic was washed with brine, dried over $Na_2SO_4$, filter, and concentrated. The oil was purified by MPLC on a 120 g silica eluted with 0% to 20% MeOH in DCM. The major UV active material was collected to provide 2-(2-(4-methoxybenzyl)-2H-tetrazol-5-yl)-4'-methyl-[1,1'-biphenyl]-3-sulfonamide. LC-MS: calculated for $C_{22}H_{21}N_5O_3S$ 435.1; observed m/e (M+H)$^+$: 436.6.

Step B: (6-(2-(4-Methoxybenzyl)-2H-tetrazol-5-yl)-4'-methyl-5-sulfamoyl-[1,1'-biphenyl]-3-yl)boronic acid (1,5-Cyclooctadiene)(methoxy)iridium(i) dimer (38.1 mg, 0.057 mmol) and BISPIN (292 mg, 1.148 mmol) were dissolved in 3 mL THF and added to a 15 mL pressure tube containing a 2 mL THF solution of 3,4,7,8-tetramethyl-1,10-phenanthroline (27.1 mg, 0.115 mmol). Finally, a 1 mL THF solution containing 2-(2-(4-methoxybenzyl)-2H-tetrazol-5-yl)-4'-methyl-[1,1'-biphenyl]-3-sulfonamide (250 mg, 0.574 mmol) was added to the pressure tube via pipette and the reaction vessel was sealed and heated in an oil bath at 80° C. for 3.5 hr. The reaction was concentrated en vacuo then purified by reverse phase HPLC on a C18 column eluted with 10% to 100% MeCN in water with 0.05% TFA. The major UV active material was collected and lyopholized to provide (6-(1-(and 2-)(4-methoxybenzyl)-2H-tetrazol-5-yl)-4'-methyl-5-sulfamoyl-[1,1'-biphenyl]-3-yl)boronic acid. LC-MS: calculated for $C_{22}H_{22}BN_5O_5S$ 479.1; observed m/e: 480.3 (M+H)$^+$;

Step C: 4'-Methyl-5-(1-oxoisoindolin-5-yl)-2-(2H-tetrazol-5-yl)-[1,1'-biphenyl]-3-sulfonamide (6-(1-(and 2-)(4-methoxybenzyl)-2H-tetrazol-5-yl)-4'-methyl-5-sulfamoyl-[1,1'-biphenyl]-3-yl)boronic acid (40 mg, 0.083 mmol) and 6-bromoisoindolin-1-one (19.47 mg, 0.092 mmol) was suspended in ethanol (835 µl) and potassium phosphate tribasic (250 µl, 0.250 mmol). The reaction mixture was sparged with $N_2$ for 5 min. 1,1'-bis(di-tert-butylphosphino)ferrocene palladium dichloride (5.44 mg, 8.35 µmol) was added and the reaction mixture microwaved at 110° C. for 90 min. The crude reaction mixture was diluted with EtOAc and water. The aqueous phase was extract with EtOAc (×2), then the combined extracts were washed with brine, dried over $Na_2SO_4$, filtered, and concentrated. The reaction mixture was purified by reverse phase HPLC on a $C_{18}$ column and then eluted with 10% to 100% MeCN in water. The major UV active material was lyopholized to provide a white solid that was utilized directly in the deprotection. LC-MS: calculated for $C_{30}H_{26}N_6O_4S$ 566.2; observed m/e: 467.5 (M+H)$^+$. The resulting solid was dissolved in TFA and heated to 45° C. overnight, then concentrated. The residue was purified by reverse phase HPLC on a $C_{18}$ column eluted with 0% to 80% MeCN in water. The major UV active material was lyopholized to provide 4'-methyl-5-(1-oxoisoindolin-5-yl)-2-(2H-tetrazol-5-yl)-[1,1'-biphenyl]-3-sulfonamide. LC-MS: calculated for $C_{22}H_{18}N_6O_3S$ 446.1; observed m/e: 447.4 (M+H)$^+$; $^1$H NMR δ (ppm) (DMSO): 8.72 (s, 1H), 8.44 (s, 1H), 8.16 (s, 1H), 8.12 (d, 1H), 8.05 (s, 1H), 7.77 (d, 1H), 7.60 (s, 2H), 7.11-7.05 (m, 4H), 4.48 (s, 2H), 2.27 (s, 3H).

EXAMPLES 291-296

Parallel synthesis of 5-substituted 4'-methyl-2-(1H-tetrazol-5-yl)-[1,1'-biphenyl]-3-sulfonamides

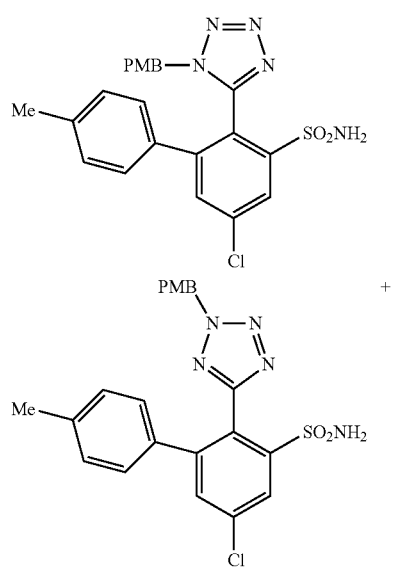

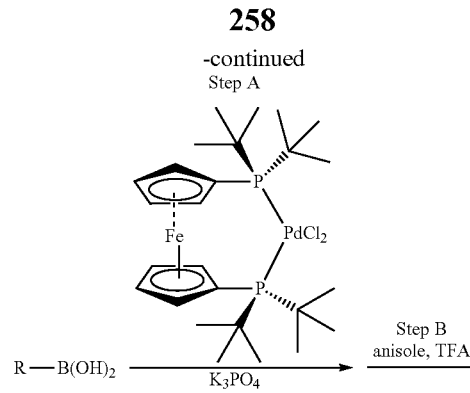

-continued
Step A

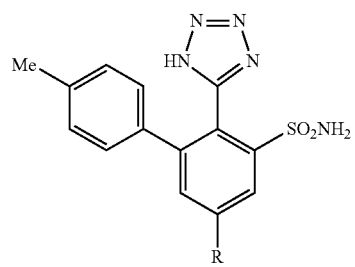

Step A: Palladium Catalyzed C—C Coupling of Arylbromide and Boronic Acids or Boronic Esters Into a mixture of boronic acid (commercially available, known, or prepared as described herein, 10.9 mg, 0.080 mmol) and 1,1'-bis(di-tert-butylphosphino) ferrocene palladium dichloride (2.08 mg, 3.19 µmol) in vials were added a solution of isomeric mixture 5-chloro-2-(1-(4-methoxybenzyl)-1H-tetrazol-5-yl)-4'-methyl-[1,1'-biphenyl]-3-sulfonamide and 5-chloro-2-(2-(4-methoxybenzyl)-2H-tetrazol-5-yl)-4'-methyl-[1,1'-biphenyl]-3-sulfonamide (25 mg, 0.053 mmol) in 2 mL of EtOH and 0.5 mL of THF, followed by a 1.0 M solution of potassium phosphate (0.213 mL, 0.213 mmol). The mixtures were heated at 70° C. for 18 hr. The solvent was removed under reduced pressure. Into the residue in each vial was added 800 µL of water and 2.4 mL of ethyl acetate. The organic layers were transferred into 2 dram vials and the solvent was removed under reduced pressure.

Step B: Removal of the p-methoxybenzyl (PMB) Protecting Group Under Acidic Conditions Into the residues were added a mixture of TFA (0.6 mL, 0.053 mmol) and anisole (58 mg) in 0.4 mL of DCM. The mixtures were heated at 50° C. for 20 hr. After cooling to room temperature, the solvent was removed under reduced pressure. The residue was dissolved in 1.4 mL of DMSO. The crude solution was filtered through a filter plate. These crude materials were purified by HPLC to afford Examples 291-296.

| Ex. No. | Structure | Name | Calc'd Mass [M + H]+ | LC/MS m/e [M + H]+ |
|---|---|---|---|---|
| 291 | 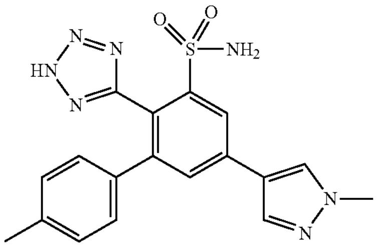 | 4'-methyl-5-(1-methyl-1H-pyrazol-4-yl)-2-(2H-tetrazol-5-yl)-[1,1'-biphenyl]-3-sulfonamide | 396 | 396 |
| 292 | 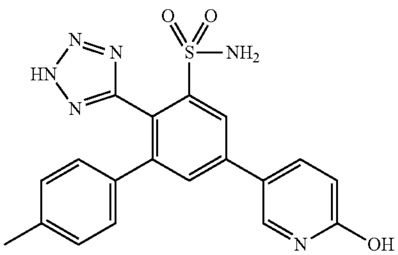 [SMILES: Cc1ccc(-c2cc(-c3ccc(O)nc3)cc(S(N)(=O)=O)c2-c2nn[nH]n2)cc1] | 5-(6-hydroxypyridin-3-yl)-4'-methyl-2-(2H-tetrazol-5-yl)-[1,1'-biphenyl]-3-sulfonamide | 409 | 409 |
| 293 | 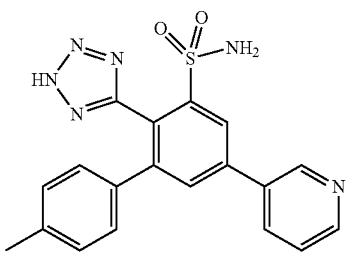 [SMILES: Cc1ccc(-c2cc(-c3cccnc3)cc(S(N)(=O)=O)c2-c2nn[nH]n2)cc1] | 4'-methyl-5-(pyridin-3-yl)-2-(2H-tetrazol-5-yl)-[1,1'-biphenyl]-3-sulfonamide | 393 | 393 |
| 294 | 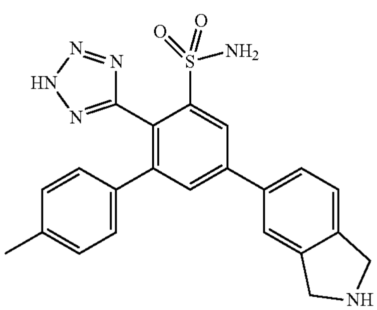 [SMILES: Cc1ccc(-c2cc(-c3ccc4c(c3)CNC4)cc(S(N)(=O)=O)c2-c2nn[nH]n2)cc1] | 5-(isoindolin-5-yl)-4'-methyl-2-(2H-tetrazol-5-yl)-[1,1'-biphenyl]-3-sulfonamide | 433 | 433 |
| 295 | 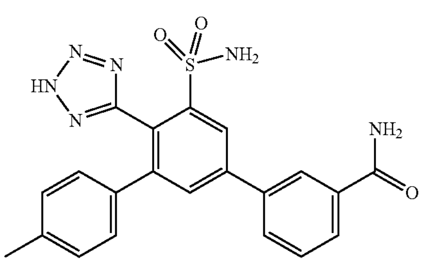 [SMILES: Cc1ccc(-c2cc(-c3cccc(C(N)=O)c3)cc(S(N)(=O)=O)c2-c2nn[nH]n2)cc1] | 4''-methyl-5'-sulfamoyl-4'-(2H-tetrazol-5-yl)-[1,1':3',1''-terphenyl]-3-carboxamide | 435 | 435 |

-continued

| Ex. No. | Structure | Name | Calc'd Mass [M + H]+ | LC/MS m/e [M + H]+ |
|---|---|---|---|---|
| 296 | 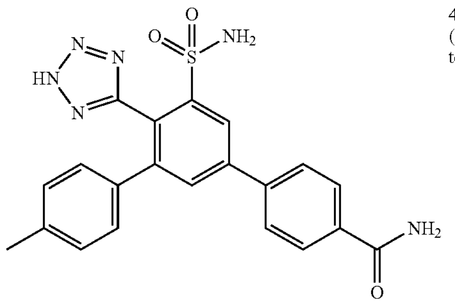 | 4''-methyl-5'-sulfamoyl-4'-(2H-tetrazol-5-yl)-[1,1':3',1''-terphenyl]-4-carboxamide | 435 | 435 |

EXAMPLE 297

3-Sulfamoyl-2-(2H-tetrazol-5-yl)benzoic acid

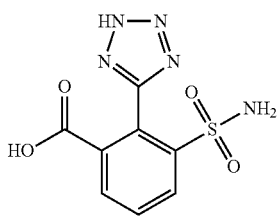 [SMILES: NS(=O)(=O)c1cccc(C(=O)O)c1-c1nn[nH]n1]

Step A: 3-Cyano-2-(2-(4-methoxybenzyl)-2H-tetrazol-5-yl) benzenesulfonamide

The mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide amide (650 mg, 1.532 mmol) was dissolved in DMA (7660 μL). Zinc cyanide (360 mg, 3.06 mmol) was added and the reaction was sparged with N₂ for 5 min. Tetrakis(triphenylphosphine)palladium(0) (354 mg, 0.306 mmol) was added and the reaction mixture was heated to 110° C. overnight. The crude reaction mixture was diluted with water and EtOAc. The aqueous phase was extracted with EtOAc (×2) and the combined extracts were washed with brine, dried over Na₂SO₄, filtered, and concentrated. The residue was purified by MPLC on a 80 g silica column eluted with 10% to 100% EtOAc in hexane. The solution was concentrated to provide 3-cyano-2-(2-(4-methoxybenzyl)-2H-tetrazol-5-yl) benzenesulfonamide. LC-MS: calculated for C₁₆H₁₄N₆O₃SC₂₈H₃₃N₉O₅S 370.1; observed m/e: 371.3 (M+H)+ (Rt 0.9/2 min)

Step B: 3-Sulfamoyl-2-(2H-tetrazol-5-yl)benzoic acid 3-cyano-2-(2-(4-methoxybenzyl)-2H-tetrazol-5-yl)benzenesulfonamide (50 mg, 0.135 mmol) was dissolved in dioxane (675 μl), MeOH (675 μl), and NaOH (225 μl, 1.350 mmol) was added. The reaction mixture was then heated to 90° C. overnight. TFA (104 μl, 1.350 mmol) was added and the reaction was concentrate to provide a white solid. The white solid was dissolved in 2 mL TFA and heated to 45° C. overnight then concentrated. The residue was purified by reverse phase HPLC with Phenomenex Polar-RP column eluted with 0% to 50% MeCN in water. The major UV active material was lyopholized to provide 3-sulfamoyl-2-(2H-tetrazol-5-yl)benzoic acid. LC-MS: calculated for C₈H₇N₅O₄S 269.0; observed m/e: 270.2 (M)+; ¹H NMR δ (ppm) (MeOH): 8.38-8.35 (m, 2H), 7.89 (t, 1H).

EXAMPLE 298

3-(6-Aminopyridin-3-yl)-2-(1H-tetrazol-5-yl)benzene sulfonamide, TFA salt

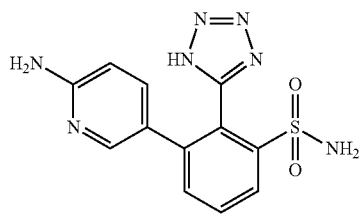 [SMILES: Nc1ccc(-c2cccc(S(N)(=O)=O)c2-c2nnn[nH]2)cn1]

Step A: 3-(6-Aminopyridin-3-yl)-1-(and 2-)(4-methoxybenzyl)-2-(1H-tetrazol-5-yl)benzene sulfonamide A 20 mL microwave reaction vial was charged with a mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (200 mg, 0.471 mmol), (6-aminopyridin-3-yl)boronic acid hydrochloride (164 mg, 0.943 mmol), 1,1'-Bis(di-tert-butylphosphino)ferrocene palladium (38.5 mg, 0.047 mmol), potassium carbonate (saturated aqueous solution, 3 mL, 0.471 mmol) and ethanol (8 mL). The vial was capped, and the reaction was heated to 120° C. for 20 minutes in a microwave. The excess catalyst was filtered off and the reaction was concentrated. The residue was purified by normal phase ISCO on a 24 g column eluted with 0% to 100% ethyl acetate in hexane. The pure fractions were concentrated to afford a mixture of 3-(6-aminopyridin-3-yl)-1-(and 2-)(4-methoxybenzyl)-2-(1H-tetrazol-5-yl)benzene sulfonamide. LC-MS: calculated for C₂₀H₁₉N₇O₃S 437.5; observed m/e: 438.4 (M+H)+.

Step B: 3-(6-Aminopyridin-3-yl)-2-(1H-tetrazol-5-yl)benzene sulfonamide, TFA salt The residue was dissolved in TFA (2 mL) and anisole (198 mg, 1.829 mmol) and heated to 45° C. via an oil bath for 18 hr. The reaction mixture was purified by reverse phase HPLC column (acetonitrile/water/0.05% TFA system) and eluted with 0% to 20% MeCN in water. The solution was concentrated to afford 3-(6-aminopyridin-3-yl)-2-(1H-tetrazol-5-yl)benzene sulfonamide, TFA salt. LC-MS: calculated for C₁₂H₁₁N₇O₂S 317.3; observed m/e: 318.3 (M+H)+; ¹H NMR δ (ppm) (MeOH): 8.27 (d, 1H), 7.89 (t, 1H), 7.8 (d, 1H), 7.63 (d, 1H), 7.52-7.56 (m, 1H), 6.87 (d, 1H).

EXAMPLES 299-316

The following Examples 299-316 were prepared from the mixture of 3-bromo-2-(1-(and 2-)(4-methoxybenzyl)-2H-tetrazol-5-yl)benzenesulfonamide and the appropriate substituted aryl or heteroaryl boronic acid esters (from commercially available sources or prepared as described herein) according to the method described in Example 298 (except that boronic esters are used in place of the boronic acid).

| Ex. No. | Structure | Name | Calc'd. Mass [M + H]⁺ | LC/MS m/e (M + H)⁺ |
|---|---|---|---|---|
| 299 | 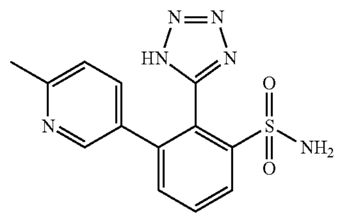 [SMILES: Cc1ccc(-c2cccc(S(N)(=O)=O)c2-c2nnn[nH]2)cn1] | 3-(6-methylpyridin-3-yl)-2-(1H-tetrazol-5-yl)benzenesulfonamide | 317.3 | 317.2 |
| 300 | 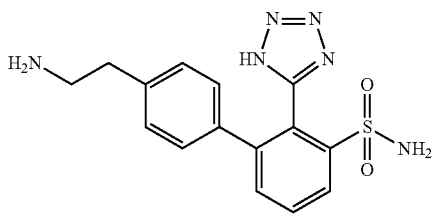 [SMILES: NCCc1ccc(-c2cccc(S(N)(=O)=O)c2-c2nnn[nH]2)cc1] | 4'-(2-aminoethyl)-2-(1H-tetrazol-5-yl)-[1,1'-biphenyl]-3-sulfonamide | 345.4 | 345.3 |
| 301 | 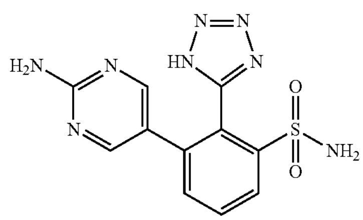 [SMILES: Nc1ncc(-c2cccc(S(N)(=O)=O)c2-c2nnn[nH]2)cn1] | 3-(2-aminopyrimidin-5-yl)-2-(1H-tetrazol-5-yl)benzenesulfonamide | 319.3 | 319.3 |
| 302 | 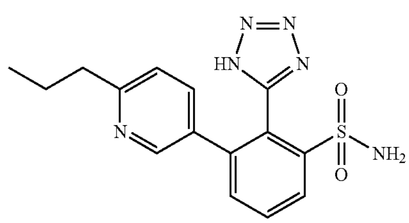 | 3-(6-propylpyridin-3-yl)-2-(1H-tetrazol-5-yl)benzenesulfonamide | 345.4 | 345.3 |
| 303 | 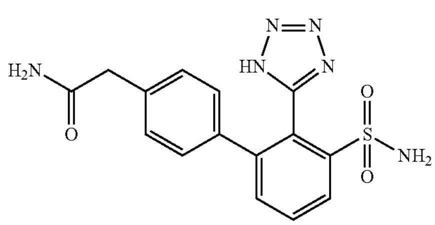 [SMILES: NC(=O)Cc1ccc(-c2cccc(S(N)(=O)=O)c2-c2nnn[nH]2)cc1] | 2-(3'-sulfamoyl-2'-(1H-tetrazol-5-yl)-[1,1'-biphenyl]-4-yl)acetamide | 359.4 | 359.3 |
| 304 | 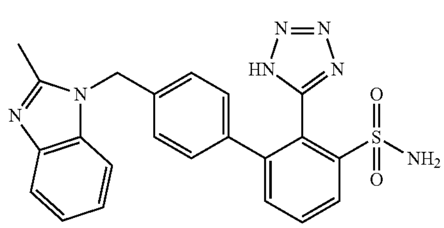 [SMILES: Cc1nc2ccccc2n1Cc1ccc(-c2cccc(S(N)(=O)=O)c2-c2nnn[nH]2)cc1] | 4'-((2-methyl-1H-benzo[d]imidazol-1-yl)methyl)-2-(1H-tetrazol-5-yl)-[1,1'-biphenyl]-3-sulfonamide | 446.5 | 446.3 |

-continued

| Ex. No. | Structure | Name | Calc'd. Mass [M + H]+ | LC/MS m/e (M + H)+ |
|---|---|---|---|---|
| 305 | 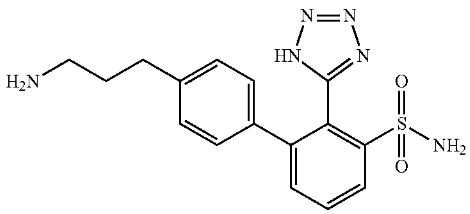 [SMILES: NCCCc1ccc(-c2cccc(S(N)(=O)=O)c2-c2nnn[nH]2)cc1] | 4'-(3-aminopropyl)-2-(1H-tetrazol-5-yl)-[1,1'-biphenyl]-3-sulfonamide | 359.4 | 359.3 |
| 306 | 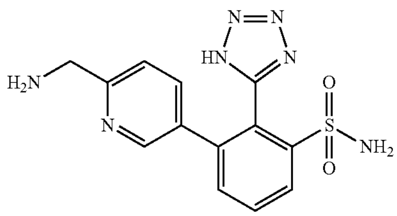 [SMILES: NCc1ccc(-c2cccc(S(N)(=O)=O)c2-c2nnn[nH]2)cn1] | 3-(6-(aminomethyl)pyridin-3-yl)-2-(1H-tetrazol-5-yl)benzenesulfonamide | 332.4 | 332.4 |
| 307 | 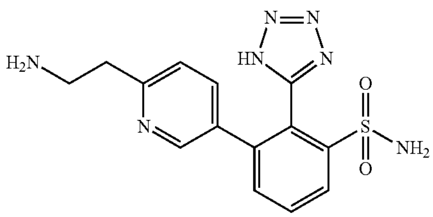 | 3-(6-(2-aminoethyl)pyridin-3-yl)-2-(1H-tetrazol-5-yl)benzenesulfonamide | 346.4 | 346.3 |
| 308 | 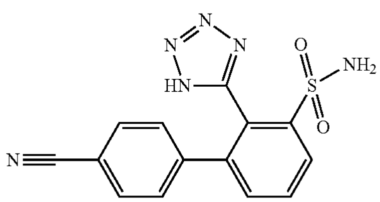 [SMILES: N#Cc1ccc(-c2cccc(S(N)(=O)=O)c2-c2nnn[nH]2)cc1] | 4'-cyano-2-(1H-tetrazol-5-yl)-[1,1'-biphenyl]-3-sulfonamide | 327 | 327 |
| 309 | 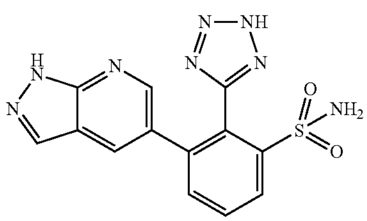 [SMILES: NS(=O)(=O)c1cccc(-c2cnc3[nH]ncc3c2)c1-c1nn[nH]n1] | 3-(1H-pyrazolo[3,4-b]pyridin-5-yl)-2-(2H-tetrazol-5-yl)benzenesulfonamide | 343 | 343 |
| 310 | 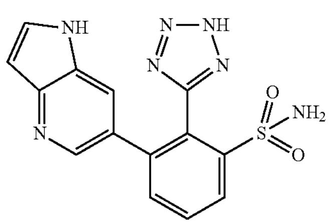 [SMILES: NS(=O)(=O)c1cccc(-c2cnc3cc[nH]c3c2)c1-c1nn[nH]n1] | 3-(1H-pyrrolo[3,2-b]pyridin-6-yl)-2-(2H-tetrazol-5-yl)benzenesulfonamide | 342 | 342 |
| 311 | 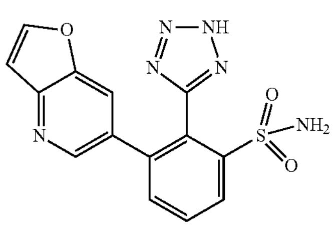 [SMILES: NS(=O)(=O)c1cccc(-c2cnc3ccoc3c2)c1-c1nn[nH]n1] | 3-(furo[3,2-b]pyridin-6-yl)-2-(2H-tetrazol-5-yl)benzenesulfonamide | 343 | 343 |

| Ex. No. | Structure | Name | Calc'd. Mass [M + H]+ | LC/MS m/e (M + H)+ |
|---|---|---|---|---|
| 312 | 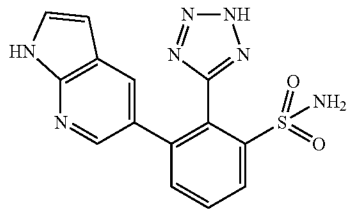 [SMILES: NS(=O)(=O)c1cccc(-c2cnc3[nH]ccc3c2)c1-c1nn[nH]n1] | 3-(1H-pyrrolo[2,3-b]pyridin-5-yl)-2-(2H-tetrazol-5-yl)benzenesulfonamide | 342 | 342 |
| 313 | 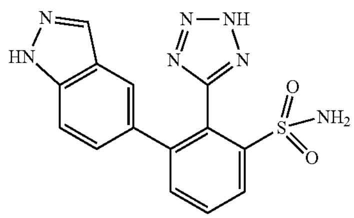 [SMILES: NS(=O)(=O)c1cccc(-c2ccc3[nH]ncc3c2)c1-c1nn[nH]n1] | 3-(1H-indazol-5-yl)-2-(2H-tetrazol-5-yl)benzenesulfonamide | 342 | 342 |
| 314 | 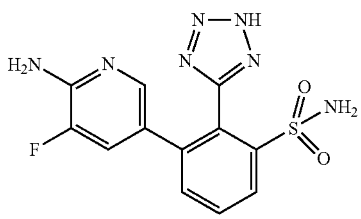 [SMILES: Nc1ncc(-c2cccc(S(N)(=O)=O)c2-c2nn[nH]n2)cc1F] | 3-(6-amino-5-fluoropyridin-3-yl)-2-(2H-tetrazol-5-yl)benzenesulfonamide | 336 | 336 |
| 315 | 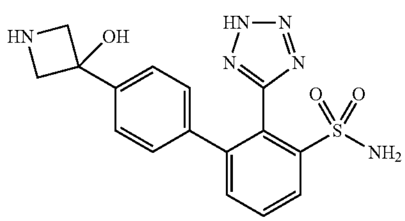 [SMILES: NS(=O)(=O)c1cccc(-c2ccc(C3(O)CNC3)cc2)c1-c1nn[nH]n1] | 4'-(3-hydroxyazetidin-3-yl)-2-(2H-tetrazol-5-yl)-[1,1'-biphenyl]-3-sulfonamide | 373 | 373 |
| 316 | 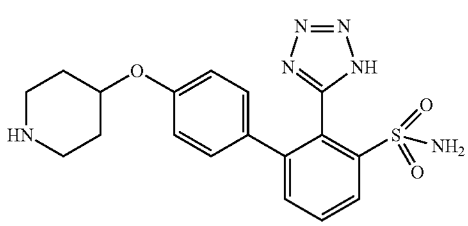 [SMILES: NS(=O)(=O)c1cccc(-c2ccc(OC3CCNCC3)cc2)c1-c1nnn[nH]1] | 4'-(piperidin-4-yloxy)-2-(1H-tetrazol-5-yl)-[1,1'-biphenyl]-3-sulfonamide | 401 | 401 |

EXAMPLES 317-319

The following Examples 317-319 were prepared from the mixture of 3-bromo-2-(1-(and 2-)(4-methoxybenzyl)-2H-tetrazol-5-yl)benzenesulfonamide and the appropriate substituted aryl or heteroaryl boronic acids (from commercially available sources or prepared as described herein) according to the method described in Example 298.

| Ex. No. | Structure | Name | Calc'd. MW [M + H]+ | LC/MS m/e (M + H)+ |
|---|---|---|---|---|
| 317 | 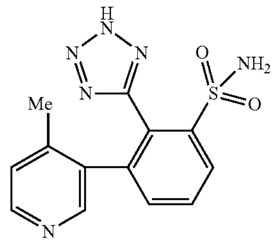 [SMILES: Cc1ccncc1-c1cccc(S(N)(=O)=O)c1-c1nn[nH]n1] | 3-(4-methylpyridin-3-yl)-2-(2H-tetrazol-5-yl)benzenesulfonamide | 317 | 317 |
| 318 | 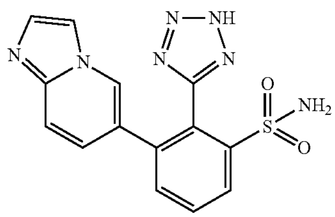 [SMILES: NS(=O)(=O)c1cccc(-c2ccc3nccn3c2)c1-c1nn[nH]n1] | 3-(imidazo[1,2-a]pyridin-6-yl)-2-(2H-tetrazol-5-yl)benzenesulfonamide | 342 | 342 |
| 319 | 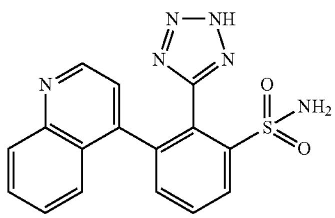 [SMILES: NS(=O)(=O)c1cccc(-c2ccnc3ccccc23)c1-c1nn[nH]n1] | 3-(quinolin-4-yl)-2-(2H-tetrazol-5-yl)benzenesulfonamide | 353 | 353 |

EXAMPLE 320

3-(2-(Piperazin-1-yl)pyrimidin-5-yl)-2-(2H-tetrazol-5-yl)benzenesulfonamide

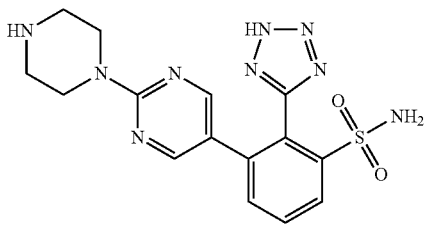 [SMILES: NS(=O)(=O)c1cccc(-c2cnc(N3CCNCC3)nc2)c1-c1nn[nH]n1]

Step A: 3-(2-(Piperazin-1-yl)pyrimidin-5-yl)-2-(1-(and 2-)2-(4-methoxybenzyl)-2H-tetrazol-5-yl)benzenesulfonamide A microwave reaction vial was charged with tert-butyl 4-(5-(4,4,5,5-tetramethyl-1,3,2-dioxaborolan-2-yl)pyrimidin-2-yl)piperazine-1-carboxylate (259 mg, 0.663 mmol) and a mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (225 mg, 0.530 mmol). EtOH (5303 µl) and potassium phosphate tribasic (1 M aq. solution, 1591 µL, 1.591 mmol) were added and the reaction mixture was sparged with N₂ for 10 min. 1,1'-bis(di-tert-butylphosphino)ferrocene palladium dichloride (34.6 mg, 0.053 mmol) was added and the reaction vessel was sealed and heated to 100° C. for 1 hr in a microwave. The crude reaction mixture was diluted with water and EtOAc. The organic was washed with brine, dried over Na₂SO₄, filtered and concentrated. The residue was purified by reverse phase HPLC on a C18 column eluted with 5% to 90% MeCN in water with 0.05% TFA. The solution was concentrated to provide a mixture of 3-(2-(piperazin-1-yl)pyrimidin-5-yl)-2-(1-(and 2-)2-(4-methoxybenzyl)-2H-tetrazol-5-yl)benzenesulfonamide. LC-MS: calculated for C₂₈H₃₃N₉O₅S 607.2; observed m/e: 608.6 (M+H)+;

Step B: 3-(2-(Piperazin-1-yl)pyrimidin-5-yl)-2-(2H-tetrazol-5-yl)benzenesulfonamide The mixture of 3-(2-(piperazin-1-yl)pyrimidin-5-yl)-2-(1-(and 2-)2-(4-methoxybenzyl)-2H-tetrazol-5-yl)benzenesulfonamide was dissolved in TFA (2 mL) and anisole (200 µL) and heated to 45° C. overnight. Purification by reverse phase HPLC with Phenomenex Polar RP column eluted with 0% to 80% MeCN in water. The solution was lyopholized to provide the title compound. LC-MS: calculated for C₁₅H₁₂N₉O₂S 387.4; observed m/e: 387.4 (M+H)+; ¹HNMR δ (ppm) (DMSO): 8.75 (br s, 1H), 8.05-8.03 (m, 1H), 7.98 (s, 2H), 7.81 (br s, 1H), 7.70-7.69 (m, 1H), 3.90 (t, 2H), 3.17 (t, 2H).

EXAMPLES 321-326

The following Examples 321-326 were prepared from the mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide and the appropriate substituted aryl boronic acid esters (from commercially available sources or prepared as described herein) according to the method described in Example 320.

| Ex. No. | Structure | Name | Calc'd. MW [M + H]+ | LC/MS m/e (M + H)+ |
|---|---|---|---|---|
| 321 | 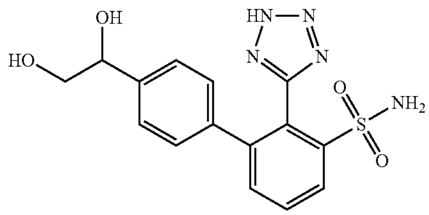 [SMILES: NS(=O)(=O)c1cccc(-c2ccc(C(O)CO)cc2)c1-c1nn[nH]n1] | 4'-(1,2-dihydroxyethyl)-2-(2H-tetrazol-5-yl)-[1,1'-biphenyl]-3-sulfonamide | 362.4 | 362.2 |
| 322 | 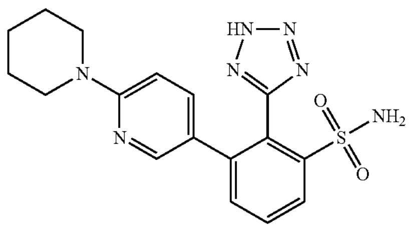 [SMILES: NS(=O)(=O)c1cccc(-c2ccc(N3CCCCC3)nc2)c1-c1nn[nH]n1] | 3-(6-(piperidin-1-yl)pyridin-3-yl)-2-(2H-tetrazol-5-yl)benzenesulfonamide | 386.5 | 386.3 |
| 323 | 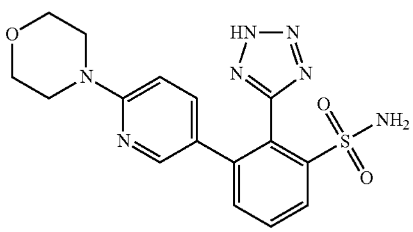 [SMILES: NS(=O)(=O)c1cccc(-c2ccc(N3CCOCC3)nc2)c1-c1nn[nH]n1] | 3-(6-morpholinopyridin-3-yl)-2-(2H-tetrazol-5-yl)benzenesulfonamide | 388.4 | 388.3 |
| 324 | 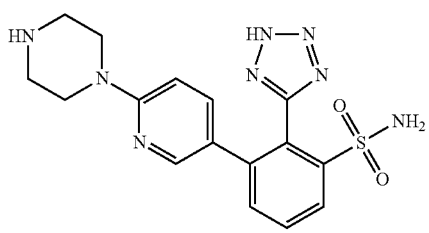 | 3-(6-(piperazin-1-yl)pyridin-3-yl)-2-(2H-tetrazol-5-yl)benzenesulfonamide | 387.4 | 387.3 |
| 325 | 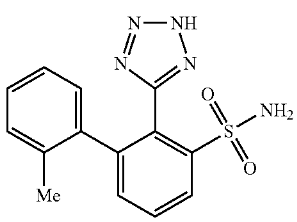 [SMILES: Cc1ccccc1-c1cccc(S(N)(=O)=O)c1-c1nn[nH]n1] | 2'-methyl-2-(2H-tetrazol-5-yl)-[1,1'-biphenyl]-3-sulfonamide | 316.4 | 316.3 |
| 326 | 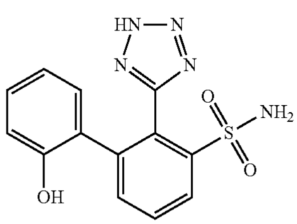 [SMILES: NS(=O)(=O)c1cccc(-c2ccccc2O)c1-c1nn[nH]n1] | 2'-hydroxy-2-(2H-tetrazol-5-yl)-[1,1'-biphenyl]-3-sulfonamide | 318.3 | 318.2 |

EXAMPLE 327

4'-((Dimethylamino)methyl)-2-(1H-tetrazol-5-yl)-[1,1'-biphenyl]-3-sulfonamide, TFA salt

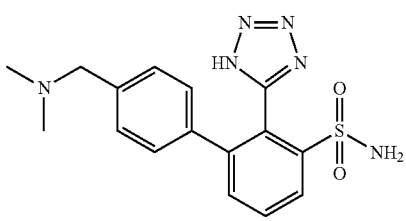 [SMILES: CN(C)Cc1ccc(-c2cccc(S(N)(=O)=O)c2-c2nnn[nH]2)cc1]

Step A: 4'-((Dimethylamino)methyl)-2-(1-(and 2-)(4-methoxybenzyl)-2-(1H-tetrazol-5-yl)-[1,1'-biphenyl]-3-sulfonamide A 40 mL reaction vial was charged with the mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (35 mg, 0.082 mmol), (4-((dimethylamino)methyl)phenyl)boronic acid (44.3 mg, 0.247 mmol), potassium phosphate (52.5 mg, 0.247 mmol), diacetoxypalladium (5.56 mg, 0.025 mmol) and SPhos-Pd-G2 (20.32 mg, 0.049 mmol). The vial was capped via a red sure-seal cap, and the reaction was degassed via vacuum/nitrogen flushes (line with needle from manifold). THF (4 mL) was added via syringe, and again, the reaction was degassed via vacuum/nitrogen flushes. The reaction stirred at room temp for 15 minutes, and was then heated at 90° C. via an oil bath for 18 hours. The excess catalyst was filtered off and the reaction was concentrated, and then purified by reverse phase HPLC column (acetonitrile/water/0.05% TFA system) and eluted with 5% to 100% MeCN in water. The solution was concentrated to afford product. LC-MS: calculated for $C_{24}H_{26}N_6O_3S$ 478.6; observed m/e: 479.2 (M+H)$^+$ (Rt 0.79/2 min).

Step B: 4'-((Dimethylamino)methyl)-2-(1H-tetrazol-5-yl)-[1,1'-biphenyl]-3-sulfonamide, TFA salt The residue was dissolved in TFA (500 μL) and anisole (7.23 mg, 0.067 mmol) and heated to 45° C. for 18 hr. The reaction mixture was purified by reverse phase HPLC column (acetonitrile/water/0.05% TFA system) and eluted with 0% to 20% MeCN in water. The solution was concentrated to afford 4'-((dimethylamino)methyl)-2-(1H-tetrazol-5-yl)-[1,1'-biphenyl]-3-sulfonamide, TFA salt. LC-MS: calculated for $C_{16}H_{18}N_6O_2S$ 358.4; observed m/e: 359.3 (M+H)$^+$; $^1$H NMR δ (ppm) (MeOH): 8.24 (d, 1H), 7.88 (t, 1H), 7.78 (d, 1H), 7.40 (d, 2H), 7.22 (d, 2H), 4.26 (s, 2H), 2.80 (s, 6H).

EXAMPLES 328-396

Parallel Synthesis of 4'-(aminomethyl)-2-(1H-tetrazol-5-yl)-[1,1'-biphenyl]-3-sulfonamides by Reductive Amination Reaction

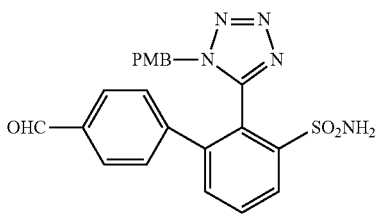

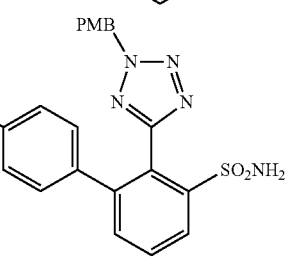

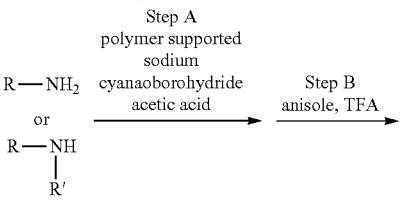

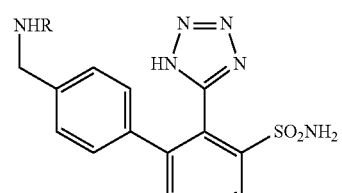

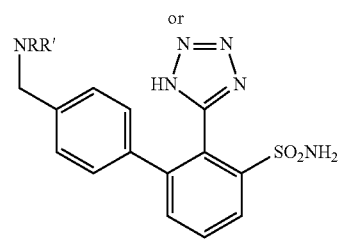

Step A: Reductive Amination of the Isomer Mixture 4'-formyl-2-(1-(4-methoxybenzyl)-1H-tetrazol-5-yl)-[1,1'-biphenyl]-3-sulfonamide and 4'-formyl-2-(2-(4-methoxybenzyl)-2H-tetrazol-5-yl)-[1,1'-biphenyl]-3-sulfonamide (Reference Example 13) with Primary and Secondary Amines 4'-formyl-2-(1-(4-methoxybenzyl)-1H-tetrazol-5-yl)-[1,1'-biphenyl]-3-sulfonamide and 4'-formyl-2-(2-(4-methoxybenzyl)-2H-tetrazol-5-yl)-[1,1'-biphenyl]-3-sulfonamide (Reference Example 13) (25 mg, 0.056 mmol) and commercially available primary and secondary amines (0.111 mmol) in MeOH (0.5 mL) and tetrahydrofuran (0.5 mL) were treated with acetic acid (0.016 mL, 0.278 mmol). An excess of polymer supported sodium cyanaoborohydride was added and the mixtures were stirred for 18 hours. The mixtures were filtered and the filtrates were concentrated.

Step B: Removal of the PMB Protective Group Under Acidic Conditions

To remove the PMB protecting group the residues from Step A were each dissolved in TFA (0.5 mL) and treated with Anisole (0.018 mL, 0.167 mmol). The mixtures were stirred at 50° C. for 18 hours. The mixtures were concentrated under reduced pressure. DMSO (1 mL) was added to each crude product and the mixtures were filtered through a 0.4 micron filter. Purification by mass directed reverse phase HPLC afforded Examples 330-398.

| Ex. No. | Structure | Name | Calc'd. MW [M + H]+ | LC/MS m/e (M + H)+ |
|---|---|---|---|---|
| 328 | 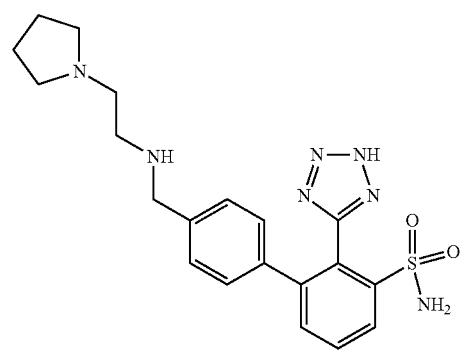 [SMILES: NS(=O)(=O)c1cccc(-c2ccc(CNCCN3CCCC3)cc2)c1-c1nn[nH]n1] | 4'-(((2-(pyrrolidin-1-yl)ethyl)amino)methyl)-2-(2H-tetrazol-5-yl)-[1,1'-biphenyl]-3-sulfonamide | 428 | 428 |
| 329 | 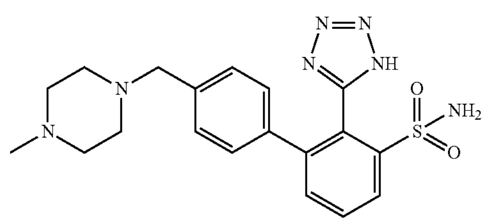 [SMILES: CN1CCN(Cc2ccc(-c3cccc(S(N)(=O)=O)c3-c3nnn[nH]3)cc2)CC1] | 4'-((4-methylpiperazin-1-yl)methyl)-2-(1H-tetrazol-5-yl)-[1,1'-biphenyl]-3-sulfonamide | 414 | 414 |
| 330 | 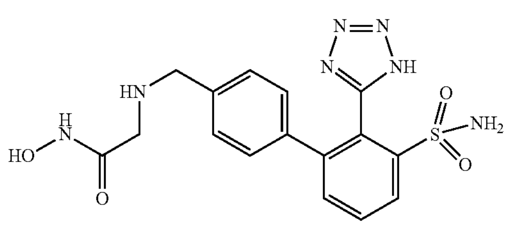 [SMILES: NS(=O)(=O)c1cccc(-c2ccc(CNCC(=O)NO)cc2)c1-c1nnn[nH]1] | N-hydroxy-2-(((3'-sulfamoyl-2'-(1H-tetrazol-5-yl)-[1,1'-biphenyl]-4-yl)methyl)amino)acetamide | 404 | 404 |
| 331 | 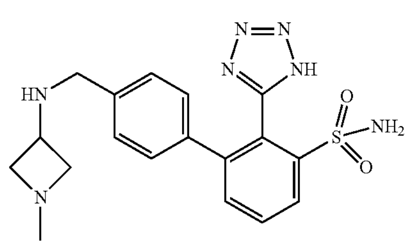 [SMILES: CN1CC(NCc2ccc(-c3cccc(S(N)(=O)=O)c3-c3nnn[nH]3)cc2)C1] | 4'-(((1-methylazetidin-3-yl)amino)methyl)-2-(1H-tetrazol-5-yl)-[1,1'-biphenyl]-3-sulfonamide | 400 | 400 |
| 332 | 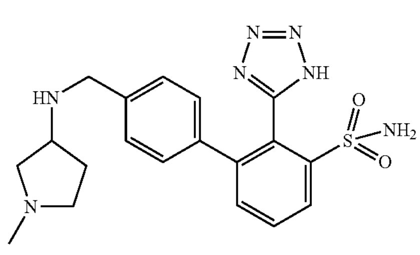 [SMILES: CN1CCC(NCc2ccc(-c3cccc(S(N)(=O)=O)c3-c3nnn[nH]3)cc2)C1] | 4'-(((1-methylpyrrolidin-3-yl)amino)methyl)-2-(1H-tetrazol-5-yl)-[1,1'-biphenyl]-3-sulfonamide | 414 | 414 |

-continued

| Ex. No. | Structure | Name | Calc'd. MW [M + H]+ | LC/MS m/e (M + H)+ |
|---|---|---|---|---|
| 333 | 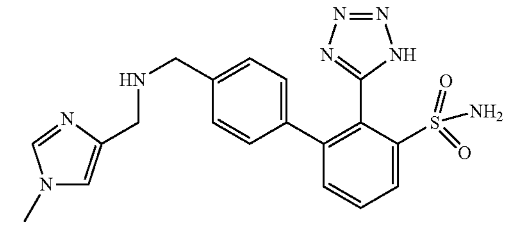 [SMILES: Cn1cnc(CNCc2ccc(-c3cccc(S(N)(=O)=O)c3-c3nnn[nH]3)cc2)c1] | 4'-((((1-methyl-1H-imidazol-4-yl)methyl)amino)methyl)-2-(1H-tetrazol-5-yl)-[1,1'-biphenyl]-3-sulfonamide | 425 | 425 |
| 334 | 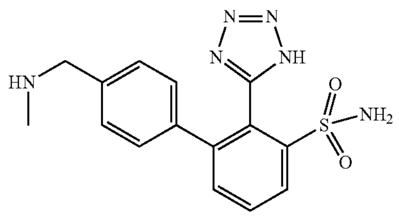 [SMILES: CNCc1ccc(-c2cccc(S(N)(=O)=O)c2-c2nnn[nH]2)cc1] | 4'-((methylamino)methyl)-2-(1H-tetrazol-5-yl)-[1,1'-biphenyl]-3-sulfonamide | 345 | 345 |
| 335 | 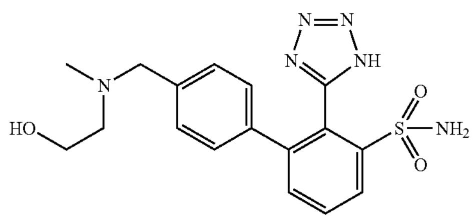 [SMILES: CN(CCO)Cc1ccc(-c2cccc(S(N)(=O)=O)c2-c2nnn[nH]2)cc1] | 4'-(((2-hydroxyethyl)(methyl)amino)methyl)-2-(1H-tetrazol-5-yl)-[1,1'-biphenyl]-3-sulfonamide | 389 | 389 |
| 336 | 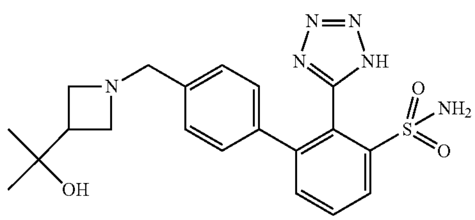 [SMILES: CC(C)(O)C1CN(Cc2ccc(-c3cccc(S(N)(=O)=O)c3-c3nnn[nH]3)cc2)C1] | 4'-((3-(2-hydroxypropan-2-yl)azetidin-1-yl)methyl)-2-(1H-tetrazol-5-yl)-[1,1'-biphenyl]-3-sulfonamide | 429 | 429 |
| 337 | 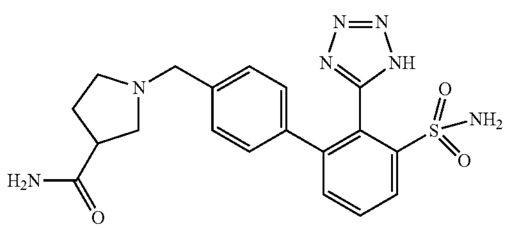 [SMILES: NC(=O)C1CCN(Cc2ccc(-c3cccc(S(N)(=O)=O)c3-c3nnn[nH]3)cc2)C1] | 1-((3'-sulfamoyl-2'-(1H-tetrazol-5-yl)-[1,1'-biphenyl]-4-yl)methyl)pyrrolidine-3-carboxamide | 428 | 428 |
| 338 | 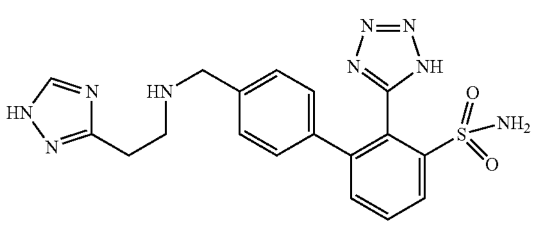 [SMILES: NS(=O)(=O)c1cccc(-c2ccc(CNCCc3nc[nH]n3)cc2)c1-c1nnn[nH]1] | 4'-(((2-(1H-1,2,4-triazol-3-yl)ethyl)amino)methyl)-2-(1H-tetrazol-5-yl)-[1,1'-biphenyl]-3-sulfonamide | 426 | 426 |
| 339 | 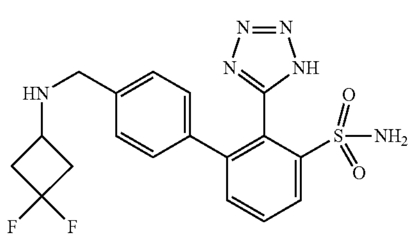 [SMILES: NS(=O)(=O)c1cccc(-c2ccc(CNC3CC(F)(F)C3)cc2)c1-c1nnn[nH]1] | 4'-(((3,3-difluorocyclobutyl)amino)methyl)-2-(1H-tetrazol-5-yl)-[1,1'-biphenyl]-3-sulfonamide | 421 | 421 |

-continued

| Ex. No. | Structure | Name | Calc'd. MW [M + H]⁺ | LC/MS m/e (M + H)⁺ |
|---|---|---|---|---|
| 340 | 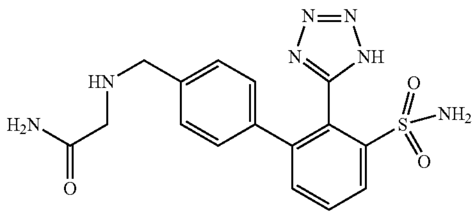 [SMILES: NC(=O)CNCc1ccc(-c2cccc(S(N)(=O)=O)c2-c2nnn[nH]2)cc1] | 2-(((3'-sulfamoyl-2'-(1H-tetrazol-5-yl)-[1,1'-biphenyl]-4-yl)methyl)amino)acetamide | 388 | 388 |
| 341 | 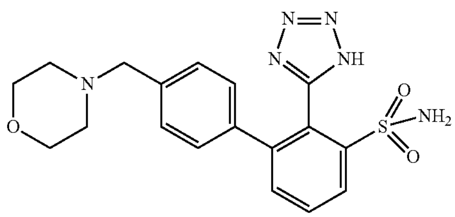 [SMILES: NS(=O)(=O)c1cccc(-c2ccc(CN3CCOCC3)cc2)c1-c1nnn[nH]1] | 4'-(morpholin-4-ylmethyl)-2-(1H-tetrazol-5-yl)biphenyl-3-sulfonamide | 401 | 401 |
| 342 | 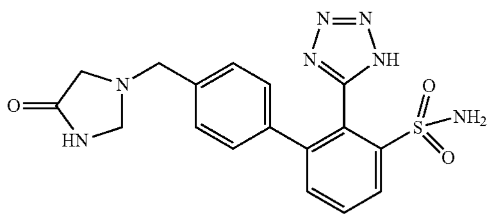 [SMILES: NS(=O)(=O)c1cccc(-c2ccc(CN3CNC(=O)C3)cc2)c1-c1nnn[nH]1] | 4'-[(4-oxoimidazolidin-1-yl)methyl]-2-(1H-tetrazol-5-yl)biphenyl-3-sulfonamide | 400 | 400 |
| 343 | 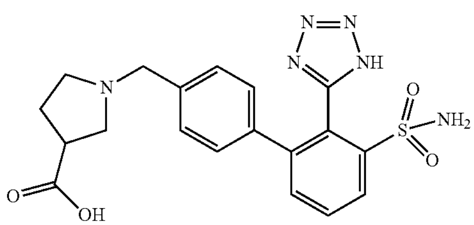 [SMILES: NS(=O)(=O)c1cccc(-c2ccc(CN3CCC(C(=O)O)C3)cc2)c1-c1nnn[nH]1] | 1-{[3'-sulfamoyl-2'-(1H-tetrazol-5-yl)biphenyl-4-yl]methyl}pyrrolidine-3-carboxylic acid | 429 | 429 |
| 344 | 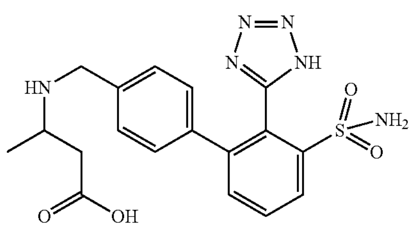 [SMILES: CC(CC(=O)O)NCc1ccc(-c2cccc(S(N)(=O)=O)c2-c2nnn[nH]2)cc1] | 3-({[3'-sulfamoyl-2'-(1H-tetrazol-5-yl)biphenyl-4-yl]methyl}amino)butanoic acid | 417 | 417 |
| 345 | 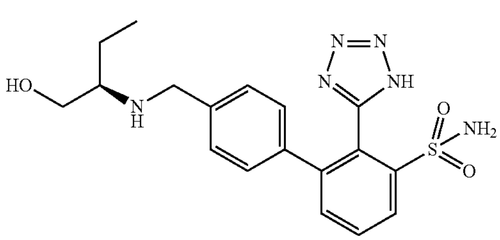 [SMILES: CC[C@H](CO)NCc1ccc(-c2cccc(S(N)(=O)=O)c2-c2nnn[nH]2)cc1] | 4'-({[(1S)-1-(hydroxymethyl)propyl]amino}methyl)-2-(1H-tetrazol-5-yl)biphenyl-3-sulfonamide | 403 | 403 |

| Ex. No. | Structure | Name | Calc'd. MW [M + H]+ | LC/MS m/e (M + H)+ |
|---|---|---|---|---|
| 346 | 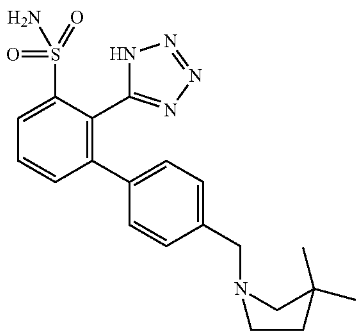 [SMILES: CC1(C)CCN(Cc2ccc(-c3cccc(S(N)(=O)=O)c3-c3nnn[nH]3)cc2)C1] | 4'-[(3,3-dimethylpyrrolidin-1-yl)methyl]-2-(1H-tetrazol-5-yl)biphenyl-3-sulfonamide | 413 | 413 |
| 347 | 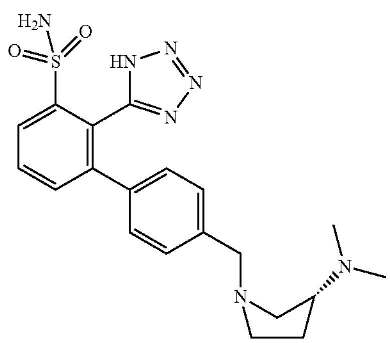 | 4'-{[(3R)-3-(dimethylamino)pyrrolidin-1-yl]methyl}-2-(1H-tetrazol-5-yl)biphenyl-3-sulfonamide | 428 | 428 |
| 348 | 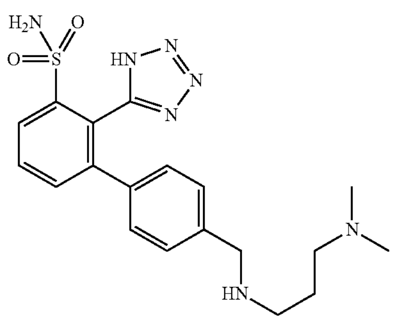 [SMILES: CN(C)CCCNCc1ccc(-c2cccc(S(N)(=O)=O)c2-c2nnn[nH]2)cc1] | 4'-({[3-(dimethylamino)propyl]amino}methyl)-2-(1H-tetrazol-5-yl)biphenyl-3-sulfonamide | 416 | 416 |
| 349 | 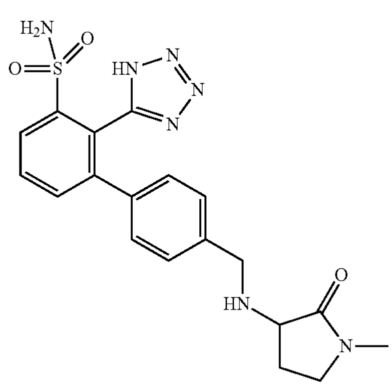 [SMILES: CN1CCC(NCc2ccc(-c3cccc(S(N)(=O)=O)c3-c3nnn[nH]3)cc2)C1=O] | 4'-{[(1-methyl-2-oxopyrrolidin-3-yl)amino]methyl}-2-(1H-tetrazol-5-yl)biphenyl-3-sulfonamide | 428 | 428 |

-continued

| Ex. No. | Structure | Name | Calc'd. MW [M + H]+ | LC/MS m/e (M + H)+ |
|---|---|---|---|---|
| 350 | 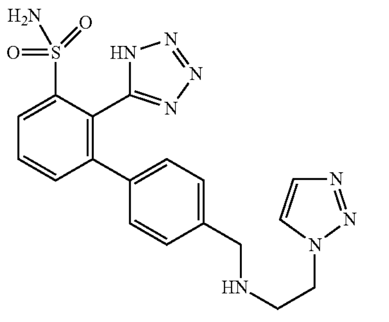 [SMILES: NS(=O)(=O)c1cccc(-c2ccc(CNCCn3ccnn3)cc2)c1-c1nnn[nH]1] | 2-(1H-tetrazol-5-yl)-4'-({[2-(1H-1,2,3-triazol-1-yl)ethyl]amino}methyl) biphenyl-3-sulfonamide | 426 | 426 |
| 351 | 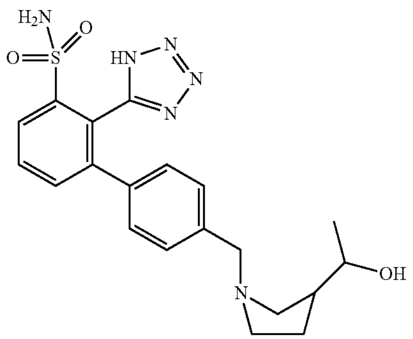 [SMILES: CC(O)C1CCN(Cc2ccc(-c3cccc(S(N)(=O)=O)c3-c3nnn[nH]3)cc2)C1] | 4'-{[3-(1-hydroxyethyl)pyrrolidin-1-yl]methyl}-2-(1H-tetrazol-5-yl)biphenyl-3-sulfonamide | 429 | 429 |
| 352 | 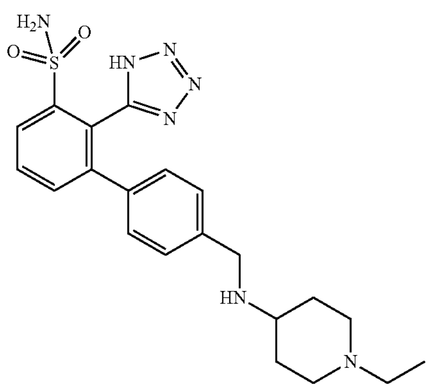 [SMILES: CCN1CCC(NCc2ccc(-c3cccc(S(N)(=O)=O)c3-c3nnn[nH]3)cc2)CC1] | 4'-{[(1-ethylpiperidin-4-yl)amino]methyl}-2-(1H-tetrazol-5-yl)biphenyl-3-sulfonamide | 442 | 442 |
| 353 | 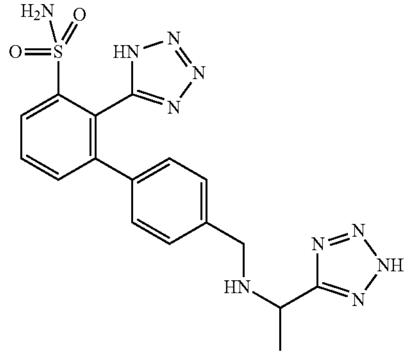 [SMILES: CC(NCc1ccc(-c2cccc(S(N)(=O)=O)c2-c2nnn[nH]2)cc1)c1nn[nH]n1] | 2-(1H-tetrazol-5-yl)-4'-({[1-(2H-tetrazol-5-yl)ethyl]amino}methyl) biphenyl-3-sulfonamide | 427 | 427 |

| Ex. No. | Structure | Name | Calc'd. MW [M + H]+ | LC/MS m/e (M + H)+ |
|---|---|---|---|---|
| 354 | 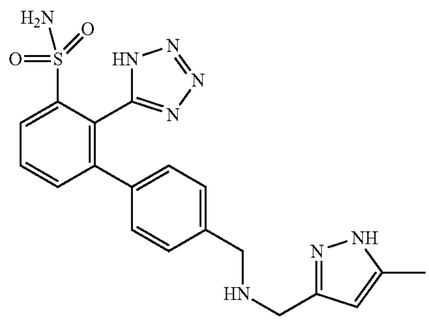 [SMILES: Cc1cc(CNCc2ccc(-c3cccc(S(N)(=O)=O)c3-c3nnn[nH]3)cc2)n[nH]1] | 4'-({[(5-methyl-1H-pyrazol-3-yl)methyl]amino}methyl)-2-(1H-tetrazol-5-yl)biphenyl-3-sulfonamide | 425 | 425 |
| 355 | 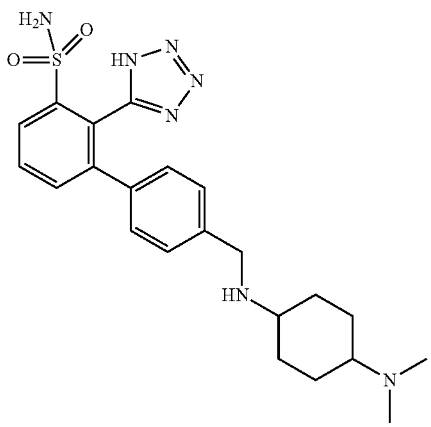 [SMILES: CN(C)C1CCC(NCc2ccc(-c3cccc(S(N)(=O)=O)c3-c3nnn[nH]3)cc2)CC1] | 4'-({[4-(dimethylamino)cyclohexyl]amino}methyl)-2-(1H-tetrazol-5-yl)biphenyl-3-sulfonamide | 456 | 456 |
| 356 | 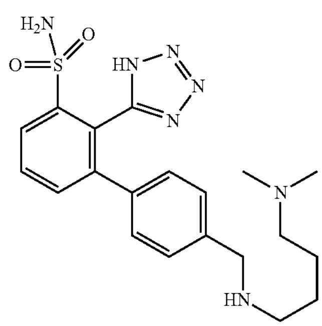 [SMILES: CN(C)CCCCNCc1ccc(-c2cccc(S(N)(=O)=O)c2-c2nnn[nH]2)cc1] | 4'-({[4-(dimethylamino)butyl]amino}methyl)-2-(1H-tetrazol-5-yl)biphenyl-3-sulfonamide | 430 | 430 |
| 357 | 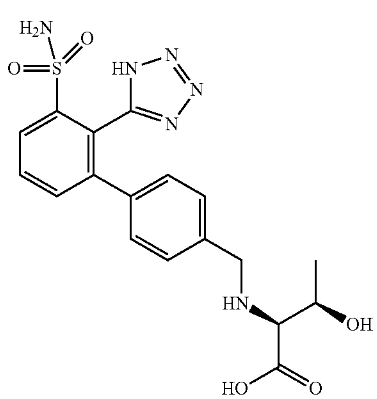 [SMILES: C[C@@H](O)[C@H](NCc1ccc(-c2cccc(S(N)(=O)=O)c2-c2nnn[nH]2)cc1)C(=O)O] | N-{[3'-sulfamoyl-2'-(1H-tetrazol-5-yl)biphenyl-4-yl]methyl}-L-threonine | 433 | 433 |

| Ex. No. | Structure | Name | Calc'd. MW [M + H]+ | LC/MS m/e (M + H)+ |
|---|---|---|---|---|
| 358 | 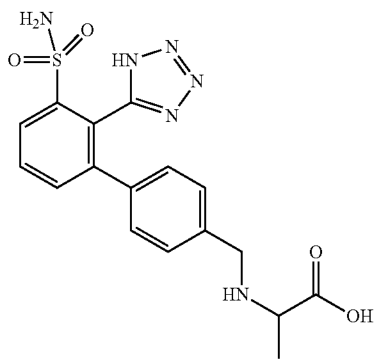 [SMILES: CC(NCc1ccc(-c2cccc(S(N)(=O)=O)c2-c2nnn[nH]2)cc1)C(=O)O] | N-{[3'-sulfamoyl-2'-(1H-tetrazol-5-yl)biphenyl-4-yl]methyl}alanine | 403 | 403 |
| 359 | 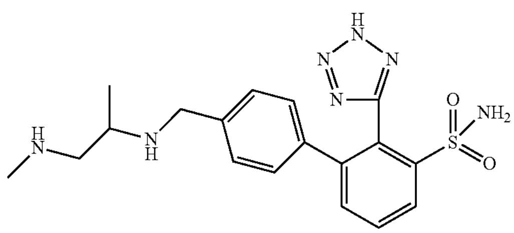 [SMILES: CNCC(C)NCc1ccc(-c2cccc(S(N)(=O)=O)c2-c2nn[nH]n2)cc1] | 4'-({[1-methyl-2-(methylamino)ethyl]amino}methyl)-2-(2H-tetrazol-5-yl)biphenyl-3-sulfonamide | 402 | 402 |
| 360 | 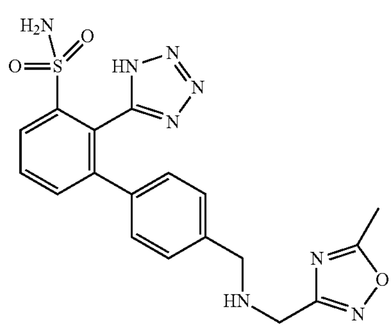 [SMILES: Cc1nc(CNCc2ccc(-c3cccc(S(N)(=O)=O)c3-c3nnn[nH]3)cc2)no1] | 4'-({[(5-methyl-1,2,4-oxadiazol-3-yl)methyl]amino}methyl)-2-(1H-tetrazol-5-yl)biphenyl-3-sulfonamide | 427 | 427 |
| 361 | 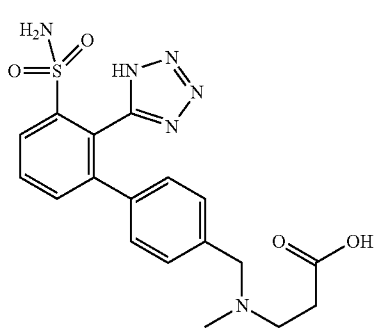 [SMILES: CN(CCC(=O)O)Cc1ccc(-c2cccc(S(N)(=O)=O)c2-c2nnn[nH]2)cc1] | N-methyl-N-{[3'-sulfamoyl-2'-(1H-tetrazol-5-yl)biphenyl-4-yl]methyl}-beta-alanine | 417 | 417 |

| Ex. No. | Structure | Name | Calc'd. MW [M + H]+ | LC/MS m/e (M + H)+ |
|---|---|---|---|---|
| 362 | 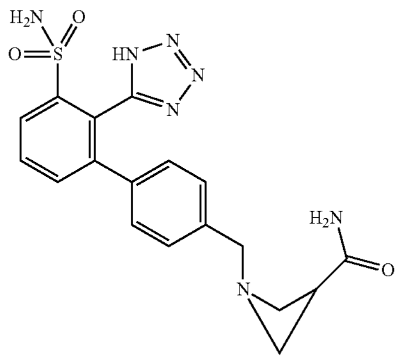 [SMILES: NC(=O)C1CN(Cc2ccc(-c3cccc(S(N)(=O)=O)c3-c3nnn[nH]3)cc2)C1] | 1-{[3'-sulfamoyl-2'-(1H-tetrazol-5-yl)biphenyl-4-yl]methyl}azetidine-3-carboxamide | 414 | 414 |
| 363 | 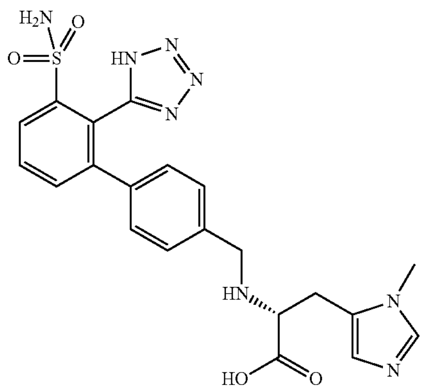 [SMILES: Cn1cncc1C[C@@H](NCc1ccc(-c2cccc(S(N)(=O)=O)c2-c2nnn[nH]2)cc1)C(=O)O] | 3-methyl-N-{[3'-sulfamoyl-2'-(1H-tetrazol-5-yl)biphenyl-4-yl]methyl}-D-histidine | 483 | 483 |
| 364 | 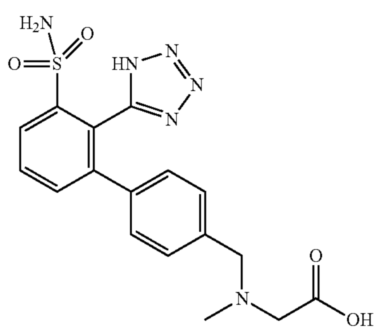 [SMILES: CN(CC(=O)O)Cc1ccc(-c2cccc(S(N)(=O)=O)c2-c2nnn[nH]2)cc1] | N-methyl-N-{[3'-sulfamoyl-2'-(1H-tetrazol-5-yl)biphenyl-4-yl]methyl}glycine | 403 | 403 |
| 365 | 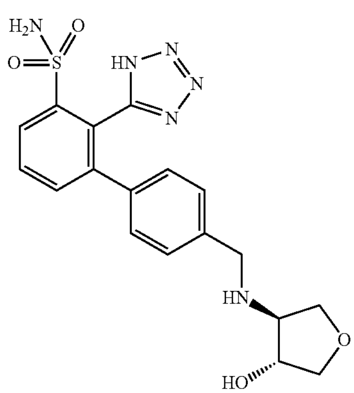 [SMILES: NS(=O)(=O)c1cccc(-c2ccc(CN[C@H]3COC[C@@H]3O)cc2)c1-c1nnn[nH]1] | 4'-({[(3S,4R)-4-hydroxytetrahydrofuran-3-yl]amino}methyl)-2-(1H-tetrazol-5-yl)biphenyl-3-sulfonamide | 417 | 417 |

-continued

| Ex. No. | Structure | Name | Calc'd. MW [M + H]+ | LC/MS m/e (M + H)+ |
|---|---|---|---|---|
| 366 | 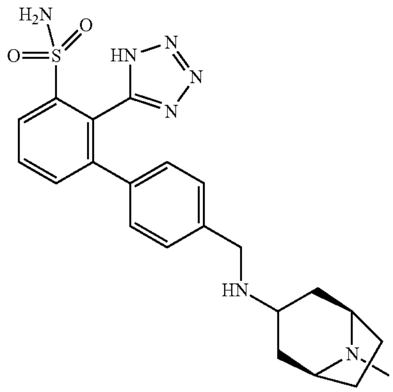 [SMILES: CN1[C@@H]2CC[C@H]1CC(NCc1ccc(-c3cccc(S(N)(=O)=O)c3-c3nnn[nH]3)cc1)C2] | 4'-({[(3-endo)-8-methyl-8-azabicyclo[3.2.1]oct-3-yl]amino}methyl)-2-(1H-tetrazol-5-yl)biphenyl-3-sulfonamide | 454 | 454 |
| 367 | 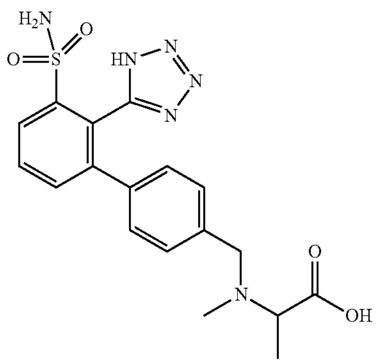 [SMILES: CC(C(=O)O)N(C)Cc1ccc(-c2cccc(S(N)(=O)=O)c2-c2nnn[nH]2)cc1] | N-methyl-N-{[3'-sulfamoyl-2'-(1H-tetrazol-5-yl)biphenyl-4-yl]methyl}alanine | 417 | 417 |
| 368 | 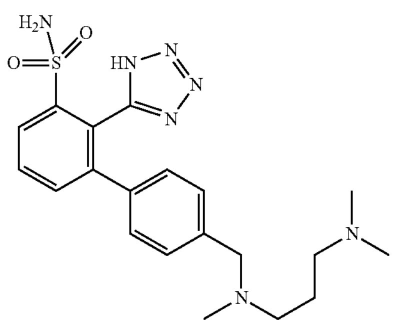 [SMILES: CN(C)CCCN(C)Cc1ccc(-c2cccc(S(N)(=O)=O)c2-c2nnn[nH]2)cc1] | 4'-({[3-(dimethylamino)propyl](methyl)amino}methyl)-2-(1H-tetrazol-5-yl)biphenyl-3-sulfonamide | 430 | 430 |
| 369 | 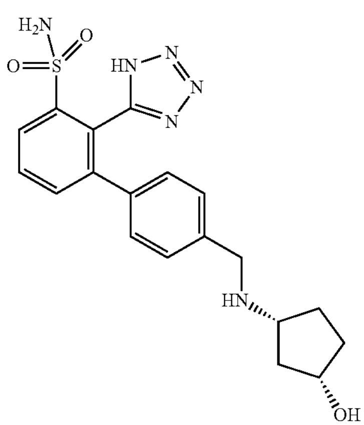 [SMILES: NS(=O)(=O)c1cccc(-c2ccc(CN[C@@H]3CC[C@H](O)C3)cc2)c1-c1nnn[nH]1] | 4'-({[(1R,3S)-3-hydroxycyclopentyl]amino}methyl)-2-(1H-tetrazol-5-yl)biphenyl-3-sulfonamide | 415 | 415 |

| Ex. No. | Structure | Name | Calc'd. MW [M + H]+ | LC/MS m/e (M + H)+ |
|---|---|---|---|---|
| 370 | 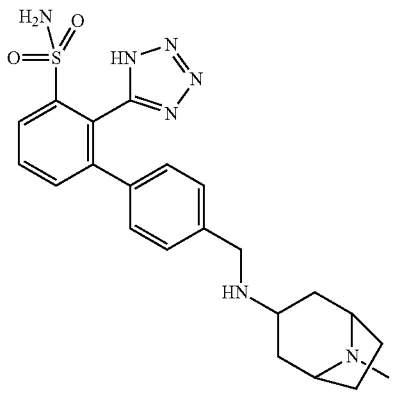 [SMILES: CN1C2CCC1CC(NCc1ccc(-c3cccc(S(N)(=O)=O)c3-c3nnn[nH]3)cc1)C2] | 4'-{[(8-methyl-8-azabicyclo[3.2.1]oct-3-yl)amino]methyl}-2-(1H-tetrazol-5-yl)biphenyl-3-sulfonamide | 454 | 454 |
| 371 | 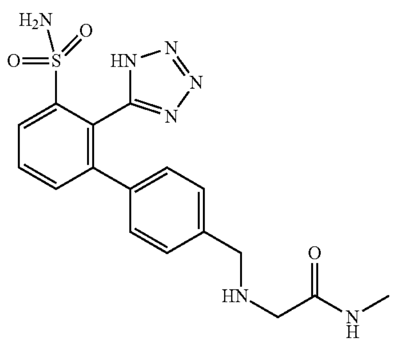 [SMILES: CNC(=O)CNCc1ccc(-c2cccc(S(N)(=O)=O)c2-c2nnn[nH]2)cc1] | N-methyl-N~2~-{[3'-sulfamoyl-2'-(1H-tetrazol-5-yl)biphenyl-4-yl]methyl}glycinamide | 402 | 402 |
| 372 | 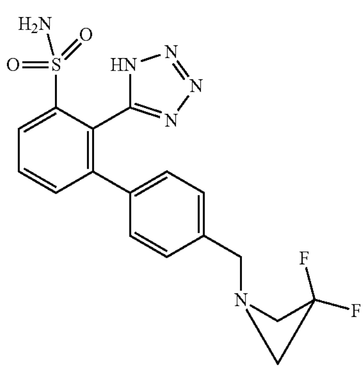 [SMILES: NS(=O)(=O)c1cccc(-c2ccc(CN3CC(F)(F)C3)cc2)c1-c1nnn[nH]1] | 4'-[(3,3-difluoroazetidin-1-yl)methyl]-2-(1H-tetrazol-5-yl)biphenyl-3-sulfonamide | 407 | 407 |
| 373 | 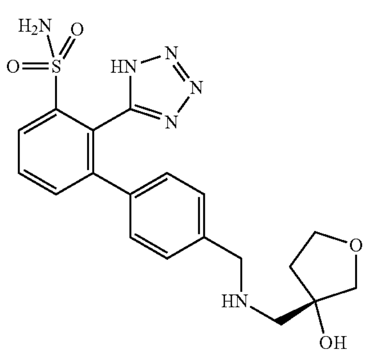 [SMILES: NS(=O)(=O)c1cccc(-c2ccc(CNC[C@@]3(O)CCOC3)cc2)c1-c1nnn[nH]1] | 4'-[({[(3S)-3-hydroxytetrahydrofuran-3-yl]methyl}amino)methyl]-2-(1H-tetrazol-5-yl)biphenyl-3-sulfonamide | 431 | 431 |

-continued

| Ex. No. | Structure | Name | Calc'd. MW [M + H]+ | LC/MS m/e (M + H)+ |
|---|---|---|---|---|
| 374 | 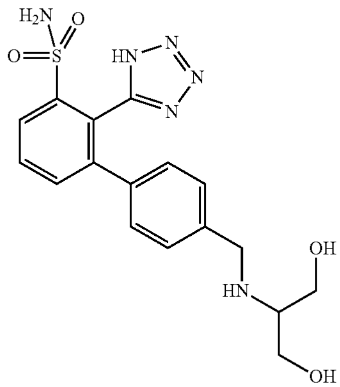 [SMILES: NS(=O)(=O)c1cccc(-c2ccc(CNC(CO)CO)cc2)c1-c1nnn[nH]1] | 4'-({[2-hydroxy-1-(hydroxymethyl)ethyl]amino}methyl)-2-(1H-tetrazol-5-yl)biphenyl-3-sulfonamide | 405 | 405 |
| 375 | 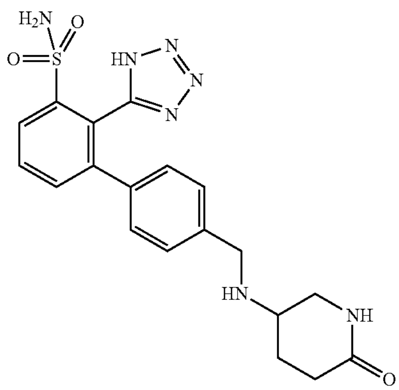 [SMILES: NS(=O)(=O)c1cccc(-c2ccc(CNC3CCC(=O)NC3)cc2)c1-c1nnn[nH]1] | 4'-{[(6-oxopiperidin-3-yl)amino]methyl}-2-(1H-tetrazol-5-yl)biphenyl-3-sulfonamide | 428 | 428 |
| 376 | 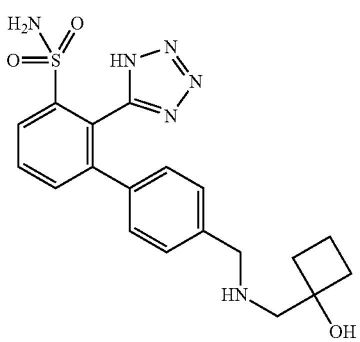 [SMILES: NS(=O)(=O)c1cccc(-c2ccc(CNCC3(O)CCC3)cc2)c1-c1nnn[nH]1] | 4'-({[(1-hydroxycyclobutyl)methyl]amino}methyl)-2-(1H-tetrazol-5-yl)biphenyl-3-sulfonamide | 415 | 415 |
| 377 | 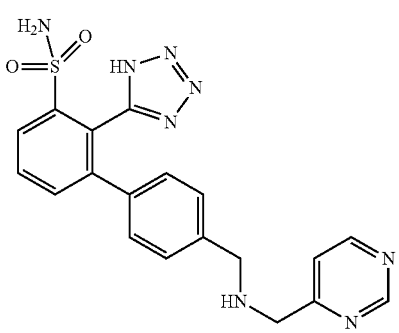 [SMILES: NS(=O)(=O)c1cccc(-c2ccc(CNCc3ccncn3)cc2)c1-c1nnn[nH]1] | 4'-{[(pyrimidin-4-ylmethyl)amino]methyl}-2-(1H-tetrazol-5-yl)biphenyl-3-sulfonamide | 423 | 423 |

| Ex. No. | Structure | Name | Calc'd. MW [M + H]+ | LC/MS m/e (M + H)+ |
|---|---|---|---|---|
| 378 | 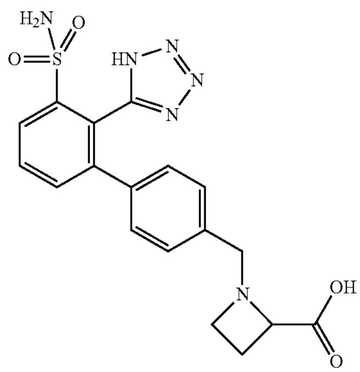 [SMILES: NS(=O)(=O)c1cccc(-c2ccc(CN3CCC3C(=O)O)cc2)c1-c1nnn[nH]1] | 1-{[3'-sulfamoyl-2'-(1H-tetrazol-5-yl)biphenyl-4-yl]methyl}azetidine-2-carboxylic acid | 415 | 415 |
| 379 | 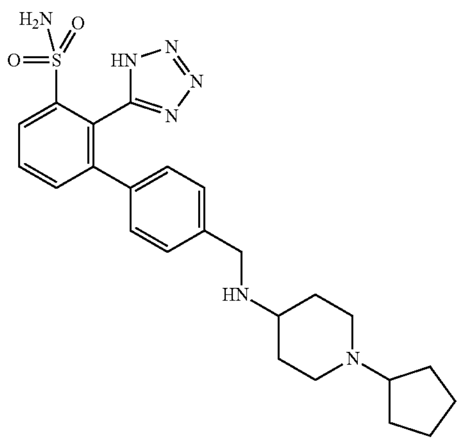 [SMILES: NS(=O)(=O)c1cccc(-c2ccc(CNC3CCN(C4CCCC4)CC3)cc2)c1-c1nnn[nH]1] | 4'-{[(1-cyclopentylpiperidin-4-yl)amino]methyl}-2-(1H-tetrazol-5-yl)biphenyl-3-sulfonamide | 482 | 482 |
| 380 | 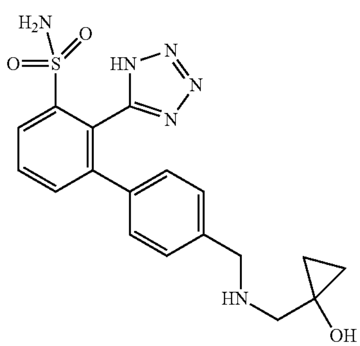 [SMILES: NS(=O)(=O)c1cccc(-c2ccc(CNCC3(O)CC3)cc2)c1-c1nnn[nH]1] | 4'-({[(1-hydroxycyclopropyl)methyl]amino}methyl)-2-(1H-tetrazol-5-yl)biphenyl-3-sulfonamide | 401 | 401 |
| 381 | 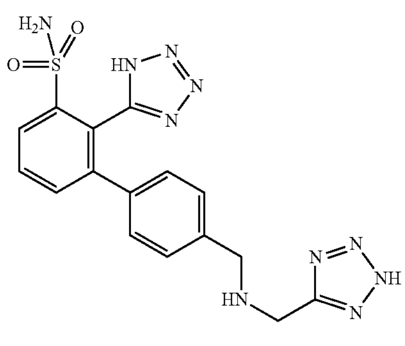 [SMILES: NS(=O)(=O)c1cccc(-c2ccc(CNCc3nn[nH]n3)cc2)c1-c1nnn[nH]1] | 2-(1H-tetrazol-5-yl)-4'-{[[(2H-tetrazol-5-ylmethyl)amino]methyl}biphenyl-3-sulfonamide | 413 | 413 |

| Ex. No. | Structure | Name | Calc'd. MW [M + H]+ | LC/MS m/e (M + H)+ |
|---|---|---|---|---|
| 382 | 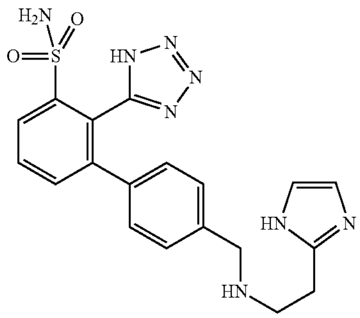 [SMILES: NS(=O)(=O)c1cccc(-c2ccc(CNCCc3ncc[nH]3)cc2)c1-c1nnn[nH]1] | 4'-({[2-(1H-imidazol-2-yl)ethyl]amino}methyl)-2-(1H-tetrazol-5-yl)biphenyl-3-sulfonamide | 425 | 425 |
| 383 | 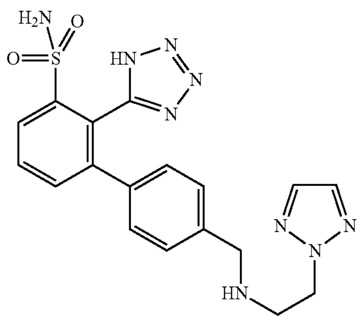 [SMILES: NS(=O)(=O)c1cccc(-c2ccc(CNCCn3nccn3)cc2)c1-c1nnn[nH]1] | 2-(1H-tetrazol-5-yl)-4'-({[2-(2H-1,2,3-triazol-2-yl)ethyl]amino}methyl)biphenyl-3-sulfonamide | 426 | 426 |
| 384 | 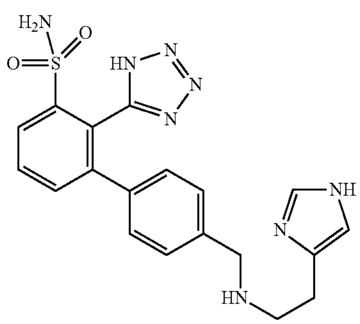 [SMILES: NS(=O)(=O)c1cccc(-c2ccc(CNCCc3c[nH]cn3)cc2)c1-c1nnn[nH]1] | 4'-({[2-(1H-imidazol-4-yl)ethyl]amino}methyl)-2-(1H-tetrazol-5-yl)biphenyl-3-sulfonamide | 425 | 425 |
| 385 | 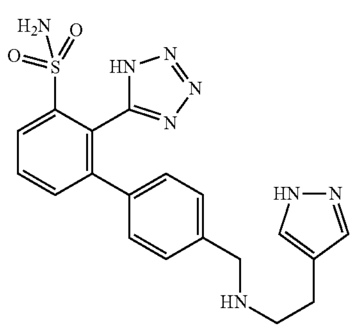 [SMILES: NS(=O)(=O)c1cccc(-c2ccc(CNCCc3cn[nH]c3)cc2)c1-c1nnn[nH]1] | 4'-({[2-(1H-pyrazol-4-yl)ethyl]amino}methyl)-2-(1H-tetrazol-5-yl)biphenyl-3-sulfonamide | 425 | 425 |

| Ex. No. | Structure | Name | Calc'd. MW [M + H]⁺ | LC/MS m/e (M + H)⁺ |
|---|---|---|---|---|
| 386 | 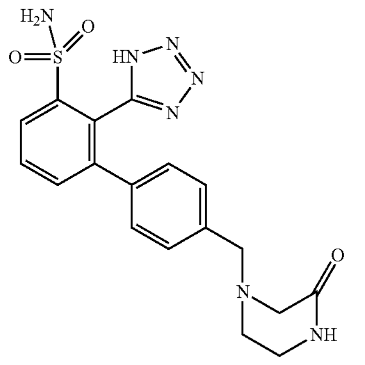 [SMILES: NS(=O)(=O)c1cccc(-c2ccc(CN3CCNC(=O)C3)cc2)c1-c1nnn[nH]1] | 4'-[(3-oxopiperazin-1-yl)methyl]-2-(1H-tetrazol-5-yl)biphenyl-3-sulfonamide | 414 | 414 |
| 387 | 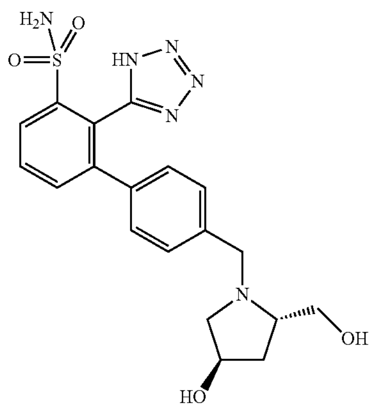 [SMILES: NS(=O)(=O)c1cccc(-c2ccc(CN3C[C@H](O)C[C@H]3CO)cc2)c1-c1nnn[nH]1] | 4'-{[(2S,4R)-4-hydroxy-2-(hydroxymethyl)pyrrolidin-1-yl]methyl}-2-(1H-tetrazol-5-yl)biphenyl-3-sulfonamide | 431 | 431 |
| 388 | 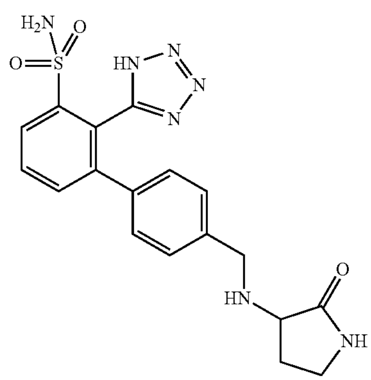 [SMILES: NS(=O)(=O)c1cccc(-c2ccc(CNC3CCNC3=O)cc2)c1-c1nnn[nH]1] | 4'-{[(2-oxopyrrolidin-3-yl)amino]methyl}-2-(1H-tetrazol-5-yl)biphenyl-3-sulfonamide | 414 | 414 |
| 389 | 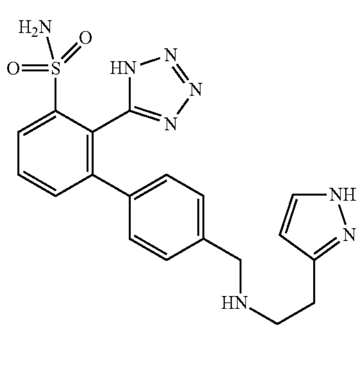 [SMILES: NS(=O)(=O)c1cccc(-c2ccc(CNCCc3cc[nH]n3)cc2)c1-c1nnn[nH]1] | 4'-({[2-(1H-pyrazol-3-yl)ethyl]amino}methyl)-2-(1H-tetrazol-5-yl)biphenyl-3-sulfonamide | 425 | 425 |

-continued

| Ex. No. | Structure | Name | Calc'd. MW [M + H]+ | LC/MS m/e (M + H)+ |
|---|---|---|---|---|
| 390 | 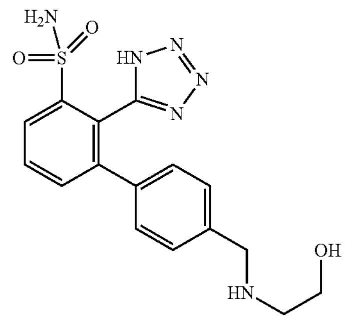 [SMILES: NS(=O)(=O)c1cccc(-c2ccc(CNCCO)cc2)c1-c1nnn[nH]1] | 4'-{[(2-hydroxyethyl)amino]methyl}-2-(1H-tetrazol-5-yl)biphenyl-3-sulfonamide | 375 | 375 |
| 391 | 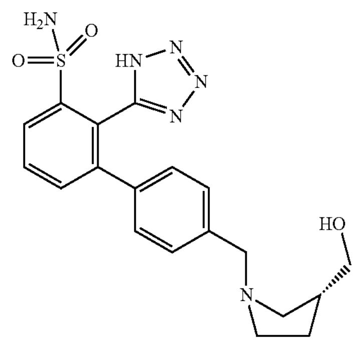 | 4'-{[(3S)-3-(hydroxymethyl)pyrrolidin-1-yl]methyl}-2-(1H-tetrazol-5-yl)biphenyl-3-sulfonamide | 415 | 415 |
| 392 | 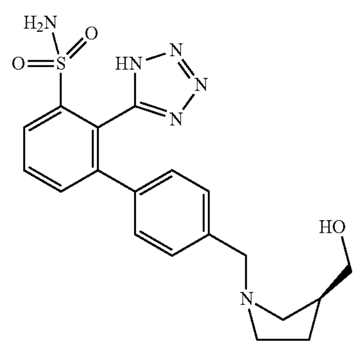 | 4'-{[(3S)-3-(hydroxymethyl)pyrrolidin-1-yl]methyl}-2-(1H-tetrazol-5-yl)biphenyl-3-sulfonamide | 415 | 415 |
| 393 | 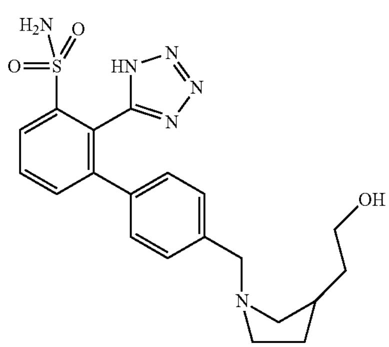 [SMILES: NS(=O)(=O)c1cccc(-c2ccc(CN3CCC(CCO)C3)cc2)c1-c1nnn[nH]1] | 4'-{[3-(2-hydroxyethyl)pyrrolidin-1-yl]methyl}-2-(1H-tetrazol-5-yl)biphenyl-3-sulfonamide | 429 | 429 |

| Ex. No. | Structure | Name | Calc'd. MW [M + H]+ | LC/MS m/e (M + H)+ |
|---|---|---|---|---|
| 394 | 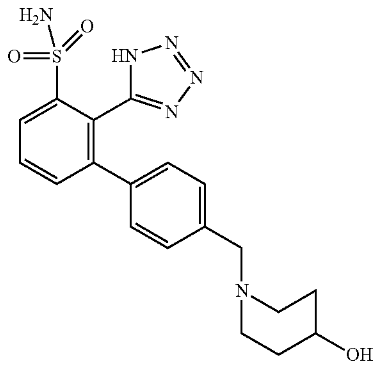 [SMILES: NS(=O)(=O)c1cccc(-c2ccc(CN3CCC(O)CC3)cc2)c1-c1nnn[nH]1] | 4'-[(4-hydroxypiperidin-1-yl)methyl]-2-(1H-tetrazol-5-yl)biphenyl-3-sulfonamide | 415 | 415 |
| 395 | 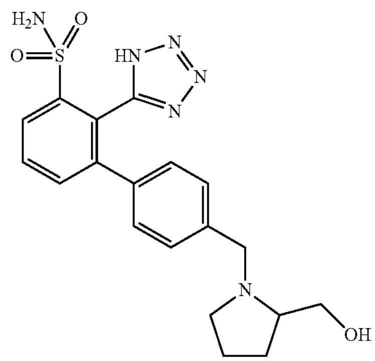 [SMILES: NS(=O)(=O)c1cccc(-c2ccc(CN3CCCC3CO)cc2)c1-c1nnn[nH]1] | 4'-{[2-(hydroxymethyl)pyrrolidin-1-yl]methyl}-2-(1H-tetrazol-5-yl)biphenyl-3-sulfonamide | 415 | 415 |
| 396 | 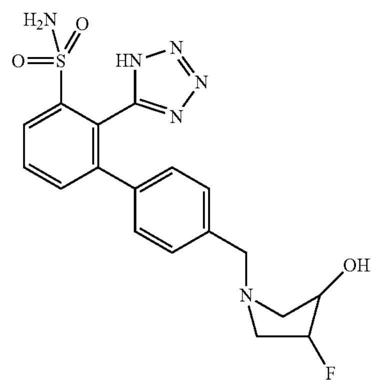 [SMILES: NS(=O)(=O)c1cccc(-c2ccc(CN3CC(O)C(F)C3)cc2)c1-c1nnn[nH]1] | 4'-[(3-fluoro-4-hydroxypyrrolidin-1-yl)methyl]-2-(1H-tetrazol-5-yl)biphenyl-3-sulfonamide | 419 | 419 |

EXAMPLE 397

4'-(Ethoxymethyl)-2-(1H-tetrazol-5-yl)-[1,1'-biphenyl]-3-sulfonamide

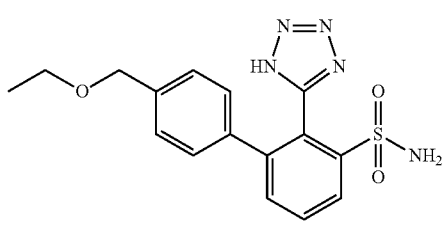 [SMILES: CCOCc1ccc(-c2cccc(S(N)(=O)=O)c2-c2nnn[nH]2)cc1]

Step A: 4'-(Ethoxymethyl)-1-(and 2-)(4-methoxybenzyl)-2-(1H-tetrazol-5-yl)-[1,1'-biphenyl]-3-sulfonamide A 4 mL microwave reaction vial was charged with the mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (150 mg, 0.354 mmol), (4-(chloromethyl)phenyl)boronic acid (120 mg, 0.707 mmol), 1,1'-Bis(di-tert-butylphosphino)ferrocene palladium (28.9 mg, 0.035 mmol), potassium carbonate (saturated aqueous solution, 1.5 ml, 0.354 mmol) and ethanol (3 mL). The vial was capped, and heated in a microwave at 120° C. for 20 minutes. The excess catalyst was filtered off, and the solution was concentrated and then purified by reverse phase HPLC column (acetonitrile/water/0.05% TFA system) eluted with 10% to 100% MeCN in water. The solution was concentrated to afford product. LC-MS: calculated for $C_{24}H_{25}N_5O_4S$ 479.5; observed m/e: 480.4 (M+H)+.

Step B: 4'-(Ethoxymethyl)-2-(1H-tetrazol-5-yl)-[1,1'-biphenyl]-3-sulfonamide

The residue was dissolved in TFA (1.5 uL) and anisole (108 mg, 1.001 mmol) and heated to 45° C. for 18 hr. The reaction mixture was purified by reverse phase HPLC column (acetonitrile/water/0.05% TFA system) and eluted with 0% to 20% MeCN in water. The solution was concentrated to afford product. LC-MS: calculated for $C_{16}H_{17}N_5O_3S$ 359.4; observed m/e: 360.3 (M+H)+; $^1$H NMR δ (ppm) (MeOH): 8.2 (d, 1H), 7.84 (t, 1H), 7.76 (d, 1H), 7.25 (d, 2H), 7.06 (d, 2H), 4.45 (s, 2H), 3.51 (q, 2H), 1.19 (t, 3H).

EXAMPLE 398

3-(5-Methylpyridin-2-yl)-2-(1H-tetrazol-5-yl)benzenesulfonamide, TFA Salt

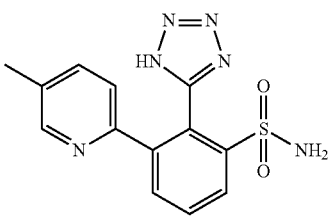

Step A: 3-(5-Methylpyridin-2-yl)-2-(1-(4-methoxybenzyl) (1H-tetrazol-5-yl))benzenesulfonamide and 3-(5-methylpyridin-2-yl)-2-(2-(4-methoxybenzyl)(1H-tetrazol-5-yl)) benzenesulfonamide A 40 mL reaction vial was charged with the mixture of 3-bromo-2-(1-(4-methoxybenzyl)(1H-tetrazol-5-yl))benzenesulfonamide and 3-bromo-2-(2-(4-methoxybenzyl)(1H-tetrazol-5-yl))benzenesulfonamide (50 mg, 0.118 mmol), and RuPhos precatalyst (18.31 mg, 0.024 mmol). The vial was capped via a red sure seal and degassed three times with vacuum/nitrogen (line with needle connected to manifold). Then, DMA (3 mL), THF (1.5 mL) and (5-methylpyridin-2-yl)zinc(II) bromide (0.471 ml, 0.236 mmol) were syringed into the vial. Again, the vial was degassed three times with vacuum/nitrogen (line with needle connected to manifold). After stirring at room temp for 10 minutes, the reaction was allowed to stir at 80° C. via an oil bath for 18 hours. The reaction was diluted with ethyl acetate and quenched with NH$_4$Cl (saturated aqueous solution). The organic layer was extracted out and concentrated. The residue was purified by normal phase ISCO on a 4 g column eluted with 0% to 100% ethyl acetate in hexane. The pure fractions were concentrated to afford product. LC-MS: calculated for $C_{21}H_{20}N_6O_3S$ 436.5; observed m/e: 437.3 (M+H)+ (Rt 0.96/2 min)

Step B: 3-(5-Methylpyridin-2-yl)-2-(1H-tetrazol-5-yl)benzenesulfonamide, TFA Salt The residue was dissolved in TFA (800 uL) and anisole (9.29 mg, 0.086 mmol) and heated to 45° C. for 18 hr. Purification by reverse phase HPLC column (acetonitrile/water/0.05% TFA system) eluted with 0% to 20% MeCN in water. The solution was concentrated to afford 3-(5-methylpyridin-2-yl)-2-(1H-tetrazol-5-yl)benzenesulfonamide, TFA salt. LC-MS: calculated for $C_{13}H_{12}N_6O_2$ 316.3; observed m/e: 317.2 (M+H)+ (Rt 0.32/2 min); $^1$H NMR δ (ppm) (MeOH): 8.27-8.32 (m, 2H), 7.87-7.95 (m, 2H), 7.67 (d, 1H), 7.22 (d, 1H), 2.33 (s, 3H).

EXAMPLE 399

1-(1H-tetrazol-5-yl)naphthalene-2-sulfonamide

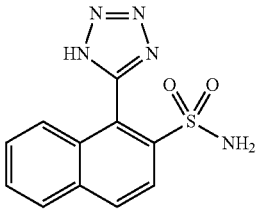 [SMILES: NS(=O)(=O)c1ccc2ccccc2c1-c1nnn[nH]1]

Step A: 2-((2-(trimethylsilyl)ethyl)thio)-1-naphthonitrile

A solution of n-butyllithium (2.5M in Hexane) (2.74 ml, 6.8 mmol) was added drop wise to a solution of 2,2,6,6-tetramethylpiperidine (1.15 ml, 6.8 mmol) in THF (5 mL) while maintaining the temperature at 0° C. After 30 minutes of stirring, the reaction mixture was cooled to −78° C. and a solution of 1-naphthonitrile (1 g, 6.53 mmol) in THF (3 mL) was added drop wise. The resulting dark solution was maintained at −78° C. and stirred for 2 hours. A solution of iodine (1.74 g, 6.8 mmol) in THF (3 mL) was added drop wise and stirred at −78° C. for 2 hours, then allowed to warm to room temperature overnight. The reaction mixture was quenched with H$_2$O and resulting mixture was extracted with EtOAc. The combined organic extracts were dried over Na$_2$SO$_4$, filtered and concentrated. The resulting crude, 2-iodo-1-naphthonitrile (1.7 g, 6.1 mmol) and potassium carbonate (1.01 g, 7.3 mmol) were dissolved in DMF (10 ml). To that mixture, 2-(trimethylsilyl)ethanethiol (1.46 ml, 9.1 mmol) was added and stirred at room temperature under N$_2$ overnight. The reaction mixture was washed with water and organic was extracted with EtOAc. The combined organic layer was dried over Na$_2$SO$_4$, filtered and concentrated under vacuum. The crude was purified by MPLC with hexanes and EtOAc to give desired compound. $^1$H NMR (MeOD): δ 0.11 ppm (s, 9H), 1.03 ppm (m, 2H), 3.28 ppm (m, 2H), 7.61 ppm (dd, J=8.2 Hz, 1H), 7.64 ppm (d, J=8.8 Hz, 1H), 7.73 ppm (d, J=7.1 Hz, 1H), 7.98 ppm (d, J=8.2 Hz, 1H), 8.03 ppm (d, J=8.8 Hz, 1H), 8.09 ppm, (d, J=8.5 Hz, 1H).

Step B: 2-((2-(trimethylsilyl)ethyl)sulfonyl)-1-naphthonitrile

To a solution of 2-((2-(trimethylsilyl)ethyl)thio)-1-naphthonitrile (1.35 g, 4.7 mmol) in DCM (50 ml) was added 3-chloroperoxybenzoic acid (2.9 g, 16.6 mmol). The mixture was stirred at room temperature under N$_2$ for 4 hours. The TLC indicated complete consumption of starting material. To a reaction mixture, sat. Na$_2$S$_2$O$_3$ was added and stirred for 15 minutes and then sat. NaHCO$_3$ was added stirred for another 15 more minutes. The organic was extracted with DCM, dried over NaSO$_4$, filtered and concentrated under vacuum. The crude was purified by MPLC with hexanes and EtOAc to give desired compound. $^1$H NMR (MeOD): δ 0.06 ppm (9 H, s), 0.96 ppm (2 H, m), 3.48 ppm (2 H, m), 7.90 ppm (ddd, J=8.2 Hz, 1H), 7.96 ppm (ddd, J=8.5 Hz, 1H), 8.20 (d, J=8.7, 1 H), 8.23 ppm (d, J=8.2 Hz, 1H), 8.46 ppm (d, J=8.2 Hz, 1H), 8.49 ppm (d, J=8.7 Hz, 1H).

Step C: 5-(2-((2-(trimethylsilyl)ethyl)sulfonyl)naphthalen-1-yl)-1H-tetrazole

A solution of 2-((2-(trimethylsilyl)ethyl)sulfonyl)-1-naphthonitrile (113 mg, 0.36 mmol) and azidotrimethyltin (370 mg, 1.78 mmol) in toluene (3 ml) was microwaved at 140° C. for 1 hour. The reaction mixture was filtered and concentrated. The crude was dissolved in water/ACN and purified by HPLC with ACN and water with 0.05% TFA to afford the desired compound. LC-MS [M+1]+: 361.

Step D: 1-(1H-tetrazol-5-yl)naphthalene-2-sulfonamide

To a solution of 5-(2-((2-(trimethylsilyl)ethyl)sulfonyl)naphthalen-1-yl)-1H-tetrazole (50 mg, 0.139 mmol) in THF (5 ml) was added tetrabutylammonium fluoride (0.42 ml, 0.42 mmol). The mixture was stirred for 16 hours at room temperature under N$_2$. A solution of sodium acetate (57 mg, 0.69 mmol) in water (0.32 ml, 18 mmol) and hydroxylamine-o-sulfonic acid (78 mg, 0.69 mmol) were added sequentially, and the mixture was allowed to stir at room temperature for 3 hours. The solvent was removed under vacuum and the crude was dissolved in water/ACN and purified by HPLC with ACN and water with 0.05% TFA to give desire compound as ammonium salt. The compound was dissolved in H$_2$O and acetone (minimum amount) and ran through a packed resin column (Dowex 50wx8, 100-200 mesh, ion-exchange resin, cas#11119-67-8) which was washed with 1N NaOH and neutralized to pH~7) to give pure compound. LC-MS [M+H]+: 276.1.

EXAMPLE 400

3-(1-aminoisoquinolin-7-yl)-2-(1H-tetrazol-5-yl)benzenesulfonamide

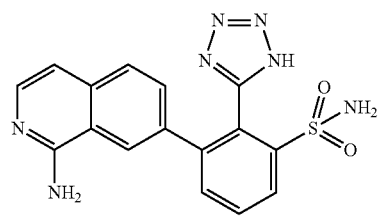 [SMILES: Nc1nccc2ccc(-c3cccc(S(N)(=O)=O)c3-c3nnn[nH]3)cc12]

3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide (80 mg, 0.12 mmol), Chloro[(Di(1-Adamantyl)-N-Butylphosphine)-2-(2-Aminobiphenyl)]Palladium(II) (7.7 mg, 0.011 mmol), Cesium Carbonate (112 mg, 0.344 mmol) and 7-Bromoisoquinolin-1-Amine (25.6 mg, 0.115 mmol) were weighed into a 1 dram vial and taken into the glove box. Toluene (1 mL) and Water (0.1 mL) were added and the mixture stirred at 110° C. for 18 hours. The organics were removed in the genevac under reduced pressure.

To remove the PMB protecting group, TFA (1 mL) and Anisole (0.050 mL, 0.459 mmol) was added to the residue and the mixture stirred at 65° C. for 2.5 hours. The mixture was allowed to cool, and the volatile organics were removed in the genevac under reduced pressure. The crude product was purified using mass directed reverse phase HPLC. LC-MS [M+H]+: 368.

EXAMPLES 401-415

Examples 401-415 in the following table were prepared in the same fashion as described for 3-(1-amino-7-isoquinolyl)-2-(1H-tetrazol-5-yl)benzenesulfonamide (EXAMPLE 400) above starting from 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and heteroaryl bromides (commercially available, known, or prepared as described herein).

| Ex. No. | Structure | Name | Calc'd. MW [M + H]+ | LC/MS m/e (M + H)+ |
|---|---|---|---|---|
| 401 | 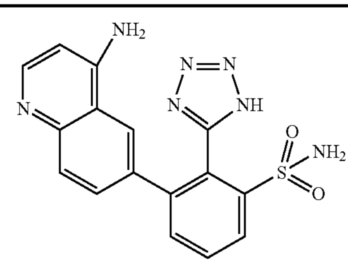 | 3-(4-amino-6-quinolyl)-2-(1H-tetrazol-5-yl)benzenesulfonamide | 368 | 368 |
| 402 | 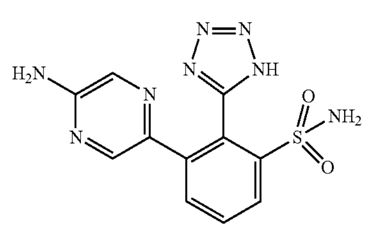 [SMILES: Nc1cnc(-c2cccc(S(N)(=O)=O)c2-c2nnn[nH]2)cn1] | 3-(5-aminopyrazin-2-yl)-2-(1H-tetrazol-5-yl)benzenesulfonamide | 319 | 319 |

-continued

| Ex. No. | Structure | Name | Calc'd. MW [M + H]⁺ | LC/MS m/e (M + H)⁺ |
|---|---|---|---|---|
| 403 | 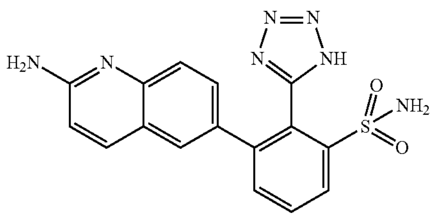 [SMILES: Nc1ccc2cc(-c3cccc(S(N)(=O)=O)c3-c3nnn[nH]3)ccc2n1] | 3-(2-amino-6-quinolyl)-2-(1H-tetrazol-5-yl)benzenesulfonamide | 368 | 368 |
| 404 | 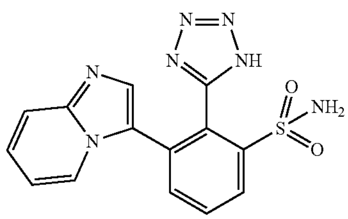 [SMILES: NS(=O)(=O)c1cccc(-c2cnc3ccccn23)c1-c1nnn[nH]1] | 3-imidazo[1,2-a]pyridin-3-yl-2-(1H-tetrazol-5-yl)benzenesulfonamide | 342 | 342 |
| 405 | 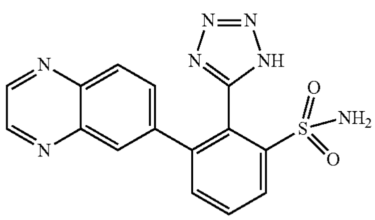 [SMILES: NS(=O)(=O)c1cccc(-c2ccc3nccnc3c2)c1-c1nnn[nH]1] | 3-quinoxalin-6-yl-2-(1H-tetrazol-5-yl)benzenesulfonamide | 354 | 354 |
| 406 | 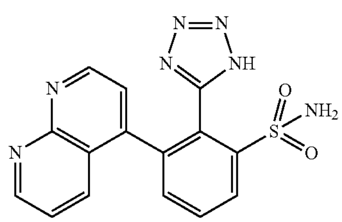 [SMILES: NS(=O)(=O)c1cccc(-c2ccnc3ncccc23)c1-c1nnn[nH]1] | 3-(1,8-naphthyridin-4-yl)-2-(1H-tetrazol-5-yl)benzenesulfonamide | 354 | 354 |
| 407 | 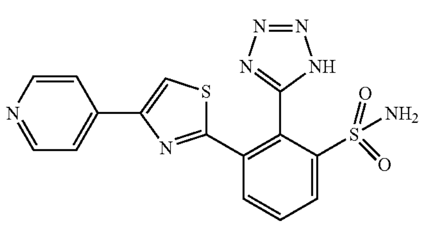 [SMILES: NS(=O)(=O)c1cccc(-c2nc(-c3ccncc3)cs2)c1-c1nnn[nH]1] | 3-[4-(4-pyridyl)thiazol-2-yl]-2-(1H-tetrazol-5-yl)benzenesulfonamide | 386 | 386 |
| 408 | 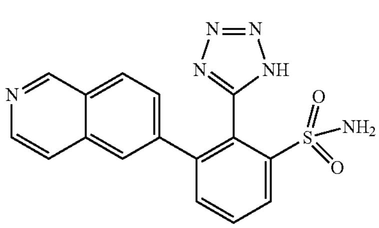 [SMILES: NS(=O)(=O)c1cccc(-c2ccc3cnccc3c2)c1-c1nnn[nH]1] | 3-(6-isoquinolyl)-2-(1H-tetrazol-5-yl)benzenesulfonamide | 353 | 353 |

-continued

| Ex. No. | Structure | Name | Calc'd. MW [M + H]+ | LC/MS m/e (M + H)+ |
|---|---|---|---|---|
| 409 | 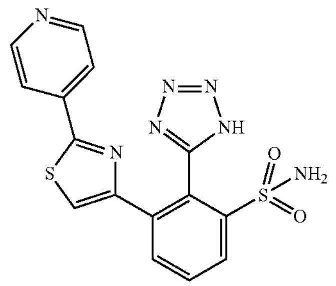 [SMILES: NS(=O)(=O)c1cccc(-c2csc(-c3ccncc3)n2)c1-c1nnn[nH]1] | 3-[2-(4-pyridyl)thiazol-4-yl]-2-(1H-tetrazol-5-yl)benzenesulfonamide | 386 | 386 |
| 410 | 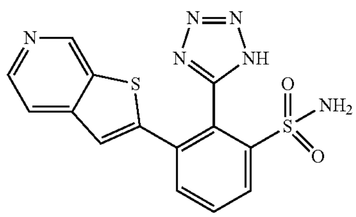 [SMILES: NS(=O)(=O)c1cccc(-c2cc3ccncc3s2)c1-c1nnn[nH]1] | 2-(1H-tetrazol-5-yl)-3-thieno[2,3-c]pyridin-2-yl-benzenesulfonamide | 359 | 359 |
| 411 | 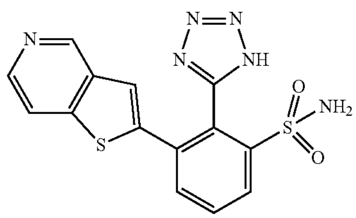 [SMILES: NS(=O)(=O)c1cccc(-c2cc3cnccc3s2)c1-c1nnn[nH]1] | 2-(1H-tetrazol-5-yl)-3-thieno[3,2-c]pyridin-2-yl-benzenesulfonamide | 359 | 359 |
| 412 | 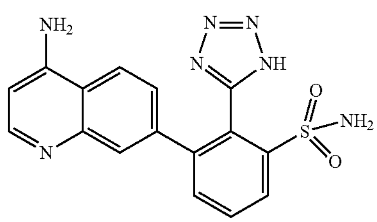 [SMILES: Nc1ccnc2cc(-c3cccc(S(N)(=O)=O)c3-c3nnn[nH]3)ccc12] | 3-(4-amino-7-quinolyl)-2-(1H-tetrazol-5-yl)benzenesulfonamide | 368 | 368 |
| 413 | 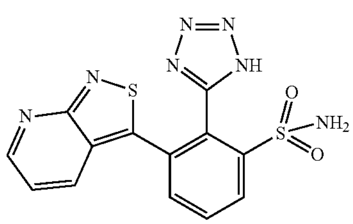 [SMILES: NS(=O)(=O)c1cccc(-c2snc3ncccc23)c1-c1nnn[nH]1] | 3-isothiazolo[3,4-b]pyridin-3-yl-2-(1H-tetrazol-5-yl)benzenesulfonamide | 360 | 360 |
| 414 | 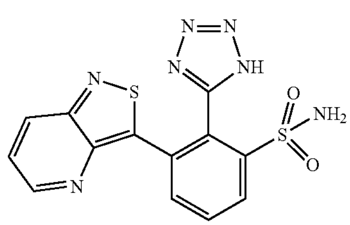 [SMILES: NS(=O)(=O)c1cccc(-c2snc3cccnc23)c1-c1nnn[nH]1] | 3-isothiazolo[4,3-b]pyridin-3-yl-2-(1H-tetrazol-5-yl)benzenesulfonamide | 360 | 360 |

-continued

| Ex. No. | Structure | Name | Calc'd. MW [M + H]+ | LC/MS m/e (M + H)+ |
|---|---|---|---|---|
| 415 | 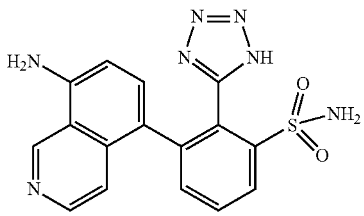 [SMILES: Nc1ccc(-c2cccc(S(N)(=O)=O)c2-c2nnn[nH]2)c2ccncc12] | 3-(8-amino-5-isoquinolyl)-2-(1H-tetrazol-5-yl)benzenesulfonamide | 368 | 368 |

EXAMPLES 416-419

Parallel Synthesis of 3-Substituted 2-(1H-tetrazol-5-yl)benzenesulfonamides

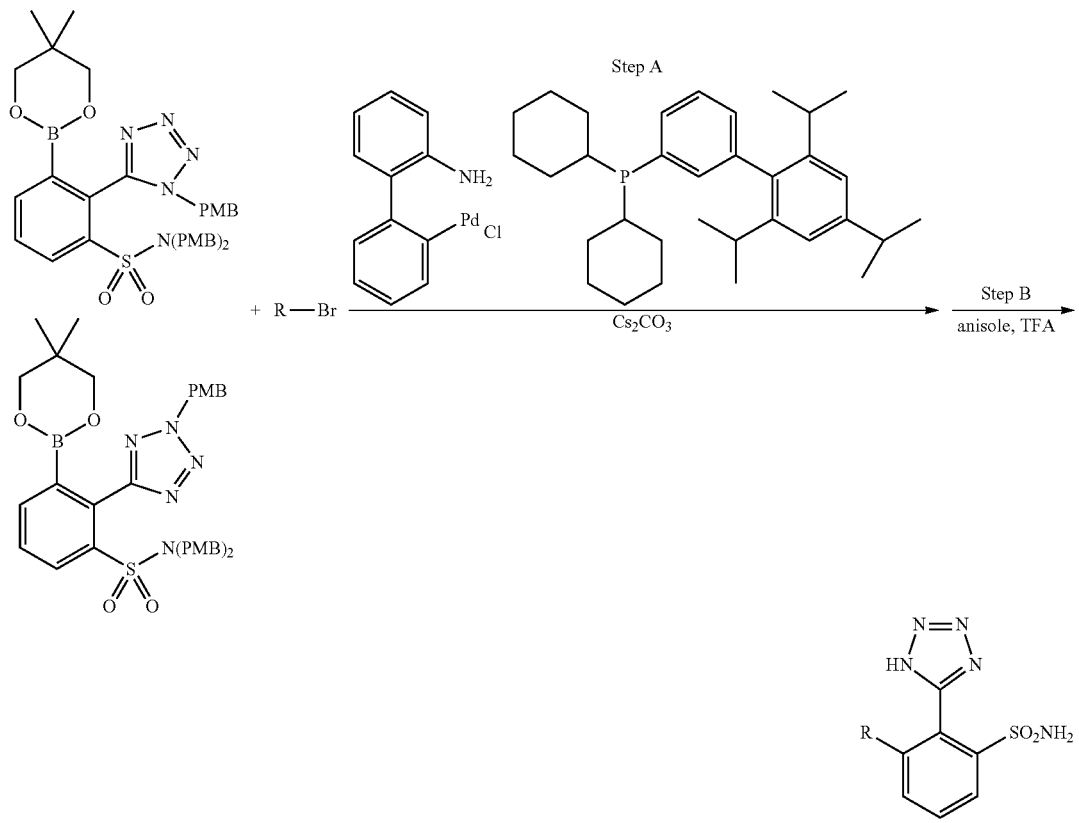

Step A: Palladium Catalyzed C—C Coupling of Arylboronic Ester with Bromides

An isomeric mixture of 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl) benzenesulfonamide, Reference Example 9, (80 mg, 0.12 mmol), were combined with commercially available or known aryl or heteroaryl bromides (0.138 mmol), cesium carbonate (112 mg, 0.344 mmol) and 2nd Generation Xphos Precatalyst (13.5 mg, 17 μmol) in a 1 dram vial and taken into the glove box. Dioxane (0.8 mL) and water (0.2 mL) were added and the mixture stirred at 85° C. for 18 hours. Then 2 mL DCM and 1 mL saturated ammonium chloride was added and the mixtures were stirred for 5 minutes. The aqeuous layer was removed by pipette and the remaining organics concentrated under reduced pressure in the genevac.

Step B: Removal of the p-methoxybenzyl (PMB) Protecting Group Under Acidic Conditions To each vial from Step A was added Anisole (0.125 ml, 1.15 mmol) and TFA (1 mL) and the mixture stirred at 60° C. for 4 hours. The mixture was allowed to cool and the volatile organics removed in the genevac. DMSO (1 mL) was added and the mixtures were filtered through a 96 well 0.4 micron filter plate. These crude materials and others made in the same way were purified by mass directed reverse phase HPLC to afford Examples 416-419.

| Ex. No. | Structure | Name | Calc'd. Mass [M + H]+ | LC/MS m/e [M + H]+ |
|---|---|---|---|---|
| 416 | 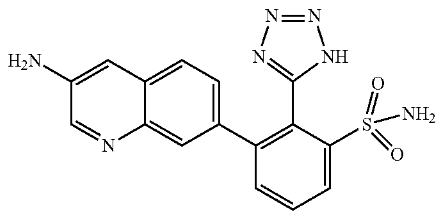 [SMILES: Nc1cnc2cc(-c3cccc(S(N)(=O)=O)c3-c3nnn[nH]3)ccc2c1] | 3-(3-amino-7-quinolyl)-2-(1H-tetrazol-5-yl)benzenesulfonamide | 368 | 368 |
| 417 | 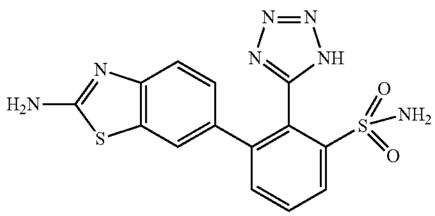 [SMILES: Nc1nc2ccc(-c3cccc(S(N)(=O)=O)c3-c3nnn[nH]3)cc2s1] | 3-(2-amino-1,3-benzothiazol-6-yl)-2-(1H-tetrazol-5-yl)benzenesulfonamide | 374 | 374 |
| 418 | 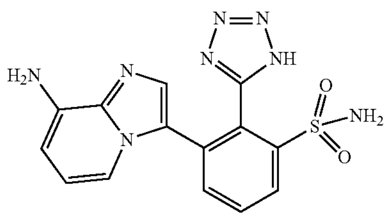 [SMILES: Nc1cccn2c(-c3cccc(S(N)(=O)=O)c3-c3nnn[nH]3)cnc12] | 3-(8-aminoimidazo[1,2-a]pyridin-3-yl)-2-(1H-tetrazol-5-yl)benzenesulfonamide | 357 | 357 |
| 419 | 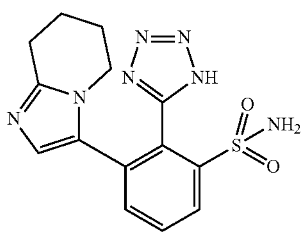 [SMILES: NS(=O)(=O)c1cccc(-c2cnc3n2CCCC3)c1-c1nnn[nH]1] | 3-(5,6,7,8-tetrahydroimidazo[1,2-a]pyridin-3-yl)-2-(1H-tetrazol-5-yl)benzenesulfonamide | 346 | 346 |

EXAMPLE 420

3-(2-Aminoquinazolin-7-yl)-2-(1H-tetrazol-5-yl)benzenesulfonamide

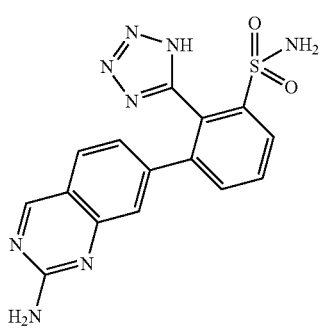 [SMILES: Nc1ncc2ccc(-c3cccc(S(N)(=O)=O)c3-c3nnn[nH]3)cc2n1]

Step A: 3-(2-Aminoquinazolin-7-yl)-N,N-bis(4-methoxybenzyl)-2-(1-(4-methoxybenzyl)-1H-tetrazol-5-yl)benzenesulfonamide and 3-(2-aminoquinazolin-7-yl)-N,N-bis(4-methoxybenzyl)-2-(2-(4-methoxybenzyl)-2H-tetrazol-5-yl)benzenesulfonamide A mixture of 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide (200 mg, 0.287 mmol), 7-bromoquinazolin-2-amine (96 mg, 0.430 mmol), cesium carbonate (280 mg, 0.860 mmol), Xphos Pd G2 (33.8 mg, 0.043 mmol) were placed in a microwave tube. Dioxane (2294 μl) and water (573 μl) were added to this tube. After degassing, the reaction mixture was heated at 85° C. overnight. The reaction mixture was purified by column chromatography (0-10% MeOH/EtOAc) to afford the title compounds. LC/MS (M+1)+=729.5.

Step B: 3-(2-Aminoquinazolin-7-yl)-2-(1H-tetrazol-5-yl)benzenesulfonamide 3-(2-Aminoquinazolin-7-yl)-N,N-bis(4-methoxybenzyl)-2-(1-(4-methoxybenzyl)-1H-tetrazol-5-yl)benzenesulfonamide and 3-(2-aminoquinazolin-7-yl)-N,N-bis(4-methoxybenzyl)-2-(2-(4-methoxybenzyl)-2H-tetrazol-5-yl)benzenesulfonamide (133 mg, 0.182 mmol) was heated in TFA at 60° C. for 2 hr. After cooling, the reaction mixture was concentrated and purified with Gilson (2-40% CH3CN/water with 0.1% TFA). The correct fractions were combined, concentrated and lypholized to give 3-(2-aminoquinazolin-7-yl)-2-(1H-tetrazol-5-yl)benzenesulfonamide. LC/MS (M+1)$^+$=369.3.

EXAMPLE 421

3-(2-Bromobenzo[d]thiazol-4-yl)-2-(1H-tetrazol-5-yl)benzenesulfonamide

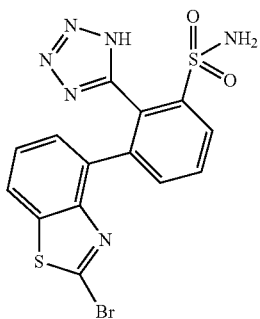 [SMILES: NS(=O)(=O)c1cccc(-c2cccc3sc(Br)nc23)c1-c1nnn[nH]1]

Step A: 3-(2-aminobenzo[d]thiazol-4-yl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-N,N-bis(4-methoxybenzyl)-2-(2-(4-methoxybenzyl)-2H-tetrazol-5-yl)benzenesulfonamide 4-Bromobenzo[d]thiazol-2-amine (600 mg, 2.62 mmol), (3-(N,N-bis(4-methoxybenzyl)sulfamoyl)-2-(1-(4-methoxybenzyl)-1H-tetrazol-5-yl)phenyl)boronic acid and (3-(N,N-bis(4-methoxybenzyl)sulfamoyl)-2-(2-(4-methoxybenzyl)-2H-tetrazol-5-yl)phenyl)boronic acid (2473 mg, 3.93 mmol), 2nd Generation Xphos Precatalyst (309 mg, 0.393 mmol), Cs$_2$CO$_3$ (2560 mg, 7.86 mmol) was placed in a reaction vessel, 1,4-Dioxane (1.40E+04 µL) and Water (3492 µL) were added. The reaction mixture was degassed for 20 min and heated at 85° C. for 20 hr. LC-MS showed the completion of the reaction. After cooling, the reaction mixture was directly loaded onto a silica gel column, eluting with 0-20% MeOH/EtOAc to give the title compounds. LC/MS (M+1)$^+$=734.4

Step B: 3-(2-Bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide 3-(2-Aminobenzo[d]thiazol-4-yl)-N,N-bis(4-methoxybenzyl)-2-(1-(4-methoxybenzyl)-1H-tetrazol-5-yl)benzenesulfonamide and 3-(2-aminobenzo[d]thiazol-4-yl)-N,N-bis(4-methoxybenzyl)-2-(2-(4-methoxybenzyl)-2H-tetrazol-5-yl)benzenesulfonamide (1.56 g, 2.13 mmol) was added portionwise to a black solution of Copper(II) Bromide (0.570 g, 2.55 mmol) and Tert-Butyl Nitrite (0.351 g, 3.40 mmol) in acetonitrile (7.87 mL) at room temperature under N$_2$. The mixture was stirred for 30 min and then diluted with 1N HCl and extracted with EtOAc. The organics were separated and purified by column chromatography (0-50% EtOAc/Hexane) to give the title compounds. LC/MS (M+1)$^+$=797.6, 799.6

Step C: 3-(2-Bromobenzo[d]thiazol-4-yl)-2-(1H-tetrazol-5-yl)benzenesulfonamide 3-(2-Bromobenzo[d]thiazol-4-yl)-N,N-bis(4-methoxybenzyl)-2-(1-(4-methoxybenzyl)-1H-tetrazol-5-yl)benzenesulfonamide (100 mg, 0.125 mmol) was heated in TFA (2 mL) at 60° C. for 3 hr. The reaction mixture was concentrated and the residue was purified with Gilson (5-70% CH$_3$CN/water) with 0.1% TFA. The correct fractions were combined, concentrated and lypholized to give 3-(2-bromobenzo[d]thiazol-4-yl)-2-(1H-tetrazol-5-yl)benzenesulfonamide. LC/MS (M+1)$^+$=437.2

EXAMPLE 422

3-(Benzo[d]thiazol-4-yl)-2-(1H-tetrazol-5-yl)benzenesulfonamide

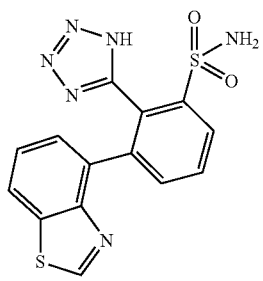 [SMILES: NS(=O)(=O)c1cccc(-c2cccc3scnc23)c1-c1nnn[nH]1]

Step A: 3-(Benzo[d]thiazol-4-yl)-N,N-bis(4-methoxybenzyl)-2-(1-(4-methoxybenzyl)-1H-tetrazol-5-yl)benzenesulfonamide and 3-(Benzo[d]thiazol-4-yl)-N,N-bis(4-methoxybenzyl)-2-(2-(4-methoxybenzyl)-2H-tetrazol-5-yl)benzenesulfonamide 3-(2-Bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide (43 mg, 0.054 mmol) was hydrogenated with a balloon in the presence of Pd(OH)$_2$ (37.8 mg, 0.054 mmol) at room temperature overnight. Another 15 mg of Pd(OH)$_2$ was added, and hydrogenation was continued for 5 hr until LC-MS showed the completion of the reaction. The reaction mixture was filtered and concentrated to give the title compounds. LC/MS (M+1)$^+$=719.8.

Step B: 3-(Benzo[d]thiazol-4-yl)-2-(1H-tetrazol-5-yl)benzenesulfonamide 3-(Benzo[d]thiazol-4-yl)-N,N-bis(4-methoxybenzyl)-2-(1-(4-methoxybenzyl)-1H-tetrazol-5-yl)benzenesulfonamide and 3-(benzo[d]thiazol-4-yl)-N,N-bis(4-methoxybenzyl)-2-(2-(4-methoxybenzyl)-2H-tetrazol-5-yl)benzenesulfonamide (37 mg, 0.051 mmol) was heated in TFA (2 mL) at 60° C. for 2 hr. The mixture was concentrated and purified with Gilson (3-80% CH$_3$CN/water with 0.1% TFA). The correct fractions were combined, concentrated and lypholized to give 3-(benzo[d]thiazol-4-yl)-2-(1H-tetrazol-5-yl)benzenesulfonamide. LC/MS (M+1)+=359.3.

EXAMPLE 423

3-(2-amino-1,3-benzothiazol-4-yl)-2-(2H-tetrazol-5-yl)-6-(trifluoromethyl)benzenesulfonamide

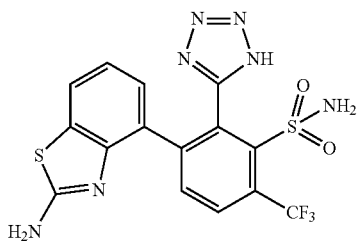 [SMILES: Nc1nc2c(-c3ccc(C(F)(F)F)c(S(N)(=O)=O)c3-c3nnn[nH]3)cccc2s1]

Step A: 3-(2-aminobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide To the reaction mixture of (3-[bis[(4-methoxyphenyl)methyl]sulfamoyl]-2-[1-[(4-methoxyphenyl)methyl]-1H-1,2,3,4-tetrazol-5-yl]-4-(trifluoromethyl)phenyl)boronic acid and (3-[bis[(4-methoxyphenyl)methyl]sulfamoyl]-2-[2-[(4-methoxyphenyl)methyl]-2H-1,2,3,4-tetrazol-5-yl]-4-(trifluoromethyl)phenyl)boronic acid (4.00 g, 5.73 mmol) was added 4-bromobenzo[d]thiazol-2-amine (1708 mg, 7.46 mmol), PdCl$_2$(dppf) (420 mg, 0.573 mmol), and Na$_2$CO$_3$ (1216 mg, 11.47 mmol) in water (1.43E+04 µl). Then 3.5 mL of dioxane was added. The reaction mixture was degassed for 20 min. The reaction mixture was sealed and heated at 85° C. overnight. After removal of the solvent under reduced pressure, the crude reaction mixture was purified by column chromatography (100% hexane to 50% EtOAc/Hexane gradient) on a 330 g ISCO column to give the title compound as an tetrazole para-methoxybenzyl isomer mixture. LC-MS [M+H]$^+$: 802.7.

Step B: 3-(2-amino-1,3-benzothiazol-4-yl)-2-(2H-tetrazol-5-yl)-6-(trifluoromethyl)benzenesulfonamide 3-(2-aminobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and its para-methoxybenzyl regioisomer (664 mg, 0.828 mmol) was heated in TFA (5 mL) at 60° C. for 2 hr. LC-MS showed the reaction was complete. The mixture was concentrated and purified using a Gilson HPLC (3-75% CH3CN/water) with 0.1% TFA. The correct fractions were combined and concentrated. The resulting TFA salt was neutralized with a scx ion exchange cartridge. Lyophilization gave the title compound. LC-MS [M+H]$^+$: 442.3.

EXAMPLE 424

3-(2-aminothiazol-5-yl)-6-bromo-2-(2H-tetrazol-5-yl)benzenesulfonamide

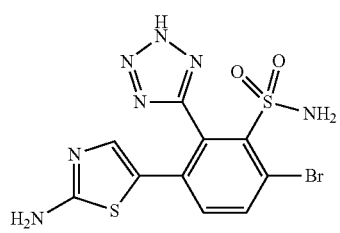 [SMILES: Nc1ncc(-c2ccc(Br)c(S(N)(=O)=O)c2-c2nn[nH]n2)s1]

Step A: 3-(2-aminothiazol-5-yl)-6-bromo-N,N-bis(4-methoxybenzyl)-2-(2-(4-methoxybenzyl)-2H-tetrazol-5-yl)benzenesulfonamide A microwave vial was charged with 6-bromo-3-iodo-N,N-bis(4-methoxybenzyl)-2-(2-(4-methoxybenzyl)-2H-tetrazol-5-yl)benzenesulfonamide (0.2 g, 0.253 mmol), 5-(4,4,5,5-tetramethyl-1,3,2-dioxaborolan-2-yl)thiazol-2-amine hydrochloride (0.266 g, 1.012 mmol), potassium carbonate (0.210 g, 1.518 mmol) and PdCl$_2$(dppf)-CH$_2$Cl$_2$ adduct (0.083 g, 0.101 mmol). The vial was sealed, degassed, and filled with dioxane (1.26 mL) and water (0.42 mL). The resulting mixture was heated overnight at 90° C. The reaction mixture was filtered over celite to removed palladium. The filtrate was diluted with EtOAc and washed with water. The organic layer was dried over anhydrous MgSO$_4$, filtered, concentrated and purified by silica gel column chromatography using 0-10% MeOH/DCM as mobile phase to afford the title compound. LC-MS (IE, m/z): 764.38 [M+2]$^+$.

Step B: 3-(2-aminothiazol-5-yl)-6-bromo-2-(2H-tetrazol-5-yl)benzenesulfonamide

To a solution of 3-(2-aminothiazol-5-yl)-6-bromo-N,N-bis(4-methoxybenzyl)-2-(2-(4-methoxybenzyl)-2H-tetrazol-5-yl)benzenesulfonamide (80 mg, 0.105 mmol) in DCM (0.52 mL) was added anisole (114 µL, 1.049 mmol) and TFA (808 µL, 10.49 mmol) at rt. The resulting mixture was heated at 80° C. for 1 hr. After removing the volatile the residue was purified by reverse phase HPLC using DMSO to load sample and 5-45% acetonitrile/water (0.1% formic acid as additive) as mobile phase over 10 min to give the title compound. LC-MS (IE, m/z): 404.01 [M+2]$^+$.

EXAMPLE 425

N-((4'-bromo-3'-sulfamoyl-2'-(2H-tetrazol-5-yl)-[1,1'-biphenyl]-4-yl)methyl)formimidamide

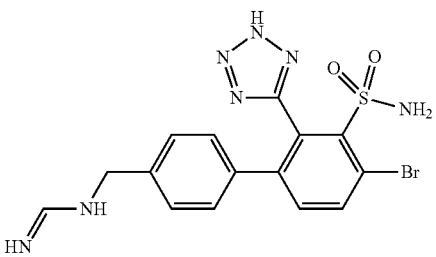 [SMILES: N=CNCc1ccc(-c2ccc(Br)c(S(N)(=O)=O)c2-c2nn[nH]n2)cc1]

Step A: tert-butyl ((4'-bromo-2'-(2-(4-methoxybenzyl)-2H-tetrazol-5-yl)-3'-sulfamoyl-[1,1'-biphenyl]-4-yl)methyl)carbamate A microwave vial was charged with 6-bromo-3-iodo-2-(2-(4-methoxybenzyl)-2H-tetrazol-5-yl)benzenesulfonamide (0.4 g, 0.727 mmol), (4-(((tert-butoxycarbonyl)amino)methyl)phenyl)boronic acid (0.402 g, 1.600 mmol), Na$_2$CO$_3$ (0.231 g, 2.181 mmol) and PdCl$_2$(dppf)-CH$_2$Cl$_2$ adduct (0.089 g, 0.109 mmol). The vial was sealed, degassed, and filled with dioxane (3.64 mL) and water (1.21 mL). The resulting mixture was heated overnight at 80° C. The reaction mixture was filtered over celite to removed palladium. The filtrate was evaporated and the residue was purified by silica gel chromatograph eluting with 0-10% MeOH/DCM to give the title compound.

Step B: 4'-(aminomethyl)-4-bromo-2-(2-(4-methoxybenzyl)-2H-tetrazol-5-yl)-[1,1'-biphenyl]-3-sulfonamide To the solution of tert-butyl ((4'-bromo-2'-(2-(4-methoxybenzyl)-2H-tetrazol-5-yl)-3'-sulfamoyl-[1,1'-biphenyl]-4-yl)methyl)carbamate (580 mg, 0.921 mmol) in DCM (18 mL) was added anisole (2.0 mL, 18.43 mmol) and TFA (7.1 mL, 92 mmol) at rt. The resulting mixture was stirred at rt for 1 hr. After removing the volatile the residue was purified by ion exchange column (load sample and rinse with MeOH, rinse out product with 2 M $NH_3$ in MeOH) to give the product as a free amine LC-MS (IE, m/z): 531.11 $[M+2]^+$.

Step C: N-((4'-bromo-2'-(2-(4-methoxybenzyl)-2H-tetrazol-5-yl)-3'-sulfamoyl-[1,1'-biphenyl]-4-yl)methyl)formimidamide 4'-(aminomethyl)-4-bromo-2-(1-(4-methoxybenzyl)-1H-tetrazol-5-yl)-[1,1'-biphenyl]-3-sulfonamide (80 mg, 0.151 mmol) in DMF (1.5 mL) was treated with ethyl formimidate hydrochloride (19.87 mg, 0.181 mmol) and DIPEA (106 µL, 0.604 mmol) at 0° C. The reaction mixture was stirred at rt overnight. LC-MS showed the reaction was not completed. More reagents were added with 20 mg ethyl formimidate hydrochloride and 0.1 mL of DIPEA. After stirring once more overnight, the reaction mixture was concentrated and purified with reverse phase HPLC eluting with 5-70% $CH_3CN$/water with 0.1% TFA to afford the title compound. LC-MS (IE, m/z): 558.28 [M+2].

Step D: N-((4'-bromo-3'-sulfamoyl-2'-(2H-tetrazol-5-yl)-[1,1'-biphenyl]-4-yl)methyl)formimidamide To the solution of N-((4'-bromo-2'-(2-(4-methoxybenzyl)-2H-tetrazol-5-yl)-3'-sulfamoyl-[1,1'-biphenyl]-4-yl)methyl) formimidamide (20 mg, 0.036 mmol) in DCM (0.72 mL) was added anisole (78 µL, 0.719 mmol) and TFA (277 µL, 3.59 mmol) at rt. The resulting mixture was heated at 80° C. for 2 hr. After removing the volatile the residue was purified by reverse phase HPLC eluting with 5-40% acetonitrile/water (0.1% formic acid) to give the title product. LC-MS (IE, m/z): 438.32 $[M+2]^+$.

EXAMPLE 426

3-(6-((2-hydroxyethyl)amino)pyridin-3-yl)-2-(2H-tetrazol-5-yl)benzenesulfonamide

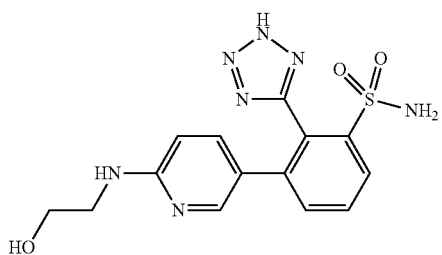 [SMILES: NS(=O)(=O)c1cccc(-c2ccc(NCCO)nc2)c1-c1nn[nH]n1]

Step A: 3-(6-((2-hydroxyethyl)amino)pyridin-3-yl)-N,N-bis(4-methoxybenzyl)-2-(2-(4-methoxybenzyl)-2H-tetrazol-5-yl)benzenesulfonamide In a MW vial, 2-aminoethanol (12 µL, 0.202 mmol), 3-(6-bromopyridin-3-yl)-N,N-bis(4-methoxybenzyl)-2-(2-(4-methoxybenzyl)-2H-tetrazol-5-yl)benzenesulfonamide (100 mg, 0.135 mmol), $Cs_2CO_3$ (88 mg, 0.270 mmol) and bis((2-isobutyrylcyclohex-1-en-1-yl)oxy)copper (21.47 mg, 0.054 mmol) were suspended in DMF (1.3 mL). The vial was sealed, and degassed with $N_2$. The reaction mixture was heated at 100° C. for 24 hr. After filtration through celite, the filtrate was concentrated and the residue was purified on silica gel column using 0-15% MeOH/DCM to give the title compound. LC-MS (IE, m/z): 722.99 $[M+1]^+$.

Step B: 3-(6-((2-hydroxyethyl)amino)pyridin-3-yl)-2-(2H-tetrazol-5-yl)benzenesulfonamide To a solution of 3-(6-((2-hydroxyethyl)amino)pyridin-3-yl)-N,N-bis(4-methoxybenzyl)-2-(2-(4-methoxybenzyl)-2H-tetrazol-5-yl)benzenesulfonamide (80 mg, 0.111 mmol) in DCM (554 µL) was added anisole (120 µL, 1.108 mmol) and TFA (854 µL, 11.08 mmol) at rt. The resulting mixture was heated at 80° C. for 1 hr. After removing the volatile the residue was purified by reverse phase HPLC using DMSO to load sample and 5-60% acetonitrile/water (0.1% TFA as additive) as mobile phase over 10 min to give the title compound. LC-MS (IE, m/z): 362.31 $[M+1]^+$.

EXAMPLE 427

3-(2-(6-aminopyridin-3-yl)ethyl)-2-(2H-tetrazol-5-yl)benzenesulfonamide

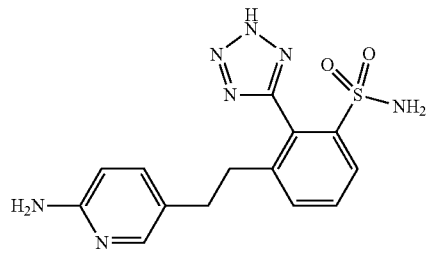 [SMILES: Nc1ccc(CCc2cccc(S(N)(=O)=O)c2-c2nn[nH]n2)cn1]

Step A: 3-bromo-N,N-bis(4-methoxybenzyl)-2-(2-(4-methoxybenzyl)-2H-tetrazol-5-yl)benzenesulfonamide To a solution of 3-bromo-2-(2-(4-methoxybenzyl)-2H-tetrazol-5-yl)benzenesulfonamide (20.0 g, 47.1 mmol) in acetone (300 mL) were added PMB-Cl (16.2 g, 104 mmol), KI (17.2 g, 104 mmol) and $K_2CO_3$ (26.1 g, 188 mmol). The resultant mixture was stirred for 3 hr at 70° C. The mixture was concentrated in vacuo and 400 mL of water was added. The mixture was extracted with ethyl acetate (100 mL×3). The organic layer was dried over anhydrous sodium sulfate, filtered and the filtrate was concentrated in vacuo to give the crude product. The crude product was purified by silica gel chromatography (20% EtOAc in petroleum ether) to give the title compound. MS (ESI): m/z $(M+H)^+$ 663.9, 665.9.

Step B: N,N-bis(4-methoxybenzyl)-2-(2-(4-methoxybenzyl)-2H-tetrazol-5-yl)-3-vinylbenzenesulfonamide To a solution of 3-bromo-N,N-bis(4-methoxybenzyl)-2-(2-(4-methoxybenzyl)-2H-tetrazol-5-yl)benzenesulfonamide (10.0 g, 15.1 mmol) in dioxane/water (120/12 mL) were added potassium vinyltrifluroborate (4.03 g, 30.2 mmol), $Na_2CO_3$ (3.19 g, 30.1 mmol) and $Pd(dppf)Cl_2$ (2.20 g, 3.01 mmol) under nitrogen atmosphere. The mixture was stirred for overnight at 110° C. The mixture was filtered and the filtrate was concentrated in vacuo, the residue was purified by silica gel chromatography (30% EtOAc in petroleum ether) to give the title compound. MS (ESI): m/z $(M+H)^+$ 612.1.

Step C: tert-butyl (E)-(5-(3-(N,N-bis(4-methoxybenzyl)sulfamoyl)-2-(2-(4-methoxybenzyl)-2H-tetrazol-5-yl)styryl)pyridin-2-yl)carbamate In the reaction vessel tert-butyl (5-bromopyridin-2-yl)carbamate (0.035 g, 0.128 mmol), and N,N-bis(4-methoxybenzyl)-2-(2-(4-methoxybenzyl)-2H-tetrazol-5-yl)-3-vinylbenzenesulfonamide (0.094 g, 0.154 mmol) were combined, followed by tBu₃P HBF₄ (0.015 g, 0.051 mmol), Pd₂(dba)₃ (0.012 g, 0.013 mmol) and dicyclohexylmethylamine (0.041 ml, 0.192 mmol). This mixture was then evacuated and backfilled with N₂ (3 times). Then dry, degassed dioxane (1.28 mL) was added to this flask. This mixture was stirred at 100° C. overnight. The mixture was cooled, filtered and the solvent was evaporated under reduced pressure. The residue was purified by silica gel chromatography eluting with 0-100% EtOAc/hexan to give the title compound. LC-MS (IE, m/z): 804.31 [M+1]⁺.

Step D: 3-(2-(6-aminopyridin-3-yl)ethyl)-2-(2H-tetrazol-5-yl)benzenesulfonamide

To a solution of tert-butyl (5-(3-(N,N-bis(4-methoxybenzyl)sulfamoyl)-2-(2-(4-methoxybenzyl)-2H-tetrazol-5-yl)phenethyl)pyridin-2-yl)carbamate (50 mg, 0.062 mmol) in DCM (310 µL) was added anisole (67 µL, 0.620 mmol) and TFA (478 µL, 6.20 mmol) at rt. The resulting mixture was heated at 80° C. for 1 hr. After removing the volatile the residue was purified by reverse phase HPLC using DMSO to load sample and 5-55% acetonitrile/water (0.1% TFA as additive) as mobile phase over 10 min to give the title compound. LC-MS (IE, m/z): 346.12 [M+1].

EXAMPLE 428

3-(2-amino-1H-benzo[d]imidazol-7-yl)-2-(2H-tetrazol-5-yl)benzenesulfonamide

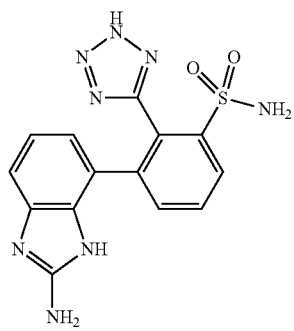 [SMILES: Nc1nc2cccc(-c3cccc(S(N)(=O)=O)c3-c3nn[nH]n3)c2[nH]1]

Step A: 3-(2-amino-1H-benzo[d]imidazol-7-yl)-N,N-bis(4-methoxybenzyl)-2-(2-(4-methoxybenzyl)-2H-tetrazol-5-yl)benzenesulfonamide A microwave vial was charged with cesium carbonate (0.280 g, 0.860 mmol), 2nd generation XPhos precatalyst (0.045 g, 0.057 mmol), 7-chloro-1H-benzo[d]imidazol-2-amine (0.072 g, 0.430 mmol) and 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide (0.2 g, 0.287 mmol). The vial was sealed, degassed, and filled with dioxane (1.529 ml) and water (0.382 ml). The resulting mixture was heated overnight at 80° C. The reaction mixture was filtered over celite to removed palladium. The filtrate was concentrated and the residue was purified by silica gel column chromatography using 0-10% MeOH/DCM as mobile phase to afford the title product. MS (ESI): m/z (M+H)⁺ 717.48.

Step B: 3-(2-amino-1H-benzo[d]imidazol-7-yl)-2-(2H-tetrazol-5-yl)benzenesulfonamide To the solution of 3-(2-amino-1H-benzo[d]imidazol-7-yl)-N,N-bis(4-methoxybenzyl)-2-(2-(4-methoxybenzyl)-2H-tetrazol-5-yl)benzenesulfonamide (200 mg, 0.279 mmol) in DCM (1.4 mL) was added anisole (303 µL, 2.79 mmol) and TFA (2150 µL, 27.9 mmol) at rt. The resulting mixture was stirred at 80° C. for 1 hr. After removing the volatile the residue was purified by reverse phase HPLC (5-35% ACN/water, 0.1% TFA as additive) to give the title compound. MS (ESI): m/z (M+H)⁺ 357.31

EXAMPLE 429

EXAMPLE 429 was prepared in an analogous fashion to EXAMPLE 428, 3-(2-amino-1H-benzo[d]imidazol-7-yl)-2-(2H-tetrazol-5-yl)benzenesulfonamide, starting from 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide and corresponding halides listed below.

| EX. NO. | INTERMEDIATES | EXAMPLE STRUCTURE/NAME | Characterization, LC/MS |
|---|---|---|---|
| 429 | 6-bromo-1H-benzo[d]imidazol-2-amine | 3-(2-amino-1H-benzo[d]imidazol-6-yl)-2-(2H-tetrazol-5-yl)benzenesulfonamide | [M + 1]⁺: 357.24 |

EXAMPLE 430

3,6-bis[4-(4-piperidyl)phenyl]-2-(2H-tetrazol-5-yl)benzenesulfonamide

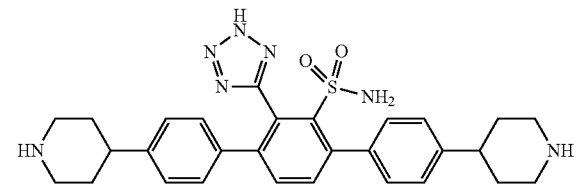 [SMILES: NS(=O)(=O)c1c(-c2ccc(C3CCNCC3)cc2)ccc(-c2ccc(C3CCNCC3)cc2)c1-c1nn[nH]n1]

Step A: di-tert-butyl 4,4'-(2'-(N,N-bis(4-methoxybenzyl)sulfamoyl)-3'-(2-(4-methoxybenzyl)-2H-tetrazol-5-yl)-[1,1':4',1''-terphenyl]-4,4''-diyl)bis(piperidine-1-carboxylate)

A microwave vial was charged with 6-bromo-3-iodo-N,N-bis(4-methoxybenzyl)-2-(2-(4-methoxybenzyl)-2H-tetrazol-5-yl)benzenesulfonamide (0.5 g, 0.633 mmol), tert-butyl 4-(4-(4,4,5,5-tetramethyl-1,3,2-dioxaborolan-2-yl)phenyl)piperidine-1-carboxylate (0.294 g, 0.759 mmol), PdCl₂(dppf)-CH₂Cl₂ adduct (0.052 g, 0.063 mmol) and sodium carbonate (0.201 g, 1.898 mmol). The vial was sealed, degassed, and filled with dioxane (3.37 mL) and water (0.84 mL). The resulting mixture was heated overnight at 70° C. The reaction mixture was filtered over celite to removed palladium. The filtrate was diluted with EtOAc and washed with water. The organic layer was dried over anhydrous MgSO₄, filtered, concentrated and purified by silica gel column chromatography using 0-100% EtOAc/Hexanes as mobile phase to afford the title product. LC-MS (IE, m/z): 1105.6 [M+1]+.

Step B: 3,6-bis[4-(4-piperidyl)phenyl]-2-(2H-tetrazol-5-yl)benzenesulfonamide

To the solution of di-tert-butyl 4,4'-(2'-(N,N-bis(4-methoxybenzyl)sulfamoyl)-3'-(2-(4-methoxybenzyl)-2H-tetrazol-5-yl)-[1,1':4',1''-terphenyl]-4,4''-diyl)bis(piperidine-1-carboxylate) (200 mg, 0.181 mmol) in DCM (3.6 mL) was added anisole (394 μL, 3.62 mmol) and TFA (1.4 mL, 18.11 mmol) at 0° C. The resulting mixture was heated at rt for 1 hr. After completely removing the volatile, the residue was redissolved in DCM (3.6 mL). Anisole (394 μL, 3.62 mmol) and TFA (1.4 mL, 18.11 mmol) were added, and the reaction mixture was heated at 80° C. for 1 hr. After removing the volatile the residue was purified (DMSO loading) on reverse phase HPLC using 5-70% acetonitrile/water (0.1% formic acid) as eluent over 10 min to give the title compound. LC-MS (IE, m/z): 544.49[M+1]+.

EXAMPLES 431 and 432

431 (Fast Eluting Isomer): 3-(2-((1r,4s)-4-aminocyclohexyl)ethyl)-2-(2H-tetrazol-5-yl)-6-(trifluoromethyl)benzenesulfonamide 432 (Slow Eluting Isomer): 3-(2-((1s,4r)-4-aminocyclohexyl)ethyl)-2-(2H-tetrazol-5-yl)-6-(trifluoromethyl)benzenesulfonamide

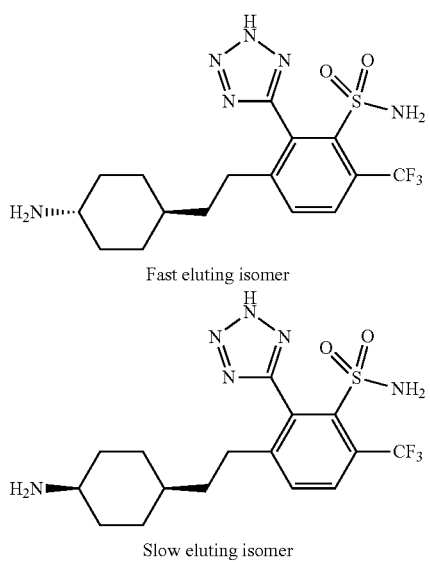

Fast eluting isomer

Slow eluting isomer

Step A: tert-butyl (4-(3-(N,N-bis(4-methoxybenzyl)sulfamoyl)-2-(2-(4-methoxybenzyl)-2H-tetrazol-5-yl)-4-(trifluoromethyl)phenethyl)cyclohexyl)carbamate A microwave vial was charged with nickel(II) iodide (25.6 mg, 0.082 mmol), manganese (90 mg, 1.638 mmol), tert-butyl (4-(2-iodoethyl)cyclohexyl)carbamate (289 mg, 0.819 mmol), bathophenanthroline (27.2 mg, 0.082 mmol) and 3-bromo-N,N-bis(4-methoxybenzyl)-2-(2-(4-methoxybenzyl)-2H-tetrazol-5-yl)-6-(trifluoromethyl)benzenesulfonamide (400 mg, 0.546 mmol). The vial was sealed, purged with N2 for 10 min, and filled with DMA (3640 μl). The resulting mixture was purged with N2 for another 10 min and heated overnight at 80° C. The reaction mixture was filtered over celite to remove metal. The filtrate was concentrated and purified by silica gel column chromatography using 0-100% EtOAc/hexane as mobile phase to afford the title compound. LC-MS (IE, m/z): 879.76 [M+1]+.

Step B: 431 (Fast Eluting Isomer): 3-(2-((1r,4s)-4-aminocyclohexyl)ethyl)-2-(2H-tetrazol-5-yl)-6-(trifluoromethyl)benzenesulfonamide 432 (Slow Eluting Isomer): 3-(2-((1s,4r)-4-aminocyclohexyl)ethyl)-2-(2H-tetrazol-5-yl)-6-(trifluoromethyl)benzenesulfonamide To tert-butyl (4-(3-(N,N-bis(4-methoxybenzyl)sulfamoyl)-2-(2-(4-methoxybenzyl)-2H-tetrazol-5-yl)-4-(trifluoromethyl)phenethyl)cyclohexyl)carbamate (330 mg, 0.375 mmol) was added anisole (204 μL, 1.877 mmol) and TFA (2.9 mL, 37.5 mmol) at rt (neat TFA, no solvent). The resulting mixture was stirred at rt for 2 hr. After removing the volatile the residue was passed through SCX ion exchange column to remove debromide side product from the coupling reaction. To the free amine was added anisole (204 μL, 1.877 mmol) and TFA (2.9 mL, 37.5 mmol) at rt (neat TFA, no solvent). The resulting mixture was heated at 80° C. for 2 hr. After removing the volatile the residue was purified (DMSO loading) on reverse phase HPLC using 5-40% acetonitrile/water (0.1% NH4OH as additive) to give the title compounds. 431 LC-MS (IE, m/z): 419.40 [M+1]+. 432 LC-MS (IE, m/z): 419.43 [M+1]+.

EXAMPLE 433

4'-(azetidin-3-yl)-2-(2H-tetrazol-5-yl)-4-(trifluoromethyl)-[1,1'-biphenyl]-3-sulfonamide

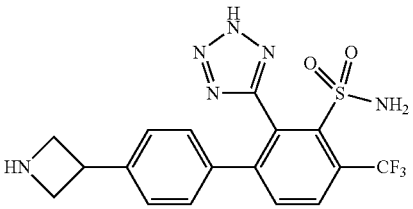 [SMILES: NS(=O)(=O)c1c(C(F)(F)F)ccc(-c2ccc(C3CNC3)cc2)c1-c1nn[nH]n1]

Step A: 4'-(azetidin-3-yl)-N,N-bis(4-methoxybenzyl)-2-(2-(4-methoxybenzyl)-2H-tetrazol-5-yl)-4-(trifluoromethyl)-[1,1'-biphenyl]-3-sulfonamide The mixture of 2nd generation PCy3 precatalyst (81 mg, 0.137 mmol), potassium acetate (402 mg, 4.10 mmol), 3-bromo-N,N-bis(4-methoxybenzyl)-2-(2-(4-methoxybenzyl)-2H-tetrazol-5-yl)-6-(trifluoromethyl)benzenesulfonamide (1000 mg, 1.365 mmol) and 5,5,5',5'-tetramethyl-2,2'-bi(1,3,2-dioxaborinane) (925 mg, 4.10 mmol) in dioxane (6.8 mL) was degassed with N2. The resulting mixture was heated at 75° C. for 6 hr. LCMS indicated complete conversion to boronic acid. 3-(4-chlorophenyl)azetidine (343 mg, 2.048 mmol), potassium carbonate (943 mg, 6.83 mmol) and 2nd generation XPhos precatalyst (161 mg, 0.205 mmol) were added followed by 2 mL water. The reaction mixture was degassed with N2 and heated at 90° C. overnight. After cooling to rt the mixture was filtered through celite, the filtrate was concentrated and the residue was purified by silica gel column chromatography using 0-10% MeOH/DCM (with NH3 as additive) as mobile phase to afford the title compound. LC-MS (IE, m/z): 785.86 [M+1]+.

Step B: 4'-(azetidin-3-yl)-2-(2H-tetrazol-5-yl)-4-(trifluoromethyl)-[1,1'-biphenyl]-3-sulfonamide To a solution of 4'-(azetidin-3-yl)-N,N-bis(4-methoxybenzyl)-2-(2-(4-methoxybenzyl)-2H-tetrazol-5-yl)-4-(trifluoromethyl)-[1,1'-biphenyl]-3-sulfonamide (90 mg, 0.115 mmol) in DCM (573 μL) was added anisole (125 μL, 1.147 mmol) and TFA (883 μL, 11.47 mmol) at rt. The resulting mixture was stirred at 80° C. for 1 hr to remove the PMB protection. After removing the volatile the residue was purified by reverse phase HPLC using DMSO to load sample and 5-55% acetonitrile/water (0.1% TFA as additive) as mobile phase over 10 min to give the final product. LC-MS (IE, m/z): 425.42 [M+1]$^+$.

EXAMPLE 434

3-(3'-sulfamoyl-2'-(2H-tetrazol-5-yl)-4'-(trifluoromethyl)-[1,1'-biphenyl]-4-yl)azetidine-1-carboximidamide

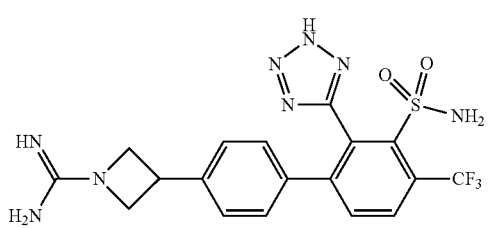

Step A: tert-butyl 4-(4'-chloro-3'-sulfamoyl-2'-(2H-tetrazol-5-yl)-[1,1'-biphenyl]-4-yl)piperidine-1-carboxylate 4'-(azetidin-3-yl)-N,N-bis(4-methoxybenzyl)-2-(1-(4-methoxybenzyl)-1H-tetrazol-5-yl)-4-(trifluoromethyl)-[1,1'-biphenyl]-3-sulfonamide (60 mg, 0.076 mmol) in DMF (1.5 mL) was treated with 1H-pyrazole-1-carboxamidine hydrochloride (17.93 mg, 0.122 mmol) and DIPEA (66.8 μl, 0.382 mmol). The reaction mixture was stirred at rt overnight. LC-MS showed the reaction was not completed. More reagents were added with 1H-pyrazole-1-carboxamidine hydrochloride (17.93 mg, 0.122 mmol) and DIPEA (66.8 μl, 0.382 mmol). After once more overnight, the reaction mixture was purified with reverse phase HPLC (10-90% MeCN/water as gradient) to afford the title compound. LC-MS (IE, m/z): 827.69 [M+1]$^+$.

Step B: 4-chloro-4'-(piperidin-4-yl)-2-(2H-tetrazol-5-yl)-[1,1'-biphenyl]-3-sulfonamide To the solution of 3-(2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-yl)azetidine-1-carboximidamide (30 mg, 0.042 mmol) in DCM (212 μL) was added anisole (46.1 μl, 0.424 mmol) and TFA (327 μl, 4.24 mmol) at rt. The resulting mixture was stirred at 80° C. for 1 hr. After removing the volatile the residue was purified by reverse phase HPLC (5-60% ACN/water, 0.1% TFA as additive) to give the title compound. LC-MS (IE, m/z): 467.39 [M+1]$^+$.

EXAMPLE 435

1,1-dimethyl-3-(3'-sulfamoyl-2'-(2H-tetrazol-5-yl)-4'-(trifluoromethyl)-[1,1'-biphenyl]-4-yl)azetidin-1-ium

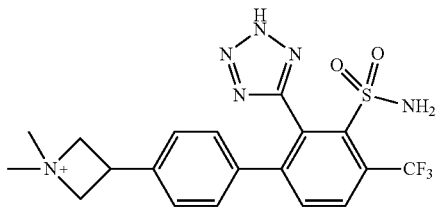

Step A: 3-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)-1,1-dimethylazetidin-1-ium To the solution of 4'-(azetidin-3-yl)-N,N-bis(4-methoxybenzyl)-2-(2-(4-methoxybenzyl)-2H-tetrazol-5-yl)-4-(trifluoromethyl)-[1,1'-biphenyl]-3-sulfonamide (60 mg, 0.076 mmol) in acetone (2 ml) was added K$_2$CO$_3$ (63.4 mg, 0.459 mmol) and MeI (0.029 ml, 0.459 mmol). The resulting mixture was stirred at rt overnight. After concentration the residue was purified on reverse phase HPLC using 40-100% acetonitrile/water (0.05% TFA) to give the title compound. LC-MS (IE, m/z): 813.64 [M]$^+$.

Step B: 1,1-dimethyl-3-(3'-sulfamoyl-2'-(2H-tetrazol-5-yl)-4'-(trifluoromethyl)-[1,1'-biphenyl]-4-yl)azetidin-1-ium To the solution of 3-(2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-yl)-1,1-dimethylazetidin-1-ium (20 mg, 0.029 mmol) in DCM (144 μL) was added anisole (31.3 μL, 0.288 mmol) and TFA (222 μL, 2.88 mmol) at rt. The resulting mixture was stirred at 80° C. for 1 hr. After removing the volatile the residue was purified by reverse phase HPLC (5-50% ACN/water, 0.1% TFA as additive) to give the title compound. LC-MS (IE, m/z): 453.36 [M]$^+$.

EXAMPLE 436

4'-(4-aminopiperidin-4-yl)-2-(2H-tetrazol-5-yl)-4-(trifluoromethyl)-[1,1'-biphenyl]-3-sulfonamide

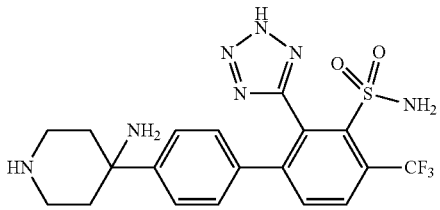 [SMILES: NC1(c2ccc(-c3ccc(C(F)(F)F)c(S(N)(=O)=O)c3-c3nn[nH]n3)cc2)CCNCC1]

Step A: tert-butyl 4-amino-4-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)piperidine-1-carboxylate The mixture of 5,5,5',5'-tetramethyl-2,2'-bi(1,3,2-dioxaborinane) (370 mg, 1.638 mmol), 3-bromo-N,N-bis(4-methoxybenzyl)-2-(2-(4-methoxybenzyl)-2H-tetrazol-5-yl)-6-(trifluoromethyl)benzenesulfonamide (400 mg, 0.546 mmol), PCy$_3$ 2nd generation precatalyst (32.2 mg, 0.055 mmol) and potassium acetate (161 mg, 1.638 mmol) in dioxane (5.5 mL) was degassed with N₂. The resulting mixture was heated at 75° C. for 6 hr. LCMS indicated complete conversion to boronic acid. Tert-butyl 4-amino-4-(4-bromophenyl)piperidine-1-carboxylate (which can be prepared in an analogous fashion as described for tert-butyl 4-amino-4-(4-chlorophenyl)piperidine-1-carboxylate in Example 283, Steps A-F; 233 mg, 0.655 mmol), Pd(dppf)Cl₂ (44.6 mg, 0.055 mmol), and potassium carbonate (377 mg, 2.73 mmol) were added followed by 1.5 mL water. The reaction mixture was degassed with N₂ and heated at 90° C. overnight. After cooling to rt, the mixture was filtered through celite, the filtrate was concentrated and the residue was purified by silica gel column chromatography using 0-10% MeOH/DCM as mobile phase to give the title compound. LC-MS (IE, m/z): 928.74 [M+1]⁺.

Step B: 4'-(4-aminopiperidin-4-yl)-N-(4-methoxybenzyl)-2-(2-(4-methoxybenzyl)-2H-tetrazol-5-yl)-4-(trifluoromethyl)-[1,1'-biphenyl]-3-sulfonamide To the solution of tert-butyl 4-amino-4-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)piperidine-1-carboxylate (100 mg, 0.108 mmol) in DCM (539 µL) was added anisole (117 µL, 1.078 mmol) and TFA (830 µL, 10.78 mmol) at rt. After 2 hr the reaction mixture was treated with ion exchange column (load sample and rinse with MeOH, rinse out product with 2 M NH₃ in MeOH) to give the title compound. LC-MS (IE, m/z): 708.52 [M+1]⁺.

Step C: 4'-(4-aminopiperidin-4-yl)-2-(2H-tetrazol-5-yl)-4-(trifluoromethyl)-[1,1'-biphenyl]-3-sulfonamide To the solution of 4'-(4-aminopiperidin-4-yl)-N-(4-methoxybenzyl)-2-(2-(4-methoxybenzyl)-2H-tetrazol-5-yl)-4-(trifluoromethyl)-[1,1'-biphenyl]-3-sulfonamide (153 mg, 0.216 mmol) in DCM (1.1 mL) was added anisole (234 µL, 2.155 mmol) and TFA (2.5 µL, 32.3 mmol) at rt. The resulting mixture was stirred at 80° C. for 1 hr. After removing the volatile the residue was purified by reverse phase HPLC (DMSO loading sample; 5-35% ACN/water, 0.1% TFA as additive) to give the title compound. LC-MS (IE, m/z): 468.32 [M+1]⁺.

EXAMPLE 437

4'-(4-amino-1-(iminomethyl)piperidin-4-yl)-2-(2H-tetrazol-5-yl)-4-(trifluoromethyl)-[1,1'-biphenyl]-3-sulfonamide

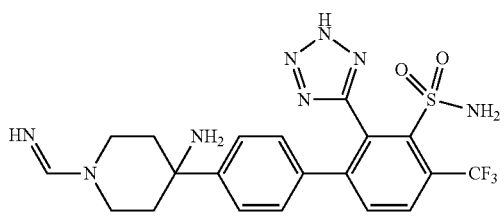 [SMILES: N=CN1CCC(N)(c2ccc(-c3ccc(C(F)(F)F)c(S(N)(=O)=O)c3-c3nn[nH]n3)cc2)CC1]

Step A: 4'-(4-amino-1-(iminomethyl)piperidin-4-yl)-N,N-bis(4-methoxybenzyl)-2-(2-(4-methoxybenzyl)-2H-tetrazol-5-yl)-4-(trifluoromethyl)-[1,1'-biphenyl]-3-sulfonamide 4'-(4-aminopiperidin-4-yl)-N-(4-methoxybenzyl)-2-(1-(4-methoxybenzyl)-1H-tetrazol-5-yl)-4-(trifluoromethyl)-[1,1'-biphenyl]-3-sulfonamide (30 mg, 0.042 mmol) in DMF (424 µL) was treated with ethyl formimidate hydrochloride (5.57 mg, 0.051 mmol) and DIPEA (29.6 µL, 0.170 mmol) at rt. After overnight LC-MS showed the reaction was not completed. Additional reagents with ethyl formimidate hydrochloride (5.57 mg, 0.051 mmol) and DIPEA (29.6 µL, 0.170 mmol) were added and the reaction was monitored carefully by LCMS. The reaction was complete in another 7 hr, and purified by reverse phase HPLC (10-90% MeCN/water as gradient, 0.1% TFA as additive) to give the title compound. LC-MS (IE, m/z): 735.64 [M+1]⁺.

Step B: 4'-(4-amino-1-(iminomethyl)piperidin-4-yl)-2-(2H-tetrazol-5-yl)-4-(trifluoromethyl)-[1,1'-biphenyl]-3-sulfonamide To the solution of 4'-(4-amino-1-(iminomethyl)piperidin-4-yl)-N-(4-methoxybenzyl)-2-(2-(4-methoxybenzyl)-2H-tetrazol-5-yl)-4-(trifluoromethyl)-[1,1'-biphenyl]-3-sulfonamide (15 mg, 0.020 mmol) in DCM (102 µL) was added anisole (22.19 µL, 0.204 mmol) and TFA (157 µL, 2.041 mmol) at rt. The resulting mixture was stirred at 80° C. for 1 hr. After removing the volatile the residue was purified by reverse phase HPLC (5-50% ACN/water, 0.1% TFA as additive) to give the title compound. LC-MS (IE, m/z): 495.47 [M+1]⁺.

EXAMPLE 438

4-amino-4-(3'-sulfamoyl-2'-(2H-tetrazol-5-yl)-4'-(trifluoromethyl)-[1,1'-biphenyl]-4-yl)piperidine-1-carboximidamide

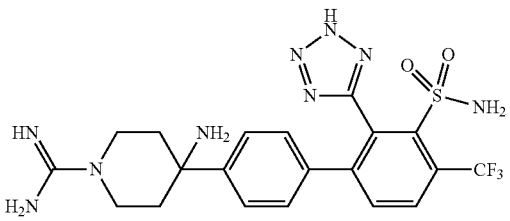 [SMILES: N=C(N)N1CCC(N)(c2ccc(-c3ccc(C(F)(F)F)c(S(N)(=O)=O)c3-c3nn[nH]n3)cc2)CC1]

Step A: 4-amino-4-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)piperidine-1-carboximidamide 4'-(4-aminopiperidin-4-yl)-N-(4-methoxybenzyl)-2-(1-(4-methoxybenzyl)-1H-tetrazol-5-yl)-4-(trifluoromethyl)-[1,1'-biphenyl]-3-sulfonamide (30 mg, 0.042 mmol) in DMF (848 µL) was treated with 1H-pyrazole-1-carboxamidine hydrochloride (9.94 mg, 0.068 mmol) and DIPEA (37.0 µL, 0.212 mmol). After overnight LC-MS showed the reaction was not completed. More reagents were added with 1H-pyrazole-1-carboxamidine hydrochloride (9.94 mg, 0.068 mmol) and DIPEA (37.0 µL, 0.212 mmol). After once more overnight the reaction mixture was purified with reverse phase HPLC (10-90% MeCN/water as gradient, 0.1% TFA as additive) to give the title compound. LC-MS (IE, m/z): 750.68 [M+1]⁺.

Step B: 4-amino-4-(3'-sulfamoyl-2'-(2H-tetrazol-5-yl)-4'-(trifluoromethyl)-[1,1'-biphenyl]-4-yl)piperidine-1-carboximidamide To the solution of 4-amino-4-(2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-yl)piperidine-1-carboximidamide (15 mg, 0.020 mmol) in DCM (100 µL) was added anisole (21 µL, 0.200 mmol) and TFA (154 µL, 2.001 mmol) at rt. The resulting mixture was stirred at 80° C. for 1 hr. After removing the volatile the residue was purified by reverse phase HPLC (5-50% ACN/water, 0.1% TFA as additive) to give the title compound. LC-MS (IE, m/z): 510.44 [M+1]$^+$.

EXAMPLE 439

4'-(aminomethyl)-2-(2H-tetrazol-5-yl)-4-(trifluoromethyl)-[1,1'-biphenyl]-3-sulfonamide

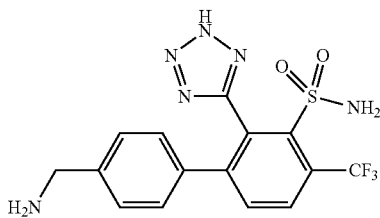 [SMILES: NCc1ccc(-c2ccc(C(F)(F)F)c(S(N)(=O)=O)c2-c2nn[nH]n2)cc1]

Step A: tert-butyl ((3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)methyl)carbamate A microwave vial was charged with 3-bromo-N,N-bis(4-methoxybenzyl)-2-(2-(4-methoxybenzyl)-2H-tetrazol-5-yl)-6-(trifluoromethyl)benzenesulfonamide (0.4 g, 0.546 mmol), (4-(((tert-butoxycarbonyl)amino)methyl)phenyl)boronic acid (0.151 g, 0.601 mmol), Na$_2$CO$_3$ (0.174 g, 1.638 mmol) and PdCl$_2$(dppf)-CH$_2$Cl$_2$ adduct (0.067 g, 0.082 mmol). The vial was sealed, degassed, and filled with dioxane (2.91 mL) and water (0.728 mL). The resulting mixture was heated overnight at 80° C. The reaction mixture was filtered over celite to remove palladium. The filtrate was diluted with EtOAc and washed with water. The organic layer was dried over anhydrous MgSO$_4$, filtered, concentrated and purified by silica gel column chromatography using 0-100% EtOAc/Hexanes as mobile phase to give the title compound. LC-MS (IE, m/z): 859.58 [M+1]$^+$.

Step B: 4'-(aminomethyl)-N-(4-methoxybenzyl)-2-(2-(4-methoxybenzyl)-2H-tetrazol-5-yl)-4-(trifluoromethyl)-[1,1'-biphenyl]-3-sulfonamide To the solution of tert-butyl ((3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)methyl)carbamate (490 mg, 0.570 mmol) in DCM (2.8 mL) was added anisole (620 μL, 5.70 mmol) and TFA (4.4 mL, 57.0 mmol) at rt. The resulting mixture was stirred at rt for 1 hr. After removing the volatile the residue was purified by ion exchange column (load sample and rinse with MeOH, rinse out product with 2 M NH$_3$ in MeOH) to give the title product as a free amine LC-MS (IE, m/z): 639.40 [M+1]$^+$.

Step C: 4'-(aminomethyl)-2-(2H-tetrazol-5-yl)-4-(trifluoromethyl)-[1,1'-biphenyl]-3-sulfonamide To the solution of 4'-(aminomethyl)-N-(4-methoxybenzyl)-2-(2-(4-methoxybenzyl)-2H-tetrazol-5-yl)-4-(trifluoromethyl)-[1,1'-biphenyl]-3-sulfonamide (80 mg, 0.125 mmol) in DCM (626 μL) was added anisole (136 μL, 1.253 mmol) and TFA (965 μL, 12.53 mmol) at rt. The resulting mixture was stirred at 80° C. for 1 hr. After removing the volatile the residue was purified by reverse phase HPLC (5-60% ACN/water, 0.1% TFA as additive) to give the title compound. LC-MS (IE, m/z): 399.22 [M+1]$^+$.

EXAMPLE 440

4'-(guanidinomethyl)-2-(2H-tetrazol-5-yl)-4-(trifluoromethyl)-[1,1'-biphenyl]-3-sulfonamide

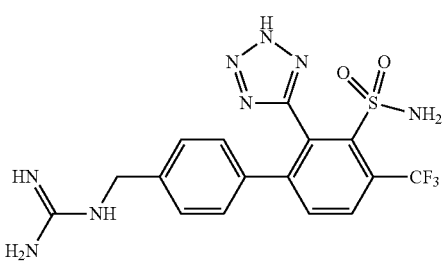 [SMILES: N=C(N)NCc1ccc(-c2ccc(C(F)(F)F)c(S(N)(=O)=O)c2-c2nn[nH]n2)cc1]

Step A: 4'-(guanidinomethyl)-N-(4-methoxybenzyl)-2-(2-(4-methoxybenzyl)-2H-tetrazol-5-yl)-4-(trifluoromethyl)-[1,1'-biphenyl]-3-sulfonamide 4'-(aminomethyl)-N-(4-methoxybenzyl)-2-(1-(4-methoxybenzyl)-1H-tetrazol-5-yl)-4-(trifluoromethyl)-[1,1'-biphenyl]-3-sulfonamide (0009) (60 mg, 0.094 mmol) in DMF (1879 μl) was treated with 1H-pyrazole-1-carboxamidine hydrochloride (22.03 mg, 0.150 mmol) and DIPEA (82 μl, 0.470 mmol). After stirring overnight LC-MS showed that the reaction was not completed. More reagents were added with 1H-pyrazole-1-carboxamidine hydrochloride (22.03 mg, 0.150 mmol) and DIPEA (82 μl, 0.470 mmol). After once more overnight the reaction mixture was purified with reverse phase HPLC (10-90% MeCN/water as gradient, 0.1% TFA as additive) to give the title compound. LC-MS (IE, m/z): 681.49 [M+1]$^+$.

Step B: 4'-(guanidinomethyl)-2-(2H-tetrazol-5-yl)-4-(trifluoromethyl)-[1,1'-biphenyl]-3-sulfonamide To the solution of 4'-(guanidinomethyl)-N-(4-methoxybenzyl)-2-(2-(4-methoxybenzyl)-2H-tetrazol-5-yl)-4-(trifluoromethyl)-[1,1'-biphenyl]-3-sulfonamide (50 mg, 0.073 mmol) in DCM (367 μL) was added anisole (80 μL, 0.735 mmol) and TFA (566 μL, 7.35 mmol) at rt. The resulting mixture was stirred at 80° C. for 1 hr. After removing the volatile the residue was purified by reverse phase HPLC (5-60% ACN/water, 0.1% TFA as additive) to give the title compound. LC-MS (IE, m/z): 441.32 [M+1]$^+$.

EXAMPLES 441-447

The following compounds were prepared in an analogous fashion to EXAMPLES 433-440 starting from 3-bromo-N,N-bis(4-methoxybenzyl)-2-(2-(4-methoxybenzyl)-2H-tetrazol-5-yl)-6-(trifluoromethyl)benzenesulfonamide and corresponding coupling partners as listed below. As quite a few different sets of conditions were used for EXAMPLES 441-447 depending on structural feature (amine, non-amine, amidine, guanidine, quaternary amine etc.), the method will be listed for the following analogs.

| EX. NO. | INTERMEDIATES | EXAMPLE STRUCTURE/NAME | Characterization, LC/MS |
|---|---|---|---|
| 441; same method as Ex. 439 | tert-butyl 5-(4,4,5,5-tetramethyl-1,3,2-dioxaborolan-2-yl)isoindoline-2-carboxylate | 3-(isoindolin-5-yl)-2-(2H-tetrazol-5-yl)-6-(trifluoromethyl)benzenesulfonamide | [M + 1]$^+$: 411.20 |
| 442; same method as Ex. 439 | tert-butyl (5-(4,4,5,5-tetramethyl-1,3,2-dioxaborolan-2-yl)-2,3-dihydro-1H-inden-2-yl)carbamate | 3-(2-amino-2,3-dihydro-1H-inden-5-yl)-2-(2H-tetrazol-5-yl)-6-(trifluoromethyl)benzenesulfonamide | [M + 1]$^+$: 425.21 |
| 443; same method as Ex. 439 | 3-(4-chlorophenyl)pyrrolidine | 4'-(pyrrolidin-3-yl)-2-(2H-tetrazol-5-yl)-4-(trifluoromethyl)-[1,1'-biphenyl]-3-sulfonamide | [M + 1]$^+$: 439.23 |
| 444; same method as Ex. 435 | 3-(4-chlorophenyl)pyrrolidine | 1,1-dimethyl-3-(3'-sulfamoyl-2'-(2H-tetrazol-5-yl)-4'-(trifluoromethyl)-[1,1'-biphenyl]-4-yl)pyrrolidin-1-ium | [M]$^+$: 467.40 |
| 445; same method as Ex. 439 | (4-(hydroxymethyl)phenyl)boronic acid | 4'-(hydroxymethyl)-2-(2H-tetrazol-5-yl)-4-(trifluoromethyl)-[1,1'-biphenyl]-3-sulfonamide | [M + 1]$^+$: 400.36 |

| EX. NO. | INTERMEDIATES | EXAMPLE STRUCTURE/NAME | Characterization, LC/MS |
|---|---|---|---|
| 446; same method as Ex. 440 | tert-butyl 5-(4,4,5,5-tetramethyl-1,3,2-dioxaborolan-2-yl)isoindoline-2-carboxylate | 5-(3-sulfamoyl-2-(2H-tetrazol-5-yl)-4-(trifluoromethyl)phenyl)isoindoline-2-carboximidamide | [M + 1]⁺: 453.36 |
| 447; same method as Ex. 440 | tert-butyl (5-(4,4,5,5-tetramethyl-1,3,2-dioxaborolan-2-yl)-2,3-dihydro-1H-inden-2-yl)carbamate | 3-(2-guanidino-2,3-dihydro-1H-inden-5-yl)-2-(2H-tetrazol-5-yl)-6-(trifluoromethyl)benzenesulfonamide | [M + 1]⁺: 467.37 |

EXAMPLE 448

2-(3'-sulfamoyl-2'-(2H-tetrazol-5-yl)-4'-(trifluoromethyl)-[1,1'-biphenyl]-4-yl)acetamide

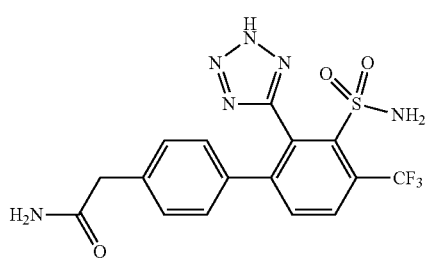 [SMILES: NC(=O)Cc1ccc(-c2ccc(C(F)(F)F)c(S(N)(=O)=O)c2-c2nn[nH]n2)cc1]

Step A: 2-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)acetamide The mixture of 4,4,4',4',5,5,5',5'-octamethyl-2,2'-bi(1,3,2-dioxaborolane) (125 mg, 0.491 mmol), 2-(4-bromophenyl)acetimidamide (87 mg, 0.410 mmol), PCy₃ 2nd generation precatalyst (16.12 mg, 0.027 mmol) and potassium acetate (107 mg, 1.092 mmol) in dioxane (2.7 mL) was degassed with N₂. The resulting mixture was heated at 100° C. for overnight. LCMS indicated complete coversion to boronic acid. 3-bromo-N,N-bis(4-methoxybenzyl)-2-(2-(4-methoxybenzyl)-2H-tetrazol-5-yl)-6-(trifluoromethyl)benzenesulfonamide (200 mg, 0.273 mmol), Pd(dppf)Cl₂ (22.30 mg, 0.027 mmol), and sodium carbonate (116 mg, 1.092 mmol) were added followed by 1.0 mL water. The reaction mixture was degassed with N₂ and heated at 90° C. overnight. After cooling to rt the mixture was filtered through celite, the filtrate was concentrated and the residue was purified by silica gel column chromatography using 0-10% MeOH/DCM as mobile phase to give the title compound. LC-MS (IE, m/z): 787.70 [M+1]⁺.

Step B: 2-(3'-sulfamoyl-2'-(2H-tetrazol-5-yl)-4'-(trifluoromethyl)-[1,1'-biphenyl]-4-yl)acetamide To the solution of 2-(3'-(N,N-bis(4-methoxybenzyl)sulfamoyl)-2'-(2-(4-methoxybenzyl)-2H-tetrazol-5-yl)-4'-(trifluoromethyl)-[1,1'-biphenyl]-4-yl)acetimidamide (100 mg, 0.127 mmol) in DCM (636 μL) was added anisole (138 μL, 1.273 mmol) and TFA (980 μL, 12.73 mmol) at rt. The resulting mixture was stirred at 80° C. for 1 hr. After removing the volatile the residue was purified by reverse phase HPLC (5-60% ACN/water, 0.1% TFA as additive) to give the title compound.

LC-MS (IE, m/z): 427.28 [M+1]⁺.

EXAMPLE 449

3-(3'-sulfamoyl-2'-(2H-tetrazol-5-yl)-4'-(trifluoromethyl)-[1,1'-biphenyl]-4-yl)propanamide

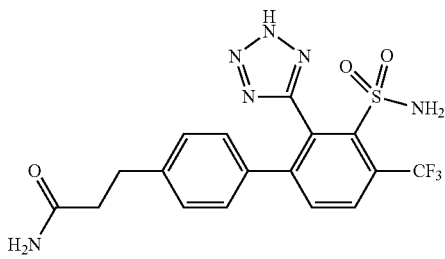 [SMILES: NC(=O)CCc1ccc(-c2ccc(C(F)(F)F)c(S(N)(=O)=O)c2-c2nn[nH]n2)cc1]

The title compound was prepared in an analogous fashion to 2-(3'-sulfamoyl-2'-(2H-tetrazol-5-yl)-4'-(trifluoromethyl)-[1,1'-biphenyl]-4-yl)acetamide starting from 3-bromo-N,N-bis(4-methoxybenzyl)-2-(2-(4-methoxybenzyl)-2H-tetrazol-5-yl)-6-(trifluoromethyl)benzenesulfonamide and 3-(4-chlorophenyl)propanimidamide. LC-MS (IE, m/z): 441.33 [M+1]$^+$.

EXAMPLE 450

3-(4-(4-(hydroxymethyl)phenyl)piperidin-1-yl)-2-(2H-tetrazol-5-yl)-6-(trifluoromethyl)benzenesulfonamide

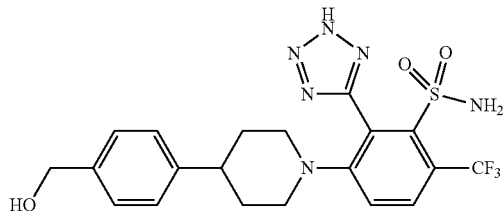 [SMILES: NS(=O)(=O)c1c(C(F)(F)F)ccc(N2CCC(c3ccc(CO)cc3)CC2)c1-c1nn[nH]n1]

Step A: tert-butyl 4-(4-(hydroxymethyl)phenyl)piperidine-1-carboxylate

To a solution of tert-butyl 4-(4-(hydroxymethyl)phenyl)piperidine-1-carboxylate (1000 mg, 3.43 mmol) in DCM (17 mL) was added anisole (1.9 mL, 17.16 mmol) and TFA (26 mL, 343 mmol) at rt. The resulting mixture was stirred at rt for 1 hr to remove Boc protection. After removing the volatile the residue was purified by SCX ion exchange column to give the desired product.

Step B: 3-(4-(4-(hydroxymethyl)phenyl)piperidin-1-yl)-N,N-bis(4-methoxybenzyl)-2-(2-(4-methoxybenzyl)-2H-tetrazol-5-yl)-6-(trifluoromethyl)benzenesulfonamide To 3-bromo-N,N-bis(4-methoxybenzyl)-2-(1-(4-methoxybenzyl)-1H-tetrazol-5-yl)-6-(trifluoromethyl)benzenesulfonamide (1000 mg, 1.365 mmol), potassium carbonate (1132 mg, 8.19 mmol) and (4-(piperidin-4-yl)phenyl)methanol (522 mg, 2.73 mmol) in a microwave vial was added DMF (4.5 mL). The mixture was MW at 140° C. for 3 hr. LCMS indicated a complete reaction. The mixtures were diluted with water, extracted with EtOAc (2×), washed with brine, dried (MgSO$_4$), and concentrated. The residue was purified by column chromatography (0-100 EtOAc/hex) to give the title compound. LC-MS (IE, m/z): 843.77 [M+1]$^+$.

Step C: 3-(4-(4-(hydroxymethyl)phenyl)piperidin-1-yl)-2-(2H-tetrazol-5-yl)-6-(trifluoromethyl)benzenesulfonamide To the solution of 3-(4-(4-(hydroxymethyl)phenyl)piperidin-1-yl)-N,N-bis(4-methoxybenzyl)-2-(2-(4-methoxybenzyl)-2H-tetrazol-5-yl)-6-(trifluoromethyl)benzenesulfonamide (50 mg, 0.059 mmol) in DCM (297 µL) was added anisole (64 µL, 0.593 mmol) and TFA (457 µL, 5.93 mmol) at rt. The resulting mixture was stirred at 80° C. for 1 hr. After removing the volatile the residue was purified by reverse phase HPLC (5-60% ACN/water, 0.1% TFA as additive) to give the title compound. LC-MS (IE, m/z): 483.41 [M+1]$^+$.

EXAMPLE 451

6-(((1s,4s)-4-aminocyclohexyl)methyl)-3-(quinolin-4-yl)-2-(2H-tetrazol-5-yl)benzenesulfonamide

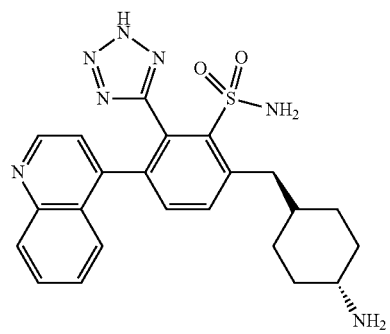

Step A: 6-bromo-N,N-bis(4-methoxybenzyl)-2-(2-(4-methoxybenzyl)-2H-tetrazol-5-yl)-3-(quinolin-4-yl)benzenesulfonamide A microwave vial was charged with 6-bromo-3-iodo-N,N-bis(4-methoxybenzyl)-2-(2-(4-methoxybenzyl)-2H-tetrazol-5-yl)benzenesulfonamide (0030 and 0125) (1 g, 1.265 mmol), quinolin-4-ylboronic acid (0.656 g, 3.80 mmol), PdCl$_2$(dppf)-CH$_2$Cl$_2$ adduct (0.155 g, 0.190 mmol) and sodium carbonate (0.536 g, 5.06 mmol). The vial was sealed, degassed, and filled with dioxane (6.33 mL) and water (2.11 mL). The resulting mixture was heated overnight at 90° C. The reaction mixture was filtered over celite to removed palladium. The filtrate was diluted with EtOAc and washed with water. The organic layer was dried over anhydrous MgSO$_4$, filtered, concentrated and purified by silica gel column chromatography using 0-100% EtOAc/Hexanes as mobile phase to give the desired product. LC-MS (IE, m/z): 793.2 [M+2]$^+$.

Step B: 6-(((1s,4s)-4-aminocyclohexyl)methyl)-N-(4-methoxybenzyl)-2-(2-(4-methoxybenzyl)-2H-tetrazol-5-yl)-3-(quinolin-4-yl)benzenesulfonamide A microwave vial was charged with tert-butyl ((1r,4r)-4-(bromomethyl)cyclohexyl)carbamate (prepared in an analogous fashion to that described for tert-butyl (1s,4s)-4-(iodomethyl)cyclohexylcarbamate, Reference Example 35, except starting from (1r,4r)-4-((tert-butoxycarbonyl)amino)cyclohexanecarboxylic acid; 55.4 mg, 0.189 mmol), nickel (II) iodide (5.92 mg, 0.019 mmol), manganese (20.82 mg, 0.379 mmol), bathophenanthroline (6.30 mg, 0.019 mmol) and 6-bromo-N,N-bis(4-methoxybenzyl)-2-(2-(4-methoxybenzyl)-2H-tetrazol-5-yl)-3-(quinolin-4-yl)benzenesulfonamide (100 mg, 0.126 mmol). The vial was sealed, purged with N$_2$ for 10 min, and filled with DMA (1.3 mL). The resulting mixture was purged with N₂ for another 10 min and heated overnight at 80° C. The reaction mixture was filtered over celite to remove metal. The filtrate was treated with TFA (0.973 mL, 12.63 mmol) and anisole (0.069 mL, 0.632 mmol) in DCM (2 mL) to remove the Boc group, and the title compound as a free amine was obtained by passing through an ion exchange column. LC-MS (IE, m/z): 704.42 [M+1]⁺.

Step C: 6-(((1s,4s)-4-aminocyclohexyl)methyl)-3-(quinolin-4-yl)-2-(2H-tetrazol-5-yl)benzenesulfonamide To a solution of 6-(((1r,4r)-4-aminocyclohexyl)methyl)-N-(4-methoxybenzyl)-2-(2-(4-methoxybenzyl)-2H-tetrazol-5-yl)-3-(quinolin-4-yl)benzenesulfonamide (89 mg, 0.126 mmol) in DCM (632 µL) was added anisole (138 µL, 1.264 mmol) and TFA (974 µL, 12.64 mmol) at rt. The resulting mixture was heated at 80° C. for 1 hr. After removing the volatile the residue was purified by reverse phase HPLC using DMSO to load sample and 5-35% acetonitrile/water (0.1% TFA as additive) as mobile phase over 10 min to give the title compound. LC-MS (IE, m/z): 464.38 [M+1]⁺.

EXAMPLE 452

6-(2-(piperidin-4-yl)ethyl)-3-(quinolin-4-yl)-2-(2H-tetrazol-5-yl)benzenesulfonamide

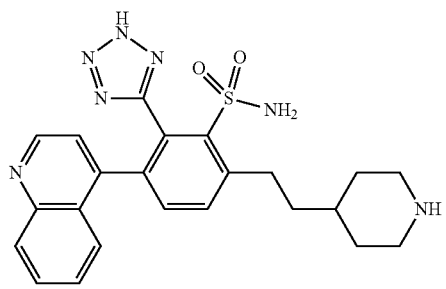 [SMILES: NS(=O)(=O)c1c(CCC2CCNCC2)ccc(-c2ccnc3ccccc23)c1-c1nn[nH]n1]

The title compound was prepared in an analogous fashion to 6-(((1s,4s)-4-aminocyclohexyl)methyl)-3-(quinolin-4-yl)-2-(2H-tetrazol-5-yl)benzenesulfonamide using 6-bromo-N,N-bis(4-methoxybenzyl)-2-(2-(4-methoxybenzyl)-2H-tetrazol-5-yl)-3-(quinolin-4-yl)benzenesulfonamide and tert-butyl 4-(2-iodoethyl)piperidine-1-carboxylate. LC-MS (IE, m/z): 441.33 [M+1]⁺.

EXAMPLE 453

6-(2-cyanoethyl)-3-(quinolin-4-yl)-2-(2H-tetrazol-5-yl)benzenesulfonamide

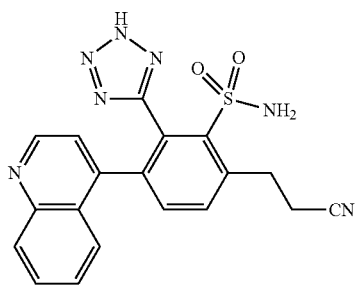 [SMILES: N#CCCc1ccc(-c2ccnc3ccccc23)c(-c2nn[nH]n2)c1S(N)(=O)=O]

Step A: 6-(2-cyanoethyl)-N-(4-methoxybenzyl)-2-(2-(4-methoxybenzyl)-2H-tetrazol-5-yl)-3-(quinolin-4-yl)benzenesulfonamide A microwave vial was charged with 6-bromo-N,N-bis(4-methoxybenzyl)-2-(2-(4-methoxybenzyl)-2H-tetrazol-5-yl)-3-(quinolin-4-yl)benzenesulfonamide (0.12 g, 0.152 mmol), and t-Bu-XPhos 1st generation precatalyst (0.021 g, 0.030 mmol). The vial was sealed, degased, and filled with THF (1.516 ml) and (2-cyanoethyl)zinc(II) bromide (1.213 ml, 0.606 mmol). The resulting mixture was heated overnight at 60° C. The reaction mixture was filtered over celite to remove palladium. The filtrate was concentrated and purified by silica gel column chromatography using (20-80)% EtOAc/Hexanes as mobile phase to give the desired product. LC-MS (IE, m/z): 766.25 [M+1]⁺.

Step B: 6-(2-cyanoethyl)-3-(quinolin-4-yl)-2-(2H-tetrazol-5-yl)benzenesulfonamide To the solution of 6-(2-cyanoethyl)-N,N-bis(4-methoxybenzyl)-2-(2-(4-methoxybenzyl)-2H-tetrazol-5-yl)-3-(quinolin-4-yl)benzenesulfonamide (80 mg, 0.104 mmol) in DCM (2089 µl) was added TFA (805 µL, 10.45 mmol) and anisole (227 µL, 2.089 mmol), and the reaction mixture was heated at 80° C. for 1 hr. After removing the volatile the residue was purified (DMSO loading) on reverse phase HPLC using 5-70% acetonitrile/water (0.1% formic acid) over 10 min to give the title compound. LC-MS (IE, m/z): 406.28 [M+1]⁺.

EXAMPLE 454

6-cyclohexyl-3-(quinolin-4-yl)-2-(2H-tetrazol-5-yl)benzenesulfonamide

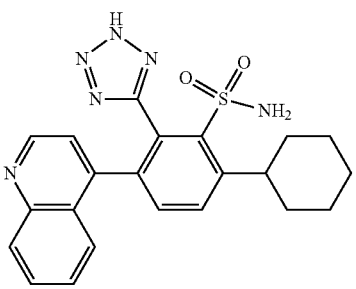 [SMILES: NS(=O)(=O)c1c(C2CCCCC2)ccc(-c2ccnc3ccccc23)c1-c1nn[nH]n1]

6-cyclohexyl-3-(quinolin-4-yl)-2-(2H-tetrazol-5-yl)benzenesulfonamide was prepared in an analogous fashion to 6-(2-cyanoethyl)-3-(quinolin-4-yl)-2-(2H-tetrazol-5-yl)benzenesulfonamide using 6-bromo-N,N-bis(4-methoxybenzyl)-2-(2-(4-methoxybenzyl)-2H-tetrazol-5-yl)-3-(quinolin-4-yl)benzenesulfonamide and cyclohexylzinc(II) bromide. LC-MS (IE, m/z): 435.32 [M+1]⁺.

EXAMPLE 455

4-(((1s,4s)-4-aminocyclohexyl)methyl)-4'-(piperidin-4-yl)-2-(2H-tetrazol-5-yl)-[1,1'-biphenyl]-3-sulfonamide

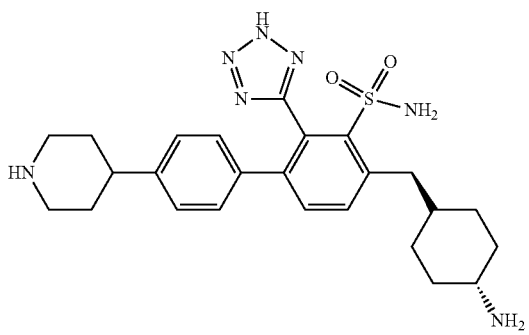

Step A: tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate A thick-wall flask was charged with tert-butyl 4-(4-(4,4,5,5-tetramethyl-1,3,2-dioxaborolan-2-yl)phenyl)piperidine-1-carboxylate (4.04 g, 10.44 mmol), 6-bromo-3-iodo-N,N-bis(4-methoxybenzyl)-2-(2-(4-methoxybenzyl)-2H-tetrazol-5-yl)benzenesulfonamide (5.5 g, 6.96 mmol), sodium carbonate (2.212 g, 20.87 mmol) and tetrakis(triphenylphosphine)palladium(0) (0.402 g, 0.348 mmol). The vial was degassed, sealed, and filled with dioxane (20.87 ml) and water (6.96 ml). The resulting mixture was heated for 16 hr at 80° C. The reaction mixture was filtered over celite to remove palladium. The filtrate was diluted with EtOAc and washed with water. The organic layer was dried over anhydrous MgSO$_4$, filtered, concentrated. The residue was purified by silica gel column chromatography using 0-100% EtOAc/Hexanes as mobile phase to give the title compound. LC-MS (IE, m/z): 925.75 [M+2]$^+$.

Step B: tert-butyl 4-(3'-(N,N-bis(4-methoxybenzyl)sulfamoyl)-4'-(((1s,4s)-4-((tert-butoxycarbonyl)amino)cyclohexyl)methyl)-2'-(2-(4-methoxybenzyl)-2H-tetrazol-5-yl)-[1,1'-biphenyl]-4-yl)piperidine-1-carboxylate A microwave vial was charged with tert-butyl ((1r,4r)-4-(bromomethyl)cyclohexyl)carbamate (47.4 mg, 0.162 mmol), nickel(II) iodide (5.07 mg, 0.016 mmol), manganese (17.84 mg, 0.325 mmol), bathophenanthroline (5.40 mg, 0.016 mmol) and tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate (100 mg, 0.108 mmol). The vial was sealed, purged with N$_2$ for 10 min, and filled with DMA (1.3 mL). The resulting mixture was purged with N$_2$ for another 10 min and heated overnight at 70° C. The reaction mixture was filtered over celite to removed metal. The filtrate was concentrated and purified by silica gel chromatography (0-100% EtOAc/hexane as gradient) to afford the title compound. LC-MS (IE, m/z): 1056.87 [M+1]$^+$.

Step C: 4-(((1s,4s)-4-aminocyclohexyl)methyl)-4'-(piperidin-4-yl)-2-(2H-tetrazol-5-yl)-[1,1'-biphenyl]-3-sulfonamide To tert-butyl 4-(3'-(N,N-bis(4-methoxybenzyl)sulfamoyl)-4'-(((1r,4r)-4-((tert-butoxycarbonyl)amino)cyclohexyl)methyl)-2'-(2-(4-methoxybenzyl)-2H-tetrazol-5-yl)-[1,1'-biphenyl]-4-yl)piperidine-1-carboxylate (90 mg, 0.085 mmol) was added anisole (93 μL, 0.852 mmol) and TFA (656 μL, 8.52 mmol) at rt. The resulting mixture was stirred at rt for 1 hr to remove both Boc and both PMB protection. After removing the volatile the residue was purified by reverse phase HPLC using DMSO to load sample and 5-60% acetonitrile/water (0.1% TFA as additive) as mobile phase over 10 min to separate the desired product from debromide side-product from the coupling reaction. To a solution of the desired product in DCM (426 μL) was added anisole (93 μL, 0.852 mmol) and TFA (656 μL, 8.52 mmol) at rt. The resulting mixture was stirred at 80° C. for 1 hr to remove the final PMB protection. After removing the volatile the residue was purified by reverse phase HPLC using DMSO to load sample and 5-40% acetonitrile/water (0.1% TFA as additive) as mobile phase over 10 min to give the final product. LC-MS (IE, m/z): 496.61 [M+1]$^+$.

EXAMPLE 456

4'-(piperidin-4-yl)-4-(piperidin-4-ylmethyl)-2-(2H-tetrazol-5-yl)-[1,1'-biphenyl]-3-sulfonamide

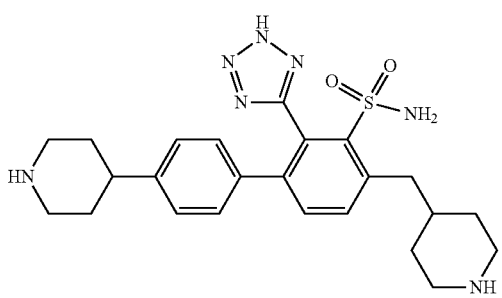 [SMILES: NS(=O)(=O)c1c(CC2CCNCC2)ccc(-c2ccc(C3CCNCC3)cc2)c1-c1nn[nH]n1]

Step A: tert-butyl 4-(3'-(N,N-bis(4-methoxybenzyl)sulfamoyl)-4'-((1-(tert-butoxycarbonyl)piperidin-4-yl)methyl)-2'-(2-(4-methoxybenzyl)-2H-tetrazol-5-yl)-[1,1'-biphenyl]-4-yl)piperidine-1-carboxylate A microwave vial was charged with bathophenanthroline (27.0 mg, 0.081 mmol), tert-butyl 4-(iodomethyl)piperidine-1-carboxylate (Synnovator) (528 mg, 1.62 mmol), nickel(II) iodide (50.7 mg, 0.162 mmol), tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate (500 mg, 0.541 mmol) and manganese (89 mg, 1.624 mmol). The vial was sealed, purged with N$_2$ for 10 min, and filled with DMAc (2.2 mL). The reaction mixture was purged with N$_2$ for 10 min, and benzonitrile (11 μL, 0.108 mmol) (added 0.1 mL stock solution, which was prepared by dissolving 0.22 mL benzonitrile in 2 mL DMAc), and TMSCl (14 μL, 0.108 mmol) (added 0.1 mL stock solution, which was prepared by dissolving 0.27 mL benzonitrile in 2 mL DMAc). The resulting mixture was purged with N$_2$ for another 10 min, and heated for 1 hr at 40° C. The reaction mixture was directly purified by silica gel column chromatography using 0-100% EtOAc/hexane as mobile phase (isostatic at 20% and 40% for a while, removed debromide side-product, which came out first) to afford the title product. LC-MS (IE, m/z): 1043.10 [M+1]$^+$.

Step B: 4'-(piperidin-4-yl)-4-(piperidin-4-ylmethyl)-2-(2H-tetrazol-5-yl)-[1,1'-biphenyl]-3-sulfonamide To tert-butyl 4-(3'-(N,N-bis(4-methoxybenzyl)sulfamoyl)-4'-((1-(tert-butoxycarbonyl)piperidin-4-yl)methyl)-2'-(2-(4-methoxybenzyl)-2H-tetrazol-5-yl)-[1,1'-biphenyl]-4-yl)piperidine-1-carboxylate (1950 mg, 1.871 mmol) was added anisole (2.0 mL, 18.71 mmol) and TFA (14 mL, 187 mmol) (neat TFA, no DCM) at rt. The resulting mixture was stirred at rt for 1 hr to remove both Boc and both PMB protection. After removing the volatile the residue was purified by reverse phase HPLC using DMSO to load sample and 5-55% acetonitrile/water (0.1% TFA as additive) as mobile phase over 10 min to separate the desired product from side products. To a solution of the desired mono-PMB product in DCM (19 mL) was added anisole (2.0 mL, 18.71 mmol) and TFA (14 mL, 187 mmol) at rt. The resulting mixture was stirred at 80° C. for 1 h to remove the final PMB protection. After removing the volatile the residue was purified by reverse phase HPLC using DMSO to load sample and 5-40% acetonitrile/water (0.1% TFA as additive) as mobile phase over 10 min to give the title compound. LC-MS (IE, m/z): 482.56 [M+1]$^+$.

EXAMPLE 457

4-(((1r,4r)-4-(aminomethyl)cyclohexyl)methyl)-4'-(piperidin-4-yl)-2-(2H-tetrazol-5-yl)-[1,1'-biphenyl]-3-sulfonamide

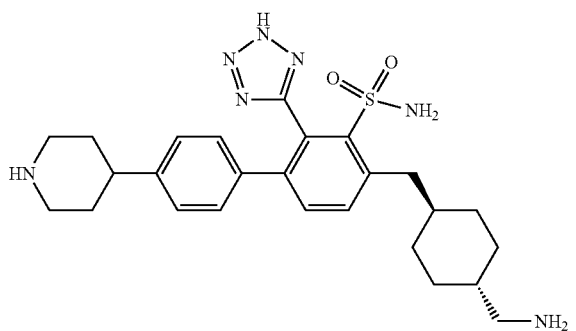 [SMILES: NC[C@H]1CC[C@H](Cc2ccc(-c3ccc(C4CCNCC4)cc3)c(-c3nn[nH]n3)c2S(N)(=O)=O)CC1]

Step A: tert-butyl (((1r,4r)-4-(iodomethyl)cyclohexyl)methyl)carbamate

Triphenylphosphine (701 mg, 2.67 mmol) and tert-butyl (((1r,4r)-4-(hydroxymethyl)cyclohexyl)methyl)carbamate (500 mg, 2.055 mmol) in acetonitrile (2.5 ml) and diethyl ether (7.5 ml) were added imidazole (182 mg, 2.67 mmol) at 0° C., and then stirred at room temperature for 15 minutes. tert-Butyl (((1r,4r)-4-(hydroxymethyl)cyclohexyl)methyl) carbamate (500 mg, 2.055 mmol) in the same solvent system (2 mL) was added dropwise at 0° C. After finished, the solution was stirred at rt overnight. The reaction mixture was evaporated, and added DCM (5 mL). The suspension was filtered and evaporated to get the crude product. The crude was purified by column chromatography on silica gel, eluting with 0-10% MeOH/DCM (254 nm has weak absorption, out early) to give the desired product. LC-MS (IE, m/z): 354.32 [M+1]$^+$.

Step B: tert-butyl 4-(3'-(N,N-bis(4-methoxybenzyl)sulfamoyl)-4'-(((1r,4r)-4-(((tert-butoxycarbonyl)amino)methyl)cyclohexyl)methyl)-2'-(2-(4-methoxybenzyl)-2H-tetrazol-5-yl)-[1,1'-biphenyl]-4-yl)piperidine-1-carboxylate A microwave vial was charged with 4,5-diazafluoren-9-one (2.96 mg, 0.016 mmol), manganese (17.84 mg, 0.325 mmol), pyridine (1.751 µl, 0.022 mmol), tert-butyl (((1r,4r)-4-(iodomethyl)cyclohexyl)methyl)carbamate (76 mg, 0.216 mmol), tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate (100 mg, 0.108 mmol) and nickel(II) iodide (5.07 mg, 0.016 mmol). The vial was sealed, purged with N$_2$ for 10 min, and filled with DMA (1.3 mL). The resulting mixture was purged with N$_2$ for another 10 min and heated overnight at 70° C. The reaction mixture was filtered over celite to remove metal. The filtrate was concentrated and purified by silica gel chromatography (0-100% EtOAc/hexane as gradient) to afford the title compound. LC-MS (IE, m/z): 1071.00 [M+1]$^+$.

Step C: 4-(((1r,4r)-4-(aminomethyl)cyclohexyl)methyl)-4'-(piperidin-4-yl)-2-(2H-tetrazol-5-yl)-[1,1'-biphenyl]-3-sulfonamide To tert-butyl 4-(3'-(N,N-bis(4-methoxybenzyl)sulfamoyl)-4'-(((1r,4r)-4-(((tert-butoxycarbonyl)amino)methyl)cyclohexyl)methyl)-2'-(2-(4-methoxybenzyl)-2H-tetrazol-5-yl)-[1,1'-biphenyl]-4-yl)piperidine-1-carboxylate (140 mg, 0.131 mmol) was added anisole (143 µL, 1.308 mmol) and TFA (1.0 mL, 13.08 mmol) at rt. The resulting mixture was stirred at rt for 1 hr to remove both Boc and both PMB protection. After removing the volatile the residue was purified by reverse phase HPLC using DMSO to load sample and 5-60% acetonitrile/water (0.1% TFA as additive) as mobile phase over 10 min to separate the desired product from the debromide side-product from the coupling reaction. To a solution of the desired mono-PMB product in DCM (1.3 mL) was added anisole (143 µL, 1.308 mmol) and TFA (1.0 mL, 13.08 mmol) at rt. The resulting mixture was stirred at 80° C. for 1 hr to remove the final PMB protection. After removing the volatile the residue was purified by reverse phase HPLC using DMSO to load sample and 5-40% acetonitrile/water (0.1% TFA as additive) as mobile phase over 10 min to give the final product. LC-MS (IE, m/z): 510.3 [M+1]$^+$.

EXAMPLES 458-469

The following compounds were prepared in an analogous fashion to EXAMPLES 455-457 starting from tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate and corresponding halides as coupling partners as listed below. As there is evolution of Ni reductive coupling conditions, the method will be listed for the following analogs, which is similar either to Example 456 or 457. Although many halides are commercially available, some were prepared. For the latter ones they were prepared following the condition shown in Step A of Example 457.

| EX. NO. | INTER-MEDIATES | EXAMPLE STRUCTURE/NAME | Characterization, LC/MS |
|---|---|---|---|
| 458; same method as Ex. 456 | 1,1,1-trifluoro-2-iodoethane | 4'-(piperidin-4-yl)-2-(2H-tetrazol-5-yl)-4-(2,2,2-trifluoroethyl)-[1,1'-biphenyl]-3-sulfonamide | $[M + 1]^+$: 467.41 |
| 459; same method as Ex. 456 | tert-butyl (4-iodocyclohexyl)carbamate | 4-(4-aminocyclohexyl)-4'-(piperidin-4-yl)-2-(2H-tetrazol-5-yl)-[1,1'-biphenyl]-3-sulfonamide | $[M + 1]^+$: 482.65 |
| 460; same method as Ex. 456 | tert-butyl 4-(2-iodoethyl)piperidine-1-carboxylate | 4'-(piperidin-4-yl)-4-(2-(piperidin-4-yl)ethyl)-2-(2H-tetrazol-5-yl)-[1,1'-biphenyl]-3-sulfonamide | $[M + 1]^+$: 496.21 |
| 461, fast eluting isomer; same method as Ex. 456 | tert-butyl (4-(2-iodoethyl)cyclohexyl)carbamate | Fast eluting isomer: 4-(2-((1r,4s)-4-aminocyclohexyl)ethyl)-4'-(piperidin-4-yl)-2-(2H-tetrazol-5-yl)-[1,1'-biphenyl]-3-sulfonamide | $[M + 1]^+$: 510.5 |
| 462, slow eluting isomer; same method as Ex. 456 | tert-butyl (4-(2-iodoethyl)cyclohexyl)carbamate | Slow eluting isomer: 4-(2-((1s,4r)-4-aminocyclohexyl)ethyl)-4'-(piperidin-4-yl)-2-(2H-tetrazol-5-yl)-[1,1'-biphenyl]-3-sulfonamide | $[M + 1]^+$: 510.7 |

-continued

| EX. NO. | INTER-MEDIATES | EXAMPLE STRUCTURE/NAME | Characterization, LC/MS |
|---|---|---|---|
| 463; same method as Ex. 456 | tert-butyl ((1s,4s)-4-(hydroxymethyl) cyclohexyl) carbamate | 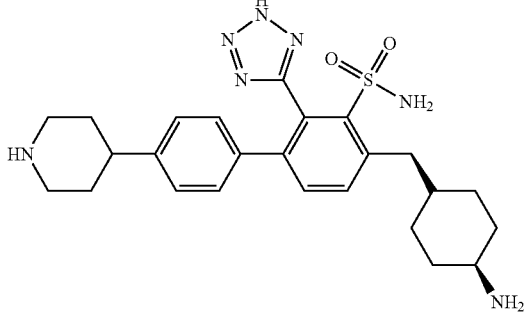<br>4-(((1r,4r)-4-aminocyclohexyl)methyl)-4'-(piperidin-4-yl)-2-(2H-tetrazol-5-yl)-[1,1'-biphenyl]-3-sulfonamide | [M + 1]$^+$: 496.68 |
| 464; same method as Ex. 457 | tert-butyl 4-fluoro-4-(hydroxymethyl) piperidine-1-carboxylate | 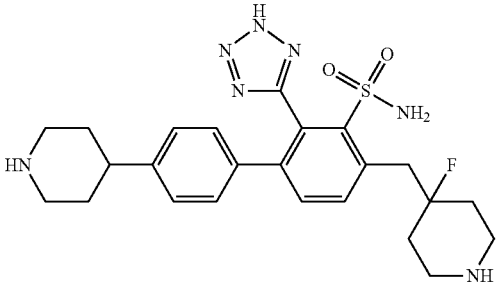 [SMILES: NS(=O)(=O)c1c(CC2(F)CCNCC2)ccc(-c2ccc(C3CCNCC3)cc2)c1-c1nn[nH]n1]<br>4-((4-fluoropiperidin-4-yl)methyl)-4'-(piperidin-4-yl)-2-(2H-tetrazol-5-yl)-[1,1'-biphenyl]-3-sulfonamide | [M + 1]$^+$: 500.10 |
| 465; same method as Ex. 457 | tert-butyl 3,3-difluoro-4-(hydroxymethyl) piperidine-1-carboxylate | 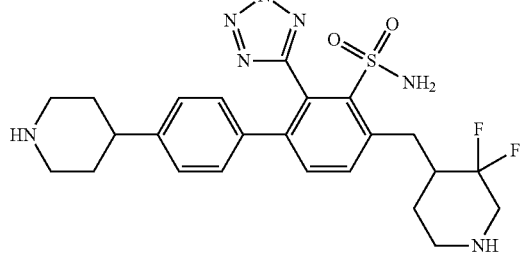<br>4-((3,3-difluoropiperidin-4-yl)methyl)-4'-(piperidin-4-yl)-2-(2H-tetrazol-5-yl)-[1,1'-biphenyl]-3-sulfonamide | [M + 1]$^+$: 518.66 |
| 466; same method as Ex. 457 | tert-butyl 3-(2-iodoethyl) azetidine-1-carboxylate | 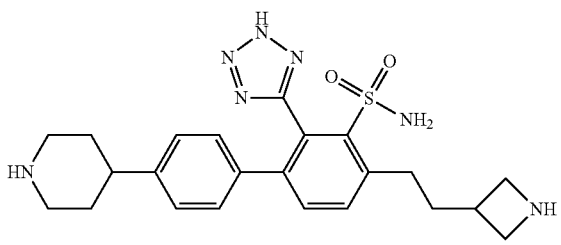 [SMILES: NS(=O)(=O)c1c(CCC2CNC2)ccc(-c2ccc(C3CCNCC3)cc2)c1-c1nn[nH]n1]<br>4-(2-(azetidin-3-yl)ethyl)-4'-(piperidin-4-yl)-2-(2H-tetrazol-5-yl)-[1,1'-biphenyl]-3-sulfonamide | [M + 1]$^+$: 468.6 |

| EX. NO. | INTER-MEDIATES | EXAMPLE STRUCTURE/NAME | Character-ization, LC/MS |
|---|---|---|---|
| 467; same method as Ex. 457 | tert-butyl 3-fluoro-3-(hydroxymethyl) pyrrolidine-1-carboxylate | 4-((3-fluoropyrrolidin-3-yl)methyl)-4'-(piperidin-4-yl)-2-(2H-tetrazol-5-yl)-[1,1'-biphenyl]-3-sulfonamide | [M + 1]⁺: 486.39 |
| 468; same method as Ex. 457 | tert-butyl 3-(iodomethyl) pyrrolidine-1-carboxylate | 4'-(piperidin-4-yl)-4-(pyrrolidin-3-ylmethyl)-2-(2H-tetrazol-5-yl)-[1,1'-biphenyl]-3-sulfonamide | [M + 1]⁺: 468.48 |
| 469; same method as Ex. 457 | tert-butyl 3-(iodomethyl) azetidine-1-carboxylate | 4-(azetidin-3-ylmethyl)-4'-(piperidin-4-yl)-2-(2H-tetrazol-5-yl)-[1,1'-biphenyl]-3-sulfonamide | [M + 1]⁺: 454.50 |

EXAMPLE 470

4'-(1-(azetidin-3-ylmethyl)piperidin-4-yl)-4-(piperidin-4-ylmethyl)-2-(2H-tetrazol-5-yl)-[1,1'-biphenyl]-3-sulfonamide

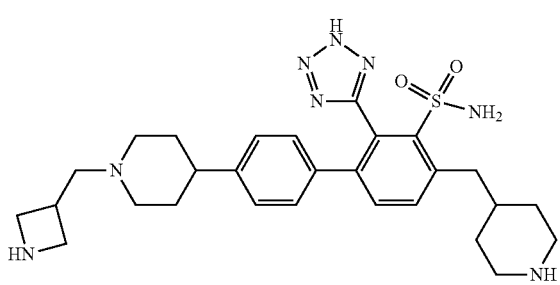 [SMILES: NS(=O)(=O)c1c(CC2CCNCC2)ccc(-c2ccc(C3CCN(CC4CNC4)CC3)cc2)c1-c1nn[nH]n1]

Step A: benzyl 4-((3-(N,N-bis(4-methoxybenzyl)sulfamoyl)-4'-(1-(tert-butoxycarbonyl)piperidin-4-yl)-2-(2-(4-methoxybenzyl)-2H-tetrazol-5-yl)-[1,1'-biphenyl]-4-yl)methyl)piperidine-1-carboxylate A microwave vial was charged with bathophenanthroline (27.0 mg, 0.081 mmol), benzyl 4-(iodomethyl)piperidine-1-carboxylate (583 mg, 1.624 mmol), nickel(II) iodide (50.7 mg, 0.162 mmol), tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate (500 mg, 0.541 mmol) and manganese (89 mg, 1.624 mmol). The vial was sealed, purged with $N_2$ for 10 min, and filled with DMAc (2.2 mL), purged with $N_2$ for 10 min, and then benzonitrile (11 μL, 0.108 mmol) (added 0.1 mL stock solution, which was prepared by dissolving 0.22 mL benzonitrile in 2 mL DMAc), and TMSCl (14 μL, 0.108 mmol) (added 0.1 mL stock solution, which was prepared by dissolving 0.27 mL benzonitrile in 2 mL DMAc). The resulting mixture was purged with $N_2$ for another 10 min, and heated for 1 hr at 40° C. The reaction mixture was directly purified by silica gel column chromatography using 0-100% EtOAc/hexane as mobile phase (isostatic at 20% and 40% for a while, removed some des-Br product, which came out first) to afford the title product. LC-MS (IE, m/z): 1077.11 [M+1]⁺.

Step B: benzyl 4-((2-(2-(4-methoxybenzyl)-2H-tetrazol-5-yl)-3-(N-(4-methoxybenzyl)sulfamoyl)-4'-(piperidin-4-yl)-[1,1'-biphenyl]-4-yl)methyl)piperidine-1-carboxylate To the solution of benzyl 4-((3-(N,N-bis(4-methoxybenzyl)sulfamoyl)-4'-(1-(tert-butoxycarbonyl)piperidin-4-yl)-2-(2-(4-methoxybenzyl)-2H-tetrazol-5-yl)-[1,1'-biphenyl]-4-yl)methyl)piperidine-1-carboxylate (220 mg, 0.204 mmol) in DCM (2.0 mL) was added anisole (222 µL, 2.044 mmol) and TFA (1.6 mL, 20.44 mmol) at rt. The resulting mixture was stirred at rt for 1 hr. After removing the volatile the residue was purified by SCX ion exchange column (load sample and rinse with MeOH, rinse out product with 2 M NH3 in MeOH) to give the desired product as a free amine LC-MS (IE, m/z): 856.91 [M+1]⁺.

Step C: benzyl 4-((4'-(1-((1-(tert-butoxycarbonyl)azetidin-3-yl)methyl)piperidin-4-yl)-2-(2-(4-methoxybenzyl)-2H-tetrazol-5-yl)-3-(N-(4-methoxybenzyl)sulfamoyl)-[1,1'-biphenyl]-4-yl)methyl)piperidine-1-carboxylate To benzyl 4-((2-(2-(4-methoxybenzyl)-2H-tetrazol-5-yl)-4'-(piperidin-4-yl)-3-sulfamoyl-[1,1'-biphenyl]-4-yl)methyl)piperidine-1-carboxylate (80 mg, 0.109 mmol) and tert-butyl 3-formylazetidine-1-carboxylate (30.2 mg, 0.163 mmol) in DCM (1.1 mL) was added acetic acid (37 µL, 0.652 mmol) and, after 5 min sodium triacetoxyborohydride (92 mg, 0.435 mmol). After being stirred at rt for 1 hr, the reaction mixture was purified by silica gel column chromatography (0-10% MeOH/DCM as eluent) to afford the title compound.

LC-MS (IE, m/z): 1026.29 [M+1]⁺.

Step D: 4'-(1-(azetidin-3-ylmethyl)piperidin-4-yl)-4-(piperidin-4-ylmethyl)-2-(2H-tetrazol-5-yl)-[1,1'-biphenyl]-3-sulfonamide To the solution benzyl 4-((4'-(1-((1-(tert-butoxycarbonyl) azetidin-3-yl)methyl)piperidin-4-yl)-2-(2-(4-methoxybenzyl)-2H-tetrazol-5-yl)-3-(N-(4-methoxybenzyl)sulfamoyl)-[1,1'-biphenyl]-4-yl)methyl)piperidine-1-carboxylate (100 mg, 0.098 mmol) in MeOH (2 mL) was added Pd—C (10.38 mg, 0.098 mmol). The reaction mixture was stirred under H₂ atmosphere with a H₂ balloon for 2 hr. After filtration through celite, the filtrate was concentrated. To the solution of this residue in DCM (975 µL) was added anisole (106 µL, 0.975 mmol) and TFA (751 µL, 9.75 mmol) at rt. The resulting mixture was stirred at rt for 1 hr. After removing the volatile the residue was purified by SCX ion exchange column (load sample and rinse with MeOH, rinse out product with 2 M NH₃ in MeOH) to give a free amine. The free amine was then treated with anisole (106 µL, 0.975 mmol) and TFA (751 µL, 9.75 mmol) at 80° C. for 1 hr. After removing the volatile the residue was purified by reverse phase HPLC using DMSO to load sample and 3-30% acetonitrile/water (0.1% TFA as additive) as mobile phase over 10 min to give the title compound. LC-MS (IE, m/z): 551.87 [M+1]⁺.

EXAMPLE 471

4-((1-(azetidin-3-ylmethyl)piperidin-4-yl)methyl)-4'-(piperidin-4-yl)-2-(2H-tetrazol-5-yl)-[1,1'-biphenyl]-3-sulfonamide

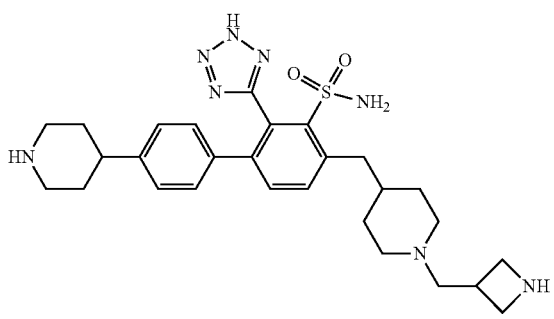 [SMILES: NS(=O)(=O)c1c(CC2CCN(CC3CNC3)CC2)ccc(-c2ccc(C3CCNCC3)cc2)c1-c1nn[nH]n1]

Step A: tert-butyl 4-(2'-(2-(4-methoxybenzyl)-2H-tetrazol-5-yl)-3'-(N-(4-methoxybenzyl)sulfamoyl)-4'-(piperidin-4-ylmethyl)-[1,1'-biphenyl]-4-yl)piperidine-1-carboxylate To the solution of benzyl 4-((3-(N,N-bis(4-methoxybenzyl)sulfamoyl)-4'-(1-(tert-butoxycarbonyl)piperidin-4-yl)-2-(2-(4-methoxybenzyl)-2H-tetrazol-5-yl)-[1,1'-biphenyl]-4-yl)methyl)piperidine-1-carboxylate (220 mg, 0.204 mmol) in MeOH (2044 µl) was added Pd—C (218 mg, 0.204 mmol) and equipped with H₂ balloon at rt. The resulting mixture was stirred at rt for 1 hr. After removing the volatile, the residue was purified by SCX ion exchange column (load sample and rinse with MeOH, rinse out product with 2 M NH₃ in MeOH) to give the title product as a free amine LC-MS (IE, m/z): 943.38 [M+1]⁺.

Step B: tert-butyl 4-(4'-((1-((1-(tert-butoxycarbonyl)azetidin-3-yl)methyl)piperidin-4-yl)methyl)-2'-(2-(4-methoxybenzyl)-2H-tetrazol-5-yl)-3'-(N-(4-methoxybenzyl)sulfamoyl)-[1,1'-biphenyl]-4-yl)piperidine-1-carboxylate To tert-butyl 4-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)piperidine-1-carboxylate (80 mg, 0.085 mmol) and tert-butyl 3-formylazetidine-1-carboxylate (23.59 mg, 0.127 mmol) in DCM (0.9 mL) was added acetic acid (29 µL, 0.509 mmol) and, after 5 min sodium triacetoxyborohydride (72.0 mg, 0.340 mmol). After being stirred at rt for 1 hr, the reaction mixture was purified by silica gel column chromatography (0-10% MeOH/DCM) to give the title compound. LC-MS (IE, m/z): 1112.44 [M+1]⁺.

Step C: 4'-(1-(azetidin-3-ylmethyl)piperidin-4-yl)-4-(piperidin-4-ylmethyl)-2-(2H-tetrazol-5-yl)-[1,1'-biphenyl]-3-sulfonamide To the solution of tert-butyl 4-(4'-((1-((1-(tert-butoxycarbonyl)azetidin-3-yl)methyl)piperidin-4-yl)methyl)-2'-(2-(4-methoxybenzyl)-2H-tetrazol-5-yl)-3'-(N-(4-methoxybenzyl)sulfamoyl)-[1,1'-biphenyl]-4-yl)piperidine-1-carboxylate (50 mg, 0.050 mmol) in DCM (504 µL) was added anisole (55 µL, 0.504 mmol) and TFA (390 µL, 5.04 mmol) at rt. The resulting mixture was stirred at rt for 1 hr. After removing the volatile the residue was treated with anisole (55 µL, 0.504 mmol) and TFA (390 µL, 5.04 mmol) at 80° C. for 1 hr. After removing the volatile the residue was purified by reverse phase HPLC using DMSO to load sample and 3-30% acetonitrile/water (0.1% TFA as additive) as mobile phase over 10 min to give the title compound.

LC-MS (IE, m/z): 551.86 [M+1]⁺.

EXAMPLE 472

4-(4'-(2-(4-guanidinocyclohexyl)ethyl)-3'-sulfamoyl-2'-(2H-tetrazol-5-yl)-[1,1'-biphenyl]-4-yl)piperidine-1-carboximidamide

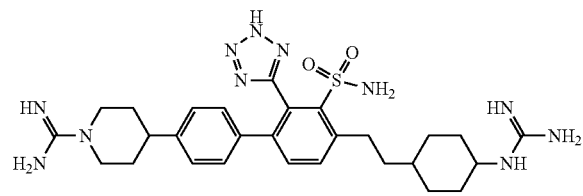 [SMILES: N=C(N)NC1CCC(CCc2ccc(-c3ccc(C4CCN(C(=N)N)CC4)cc3)c(-c3nn[nH]n3)c2S(N)(=O)=O)CC1]

Step A: 4-(4'-(2-(4-guanidinocyclohexyl)ethyl)-2'-(2-(4-methoxybenzyl)-2H-tetrazol-5-yl)-3'-sulfamoyl-[1,1'-biphenyl]-4-yl)piperidine-1-carboximidamide To a solution of 4-(2-(4-aminocyclohexyl)ethyl)-2-(1-(4-methoxybenzyl)-1H-tetrazol-5-yl)-4'-(piperidin-4-yl)-[1,1'-biphenyl]-3-sulfonamide (Intermediate of Example 38) (30 mg, 0.048 mmol) in DMF (953 μL) was added 1H-pyrazole-1-carboxamidine hydrochloride (41.9 mg, 0.286 mmol) and DIPEA (100 μL, 0.572 mmol). The reaction mixture was stirred at rt overnight, and purified by reverse phase HPLC (10-80% MeCN/water as gradient, 0.1% TFA as additive) to afford the title compound.

Steps B: 4-(4'-(2-(4-guanidinocyclohexyl)ethyl)-3'-sulfamoyl-2'-(2H-tetrazol-5-yl)-[1,1'-biphenyl]-4-yl)piperidine-1-carboximidamide To a solution of 4-(4'-(2-(4-guanidinocyclohexyl)ethyl)-2'-(2-(4-methoxybenzyl)-2H-tetrazol-5-yl)-3'-sulfamoyl-[1,1'-biphenyl]-4-yl)piperidine-1-carboximidamide (25 mg, 0.035 mmol) in DCM (175 μL) was added anisole (38 μL, 0.350 mmol) and TFA (270 μL, 3.50 mmol) at rt. The resulting mixture was stirred at 80° C. for 1 hr to remove the final PMB protection. After removing the volatile the residue was purified by reverse phase HPLC using DMSO to load sample and 5-40% acetonitrile/water (0.1% TFA as additive) as mobile phase over 10 min to give the title compound. LC-MS (IE, m/z): 594.8 [M+1]⁺.

EXAMPLE 473

4'-(piperidin-4-yl)-2-(2H-tetrazol-5-yl)-4-(3,3,3-trifluoropropyl)-[1,1'-biphenyl]-3-sulfonamide

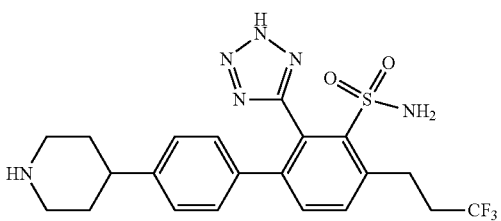

Step A: tert-butyl 4-(3'-(N,N-bis(4-methoxybenzyl)sulfamoyl)-2'-(2-(4-methoxybenzyl)-2H-tetrazol-5-yl)-4'-(3,3,3-trifluoropropyl)-[1,1'-biphenyl]-4-yl)piperidine-1-carboxylate A microwave vial was charged with potassium trifluoro (3,3,3-trifluoropropyl)borate (0.066 g, 0.325 mmol), chloro [(di(1-adamantyl)-N-butylphosphine)-2-(2-aminobiphenyl)]palladium(II) (0.022 g, 0.032 mmol), and tert-butyl 4-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)piperidine-1-carboxylate (0.1 g, 0.108 mmol). The vial was sealed and purged with N₂, and dioxane (0.87 mL) and water (0.22 mL) were added. The resulting mixture was heated overnight at 100° C. The reaction mixture was filtered over celite to remove palladium. The filtrate was concentrated and purified by silica gel column chromatography using 0-100% EtOAc/Hexanes as mobile phase to afford the title compound.

LC-MS (IE, m/z): 941.97 [M+1]⁺.

Steps B: 4'-(piperidin-4-yl)-2-(2H-tetrazol-5-yl)-4-(3,3,3-trifluoropropyl)-[1,1'-biphenyl]-3-sulfonamide To tert-butyl 4-(3'-(N,N-bis(4-methoxybenzyl)sulfamoyl)-2'-(2-(4-methoxybenzyl)-2H-tetrazol-5-yl)-4'-(3,3,3-trifluoropropyl)-[1,1'-biphenyl]-4-yl)piperidine-1-carboxylate (80 mg, 0.085 mmol) was added anisole (93 μL, 0.850 mmol) and TFA (655 μL, 8.50 mmol) at rt. The resulting mixture was stirred at rt for 2 hr to remove both Boc and PMB protection. After removing the volatile the residue was purified by reverse phase HPLC using DMSO to load sample and 5-60% acetonitrile/water (0.1% TFA as additive) as mobile phase over 10 min to separate the desired product from des-Br product (from the coupling reaction).

To a solution of the desired product in DCM (425 μL) was added anisole (93 μL, 0.850 mmol) and TFA (655 μL, 8.50 mmol) at rt. The resulting mixture was stirred at 80° C. for 1 hr to remove the final PMB protection. After removing the volatile the residue was purified by reverse phase HPLC using DMSO to load sample and 5-40% acetonitrile/water (0.1% TFA as additive) as mobile phase over 10 min to give the title compound. LC-MS (IE, m/z): 481.36 [M+1]⁺.

EXAMPLES 474-481

Parallel Synthesis of 3-aryl- or 3-heteroaryl-2-(1H-tetrazol-5-yl)-6-(trifluoromethyl)benzenesulfonamides

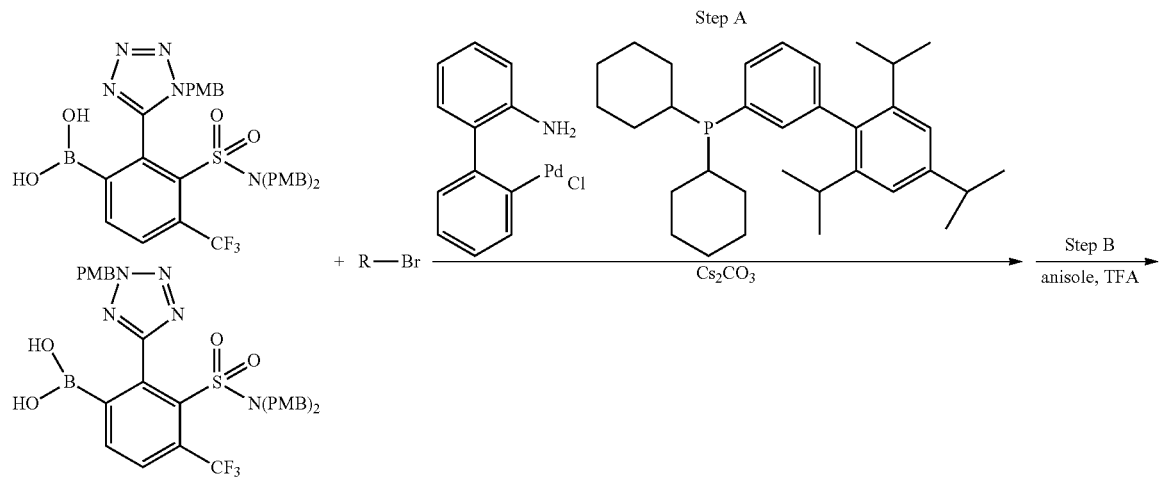

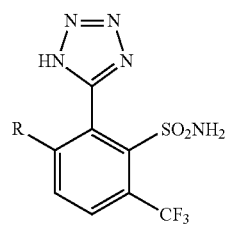

Step A: Suzuki Coupling of a Mixture of (3-[bis[(4-methoxyphenyl)methyl]sulfamoyl]-2-[1-[(4-methoxyphenyl)methyl]-1H-1,2,3,4-tetrazol-5-yl]-4-(trifluoromethyl)phenyl)boronic acid and (3-[bis[(4-methoxyphenyl)methyl]sulfamoyl]-2-[2-[(4-methoxyphenyl)methyl]-2H-1,2,3,4-tetrazol-5-yl]-4-(trifluoromethyl)phenyl)boronic acid with aryl and heteroaryl halides A solution of (3-[bis[(4-methoxyphenyl)methyl]sulfamoyl]-2-[1-[(4-methoxyphenyl)methyl]-1H-1,2,3,4-tetrazol-5-yl]-4-(trifluoromethyl)phenyl)boronic acid and (3-[bis[(4-methoxyphenyl)methyl]sulfamoyl]-2-[2-[(4-methoxyphenyl)methyl]-2H-1,2,3,4-tetrazol-5-yl]-4-(trifluoromethyl)phenyl)boronic acid (80 mg, 0.104 mmol) and 2nd Generation Xphos Precatalyst (12.33 mg, 0.016 mmol) in 1.2 mL of dioxane was added to 1 dram vials containing commercially available or known aryl or heteroaryl bromides (0.125 mmol). Then Cesium Carbonate (0.209 ml, 0.313 mmol) was added and the mixtures were stirred at 85° C. for 18 hr. The mixtures were allowed to cool. DCM (1 mL) and water (1 mL) was added and the mixtures were stirred for 5 minutes. The aqeuous layer was removed by pipette and the remaining organics concentrated under reduced pressure in the genevac.

Step B: Removal of the Paramethoxybenzyl Protective Groups

Anisole (0.114 mL, 1.045 mmol) and TFA (1 mL) were added to the residues and the mixtures were stirred at 60° C. for 4 hr. The mixtures were allowed to cool and the volatile organics were removed in the genevac under reduced pressure. DMSO (1 mL) was added to the residues and the mixtures were purified using mass directed reverse phase HPLC to afford the examples in the Table below.

| Ex. No. | Structure | Name | Calc'd. MW [M + H]+ | LC/MS m/e (M + H)+ |
|---|---|---|---|---|
| 474 | 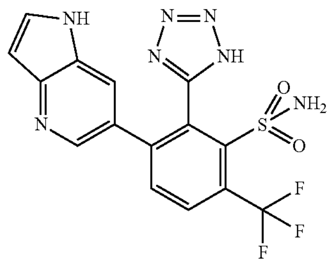 [SMILES: NS(=O)(=O)c1c(C(F)(F)F)ccc(-c2cnc3cc[nH]c3c2)c1-c1nnn[nH]1] | 3-(1H-pyrrolo[3,2-b]pyridin-6-yl)-2-(1H-tetrazol-5-yl)-6-(trifluoromethyl)benzenesulfonamide | 410 | 410 |
| 475 | 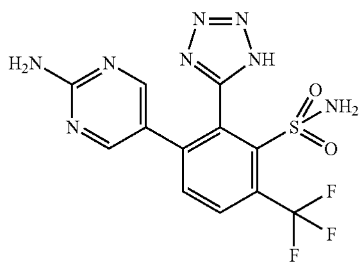 [SMILES: Nc1ncc(-c2ccc(C(F)(F)F)c(S(N)(=O)=O)c2-c2nnn[nH]2)cn1] | 3-(2-aminopyrimidin-5-yl)-2-(1H-tetrazol-5-yl)-6-(trifluoromethyl)benzenesulfonamide | 387 | 387 |
| 476 | 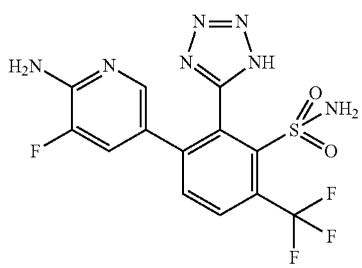 [SMILES: Nc1ncc(-c2ccc(C(F)(F)F)c(S(N)(=O)=O)c2-c2nnn[nH]2)cc1F] | 3-(6-amino-5-fluoro-3-pyridyl)-2-(1H-tetrazol-5-yl)-6-(trifluoromethyl)benzenesulfonamide | 404 | 404 |
| 477 | 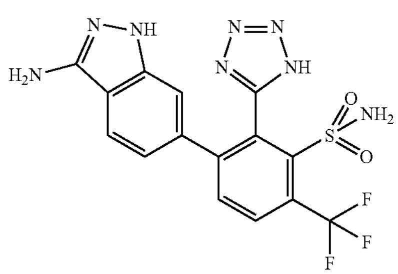 [SMILES: Nc1n[nH]c2cc(-c3ccc(C(F)(F)F)c(S(N)(=O)=O)c3-c3nnn[nH]3)ccc12] | 3-(3-amino-1H-indazol-6-yl)-2-(1H-tetrazol-5-yl)-6-(trifluoromethyl)benzenesulfonamide | 425 | 425 |
| 478 | 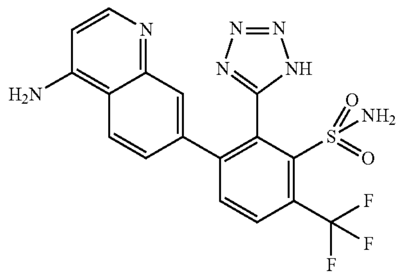 [SMILES: Nc1ccnc2cc(-c3ccc(C(F)(F)F)c(S(N)(=O)=O)c3-c3nnn[nH]3)ccc12] | 3-(4-amino-7-quinolyl)-2-(1-tetrazol-5-yl)-6-(trifluoromethyl)benzenesulfonamide | 436 | 436 |

| Ex. No. | Structure | Name | Calc'd. MW [M + H]+ | LC/MS m/e (M + H)+ |
|---|---|---|---|---|
| 479 | 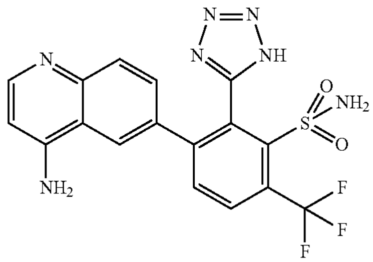 [SMILES: Nc1ccnc2ccc(-c3ccc(C(F)(F)F)c(S(N)(=O)=O)c3-c3nnn[nH]3)cc12] | 3-(4-amino-6-quinolyl)-2-(1H-tetrazol-5-yl)-6-(trifluoromethyl)benzenesulfonamide | 436 | 436 |
| 480 | 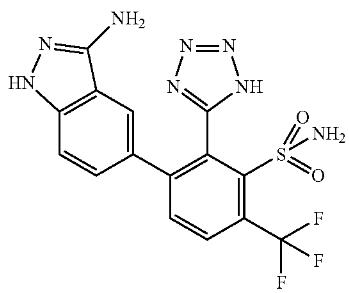 [SMILES: Nc1n[nH]c2ccc(-c3ccc(C(F)(F)F)c(S(N)(=O)=O)c3-c3nnn[nH]3)cc12] | 3-(3-amino-1H-indazol-5-yl)-2-(1H-tetrazol-5-yl)-6-(trifluoromethyl)benzenesulfonamide | 425 | 425 |
| 481 | 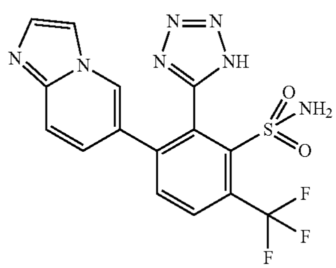 [SMILES: NS(=O)(=O)c1c(C(F)(F)F)ccc(-c2ccc3nccn3c2)c1-c1nnn[nH]1] | 3-imidazo[1,2-a]pyridin-6-yl-2-(1H-tetrazol-5-yl)-6-(trifluoromethyl)benzenesulfonamide | 410 | 410 |

EXAMPLE 482

4-(3-Sulfamoyl-2-(1H-tetrazol-5-yl)-4-(trifluoromethyl)phenyl)benzo[d]thiazole-2-carboximidamide

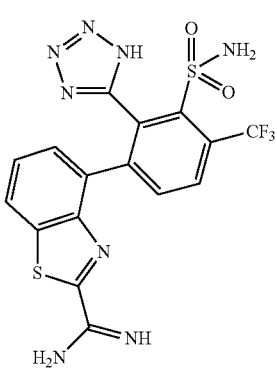 [SMILES: N=C(N)c1nc2c(-c3ccc(C(F)(F)F)c(S(N)(=O)=O)c3-c3nnn[nH]3)cccc2s1]

Step A: 3-(2-Bromobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-bromobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide 3-(2-Bromobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-bromobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide was prepared in an analogous way to that of 3-(2-bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide. LC/MS (M+1)+=866, 868.

Step B: 3-(2-Cyanobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-cyanobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide 3-(2-Bromobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-bromobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide (285 mg, 0.329 mmol) was dissolved in pyridine (329 μL), and Copper(I) Cyanide (59.0 mg, 0.658 mmol) was added. The mixture was heated at 100° C. for 2 hr. LC-MS showed the reaction was completed. The reaction mixture was concentrated to remove pyridine and the residue was purified by column chromatography (0-55% EtOAc/Hexane) to give the title compounds. LC/MS (M+1)+=812.8

Step C: 4-(3-(N,N-bis(4-methoxybenzyl)sulfamoyl)-2-(1-(4-methoxybenzyl)-1H-tetrazol-5-yl)-4-(trifluoromethyl)phenyl)benzo[d]thiazole-2-carboximidamide and 4-(3-(N,N-bis(4-methoxybenzyl)sulfamoyl)-2-(2-(4-methoxybenzyl)-2H-tetrazol-5-yl)-4-(trifluoromethyl)phenyl)benzo[d]thiazole-2-carboximidamide 3-(2-Cyanobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-cyanobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide (98 mg, 0.12 mmol) was suspended in MeOH (1 mL) and THF (0.5 mL) was added to aid the solubility. Then Sodium Methoxide (2.61 mg, 0.012 mmol) was added at room temperature. The mixture was stirred at room temperature for 1 hr. Ammonium Chloride (12.9 mg, 0.241 mmol) was then added and the mixture was stirred at room temperature for about 36 hr. LC-MS showed that the desired product was the major product. The reaction mixture was directly loaded onto a 40 g ESCO column and eluted with 0-10% MeOH/EtOAC. The correct fractions were combined and concentrated to give the title compounds. LC/MS (M+1)+=830.05.

Step D: 4-(3-Sulfamoyl-2-(1H-tetrazol-5-yl)-4-(trifluoromethyl)phenyl)benzo[d]thiazole-2-carboximidamide 4-(3-(N,N-bis(4-methoxybenzyl)sulfamoyl)-2-(1-(4-methoxybenzyl)-1H-tetrazol-5-yl)-4-(trifluoromethyl)phenyl)benzo[d]thiazole-2-carboximidamide and 4-(3-(N,N-bis(4-methoxybenzyl)sulfamoyl)-2-(2-(4-methoxybenzyl)-2H-tetrazol-5-yl)-4-(trifluoromethyl)phenyl)benzo[d]thiazole-2-carboximidamide (48 mg, 0.058 mmol) was heated in TFA (2 mL) at 60° C. for 2 hr. The reaction was concentrated to remove TFA and the residue was purified with Gilson (3-80% CH$_3$CN/water with 0.1% TFA). The correct fractions were combined, concentrated and lypholized from CH$_3$CN/water to give 4-(3-Sulfamoyl-2-(1H-tetrazol-5-yl)-4-(trifluoromethyl)phenyl)benzo[d]thiazole-2-carboximidamide. LC/MS (M+1)+=469.5

EXAMPLE 483

3-(2-Cyanobenzo[d]thiazol-4-yl)-2-(1H-tetrazol-5-yl)-6-(trifluoromethyl)benzenesulfonamide

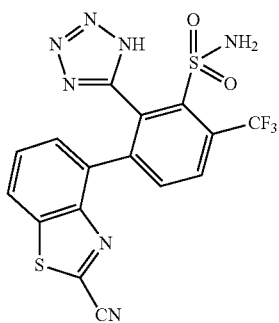 [SMILES: N#Cc1nc2c(-c3ccc(C(F)(F)F)c(S(N)(=O)=O)c3-c3nnn[nH]3)cccc2s1]

3-(2-Cyanobenzo[d]thiazol-4-yl)-N,N-bis(4-methoxybenzyl)-2-(1-(4-methoxybenzyl)-1H-tetrazol-5-yl)-6-(trifluoromethyl)benzenesulfonamide and 3-(2-cyanobenzo[d]thiazol-4-yl)-N,N-bis(4-methoxybenzyl)-2-(2-(4-methoxybenzyl)-2H-tetrazol-5-yl)-6-(trifluoromethyl)benzenesulfonamide (65 mg, 0.080 mmol) was heated in TFA (2 mL) for 2 hr. The reaction was concentrated and the residue was purified with Gilson (3-90% CH$_3$CN/water with 0.1% TFA). The correct fractions were concentrated and lypholized to give 3-(2-cyanobenzo[d]thiazol-4-yl)-2-(1H-tetrazol-5-yl)-6-(trifluoromethyl)benzenesulfonamide. LC/MS (M+1)+=452.3.

EXAMPLE 484

3-(Imidazo[1,2-a]pyridin-6-yl)-2-(1H-tetrazol-5-yl)-6-(trifluoromethyl)benzenesulfonamide

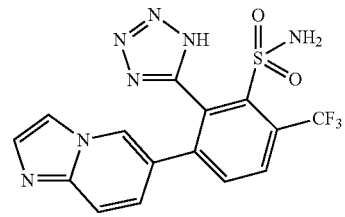 [SMILES: NS(=O)(=O)c1c(C(F)(F)F)ccc(-c2ccc3nccn3c2)c1-c1nnn[nH]1]

Step A: 3-(Imidazo[1,2-a]pyridin-6-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,2-a]pyridin-6-yl)-N,N-bis(4-methoxybenzyl)-2-(2-(4-methoxybenzyl)-2H-tetrazol-5-yl)-6-(trifluoromethyl)benzenesulfonamide 3-(Imidazo[1,2-a]pyridin-6-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,2-a]pyridin-6-yl)-N,N-bis(4-methoxybenzyl)-2-(2-(4-methoxybenzyl)-2H-tetrazol-5-yl)-6-(trifluoromethyl)benzenesulfonamide was synthesized in an analogous way to that of 3-(Imidazo[1,5-a]pyridin-7-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,5-a]pyridin-7-yl)-N,N-bis(4-methoxybenzyl)-2-(2-(4-methoxybenzyl)-2H-tetrazol-5-yl)-6-(trifluoromethyl)benzenesulfonamide. LC/MS (M+1)+=770.5.

Step B: 3-(Imidazo[1,2-a]pyridin-6-yl)-2-(1H-tetrazol-5-yl)-6-(trifluoromethyl)benzenesulfonamide 3-(Imidazo[1,2-a]pyridin-6-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,2-a]pyridin-6-yl)-N,N-bis(4-methoxybenzyl)-2-(2-(4-methoxybenzyl)-2H-tetrazol-5-yl)-6-(trifluoromethyl)benzenesulfonamide (609 mg, 0.791 mmol) were heated at 60° C. in TFA for 2 hr. After cooling, the reaction mixture was concentrated and purified with Gilson (2-55% CH$_3$CN/water with 0.1% TFA). The correct fractions were combined, concentrated and lypholized to give 3-(imidazo[1,2-a]pyridin-6-yl)-2-(1H-tetrazol-5-yl)-6-(trifluoromethyl)benzenesulfonamide. LC/MS (M+1)+=410.2

EXAMPLE 485

3-(Imidazo[1,5-a]pyridin-8-yl)-2-(1H-tetrazol-5-yl)-6-(trifluoromethyl)benzenesulfonamide

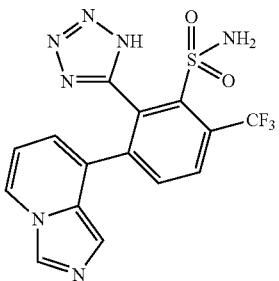 [SMILES: NS(=O)(=O)c1c(C(F)(F)F)ccc(-c2cccn3cncc23)c1-c1nnn[nH]1]

3-(Imidazo[1,5-a]pyridin-8-yl)-2-(1H-tetrazol-5-yl)-6-(trifluoromethyl)benzenesulfonamide was prepared in an analogous way to that of 3-(imidazo[1,2-a]pyridin-6-yl)-2-(1H-tetrazol-5-yl)-6-(trifluoromethyl)benzenesulfonamide (immediately above). LC/MS (M+1)$^+$=410.4.

EXAMPLE 486

3-(Quinolin-5-yl)-2-(2H-tetrazol-5-yl)-6-(trifluoromethyl)benzenesulfonamide

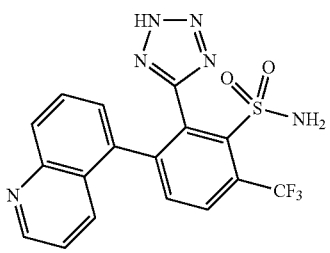 [SMILES: NS(=O)(=O)c1c(C(F)(F)F)ccc(-c2cccc3ncccc23)c1-c1nn[nH]n1]

Step A: 6-Bromo-N,N-bis(4-methoxybenzyl)-2-(1-(4-methoxybenzyl)-1H-tetrazol-5-yl)-3-(quinolin-5-yl)benzenesulfonamide compound with 6-bromo-N,N-bis(4-methoxybenzyl)-2-(2-(4-methoxybenzyl)-2H-tetrazol-5-yl)-3-(quinolin-5-yl)benzenesulfonamide A microwave vial was charged with 6-bromo-3-iodo-N,N-bis(4-methoxybenzyl)-2-(2-(4-methoxybenzyl)-2H-tetrazol-5-yl)benzenesulfonamide and 6-bromo-3-iodo-N,N-bis(4-methoxybenzyl)-2-(1-(4-methoxybenzyl)-1H-tetrazol-5-yl)benzenesulfonamide (1.24 g, 1.569 mmol), quinoline-5-boronic acid (0.271 g, 1.569 mmol), sodium carbonate (0.333 g, 3.14 mmol) and PdCl$_2$(dppf)-CH$_2$Cl$_2$ adduct (0.128 g, 0.157 mmol). The vial was sealed, degassed, and filled with dioxane (4.71 ml) and water (1.569 ml) and degassed with nitrogen. The resulting mixture was heated at 90° C. for 16 hr. The reaction mixture was filtered over celite and diluted with ethyl acetate (50 mL) and washed with water (2×15 mL). The organic layer was dried over anhydrous magnesium sulfate, filtered, concentrated and purified by silica gel column chromatography and the title compounds was isolated very light yellow colored foam. LC/MS [M+H]$^+$: 791, 793.

Step B: N,N-Bis(4-methoxybenzyl)-2-(1-(4-methoxybenzyl)-1H-tetrazol-5-yl)-3-(quinolin-5-yl)-6-(trifluoromethyl)benzenesulfonamide compound with N,N-bis(4-methoxybenzyl)-2-(2-(4-methoxybenzyl)-2H-tetrazol-5-yl)-3-(quinolin-5-yl)-6-(trifluoromethyl)benzenesulfonamide To a microwave vial was added "Trifluoromethylator" (79 mg, 0.253 mmol), 6-bromo-N,N-bis(4-methoxybenzyl)-2-(1-(4-methoxybenzyl)-1H-tetrazol-5-yl)-3-(quinolin-5-yl)benzenesulfonamide compound with 6-bromo-N,N-bis(4-methoxybenzyl)-2-(2-(4-methoxybenzyl)-2H-tetrazol-5-yl)-3-(quinolin-5-yl)benzenesulfonamide (100 mg, 0.126 mmol), CuI (48.1 mg, 0.253 mmol), and DMF (1263 µl). The vial was sealed, degassed with N$_2$, and heated at 80° C. for 16 hr. The reaction mixture was added to EtOAc (20 mL) and filtered through celite. The organic was washed with brine (10 mL) and the residue loaded was purified with silica gel chromatography to give the title compounds. LC/MS [M+H]$^+$: 781.71.

Step C: 3-(Quinolin-5-yl)-2-(2H-tetrazol-5-yl)-6-(trifluoromethyl)benzenesulfonamide To the solution of N,N-bis(4-methoxybenzyl)-2-(2-(4-methoxybenzyl)-2H-tetrazol-5-yl)-3-(quinolin-5-yl)-6-(trifluoromethyl)benzenesulfonamide and N,N-bis(4-methoxybenzyl)-2-(1-(4-methoxybenzyl)-1H-tetrazol-5-yl)-3-(quinolin-5-yl)-6-(trifluoromethyl)benzenesulfonamide (40 mg, 0.051 mmol) in DCM (1.5 mL) was added TFA (0.395 mL, 5.12 mmol) and anisole (0.056 mL, 0.512 mmol. The reaction mixture was heated at 80° C. for 1 hr. After removing the volatile the residue was purified by HPLC and then lyophilized to give the title compound. LC/MS [M+H]$^+$: 421.08.

EXAMPLES 487-492

Parallel Synthesis of 3-alkyl- or 3-cycloalkyl-2-(1H-tetrazol-5-yl)-6-(trifluoromethyl)benzenesulfonamides

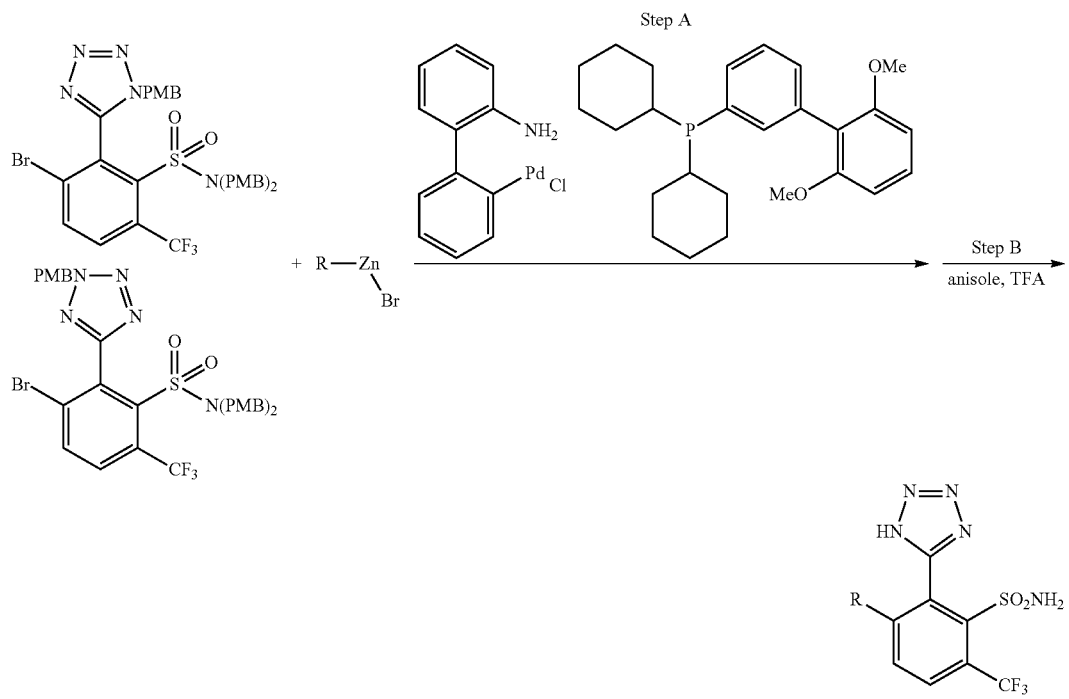

Step A: Negishi Coupling of 3-bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide with Commercially Available Alkyl and Cycloalkyl Zinc Reagents In a glove box, a mixture of 3-bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(1-(4-methoxybenzyl)-2H-tetrazol-5-yl)-6-(trifluoromethyl)benzenesulfonamide (80 mg, 0.109 mmol)) and G2 SPhos precatalyst (3.15 mg, 4.37 µmol)) in 2 mL of THF was combined with commercially available alkyl and cycloalkyl zincate reagents (0.437 mmol) and stirred at 55° C. for 18 hours. The mixtures were allowed to cool. Saturated ammonium chloride solution (1 mL) and DCM (1 mL) were added. The mixtures were stirred for 20 minutes. The organics layers were separated and the volatile organics removed under reduced pressure in the genevac.

Step B: Removal of the Para-Methoxybenzyl Protective Groups

The mixtures from Step A were treated with Anisole (0.048 mL, 0.44 mmol) and TFA (0.5 mL). The mixtures were stirred uncapped for 2 hr at 65° C. The mixtures were allowed to cool and the volatile organics removed under reduced pressure in the genevac. DMSO (1 mL) was added and the mixtures were filtered through a MTP (96 well) 0.4 micron filter plate and the filtrates were purified by mass directed reverse phase HPLC to afford the compounds in the Table below.

| Ex. No. | Structure | Name | Calc'd. MW $[M + H]^+$ | LC/MS m/e $(M + H)^+$ |
|---|---|---|---|---|
| 487 | (structure) | 3-methyl-2-(1H-tetrazol-5-yl)-6-(trifluoromethyl)benzenesulfonamide | 308 | 308 |

-continued

| Ex. No. | Structure | Name | Calc'd. MW [M + H]+ | LC/MS m/e (M + H)+ |
|---|---|---|---|---|
| 488 | 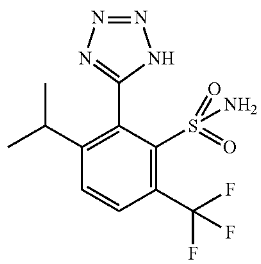 [SMILES: CC(C)c1ccc(C(F)(F)F)c(S(N)(=O)=O)c1-c1nnn[nH]1] | 3-isopropyl-2-(1H-tetrazol-5-yl)-6-(trifluoromethyl)benzenesulfonamide | 336 | 336 |
| 489 | 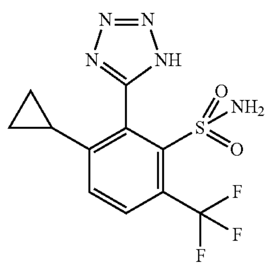 [SMILES: NS(=O)(=O)c1c(C(F)(F)F)ccc(C2CC2)c1-c1nnn[nH]1] | 3-cyclopropyl-2-(1H-tetrazol-5-yl)-6-(trifluoromethyl)benzenesulfonamide | 334 | 334 |
| 490 | 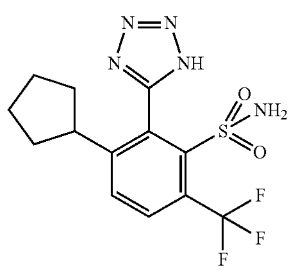 [SMILES: NS(=O)(=O)c1c(C(F)(F)F)ccc(C2CCCC2)c1-c1nnn[nH]1] | 3-cyclopentyl-2-(1H-tetrazol-5-yl)-6-(trifluoromethyl)benzenesulfonamide | 362 | 362 |
| 491 | 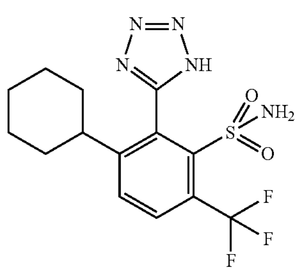 [SMILES: NS(=O)(=O)c1c(C(F)(F)F)ccc(C2CCCCC2)c1-c1nnn[nH]1] | 3-cyclohexyl-2-(1H-tetrazol-5-yl)-6-(trifluoromethyl)benzenesulfonamide | 376 | 376 |
| 492 | 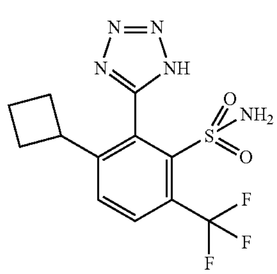 [SMILES: NS(=O)(=O)c1c(C(F)(F)F)ccc(C2CCC2)c1-c1nnn[nH]1] | 3-cyclobutyl-2-(1H-tetrazol-5-yl)-6-(trifluoromethyl)benzenesulfonamide | 348 | 348 |

EXAMPLE 493

3-(1,2,3,4-Tetrahydroquinolin-4-yl)-2-(1H-tetrazol-5-yl)-6-(trifluoromethyl)benzenesulfonamide

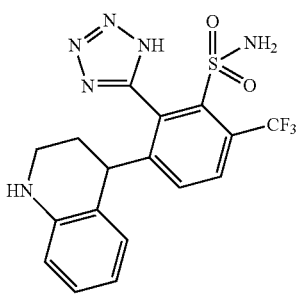 [SMILES: NS(=O)(=O)c1c(C(F)(F)F)ccc(C2CCNc3ccccc32)c1-c1nnn[nH]1]

Step A: 6-Bromo-2-(1-(4-methoxybenzyl)-1H-tetrazol-5-yl)-3-(quinolin-4-yl)benzenesulfonamide Quinolin-4-ylboronic acid (0.629 g, 3.64 mmol), 6-bromo-3-iodo-2-(1-(4-methoxybenzyl)-1H-tetrazol-5-yl)benzenesulfonamide (1 g, 1.818 mmol), $Na_2CO_3$ (0.385 g, 3.64 mmol), $PdCl_2$(dppf) (0.133 g, 0.182 mmol) was placed in a reaction vessell, and 1,4-dioxane (9.09 ml) and water (3.03 ml) were added. The reaction was sealed, degassed for 20 min and then heated at 85° C. overnight. After cooling to room temperature, the reaction mixture was diluted with EtOAc and washed with water. The organic phase was separated and concentrated. The resulting residue was purified by column chromatography (0% to 90% EtOAc/Hexane) to give 6-bromo-2-(1-(4-methoxybenzyl)-1H-tetrazol-5-yl)-3-(quinolin-4-yl)benzenesulfonamide.

Step B: 2-(1-(4-Methoxybenzyl)-1H-tetrazol-5-yl)-3-(quinolin-4-yl)-6-(trifluoromethyl)benzenesulfonamide A mixture of 6-bromo-2-(1-(4-methoxybenzyl)-1H-tetrazol-5-yl)-3-(quinolin-4-yl)benzenesulfonamide (0.43 g, 0.780 mmol), trifluoromethlator (0.488 g, 1.560 mmol), and Copper(I) Iodide (0.297 g, 1.560 mmol) in DMF (8 mL) was degassed and heated at 80° C. overnight. LC-MS analysis suggested that the stating material was consumed and the desired product was formed. The reaction mixture was cooled to room temperature and then loaded onto a silica gel column eluting with 0-100% EtOAc/hexane to give 2-(1-(4-methoxybenzyl)-1H-tetrazol-5-yl)-3-(quinolin-4-yl)-6-(trifluoromethyl)benzenesulfonamide.

Step C: 2-(1-(4-Methoxybenzyl)-1H-tetrazol-5-yl)-3-(1,2,3,4-tetrahydroquinolin-4-yl)-6-(trifluoromethyl)benzenesulfonamide 2-(1-(4-Methoxybenzyl)-1H-tetrazol-5-yl)-3-(quinolin-4-yl)-6-(trifluoromethyl)benzenesulfonamide (167 mg, 0.309 mmol) was stirred with $Pd(OH)_2$ (217 mg, 0.309 mmol) under $H_2$ atmosphere (balloon) at room temperature for 36 hr. The reaction mixture was then filtered. The filtrates were concentrated and the residue purified by column chromatography (0-100% EtOAc/Hexane) to give 2-(1-(4-methoxybenzyl)-1H-tetrazol-5-yl)-3-(1,2,3,4-tetrahydroquinolin-4-yl)-6-(trifluoromethyl)benzenesulfonamide.

Step D: 3-(1,2,3,4-Tetrahydroquinolin-4-yl)-2-(1H-tetrazol-5-yl)-6-(trifluoromethyl)benzenesulfonamide 2-(1-(4-Methoxybenzyl)-1H-tetrazol-5-yl)-3-(1,2,3,4-tetrahydroquinolin-4-yl)-6-(trifluoromethyl)benzenesulfonamide (40 mg, 0.073 mmol) was heated in neat TFA (2 mL) at 80° C. for 3 hr. The reaction was concentrated and purified with reverse phase HPLC eluted with 3-90% $CH_3CN$/water with 0.1% TFA to give 3-(1,2,3,4-tetrahydroquinolin-4-yl)-2-(1H-tetrazol-5-yl)-6-(trifluoromethyl)benzenesulfonamide. LC/MS (M+1)+=425.3

EXAMPLE 494

3-(5,6,7,8-Tetrahydroimidazo[1,5-a]pyridin-7-yl)-2-(1H-tetrazol-5-yl)-6-(trifluoromethyl)benzenesulfonamide

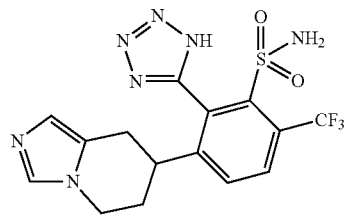 [SMILES: NS(=O)(=O)c1c(C(F)(F)F)ccc(C2CCn3cncc3C2)c1-c1nnn[nH]1]

Step A: 3-(Imidazo[1,5-a]pyridin-7-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,5-a]pyridin-7-yl)-N,N-bis(4-methoxybenzyl)-2-(2-(4-methoxybenzyl)-2H-tetrazol-5-yl)-6-(trifluoromethyl)benzenesulfonamide In a reaction vessel, 7-bromoimidazo[1,5-a]pyridine (200 mg, 1.015 mmol) and bispinacolatodiboron (773 mg, 3.05 mmol) were combined, followed by potassium acetate (299 mg, 3.05 mmol) and PCy3 Pd G2 (59.9 mg, 0.102 mmol). Then anhydrous dioxane (5075 µl) was added to this flask. This mixture was degassed and then heated at 80° C. for 12 hr. LC-MS analysis showed the desired mass. After cooled to rt, to this reaction mixture, was added a mixture of 3-bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide (744 mg, 1.015 mmol), $PdCl_2$(dppf)-$CH_2Cl_2$ Adduct (83 mg, 0.102 mmol), and $K_2CO_3$ (842 mg, 6.09 mmol) dissolved in water (1.2 mL). The mixture was degassed for 10 min, and then heated at 85° C. overnight. After cooled to room temperature, the reaction mixture was diluted with EtOAc, washed with water. The organic layer was separated and evaporated under the reduced pressure. The residue was purified by column chromatography on silica gel (80 g), eluting with 0 to 5% MeOH/EtOAc to give the title compounds. LC/MS (M+1)+: 770.7.

Step B: 3-(5,6,7,8-Tetrahydroimidazo[1,5-a]pyridin-7-yl)-2-(1H-tetrazol-5-yl)-6-(trifluoromethyl)benzenesulfonamide 3-(Imidazo[1,5-a]pyridin-7-yl)-N,N-bis(4-methoxybenzyl)-2-(1-(4-methoxybenzyl)-1H-tetrazol-5-yl)-6-(trifluoromethyl)benzenesulfonamide and 3-(imidazo[1,5-a]pyridin-7-yl)-N,N-bis(4-methoxybenzyl)-2-(2-(4-methoxybenzyl)-2H-tetrazol-5-yl)-6-(trifluoromethyl)benzenesulfonamide (240 mg, 0.312 mmol) was dissolved in MeOH (3118 µl), to which, was added 2 drops of conc. HCl followed by Pd—C (120 mg). The reaction head space was vacuumed and filled with $H_2$ a couple of times. The mixture was stirred at room temperature under $H_2$ for 48 hr before it was filtered. The filtrates were concentrated to give a crude partially hydrogenated product. LC/MS (M+1)+=772.7. The crude product was heated in TFA (2 mL) at 60° C. for 2 hr to remove protecting group and then concentrated to afford an oil. LC/MS (M+1)+=412.3. This crude oil was dissolved in EtOH/DCM (1/1, 3 mL) with TFA (3 mL) and Platinum(IV) Oxide (41.25 mg, 0.181 mmol) was added. The hydrogenation was carried out using a par shaker (40 psi) at room temperature for 6 hr. LC-MS showed the completion of the reaction. The reaction mixture was filtered and the filtrates were concentrated, the resulting residue was purified with Gilson (2-50% CH$_3$CN/water with 0.1% TFA). The product was neutralized with a SCX cartridge and lypholized to afford 3-(5,6,7,8-Tetrahydroimidazo[1,5-a]pyridin-7-yl)-2-(1H-tetrazol-5-yl)-6-(trifluoromethyl)benzenesulfonamide. LC/MS (M+1)$^+$=414.3.

EXAMPLE 495 and 496

3-((cis 4-hydroxycyclohexyl)-2-(1H-tetrazol-5-yl)-6-(trifluoromethyl)benzenesulfonamide and 3-((trans 4-hydroxycyclohexyl)-2-(1H-tetrazol-5-yl)-6-(trifluoromethyl)benzenesulfonamide

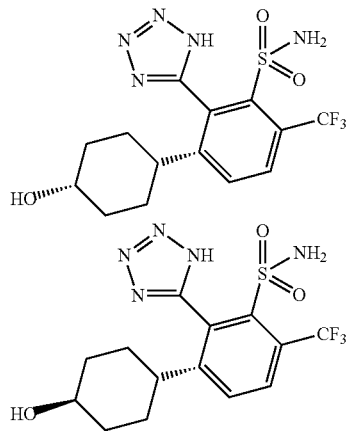

Step A: 4-Bromo-4'-hydroxy-2-(1-(4-methoxybenzyl)-1H-tetrazol-5-yl)-2',3',4',5'-tetrahydro-[1,1'-biphenyl]-3-sulfonamide and 4-bromo-4'-hydroxy-2-(2-(4-methoxybenzyl)-2H-tetrazol-5-yl)-2',3',4',5'-tetrahydro-[1,1'-biphenyl]-3-sulfonamide 4-Bromo-4'-hydroxy-2-(1-(4-methoxybenzyl)-1H-tetrazol-5-yl)-2',3',4',5'-tetrahydro-[1,1'-biphenyl]-3-sulfonamide and 4-bromo-4'-hydroxy-2-(2-(4-methoxybenzyl)-2H-tetrazol-5-yl)-2',3',4',5'-tetrahydro-[1,1'-biphenyl]-3-sulfonamide were prepared in an analogous way to that of 3-(2-Aminoquinazolin-7-yl)-N,N-bis(4-methoxybenzyl)-2-(1-(4-methoxybenzyl)-1H-tetrazol-5-yl)benzenesulfonamide and 3-(2-aminoquinazolin-7-yl)-N,N-bis(4-methoxybenzyl)-2-(2-(4-methoxybenzyl)-2H-tetrazol-5-yl)benzenesulfonamide (Step A). LC/MS (M+1)$^+$=520.0, 522.0.

Step B: 4'-Hydroxy-2-(1-(4-methoxybenzyl)-1H-tetrazol-5-yl)-4-(trifluoromethyl)-2',3',4',5'-tetrahydro-[1,1'-biphenyl]-3-sulfonamide and 4'-hydroxy-2-(2-(4-methoxybenzyl)-2H-tetrazol-5-yl)-4-(trifluoromethyl)-2',3',4',5'-tetrahydro-[1,1'-biphenyl]-3-sulfonamide Trifluoromethyl(1,10-Phenanthroline)Copper (1.29 g, 4.11 mmol), 4-bromo-4'-hydroxy-2-(1-(4-methoxybenzyl)-1H-tetrazol-5-yl)-2',3',4',5'-tetrahydro-[1,1'-biphenyl]-3-sulfonamide and 4-bromo-4'-hydroxy-2-(2-(4-methoxybenzyl)-2H-tetrazol-5-yl)-2',3',4',5'-tetrahydro-[1,1'-biphenyl]-3-sulfonamide (1.07 g, 2.06 mmol), Copper(I) Iodide (0.783 g, 4.11 mmol) and DMF (20.56 mL) were added to a microwave vial. The reaction mixture was sealed, degassed, and heated at 80° C. overnight. After cooling to room temperature, the reaction mixture was loaded onto a silica gel column, eluting with 0-80% EtOAc/hexanes, to give the title compounds. LC/MS (M+1)$^+$=510.2

Step C: 3-(4-Hydroxycyclohexyl)-2-(1-(4-methoxybenzyl)-1H-tetrazol-5-yl)-6-(trifluoromethyl)benzenesulfonamide and 3-(4-hydroxycyclohexyl)-2-(2-(4-methoxybenzyl)-2H-tetrazol-5-yl)-6-(trifluoromethyl)benzenesulfonamide 4'-hydroxy-2-(1-(4-methoxybenzyl)-1H-tetrazol-5-yl)-4-(trifluoromethyl)-2',3',4',5'-tetrahydro-[1,1'-biphenyl]-3-sulfonamide and 4'-hydroxy-2-(2-(4-methoxybenzyl)-2H-tetrazol-5-yl)-4-(trifluoromethyl)-2',3',4',5'-tetrahydro-[1,1'-biphenyl]-3-sulfonamide (447 mg, 0.877 mmol) was dissolved in MeOH (2 mL) and Palladium Hydroxide on Carbon (616 mg, 0.877 mmol) was added. The mixture was stirred under hydrogen atmosphere overnight. The mixture was then filtered and the filtrates were concentrated to give the crude 3-(4-hydroxycyclohexyl)-2-(1-(4-methoxybenzyl)-1H-tetrazol-5-yl)-6-(trifluoromethyl)benzenesulfonamide and 3-(4-hydroxycyclohexyl)-2-(2-(4-methoxybenzyl)-2H-tetrazol-5-yl)-6-(trifluoromethyl)benzenesulfonamide. LC/MS (M+1)$^+$=512.1.

Step D: 3-((cis 4-Hydroxycyclohexyl)-2-(1H-tetrazol-5-yl)-6-(trifluoromethyl)benzenesulfonamide and 3-((trans 4-hydroxycyclohexyl)-2-(1H-tetrazol-5-yl)-6-(trifluoromethyl)benzenesulfonamide The crude 3-(4-hydroxycyclohexyl)-2-(1-(4-methoxybenzyl)-1H-tetrazol-5-yl)-6-(trifluoromethyl)benzenesulfonamide and 3-(4-hydroxycyclohexyl)-2-(2-(4-methoxybenzyl)-2H-tetrazol-5-yl)-6-(trifluoromethyl)benzenesulfonamide was treated with TFA at 80° C. for 3 hr. The reaction was concentrated after cooled to room temperature and the residue was purified with Gilson (3-100% CH$_3$CN/water with 0.1% TFA) to give the product as a mixture of trans/cis isomers, which were separated by SFC chiral separations (IC column, 15% MeOH with 0.1% NH$_4$OH/CO$_2$). LC/MS (M+1)$^+$=392.1.

EXAMPLE 497

3-(4-Amino-4-(aminomethyl)cyclohexyl)-2-(1H-tetrazol-5-yl)-6-(trifluoromethyl)benzenesulfonamide

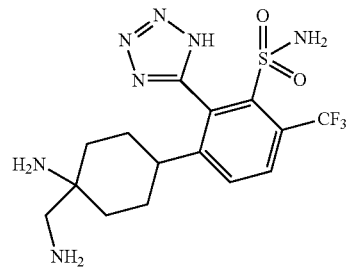 [SMILES: NCC1(N)CCC(c2ccc(C(F)(F)F)c(S(N)(=O)=O)c2-c2nnn[nH]2)CC1]

Step A: 4'-Hydroxy-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide and 4'-hydroxy-N,N-bis(4-methoxybenzyl)-2-(2-(4-methoxybenzyl)-2H-tetrazol-5-yl)-4-(trifluoromethyl)-2',3',4',5'-tetrahydro-[1,1'-biphenyl]-3-sulfonamide 4-(4,4,5,5-tetramethyl-1,3,2-dioxaborolan-2-yl)cyclohex-3-enol (1.2 g, 5.4 mmol), 3-bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide (2.5 g, 3.4 mmol), sodium carbonate (0.723 g, 6.83 mmol), PdCl$_2$(dppf) (0.250 g, 0.341 mmol) were placed in a reaction vessel. Dioxane (25.6 mL) and water (8.53 mL) were added. The reaction mixture was degassed for 20 min and then heated at 85° C. overnight. LC-MS showed the reaction was completed. The reaction was then diluted with water and extracted with EtOAc. The organics were combined, washed with brine, separated and concentrated and the residue was purified by column chromatography (0-100% EtOAc/Hexane) to give the title compounds. LC/MS (M+1)$^+$=750.6

Step B: 3-(4-Hydroxycyclohexyl)-N,N-bis(4-methoxybenzyl)-2-(1-(4-methoxybenzyl)-1H-tetrazol-5-yl)-6-(trifluoromethyl)benzenesulfonamide and 3-(4-hydroxycyclohexyl)-N,N-bis(4-methoxybenzyl)-2-(2-(4-methoxybenzyl)-2H-tetrazol-5-yl)-6-(trifluoromethyl)benzenesulfonamide 4'-Hydroxy-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide and 4'-hydroxy-N,N-bis(4-methoxybenzyl)-2-(2-(4-methoxybenzyl)-2H-tetrazol-5-yl)-4-(trifluoromethyl)-2',3',4',5'-tetrahydro-[1,1'-biphenyl]-3-sulfonamide (2.45 g, 3.27 mmol) was stirred with Palladium Hydroxide on Carbon (2.29 g, 3.27 mmol) under H$_2$ (balloon) overnight. The reaction mixture was filtered and the filtrates were concentrated to give the title compounds.

Step C: N,N-bis(4-Methoxybenzyl)-2-(1-(4-methoxybenzyl)-1H-tetrazol-5-yl)-3-(4-oxocyclohexyl)-6-(trifluoromethyl)benzenesulfonamide and N,N-bis(4-methoxybenzyl)-2-(2-(4-methoxybenzyl)-2H-tetrazol-5-yl)-3-(4-oxocyclohexyl)-6-(trifluoromethyl)benzenesulfonamide NMO (467 mg, 3.99 mmol) and 4A molecular sieves (160 mg) were added to a solution of 3-(4-hydroxycyclohexyl)-N,N-bis(4-methoxybenzyl)-2-(1-(4-methoxybenzyl)-1H-tetrazol-5-yl)-6-(trifluoromethyl)benzenesulfonamide and 3-(4-hydroxycyclohexyl)-N,N-bis(4-methoxybenzyl)-2-(2-(4-methoxybenzyl)-2H-tetrazol-5-yl)-6-(trifluoromethyl)benzenesulfonamide (2000 mg, 2.66 mmol) in CH$_2$Cl$_2$ (26 mL). The mixture was stirred at room temperature under N$_2$ for 0.5 hr, then TPAP (93 mg, 0.27 mmol) was added. The mixture was continued to stir at room temperature under N$_2$ for 1.5 hr, and then filtered. The filtrates were concentrated and the residue was purified by column chromatography (100% hexane to 70% EtOAc/Hexane) to give the title compounds. LC-MS (M+1)$^+$=750.6

Step D: 3-(4-Amino-4-cyanocyclohexyl)-N,N-bis(4-methoxybenzyl)-2-(1-(4-methoxybenzyl)-1H-tetrazol-5-yl)-6-(trifluoromethyl)benzenesulfonamide and 3-(4-amino-4-cyanocyclohexyl)-N,N-bis(4-methoxybenzyl)-2-(2-(4-methoxybenzyl)-2H-tetrazol-5-yl)-6-(trifluoromethyl)benzenesulfonamide N,N-bis(4-Methoxybenzyl)-2-(1-(4-methoxybenzyl)-1H-tetrazol-5-yl)-3-(4-oxocyclohexyl)-6-(trifluoromethyl)benzenesulfonamide and N,N-bis(4-methoxybenzyl)-2-(2-(4-methoxybenzyl)-2H-tetrazol-5-yl)-3-(4-oxocyclohexyl)-6-(trifluoromethyl)benzenesulfonamide (300 mg, 0.400 mmol) in conc NH$_4$OH/MeOH (1/1, 3 mL) was treated with KCN (52.1 mg, 0.800 mmol) and Ammonium Chloride (86 mg, 1.6 mmol). The mixture was heated in a sealed reaction vessel overnight. After cooling to rt, the reaction mixture was partitioned between EtOAc and water. The organic layer was separated and concentrated. The residue was purified by column chromatography (0-80% EtOAc/Hexane) to give the title compounds. LC/MS (M+1)$^+$=776.6.

Step E: 3-(4-Amino-4-(aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-amino-4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide 3-(4-Amino-4-cyanocyclohexyl)-N,N-bis(4-methoxybenzyl)-2-(1-(4-methoxybenzyl)-1H-tetrazol-5-yl)-6-(trifluoromethyl)benzenesulfonamide and 3-(4-amino-4-cyanocyclohexyl)-N,N-bis(4-methoxybenzyl)-2-(2-(4-methoxybenzyl)-2H-tetrazol-5-yl)-6-(trifluoromethyl)benzenesulfonamide (222 mg, 0.286 mmol) was dissolved in acetic acid (1.5 mL), EtOH (1 mL), and DCM (2 mL). Platinum(IV) Oxide (38 mg, 0.167 mmol) was added. The mixture was hydrogenated using a par shaker (40 psi) overnight. LC-MS showed the completion of the reaction. The reaction mixture was filtered and the filtrates were concentrated to give the crude title compounds, which were used directly in the next step. LC/MS (M+1)$^+$=780.7.

Step F: 3-(4-Amino-4-(aminomethyl)cyclohexyl)-2-(1H-tetrazol-5-yl)-6-(trifluoromethyl)benzenesulfonamide 3-(4-Amino-4-(aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-amino-4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide (223 mg, 0.286 mmol) was heated in TFA at 60° C. for 2 hr. The reaction mixture was concentrated and the residue purified with Gilson (2-45% CH$_3$CN/water with 0.1% TFA) to afford 3-(4-amino-4-(aminomethyl)cyclohexyl)-2-(1H-tetrazol-5-yl)-6-(trifluoromethyl)benzenesulfonamide. LC/MS (M+1)$^+$=420.3.

EXAMPLE 498 and 499

3-(cis 4-(2-aminoethyl)cyclohexyl)-2-(1H-tetrazol-5-yl)-6-(trifluoromethyl)benzenesulfonamide and 3-(trans 4-(2-aminoethyl)cyclohexyl)-2-(1H-tetrazol-5-yl)-6-(trifluoromethyl)benzenesulfonamide

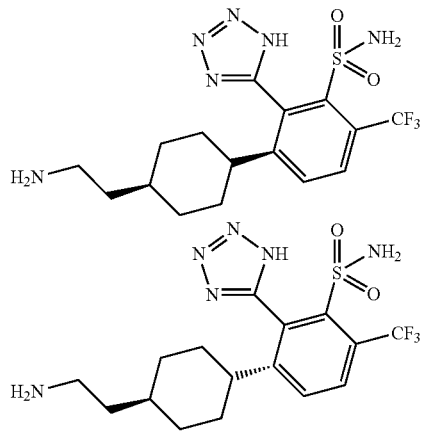

Step A: 3-(4-(Cyanomethylene)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(cyanomethylene)cyclohexyl)-N,N-bis(4-methoxybenzyl)-2-(2-(4-methoxybenzyl)-2H-tetrazol-5-yl)-6-(trifluoromethyl)benzenesulfonamide To a solution of Potassium Tert-Butoxide (2.8 mL, 2.80 mmol) in THF (0.8 mL) was added Diethyl Cyanomethylphosphonate (500 mg, 2.82 mmol) in THF (0.5 mL). The resulting pale yellow solution was aged for 60 min and a solution of N,N-bis(4-methoxybenzyl)-2-(1-(4-methoxybenzyl)-1H-tetrazol-5-yl)-3-(4-oxocyclohexyl)-6-(trifluoromethyl)benzenesulfonamide and N,N-bis(4-methoxybenzyl)-2-(2-(4-methoxybenzyl)-2H-tetrazol-5-yl)-3-(4-oxocyclohexyl)-6-(trifluoromethyl)benzenesulfonamide (300 mg, 0.400 mmol) in THF (3 mL) was added while maintaining the temp at 0° C. The reaction turned yellow thick solution during the addition. The reaction was allowed to warm up to rt and stirred overnight. Ether and water were added, and the layers were separated. The product was extracted from water layer twice with ether. The combined organic extracts were dried over $Na_2SO_4$, filtered, and concentrated. The resulting residue was purified by column chromatography (0-50% EtOAc/Hexane) to give the title compounds. LC/MS $(M+1)^+=773.7$.

Step B: 3-(4-(2-Aminoethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(2-aminoethyl)cyclohexyl)-N,N-bis(4-methoxybenzyl)-2-(2-(4-methoxybenzyl)-2H-tetrazol-5-yl)-6-(trifluoromethyl)benzenesulfonamide 3-(4-(Cyanomethylene)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(cyanomethylene)cyclohexyl)-N,N-bis(4-methoxybenzyl)-2-(2-(4-methoxybenzyl)-2H-tetrazol-5-yl)-6-(trifluoromethyl)benzenesulfonamide (257 mg, 0.333 mmol) was hydrogenated with Pd—C (354 mg, 0.333 mmol) with a $H_2$ balloon overnight. The reaction mixture was filtered and the filtrates were concentrated to give an crude oil, which was dissolved in 1.5 mL of acetic acid, 1 mL of EtOH, and 2 mL of DCM. Platinum(IV) Oxide (53 mg, 0.233 mmol) was added. The mixture was hydrogenated with a par shaker (40 psi) overnight. LC-MS showed the completion of the reaction. The reaction was filtered and the filtrates were concentrated to give the crude products. LC/MS $(M+1)^+=779.8$ Step C: 3-(cis 4-(2-Aminoethyl)cyclohexyl)-2-(1H-tetrazol-5-yl)-6-(trifluoromethyl)benzenesulfonamide and 3-(trans 4-(2-aminoethyl)cyclohexyl)-2-(1H-tetrazol-5-yl)-6-(trifluoromethyl)benzenesulfonamide 3-(4-(2-Aminoethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(2-aminoethyl)cyclohexyl)-N,N-bis(4-methoxybenzyl)-2-(2-(4-methoxybenzyl)-2H-tetrazol-5-yl)-6-(trifluoromethyl)benzenesulfonamide (238 mg, 0.306 mmol) was heated in TFA (4 mL) at 60° C. for 2 hr. After cooling to room temperature, the reaction mixture was concentrated and the residue was dissolved in DMSO (5 mL, 1 mL per injection) and purified with Gilson (2-52% $CH_3CN$/water with 0.1% TFA, 15 min gradient time). The correct fractions were combined, concentrated and lypholized to give 3-(cis 4-(2-aminoethyl)cyclohexyl)-2-(1H-tetrazol-5-yl)-6-(trifluoromethyl)benzenesulfonamide LC/MS $(M+1)^+=419.5$; and 3-(trans 4-(2-aminoethyl)cyclohexyl)-2-(1H-tetrazol-5-yl)-6-(trifluoromethyl)benzenesulfonamide. LC/MS $(M+1)^+=419.5$ EXAMPLES 500 and 501

3-(cis 4-(Aminomethyl)cyclohexyl)-2-(1H-tetrazol-5-yl)-6-(trifluoromethyl)benzenesulfonamide and 3-(trans 4-(aminomethyl)cyclohexyl)-2-(1H-tetrazol-5-yl)-6-(trifluoromethyl)benzenesulfonamide

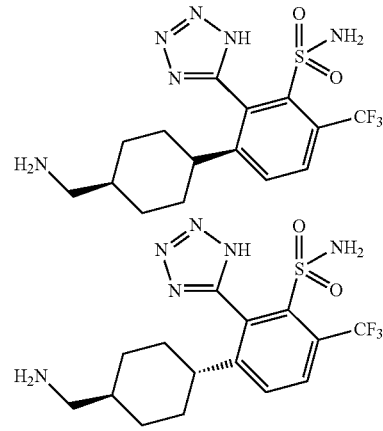

Step A: 4'-Cyano-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide and 4'-cyano-N,N-bis(4-methoxybenzyl)-2-(2-(4-methoxybenzyl)-2H-tetrazol-5-yl)-4-(trifluoromethyl)-2',3',4',5'-tetrahydro-[1,1'-biphenyl]-3-sulfonamide 3-Bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide (1500 mg, 2.048 mmol), 4-(4,4,5,5-tetramethyl-1,3,2-dioxaborolan-2-yl)cyclohex-3-enecarbonitrile (716 mg, 3.07 mmol), $PdCl_2(dppf)$ (150 mg, 0.205 mmol) and sodium carbonate (434 mg, 4.10 mmol) were placed in a reaction vial. Dioxane (1.54E+04 μL) and Water (5119 μL) were added. The reaction was sealed and degassed and heated at 80° C. over a weekend. The reaction mixture was purified by column chromatography (0-60% EtOAc/Hexane) to give the title compounds. LC/MS $(M+1)^+=759.5$ Step B: 3-(4-(Aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide 4'-Cyano-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide and 4'-cyano-N,N-bis(4-methoxybenzyl)-2-(2-(4-methoxybenzyl)-2H-tetrazol-5-yl)-4-(trifluoromethyl)-2',3',4',5'-tetrahydro-[1,1'-biphenyl]-3-sulfonamide (1.2 g, 1.581 mmol) was hydrogenated with $Pd(OH)_2$ (1.4 g) as the catalyst at 46 psi for 36 hr. LC-MS showed cyclohexene was reduced, and some of which the CN group was also reduced. The two types of the products were separated with a SCX cartridge to afford 3-(4-cyanocyclohexyl)-N,N-bis(4-methoxybenzyl)-2-(1-(4-methoxybenzyl)-1H-tetrazol-5-yl)-6-(trifluoromethyl)benzenesulfonamide and 3-(4-cyanocyclohexyl)-N,N-bis(4-methoxybenzyl)-2-(2-(4-methoxybenzyl)-2H- tetrazol-5-yl)-6-(trifluoromethyl)benzenesulfonamide, LC/MS (M+1)⁺=761.7; 3-(4-(aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide. LC/MS (M+1)⁺=765.9

Step C: 3-(cis-4-(Aminomethyl)cyclohexyl)-2-(1H-tetrazol-5-yl)-6-(trifluoromethyl)benzenesulfonamide and 3-(trans 4-(aminomethyl)cyclohexyl)-2-(1H-tetrazol-5-yl)-6-(trifluoromethyl)benzenesulfonamide 3-(4-(Aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide (310 mg, 0.405 mmol) was heated in TFA (3000 µL, 38.9 mmol) at 60° C. for 2 hr. After cooling to room temperature, the reaction mixture was concentrated and the residue was purified with Gilson (3-50% CH₃CN/water with 0.1% TFA) to afford the title compounds. LC/MS (M+1)⁺=405.4 for both isomers.

EXAMPLES 502 and 503

3-(cis 4-(guanidinomethyl)cyclohexyl)-2-(1H-tetrazol-5-yl)-6-(trifluoromethyl)benzenesulfonamide and 3-(trans 4-(guanidinomethyl)cyclohexyl)-2-(1H-tetrazol-5-yl)-6-(trifluoromethyl)benzenesulfonamide

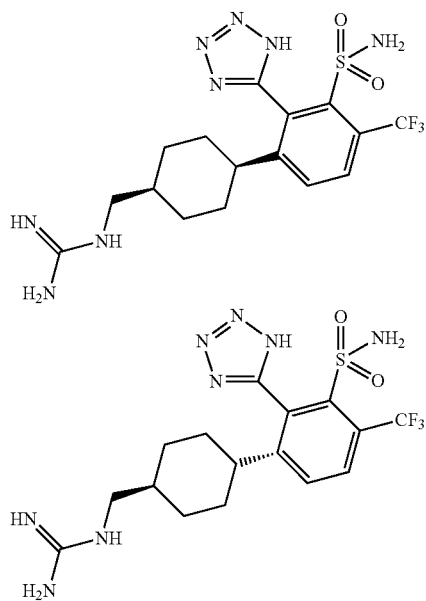

Step A: 3-(4-(Guanidinomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(guanidinomethyl)cyclohexyl)-N,N-bis(4-methoxybenzyl)-2-(2-(4-methoxybenzyl)-2H-tetrazol-5-yl)-6-(trifluoromethyl)benzenesulfonamide 3-(4-(Aminomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(aminomethyl)cyclohexyl)-N,N-bis(4-methoxybenzyl)-2-(2-(4-methoxybenzyl)-2H-tetrazol-5-yl)-6-(trifluoromethyl)benzenesulfonamide (135 mg, 0.177 mmol) was dissolved in THF (2 mL), to which, was added 1H-Pyrazole-1-Carboxamidine Hydrochloride (150 mg, 1.023 mmol), and DIEA (250 µL, 1.431 mmol). The mixture was stirred at room temperature under N₂ for 48 hr. The reaction mixture was diluted with DCM and washed with a small amount of water. The oragnics were filtered through a pad of Na₂SO₄. The filtrates were concentrated to give the crude title compounds which were used directly in the next step.

Step B: 3-(cis 4-(guanidinomethyl)cyclohexyl)-2-(1H-tetrazol-5-yl)-6-(trifluoromethyl)benzenesulfonamide and 3-(trans 4-(guanidinomethyl)cyclohexyl)-2-(1H-tetrazol-5-yl)-6-(trifluoromethyl)benzenesulfonamide The crude 3-(4-(guanidinomethyl)cyclohexyl)-N,N-bis(4-methoxybenzyl)-2-(1-(4-methoxybenzyl)-1H-tetrazol-5-yl)-6-(trifluoromethyl)benzenesulfonamide and 3-(4-(guanidinomethyl)cyclohexyl)-N,N-bis(4-methoxybenzyl)-2-(2-(4-methoxybenzyl)-2H-tetrazol-5-yl)-6-(trifluoromethyl)benzenesulfonamide was heated in TFA (2 mL) at 60° C. for 2 hr. After being cooled to room temperature, the reaction was concentrated to remove TFA and the residue was purified with Gilson (2-52% CH₃CN/water with 0.1% TFA). The correct fractions were combined, concentrated and lypholized to afford 3-(cis 4-(guanidinomethyl)cyclohexyl)-2-(1H-tetrazol-5-yl)-6-(trifluoromethyl)benzenesulfonamide and 3-(trans 4-(guanidinomethyl)cyclohexyl)-2-(1H-tetrazol-5-yl)-6-(trifluoromethyl)benzenesulfonamide. LC/MS (M+1)⁺=447.5 for both isomers.

EXAMPLE 504

4-(3-Sulfamoyl-2-(1H-tetrazol-5-yl)-4-(trifluoromethyl)phenyl)cyclohexane-1-carboximidamide

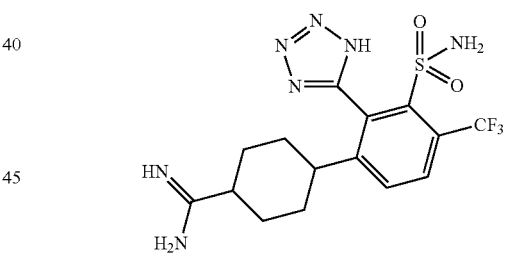

Step A: 4-(3-(N,N-Bis(4-methoxybenzyl)sulfamoyl)-2-(1-(4-methoxybenzyl)-1H-tetrazol-5-yl)-4-(trifluoromethyl)phenyl)-N-hydroxycyclohexane-1-carboximidamide and 4-(3-(N,N-bis(4-methoxybenzyl)sulfamoyl)-2-(2-(4-methoxybenzyl)-2H-tetrazol-5-yl)-4-(trifluoromethyl)phenyl)-N-hydroxycyclohexane-1-carboximidamide 4'-Cyano-N,N-bis(4-methoxybenzyl)-2-(1-(4-methoxybenzyl)-1H-tetrazol-5-yl)-4-(trifluoromethyl)-2',3',4',5'-tetrahydro-[1,1'-biphenyl]-3-sulfonamide and 4'-cyano-N,N-bis(4-methoxybenzyl)-2-(2-(4-methoxybenzyl)-2H-tetrazol-5-yl)-4-(trifluoromethyl)-2',3',4',5'-tetrahydro-[1,1'-biphenyl]-3-sulfonamide (0.376 g, 0.496 mmol) were placed in a flask and EtOH (5 mL) and then THF (5 mL) were added. Hydroxylamine (0.607 mL, 9.91 mmol) was added. It was observed that some solid precipitated out. DMF (2 mL) was then added. The reaction was heated at 80° C. with a relux condenser under N₂ overnight. The reaction mixture was concentrated and the residue was purified by column chromatography (0-10% MeOH/EtOAc) to give the title compounds. LC/MS (M+1)⁺=792.6

Step B: 4-(3-(N,N-Bis(4-Methoxybenzyl)sulfamoyl)-2-(1-(4-methoxybenzyl)-1H-tetrazol-5-yl)-4-(trifluoromethyl) phenyl)cyclohexane-1-carboximidamide and 4-(3-(N,N-bis (4-methoxybenzyl)sulfamoyl)-2-(2-(4-methoxybenzyl)-2H-tetrazol-5-yl)-4-(trifluoromethyl)phenyl)cyclohexane-1-carboximidamide 4-(3-(N,N-Bis(4-methoxybenzyl)sulfamoyl)-2-(1-(4-methoxybenzyl)-1H-tetrazol-5-yl)-4-(trifluoromethyl)phenyl)-N-hydroxycyclohexane-1-carboximidamide and 4-(3-(N,N-bis(4-methoxybenzyl)sulfamoyl)-2-(2-(4-methoxybenzyl)-2H-tetrazol-5-yl)-4-(trifluoromethyl) phenyl)-N-hydroxycyclohexane-1-carboximidamide (183 mg, 0.231 mmol) were dissolved in AcOH (1156 μL), to which solution, was added Ammonium Formate (146 mg, 2.31 mmol), and Pd—C (100 mg, 0.094 mmol). The reaction mixture was heated at 120° C. for 12 hr. Additional amount of ammonium formate was added and heating was continued at 120° C. for 3 hr until LC-MS analysis showed that the starting material was consumed. The reaction mixture was cooled and concentrated. The residue was partitioned between saturated NaHCO₃ aqueous solution and DCM. The organics were separated, washed with brine, dried (Na₂SO₄), filtered and concentrated. The residue was purified by column chromatography (0-10% MeOH/EtOAc) to give the title compounds. LC/MS (M+1)⁺=777.6

Step C: 4-(3-Sulfamoyl-2-(1H-tetrazol-5-yl)-4-(trifluoromethyl)phenyl)cyclohexane-1-carboximidamide 4-(3-(N,N-bis(4-methoxybenzyl)sulfamoyl)-2-(1-(4-methoxybenzyl)-1H-tetrazol-5-yl)-4-(trifluoromethyl)phenyl)cyclohexanecarboximidamide and 4-(3-(N,N-bis(4-methoxybenzyl)sulfamoyl)-2-(2-(4-methoxybenzyl)-2H-tetrazol-5-yl)-4-(trifluoromethyl)phenyl)cyclohexane-1-carboximidamide (27 mg, 0.035 mmol) was heated in TFA at 60° C. for 2 hr. The reaction mixture was concentrated and the residue was dissolved in DMSO and purified with Gilson (2-80% CH₃CN/water with 0.1% TFA). The correct fractions were combined and lyophilized to give 4-(3-Sulfamoyl-2-(1H-tetrazol-5-yl)-4-(trifluoromethyl)phenyl)cyclohexane-1-carboximidamide. LC/MS (M+1)⁺=417.2.

EXAMPLES 505 and 506 cis and trans 3-(cis 4-(4,5-dihydro-1H-imidazol-2-yl)cyclohexyl)-2-(1H-tetrazol-5-yl)-6-(trifluoromethyl)benzenesulfonamide and 3-(trans 4-(4,5-dihydro-1H-imidazol-2-yl)cyclohexyl)-2-(1H-tetrazol-5-yl)-6-(trifluoromethyl)benzenesulfonamide

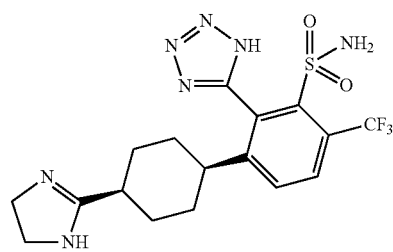

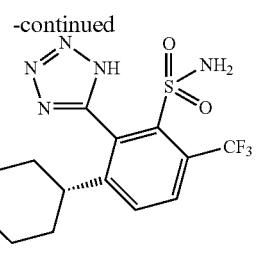

3-(4-Cyanocyclohexyl)-N,N-bis(4-methoxybenzyl)-2-(1-(4-methoxybenzyl)-1H-tetrazol-5-yl)-6-(trifluoromethyl) benzenesulfonamide and 3-(4-cyanocyclohexyl)-N,N-bis(4-methoxybenzyl)-2-(2-(4-methoxybenzyl)-2H-tetrazol-5-yl)-6-(trifluoromethyl)benzenesulfonamide (197 mg, 0.259 mmol) was dissolved in MeOH (2589 μL) and cooled to 0° C. The reaction mixture was saturated with HCl gas and then sealed. The mixture was stirred at 0° C. and warmed up to room temperature overnight. The mixture was concentrated to give the crude oil. This crude oil (0.205 g, 0.259 mmol) was dissolved in MeOH (2 mL), and treated with tert-butyl (2-aminoethyl)carbamate (0.041 g, 0.259 mmol) and DIEA (0.045 mL, 0.259 mmol). The mixture was stirred at room temperature overnight, and then concentrated to give an oil, which was dissolved in TFA (2 mL) and stirred at room temperature for 2 hr. LC-MS showed the boc group was removed. The reaction mixture was concentrated and stripped with toluene/MeOH several times. TFA (4 mL) and Anisole (0.283 ml, 2.59 mmol) were added to the residue and heated at 60° C. for 2 hr. After cooling, the reaction mixture was concentrated to remove TFA. The residue was taken up in DMSO and purified with Gilson (2-45% CH₃CN/water) with 0.1% TFA. The fractions for fast moving isomer and slow moving isomer were combined and concentrated respectively, neutralized with SCX cartridges, then lyophilized. LC/MS (M+1)⁺=444.4 for fast moving isomer; LC/MS (M+1)⁺=444.3 for slow moving isomer.

EXAMPLE 507

3-((6-Amino-5-(hydroxymethyl)pyridin-3-yl)ethynyl)-2-(2H-tetrazol-5-yl)-6-(trifluoromethyl)benzenesulfonamide

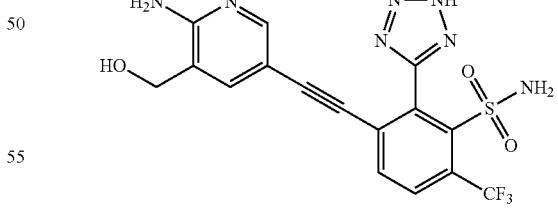

Step A: N,N-Bis(4-methoxybenzyl)-2-(2-(4-methoxybenzyl)-2H-tetrazol-5-yl)-6-(trifluoromethyl)-3-((trimethylsilyl)ethynyl)benzenesulfonamide and N,N-bis(4-methoxybenzyl)-2-(1-(4-methoxybenzyl)-1H-tetrazol-5-yl)-6-(trifluoromethyl)-3-((trimethylsilyl)ethynyl) benzenesulfonamide 3-Bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4- methoxybenzyl)-1H-tetrazol-5-yl)-6-(trifluoromethyl) benzenesulfonamide (1.00 g, 1.37 mmol) was combined with Pd(PPh₃)₄ (0.137 mmol), ethynyltrimethylsilane (4.11 mmol), triethylamine (6.85 mmol) and CuI (0.274 mmol) in dioxane (20 mL) was stirred at 80° C. under nitrogen for 16 hr. The reaction was quenched by brine (2 mL) and extracted with ethyl acetate (3×6 mL). The combined organic layers were washed with brine (6 mL). The solution was dried over anhydrous Na₂SO₄, filtered and concentrated under reduced pressure to give a residue, which was purified by a silica gel column to afford title compounds. LC/MS [M+H]⁺: 750.35

Step B: 3-Ethynyl-N,N-bis(4-methoxybenzyl)-2-(2-(4-methoxybenzyl)-2H-tetrazol-5-yl)-6-(trifluoromethyl)benzenesulfonamide and 3-ethynyl-N,N-bis(4-methoxybenzyl)-2-(1-(4-methoxybenzyl)-1H-tetrazol-5-yl)-6-(trifluoromethyl)benzenesulfonamide Sodium carbonate (274 mg, 2.59 mmol) was added to a rapidly stirred solution of N,N-bis(4-methoxybenzyl)-2-(2-(4-methoxybenzyl)-2H-tetrazol-5-yl)-6-(trifluoromethyl)-3-((trimethylsilyl)ethynyl)benzenesulfonamide and N,N-bis(4-methoxybenzyl)-2-(1-(4-methoxybenzyl)-1H-tetrazol-5-yl)-6-(trifluoromethyl)-3-((trimethylsilyl)ethynyl) benzenesulfonamide (970 mg, 1.294 mmol) in methanol (15 mL) at room temperature. The mixture and was stirred for 90 min. After this time the reaction was poured into water (10 mL) and extracted with diethyl ether (2×30 mL). The organic phase was washed with saturated brine (20 mL), dried (Na₂SO₄), filtered and concentrated in vacuo. The material was used without further purification. LC/MS [M+H]⁺: 678.33.

Step C: 3-((6-Amino-5-(hydroxymethyl)pyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)-6-(trifluoromethyl)benzenesulfonamide A solution of 3-ethynyl-N,N-bis(4-methoxybenzyl)-2-(2-(4-methoxybenzyl)-2H-tetrazol-5-yl)-6-(trifluoromethyl) benzenesulfonamide and 3-ethynyl-N,N-bis(4-methoxybenzyl)-2-(1-(4-methoxybenzyl)-1H-tetrazol-5-yl)-6-(trifluoromethyl)benzenesulfonamide (300 mg, 0.443 mmol), (2-amino-5-iodopyridin-3-yl)methanol (133 mg, 0.531 mmol), Pd(PPh₃)₄ (0.044 mmol), TEA (2.66 mmol), and CuI (0.044 mmol) in THF (5 mL) was stirred for 4 hr at 80° C. under a nitrogen atmosphere. The reaction was quenched by brine (15 mL), extracted with ethyl acetate (3×30 mL). The combined organic layers were washed with brine (30 mL), dried over anhydrous Na₂SO₄, filtered, and concentrated under reduced pressure to give a residue, which was purified by a silica gel column to isolate title compounds. LC/MS [M+H]⁺: 800.37.

Step D: 3-((6-Amino-5-(hydroxymethyl)pyridin-3-yl)ethynyl)-2-(2H-tetrazol-5-yl)-6-(trifluoromethyl)benzenesulfonamide To a solution of 3-((6-amino-5-(hydroxymethyl)pyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)-6-(trifluoromethyl) benzenesulfonamide (100 mg, 0.125 mmol) in DCM (4 mL) was added TFA (12.5 mmol) and anisole (1.25 mmol). The reaction mixture was heated at 80° C. for 1 hr. After removing the volatile the residue was purified by HPLC and then lyophilized to give the title compound. LC/MS [M+H]⁺: 440.16.

EXAMPLE 508

3-(2-(6-Amino-5-(hydroxymethyl)pyridin-3-yl) ethyl)-2-(2H-tetrazol-5-yl)-6-(trifluoromethyl)benzenesulfonamide

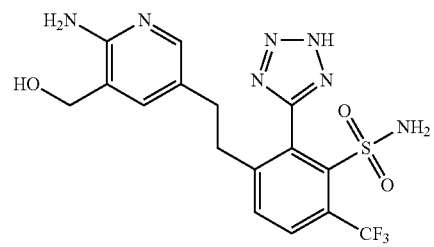 [SMILES: Nc1ncc(CCc2ccc(C(F)(F)F)c(S(N)(=O)=O)c2-c2nn[nH]n2)cc1CO]

Step A: 3-(2-(6-Amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide and 3-(2-(6-amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide 3-((6-Amino-5-(hydroxymethyl)pyridin-3-yl)ethynyl)-N,N-bis(4-methoxybenzyl)-2-(2-(4-methoxybenzyl)-2H-tetrazol-5-yl)-6-(trifluoromethyl)benzenesulfonamide and 3-((6-amino-5-(hydroxymethyl)pyridin-3-yl)ethynyl)-N,N-bis(4-methoxybenzyl)-2-(1-(4-methoxybenzyl)-1H-tetrazol-5-yl)-6-(trifluoromethyl)benzenesulfonamide (1000 mg, 1.250 mmol) and platinum(IV) oxide (142 mg, 0.625 mmol) in AcOH (20 mL) were stirred under a hydrogen atmosphere for 16 hr. The solution was filtered through celite and then concentrated and the title compounds were used without further purification. LC/MS [M+H]⁺: 804.48

Step B: 3-(2-(6-Amino-5-(hydroxymethyl)pyridin-3-yl) ethyl)-2-(2H-tetrazol-5-yl)-6-(trifluoromethyl)benzenesulfonamide 3-(2-(6-Amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide and 3-(2-(6-amino-5-(hydroxymethyl)pyridin-3-yl)ethyl)-N,N-bis(4-methoxybenzyl)-2-(2-(4-methoxybenzyl)-2H-tetrazol-5-yl)-6-(trifluoromethyl)benzenesulfonamide were deprotected in the same fashion as in the preceding EXAMPLE with TFA and anisole (1.25 mmol) at 80° C. for 1 hr. After removing the volatiles the residue was purified by HPLC and then lyophilized to give the title compound. LC/MS [M+H]⁺: 444.20.

EXAMPLE 509

4'-(1,3-Diaminopropan-2-yl)-2-(1H-tetrazol-5-yl)-[1,1'-biphenyl]-3-sulfonamide

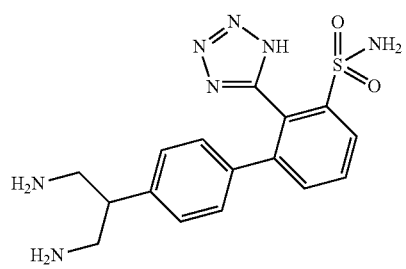 [SMILES: NCC(CN)c1ccc(-c2cccc(S(N)(=O)=O)c2-c2nnn[nH]2)cc1]

Step A: diethyl 2-(3'-(N,N-bis(4-methoxybenzyl)sulfamoyl)-2'-(1-(4-methoxybenzyl)-1H-tetrazol-5-yl)-[1,1'-biphenyl]-4-yl)malonate and diethyl 2-(3'-(N,N-bis(4-methoxybenzyl)sulfamoyl)-2'-(2-(4-methoxybenzyl)-2H-tetrazol-5-yl)-[1,1'-biphenyl]-4-yl)malonate 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide (1000 mg, 1.433 mmol), Xphos precatalyst G2 (169 mg, 0.215 mmol), diethyl 2-(4-bromophenyl)malonate (452 mg, 1.43 mmol), and cesium carbonate (1400 mg, 4.30 mmol) were placed into a microwave vial. Dioxane (1.15E+04 μL) and Water (2867 μL) were added. The mixture was degassed for 15 min and then heated at 85° C. overnight. The reaction mixture was loaded onto a 80 g ESCO column and eluted with 0-50% EtOAc/hexane to give the title compounds. LC/MS (M+1)$^+$=820.8

Step B: 4'-(1,3-Dihydroxypropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-dihydroxypropan-2-yl)-N,N-bis(4-methoxybenzyl)-2-(2-(4-methoxybenzyl)-2H-tetrazol-5-yl)-[1,1'-biphenyl]-3-sulfonamide Diethyl 243'-(N,N-bis(4-methoxybenzyl)sulfamoyl)-2'-(1-(4-methoxybenzyl)-1H-tetrazol-5-yl)-[1,1'-biphenyl]-4-yl)malonate and diethyl 2-(3'-(N,N-bis(4-methoxybenzyl)sulfamoyl)-2'-(2-(4-methoxybenzyl)-2H-tetrazol-5-yl)-[1,1'-biphenyl]-4-yl)malonate (1.03 g, 1.26 mmol) was dissolved in THF (10 mL), cooled to −78° C. Under $N_2$, DIBAL-H (6.28 mL, 6.28 mmol) was added dropwise. The reaction mixture was allowed to warm up to room temperature overnight. The reaction was quenched by adding $NH_4Cl$ aqueous solution. Celite was added to the reaction mixture and the resulting mixture was stirred at room temperature for 30 min. The mixture was filtered. The filtrates were concentrated and the residue was purified by column chromatography (0-100% EtOAc/hexane) to give the title compounds. LC/MS (M+1)$^+$=736.7

Step C: 4'-(1,3-Diazidopropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-diazidopropan-2-yl)-N,N-bis(4-methoxybenzyl)-2-(2-(4-methoxybenzyl)-2H-tetrazol-5-yl)-[1,1'-biphenyl]-3-sulfonamide 4'-(1,3-dihydroxypropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-dihydroxypropan-2-yl)-N,N-bis(4-methoxybenzyl)-2-(2-(4-methoxybenzyl)-2H-tetrazol-5-yl)-[1,1'-biphenyl]-3-sulfonamide (167 mg, 0.227 mmol) was dissolved in DCM (3 mL), at 0° C., DIEA (198 μL, 1.14 mmol) was added followed by methanesulfonyl chloride (53.1 μL, 0.681 mmol) dropwise. The reaction mixture was warmed to room temperature overnight. The reaction mixture was partitioned between DCM and $NaHCO_3$. The organics were washed with brine, dried over $Na_2SO_4$, filtered and concentrated to give a crude product. This crude product (202 mg, 0.227 mmol) was dissolved in DMF (2270 μl). Sodium Azide (44.3 mg, 0.681 mmol) was added. The mixture was heated at 70° C. overnight. LC-MS showed the reaction was completed. The reaction mixture was diluted with ether and washed with water. The organics were concentrated and purified by column chromatography (0-50% EtOAc/Hexane) to give the title compounds. LC/MS (M+1)$^+$=786.8.

Step D: 4'-(1,3-Diaminopropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-diaminopropan-2-yl)-N,N-bis(4-methoxybenzyl)-2-(2-(4-methoxybenzyl)-2H-tetrazol-5-yl)-[1,1'-biphenyl]-3-sulfonamide 4'-(1,3-Diazidopropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-diazidopropan-2-yl)-N,N-bis(4-methoxybenzyl)-2-(2-(4-methoxybenzyl)-2H-tetrazol-5-yl)-[1,1'-biphenyl]-3-sulfonamide (130 mg, 0.165 mmol) was dissolved in DCM (1 mL) and MeOH (1 mL). Pd—C (56 mg, 0.526 mmol) was added and the reaction mixture was stirred under an atmosphere of hydrogen for 2 hr. The reaction mixture was filtered and the filtrates were concentrated to give the title compounds, which were used directly in the next step. LC-MS (M+1)$^+$=734.9

Step E: 4'-(1,3-Diaminopropan-2-yl)-2-(1H-tetrazol-5-yl)-[1,1'-biphenyl]-3-sulfonamide 4'-(1,3-Diaminopropan-2-yl)-N,N-bis(4-methoxybenzyl)-2-(1-(4-methoxybenzyl)-1H-tetrazol-5-yl)-[1,1'-biphenyl]-3-sulfonamide and 4'-(1,3-diaminopropan-2-yl)-N,N-bis(4-methoxybenzyl)-2-(2-(4-methoxybenzyl)-2H-tetrazol-5-yl)-[1,1'-biphenyl]-3-sulfonamide (121 mg, 0.165 mmol) were heated at 60° C. for 3 hr. The reaction mixture was cooled and concentrated. The residue was purified with Gilson 3-45% $CH_3CN$/water with 0.1% TFA to give 4'-(1,3-diaminopropan-2-yl)-2-(1H-tetrazol-5-yl)-[1,1'-biphenyl]-3-sulfonamide. LC/MS (M+1)+=374.4

EXAMPLE 510

4-(3-Sulfamoyl-2-(1H-tetrazol-5-yl)-4-(trifluoromethyl)phenyl)-4,5,6,7-tetrahydrobenzo[d]thiazole-2-carboxylic acid

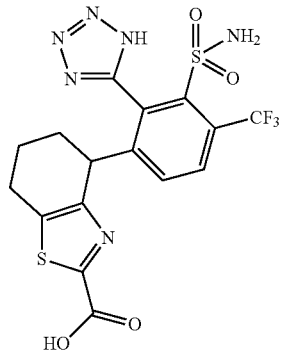 [SMILES: NS(=O)(=O)c1c(C(F)(F)F)ccc(C2CCCc3sc(C(=O)O)nc32)c1-c1nnn[nH]1]

Step A: Ethyl 4-oxo-4,5,6,7-tetrahydrobenzo[d]thiazole-2-carboxylate

Bromine (2.32 g, 14.5 mmol) was added dropwise to a solution of cyclohexane-1,2-dione (1.63 g, 14.5 mmol) in diethyl ether (14.5 mL) at 0° C. over 10 min. When the addition was complete, the reaction was allowed to come to room temperature and stirred for 15 min. The reaction mixture was concentrated in vacuo. The resulting dark oil was dissolved in DCM and purified by column chromatography (100% DCM) to give a yellow solid, which was triturated in a small amount of ether. Filtration gave an off white solid. The mother liquid was purified again with column chromatography eluting with 0-30% EtOAc/hexane to give a pale yellow solid. Two batches of solid were combined to give 3-bromocyclohexane-1,2-dione. This 3-bromocyclohexane-1,2-dione (1399 mg, 7.32 mmol) and ethyl 2-amino-2-thioxoacetate (650 mg, 4.88 mmol) were added to ethanol (1.63E+04 μL) and the mixture was heated at 80° C. in a sealed tube overnight. LC-MS indicated this reaction was a very clean conversion. After being cooled to room temperature, the reaction mixture was purified with an 80 g ISCO column with solid loading and eluted with 0-5% MeOH/EtOAc. The correct fractions combined and concentrated to give ethyl 4-oxo-4,5,6,7-tetrahydrobenzo[d]thiazole-2-carboxylate. LC/MS (M+1)⁺=226.0

Step B: (2-(Ethoxycarbonyl)-6,7-dihydrobenzo[d]thiazol-4-yl)boronic acid

Ethyl 4-oxo-4,5,6,7-tetrahydrobenzo[d]thiazole-2-carboxylate (627 mg, 2.78 mmol) was dissolved in THF (15 mL), and under N₂, NaHMDS (3618 µl, 3.62 mmol) was added at −78° C., dropwise. The resulting mixture was kept stirring at this temperature for 1 hr, and N,N-Bis(Trifluoromethylsulfonyl)Aniline (1392 mg, 3.90 mmol) was added. The reaction was stirred at −78° C. for 1 hr, and then the reaction mixture was allowed to warm up gradually to room temperature. The reaction mixture was concentrated and purified by column chromatography (0-40% EtOAc/hexane) to give ethyl 4-(((trifluoromethyl)sulfonyl)oxy)-6,7-dihydrobenzo[d]thiazole-2-carboxylate. In the reaction vessel was placed ethyl 4-(((trifluoromethyl)sulfonyl)oxy)-6,7-dihydrobenzo[d]thiazole-2-carboxylate (198 mg, 0.554 mmol), 4,4,4',4',5,5,5',5'-octamethyl-2,2'-bi(1,3,2-dioxaborolane) (422 mg, 1.66 mmol), potassium acetate (163 mg, 1.66 mmol) and PCy3 Pd G2 (33 mg, 0.055 mmol). Then dry dioxane (2.18E+04 µL) was added to this flask. This mixture was degassed and then heated at 80° C. for 12 hr. LC-MS showed the desired mass. The mixture was cooled, filtered and concentrated. The resulting residue was purified by column chromatography on silica gel (120 g), eluting first with 0-100% then with 0-30% MeOH/EtOAc to give the desired product (2-(Ethoxycarbonyl)-6,7-dihydrobenzo[d]thiazol-4-yl)boronic acid. LC/MS (M+1)⁺=254.2

Step C: 4-(3-(N,N-bis(4-methoxybenzyl)sulfamoyl)-2-(1-(4-methoxybenzyl)-1H-tetrazol-5-yl)-4-(trifluoromethyl)phenyl)-6,7-dihydrobenzo[d]thiazole-2-carboxylic acid and 4-(3-(N,N-bis(4-methoxybenzyl)sulfamoyl)-2-(2-(4-methoxybenzyl)-2H-tetrazol-5-yl)-4-(trifluoromethyl)phenyl)-6,7-dihydrobenzo[d]thiazole-2-carboxylic acid 3-Bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide (300 mg, 0.410 mmol), (2-(ethoxycarbonyl)-6,7-dihydrobenzo[d]thiazol-4-yl)boronic acid (124 mg, 0.491 mmol), PdCl₂(dppf) (30.0 mg, 0.041 mmol) and sodium carbonate (87 mg, 0.82 mmol) were placed in a reaction vial. Dioxane (3071 µL) and Water (1024 µL) were added. The reaction vessel was sealed and degassed and heated at 80° C. overnight. LC-MS showed there were still starting material present. After the reaction mixture cooled to room temperature, more catalyst (16 mg) was added. The reaction was degassed and heated at 80° C. for 20 hr. After the reaction cooled to rt, the mixture was loaded onto the ISCO column and eluted with 0-50% EtOAc/hexane, then with 0-20% MeOH/EtOAc to give the title compounds. LC/MS (M+1)⁺=833.8.

Step D: 4-(3-(N,N-Bis(4-methoxybenzyl)sulfamoyl)-2-(1-(4-methoxybenzyl)-1H-tetrazol-5-yl)-4-(trifluoromethyl) phenyl)-4,5,6,7-tetrahydrobenzo[d]thiazole-2-carboxylic acid and 4-(3-(N,N-bis(4-methoxybenzyl)sulfamoyl)-2-(2-(4-methoxybenzyl)-2H-tetrazol-5-yl)-4-(trifluoromethyl) phenyl)-4,5,6,7-tetrahydrobenzo[d]thiazole-2-carboxylic acid 4-(3-(N,N-bis(4-methoxybenzyl)sulfamoyl)-2-(1-(4-methoxybenzyl)-1H-tetrazol-5-yl)-4-(trifluoromethyl)phenyl)-6,7-dihydrobenzo[d]thiazole-2-carboxylic acid and 4-(3-(N,N-bis(4-methoxybenzyl)sulfamoyl)-2-(2-(4-methoxybenzyl)-2H-tetrazol-5-yl)-4-(trifluoromethyl)phenyl)-6,7-dihydrobenzo[d]thiazole-2-carboxylic (70 mg, 0.084 mmol) was dissolved in MeOH (1 mL) and EtOAc (1 mL). Pd(OH)₂ (35.4 mg, 0.050 mmol) was added. The mixture was hydrogenated at 50 psi for 22 hr. LC-MS showed about 50% conversion to the desired product. The reaction was filtered and the filtrates were concentrated. The crude product was subjected to hydrogenation again (50 psi) at room temperature for 26 hr in MeOH (1 mL), EtOAc (1 mL) with Pd (OH)₂ (41 mg). LC-MS showed the reaction was completed. The reaction was diluted with EtOAc and MeOH, filtered through a Celite pad. The filtrates were concentrated to give the title compounds. LC/MS (M+1)⁺=835.8

Step E: 4-(3-Sulfamoyl-2-(1H-tetrazol-5-yl)-4-(trifluoromethyl)phenyl)-4,5,6,7-tetrahydrobenzo[d]thiazole-2-carboxylic acid 4-(3-(N,N-bis(4-methoxybenzyl)sulfamoyl)-2-(1-(4-methoxybenzyl)-1H-tetrazol-5-yl)-4-(trifluoromethyl)phenyl)-4,5,6,7-tetrahydrobenzo[d]thiazole-2-carboxylic acid and 4-(3-(N,N-bis(4-methoxybenzyl)sulfamoyl)-2-(2-(4-methoxybenzyl)-2H-tetrazol-5-yl)-4-(trifluoromethyl)phenyl)-4,5,6,7-tetrahydrobenzo[d]thiazole-2-carboxylic acid (50 mg, 0.060 mmol) was heated in TFA (2 mL) at 60° C. for 1.5 hr. The reaction was concentrated and the residue was purified with Gilson (3-75% CH₃CN/water) with 0.1% TFA. The correct fraction was concentrated and lypholized to give 4-(3-sulfamoyl-2-(1H-tetrazol-5-yl)-4-(trifluoromethyl) phenyl)-4,5,6,7-tetrahydrobenzo[d]thiazole-2-carboxylic acid. LC/MS (M+1)⁺=475.4.

EXAMPLE 511

4'-(2-Amino-1,4,5,6-tetrahydropyrimidin-5-yl)-2-(1H-tetrazol-5-yl)-[1,1'-biphenyl]-3-sulfonamide

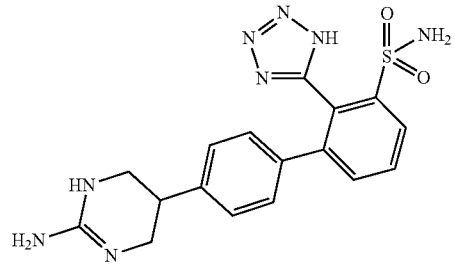 [SMILES: NC1=NCC(c2ccc(-c3cccc(S(N)(=O)=O)c3-c3nnn[nH]3)cc2)CN1]

4'-(1,3-diaminopropan-2-yl)-2-(1H-tetrazol-5-yl)-[1,1'-biphenyl]-3-sulfonamide bis(2,2,2-trifluoroacetate) (42 mg, 0.070 mmol) in MeOH (3491 µL) was treated with cyanic bromide (7.4 mg, 0.070 mmol) followed by DIEA (24.39 µL, 0.140 mmol). The mixture was stirred at room temperature overnight. The reaction mixture was concentrated and purified with Gilson (2-65% CH₃CN/water with 0.1% TFA). The correct fractions were combined, concentrated and lypholized to give 4'-(2-Amino-1,4,5,6-tetrahydropyrimidin-5-yl)-2-(1H-tetrazol-5-yl)-[1,1'-biphenyl]-3-sulfonamide. LC/MS (M+1)⁺=399.5.

EXAMPLES 512-543

Removal of the p-methoxybenzyl protecting groups on REFERENCE EXAMPLES 38-71 immediately above by trifluoroacetic acid.

The previous list of generated PMB protected REFERENCE EXAMPLES 38-71 were dissolved into TFA (100 equivalents) and anisole (10 equivalents). The reaction mixture was heated at 80° C. for 1-3 hr. After removing the volatiles the crude products were purified by HPLC and then lyophilized to give the corresponding title compounds in the following Table.

| Ex. No. | Structure | Name | LC/MS m/e [M + H]+ |
|---|---|---|---|
| 512 | 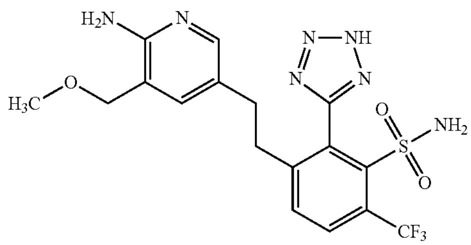 [SMILES: COCc1cc(CCc2ccc(C(F)(F)F)c(S(N)(=O)=O)c2-c2nn[nH]n2)cnc1N] | 3-(2-(6-Amino-5-(methoxymethyl)pyridin-3-yl)ethyl)-2-(2H-tetrazol-5-yl)-6-(trifluoromethyl)benzenesulfonamide | 458.34 |
| 513 | 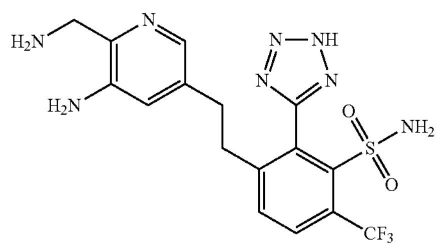 [SMILES: NCc1ncc(CCc2ccc(C(F)(F)F)c(S(N)(=O)=O)c2-c2nn[nH]n2)cc1N] | 3-(2-(5-Amino-6-(aminomethyl)pyridin-3-yl)ethyl)-2-(2H-tetrazol-5-yl)-6-(trifluoromethyl)benzenesulfonamide | 443.3 |
| 514 | 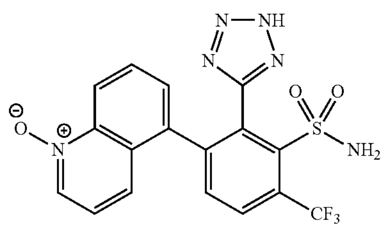 [SMILES: NS(=O)(=O)c1c(C(F)(F)F)ccc(-c2cccc3c2ccc[n+]3[O-])c1-c1nn[nH]n1] | 5-(3-Sulfamoyl-2-(2H-tetrazol-5-yl)-4-(trifluoromethyl)phenyl)quinoline 1-oxide | 437.18 |
| 515 | 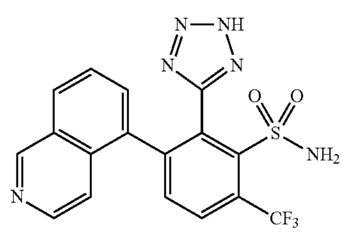 [SMILES: NS(=O)(=O)c1c(C(F)(F)F)ccc(-c2cccc3cnccc23)c1-c1nn[nH]n1] | 3-(Isoquinolin-5-yl)-2-(2H-tetrazol-5-yl)-6-(trifluoromethyl)benzenesulfonamide | 421.32 |
| 516 | 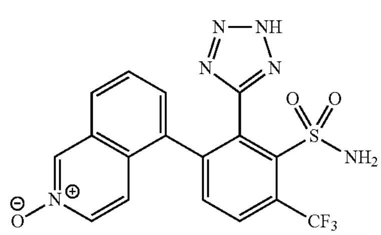 [SMILES: NS(=O)(=O)c1c(C(F)(F)F)ccc(-c2cccc3c[n+]([O-])ccc23)c1-c1nn[nH]n1] | 5-(3-Sulfamoyl-2-(2H-tetrazol-5-yl)-4-(trifluoromethyl)phenyl)isoquinoline 2-oxide | 437.37 |

-continued

| Ex. No. | Structure | Name | LC/MS m/e [M + H]+ |
|---|---|---|---|
| 517 | 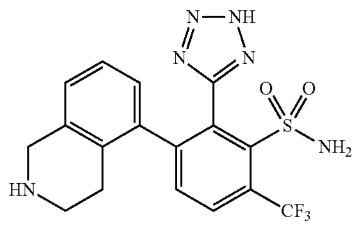 [SMILES: NS(=O)(=O)c1c(C(F)(F)F)ccc(-c2cccc3c2CCNC3)c1-c1nn[nH]n1] | 3-(1,2,3,4-Tetrahydroisoquinolin-5-yl)-2-(2H-tetrazol-5-yl)-6-(trifluoromethyl)benzenesulfonamide | 425.21 |
| 518 | 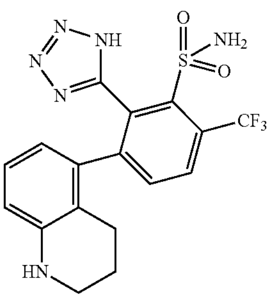 [SMILES: NS(=O)(=O)c1c(C(F)(F)F)ccc(-c2cccc3c2CCCN3)c1-c1nnn[nH]1] | 3-(1,2,3,4-Tetrahydroquinolin-5-yl)-2-(1H-tetrazol-5-yl)-6-(trifluoromethyl)benzenesulfonamide | 425.45 |
| 519 | 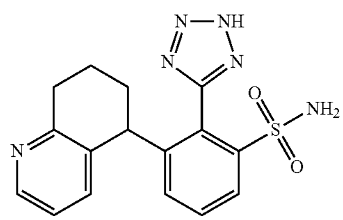 [SMILES: NS(=O)(=O)c1cccc(C2CCCc3ncccc32)c1-c1nn[nH]n1] | 3-(5,6,7,8-Tetrahydroquinolin-5-yl)-2-(2H-tetrazol-5-yl)benzenesulfonamide | 357.07 |
| 520 | 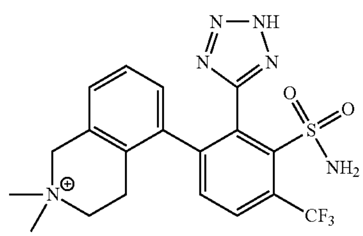 [SMILES: C[N+]1(C)CCc2c(cccc2-c2ccc(C(F)(F)F)c(S(N)(=O)=O)c2-c2nn[nH]n2)C1] | 2,2-Dimethyl-5-(3-sulfamoyl-2-(2H-tetrazol-5-yl)-4-(trifluoromethyl)phenyl)-1,2,3,4-tetrahydroisoquinolin-2-ium | 453.24 |
| 521 | 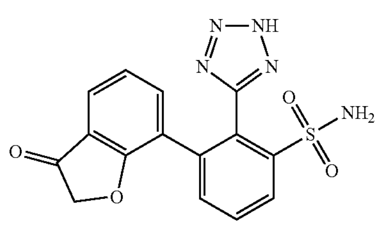 [SMILES: NS(=O)(=O)c1cccc(-c2cccc3c2OCC3=O)c1-c1nn[nH]n1] | 3-(3-Oxo-2,3-dihydrobenzofuran-7-yl)-2-(2H-tetrazol-5-yl)benzenesulfonamide | 358.31 |
| 522 | 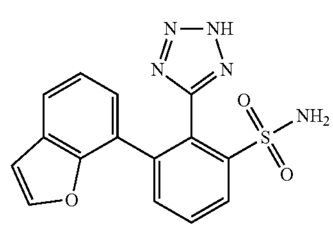 [SMILES: NS(=O)(=O)c1cccc(-c2cccc3ccoc23)c1-c1nn[nH]n1] | 3-(Benzofuran-7-yl)-2-(2H-tetrazol-5-yl)benzenesulfonamide | 342.12 |

| Ex. No. | Structure | Name | LC/MS m/e [M + H]+ |
|---|---|---|---|
| 523 | 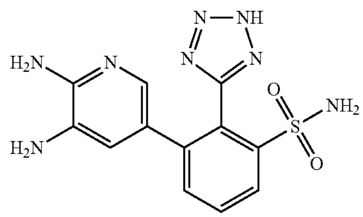 [SMILES: Nc1cc(-c2cccc(S(N)(=O)=O)c2-c2nn[nH]n2)cnc1N] | 3-(5,6-Diaminopyridin-3-yl)-2-(2H-tetrazol-5-yl)benzenesulfonamide | 333.26 |
| 524 | 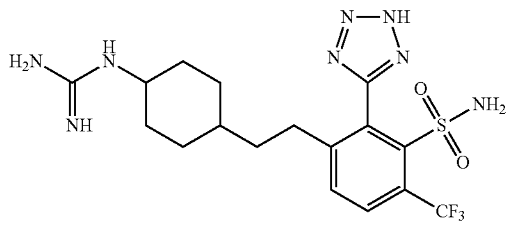 [SMILES: N=C(N)NC1CCC(CCc2ccc(C(F)(F)F)c(S(N)(=O)=O)c2-c2nn[nH]n2)CC1] | 3-(2-(4-Guanidinocyclohexyl)ethyl)-2-(2H-tetrazol-5-yl)-6-(trifluoromethyl)benzenesulfonamide | 461.48 |
| 525 | 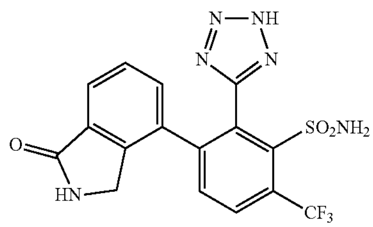 [SMILES: NS(=O)(=O)c1c(C(F)(F)F)ccc(-c2cccc3c2CNC3=O)c1-c1nn[nH]n1] | 3-(1-Oxoisoindolin-4-yl)-2-(2H-tetrazol-5-yl)-6-(trifluoromethyl)benzenesulfonamide | 425.33 |
| 526 | 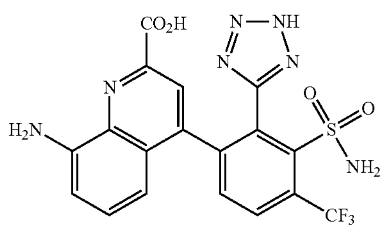 [SMILES: Nc1cccc2c(-c3ccc(C(F)(F)F)c(S(N)(=O)=O)c3-c3nn[nH]n3)cc(C(=O)O)nc12] | 8-Amino-4-(3-sulfamoyl-2-(2H-tetrazol-5-yl)-4-(trifluoromethyl)phenyl)quinoline-2-carboxylic acid | 480.34 |
| 527 | 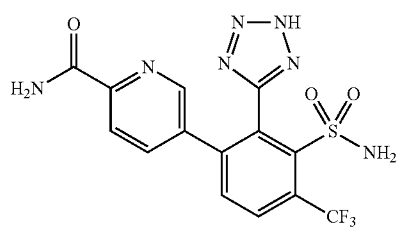 [SMILES: NC(=O)c1ccc(-c2ccc(C(F)(F)F)c(S(N)(=O)=O)c2-c2nn[nH]n2)cn1] | 5-(3-Sulfamoyl-2-(2H-tetrazol-5-yl)-4-(trifluoromethyl)phenyl)picolinamide | 414.3 |
| 528 | 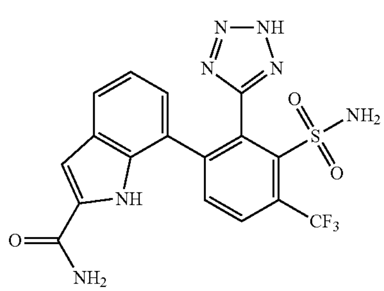 [SMILES: NC(=O)c1cc2cccc(-c3ccc(C(F)(F)F)c(S(N)(=O)=O)c3-c3nn[nH]n3)c2[nH]1] | 7-(3-Sulfamoyl-2-(2H-tetrazol-5-yl)-4-(trifluoromethyl)phenyl)-1H-indole-2-carboxamide | 452.36 |

| Ex. No. | Structure | Name | LC/MS m/e [M + H]+ |
|---|---|---|---|
| 529 | 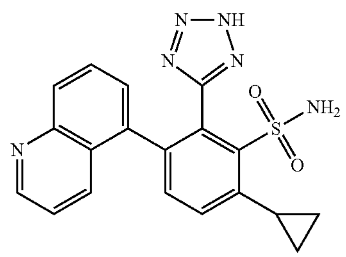 [SMILES: NS(=O)(=O)c1c(C2CC2)ccc(-c2cccc3ncccc23)c1-c1nn[nH]n1] | 6-Cyclopropyl-3-(quinolin-5-yl)-2-(2H-tetrazol-5-yl)benzenesulfonamide | 393.25 |
| 530 | 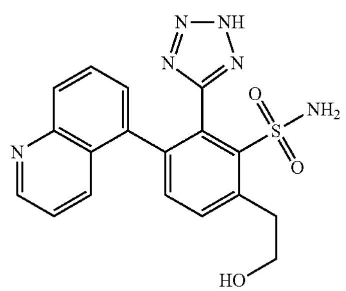 [SMILES: NS(=O)(=O)c1c(CCO)ccc(-c2cccc3ncccc23)c1-c1nn[nH]n1] | 6-(2-Hydroxyethyl)-3-(quinolin-5-yl)-2-(2H-tetrazol-5-yl)benzenesulfonamide | 397.28 |
| 531 | 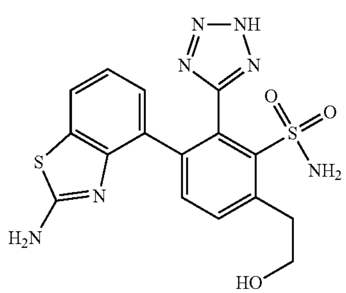 [SMILES: Nc1nc2c(-c3ccc(CCO)c(S(N)(=O)=O)c3-c3nn[nH]n3)cccc2s1] | 3-(2-Aminobenzo[d]thiazol-4-yl)-6-(2-hydroxyethyl)-2-(2H-tetrazol-5-yl)benzenesulfonamide | 418.33 |
| 532 | 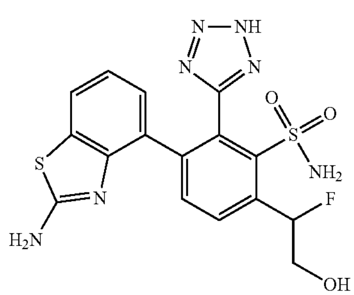 [SMILES: Nc1nc2c(-c3ccc(C(F)CO)c(S(N)(=O)=O)c3-c3nn[nH]n3)cccc2s1] | 3-(2-Aminobenzo[d]thiazol-4-yl)-6-(1-fluoro-2-hydroxyethyl)-2-(2H-tetrazol-5-yl)benzenesulfonamide | 436.35 |
| 533 | 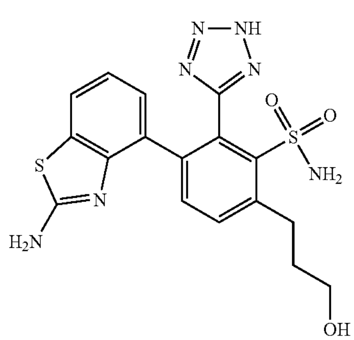 [SMILES: Nc1nc2c(-c3ccc(CCCO)c(S(N)(=O)=O)c3-c3nn[nH]n3)cccc2s1] | 3-(2-Aminobenzo[d]thiazol-4-yl)-6-(3-hydroxypropyl)-2-(2H-tetrazol-5-yl)benzenesulfonamide | 432.37 |

-continued

| Ex. No. | Structure | Name | LC/MS m/e [M + H]+ |
|---|---|---|---|
| 534 | 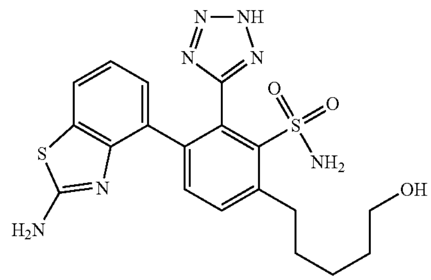 [SMILES: Nc1nc2c(-c3ccc(CCCCCO)c(S(N)(=O)=O)c3-c3nn[nH]n3)cccc2s1] | 3-(2-Aminobenzo[d]thiazol-4-yl)-6-(5-hydroxypentyl)-2-(2H-tetrazol-5-yl)benzenesulfonamide | 460.41 |
| 535 | 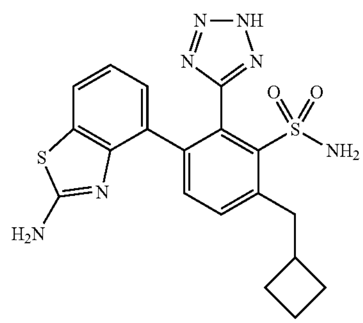 [SMILES: Nc1nc2c(-c3ccc(CC4CCC4)c(S(N)(=O)=O)c3-c3nn[nH]n3)cccc2s1] | 3-(2-Aminobenzo[d]thiazol-4-yl)-6-(cyclobutylmethyl)-2-(2H-tetrazol-5-yl)benzenesulfonamide | 442.37 |
| 536 | 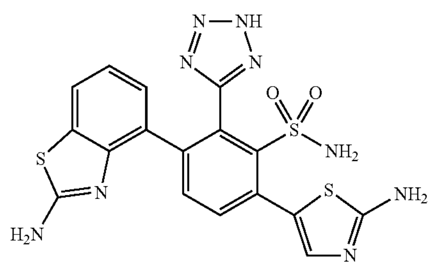 [SMILES: Nc1ncc(-c2ccc(-c3cccc4sc(N)nc34)c(-c3nn[nH]n3)c2S(N)(=O)=O)s1] | 3-(2-Aminobenzo[d]thiazol-4-yl)-6-(2-aminothiazol-5-yl)-2-(2H-tetrazol-5-yl)benzenesulfonamide | 472.32 |
| 537 | 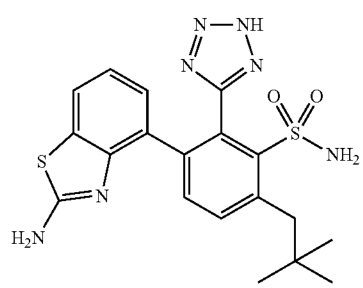 [SMILES: CC(C)(C)Cc1ccc(-c2cccc3sc(N)nc23)c(-c2nn[nH]n2)c1S(N)(=O)=O] | 3-(2-Aminobenzo[d]thiazol-4-yl)-6-neopentyl-2-(2H-tetrazol-5-yl)benzenesulfonamide | 442.18 |
| 538 | 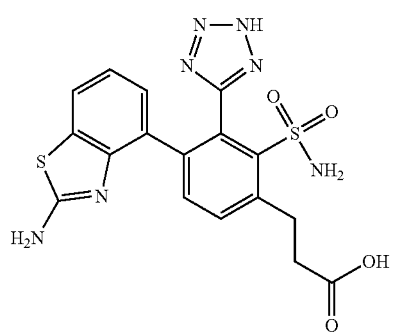 [SMILES: Nc1nc2c(-c3ccc(CCC(=O)O)c(S(N)(=O)=O)c3-c3nn[nH]n3)cccc2s1] | 3-(4-(2-Aminobenzo[d]thiazol-4-yl)-2-sulfamoyl-3-(2H-tetrazol-5-yl)phenyl)propanoic acid | 446.31 |

-continued

| Ex. No. | Structure | Name | LC/MS m/e [M + H]+ |
|---|---|---|---|
| 539 | 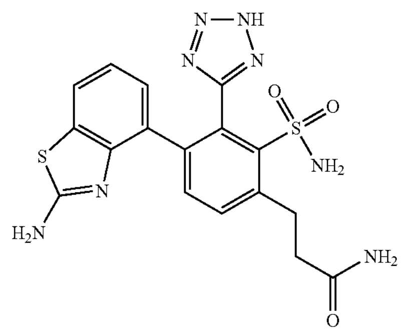 [SMILES: NC(=O)CCc1ccc(-c2cccc3sc(N)nc23)c(-c2nn[nH]n2)c1S(N)(=O)=O] | 3-(4-(2-Aminobenzo[d]thiazol-4-yl)-2-sulfamoyl-3-(2H-tetrazol-5-yl)phenyl)propanamide | 445.40 |
| 540 | 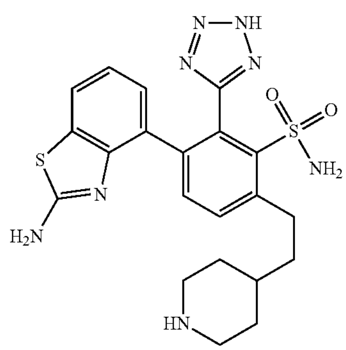 [SMILES: Nc1nc2c(-c3ccc(CCC4CCNCC4)c(S(N)(=O)=O)c3-c3nn[nH]n3)cccc2s1] | 3-(2-Aminobenzo[d]thiazol-4-yl)-6-(2-(piperidin-4-yl)ethyl)-2-(2H-tetrazol-5-yl)benzenesulfonamide | 483.38 |
| 541 | 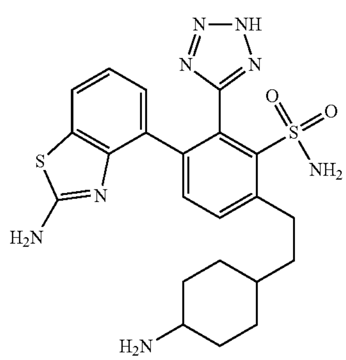 [SMILES: Nc1nc2c(-c3ccc(CCC4CCC(N)CC4)c(S(N)(=O)=O)c3-c3nn[nH]n3)cccc2s1] | 3-(2-Aminobenzo[d]thiazol-4-yl)-6-(2-(4-aminocyclohexyl)ethyl)-2-(2H-tetrazol-5-yl)benzenesulfonamide | 499.45 |
| 542 | 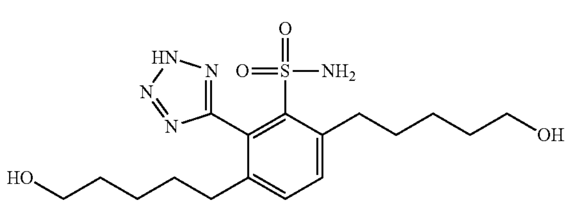 [SMILES: NS(=O)(=O)c1c(CCCCCO)ccc(CCCCCO)c1-c1nn[nH]n1] | 3,6-Bis(5-hydroxypentyl)-2-(2H-tetrazol-5-yl)benzenesulfonamide | 398.41 |
| 543 | 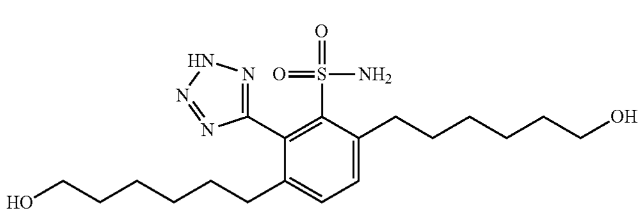 [SMILES: NS(=O)(=O)c1c(CCCCCCO)ccc(CCCCCCO)c1-c1nn[nH]n1] | 3,6-Bis(6-hydroxyhexyl)-2-(2H-tetrazol-5-yl)benzenesulfonamide | 426.47 |

EXAMPLE 544

3-(2-aminobenzo[d]thiazol-4-yl)-6-(piperidin-4-ylmethyl)-2-(2H-tetrazol-5-yl)benzenesulfonamide

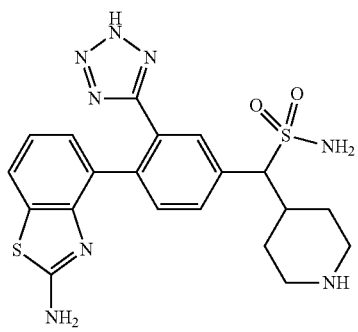 [SMILES: Nc1nc2c(-c3ccc(C(C4CCNCC4)S(N)(=O)=O)cc3-c3nn[nH]n3)cccc2s1]

Step A: 3-(2-(bis(4-methoxybenzyl)amino)benzo[d]thiazol-4-yl)-6-bromo-N,N-bis(4-methoxybenzyl)-2-(2-(4-methoxybenzyl)-2H-tetrazol-5-yl)benzenesulfonamide To a mixture of 3-(2-aminobenzo[d]thiazol-4-yl)-6-bromo-N,N-bis(4-methoxybenzyl)-2-(1-(4-methoxybenzyl)-1H-tetrazol-5-yl)benzenesulfonamide (250 mg, 0.308 mmol), 1-(chloromethyl)-4-methoxybenzene (106 mg, 0.677 mmol) in 2-butanone (1.5 mL) at rt 1-(chloromethyl)-4-methoxybenzene (106 mg, 0.677 mmol) was added, followed by potassium carbonate (170 mg, 1.23 mmol) and sodium iodide (101 mg, 0.677 mmol). The reaction was stirred under nitrogen overnight at 80° C. and monitored by LCMS. More reagents were added until starting material was consumed. The reaction mixture was then filtered, and rinsed by EtOAc. The combined organic layer was evaporated, and the crude product was purified by silica gel column chromatography with EtOAc/Hex (0-100%) as eluent to give the title compound. LC-MS (IE, m/z): 1054.75 [M+2]$^+$.

Step B: tert-butyl 4-(4-(2-(bis(4-methoxybenzyl)amino)benzo[d]thiazol-4-yl)-2-(N,N-bis(4-methoxybenzyl)sulfamoyl)-3-(2-(4-methoxybenzyl)-2H-tetrazol-5-yl)benzyl)piperidine-1-carboxylate A microwave vial was charged with tert-butyl 4-(iodomethyl)piperidine-1-carboxylate (67.9 mg, 0.209 mmol), Nickel(II) Iodide (9.79 mg, 0.031 mmol), Manganese (17.22 mg, 0.313 mmol), Bathophenanthroline (5.21 mg, 0.016 mmol) and 3-(2-(bis(4-methoxybenzyl)amino)benzo[d]thiazol-4-yl)-6-bromo-N,N-bis(4-methoxybenzyl)-2-(2-(4-methoxybenzyl)-2H-tetrazol-5-yl)benzenesulfonamide (110 mg, 0.104 mmol). The vial was sealed, purged with N$_2$ for 10 min, and filled with DMA (522 μL). The resulting mixture was purged with N$_2$ for another 10 min and heated over the weekend at 80° C. The reaction mixture was filtered over celite to remove the metal. The filtrate was concentrated and purified by silica gel column chromatography (RediSep gold column, 120 g gold column) using 0-100% EtOAc/hexane as mobile phase (isocratic at 20% and 40% for a while, removed some des-Br product, which came out first) to afford the product. LCMS: (M+H)$^+$ 1172.46.

Step C: 3-(2-aminobenzo[d]thiazol-4-yl)-6-(piperidin-4-ylmethyl)-2-(2H-tetrazol-5-yl)benzenesulfonamide To tert-butyl 4-(4-(2-(bis(4-methoxybenzyl)amino)benzo[d]thiazol-4-yl)-2-(N,N-bis(4-methoxybenzyl)sulfamoyl)-3-(2-(4-methoxybenzyl)-2H-tetrazol-5-yl)benzyl)piperidine-1-carboxylate (90 mg, 0.077 mmol) was added Anisole (84 μL, 0.768 mmol) and TFA (592 μL, 7.68 mmol) at rt. The resulting mixture was stirred at rt for 1 hr to remove both Boc and both PMB protection. After removing the volatiles the residue was purified by reverse phase HPLC using DMSO to load sample and 5-55% acetonitrile/water (0.1% TFA as additive) as mobile phase over 10 min to separate desired product from des-Br product. To a solution of the desired mono-PMB intermediate product in DCM (768 μL) was added Anisole (84 μL, 0.768 mmol) and TFA (592 μL, 7.68 mmol) at rt. The resulting mixture was stirred at 80° C. for 1 hr to remove the final PMB protection. After removing the volatiles the residue was purified by reverse phase HPLC using DMSO to load sample and 5-40% acetonitrile/water (0.1% TFA as additive) as mobile phase over 10 min to give the final product. LC-MS (IE, m/z): 471.4 [M+1]$^+$.

EXAMPLE 545

3-(2-aminobenzo[d]thiazol-4-yl)-6-(azetidin-3-ylmethyl)-2-(2H-tetrazol-5-yl)benzenesulfonamide

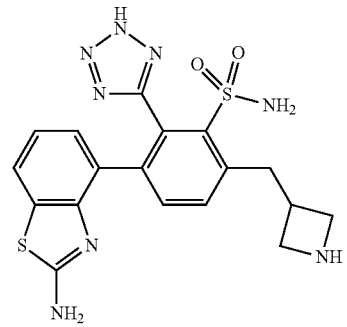 [SMILES: Nc1nc2c(-c3ccc(CC4CNC4)c(S(N)(=O)=O)c3-c3nn[nH]n3)cccc2s1]

The title compound was prepared in an analogous fashion to that described for the preparation of 4'-(piperidin-4-yl)-4-(piperidin-4-ylmethyl)-2-(2H-tetrazol-5-yl)-[1,1'-biphenyl]-3-sulfonamide (immediately above) using intermediate 3-(2-(bis(4-methoxybenzyl)amino)-1H-benzo[d]imidazol-4-yl)-6-bromo-N,N-bis(4-methoxybenzyl)-2-(2-(4-methoxybenzyl)-2H-tetrazol-5-yl)benzenesulfonamide and tert-butyl 3-(iodomethyl)azetidine-1-carboxylate. LC-MS (IE, m/z): 443.50 [M+1]$^+$.

EXAMPLE 546

6-(azetidin-3-ylmethyl)-3-(imidazo[1,2-a]pyridin-3-yl)-2-(2H-tetrazol-5-yl)benzenesulfonamide

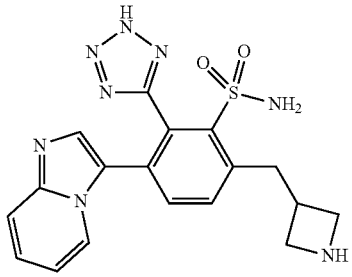 [SMILES: NS(=O)(=O)c1c(CC2CNC2)ccc(-c2cnc3ccccn23)c1-c1nn[nH]n1]

The title compound was prepared in an analogous fashion to that described for the preparation of 4'-(piperidin-4-yl)-

4-(piperidin-4-ylmethyl)-2-(2H-tetrazol-5-yl)-[1,1'-biphenyl]-3-sulfonamide using intermediates 6-bromo-3-iodo-N,N-bis(4-methoxybenzyl)-2-(2-(4-methoxybenzyl)-2H-tetrazol-5-yl)benzenesulfonamide, 3-(4,4,5,5-tetramethyl-1,3,2-dioxaborolan-2-yl)imidazo[1,2-a]pyridine, and tert-butyl 3-(iodomethyl)azetidine-1-carboxylate. LC-MS (IE, m/z): 411.58 [M+1]$^+$.

EXAMPLES 547-562

Synthesis of 4'-substituted 2-(2H-tetrazol-5-yl)-4-(trifluoromethyl)biphenyl-3-sulfonamides

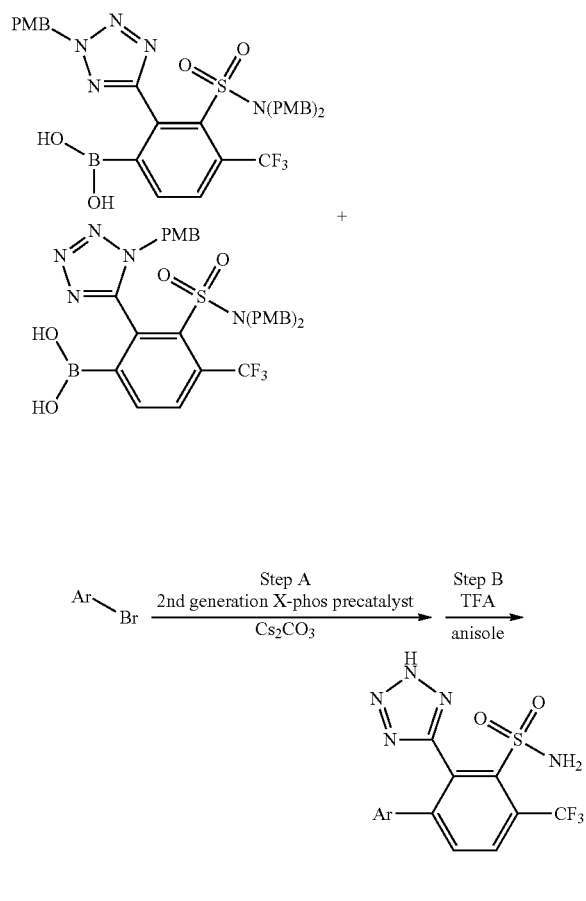

Step A: Palladium Catalyzed C—C Coupling of Aryl-herterocyclicbromide and Boronic Acids or Boronic Esters (Such as Pinacol Esters)

Into a 50 mL three necked round bottom flask was placed a solution of 3-(N,N-bis(4-methoxybenzyl)sulfamoyl)-2-(2-(4-methoxybenzyl)-2H-tetrazol-5-yl)-4-(trifluoromethyl)phenylboronic acid (0.18 g, 0.26 mmol), 2nd generation X-phos precatalyst (30 mg, 0.04 mmol), heterocycle bromide (commercially available, known from the literature, or prepared as described herein) and $Cs_2CO_3$ (0.25 g, 0.77 mmol) in dioxane (1.5 mL) and water (0.4 mL). The resulting mixture was degassed with nitrogen for 3 times and stirred for 16 hr at 80° C. The reaction was quenched with water (8 mL) and extracted with EtOAc (3×15 mL). The combined organic layers was washed with water (2×20 mL) and brine (2×20 mL), dried over anhydrous $Na_2SO_4$ and filtered. The filtrate was concentrated under vacuum. The residue was purified by silica gel column chromatography to afford the coupled products.

Step B: Removal of the p-methoxybenzyl (PMB) Protecting Group by TFA

Into a 50 mL round bottom flask was placed a solution of the coupled products from Step A (0.16 mmol) in DCM (2.0 mL) followed by the additional of TFA (1.0 mL). After the resulting mixture was stirred at ambient temperature for 3 hr, the solvent was removed under vacuum. The residue was dissolved in DCM (0.2 mL), to which was added anisole (1.0 mL, 0.16 mmol) and TFA (2.0 mL, 26.0 mmol). The resulting mixture was stirred at 80° C. for 6 hr. After the solvent was removed under vacuum, the residue was purified by Prep-HPLC, typically with the following conditions: Column: X Bridge RP18, 19×150 mm, 5 µm; Mobile Phase A: water (0.05% TFA), Mobile Phase B: ACN; Flow rate: 20 mL/min; Gradient: 10% B to 40% B in 7 min; Detection: UV 254 nm to afford the title compounds in the Table immediately below. Note that when the Aryl group contains a Boc protective group, this group is removed under the conditions of Step B.

| Ex. No. | Structure | Name | Calc'd. MW [M + H]$^+$ | LC/MS m/e [M + H]$^+$ |
|---|---|---|---|---|
| 547 | 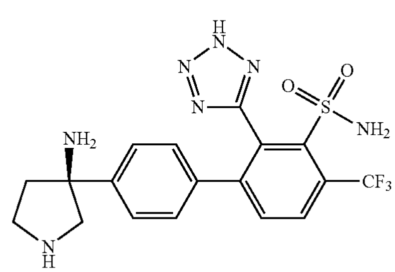 [SMILES: N[C@]1(c2ccc(-c3ccc(C(F)(F)F)c(S(N)(=O)=O)c3-c3nn[nH]n3)cc2)CCNC1] | 3-[4-[(3S)-3-aminopyrrolidin-3-yl]phenyl]-2-(2H-tetrazol-5-yl)-6-(trifluoromethyl)benzenesulfonamide | 454.1 | 454.2 |

-continued

| Ex. No. | Structure | Name | Calc'd. MW [M + H]+ | LC/MS m/e [M + H]+ |
|---|---|---|---|---|
| 548 | 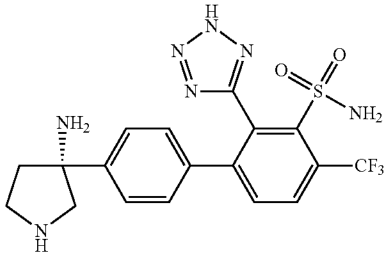 [SMILES: N[C@@]1(c2ccc(-c3ccc(C(F)(F)F)c(S(N)(=O)=O)c3-c3nn[nH]n3)cc2)CCNC1] | 3-[4-[(3R)-3-aminopyrrolidin-3-yl]phenyl]-2-(2H-tetrazol-5-yl)-6-(trifluoromethyl)benzenesulfonamide | 454.1 | 454.2 |
| 549 | 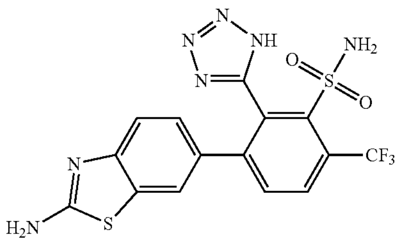 [SMILES: Nc1nc2ccc(-c3ccc(C(F)(F)F)c(S(N)(=O)=O)c3-c3nnn[nH]3)cc2s1] | 3-(2-amino-1,3-benzothiazol-6-yl)-2-(1H-tetrazol-5-yl)-6-(trifluoromethyl)benzenesulfonamide | 442.4 | 442.2 |
| 550 | 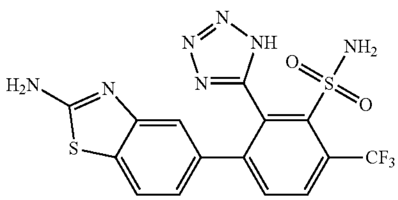 [SMILES: Nc1nc2cc(-c3ccc(C(F)(F)F)c(S(N)(=O)=O)c3-c3nnn[nH]3)ccc2s1] | 3-(2-amino-1,3-benzothiazol-5-yl)-2-(1H-tetrazol-5-yl)-6-(trifluoromethyl)benzenesulfonamide | 442.4 | 442.8 |
| 551 | 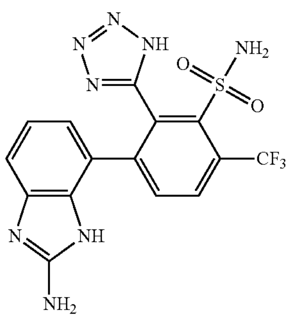 [SMILES: Nc1nc2cccc(-c3ccc(C(F)(F)F)c(S(N)(=O)=O)c3-c3nnn[nH]3)c2[nH]1] | 3-(2-amino-3H-benzimidazol-4-yl)-2-(1H-tetrazol-5-yl)-6-(trifluoromethyl)benzenesulfonamide | 425.4 | 425.1 |
| 552 | 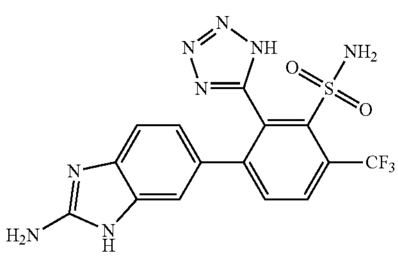 [SMILES: Nc1nc2ccc(-c3ccc(C(F)(F)F)c(S(N)(=O)=O)c3-c3nnn[nH]3)cc2[nH]1] | 3-(2-amino-3H-benzimidazol-5-yl)-2-(1H-tetrazol-5-yl)-6-(trifluoromethyl)benzenesulfonamide | 425.4 | 425.0 |
| 553 | 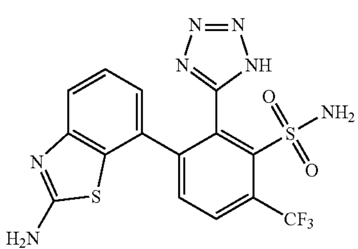 [SMILES: Nc1nc2cccc(-c3ccc(C(F)(F)F)c(S(N)(=O)=O)c3-c3nnn[nH]3)c2s1] | 3-(2-amino-1,3-benzothiazol-7-yl)-2-(1H-tetrazol-5-yl)-6-(trifluoromethyl)benzenesulfonamide | 442.4 | 442.0 |

-continued

| Ex. No. | Structure | Name | Calc'd. MW [M + H]+ | LC/MS m/e [M + H]+ |
|---|---|---|---|---|
| 554 | 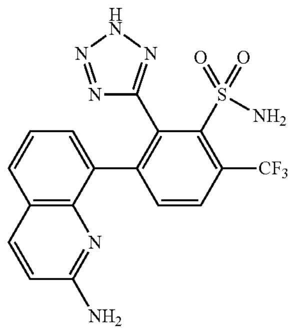 [SMILES: Nc1ccc2cccc(-c3ccc(C(F)(F)F)c(S(N)(=O)=O)c3-c3nn[nH]n3)c2n1] | 3-(2-amino-8-quinolyl)-2-(2H-tetrazol-5-yl)-6-(trifluoromethyl)benzenesulfonamide | 436.38 | 436.0 |
| 555 | 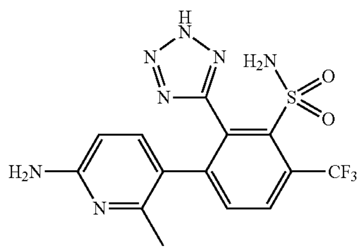 [SMILES: Cc1nc(N)ccc1-c1ccc(C(F)(F)F)c(S(N)(=O)=O)c1-c1nn[nH]n1] | 3-(6-amino-2-methyl-3-pyridyl)-2-(2H-tetrazol-5-yl)-6-(trifluoromethyl)benzenesulfonamide | 399.35 | 399.1 |
| 556 | 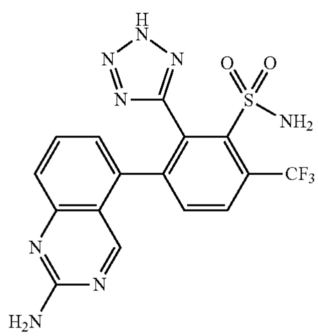 [SMILES: Nc1ncc2c(-c3ccc(C(F)(F)F)c(S(N)(=O)=O)c3-c3nn[nH]n3)cccc2n1] | 3-(2-aminoquinazolin-5-yl)-2-(2H-tetrazol-5-yl)-6-(trifluoromethyl)benzenesulfonamide | 437.3 | 436.9 |
| 557 | 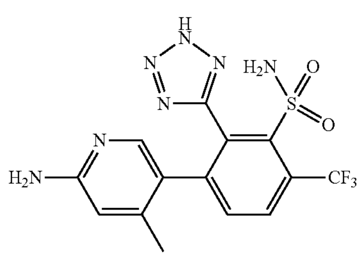 [SMILES: Cc1cc(N)ncc1-c1ccc(C(F)(F)F)c(S(N)(=O)=O)c1-c1nn[nH]n1] | 3-(6-amino-4-methyl-3-pyridyl)-2-(2H-tetrazol-5-yl)-6-(trifluoromethyl)benzenesulfonamide | 399.35 | 399.4 |
| 558 | 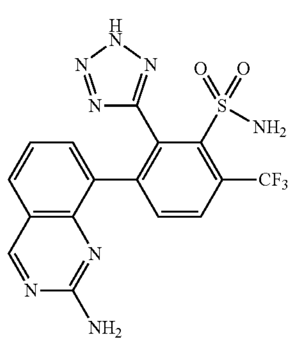 [SMILES: Nc1ncc2cccc(-c3ccc(C(F)(F)F)c(S(N)(=O)=O)c3-c3nn[nH]n3)c2n1] | 3-(2-aminoquinazolin-8-yl)-2-(2H-tetrazol-5-yl)-6-(trifluoromethyl)benzenesulfonamide | 437.37 | 437.0 |

-continued

| Ex. No. | Structure | Name | Calc'd. MW [M + H]+ | LC/MS m/e [M + H]+ |
|---|---|---|---|---|
| 559 | 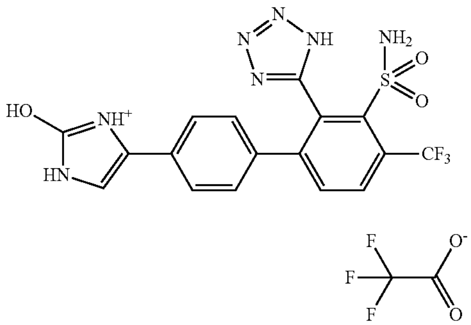 [SMILES: NS(=O)(=O)c1c(C(F)(F)F)ccc(-c2ccc(-c3c[nH]c(O)[nH+]3)cc2)c1-c1nnn[nH]1 ; O=C([O-])C(F)(F)F] | 3-[4-(2-hydroxy-1H-imidazol-4-yl)phenyl]-2-(1H-tetrazol-5-yl)-6-(trifluoromethyl)benzenesulfonamide | 452 | 452.34 |
| 560 | 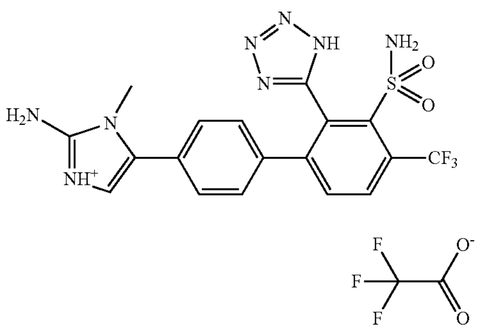 [SMILES: Cn1c(-c2ccc(-c3ccc(C(F)(F)F)c(S(N)(=O)=O)c3-c3nnn[nH]3)cc2)c[nH+]c1N ; O=C([O-])C(F)(F)F] | 3-[4-(2-amino-3-methyl-imidazol-4-yl)phenyl]-2-(1H-tetrazol-5-yl)-6-(trifluoromethyl)benzenesulfonamide | 465 | 465.39 |
| 561 | 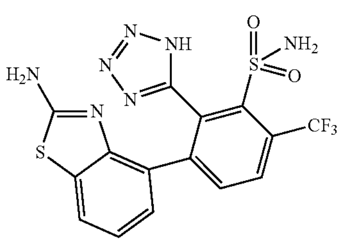 [SMILES: Nc1nc2c(-c3ccc(C(F)(F)F)c(S(N)(=O)=O)c3-c3nnn[nH]3)cccc2s1] | 3-(2-aminobenzo[d]thiazol-4-yl)-2-(1H-tetrazol-5-yl)-6-(trifluoromethyl)benzenesulfonamide | 442 | 442 |
| 562 | 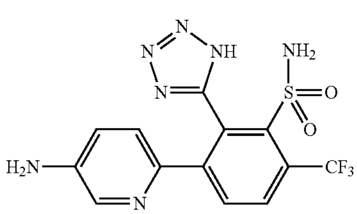 [SMILES: Nc1ccc(-c2ccc(C(F)(F)F)c(S(N)(=O)=O)c2-c2nnn[nH]2)nc1] | 3-(5-aminopyridin-2-yl)-2-(1H-tetrazol-5-yl)-6-(trifluoromethyl)benzenesulfonamide | 386 | 386 |

EXAMPLE 563

N-(azetidin-3-yl)-3'-sulfamoyl-2'-(2H-tetrazol-5-yl)-4'-(trifluoromethyl)biphenyl-4-carboximidamide

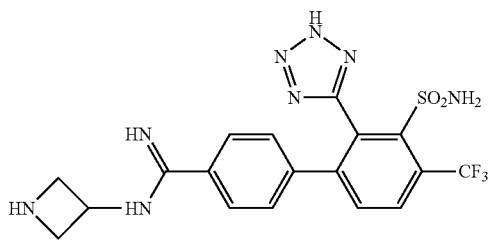 [SMILES: N=C(NC1CNC1)c1ccc(-c2ccc(C(F)(F)F)c(S(N)(=O)=O)c2-c2nn[nH]n2)cc1]

Step A: 4'-cyano-N,N-bis(4-methoxybenzyl)-2-(2-(4-methoxybenzyl)-2H-tetrazol-5-yl)-4-(trifluoromethyl)biphenyl-3-sulfonamide Into a 25-mL round-bottom flask purged and maintained with an inert atmosphere of argon, was placed a solution of 3-bromo-N,N-bis(4-methoxybenzyl)-2-(1-(4-methoxybenzyl)-1H-tetrazol-5-yl)-6-(trifluoromethyl)benzenesulfonamide (0.20 g, 0.27 mmol) in dioxane/water (v:v=4:1, 4 mL). This was followed by the addition of 4-(4,4,5,5-tetramethyl-1,3,2-dioxaborolan-2-yl)benzonitrile (0.13 g, 0.55 mmol), [1,1'-bis(diphenylphosphino)ferrocene]dichloropalladium (II) (20 mg, 0.03 mmol), Na$_2$CO$_3$ (87 mg, 0.82 mmol) at ambient temperature. The reaction mixture was stirred at 80° C. for 2 hr under argon atmosphere. The resulting mixture was cooled down to 20° C. and the solvent was evaporated under vacuum. The residue was purified by Prep-TLC with EtOAc/petroleum ether (1/2) to afford the title compound: LCMS (ESI) calc'd for C$_{39}$H$_{33}$F$_3$N$_6$O$_5$S [M+H]$^+$: 755, found 755.

Step B: methyl 2'-(2-(4-methoxybenzyl)-2H-tetrazol-5-yl)-3'-(N-(4-methoxybenzyl)sulfamoyl)-4'-(trifluoromethyl)biphenyl-4-carbimidate Into a solution of 4'-cyano-N,N-bis(4-methoxybenzyl)-2-(1-(4-methoxybenzyl)-1H-tetrazol-5-yl)-4-(trifluoromethyl)-[1,1'-biphenyl]-3-sulfonamide (100 mg, 0.132 mmol) in dry MeOH (20 mL) was bubbled with dry HCl (g) at ambient temperature. The saturated HCl solution was stirred for 5 hr at ambient temperature. The solvent was evaporated under vacuum to afford the crude title compound, which was used directly in the next step without further purification: LCMS (ESI) calc'd for C$_{32}$H$_{29}$F$_3$N$_6$O$_5$S [M+H]$^+$: 667, found 667.

Step C: tert-butyl 3-(2'-(2-(4-methoxybenzyl)-2H-tetrazol-5-yl)-3'-(N-(4-methoxybenzyl)sulfamoyl)-4'-(trifluoromethyl)biphenyl-4-ylcarboximidamido)azetidine-1-carboxylate Into a 25-mL round-bottom flask purged and maintained with an inert atmosphere of argon, was placed a solution of methyl 2'-(1-(4-methoxybenzyl)-1H-tetrazol-5-yl)-3'-(N-(4-methoxybenzyl)sulfamoyl)-4'-(trifluoromethyl)-[1,1'-biphenyl]-4-carbimidate (0.14 g, 0.13 mmol) in DCM (2 mL). This was followed by the addition of N,N-diisopropylethylamine (65 mg, 0.50 mmol) and tert-butyl 3-aminoazetidine-1-carboxylate (43 mg, 0.25 mmol) at 0° C. The resulting mixture was stirred at 20° C. for 24 hr under argon atmosphere. The solvent was evaporated under vacuum and the residue was purified by silica gel column chromatography, eluted with EtOAc/PE (1:2) to afford the title compound: LCMS (ESI) calc'd for C$_{39}$H$_{41}$F$_3$N$_8$O$_6$S [M+H]$^+$: 807, found 807.

Step D: N-(azetidin-3-yl)-2'-(2-(4-methoxybenzyl)-2H-tetrazol-5-yl)-3'-(N-(4-methoxybenzyl)sulfamoyl)-4'-(trifluoromethyl)biphenyl-4-carboximidamide To a solution of tert-butyl 3-(2'-(1-(4-methoxybenzyl)-1H-tetrazol-5-yl)-3'-(N-(4-methoxybenzyl)sulfamoyl)-4'-(trifluoromethyl)-[1,1'-biphenyl]-4-ylcarboximidamido)azetidine-1-carboxylate (0.12 g, 0.12 mmol) in anisole (1 mL) was added TFA (1 mL) at 0° C. The resulting mixture was stirred at 0° C. for 1 hr and then the solvent was evaporated under vacuum. The residue was used directly in the next step without further purification: LCMS (ESI) calc'd for C$_{34}$H$_{33}$F$_3$N$_8$O$_4$S [M+H]$^+$: 707, found 707.

Step E: N-(azetidin-3-yl)-3'-sulfamoyl-2'-(2H-tetrazol-5-yl)-4'-(trifluoromethyl)biphenyl-4-carboximidamide To a solution of N-(azetidin-3-yl)-2'-(1-(4-methoxybenzyl)-1H-tetrazol-5-yl)-3'-(N-(4-methoxybenzyl)sulfamoyl)-4'-(trifluoromethyl)-[1,1'-biphenyl]-4-carboximidamide (0.10 g, 0.11 mmol) in anisole (0.5 mL) was added TFA (3 mL) at ambient temperature. The resulting mixture was stirred at 80° C. for 16 hr. The resulting mixture was cooled down to 20° C. and the solvent was evaporated under vacuum. The residue was purified by Prep-HPLC with the following conditions: Column: X Bridge C18, 19×150 mm, 5 μm; Mobile Phase A: water (10 mM NH$_4$HCO$_3$); Mobile Phase B: ACN; Flow rate: 20 mL/min; Gradient: 10-18% B in 8 min; Detection: at 254 nm; Retention time: 6.6 min. The collected fractions were combined and concentrated under reduced pressure to afford the title compound: LCMS (ESI) calc'd for C$_{18}$H$_{17}$F$_3$N$_8$O$_2$S [M+H]$^+$: 467, found 467.

EXAMPLE 564

N-(pyrrolidin-3-yl)-3'-sulfamoyl-2'-(2H-tetrazol-5-yl)-4'-(trifluoromethyl)biphenyl-4-carboximidamide

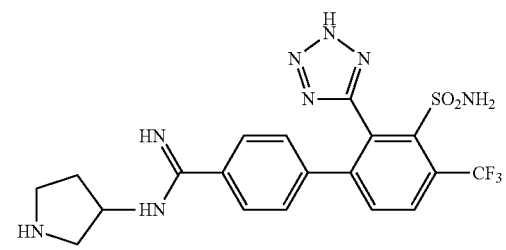 [SMILES: N=C(NC1CCNC1)c1ccc(-c2ccc(C(F)(F)F)c(S(N)(=O)=O)c2-c2nn[nH]n2)cc1]

Step A: tert-butyl 3-(2'-(2-(4-methoxybenzyl)-2H-tetrazol-5-yl)-3'-(N-(4-methoxybenzyl)sulfamoyl)-4'-(trifluoromethyl)biphenyl-4-ylcarboximidamido)pyrrolidine-1-carboxylate To a stirred solution of methyl 2'-(1-(4-methoxybenzyl)-1H-tetrazol-5-yl)-3'-(N-(4-methoxybenzyl)sulfamoyl)-4'-(trifluoromethyl)-[1,1'-biphenyl]-4-carbimidate (0.35 g, 0.34 mmol) in DCM (3 mL) and MeOH (1 mL) were added DIEA (0.60 ml, 3.41 mmol) and tert-butyl 3-aminopyrrolidine-1-carboxylate (0.32 g, 1.71 mmol) at 0° C. under argon atmosphere. The resulting mixture was stirred at ambient temperature for 24 hr under argon atmosphere. The solvent was evaporated under vacuum and the residue was purified by Prep-TLC, eluted with EtOAcA/PE (1:2) to afford the title compound: LCMS (ESI) calc'd for C$_{40}$H$_{43}$F$_3$N$_8$O$_6$S [M+H]$^+$: 821, found 821.

Step B: 2'-(2-(4-methoxybenzyl)-2H-tetrazol-5-yl)-3'-(N-(4-methoxybenzyl)sulfamoyl)-N-(pyrrolidin-3-yl)-4'-(trifluoromethyl)biphenyl-4-carboximidamide A solution of tert-butyl 3-(2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-ylcarboximidamido)pyrrolidine-1-carboxylate (0.26 g, 0.22 mmol) in anisole (1 mL) and TFA (1 mL) was stirred at ambient temperature for 1 hr. The solvent was evaporated under vacuum and the residue was used directly in the next step without further purification: LCMS (ESI) calc'd for $C_{35}H_{35}F_3N_8O_4S$ [M+H]$^+$: 721, found 721.

Step C: N-(pyrrolidin-3-yl)-3'-sulfamoyl-2'-(2H-tetrazol-5-yl)-4'-(trifluoromethyl)biphenyl-4-carboximidamide A solution of 2'-(2-(4-methoxybenzyl)-2H-tetrazol-5-yl)-3'-(N-(4-methoxybenzyl)sulfamoyl)-N-(pyrrolidin-3-yl)-4'-(trifluoromethyl)-[1,1'-biphenyl]-4-carboximidamide (0.22 g, 0.18 mmol) in anisole (1 mL) and TFA (3 mL) was stirred at 80° C. for 16 hr. The resulting mixture was cooled down to 20° C. and the solvent was evaporated under vacuum. The residue was purified by Prep-HPLC with the following conditions: Column: X Bridge C18, 19×150 mm, 5 μm; Mobile Phase A: water (10 mM NH$_4$HCO$_3$), Mobile Phase B: ACN; Flow rate: 20 mL/min; Gradient: 10-18% B in 8 min; Detection: at 254 nm; Retention time: 6.0 min. The collected fractions were combined and concentrated under reduced pressure to afford the title compound: LCMS (ESI) calc'd for $C_{19}H_{19}F_3N_8O_2S$ [M+H]$^+$: 481, found 481.

EXAMPLE 565

N-(3-aminopropyl)-3'-sulfamoyl-2'-(2H-tetrazol-5-yl)-4'-(trifluoromethyl)biphenyl-4-carboximidamide

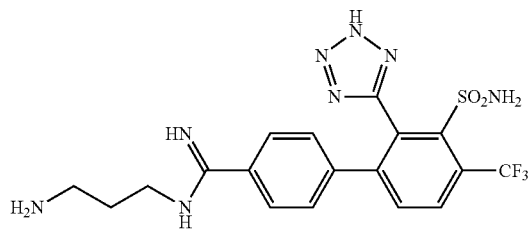 [SMILES: N=C(NCCCN)c1ccc(-c2ccc(C(F)(F)F)c(S(N)(=O)=O)c2-c2nn[nH]n2)cc1]

Step A: tert-butyl 3-(2'-(2-(4-methoxybenzyl)-2H-tetrazol-5-yl)-3'-(N-(4-methoxybenzyl)sulfamoyl)-4'-(trifluoromethyl)biphenyl-4-ylcarboximidamido)propylcarbamate To a solution of methyl 2'-(1-(4-methoxybenzyl)-1H-tetrazol-5-yl)-3'-(N-(4-methoxybenzyl)sulfamoyl)-4'-(trifluoromethyl)-[1,1'-biphenyl]-4-carbimidate (0.18 g, 0.21 mmol) in DCM (5 mL) were added DIEA (0.18 mL, 1.05 mmol) and tert-butyl (3-aminopropyl)carbamate (0.15 g, 0.84 mmol) at 0° C. under nitrogen. The mixture was stirred at ambient temperature for 36 hr under argon atmosphere. The solvent was evaporated under vacuum and the residue was purified by Prep-TLC, eluted with EtOAc/PE (1:2) to afford the crude title compound: LCMS (ESI) calc'd for $C_{39}H_{43}F_3N_8O_6S$ [M+H]$^+$: 809, found 809.

Step B: N-(3-aminopropyl)-2'-(2-(4-methoxybenzyl)-2H-tetrazol-5-yl)-3'-(N-(4-methoxybenzyl)sulfamoyl)-4'-(trifluoromethyl)biphenyl-4-carboximidamide A solution of tert-butyl (3-(2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-ylcarboximidamido)propyl)carbamate (0.20 g, 0.20 mmol) in DCM (2 mL) was added TFA (0.5 ml, 6.49 mmol) at 0° C. The resulting mixture was stirred at 0° C. for 2 hr. The solvent was evaporated under vacuum and the residue was used directly in the next step without further purification: LCMS (ESI) calc'd for $C_{34}H_{35}F_3N_8O_4S$ [M+H]$^+$: 709, found 709.

Step C: N-(3-aminopropyl)-3'-sulfamoyl-2'-(2H-tetrazol-5-yl)-4'-(trifluoromethyl)biphenyl-4-carboximidamide To a solution of N-(3-aminopropyl)-2'-(2-(4-methoxybenzyl)-2H-tetrazol-5-yl)-3'-(N-(4-methoxybenzyl)sulfamoyl)-4'-(trifluoromethyl)-[1,1'-biphenyl]-4-carboximidamide (0.18 g, 0.20 mmol) in anisole (0.5 mL) was added TFA (3 mL, 38.9 mmol) at ambient temperature. The resulting mixture was stirred at 80° C. for 3 hr. The reaction mixture was cooled down to 20° C. and the solvent was evaporated under vacuum. The residue was purified by Prep-HPLC with the following conditions: Column: X Bridge C18, 19×150 mm, 5 μm; Mobile Phase A: water (0.05% TFA), Mobile Phase B: ACN; Flow rate: 20 mL/min; Gradient: 30% B to 70% B in 10 min; Detection: at 254 nm. The collected fractions were combined and concentrated under reduced pressure to afford the title compound: LCMS (ESI) calc'd for $C_{18}H_{19}F_3N_8O_2S$ [M+H]$^+$: 469, found 469.

EXAMPLE 566

3-(2-amino-5-fluoro-1H-benzo[d]imidazol-7-yl)-2-(1H-tetrazol-5-yl)-6-(trifluoromethyl)benzenesulfonamide

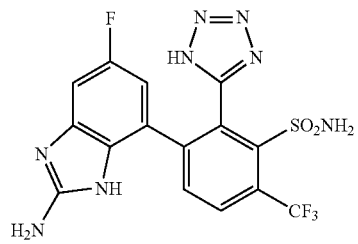 [SMILES: Nc1nc2cc(F)cc(-c3ccc(C(F)(F)F)c(S(N)(=O)=O)c3-c3nnn[nH]3)c2[nH]1]

Step A: 7-bromo-5-fluoro-1H-benzo[d]imidazol-2-amine

To a 25 mL microwave tube was added a solution of 3-bromo-5-fluorobenzene-1,2-diamine (0.410 g, 2.0 mmol) in 6 mL of methanol, followed by addition of cyanic bromide (0.254 g, 2.40 mmol) and 4 mL of water. The mixture was stirred for 16 hr. TLC showed most SM was converted. The reaction mixture was heated at 80° C. for 1 hr and no SM was left. The solvent was removed via rotavapor and the residue was purified via column chromatography (ISCO RediSep gold column, 40 g) using 0-10% MeOH/DCM as mobile phase to afford the title compound. LC-MS (M+H)$^+$: 230.08.

Step B: 3-(2-amino-5-fluoro-1H-benzo[d]imidazol-7-yl)-N,N-bis(4-methoxybenzyl)-2-(1-(4-methoxybenzyl)-1H-tetrazol-5-yl)-6-(trifluoromethyl)benzenesulfonamide and 3-(2-amino-5-fluoro-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide To a 10 mL RBF was added cesium carbonate (63.8 mg, 0.196 mmol), 7-bromo-5-fluoro-1H-benzo[d]imidazol-2-amine (15.77 mg, 0.069 mmol), 3-(5,5-dimethyl-1,3,2-dioxaborinan-2-yl)-N,N-bis(4-methoxybenzyl)-2-(2-(4-methoxybenzyl)-2H-tetrazol-5-yl)-6-trifluoromethyl) benzenesulfonamide (50 mg, 0.065 mmol) and Xphos Pd G2 (10.28 mg, 0.013 mmol). The flask was sealed, degassed, and filled with dioxane (0.8 ml) and water (0.200 ml). The resulting mixture was heated at 80° C. for overnight. The reaction mixture was filtered through a celite pad to removed palladium. The filtrate was diluted with EtOAc and washed with water. The organic layer was dried over anhydrous MgSO$_4$, filtered, concentrated and purified by silica gel column chromatography (ISCO RediSep gold column, 40 g) using 0-10% MeOH/DCM as mobile phase and the title compound was isolated. LC/MS (M+H)$^+$: 799.7.

Step C: 3-(2-amino-5-fluoro-1H-benzo[d]imidazol-7-yl)-2-(1H-tetrazol-5-yl)-6-(trifluoromethyl)benzenesulfonamide To a solution of 3-(2-amino-5-fluoro-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide (15 mg, 0.019 mmol) in DCM (200 μl) was added anisole (20 μl, 0.187 mmol) and TFA (144 μl, 1.868 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA) to afford the title compound. LC/MS (M+H)$^+$: 443.34.

EXAMPLE 567

3-(2-amino-5-(trifluoromethyl)-1H-benzo[d]imidazol-7-yl)-N,N-bis(4-methoxybenzyl)-2-(2-(4-methoxybenzyl)-2H-tetrazol-5-yl)-6-(trifluoromethyl) benzenesulfonamide

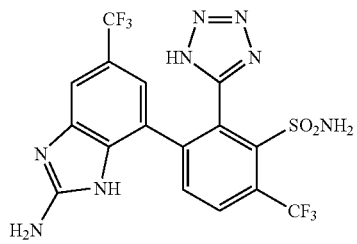 [SMILES: Nc1nc2cc(C(F)(F)F)cc(-c3ccc(C(F)(F)F)c(S(N)(=O)=O)c3-c3nnn[nH]3)c2[nH]1]

Step A: 7-bromo-5-(trifluoromethyl)-1H-benzo[d]imidazol-2-amine

To a 25 mL microwave tube was added a solution of 3-bromo-5-(trifluoromethyl)benzene-1,2-diamine (0.510 g, 2.0 mmol) in 6 mL of methanol, followed by addition of cyanic bromide (0.254 g, 2.40 mmol) and 4 mL of water. The mixture was stirred for 16 hr. TLC showed most SM was converted. The reaction mixture was heated at 80° C. for 1 hr and no SM was left. The solvent was removed via rotavapor and the residue was purified via column chromatography (ISCO RediSep gold column, 40 g) using 0-10% MeOH/DCM as mobile phase to afford the title compound. LC-MS (M+H)$^+$: 280.10.

Step B: 3-(2-amino-5-(trifluoromethyl)-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide and 3-(2-amino-5-(trifluoromethyl)-1H-benzo[d]imidazol-7-yl)-N,N-bis(4-methoxybenzyl)-2-(1-(4-methoxybenzyl)-1H-tetrazol-5-yl)-6-(trifluoromethyl) benzenesulfonamide To a 10 mL RBF was added cesium carbonate (63.8 mg, 0.196 mmol), 7-bromo-5-(trifluoromethyl)-1H-benzo[d]imidazol-2-amine (19.20 mg, 0.069 mmol), 3-(5,5-dimethyl-1,3,2-dioxaborinan-2-yl)-N,N-bis(4-methoxybenzyl)-2-(2-(4-methoxybenzyl)-2H-tetrazol-5-yl)-6-(trifluoromethyl)benzenesulfonamide (50 mg, 0.065 mmol) and Xphos Pd G2 (10.28 mg, 0.013 mmol). The flask was sealed, degassed, and filled with dioxane (0.8 ml) and water (0.2 ml). The resulting mixture was heated at 80° C. for overnight. The reaction mixture was filtered through a celite pad to removed palladium. The filtrate was diluted with EtOAc and washed with water. The organic layer was dried over anhydrous MgSO$_4$, filtered, concentrated and purified by silica gel column chromatography (ISCO RediSep gold column, 40 g) using 0-10% MeOH/DCM as mobile phase and the title compound was isolated. LC/MS (M+H)$^+$: 853.84.

Step C: 3-(2-amino-5-(trifluoromethyl)-1H-benzo[d]imidazol-7-yl)-N,N-bis(4-methoxybenzyl)-2-(2-(4-methoxybenzyl)-2H-tetrazol-5-yl)-6-(trifluoromethyl) benzenesulfonamide To a solution of 3-(2-amino-5-trifluoromethyl-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide (20 mg, 0.023 mmol) in DCM (0.2 ml) was added anisole (26 μl, 0.24 mmol) and TFA (181 μl, 2.35 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA) to afford the title compound. LC/MS (M+H)$^+$: 493.36.

EXAMPLE 568

3-(2-amino-4-methyl-1H-benzo[d]imidazol-7-yl)-2-(1H-tetrazol-5-yl)-6-(trifluoromethyl)benzenesulfonamide

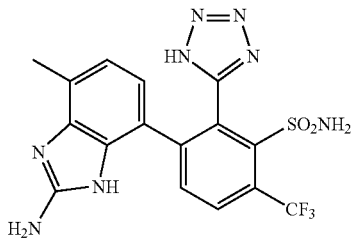 [SMILES: Cc1ccc(-c2ccc(C(F)(F)F)c(S(N)(=O)=O)c2-c2nnn[nH]2)c2[nH]c(N)nc12]

Step A: 7-bromo-4-methyl-1H-benzo[d]imidazol-2-amine

To a 25 mL microwave tube was added a solution of 3-bromo-4-methylbenzene-1,2-diamine (201 mg, 1.0 mmol) in 6 mL of methanol, followed by addition of cyanic bromide (127 mg, 1.20 mmol) and 4 mL of water. The mixture was stirred for 16 hr. TLC showed most SM was converted. The reaction mixture was heated at 80° C. for 1 hr and no SM was left. The solvent was removed via rotavapor and the residue was purified via column chromatography (ISCO RediSep gold column, 40 g) using 0-10% MeOH/DCM as mobile phase to afford the title compound. LC-MS (M+H)$^+$: 228.10.

Step B: 3-(2-amino-4-methyl-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide and 3-(2-amino-4-methyl-1H-benzo[d]imidazol-7-yl)-N,N-bis(4-methoxybenzyl)-2-(1-(4-methoxybenzyl)-1H-tetrazol-5-yl)-6-(trifluoromethyl)benzenesulfonamide To a 10 mL RBF was added cesium carbonate (63.8 mg, 0.196 mmol), 7-bromo-4-methyl-1H-benzo[d]imidazol-2-amine (15.5 mg, 0.069 mmol), 3-(5,5-dimethyl-1,3,2-dioxaborinan-2-yl)-N,N-bis(4-methoxybenzyl)-2-(2-(4-methoxybenzyl)-2H-tetrazol-5-yl)-6-(trifluoromethyl) benzenesulfonamide (and its tetrazole PMB isomer) (50 mg, 0.065 mmol) and Xphos Pd G2 (10.28 mg, 0.013 mmol). The RBF was sealed, degassed, and filled with dioxane (0.8 ml) and water (0.2 ml). The resulting mixture was heated at 80° C. for overnight, then was cooled and filtered through a celite pad to removed palladium. The filtrate was diluted with EtOAc, then was washed with water. The organic layer was dried over anhydrous MgSO$_4$, filtered, concentrated and purified by silica gel column chromatography (ISCO RediSep gold column, 40 g) using 0-10% MeOH/DCM as mobile phase to afford the title compounds. LC/MS (M+H)$^+$: 799.9.

Step C: 3-(2-amino-4-methyl-1H-benzo[d]imidazol-7-yl)-2-(1H-tetrazol-5-yl)-6-(trifluoromethyl)benzenesulfonamide To a solution of 3-(2-amino-4-methyl-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide (20 mg, 0.025 mmol) in DCM (200 µl) was added anisole (27.2 µl, 0.250 mmol) and TFA (193 µl, 2.504 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA). LC/MS (M+H)$^+$: 439.33.

EXAMPLE 569

3-(2-amino-5-cyano-1H-benzo[d]imidazol-7-yl)-2-(1H-tetrazol-5-yl)-6-(trifluoromethyl)benzenesulfonamide

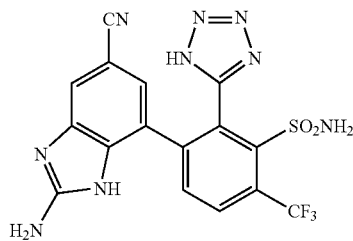 [SMILES: N#Cc1cc(-c2ccc(C(F)(F)F)c(S(N)(=O)=O)c2-c2nnn[nH]2)c2[nH]c(N)nc2c1]

Step A: 2-amino-7-bromo-1H-benzo[d]imidazole-5-carbonitrile

To a 25 mL microwave tube was added a solution of 3,4-diamino-5-bromobenzonitrile (212 mg, 1.0 mmol) in 6 mL of methanol, followed by addition of cyanic bromide (127 mg, 1.20 mmol) and 4 mL of water. The mixture was stirred for 16 hr. TLC showed most SM was converted. The reaction mixture was heated at 80° C. for 1 hr and no SM was left. The solvent was removed via rotavapor and the residue was purified via column chromatography (ISCO RediSep gold column, 40 g) using 0-10% MeOH/DCM as mobile phase to afford the title compound. LC-MS (M+H)$^+$: 238.89.

Step B: 3-(2-amino-5-cyano-1H-benzo[d]imidazol-7-yl)-N,N-bis(4-methoxybenzyl)-2-(1-(4-methoxybenzyl)-1H-tetrazol-5-yl)-6-(trifluoromethyl)benzenesulfonamide and 3-(2-amino-5-cyano-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide To a 10 mL RBF was added cesium carbonate (63.8 mg, 0.196 mmol), 2-amino-7-bromo-1H-benzo[d]imidazole-5-carbonitrile (16.26 mg, 0.069 mmol), 3-(5,5-dimethyl-1,3,2-dioxaborinan-2-yl)-N,N-bis(4-methoxybenzyl)-2-(2-(4-methoxybenzyl)-2H-tetrazol-5-yl)-6-(trifluoromethyl) benzenesulfonamide (50 mg, 0.065 mmol) and Xphos Pd G2 (10.28 mg, 0.013 mmol). The vial was sealed, degassed, and filled with Dioxane (0.8 ml) and Water (0.200 ml). The resulting mixture was heated at 80° C. overnight. The reaction mixture was filtered through a celite pad to remove palladium. The filtrate was diluted with EtOAc and washed with water. The organic layer was dried over anhydrous MgSO$_4$, filtered, concentrated and purified by silica gel column chromatography (ISCO RediSep gold column, 40 g) using 0-20% MeOH/DCM as mobile phase to afford the title compound. LC/MS (M+H)$^+$: 810.8.

Step C: 3-(2-amino-5-cyano-1H-benzo[d]imidazol-7-yl)-2-(1H-tetrazol-5-yl)-6-(trifluoromethyl)benzenesulfonamide To a solution of 3-(2-amino-5-cyano-1H-benzo[d]imidazol-7-yl)-N,N-bis(4-methoxybenzyl)-2-(1-(4-methoxybenzyl)-1H-tetrazol-5-yl)-6-(trifluoromethyl)benzenesulfonamide and 3-(2-amino-5-cyano-1H-benzo[d]imidazol-7-yl)-N,N-bis(4-methoxybenzyl)-2-(2-(4-methoxybenzyl)-2H-tetrazol-5-yl)-6-(trifluoromethyl)benzenesulfonamide (20 mg, 0.025 mmol) in DCM (200 µl) was added anisole (26.8 µl, 0.247 mmol) and TFA (190 µl, 2.470 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA). LC/MS (M+H)$^+$: 450.37.

EXAMPLE 570

3-(2-amino-1H-imidazo[4,5-b]pyridin-7-yl)-2-(1H-tetrazol-5-yl)-6-(trifluoromethyl)benzenesulfonamide

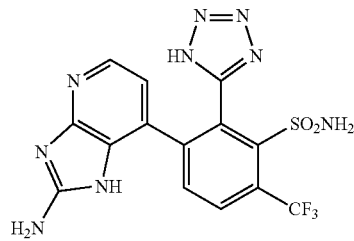 [SMILES: Nc1nc2nccc(-c3ccc(C(F)(F)F)c(S(N)(=O)=O)c3-c3nnn[nH]3)c2[nH]1]

Step A: 3-(2,3-diaminopyridin-4-yl)-N,N-bis(4-methoxybenzyl)-2-(1-(4-methoxybenzyl)-1H-tetrazol-5-yl)-6-(trifluoromethyl)benzenesulfonamide and 3-(2,3-diaminopyridin-4-yl)-N,N-bis(4-methoxybenzyl)-2-(2-(4-methoxybenzyl)-2H-tetrazol-5-yl)-6-(trifluoromethyl)benzenesulfonamide To a 10 mL RBF was added cesium carbonate (280 mg, 0.860 mmol), 2-bromopyridine-3,4-diamine (53.9 mg, 0.287 mmol), (3-(N,N-bis(4-methoxybenzyl)sulfamoyl)-2-(2-(4-methoxybenzyl)-2H-tetrazol-5-yl)-4-(trifluoromethyl)phenyl)boronic acid (200 mg, 0.287 mmol) and Xphos Pd G2 (22.56 mg, 0.029 mmol). The vial was sealed, degassed, and filled with dioxane (2.4 ml) and water (0.6 ml). The resulting mixture was heated at 80° C. for 2 hr. The reaction mixture was filtered through a celite pad. The filtrate was diluted with EtOAc and washed with water. The organic layer was dried over anhydrous MgSO$_4$, filtered, concentrated and purified by silica gel column chromatography (ISCO RediSep gold column, 24 g) using 0-10% MeOH/DCM as mobile phase (3% and 6% isostatic) to afford the title compound. LC/MS (M+H)$^+$: 761.37.

Step B: 3-(2-amino-1H-imidazo[4,5-b]pyridin-7-yl)-N,N-bis(4-methoxybenzyl)-2-(1-(4-methoxybenzyl)-1H-tetrazol-5-yl)-6-(trifluoromethyl)benzenesulfonamide and 3-(2-amino-1H-imidazo[4,5-b]pyridin-7-yl)-N,N-bis(4-methoxybenzyl)-2-(2-(4-methoxybenzyl)-2H-tetrazol-5-yl)-6-(trifluoromethyl)benzenesulfonamide To a 10 mL microwave tube was added a solution of 3-(2,3-diaminopyridin-4-yl)-N,N-bis(4-methoxybenzyl)-2-(1-(4-methoxybenzyl)-1H-tetrazol-5-yl)-6-(trifluoromethyl)benzenesulfonamide and 3-(2,3-diaminopyridin-4-yl)-N,N-bis(4-methoxybenzyl)-2-(2-(4-methoxybenzyl)-2H-tetrazol-5-yl)-6-(trifluoromethyl)benzenesulfonamide (82 mg, 0.108 mmol) and di(1H-imidazol-1-yl)methanimine (17.37 mg, 0.108 mmol) in 2 mL of DMF. The mixture was refluxed at 120° C. for overnight. LC-MS showed formation of the desired product. DMF was removed under vacuum and the residual was chromatographed by silica gel column chromatography (ISCO RediSep gold column 24 g) using 0-20% methanol/DCM as mobile phase to afford the title compound. LC/MS (M+H)$^+$: 786.78.

Step C: 3-(2-amino-1H-imidazo[4,5-b]pyridin-7-yl)-2-(1H-tetrazol-5-yl)-6-(trifluoromethyl)benzenesulfonamide To a solution of 3-(2-amino-1H-imidazo[4,5-b]pyridin-7-yl)-N,N-bis(4-methoxybenzyl)-2-(2-(4-methoxybenzyl)-2H-tetrazol-5-yl)-6-(trifluoromethyl)benzenesulfonamide (17 mg, 0.022 mmol) in DCM (0.2 mL) was added anisole (23.51 µL, 0.216 mmol) and TFA (167 µL, 2.163 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA) to afford the title compound. LC/MS (M+H)$^+$: 426.38.

EXAMPLE 571

3-(2-amino-1H-imidazo[4,5-c]pyridin-7-yl)-2-(1H-tetrazol-5-yl)-6-(trifluoromethyl)benzenesulfonamide

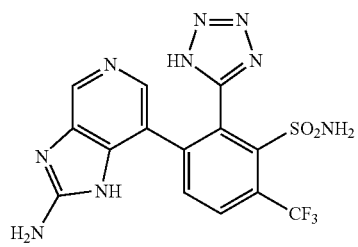 [SMILES: Nc1nc2cncc(-c3ccc(C(F)(F)F)c(S(N)(=O)=O)c3-c3nnn[nH]3)c2[nH]1]

Step A: 3-(4,5-diaminopyridin-3-yl)-N,N-bis(4-methoxybenzyl)-2-(1-(4-methoxybenzyl)-1H-tetrazol-5-yl)-6-(trifluoromethyl)benzenesulfonamide and 3-(4,5-diaminopyridin-3-yl)-N,N-bis(4-methoxybenzyl)-2-(2-(4-methoxybenzyl)-2H-tetrazol-5-yl)-6-(trifluoromethyl)benzenesulfonamide To a 10 ml RBF was added cesium carbonate (140 mg, 0.430 mmol), 5-bromopyridine-3,4-diamine (27.0 mg, 0.143 mmol), (3-(N,N-bis(4-methoxybenzyl)sulfamoyl)-2-(2-(4-methoxybenzyl)-2H-tetrazol-5-yl)-4-(trifluoromethyl)phenyl)boronic acid (100 mg, 0.143 mmol) and Xphos Pd G2 (11.28 mg, 0.014 mmol). The RBF was sealed, degassed, and filled with dioxane (1.2 ml) and water (0.3 ml). The resulting mixture was heated at 80° C. for 2 hr. The reaction mixture was filtered through a celite pad. The filtrate was diluted with EtOAc and washed with water. The organic layer was dried over anhydrous MgSO$_4$, filtered, concentrated and purified by silica gel column chromatography (ISCO RediSep gold column, 24 g) using 0-10% MeOH/DCM as mobile phase (3% and 6% isostatic) to afford the title compounds. LC/MS (M+H)$^+$: 761.71.

Step B: 3-(2-amino-1H-imidazo[4,5-c]pyridin-7-yl)-N,N-bis(4-methoxybenzyl)-2-(1-(4-methoxybenzyl)-1H-tetrazol-5-yl)-6-(trifluoromethyl)benzenesulfonamide and 3-(2-amino-1H-imidazo[4,5-c]pyridin-7-yl)-N,N-bis(4-methoxybenzyl)-2-(2-(4-methoxybenzyl)-2H-tetrazol-5-yl)-6-(trifluoromethyl)benzenesulfonamide To a 10 mL sealed tube was added a solution of 3-(4,5-diaminopyridin-3-yl)-N,N-bis(4-methoxybenzyl)-2-(1-(4-methoxybenzyl)-1H-tetrazol-5-yl)-6-(trifluoromethyl)benzenesulfonamide and 3-(4,5-diaminopyridin-3-yl)-N,N-bis(4-methoxybenzyl)-2-(2-(4-methoxybenzyl)-2H-tetrazol-5-yl)-6-(trifluoromethyl)benzenesulfonamide (42 mg, 0.055 mmol) and di(1H-imidazol-1-yl)methanimine (8.90 mg, 0.055 mmol) in DMF (3 mL). The mixture was stirred for overnight at 120° C. The solvent was removed in vacuum and the residue was purified by column chromatography (ISCO RediSep Gold column 24 g) using 0-20% methanol/DCM as mobile phase to afford the title compounds. LC/MS (M+H)$^+$: 786.68.

Step C: 3-(2-amino-1H-imidazo[4,5-c]pyridin-7-yl)-2-(1H-tetrazol-5-yl)-6-(trifluoromethyl)benzenesulfonamide To a solution of 3-(2-amino-1H-imidazo[4,5-c]pyridin-7-yl)-N,N-bis(4-methoxybenzyl)-2-(2-(4-methoxybenzyl)-2H-tetrazol-5-yl)-6-(trifluoromethyl)benzenesulfonamide (17 mg, 0.022 mmol) in DCM (0.2 ml) was added anisole (23.51 µl, 0.216 mmol) and TFA (167 µl, 2.163 mmol) at 0° C. The reaction mixture was stirred at 80° C. for 1 hr. After removing the volatile, the residue was dissolved in 1 mL of DMSO and purified by Gilson using 3 to 60% water (0.05% TFA) in acetonitrile (0.05% TFA). LC/MS (M+H)$^+$: 426.48.

EXAMPLE 572

3-((6-amino-2-methylpyridin-3-yl)methyl)-2-(2H-tetrazol-5-yl)benzenesulfonamide

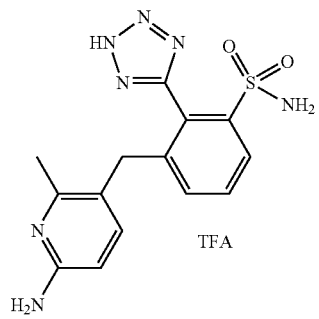 [SMILES: Cc1nc(N)ccc1Cc1cccc(S(N)(=O)=O)c1-c1nn[nH]n1]

Step A: N,N-bis(4-methoxybenzyl)-2-(2-(4-methoxybenzyl)-2H-tetrazol-5-yl)-3-vinylbenzenesulfonamide Into a 100 mL three necked round bottom flask was placed a solution of 3-bromo-N,N-bis(4-methoxybenzyl)-2-(2-(4-methoxybenzyl)-2H-tetrazol-5-yl)benzenesulfonamide (1.00 g, 1.51 mmol), potassium vinyltrifluoroborate (0.40 g, 3.01 mmol), PdCl$_2$(dppf) (0.11 g, 0.15 mmol) and Na$_2$CO$_3$ (0.48 g, 4.51 mmol) in dioxane (12 mL) and water (2.5 mL). The resulting mixture was degassed with nitrogen for 3 times and stirred for overnight at 90° C. The solvent was removed under reduced pressure. The residue was diluted with EtOAc (100 mL), washed with water (2×30 mL) and brine (30 mL), dried over anhydrous $Na_2SO_4$ and filtered. The filtrate was concentrated under reduced and the residue was purified by silica gel column chromatography, eluted with EtOAc/PE (1:2) to give the title compound: LCMS (ESI) calc'd for $C_{33}H_{33}N_5O_5S$ [M+H]$^+$: 612, found 612;

Step B: 3-formyl-N,N-bis(4-methoxybenzyl)-2-(2-(4-methoxybenzyl)-2H-tetrazol-5-yl)benzenesulfonamide Into a 100 mL round bottom flask was placed a solution of N,N-bis(4-methoxybenzyl)-2-(2-(4-methoxybenzyl)-2H-tetrazol-5-yl)-3-vinylbenzenesulfonamide (0.65 g, 1.06 mmol) and 4-methylmorpholine N-oxide (0.16 g, 1.38 mmol) in ACN (9 mL) and water (1.8 mL) followed by the additional of a solution of $OsO_4$ (30 mg) in water (0.5 mL) with stirring at ambient temperature. After the resulting mixture was stirred at ambient temperature for 1 hr, $NaIO_4$ (0.68 g, 3.19 mmol) was added and the resulting mixture was stirred at ambient temperature for 1 hr. The reaction mixture with heavy precipitate was filtered through celite, washed with EtOAc (20 mL). The combined organic layers were concentrated under vacuum to give the title compound: LCMS (ESI) calc'd for $C_{32}H_{31}N_5O_6S$ [M+H]$^+$: 614, found 614;

Step C: 3-(hydroxymethyl)-N,N-bis(4-methoxybenzyl)-2-(2-(4-methoxybenzyl)-2H-tetrazol-5-yl)benzenesulfonamide Into a 100 mL round bottom flask was placed a solution of 3-formyl-N,N-bis(4-methoxybenzyl)-2-(2-(4-methoxybenzyl)-2H-tetrazol-5-yl)benzenesulfonamide (0.63 g, 1.03 mmol) in MeOH (10 mL), $NaBH_4$ (78 mg, 2.06 mmol) was added in portions at 0° C. The reaction mixture was stirred at ambient temperature for 1 hr and then quenched with ice water (5 mL), diluted with water (10 mL) and extracted with ethyl acetate (3×20 mL). The combined organic layers were washed with water (30 mL) and brine (30 mL), dried over anhydrous $Na_2SO_4$ and filtered. The filtrate was concentrated under reduced pressure. The residue was purified by silica gel column chromatography, eluting with EtOAc/PE (2:1) to give the title compound: LCMS (ESI) calc'd for $C_{32}H_{33}N_5O_6S$ [M+H]$^+$: 616, found 616;

Step D: 3-(bromomethyl)-N,N-bis(4-methoxybenzyl)-2-(2-(4-methoxybenzyl)-2H-tetrazol-5-yl)benzenesulfonamide Into a 100 mL round bottom flask was placed a solution of 3-(hydroxymethyl)-N,N-bis(4-methoxybenzyl)-2-(2-(4-methoxybenzyl)-2H-tetrazol-5-yl)benzenesulfonamide (0.43 g, 0.70 mmol) in DCM (10 mL). To this solution was added $PBr_3$ (0.20 mL, 2.01 mmol) with stirring at 0° C. The resulting mixture was stirred at ambient temperature for 30 min. and then quenched with water (5 mL), diluted with water (10 mL) and extracted with EtOAc (3×20 mL). The combined organic layers were washed with water (20 mL), brine (20 mL), dried over anhydrous $Na_2SO_4$ and filtered. The filtrate was concentrated under reduced pressure and the residue was purified by silica gel column chromatography, eluted with EtOAc/PE (1:3) to give the title compound: LCMS (ESI) calc'd for $C_{32}H_{32}BrN_5O_5S$ [M+H]$^+$: 678, 680 (1:1), found 678, 680 (1:1);

Step E: 3-((6-amino-2-methylpyridin-3-yl)methyl)-N,N-bis(4-methoxybenzyl)-2-(2-(4-methoxybenzyl)-2H-tetrazol-5-yl)benzenesulfonamide Into a 50 mL three necked round bottom flask were placed 3-(bromomethyl)-N,N-bis(4-methoxybenzyl)-2-(2-(4-methoxybenzyl)-2H-tetrazol-5-yl)benzenesulfonamide (0.27 g, 0.40 mmol), 6-methyl-5-(4,4,5,5-tetramethyl-1,3,2-dioxaborolan-2-yl)pyridin-2-amine (0.14 g, 0.60 mmol), $PdCl_2(dppf)$ (29 mg, 0.04 mmol) and $Na_2CO_3$ (0.13 g, 1.20 mmol) in Dioxane (5 mL) and water (1.0 mL). The reaction mixture was degassed with nitrogen for 3 times and stirred for 4 hr at 80° C. The resulting mixture was poured into water (5 mL), extracted with EtOAc (3×15 mL). The combined organic layers were washed with water (15 mL), brine (15 mL), dried over anhydrous $Na_2SO_4$ and filtered. The filtrate was concentrated under reduced pressure and the residue was purified by silica gel column chromatography, eluted with EtOAc/PE (1:1) to give the title compound: LCMS (ESI) calc'd for $C_{38}H_{39}N_7O_5S$ [M+H]$^+$: 706, found 706;

Step F: 3-((6-amino-2-methylpyridin-3-yl)methyl)-2-(2H-tetrazol-5-yl)benzenesulfonamide Into a 50 mL round bottom flask was placed a solution of 3-((6-amino-2-methylpyridin-3-yl)methyl)-N,N-bis(4-methoxybenzyl)-2-(2-(4-methoxybenzyl)-2H-tetrazol-5-yl)benzenesulfonamide (0.20 g, 0.28 mmol) in DCM (2.0 mL), anisole (2.0 mL) and TFA (4.0 mL). The resulting mixture was stirred at 85° C. for 16 hr. The solvent was removed under reduced and the residue was purified by Prep-HPLC with the following conditions: Column: T 3, 19×150 mm, 5 μm; Mobile Phase A: water (0.05% TFA), Mobile Phase B: ACN; Flow rate: 20 mL/min; Gradient: 5% B to 30% B in 8 min; Detection: UV 254 nm. The collected fractions were combined and concentrated under reduced pressure to give the title compound: LCMS (ESI) calc'd for $C_{14}H_{15}N_7O_2S$ [M+H]$^+$: 346, found 346;

EXAMPLE 573

3-((6-amino-4-methylpyridin-3-yl)methyl)-2-(2H-tetrazol-5-yl)benzenesulfonamide

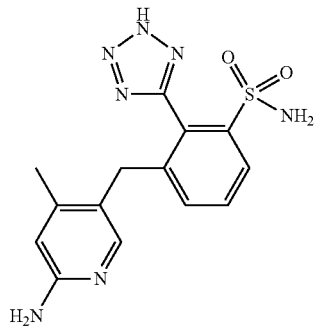 [SMILES: Cc1cc(N)ncc1Cc1cccc(S(N)(=O)=O)c1-c1nn[nH]n1]

Step A: 3-((6-amino-4-methylpyridin-3-yl)methyl)-N,N-bis(4-methoxybenzyl)-2-(2-(4-methoxybenzyl)-2H-tetrazol-5-yl)benzenesulfonamide To a stirred solution of 3-(bromomethyl)-N,N-bis(4-methoxybenzyl)-2-(2-(4-methoxybenzyl)-2H-tetrazol-5-yl)benzene sulfonamide (0.20 g, 0.30 mmol) in dioxane/water (4/1) (5 ml) were added 1,1'-bis(diphenyl phosphino)ferrocene]dichloropalladium (22 mg, 0.03 mmol), 4-methyl-5-(4,4,5,5-tetramethyl-1,3,2-dioxaborolan-2-yl) pyridin-2-amine (0.10 g, 0.44 mmol), $Na_2CO_3$ (94 mg, 0.88 mmol) at ambient temperature. After the resulting mixture was degassed with nitrogen for 3 times and stirred at 80° C. for 2 hr under nitrogen, it was cooled down to room temperature and the solids were filtered out. The filtrate was concentrated and the residue was purified by silica gel column chromatography, eluteding with EtOAc/PE (10/1) to give the title compound: LCMS (ESI) calc'd for $C_{38}H_{39}N_7O_5S$ [M+H]$^+$: 706, found 706.

Step B: 3-((6-amino-4-methylpyridin-3-yl)methyl)-2-(2H-tetrazol-5-yl)benzenesulfonamide To a stirred solution of 3-((6-amino-4-methylpyridin-3-yl)methyl)-N, N-bis(4-methoxybenzyl)-2-(2-(4-methoxybenzyl)-2H-tetrazol-5-yl) benzenesulfonamide (0.16 g, 0.18 mmol) in DCM (2 ml) and anisole (2 ml) was added TFA (0.10 g, 0.89 mmol) at ambient temperature. The resulting mixture was stirred at 80° C. for 16 hr and then concentrated under reduced pressure. The residue was purified by Prep-HPLC with the following conditions: Column, Xbridge C18, 19×150 mm; mobile phase: water (0.05% TFA) and acetonitrile (hold 34% acetonitrile for 8 min, hold 100% for 2 min, down to 34% in 2 min); Detector, UV 220 and 254 nm; retention time: 6.18 min. The collected fractions were combined and concentrated under reduced pressure to afford 30 mg (37%) of 3-((6-amino-4-methylpyridin-3-yl)methyl)-2-(2H-tetrazol-5-yl)benzenesulfonamide 2,2,2-trifluoroacetate as a colorless solid: LCMS (ESI) calc'd for $C_{14}H_{15}N_7O_2S$ [M+H]$^+$: 346, found 346.

EXAMPLE 574

6-(((1s,4s)-4-aminocyclohexyl)methyl)-3-(6-aminopyridin-3-yl)-2-(2H-tetrazol-5-yl)benzenesulfonamide

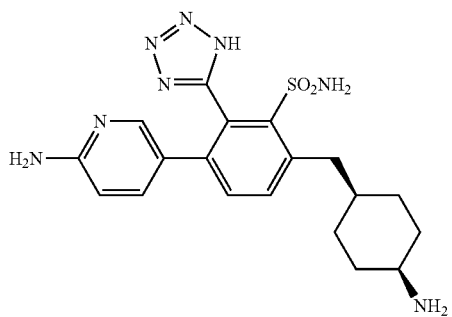 [SMILES: Nc1ccc(-c2ccc(C[C@H]3CC[C@@H](N)CC3)c(S(N)(=O)=O)c2-c2nnn[nH]2)cn1]

Step A: 3-(6-aminopyridin-3-yl)-6-bromo-N,N-bis(4-methoxybenzyl)-2-(2-(4-methoxybenzyl)-2H-tetrazol-5-yl)benzenesulfonamide Into a 100-mL round bottom flask was placed a solution of 6-bromo-3-iodo-N,N-bis(4-methoxybenzyl)-2-(2-(4-methoxybenzyl)-2H-tetrazol-5-yl)benzenesulfonamide (2.00 g, 2.53 mmol), 5-(4,4,5,5-tetramethyl-1,3,2-dioxaborolan-2-yl)pyridin-2-amine (0.89 g, 4.05 mmol) and Pd(PPh$_3$)$_4$ (0.29 g, 0.25 mmol) and Na$_2$CO3 (0.81 g, 7.59 mmol) in dioxane (40 mL) and water (8 mL) at ambient temperature. The resulting mixture was degassed with nitrogen and stirred at 80° C. for 16 hr under nitrogen and then quenched with water (200 mL) and extracted with EtOAC (3×200 mL). The combined organics were washed with brine (500 mL), dried over anhydrous Na$_2$SO$_4$ and filtered. The filtrate was evaporated under reduced pressure and the residue was purified by a silica gel column chromatography, eluted with EtOAc/petroleum ether (4/1) to afford the title compound: LCMS (ESI) calc'd for $C_{36}H_{34}BrN_7O_5S$ [M+H]$^+$: 756, 758 (1:1), found 756, 758 (1:1).

Step B: 3-(6-(bis(4-methoxybenzyl)amino)pyridin-3-yl)-6-bromo-N,N-bis(4-methoxybenzyl)-2-(2-(4-methoxybenzyl)-2H-tetrazol-5-yl)benzenesulfonamide To a stirred solution of 3-(6-aminopyridin-3-yl)-6-bromo-N,N-bis(4-methoxybenzyl)-2-(2-(4-methoxybenzyl)-2H-tetrazol-5-yl)benzenesulfonamide (2.00 g, 2.64 mmol) in DMF (30 mL) was added NaH (0.19 g, 7.93 mmol) at 0° C. The resulting mixture was stirred for 30 min at ambient temperature, and then 4-methoxybenzyl bromide (1.59 g, 7.93 mmol) was added dropwise at 0° C. After the resulting mixture was stirred for 3 hours at ambient temperature, the reaction was quenched with water (20 mL) and extracted with EtOAc (3×20 mL). The combined organic layers were washed with brine (2×20 mL), dried over anhydrous Na$_2$SO$_4$ and filtered. The filtrate was concentrated under reduced pressure and the residue was purified by silica gel chromatography, eluted with EtOAc/PE (1/3) to give the title compound: LCMS (ESI) calc'd for $C_{52}H_{50}BrN_7O_7S$ [M+H]$^+$: 996, 998 (1:1), found 996, 998 (1:1).

Step C: tert-butyl (1s,4s)-4-(4-(6-(bis(4-methoxybenzyl)amino)pyridin-3-yl)-2-(N,N-bis(4-methoxybenzyl)sulfamoyl)-3-(2-(4-methoxybenzyl)-2H-tetrazol-5-yl)benzyl)cyclohexylcarbamate Into a 50 mL round bottom flask was placed a solution of 3-(6-(bis(4-methoxybenzyl)amino)pyridin-3-yl)-6-bromo-N,N-bis(4-methoxybenzyl)-2-(2-(4-methoxybenzyl)-2H-tetrazol-5-yl)benzenesulfonamide (0.20 g, 0.20 mmol), tert-butyl ((1S,4S)-4-(iodomethyl)cyclohexyl)carbamate (0.14 g, 0.40 mmol), Mn (22 mg, 0.40 mmol), NiI$_2$ (12 mg, 0.04 mmol), bathophenanthroline (10 mg, 0.03 mmol) and benzonitrile (4 mg, 0.04 mmol) in DMA (1.2 mL). The resulting mixture was degassed with nitrogen for 3 times, then TMSCl (5 µL, 0.04 mmol) was added at 0° C. and stirred for 2 hr at 60° C. The reaction mixture was quenched with water (10 mL) and extracted with EtOAc (3×5 mL). The combined organic layers were washed with water (25 mL), brine (25 mL), dried over anhydrous Na$_2$SO$_4$ and filtered. The filtrate was concentrated under vacuum and the residue was purified by Prep-HPLC with the following conditions: Column: X Bridge RP18, 19×150 mm, 5 µm; Mobile Phase A: water (0.05% TFA), Mobile Phase B: ACN; Flow rate: 20 mL/min; Gradient: 52% B to 90% B in 10 min; Detection: UV 254 nm. The collected fractions were concentrated under vacuum to afford the title compound: LCMS (ESI) calc'd for $C_{64}H_{72}N_8O_9S$ [M+H]$^+$: 1129, found 1129.

Step D: 6-(((1s,4s)-4-aminocyclohexyl)methyl)-3-(6-aminopyridin-3-yl)-2-(2H-tetrazol-5-yl)benzenesulfonamide Into a 10 mL round bottom flask was placed a solution of tert-butyl ((1s,4s)-4-(4-(6-(bis(4-methoxybenzyl)amino)pyridin-3-yl)-2-(N,N-bis(4-methoxybenzyl)sulfamoyl)-3-(2-(4-methoxybenzyl)-2H-tetrazol-5-yl)benzyl)cyclohexyl)carbamate (0.15 g, 0.13 mmol) in DCM (2 mL), TFA (1 mL, 26.00 mmol) was added. After the resulting mixture was stirred at ambient temperature for 2 hr, the solvent was removed under vacuum. The residue was dissolved in DCM (0.5 mL), and then anisole (1 mL) and trifluoroacetic acid (2 mL, 26.0 mmol) was added sequentially. The resulting mixture was stirred at 80° C. for 16 hr. The solvent was removed under reduced pressure and the residue was purified by Prep-HPLC with the following conditions: Column: X Bridge RP18, 19×150 mm, 5 µm; Mobile Phase A: water (0.05% NH$_4$HCO$_3$), Mobile Phase B: ACN; Flow rate: 20 mL/min; Gradient: 5% B to 16% B in 7 min; Detection: UV 254 nm. The collected fractions were concentrated under reduced pressure to afford the title compound: LCMS (ESI) calc'd for $C_{19}H_{24}N_8O_2S$ [M+H]$^+$: 429, found 429.

EXAMPLES 575-581

In the similar way to 6-(((1s,4s)-4-aminocyclohexyl)methyl)-3-(6-aminopyridin-3-yl)-2-(2H-tetrazol-5-yl)benzenesulfonamide, the following compounds were synthesized starting from 3-(6-(bis(4-methoxybenzyl)amino)pyridin-3-yl)-6-bromo-N,N-bis(4-methoxybenzyl)-2-(2-(4-methoxybenzyl)-2H-tetrazol-5-yl)benzenesulfonamide and using alkyl halides prepared as described above.

| Ex. No. | Structure | Name | Calc'd. MW [M + H]+ | LC/MS m/e [M + H]+ |
|---|---|---|---|---|
| 575 | 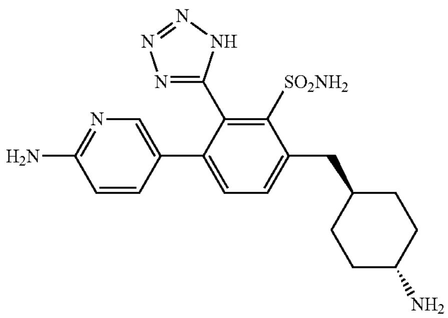 [SMILES: Nc1ccc(-c2ccc(C[C@H]3CC[C@H](N)CC3)c(S(N)(=O)=O)c2-c2nnn[nH]2)cn1] | 6-(((1r,4r)-4-aminocyclohexyl)methyl)-3-(6-aminopyridin-3-yl)-2-(1H-tetrazol-5-yl)benzenesulfonamide | 429.17 | 429.1 |
| 576 | 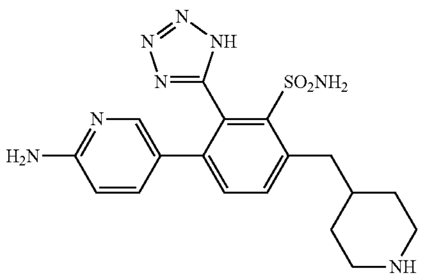 [SMILES: Nc1ccc(-c2ccc(CC3CCNCC3)c(S(N)(=O)=O)c2-c2nnn[nH]2)cn1] | 3-(6-amino-3-pyridyl)-6-(4-piperidylmethyl)-2-(1H-tetrazol-5-yl)benzenesulfonamide | 415.48 | 441.5 |
| 577 | 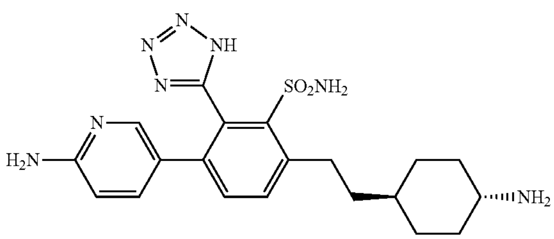 [SMILES: Nc1ccc(-c2ccc(CC[C@H]3CC[C@H](N)CC3)c(S(N)(=O)=O)c2-c2nnn[nH]2)cn1] | 6-(2-((1r,4s)-4-aminocyclohexyl)ethyl)-3-(6-aminopyridin-3-yl)-2-(1H-tetrazol-5-yl)benzenesulfonamide | 443.19 | 443.2 |
| 578 | 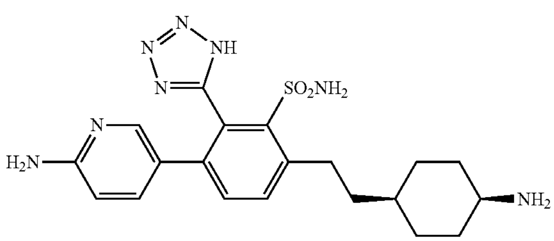 [SMILES: Nc1ccc(-c2ccc(CC[C@H]3CC[C@@H](N)CC3)c(S(N)(=O)=O)c2-c2nnn[nH]2)cn1] | 6-(2-((1s,4r)-4-aminocyclohexyl)ethyl)-3-(6-amino-3-pyridyl)-2-(1H-tetrazol-5-yl)benzenesulfonamide | 442.19 | 443.2 |
| 579 | 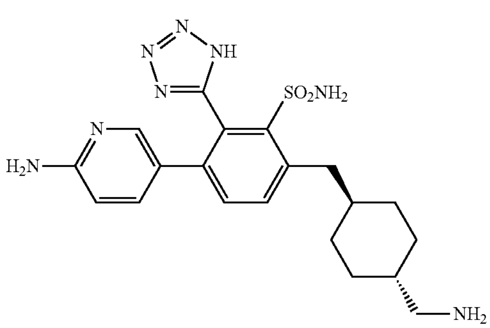 [SMILES: NC[C@H]1CC[C@H](Cc2ccc(-c3ccc(N)nc3)c(-c3nnn[nH]3)c2S(N)(=O)=O)CC1] | 6-(((1r,4r)-4-(aminomethyl)cyclohexyl)methyl)-3-(6-aminopyridin-3-yl)-2-(1H-tetrazol-5-yl)benzenesulfonamide | 443.19 | 443.1 |

| Ex. No. | Structure | Name | Calc'd. MW [M + H]+ | LC/MS m/e [M + H]+ |
|---|---|---|---|---|
| 580 | 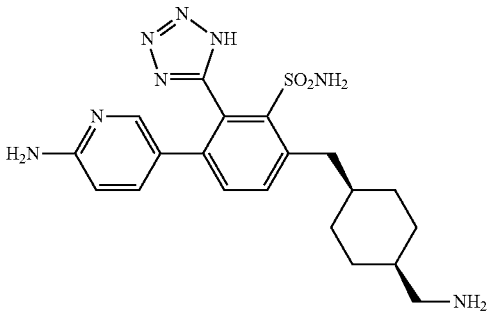 [SMILES: NC[C@H]1CC[C@@H](Cc2ccc(-c3ccc(N)nc3)c(-c3nnn[nH]3)c2S(N)(=O)=O)CC1] | 6-(((1s,4s)-4-(aminomethyl)cyclohexyl)methyl)-3-(6-aminopyridin-3-yl)-2-(1H-tetrazol-5-yl)benzenesulfonamide | 443.19 | 443.2 |
| 581 | 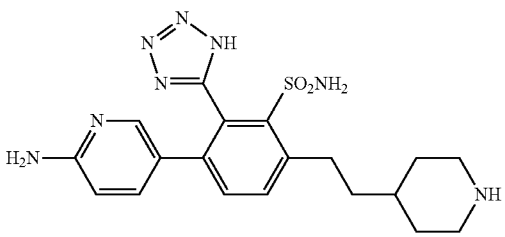 [SMILES: Nc1ccc(-c2ccc(CCC3CCNCC3)c(S(N)(=O)=O)c2-c2nnn[nH]2)cn1] | 3-(6-aminopyridin-3-yl)-6-(2-(piperidin-4-yl)ethyl)-2-(1H-tetrazol-5-yl)benzenesulfonamide | 429 | 429 |

EXAMPLE 582

4-(((1r,4r)-4-aminocyclohexyl)methyl)-4'-(pyrrolidin-3-yl)-2-(2H-tetrazol-5-yl)-[1,1'-biphenyl]-3-sulfonamide

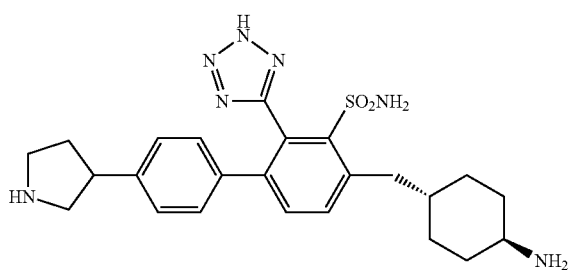 [SMILES: NS(=O)(=O)c1c(C[C@H]2CC[C@H](N)CC2)ccc(-c2ccc(C3CCNC3)cc2)c1-c1nn[nH]n1]

Step A: tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)pyrrolidine-1-carboxylate Into a 50-mL round bottom flask was added a solution of sodium carbonate (0.40 g, 3.79 mmol) in dioxane (10 mL)/water (2.5 mL) (v/v 4:1) at ambient temperature. Then tetrakis(triphenylphosphine)palladium(0) (0.15 g, 0.13 mmol), tert-butyl 3-(4-(4,4,5,5-tetramethyl-1,3,2-dioxaborolan-2-yl)phenyl)pyrrolidine-1-carboxylate (0.76 g, 2.02 mmol) and 6-bromo-3-iodo-N,N-bis(4-methoxybenzyl)-2-(2-(4-methoxybenzyl)-2H-tetrazol-5-yl)benzenesulfonamide (1.00 g, 1.26 mmol) were added sequentially. The resulting mixture was degassed with nitrogen for 3 times and then stirred for 4 hr at 100° C. under nitrogen. The resulting mixture was quenched and extracted by EtOAc (3×20 mL). The organic layers were combined and concentrated under reduced pressure. The residue was purified by a silica gel column chromatography, eluted with EtOAc/DCM/petroleum ether (1/1/5) to afford the title compound: LCMS (ESI) calc'd for $C_{46}H_{49}BrN_6O_7S$ [M+H]+: 909, 911 (1:1), found 909, 911 (1:1).

Step B: tert-butyl 3-(3'-(N,N-bis(4-methoxybenzyl)sulfamoyl)-4'-(((1r,4r)-4-(tert-butoxycarbonylamino)cyclohexyl)methyl)-2'-(2-(4-methoxybenzyl)-2H-tetrazol-5-yl)biphenyl-4-yl)pyrrolidine-1-carboxylate Into a 50 mL round bottom flask were placed tert-butyl 3-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)pyrrolidine-1-carboxylate (0.30 g, 0.33 mmol), tert-butyl ((1R,4R)-4-(iodomethyl)cyclohexyl)carbamate (0.45 g, 1.32 mmol), bathophenanthroline (16 mg, 0.049 mmol), manganese (36 mg, 0.659 mmol), nickel (II) iodide (21 mg, 0.07 mmol), and dry pyridine (5 µL, 0.07 mmol) in DMA (2 mL). The resulting mixture was degassed with nitrogen for 3 times and stirred for 18 hr at 80° C. The reaction mixture was quenched with water (5 mL) and extracted with EtOAc (3×15 mL). The combined organic layers were washed with water (15 mL) and brine (15 mL), dried over anhydrous sodium sulfate and filtered. The filtrate was concentrated under vacuum. The residue was purified by Prep-TLC with EtOAc/DCM/petroleum ether (1/1/2) to give the title compound: LCMS (ESI) calc'd for $C_{58}H_{71}N_7O_9S$ [M+H]+: 1042, found 1042.

Step C: 4-(((1r,4r)-4-aminocyclohexyl)methyl)-4'-(pyrrolidin-3-yl)-2-(2H-tetrazol-5-yl)-[1,1'-biphenyl]-3-sulfonamide Into a 50 mL three necked round bottom flask were placed a solution of tert-butyl 3-(3'-(N,N-bis(4-methoxybenzyl)sulfamoyl)-4'-(((1R,4R)-4-((tert-butoxycarbonyl)amino)cyclohexyl)methyl)-2'-(2-(4-methoxybenzyl)-2H-tetrazol-5-yl)-[1,1'-biphenyl]-4-yl)pyrrolidine-1-carboxylate (0.11 g, 0.11 mmol) in DCM (2 mL), trifluoroacetic acid (2 mL, 26.00 mmol). The resulting mixture was stirred at ambient temperature for 2 hr and then the solvent was removed under reduced pressure. The residue was dissolved in DCM (1 mL), and then Anisole (1 mL, 0.11 mmol), trifluoroacetic acid (2 mL, 26.0 mmol) was added sequentially. After the reaction mixture was stirred at 80° C. for 16 hr, the solvent was removed under reduced pressure. The residue was purified by Prep-HPLC with the following conditions: Column: X Bridge C18, 19×150 mm, 5 nm; Mobile Phase A: water (0.05% TFA), Mobile Phase B: ACN; Flow rate: 20 mL/min; Gradient: 30% B to 70% B in 10 min; Detection: UV 254 nm. The collected fractions were combined and concentrated under reduced pressure to afford the title compound: LCMS (ESI) calc'd for $C_{24}H_{31}N_7O_2S$ [M+H]$^+$: 482, found 482.

EXAMPLES 583-588

In the similar way to 4-(((1r,4r)-4-aminocyclohexyl)methyl)-4'-(pyrrolidin-3-yl)-2-(2H-tetrazol-5-yl)-[1,1'-biphenyl]-3-sulfonamide, the following compounds were synthesized starting from tert-butyl 3-(3'-(N,N-bis(4-methoxybenzyl)sulfamoyl)-4'-bromo-2'-(2-(4-methoxybenzyl)-2H-tetrazol-5-yl)biphenyl-4-yl)pyrrolidine-1-carboxylate.

| Ex. No. | Structure | Name | Calc'd. MW [M + H]$^+$ | LC/MS m/e [M + H]$^+$ |
|---|---|---|---|---|
| 583 | 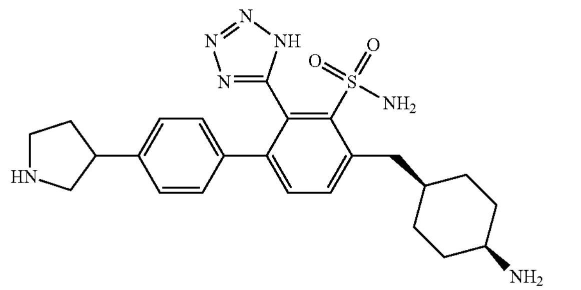 [SMILES: NS(=O)(=O)c1c(C[C@H]2CC[C@@H](N)CC2)ccc(-c2ccc(C3CCNC3)cc2)c1-c1nnn[nH]1] | 4-(((1s,4s)-4-aminocyclohexyl)methyl)-4'-(pyrrolidin-3-yl)-2-(1H-tetrazol-5-yl)-[1,1'-biphenyl]-3-sulfonamide | 482.23 | 482.2 |
| 584 | 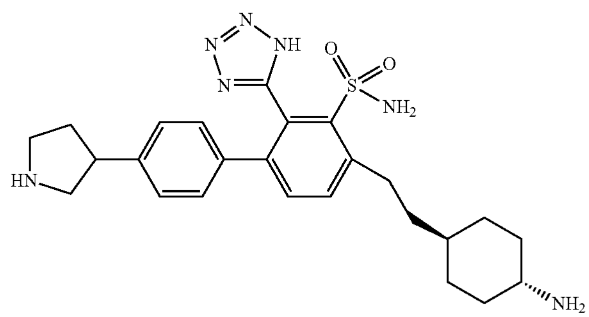 [SMILES: NS(=O)(=O)c1c(CC[C@H]2CC[C@H](N)CC2)ccc(-c2ccc(C3CCNC3)cc2)c1-c1nnn[nH]1] | 4-(2-((1r,4s)-4-aminocyclohexyl)ethyl)-4'-(pyrrolidin-3-yl)-2-(1H-tetrazol-5-yl)-[1,1'-biphenyl]-3-sulfonamide | 496.24 | 496.3 |
| 585 | 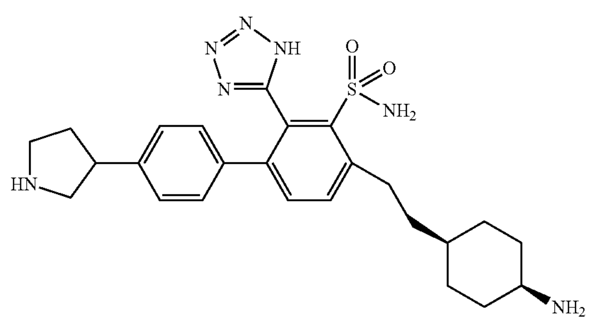 [SMILES: NS(=O)(=O)c1c(CC[C@H]2CC[C@@H](N)CC2)ccc(-c2ccc(C3CCNC3)cc2)c1-c1nnn[nH]1] | 4-(2-((1s,4r)-4-aminocyclohexyl)ethyl)-4'-(pyrrolidin-3-yl)-2-(1H-tetrazol-5-yl)-[1,1'-biphenyl]-3-sulfonamide | 496.24 | 496.3 |
| 586 | 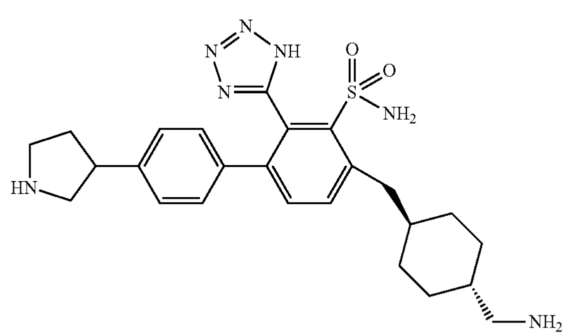 [SMILES: NC[C@H]1CC[C@H](Cc2ccc(-c3ccc(C4CCNC4)cc3)c(-c3nnn[nH]3)c2S(N)(=O)=O)CC1] | 4-(((1r,4r)-4-(aminomethyl)cyclohexyl)methyl)-4'-(pyrrolidin-3-yl)-2-(1H-tetrazol-5-yl)-[1,1'-biphenyl]-3-sulfonamide | 496.24 | 496.4 |

| Ex. No. | Structure | Name | Calc'd. MW [M + H]+ | LC/MS m/e [M + H]+ |
|---|---|---|---|---|
| 587 | 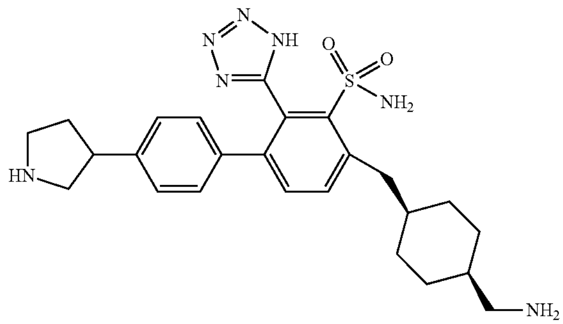 [SMILES: NC[C@H]1CC[C@@H](Cc2ccc(-c3ccc(C4CCNC4)cc3)c(-c3nnn[nH]3)c2S(N)(=O)=O)CC1] | 4-(((1s,4s)-4-(aminomethyl)cyclohexyl)methyl)-4'-(pyrrolidin-3-yl)-2-(1H-tetrazol-5-yl)-[1,1'-biphenyl]-3-sulfonamide | 496.24 | 496.2 |
| 588 | 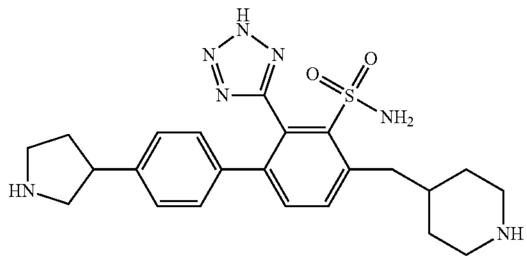 [SMILES: NS(=O)(=O)c1c(CC2CCNCC2)ccc(-c2ccc(C3CCNC3)cc2)c1-c1nn[nH]n1] | 4-(piperidin-4-ylmethyl)-4'-(pyrrolidin-3-yl)-2-(2H-tetrazol-5-yl)-[1,1'-biphenyl]-3-sulfonamide | 468.21 | 468.3 |

EXAMPLES 589 and 590

3-((1r,4r)-4-(aminomethyl)cyclohexyl)-6-(piperidin-4-ylmethyl)-2-(2H-tetrazol-5-yl)benzenesulfonamide and 3-((1r,4r)-4-(aminomethyl)cyclohexyl)-6-(piperidin-4-ylmethyl)-2-(2H-tetrazol-5-yl)benzenesulfonamide

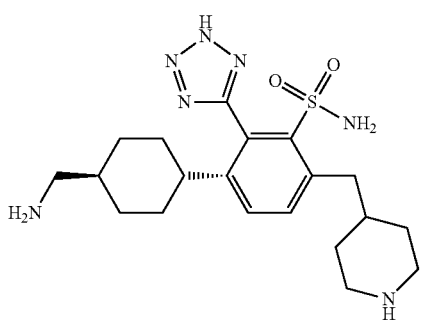

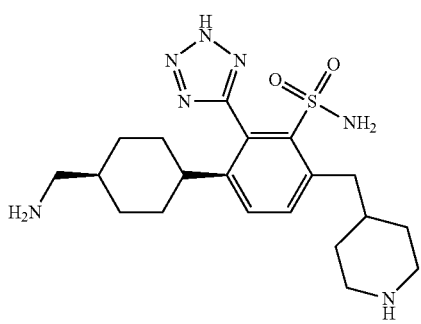

Step A: 6-bromo-3-(4-cyanocyclohex-1-enyl)-N,N-bis(4-methoxybenzyl)-2-(2-(4-methoxybenzyl)-2H-tetrazol-5-yl)benzenesulfonamide A degassed solution of tetrakis(triphenylphosphine) palladium (0) (14.62 mg, 0.013 mmol), sodium carbonate (40 mg, 0.38 mmol), 4-(4,4,5,5-tetramethyl-1,3,2-dioxaborolan-2-yl)cyclohex-3-enecarbonitrile (35 mg, 0.15 mmol), 6-bromo-3-iodo-N,N-bis(4-methoxybenzyl)-2-(1-(4-methoxybenzyl)-1H-tetrazol-5-yl)benzenesulfonamide (0.10 g, 0.127 mmol) in dioxane/water (4/1) (4 mL) was stirred at 80° C. for 2 hr under nitrogen. The mixture was concentrated under vacuum and the residue was purified by Prep-TLC with EtOAc/PE (1/2) to afford the title compound: LCMS (ESI) calc'd for $C_{38}H_{37}BrN_6O_5S$ [M+H]+: 769, 771 (1:1), found: 769, 771 (1:1).

Step B: tert-butyl 4-(2-(N,N-bis(4-methoxybenzyl)sulfamoyl)-4-(4-cyanocyclohex-1-enyl)-3-(2-(4-methoxybenzyl)-2H-tetrazol-5-yl)benzyl)piperidine-1-carboxylate In the 10 mL sealed tube, tert-butyl 4-(iodomethyl)piperidine-1-carboxylate (1.01 g, 3.12 mmol), 4,7-diphenyl-1,10-phenanthroline (0.08 g, 0.23 mmol), nickel(II) iodide (0.15 g, 0.47 mmol), manganese (0.26 g, 4.68 mmol) was added to a stirred mixture of 4-bromo-4'-cyano-N,N-bis(4-methoxybenzyl)-2-(1-(4-methoxybenzyl)-1H-tetrazol-5-yl)-2',3',4',5'-tetrahydro-[1,1'-biphenyl]-3-sulfonamide (1.20 g, 1.56 mmol) in DMAc (3 mL) at ambient temperature. The resulting mixture was bubbled with argon for 10 min and then stirred for 16 hr at 80° C. under argon and then quenched with water (10 mL). The resulting mixture was extracted with EtOAc (3×50 mL), dried over anhydrous $Na_2SO_4$ and concentrated under reduced pressure. The residue was purified by silica gel column chromatography, eluted with EtOAc/PE (1/2) to afford the residue which was purified by Prep-HPLC with the following conditions: Column: X bridge C18, 19×150 mm, 5 μm; Mobile phase A: water (10 mM $NH_4HCO_3$) and Mobile phase B: ACN; Flow rate: 20 mL/min; Gradient: 75-85% B in 8 min; Detection:

UV 220 and 254 nm. The collected fractions were combined and concentrated under reduced pressure to afford the title compound: LCMS (ESI) calc'd for $C_{49}H_{57}N_7O_7S$ [M+H]$^+$: 888, found: 888.

Step C: tert-butyl 4-(2-(N,N-bis(4-methoxybenzyl)sulfamoyl)-4-(4-(((tert-butoxycarbonylamino)methyl)cyclohex-1-enyl)-3-(2-(4-methoxybenzyl)-2H-tetrazol-5-yl)benzyl)piperidine-1-carboxylate In the 25 mL round bottom flask, di-tert-butyl dicarbonate (74 mg, 0.34 mmol) was added to a stirred mixture of tert-butyl 4-((3-(N,N-bis(4-methoxybenzyl)sulfamoyl)-4'-cyano-2-(1-(4-methoxybenzyl)-1H-tetrazol-5-yl)-2',3',4',5'-tetrahydro-[1,1'-biphenyl]-4-yl)methyl)piperidine-1-carboxylate (0.15 g, 0.17 mmol) in MeOH (3 mL) at ambient temperature under hydrogen (2 atm). The resulting mixture was stirred for 2 hr at ambient temperature under hydrogen and then the solids were filtered out. The filtrate was concentrated and the residue was purified by Prep-TLC with EtOAC/PE (1/2) to afford the title compound: LCMS (ESI) calc'd for $C_{54}H_{69}N_7O_9S$ [M+H]$^+$: 992, found: 992.

Step D: tert-butyl 4-(2-(N,N-bis(4-methoxybenzyl)sulfamoyl)-4-(4-(((tert-butoxycarbonylamino)methyl)cyclohexyl)-3-(2-(4-methoxybenzyl)-2H-tetrazol-5-yl)benzyl)piperidine-1-carboxylate In the 20 sealed tube, dihydroxypalladium (0.16 g, 0.23 mmol) was added to a stirred mixture of tert-butyl 4-((3-(N,N-bis(4-methoxybenzyl)sulfamoyl)-4'-(((tert-butoxycarbonyl)amino)methyl)-2-(2-(4-methoxybenzyl)-2H-tetrazol-5-yl)-2',3',4',5'-tetrahydro-[1,1'-biphenyl]-4-yl)methyl)piperidine-1-carboxylate (0.15 g, 0.15 mmol) in MeOH (3 mL) at ambient temperature. After the resulting mixture was stirred at ambient temperature for 16 hr under hydrogen at 15 atm, the solids were filtered out and the filtrate was concentrated under vacuum to afford the title compound: LCMS (ESI) calc'd for $C_{54}H_{71}N_7O_9S$ [M+H]$^+$: 994, found: 994.

Step E: 3-(4-(aminomethyl)cyclohexyl)-N,N-bis(4-methoxybenzyl)-2-(2-(4-methoxybenzyl)-2H-tetrazol-5-yl)-6-(piperidin-4-ylmethyl)benzenesulfonamide In the 25 round bottom flask, 2,2,2-trifluoroacetic acid (14.91 mg, 0.13 mmol) was added dropwise to a stirred mixture of tert-butyl 4-(2-(N,N-bis(4-methoxybenzyl)sulfamoyl)-4-(4-(((tert-butoxycarbonyl)amino)methyl)cyclohexyl)-3-(2-(4-methoxybenzyl)-2H-tetrazol-5-yl)benzyl)piperidine-1-carboxylate (0.13 g, 0.13 mmol) in anisole (1 mL) at ambient temperature. The resulting mixture was stirred at ambient temperature for 1 hr and then concentrated under vacuum. The residue was used in the next step directly without further purification: LCMS (ESI) calc'd for $C_{44}H_{55}N_7O_5S$ [M+H]$^+$: 794, found: 794.

Step F: 3-((1r,4r)-4-(aminomethyl)cyclohexyl)-6-(piperidin-4-ylmethyl)-2-(2H-tetrazol-5-yl)benzenesulfonamide and 3-((1r,4r)-4-(aminomethyl)cyclohexyl)-6-(piperidin-4-ylmethyl)-2-(2H-tetrazol-5-yl)benzenesulfonamide In the 100 mL round bottom flask, 2,2,2-trifluoroacetic acid (0.14 g, 1.26 mmol) was added dropwise to a stirred mixture of 3-(2-aminoquinolin-8-yl)-N,N-bis(4-methoxybenzyl)-2-(2-(4-methoxybenzyl)-2H-tetrazol-5-yl)-6-(trifluoromethyl)benzenesulfonamide (0.10 g, 0.13 mmol) in anisole and DCM (1/1) (2 mL) at ambient temperature. The resulting mixture was stirred for 16 hr at 80° C. and then concentrated under vacuum. The residue was purified by Prep-HPLC with the following conditions: Column: X Bridge C18, 19×150 mm, 5 µm; Mobile Phase A: water (10 mM NH$_4$HCO$_3$), Mobile Phase B: ACN; Flow rate: 20 mL/min; Gradient: 10-36% B in 8 min; Detection: UV 254 nm. The collected fractions were combined and concentrated under reduced pressure to afford the faster eluting isomer: LCMS (ESI) calc'd for $C_{20}H_{31}N_7O_2S$ [M+H]$^+$: 434, found: 434; $^1$H NMR (300 MHz, CD$_3$OD): 7.58 (d, J=5.4 Hz, 1H), 7.39 (d, J=6.3 Hz, 1H), 3.33-3.31 (m, 2H), 3.15-3.12 (m, 2H), 2.97 (d, J=5.7 Hz, 1H), 2.87-2.76 (m, 2H), 1.99-1.96 (m, 2H), 1.88-1.71 (m, 3H), 1.71-1.61 (m, 2H) 1.53-1.35 (m, 9H) and the slower eluting isomer: LCMS (ESI) calc'd for $C_{20}H_{31}N_7O_2S$ [M+H]$^+$: 434, found: 434; $^1$H NMR (300 MHz, CD$_3$OD): 7.58 (d, J=3.9 Hz, 1H), 7.39 (d, J=9.0 Hz, 1H), 3.31-3.11 (m, 3H), 2.90-2.79 (m, 2H), 2.66 (d, J=5.1 Hz, 1H), 1.95-1.77 (m, 8H), 1.68-1.41 (m, 7H), 0.88-0.72 (m, 2H).

EXAMPLES 591-592

In the similar way to 3-((1r,4r)-4-(aminomethyl)cyclohexyl)-6-(piperidin-4-ylmethyl)-2-(2H-tetrazol-5-yl)benzenesulfonamide and 3-((1r,4r)-4-(aminomethyl)cyclohexyl)-6-(piperidin-4-ylmethyl)-2-(2H-tetrazol-5-yl)benzenesulfonamide, the following compounds were synthesized.

| Ex. No. | Structure | Name | Calc'd. MW [M + H]$^+$ | LC/MS m/e [M + H]$^+$ |
|---|---|---|---|---|
| 591 | 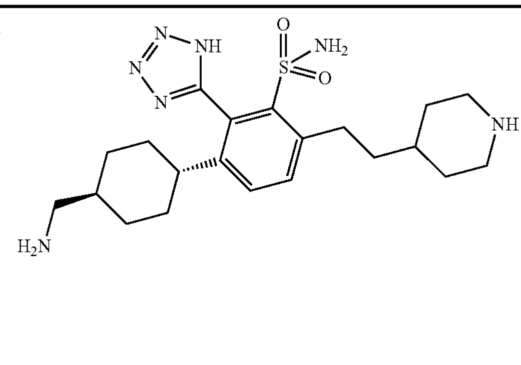 | 3-((1r,4r)-4-(aminomethyl)cyclohexyl)-6-(2-(piperidin-4-yl)ethyl)-2-(1H-tetrazol-5-yl)benzenesulfonamide | 448.24 | 448.3 |

| Ex. No. | Structure | Name | Calc'd. MW [M + H]+ | LC/MS m/e [M + H]+ |
|---|---|---|---|---|
| 592 | 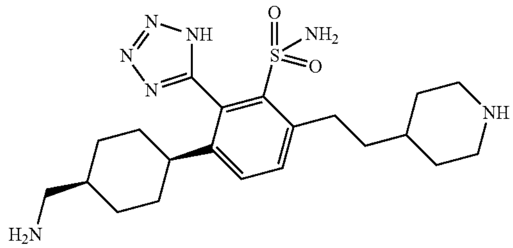 [SMILES: NC[C@H]1CC[C@@H](c2ccc(CCC3CCNCC3)c(S(N)(=O)=O)c2-c2nnn[nH]2)CC1] | 3-((1s,4s)-4-(aminomethyl)cyclohexyl)-6-(2-(piperidin-4-yl)ethyl)-2-(1H-tetrazol-5-yl)benzenesulfonamide | 448.24 | 448.3 |

EXAMPLE 593

4'-(aminomethyl)-4-(piperidin-4-ylmethyl)-2-(2H-tetrazol-5-yl)biphenyl-3-sulfonamide

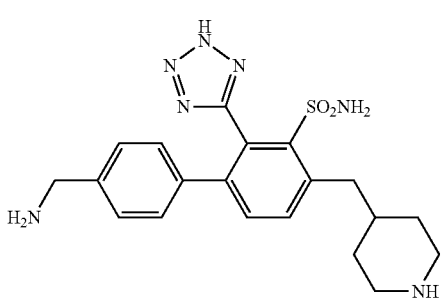 [SMILES: NCc1ccc(-c2ccc(CC3CCNCC3)c(S(N)(=O)=O)c2-c2nn[nH]n2)cc1]

Step A: benzyl 4-((3-(N,N-bis(4-methoxybenzyl)sulfamoyl)-4'-cyano-2-(2-(4-methoxybenzyl)-2H-tetrazol-5-yl)biphenyl-4-yl)methyl)piperidine-1-carboxylate To a stirred mixture of 4-bromo-4'-cyano-N,N-bis(4-methoxybenzyl)-2-(1-(4-methoxybenzyl)-1H-tetrazol-5-yl)-[1,1'-biphenyl]-3-sulfonamide (0.20 g, 0.26 mmol) in DMA (2.6 mL) was added benzyl 4-(iodomethyl)piperidine-1-carboxylate (0.38 mg, 1.05 mmol) at ambient temperature under Ar. To the reaction mixture were added 4,7-diphenyl-1,10-phenanthroline (17 mg, 0.05 mmol), nickel (II) iodide (16 mg, 0.05 mmol), manganese (29 mg, 0.52 mmol), benzonitrile (5 mg, 0.05 mmol) and chlorotrimethylsilane (6 mg, 0.05 mmol) sequentially. After the resulting mixture was heated for 2 hr at 40° C. under Ar, it was quenched with water (5 mL) and extracted with EtOAc (3×10 mL). The combined organic layers were washed with brine (2×10 mL), dried over anhydrous $Na_2SO_4$, concentrated under reduced pressure. The residue was purified by Prep-TLC with EtOAc/PE (1/1) to afford the title compound, which was used in the next reaction directly. LCMS (ESI) calc'd for $C_{52}H_{51}N_7O_7S$ [M+1]+: 918, found 918.

Step B: 4'-(aminomethyl)-N,N-bis(4-methoxybenzyl)-2-(2-(4-methoxybenzyl)-2H-tetrazol-5-yl)-4-(piperidin-4-ylmethyl)biphenyl-3-sulfonamide To a stirred solution of benzyl 4-((3-(N,N-bis(4-methoxybenzyl)sulfamoyl)-4'-cyano-2-(2-(4-methoxybenzyl)-2H-tetrazol-5-yl)-[1,1'-biphenyl]-4-yl)methyl)piperidine-1-carboxylate (0.11 g, 0.12 mmol) in EtOAc (3 mL) was added dihydroxypalladium (8 mg, 0.012 mmol) and five drops of HCl (1 N, aq.) at ambient temperature. The reaction mixture was stirred under hydrogen (1.5 atm) for 48 hr at ambient temperature, and then filtered through celite. The filtrate was concentrated under reduced pressure to afford the title compound, which was used in the next step directly without further purification. LCMS (ESI) calc'd for $C_{36}H_{41}N_7O_4S$ [M+1]+: 668, found 668.

Step C: 4'-(aminomethyl)-4-(piperidin-4-ylmethyl)-2-(2H-tetrazol-5-yl)biphenyl-3-sulfonamide To a stirred solution of 4'-(aminomethyl)-N,N-bis(4-methoxybenzyl)-2-(2-(4-methoxybenzyl)-2H-tetrazol-5-yl)-4-(piperidin-4-ylmethyl)-[1,1'-biphenyl]-3-sulfonamide (60 mg, 0.08 mmol) (crude) in anisole (2 mL, 0.08 mmol) was added TFA (4 mL, 0.08 mmol) at 0° C. The reaction mixture was heated for 16 hr at 80° C. and then concentrated under reduced pressure. The residue was purified by Prep-HPLC with the following conditions: Column, X bridge C18, 19×150 mm; Mobile phase: water (0.05% $NH_4HCO_3$) and acetonitrile; Gradient: hold 34% acetonitrile for 8 min, hold 100% for 2 min, down to 34% in 2 min; Detector: UV 220 and 254 nm. The collected fractions was concentrated under reduced pressure to afford the title compound: LCMS (ESI) calc'd for $C_{20}H_{25}N_7O_2S$ [M+1]+: 428, found 428.

EXAMPLE 594

4'-(guanidinomethyl)-4-(piperidin-4-ylmethyl)-2-(2H-tetrazol-5-yl)biphenyl-3-sulfonamide

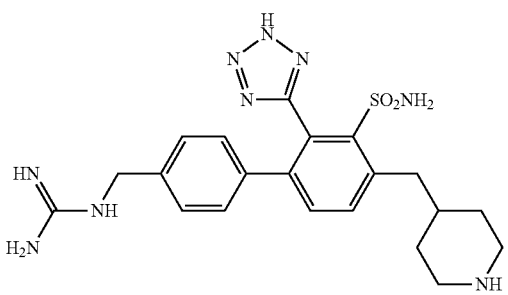 [SMILES: N=C(N)NCc1ccc(-c2ccc(CC3CCNCC3)c(S(N)(=O)=O)c2-c2nn[nH]n2)cc1]

Step A: tert-butyl 4-((4'-(aminomethyl)-3-(N,N-bis(4-methoxybenzyl)sulfamoyl)-2-(2-(4-methoxybenzyl)-2H-tetrazol-5-yl)biphenyl-4-yl)methyl)piperidine-1-carboxylate

437

To a stirred solution of tert-butyl 4-((3-(N,N-bis(4-methoxybenzyl)sulfamoyl)-4'-cyano-2-(2-(4-methoxybenzyl)-2H-tetrazol-5-yl)-[1,1'-biphenyl]-4-yl)methyl)piperidine-1-carboxylate (0.11 g, 0.12 mmol) in EtOAc (3 mL), dihydroxypalladium (8 mg, 0.01 mmol) and five drops of HCl (1 N, aq.) were added at ambient temperature. The reaction mixture was stirred under hydrogen (15 atm) for 48 hr at ambient temperature, and then filtered and concentrated to afford the title compound, which was used in the next reaction directly without further purification. LCMS (ESI) calc'd for $C_{49}H_{57}N_7O_7S$ [M+1]$^+$: 888, found 888.

Step B: tert-butyl 4-((3-(N,N-bis(4-methoxybenzyl)sulfamoyl)-4'-(guanidinomethyl)-2-(2-(4-methoxybenzyl)-2H-tetrazol-5-yl)biphenyl-4-yl)methyl)piperidine-1-carboxylate To a stirred mixture of tert-butyl 4-((4'-(aminomethyl)-3-(N,N-bis(4-methoxybenzyl)sulfamoyl)-2-(2-(4-methoxybenzyl)-2H-tetrazol-5-yl)-[1,1'-biphenyl]-4-yl)methyl)piperidine-1-carboxylate (60 mg, 0.07 mmol) and 1H-pyrazole-1-carboximidamide (22 mg, 0.20 mmol) in DMF (1 mL), DIEA (26 mg, 0.20 mmol) was added dropwise at 0° C. The resulting mixture was stirred for 4 h at ambient temperature and then quenched with water (5 mL), extracted with EtOAc (2×10 mL). The combined organic layers were washed with brine (2×10 mL), dried over anhydrous $Na_2SO_4$ and concentrated under reduced pressure. The residue was purified Prep-TLC, eluted with DCM/MeOH (5/1) to afford the title compound, which was used in the next step directly. LCMS (ESI) calc'd for $C_{50}H_{59}N_9O_7S$ [M+1]$^+$: 930, found 930.

Step C: 4'-(guanidinomethyl)-4-(piperidin-4-ylmethyl)-2-(2H-tetrazol-5-yl)biphenyl-3-sulfonamide To a stirred solution of tert-butyl 4-((3-(N,N-bis(4-methoxybenzyl)sulfamoyl)-4'-(guanidinomethyl)-2-(2-(4-methoxybenzyl)-2H-tetrazol-5-yl)-[1,1'-biphenyl]-4-yl)methyl)piperidine-1-carboxylate (40 mg, 0.04 mmol) in anisole (1 mL, 0.04 mmol), TFA (1 mL, 0.04 mmol) was added dropwise at 0° C. After the reaction mixture was stirred for 2 hr at ambient temperature, it was concentrated to afford 60 mg crude of 4'-(guanidinomethyl)-N-(4-methoxybenzyl)-2-(2-(4-methoxybenzyl)-2H-tetrazol-5-yl)-4-(piperidin-4-ylmethyl)-[1,1'-biphenyl]-3-sulfonamide which was used directly in the next step without further purification. LCMS (ESI) calc'd for $C_{37}H_{43}N_9O_4S$ [M+1]$^+$: 710, found 710.

To a stirred solution of 4'-(guanidinomethyl)-N-(4-methoxybenzyl)-2-(2-(4-methoxybenzyl)-2H-tetrazol-5-yl)-4-(piperidin-4-ylmethyl)-[1,1'-biphenyl]-3-sulfonamide (60 mg, 0.09 mmol) (crude) in anisole (5 mL) was added TFA (10 mL, 0.09 mmol) at 0° C. The resulting mixture was heated for 16 hr at 80° C. and then concentrated under reduced pressure. The residue was purified by Prep-HPLC with the following conditions: Column, X bridge C18, 19×150 mm; mobile phase: water (0.05% $NH_4HCO_3$) and acetonitrile; Gradient: hold 34% acetonitrile for 8 min, hold 100% for 2 min, down to 34% in 2 min; Detector: UV 220 and 254 nm. The collected fractions were concentrated under reduced pressure to afford the title compound: LCMS (ESI) calc'd for $C_{21}H_{27}N_9O_2S$ [M+1]$^+$: 470, found 470.

438

EXAMPLE 595

4-(((1r,4r)-4-aminocyclohexyl)methyl)-4'-(azetidin-3-yl)-2-(2H-tetrazol-5-yl)-[1,1'-biphenyl]-3-sulfonamide

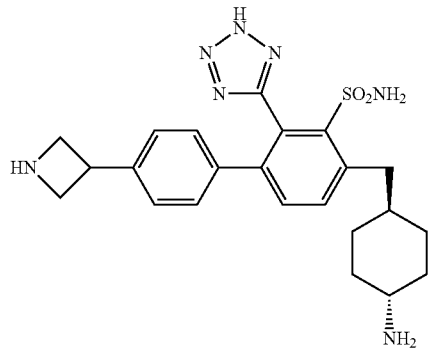 [SMILES: NS(=O)(=O)c1c(C[C@H]2CC[C@H](N)CC2)ccc(-c2ccc(C3CNC3)cc2)c1-c1nn[nH]n1]

Step A: tert-butyl (1r,4r)-4-(hydroxymethyl)cyclohexylcarbamate

To a stirred solution of (1R,4R)-4-((tert-butoxycarbonyl)amino)cyclohexanecarboxylic acid (2.00 g, 8.22 mmol) in THF (20 mL), borane (8.22 mL, 16.44 mmol) was added dropwise at 0° C. After the resulting mixture was stirred for 6 hr at ambient temperature, it was quenched with water (20 mL) and extracted with EtOAc (2×40 mL). The combined organic layers were washed brine (2×30 mL), dried over anhydrous $Na_2SO_4$ and concentrated under reduced pressure to afford the title compound: $^1$H NMR (400 MHz, $CDCl_3$): δ 4.62 (s, 1H), 3.48 (d, J=6.4 Hz, 2H), 3.01-2.98 (m, 2H), 1.89-1.71 (m, 4H), 1.70-1.61 (m, 1H), 1.49 (s, 9H), 1.05-0.90 (m, 4H).

Step B: tert-butyl (1r,4r)-4-(iodomethyl)cyclohexylcarbamate

To a stirred mixture of tert-butyl ((1R,4R)-4-(hydroxymethyl)cyclohexyl)carbamate (1.70 g, 7.41 mmol), triphenylphosphine (2.33 g, 8.90 mmol) and 1H-imidazole (0.60 g, 8.90 mmol) in THF (30 mL), $I_2$ (2.26 g, 8.90 mmol) in 10 mL of THF was added dropwise at 0° C. After the resulting mixture was stirred 12 hr at ambient temperature, it was quenched with water (50 mL) and extracted with EtOAc (3×50 mL). The combined organic layers were washed with aqueous $Na_2SO_3$ (aq.) (2×50 mL), dried over anhydrous $Na_2SO_4$ and concentrated under reduced pressure. The residue was purified by silica gel column chromatography, eluting with EtOAc/PE (1/5) to afford the title compound: $^1$H NMR (400 MHz, $CDCl_3$): δ 4.46 (s, 1H), 3.45 (s, 1H), 3.11 (d, J=8.4 Hz, 2H), 2.12-1.89 (m, 4H), 1.45 (s, 9H), 1.18-1.01 (m, 4H).

Step C: tert-butyl 3-(3'-(N,N-bis(4-methoxybenzyl)sulfamoyl)-4'-(((1 r,4r)-4-(tert-butoxycarbonylamino)cyclohexyl)methyl)-2'-(2-(4-methoxybenzyl)-2H-tetrazol-5-yl)biphenyl-4-yl)azetidine-1-carboxylate To a stirred mixture of tert-butyl 3-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)azetidine-1-carboxylate (0.30 g, 0.34 mmol) and tert-butyl ((1R,4R)-4-(iodomethyl)cyclohexyl)carbamate (0.23 g, 0.67 mmol) in DMA (3.9 mL), 4,7-diphenyl-1,10-phenanthroline (17 mg, 0.05 mmol), nickel (II) iodide (21 mg, 0.07 mmol), manganese (37 mg, 0.67 mmol) and pyridine (5 μL, 0.07 mmol) was added at ambient temperature under Ar sequentially.

The resulting mixture was heated for 24 hr at 80° C. under Ar and then quenched with water (5 mL) and extracted with EtOAc (3×10 mL). The combined organic layers were washed with brine (2×10 mL), dried over anhydrous $Na_2SO_4$ and concentrated under reduced pressure. The residue was purified by Prep-TLC and the combined organic fractions were concentrated under reduced pressure to afford the title compound, which was used in the next step directly. LCMS (ESI) calc'd for $C_{57}H_{69}N_7O_9S$ [M+H]$^+$: 1028, found: 1028.

Step D: tert-butyl 3-(3'-(N,N-bis(4-methoxybenzyl)sulfamoyl)-4'-(((1r,4r)-4-(tert-butoxycarbonylamino)cyclohexyl)methyl)-2'-(2-(4-methoxybenzyl)-2H-tetrazol-5-yl)biphenyl-4-yl)azetidine-1-carboxylate To a stirred solution of tert-butyl 3-(3'-(N,N-bis(4-methoxybenzyl)sulfamoyl)-4'-(((1R,4R)-4-((tert-butoxycarbonyl)amino)cyclohexyl)methyl)-2'-(2-(4-methoxybenzyl)-2H-tetrazol-5-yl)-[1,1'-biphenyl]-4-yl)azetidine-1-carboxylate (90 mg, 0.09 mmol) in anisole (1 mL), TFA (1.4 mL, 17.51 mmol) was added dropwise at 0° C. After the resulting solution was stirred at 0° C. for 2 hr, it was concentrated under reduced pressure. The residue was evaporated with anisole (10 mL) for 3 times under reduced pressure and used in the next step directly.

Step E: 6-[(4-aminocyclohexyl)methyl]-3-[4-(azetidin-3-yl)phenyl]-2-(1H-tetrazol-5-yl)benzenesulfonamide To a stirred solution of 4-(((1R,4R)-4-aminocyclohexyl)methyl)-4'-(azetidin-3-yl)-N-(4-methoxybenzyl)-2-(2-(4-methoxybenzyl)-2H-tetrazol-5-yl)-[1,1'-biphenyl]-3-sulfonamide (0.10 g, 0.14 mmol, crude) in anisole (0.2 mL) TFA (2 mL, 28.30 mmol) was added at ambient temperature. After the resulting mixture was heated at 80° C. for 16 hr, it was concentrated under reduced pressure. The residue was purified by Prep-HPLC with following condition: Column: X Bridge C18, 19×150 mm, 5 μm; Mobile Phase A: water (0.05% TFA), Mobile Phase B: ACN; Flow rate: 20 mL/min; Gradient: 5-15% B in 8 min; Detected: at UV 254 nm and 220 nm. The collected fractions were concentrated under reduced pressure to afford the title compound: LCMS (ESI) calc'd for $C_{23}H_{29}N_7O_2S$ [M+H]$^+$: 468, found: 468.

EXAMPLES 596-602

In the similar way to 4-(((1r,4r)-4-aminocyclohexyl)methyl)-4'-(azetidin-3-yl)-2-(2H-tetrazol-5-yl)-[1,1'-biphenyl]-3-sulfonamide, the following compounds were synthesized starting from tert-butyl 3-(3'-(N,N-bis(4-methoxybenzyl)sulfamoyl)-4'-bromo-2'-(1-(4-methoxybenzyl)-1H-tetrazol-5-yl)-[1,1'-biphenyl]-4-yl)azetidine-1-carboxylate and alkyl halides prepared as described herein.

| Ex. No. | Structure | Name | Calc'd. MW [M + H]$^+$ | LC/MS m/e [M + H]$^+$ |
|---|---|---|---|---|
| 596 | 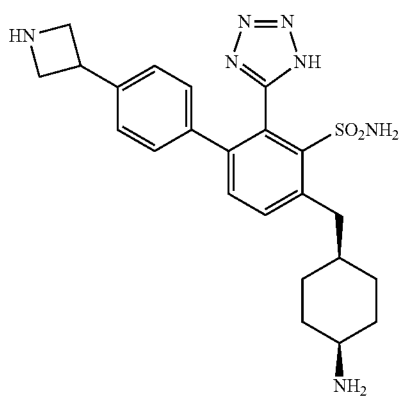 [SMILES: NS(=O)(=O)c1c(C[C@H]2CC[C@@H](N)CC2)ccc(-c2ccc(C3CNC3)cc2)c1-c1nnn[nH]1] | 4-(((1s,4s)-4-aminocyclohexyl)methyl)-4'-(azetidin-3-yl)-2-(1H-tetrazol-5-yl)-[1,1'-biphenyl]-3-sulfonamide | 468.21 | 468.2 |
| 597 | 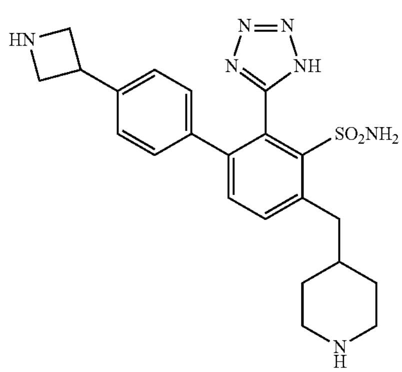 [SMILES: NS(=O)(=O)c1c(CC2CCNCC2)ccc(-c2ccc(C3CNC3)cc2)c1-c1nnn[nH]1] | 3-[4-(azetidin-3-yl)phenyl]-6-(4-piperidylmethyl)-2-(1H-tetrazol-5-yl)benzenesulfonamide | 454.19 | 454.2 |

| Ex. No. | Structure | Name | Calc'd. MW [M + H]+ | LC/MS m/e [M + H]+ |
|---|---|---|---|---|
| 598 | 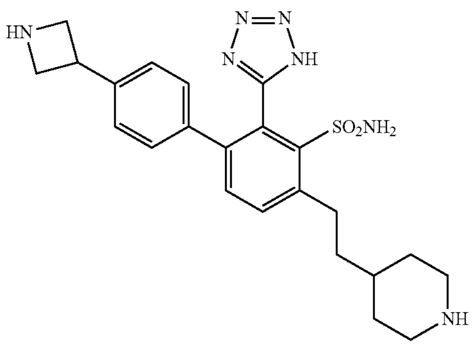 [SMILES: NS(=O)(=O)c1c(CCC2CCNCC2)ccc(-c2ccc(C3CNC3)cc2)c1-c1nnn[nH]1] | 3-[4-(azetidin-3-yl)phenyl]-6-[2-(4-piperidyl)ethyl]-2-(1H-tetrazol-5-yl)benzenesulfonamide | 467.21 | 466.8 |
| 599 | 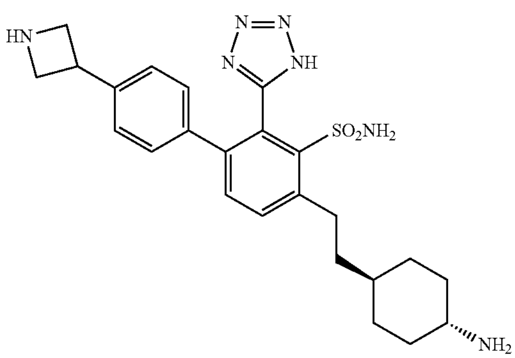 [SMILES: NS(=O)(=O)c1c(CC[C@H]2CC[C@H](N)CC2)ccc(-c2ccc(C3CNC3)cc2)c1-c1nnn[nH]1] | 4-(2-((1r,4s)-4-aminocyclohexyl)ethyl)-4'-(azetidin-3-yl)-2-(1H-tetrazol-5-yl)-[1,1'-biphenyl]-3-sulfonamide | 482.23 | 482.4 |
| 600 | 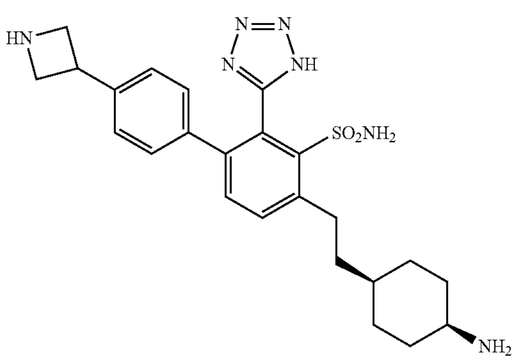 [SMILES: NS(=O)(=O)c1c(CC[C@H]2CC[C@@H](N)CC2)ccc(-c2ccc(C3CNC3)cc2)c1-c1nnn[nH]1] | 4-(2-((1s,4r)-4-aminocyclohexyl)ethyl)-4'-(azetidin-3-yl)-2-(1H-tetrazol-5-yl)-[1,1'-biphenyl]-3-sulfonamide | 482.23 | 482.2 |
| 601 | 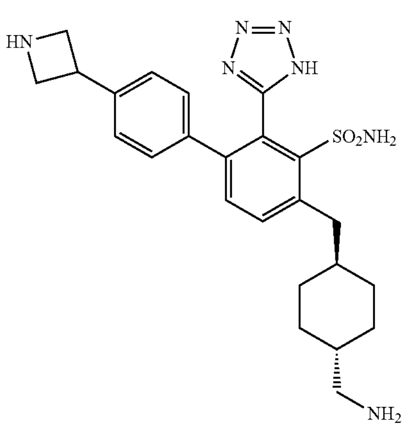 [SMILES: NC[C@H]1CC[C@H](Cc2ccc(-c3ccc(C4CNC4)cc3)c(-c3nnn[nH]3)c2S(N)(=O)=O)CC1] | 4-(((1r,4r)-4-(aminomethyl)cyclohexyl)methyl)-4'-(azetidin-3-yl)-2-(1H-tetrazol-5-yl)-[1,1'-biphenyl]-3-sulfonamide | 482.23 | 482.3 |

| Ex. No. | Structure | Name | Calc'd. MW [M + H]+ | LC/MS m/e [M + H]+ |
|---|---|---|---|---|
| 602 | 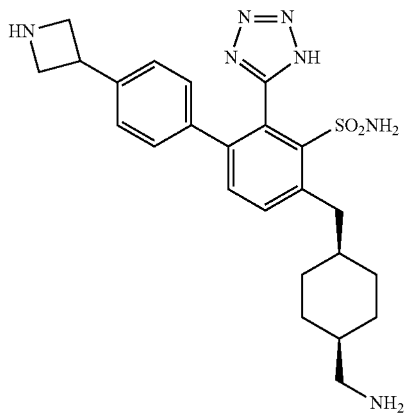 [SMILES: NC[C@H]1CC[C@@H](Cc2ccc(-c3ccc(C4CNC4)cc3)c(-c3nnn[nH]3)c2S(N)(=O)=O)CC1] | 4-(((1s,4s)-4-(aminomethyl)cyclohexyl)methyl)-4'-(azetidin-3-yl)-2-(1H-tetrazol-5-yl)-[1,1'-biphenyl]-3-sulfonamide | 482.23 | 482.2 |

EXAMPLE 603

3-[4-[4-(4-piperidylmethyl)-3-sulfamoyl-2-(2H-tetrazol-5-yl)phenyl]phenyl]azetidine-1-carboxamidine

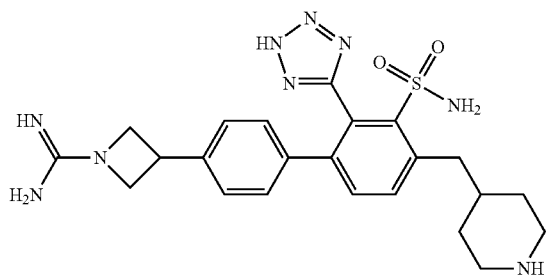 [SMILES: N=C(N)N1CC(c2ccc(-c3ccc(CC4CCNCC4)c(S(N)(=O)=O)c3-c3nn[nH]n3)cc2)C1]

Step A: benzyl 4-(iodomethyl)piperidine-1-carboxylate

A solution of $I_2$ (9.77 g, 38.50 mmol) in THF (5 mL) was added in dropwise to a stirred solution of benzyl 4-(hydroxymethyl)piperidine-1-carboxylate (8.00 g, 32.10 mmol), 1H-imidazole (2.62 g, 38.50 mmol) and triphenylphosphine (10.10 g, 38.50 mmol) in THF (15 mL) at ambient temperature in a period of 4 hr. The reaction mixture was then quenched with water (30 mL), diluted with water (40 mL) and extracted with EtOAc (3×40 mL). The combined organic layers were washed with water (20 mL) and brine (20 mL), dried over anhydrous $Na_2SO_4$ and concentrated under reduced pressure. The residue was purified by silica gel, eluted with EtOAc/PE (1/10) to afford the title compound: LCMS (ESI) calc'd for $C_{14}H_{18}INO_2$ [M+H]+: 360, found 360.

Step B: benzyl 4-((3-(N,N-bis(4-methoxybenzyl)sulfamoyl)-4'-(1-(tert-butoxycarbonyl)azetidin-3-yl)-2-(2-(4-methoxybenzyl)-2H-tetrazol-5-yl)biphenyl-4-yl)methyl)piperidine-1-carboxylate To the solution mixture of tert-butyl 3-(3'-(N,N-bis(4-methoxybenzyl)sulfamoyl)-4'-bromo-2'-(2-(4-methoxybenzyl)-2H-tetrazol-5-yl)-[1,1'-biphenyl]-4-yl)azetidine-1-carboxylate (0.50 g, 0.56 mmol), benzyl 4-(iodomethyl)piperidine-1-carboxylate (0.40 g, 1.12 mmol), nickel iodide (35 mg, 0.11 mmol), 4,7-diphenyl-1,10-phenanthroline (28 mg, 0.08 mmol) and manganese (61 mg, 1.12 mmol) in DMA (5 mL) were added benzonitrile (12 mg, 0.112 mmol) (one drop) and chlorotrimethylsilane (12 mg, 0.112 mmol) (one drop) at ambient temperature under Argon sequencely. The resulting mixture was stirred at 40° C. for 2 hr under Argon and then filtered. The filtrate was concentrated under reduced pressure and the residue was purified by silica gel, eluted with EtOAc/PE (40/60) to afford the title compound: LCMS (ESI) calc'd for $C_{59}H_{65}N_7O_9S$ [M+H]+: 1048, found 1048.

Step C: benzyl 4-((4'-(azetidin-3-yl)-2-(2-(4-methoxybenzyl)-2H-tetrazol-5-yl)-3-(N-(4-methoxybenzyl)sulfamoyl)biphenyl-4-yl)methyl)piperidine-1-carboxylate To the solution of benzyl 4-((3-(N,N-bis(4-methoxybenzyl)sulfamoyl)-4'-(1-(tert-butoxycarbonyl)azetidin-3-yl)-2-(2-(4-methoxybenzyl)-2H-tetrazol-5-yl)-[1,1'-biphenyl]-4-yl)methyl)piperidine-1-carboxylate (0.16 g, 0.15 mmol) in DCM (16 mL) was added TFA (1.6 mL, 20.77 mmol) at 0° C. and stirred at 0° C. for 2 hr. The reaction was quenched with water (5 mL) and adjusted to pH 10 with $NaHCO_3$, extracted with DCM (3×20 mL). The combined organic layers were washed with water (20 mL) and brine (20 mL), dried over anhydrous $Na_2SO_4$ and concentrated under vacuum to afford the title compound. LCMS (ESI) calc'd for $C_{46}H_{49}N_7O_6S$ [M+H]+: 828, found 828.

Step D: benzyl 4-((4'-(1-carbamimidoylazetidin-3-yl)-2-(2-(4-methoxybenzyl)-2H-tetrazol-5-yl)-3-(N-(4-methoxybenzyl)sulfamoyl)biphenyl-4-yl)methyl)piperidine-1-carboxylate The solution of benzyl 4-((4'-(azetidin-3-yl)-2-(2-(4-methoxybenzyl)-2H-tetrazol-5-yl)-3-(N-(4-methoxybenzyl)sulfamoyl)-[1,1'-biphenyl]-4-yl)methyl)piperidine-1-carboxylate (0.13 g, 0.15 mmol), DIEA (0.11 mL, 0.60 mmol) and 1H-pyrazole-1-carboxamidine hydrochloride (89 mg, 0.60 mmol) in DMF (3 mL) was stirred at ambient temperature for 3 hr under nitrogen and then quenched with water (30 mL), diluted with water (30 mL) and extracted with EtOAc (3×20 mL). The combined organic layers were washed with water (20 mL) and brine (20 mL), dried over anhydrous $Na_2SO_4$ and concentrated under reduced pressure. The residue was purified by silica gel, eluted with MeOH/DCM (10/90) to afford the title compound: LCMS (ESI) calc'd for $C_{47}H_{51}N_9O_6S$ [M+H]+: 870, found 870.

Step E: 3-(2'-(2-(4-methoxybenzyl)-2H-tetrazol-5-yl)-3'-(N-(4-methoxybenzyl)sulfamoyl)-4'-(piperidin-4-ylmethyl)biphenyl-4-yl)azetidine-1-carboximidamide To a stirred solution of benzyl 4-((4'-(1-carbamimidoylazetidin-3-yl)-2-(2-(4-methoxybenzyl)-2H-tetrazol-5-yl)-3-(N-(4-methoxybenzyl)sulfamoyl)-[1,1'-biphenyl]-4-yl)methyl)piperidine-1-carboxylate (50 mg, 0.06 mmol) in MeOH (5 mL) was added Pd(OH)$_2$ (40 mg, 0.06 mmol) at ambient temperature. After the reaction mixture was degassed with hydrogen for 3 times and stirred under hydrogen for 1 hr at ambient temperature, the resulting mixture was filtered and the filter cake was washed with DCM (3×10 mL). The combined organic layers were concentrated under reduced pressure to afford the title compound: LCMS (ESI) calc'd for $C_{39}H_{45}N_9O_4S$ [M+H]$^+$: 736, found 736.

Step F: 3-[4-[4-(4-piperidylmethyl)-3-sulfamoyl-2-(2H-tetrazol-5-yl)phenyl]phenyl]azetidine-1-carboxamidine A mixture solution of 3-(2'-(2-(4-methoxybenzyl)-2H-tetrazol-5-yl)-3'-(N-(4-methoxybenzyl)sulfamoyl)-4'-(piperidin-4-ylmethyl)-[1,1'-biphenyl]-4-yl)azetidine-1-carboximidamide (45 mg, 0.06 mmol) and TFA (5 mL) in DCM (1 mL) was stirred at 80° C. for 16 hr. The resulting solution was concentrated under reduced pressure and the residue was dissolved with water (50 mL), extracted with EtOAc (3×20 mL) and concentrated to afford the crude product. The crude product was purified by Prep-HPLC with the following conditions: Column, Sunfire C18, 19×150 mm; Mobile phase: water (0.05% NH$_4$HCO$_3$) and acetonitrile; Gradient time: 7 min. B %: 40%-80%; Detector; UV 220 and 254 nm. The collected fractions were combined and concentrated under reduced pressure to afford the title compound. LCMS (ESI) calc'd for $C_{23}H_{29}N_9O_2S$ [M+H]$^+$: 496, found 496. $^1$H NMR (400 MHz, DMSO-d$_6$): δ 7.83 (s, 2H), 7.40 (d, J=8.0 Hz, 1H), 7.32 (d, J=8.0 Hz, 1H), 7.27 (s, 2H), 7.11 (d, J=8.4 Hz, 2H), 6.85 (d, J=8.4 Hz, 2H), 4.41-4.37 (m, 2H), 3.97-3.94 (m, 2H), 3.88-3.81 (m, 1H), 3.04-3.00 (m, 2H), 2.91-2.88 (m, 2H), 2.42-2.37 (m, 2H), 1.74-1.70 (m, 1H), 1.57-1.54 (m, 2H), 1.14-1.09 (m, 2H).

EXAMPLE 604

4-[[4-[4-(azetidin-3-yl)phenyl]-2-sulfamoyl-3-(2H-tetrazol-5-yl)phenyl]methyl]piperidine-1-carboxamidine

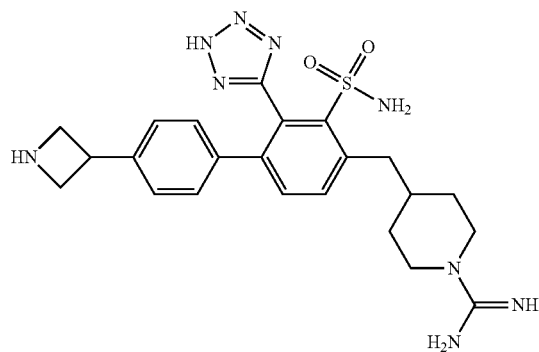 [SMILES: N=C(N)N1CCC(Cc2ccc(-c3ccc(C4CNC4)cc3)c(-c3nn[nH]n3)c2S(N)(=O)=O)CC1]

Step A: tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)biphenyl-4-yl)azetidine-1-carboxylate The solution of benzyl 4-((3-(N,N-bis(4-methoxybenzyl)sulfamoyl)-4'-(1-(tert-butoxycarbonyl)azetidin-3-yl)-2-(2-(4-methoxybenzyl)-2H-tetrazol-5-yl)-[1,1'-biphenyl]-4-yl)methyl)piperidine-1-carboxylate (1.10 g, 1.05 mmol), Pd(OH)$_2$ (0.74 g, 1.05 mmol) and HCl (two drops, 1 N) in MeOH (4 mL) and DCM (5 mL) was degassed with H$_2$ for 3 times and stirred under H$_2$ atmosphere for 1 hr at ambient temperature. The resulting mixture was filtered and the filtrate was concentrated under vacuum to afford the title compound: LCMS (ESI) calc'd for $C_{51}H_{59}N_7O_7S$ [M+1]$^+$: 914, found 914.

Step B: tert-butyl 3-(3'-(N,N-bis(4-methoxybenzyl)sulfamoyl)-4'-((1-carbamimidoylpiperidin-4-yl)methyl)-2'-(2-(4-methoxybenzyl)-2H-tetrazol-5-yl)biphenyl-4-yl)azetidine-1-carboxylate A mixture solution of tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)azetidine-1-carboxylate (0.21 g, 0.23 mmol), DIEA (0.24 mL, 1.38 mmol) and 1H-pyrazole-1-carboxamidine hydrochloride (0.15 g, 1.03 mmol) in DMF (5 mL) was stirred at ambient temperature for 16 hr. The resulting mixture was quenched with water (20 mL), diluted with water (20 mL) and extracted with EtOAc (3×30 mL). The combined organic layers were washed with water (20 mL) and brine (20 mL), dried over anhydrous sodium sulfate and concentrated under reduced pressure to afford the title compound: LCMS (ESI) calc'd for $C_{52}H_{61}N_9O_7S$ [M+1]$^+$: 956, found 956.

Step C: 4-((4'-(azetidin-3-yl)-2-(2-(4-methoxybenzyl)-2H-tetrazol-5-yl)-3-(N-(4-methoxybenzyl)sulfamoyl)biphenyl-4-yl)methyl)piperidine-1-carboximidamide A mixture solution of tert-butyl-3-(3'-(N,N-bis(4-methoxybenzyl)sulfamoyl)-4'-((1-carbamimidoylpiperidin-4-yl)methyl)-2'-(2-(4-methoxybenzyl)-2H-tetrazol-5-yl)-[1,1'-biphenyl]-4-yl)azetidine-1-carboxylate (0.10 g, 0.11 mmol) and TFA (2 mL, 26.00 mmol) in DCM (3 mL) was stirred at ambient temperature for 1 hr. The resulting mixture was concentrated under reduced pressure to afford the crude title compound: LCMS (ESI) calc'd for $C_{39}H_{45}N_9O_4S$ [M+1]$^+$: 736, found 736.

Step D: 4-[[4-[4-(azetidin-3-yl)phenyl]-2-sulfamoyl-3-(2H-tetrazol-5-yl)phenyl]methyl]piperidine-1-carboxamidine A solution of 4-((4'-(azetidin-3-yl)-2-(2-(4-methoxybenzyl)-2H-tetrazol-5-yl)-3-(N-(4-methoxybenzyl)sulfamoyl)-[1,1'-biphenyl]-4-yl)methyl)piperidine-1-carboximidamide (0.10 g, 0.14 mmol), TFA (5 mL, 64.90 mmol) and anisole (0.5 mL, 4.58 mmol) in DCM (0.5 mL) was stirred at 80° C. for 16 hr. The resulting mixture was concentrated under reduced pressure and the residue was purified by Prep-HPLC with the following conditions: Column: X Bridge RP18, 19×150 mm, 5 μm; Mobile Phase A: water (0.05% NH$_4$HCO$_3$); Mobile Phase B: ACN; Flow rate: 20 mL/min; Gradient: 5% B to 35% B in 7 min; Detection: UV 254 nm. The collected fractions were combined and concentrated under vacuum to afford the title compound: LCMS (ESI) calc'd for $C_{23}H_{29}N_9O_2S$ [M+1]$^+$: 496, found 496.

EXAMPLE 605

3-[4-(azetidin-3-yl)phenyl]-6-[(1,1-dimethylpiperidin-1-ium-4-yl)methyl]-2-(2H-tetrazol-5-yl)benzenesulfonamide

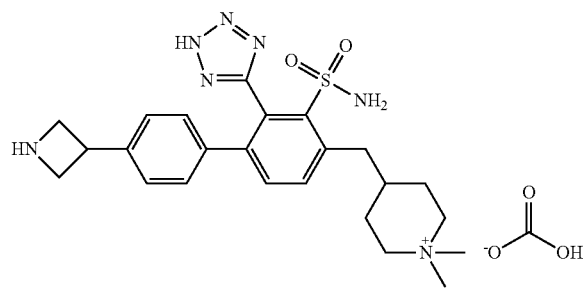

Step A: 4-((3-(N,N-bis(4-methoxybenzyl)sulfamoyl)-4'-(1-(tert-butoxycarbonyl)azetidin-3-yl)-2-(2-(4-methoxybenzyl)-2H-tetrazol-5-yl)biphenyl-4-yl)methyl)-1,1-dimethylpiperidinium A mixture solution of tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)azetidine-1-carboxylate (0.20 g, 0.22 mmol), $K_2CO_3$ (0.18 g, 1.31 mmol) and MeI (0.08 mL, 1.31 mmol) in acetone (4 mL) was stirred at ambient temperature for 1 hr. The resulting mixture was filtered and the filtrate was concentrated under reduced pressure to afford the title compound: LCMS (ESI) calc'd for $C_{53}H_{64}N_7O_7S^+$ [M]$^+$: 942, found 942.

Step B: 4-((4'-(azetidin-3-yl)-2-(2-(4-methoxybenzyl)-2H-tetrazol-5-yl)-3-(N-(4-methoxybenzyl)sulfamoyl)biphenyl-4-yl)methyl)-1,1-dimethylpiperidinium A mixture solution of 4-((3-(N,N-bis(4-methoxybenzyl)sulfamoyl)-4'-(1-(ten-butoxycarbonyl)azetidin-3-yl)-2-(2-(4-methoxybenzyl)-2H-tetrazol-5-yl)-[1,1'-biphenyl]-4-yl)methyl)-1,1-dimethylpiperidin-1-ium (0.20 g, 0.21 mmol) and TFA (3 mL, 38.90 mmol) in DCM (2 mL) was stirred at ambient temperature for 1 hr. The resulting mixture was concentrated under reduced pressure to afford the title compound, which was used in the next step directly: LCMS (ESI) calc'd for $C_{40}H_{48}N_7O_4S^+$ [M]$^+$: 722, found 722.

Step C: 3-[4-(azetidin-3-yl)phenyl]-6-[(1,1-dimethylpiperidin-1-ium-4-yl)methyl]-2-(2H-tetrazol-5-yl)benzenesulfonamide A mixture solution of 4-((4'-(azetidin-3-yl)-2-(2-(4-methoxybenzyl)-2H-tetrazol-5-yl)-3-(N-(4-methoxybenzyl)sulfamoyl)-[1,1'-biphenyl]-4-yl)methyl)-1,1-dimethylpiperidin-1-ium (0.20 g, 0.28 mmol), TFA (10 mL, 130 mmol) and anisole (0.5 mL, 4.58 mmol) in DCM (1 mL) was stirred at 80° C. for 16 hr. The resulting mixture was concentrated under reduced pressure and the residue was purified by Prep-HPLC with the following conditions: Column: X Bridge C18, 19×250 mm, 5 μm; Mobile Phase A: water (0.05% $NH_4HCO_3$), Mobile Phase B: ACN; Flow rate: 20 mL/min; Gradient: 28% B to 85% B in 8 min; Detection: UV 254 nm. The collected fractions were combined and concentrated under reduced pressure to afford the title compound. LCMS (ESI) calc'd for $C_{24}H_{32}N_7O_2S^+$ [M+H]$^+$: 482, found 482. $^1$H NMR (400 MHz, DMSO-d$_6$): δ 7.85 (brs, 2H), 7.46 (d, J=8.0 Hz, 1H), 7.36 (d, J=8.0 Hz, 1H), 7.06 (d, J=8.0 Hz, 2H), 6.79 (d, J=8.0 Hz, 2H), 3.73-3.68 (m, 3H), 3.57-3.51 (m, 2H), 3.41-3.35 (m, 4H), 3.15-3.06 (m, 8H), 1.97-1.95 (m, 1H), 1.79-1.69 (m, 4H).

EXAMPLE 606

6-[[1-(2-aminoethyl)-4-piperidyl]methyl]-3-[4-(azetidin-3-yl)phenyl]-2-(2H-tetrazol-5-yl)benzenesulfonamide

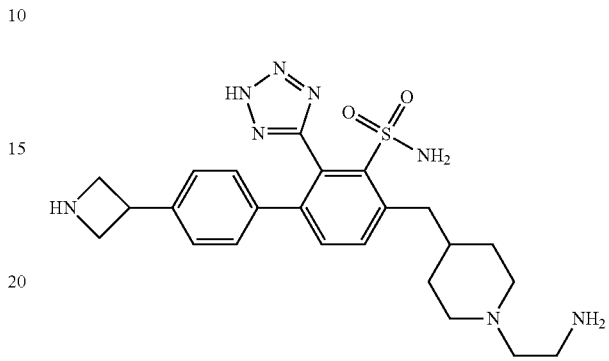

Step A: tert-butyl 3-(3'-(N,N-bis(4-methoxybenzyl)sulfamoyl)-4'-((1-(2-(tert-butoxycarbonylamino)ethyl)piperidin-4-yl)methyl)-2'-(2-(4-methoxybenzyl)-2H-tetrazol-5-yl)biphenyl-4-yl) azetidine-1-carboxylate A mixture solution of tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)azetidine-1-carboxylate (0.15 g, 0.16 mmol), $MgSO_4$ (0.19 g, 1.64 mmol), acetic acid (10 mg, 0.16 mmol), tert-butyl-2-oxoethylcarbamate (0.13 g, 0.82 mmol) and sodium triacetoxyborohydride (70 mg, 0.33 mmol) in MeOH (0.5 mL) was stirred at ambient temperature for 16 hr. The reaction mixture was quenched with water (20 mL), diluted with water (20 mL) and extracted with EtOAc (3×20 mL). The combined organic layers were washed with water (20 mL) and brine (20 mL), dried over anhydrous $Na_2SO_4$ and concentrated under reduced pressure to afford the title compound: LCMS (ESI) calc'd for $C_{58}H_{72}N_8O_9S$ [M+H]$^+$: 1057, found 1057.

Step B: 4-((1-(2-aminoethyl)piperidin-4-yl)methyl)-4'-(azetidin-3-yl)-N-(4-methoxybenzyl)-2-(2-(4-methoxybenzyl)-2H-tetrazol-5-yl)biphenyl-3-sulfonamide To a stirred solution of tert-butyl 3-(3'-(N,N-bis(4-methoxybenzyl)sulfamoyl)-4'-((1-(2-((tert-butoxycarbonyl)amino)ethyl)piperidin-4-yl)methyl)-2'-(2-(4-methoxybenzyl)-2H-tetrazol-5-yl)-[1,1'-biphenyl]-4-yl)azetidine-1-carboxylate (0.17 g, 0.16 mmol) in DCM (10 mL) was added dropwise TFA (1 mL, 12.98 mmol) at 0° C. and stirred at 0° C. for 2 hr. The resulting mixture was concentrated under reduced pressure to afford the title compound, which was used in the next step directly: LCMS (ESI) calc'd for $C_{40}H_{48}N_8O_4S$ [M+H]$^+$: 737, found 737.

Step C: 6-[[1-(2-aminoethyl)-4-piperidyl]methyl]-3-[4-(azetidin-3-yl)phenyl]-2-(2H-tetrazol-5-yl)benzenesulfonamide A solution of 4-((1-(2-aminoethyl)piperidin-4-yl)methyl)-4'-(azetidin-3-yl)-N-(4-methoxybenzyl)-2-(2-(4-methoxybenzyl)-2H-tetrazol-5-yl)-[1,1'-biphenyl]-3-sulfonamide (0.10 g, 0.14 mmol), TFA (10 mL, 130 mmol) and anisole (0.015 mL, 0.136 mmol) in DCM (1 mL) was stirred at 80° C. for 3 hr. The reaction mixture was concentrated under reduced pressure and the residue was purified by Prep-HPLC with the following conditions: Column: X Bridge RP18, 19×150 mm, 5 μm; Mobile Phase A: water (0.05%

EXAMPLE 607

3-[4-(azetidin-3-yl)phenyl]-6-[[1-(2-hydroxyethyl)-4-piperidyl]methyl]-2-(2H-tetrazol-5-yl)benzenesulfonamide

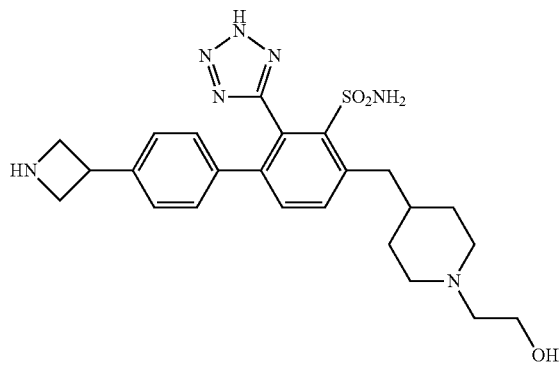 [SMILES: NS(=O)(=O)c1c(CC2CCN(CCO)CC2)ccc(-c2ccc(C3CNC3)cc2)c1-c1nn[nH]n1]

Step A: tert-butyl 3-(4'-((1-(2-(benzyloxy)ethyl)piperidin-4-yl)methyl)-3'-(N,N-bis(4-methoxybenzyl)sulfamoyl)-2'-(2-(4-methoxybenzyl)-2H-tetrazol-5-yl)biphenyl-4-yl)azetidine-1-carboxylate A mixture solution of tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)azetidine-1-carboxylate (0.10 g, 0.11 mmol), $Mg_2SO_4$ (0.13 g, 1.09 mmol), acetic acid (7 mg, 0.12 mmol), benzyloxyacetaldehyde (82 mg, 0.55 mmol) and sodium triacetoxyborohydride (46 mg, 0.22 mmol) in MeOH (0.5 mL) was stirred at ambient temperature for 16 hr, and then the resulting mixture was quenched with water (20 mL), diluted with water (20 mL) and extracted with EtOAc (3×20 mL). The combined organic layers were washed with water (20 mL) and brine (20 mL), dried over anhydrous $Na_2SO_4$ and concentrated under reduced pressure to afford the tittle compound, which was used in the next reaction directly: LCMS (ESI) calc'd for $C_{60}H_{69}N_7O_8S$ [M+H]$^+$: 1048, found 1048.

Step B: tert-butyl 3-(3'-(N,N-bis(4-methoxybenzyl)sulfamoyl)-4'-((1-(2-hydroxyethyl)piperidin-4-yl)methyl)-2'-(2-(4-methoxybenzyl)-2H-tetrazol-5-yl)biphenyl-4-yl)azetidine-1-carboxylate A mixture solution of tert-butyl 3-(4'-((1-(2-(benzyloxy)ethyl)piperidin-4-yl)methyl)-3'-(N,N-bis(4-methoxybenzyl)sulfamoyl)-2'-(2-(4-methoxybenzyl)-2H-tetrazol-5-yl)-[1,1'-biphenyl]-4-yl)azetidine-1-carboxylate (70 mg, 0.07 mmol), Pd(OH)$_2$ (47 mg, 0.07 mmol) and AcOH (4 µl, 0.07 mmol) in MeOH (4 mL) was stirred at ambient temperature for 16 hr under hydrogen at 1.5 atm. The resulting mixture was filtered and the filtrate was concentrated to afford the title compound, which was used in the next reaction directly: LCMS (ESI) calc'd for $C_{53}H_{63}N_7O_8S$ [M+H]$^+$: 958, found 958.

Step C: 4'-(azetidin-3-yl)-4-((1-(2-hydroxyethyl)piperidin-4-yl)methyl)-N-(4-methoxybenzyl)-2-(2-(4-methoxybenzyl)-2H-tetrazol-5-yl)biphenyl-3-sulfonamide A mixture solution of tert-butyl-3-(3'-(N,N-bis(4-methoxybenzyl)sulfamoyl)-4'-((1-(2-hydroxyethyl)piperidin-4-yl)methyl)-2'-(2-(4-methoxybenzyl)-2H-tetrazol-5-yl)-[1,1'-biphenyl]-4-yl)azetidine-1-carboxylate (60 mg, 0.06 mmol) and TFA (1 mL, 12.98 mmol) in DCM (10 mL) was stirred at ambient temperature for 1 hr. The reaction mixture was concentrated under reduced pressure to afford the title compound, which was used in the next step directly. LCMS (ESI) calc'd for $C_{40}H_{47}N_7O_5S$ [M+H]$^+$: 738, found 738.

Step D: 3-[4-(azetidin-3-yl)phenyl]-6-[[1-(2-hydroxyethyl)-4-piperidyl]methyl]-2-(2H-tetrazol-5-yl)benzenesulfonamide A mixture solution of 4'-(azetidin-3-yl)-4-((1-(2-hydroxyethyl)piperidin-4-yl)methyl)-N-(4-methoxybenzyl)-2-(2-(4-methoxybenzyl)-2H-tetrazol-5-yl)-[1,1'-biphenyl]-3-sulfonamide (50 mg, 0.07 mmol) in anisole (0.5 mL), TFA (10 mL) and DCM (0.5 mL) was stirred at 80° C. for 4 hr. The reaction mixture was concentrated under vacuum and the residue was purified by Prep-HPLC with the following conditions: Column: X Bridge C18, 19×250 mm, 5 µm; Mobile Phase A: water (0.05% $NH_4HCO_3$), Mobile Phase B: ACN; Flow rate: 20 mL/min; Gradient: 5% B to 20% B in 8 min; Detection: UV 254 nm. The collected fractions were combined and concentrated under vacuum to afford the title compound: LCMS (ESI) calc'd for $C_{24}H_{31}N_7O_3S$ [M+H]$^+$: 498, found 498; $^1$H NMR (400 MHz, DMSO-d$_6$): 7.82 (brs, 2H), 7.41 (d, J=8.0 Hz, 1H), 7.34 (d, J=8.0 Hz, 1H), 7.13 (d, J=8.1 Hz, 2H), 6.87 (d, J=8.1 Hz, 2H), 4.42 (brs, 1H), 4.15-4.11 (m, 2H), 3.97-3.92 (m, 3H), 3.51-3.49 (m, 2H), 3.05 (d, J=6.4 Hz, 2H), 2.90-2.83 (m, 2H), 2.49-2.42 (m, 2H), 2.03-1.95 (m, 2H), 1.71-1.58 (m, 3H), 1.32-1.25 (m, 2H).

EXAMPLE 608

3-[4-[1-(2-hydroxyethyl)azetidin-3-yl]phenyl]-6-(4-piperidylmethyl)-2-(2H-tetrazol-5-yl)benzenesulfonamide

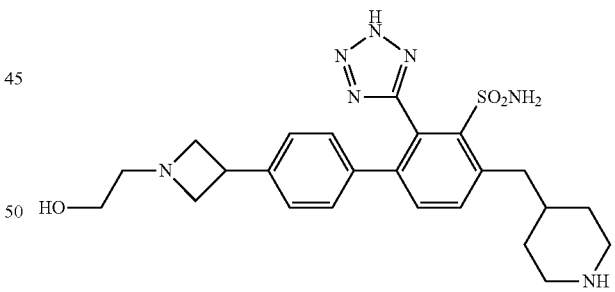

Step A: 4'-(1-(2-hydroxyethyl)azetidin-3-yl)-4-(piperidin-4-ylmethyl)-2-(2H-tetrazol-5-yl)biphenyl-3-sulfonamide A mixture solution of benzyl 4-((4'-(azetidin-3-yl)-2-(2-(4-methoxybenzyl)-2H-tetrazol-5-yl)-3-(N-(4-methoxybenzyl)sulfamoyl)biphenyl-4-yl)methyl)piperidine-1-carboxylate (0.15 mg, 0.18 mmol), $Mg_2SO_4$ (0.13 g, 1.09 mmol), acetic acid (7 mg, 0.11 mmol), 2-(tert-butyldimethylsilyloxy)acetaldehyde (0.32 mg, 1.81 mmol) and sodium triacetoxyborohydride (46 mg, 0.22 mmol) in MeOH (0.5 mL) was stirred at ambient temperature for 16 hr. The reaction mixture was quenched with water (20 mL), diluted with water (20 mL) and extracted with EtOAc (3×20 mL). The combined organic layers were washed with water (20 mL)

and then brine (20 mL), dried over anhydrous Na$_2$SO$_4$ and concentrated under reduced pressure to afford the title compound, which was used in next step directly: LCMS (ESI) calc'd for C$_{54}$H$_{67}$N$_7$O$_7$SSi [M+H]$^+$: 986, found 986.

Step B: 4'-(1-(2-(tert-butyldimethylsilyloxy)ethyl)azetidin-3-yl)-N-(4-methoxybenzyl)-2-(2-(4-methoxybenzyl)-2H-tetrazol-5-yl)-4-(piperidin-4-ylmethyl)biphenyl-3-sulfonamide A mixture solution of benzyl-4-((4'-(1-(2-(tert-butyldimethylsilyloxy)ethyl)azetidin-3-yl)-2-(2-(4-methoxybenzyl)-2H-tetrazol-5-yl)-3-(N-(4-methoxybenzyl)sulfamoyl)biphenyl-4-yl)methyl)piperidine-1-carboxylate (67 mg, 0.07 mmol), Pd(OH)$_2$ (47 mg, 0.07 mmol) and AcOH (4 µL, 0.07 mmol) in MeOH (4 mL) was stirred at ambient temperature for 16 hr. The resulting mixture was filtered and the filtrate was concentrated under reduced pressure to afford the title compound, which was used in the next step directly: LCMS (ESI) calc'd for C$_{46}$H$_{61}$N$_7$O$_5$SSi [M+H]$^+$: 852, found 852.

Step C: 4'-(1-(2-hydroxyethyl)azetidin-3-yl)-N-(4-methoxybenzyl)-2-(2-(4-methoxybenzyl)-2H-tetrazol-5-yl)-4-(piperidin-4-ylmethyl)biphenyl-3-sulfonamide A mixture solution of 4'-(1-(2-(tert-butyldimethylsilyloxy)ethyl)azetidin-3-yl)-N-(4-methoxybenzyl)-2-(2-(4-methoxybenzyl)-2H-tetrazol-5-yl)-4-(piperidin-4-ylmethyl)biphenyl-3-sulfonamide (50 mg, 0.06 mmol) and TBAF (0.15 g, 0.58 mmol) in THF (10 mL) was stirred at ambient temperature for 1 hr and then the resulting mixture was concentrated under reduced pressure and the residue was purified by Prep-HPLC with the following conditions: Column: X Bridge C18, 19×250 mm, 5 µm; Mobile Phase A: water (0.05% TFA), Mobile Phase B: ACN; Flow rate: 20 mL/min; Gradient: 30% B to 70% B in 10 min; Detection: UV 254 nm; Retention time: 5.8 min. The collected fractions were combined and concentrated to afford the title compound, which was used in next step directly: LCMS (ESI) calc'd for C$_{40}$H$_{47}$N$_7$O$_5$S [M+H]$^+$: 738, found 738.

Step D: 3-[4-[1-(2-hydroxyethyl)azetidin-3-yl]phenyl]-6-(4-piperidylmethyl)-2-(2H-tetrazol-5-yl)benzenesulfonamide A mixture solution of 4'-(1-(2-hydroxyethyl)azetidin-3-yl)-N-(4-methoxybenzyl)-2-(2-(4-methoxybenzyl)-2H-tetrazol-5-yl)-4-(piperidin-4-ylmethyl)biphenyl-3-sulfonamide (30 mg, 0.04 mmol), anisole (0.5 mL, 4.58 mmol) and TFA (10 mL, 0.13 mmol) in DCM (0.5 mL) was stirred at ambient temperature for 4 hr. The resulting mixture was concentrated under vacuum and the residue was purified by Prep-HPLC with the following conditions: Column: X Bridge C18, 19×250 mm, 5 µm; Mobile Phase A: water (0.05% NH$_4$HCO$_3$), Mobile Phase B: ACN; Flow rate: 20 mL/min; Gradient: 5% B to 20% B in 8 min; Detection: UV 254 nm. The collected fractions were combined and concentrated under reduced pressure to afford the title compound: LCMS (ESI) calc'd for C$_{24}$H$_{31}$N$_7$O$_3$S [M+H]$^+$: 498, found 498. $^1$H NMR (400 MHz, DMSO-d$_6$): 7.53-7.47 (m, 2H), 7.10 (d, J=8.0 Hz, 2H), 6.97 (d, J=8.4 Hz, 2H), 3.93-3.85 (m, 2H), 3.79-3.71 (m, 1H), 3.62-3.59 (m, 2H), 3.37-3.32 (m, 2H), 3.23-3.16 (m, 2H), 2.94-2.88 (m, 2H), 2.76-2.72 (m, 2H), 2.12-2.03 (m, 1H), 1.96-1.90 (m, 2H), 1.59-1.30 (m, 4H).

EXAMPLE 609

2-[4-[[4-[4-(azetidin-3-yl)phenyl]-2-sulfamoyl-3-(2H-tetrazol-5-yl)phenyl]methyl]-1-piperidyl]acetamide

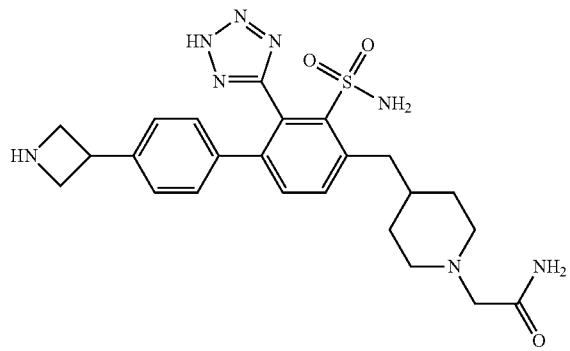 [SMILES: NC(=O)CN1CCC(Cc2ccc(-c3ccc(C4CNC4)cc3)c(-c3nn[nH]n3)c2S(N)(=O)=O)CC1]

Step A: tert-butyl 3-(4'-((1-(2-amino-2-oxoethyl)piperidin-4-yl)methyl)-3'-(N,N-bis(4-methoxybenzyl)sulfamoyl)-2'-(2-(4-methoxybenzyl)-2H-tetrazol-5-yl)biphenyl-4-yl)azetidine-1-carboxylate A solution mixture of tert-butyl 3-(3'-(N,N-bis(4-methoxybenzyl)sulfamoyl)-2'-(2-(4-methoxybenzyl)-2H-tetrazol-5-yl)-4'-(piperidin-4-ylmethyl)-[1,1'-biphenyl]-4-yl)azetidine-1-carboxylate (0.15 g, 0.16 mmol), K$_2$CO$_3$ (0.11 mg, 0.82 mmol) and 2-chloroacetamide (77 mg, 0.82 mmol) in DMF (10 mL) was stirred at 60° C. for 3 hr. The resulting mixture was quenched with water (20 mL), diluted with water (60 mL) and extracted with EtOAc (3×40 mL). The combined organic layers were washed with water (20 mL) and brine (20 mL), dried over anhydrous Na$_2$SO$_4$ and concentrated under vacuum to afford the title compound, which was used in next step directly: LCMS (ESI) calc'd for C$_{53}$H$_{62}$N$_8$O$_8$S [M+H]$^+$: 971, found 971.

Step B: 2-(4-((4'-(azetidin-3-yl)-3-(N,N-bis(4-methoxybenzyl)sulfamoyl)-2-(2-(4-methoxybenzyl)-2H-tetrazol-5-yl)biphenyl-4-yl)methyl)piperidin-1-yl)acetamide A solution of tert-butyl-3-(4'-((1-(2-amino-2-oxoethyl)piperidin-4-yl)methyl)-3'-(N,N-bis(4-methoxybenzyl)sulfamoyl)-2'-(2-(4-methoxybenzyl)-2H-tetrazol-5-yl)-[1,1'-biphenyl]-4-yl)azetidine-1-carboxylate (0.15 g, 0.15 mmol) and TFA (2.5 mL, 32.40 mmol) in DCM (20 mL) was stirred at ambient temperature for 30 min and then it was concentrated under reduced pressure to afford the title compound, which was used in next step directly: LCMS (ESI) calc'd for C$_{48}$H$_{54}$N$_8$O$_6$S [M+H]$^+$: 871, found 871.

Step C: 2-[4-[[4-[4-(azetidin-3-yl)phenyl]-2-sulfamoyl-3-(2H-tetrazol-5-yl)phenyl]methyl]-1-piperidyl]acetamide A solution of 2-(4-((4'-(azetidin-3-yl)-3-(N,N-bis(4-methoxybenzyl)sulfamoyl)-2-(2-(4-methoxybenzyl)-2H-tetrazol-5-yl)-[1,1'-biphenyl]-4-yl)methyl)piperidin-1-yl)acetamide (0.13 g, 0.15 mmol) in TFA (10 mL, 130 mmol) was stirred at 80° C. for 2 hr and then the resulting mixture was concentrated under vacuum and the residue was purified by Prep-HPLC with the following conditions: Column: X Bridge RP18, 19×150 mm, 5 µm; Mobile Phase A: water (0.05% NH$_4$HCO$_3$), Mobile Phase B: ACN; Flow rate: 20 mL/min; Gradient: 5% B to 25% B in 7 min; Detection: UV 254 nm. The collected fractions were combined and concentrated under vacuum to afford the title compound: LCMS (ESI) calc'd for C$_{24}$H$_{30}$N$_8$O$_3$S [M+H]$^+$: 511. found 511; $^1$H NMR (300 MHz, DMSO-$d_6$): δ 8.51 (brs, 1H), 7.82 (s, 2H), 7.43-7.32 (m, 2H), 7.14-7.11 (m, 4H), 6.87 (d, J=10.8 Hz, 2H), 4.17 (s, 2H), 3.97-3.96 (m, 3H), 3.06 (d, J=8.0 Hz, 2H), 2.81-2.71 (m, 4H), 2.01-1.93 (m, 2H), 1.65-1.57 (m, 3H), 1.38-1.34 (m, 2H).

EXAMPLE 610

3-(2-amino-3H-benzo[d]imidazol-5-yl)-6-(piperidin-4-ylmethyl)-2-(2H-tetrazol-5-yl)benzenesulfonamide

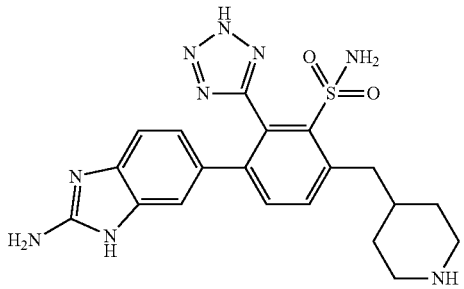 [SMILES: Nc1nc2ccc(-c3ccc(CC4CCNCC4)c(S(N)(=O)=O)c3-c3nn[nH]n3)cc2[nH]1]

Step A: 2-nitro-4-(4,4,5,5-tetramethyl-1,3,2-dioxaborolan-2-yl)benzenamine

Into a 500-mL round-bottom flask purged and maintained with an inert atmosphere of argon, was placed a solution of 4,4,4',4',5,5,5',5'-octamethyl-2,2'-bi(1,3,2-dioxaborolane) (25.70 g, 101.00 mmol), 4-bromo-2-nitroaniline (20.00 g, 92.00 mmol) and potassium acetate (27.10 g, 276.00 mmol) in DMF (250 mL). This was followed by the addition of PdOAc$_2$ (0.62 g, 2.76 mmol) at ambient temperature. The resulting mixture was stirred at 85° C. for 20 hr under argon and then it was cool down to 20° C., quenched with water (200 mL) and filtered. The filtrate was concentrated under reduced pressure and the residue was purified by silica gel column chromatography, eluted with EA in PE (50%) to afford the crude product. The crude was recrystallized from PE/EtOAc (200 mL/10 mL) and dried over in vacuum to afford the title compound: LCMS (ESI) calc'd for $C_{12}H_{12}BN_2O_4$ [M+H]$^+$: 265, found 265. $^1$H NMR (400 MHz, DMSO-$d_6$): δ 8.26 (s, 1H), 7.70 (s, 2H), 7.55 (d, J=8.4 Hz, 1H), 6.97 (d, J=8.4 Hz, 1H), 1.27 (s, 12H).

Step B: 4-(4,4,5,5-tetramethyl-1,3,2-dioxaborolan-2-yl)benzene-1,2-diamine

Into a 250-mL round-bottom flask, was placed a solution of 2-nitro-4-(4,4,5,5-tetramethyl-1,3,2-dioxaborolan-2-yl) aniline (7.40 g, 25.20 mmol) in MeOH (50 mL) and DCM (50 mL). This was followed by the additional of Pd/C (134 g, 126 mmol, wet 10%) at ambient temperature. The reaction mixture was degassed with nitrogen for 3 times and stirred under hydrogen for 16 hr at ambient temperature. The resulting mixture was filtered and the filter cake was washed with DCM (3×10 mL). The combined organic layers were concentrated in vacuo and purified by silica gel column chromatography, eluted with EA in PE (30%) to afford the title compound: LCMS (ESI) calc'd for $C_{12}H_{19}BN_2O_2$ [M+H]$^+$: 235, found 235. $^1$H NMR (400 MHz, CD$_3$Cl): δ 7.23 (d, J=7.6 Hz, 1H), 7.17 (s, 1H), 6.70 (d, J=8.0 Hz, 1H), 3.19 (br, 4H), 1.32 (s, 12H).

Step C: 6-(4,4,5,5-tetramethyl-1,3,2-dioxaborolan-2-yl)-1H-benzo[d]imidazol-2-amine Into a 50-mL round-bottom flask purged and maintained with an inert atmosphere of argon, was placed a solution of 4-(4,4,5,5-tetramethyl-1,3,2-dioxaborolan-2-yl)benzene-1, 2-diamine (2.00 g, 7.69 mmol) in MeOH (10 mL). This was followed by the additional of cyanogen bromide (0.83 g, 7.69 mmol) at 0° C. The resulting mixture was stirred at 0° C. for 2 hr under argon and then it was quenched with aqueous saturated Na$_2$CO$_3$ (30 mL) and extracted with EtOAc (3×30 mL). The combined organic layers were washed with brine (70 mL), dried over anhydrous Na$_2$SO$_4$ and concentrated in vacuo. The residue was recrystallized from DCM (100 mL) to afford the title compound: LCMS (ESI) calc'd for $C_{13}H_{18}BN_3O_2$ [M+H]$^+$: 260, found 260; $^1$H NMR (400 MHz, DMSO-$d_6$): δ 10.70 (br, 1H), 7.40 (s, 1H), 7.23 (d, J=8.0 Hz, 1H), 7.06 (d, J=7.6 Hz, 1H), 6.24 (s, 2H), 1.23 (s, 12H).

Step D: 3-(2-amino-3H-benzo[d]imidazol-5-yl)-6-bromo-N,N-bis(4-methoxybenzyl)-2-(2-(4-methoxybenzyl)-2H-tetrazol-5-yl)benzenesulfonamide Into a 25-mL round-bottom flask purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (0.63 g, 0.80 mmol), 6-(4,4,5,5-tetramethyl-1,3,2-dioxaborolan-2-yl)-1H-benzo[d]imidazol-2-amine (0.25 g, 0.96 mmol) and Pd(PPh$_3$)$_4$ (0.14 g, 0.12 mmol) in dioxane (7 mL). This was followed by the addition of Na$_2$CO$_3$ (0.26 g, 2.41 mmol) in water (1.5 mL) at ambient temperature. After the resulting mixture was stirred at 80° C. for 18 hr under argon, it was cooled down to 20° C., quenched with water (50 mL) and extracted with EtOAc (3×50 mL). The combined organics were washed with brine (2×50 mL), dried over anhydrous Na$_2$SO$_4$ and concentrated in vacuo. The residue was purified by silica gel column chromatography, eluted with EtOAc/PE (100/1) to afford the title compound: LCMS (ESI) calc'd for $C_{38}H_{35}BrN_8O_5S$ [M+H]$^+$: 795, 797 (1:1), found 795, 797 (1:1).

Step E: tert-butyl 4-(4-(2-amino-3H-benzo[d]imidazol-5-yl)-2-(N,N-bis(4-methoxybenzyl)sulfamoyl)-3-(2-(4-methoxybenzyl)-2H-tetrazol-5-yl)benzyl)piperidine-1-carboxylate Into a 10-mL round-bottom flask purged and maintained with an inert atmosphere of argon, was placed a solution of 3-(2-amino-1H-benzo[d]imidazol-6-yl)-6-bromo-N,N-bis(4-methoxybenzyl)-2-(2-(4-methoxybenzyl)-2H-tetrazol-5-yl)benzenesulfonamide (0.10 g, 0.13 mmol). tert-butyl 4-(iodomethyl)piperidine-1-carboxylate (82 mg, 0.25 mmol), 4,7-diphenyl-1,10-phenanthroline (8.35 mg, 0.025 mmol), nickel iodine (7.85 mg, 0.03 mmol) and manganese (14 mg, 0.25 mmol) in DMA (1 mL). This was followed by the addition of benzonitrile (1.30 mg, 0.013 mmol) at ambient temperature and chlorotrimethylsilane (0.14 mg, 1.26 µmol) at 0° C. The resulting mixture was stirred at 40° C. for 2 hr under argon and then cooled down to 20° C., quenched with water (10 mL) and extracted with EtOAc (3×10 mL). The combined organic phases were washed with brine (2×20 mL), dried over anhydrous Na$_2$SO$_4$ and concentrated in vacuo. The residue was purified by Prep-HPLC: Column: X Bridge C18, 19×150 mm, 5 µm; Mobile Phase A: water (0.05% TFA), Mobile Phase B: ACN; Flow rate: 20 mL/min; Gradient: 30% B to 70% B in 10 min; Detection: UV 254 nm. to afford the title compound: LCMS (ESI) calc'd for $C_{49}H_{55}N_9O_7S$ [M+H]$^+$: 914, found 914.

Step F: 3-(2-amino-3H-benzo[d]imidazol-5-yl)-N,N-bis(4-methoxybenzyl)-2-(2-(4-methoxybenzyl)-2H-tetrazol-5-yl)-6-(piperidin-4-ylmethyl)benzenesulfonamide Into a 25-mL round-bottom flask, was placed a solution of tert-butyl 4-(4-(2-amino-1H-benzo[d]imidazol-6-yl)-2-(N, N-bis(4-methoxybenzyl)sulfamoyl)-3-(2-(4-methoxybenzyl)-2H-tetrazol-5-yl)benzyl)piperidine-1-carboxylate (25 mg, 0.03 mmol) in DCM (2 mL). This was followed by the addition of TFA (0.5 mL, 6.49 mmol) dropwise with stirring at 0° C. The resulting mixture was stirred at 0° C. for 1 hr and then the solvent was evaporated in vacuo to afford the title compound. The crude product was used directly in the next step without further purification: LCMS (ESI) calc'd for $C_{44}H_{47}N_9O_5S$ [M+H]$^+$: 814, found 814.

Step G: 3-(2-amino-3H-benzo[d]imidazol-5-yl)-6-(piperidin-4-ylmethyl)-2-(2H-tetrazol-5-yl)benzenesulfonamide To a stirred solution of 3-(2-amino-1H-benzo[d]imidazol-6-yl)-N,N-bis(4-methoxybenzyl)-2-(2-(4-methoxybenzyl)-2H-tetrazol-5-yl)-6-(piperidin-4-ylmethyl)benzenesulfonamide (20 mg, 0.02 mmol) in anisole (1 mL) was added TFA (3 mL, 38.9 mmol) at ambient temperature. The resulting mixture was stirred at 80° C. for 3 hr and then cool down to 20° C. The solvent was evaporated and the residue was purified by Prep-HPLC with the following conditions: Column: X Bridge RP18, 19×150 mm, 5 μm; Mobile Phase A: water (0.05% NH$_4$HCO$_3$), Mobile Phase B: ACN; Flow rate: 20 mL/min; Gradient: 3% B to 18% B in 7 min; Detection: UV 254 nm. The collected fractions were combined and concentrated in vacuo to give the title compound: LCMS (ESI) calc'd for $C_{20}H_{23}N_9O_2S$ [M−H]$^-$: 452, found 452. $^1$H NMR (400 MHz, DMSO-d$_6$): δ 7.83 (s, 2H), 7.44 (d, J=8.0 Hz, 1H), 7.32 (d, J=8.0 Hz, 1H), 6.78 (d, J=8.0 Hz, 1H), 6.64 (s, 1H), 6.42 (s, 1H), 6.01 (s, 2H), 3.20-3.10 (s, 2H), 3.07 (d, J=6.4 Hz, 2H), 2.76-2.73 (m, 2H), 1.98-1.82 (m, 1H), 1.75-1.71 (m, 2H), 1.40-1.37 (m, 2H).

EXAMPLE 611

3-(2-amino-3H-benzo[d]imidazol-5-yl)-6-(azetidin-3-ylmethyl)-2-(2H-tetrazol-5-yl)benzenesulfonamide

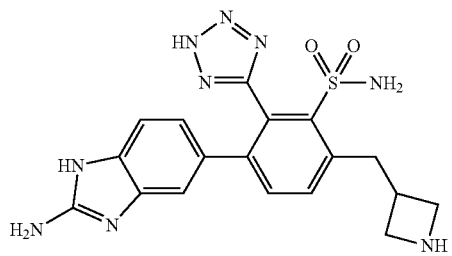 [SMILES: Nc1nc2cc(-c3ccc(CC4CNC4)c(S(N)(=O)=O)c3-c3nn[nH]n3)ccc2[nH]1]

Step A: tert-butyl 3-(4-(2-amino-3H-benzo[d]imidazol-5-yl)-2-(N,N-bis(4-methoxybenzyl)sulfamoyl)-3-(2-(4-methoxybenzyl)-2H-tetrazol-5-yl)benzyl)azetidine-1-carboxylate To a stirred mixture of 3-(2-amino-3a,7a-dihydro-1H-benzo[d]imidazol-6-yl)-6-bromo-N,N-bis(4-methoxybenzyl)-2-(1-(4-methoxybenzyl)-1H-tetrazol-5-yl)benzenesulfonamide (0.10 g, 0.13 mmol) in DMA (1.3 mL) was added tert-butyl 3-(iodomethyl)azetidine-1-carboxylate (0.15 g, 0.50 mmol) at ambient temperature under Ar. To the resulting mixture was added 4,7-diphenyl-1,10-phenanthroline (17 mg, 0.05 mmol), nickel (II) iodide (16 mg, 0.05 mmol), manganese (28 mg, 0.50 mmol), benzonitrile (5 mg, 0.05 mmol) and chlorotrimethylsilane (6 mg, 0.05 mmol) at ambient temperature. After the resulting mixture was heated for 2 hr at 60° C. under Ar, the reaction was quenched with water (5 mL) and extracted with EtOAc (3×10 mL). The combined organic layers were washed with brine (2×10 mL), dried over anhydrous Na$_2$SO$_4$ and concentrated in vacuo. The residue was purified by Prep-TLC with DCM/MeOH (15/1) to afford the title compound, which was used in the next reaction directly. LCMS (ESI) calc'd for $C_{47}H_{51}N_9O_7S$ [M+1]$^+$: 886, found 886.

Step B: 3-(2-amino-3H-benzo[d]imidazol-5-yl)-6-(azetidin-3-ylmethyl)-N-(4-methoxybenzyl)-2-(2-(4-methoxybenzyl)-2H-tetrazol-5-yl)benzenesulfonamide To a stirred solution of tert-butyl 3-(4-(2-amino-1H-benzo[d]imidazol-6-yl)-2-(N,N-bis(4-methoxybenzyl)sulfamoyl)-3-(2-(4-methoxybenzyl)-2H-tetrazol-5-yl)benzyl)azetidine-1-carboxylate (60 mg, 0.07 mmol) in anisole (1 mL, 0.07 mmol) was dropwise added TFA (1 mL, 0.07 mmol) at 0° C. The reaction mixture was stirred for 2 hr at ambient temperature and concentrated in vacuo to afford the title compound, which was used directly: LCMS (ESI) calc'd for $C_{39}H_{35}N_9O_4S$ [M+1]$^+$: 666, found 666.

Step C: 3-(2-amino-3H-benzo[d]imidazol-5-yl)-6-(azetidin-3-ylmethyl)-2-(2H-tetrazol-5-yl)benzenesulfonamide To a stirred mixture of 3-(2-amino-1H-benzo[d]imidazol-6-yl)-6-(azetidin-3-ylmethyl)-N,N-bis(4-methoxybenzyl)-2-(2-(4-methoxybenzyl)-2H-tetrazol-5-yl)benzenesulfonamide (70 mg, 0.00 mmol) (crude) in anisole (1 mL) was added TFA (2 mL) at ambient temperature. The resulting solution was stirred for 3 hr at 80° C. and then concentrated in vacuo. The residue was purified by Prep-HPLC with the following conditions: Column, X bridge C18, 19×150 mm; Mobile phase A: water (0.05% NH$_4$HCO$_3$), Mobile phase A: acetonitrile; Gradient: (hold 34% acetonitrile for 8 min, hold 100% for 2 min, down to 34% in 2 min; Detector: UV 220 and 254 nm. The collected fractions were concentrated in vacuo to afford the title compound: LCMS (ESI) calc'd for $C_{18}H_{19}N_9O_2S$ [M+1]$^+$: 426, found 426. $^1$H NMR (400 MHz, CD$_3$OD): δ 7.59 (d, J=8.0 Hz, 1H), 7.54-7.51 (m, 1H), 6.99 (d, J=8.4 Hz, 1H), 6.84 (d, J=8.8 Hz, 1H), 6.76 (d, J=6.4 Hz, 1H), 4.10-3.99 (m, 3H), 3.66-3.48 (m, 4H).

EXAMPLE 612

3-(2-amino-3H-benzo[d]imidazol-4-yl)-6-(piperidin-4-ylmethyl)-2-(2H-tetrazol-5-yl)benzenesulfonamide

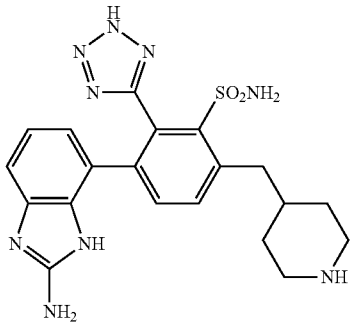 [SMILES: Nc1nc2cccc(-c3ccc(CC4CCNCC4)c(S(N)(=O)=O)c3-c3nn[nH]n3)c2[nH]1]

Step A: 2-nitro-3-(4,4,5,5-tetramethyl-1,3,2-dioxaborolan-2-yl)benzenamine

Into a 50-mL round-bottom flask purged and maintained with an inert atmosphere of argon, was placed a solution of 3-bromo-2-nitroaniline (20.00 g, 92 mmol) in 1,4-dioxane (300 mL). This was followed by the addition of [1,1'-bis(diphenylphosphino)ferrocene]dichloropalladium(II) (3.37 g, 4.61 mmol), potassium acetate (27.10 g, 276 mmol) and 4,4,4',4',5,5,5',5'-octamethyl-2,2'-bi(1,3,2-dioxaborolane) (35.10 g, 138 mmol) at ambient temperature. After the resulting mixture was stirred at 85° C. for 16 hr under argon, it was filtered out and the filtrate was concentrated in vacuo. The residue was purified by silica gel column chromatography, eluted with EtOAc/PE (1/1) to afford the title compound: LCMS (ESI) calc'd for $C_{12}H_{17}BN_2O_4$ [M+H]$^+$: 265, found 265.

Step B: 3-(4,4,5,5-tetramethyl-1,3,2-dioxaborolan-2-yl)benzene-1,2-diamine

Into a 250-mL round-bottom flask, was placed a solution of 2-nitro-3-(4,4,5,5-tetramethyl-1,3,2-dioxaborolan-2-yl)aniline (5.00 g, 18.93 mmol) in DCM (20 mL) and MeOH (20 mL). This was followed by the additional of Pd/C (20.15 g, 18.93 mmol) at ambient temperature. The resulting mixture was degassed with nitrogen for 3 times, and then bubbled with hydrogen for 3 times. After the resulting mixture was stirred under hydrogen for 16 hr at ambient temperature at 1.5 atm, it was filtered and the filter cake was washed with DCM (3×10 mL). The combined organic layers were concentrated in vacuo and purified by silica gel column chromatography, eluted with EtOAc/PE (2/3) to afford the title compound: LCMS (ESI) calc'd for $C_{12}H_{19}BN_2O_2$ [M+H]$^+$: 235, found 235.

Step C: 5',6'-diamino-4-bromo-N,N-bis(4-methoxybenzyl)-2-(2-(4-methoxybenzyl)-2H-tetrazol-5-yl)biphenyl-3-sulfonamide Into a 50-mL round-bottom flask purged and maintained with an inert atmosphere of argon, was placed a solution of 6-bromo-3-iodo-N,N-bis(4-methoxybenzyl)-2-(2-(4-methoxybenzyl)-2H-tetrazol-5-yl)benzenesulfonamide (0.77 g, 0.97 mmol), 3-(4,4,5,5-tetramethyl-1,3,2-dioxaborolan-2-yl)benzene-1,2-diamine (0.50 g, 2.13 mmol) and Pd(Ph$_3$P)$_4$ (0.11 g, 0.10 mmol) in dioxane (10 mL). This was followed by the addition of Na$_2$CO$_3$ (0.31 g, 2.90 mmol) in water (1 mL) at ambient temperature. The resulting mixture was stirred at 80° C. for 18 hr under argon and then was cooled down to 20° C., quenched with water (50 mL) and extracted with EtOAc (3×50 mL). The combined organic phase was washed with brine (3×50 mL), dried over anhydrous Na$_2$SO$_4$ and concentrated under reduced pressure. The residue was purified by silica gel column chromatography, eluted with EA/PE (3/2) to afford the title compound, which was used in the next step directly. LCMS (ESI) calc'd for $C_{37}H_{36}BrN_7O_5S$ [M+H]$^+$: 770, 772 (1:1), found 770, 772 (1:1).

Step D: 3-(2-amino-3H-benzo[d]imidazol-4-yl)-6-bromo-N,N-bis(4-methoxybenzyl)-2-(2-(4-methoxybenzyl)-2H-tetrazol-5-yl)benzenesulfonamide Into a 25-mL round-bottom flask purged and maintained with an inert atmosphere of argon, was placed a solution of 2',3'-diamino-4-bromo-N,N-bis(4-methoxybenzyl)-2-(2-(4-methoxybenzyl)-2H-tetrazol-5-yl)-[1,1'-biphenyl]-3-sulfonamide (1.4 g, 1.82 mmol) in MeOH (5 mL) and DCM (5 mL). This was followed by the addition of cyanogen bromide (0.19 g, 1.82 mmol) at 0° C. The resulting mixture was stirred at 25° C. for 16 hr under a atmosphere of argon. The reaction was quenched with aqueous saturated sodium bicarbonate (50 mL) and extracted with EtOAc (3×50 mL). The combined organic layers were washed with brine (2×50 mL), dried over anhydrous Na$_2$SO$_4$ and concentrated under reduced pressure. The residue was recrystallized from DCM/EA/PE (10 mL/10 mL/50 mL). The solid was collected by filtration and dried in vacuo and then was purified by silica gel column chromatography, eluted with EtOAc in Petroleum ether (80%) to afford the title compound: LCMS (ESI) calc'd for $C_{38}H_{35}BrN_8O_5S$ [M+H]$^+$: 795, 797 (1:1), found 795, 797 (1:1).

Step E: tert-butyl 4-(4-(2-amino-3H-benzo[d]imidazol-4-yl)-2-(N,N-bis(4-methoxybenzyl)sulfamoyl)-3-(2-(4-methoxybenzyl)-2H-tetrazol-5-yl)benzyl)piperidine-1-carboxylate Into a 10-mL round-bottom flask purged and maintained with an inert atmosphere of argon, was placed a solution of 3-(2-amino-1H-benzo[d]imidazol-7-yl)-6-bromo-N,N-bis(4-methoxybenzyl)-2-(2-(4-methoxybenzyl)-2H-tetrazol-5-yl)benzenesulfonamide (0.20 g, 0.25 mmol) tert-butyl 4-(iodomethyl)piperidine-1-carboxylate (0.33 g, 1.01 mmol), 4,7-diphenyl-1,10-phenanthroline (33 mg, 0.10 mmol), nickel iodide (17 mg, 0.05 mmol) and manganese (55 mg, 1.01 mmol) in DMA (3 mL). This was followed by the addition of benzonitrile (26 mg, 0.25 mmol) at ambient temperature and chlorotrimethylsilane (27.3 mg, 0.251 mmol) at 0° C. The resulting mixture was stirred at 60° C. for 2 hr under a atmosphere of argon. The reaction mixture was allowed to cool to 20° C., quenched with water (10 mL) and extracted with EtOAc (3×10 mL), the combined organic layers were washed with brine (2×20 mL), dried over anhydrous Na$_2$SO$_4$ and filtered. The filtrate was evaporated under reduced pressure and the residue was purified by Prep-HPLC with the following conditions: Column: X Bridge RP C18, 19×150 mm, 5 µm; Mobile Phase A: water (10 mM NH$_4$HCO$_3$), Mobile Phase B: ACN; Flow rate: 20 mL/min; Gradient: 65-65% B in 12 min; Detection: at 254 nm. The collected fractions were combined and concentrated in vacuo to afford the title compound: LCMS (ESI) calc'd for $C_{49}H_{55}N_9O_7S$ [M+H]$^+$: 914, found 914.

Step F: 3-(2-amino-3H-benzo[d]imidazol-4-yl)-N,N-bis(4-methoxybenzyl)-2-(2-(4-methoxybenzyl)-2H-tetrazol-5-yl)-6-(piperidin-4-ylmethyl)benzenesulfonamide Into a 25-mL round-bottom flask, was placed a solution of tert-butyl 4-(4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)benzyl)piperidine-1-carboxylate (0.10 g, 0.11 mmol) in DCM (2 mL). This was followed by the addition of TFA (0.5 mL, 6.49 mmol) dropwise with stirring at 0° C. The resulting mixture was stirred at 0° C. for 1 hr and then evaporated under reducing pressure to afford the title compound, which was used directly in the next step without further purification: LCMS (ESI) calc'd for $C_{44}H_{47}N_9O_5S$ [M+H]$^+$: 814, found 814.

Step G: 3-(2-amino-3H-benzo[d]imidazol-4-yl)-6-(piperidin-4-ylmethyl)-2-(2H-tetrazol-5-yl)benzenesulfonamide To a solution of 3-(2-amino-1H-benzo[d]imidazol-7-yl)-N,N-bis(4-methoxybenzyl)-2-(2-(4-methoxybenzyl)-2H-tetrazol-5-yl)-6-(piperidin-4-ylmethyl)benzenesulfonamide (90 mg, 0.09 mmol) in anisole (0.5 mL) was added TFA (3 mL, 38.9 mmol) at ambient temperature. After the resulting mixture was stirred at 80° C. for 2 hr, it was cooled down to 20° C. and the solvent was evaporated. The residue was purified by Prep-HPLC with the following conditions: Column: X Bridge RP C18, 19×150 mm, 5 µm; Mobile Phase A: water (10 mM NH$_4$HCO$_3$), Mobile Phase B: ACN; Flow rate: 20 mL/min; Gradient: 5-25% B in 8 min; Detection: at 254 nm. The collected fractions were combined and concentrated under reducing pressure to afford the title compound: LCMS (ESI) calc'd for $C_{20}H_{23}N_9O_2S$ [M−H]$^-$: 452, found 452; $^1$H NMR (400 MHz, DMSO-d$_6$): δ 7.86 (s, 2H), 7.63 (s, 1H), 7.35 (d, J=8.4 Hz, 1H), 6.85 (d, J=8.4 Hz, 1H), 6.44 (s, 1H), 6.08 (s, 1H), 6.04 (d, J=8.0 Hz, 2H), 3.17-3.08 (m, 4H), 2.51-2.49 (m, 2H), 1.80 (s, 1H), 1.67-1.51 (m, 2H), 1.42-1.33 (m, 2H).

EXAMPLES 613-621

Parallel synthesis of N-substituted 4'-(piperidin-4-yl)-2-(1H-tetrazol-5-yl)-[1,1'-biphenyl]-3-sulfonamides

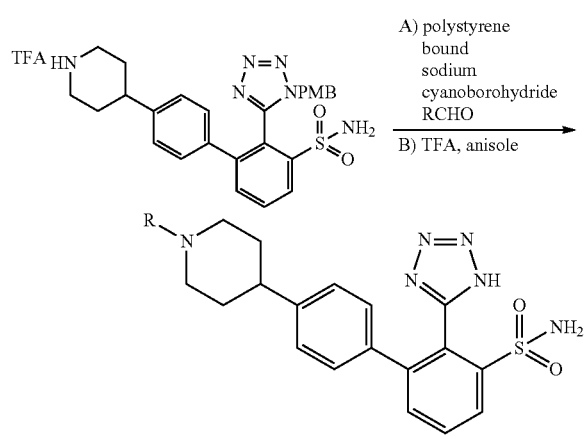

Step A: 2-(1-(4-methoxybenzyl)-1H-tetrazol-5-yl)-4'-(piperidin-4-yl)-[1,1'-biphenyl]-3-sulfonamide 2,2,2-trifluoroacetate and 2-(2-(4-methoxybenzyl)-2H-tetrazol-5-yl)-4'-(piperidin-4-yl)-[1,1'-biphenyl]-3-sulfonamide 2,2,2-trifluoroacetate (47 mg, 0.076 mmol) in MeOH (0.500 mL) and Tetrahydrofuran (0.5 mL) were treated with an excess of polystyrene bound sodium cyanoborohydride. Then commercially available or known tert-butoxycarbonyl protected aminoaldehydes (2 equivalents, 0.152 mmol) were added in separate vials prepared as described and each of these mixtures was stirred for 3 hours. The organics were removed via pipette to leave behind the resin. The solvents were removed in the genevac under reduced pressure.

Step B: To firstly remove the boc-protecting group, ANISOLE (0.100 mL, 0.912 mmol), $CH_2Cl_2$ (0.7 mL) and TFA (0.3 mL) were added and the mixtures were stirred at room temperature for 2 hours. Then TFA (1 mL) was added and the mixtures were stirred at 65° C. for 2.5 hours. The mixtures were allowed to cool, and the volatile organics were removed in the genenvac. 1 mL of DMSO was added to each vial and the mixtures were purified using mass directed reverse phase HPLC to afford the examples in the table below.

| Ex. No. | Structure | Name | Cal'd MW $[M + H]^+$ | LC/MS m/e $(M + H)^+$ |
|---|---|---|---|---|
| 613 | 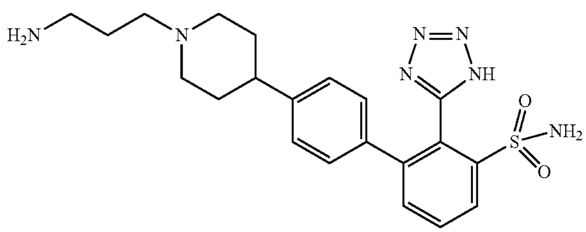 [SMILES: NCCCN1CCC(c2ccc(-c3cccc(S(N)(=O)=O)c3-c3nnn[nH]3)cc2)CC1] | 3-[4-[1-(3-aminopropyl)-4-piperidyl]phenyl]-2-(1H-tetrazol-5-yl)benzenesulfonamide | 442 | 442 |
| 614 | 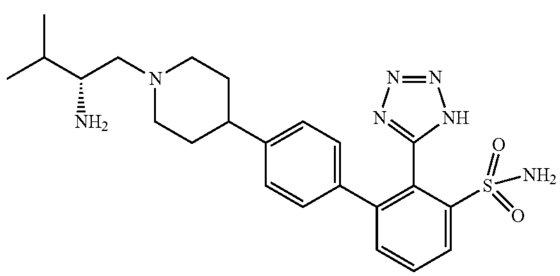 [SMILES: CC(C)[C@@H](N)CN1CCC(c2ccc(-c3cccc(S(N)(=O)=O)c3-c3nnn[nH]3)cc2)CC1] | 3-[4-[1-[(2R)-2-amino-3-methyl-butyl]-4-piperidyl]phenyl]-2-(1H-tetrazol-5-yl)benzenesulfonamide | 470 | 470 |
| 615 | 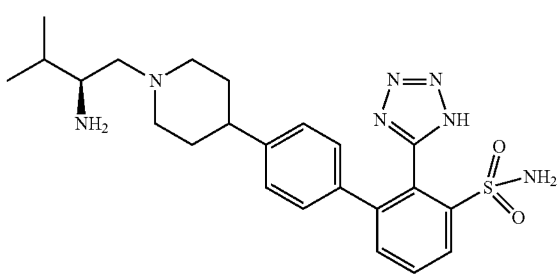 [SMILES: CC(C)[C@H](N)CN1CCC(c2ccc(-c3cccc(S(N)(=O)=O)c3-c3nnn[nH]3)cc2)CC1] | 3-[4-[1-[(2S)-2-amino-3-methyl-butyl]-4-piperidyl]phenyl]-2-(1H-tetrazol-5-yl)benzenesulfonamide | 470 | 470 |

| Ex. No. | Structure | Name | Cal'd MW [M + H]+ | LC/MS m/e (M + H)+ |
|---|---|---|---|---|
| 616 | 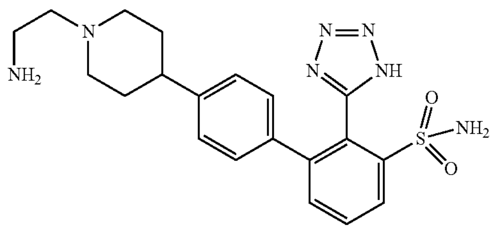 [SMILES: NCCN1CCC(c2ccc(-c3cccc(S(N)(=O)=O)c3-c3nnn[nH]3)cc2)CC1] | 3-[4-[1-(2-aminoethyl)-4-piperidyl]phenyl]-2-(1H-tetrazol-5-yl)benzenesulfonamide | 428 | 428 |
| 617 | 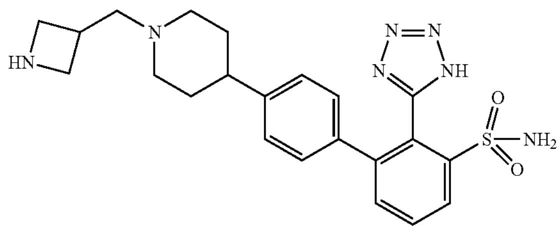 [SMILES: NS(=O)(=O)c1cccc(-c2ccc(C3CCN(CC4CNC4)CC3)cc2)c1-c1nnn[nH]1] | 3-[4-[1-(azetidin-3-ylmethyl)-4-piperidyl]phenyl]-2-(1H-tetrazol-5-yl)benzenesulfonamide | 454 | 454 |
| 618 | 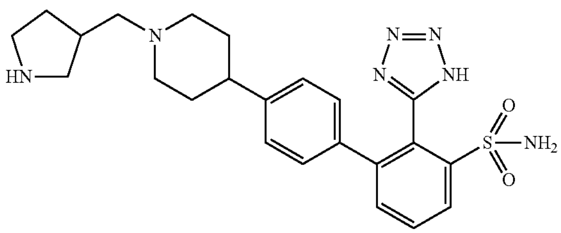 [SMILES: NS(=O)(=O)c1cccc(-c2ccc(C3CCN(CC4CCNC4)CC3)cc2)c1-c1nnn[nH]1] | 3-[4-[1-(pyrrolidin-3-ylmethyl)-4-piperidyl]phenyl]-2-(1H-tetrazol-5-yl)benzenesulfonamide | 468 | 468 |
| 619 | 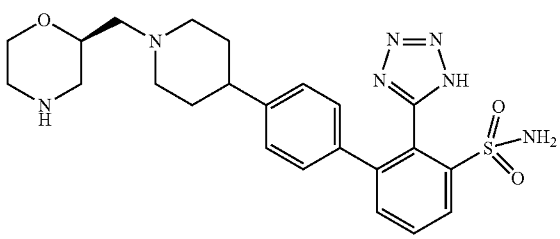 [SMILES: NS(=O)(=O)c1cccc(-c2ccc(C3CCN(C[C@H]4CNCCO4)CC3)cc2)c1-c1nnn[nH]1] | 3-[4-[1-[(2R)-morpholin-2-yl]methyl]-4-piperidyl]phenyl]-2-(1H-tetrazol-5-yl)benzenesulfonamide | 484 | 484 |
| 620 | 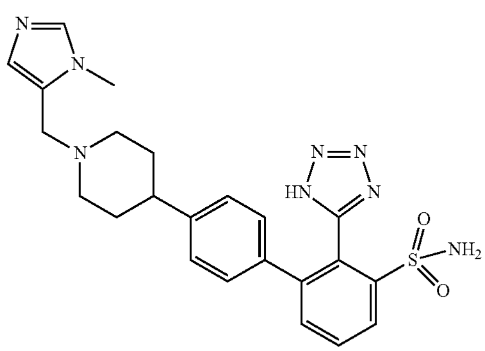 [SMILES: Cn1cncc1CN1CCC(c2ccc(-c3cccc(S(N)(=O)=O)c3-c3nnn[nH]3)cc2)CC1] | 3-[4-[1-[(3-methylimidazol-4-yl)methyl]-4-piperidyl]phenyl]-2-(1H-tetrazol-5-yl)benzenesulfonamide | 478 | 478 |

| Ex. No. | Structure | Name | Cal'd MW [M + H]+ | LC/MS m/e (M + H)+ |
|---|---|---|---|---|
| 621 | 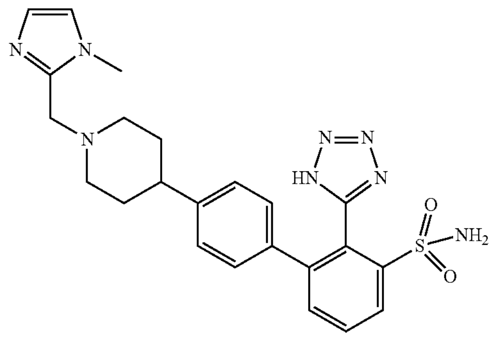 [SMILES: Cn1ccnc1CN1CCC(c2ccc(-c3cccc(S(N)(=O)=O)c3-c3nnn[nH]3)cc2)CC1] | 3-[4-[1-[(1-methylimidazol-2-yl)methyl]-4-piperidyl]phenyl]-2-(1H-tetrazol-5-yl)benzenesulfonamide | 478 | 478 |

EXAMPLES 622-638

Parallel Synthesis of 3-(6-aminopyridin-3-yl)-2-(2H-tetrazol-5-yl)benzenesulfonamides

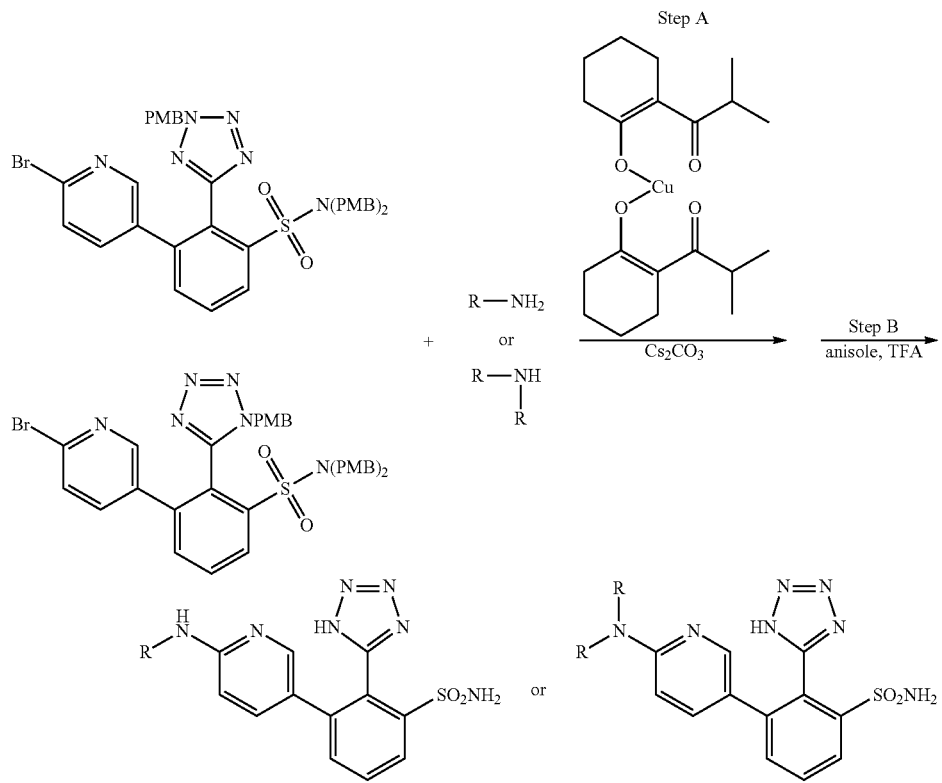

Step A: Copper Catalyzed C—N Coupling of Pyridyl Bromide with Primary and Secondary Amines 3-(6-bromopyridin-3-yl)-N,N-bis(4-methoxybenzyl)-2-(1-(4-methoxybenzyl)-1H-tetrazol-5-yl)benzenesulfonamide (40 mg, 0.054 mmol), Bis(2-isobutyrylcyclohexanone)copper(II) (commercially available from Aldrich; 9.23 mg, 0.022 mmol) and commercially available or known primary and secondary amines (0.054 mmol) were stirred at 100° C. for 18 hours. The mixtures were allowed to cool. Then 1 mL DCM and 1 mL water were added. The organics were separated and concentrated in vacuo.

Step B: Removal of the Para-Methoxybenzyl Protective Groups

The residue from Step A was dissolved in TFA (1 mL) and treated with anisole (0.029 mL, 0.270 mmol). The mixture was stirred at 65° C. for 2 hr. The mixtures were allowed to cool. The volatile organics were removed under reduced pressure in the genevac. Then 1 ml DMSO was added and the crude materials and others made in the same way were purified by mass directed reverse phase HPLC to afford Examples 622-638.

| Ex. No. | Structure | Name | Calc'd Mass [M + H]+ | LC/MS m/e [M + H]+ |
|---|---|---|---|---|
| 622 | 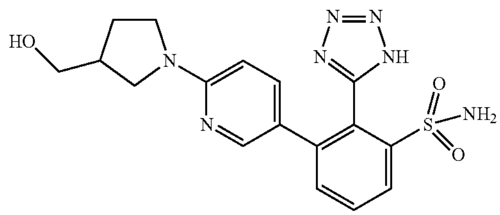 [SMILES: NS(=O)(=O)c1cccc(-c2ccc(N3CCC(CO)C3)nc2)c1-c1nnn[nH]1] | 3-[6-[3-(hydroxymethyl)pyrrolidin-1-yl]-3-pyridyl]-2-(1H-tetrazol-5-yl)benzenesulfonamide | 402 | 402 |
| 623 | 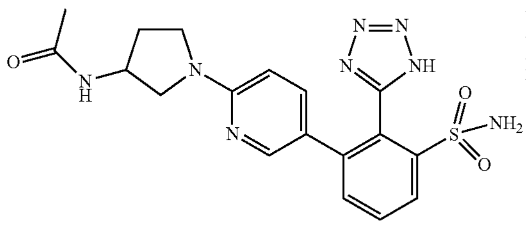 [SMILES: CC(=O)NC1CCN(c2ccc(-c3cccc(S(N)(=O)=O)c3-c3nnn[nH]3)cn2)C1] | N-[1-[5-[3-sulfamoyl-2-(1H-tetrazol-5-yl)phenyl]-2-pyridyl]pyrrolidin-3-yl]acetamide | 429 | 429 |
| 624 | 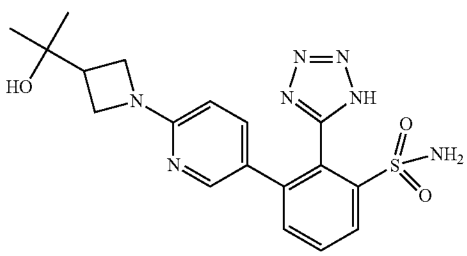 [SMILES: CC(C)(O)C1CN(c2ccc(-c3cccc(S(N)(=O)=O)c3-c3nnn[nH]3)cn2)C1] | 3-[6-[3-(1-hydroxy-1-methyl-ethyl)azetidin-1-yl]-3-pyridyl]-2-(1H-tetrazol-5-yl)benzenesulfonamide | 416 | 416 |
| 625 | 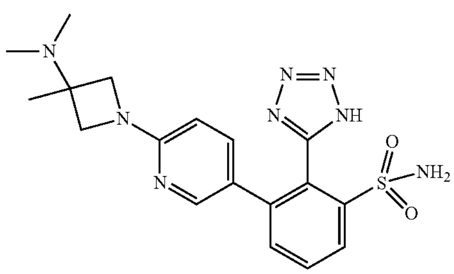 [SMILES: CN(C)C1(C)CN(c2ccc(-c3cccc(S(N)(=O)=O)c3-c3nnn[nH]3)cn2)C1] | 3-[6-[3-(dimethylamino)-3-methyl-azetidin-1-yl]-3-pyridyl]-2-(1H-tetrazol-5-yl)benzenesulfonamide | 415 | 415 |
| 626 | 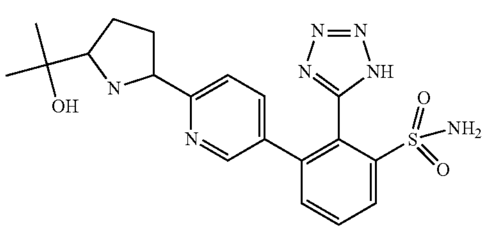 [SMILES: CC(C)(O)C1CCC(c2ccc(-c3cccc(S(N)(=O)=O)c3-c3nnn[nH]3)cn2)N1] | 3-[6-[3-(1-hydroxy-1-methyl-ethyl)pyrrolidin-1-yl]-3-pyridyl]-2-(1H-tetrazol-5-yl)benzenesulfonamide | 430 | 430 |
| 627 | 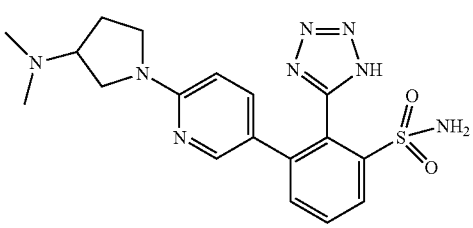 [SMILES: CN(C)C1CCN(c2ccc(-c3cccc(S(N)(=O)=O)c3-c3nnn[nH]3)cn2)C1] | 3-[6-[3-(dimethylamino)pyrrolidin-1-yl]-3-pyridyl]-2-(1H-tetrazol-5-yl)benzenesulfonamide | 415 | 415 |

-continued

| Ex. No. | Structure | Name | Calc'd Mass [M + H]⁺ | LC/MS m/e [M + H]⁺ |
|---|---|---|---|---|
| 628 | 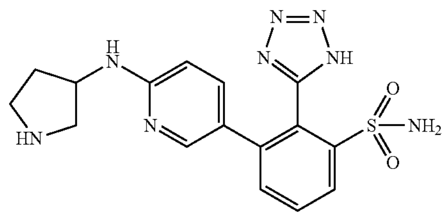 [SMILES: NS(=O)(=O)c1cccc(-c2ccc(NC3CCNC3)nc2)c1-c1nnn[nH]1] | 3-[6-(pyrrolidin-3-ylamino)-3-pyridyl]-2-(1H-tetrazol-5-yl)benzenesulfonamide | 387 | 387 |
| 629 | 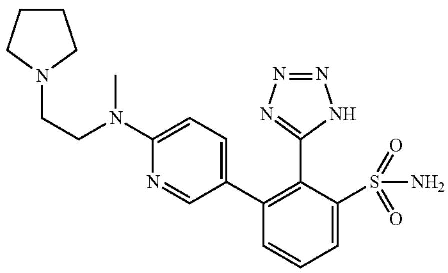 [SMILES: CN(CCN1CCCC1)c1ccc(-c2cccc(S(N)(=O)=O)c2-c2nnn[nH]2)cn1] | 3-[6-[methyl(2-pyrrolidin-1-ylethyl)amino]-3-pyridyl]-2-(1H-tetrazol-5-yl)benzenesulfonamide | 429 | 429 |
| 630 | 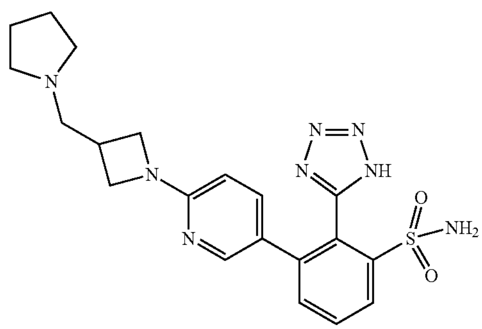 [SMILES: NS(=O)(=O)c1cccc(-c2ccc(N3CC(CN4CCCC4)C3)nc2)c1-c1nnn[nH]1] | 3-[6-[3-(pyrrolidin-1-ylmethyl)azetidin-1-yl]-3-pyridyl]-2-(1H-tetrazol-5-yl)benzenesulfonamide | 441 | 441 |
| 631 | 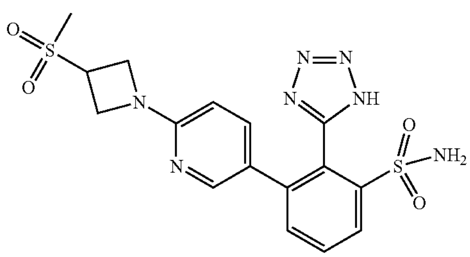 [SMILES: CS(=O)(=O)C1CN(c2ccc(-c3cccc(S(N)(=O)=O)c3-c3nnn[nH]3)cn2)C1] | 3-[6-(3-methylsulfonylazetidin-1-yl)-3-pyridyl]-2-(1H-tetrazol-5-yl)benzenesulfonamide | 436 | 436 |
| 632 | 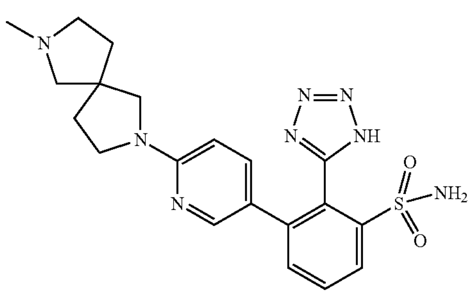 [SMILES: CN1CCC2(CCN(c3ccc(-c4cccc(S(N)(=O)=O)c4-c4nnn[nH]4)cn3)C2)C1] | 3-[6-(7-methyl-2,7-diazaspiro[4.4]nonan-2-yl)-3-pyridyl]-2-(1H-tetrazol-5-yl)benzenesulfonamide | 441 | 441 |

| Ex. No. | Structure | Name | Calc'd Mass [M + H]+ | LC/MS m/e [M + H]+ |
|---|---|---|---|---|
| 633 | 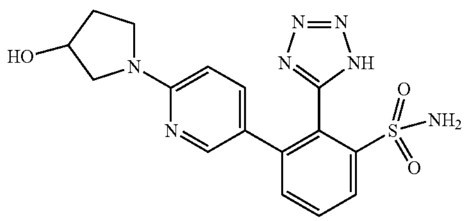 [SMILES: NS(=O)(=O)c1cccc(-c2ccc(N3CCC(O)C3)nc2)c1-c1nnn[nH]1] | 3-[6-(3-hydroxypyrrolidin-1-yl)-3-pyridyl]-2-(1H-tetrazol-5-yl)benzenesulfonamide | 388 | 388 |
| 634 | 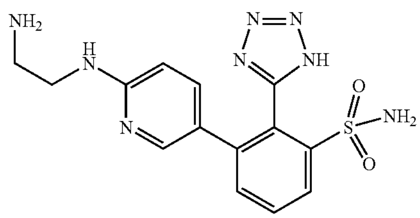 [SMILES: NCCNc1ccc(-c2cccc(S(N)(=O)=O)c2-c2nnn[nH]2)cn1] | 3-[6-(2-aminoethylamino)-3-pyridyl]-2-(1H-tetrazol-5-yl)benzenesulfonamide | 361 | 361 |
| 635 | 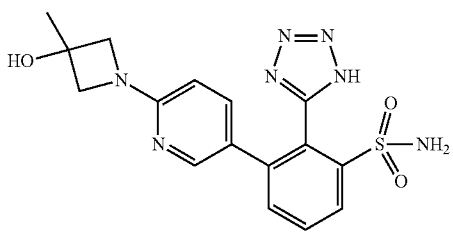 [SMILES: CC1(O)CN(c2ccc(-c3cccc(S(N)(=O)=O)c3-c3nnn[nH]3)cn2)C1] | 3-[6-(3-hydroxy-3-methyl-azetidin-1-yl)-3-pyridyl]-2-(1H-tetrazol-5-yl)benzenesulfonamide | 388 | 388 |
| 636 | 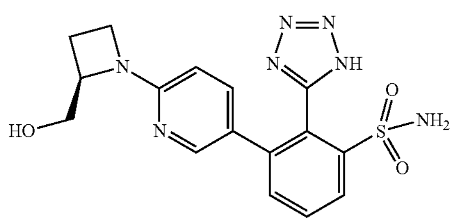 [SMILES: NS(=O)(=O)c1cccc(-c2ccc(N3CC[C@@H]3CO)nc2)c1-c1nnn[nH]1] | 3-[6-[(2S)-2-(hydroxymethyl)azetidin-1-yl]-3-pyridyl]-2-(1H-tetrazol-5-yl)benzenesulfonamide | 388 | 388 |
| 637 | 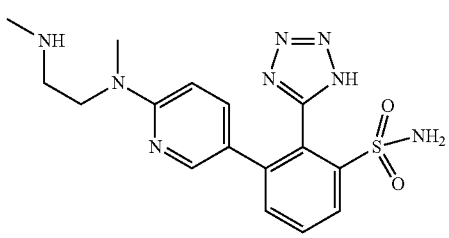 [SMILES: CNCCN(C)c1ccc(-c2cccc(S(N)(=O)=O)c2-c2nnn[nH]2)cn1] | 3-[6-[methyl-[2-(methylamino)ethyl]amino]-3-pyridyl]-2-(1H-tetrazol-5-yl)benzenesulfonamide | 389 | 389 |
| 638 | 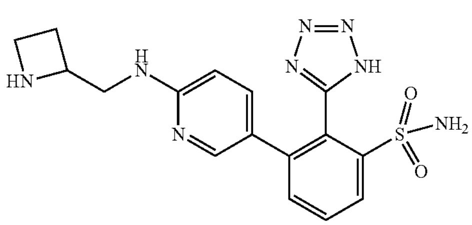 [SMILES: NS(=O)(=O)c1cccc(-c2ccc(NCC3CCN3)nc2)c1-c1nnn[nH]1] | 3-[6-(azetidin-2-ylmethylamino)-3-pyridyl]-2-(1H-tetrazol-5-yl)benzenesulfonamide | 387 | 387 |

EXAMPLES 639-646

Parallel Synthesis of 3-(2-aminobenzo[d]thiazol-4-yl)-2-(1H-tetrazol-5-yl)benzenesulfonamides

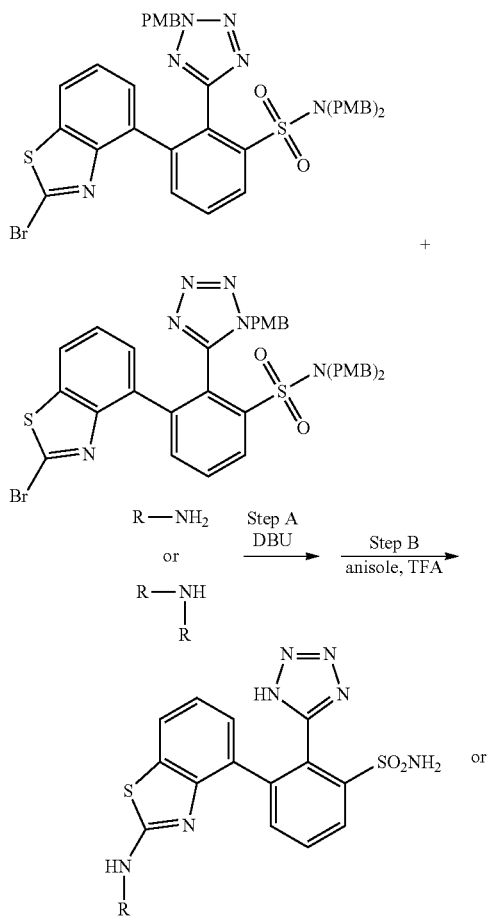

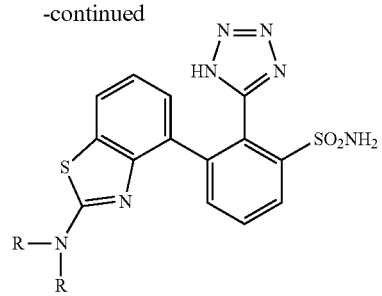

Step A: Coupling of Primary and Secondary Amines to 3-(2-bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide A mixture of 3-(2-bromobenzo[d]thiazol-4-yl)-N,N-bis(4-methoxybenzyl)-2-(1-(4-methoxybenzyl)-1H-tetrazol-5-yl)benzenesulfonamide and 3-(2-bromobenzo[d]thiazol-4-yl)-N,N-bis(4-methoxybenzyl)-2-(2-(4-methoxybenzyl)-2H-tetrazol-5-yl)benzenesulfonamide (40 mg, 0.050 mmol), DBU (0.030 mL, 0.201 mmol) and commercially available primary or secondary amines (0.100 mmol) in Dioxane (1 mL) were added to a microwave vial, and heated at 150° C. for 15 minutes. The crude reaction mixture was concentrated in the genevac under reduced pressure.

Step B: Removal of the Para-Methoxybenzyl Protective Groups

The residues from Step A were treated with TFA (1.0 mL) and stirred at 65° C. for 4 hours. The mixtures were allowed to cool and the volatile organics removed in the genevac under reduced pressure. Then 1 ml DMSO was added and the crude materials and others made in the same way were purified by mass directed reverse phase HPLC to afford Examples 639-646. Note that in some cases the amines used contained a tert-butoxycarbonyl protected amino group. In those cases when the amines used contained a second amino group protected with a tert-butoxycarbonyl protective group, this group was also removed under the para-methoxybenzyl protective group removal conditions.

| Ex. No. | Structure | Name | Calc'd Mass [M + H]+ | LC/MS m/e [M + H]+ |
|---|---|---|---|---|
| 639 | 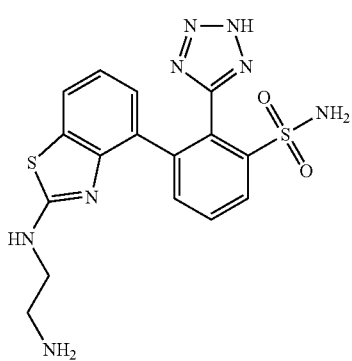 [SMILES: NCCNc1nc2c(-c3cccc(S(N)(=O)=O)c3-c3nn[nH]n3)cccc2s1] | 3-[2-(2-aminoethylamino)-1,3-benzothiazol-4-yl]-2-(2H-tetrazol-5-yl)benzenesulfonamide | 417 | 417 |

-continued

| Ex. No. | Structure | Name | Calc'd Mass [M + H]⁺ | LC/MS m/e [M + H]⁺ |
|---|---|---|---|---|
| 640 | 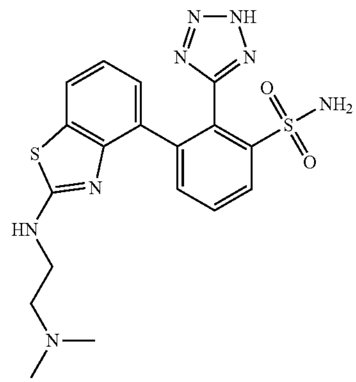 [SMILES: CN(C)CCNc1nc2c(-c3cccc(S(N)(=O)=O)c3-c3nn[nH]n3)cccc2s1] | 3-[2-[2-(dimethylamino)ethylamino]-1,3-benzothiazol-4-yl]-2-(2H-tetrazol-5-yl)benzenesulfonamide | 445 | 445 |
| 641 | 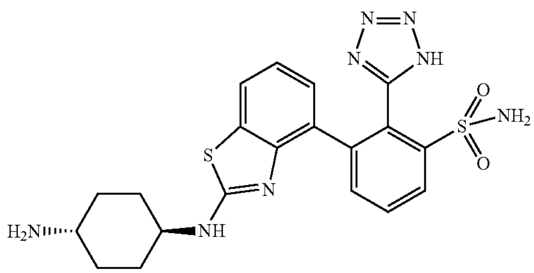 [SMILES: NS(=O)(=O)c1cccc(-c2cccc3sc(N[C@H]4CC[C@H](N)CC4)nc23)c1-c1nnn[nH]1] | 3-[2-[(4-aminocyclohexyl)amino]-1,3-benzothiazol-4-yl]-2-(1H-tetrazol-5-yl)benzenesulfonamide | 471 | 471 |
| 642 | 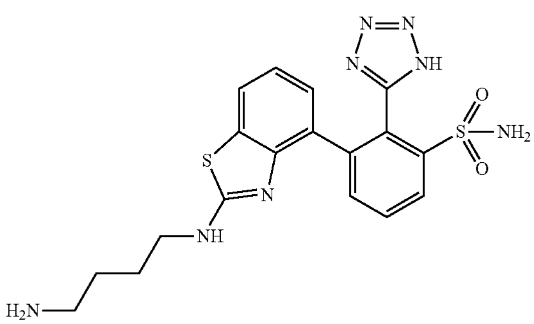 [SMILES: NCCCCNc1nc2c(-c3cccc(S(N)(=O)=O)c3-c3nnn[nH]3)cccc2s1] | 3-[2-(4-aminobutylamino)-1,3-benzothiazol-4-yl]-2-(1H-tetrazol-5-yl)benzenesulfonamide | 445 | 445 |
| 643 | 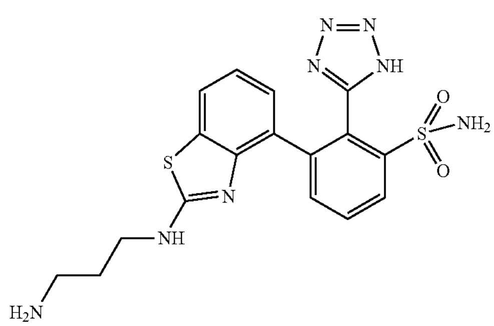 [SMILES: NCCCNc1nc2c(-c3cccc(S(N)(=O)=O)c3-c3nnn[nH]3)cccc2s1] | 3-[2-(3-aminopropylamino)-1,3-benzothiazol-4-yl]-2-(1H-tetrazol-5-yl)benzenesulfonamide | 431 | 431 |

-continued

| Ex. No. | Structure | Name | Calc'd Mass [M + H]+ | LC/MS m/e [M + H]+ |
|---|---|---|---|---|
| 644 | 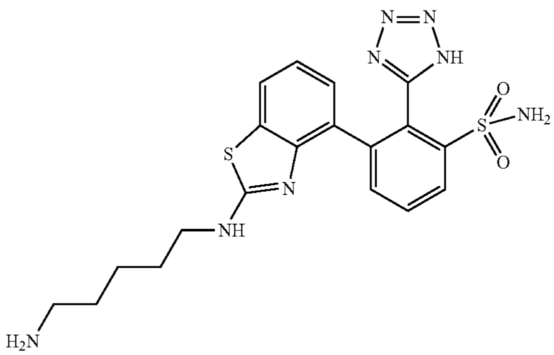 [SMILES: NCCCCCNc1nc2c(-c3cccc(S(N)(=O)=O)c3-c3nnn[nH]3)cccc2s1] | 3-[2-(5-aminopentylamino)-1,3-benzothiazol-4-yl]-2-(1H-tetrazol-5-yl)benzenesulfonamide | 459 | 459 |
| 645 | 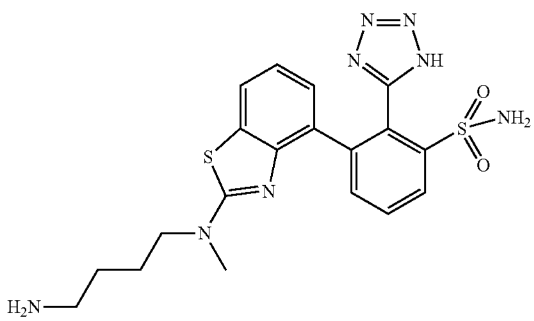 [SMILES: CN(CCCCN)c1nc2c(-c3cccc(S(N)(=O)=O)c3-c3nnn[nH]3)cccc2s1] | 3-[2-[4-aminobutyl(methyl)amino]-1,3-benzothiazol-4-yl]-2-(1H-tetrazol-5-yl)benzenesulfonamide | 459 | 459 |
| 646 | 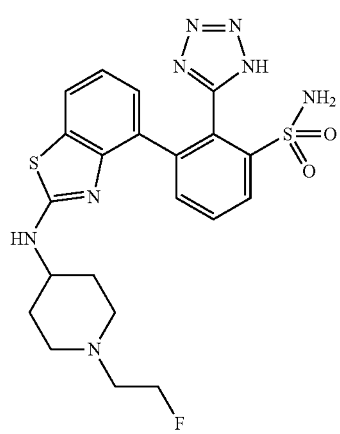 [SMILES: NS(=O)(=O)c1cccc(-c2cccc3sc(NC4CCN(CCF)CC4)nc23)c1-c1nnn[nH]1] | 3-[2-[[1-(2-fluoroethyl)-4-piperidyl]amino]-1,3-benzothiazol-4-yl]-2-(1H-tetrazol-5-yl)benzenesulfonamide | 503 | 503 |

EXAMPLES 647-652

Parallel Synthesis of 3-Substituted 2-(1H-tetrazol-5-yl)benzenesulfonamides

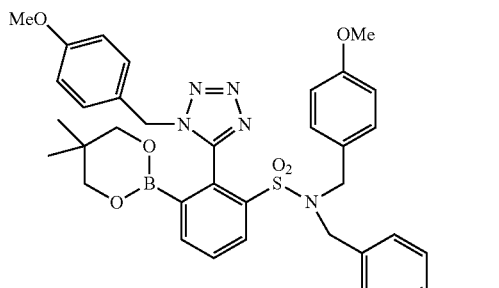

+

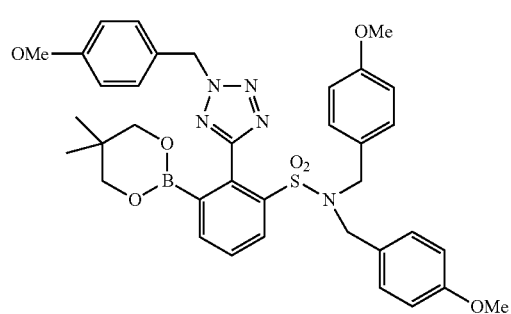

Step A

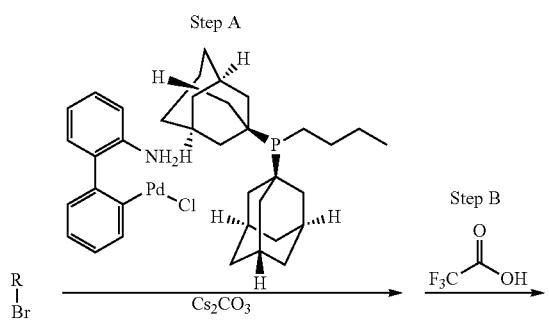

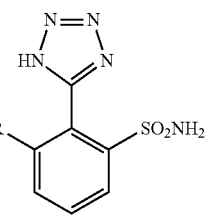

Step A: Palladium Catalyzed C—C Coupling of Arylboronic Ester and Arylbromides

In a glove box under a dry nitrogen atmosphere, arylbromides (0.3 mmol) (commercially available, known from the literature) and Ad$_2$nBuP Biphenyl Pre-Catalyst (6.71 mg, 10.0 µmol) and 200 µL of 1.5 N degassed aq. Cs$_2$CO$_3$ solution were added into 2 drum vials. 1.0 mL of a solution of the mixture of 3-(5,5-dimethyl-1,3,2-dioxaborinan-2-yl)-N,N-bis(4-methoxybenzyl)-2-(2-(4-methoxybenzyl)-2H-tetrazol-5-yl)benzenesulfonamide and 3-(5,5-dimethyl-1,3,2-dioxaborinan-2-yl)-N,N-bis(4-methoxybenzyl)-2-(1-(4-methoxybenzyl)-1H-tetrazol-5-yl)benzenesulfonamide from Reference Example 9 (70 mg, 0.1 mmol) in Toluene were added into each vial. The vials were capped and heated at 110° C. with stirring for 20 hr. After the vials were cooled to room temperature, the solvent was removed in a GeneVac. Into each residue was added 600 µL of H$_2$O and 2 mL of EtOAc. The organic layers were transferred into 2 dram vials. The organic solvent was removed in GeneVac to afford the crude intermediates which were deprotected without further purification in the subsequent step.

Step B: Removal of the p-methoxybenzyl (PMB) Protecting Group by TFA Treatment

The residues from Step A were each added TFA 0.7 mL alone with anilsole (0.3 mL). The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 µm, 19×100 mm; solvent: gradient range 3-28% initial to 60-95% final MeCN (0.1% TFA) in water (0.1% TFA) 50 or 70 mL/min; 8 min run time] to afford EXAMPLES 647 to 652.

| Ex. No. | Structure | Name | Calc'd. MW [M + H]$^+$ | LC/MS m/e [M + H]$^+$ |
|---|---|---|---|---|
| 647 | 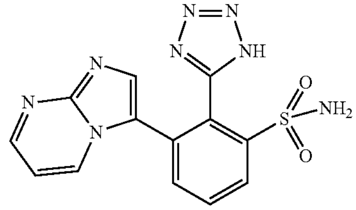 [SMILES: NS(=O)(=O)c1cccc(-c2cnc3ncccn23)c1-c1nnn[nH]1] | 3-imidazo[1,2-a]pyrimidin-3-yl-2-(1H-tetrazol-5-yl)benzenesulfonamide | 343.07 | 343.07 |

-continued

| Ex. No. | Structure | Name | Calc'd. MW [M + H]+ | LC/MS m/e [M + H]+ |
|---|---|---|---|---|
| 648 | 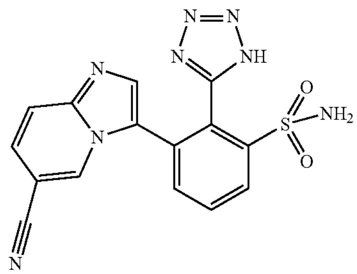 [SMILES: N#Cc1ccc2ncc(-c3cccc(S(N)(=O)=O)c3-c3nnn[nH]3)n2c1] | 3-(6-cyanoimidazo[1,2-a]pyridin-3-yl)-2-(1H-tetrazol-5-yl)benzenesulfonamide | 367.07 | 367.07 |
| 649 | 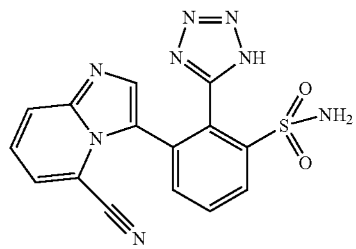 [SMILES: N#Cc1cccc2ncc(-c3cccc(S(N)(=O)=O)c3-c3nnn[nH]3)n12] | 3-(5-cyanoimidazo[1,2-a]pyridin-3-yl)-2-(1H-tetrazol-5-yl)benzenesulfonamide | 367.07 | 367.07 |
| 650 | 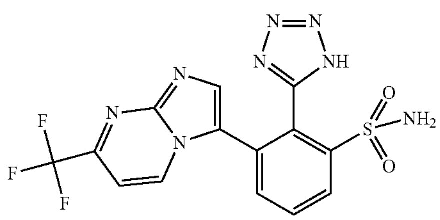 [SMILES: NS(=O)(=O)c1cccc(-c2cnc3nc(C(F)(F)F)ccn23)c1-c1nnn[nH]1] | 2-(1H-tetrazol-5-yl)-3-[7-(trifluoromethyl)imidazo[1,2-a]pyrimidin-3-yl]benzenesulfonamide | 411.06 | 411.05 |
| 651 | 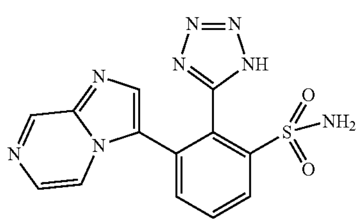 [SMILES: NS(=O)(=O)c1cccc(-c2cnc3cnccn23)c1-c1nnn[nH]1] | 3-imidazo[1,2-a]pyrazin-3-yl-2-(1H-tetrazol-5-yl)benzenesulfonamide | 343.07 | 343.07 |
| 652 | 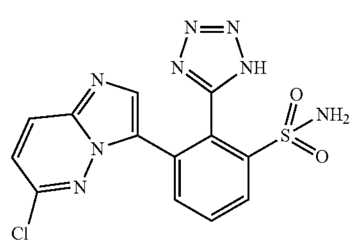 [SMILES: NS(=O)(=O)c1cccc(-c2cnc3ccc(Cl)nn23)c1-c1nnn[nH]1] | 3-(6-chloroimidazo[1,2-b]pyridazin-3-yl)-2-(1H-tetrazol-5-yl)benzenesulfonamide | 377.03 | 377.03 |

EXAMPLES 653-667

Parallel Synthesis of 3-N-substituted-2-(1H-tetrazol-5-yl)-6-(trifluromethyl)benzenesulfonamides

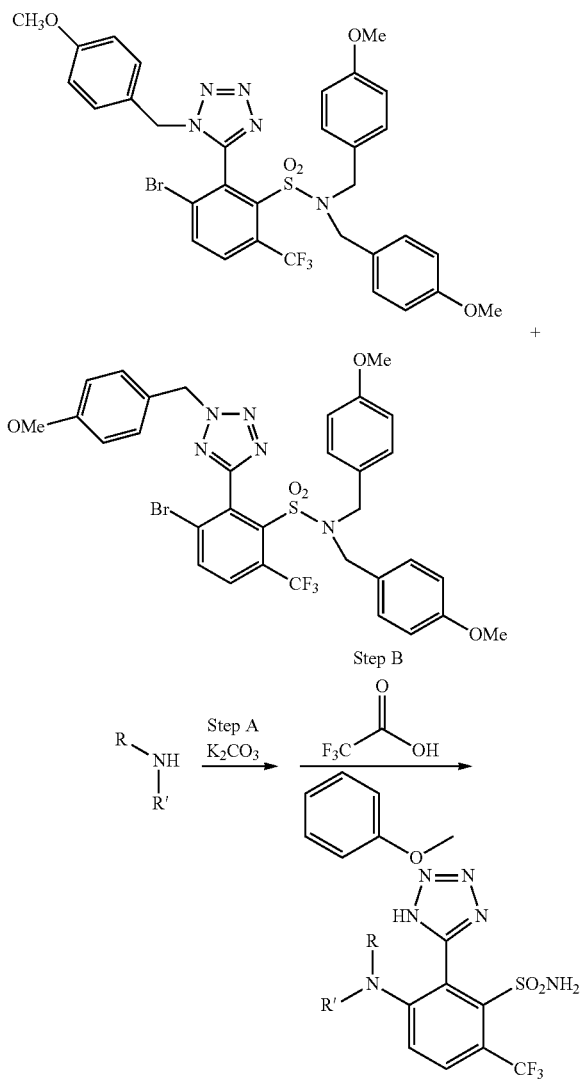

Step A: C—N Displacement of Secondary Amines on Arylbromide

To 5-mL microwave vials, secondary amines (0.164 mmol) (commercially available, known from the literature) and $K_2CO_3$ solid (37.7 mg, 0.273 mmol) were added followed by addition of 1 mL DMF solution of the mixture of 3-bromo-N,N-bis(4-methoxybenzyl)-2-(1-(4-methoxybenzyl)-1H-tetrazol-5-yl)-6-(trifluoromethyl)benzenesulfonamide and 3-bromo-N,N-bis(4-methoxybenzyl)-2-(2-(4-methoxybenzyl)-2H-tetrazol-5-yl)-6-(trifluoromethyl)benzenesulfonamide from Reference Example 24 (40 mg, 0.055 mmol). The vials were capped and heated at 140° C. with stirring for 2 hr. After the vials were cooled to room temperature, the solvent was removed in a GeneVac. Into each residue was added 500 µL of 3 N HCl and 2 mL of EtOAc. The organic layers were transferred into 2 dram vials. The organic solvent was removed in GeneVac to afford the crude intermediates which were deprotected without further purification in the subsequent step.

Step B: Removal of the p-methoxybenzyl (PMB) Protecting Group by TFA Treatment

The residues from Step A were each added TFA 0.7 mL alone with anilsole (0.3 mL). The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 µm, 19×100 mm; solvent: gradient range 10-35% initial to 45-95% final MeCN (0.1% TFA) in water (0.1% TFA) 50 or 70 mL/min; 8 min run time] to afford Examples 653-667.

| Ex. No. | Structure | Name | Calc'd. MW $[M + H]^+$ | LC/MS m/e $[M + H]^+$ |
|---|---|---|---|---|
| 653 | 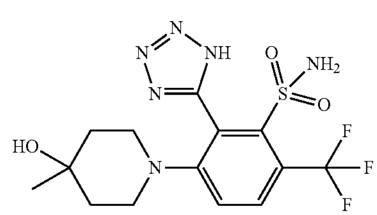 [SMILES: CC1(O)CCN(c2ccc(C(F)(F)F)c(S(N)(=O)=O)c2-c2nnn[nH]2)CC1] | 3-(4-hydroxy-4-methypiperidin-1-yl)-2-(1H-tetrazol-5-yl)-6-(trifluoromethyl)benzenesulfonamide | 407.11 | 407.1 |

-continued

| Ex. No. | Structure | Name | Calc'd. MW [M + H]⁺ | LC/MS m/e [M + H]⁺ |
|---|---|---|---|---|
| 654 | 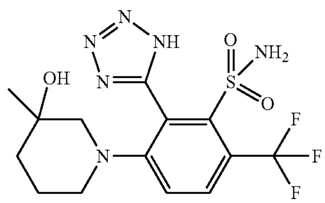 [SMILES: CC1(O)CCCN(c2ccc(C(F)(F)F)c(S(N)(=O)=O)c2-c2nnn[nH]2)C1] | 3-(3-hydroxy-3-methylpiperidin-1-yl)-2-(1H-tetrazol-5-yl)-6-(trifluoromethyl)benzenesulfonamide | 407.11 | 407.1 |
| 655 | 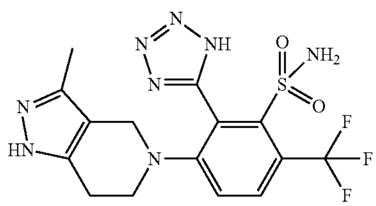 [SMILES: Cc1n[nH]c2c1CN(c1ccc(C(F)(F)F)c(S(N)(=O)=O)c1-c1nnn[nH]1)CC2] | 3-(3-methyl-1,4,6,7-tetrahydro-5H-pyrazolo[4,3-c]pyridin-5-yl)-2-(1H-tetrazol-5-yl)-6-trifluoromethyl)benzenesulfonamide | 429.11 | 429.0 |
| 656 | 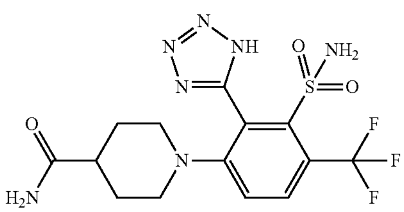 [SMILES: NC(=O)C1CCN(c2ccc(C(F)(F)F)c(S(N)(=O)=O)c2-c2nnn[nH]2)CC1] | 1-[3-sulfamoyl-2-(1H-tetrazol-5-yl)-4-(trifluoromethyl)phenyl]piperidine-4-carboxamide | 420.11 | 420.1 |
| 657 | 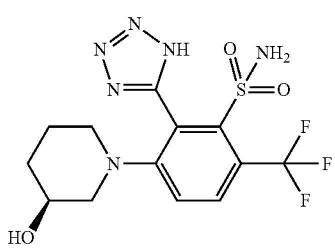 [SMILES: NS(=O)(=O)c1c(C(F)(F)F)ccc(N2CCC[C@H](O)C2)c1-c1nnn[nH]1] | 3-[(3S)-3-hydroxypiperidin-1-yl]-2-(1H-tetrazol-5-yl)-6-(trifluoromethyl)benzenesulfonamide | 393.1 | 393.09 |
| 658 | 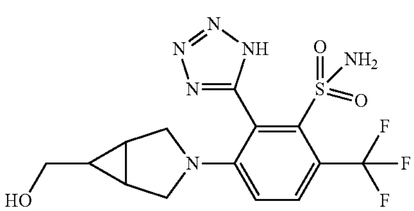 [SMILES: NS(=O)(=O)c1c(C(F)(F)F)ccc(N2CC3C(CO)C3C2)c1-c1nnn[nH]1] | 3-[6-(hydroxymethyl)-3-azabicyclo[3.1.0]hex-3-yl]-2-(1H-tetrazol-5-yl)-6-(trifluoromethyl)benzenesulfonamide | 405.1 | 405.09 |
| 659 | 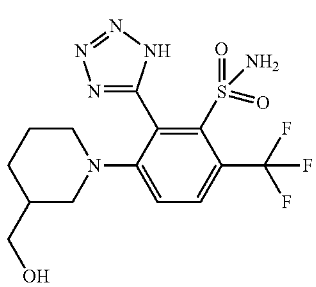 [SMILES: NS(=O)(=O)c1c(C(F)(F)F)ccc(N2CCCC(CO)C2)c1-c1nnn[nH]1] | 3-[3-(hydroxymethyl)piperidin-1-yl]-2-(1H-tetrazol-5-yl)-6-(trifluoromethyl)benzenesulfonamide | 407.11 | 407.1 |

| Ex. No. | Structure | Name | Calc'd. MW [M + H]+ | LC/MS m/e [M + H]+ |
|---|---|---|---|---|
| 660 | 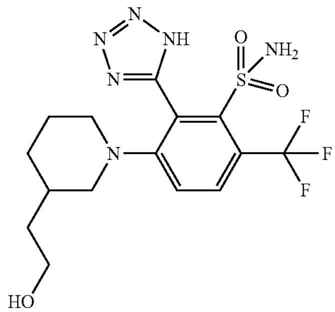 [SMILES: NS(=O)(=O)c1c(C(F)(F)F)ccc(N2CCCC(CCO)C2)c1-c1nnn[nH]1] | 3-[3-(2-hydroxyethyl)piperidin-1-yl]-2-(1H-tetrazol-5-yl)-6-(trifluoromethyl)benzenesulfonamide | 421.13 | 421.12 |
| 661 | 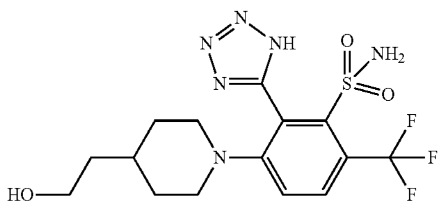 [SMILES: NS(=O)(=O)c1c(C(F)(F)F)ccc(N2CCC(CCO)CC2)c1-c1nnn[nH]1] | 3-[4-(2-hydroxyethyl)piperidin-1-yl]-2-(1H-tetrazol-5-yl)-6-(trifluoromethyl)benzenesulfonamide | 421.13 | 421.12 |
| 662 | 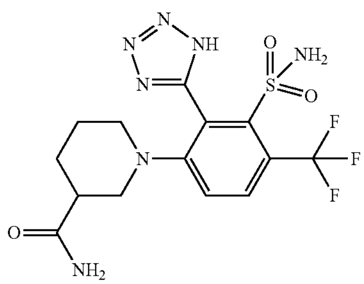 [SMILES: NC(=O)C1CCCN(c2ccc(C(F)(F)F)c(S(N)(=O)=O)c2-c2nnn[nH]2)C1] | 1-[3-sulfamoyl-2-(1H-tetrazol-5-yl)-4-(trifluoromethyl)phenyl]piperidine-3-carboxamide | 420.11 | 420.1 |
| 663 | 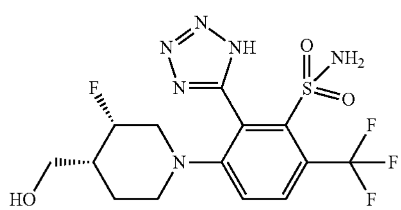 [SMILES: NS(=O)(=O)c1c(C(F)(F)F)ccc(N2CC[C@H](CO)[C@H](F)C2)c1-c1nnn[nH]1] | 3-[(3S,4R)-3-fluoro-4-(hydroxymethyl)piperidin-1-yl]-2-(1H-tetrazol-5-yl)-6-(trifluoromethyl)benzenesulfonamide | 425.1 | 425.09 |
| 664 | 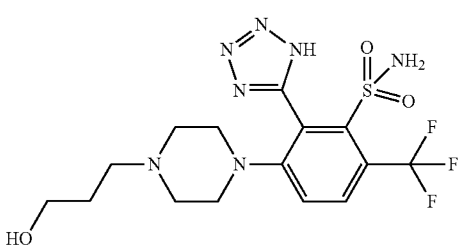 [SMILES: NS(=O)(=O)c1c(C(F)(F)F)ccc(N2CCN(CCCO)CC2)c1-c1nnn[nH]1] | 3-[4-(3-hydroxypropyl)piperazin-1-yl]-2-(1H-tetrazol-5-yl)-6-(trifluoromethyl)benzenesulfonamide | 436.14 | 436.13 |
| 665 | 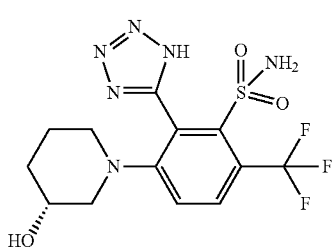 [SMILES: NS(=O)(=O)c1c(C(F)(F)F)ccc(N2CCC[C@@H](O)C2)c1-c1nnn[nH]1] | 3-[(3R)-3-hydroxypiperidin-1-yl]-2-(1H-tetrazol-5-yl)-6-(trifluoromethyl)benzenesulfonamide | 393.1 | 393.09 |

| Ex. No. | Structure | Name | Calc'd. MW [M + H]+ | LC/MS m/e [M + H]+ |
|---|---|---|---|---|
| 666 | 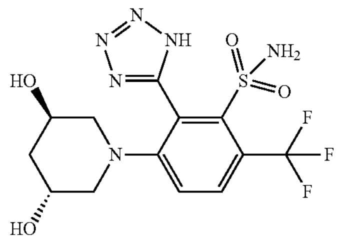 [SMILES: NS(=O)(=O)c1c(C(F)(F)F)ccc(N2C[C@H](O)C[C@@H](O)C2)c1-c1nnn[nH]1] | 3-[(3R,5R)-3,5-dihydroxypiperidin-1-yl]-2-(1H-tetrazol-5-yl)-6-(trifluoromethyl)benzenesulfonamide | 409.09 | 409.08 |
| 667 | 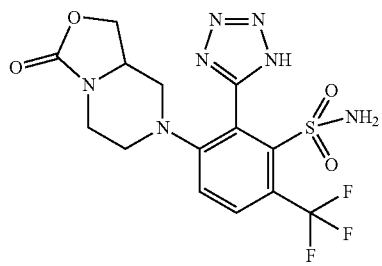 [SMILES: NS(=O)(=O)c1c(C(F)(F)F)ccc(N2CCN3C(=O)OCC3C2)c1-c1nnn[nH]1] | 3-(3-oxotetrahydro[1,3]oxazolo[3,4-a]pyrazin-7(1H)-yl)-2-(1H-tetrazol-5-yl)-6-(trifluoromethyl)benzenesulfonamide | 434.09 | 434.08 |

EXAMPLES 668-678

Parallel Synthesis of 4'-[N-substituted piperidin-4-yl]-2-(1H-tetrazol-5-yl)-4-(trifluoromethyl)biphenyl-3-sulfonamides

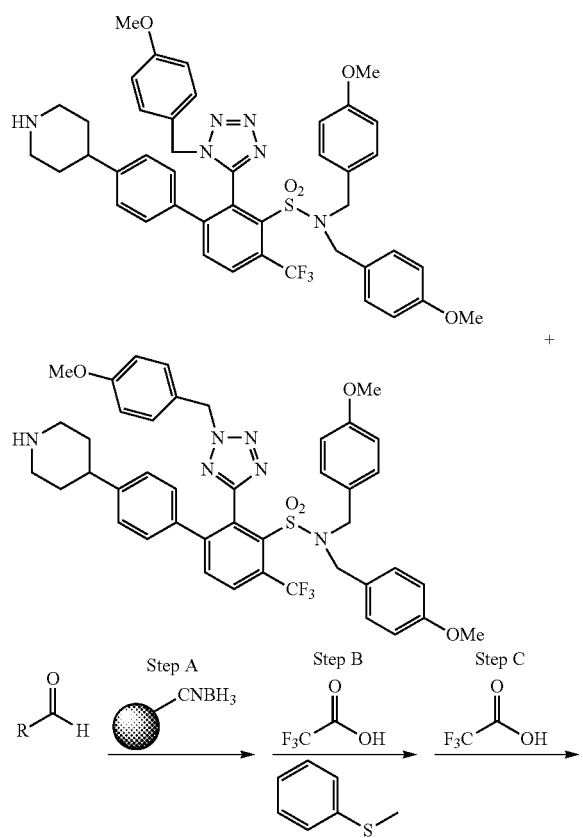

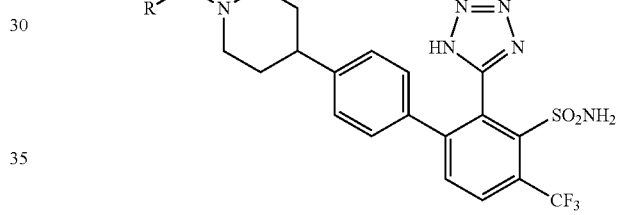

Step A: Reductive Amination of Aldehydes on Piperidin

To 2 dram vials, aldehydes (0.13 mmol) (commercially available, known from the literature) was added into 1 mL MeOH solution of the mixture of N,N-bis(4-methoxybenzyl)-2-(1-(4-methoxybenzyl)-1H-tetrazol-5-yl)-4'-(piperidin-4-yl)-4-(trifluoromethyl)-[1,1'-biphenyl]-3-sulfonamide and N,N-bis(4-methoxybenzyl)-2-(2-(4-methoxybenzyl)-2H-tetrazol-5-yl)-4'-(piperidin-4-yl)-4-(trifluoromethyl)-[1,1'-biphenyl]-3-sulfonamide from Example 269, prior to TFA removal of the para-methoxybenzyl protective groups, (30 mg, 0.043 mmol) followed by addition of 2 drops of acetic acid. The vials were capped and stirring at room temperature for 20 min. MP-CNBH₃ (90 mg, 2.4 mmol/g) was then added to each vial. The vials were capped and stirring at room temperature for 20 hr. The crude reactions were monitored by UPLC. Once the reaction was finished, the mixture were filtered and the solvent were removed in a GeneVac to afford the crude intermediates which were deprotected without further purification in the subsequent step.

Step B: Removal of the Boc and p-methoxybenzyl (PMB) Protecting Group by TFA Treatment The residues from Step A were each added TFA 0.7 mL alone with thioanilsole (0.3 mL). The vials were sealed and stirred at room temperature. After 5 hr, the reactions were monitored by UPLC. The mixtures were concentrated in a GeneVac. The residues were dissolved in DMSO. Each crude mixture was filtered into a 96-well tray and purified with HPLC. The crude products were purified by mass triggered reverse phase HPLC to afford corresponding intermediates.

Step C: Removal of the p-methoxybenzyl (PMB) Protecting Group by TFA Treatment

To the intermediates from Step B, was added TFA 0.7 mL. The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 μm, 19×100 mm; solvent: gradient range 3-28% initial to 45-100% final MeCN (0.1% TFA) in water (0.1% TFA) 50 or 70 mL/min; 8 min run time] to afford Examples 668-678.

| Ex. No. | Structure | Name | Calc'd. MW [M + H]$^+$ | LC/MS m/e [M + H]$^+$ |
|---|---|---|---|---|
| 668 | 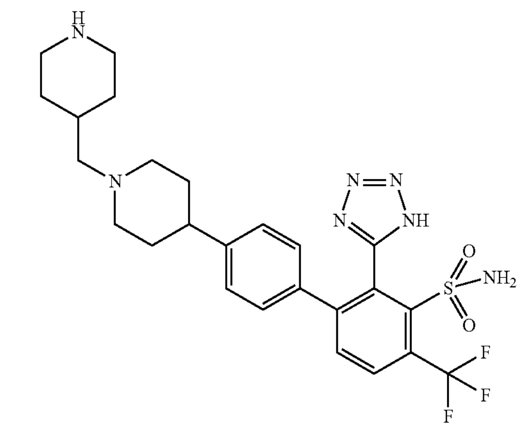 [SMILES: NS(=O)(=O)c1c(C(F)(F)F)ccc(-c2ccc(C3CCN(CC4CCNCC4)CC3)cc2)c1-c1nnn[nH]1] | 4'-[1-(piperidin-4-ylmethyl)piperidin-4-yl]-2-(1H-tetrazol-5-yl)-4-(trifluoromethyl)biphenyl-3-sulfonamide | 550.22 | 550.21 |
| 669 | 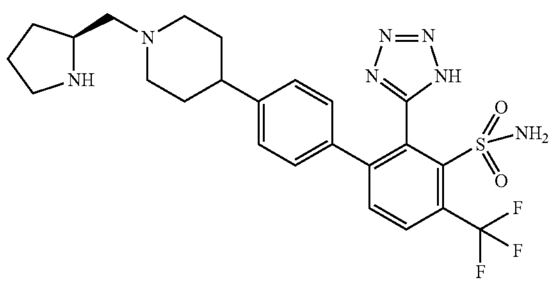 [SMILES: NS(=O)(=O)c1c(C(F)(F)F)ccc(-c2ccc(C3CCN(C[C@@H]4CCCN4)CC3)cc2)c1-c1nnn[nH]1] | 4'-{1-[(2S)-pyrrolidin-2-ylmethyl]piperidin-4-yl}-2-(1H-tetrazol-5-yl)-4-(trifluoromethyl)biphenyl-3-sulfonamide | 536.21 | 536.2 |
| 670 | 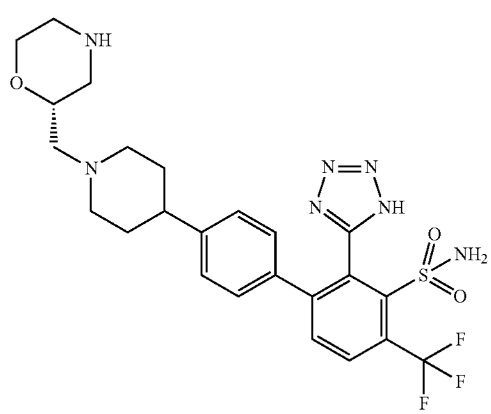 [SMILES: NS(=O)(=O)c1c(C(F)(F)F)ccc(-c2ccc(C3CCN(C[C@H]4CNCCO4)CC3)cc2)c1-c1nnn[nH]1] | 4'-{1-[(2R)-morpholin-2-ylmethyl]piperidin-4-yl}-2-(1H-tetrazol-5-yl)-4-(trifluoromethyl)biphenyl-3-sulfonamide | 552.2 | 552.19 |

-continued

| Ex. No. | Structure | Name | Calc'd. MW [M + H]+ | LC/MS m/e [M + H]+ |
|---|---|---|---|---|
| 671 | 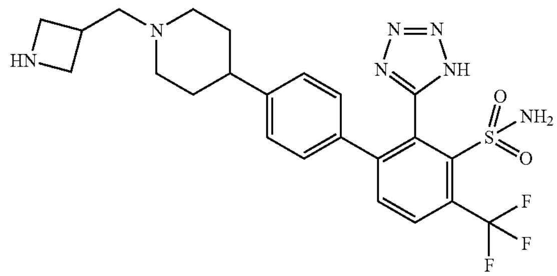 [SMILES: NS(=O)(=O)c1c(C(F)(F)F)ccc(-c2ccc(C3CCN(CC4CNC4)CC3)cc2)c1-c1nnn[nH]1] | 4'-[1-(azetidin-3-ylmethyl)piperidin-4-yl]-2-(1H-tetrazol-5-yl)-4-(trifluoromethyl)biphenyl-3-sulfonamide | 522.19 | 522.18 |
| 672 | 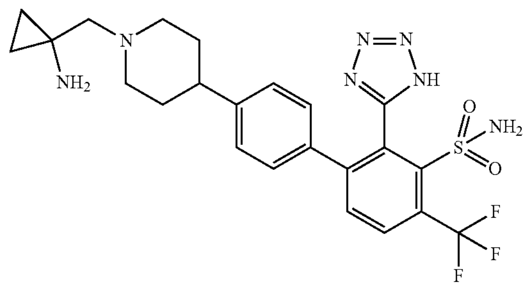 [SMILES: NC1(CN2CCC(c3ccc(-c4ccc(C(F)(F)F)c(S(N)(=O)=O)c4-c4nnn[nH]4)cc3)CC2)CC1] | 4'-{1-[(1-aminocyclopropyl)methyl]piperidin-4-yl}-2-(1H-tetrazol-5-yl)-4-(trifluoromethyl)biphenyl-3-sulfonamide | 522.19 | 522.18 |
| 673 | 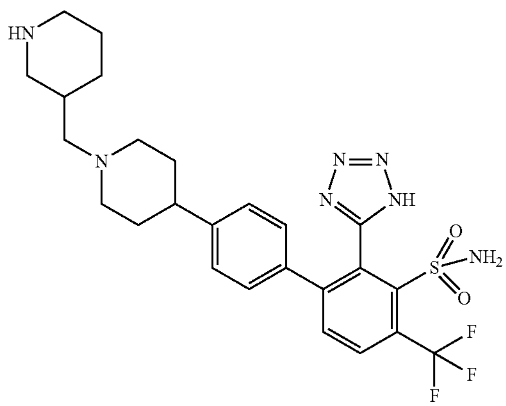 [SMILES: NS(=O)(=O)c1c(C(F)(F)F)ccc(-c2ccc(C3CCN(CC4CCCNC4)CC3)cc2)c1-c1nnn[nH]1] | 4'-[1-(piperidin-3-ylmethyl)piperidin-4-yl]-2-(1H-tetrazol-5-yl)-4-(trifluoromethyl)biphenyl-3-sulfonamide | 550.22 | 550.21 |
| 674 | 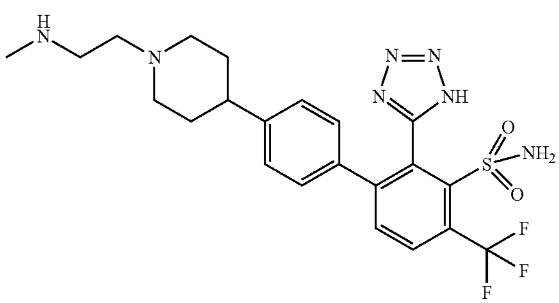 [SMILES: CNCCN1CCC(c2ccc(-c3ccc(C(F)(F)F)c(S(N)(=O)=O)c3-c3nnn[nH]3)cc2)CC1] | 4'-{1-[2-(methylamino)ethyl]piperidin-4-yl}-2-(1H-tetrazol-5-yl)-4-(trifluoromethyl)biphenyl-3-sulfonamide | 510.19 | 510.18 |
| 675 | 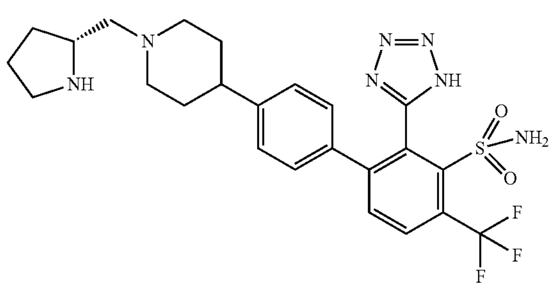 [SMILES: NS(=O)(=O)c1c(C(F)(F)F)ccc(-c2ccc(C3CCN(C[C@H]4CCCN4)CC3)cc2)c1-c1nnn[nH]1] | 4'-{1-[(2R)-pyrrolidin-2-ylmethyl]piperidin-4-yl}-2-(1H-tetrazol-5-yl)-4-(trifluoromethyl)biphenyl-3-sulfonamide | 536.21 | 536.2 |

| Ex. No. | Structure | Name | Calc'd. MW [M + H]+ | LC/MS m/e [M + H]+ |
|---|---|---|---|---|
| 676 | 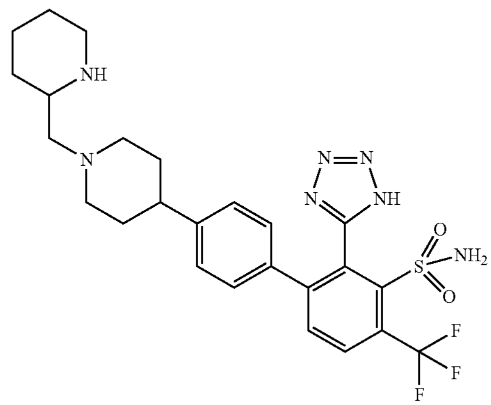 [SMILES: NS(=O)(=O)c1c(C(F)(F)F)ccc(-c2ccc(C3CCN(CC4CCCCN4)CC3)cc2)c1-c1nnn[nH]1] | 4'-[1-(piperidin-2-ylmethyl)piperidin-4-yl]-2-(1H-tetrazol-5-yl)-4-(trifluoromethyl)biphenyl-3-sulfonamide | 550.22 | 550.21 |
| 677 | 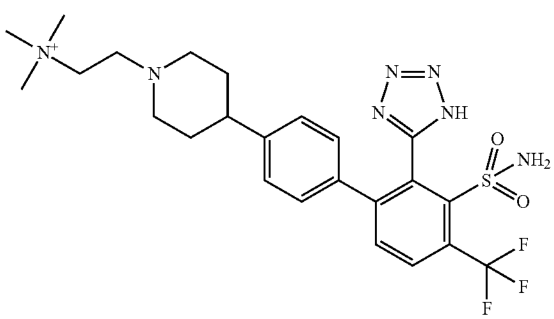 [SMILES: C[N+](C)(C)CCN1CCC(c2ccc(-c3ccc(C(F)(F)F)c(S(N)(=O)=O)c3-c3nnn[nH]3)cc2)CC1] | N,N,N-trimethyl-2-{4-[3'-sulfamoyl-2'-(1H-tetrazol-5-yl)-4'-(trifluoromethyl)biphenyl-4-yl]piperidin-1-yl}ethanaminium | 539.23 | 539.22 |
| 678 | 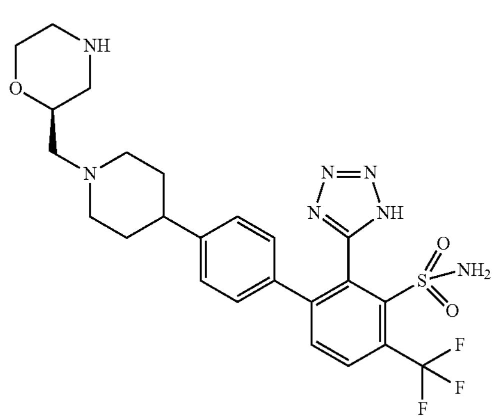 [SMILES: NS(=O)(=O)c1c(C(F)(F)F)ccc(-c2ccc(C3CCN(C[C@@H]4CNCCO4)CC3)cc2)c1-c1nnn[nH]1] | 4'-{1-[(2S)-morpholin-2-ylmethyl]piperidin-4-yl}-2-(1H-tetrazol-5-yl)-4-(trifluoromethyl)biphenyl-3-sulfonamide | 552.2 | 552.19 |

EXAMPLES 679-705

Parallel Synthesis of trans-4'-N-substituted cyclohexyl-2-(1H-tetrazol-5-yl)-6-(trifluoromethyl)benzensulfonamides

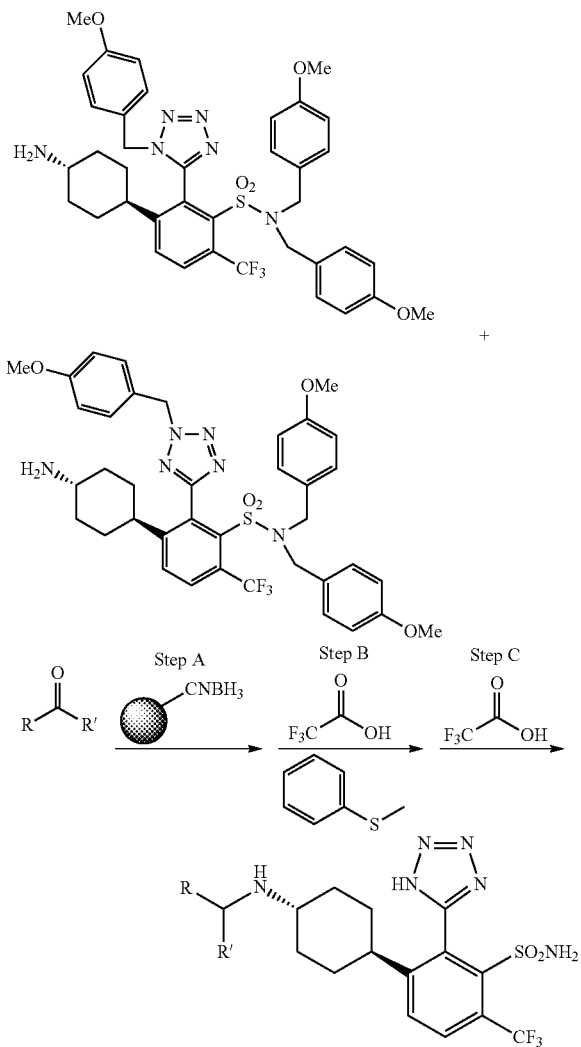

Step A: Reductive Amination of Ketones on Cyclohexylamine

To 2 dram vials, ketones (0.12 mmol) (commercially available, known from the literature) was added into 1 mL MeOH solution of the mixture (S)-3-((1r,4S)-4-aminocyclohexyl)-N,N-bis(4-methoxybenzyl)-2-(1-(4-methoxybenzyl)-1H-tetrazol-5-yl)-6-(trifluoromethyl)benzenesulfonamide and 3-((1r,4r)-4-aminocyclohexyl)-N,N-bis(4-methoxybenzyl)-2-(2-(4-methoxybenzyl)-2H-tetrazol-5-yl)-6-(trifluoromethyl)benzenesulfonamide from Example 820, prior to removal of the para-methoxybenzyl protective groups, (30 mg, 0.04 mmol) followed by addition of 2 drops of acetic acid. The vials were capped and stirring at room temperature for 20 min. MP-CNBH$_3$ (90 mg, 2.4 mmol/g) was then added to each vial. The vials were capped and stirring at room temperature for 20 hr. The crude reactions were monitored by UPLC. Once reactions were finished, the mixture were filtered and the solvent were removed in a GeneVac to afford the crude intermediates which were deprotected without further purification in the subsequent step.

Step B: Removal of the Boc and p-methoxybenzyl (PMB) Protecting Group by TFA Treatment To the residues from Step A, were each added TFA 0.7 mL and thioanilsole (0.3 mL). The vials were sealed and stirred at room temperature. After 5 hr, the reactions were monitored by UPLC. The mixtures were concentrated in a GeneVac. The residues were dissolved in DMSO. Each crude mixture was filtered into a 96-well tray and purified with HPLC. The crude products were purified by mass triggered reverse phase HPLC to afford corresponding intermediates.

Step C: Removal of the p-methoxybenzyl (PMB) Protecting Group by TFA Treatment

To the intermediates from Step B were added TFA 0.7 mL. The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 µm, 19×100 mm; solvent: gradient range 3-45% initial to 45-100% final MeCN (0.1% TFA) in water (0.1% TFA) 50 or 70 mL/min; 8 min run time] to afford Examples 679-705.

| Ex. No. | Structure | Name | Calc'd. MW [M + H]$^+$ | LC/MS m/e [M + H]$^+$ |
|---|---|---|---|---|
| 679 | 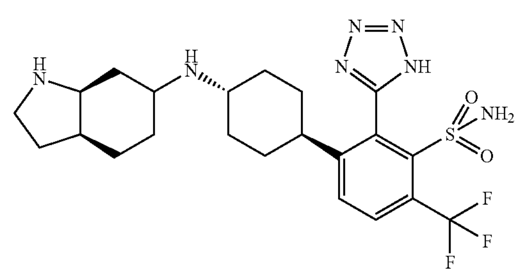 | 3-{4-[(3aS,6S,7aS)-octahydro-1H-indol-6-ylamino]cyclohexyl}-2-(1H-tetrazol-5-yl)-6-(trifluoromethyl)benzenesulfonamide | 514.22 | 514.21 |

| Ex. No. | Structure | Name | Calc'd. MW [M + H]+ | LC/MS m/e [M + H]+ |
|---|---|---|---|---|
| 680 | 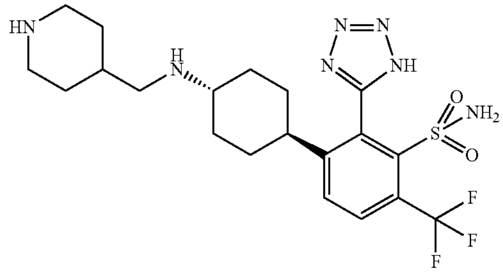 [SMILES: NS(=O)(=O)c1c(C(F)(F)F)ccc([C@H]2CC[C@H](NCC3CCNCC3)CC2)c1-c1nnn[nH]1] | 3-{4-[(piperidin-4-ylmethyl)amino]cyclohexyl}-2-(1H-tetrazol-5-yl)-6-(trifluoromethyl)benzenesulfonamide | 488.21 | 488.2 |
| 681 | 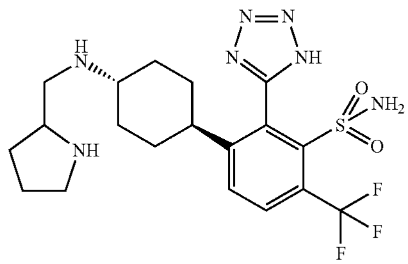 [SMILES: NS(=O)(=O)c1c(C(F)(F)F)ccc([C@H]2CC[C@H](NCC3CCCN3)CC2)c1-c1nnn[nH]1] | 3-{4-[(pyrrolidin-2-ylmethyl)amino]cyclohexyl}-2-(1H-tetrazol-5-yl)-6-(trifluoromethyl)benzenesulfonamide | 474.19 | 474.18 |
| 682 | 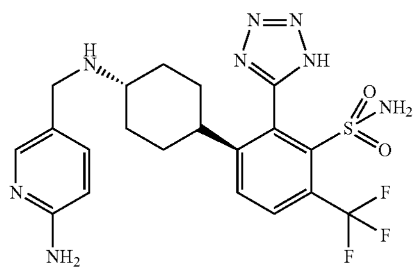 | 3-(4-{[(6-aminopyridin-3-yl)methyl]amino}cyclohexyl)-2-(1H-tetrazol-5-yl)-6-(trifluoromethyl)benzenesulfonamide | 497.17 | 497.16 |
| 683 | 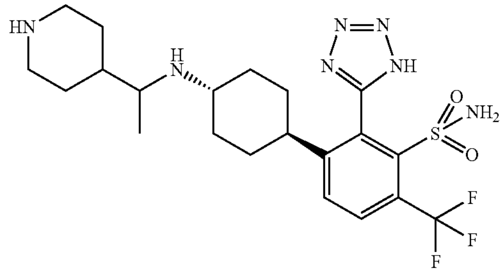 [SMILES: CC(N[C@H]1CC[C@H](c2ccc(C(F)(F)F)c(S(N)(=O)=O)c2-c2nnn[nH]2)CC1)C1CCNCC1] | 3-{4-[(1-piperidin-4-ylethyl)amino]cyclohexyl}-2-(1H-tetrazol-5-yl)-6-(trifluoromethyl)benzenesulfonamide | 502.22 | 502.21 |
| 684 | 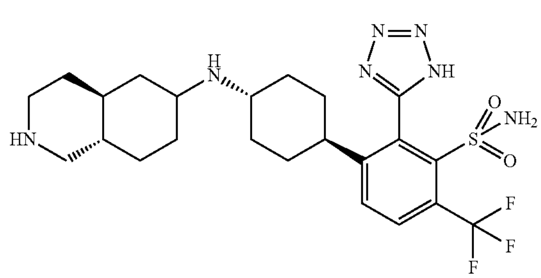 [SMILES: NS(=O)(=O)c1c(C(F)(F)F)ccc([C@H]2CC[C@H](NC3CC[C@@H]4CNCC[C@H]4C3)CC2)c1-c1nnn[nH]1] | 3-{4-[(4aS,8aS)-decahydroisoquinolin-6-ylamino]cyclohexyl}-2-(1H-tetrazol-5-yl)-6-(trifluoromethyl)benzenesulfonamide | 528.24 | 528.23 |

-continued

| Ex. No. | Structure | Name | Calc'd. MW [M + H]+ | LC/MS m/e [M + H]+ |
|---|---|---|---|---|
| 685 | 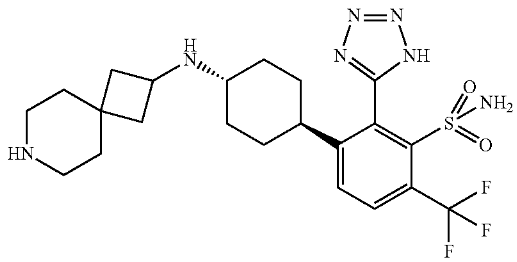 [SMILES: NS(=O)(=O)c1c(C(F)(F)F)ccc([C@H]2CC[C@H](NC3CC4(CCNCC4)C3)CC2)c1-c1nnn[nH]1] | 3-[4-(7-azaspiro[3.5]non-2-ylamino)cyclohexyl]-2-(1H-tetrazol-5-yl)-6-(trifluoromethyl)benzenesulfonamide | 514.22 | 514.21 |
| 686 | 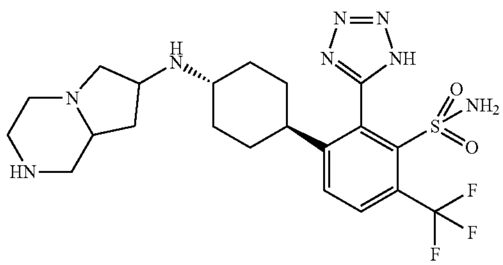 [SMILES: NS(=O)(=O)c1c(C(F)(F)F)ccc([C@H]2CC[C@H](NC3CC4CNCCN4C3)CC2)c1-c1nnn[nH]1] | 3-[4-(octahydropyrrolo[1,2-a]pyrazin-7-ylamino)cyclohexyl]-2-(1H-tetrazol-5-yl)-6-(trifluoromethyl)benzenesulfonamide | 515.22 | 515.21 |
| 687 | 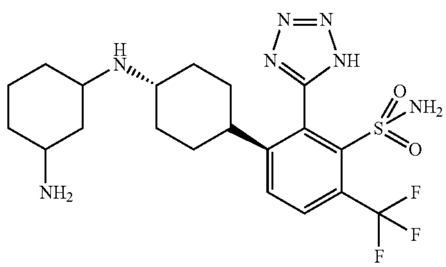 | 3-{4-[(3-aminocyclohexyl)amino]cyclohexyl}-2-(1H-tetrazol-5-yl)-6-(trifluoromethyl)benzenesulfonamide | 488.21 | 488.2 |
| 688 | 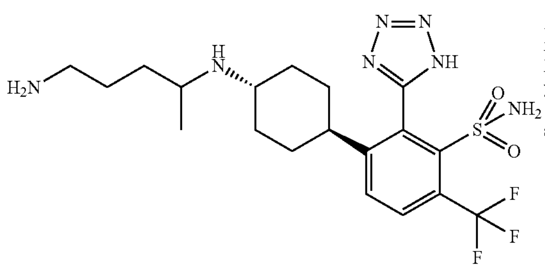 | 3-{4-[(4-amino-1-methylbutyl)amino]cyclohexyl)-2-(1H-tetrazol-5-yl)-6-(trifluoromethyl)benzenesulfonamide | 476.21 | 476.2 |
| 689 | 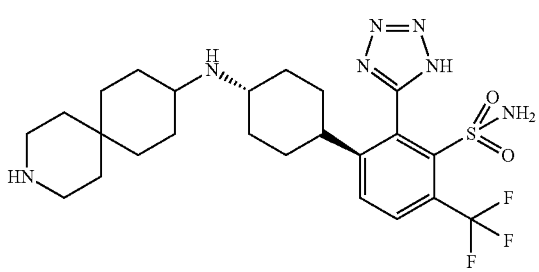 | 3-[4-(3-azaspiro[5.5]undec-9-ylamino)cyclohexyl]-2-(1H-tetrazol-5-yl)-6-(trifluoromethyl)benzenesulfonamide | 542.25 | 542.24 |

| Ex. No. | Structure | Name | Calc'd. MW [M + H]⁺ | LC/MS m/e [M + H]⁺ |
|---|---|---|---|---|
| 690 | 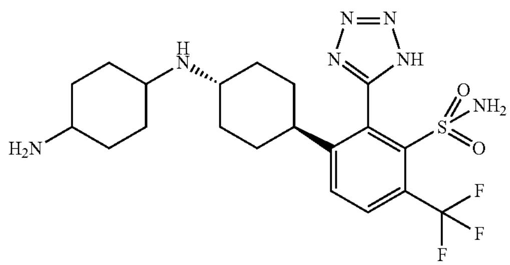 [SMILES: NC1CCC(N[C@H]2CC[C@H](c3ccc(C(F)(F)F)c(S(N)(=O)=O)c3-c3nnn[nH]3)CC2)CC1] | 3-{4-[(4-aminocyclohexyl)amino]cyclohexyl}-2-(1H-tetrazol-5-yl)-6-(trifluoromethyl)benzenesulfonamide | 488.21 | 488.2 |
| 691 | 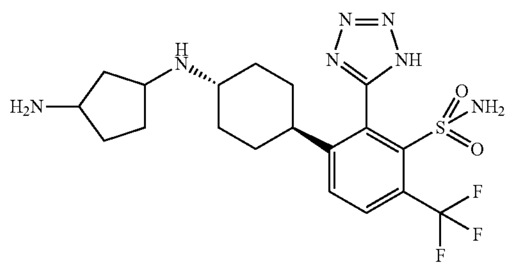 [SMILES: NC1CCC(N[C@H]2CC[C@H](c3ccc(C(F)(F)F)c(S(N)(=O)=O)c3-c3nnn[nH]3)CC2)C1] | 3-{4-[(3-aminocyclopentyl)amino]cyclohexyl}-2-(1H-tetrazol-5-yl)-6-(trifluoromethyl)benzenesulfonamide | 474.19 | 474.18 |
| 692 | 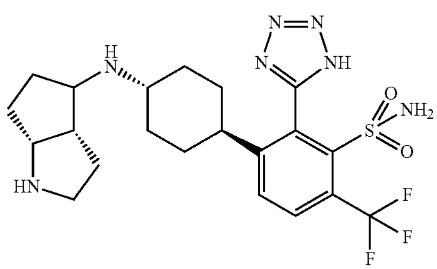 | 3-{4-[(3aR,6aR)-octahydrocyclopenta[b]pyrrol-4-ylamino]cyclohexyl}-2-(1H-tetrazol-5-yl)-6-(trifluoromethyl)benzenesulfonamide | 500.21 | 500.2 |
| 693 | 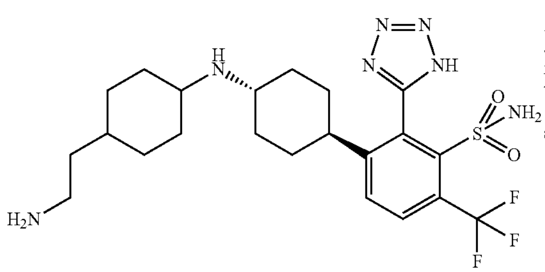 | 3-(4-{[4-(2-aminoethyl)cyclohexyl]amino}cyclohexyl)-2-(1H-tetrazol-5-yl)-6-(trifluoromethyl)benzenesulfonamide | 516.24 | 516.23 |
| 694 | 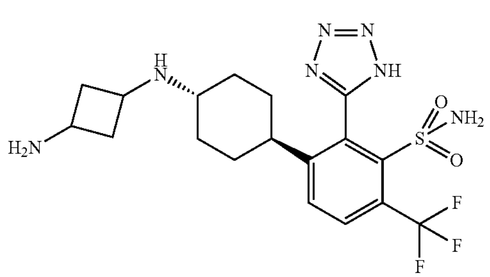 [SMILES: NC1CC(N[C@H]2CC[C@H](c3ccc(C(F)(F)F)c(S(N)(=O)=O)c3-c3nnn[nH]3)CC2)C1] | 3-{4-[(3-aminocyclobutyl)amino]cyclohexyl}-2-(1H-tetrazol-5-yl)-6-(trifluoromethyl)benzenesulfonamide | 460.17 | 460.16 |

-continued

| Ex. No. | Structure | Name | Calc'd. MW [M + H]+ | LC/MS m/e [M + H]+ |
|---|---|---|---|---|
| 695 | 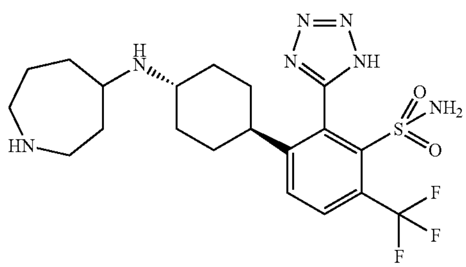 [SMILES: NS(=O)(=O)c1c(C(F)(F)F)ccc([C@H]2CC[C@H](NC3CCCNCC3)CC2)c1-c1nnn[nH]1] | 3-[4-(azepan-4-ylamino)cyclohexyl]-2-(1H-tetrazol-5-yl)-6-(trifluoromethyl)benzene sulfonamide | 488.21 | 488.2 |
| 696 | 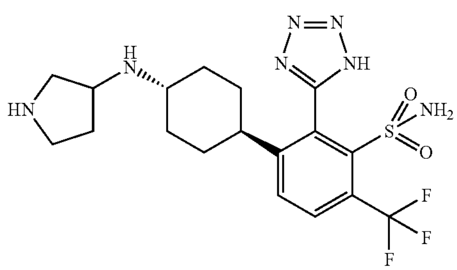 [SMILES: NS(=O)(=O)c1c(C(F)(F)F)ccc([C@H]2CC[C@H](NC3CCNC3)CC2)c1-c1nnn[nH]1] | 3-[4-(pyrrolidin-3-ylamino)cyclohexyl]-2-(1H-tetrazol-5-yl)-6-(trifluoromethyl)benzene sulfonamide | 460.17 | 460.17 |
| 697 | 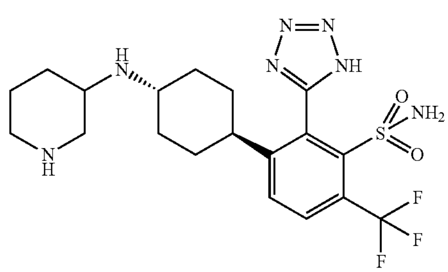 [SMILES: NS(=O)(=O)c1c(C(F)(F)F)ccc([C@H]2CC[C@H](NC3CCCNC3)CC2)c1-c1nnn[nH]1] | 3-[4-(piperidin-3-ylamino)cyclohexyl]-2-(1H-tetrazol-5-yl)-6-(trifluoromethyl)benzene sulfonamide | 474.19 | 474.18 |
| 698 | 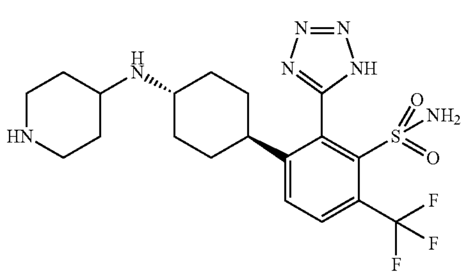 [SMILES: NS(=O)(=O)c1c(C(F)(F)F)ccc([C@H]2CC[C@H](NC3CCNCC3)CC2)c1-c1nnn[nH]1] | 3-[4-(piperidin-4-ylamino)cyclohexyl]-2-(1H-tetrazol-5-yl)-6-(trifluoromethyl)benzene sulfonamide | 474.19 | 474.18 |
| 699 | 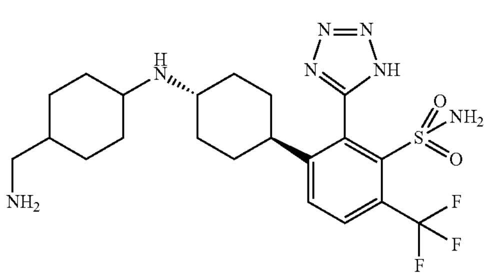 [SMILES: NCC1CCC(N[C@H]2CC[C@H](c3ccc(C(F)(F)F)c(S(N)(=O)=O)c3-c3nnn[nH]3)CC2)CC1] | 3-(4-{[4-(aminomethyl)cyclohexyl]amino}cyclohexyl)-2-(1H-tetrazol-5-yl)-6-(trifluoromethyl)benzene sulfonamide | 502.22 | 502.21 |

-continued

| Ex. No. | Structure | Name | Calc'd. MW [M + H]+ | LC/MS m/e [M + H]+ |
|---|---|---|---|---|
| 700 | 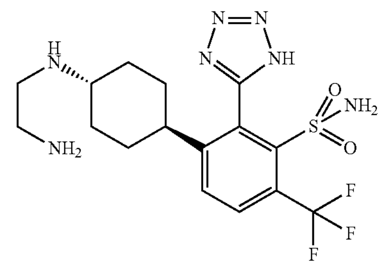 [SMILES: NCCN[C@H]1CC[C@H](c2ccc(C(F)(F)F)c(S(N)(=O)=O)c2-c2nnn[nH]2)CC1] | 3-{4-[(2-aminoethyl)amino]cyclohexyl}-2-(1H-tetrazol-5-yl)-6-(trifluoromethyl)benzenesulfonamide | 434.16 | 434.15 |
| 701 | 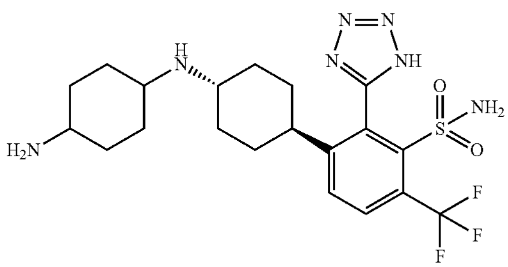 [SMILES: NC1CCC(N[C@H]2CC[C@H](c3ccc(C(F)(F)F)c(S(N)(=O)=O)c3-c3nnn[nH]3)CC2)CC1] | 3-{4-[(4-aminocyclohexyl)amino]cyclohexyl}-2-(1H-tetrazol-5-yl)-6-(trifluoromethyl)benzenesulfonamide | 488.21 | 488.2 |
| 702 | 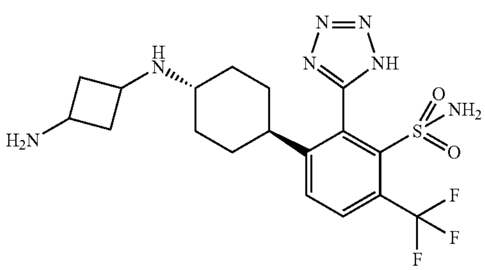 [SMILES: NC1CC(N[C@H]2CC[C@H](c3ccc(C(F)(F)F)c(S(N)(=O)=O)c3-c3nnn[nH]3)CC2)C1] | 3-{4-[(3-aminocyclobutyl)amino]cyclohexyl}-2-(1H-tetrazol-5-yl)-6-(trifluoromethyl)benzenesulfonamide | 460.17 | 460.17 |
| 703 | 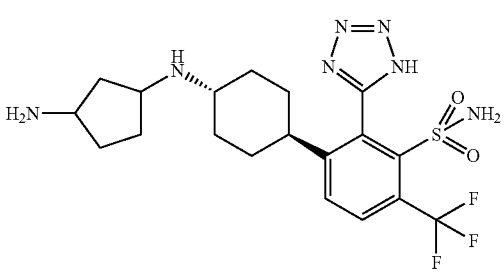 [SMILES: NC1CCC(N[C@H]2CC[C@H](c3ccc(C(F)(F)F)c(S(N)(=O)=O)c3-c3nnn[nH]3)CC2)C1] | 3-{4-[(3-aminocyclopentyl)amino]cyclohexyl}-2-(1H-tetrazol-5-yl)-6-(trifluoromethyl)benzenesulfonamide | 474.19 | 474.18 |
| 704 | 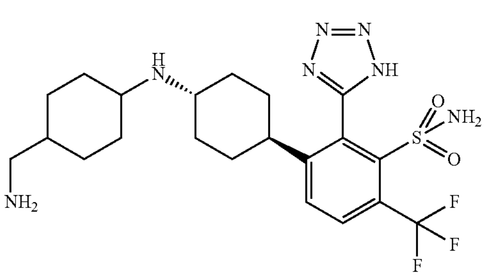 [SMILES: NCC1CCC(N[C@H]2CC[C@H](c3ccc(C(F)(F)F)c(S(N)(=O)=O)c3-c3nnn[nH]3)CC2)CC1] | 3-(4-{[4-(aminomethyl)cyclohexyl]amino}cyclohexyl)-2-(1H-tetrazol-5-yl)-6-(trifluoromethyl)benzenesulfonamide | 502.22 | 502.21 |

| Ex. No. | Structure | Name | Calc'd. MW [M + H]+ | LC/MS m/e [M + H]+ |
|---|---|---|---|---|
| 705 | 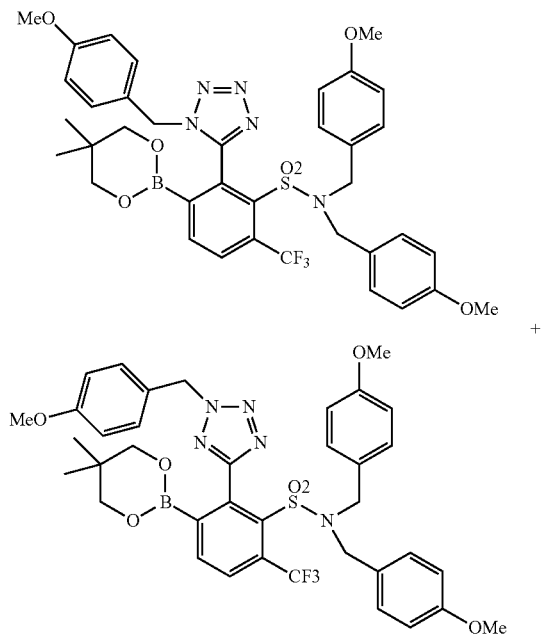 | 3-(4-{[4-(2-aminoethyl)cyclohexyl]amino}cyclohexyl)-2-(1H-tetrazol-5-yl)-6-(trifluoromethyl)benzenesulfonamide | 516.24 | 516.23 |

EXAMPLES 706-753

Parallel Synthesis of 3-substituted 2-(1H-tetrazol-5-yl)-6-(trifluromethyl)benzenesulfonamides

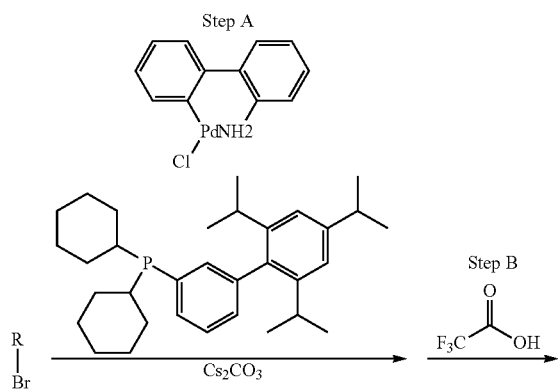

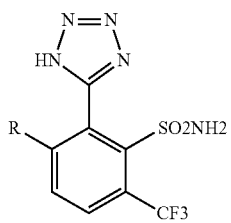

Step A: Palladium Catalyzed C—C Coupling of Arylboronic Ester and Arylbromides

In a glove box under a dry nitrogen atmosphere, arylbromides (0.133 mmol) (commercially available, known from the literature) and $2^{nd}$ Generation Xphos Pre-Catalyst (5.23 mg, 6.65 μmol) and 266 μL of 1N degassed aq. $Cs_2CO3$ solution were added into 2 dram vials. 1.0 mL of a solution of the mixture of 3-(5,5-dimethyl-1,3,2-dioxaborinan-2-yl)-N,N-bis(4-methoxybenzyl)-2-(1-(4-methoxybenzyl)-1H-tetrazol-5-yl)-6-(trifluoromethyl)benzenesulfonamide and 3-(5,5-dimethyl-1,3,2-dioxaborinan-2-yl)-N,N-bis(4-methoxybenzyl)-2-(2-(4-methoxybenzyl)-2H-tetrazol-5-yl)-6-(trifluoromethyl)benzenesulfonamide (50 mg, 0.067 mmol) in 1,4-Dioxane were added into each vial. The vials were capped and heated at 85° C. with stirring for 20 hr. After the vials were cooled to room temperature, the solvent was removed in a GeneVac. Into each residue was added 600 μL of $H_2O$ and 2 mL of EtOAc. The organic layers were transferred into 2 dram vials. The organic solvent was removed in GeneVac to afford the crude intermediates which were deprotected without further purification in the subsequent step.

Step B: Removal of the p-methoxybenzyl (PMB) Protecting Group by TFA Treatment

To the residues from Step A were each added TFA 0.7 mL and anisole (0.3 mL). The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 μm, 19×100 mm; solvent: gradient range 3-28% initial to 45-95% final MeCN (0.1% TFA) in water (0.1% TFA) 50 or 70 mL/min; 8 min run time] to afford EXAMPLES 706-753. Note that some aryl halides included tert-butoxycarbonyl protected amino groups; in these instances TFA treatment also led to removal of the tert-butoxycarbonyl protective group.

| Ex. No. | Structure | Name | Calc'd. MW [M + H]+ | LC/MS m/e [M + H]+ |
|---|---|---|---|---|
| 706 | 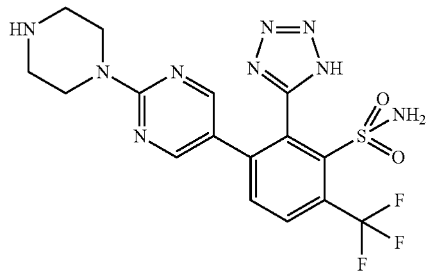 [SMILES: NS(=O)(=O)c1c(C(F)(F)F)ccc(-c2cnc(N3CCNCC3)nc2)c1-c1nnn[nH]1] | 3-(2-piperazin-1-ylpyrimidin-5-yl)-2-(1H-tetrazol-5-yl)-6-(trifluoromethyl)benzenesulfonamide | 456.12 | 456.11 |
| 707 | 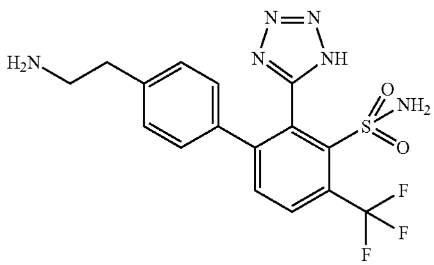 [SMILES: NCCc1ccc(-c2ccc(C(F)(F)F)c(S(N)(=O)=O)c2-c2nnn[nH]2)cc1] | 4'-(2-aminoethyl)-2-(1H-tetrazol-5-yl)-4-(trifluoromethyl)biphenyl-3-sulfonamide | 413.1 | 413.09 |
| 708 | 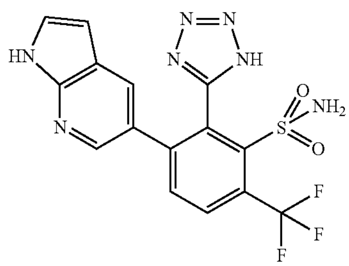 [SMILES: NS(=O)(=O)c1c(C(F)(F)F)ccc(-c2cnc3[nH]ccc3c2)c1-c1nnn[nH]1] | 3-(1H-pyrrolo[2,3-b]pyridin-5-yl)-2-(1H-tetrazol-5-yl)-6-(trifluoromethyl)benzenesulfonamide | 410.06 | 410.06 |
| 709 | 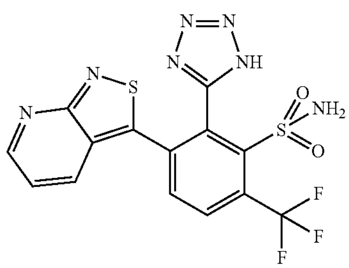 [SMILES: NS(=O)(=O)c1c(C(F)(F)F)ccc(-c2snc3ncccc23)c1-c1nnn[nH]1] | 3-isothiazolo[3,4-b]pyridin-3-yl-2-(1H-tetrazol-5-yl)-6-(trifluoromethyl)benzenesulfonamide | 428.02 | 428.01 |
| 710 | 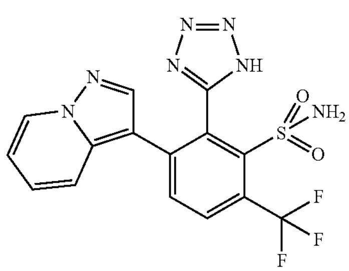 [SMILES: NS(=O)(=O)c1c(C(F)(F)F)ccc(-c2cnn3ccccc23)c1-c1nnn[nH]1] | 3-pyrazolo[1,5-a]pyridin-3-yl-2-(1H-tetrazol-5-yl)-6-(trifluoromethyl)benzenesulfonamide | 410.06 | 410.06 |

-continued

| Ex. No. | Structure | Name | Calc'd. MW [M + H]+ | LC/MS m/e [M + H]+ |
|---|---|---|---|---|
| 711 | 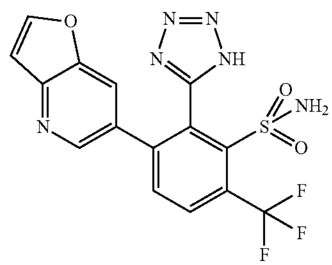 [SMILES: NS(=O)(=O)c1c(C(F)(F)F)ccc(-c2cnc3ccoc3c2)c1-c1nnn[nH]1] | 3-furo[3,2-b]pyridin-6-yl-2-(1H-tetrazol-5-yl)-6-(trifluoromethyl)benzenesulfonamide | 411.05 | 411.04 |
| 712 | 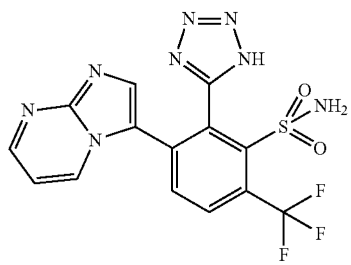 [SMILES: NS(=O)(=O)c1c(C(F)(F)F)ccc(-c2cnc3ncccn23)c1-c1nnn[nH]1] | 3-imidazo[1,2-a]pyrimidin-3-yl-2-(1H-tetrazol-5-yl)-6-(trifluoromethyl)benzenesulfonamide | 411.06 | 411.05 |
| 713 | 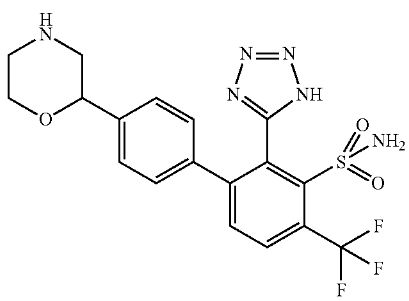 [SMILES: NS(=O)(=O)c1c(C(F)(F)F)ccc(-c2ccc(C3CNCCO3)cc2)c1-c1nnn[nH]1] | 4'-morpholin-2-yl-2-(1H-tetrazol-5-yl)-4-(trifluoromethyl)biphenyl-3-sulfonamide | 455.11 | 455.1 |
| 714 | 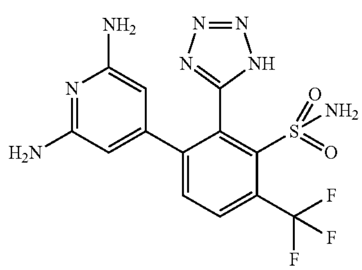 [SMILES: Nc1cc(-c2ccc(C(F)(F)F)c(S(N)(=O)=O)c2-c2nnn[nH]2)cc(N)n1] | 3-(2,6-diaminopyridin-4-yl)-2-(1H-tetrazol-5-yl)-6-(trifluoromethyl)benzenesulfonamide | 401.08 | 401.07 |
| 715 | 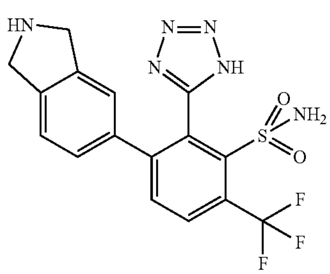 [SMILES: NS(=O)(=O)c1c(C(F)(F)F)ccc(-c2ccc3c(c2)CNC3)c1-c1nnn[nH]1] | 3-(2,3-dihydro-1H-isoindol-5-yl)-2-(1H-tetrazol-5-yl)-6-(trifluoromethyl)benzenesulfonamide | 411.09 | 411.08 |

-continued

| Ex. No. | Structure | Name | Calc'd. MW [M + H]+ | LC/MS m/e [M + H]+ |
|---|---|---|---|---|
| 716 | 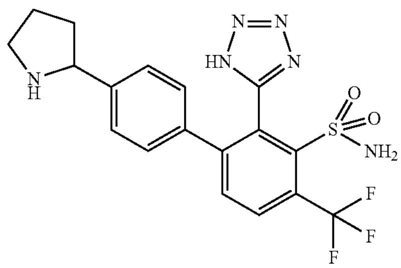 [SMILES: NS(=O)(=O)c1c(C(F)(F)F)ccc(-c2ccc(C3CCCN3)cc2)c1-c1nnn[nH]1] | 4'-pyrrolidin-2-yl-2-(1H-tetrazol-5-yl)-4-(trifluoromethyl)biphenyl-3-sulfonamide | 439.12 | 439.11 |
| 717 | 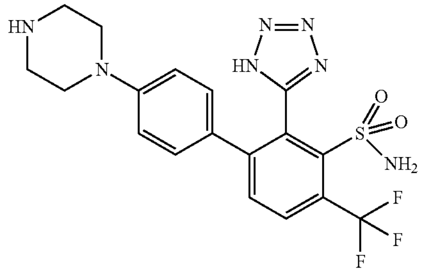 [SMILES: NS(=O)(=O)c1c(C(F)(F)F)ccc(-c2ccc(N3CCNCC3)cc2)c1-c1nnn[nH]1] | 4'-piperazin-1-yl-2-(1H-tetrazol-5-yl)-4-(trifluoromethyl)biphenyl-3-sulfonamide | 454.13 | 454.12 |
| 718 | 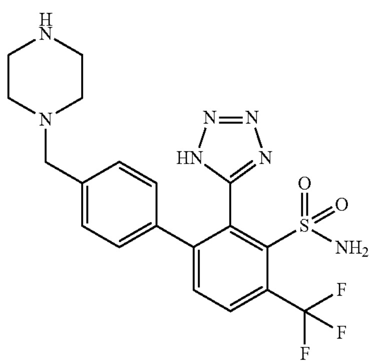 [SMILES: NS(=O)(=O)c1c(C(F)(F)F)ccc(-c2ccc(CN3CCNCC3)cc2)c1-c1nnn[nH]1] | 4'-(piperazin-1-ylmethyl)-2-(1H-tetrazol-5-yl)-4-(trifluoromethyl)biphenyl-3-sulfonamide | 468.14 | 468.14 |
| 719 | 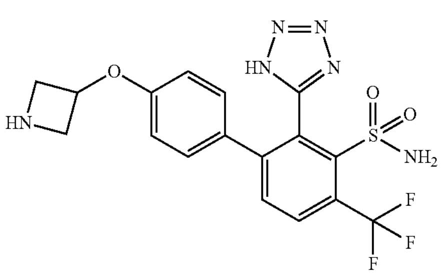 [SMILES: NS(=O)(=O)c1c(C(F)(F)F)ccc(-c2ccc(OC3CNC3)cc2)c1-c1nnn[nH]1] | 4'-(azetidin-3-yloxy)-2-(1H-tetrazol-5-yl)-4-(trifluoromethyl)biphenyl-3-sulfonamide | 441.1 | 441.09 |
| 720 | 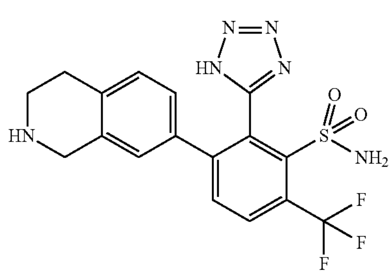 [SMILES: NS(=O)(=O)c1c(C(F)(F)F)ccc(-c2ccc3c(c2)CNCC3)c1-c1nnn[nH]1] | 3-(1,2,3,4-tetrahydroisoquinolin-7-yl)-2-(1H-tetrazol-5-yl)-6-(trifluoromethyl)benzenesulfonamide | 425.1 | 425.09 |

-continued

| Ex. No. | Structure | Name | Calc'd. MW [M + H]+ | LC/MS m/e [M + H]+ |
|---|---|---|---|---|
| 721 | 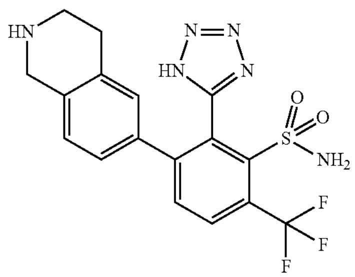 [SMILES: NS(=O)(=O)c1c(C(F)(F)F)ccc(-c2ccc3c(c2)CCNC3)c1-c1nnn[nH]1] | 3-(1,2,3,4-tetrahydroisoquinolin-6-yl)-2-(1H-tetrazol-5-yl)-6-(trifluoromethyl)benzenesulfonamide | 425.1 | 425.09 |
| 722 | 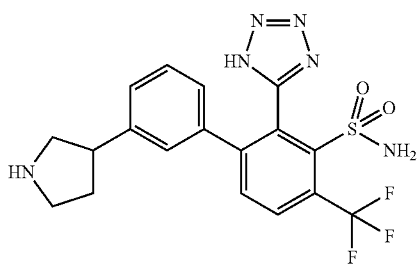 [SMILES: NS(=O)(=O)c1c(C(F)(F)F)ccc(-c2cccc(C3CCNC3)c2)c1-c1nnn[nH]1] | 3'-pyrrolidin-3-yl-2-(1H-tetrazol-5-yl)-4-(trifluoromethyl)biphenyl-3-sulfonamide | 439.12 | 439.11 |
| 723 | 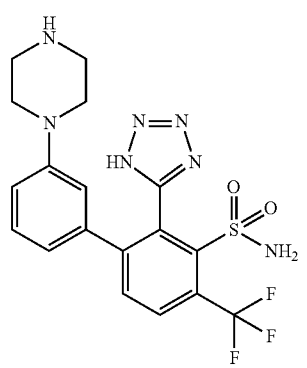 [SMILES: NS(=O)(=O)c1c(C(F)(F)F)ccc(-c2cccc(N3CCNCC3)c2)c1-c1nnn[nH]1] | 3'-piperazin-1-yl-2-(1H-tetrazol-5-yl)-4-(trifluoromethyl)biphenyl-3-sulfonamide | 454.13 | 454.12 |
| 724 | 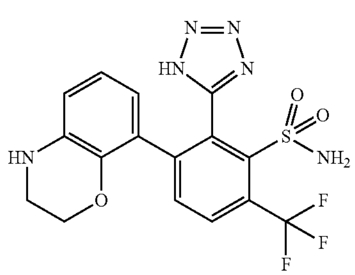 [SMILES: NS(=O)(=O)c1c(C(F)(F)F)ccc(-c2cccc3c2OCCN3)c1-c1nnn[nH]1] | 3-(3,4-dihydro-2H-1,4-benzoxazin-8-yl)-2-(1H-tetrazol-5-yl)-6-(trifluoromethyl)benzenesulfonamide | 427.08 | 427.07 |
| 725 | 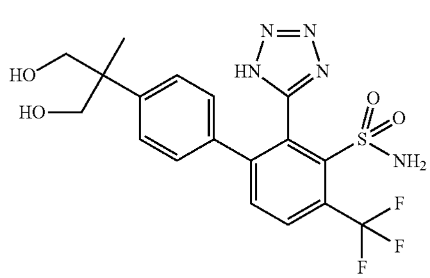 [SMILES: CC(CO)(CO)c1ccc(-c2ccc(C(F)(F)F)c(S(N)(=O)=O)c2-c2nnn[nH]2)cc1] | 4'-[2-hydroxy-1-(hydroxymethyl)-1-methylethyl]-2-(1H-tetrazol-5-yl)-4-(trifluoromethyl)biphenyl-3-sulfonamide | 458.11 | 458.1 |

-continued

| Ex. No. | Structure | Name | Calc'd. MW [M + H]⁺ | LC/MS m/e [M + H]⁺ |
|---|---|---|---|---|
| 726 | 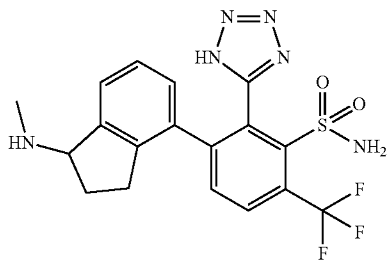 [SMILES: CNC1CCc2c(-c3ccc(C(F)(F)F)c(S(N)(=O)=O)c3-c3nnn[nH]3)cccc21] | 3-[1-(methylamino)-2,3-dihydro-1H-inden-4-yl]-2-(1H-tetrazol-5-yl)-6-(trifluoromethyl)benzenesulfonamide | 439.12 | 439.11 |
| 727 | 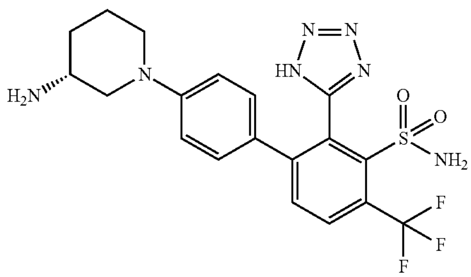 [SMILES: N[C@@H]1CCCN(c2ccc(-c3ccc(C(F)(F)F)c(S(N)(=O)=O)c3-c3nnn[nH]3)cc2)C1] | 4'-[(3R)-3-aminopiperidin-1-yl]-2-(1H-tetrazol-5-yl)-4-(trifluoromethyl)biphenyl-3-sulfonamide | 468.14 | 468.14 |
| 728 | 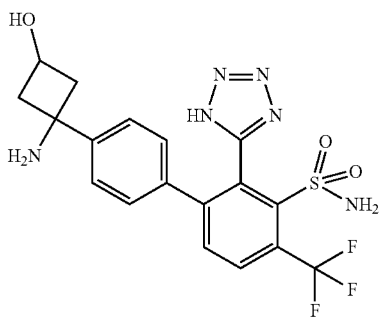 [SMILES: NC1(c2ccc(-c3ccc(C(F)(F)F)c(S(N)(=O)=O)c3-c3nnn[nH]3)cc2)CC(O)C1] | 4'-(1-amino-3-hydroxycyclobutyl)-2-(1H-tetrazol-5-yl)-4-(trifluoromethyl)biphenyl-3-sulfonamide | 455.11 | 455.1 |
| 729 | 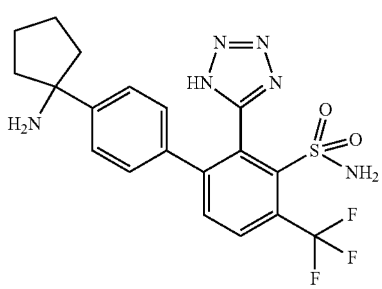 [SMILES: NC1(c2ccc(-c3ccc(C(F)(F)F)c(S(N)(=O)=O)c3-c3nnn[nH]3)cc2)CCCC1] | 4'-(1-aminocyclopentyl)-2-(1H-tetrazol-5-yl)-4-(trifluoromethyl)biphenyl-3-sulfonamide | 453.13 | 453.12 |
| 730 | 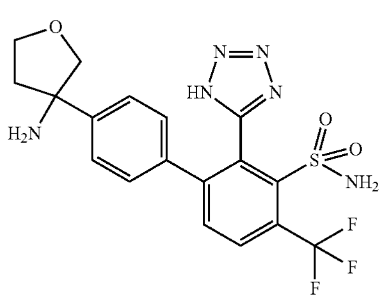 [SMILES: NC1(c2ccc(-c3ccc(C(F)(F)F)c(S(N)(=O)=O)c3-c3nnn[nH]3)cc2)CCOC1] | 4'-(3-aminotetrahydrofuran-3-yl)-2-(1H-tetrazol-5-yl)-4-(trifluoromethyl)biphenyl-3-sulfonamide | 455.11 | 455.1 |

| Ex. No. | Structure | Name | Calc'd. MW [M + H]⁺ | LC/MS m/e [M + H]⁺ |
|---|---|---|---|---|
| 731 | 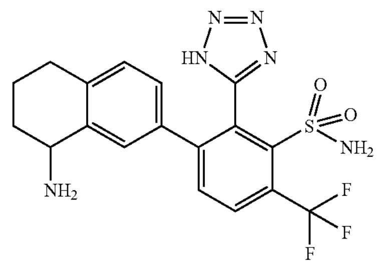 [SMILES: NC1CCCc2ccc(-c3ccc(C(F)(F)F)c(S(N)(=O)=O)c3-c3nnn[nH]3)cc21] | 3-(8-amino-5,6,7,8-tetrahydronaphthalen-2-yl)-2-(1H-tetrazol-5-yl)-6-(trifluoromethyl)benzenesulfonamide | 439.12 | 439.11 |
| 732 | 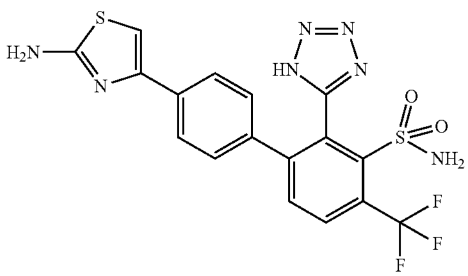 [SMILES: Nc1nc(-c2ccc(-c3ccc(C(F)(F)F)c(S(N)(=O)=O)c3-c3nnn[nH]3)cc2)cs1] | 4'-(2-amino-1,3-thiaozl-4-yl)-2-(1H-tetrazol-5-yl)-4-(trifluoromethyl)biphenyl-3-sulfonamide | 468.05 | 468.05 |
| 733 | 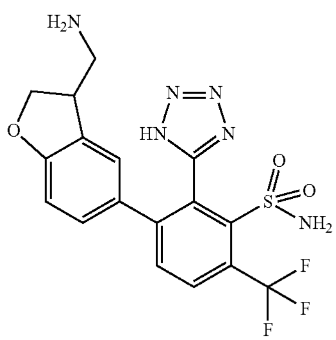 [SMILES: NCC1COc2ccc(-c3ccc(C(F)(F)F)c(S(N)(=O)=O)c3-c3nnn[nH]3)cc21] | 3-[3-(aminomethyl)-2,3-dihydro-1-benzofuran-5-yl]-2-(1H-tetrazol-5-yl)-6-(trifluoromethyl)benzenesulfonamide | 441.1 | 441.09 |
| 734 | 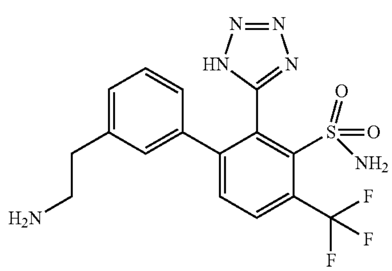 [SMILES: NCCc1cccc(-c2ccc(C(F)(F)F)c(S(N)(=O)=O)c2-c2nnn[nH]2)c1] | 3'-(2-aminoethyl)-2-(1H-tetraozl-5-yl)-4-(trifluoromethyl)biphenyl-3-sulfonamide | 413.1 | 413.09 |
| 735 | 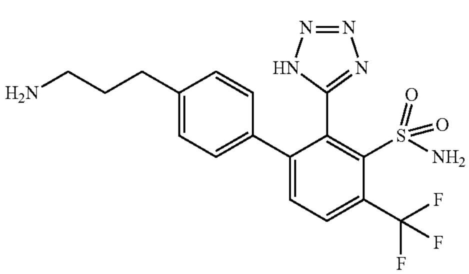 [SMILES: NCCCc1ccc(-c2ccc(C(F)(F)F)c(S(N)(=O)=O)c2-c2nnn[nH]2)cc1] | 4'-(3-aminopropyl)-2-(1H-tetrazol-5-yl)-4-(trifluoromethyl)biphenyl-3-sulfonamide | 427.12 | 427.11 |

-continued

| Ex. No. | Structure | Name | Calc'd. MW [M + H]+ | LC/MS m/e [M + H]+ |
|---|---|---|---|---|
| 736 | 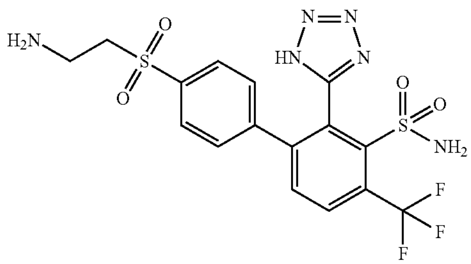 [SMILES: NCCS(=O)(=O)c1ccc(-c2ccc(C(F)(F)F)c(S(N)(=O)=O)c2-c2nnn[nH]2)cc1] | 4'-[(2-aminoethyl)sulfonyl]-2-(1H-tetrazol-5-yl)-4-(trifluoromethyl)biphenyl-3-sulfonamide | 477.06 | 477.05 |
| 737 | 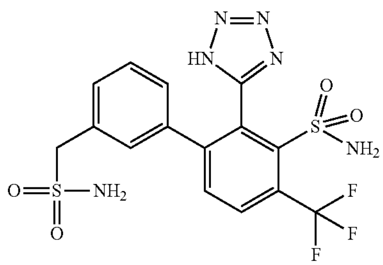 [SMILES: NS(=O)(=O)Cc1cccc(-c2ccc(C(F)(F)F)c(S(N)(=O)=O)c2-c2nnn[nH]2)c1] | 3'-(sulfamoylmethyl)-2-(1H-tetrazol-5-yl)-4-(trifluoromethyl)biphenyl-3-sulfonamide | 463.05 | 463.04 |
| 738 | 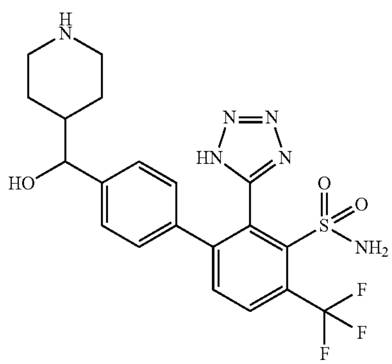 [SMILES: NS(=O)(=O)c1c(C(F)(F)F)ccc(-c2ccc(C(O)C3CCNCC3)cc2)c1-c1nnn[nH]1] | 4'-[hydroxy(piperidin-4-yl)methyl]-2-(1H-tetrazol-5-yl)-4-(trifluoromethyl)biphenyl-3-sulfonamide | 483.14 | 483.14 |
| 739 | 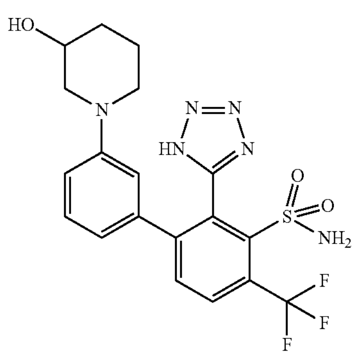 [SMILES: NS(=O)(=O)c1c(C(F)(F)F)ccc(-c2cccc(N3CCCC(O)C3)c2)c1-c1nnn[nH]1] | 3'-(3-hydroxypiperidin-1-yl)-2-(1H-tetrazol-5-yl)-4-(trifluoromethyl)biphenyl-3-sulfonamide | 469.13 | 469.12 |
| 740 | 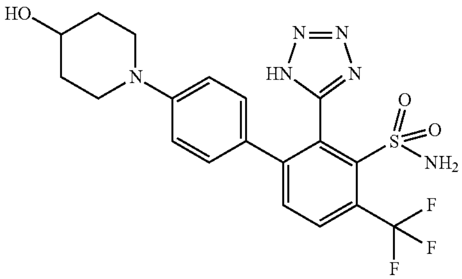 [SMILES: NS(=O)(=O)c1c(C(F)(F)F)ccc(-c2ccc(N3CCC(O)CC3)cc2)c1-c1nnn[nH]1] | 4'-(4-hydroxypiperidin-1-yl)-2-(1H-tetrazol-5-yl)-4-(trifluoromethyl)biphenyl-3-sulfonamide | 469.13 | 469.12 |

-continued

| Ex. No. | Structure | Name | Calc'd. MW [M + H]+ | LC/MS m/e [M + H]+ |
|---|---|---|---|---|
| 741 | 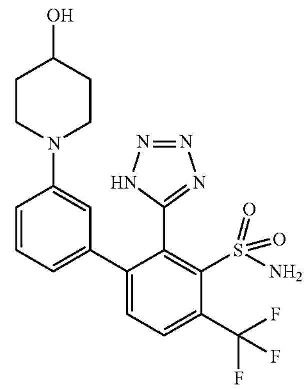 [SMILES: NS(=O)(=O)c1c(C(F)(F)F)ccc(-c2cccc(N3CCC(O)CC3)c2)c1-c1nnn[nH]1] | 3'-(4-hydroxypiperidin-1-yl)-2-(1H-tetrazol-5-yl)-4-(trifluoromethyl)biphenyl-3-sulfonamide | 469.13 | 469.12 |
| 742 | 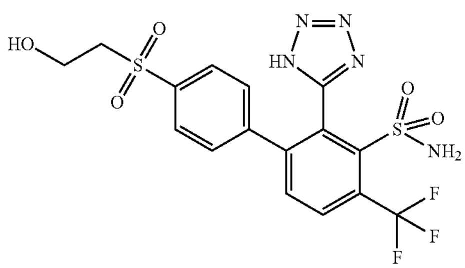 [SMILES: NS(=O)(=O)c1c(C(F)(F)F)ccc(-c2ccc(S(=O)(=O)CCO)cc2)c1-c1nnn[nH]1] | 4'-[(2-hydroxyethyl)sulfonyl]-2-(1H-tetrazol-5-yl)-4-(trifluoromethyl)biphenyl-3-sulfonamide | 478.05 | 478.04 |
| 743 | 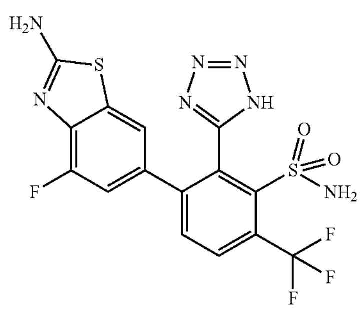 [SMILES: Nc1nc2c(F)cc(-c3ccc(C(F)(F)F)c(S(N)(=O)=O)c3-c3nnn[nH]3)cc2s1] | 3-(2-amino-4-fluoro-1,3-benzothiazol-6-yl)-2-(1H-tetrazol-5-yl)-6-(trifluoromethyl)benzenesulfonamide | 460.03 | 460.02 |
| 744 | 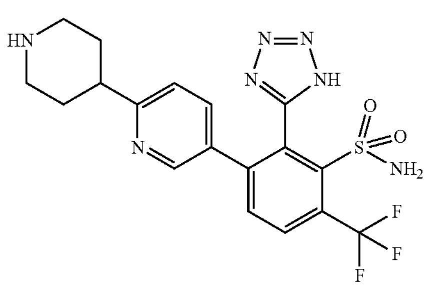 [SMILES: NS(=O)(=O)c1c(C(F)(F)F)ccc(-c2ccc(C3CCNCC3)nc2)c1-c1nnn[nH]1] | 3-(6-piperidin-4-ylpyridin-3-yl)-2-(1H-tetrazol-5-yl)-6-(trifluoromethyl)benzenesulfonamide | 454.13 | 454.12 |
| 745 | 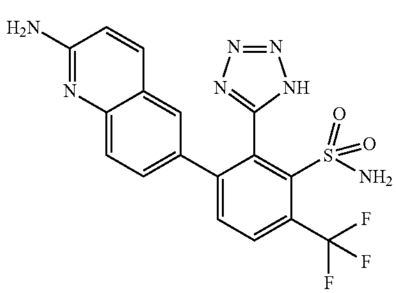 [SMILES: Nc1ccc2cc(-c3ccc(C(F)(F)F)c(S(N)(=O)=O)c3-c3nnn[nH]3)ccc2n1] | 3-(2-aminoquinolin-6-yl)-2-(1H-tetrazol-5-yl)-6-(trifluoromethyl)benzenesulfonamide | 436.08 | 436.07 |

-continued

| Ex. No. | Structure | Name | Calc'd. MW [M + H]⁺ | LC/MS m/e [M + H]⁺ |
|---|---|---|---|---|
| 746 | 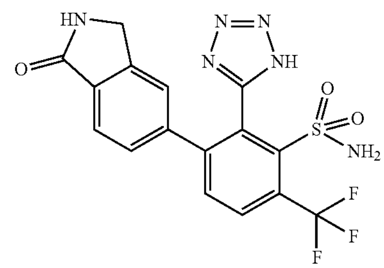 [SMILES: NS(=O)(=O)c1c(C(F)(F)F)ccc(-c2ccc3c(c2)CNC3=O)c1-c1nnn[nH]1] | 3-(1-oxo-2,3-dihydro-1H-isoindol-5-yl)-2-(1H-tetrazol-5-yl)-6-(trifluoromethyl)benzenesulfonamide | 425.06 | 425.06 |
| 747 | 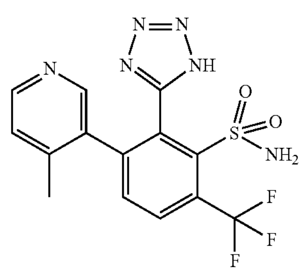 [SMILES: Cc1ccncc1-c1ccc(C(F)(F)F)c(S(N)(=O)=O)c1-c1nnn[nH]1] | 3-(4-methylpyridin-3-yl)-2-(1H-tetrazol-5-yl)-6-(trifluoromethyl)benzenesulfonamide | 385.07 | 385.06 |
| 748 | 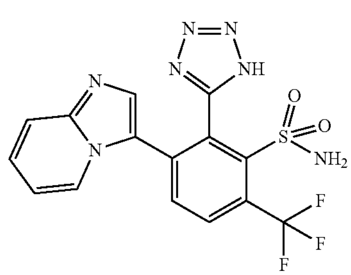 [SMILES: NS(=O)(=O)c1c(C(F)(F)F)ccc(-c2cnc3ccccn23)c1-c1nnn[nH]1] | 3-imidazo[1,2-a]pyridin-3-yl-2-(1H-tetrazol-5-yl)-6-(trifluoromethyl)benzenesulfonamide | 410.06 | 410.06 |
| 749 | 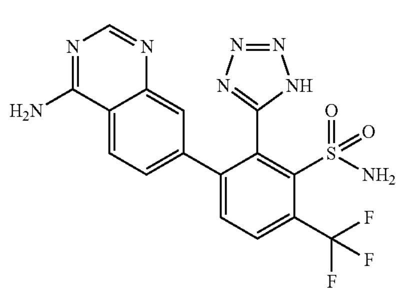 [SMILES: Nc1ncnc2cc(-c3ccc(C(F)(F)F)c(S(N)(=O)=O)c3-c3nnn[nH]3)ccc12] | 3-(4-aminoquinazolin-7-yl)-2-(1H-tetrazol-5-yl)-6-(trifluoromethyl)benzenesulfonamide | 437.08 | 437.07 |

-continued

| Ex. No. | Structure | Name | Calc'd. MW [M + H]+ | LC/MS m/e [M + H]+ |
|---|---|---|---|---|
| 750 | 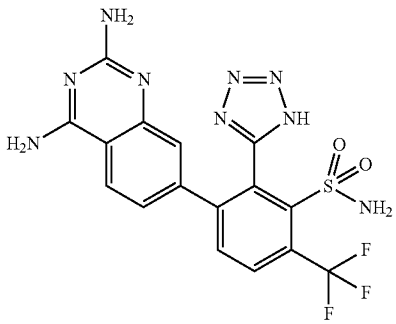 [SMILES: Nc1nc(N)c2ccc(-c3ccc(C(F)(F)F)c(S(N)(=O)=O)c3-c3nnn[nH]3)cc2n1] | 3-(2,4-diaminoquinazolin-7-yl)-2-(1H-tetrazol-5-yl)-6-(trifluoromethyl)benzenesulfonamide | 452.09 | 452.08 |
| 751 | 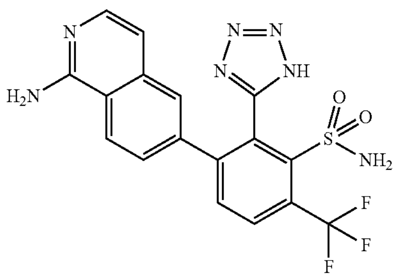 [SMILES: Nc1nccc2cc(-c3ccc(C(F)(F)F)c(S(N)(=O)=O)c3-c3nnn[nH]3)ccc12] | 3-(1-aminoisoquinolin-6-yl)-2-(1H-tetrazol-5-yl)-6-(trifluoromethyl)benzenesulfonamide | 436.08 | 436.08 |
| 752 | 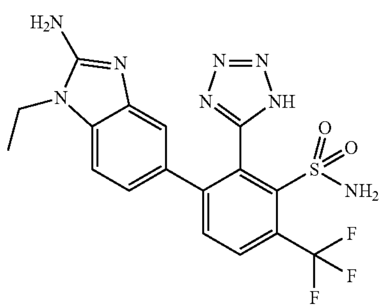 [SMILES: CCn1c(N)nc2cc(-c3ccc(C(F)(F)F)c(S(N)(=O)=O)c3-c3nnn[nH]3)ccc21] | 3-(2-amino-1-ethyl-1H-benzimidazol-5-yl)-2-(1H-tetrazol-5-yl)-6-(trifluoromethyl)benzenesulfonamide | 453.11 | 453.1 |
| 753 | 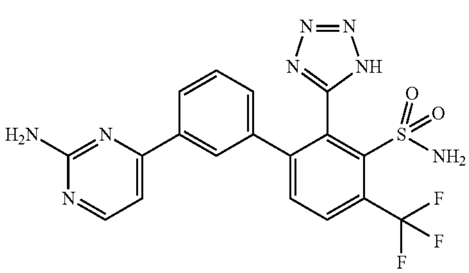 [SMILES: Nc1nccc(-c2cccc(-c3ccc(C(F)(F)F)c(S(N)(=O)=O)c3-c3nnn[nH]3)c2)n1] | 3'-(2-aminopyrimidin-4-yl)-2-(1H-tetrazol-5-yl)-4-(trifluoromethyl)biphenyl-3-sulfonamdie | 463.09 | 463.08 |

Examples 754-784

Parallel Synthesis of 3-N-substituted-2-(1H-tetrazol-5-yl)-6-(trifluromethyl)benzenesulfonamides

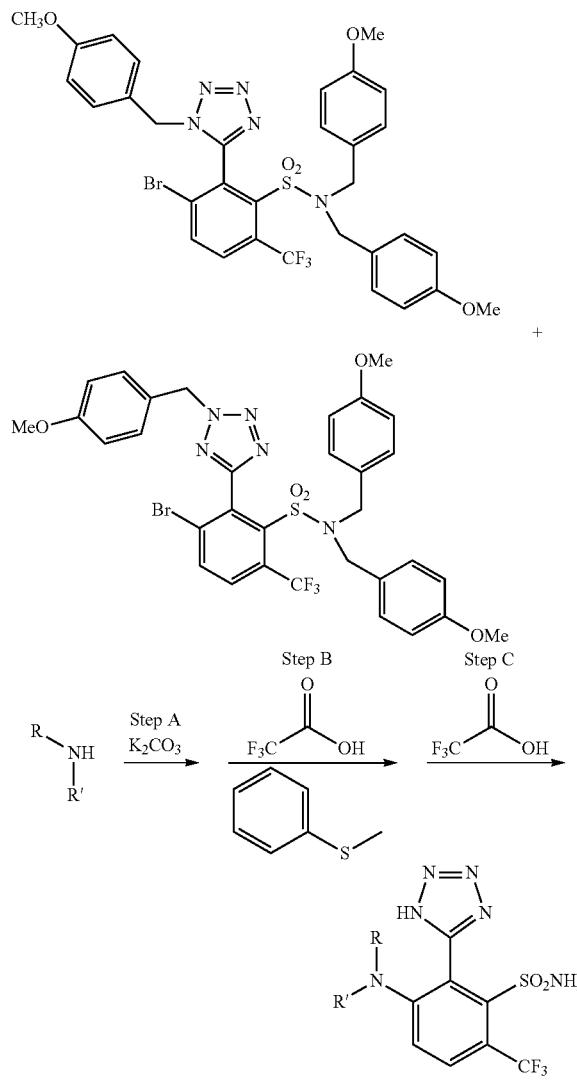

Step A: C—N Displacement of Secondary Amines on Arylbromide

To 5-mL microwave vials, secondary amines (0.164 mmol) (commercially available, known from the literature) and $K_2CO_3$ solid (37.7 mg, 0.273 mmol) were added followed by addition of 1 mL DMF solution of the mixture of 3-bromo-N,N-bis(4-methoxybenzyl)-2-(2-(4-methoxybenzyl)-2H-tetrazol-5-yl)-6-(trifluoromethyl)benzenesulfonamide and 3-bromo-N,N-bis(4-methoxybenzyl)-2-(1-(4-methoxybenzyl)-1H-tetrazol-5-yl)-6-(trifluoromethyl)benzenesulfonamide from Reference Example 24 (40 mg, 0.055 mmol). The vials were capped and heated at 140° C. with stirring for 2 hr. After the vials were cooled to room temperature, the solvent was removed in a GeneVac. Into each residue was added 500 µL of 3 N HCl and 2 mL of EtOAc. The organic layers were transferred into 2 dram vials. The organic solvent was removed in GeneVac to afford the crude intermediates which were deprotected without further purification in the subsequent step.

Step B: Removal of the Boc and p-methoxybenzyl (PMB) Protecting Group by TFA Treatment To the residues from Step A were each added TFA 0.7 mL and thioanisole (0.3 mL). The vials were sealed and stirred at room temperature. After 5 hr, the reactions were monitored by UPLC. The mixtures were concentrated in a GeneVac. The residues were dissolved in DMSO. Each crude mixture was filtered into a 96-well tray and purified with HPLC. The crude products were purified by mass triggered reverse phase HPLC to afford corresponding intermediates.

Step C: Removal of the p-methoxybenzyl (PMB) Protecting Group by TFA Treatment

To the intermediates from Step B were added TFA 0.7 mL. The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 µm, 19×100 mm; solvent: gradient range 3-45% initial to 45-100% final MeCN (0.1% TFA) in water (0.1% TFA) 50 or 70 mL/min; 8 min run time] to afford EXAMPLES 754-784.

| Ex. No. | Structure | Name | Calc'd. MW $[M + H]^+$ | LC/MS m/e $[M + H]^+$ |
|---|---|---|---|---|
| 754 | 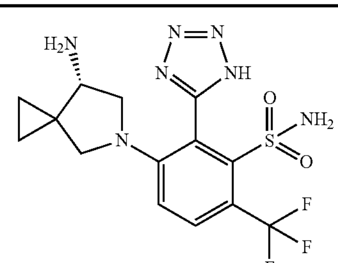 | 3-[(7S)-7-amino-5-azaspiro[2.4]hept-5-yl]-2-(1H-tetrazol-5-yl)-6-(trifluoromethyl)benzenesulfonamide | 404.11 | 404.1 |

-continued

| Ex. No. | Structure | Name | Calc'd. MW [M + H]+ | LC/MS m/e [M + H]+ |
|---|---|---|---|---|
| 755 | 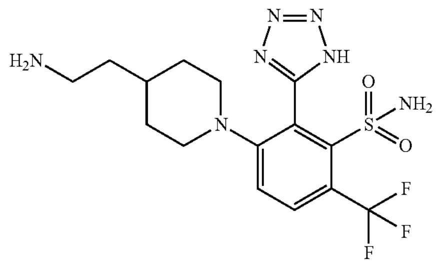 [SMILES: NCCC1CCN(c2ccc(C(F)(F)F)c(S(N)(=O)=O)c2-c2nnn[nH]2)CC1] | 3-[4-(2-aminoethyl)piperidin-1-yl]-2-(1H-tetrazol-5-yl)-6-(trifluoromethyl)benzenesulfonamide | 420.14 | 420.14 |
| 756 | 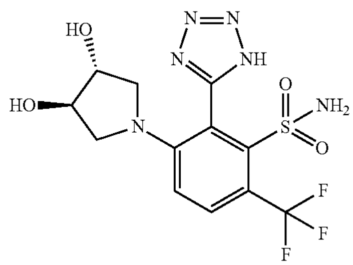 [SMILES: NS(=O)(=O)c1c(C(F)(F)F)ccc(N2C[C@@H](O)[C@H](O)C2)c1-c1nnn[nH]1] | 3-[(3R,4R)-3,4-dihydroxypyrrolidin-1-yl]-2-(1H-tetrazol-5-yl)-6-(trifluoromethyl)benzenesulfonamide | 395.07 | 395.07 |
| 757 | 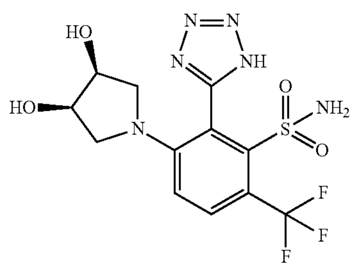 [SMILES: NS(=O)(=O)c1c(C(F)(F)F)ccc(N2C[C@@H](O)[C@@H](O)C2)c1-c1nnn[nH]1] | 3-[(3R,4S)-3,4-dihydroxypyrrolidin-1-yl]-2-(1H-tetrazol-5-yl)-6-(trifluoromethyl)benzenesulfonamide | 395.07 | 395.07 |
| 758 | 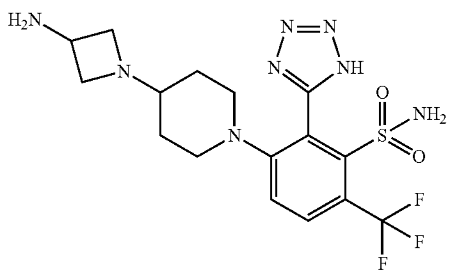 [SMILES: NC1CN(C2CCN(c3ccc(C(F)(F)F)c(S(N)(=O)=O)c3-c3nnn[nH]3)CC2)C1] | 3-[4-(3-aminoazetidin-1-yl)piperidin-1-yl]-2-(1H-tetrazol-5-yl)-6-(trifluoromethyl)benzenesulfonamide | 447.15 | 447.15 |
| 759 | 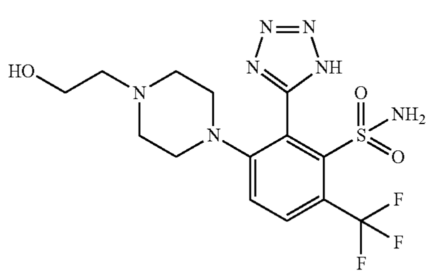 [SMILES: NS(=O)(=O)c1c(C(F)(F)F)ccc(N2CCN(CCO)CC2)c1-c1nnn[nH]1] | 3-[4-(2-hydroxyethyl)piperazin-1-yl]-2-(1H-tetrazol-5-yl)-6-(trifluoromethyl)benzenesulfonamide | 422.12 | 422.11 |

| Ex. No. | Structure | Name | Calc'd. MW [M + H]+ | LC/MS m/e [M + H]+ |
|---|---|---|---|---|
| 760 | 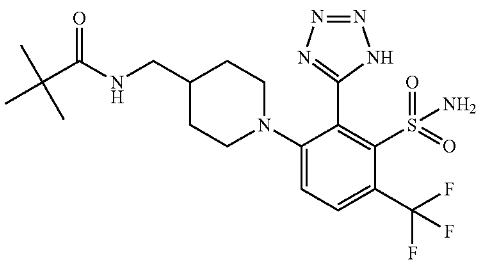 [SMILES: CC(C)(C)C(=O)NCC1CCN(c2ccc(C(F)(F)F)c(S(N)(=O)=O)c2-c2nnn[nH]2)CC1] | 2,2-dimethyl-N-({1-[3-sulfamoyl-2-(1H-tetrazol-5-yl)-4-(trifluoromethyl)phenyl]piperidin-4-yl}methyl)propanamide | 490.18 | 490.18 |
| 761 | 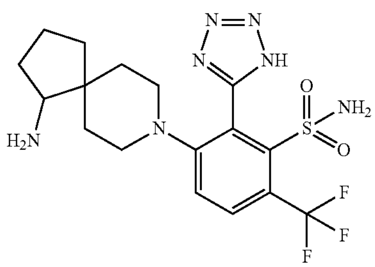 [SMILES: NC1CCCC12CCN(c1ccc(C(F)(F)F)c(S(N)(=O)=O)c1-c1nnn[nH]1)CC2] | 3-(1-amino-8-azaspiro[4.5]dec-8-yl)-2-(1H-tetrazol-5-yl)-6-(trifluoromethyl)benzenesulfonamide | 446.16 | 446.15 |
| 762 | 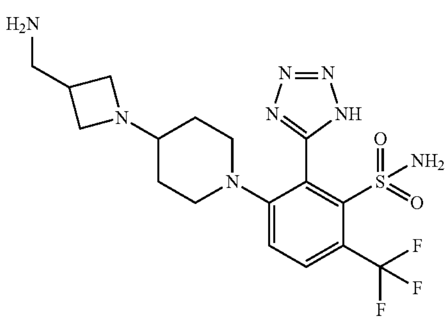 [SMILES: NCC1CN(C2CCN(c3ccc(C(F)(F)F)c(S(N)(=O)=O)c3-c3nnn[nH]3)CC2)C1] | 3-{4-[3-(aminomethyl)azetidin-1-yl]piperidin-1-yl}-2-(1H-tetrazol-5-yl)-6-(trifluoromethyl)benzenesulfonamide | 461.17 | 461.16 |
| 763 | 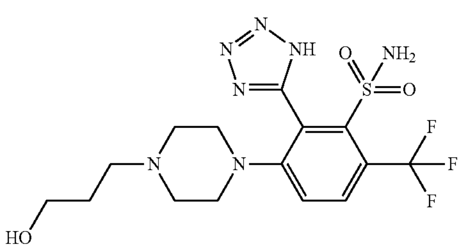 [SMILES: NS(=O)(=O)c1c(C(F)(F)F)ccc(N2CCN(CCCO)CC2)c1-c1nnn[nH]1] | 3-[4-(3-hydroxypropyl)piperazin-1-yl]-2-(1H-tetrazol-5-yl)-6-(trifluoromethyl)benzenesulfonamide | 436.14 | 436.13 |
| 764 | 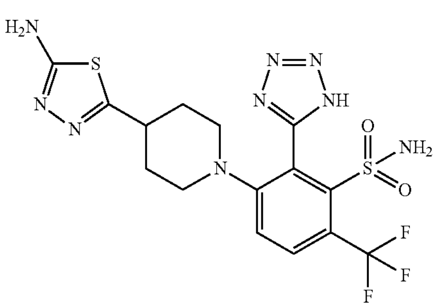 [SMILES: Nc1nnc(C2CCN(c3ccc(C(F)(F)F)c(S(N)(=O)=O)c3-c3nnn[nH]3)CC2)s1] | 3-[4-(5-amino-1,3,4-thiadiazol-2-yl)piperidin-1-yl]-2-(1H-tetrazol-5-yl)-6-(trifluoromethyl)benzenesulfonamide | 476.09 | 476.08 |

-continued

| Ex. No. | Structure | Name | Calc'd. MW [M + H]+ | LC/MS m/e [M + H]+ |
|---|---|---|---|---|
| 765 | 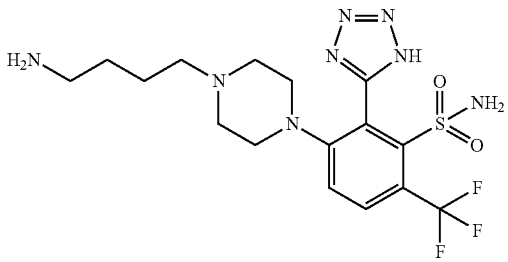 [SMILES: NCCCCN1CCN(c2ccc(C(F)(F)F)c(S(N)(=O)=O)c2-c2nnn[nH]2)CC1] | 3-[4-(4-aminobutyl)piperazin-1-yl]-2-(1H-tetrazol-5-yl)-6-(trifluoromethyl)benzenesulfonamide | 449.17 | 449.16 |
| 766 | 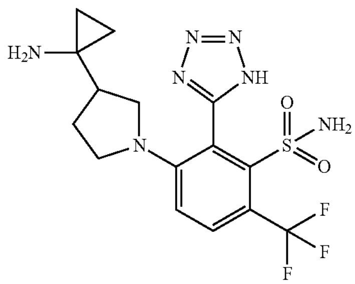 [SMILES: NC1(C2CCN(c3ccc(C(F)(F)F)c(S(N)(=O)=O)c3-c3nnn[nH]3)C2)CC1] | 3-[3-(1-aminocyclopropyl)pyrrolidin-1-yl]-2-(1H-tetrazol-5-yl)-6-(trifluoromethyl)benzenesulfonamide | 418.13 | 418.12 |
| 767 | 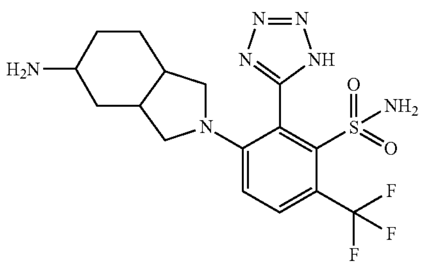 [SMILES: NC1CCC2CN(c3ccc(C(F)(F)F)c(S(N)(=O)=O)c3-c3nnn[nH]3)CC2C1] | 3-(5-aminooctahydro-2H-isoindol-2-yl)-2-(1H-tetrazol-5-yl)-6-(trifluoromethyl)benzenesulfonamide | 432.14 | 432.14 |
| 768 | 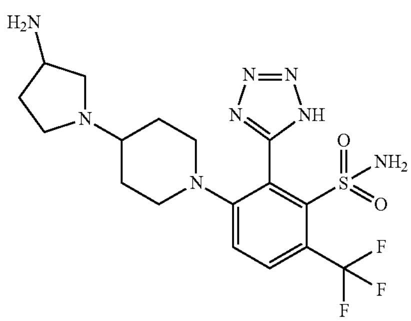 [SMILES: NC1CCN(C2CCN(c3ccc(C(F)(F)F)c(S(N)(=O)=O)c3-c3nnn[nH]3)CC2)C1] | 3-[4-(3-aminopyrrolidin-1-yl)piperidin-1-yl]-2-(1H-tetrazol-5-yl)-6-(trifluoromethyl)benzenesulfonamide | 461.17 | 461.16 |
| 769 | 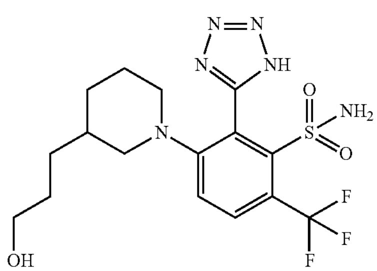 [SMILES: NS(=O)(=O)c1c(C(F)(F)F)ccc(N2CCCC(CCCO)C2)c1-c1nnn[nH]1] | 3-[3-(3-hydroxypropyl)piperidin-1-yl]-2-(1H-tetrazol-5-yl)-6-(trifluoromethyl)benzenesulfonamide | 435.14 | 435.14 |

-continued

| Ex. No. | Structure | Name | Calc'd. MW [M + H]+ | LC/MS m/e [M + H]+ |
|---|---|---|---|---|
| 770 | 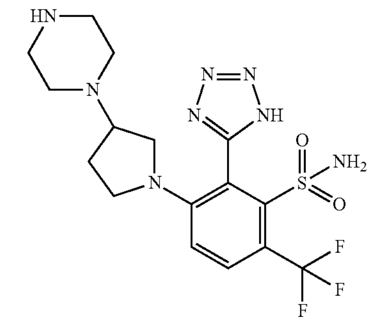 [SMILES: NS(=O)(=O)c1c(C(F)(F)F)ccc(N2CCC(N3CCNCC3)C2)c1-c1nnn[nH]1] | 3-(3-piperazin-1-ylpyrrolidin-1-yl)-2-(1H-tetrazol-5-yl)-6-(trifluoromethyl)benzenesulfonamide | 447.15 | 447.15 |
| 771 | 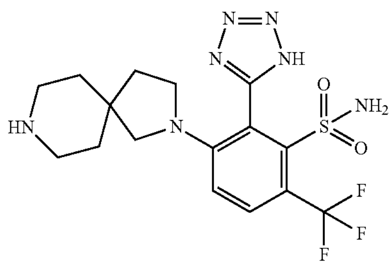 [SMILES: NS(=O)(=O)c1c(C(F)(F)F)ccc(N2CCC3(CCNCC3)C2)c1-c1nnn[nH]1] | 3-(2,8-diazaspiro[4.5]dec-2-yl)-2-(1H-tetrazol-5-yl)-6-(trifluoromethyl)benzenesulfonamide | 432.14 | 432.14 |
| 772 | 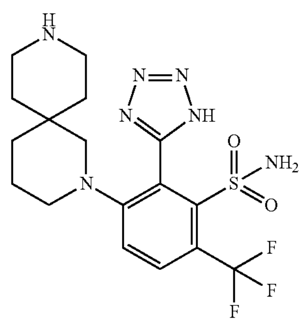 [SMILES: NS(=O)(=O)c1c(C(F)(F)F)ccc(N2CCCC3(CCNCC3)C2)c1-c1nnn[nH]1] | 3-(2,9-diazaspiro[5.5]undec-2-yl)-2-(1H-tetrazol-5-yl)-6-(trifluoromethyl)benzenesulfonamide | 446.16 | 446.15 |
| 773 | 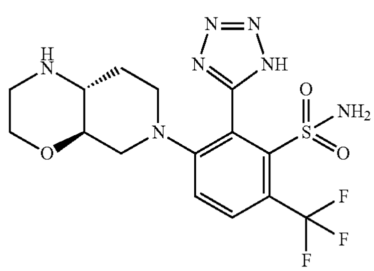 [SMILES: NS(=O)(=O)c1c(C(F)(F)F)ccc(N2CC[C@H]3NCCO[C@@H]3C2)c1-c1nnn[nH]1] | 3-[(4aR,8aR)-octahydro-6H-pyrido[3,4-b][1,4]oxazin-6-yl]-2-(1H-tetrazol-5-yl)-6-(trifluoromethyl)benzenesulfonamide | 434.12 | 434.11 |
| 774 | 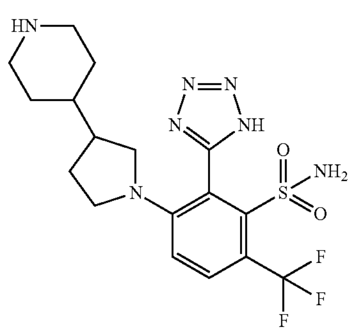 | 3-(3-piperidin-4-ylpyrrolidin-1-yl)-2-(1H-tetrazol-5-yl)-6-(trifluoromethyl)benzenesulfonamide | 446.16 | 446.15 |

| Ex. No. | Structure | Name | Calc'd. MW [M + H]⁺ | LC/MS m/e [M + H]⁺ |
|---|---|---|---|---|
| 775 | 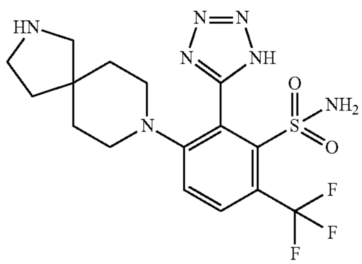 [SMILES: NS(=O)(=O)c1c(C(F)(F)F)ccc(N2CCC3(CCNC3)CC2)c1-c1nnn[nH]1] | 3-(2,8-diazaspiro[4.5]dec-8-yl)-2-(1H-tetrazol-5-yl)-6-(trifluoromethyl)benzenesulfonamide | 432.14 | 432.14 |
| 776 | 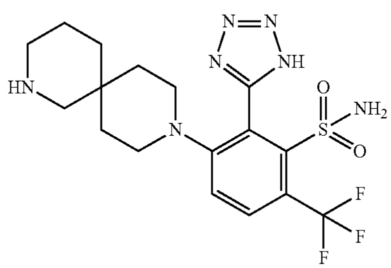 [SMILES: NS(=O)(=O)c1c(C(F)(F)F)ccc(N2CCC3(CCCNC3)CC2)c1-c1nnn[nH]1] | 3-(2,9-diazaspiro[5.5]undec-9-yl)-2-(1H-tetrazol-5-yl)-6-(trifluoromethyl)benzenesulfonamide | 446.16 | 446.15 |
| 777 | 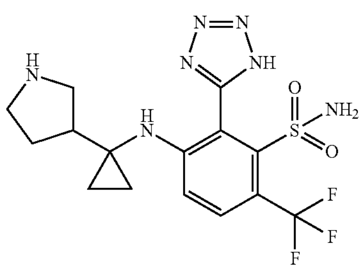 [SMILES: NS(=O)(=O)c1c(C(F)(F)F)ccc(NC2(C3CCNC3)CC2)c1-c1nnn[nH]1] | 3-[(1-pyrrolidin-3-ylcyclopropyl)amino]-2-(1H-tetrazol-5-yl)-6-(trifluoromethyl)benzenesulfonamide | 418.13 | 418.12 |
| 778 | 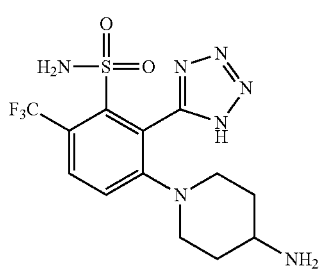 [SMILES: NC1CCN(c2ccc(C(F)(F)F)c(S(N)(=O)=O)c2-c2nnn[nH]2)CC1] | 3-(4-amino-1-piperidyl)-2-(1H-tetrazol-5-yl)-6-(trifluoromethyl)benzenesulfonamide | 392 | 392.28 |
| 779 | 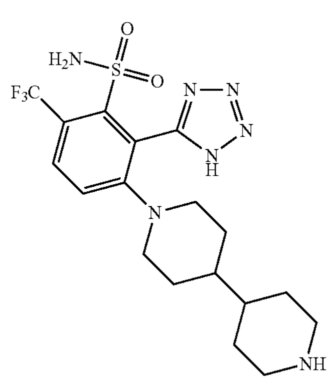 [SMILES: NS(=O)(=O)c1c(C(F)(F)F)ccc(N2CCC(C3CCNCC3)CC2)c1-c1nnn[nH]1] | 3-[4-(4-piperidyl)-1-piperidyl]-2-(1H-tetrazol-5-yl)-6-(trifluoromethyl)benzenesulfonamide | 460 | 460.24 |

| Ex. No. | Structure | Name | Calc'd. MW [M + H]⁺ | LC/MS m/e [M + H]⁺ |
|---|---|---|---|---|
| 780 | 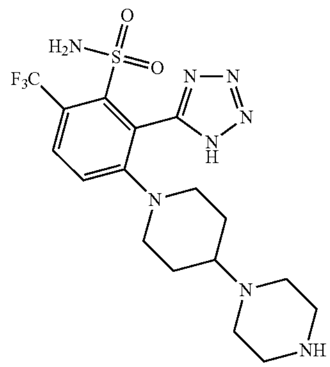 [SMILES: NS(=O)(=O)c1c(C(F)(F)F)ccc(N2CCC(N3CCNCC3)CC2)c1-c1nnn[nH]1] | 3-(4-piperazin-1-yl-1-piperidyl)-2-(1H-tetrazol-5-yl)-6-(trifluoromethyl)benzenesulfonamide | 461 | 461.43 |
| 781 | 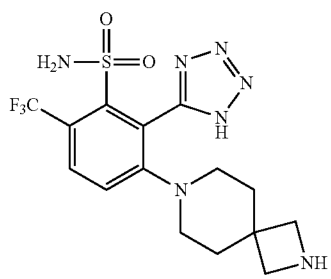 [SMILES: NS(=O)(=O)c1c(C(F)(F)F)ccc(N2CCC3(CC2)CNC3)c1-c1nnn[nH]1] | 3-(2,8-diazaspiro[3.5]nonan-8-yl)-2-(1H-tetrazol-5-yl)-6-(trifluoromethyl)benzenesulfonamide | 418 | 418.38 |
| 782 | 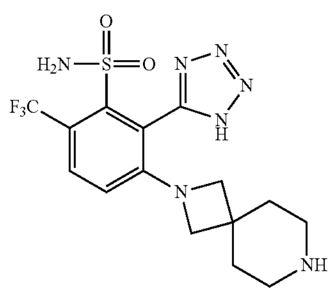 [SMILES: NS(=O)(=O)c1c(C(F)(F)F)ccc(N2CC3(CCNCC3)C2)c1-c1nnn[nH]1] | 3-(2,8-diazaspiro[3.5]nonan-2-yl)-2-(1H-tetrazol-5-yl)-6-(trifluoromethyl)benzenesulfonamide | 418 | 418.25 |
| 783 | 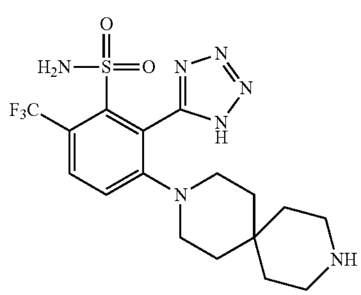 [SMILES: NS(=O)(=O)c1c(C(F)(F)F)ccc(N2CCC3(CCNCC3)CC2)c1-c1nnn[nH]1] | 3-(3,9-diazaspiro[5.5]undecan-3-yl)-2-(1H-tetrazol-5-yl)-6-(trifluoromethyl)benzenesulfonamide | 446 | 446.35 |
| 784 | 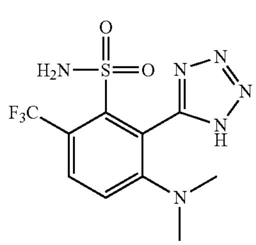 [SMILES: CN(C)c1ccc(C(F)(F)F)c(S(N)(=O)=O)c1-c1nnn[nH]1] | 3-(dimethylamino)-2-(1H-tetrazol-5-yl)-6-(trifluoromethyl)benzenesulfonamide | 337 | 337.33 |

EXAMPLES 785-799

Parallel Synthesis of N-substituted 4'-piperidin-2-(1H-tetrazol-5-yl)-[1,1'-biphenyl]-4-(trifluromethyl)-3-sulfonamides

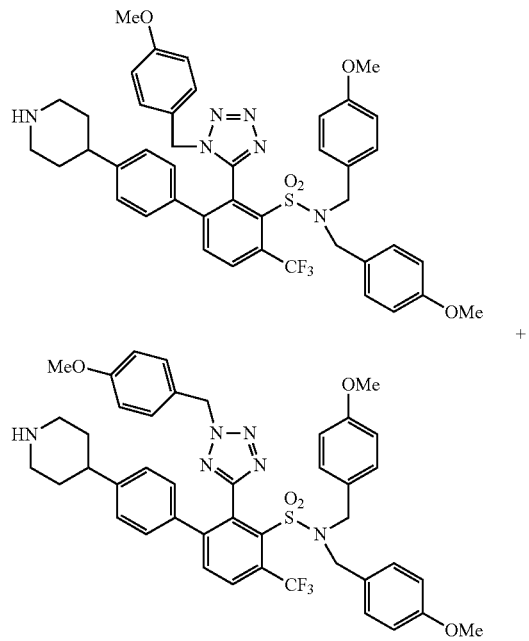

+

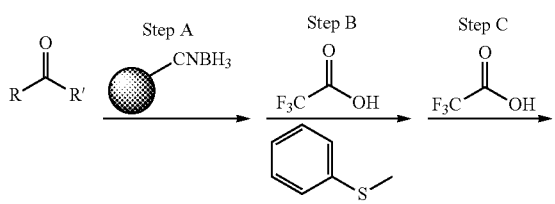

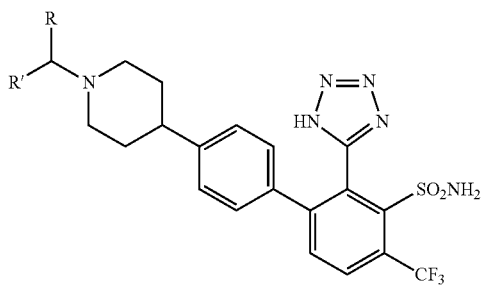

Step A: Reductive Amination of Ketones on Piperidine

To 2 dram vials, ketones (0.246 mmol) (commercially available, known from the literature) was added into 1 mL MeOH solution of the mixture of N,N-bis(4-methoxybenzyl)-2-(1-(4-methoxybenzyl)-1H-tetrazol-5-yl)-4'-(piperidin-4-yl)-4-(trifluoromethyl)-[1,1'-biphenyl]-3-sulfonamide and 3-((trans-4-aminocyclohexyl)-N,N-bis(4-methoxybenzyl)-2-(1-(4-methoxyhenzyl)-1H-tetrazol-5-yl)-4-(trifluromethyl)-[1,1'-biphenyl]-3-sulfonamide and N,N-bis(4-methoxybenzyl)-2-(2-(4-methoxybenzyl)-2H-tetrazol-5-yl)-4'-(piperidin-4-yl)-4-(trifluoromethyl)-[1,1'-biphenyl]-3-sulfonamide from Reference Example (50 mg, 0.062 mmol) followed by addition of 2 drops of acetic acid. The vials were capped and stirring at room temperature for 20 min. MP-CNBH$_3$ (120 mg, 2.4 mmol/g) was then added to each vial. The vials were capped and stirring at room temperature for 20 hr. The crude reactions were monitored by UPLC. Once reactions were finished, the mixtures were filtered and the solvent were removed in a GeneVac to afford the crude intermediates which were deprotected without further purification in the subsequent step.

Step B: Removal of the Boc and p-methoxybenzyl (PMB) Protecting Group by TFA Treatment To the residues from Step A were each added TFA 0.7 mL and thioanisole (0.3 mL). The vials were sealed and stirred at room temperature. After 5 hr, the reactions were monitored by UPLC. The mixtures were concentrated in a GeneVac. The residues were dissolved in DMSO. Each crude mixture was filtered into a 96-well tray and purified with HPLC. The crude products were purified by mass triggered reverse phase HPLC to afford corresponding intermediates.

Step C: Removal of the p-methoxybenzyl (PMB) Protecting Group by TFA Treatment

To the intermediates from Step B were added TFA 0.7 mL. The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 μm, 19×100 mm; solvent: gradient range 3-45% initial to 45-100% final MeCN (0.1% TFA) in water (0.1% TFA) 50 or 70 mL/min; 8 min run time] to afford EXAMPLES 785-799.

| Ex. No. | Structure | Name | Calc'd. MW [M + H]+ | LC/MS m/e [M + H]+ |
|---|---|---|---|---|
| 785 | 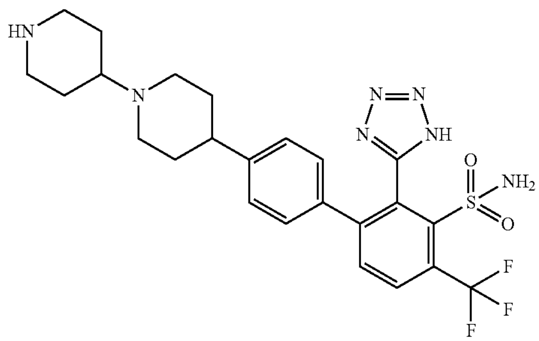 [SMILES: NS(=O)(=O)c1c(C(F)(F)F)ccc(-c2ccc(C3CCN(C4CCNCC4)CC3)cc2)c1-c1nnn[nH]1] | 4'-(1,4'-bipiperidin-4-yl)-2-(1H-tetrazol-5-yl)-4-(trifluoromethyl)biphenyl-3-sulfonamide | 536.21 | 536.2 |
| 786 | 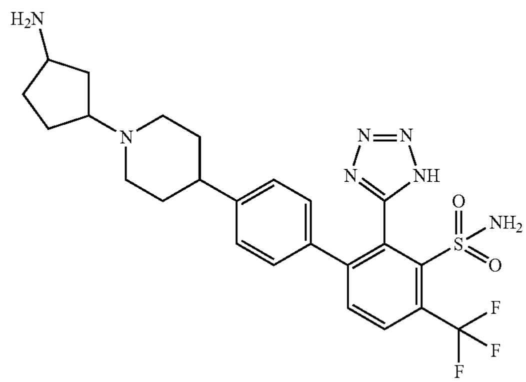 [SMILES: NC1CCC(N2CCC(c3ccc(-c4ccc(C(F)(F)F)c(S(N)(=O)=O)c4-c4nnn[nH]4)cc3)CC2)C1] | 4'-[1-(3-aminocyclopentyl)piperidin-4-yl]-2-(1H-tetrazol-5-y)-4-(trifluoromethyl)biphenyl-3-sulfonamide | 536.21 | 536.2 |
| 787 | 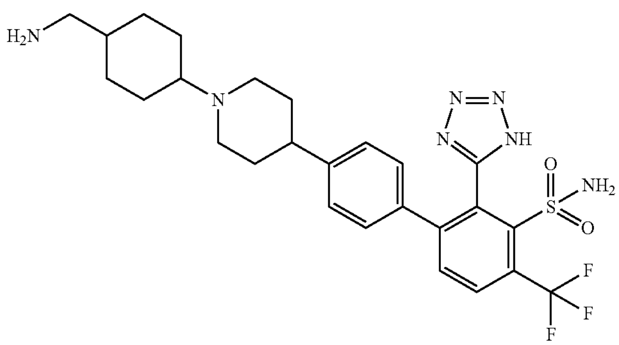 [SMILES: NCC1CCC(N2CCC(c3ccc(-c4ccc(C(F)(F)F)c(S(N)(=O)=O)c4-c4nnn[nH]4)cc3)CC2)CC1] | 4'-{1-[4-(aminomethyl)cyclohexyl]piperidin-4-yl}-2-(1H-tetrazol-5-yl)-4-(trifluoromethyl)biphenyl-3-sulfonamide | 564.24 | 564.23 |
| 788 | 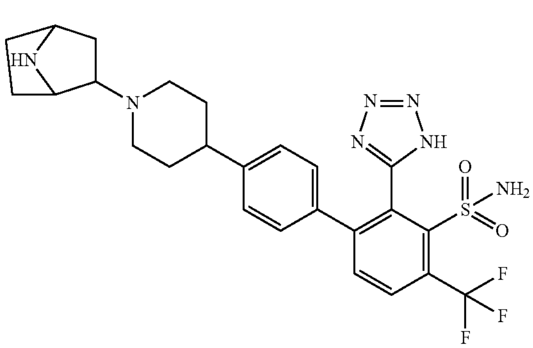 [SMILES: NS(=O)(=O)c1c(C(F)(F)F)ccc(-c2ccc(C3CCN(C4CC5CCC4N5)CC3)cc2)c1-c1nnn[nH]1] | 4'-[1-(7-azabicyclo[2.2.1]hept-2-yl)piperidin-4-yl]-2-(1H-tetrazol-5-yl)-4-(trifluoromethyl)biphenyl-3-sulfonamide | 548.21 | 548.2 |

-continued

| Ex. No. | Structure | Name | Calc'd. MW [M + H]+ | LC/MS m/e [M + H]+ |
|---|---|---|---|---|
| 789 | 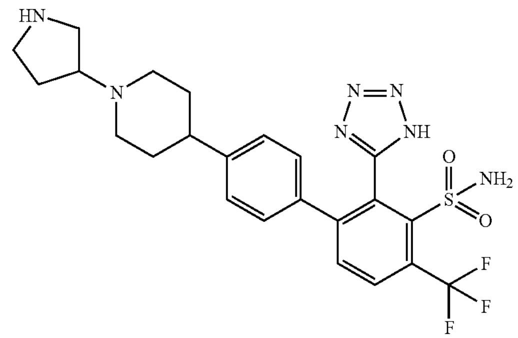 [SMILES: NS(=O)(=O)c1c(C(F)(F)F)ccc(-c2ccc(C3CCN(C4CCNC4)CC3)cc2)c1-c1nnn[nH]1] | 4'-(1-pyrrolidin-3-ylpiperidin-4-yl)-2-(1H-tetrazol-5-yl)-4-(trifluoromethyl)biphenyl-3-sulfonamide | 522.19 | 522.18 |
| 790 | 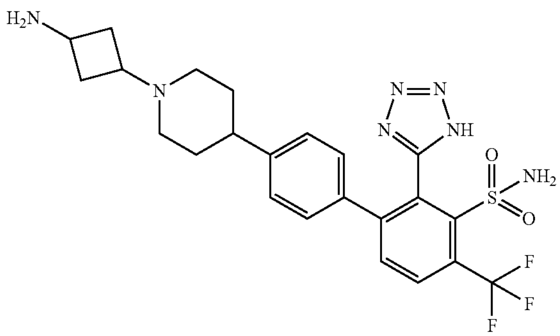 [SMILES: NC1CC(N2CCC(c3ccc(-c4ccc(C(F)(F)F)c(S(N)(=O)=O)c4-c4nnn[nH]4)cc3)CC2)C1] | 4'-[1-(3-aminocyclobutyl)piperidin-4-yl]-2-(1H-tetrazol-5-yl)-4-(trifluoromethyl)biphenyl-3-sulfonamide | 522.19 | 522.18 |
| 791 | 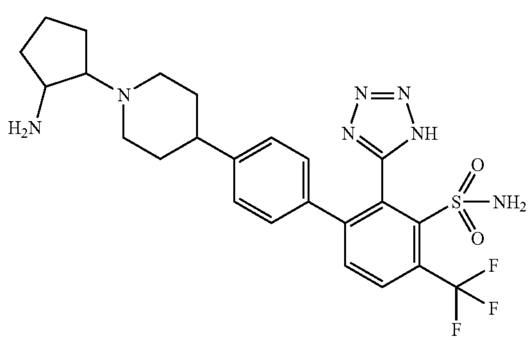 [SMILES: NC1CCCC1N1CCC(c2ccc(-c3ccc(C(F)(F)F)c(S(N)(=O)=O)c3-c3nnn[nH]3)cc2)CC1] | 4'-[1-(2-aminocyclopentyl)piperidin-4-yl]-2-(1H-tetrazol-5-yl)-4-(trifluoromethyl)biphenyl-3-sulfonamide | 536.21 | 536.2 |
| 792 | 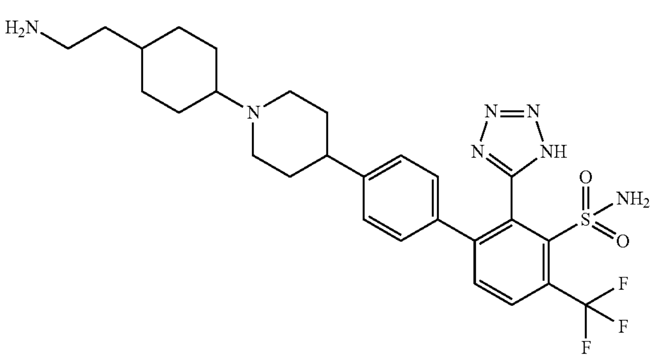 [SMILES: NCCC1CCC(N2CCC(c3ccc(-c4ccc(C(F)(F)F)c(S(N)(=O)=O)c4-c4nnn[nH]4)cc3)CC2)CC1] | 4'-{1-[4-(2-aminoethyl)cyclohexyl]piperidin-4-yl}-2-(1H-tetrazol-5-yl)-4-(trifluoromethyl)biphenyl-3-sulfonamide | 578.25 | 578.24 |

| Ex. No. | Structure | Name | Calc'd. MW [M + H]+ | LC/MS m/e [M + H]+ |
|---|---|---|---|---|
| 793 | 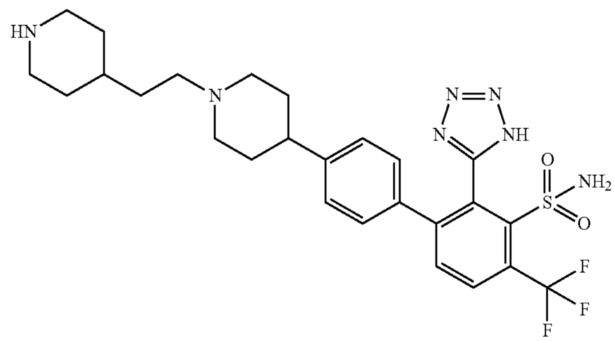 [SMILES: NS(=O)(=O)c1c(C(F)(F)F)ccc(-c2ccc(C3CCN(CCC4CCNCC4)CC3)cc2)c1-c1nnn[nH]1] | 4'-[1-(2-piperidin-4-ylethyl)piperidin-4-yl]-2-(1H-tetrazol-5-yl)-4-(trifluoromethyl)biphenyl-3-sulfonamide | 564.24 | 564.23 |
| 794 | 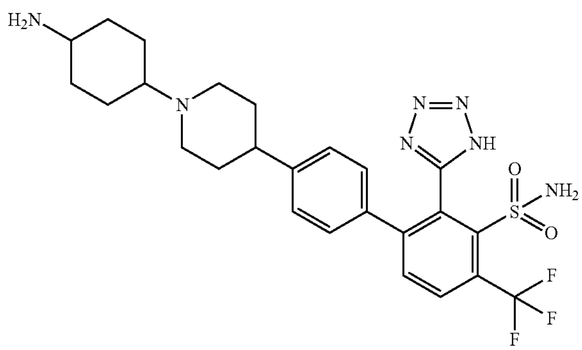 [SMILES: NC1CCC(N2CCC(c3ccc(-c4ccc(C(F)(F)F)c(S(N)(=O)=O)c4-c4nnn[nH]4)cc3)CC2)CC1] | 4'-[1-(4-aminocyclohexyl)piperidin-4-yl]-2-(1H-tetrazol-5-yl)-4-(trifluoromethyl)biphenyl-3-sulfonamide | 550.22 | 550.21 |
| 795 | 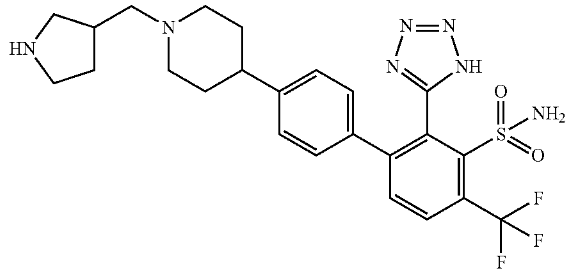 [SMILES: NS(=O)(=O)c1c(C(F)(F)F)ccc(-c2ccc(C3CCN(CC4CCNC4)CC3)cc2)c1-c1nnn[nH]1] | 4'-[1-(pyrrolidin-3-ylmethyl)piperidin-4-yl]-2-(1H-tetrazol-5-yl)-4-(trifluoromethyl)biphenyl-3-sulfonamide | 536.21 | 536.2 |
| 796 | 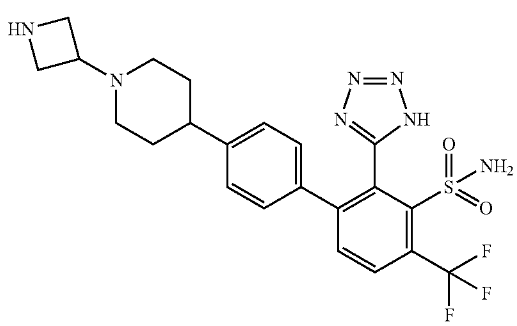 [SMILES: NS(=O)(=O)c1c(C(F)(F)F)ccc(-c2ccc(C3CCN(C4CNC4)CC3)cc2)c1-c1nnn[nH]1] | 4'-(1-azetidin-3-ylpiperidin-4-yl)-2-(1H-tetrazol-5-yl)-4-(trifluoromethyl)biphenyl-3-sulfonamide | 508.17 | 508.16 |

-continued

| Ex. No. | Structure | Name | Calc'd. MW [M + H]+ | LC/MS m/e [M + H]+ |
|---|---|---|---|---|
| 797 | 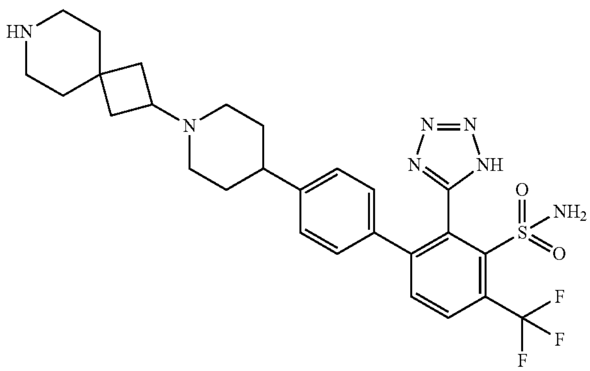 [SMILES: NS(=O)(=O)c1c(C(F)(F)F)ccc(-c2ccc(C3CCN(C4CC5(CCNCC5)C4)CC3)cc2)c1-c1nnn[nH]1] | 4'-[1-(7-azaspiro[3.5]non-2-yl)piperidin-4-yl]-2-(1H-tetrazol-5-yl)-4-(trifluoromethyl)biphenyl-3-sulfonamide | 576.24 | 576.23 |
| 798 | 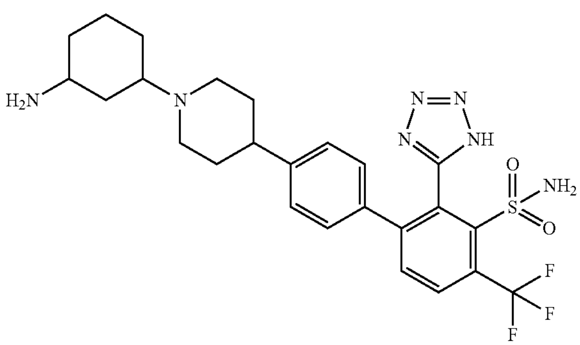 [SMILES: NC1CCCC(N2CCC(c3ccc(-c4ccc(C(F)(F)F)c(S(N)(=O)=O)c4-c4nnn[nH]4)cc3)CC2)C1] | 4'-[1-(3-aminocyclohexyl)piperidin-4-yl]-2-(1H-tetrazol-5-yl)-4-(trifluoromethyl)biphenyl-3-sulfonamide | 550.22 | 550.21 |
| 799 | 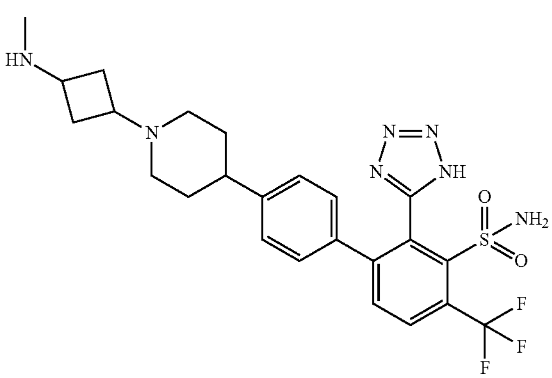 [SMILES: CNC1CC(N2CCC(c3ccc(-c4ccc(C(F)(F)F)c(S(N)(=O)=O)c4-c4nnn[nH]4)cc3)CC2)C1] | 4'-{1-[3-(methylamino)cyclobutyl]piperidin-4-yl}-2-(1H-tetrazol-5-yl)-4-(trifluoromethyl)biphenyl-3-sulfonamide | 536.21 | 536.2 |

EXAMPLES 800-818

Parallel Synthesis of 4'-(1-substituted-azetidin-3-yl)-2-(1H-tetrazol-5-yl)-4-(trifluoromethyl)biphenyl-3-sulfonamides

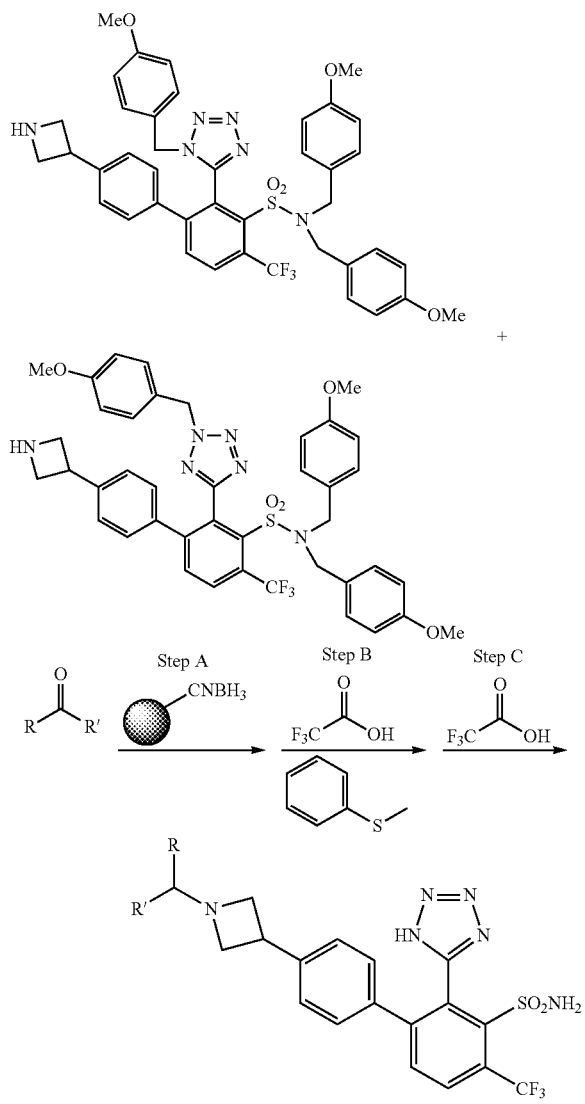

Step A: Reductive Amination of Ketones on Azetidine

To 2 dram vials, ketones (0.255 mmol) (commercially available, known from the literature) was added into 1 mL MeOH solution of the mixture of 4'-(azetidin-3-yl)-N,N-bis(4-methoxybenzyl)-2-(1-(4-methoxybenzyl)-1H-tetrazol-5-yl)-4-(trifluoromethyl)-[1,1'-biphenyl]-3-sulfonamide and 4'-(azetidin-3-yl)-N,N-bis(4-methoxybenzyl)-2-(2-(4-methoxybenzyl)-2H-tetrazol-5-yl)-4-(trifluoromethyl)-[1,1'-biphenyl]-3-sulfonamide from Example 433, prior to removal of the para-methoxybenzyl protective groups (50 mg, 0.064 mmol) followed by addition of 2 drops of acetic acid. The vials were capped and stirring at room temperature for 20 min. MP-CNBH$_3$ (120 mg, 2.4 mmol/g) was then added to each vial. The vials were capped and stirring at room temperature for 20 hr. The crude reactions were monitored by UPLC. Once the reaction was finished, the mixtures were filtered and the solvent were removed in a GeneVac to afford the crude intermediates which were deprotected without further purification in the subsequent step.

Step B: Removal of the Boc and p-methoxybenzyl (PMB) Protecting Group by TFA Treatment The residues from Step A were each added TFA 0.7 mL alone with thioanilsole (0.3 mL). The vials were sealed and stirred at room temperature. After 5 hr, the reactions were monitored by UPLC. The mixtures were concentrated in a GeneVac. The residues were dissolved in DMSO. Each crude mixture was filtered into a 96-well tray and purified with HPLC. The crude products were purified by mass triggered reverse phase HPLC to afford corresponding intermediates.

Step C: Removal of the p-methoxybenzyl (PMB) Protecting Group by TFA Treatment To the intermediates from Step B was added TFA 0.7 mL. The vials were sealed and heated at 55° C. under stirring. The pressure was released periodically by unscrewing the cap. After 5 hr, the reactions were monitored by UPLC. The mixtures were cooled to room temperature and filtered through filters. The filtrates were concentrated in a GeneVac. The residues were dissolved in DMSO. Each crude mixture was filtered into a 96-well tray and purified with HPLC. The crude products were purified by mass triggered reverse phase HPLC using the following conditions: [column: Waters XBridge C18, or Waters Sunfire C18, 5 µm, 19×100 mm; solvent: gradient range 3-45% initial to 45-100% final MeCN (0.1% TFA) in water (0.1% TFA) 50 or 70 mL/min; 8 min run time] to afford EXAMPLES 800-818.

| Ex. No. | Structure | Name | Calc'd. MW [M + H]$^+$ | LC/MS m/e [M + H]$^+$ |
|---|---|---|---|---|
| 800 | 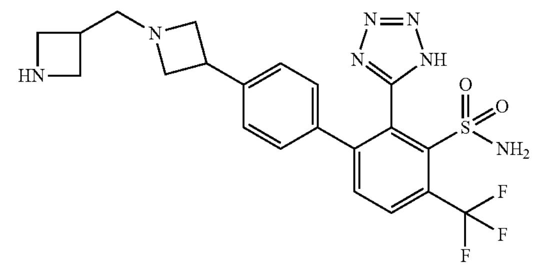 [SMILES: NS(=O)(=O)c1c(C(F)(F)F)ccc(-c2ccc(C3CN(CC4CNC4)C3)cc2)c1-c1nnn[nH]1] | 4'-[1-(azetidin-3-ylmethyl)azetidin-3-yl]-2-(1H-tetrazol-5-yl)-4-(trifluoromethyl)biphenyl-3-sulfonamide | 494.16 | 494.15 |

-continued

| Ex. No. | Structure | Name | Calc'd. MW [M + H]⁺ | LC/MS m/e [M + H]⁺ |
|---|---|---|---|---|
| 801 | 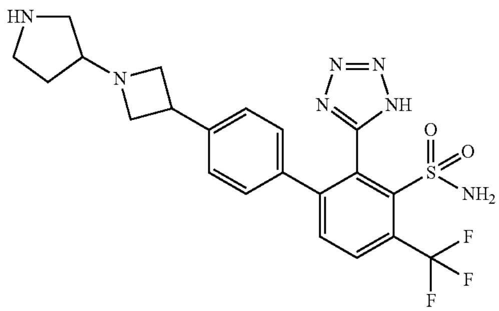 [SMILES: NS(=O)(=O)c1c(C(F)(F)F)ccc(-c2ccc(C3CN(C4CCNC4)C3)cc2)c1-c1nnn[nH]1] | 4'-(1-pyrrolidin-3-ylazetidin-3-yl)-2-(1H-tetrazol-5-yl)-4-(trifluoromethyl)biphenyl-3-sulfonamide | 494.16 | 494.15 |
| 802 | 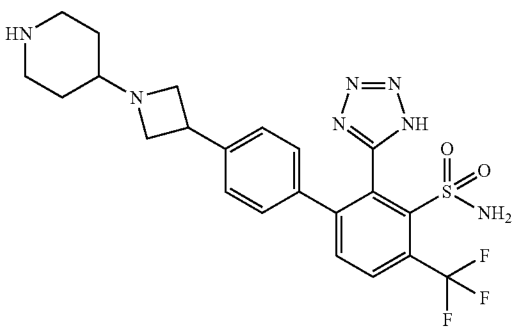 [SMILES: NS(=O)(=O)c1c(C(F)(F)F)ccc(-c2ccc(C3CN(C4CCNCC4)C3)cc2)c1-c1nnn[nH]1] | 4'-(1-piperidin-4-ylazetidin-3-yl)-2-(1H-tetrazol-5-yl)-4-(trifluoromethyl)biphenyl-3-sulfonamide | 508.17 | 508.17 |
| 803 | 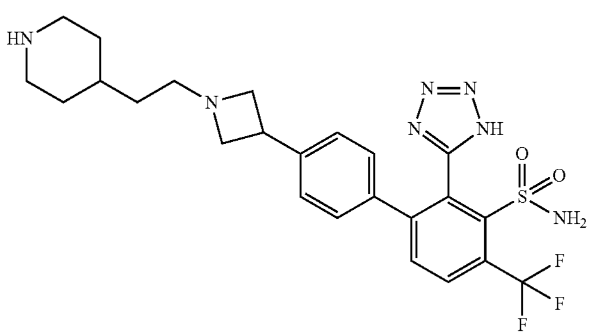 [SMILES: NS(=O)(=O)c1c(C(F)(F)F)ccc(-c2ccc(C3CN(CCC4CCNCC4)C3)cc2)c1-c1nnn[nH]1] | 4'-[1-(2-piperidin-4-ylethyl)azetidin-3-yl]-2-(1H-tetrazol-5-yl)-4-(trifluoromethyl)biphenyl-3-sulfonamide | 536.21 | 536.2 |
| 804 | 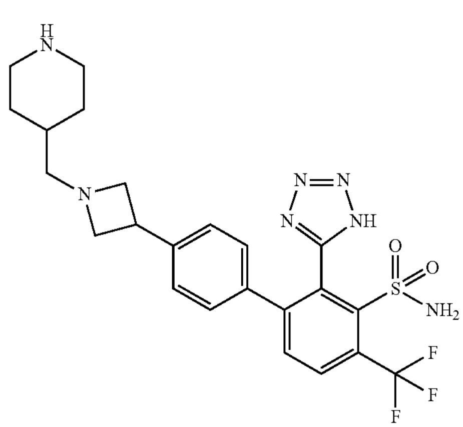 [SMILES: NS(=O)(=O)c1c(C(F)(F)F)ccc(-c2ccc(C3CN(CC4CCNCC4)C3)cc2)c1-c1nnn[nH]1] | 4'-[1-(piperidin-4-ylmethyl)azetidin-3-yl]-2-(1H-tetrazol-5-yl)-4-(trifluoromethyl)biphenyl-3-sulfonamide | 522.19 | 522.18 |

-continued

| Ex. No. | Structure | Name | Calc'd. MW [M + H]⁺ | LC/MS m/e [M + H]⁺ |
|---|---|---|---|---|
| 805 | 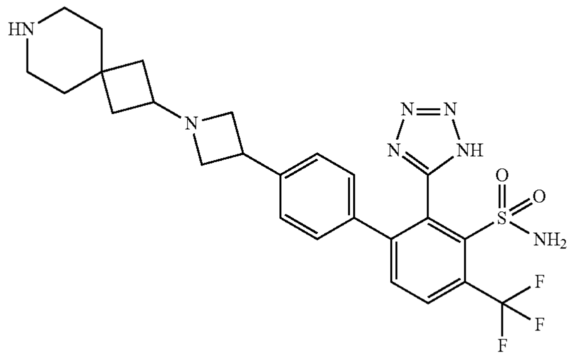 [SMILES: NS(=O)(=O)c1c(C(F)(F)F)ccc(-c2ccc(C3CN(C4CC5(CCNCC5)C4)C3)cc2)c1-c1nnn[nH]1] | 4'-[1-(7-azaspiro[3.5]non-2-yl)azetidin-3-yl]-2-(1H-tetrazol-5-yl)-4-(trifluoromethyl)biphenyl-3-sulfonamide | 548.21 | 548.2 |
| 806 | 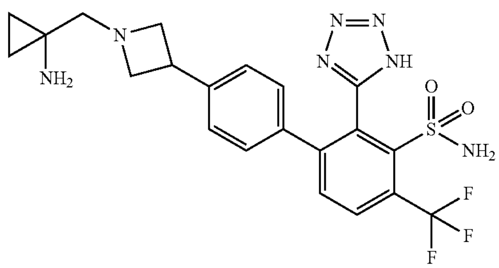 [SMILES: NC1(CN2CC(c3ccc(-c4ccc(C(F)(F)F)c(S(N)(=O)=O)c4-c4nnn[nH]4)cc3)C2)CC1] | 4'-{1-[(1-aminocyclopropyl)methyl]azetidin-3-yl}-2-(1H-tetrazol-5-yl)-4-(trifluoromethyl)biphenyl-3-sulfonamide | 494.16 | 494.15 |
| 807 | 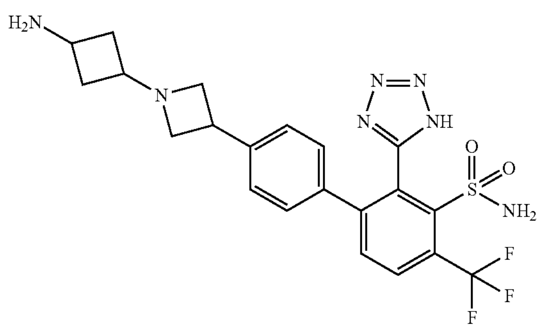 [SMILES: NC1CC(N2CC(c3ccc(-c4ccc(C(F)(F)F)c(S(N)(=O)=O)c4-c4nnn[nH]4)cc3)C2)C1] | 4'-[1-(3-aminocyclobutyl)azetidin-3-yl]-2-(1H-tetrazol-5-yl)-4-(trifluuromethyl)biphenyl-3-sulfonamide | 494.16 | 494.15 |
| 808 | 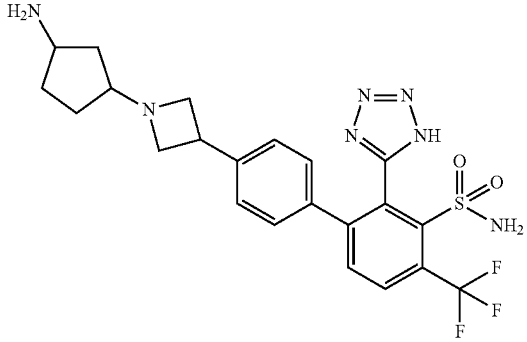 [SMILES: NC1CCC(N2CC(c3ccc(-c4ccc(C(F)(F)F)c(S(N)(=O)=O)c4-c4nnn[nH]4)cc3)C2)C1] | 4'-[1-(3-aminocyclopentyl)azetidin-3-yl]-2-(1H-tetrazol-5-yl)-4-(trifluoromethyl)biphenyl-3-sulfonamide | 508.17 | 508.17 |

-continued

| Ex. No. | Structure | Name | Calc'd. MW [M + H]+ | LC/MS m/e [M + H]+ |
|---|---|---|---|---|
| 809 | 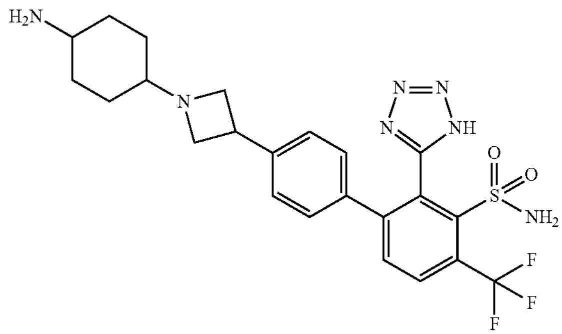 [SMILES: NC1CCC(N2CC(c3ccc(-c4ccc(C(F)(F)F)c(S(N)(=O)=O)c4-c4nnn[nH]4)cc3)C2)CC1] | 4'-[1-(4-aminocyclohexyl)azetidin-3-yl]-2-(1H-tetrazol-5-yl)-4-(trifluoromethyl)biphenyl-3-sulfonamide | 522.19 | 522.18 |
| 810 | 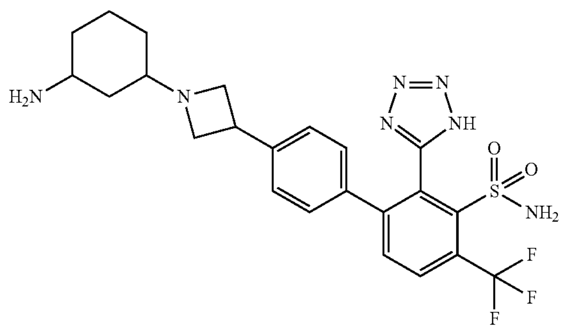 [SMILES: NC1CCCC(N2CC(c3ccc(-c4ccc(C(F)(F)F)c(S(N)(=O)=O)c4-c4nnn[nH]4)cc3)C2)C1] | 4'-[1-(3-aminocyclohexyl)azetidin-3-yl]-2-(1H-tetrazol-5-yl)-4-(trifluoromethyl)biphenyl-3-sulfonamide | 522.19 | 522.18 |
| 811 | 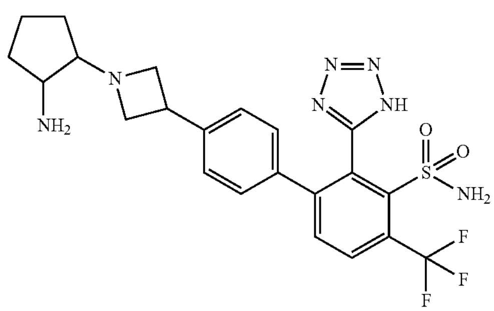 [SMILES: NC1CCCC1N1CC(c2ccc(-c3ccc(C(F)(F)F)c(S(N)(=O)=O)c3-c3nnn[nH]3)cc2)C1] | 4'-[1-(2-aminocyclopentyl)azetidin-3-yl]-2-(1H-tetrazol-5-yl)-4-(trifluoromethyl)biphenyl-3-sulfonamide | 508.17 | 508.17 |
| 812 | 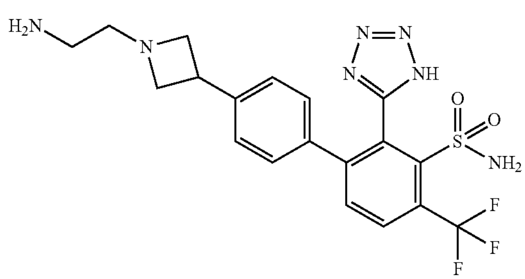 [SMILES: NCCN1CC(c2ccc(-c3ccc(C(F)(F)F)c(S(N)(=O)=O)c3-c3nnn[nH]3)cc2)C1] | 4'-[1-(2-aminoethyl)azetidin-3-yl]-2-(1H-tetrazol-5-yl)-4-(trifluoromethyl)biphenyl-3-sulfonamide | 468.14 | 468.14 |

-continued

| Ex. No. | Structure | Name | Calc'd. MW [M + H]+ | LC/MS m/e [M + H]+ |
|---|---|---|---|---|
| 813 | 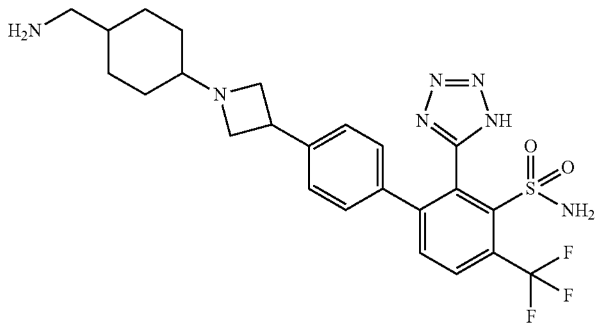 [SMILES: NCC1CCC(N2CC(c3ccc(-c4ccc(C(F)(F)F)c(S(N)(=O)=O)c4-c4nnn[nH]4)cc3)C2)CC1] | 4'-{1-[4-(aminomethyl)cyclohexyl]azetidin-3-yl}-2-(1H-tetrazol-5-yl)-4-(trifluoromethyl)biphenyl-3-sulfonamide | 536.21 | 536.2 |
| 814 | 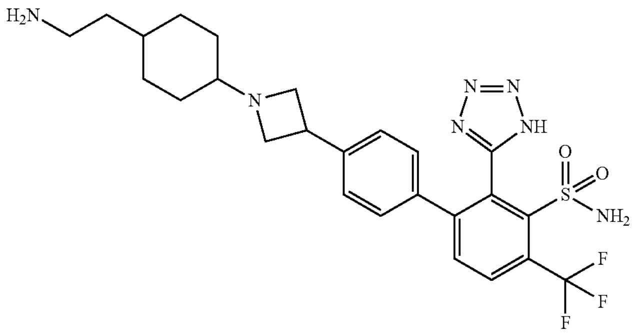 [SMILES: NCCC1CCC(N2CC(c3ccc(-c4ccc(C(F)(F)F)c(S(N)(=O)=O)c4-c4nnn[nH]4)cc3)C2)CC1] | 4'-{1-[4-(2-aminoethyl)cyclohexyl]azetidin-3-yl}-2-(1H-tetrazol-5-yl)-4-(trifluoromethyl)biphenyl-3-sulfonamide | 550.22 | 550.21 |
| 815 | 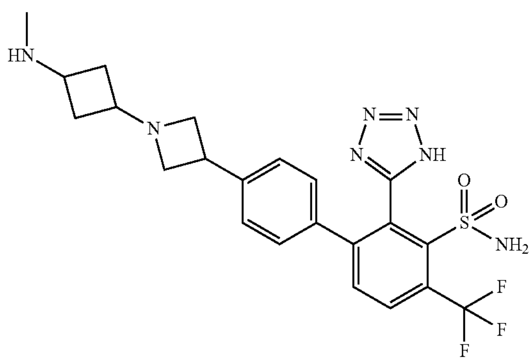 [SMILES: CNC1CC(N2CC(c3ccc(-c4ccc(C(F)(F)F)c(S(N)(=O)=O)c4-c4nnn[nH]4)cc3)C2)C1] | 4'-{1-[3-(methylamino)cyclobutyl]azetidin-3-yl}-2-(1H-tetrazol-5-yl)-4-(trifluoromethyl)biphenyl-3-sulfonamide | 508.17 | 508.17 |
| 816 | 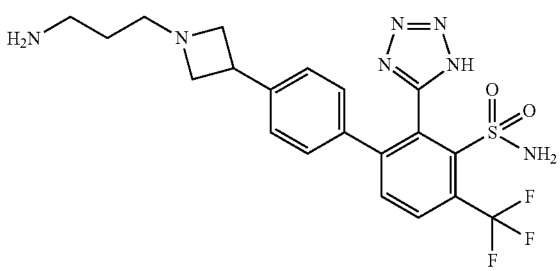 [SMILES: NCCCN1CC(c2ccc(-c3ccc(C(F)(F)F)c(S(N)(=O)=O)c3-c3nnn[nH]3)cc2)C1] | 4'-[1-(3-aminopropyl)azetidin-3-yl]-2-(1H-tetrazol-5-yl)-4-(trifluoromethyl)biphenyl-3-sulfonamide | 482.16 | 482.15 |
| 817 | 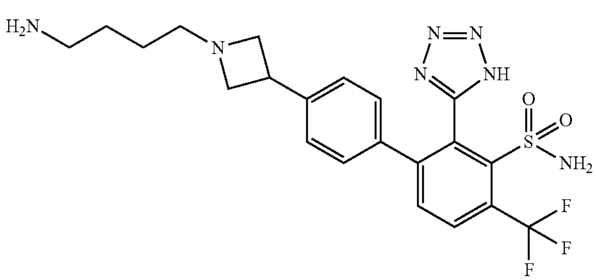 [SMILES: NCCCCN1CC(c2ccc(-c3ccc(C(F)(F)F)c(S(N)(=O)=O)c3-c3nnn[nH]3)cc2)C1] | 4'-[1-(4-aminobutyl)azetidin-3-yl]-2-(1H-tetrazol-5-yl)-4-(trifluoromethyl)biphenyl-3-sulfonamide | 496.17 | 496.17 |

| Ex. No. | Structure | Name | Calc'd. MW [M + H]+ | LC/MS m/e [M + H]+ |
|---|---|---|---|---|
| 818 | 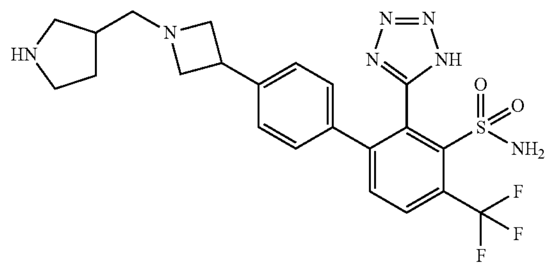 [SMILES: NS(=O)(=O)c1c(C(F)(F)F)ccc(-c2ccc(C3CN(CC4CCNC4)C3)cc2)c1-c1nnn[nH]1] | 4'-[1-(pyrrolidin-3-ylmethyl)azetidin-3-yl]-2-(1H-tetrazol-5-yl)-4-(trifluoromethyl)biphenyl-3-sulfonamide | 508.17 | 508.17 |

The following General Methods were used in making EXAMPLES 819-840

Method 1: General Coupling Procedure Between an Aryl Halide Core Substrate and an Aryl Boronic Ester or Acid

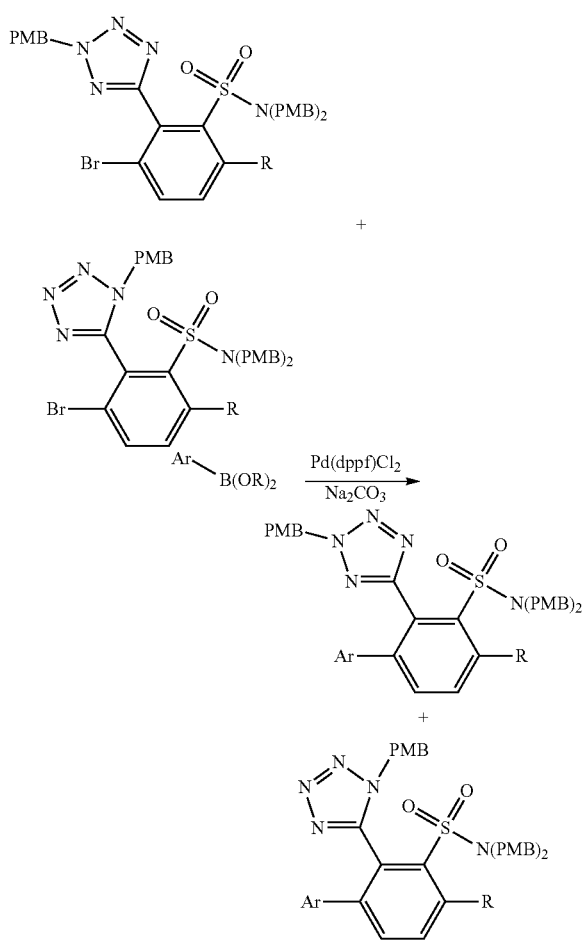

Method 2: General Coupling Procedure Between an Aryl Boronic Ester or Acid Core Substrate and an Aryl Halide

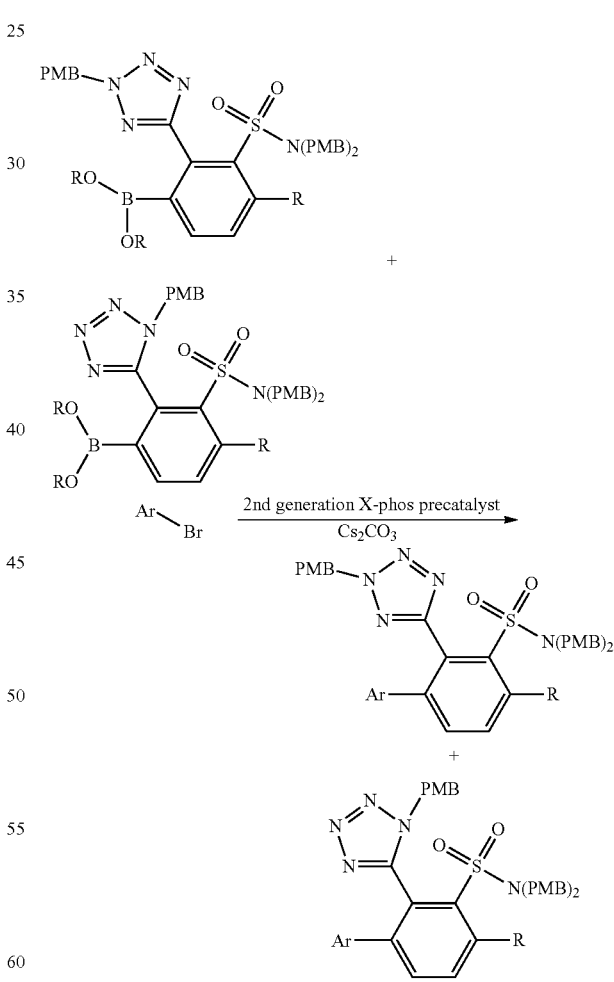

The aryl halide core substrate (1.0 mmol), an aryl boronic ester or acid (1.2 mmol), sodium carbonate (2.5 mmol) and Pd(dppf)Cl$_2$ (0.1 mmol) were placed in a reaction vessel. To the reaction vessel was added 1,4-Dioxane (6 ml) and Water (1.5 ml). N$_2$ was bubbled through for 10 min. Then the reaction was heated at 80° C. overnight. The reaction mixture was diluted with water (60 ml) and extracted with EtOAc (2×50 ml). The organic phase was concentrated by reduced pressure. The residue was purified by column chromatography to give the product.

To a reaction flask was added an aryl boronic ester (0.3 mmol) core substrate, an aryl halide compound (0.6 mmol), Cs$_2$CO$_3$ (0.9 mmol) and second generation xphos precatalyst (0.06 mmol). Dioxane (2 ml) and water (0.5 ml) were added to this flask. N$_2$ was bubbled through for 10 min. This mixture was then heated at 75° C. overnight. The mixture was cooled, saturated NaHCO₃ was added to the reaction mixture which was then extracted with EtOAc (2×60 ml). The combined organic phase was concentrated under reduced pressure. The residue was purified by column chromatography on silica gel to give the product.

Method 3: General Procedure for Remove Boc Protecting Group on Nitrogen

This method is used when in addition to PMB protection on tetrazole and sulfonamide there is also Boc protection on an amino group present in the intermediate.

The N-Boc protected starting material (0.7 mmol) was dissolved in DCM (4 ml). TFA (8 ml) was added at room temperature and the mixture was stirred at room temperature for 2 hr. The reaction mixture was concentrated to afford the crude Boc fall off product. The crude material was placed on the vacuum for 3 hours and used as is.

Method 4: General Procedure for Remove N-PMB Protecting Group on Nitrogen

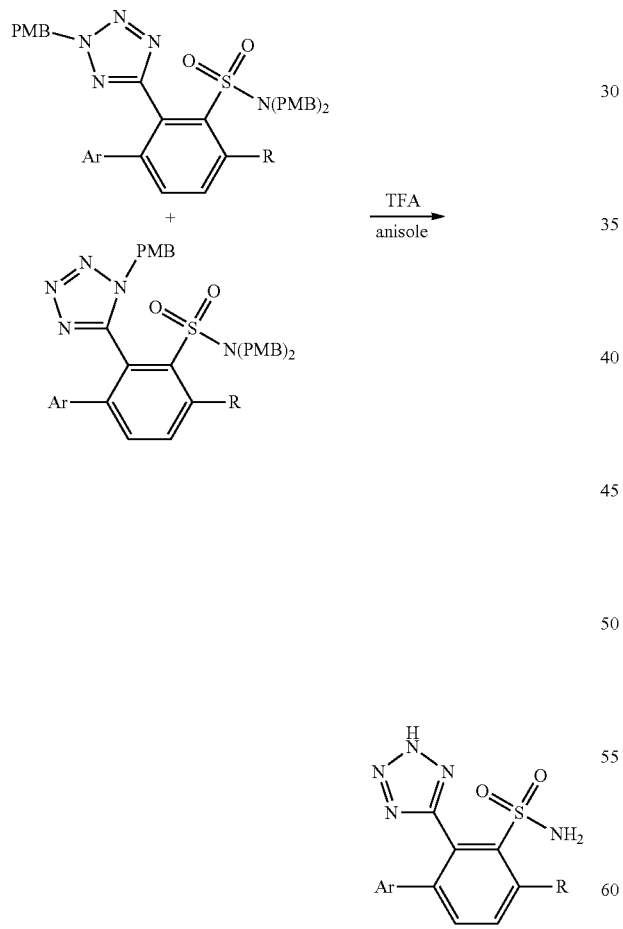

The N-PMB protected starting material (0.16 mmol) was dissolved in 3 ml of TFA, heated to 80° C. for 2 hr. The reaction mixture was concentrated. The residue was purified by Gilson reverse phase HPLC to give the pure product.

Method 5: General Reaction Procedure Between an Aryl Halide Core Substrate and an Amine

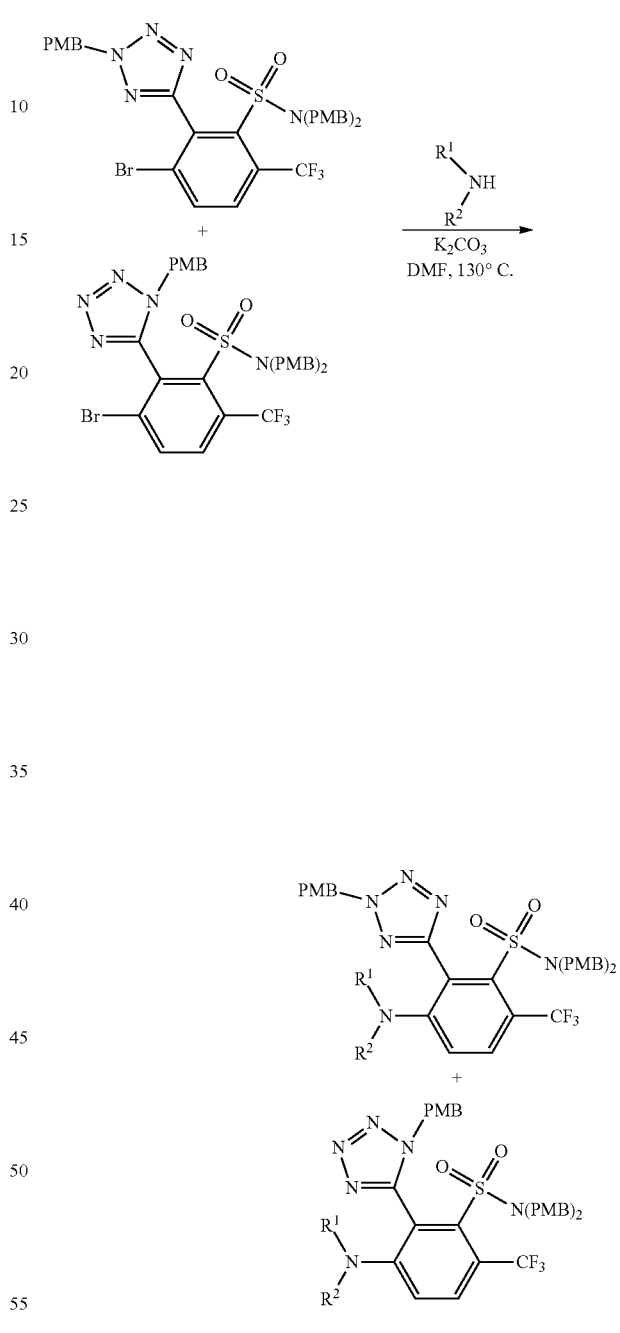

To an aryl halide core (210 mg, 0.287 mmol) in DMF (3 ml), were added potassium carbonate (238 mg, 1.720 mmol) and an amine (115 mg, 0.573 mmol) in a microwave vial. The mixture was stirred in a microwave reactor at 130° C. for 1 hour. The mixtures were diluted with water (25 ml), extracted with EtOAc (2×25 ml). The combined organic phase was dried (MgSO₄), concentrated under reduced pressure. The residue was purified by column chromatography on silica gel, eluting with EtOAc/isohexane to give the product.

EXAMPLE 819 and 820

3-((1s,4s)-4-aminocyclohexyl)-2-(1H-tetrazol-5-yl)-6-(trifluoromethyl)benzenesulfonamide and 3-((1r,4r)-4-aminocyclohexyl)-2-(1H-tetrazol-5-yl)-6-(trifluoromethyl)benzenesulfonamide

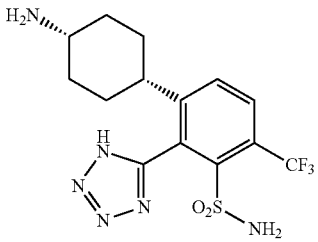

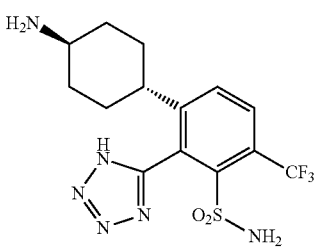

Step A: tert-butyl (3'-(N,N-bis(4-methoxybenzyl)sulfamoyl)-2'-(1-(4-methoxybenzyl)-1H-tetrazol-5-yl)-4'-(trifluoromethyl)-2,3,4,5-tetrahydro-[1,1'-biphenyl]-4-yl)carbamate Starting from 3-bromo-N,N-bis(4-methoxybenzyl)-2-(1-(4-methoxybenzyl)-1H-tetrazol-5-yl)-6-(trifluoromethyl)benzenesulfonamide and tert-butyl (4-(4,4,5,5-tetramethyl-1,3,2-dioxaborolan-2-yl)cyclohex-3-en-1-yl)carbamates, Method 1 was used to provide the title compound.

Step B: tert-butyl (4-(3-(N,N-bis(4-methoxybenzyl)sulfamoyl)-2-(1-(4-methoxybenzyl)-1H-tetrazol-5-yl)-4-(trifluoromethyl)phenyl)cyclohexyl)carbamate Palladium hydroxide (176 mg, 0.251 mmol) was added to a stirred solution of tert-butyl (3'-(N,N-bis(4-methoxybenzyl)sulfamoyl)-2'-(1-(4-methoxybenzyl)-1H-tetrazol-5-yl)-4'-(trifluoromethyl)-2,3,4,5-tetrahydro-[1,1'-biphenyl]-4-yl)carbamate (710 mg, 0.836 mmol) in methanol (10 ml) and DCM (6 ml) at RT. The mixture solution was degased by reduced pressure and refilled with N₂ and vacuum applied again. Then the reaction mixture was hydrogenated (balloon or 45 PSI) at room temperature overnight. The reaction mixture was filtered through a celite pad and washed with EtOAc. The filtrate was concentrated and the residue was purified by column chromatography on silica gel, eluting with EtOAc/isohexane to give the title compound.

Step C: 3-((1s,4s)-4-aminocyclohexyl)-2-(1H-tetrazol-5-yl)-6-(trifluoromethyl)benzenesulfonamide and 3-((1r,4r)-4-aminocyclohexyl)-2-(1H-tetrazol-5-yl)-6-(trifluoromethyl)benzenesulfonamide Starting from tert-butyl (4-(3-(N,N-bis(4-methoxybenzyl)sulfamoyl)-2-(1-(4-methoxybenzyl)-1H-tetrazol-5-yl)-4-(trifluoromethyl)phenyl)cyclohexyl)carbamates, Methods 3 and 4 were applied to give, after HPLC separation, the separated cis and trans title compounds.

EXAMPLE 821

3-[4-(aminomethyl)-1-piperidyl]-2-(1H-tetrazol-5-yl)-6-(trifluoromethyl)benzenesulfonamide

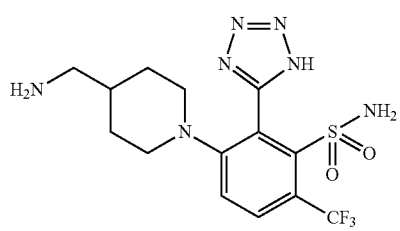 [SMILES: NCC1CCN(c2ccc(C(F)(F)F)c(S(N)(=O)=O)c2-c2nnn[nH]2)CC1]

Step A: 3-(4-cyanopiperidin-1-yl)-N,N-bis(4-methoxybenzyl)-2-(1-(4-methoxybenzyl)-1H-tetrazol-5-yl)-6-(trifluoromethyl)benzenesulfonamide Starting from 3-bromo-N,N-bis(4-methoxybenzyl)-2-(1-(4-methoxybenzyl)-1H-tetrazol-5-yl)-6-(trifluoromethyl)benzenesulfonamide and piperidine-4-carbonitrile, the title compound was obtained by using Method 5.

Step B: 3-(4-(aminomethyl)piperidin-1-yl)-N,N-bis(4-methoxybenzyl)-2-(1-(4-methoxybenzyl)-1H-tetrazol-5-yl)-6-(trifluoromethyl)benzenesulfonamide Platinum(IV) oxide (22 mg, 0.098 mmol) was added to a stirred solution of 3-(4-cyanopiperidin-1-yl)-N,N-bis(4-methoxybenzyl)-2-(1-(4-methoxybenzyl)-1H-tetrazol-5-yl)-6-(trifluoromethyl)benzenesulfonamide (150 mg, 0.197 mmol) in HOAc (1 mL), methanol (1 mL) and DCM (1 ml) at rt. The mixture solution was degased by reduced pressure and then hydrogenated (using small balloon) at room temperature overnight. The reaction mixture was filtered through celite and washed with DCM and MeOH. The filtrate was concentrated to afford the title compound.

Step C: 3-[4-(aminomethyl)-1-piperidyl]-2-(1H-tetrazol-5-yl)-6-(trifluoromethyl)benzenesulfonamide Starting from 3-(4-(aminomethyl)piperidin-1-yl)-N,N-bis(4-methoxybenzyl)-2-(1-(4-methoxybenzyl)-1H-tetrazol-5-yl)-6-(trifluoromethyl)benzenesulfonamide, method 4 was applied to afford the title compound. LC/MS: Cal'd mass: 405.12; Observed mass 406.52 (M+H)⁺.

General Procedure for the Synthesis of Guanidine Containing Analogs from the Corresponding Amines:

To a corresponding core substrate containing an amine (0.2 mmol) in THF (2.0 mL) was added 1H-pyrazole-1-carboxamidine hydrochloride (0.45 mmol) and Hunig's base (1.0 mmol). The reaction mixture was stirred at rt under nitrogen overnight. The mixture was diluted with ethyl acetate (2×25 mL), washed with brine (25 mL), dried (MgSO₄), filtered and the solvent was evaporated under reduced pressure. The residue was deprotected by using Method 4 to give the crude product which was purified by Gilson HPLC to give the pure product.

| Ex. No. | Structure | Name | Calc'd. MW | LC/MS m/e [M + H]+ |
|---|---|---|---|---|
| 822 | 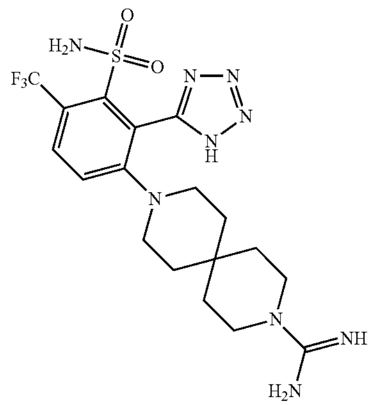 [SMILES: N=C(N)N1CCC2(CC1)CCN(c1ccc(C(F)(F)F)c(S(N)(=O)=O)c1-c1nnn[nH]1)CC2] | 9-[3-sulfamoyl-2-(1H-tetrazol-5-yl)-4-(trifluoromethyl)phenyl]-3,9-diazaspiro[5.5]undecane-3-carboxamidine | 487.17 | 488.47 |
| 823 | 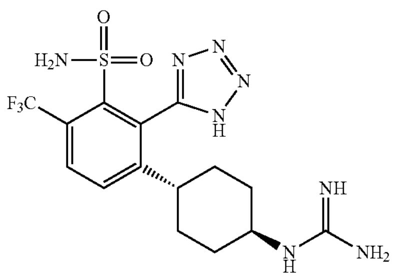 [SMILES: N=C(N)N[C@H]1CC[C@H](c2ccc(C(F)(F)F)c(S(N)(=O)=O)c2-c2nnn[nH]2)CC1] | 1-[4-[3-sulfamoyl-2-(1H-tetrazol-5-yl)-4-(trifluoromethyl)phenyl]cyclohexyl]guanidine | 432.13 | 433.30 |
| 824 | 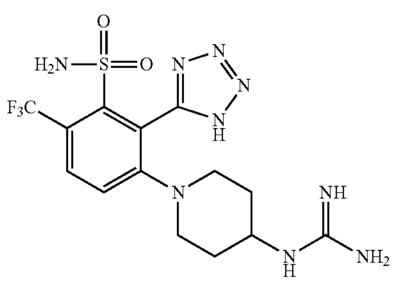 [SMILES: N=C(N)NC1CCN(c2ccc(C(F)(F)F)c(S(N)(=O)=O)c2-c2nnn[nH]2)CC1] | 1-[1-[3-sulfamoyl-2-(1H-tetrazol-5-yl)-4-(trifluoromethyl)phenyl]-4-piperidyl]guanidine | 433.13 | 434.34 |
| 825 | 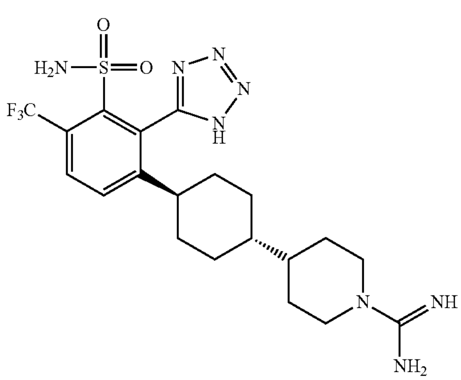 [SMILES: N=C(N)N1CCC([C@H]2CC[C@H](c3ccc(C(F)(F)F)c(S(N)(=O)=O)c3-c3nnn[nH]3)CC2)CC1] | 4-[4-[3-sulfamoyl-2-(1H-tetrazol-5-yl)-4-(trifluoromethyl)phenyl]cyclohexyl]piperidine-1-carboxamidine | 500.19 | 501.63 |

| Ex. No. | Structure | Name | Calc'd. MW | LC/MS m/e [M + H]+ |
|---|---|---|---|---|
| 826 | 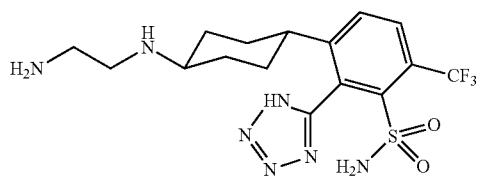 [SMILES: NCCNC1CCC(c2ccc(C(F)(F)F)c(S(N)(=O)=O)c2-c2nnn[nH]2)CC1] | 9-[3-sulfamoyl-2-(1H-tetrazol-5-yl)-4-(trifluoromethyl)phenyl]-3-azaspiro[5.5]undecane-3-carboxamidine | 486.18 | 487.46 |

EXAMPLE 827

3-[4-(trans-2-aminoethylamino)cyclohexyl]-2-(1H-tetrazol-5-yl)-6-(trifluoromethyl)benzenesulfonamide

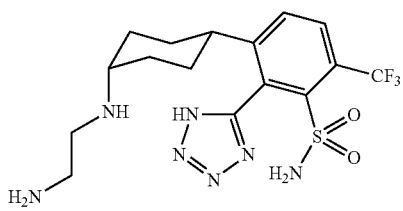 [SMILES: NCCNC1CCC(c2ccc(C(F)(F)F)c(S(N)(=O)=O)c2-c2nnn[nH]2)CC1]

tert-Butyl (2-oxoethyl)carbamate (98 mg, 0.615 mmol) and sodium cyanoborohydride (38.6 mg, 0.615 mmol) were added to a stirred solution of starting material 3-((1r,4r)-4-aminocyclohexyl)-2-(1H-tetrazol-5-yl)-6-(trifluoromethyl)benzenesulfonamide (80 mg, 0.205 mmol) in methanol at room temperature. The resulting mixture was stirred at room temperature overnight. The reaction mixture was diluted with water (3 mL) and the mixture was stirred for 30 min, filtered through a celite pad. The filtrate was concentrated to afford the crude product. Then followed by using deprotection Method 3 to afford the title product. LC/MS: Cal'd mass 433.15; Observed 434.37 [M+1]+.

EXAMPLE 828

3-((1s,4s)-4-((2-aminoethyl)amino)cyclohexyl)-2-(1H-tetrazol-5-yl)-6-(trifluoromethyl)benzenesulfonamide Step A: tert-butyl (2-(((1s,4s)-4-(3-sulfamoyl-2-(1H-tetrazol-5-yl)-4-(trifluoromethyl)phenyl)cyclohexyl)amino)ethyl)carbamate tert-butyl (2-oxoethyl)carbamate (53.8 mg, 0.338 mmol) was added to a stirred solution of starting material 3-((1s,4s)-4-aminocyclohexyl)-2-(1H-tetrazol-5-yl)-6-(trifluoromethyl)benzenesulfonamide (44 mg, 0.113 mmol) in methanol (2 ml) at room temperature and the mixture was stirred at room temperature overnight. The mixture was diluted with water (3 ml) and the mixture was stirred for 30 min and filtered through a celite pad. The filtrate was concentrated to afford the crude product, tert-butyl (2-(((1s,4s)-4-(3-sulfamoyl-2-(1H-tetrazol-5-yl)-4-(trifluoromethyl)phenyl)cyclohexyl)amino)ethyl)carbamate.

Step B: 3-((1s,4s)-4-((2-aminoethyl)amino)cyclohexyl)-2-(1H-tetrazol-5-yl)-6-(trifluoromethyl)benzenesulfonamide Using deprotection Method 3 tert-butyl (2-(((1s,4s)-4-(3-sulfamoyl-2-(1H-tetrazol-5-yl)-4-(trifluoromethyl)phenyl)cyclohexyl)amino)ethyl)carbamate was converted to the title product. LC/MS: Calc'd mass 433.15; Observed 434.30 [M+1]+.

EXAMPLE 829

3-[4-(2-aminoethylamino)-1-piperidyl]-2-(1H-tetrazol-5-yl)-6-(trifluoromethyl)benzenesulfonamide

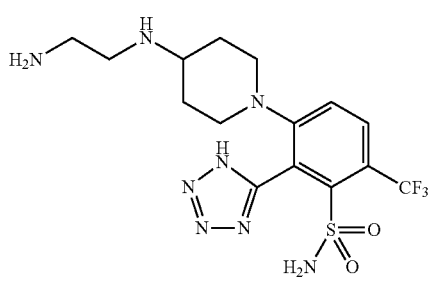 [SMILES: NCCNC1CCN(c2ccc(C(F)(F)F)c(S(N)(=O)=O)c2-c2nnn[nH]2)CC1]

Sodium acetate (26.0 mg, 0.317 mmol) was added to 3-(4-aminopiperidin-1-yl)-N-(4-methoxybenzyl)-2-(1-(4-methoxybenzyl)-1H-tetrazol-5-yl)-6-(trifluoromethyl)benzenesulfonamide (100 mg, 0.158 mmol) in THF (2 ml) and MeOH (2 ml). Followed by adding tert-butyl (2-oxoethyl)carbamate (50.4 mg, 0.317 mmol), sodium cyanotrihydroborate (49.7 mg, 0.792 mmol) and acetic acid (9.06 μl, 0.158 mmol). The mixture was stirred at rt under nitrogen overnight. To the reaction flask was added another 2 equivalent of sodium cyanotrihydroborate (49.7 mg, 0.792 mmol) and stirred for 5 hr. The mixture was diluted with ethyl acacate (30 ml), washed with brine (25 mL), the organic phase was dried (MgSO₄), filtered and the solvent was evaporated under reduced pressure. The residue was purified by column chromatography on silica gel 12 g, eluting with EtOAc/isohexane to give as the intermediate tert-butyl (2-((1-(2-(1-(4-methoxybenzyl)-1H-tetrazol-5-yl)-3-(N-(4-methoxybenzyl)sulfamoyl)-4-(trifluoromethyl)phenyl)piperidin-4-yl)amino)ethyl)carbamate. This intermediate product was treated with Method 3 and 4 to afford the titled compound. LC/MS: Calc'd mass 434.14; Observed 435.36 [M+1]⁺.

EXAMPLE 830

3-[4-[(1-aminocyclopropyl)methylamino]cyclohexyl]-2-(1H-tetrazol-5-yl)-6-(trifluoromethyl)benzenesulfonamide

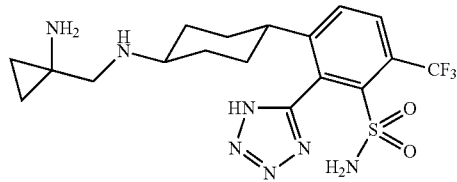 [SMILES: NC1(CNC2CCC(c3ccc(C(F)(F)F)c(S(N)(=O)=O)c3-c3nnn[nH]3)CC2)CC1]

tert-Butyl (1-formylcyclopropyl)carbamate (47.0 mg, 0.254 mmol) was added to 3-((1r,4r)-4-aminocyclohexyl)-N-(4-methoxybenzyl)-2-(1-(4-methoxybenzyl)-1H-tetrazol-5-yl)-6-(trifluoromethyl)benzenesulfonamide (80 mg, 0.127 mmol) in DCE. Followed by adding sodium triacetoxyborohydride (67.2 mg, 0.317 mmol) and acetic acid (10.89 μl, 0.190 mmol). The reaction mixture was stirred at 45° C. under N₂ for 5 hr. The mixture was diluted with water and extracted with EtOAc twice (2×30 ml). The combined organic phase was washed with saturated NaHCO₃, brine (30 mL), dried (MgSO₄), filtered and the solvent was evaporated under reduced pressure. The residue was purified by column chromatography on silica gel eluting with EtOAc/isohexane to give the intermediate tert-butyl (1-((((1r,4r)-4-(2-(1-(4-methoxybenzyl)-1H-tetrazol-5-yl)-3-(N-(4-methoxybenzyl)sulfamoyl)-4-(trifluoromethyl)phenyl)cyclohexyl)amino)methyl)cyclopropyl)carbamate. This intermediate product was treated with Method 3 and 4 to afford the title product. LC/MS: Calc'd mass 459.17; Observed mass 460.45 [M+1]⁺.

EXAMPLES 831 and 832

3-((1s,4s)-4-(piperidin-4-yl)cyclohexyl)-2-(1H-tetrazol-5-yl)-6-(trifluoromethyl)benzenesulfonamide and 3-((1r,4r)-4-(piperidin-4-yl)cyclohexyl)-2-(1H-tetrazol-5-yl)-6-(trifluoromethyl)benzenesulfonamide

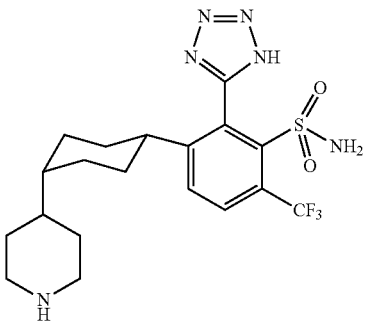

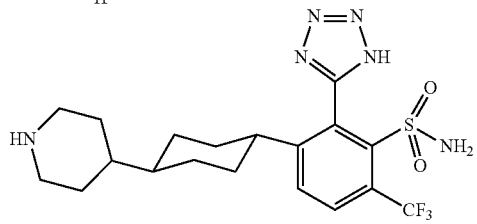

Step A: 2'-(1-(4-methoxybenzyl)-1H-tetrazol-5-yl)-3'-(N-(4-methoxybenzyl)sulfamoyl)-4'-(trifluoromethyl)-1,2,3,6-tetrahydro-[1,1'-biphenyl]-4-yl trifluoromethanesulfonate To a solution of N-(4-methoxybenzyl)-2-(1-(4-methoxybenzyl)-1H-tetrazol-5-yl)-3-(4-oxocyclohexyl)-6-(trifluoromethyl)benzenesulfonamide (190 mg, 0.302 mmol) and 1,1,1-trifluoro-N-phenyl-N-((trifluoromethyl)sulfonyl)methanesulfonamide (108 mg, 0.302 mmol) in THF (4.0 mL) was added sodium bis(trimethylsilyl)amide (0.392 ml, 0.392 mmol) at −78° C. After stirring at −78° C. for 30 min, saturated NaHCO₃ (50 ml) was added and the mixture was extracted with EtOAc (2×50 ml). The combined organic layer was washed with brine, dried over MgSO₄ and concentrated. The residue was purified by column chromatography on silica gel, eluting with EtOAc/hexane to give the title compound.

Step B: tert-butyl 4-(2'-(1-(4-methoxybenzyl)-1H-tetrazol-5-yl)-3'-(N-(4-methoxybenzyl)sulfamoyl)-4'-(trifluoromethyl)-1,2,3,6-tetrahydro-[1,1'-biphenyl]-4-yl)-3,6-dihydropyridine-1(2H)-carboxylate 2'-(1-(4-methoxybenzyl)-1H-tetrazol-5-yl)-3'-(N-(4-methoxybenzyl)sulfamoyl)-4'-(trifluoromethyl)-1,2,3,6-tetrahydro-[1,1'-biphenyl]-4-yl trifluoromethanesulfonate (71 mg, 0.093 mmol), tert-butyl 4-(4,4,5,5-tetramethyl-1,3,2-dioxaborolan-2-yl)-5,6-dihydropyridine-1(2H)-carboxylate (72.1 mg, 0.233 mmol), Pd(dppf)Cl₂ (17.05 mg, 0.023 mmol) and sodium carbonate (19.8 mg, 0.186 mmol) were placed in a reaction vessel. Dioxane (1.5 mL) and Water (0.5 mL) was added. The mixture was sealed and degassed and heated at 95° C., and stirred overnight. The reaction mixture was cooled to room temperature, filtered through a celite pad. The filtrated was concentrated and the residue was loaded onto silica gel column and eluted with EtOAc/hexane to give the title compound.

Step C: tert-butyl 4-(4-(2-(1-(4-methoxybenzyl)-1H-tetrazol-5-yl)-3-(N-(4-methoxybenzyl)sulfamoyl)-4-(trifluoromethyl)phenyl)cyclohexyl)piperidine-1-carboxylate Dihydroxypalladium (27.0 mg, 0.038 mmol) was added to a stirred solution of starting material tert-butyl 4-(2'-(1-(4-methoxybenzyl)-1H-tetrazol-5-yl)-3'-(N-(4-methoxybenzyl)sulfamoyl)-4'-(trifluoromethyl)-1,2,3,6-tetrahydro-[1,1'-biphenyl]-4-yl)-5,6-dihydropyridine-1(2H)-carboxylate (102 mg, 0.128 mmol) in methanol (2 ml) and DCM (2 ml) at RT. The mixture solution was degased by reduced pressure and then hydrogenated (using small balloon) at room temperature for overnight. The reaction mixture was filtered through a celite pad and washed with EtOAc. The filtrate was concentrated and the residue was purified by column chromatography on silica gel, eluting with EtOAc/isohexane to give the title compound.

Step 4: 3-((1s,4s)-4-(piperidin-4-yl)cyclohexyl)-2-(1H-tetrazol-5-yl)-6-(trifluoromethyl)benzenesulfonamide and 3-((1r,4r)-4-(piperidin-4-yl)cyclohexyl)-2-(1H-tetrazol-5-yl)-6-(trifluoromethyl)benzenesulfonamide Used deprotection Method 3 and 4 to afford the titled compounds after HPLC separation of the isomers. LC/MS: Calc'd mass 458.17; Observed Cis 459.35 [M+1]$^+$ and Trans 459.36 [M+1]$^+$.

EXAMPLE 833

3-(3-azaspiro[5.5]undecan-9-yl)-2-(1H-tetrazol-5-yl)-6-(trifluoromethyl)benzenesulfonamide

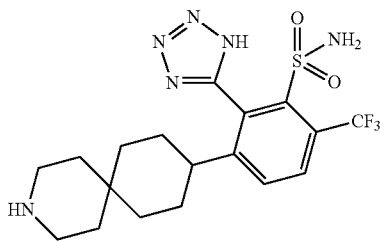 [SMILES: NS(=O)(=O)c1c(C(F)(F)F)ccc(C2CCC3(CCNCC3)CC2)c1-c1nnn[nH]1]

Step A: tert-butyl 9-(((trifluoromethyl)sulfonyl)oxy)-3-azaspiro[5.5]undec-8-ene-3-carboxylate To a solution of tert-butyl 9-oxo-3-azaspiro[5.5]undecane-3-carboxylate (1.0 g, 3.74 mmol) and in THF (20 mL) was added sodium bis(trimethylsilyl)amide (4.86 ml, 4.86 mmol) at −78° C. After stirring at −78° C. for 30 min, 1,1,1-trifluoro-N-phenyl-N-((trifluoromethyl)sulfonyl) methanesulfonamide (1.60 g, 4.49 mmol) was added as solid and stirred for 50 minutes. To the reaction was added saturated NaHCO$_3$ (100 mL) and the mixture was extracted with EtOAc (2×100 mL). The organic layer was washed with brine, dried over MgSO$_4$, filtered and concentrated. The residue was purified by column chromatography on silica gel, eluting with EtOAc/hexane to give the title compound.

Step B: tert-butyl 9-(4,4,5,5-tetramethyl-1,3,2-dioxaborolan-2-yl)-3-azaspiro[5.5]undec-8-ene-3-carboxylate 4,4,4',4',5,5,5',5'-Octamethyl-2,2'-bi(1,3,2-dioxaborolane) (0.763 g, 3.00 mmol), tert-butyl 9-(((trifluoromethyl)sulfonyl)oxy)-3-azaspiro[5.5]undec-8-ene-3-carboxylate (1.0 g, 2.504 mmol), Pd(dppf)Cl$_2$ (0.183 g, 0.250 mmol) and potassium acetate (0.737 g, 7.51 mmol) were placed in a reaction vessel. Dioxane (15 mL) was added. The mixture was sealed and degassed. The reaction was stirred at 80° C. overnight. The reaction mixture was cooled to rt and filtered through a celite pad. The filtrate was concentrated and the residue was purified by silica gel column chromatgraph and eluted with EtOAc/hexane to give the title compound.

Step C: tert-butyl 9-(3-(N,N-bis(4-methoxybenzyl)sulfamoyl)-2-(1-(4-methoxybenzyl)-1H-tetrazol-5-yl)-4-(trifluoromethyl)phenyl)-3-azaspiro[5.5]undec-8-ene-3-carboxylate Coupling Method 1 was applied tert-butyl 9-(4,4,5,5-tetramethyl-1,3,2-dioxaborolan-2-yl)-3-azaspiro[5.5]undec-8-ene-3-carboxylate and 3-bromo-N,N-bis(4-methoxybenzyl)-2-(1-(4-methoxybenzyl)-1H-tetrazol-5-yl)-6-(trifluoromethyl)benzenesulfonamide to afford the title compound.

Step D: tert-butyl 9-(3-(N,N-bis(4-methoxybenzyl)sulfamoyl)-2-(1-(4-methoxybenzyl)-1H-tetrazol-5-yl)-4-(trifluoromethyl)phenyl)-3-azaspiro[5.5]undecane-3-carboxylate Dihydroxypalladium (182 mg, 0.259 mmol) was added to a stirred solution of starting material tert-butyl 9-(3-(N,N-bis(4-methoxybenzyl)sulfamoyl)-2-(1-(4-methoxybenzyl)-1H-tetrazol-5-yl)-4-(trifluoromethyl)phenyl)-3-azaspiro[5.5]undec-8-ene-3-carboxylate (780 mg, 0.864 mmol) in methanol (6 ml) and DCM (6 mL) at RT. The mixture solution was degased by reduced pressure and then hydrogenated (using small balloon) at room temperature for overnight. The reaction mixture was filtered through celite. The filtrate was concentrated and the residue was purified by column chromatography on silica gel, eluting with EtOAc/isohexane to give the title compound.

Step E: 3-(3-azaspiro[5.5]undecan-9-yl)-2-(1H-tetrazol-5-yl)-6-(trifluoromethyl)benzenesulfonamide Used deprotection Method 3 and 4 to afford the title compound. LC/MS: Calc'd mass 444.16; Observed 445.41 [M+1]$^+$.

EXAMPLE 834

3-[3-[(1-aminocyclopropyl)methyl]-3-azaspiro[5.5]undecan-9-yl]-2-(1H-tetrazol-5-yl)-6-(trifluoromethyl)benzenesulfonamide

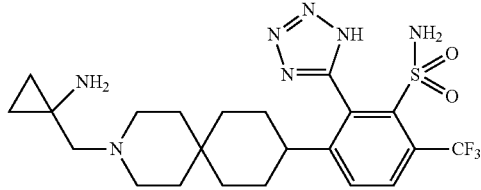 [SMILES: NC1(CN2CCC3(CCC(c4ccc(C(F)(F)F)c(S(N)(=O)=O)c4-c4nnn[nH]4)CC3)CC2)CC1]

tert-Butyl (1-formylcyclopropyl)carbamate (108 mg, 0.584 mmol) was added to N-(4-methoxybenzyl)-2-(1-(4-methoxybenzyl)-1H-tetrazol-5-yl)-3-(3-azaspiro[5.5]undecan-9-yl)-6-(trifluoromethyl)benzenesulfonamide (200 mg, 0.292 mmol) in DCE (2.5 mL). Sodium triacetoxyborohydride (155 mg, 0.730 mmol) and acetic acid (0.025 ml, 0.438 mmol) were added. The mixture was stirred at RT under nitrogen for 4 hr. Then mixture was diluted with water and extracted with EtOAc twice (50 mL). The combined organic phase was washed with saturated NaHCO3, brine (2×30 ml), dried (MgSO$_4$), filtered through a celite pad and the solvent was evaporated under reduced pressure. The residue was purified by column chromatography on silica gel, eluting with EtOAc/isohexane to give tert-butyl (1-((9-(2-(1-(4-methoxybenzyl)-1H-tetrazol-5-yl)-3-(N-(4-methoxybenzyl)sulfamoyl)-4-(trifluoromethyl)phenyl)-3-azaspiro[5.5]undecan-3-yl)methyl)cyclopropyl)carbamate. Followed by using deprotection Method 3 and 4 to afford the title product. LC/MS: Calc'd mass 513.21; Observed mass 514.50 [M+1]⁺.

EXAMPLE 835

3-[1-(4-piperidyl)-4-piperidyl]-2-(1H-tetrazol-5-yl)-6-(trifluoromethyl)benzenesulfonamide

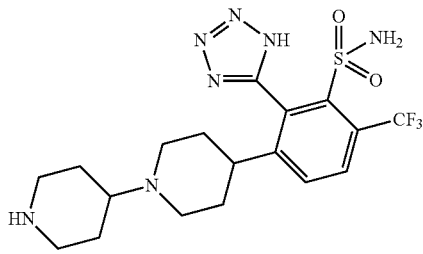 [SMILES: NS(=O)(=O)c1c(C(F)(F)F)ccc(C2CCN(C3CCNCC3)CC2)c1-c1nnn[nH]1]

Step A: tert-butyl 4-(3-(N,N-bis(4-methoxybenzyl)sulfamoyl)-2-(1-(4-methoxybenzyl)-1H-tetrazol-5-yl)-4-(trifluoromethyl)phenyl)-3,6-dihydropyridine-1(2H)-carboxylate Coupling Method 1 was applied to 3-bromo-N,N-bis(4-methoxybenzyl)-2-(1-(4-methoxybenzyl)-1H-tetrazol-5-yl)-6-(trifluoromethyl)benzenesulfonamide and tert-butyl 4-(4,4,5,5-tetramethyl-1,3,2-dioxaborolan-2-yl)-3,6-dihydropyridine-1(2H)-carboxylate to afford the title compound.

Step B: tert-butyl 4-(3-(N,N-bis(4-methoxybenzyl)sulfamoyl)-2-(1-(4-methoxybenzyl)-1H-tetrazol-5-yl)-4-(trifluoromethyl)phenyl)piperidine-1-carboxylate Dihydroxypalladium (0.303 g, 0.431 mmol) was added to a stirred solution of starting material tert-butyl 4-(3-(N,N-bis(4-methoxybenzyl)sulfamoyl)-2-(1-(4-methoxybenzyl)-1H-tetrazol-5-yl)-4-(trifluoromethyl)phenyl)-5,6-dihydropyridine-1(2H)-carboxylate (1.2 g, 1.437 mmol) in methanol (6 mL) and DCM (6 mL) at RT. The mixture solution was degased by reduced pressure. The reaction mixture was then hydrogenated (using small balloon) at room temperature overnight. The reaction mixture was filtered through celite and washed with EtOAc. The filtrate was concentrated and the residue was purified by column chromatography on silica gel, eluting with EtOAc/isohexane to give the title compound.

Step C: N-(4-methoxybenzyl)-2-(1-(4-methoxybenzyl)1H-tetrazol-5-yl)-3-(piperidin-4-yl)-6-(trifluoromethyl)benzenesulfonamide Deprotection Method 3 was applied to tert-butyl 4-(3-(N,N-bis(4-methoxybenzyl)sulfamoyl)-2-(1-(4-methoxybenzyl)-1H-tetrazol-5-yl)-4-(trifluoromethyl)phenyl)piperidine-1-carboxylate to afford the title compound.

Step D: tert-butyl 4-(2-(1-(4-methoxybenzyl)-1H-tetrazol-5-yl)-3-(N-(4-methoxybenzyl)sulfamoyl)-4-(trifluoromethyl)phenyl)-[1,4'-bipiperidine]-1'-carboxylate tert-Butyl 4-oxopiperidine-1-carboxylate (145 mg, 0.730 mmol) and titanium(iv) isopropoxide (0.288 mL, 0.973 mmol) were added to N-(4-methoxybenzyl)-2-(1-(4-methoxybenzyl)-1H-tetrazol-5-yl)-3-(piperidin-4-yl)-6-(trifluoromethyl)benzenesulfonamide (150 mg, 0.243 mmol) in EtOH (2 mL). The reaction was heated to 70° C. for overnight. The reaction was cooled to RT, and sodium cyanotrihydroborate (61.1 mg, 0.973 mmol) was added. The reaction mixture was stirred at rt under nitrogen for 1 hr. The mixture was diluted with water and extracted with EtOAc (2×30 mL). The combined organic phase was washed with saturated NaHCO₃, brine (2×30 mL), dried (MgSO₄), filtered and the solvent was evaporated under reduced pressure. The residue was purified by column chromatography on silica gel, eluting with EtOAc/isohexane to give the title compound.

Step E: 3-[1-(4-piperidyl)-4-piperidyl]-2-(1H-tetrazol-5-yl)-6-(trifluoromethyl)benzenesulfonamide Using deprotection procedure 3 and 4 was applied to tert-butyl 4-(2-(1-(4-methoxybenzyl)-1H-tetrazol-5-yl)-3-(N-(4-methoxybenzyl)sulfamoyl)-4-(trifluoromethyl)phenyl)-[1,4'-bipiperidine]-1'-carboxylate to afford the titled product. LC/MS: Calc'd mass 459.17 Observed mass 460.43 [M+1]⁺.

EXAMPLE 836

3-(2-aminoindan-4-yl)-2-(1H-tetrazol-5-yl)-6-(trifluoromethyl)benzenesulfonamide

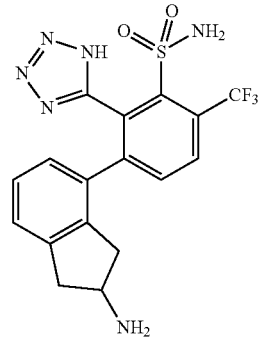 [SMILES: NC1Cc2cccc(-c3ccc(C(F)(F)F)c(S(N)(=O)=O)c3-c3nnn[nH]3)c2C1]

Step A: 3-(2-hydroxy-2,3-dihydro-1H-inden-4-yl)-N,N-bis(4-methoxybenzyl)-2-(1-(4-methoxybenzyl)-1H-tetrazol-5-yl)-6-(trifluoromethyl)benzenesulfonamide To a reaction vessel, was added (3-(N,N-bis(4-methoxybenzyl)sulfamoyl)-2-(1-(4-methoxybenzyl)-1H-tetrazol-5-yl)-4-(trifluoromethyl)phenyl) boronic acid (200 mg, 0.287 mmol), 4-bromo-2,3-dihydro-1H-inden-2-ol (122 mg, 0.573 mmol), cesium carbonate (280 mg, 0.860 mmol) and 2nd generation xphos precatalyst (45.1 mg, 0.057 mmol). Dioxane (1.5 ml) and water (0.5 ml) were added to this flask. The reaction mixture was degased with bubbled under N₂ for 10 min. This mixture was then heated at 66° C. for overnight. The mixture was cooled, diluted with saturated NaHCO₃, and extracted with EtOAc. The organic phase was concentrated under reduced pressure. The residue was purified by column chromatography on silica gel, eluting with hexane/EtOAc to give the title compound.

Step B: 4-(3-(N,N-bis(4-methoxybenzyl)sulfamoyl)-2-(1-(4-methoxybenzyl)-1H-tetrazol-5-yl)-4-(trifluoromethyl)phenyl)-2,3-dihydro-1H-inden-2-yl methanesulfonate Triethylamine (0.043 mL, 0.305 mmol) and methanesulfonyl chloride (0.012 mL, 0.153 mmol) was added to a stirred solution of starting material 3-(2-hydroxy-2,3-dihydro-1H-inden-4-yl)-N,N-bis(4-methoxybenzyl)-2-(1-(4-methoxybenzyl)-1H-tetrazol-5-yl)-6-(trifluoromethyl)benzenesulfonamide (80 mg, 0.102 mmol) in dichloromethane (2 mL) at 0° C. and the mixture was stirred at 0° C. for 5 hr. The mixture was diluted with aqueous sodium hydrogen carbonate (20 mL) and the mixture was extracted with dichloromethane (2×30 mL). The organic phase was washed with HCl (0.5M, 20 mL), dried (MgSO₄) and concentrated to give crude title compound, which was taken as is for next step.

Step C: 3-(2-azido-2,3-dihydro-1H-inden-4-yl)-N,N-bis(4-methoxybenzyl)-2-(1-(4-methoxybenzyl)-1H-tetrazol-5-yl)-6-(trifluoromethyl)benzenesulfonamide Sodium azide (33.1 mg, 0.509 mmol) was added to a stirred solution of starting material 4-(3-(N,N-bis(4-methoxybenzyl)sulfamoyl)-2-(1-(4-methoxybenzyl)-1H-tetrazol-5-yl)-4-(trifluoromethyl)phenyl)-2,3-dihydro-1H-inden-2-yl methanesulfonate (88 mg, 0.102 mmol) in dimethylsulfoxide (2 mL) at room temperature and the mixture was stirred at room temperature for overnight. The mixture was diluted with water (30 ml) and the mixture was extracted with diethyl ether (2×30 mL). The organic phase was washed with brine, dried (MgSO₄) and concentrated. The residue was purified by column chromatography on silica gel, eluting with EtOAc/isohexane to give the title compound.

Step D: 3-(2-amino-2,3-dihydro-1H-inden-4-yl)-N,N-bis(4methoxybenzyl)-2-(1-(4-methoxybenzyl)-1H-tetrazol-5-yl)-6-(trifluoromethyl)benzenesulfonamide Pd—C (27.6 mg, 0.026 mmol) was added to a stirred solution of starting material 3-(2-azido-2,3-dihydro-1H-inden-4-yl)-N,N-bis(4-methoxybenzyl)-2-(1-(4-methoxybenzyl)-1H-tetrazol-5-yl)-6-(trifluoromethyl)benzenesulfonamide (70 mg, 0.086 mmol) in DCM (1 ml) at RT and the mixture solution was degased by reduced pressure. Then the reaction mixture was hydrogenated (using small balloon) at room temperature for 2 hours. The reaction mixture was filtered through celite and washed with MeOH. The filtrate was concentrated and the residue was purified by column chromatography on silica gel, eluting with EtOAc/isohexane to give the title compound.

Step E: 3-(2-aminoindan-4-yl)-2-(1H-tetrazol-5-yl)-6-(trifluoromethyl)benzenesulfonamide 3-(2-Amino-2,3-dihydro-1H-inden-4-yl)-N,N-bis(4methoxybenzyl)-2-(1-(4-methoxybenzyl)-1H-tetrazol-5-yl)-6-(trifluoromethyl)benzenesulfonamide was subjected to deprotection Method 4 to afford the title product. LC/MS: Calc'd mass 424.09; Observed 425.18 [M+1]⁺.

EXAMPLE 837

(S)-2,3-diamino-N-((1r,4S)-4-(3-sulfamoyl-2-(1H-tetrazol-5-yl)-4-(trifluoromethyl)phenyl)cyclohexyl)propanamide

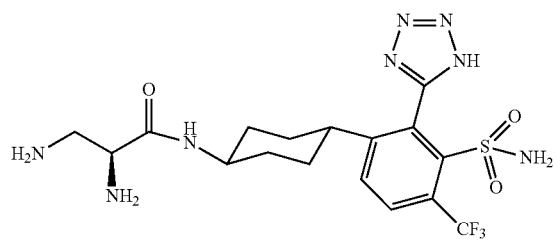 [SMILES: NC[C@H](N)C(=O)NC1CCC(c2ccc(C(F)(F)F)c(S(N)(=O)=O)c2-c2nnn[nH]2)CC1]

Step A: (S)-2,5-dioxopyrrolidin-1-yl 2,3-bis((tert-butoxycarbonyl)amino)propanoate N,N,N',N'-Tetramethyl-O—(N-succinimidyl)uronium tetrafluoroborate (193 mg, 0.641 mmol) was added to a stirred mixture of starting material(S)-2,3-bis((tert-butoxycarbonyl)amino)propanoic acid (150 mg, 0.493 mmol) in dichloromethane (2 mL) at 0° C. and the mixture was stirred at room temperature for 2 hr to give the title compound which was used as is for next step.

Step B: di-tert-butyl ((S)-3-oxo-3-(((1r,4S)-4-(3-sulfamoyl-2-(1H-tetrazol-5-yl)-4-(trifluoromethyl)phenyl)cyclohexyl)amino)propane-1,2-diyl)dicarbamate (S)-2,5-Dioxopyrrolidin-1-yl 2,3-bis((tert-butoxycarbonyl)amino)propanoate (80 mg, 0.200 mmol) was added to a stirred solution of starting material 3-((1r,4s)-4-aminocyclohexyl)-2-(1H-tetrazol-5-yl)-6-(trifluoromethyl)benzenesulfonamide (60 mg, 0.154 mmol) in dimethylformamide (2 ml) at 0° C. and the mixture was stirred at 0° C. for 2 hr. The mixture was diluted with water (30 mL), and extracted with dichloromethane (2×30 mL). The combined organic phase was dried (MgSO₄) and concentrated. The residue was used as is.

Step C: (S)-2,3-diamino-N-((1r,4S)-4-(3-sulfamoyl-2-(1H-tetrazol-5-yl)-4-(trifluoromethyl)phenyl)cyclohexyl)propanamide TFA (1.0 mL, 13 mmol) was added to a stirred solution of starting material di-tert-butyl ((S)-3-oxo-3-(((1r,4S)-4-(3-sulfamoyl-2-(1H-tetrazol-5-yl)-4-(trifluoromethyl)phenyl)cyclohexyl)amino)propane-1,2-diyl)dicarbamate (30 mg, 0.044 mmol) in dichloromethane (1 ml) at room temperature and the mixture was stirred at room temperature for 2 hr. The mixture was concentrated. The residue was purified by Gilson HPLC reverse phase (C-18), eluting with acetonitrile/water to give the title compound after lyophilization. LC/MS: Calc'd mass 476.16; Observed 477.47 [M+1]⁺.

EXAMPLE 838

3-(4-aminocyclohexyl)-6-[2-(4-piperidyl)ethyl]-2-(2H-tetrazol-5-yl)benzenesulfonamide

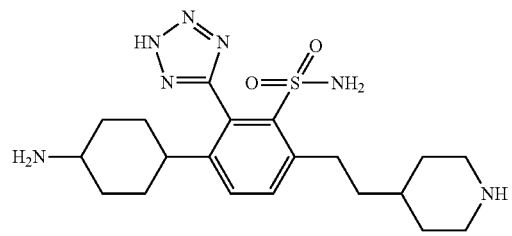 [SMILES: NC1CCC(c2ccc(CCC3CCNCC3)c(S(N)(=O)=O)c2-c2nn[nH]n2)CC1]

Step A: tert-butyl 4-(2-(3-(N,N-bis(4methoxybenzyl)sulfamoyl)-4'-((tert-butoxycarbonyl)amino)-2-(2-(4-methoxybenzyl)-2H-tetrazol-5-yl)-2',3',4',5'-tetrahydro-[1,1'-biphenyl]-4-yl)ethyl)piperidine-1-carboxylate A microwave vial was charged with 4,7-diphenyl-1,10-phenanthroline (21.86 mg, 0.066 mmol), tert-butyl 4-(2-iodoethyl)piperidine-1-carboxylate (297 mg, 0.877 mmol), nickel(II) iodide (41.1 mg, 0.132 mmol), tert-butyl (3'-(N,N-bis(4-methoxybenzyl)sulfamoyl)-4'-bromo-2'-(2-(4-methoxybenzyl)-2H-tetrazol-5-yl)-2,3,4,5-tetrahydro-[1,1'-biphenyl]-4-yl)carbamate (377 mg, 0.438 mmol) and manganese (48.2 mg, 0.877 mmol). The vial was sealed, purged with N₂ for 10 min, and filled with DMA (2 ml), benzonitrile (9.04 µl, 0.088 mmol) and chlorotrimethylsilane (0.011 ml, 0.088 mmol). The resulting mixture was purged with N₂ for another 5 min, and heated for 3 hr at 60° C. The reaction mixture was filtered over celite to remove metal. The filtrate was concentrated and purified by silica gel column chromatography to afford the title compound.

Step B: tert-butyl 4-(2-(N,N-bis(4-methoxybenzyl)sulfamoyl)-4-(4-((tert-butoxycarbonyl)amino)cyclohexyl)-3-(2-(4-methoxybenzyl)-2H-tetrazol-5-yl)phenethyl)Piperidine-1-carboxylate Dihydroxypalladium (164 mg, 0.234 mmol) was added to a stirred solution of starting material tert-butyl 4-(2-(3-(N,N-bis(4-methoxybenzyl)sulfamoyl)-4'-((tert-butoxycarbonyl)amino)-2-(2-(4-methoxybenzyl)-2H-tetrazol-5-yl)-2',3',4',5'-tetrahydro-[1,1'-biphenyl]-4-yl)ethyl)piperidine-1-carboxylate (387 mg, 0.390 mmol) in methanol (3 ml) and EtOAc (2 ml) at RT. The mixture solution was degased. And then hydrogenated (Parr shaker, 45 PSI) at room temperature overnight. The reaction mixture was filtered through celite and washed with EtOAc. The filtrate was concentrated and the residue was purified by column chromatography on silica gel, eluting with EtOAc/isohexane to give the title compound.

Step C: 3-(4-aminocyclohexyl)-N,N-bis(4-methoxybenzyl-2-(2-(4-methoxybenzyl)-2H-tetrazol-5-yl)-6-(2-(piperidin-4-yl)ethyl)benzenesulfonamide tert-Butyl 4-(2-(N,N-bis(4-methoxybenzyl)sulfamoyl)-4-(4-((tert-butoxycarbonyl)amino)cyclohexyl)-3-(2-(4-methoxybenzyl)-2H-tetrazol-5-yl)phenethyl)Piperidine-1-carboxylate was subjected to deprotection Method 3 to afford the title compound.

Step D: 3-(4-aminocyclohexyl)-6-[2-(4-piperidyl)ethyl]-2-(2H-tetrazol-5-yl)benzenesulfonamide 3-(4-Aminocyclohexyl)-N,N-bis(4-methoxybenzyl-2-(2-(4-methoxybenzyl)-2H-tetrazol-5-yl)-6-(2-(piperidin-4-yl)ethyl)benzenesulfonamide was subjected to deprotection Method 4 to afford the title compound. LC/MS: Calc'd mass 433.22; Observed 217.77 [M+2]/2.

EXAMPLE 839

3-(4-aminocyclohexyl)-6-(piperidin-4-ylmethyl)-2-(2H-tetrazol-5-yl)benzenesulfonamide

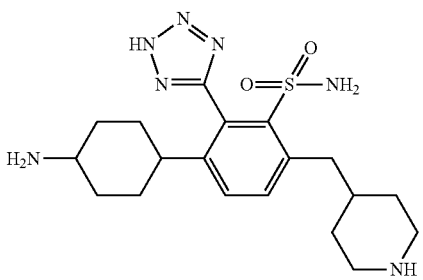 [SMILES: NC1CCC(c2ccc(CC3CCNCC3)c(S(N)(=O)=O)c2-c2nn[nH]n2)CC1]

Step A: tert-butyl 4-((3-(N,N-bis(4-methoxybenzyl)sulfamoyl)-4'-((tert-butoxycarbonyl)amino)-2-(2-(4-methoxybenzyl)-2H-tetrazol-5-yl)-2',3',4',5'-tetrahydro-[1,1'-biphenyl]-4-yl)methyl)piperidine-1-carboxylate A microwave vial was charged with 4,7-diphenyl-1,10-phenanthroline (22.91 mg, 0.069 mmol), tert-butyl 4-(iodomethyl)piperidine-1-carboxylate (448 mg, 1.378 mmol), nickel(II) iodide (43.1 mg, 0.138 mmol), tert-butyl (3'-(N,N-bis(4-methoxybenzyl)sulfamoyl)-4'-bromo-2'-(2-(4-methoxybenzyl)-2H-tetrazol-5-yl)-2,3,4,5-tetrahydro-[1,1'-biphenyl]-4-yl)carbamate (395 mg, 0.459 mmol) and manganese (50.5 mg, 0.919 mmol). The vial was sealed, purged with $N_2$ for 10 min, and filled with DMA (2 ml), benzonitrile (9.47 µl, 0.092 mmol) and chlorotrimethylsilane (0.012 ml, 0.092 mmol). The resulting mixture was purged with $N_2$ for another 5 min, and heated for 3 hr at 45° C. The reaction mixture was filtered over celite to remove metal. The filtrate was concentrated and purified by silica gel column chromatography using EtOAc/hexane as mobile phase to afford the title compound.

Step B: tert-butyl 4-(2-(N,N-bis(4-methoxybenzyl)sulfamoyl)-4-(4-((tert-butoxycarbonyl)amino)cyclohexyl)-3-(2-(4-methoxybenzyl)-2H-tetrazol-5-yl)benzyl)piperidine-1-carboxylate Dihydroxypalladium (129 mg, 0.184 mmol) was added to a solution of starting material tert-butyl 4-((3-(N,N-bis(4-methoxybenzyl)sulfamoyl)-4'-((tert-butoxycarbonyl)amino)-2-(2-(4-methoxybenzyl)-2H-tetrazol-5-yl)-2',3',4',5'-tetrahydro-[1,1'-biphenyl]-4-yl)methyl)piperidine-1-carboxylate (300 mg, 0.307 mmol) in methanol (3 ml) and EtOAc (3 ml) at RT. This was followed by adding acetic acid (0.5 ml). The mixture solution was degased, and then hydrogenated (45 PSI) at room temperature for overnight. The reaction mixture was filtered through celite and washed with MeOH. The filtrate was concentrated and the residue was purified by column chromatography on silica gel, eluting with EtOAc/isohexane to give the title compound.

Step C: 3-(4-aminocyclohexyl)-N-(4-methoxybenzyl)-2-(2-(4-methoxybenzyl)-2H-tetrazol-5-yl)-6-(piperidin-4-ylmethyl)benzenesulfonamide tert-Butyl 4-(2-(N,N-bis(4-methoxybenzyl)sulfamoyl)-4-(4-((tert-butoxycarbonyl)amino)cyclohexyl)-3-(2-(4-methoxybenzyl)-2H-tetrazol-5-yl)benzyl)piperidine-1-carboxylate was subjected to deprotection Method 3 to afford the title compound.

Step D: 3-(4-aminocyclohexyl)-6-(piperidin-4-ylmethyl)-2-(2H-tetrazol-5-yl)benzenesulfonamide 3-(4-Aminocyclohexyl)-N-(4-methoxybenzyl)-2-(2-(4-methoxybenzyl)-2H-tetrazol-5-yl)-6-(piperidin-4-ylmethyl)benzenesulfonamide was subjected to deprotection Method 4 to afford the title compound. LC/MS: Calc'd mass 419.21; Observed 210.92 [M+2]/2.

EXAMPLE 840

3-([1,2,4]triazolo[1,5-a]pyridin-8-yl)-2-(1H-tetrazol-5-yl)-6-(trifluoromethyl)benzenesulfonamide

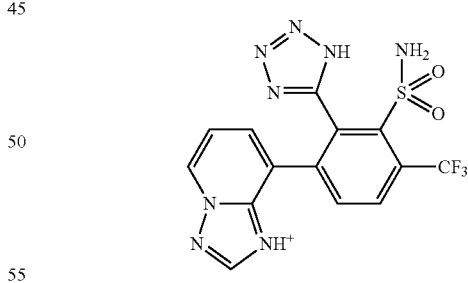

Step A: 3-([1,2,4]triazolo[1,5-a]pyridin-8-yl)-N,N-bis(4-methoxybenzyl)-2-(1-(4-methoxybenzyl)-1H-tetrazol-5-yl)-6-(trifluoromethyl)benzenesulfonamide 8-(Tributylstannyl)-[1,2,4]triazolo[1,5-a]pyridine (1.014 g, 2.484 mmol) and Pd(Ph₃P)₄ (0.221 g, 0.191 mmol) were added to a stirred solution of starting material 3-bromo-N,N-bis(4-methoxybenzyl)-2-(1-(4-methoxybenzyl)-1H-tetrazol-5-yl)-6-(trifluoromethyl)benzenesulfonamide (1.4 g, 1.9 mmol) in toluene (50 mL) at room temperature and the mixture was stirred at 70° C. for overnight. The mixture was concentrated, dissolved in EtOAc 30 ml, diluted with brine (30 mL) and the mixture was extracted with ethyl acacate (2×50 mL). The residue was purified by column chromatography on silica gel, eluting with EtOAc/isohexane to give the title compound.

Step B: 3-([1,2,4]triazolo[1,5-a]pyridin-8-yl)-2-(1H-tetrazol-5-yl)-6-(trifluoromethyl)benzenesulfonamide 3-([1,2,4]Triazolo[1,5-a]pyridin-8-yl)-N,N-bis(4-methoxybenzyl)-2-(1-(4-methoxybenzyl)-1H-tetrazol-5-yl)-6-(trifluoromethyl)benzenesulfonamide was subjected to Method 4 to afford the title compound. LC/MS: Calc'd mass 410.05; observed mass 411.30 [M+1]$^+$.

BIOLOGICAL ASSAYS

Enzyme Activity: Determination of $IC_{50}$

The Class B enzyme activities were measured in the presence of the test inhibitor in a fluorescence assay against a commercially available substrate consisting of a cephalosporin core linking 7-hydroxycoumarin to fluorescein (CCF2-FA). The enzyme (NDM-1, IMP-1 or VIM-1) and the substrate were diluted in 100 mM $KH_2PO_4$ buffer (pH 7) containing 0.005% Tween-20 and 10 μM $ZnSO_4$. In the assay, the final concentration of enzyme was 1 pM, 2 pM and 30 pM for NDM-1, IMP-1 and VIM-1, respectively, and the final concentration of CCF2-FA was 1.25 μM. The test inhibitor was dissolved in dimethylsulfoxide and diluted 1:50 in the assay, resulting in a final concentration range of 20 uM to 0.00063 uM. In a 384-well microplate, the test inhibitor was incubated with the metallo-β-lactamase enzyme and the substrate for 2 hours at 25° C. Fluorescence at 460 nm following excitation at 405 nm was measured. The $IC_{50}$ value was determined from semi-logarithmic plots of enzyme inhibition versus inhibitor concentration, with a curve generated using a 4-parameter fit.

Representative compounds of the present invention exhibit inhibition of Class B β-lactamases in this assay. For example, the compounds of Examples 1-840 were tested in this assay and were found to have the $IC_{50}$ values shown in Table 1.

Antibiotic Potentiation Activity: Determination of Synergistic Concentration

The concentrations of metallo-β-lactamase inhibitors required to restore the susceptibility of various strains of bacteria to inactive concentrations of antibiotics were determined in an assay that assessed bacterial growth by measuring the optical density at 600 nm ($OD_{600}$). The bacterial strains tested included the clinical strains *Escherichia coli* expressing NDM-1 (CLB30005, CLB30016), *Serratia marcescens* expressing IMP-1 (CL5741), and *Klebsiella pneumoniae* expressing VIM-1 (IHMA599644) Inhibitor activity was measured in the presence and absence of imipenem in a 384-well microplate.

The clinical strains CLB30016, CL5741 and IHMA599644 were grown on trypticase soy agar containing 5% sheep's blood. The clinical strain CLB30005 was grown on Mueller Hinton broth agar containing 8 ug/ml imipenem. The bacteria on agar plates were incubated at 35° C. with humidity overnight. The following day, individual colonies from each clinical strain were picked and resuspended in 5 ml saline to attain an $OD_{600}$ of 0.14, 0.11, 0.15 and 0.13, for CLB30005, CLB30016, CL5741 and IHMA599644, respectively. These were further diluted 1:100 into 1.1×CAMHB and used to inoculate the test wells as described below.

Imipenem in 10 mM 3-(N-morpholino)propanesulfonic acid (MOPS, pH 7) was stored in single use aliquots at −80° C. Test inhibitors were dissolved in dimethylsulfoxide and diluted 1:50 in the assay, resulting in a final concentration range of 200 uM to 0.195 μM. On the day of the assay, 4 μl of antibiotic was added to 45 ul of bacteria followed by 1 μl of test compound and mixed by pipetting and with an orbital shaker. The concentration of antibiotic used in the assay was 4 μg/ml, or optionally 1 μg/ml. Microplates were covered and incubated at 35° C. for 22 hours to 24 hours. At the end of the incubation, absorbance was determined using a spectrophotometer. The synergistic concentration of MBLI was determined by identifying the lowest concentration of test compound in the presence of a given concentration of antibiotic that was required to inhibit 95% of the growth of the bacteria. The results for Examples 1-840 are reported in Table 1, expressed as the concentration of compound that potentiated the action of antibiotic (imipenem) affecting 95% inhibition of bacterial growth (MITC95).

Representative compounds of the present invention do not have any or have minimal intrinsic antibacterial activity but display a synergistic effect when used in combination with a beta-lactam antibiotic. For example, in general, the compounds of Examples 1-840 were determined to restore susceptibility to imipenem for one or more of the test organisms at concentrations of 100 μM or less.

TABLE 1

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | *Serratia marcescens* expressing IMP-1 (CL5741) MITC95 μM | *Escherichia coli* expressing NDM-1 (CLB 30005) MITC95 μM | *Escherichia coli* expressing NDM-1 (CLB 30016) MITC95 μM | *Klebsiella pneumoniae* expressing VIM-1 (IHMA 599644) MITC95 μM |
|---|---|---|---|---|---|---|---|
| 1 | 64.78 | 3.765 | 57.56 | 11.96 | 1.489 | 0.7595 | 123.3 |
| 2 | 262.1 | 52.33 | 1907 | | | | |
| 3 | 8.919 | 1.489 | 39.89 | 1.563 | 0.7813 | | 200 |
| 4 | 11.27 | 2.843 | 196.3 | 6.25 | 0.7813 | | >200 |
| 5 | 72.27 | 3.443 | 56.53 | 12.5 | 0.7813 | | >200 |
| 6 | 39.59 | 1.959 | 42.34 | 50 | 1.563 | | >200 |
| 7 | 29.42 | 3.694 | 485.8 | 12.5 | 6.25 | | >200 |
| 8 | 78.24 | 3.99 | 79.77 | 3.125 | 0.3906 | | 200 |
| 9 | 17.24 | 1.484 | 276.9 | 12.5 | 3.125 | | >200 |
| 10 | 62.64 | 3.704 | 986.2 | 6.25 | 3.125 | | >200 |
| 11 | 109 | 6.42 | 465.6 | 12.5 | 1.563 | | >200 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 12 | 41.81 | 3.466 | 95.66 | 6.25 | 3.125 | | 200 |
| 13 | 172.8 | 5.475 | 226.2 | 200 | 1.563 | | 200 |
| 14 | 172.3 | 5.192 | 108.4 | 6.25 | 0.3906 | | 100 |
| 15 | 133.6 | 5.963 | 62.31 | 15.63 | 0.3906 | | 18.75 |
| 16 | 85.47 | 10.48 | 67.06 | 25 | 1.172 | | 75 |
| 17 | 87.48 | 8.569 | 209.1 | 53.13 | 0.7813 | | 100 |
| 18 | 23.39 | 2.038 | 326.1 | 103.1 | 3.906 | | >200 |
| 19 | 1778 | 24.54 | 269.3 | 50 | 0.3906 | | 50 |
| 20 | 331.4 | 20.35 | 362.5 | 18.75 | 1.823 | | 166.7 |
| 21 | 2273 | 63.8 | 563.6 | 100 | 12.89 | | >200 |
| 22 | 31.76 | 1.999 | 26.72 | 6.25 | 1.563 | | 200 |
| 23 | 4.356 | 0.6366 | 9.763 | 2.344 | 2.344 | | 50 |
| 24 | 17.81 | 3.645 | 123.6 | 3.125 | 1.563 | | 150 |
| 25 | 3.60 | <0.6366 | 45.53 | 12.5 | 3.125 | | >200 |
| 26 | 46.22 | 2.43 | 58.39 | 6.25 | 1.56 | | 50 |
| 27 | 13.09 | 2.232 | 77.06 | 3.125 | 3.125 | | 200 |
| 28 | 3.74 | 0.972 | 26.7 | 12.5 | 12.5 | | >200 |
| 29 | 12.12 | 1.494 | 52.8 | 6.25 | 3.125 | | 200 |
| 30 | 1668 | 132.1 | 874.7 | 50 | 3.125 | 1.563 | 200 |
| 31 | 34.39 | 4.96 | 18.83 | 1.56 | 0.781 | | 6.25 |
| 32 | 18.05 | 3.458 | 77.8 | 0.7813 | | 0.5859 | 25 |
| 33 | 70.59 | 16.62 | 832 | 1.172 | | 1.172 | 100 |
| 34 | 3094 | 150.9 | 1438 | 150 | 3.125 | | >200 |
| 35 | 2683 | 137.9 | 1011 | 50 | 1.953 | | 100 |
| 36 | 789.7 | 38.74 | 218.7 | 50 | 1.953 | | 75 |
| 37 | 1211 | 26.43 | 205.9 | 50 | 2.344 | | 200 |
| 38 | 2392 | 280.8 | 5537 | 25 | 0.7813 | | 200 |
| 39 | 2574 | 345.6 | 8139 | 50 | 1.563 | | >200 |
| 40 | 3048 | 42.2 | 560.1 | 200 | 3.125 | | 200 |
| 41 | 246.8 | 30.43 | 1151 | 9.375 | 0.3906 | | 200 |
| 42 | 10520 | 542.7 | 9964 | 200 | 1.563 | 0.7813 | >200 |
| 43 | 2094 | 309.9 | 2462 | 75 | 1.172 | | >200 |
| 44 | 293.4 | 34.59 | 293.8 | 12.5 | 0.3906 | | 37.5 |
| 45 | 1206 | 85.04 | 496.2 | 25 | 0.7813 | | 50 |
| 46 | 302 | 14.54 | 99.07 | 25 | 0.5859 | | 28.13 |
| 47 | 4156 | 344.7 | 5359 | 50 | 0.7813 | | >200 |
| 48 | 644.4 | 19.14 | 181.8 | 33.33 | 0.3906 | | 66.67 |
| 49 | 4047 | 21.58 | 61.68 | 150 | 0.5859 | | 12.5 |
| 50 | 37.87 | 2.709 | 89.13 | 12.5 | 2.344 | | 200 |
| 51 | 27.44 | 2.74 | 4193 | 31.25 | 9.375 | | >200 |
| 52 | 17.91 | 1.705 | 96.61 | 6.25 | 1.563 | | 100 |
| 53 | 73.27 | 4.411 | 37.05 | 6.25 | 0.5859 | | 37.5 |
| 54 | 204.6 | 42.28 | 937.4 | 18.75 | 2.344 | | >200 |
| 55 | 52.7 | 3.48 | 144.2 | 12.5 | 1.953 | | 200 |
| 56 | 13.23 | 1.826 | 43.98 | 14.06 | 2.344 | | 200 |
| 57 | 28.85 | 4.194 | 29.67 | 4.688 | 1.563 | | 25 |
| 58 | 227.2 | 14.54 | 189.6 | 12.5 | 0.5859 | | 100 |
| 59 | 36.12 | 4.379 | 94.95 | 6.25 | 2.344 | | 200 |
| 60 | 16.49 | 3.175 | 27.78 | 4.688 | 3.906 | | 75 |
| 61 | 58 | 6.336 | 62.03 | 6.25 | 0.5859 | | 25 |
| 62 | 211.2 | 8.475 | 186.1 | 100 | 1.563 | | 100 |
| 63 | 1557 | 48.91 | 1322 | 50 | 0.7813 | | 100 |
| 64 | 247.7 | 13.43 | 587.6 | 50 | 1.953 | | 200 |
| 65 | 20000 | 904.6 | 4994 | >200 | 4.688 | | >200 |
| 66 | 140.1 | 1.103 | 29.07 | 18.75 | 0.7813 | | 75 |
| 67 | 910.7 | 2.158 | 56.97 | 75 | 2.344 | | 62.5 |
| 68 | 81.86 | 1.99 | 33.66 | 12.5 | 2.344 | | 75 |
| 69 | 236.7 | 5.055 | 26.4 | 18.75 | 0.7813 | | 25 |
| 70 | 105.1 | 1.995 | 28.9 | 18.75 | 1.563 | | 150 |
| 71 | 78.58 | 1.22 | 14.48 | 18.75 | 0.7813 | | 75 |
| 72 | 48.66 | 0.6366 | 22.16 | 12.5 | 2.344 | | 25 |
| 73 | 156.4 | 6.489 | 66.65 | 18.75 | 1.563 | | 100 |
| 74 | 1610 | 26.44 | 474.8 | 18.75 | 0.9766 | | 50 |
| 75 | 9.964 | 4.569 | 98.08 | 3.906 | 6.25 | | >200 |
| 76 | 42.7 | 17.07 | 243.7 | 6.25 | 6.25 | | >200 |
| 77 | 53.84 | 12.04 | 2905 | 28.13 | 9.375 | | >200 |
| 78 | 202.5 | 19.32 | 147 | 18.75 | 0.7813 | | 100 |
| 79 | 3967 | 48.65 | 60.23 | 150 | 1.563 | | 25 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 80 | 2384 | 81.82 | 541.8 | 50 | 0.3906 | | 25 |
| 81 | 571.2 | 34.65 | 255.4 | 37.5 | 0.9766 | | 37.5 |
| 82 | 22.18 | 1.429 | 7.793 | 3.125 | 1.953 | 0.5859 | 12.5 |
| 83 | 520.3 | 5.974 | 43.59 | 50 | 0.3906 | | 25 |
| 84 | 707.7 | 3.079 | 23.16 | 50 | 0.7813 | | 6.25 |
| 85 | 94.61 | 1.812 | 28.02 | 37.5 | 2.344 | | 150 |
| 86 | 67.44 | 11.03 | 1073 | 3.125 | 0.7813 | | 200 |
| 87 | 907.6 | 95.45 | 2086 | 18.75 | 3.906 | | 200 |
| 88 | 87.3 | 2.983 | 243.3 | 12.5 | 1.953 | | 100 |
| 89 | 318.6 | 54.67 | 1023 | 12.5 | 4.688 | | >200 |
| 90 | 197 | 2.241 | 15.49 | 25 | 0.5859 | | 12.5 |
| 91 | 830.2 | 27.53 | 180 | 50 | 0.7813 | | 75 |
| 92 | 2530 | 41.05 | 208.5 | 50 | 0.3906 | | 37.5 |
| 93 | 330.9 | 3.166 | 89.85 | 18.75 | 0.7813 | | 25 |
| 94 | 164.1 | 6.317 | 234.4 | 12.5 | 2.344 | | 100 |
| 95 | 534 | 1.515 | 374.7 | 106.3 | 3.906 | | >200 |
| 96 | 109 | 1.306 | 3.551 | 15.63 | 1.758 | | 25 |
| 97 | 1572 | 71.14 | 1615 | 18.75 | 0.5859 | | 200 |
| 98 | 319.9 | 2.7 | 29.38 | 7.813 | 0.9766 | 0.7813 | 18.75 |
| 99 | 208 | 6.984 | 104 | 28.13 | 9.375 | | >200 |
| 100 | 145.9 | 29.57 | 940.1 | 14.06 | 7.031 | | >200 |
| 101 | 517 | 40.91 | 111.5 | 14.06 | 3.906 | | 125 |
| 102 | 173.6 | 128.1 | 524.3 | 53.13 | 9.375 | | >200 |
| 103 | 310.6 | 49.44 | 2641 | 15.63 | 9.375 | | >200 |
| 104 | 286.7 | 16.78 | 107.1 | 15.63 | 0.9766 | | 25 |
| 105 | 374.2 | 14.35 | 70.36 | 31.25 | 0.9766 | | 18.75 |
| 106 | 1799 | 9.626 | 961.8 | 62.5 | 3.906 | | 200 |
| 107 | 365.2 | 10.01 | 194 | 15.63 | 3.906 | | 200 |
| 108 | 255.1 | 5.802 | 45.02 | 18.75 | 1.172 | | 37.5 |
| 109 | 38.94 | 2.21 | 0.6366 | 12.89 | 12.5 | | 18.75 |
| 110 | 445.2 | 51.89 | 1364 | 28.13 | 9.375 | | >200 |
| 111 | | | | 9.375 | | 1.172 | 18.75 |
| 113 | 14830 | 15.44 | 313 | 200 | | 3.125 | 50 |
| 115 | 543.5 | 7.811 | 54.43 | 18.75 | 0.25 | | 37.5 |
| 116 | 225.7 | 5.428 | 1238 | 9.375 | | 1.563 | 200 |
| 117 | 133.7 | 5.179 | 134.8 | 6.25 | | 1.172 | 100 |
| 118 | 1330 | 44.2 | 491.7 | 18.75 | | 0.7813 | 50 |
| 119 | 548.4 | 16.21 | 261.4 | 18.75 | | 1.563 | 50 |
| 120 | 777 | 1.415 | 4.994 | 18.75 | | 0.7813 | 4.688 |
| 121 | 372.8 | 7.371 | 187.1 | 25 | | 3.125 | >200 |
| 122 | 63.09 | 3.08 | 248.6 | 4.688 | | 4.688 | >200 |
| 123 | 414.6 | 8.303 | 309.2 | 18.75 | | 1.563 | >200 |
| 124 | 68.93 | 4.341 | 258.6 | 6.25 | | 2.344 | >200 |
| 125 | 326 | 6.55 | 172.1 | 9.375 | | 1.953 | 25 |
| 126 | 864.2 | 166.3 | 14390 | 25 | | 6.25 | >200 |
| 127 | 157.3 | 1.112 | 84.22 | 4.688 | | 1.172 | 37.5 |
| 128 | 452.7 | 7.953 | 1140 | 9.375 | | 1.563 | >200 |
| 129 | 176 | 3.707 | 37.88 | 9.375 | | 0.7813 | 12.5 |
| 130 | 267.2 | 10.6 | 41.8 | 9.375 | | 1.172 | 37.5 |
| 131 | 187.4 | 0.7001 | 16.94 | 3.125 | | 0.7813 | 3.125 |
| 132 | 755.1 | 2.727 | 26.7 | 12.5 | | 1.172 | 6.25 |
| 133 | 4922 | 21.55 | 107.8 | 37.5 | | 0.3906 | 6.25 |
| 134 | 22.62 | 0.2802 | 11.08 | 0.7813 | | 0.5859 | 3.125 |
| 135 | 62.61 | 4.471 | 61.85 | 1.172 | | 1.172 | 18.75 |
| 136 | 1692 | 24.79 | 150.1 | 25 | | 1.563 | 37.5 |
| 137 | 2534 | 30.71 | 560.8 | 25 | | 1.172 | 25 |
| 138 | 354.3 | 6.78 | 166.3 | 37.5 | | 1.563 | >200 |
| 139 | 98.37 | 0.6366 | 5.781 | 6.25 | | 0.1953 | 12.5 |
| 140 | 160.4 | 7.677 | 388.2 | 6.25 | | 0.5859 | 50 |
| 141 | 2335 | 61.54 | 2582 | 37.5 | | 0.7813 | 200 |
| 142 | 80.95 | 8.197 | 418.8 | 6.25 | | 1.563 | >200 |
| 143 | 98.46 | 20.74 | 380 | 4.688 | | 0.7813 | 200 |
| 144 | 4500 | 121.1 | 1540 | 200 | | 3.125 | >200 |
| 145 | 2410 | 190.6 | 6409 | 75 | 0.7813 | | >200 |
| 146 | 766.4 | 65.53 | 2796 | 50 | 1.172 | | >200 |
| 147 | 103.2 | 16.43 | 1097 | 18.75 | 3.125 | | >200 |
| 148 | 550.4 | 131 | 3076 | 50 | 6.25 | | >200 |
| 149 | 492.9 | 23.67 | 861.4 | 6.25 | | 1.563 | 150 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 150 | 1940 | 147.6 | 5650 | 6.25 | | 0.7813 | 200 |
| 151 | 31.8 | 1.25 | 31.46 | 1.563 | | 1.172 | 37.5 |
| 152 | 252.4 | 14.22 | 91.39 | 12.5 | | 4.688 | 200 |
| 153 | 71.28 | 8.253 | 251.7 | 2.344 | | 4.688 | >200 |
| 154 | 10.76 | 3.28 | 80.79 | 0.3906 | | 2.344 | 100 |
| 155 | 92.66 | 2.999 | 16.17 | 2.344 | | 3.125 | 75 |
| 156 | 507.9 | 13.07 | 390.8 | 9.375 | | 0.5859 | 50 |
| 157 | 560.8 | 28.66 | 1048 | 6.25 | | 0.3906 | 50 |
| 158 | 387.1 | 15.96 | 351.9 | 12.5 | | 3.125 | 200 |
| 159 | 525.9 | 33.99 | 3390 | 18.75 | | 3.125 | >200 |
| 160 | 251 | 8.999 | 279.6 | 9.375 | | 0.7813 | 75 |
| 161 | 306.4 | 20.1 | 874.3 | 6.25 | | 1.563 | 150 |
| 162 | 571.3 | 18.93 | 690.5 | 12.5 | | 1.563 | 200 |
| 163 | 326.7 | 17.7 | 437.4 | 12.5 | | 3.125 | >200 |
| 164 | 5.498 | 2.934 | 50.63 | 0.3906 | | 1.563 | 200 |
| 165 | 213.6 | 1.243 | 11.59 | 9.375 | | 0.5859 | 37.5 |
| 166 | 74.5 | 6.892 | 18.82 | 3.906 | | 2.344 | 100 |
| 167 | 260.4 | 12.36 | 1030 | 9.375 | | 1.563 | 200 |
| 168 | 864.9 | 39.38 | 50.27 | 6.25 | | 0.25 | 2.172 |
| 169 | 111 | 3.74 | 57.59 | 3.125 | | 2.344 | 50 |
| 170 | 576.7 | 21.92 | 3470 | 9.375 | | 1.563 | 200 |
| 171 | 118.6 | 8.564 | 128.1 | 6.25 | | 2.344 | 25 |
| 172 | 720.3 | 16.52 | 420.7 | 18.75 | 4.688 | | 100 |
| 173 | 148.9 | 4.392 | 85.64 | 6.25 | 4.688 | | >200 |
| 174 | 402.8 | 4.543 | 262.4 | 12.5 | 2.344 | | 100 |
| 175 | 12370 | 552.4 | 3087 | 37.5 | 0.7813 | | 75 |
| 176 | 72.78 | 6.432 | 148.3 | | | | |
| 177 | 667.7 | 12.83 | 733 | 37.5 | 6.25 | | >200 |
| 178 | 1023 | 28.43 | 65.53 | 12.5 | | 0.25 | 9.375 |
| 179 | 405.9 | 10.82 | 1439 | 37.5 | | 3.125 | >200 |
| 180 | 112.6 | 9.911 | 22.43 | 3.125 | 0.3906 | 0.5 | 4.688 |
| 181 | 374.8 | 27.87 | 184 | 12.5 | 1.953 | 0.6727 | 18.75 |
| 182 | 348.1 | 32.41 | 91.42 | 100 | 4.688 | | 200 |
| 183 | 339.3 | 11.51 | 172.7 | 50 | 4.688 | | 75 |
| 184 | 601.5 | 66.91 | 163.7 | 37.5 | 0.5859 | | 25 |
| 185 | 1478 | 135 | 2021 | 75 | 2.344 | | >200 |
| 186 | 563.7 | 97.14 | 1859 | 100 | 18.75 | | >200 |
| 187 | 28.93 | 2.809 | 149.6 | 25 | 15.63 | | >200 |
| 188 | 767.7 | 36.5 | 4127 | 37.5 | 2.344 | | >200 |
| 189 | 704.4 | 23.25 | 685.2 | 37.5 | 1.563 | | 100 |
| 190 | 3150 | 231.8 | 1300 | 100 | 10.42 | | >200 |
| 191 | 75.98 | 7.747 | 45.87 | 15.63 | 9.375 | | 75 |
| 192 | 439.1 | 36.44 | 98.14 | 50 | 1.953 | | 50 |
| 193 | 2655 | 373.7 | 813 | 150 | 0.7813 | | 37.5 |
| 194 | 2272 | 248.1 | 906.8 | 75 | 0.7813 | | 62.5 |
| 195 | 2629 | 78.54 | 290.8 | 50 | 0.3906 | | 12.5 |
| 196 | 1590 | 45.61 | 50.31 | 125 | 1.953 | | 25 |
| 197 | 581.7 | 130.1 | 70.21 | 1.563 | 0.3906 | | 1.563 |
| 198 | 1166 | 68.38 | 101.1 | 3.125 | 0.3906 | | 2.344 |
| 199 | 324.9 | 12.96 | 24.79 | 6.25 | 0.3906 | | 3.125 |
| 200 | 962.9 | 30.23 | 35.64 | 75 | 2.083 | | 50 |
| 201 | 1447 | 66.21 | 67.11 | 50 | 0.7813 | | 18.75 |
| 202 | 23.8 | 11.51 | 118.2 | 2.344 | 0.3906 | | 25 |
| 203 | 1426 | 18.62 | 43.57 | 50 | 0.3906 | | 9.375 |
| 204 | 2855 | 59.05 | 237.8 | 37.5 | 0.3906 | | 12.5 |
| 205 | 112.9 | 14.3 | 24.13 | 6.25 | 0.3906 | | 9.375 |
| 206 | 91.45 | 11.42 | 14.18 | 4.125 | 0.1953 | 0.375 | 3.125 |
| 207 | 373.3 | 35.11 | 200.9 | 12.5 | 0.1953 | 0.5 | 18.75 |
| 208 | 588.9 | 94.73 | 568.5 | 37.5 | 3.646 | | >200 |
| 209 | 516.4 | 26.33 | 5.454 | 75 | 2.604 | | 37.5 |
| 210 | 420.9 | 11.76 | 25.48 | 25 | 0.5208 | | 15.63 |
| 211 | 537.1 | 45.57 | 242 | 31.25 | 0.3906 | | 200 |
| 212 | 414.6 | 7.909 | 13.08 | 18.75 | 0.3906 | | 3.125 |
| 213 | 564.3 | 50.98 | 62.38 | 37.5 | 1.042 | | 100 |
| 214 | 98.4 | 13.21 | 128.7 | 3.344 | 0.1953 | 0.375 | 37.5 |
| 215 | 1856 | 90.92 | 493.9 | 18.75 | 0.1953 | 0.25 | 12.5 |
| 216 | 456.3 | 40.35 | 96.66 | 12.5 | | 1.172 | 18.75 |
| 217 | 480.6 | 43.03 | 49.29 | 12.5 | | 4.688 | 150 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 218 | 484.1 | 101.9 | 105.8 | 25 | | 12.5 | 100 |
| 219 | 10410 | 1061 | 457.6 | 37.5 | | 4.688 | 12.5 |
| 220 | 2387 | 22.79 | 233.7 | 75 | | 12.5 | >200 |
| 221 | 6169 | 251.1 | 6175 | 100 | | 4.688 | 200 |
| 222 | 20000 | 5150 | 793.8 | 75 | | 12.5 | 12.5 |
| 223 | 1305 | 157.3 | 583.4 | 25 | | 4.688 | 200 |
| 224 | 1093 | 246.7 | 1181 | 18.75 | | 4.688 | 200 |
| 225 | 76.16 | 142.4 | 225.8 | 2.344 | | 9.375 | 50 |
| 226 | 3869 | 481.4 | 709.7 | 50 | | 6.25 | 12.5 |
| 227 | 7070 | 888.4 | 260.5 | 75 | | 3.125 | 6.25 |
| 228 | 3207 | 371.9 | 342.7 | 37.5 | | 1.563 | 37.5 |
| 229 | 466.3 | 204.4 | 2.221 | 50 | | 12.5 | 6.25 |
| 230 | 796.7 | 206.1 | 163.6 | 18.75 | | 1.563 | 37.5 |
| 231 | 422.7 | 10.79 | 325.7 | 18.75 | | 4.688 | >200 |
| 232 | 7638 | 892.3 | 166.2 | >200 | | 50 | 150 |
| 233 | 195.2 | 60.92 | 97.6 | 6.25 | | 0.7813 | 37.5 |
| 234 | 1448 | 24.46 | 1171 | 100 | | 4.688 | >200 |
| 235 | 3435 | 141.8 | 1728 | 200 | | 12.5 | >200 |
| 236 | 222.9 | 38.59 | 187.6 | 25 | | 18.75 | >200 |
| 237 | 580.8 | 101.6 | 239.1 | 125 | | 18.75 | >200 |
| 238 | 188.5 | 30.77 | 96.89 | 9.375 | | 3.125 | 125 |
| 239 | 3711 | 382.9 | 945.1 | 50 | | 1.563 | 50 |
| 240 | 3406 | 418.4 | 937.8 | 37.5 | | 1.172 | 25 |
| 241 | 335.1 | 67.66 | 774.2 | 12.5 | | 1.563 | >200 |
| 242 | 1115 | 102.7 | 270.2 | 25 | | 0.3906 | 6.25 |
| 243 | 1509 | 67.13 | 204.2 | 100 | | 18.75 | >200 |
| 244 | 681.9 | 51.19 | 125.4 | 18.75 | | 1.563 | 37.5 |
| 245 | 9779 | 266 | 460.1 | 50 | 0.3906 | | 12.5 |
| 246 | 2805 | 30.22 | 78.28 | 150 | | 0.5859 | 12.5 |
| 247 | 479.3 | 14.62 | 115.7 | 25 | 0.3906 | | 37.5 |
| 248 | 134 | 4.491 | 132 | 4.688 | | 0.1875 | 12.5 |
| 249 | 104.4 | 7.548 | 86.98 | 3.125 | 0.7813 | | 50 |
| 250 | 109.1 | 18.02 | 194.7 | 4.688 | 0.7813 | | 100 |
| 251 | 42.51 | 5.852 | 71.64 | 6.25 | 0.7813 | | 200 |
| 252 | 111500 | 591.1 | 156100 | | | | |
| 253 | 46290 | 440.1 | 170000 | >200 | 3.125 | | >200 |
| 254 | 20000 | 1052 | 20000 | >200 | 3.125 | | >200 |
| 255 | 20000 | 699 | 20000 | >200 | 25 | | >200 |
| 256 | 6260 | 229.7 | 8441 | 100 | 0.7813 | | >200 |
| 257 | 8277 | 546.6 | 9229 | 150 | 1.563 | | >200 |
| 258 | 887.6 | 12.87 | 147.1 | 37.5 | 1.302 | | 15.63 |
| 259 | 10.07 | 10.96 | 3.1 | 1 | 1.584 | | 3.125 |
| 260 | 6.723 | 11.17 | 0.7966 | 1.563 | 6.25 | | 6.25 |
| 261 | 1.717 | 6.586 | 10.21 | 1.563 | | 6.25 | 100 |
| 262 | 72.42 | 31.46 | 28.15 | 6.25 | | 3.125 | 25 |
| 263 | 21.02 | 3.275 | 11.46 | 0.7813 | | 0.7813 | 18.75 |
| 264 | 16.95 | 4.607 | 4.397 | 0.3828 | | 0.04688 | 1.781 |
| 265 | 6.932 | 2.653 | 1.263 | 0.4271 | | 0.125 | 4.775 |
| 266 | 12.56 | 2.082 | 0.6886 | 0.7813 | | 3.125 | 9.375 |
| 267 | 2.005 | 1.815 | 2.955 | 0.2552 | | 0.7383 | 6.25 |
| 268 | 1.639 | 2.012 | 0.898 | 0.25 | | 2.229 | 9.375 |
| 269 | 1.429 | 1.213 | 0.317 | 0.3125 | | 0.7383 | 1.969 |
| 270 | 4.864 | 2.559 | 1.684 | 0.3906 | | 1.563 | 6.25 |
| 271 | 23.44 | 11.38 | 11.7 | 0.5859 | | 0.3906 | 2.344 |
| 272 | 49.04 | 7.168 | 5.544 | 1.563 | | 0.7813 | 0.7813 |
| 273 | 3.213 | 0.5809 | 0.1648 | 0.3906 | | 4.688 | 6.25 |
| 274 | 0.6366 | 0.6366 | 0.6366 | 0.1953 | | 0.7813 | 4.688 |
| 275 | 6.702 | 3.679 | 0.6366 | 0.7813 | | 3.125 | 9.375 |
| 276 | 8.749 | 5.507 | 3.385 | 0.3906 | | 0.7813 | 1.563 |
| 277 | 5270 | 295.9 | 1226 | 125 | 12.5 | | >200 |
| 278 | 535.8 | 8.497 | 79.1 | 37.5 | 3.125 | | 100 |
| 279 | 2166 | 32.34 | 183.5 | 25 | 0.5859 | | 75 |
| 280 | 15.83 | 1.44 | 20.41 | 6.25 | | 0.5859 | 3.125 |
| 281 | 42.86 | 0.3417 | 12.16 | 3.125 | | 0.7813 | 12.5 |
| 282 | 265.9 | 21.52 | 182.9 | 1.563 | | 0.7813 | 12.5 |
| 283 | 500.1 | 32.99 | 307.8 | 2.344 | | 0.5859 | 12.5 |
| 284 | 102.2 | 12.66 | 55.52 | 1.563 | | 0.7813 | 4.688 |
| 285 | 25.08 | 2.825 | 18.02 | 0.7813 | | 0.3906 | 3.125 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 286 | 204.5 | 6.145 | 12.73 | 3.125 | | 0.7813 | 3.125 |
| 287 | 159 | 0.7338 | 33.98 | 18.75 | | 9.375 | 37.5 |
| 288 | 88.86 | 1.307 | 9.778 | 9.375 | | 1.563 | 75 |
| 289 | 120.6 | 13.54 | 452.1 | 31.25 | 3.125 | | >200 |
| 290 | 19.71 | 0.6366 | 34.29 | 19.53 | 3.516 | | >200 |
| 291 | 98.64 | 1.472 | 221.7 | 4.688 | 3.906 | | >200 |
| 292 | 416 | 3.651 | 192.6 | 18.75 | 3.516 | | >200 |
| 293 | 86.54 | 1.023 | 232.4 | 9.375 | 1.953 | | >200 |
| 294 | 29.36 | 0.6366 | 192.7 | 0.6406 | 0.3802 | | 37.5 |
| 295 | 16.06 | 0.6366 | 126.4 | 1.563 | 1.953 | | >200 |
| 296 | 54.84 | 0.6366 | 127.4 | 3.125 | 1.953 | | >200 |
| 297 | 20000 | 2479 | 20000 | >200 | 12.5 | | >200 |
| 298 | 776 | 71.66 | 250.6 | 8.333 | 0.1953 | 0.04688 | 12.5 |
| 299 | 443.9 | 11.76 | 110.4 | 18.75 | 0.1953 | | 37.5 |
| 300 | 372.7 | 37.21 | 31.55 | 12.5 | 1.172 | | 9.375 |
| 301 | 1383 | 8.195 | 281.9 | 37.5 | 0.7813 | | 25 |
| 302 | 110.5 | 5.851 | 38.47 | 3.906 | 0.3906 | | 150 |
| 303 | 58.98 | 5.063 | 44.57 | 2.344 | 0.9766 | | 18.75 |
| 304 | 50.27 | 29.19 | 102.7 | 7.031 | 6.25 | | >200 |
| 305 | 332.6 | 50.22 | 102.6 | 4.688 | 1.953 | | 18.75 |
| 306 | 3737 | 104.4 | 299.9 | 50 | 1.172 | | 25 |
| 307 | 4887 | 173.9 | 96.18 | 50 | 1.172 | | 12.5 |
| 308 | 192.1 | 11.33 | 164.2 | 9.375 | 2.344 | | 75 |
| 309 | 326.4 | 1.347 | 31.5 | 8.333 | 0.3906 | 0.7813 | 5.729 |
| 310 | 419.8 | 0.9943 | 45.98 | 9.375 | 0.1953 | 0.02344 | 4.167 |
| 311 | 128.9 | 1.108 | 8.162 | 3.906 | 0.1953 | 0.7813 | 4.688 |
| 312 | 107.4 | 0.9498 | 6.495 | 5.469 | 0.3906 | 0.5859 | 3.125 |
| 313 | 66.94 | 0.7696 | 13.44 | 3.906 | 0.4635 | 0.5859 | 7.031 |
| 314 | 291.7 | 3.652 | 26.9 | 5.469 | 0.1953 | 0.3906 | 3.906 |
| 315 | 510.1 | 11.6 | 33.39 | 4.688 | 0.3906 | | 3.125 |
| 316 | 69.27 | 5.109 | 67.73 | 2.344 | | 0.9766 | 12.5 |
| 317 | 359.9 | 5.384 | 46.03 | 9.375 | 0.125 | 0.1875 | 18.75 |
| 318 | 295.4 | 2.134 | 24.6 | 6.25 | 0.1953 | 0.0625 | 4.688 |
| 319 | 62.16 | 0.5506 | 0.8864 | 3.906 | 0.3906 | 3.906 | 3.906 |
| 320 | 294.3 | 14.41 | 35.92 | 9.375 | 0.6836 | | 6.25 |
| 321 | 93.53 | 19.25 | 199.3 | 6.25 | 1.563 | | 50 |
| 322 | 321.3 | 36.48 | 3649 | 25 | 7.813 | | 200 |
| 323 | 70.58 | 7.692 | 150.7 | 12.5 | 2.344 | | 200 |
| 324 | 1022 | 104.8 | 404.3 | 32.81 | 13.28 | | 37.5 |
| 325 | 228.3 | 1.298 | 13.12 | 25 | 3.125 | | 37.5 |
| 326 | 370 | 3.648 | 135.5 | 18.75 | 3.32 | | 37.5 |
| 327 | 534.1 | 37.73 | 215.8 | 12.5 | 0.7813 | | 100 |
| 328 | 324.9 | 20.44 | 473.4 | 6.25 | | 1.563 | 125 |
| 329 | 87.07 | 8.257 | 682.7 | 1.563 | | 0.7813 | 200 |
| 330 | 118 | 12.49 | 401.3 | 4.688 | | 1.563 | 50 |
| 331 | 392 | 30.62 | 1185 | 6.25 | | 1.172 | 150 |
| 332 | 192.5 | 11.49 | 554 | 3.125 | | 0.5859 | 100 |
| 333 | 185.7 | 10.65 | 335.1 | 4.688 | | 0.7813 | 50 |
| 334 | 385 | 10.59 | 129 | 3.125 | | 0.3906 | 9.375 |
| 335 | 228.2 | 14.99 | 226.7 | 3.125 | | 0.3906 | 25 |
| 336 | 379.3 | 34.04 | 634 | 4.688 | | 0.7813 | 100 |
| 337 | 69.83 | 4.379 | 321.1 | 2.344 | | 0.3906 | 75 |
| 338 | 75.43 | 4.526 | 151.5 | 3.125 | | 0.5859 | 25 |
| 339 | 42.33 | 4.537 | 610.7 | 1.563 | | 0.5859 | >200 |
| 340 | 90.24 | 5.137 | 158.4 | 1.563 | | 0.3906 | 25 |
| 341 | 22.13 | 2.938 | 786.3 | 1.172 | | 0.7813 | >200 |
| 342 | 46.04 | 4.643 | 80.44 | 0.7813 | | 3.125 | 25 |
| 343 | 372.9 | 24.73 | 1179 | 9.375 | | 1.563 | 100 |
| 344 | 241.6 | 32.78 | 585.2 | 4.688 | | 2.344 | 100 |
| 345 | 213.4 | 18.49 | 269.1 | 4.688 | | 1.563 | 50 |
| 346 | 232.1 | 11.74 | 407.6 | 2.344 | | 1.563 | 150 |
| 347 | 184.6 | 12.2 | 844.4 | 3.125 | | 2.344 | 200 |
| 348 | 1330 | 25.41 | 850.8 | 9.375 | | 1.172 | 75 |
| 349 | 61.08 | 4.32 | 636.6 | 2.344 | | 6.25 | >200 |
| 350 | 39.69 | 5.799 | 246.2 | 1.563 | | 1.172 | >200 |
| 351 | 331.8 | 18.1 | 414 | 3.125 | | 1.563 | 150 |
| 352 | 547.4 | 38.02 | 916.3 | 6.25 | | 1.563 | >200 |
| 353 | 28.02 | 4.098 | 689.2 | 1.172 | | 2.344 | 100 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 354 | 16.35 | 7.325 | 324.7 | 2.344 | | 2.344 | 200 |
| 355 | 466.7 | 14 | 868.7 | 4.688 | | 1.563 | 150 |
| 356 | 1536 | 24.14 | 646 | 12.5 | | 1.563 | 75 |
| 357 | 181.6 | 12.54 | 286.9 | 4.688 | | 3.125 | 25 |
| 358 | 287.8 | 32.83 | 386.8 | 4.688 | | 3.125 | 75 |
| 359 | 103.9 | 13.01 | 1865 | 3.125 | | 4.688 | >200 |
| 360 | 37.59 | 1.518 | 231.7 | 2.344 | | 2.344 | >200 |
| 361 | 138.9 | 12.94 | 271.4 | 3.125 | | 2.344 | 25 |
| 362 | 115.8 | 11.3 | 493.8 | 3.125 | | 0.7813 | 75 |
| 363 | 233 | 21.45 | 494.8 | 6.25 | | 3.125 | 100 |
| 364 | 100.1 | 9.17 | 211.7 | 3.125 | | 1.563 | 25 |
| 365 | 52.1 | 5.367 | 390.4 | 2.344 | | 1.563 | 75 |
| 366 | 257.1 | 18.23 | 1543 | 3.125 | | 1.172 | 150 |
| 367 | 60.28 | 7.525 | 1003 | 3.125 | | 3.125 | 200 |
| 368 | 417 | 23.38 | 1676 | 9.375 | | 1.563 | >200 |
| 369 | 727.6 | 25.2 | 667.4 | 12.5 | | 3.125 | 200 |
| 370 | 45.83 | 7.346 | 624.2 | 1.563 | | 1.563 | 200 |
| 371 | 78.29 | 8.504 | 370.1 | 2.344 | | 0.7813 | 100 |
| 372 | 15.7 | 4.914 | 469.8 | 1.563 | | 7.813 | >200 |
| 373 | 246.8 | 11.26 | 241 | 3.125 | | 1.563 | 50 |
| 374 | 263.5 | 16.03 | 277.2 | 3.125 | | 0.7813 | 37.5 |
| 375 | 97.6 | 6.127 | 533.3 | 3.125 | | 1.563 | >200 |
| 376 | 96.62 | 14.45 | 50.39 | 4.688 | | 2.344 | 15.63 |
| 377 | 73.73 | 5.269 | 256.4 | 3.125 | | 1.563 | 200 |
| 378 | 261.9 | 24.58 | 406.8 | 6.25 | | 3.125 | 50 |
| 379 | 318.3 | 27.28 | 639 | 4.688 | | 1.563 | 200 |
| 380 | 335.2 | 22.19 | 263.1 | 4.688 | | 1.563 | 62.5 |
| 381 | 25.42 | 2.246 | 356.8 | 0.7813 | | 1.563 | 50 |
| 382 | 212.3 | 12.77 | 220.4 | 3.125 | | 1.563 | 50 |
| 383 | 51.62 | 4.664 | 269.2 | 1.563 | | 1.563 | 200 |
| 384 | 292.7 | 13.63 | 224.9 | 4.688 | | 1.953 | 50 |
| 385 | 498.6 | 12.52 | 356.6 | 6.25 | | 1.563 | 50 |
| 386 | 32.05 | 3.228 | 120 | 1.563 | | 6.25 | >200 |
| 387 | 144.9 | 10.61 | 444.6 | 3.125 | | 2.344 | 100 |
| 388 | 48.57 | 4.275 | 272.5 | 1.563 | | 1.563 | 200 |
| 389 | 63.96 | 3.333 | 146 | 2.344 | | 1.563 | 75 |
| 390 | 482.8 | 12.16 | 221.7 | 6.25 | | 0.7813 | 62.5 |
| 391 | 348.1 | 18.85 | 400.6 | 2.344 | | 1.172 | 50 |
| 392 | 393.7 | 7.877 | 454.9 | 3.125 | | 2.344 | 75 |
| 393 | 337.7 | 10.82 | 508.6 | 4.688 | | 1.563 | 200 |
| 394 | 195.4 | 11.3 | 657.9 | 3.125 | | 2.344 | >200 |
| 395 | 225.7 | 14.43 | 343 | 3.125 | | 1.563 | 100 |
| 396 | 22.39 | 3.206 | 180.9 | 1.172 | | 1.172 | 100 |
| 397 | 37.26 | 3.926 | 246.1 | 9.375 | 3.906 | | >200 |
| 398 | 1214 | 42.99 | 312 | 50 | 1.563 | | 100 |
| 399 | 15100 | 117.3 | 12420 | >200 | 3.906 | | >200 |
| 400 | 166.1 | 1.639 | 18.45 | 12.5 | | 0.25 | 6.25 |
| 401 | 645.8 | 7.314 | 7.569 | 6.25 | | 0.09375 | 0.8906 |
| 402 | 389.4 | 8.087 | 348.8 | 6.25 | | 0.3906 | 25 |
| 403 | 184 | 2.338 | 15.45 | 4.688 | | 0.125 | 6.25 |
| 404 | 71.38 | 0.8173 | 5.411 | 1.708 | | 0.0625 | 2.563 |
| 405 | 67.64 | 4.231 | 16.87 | 1.563 | | 1.563 | 62.5 |
| 406 | 250.4 | 1.652 | 1.736 | 6.25 | | 1.172 | 3.125 |
| 407 | 114.7 | 25.75 | 133 | 3.125 | | 3.125 | >200 |
| 408 | 84.28 | 1.376 | 14.91 | 4.688 | | 0.3906 | 75 |
| 409 | 445.3 | 26.91 | 236.9 | 12.5 | | 1.563 | >200 |
| 410 | 107.3 | 4.108 | 19.24 | 3.125 | | 0.5859 | 18.75 |
| 411 | 102.3 | 4.836 | 27.76 | 3.125 | | 0.7813 | 25 |
| 412 | 1389 | 25.9 | 25.79 | 25 | | 0.3906 | 3.125 |
| 413 | 340.4 | 2.125 | 2.085 | 9.375 | | 0.5859 | 4.688 |
| 414 | 176.9 | 6.014 | 19.86 | 4.688 | | 2.344 | 18.75 |
| 415 | 32.3 | 0.5796 | 1.099 | 1.172 | | 0.5859 | 3.125 |
| 416 | 56.47 | 2.416 | 13.72 | 6.25 | | 2.344 | 25 |
| 417 | 49.78 | 0.7597 | 8.533 | 2.344 | | 1.953 | 9.375 |
| 418 | 118.2 | 1.184 | 12.96 | 6.25 | | 0.3906 | 6.25 |
| 419 | 1037 | 51.9 | 468.6 | 25 | | 0.25 | 25 |
| 420 | 217.2 | 4.742 | 30.71 | 9.375 | | 1.563 | 18.75 |
| 421 | 18.84 | 0.291 | 2.298 | 25 | | 3.125 | >200 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 422 | 55.95 | 1.305 | 22.59 | 25 | | 3.125 | 100 |
| 423 | 1.288 | 0.3783 | 0.7105 | 0.125 | | 1.086 | 3.125 |
| 424 | 80.77 | 18.89 | 32.7 | 1.563 | | 0.7813 | 15.63 |
| 425 | 15.95 | 13.52 | 4.067 | 0.5859 | | 0.3906 | 1.563 |
| 426 | 353.2 | 9.281 | 259.9 | 9.375 | | 0.4063 | 25 |
| 427 | 108.9 | 29.79 | 450.1 | 4.688 | | 0.25 | 75 |
| 428 | 345.2 | 0.6829 | 17.26 | 6.25 | | 0.0625 | 1.531 |
| 429 | 498.8 | 2.585 | 30.03 | 6.25 | | 0.0625 | 2.344 |
| 430 | 6.377 | 52.29 | 50.83 | 0.3906 | | 1.563 | 3.125 |
| 431 | 3.745 | 17.94 | 0.4318 | 0.125 | | 2.563 | 1.531 |
| 432 | 11.67 | 47.86 | 4.721 | 0.3906 | | 6.25 | 18.75 |
| 433 | 0.5632 | 0.8747 | 0.9836 | 0.1875 | | 0.6406 | 0.7656 |
| 434 | 1.853 | 1.783 | 0.1754 | 0.09375 | | 0.543 | 0.7656 |
| 435 | 11.07 | 12.04 | 2.374 | 0.25 | | 1.281 | 3.125 |
| 436 | 12.85 | 9.318 | 3.043 | 0.2552 | | 0.375 | 0.8542 |
| 437 | 7.823 | 7.947 | 8.002 | 0.3906 | | 0.3906 | 3.125 |
| 438 | 4.05 | 3.674 | 10.75 | 0.25 | | 0.125 | 2.563 |
| 439 | 20.58 | 11.88 | 4.05 | 0.5859 | | 0.7813 | 1.563 |
| 440 | 3.371 | 3.912 | 0.3572 | 0.0625 | | 0.25 | 0.7656 |
| 441 | 22.05 | 11.3 | 0.8382 | 1.563 | | 1.172 | 0.7813 |
| 442 | 16.54 | 11.78 | 0.2676 | 0.5859 | | 1.172 | 0.7813 |
| 443 | 1.341 | 0.9092 | 0.4972 | 0.09375 | | 0.7734 | 0.8906 |
| 444 | 3.275 | 2.495 | 1.349 | 0.3906 | | 2.344 | 4.688 |
| 445 | 1.169 | 1.276 | 1.339 | 0.125 | | 1.547 | 4.688 |
| 446 | 19.35 | 15.39 | 0.252 | 0.3906 | | 1.563 | 1.563 |
| 447 | 4.263 | 7.129 | 0.1712 | 0.125 | | 1.086 | 0.8906 |
| 448 | 2.165 | 2.095 | 0.9617 | 0.1953 | | 3.125 | 6.25 |
| 449 | 0.5371 | 0.6534 | 0.8151 | 0.1953 | | 0.7813 | 6.25 |
| 450 | 1.284 | 1.623 | 1.8 | 0.03125 | | 18.75 | 75 |
| 451 | 47.08 | 0.9766 | 0.4764 | 3.125 | | 1.563 | 3.125 |
| 452 | 124.8 | 1.221 | 1.984 | 9.375 | | 1.563 | 4.688 |
| 453 | 110.7 | 6.885 | 0.6651 | 12.5 | | 4.688 | 6.25 |
| 454 | 67.01 | 111.1 | 19.63 | 12.5 | | 100 | 200 |
| 454 | 1.925 | 2.019 | 1.892 | 0.0625 | | 0.7656 | 6.25 |
| 455 | 6.295 | 3.374 | 2.835 | 0.3906 | | 0.5859 | 1.563 |
| 456 | 9.795 | 4.583 | 3.441 | 0.5859 | | 0.5859 | 1.172 |
| 457 | 3.047 | 1.102 | 0.8031 | 0.1953 | | 0.3906 | 1.172 |
| 458 | 2.386 | 22.14 | 2.125 | 0.125 | | 3.125 | 3.125 |
| 459 | 86.63 | 1116 | 112.2 | 1.172 | | 6.25 | 3.125 |
| 460 | 16.58 | 3.973 | 10.38 | 0.3906 | | 0.5859 | 1.563 |
| 461 | 4.068 | 1.918 | 1.667 | 1.563 | | 1.563 | 4.688 |
| 462 | 11.52 | 3.803 | 8.131 | 1.563 | | 0.7813 | 18.75 |
| 463 | 6.579 | 4.415 | 4.419 | 0.1953 | | 0.7813 | 0.7813 |
| 464 | 18.74 | 3.821 | 1.949 | 1.563 | | 0.7813 | 1.563 |
| 465 | 3.305 | 2.703 | 1.635 | 3.125 | | 3.125 | 12.5 |
| 466 | 54.63 | 10.54 | 3.723 | 1.563 | | 0.7813 | 1.563 |
| 467 | 34.78 | 10.19 | 4.751 | 1.563 | | 0.7813 | 1.563 |
| 468 | 13.49 | 9.948 | 3.813 | 1.563 | | 0.7813 | 1.563 |
| 469 | 29.72 | 10.65 | 7.655 | 1.563 | | 0.7813 | 1.563 |
| 470 | 3.233 | 27.02 | 101.1 | 1.563 | | 0.7813 | 12.5 |
| 471 | 8.684 | 2.722 | 2.048 | 1.563 | | 0.7813 | 1.563 |
| 472 | 0.661 | 0.5053 | 13.42 | 0.7813 | | 1.172 | 75 |
| 473 | 7.296 | 4.47 | 1.416 | 0.5859 | | 4.688 | 4.688 |
| 474 | 3.913 | 0.5226 | 0.5489 | 0.4453 | | 0.09375 | 1.531 |
| 475 | 13.67 | 5.126 | 1.919 | 0.7813 | | 0.7813 | 3.125 |
| 476 | 3.982 | 1.791 | 0.2627 | 0.5859 | | 1.563 | 1.563 |
| 477 | 6.378 | 1.009 | 0.722 | 0.5859 | | 0.7813 | 6.25 |
| 478 | 88.07 | 24.6 | 0.6388 | 2.344 | | 0.7813 | 0.7813 |
| 479 | 30.32 | 6.658 | 0.373 | 1.563 | | 0.3906 | 0.7813 |
| 480 | 9.143 | 0.8705 | 0.2643 | 0.7813 | | 0.7813 | 2.344 |
| 481 | 7.106 | 1.462 | 0.4205 | 0.543 | | 0.125 | 1.922 |
| 482 | 7.239 | 0.8886 | 0.1941 | 3.125 | | 1.563 | 3.125 |
| 483 | 2.122 | 0.7548 | 0.2163 | 25 | | 6.25 | 12.5 |
| 484 | 6.585 | 1.22 | 0.322 | 0.3828 | | 0.25 | 1.708 |
| 485 | 4.977 | 1.568 | 0.1965 | 12.5 | | 3.125 | 6.25 |
| 486 | 1.191 | 0.1918 | 0.1341 | 0.1367 | | 1.208 | 4.531 |
| 487 | 56.37 | 102.5 | 70.38 | 1.563 | | 1.563 | 25 |
| 488 | 18.79 | 7.896 | 3.445 | 0.7813 | | 1.563 | 4.688 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 489 | 20.7 | 19.63 | 9.83 | 0.7813 | | 1.563 | 9.375 |
| 490 | 5.607 | 2.569 | 2.351 | 0.375 | | 1.281 | 9.375 |
| 491 | 1.107 | 0.4347 | 0.5047 | 0.0625 | | 0.6406 | 3.792 |
| 492 | 15.99 | 17.27 | 12.3 | 0.3906 | | 3.125 | 12.5 |
| 493 | 4.499 | 1.694 | 0.1333 | 0.3906 | | 1.563 | 3.125 |
| 494 | 12.97 | 4.429 | 0.4271 | 1.172 | | 0.3906 | 1.563 |
| 495 | 4.26 | 1.866 | 22.09 | 0.5859 | | 2.344 | 25 |
| 496 | 1.091 | 0.5061 | 0.3968 | 0.3906 | | 1.172 | 3.125 |
| 497 | 25.8 | 3.064 | 59.45 | 0.3906 | | 0.5859 | 6.25 |
| 498 | 5.502 | 2.148 | 6.366 | 0.1953 | | 0.3906 | 4.688 |
| 499 | 7.043 | 1.933 | 0.3277 | 0.1953 | | 0.7813 | 1.172 |
| 500 | 9.861 | 3.519 | 12.2 | 1.563 | | 2.344 | 31.25 |
| 501 | 5.388 | 1.521 | 0.5163 | 1.563 | | 1.172 | 1.563 |
| 502 | 1.188 | 0.5204 | 1.444 | 1.563 | | 1.563 | 9.375 |
| 503 | 4.202 | 1.141 | 0.1833 | 0.1953 | | 0.1953 | 0.7813 |
| 505 | 22.21 | 9.543 | 0.9368 | 6.25 | | 6.25 | 12.5 |
| 506 | 35.71 | 2.217 | 41.42 | 6.25 | | 4.688 | 100 |
| 507 | 4.313 | 11.53 | 3.272 | 0.5859 | | 4.688 | 25 |
| 508 | 2.366 | 4.554 | 1.662 | 0.0625 | | 0.8359 | 3.125 |
| 509 | 928.7 | 57.36 | 395.8 | 12.5 | | 1.563 | 50 |
| 510 | 47.35 | 3.422 | 12.81 | 200 | | 50 | >200 |
| 511 | 14.29 | 4.803 | 41.62 | 3.125 | | 3.125 | 100 |
| 512 | 46.05 | 161.7 | 3.903 | 0.9766 | | 9.375 | 2.344 |
| 513 | 3.612 | 9.349 | 1.176 | 9.375 | | 12.5 | 9.375 |
| 514 | 6.076 | 1.148 | 0.1377 | 1.172 | | 3.125 | 9.375 |
| 515 | 3.676 | 0.6027 | 0.3086 | 0.3906 | | 4.688 | 6.25 |
| 516 | 12.63 | 2.404 | 0.2769 | 0.7813 | | 6.25 | 6.25 |
| 517 | 37.21 | 5.884 | 0.937 | 3.125 | | 3.125 | 1.563 |
| 518 | 1.624 | 0.7754 | 0.3422 | 0.3906 | | 1.563 | 6.25 |
| 519 | 766.1 | 3.784 | 24.55 | 100 | | 1.563 | 37.5 |
| 520 | 52.63 | 24.82 | 1.956 | 3.125 | | 3.125 | 3.125 |
| 521 | 559.3 | 3.439 | 19.68 | 12.5 | | 1.563 | 12.5 |
| 522 | 263.3 | 3.403 | 52.89 | 18.75 | | 2.344 | 50 |
| 523 | 1210 | 20.17 | 226.3 | 9.375 | | 0.125 | 4.125 |
| 524 | 5.132 | 24.75 | 1.048 | 6.25 | | 12.5 | 12.5 |
| 525 | 6.853 | 0.5412 | 0.08968 | 12.5 | | 3.125 | 4.688 |
| 526 | 4.575 | 1.848 | 1.586 | 100 | | 25 | 50 |
| 527 | 10.64 | 7.025 | 2.894 | 12.5 | | 6.25 | 12.5 |
| 528 | 0.4248 | 0.02476 | 0.1456 | 3.125 | | 1.563 | 12.5 |
| 529 | 6.299 | 2.201 | 0.991 | 0.7813 | | 3.906 | 9.375 |
| 530 | 25.91 | 1.149 | 0.2999 | 0.5859 | | 3.125 | 4.688 |
| 531 | 32.14 | 2.069 | 8.362 | 12.5 | | 6.25 | 12.5 |
| 532 | 6.415 | 0.5975 | 3.962 | 12.5 | | 12.5 | 12.5 |
| 533 | 16.62 | 0.8776 | 2.875 | 12.5 | | 3.125 | 12.5 |
| 534 | 9.529 | 0.4442 | 0.8425 | 25 | | 6.25 | 12.5 |
| 535 | 6.855 | 0.8443 | 2.709 | 25 | | 6.25 | 50 |
| 536 | 39.36 | 2.71 | 4.121 | 50 | | 6.25 | 25 |
| 537 | 19.24 | 14.34 | 66.73 | 50 | | 50 | >200 |
| 538 | 53.75 | 1.402 | 40.3 | 50 | | 6.25 | 100 |
| 539 | 7.618 | 0.192 | 1.854 | 12.5 | | 3.125 | 25 |
| 540 | 20.82 | 0.1993 | 6.702 | 6.25 | | 1.563 | 12.5 |
| 541 | 7.207 | 0.1326 | 5.106 | 6.25 | | 3.125 | 25 |
| 542 | 7.898 | 11.49 | 6.434 | 6.25 | | 25 | 100 |
| 543 | 1.161 | 2.62 | 3.21 | 12.5 | | 50 | >200 |
| 544 | 19.21 | 0.7275 | 2.235 | 3.125 | | 0.7813 | 1.563 |
| 545 | 21.8 | 2.724 | 7.686 | 3.125 | | 0.7813 | 3.125 |
| 546 | 177.8 | 33.76 | 38.65 | 12.5 | | 1.563 | 12.5 |
| 547 | 9.136 | 9.316 | 1.175 | 3.125 | | 6.25 | 6.25 |
| 548 | 10.48 | 7.537 | 0.5188 | 3.125 | | 3.125 | 1.563 |
| 549 | 0.4723 | 0.2556 | 0.0629 | 3.125 | | 1.563 | 6.25 |
| 550 | 2.521 | 0.7533 | 0.3153 | 3.125 | | 3.125 | 12.5 |
| 551 | 3.803 | 0.1419 | 0.2602 | 0.7813 | | 0.3906 | 1.563 |
| 552 | 7.198 | 1.325 | 0.2618 | 1.563 | | 0.3906 | 1.563 |
| 553 | 0.9585 | 0.0499 | 0.0624 | 3.125 | | 3.125 | 3.125 |
| 554 | 0.8178 | 0.1151 | 0.3631 | 1.563 | | 3.125 | 3.125 |
| 555 | 8.916 | 1.962 | 0.1768 | 6.25 | | 0.5859 | 3.125 |
| 556 | 2.973 | 0.1251 | 0.1218 | 12.5 | | 25 | 12.5 |
| 557 | 8.084 | 3.052 | 0.6556 | 6.25 | | 0.3906 | 6.25 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 558 | 1.957 | 0.1447 | 0.1777 | 6.25 | | 6.25 | 6.25 |
| 559 | 0.5342 | 0.439 | 0.2124 | 6.25 | | 12.5 | 12.5 |
| 560 | 0.8979 | 0.7272 | 0.2118 | 3.125 | | 6.25 | 6.25 |
| 561 | 0.9929 | 0.1534 | 0.4339 | 0.09375 | | 0.668 | 2.563 |
| 562 | 7.55 | 5.003 | 2.35 | 0.3906 | | 0.5859 | 3.125 |
| 563 | 45.94 | 53.8 | 5.024 | 6.25 | | 3.125 | 3.125 |
| 564 | 301 | 261.8 | 36.33 | 25 | | 25 | 50 |
| 565 | 199.9 | 186.7 | 11.3 | 25 | | 12.5 | 12.5 |
| 566 | 2.676 | 0.2332 | 0.5079 | 3.125 | | 0.7813 | 3.125 |
| 567 | 3.771 | 0.2992 | 0.2251 | 6.25 | | 3.125 | 6.25 |
| 568 | 1.169 | 0.0983 | 0.1611 | 1.563 | | 0.3906 | 1.563 |
| 569 | 1.617 | 0.215 | 0.3094 | 3.125 | | 6.25 | 6.25 |
| 570 | 4.06 | 0.33 | 0.49 | 6.25 | | 3.125 | 6.25 |
| 571 | 14.85 | 1.71 | 5.06 | 3.125 | | 0.7813 | 6.25 |
| 572 | 701.4 | 14.65 | 8.979 | 25 | | 0.5859 | 6.25 |
| 573 | 668.2 | 38.65 | 41.38 | 12.5 | | 0.7813 | 12.5 |
| 574 | 35.88 | 1.495 | 7.943 | 3.125 | | 0.3906 | 3.125 |
| 575 | 59.45 | 3.149 | 6.977 | 3.125 | | 0.3906 | 6.25 |
| 576 | 164.4 | 12.32 | 24.81 | 6.323 | | 0.5969 | 4.24 |
| 577 | 29.62 | 2.47 | 10.38 | 3.125 | | 0.7813 | 12.5 |
| 578 | 47.08 | 1.852 | 11.13 | 12.5 | | 3.125 | 50 |
| 579 | 17.79 | 1.636 | 3.121 | 3.125 | | 0.7813 | 12.5 |
| 580 | 22.67 | 0.869 | 13.41 | 6.25 | | 1.563 | 12.5 |
| 581 | 267.8 | 8.228 | 36.83 | 6.25 | | 0.3906 | 12.5 |
| 582 | 17.36 | 3.986 | 1.567 | 1.563 | | 0.7813 | 1.563 |
| 583 | 12.01 | 6.527 | 23.6 | 6.25 | | 3.125 | 6.25 |
| 584 | 10.23 | 2.048 | 1.606 | 1.563 | | 1.563 | 6.25 |
| 585 | 16.99 | 2.202 | 4.583 | 3.125 | | 0.7813 | 6.25 |
| 586 | 7.143 | 2.342 | 1.164 | 1.563 | | 0.7813 | 1.563 |
| 587 | 2.829 | 0.7982 | 11.53 | 1.563 | | 0.7813 | 6.25 |
| 588 | 28.76 | 6.27 | 2.61 | 3.125 | | 1.563 | 1.563 |
| 589 | 146.4 | 8.746 | 93.88 | 4.688 | | 1.172 | 9.375 |
| 590 | 24.51 | 8.273 | 8.349 | 2.344 | | 1.172 | 2.344 |
| 591 | 320.1 | 16 | 574.4 | 6.25 | | 1.563 | 25 |
| 592 | 84.09 | 8.598 | 34.82 | 3.125 | | 1.563 | 12.5 |
| 593 | 272.7 | 38.18 | 31.56 | 6.25 | | 1.563 | 3.125 |
| 594 | 51.69 | 13.38 | 5.406 | 1.563 | | 0.7813 | 1.563 |
| 595 | 42.56 | 4.342 | 1.297 | 3.125 | | 0.7813 | 1.563 |
| 596 | 10.59 | 4.385 | 7.464 | 1.563 | | 0.7813 | 1.563 |
| 597 | 45.98 | 8.861 | 1.239 | 3.125 | | 1.563 | 1.563 |
| 598 | 135.2 | 15.25 | 4.409 | 3.125 | | 1.563 | 1.563 |
| 599 | 6.434 | 2.117 | 5.332 | 3.125 | | 1.563 | 3.125 |
| 600 | 43.77 | 2.557 | 0.8611 | 6.25 | | 1.563 | 3.125 |
| 601 | 13.06 | 1.656 | 0.5866 | 3.125 | | 1.563 | 1.563 |
| 602 | 21.02 | 3.954 | 2.472 | 3.125 | | 1.563 | 1.563 |
| 603 | 31.94 | 21.55 | 4.73 | 1.563 | | 3.125 | 1.563 |
| 604 | 41.66 | 3.315 | 0.8991 | 6.25 | | 1.563 | 1.563 |
| 605 | 159.9 | 11.7 | 3.886 | 6.25 | | 6.25 | 3.125 |
| 606 | 51.42 | 17.69 | 1.124 | 3.125 | | 0.7813 | 1.563 |
| 607 | 42.18 | 11.34 | 2.068 | 3.125 | | 1.563 | 1.563 |
| 608 | 127.1 | 30.42 | 45.01 | 6.25 | | 6.25 | 6.25 |
| 609 | 83.93 | 21.27 | 1.636 | 12.5 | | 6.25 | 3.125 |
| 610 | 114.4 | 2.918 | 6.392 | 3.125 | | 0.3906 | 1.563 |
| 611 | 343.8 | 17.69 | 20.11 | 12.5 | | 0.3906 | 1.563 |
| 612 | 65.47 | 1.63 | 7.23 | 2.563 | | 0.5 | 1.281 |
| 613 | 36.3 | 14.1 | 252.9 | 0.543 | | 0.25 | 18.75 |
| 614 | 11.6 | 5.891 | 505 | 1.563 | | 1.172 | >200 |
| 615 | 16.71 | 9.836 | 620.7 | 1.172 | | 0.7813 | >200 |
| 616 | 14.43 | 4.365 | 276 | 0.5859 | | 0.3906 | 75 |
| 617 | 9.665 | 10.02 | 334.1 | 0.2969 | | 0.25 | 37.5 |
| 618 | 16.1 | 11.67 | 345.1 | 0.3906 | | 0.3906 | 75 |
| 619 | 10.77 | 8.235 | 388.3 | 0.9766 | | 0.7813 | 150 |
| 620 | 8.364 | 10.67 | 1034 | 2.344 | | 7.813 | >200 |
| 621 | 6.018 | 2.569 | 508.4 | 1.563 | | 3.906 | >200 |
| 622 | 85.57 | 4.395 | 142.4 | 6.25 | | 0.9766 | >200 |
| 623 | 79.49 | 7.937 | 206.9 | 6.25 | | 1.953 | 150 |
| 624 | 86.23 | 10.17 | 559 | 12.5 | | 7.813 | >200 |
| 625 | 203.1 | 36.95 | 1348 | 12.5 | | 2.344 | >200 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 626 | 68.52 | 9.128 | 355.9 | 12.5 | | 4.688 | >200 |
| 627 | 415.2 | 32.89 | 830.2 | 12.5 | | 1.172 | 100 |
| 628 | 649.7 | 44.97 | 164 | 12.5 | | 0.9766 | 12.5 |
| 629 | 798.8 | 43.6 | 668.4 | 25 | | 4.688 | 100 |
| 630 | 388.3 | 32.33 | 634.9 | 12.5 | | 1.172 | 50 |
| 631 | 39.91 | 8.253 | 110 | 6.25 | | 1.953 | 25 |
| 632 | 254.3 | 26.78 | 482.2 | 6.25 | | 1.172 | 100 |
| 633 | 66.39 | 4.885 | 119.9 | 4.833 | | 0.125 | 37.5 |
| 634 | 1283 | 14.1 | 163 | 18.75 | | 0.5859 | 6.25 |
| 635 | 91.49 | 4.924 | 258.1 | 7.813 | | 2.148 | 112.5 |
| 636 | 37.25 | 1.536 | 88.91 | 4.688 | | 0.3906 | >200 |
| 637 | 924.6 | 52.02 | 452.9 | 25 | | 2.344 | 50 |
| 638 | 595.5 | 55.04 | 181.2 | 12.5 | | 0.7813 | 12.5 |
| 639 | 187 | 1.975 | 10.52 | 25 | | 1.563 | 6.25 |
| 640 | 193.7 | 0.8547 | 9.842 | 100 | | 1.563 | 100 |
| 641 | 26.5 | 1.016 | 4.462 | 25 | | 6.25 | 25 |
| 642 | 51.9 | 1.015 | 8.997 | 25 | | 1.563 | 50 |
| 643 | 101.1 | 2.338 | 12.28 | 25 | | 1.563 | 25 |
| 644 | 32.44 | 1.339 | 13.84 | 37.5 | | 4.688 | 75 |
| 645 | 88.79 | 1.157 | 5.292 | 100 | | 1.563 | 50 |
| 646 | 31.84 | 0.851 | 5.098 | 50 | | 3.125 | 100 |
| 647 | 617.6 | 14.08 | 83.94 | 18.75 | | 0.25 | 6.25 |
| 648 | 95.67 | 5.11 | 15.27 | 6.25 | | 1.563 | 12.5 |
| 649 | 48.38 | 2.868 | 12.83 | 3.125 | | 2.344 | 12.5 |
| 650 | 1262 | 22.06 | 46.84 | 100 | | 1.563 | 50 |
| 651 | 899.7 | 9.85 | 40.66 | 37.5 | | 1.172 | 6.25 |
| 652 | 167.3 | 5.372 | 27.35 | 12.5 | | 1.563 | 25 |
| 653 | 4.821 | 2.818 | 4.501 | 0.3906 | | 1.563 | 6.25 |
| 654 | 19.65 | 6.853 | 1.226 | 1.172 | | 4.688 | 9.375 |
| 655 | 7.799 | 0.9846 | 0.2252 | 0.5859 | | 2.344 | 9.375 |
| 656 | 2.838 | 1.978 | 0.8004 | 0.125 | | 0.5781 | 3.125 |
| 657 | 10.16 | 9.664 | 2.091 | 0.7813 | | 2.344 | 4.688 |
| 658 | 6.997 | 5.12 | 5.264 | 0.7813 | | 2.344 | 12.5 |
| 659 | 36.29 | 18.77 | 6.402 | 2.344 | | 15.63 | 25 |
| 660 | 10.43 | 4.699 | 1.31 | 0.3906 | | 2.344 | 6.25 |
| 661 | 0.9648 | 1.007 | 0.2195 | 0.0625 | | 2.703 | 2.75 |
| 662 | 37.11 | 11.62 | 4.585 | 1.953 | | 6.25 | 12.5 |
| 663 | 2.944 | 2.459 | 0.7899 | 0.125 | | 0.8906 | 3.125 |
| 664 | 38.5 | 18.06 | 51.96 | 0.418 | | 0.25 | 6.25 |
| 665 | 29.84 | 7.48 | 0.9985 | 1.172 | | 1.563 | 4.688 |
| 666 | 150.5 | 57.02 | 14.72 | 4.688 | | 2.344 | 12.5 |
| 667 | 75.02 | 19.68 | 1.48 | 2.344 | | 3.125 | 9.375 |
| 668 | 2.796 | 9.316 | 7.04 | 3.125 | | 1.563 | 50 |
| 669 | 0.6879 | 3.922 | 8.993 | 2.344 | | 2.344 | >200 |
| 670 | 1.076 | 4.109 | 3.529 | 3.125 | | 1.563 | 25 |
| 671 | 2.004 | 4.133 | 5.647 | 1.563 | | 1.172 | 37.5 |
| 672 | 2.513 | 3.659 | 3.381 | 4.688 | | 6.25 | 75 |
| 673 | 1.354 | 10.06 | 9.066 | 3.125 | | 3.125 | 62.5 |
| 674 | 2.469 | 6.629 | 17.39 | 6.25 | | 3.125 | 75 |
| 675 | 1.942 | 4.525 | 14.68 | 6.25 | | 4.688 | 150 |
| 676 | 1.258 | 5.589 | 9.104 | 6.25 | | 12.5 | >200 |
| 677 | 0.5406 | 4.165 | 19.37 | 12.5 | | 12.5 | >200 |
| 678 | 5.005 | 15.3 | 20.75 | 6.25 | | 9.375 | 150 |
| 679 | 75.31 | 19.79 | 21.23 | 3.125 | | 1.563 | 50 |
| 680 | 86.6 | 41.38 | 5.159 | 3.125 | | 1.563 | 6.25 |
| 681 | 16.1 | 8.72 | 7.104 | 3.125 | | 1.563 | 6.25 |
| 682 | 27.37 | 4.125 | 0.6843 | 6.25 | | 6.25 | 12.5 |
| 683 | 153.7 | 31.49 | 28.07 | 12.5 | | 3.125 | 50 |
| 684 | 75.73 | 38.65 | 10.76 | 6.25 | | 3.125 | 12.5 |
| 685 | 75.79 | 29.98 | 4.88 | 6.25 | | 1.563 | 25 |
| 686 | 31.71 | 9.53 | 15.65 | 6.25 | | 1.563 | 12.5 |
| 687 | 94.32 | 25.22 | 27.81 | 6.25 | | 3.125 | 25 |
| 688 | 158.1 | 44.06 | 13.43 | 6.25 | | 1.563 | 12.5 |
| 689 | 52.07 | 26.83 | 6.43 | 6.25 | | 6.25 | 12.5 |
| 690 | 75.86 | 12.6 | 5.259 | 3.125 | | 1.563 | 25 |
| 691 | 51.82 | 10.59 | 6.132 | 3.125 | | 0.7813 | 3.125 |
| 692 | 19.81 | 6.359 | 12.7 | 3.125 | | 1.563 | 6.25 |
| 693 | 97.84 | 36.86 | 11.6 | 6.25 | | 3.125 | 12.5 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 µM | Escherichia coli expressing NDM-1 (CLB 30005) MITC95 µM | Escherichia coli expressing NDM-1 (CLB 30016) MITC95 µM | Klebsiella pneumoniae expressing VIM-1 (IHMA 599644) MITC95 µM |
|---|---|---|---|---|---|---|---|
| 694 | 18.65 | 4.842 | 2.458 | 1.563 | | 0.3906 | 1.563 |
| 695 | 42.26 | 13.57 | 13.18 | 3.125 | | 0.7813 | 6.25 |
| 696 | 5.26 | 1.094 | 2.381 | 1.563 | | 0.3906 | 3.125 |
| 697 | 6.421 | 1.611 | 6.327 | 3.125 | | 0.7813 | 6.25 |
| 698 | 29.57 | 10.01 | 6.518 | 3.125 | | 0.7813 | 3.125 |
| 699 | 58.83 | 18 | 4.722 | 6.25 | | 3.125 | 6.25 |
| 700 | 16.69 | 3.944 | 0.9583 | 3.125 | | 0.3906 | 1.563 |
| 701 | 62.89 | 15.44 | 12.68 | 3.125 | | 0.7813 | 6.25 |
| 702 | 25.19 | 4.016 | 2.248 | 3.125 | | 0.7813 | 1.563 |
| 703 | 38.04 | 6.143 | 8.379 | 3.125 | | 0.3906 | 12.5 |
| 704 | 51.63 | 14.84 | 7.175 | 6.25 | | 1.563 | 6.25 |
| 705 | 61.14 | 18.23 | 5.7 | 4.688 | | 2.344 | 12.5 |
| 706 | 12.38 | 4.52 | 0.6321 | 6.25 | | 3.125 | 1.563 |
| 707 | 6.674 | 5.592 | 0.2492 | 6.25 | | 3.125 | 1.563 |
| 708 | 1.599 | 0.3796 | 0.1443 | 6.25 | | 1.563 | 6.25 |
| 709 | 16.4 | 6.578 | 0.2892 | 25 | | 6.25 | 6.25 |
| 710 | 2.085 | 0.8901 | 0.1679 | 6.25 | | 6.25 | 12.5 |
| 711 | 3.541 | 1.012 | 0.2237 | 12.5 | | 6.25 | 6.25 |
| 712 | 126.3 | 58.73 | 13.56 | 100 | | 25 | 50 |
| 713 | 3.535 | 3.272 | 0.8193 | 6.25 | | 3.125 | 3.125 |
| 714 | 31.73 | 5.046 | 0.7991 | 12.5 | | 1.563 | 3.125 |
| 715 | 27.37 | 25.31 | 0.7292 | 12.5 | | 6.25 | 3.125 |
| 716 | 5.435 | 8.075 | 2.792 | 3.125 | | 6.25 | 25 |
| 717 | 2.625 | 1.637 | 0.598 | 3.125 | | 1.563 | 3.125 |
| 718 | 2.396 | 1.506 | 1.732 | 6.25 | | 12.5 | 25 |
| 719 | 3.68 | 3.04 | 0.5528 | 3.125 | | 3.125 | 3.125 |
| 720 | 16.12 | 3.035 | 1.04 | 12.5 | | 6.25 | 3.125 |
| 721 | 9.18 | 3.025 | 0.8072 | 6.25 | | 6.25 | 1.563 |
| 722 | 21.66 | 20.76 | 1.457 | 25 | | 12.5 | 6.25 |
| 723 | 17.18 | 7.781 | 1.265 | 25 | | 6.25 | 12.5 |
| 724 | 2.445 | 1.152 | 0.8617 | 6.25 | | 6.25 | 12.5 |
| 725 | 0.9197 | 0.7671 | 1.271 | 6.25 | | 12.5 | 25 |
| 726 | 58.85 | 26.75 | 1.212 | 25 | | 12.5 | 3.125 |
| 727 | 1.968 | 2.131 | 0.9145 | 3.125 | | 3.125 | 25 |
| 728 | 4.156 | 2.585 | 3.996 | 6.25 | | 3.125 | 25 |
| 729 | 6.972 | 4.847 | 7.369 | 6.25 | | 6.25 | 25 |
| 730 | 3.574 | 2.797 | 5.997 | 3.125 | | 3.125 | 50 |
| 731 | 117.4 | 61.26 | 22.09 | 50 | | 25 | 50 |
| 732 | 0.3839 | 0.5336 | 0.6898 | 3.125 | | 0.7813 | 25 |
| 733 | 34.29 | 33.46 | 1.466 | 25 | | 12.5 | 6.25 |
| 734 | 34.39 | 31.35 | 3.269 | 25 | | 12.5 | 12.5 |
| 735 | 1.698 | 3.03 | 0.3883 | 3.125 | | 3.125 | 6.25 |
| 736 | 3.229 | 3.232 | 1.595 | 6.25 | | 6.25 | 6.25 |
| 737 | 3.023 | 4.951 | 4.286 | 3.125 | | 6.25 | 25 |
| 738 | 2.28 | 1.276 | 3.412 | 6.25 | | 3.125 | 50 |
| 739 | 6.822 | 3.837 | 2.767 | 25 | | 25 | >200 |
| 740 | 0.4555 | 0.2292 | 1.15 | 6.25 | | 6.25 | 50 |
| 741 | 6.115 | 4.653 | 2.739 | 25 | | 25 | >200 |
| 742 | 1.836 | 2.009 | 0.6571 | 12.5 | | 12.5 | 25 |
| 743 | 0.9012 | 0.4093 | 0.1466 | 6.25 | | 3.125 | 6.25 |
| 744 | 18.13 | 16.29 | 0.9071 | 12.5 | | 6.25 | 12.5 |
| 745 | 1.501 | 1.055 | 0.1748 | 3.125 | | 0.7813 | 3.125 |
| 746 | 2.593 | 2.269 | 0.234 | 6.25 | | 6.25 | 6.25 |
| 747 | 11.17 | 5.716 | 0.8655 | 25 | | 6.25 | 12.5 |
| 748 | 1.248 | 0.8331 | 0.2477 | 6.25 | | 0.7813 | 6.25 |
| 749 | 4.123 | 2.347 | 0.2622 | 12.5 | | 3.125 | 6.25 |
| 750 | 21.46 | 4.747 | 0.4323 | 6.25 | | 1.563 | 3.125 |
| 751 | 5.631 | 0.9619 | 0.108 | 3.125 | | 0.7813 | 3.125 |
| 752 | 6.247 | 2.327 | 0.6772 | 12.5 | | 1.563 | 25 |
| 753 | 2.022 | 1.006 | 0.7536 | 12.5 | | 12.5 | 100 |
| 754 | 868.9 | 596.1 | 7.675 | 50 | | 25 | 12.5 |
| 755 | 22.14 | 13.93 | 0.1909 | 6.25 | | 6.25 | 3.125 |
| 756 | 89.14 | 78.09 | 339.4 | 12.5 | | 12.5 | >200 |
| 757 | 110.6 | 82.79 | 352.7 | 25 | | 12.5 | >200 |
| 758 | 45.76 | 29.64 | 2.444 | 6.25 | | 6.25 | 6.25 |
| 759 | 40.9 | 22.51 | 45.64 | 3.125 | | 3.125 | 12.5 |
| 760 | 2.08 | 5.645 | 1.515 | 25 | | 100 | 100 |
| 761 | 103.7 | 46.03 | 48.31 | 100 | | 100 | >200 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 µM | Escherichia coli expressing NDM-1 (CLB 30005) MITC95 µM | Escherichia coli expressing NDM-1 (CLB 30016) MITC95 µM | Klebsiella pneumoniae expressing VIM-1 (IHMA 599644) MITC95 µM |
|---|---|---|---|---|---|---|---|
| 762 | 123.4 | 73.22 | 14.22 | 6.25 | | 3.125 | 6.25 |
| 763 | 46.4 | 37.67 | 73.58 | 3.125 | | 1.563 | 50 |
| 764 | 68.66 | 272.7 | 27.68 | 50 | | 100 | >200 |
| 765 | 131 | 93.29 | 124.7 | 3.125 | | 6.25 | 25 |
| 766 | 120.4 | 133.9 | 8.519 | 25 | | 25 | 12.5 |
| 767 | 222.6 | 208.2 | 4.579 | 50 | | 200 | 12.5 |
| 768 | 36.66 | 24.63 | 0.906 | 6.25 | | 12.5 | 3.125 |
| 769 | 11.41 | 7.478 | 0.9983 | 25 | | 100 | 50 |
| 770 | 251.4 | 366.4 | 7.51 | 50 | | 50 | 3.125 |
| 771 | 227.3 | 30.7 | 22.93 | 50 | | 25 | 50 |
| 772 | 113.6 | 33.89 | 13.89 | 50 | | 12.5 | 50 |
| 773 | 17.16 | 31.82 | 1.112 | 6.25 | | 6.25 | 3.125 |
| 774 | 29.08 | 62.59 | 1.351 | 25 | | 25 | 6.25 |
| 775 | 35.8 | 9.043 | 5.193 | 6.25 | | 3.125 | 12.5 |
| 776 | 55.86 | 15.22 | 15.92 | 50 | | 25 | 25 |
| 777 | 51.32 | 23.31 | 6.733 | 12.5 | | 12.5 | 6.25 |
| 778 | 159.9 | 146.6 | 0.6876 | 1.563 | | 3.125 | 1.172 |
| 779 | 6.701 | 6.425 | 0.1095 | 0.3906 | | 1.172 | 2.344 |
| 780 | 31.67 | 17.7 | 0.2737 | 1.563 | | 1.563 | 2.344 |
| 781 | 53.72 | 12.01 | 2.694 | 1.563 | | 0.7813 | 3.125 |
| 782 | 397.2 | 182.1 | 9.504 | 4.688 | | 6.25 | 3.125 |
| 783 | 13.4 | 4.914 | 1.927 | 0.5859 | | 1.172 | 2.344 |
| 784 | 48.28 | 41.72 | 15.54 | 3.125 | | 3.125 | 31.25 |
| 785 | 1.093 | 4.212 | 12.19 | 3.125 | | 1.563 | 25 |
| 786 | 2.084 | 6.196 | 12.03 | 3.125 | | 1.563 | 50 |
| 787 | 1.711 | 7.094 | 8.101 | 3.125 | | 1.563 | 25 |
| 788 | 0.4378 | 2.828 | 35.65 | 6.25 | | 6.25 | >200 |
| 789 | 0.4725 | 2.396 | 16.5 | 3.125 | | 3.125 | 100 |
| 790 | 0.8705 | 3.573 | 7.258 | 3.125 | | 0.7813 | 12.5 |
| 791 | 1.197 | 6.26 | 11.1 | 1.563 | | 0.7813 | 50 |
| 792 | 1.549 | 7.313 | 4.379 | 3.125 | | 3.125 | 25 |
| 793 | 1.023 | 7.004 | 4.659 | 3.125 | | 1.563 | 25 |
| 794 | 1.764 | 6.442 | 10.99 | 3.125 | | 1.563 | 50 |
| 795 | 1.098 | 5.226 | 6.57 | 3.125 | | 1.563 | 25 |
| 796 | 0.3449 | 2.062 | 17.97 | 6.25 | | 6.25 | >200 |
| 797 | 1.508 | 5.569 | 9.919 | 3.125 | | 3.125 | 25 |
| 798 | 2.351 | 6.051 | 13.3 | 3.125 | | 1.563 | 25 |
| 799 | 1.051 | 3.889 | 15.01 | 3.125 | | 3.125 | >200 |
| 800 | 5.139 | 2.683 | 14.32 | 6.25 | | 0.7813 | 12.5 |
| 801 | 2.798 | 2.217 | 9.446 | 6.25 | | 3.125 | 100 |
| 802 | 4.266 | 3.246 | 17.19 | 6.25 | | 6.25 | 100 |
| 803 | 13.03 | 4.866 | 13.22 | 6.25 | | 6.25 | 100 |
| 804 | 5.781 | 3.854 | 8.72 | 6.25 | | 3.125 | 50 |
| 805 | 7.581 | 3.769 | 19.65 | 6.25 | | 3.125 | 50 |
| 806 | 7.672 | 4.679 | 5.016 | 6.25 | | 6.25 | 12.5 |
| 807 | 5.158 | 3.974 | 19.92 | 6.25 | | 1.563 | 25 |
| 808 | 8.442 | 3.573 | 25.3 | 3.125 | | 1.563 | 25 |
| 809 | 11.35 | 4.022 | 27.9 | 6.25 | | 3.125 | 50 |
| 810 | 8.919 | 7.063 | 26.78 | 6.25 | | 3.125 | 100 |
| 811 | 9.419 | 4.775 | 27.89 | 6.25 | | 1.563 | 100 |
| 812 | 5.766 | 2.699 | 3.885 | 6.25 | | 1.563 | 12.5 |
| 813 | 9.862 | 6.273 | 20.58 | 6.25 | | 6.25 | 100 |
| 814 | 12.46 | 8.077 | 22.5 | 6.25 | | 6.25 | 100 |
| 815 | 6.014 | 4.843 | 18.01 | 3.125 | | 1.563 | 100 |
| 816 | 16.27 | 6.615 | 13.46 | 6.25 | | 1.563 | 12.5 |
| 817 | 14.99 | 4.457 | 9.501 | 6.25 | | 1.563 | 12.5 |
| 818 | 8.6 | 4.384 | 17.24 | 3.125 | | 1.563 | 12.5 |
| 819 | 97.09 | 14.29 | 27.41 | 1.823 | | 0.8464 | 3.385 |
| 820 | 39.42 | 13.52 | 0.6593 | 0.7813 | | 0.3906 | 0.7813 |
| 821 | 55.15 | 18.05 | 0.4959 | 6.25 | | 12.5 | 12.5 |
| 822 | 2.246 | 1.442 | 0.1955 | 0.0938 | | 0.6406 | 1.086 |
| 823 | 25.45 | 17.48 | 0.666 | 0.3906 | | 1.172 | 1.172 |
| 824 | 59.19 | 53.13 | 0.7024 | 0.7813 | | 1.563 | 0.7813 |
| 825 | 0.4988 | 0.1567 | 0.0805 | 1.563 | | 0.7813 | 3.125 |
| 826 | 1.453 | 0.4908 | 1.359 | 3.125 | | 1.563 | 25 |
| 827 | 22.55 | 5.718 | 2.588 | 0.3906 | | 0.3906 | 1.172 |
| 828 | 72.88 | 8.291 | 73.33 | 1.563 | | 0.7813 | 6.25 |
| 829 | 93.3 | 59.75 | 1.077 | 0.9766 | | 0.7813 | 0.7813 |

TABLE 1-continued

Inhibition of metallo-β-lactamases (IMP-1, NDM-1, VIM-1) and antibiotic potentiation vs. MBL-expressing bacteria by Examples 1-840.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB 30005) MITC95 μM | Escherichia coli expressing NDM-1 (CLB 30016) MITC95 μM | Klebsiella pneumoniae expressing VIM-1 (IHMA 599644) MITC95 μM |
|---|---|---|---|---|---|---|---|
| 830 | 3.821 | 1.934 | 0.2471 | 0.724 | | 0.25 | 0.8542 |
| 831 | 0.8916 | 0.8174 | 2.837 | 3.125 | | 2.344 | 50 |
| 832 | 1.456 | 0.5015 | 0.2118 | 3.125 | | 1.563 | 4.688 |
| 833 | 4.307 | 0.7403 | 3.335 | 3.125 | | 1.563 | 12.5 |
| 834 | 5.449 | 1.486 | 13.31 | 6.25 | | 6.25 | 50 |
| 835 | 232 | 95.98 | 190.4 | 6.25 | | 3.125 | 100 |
| 836 | 133.7 | 54.93 | 2.386 | 4.688 | | 2.344 | 1.563 |
| 837 | 21.17 | 8.677 | 2.902 | 0.5859 | | 1.563 | 6.25 |
| 838 | 1679 | 68.26 | 61.16 | 12.5 | | 3.125 | 6.25 |
| 839 | 359.2 | 56.88 | 19.33 | 6.25 | | 3.125 | 6.25 |
| 840 | 14.1 | 2.492 | 0.4603 | 12.5 | | 3.125 | 6.25 |

What is claimed:

1. A compound of formula I

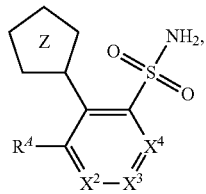

(I)

or a pharmaceutically acceptable salt thereof,
wherein:
$X^2$ is N or $CR^B$;
$X^3$ is N or $CR^C$;
$X^4$ is N or $CR^D$;
wherein no more than 2 of $X^2$, $X^3$, and $X^4$ are N;
Z is tetrazolyl, wherein Z is linked to the six membered ring through a carbon to carbon bond;
$R^A$ is H, $C_1$-$C_6$ alkyl, —$(CH_2)_{0-3}$—$C_3$-$C_8$ cycloalkyl, —$C_3$-$C_6$ cycloalkenyl, —$CF_3$, $C_1$-$C_6$ alkoxy, —$COOR^a$, —CN, —$NR^aR^b$, —$(CH_2)_{0-3}$HetA, —$(CH_2)_{0-3}$-AryA, —$(CH_2)_{0-1}$—O-AryA, —$NR^a$$(CH_2)_{0-2}$—$C_3$-$C_8$ cycloalkyl, —$NR^a(CH_2)_{1-2}$-phenyl, —C≡C-pyridinyl, —C≡C—$CH_2$-HetC, or —C≡C—$CH_2$—O-HetC; wherein the $R^A$ $C_1$-$C_6$ alkyl or any $R^A$ $C_3$-$C_8$ cycloalkyl is optionally substituted with 1, 2, or 3 substituents independently selected from $C_1$-$C_6$ alkoxy, $C_3$-$C_7$ cycloalkyl, —OH, F, —$CF_3$, —CN, —$(CH_2)_{0-3}NR^aR^b$, —C(=NH)$NH_2$; —CONR$^aR^b$, —$(CH_2)_{0-1}$NHC(=NH)$NH_2$; —NHCONR$^aR^b$, —NHCO-diamino$C_2$alkyl, —NH($CH_2)_{0-1}$—$C_3$-$C_6$cycloalkyl; —NHSO$_2$—$C_1$-$C_6$ alkyl, —SO$_2$—$C_1$-$C_6$alkyl, —SO$_2$—$C_3$-$C_6$cycloalkyl, —SO$_2NR^aR^b$, AryB, —NH($CH_2)_{0-1}$-AryB, HetB, and —NH(CHR$^a$)$_{0-1}$-HetB, and wherein any $C_3$-$C_6$cycloalkyl is optionally substituted with —$(CH_2)_{0-2}NH_2$, wherein —$C_3$-$C_6$ cycloalkenyl is optionally substituted with cyano; and the pyridinyl is optionally substituted with 1 or 2 substituents independently selected from —$CH_2OH$ and —$NH_2$;

$R^B$ is H, $C_1$-$C_6$ alkyl, —OH, $C_1$-$C_6$ alkoxy, —CN, F, Cl, Br, or —$NR^aR^b$, wherein the $R^B$ $C_1$-$C_6$ alkyl is optionally be substituted with 1, 2 or 3 substituents selected from —OH, —F, —$NR^aR^b$, —$CF_3$, $C_1$-$C_6$ alkoxy, and —CONR$^aR^b$;

or $R^A$ and $R^B$ together with the atom(s) to which they are attached form a 5-7 membered fused ring containing 0, 1, or 2 heteroatoms independently selected from N, O and S, wherein N is optionally substituted with $R^d$;

$R^C$ is H, $C_1$-$C_6$ alkyl, F, Cl, —$CF_3$, —$COOCH_3$, —C(O)$NH_2$, or AryC;

$R^D$ is H, $C_1$-$C_6$ alkyl, $C_1$-$C_6$ hydroxyalkyl, —$(CH_2)_{0-2}C_3$-$C_6$ cycloalkyl, —$C_3$-$C_6$ cycloalkenyl, —$(CH_2)_2C(O)$OH, —$CF_3$, F, Cl, Br, —$(CH_2)_{0-1}$AryA, or —$(CH_2)_{0-2}$HetA, wherein the $R^D$ $C_1$-$C_6$ alkyl or $R^D$ $C_3$-$C_6$ cycloalkyl is optionally substituted with 1, 2, or 3 substituents independently selected from $C_3$-$C_6$ cycloalkyl, —OH, F, —CN, —$(CH_2)_{0-3}NR^aR^b$, —$CF_3$, —$(CH_2)_{0-2}$HetB, —$(CH_2)_{0-2}$AryB, —$(CH_2)_{0-1}$NHC(=NH)$NH_2$; —SO$_2$—$C_1$-$C_6$alkyl, —SO$_2$—$C_3$-$C_6$cycloalkyl, —SO$_2NR^aR^b$, $C_1$-$C_6$ alkoxy, and —$(CH_2)_{0-4}CONR^aR^b$, and wherein the —$C_3$-$C_6$ cycloalkenyl is optionally substituted with cyano;

wherein when $R^A$, $R^B$, $R^C$ and $R^D$ are all present, then 1, 2 or 3 of $R^A$, $R^B$, $R^C$ and $R^D$ are H;

wherein when 1 or 2 of $X^2$, $X^3$, $X^4$ are N, then at least one of $R^A$, $R^B$, $R^C$, and $R^D$, if present, is not H;

AryA is an aromatic ring system selected from:

1) a 5-6 membered monocyclic ring with 0, 1, 2 or 3 heteroatom ring atoms independently selected from N, O and S, optionally substituted with 1, 2 or 3 substituents independently selected from:
  a) —$C_1$-$C_6$ alkyl,
  b) —$C_2$-$C_6$diaminoalkyl;
  c) —$C_1$-$C_6$ hydroxyalkyl,
  d) —$C_1$-$C_6$ dihydroxyalkyl,
  e) —$C_3$-$C_6$ cycloalkyl optionally substituted with 1 or 2 substituents selected from —OH and —$NR^aR^b$,
  f) —$C_3$-$C_6$ cycloalkenyl optionally substituted with —CN,
  g) —$(CH_2)_{0-6}NR^aR^b$,
  h) —$CH(OH)R^e$,
  i) —$CH_2OR^a$, j) —(CH$_2$)$_{0-2}$C(O)NR$^a$R$^b$,
k) —CH$_2$NR$^a$—C$_2$-C$_4$alkyl-NR$^a$R$^b$,
l) —C(=NH)NHR$^b$;
m) —CH$_2$NHCH(=NH);
n) —CH$_2$NHCH$_2$C(O)NR$^a$R$^b$,
o) —(CH$_2$)$_{0-2}$C(O)OR$^a$,
p) —CH$_2$NR$^a$—C$_1$-C$_3$alkyl-C(O)OR$^a$,
q) —CH$_2$NH—CH[C(OH)CH$_3$][C(O)OR$^a$],
r) —CH$_2$NR$^a$—C$_1$-C$_6$ hydroxyalkyl,
s) —(CH$_2$)$_{0-2}$SO$_2$—C$_1$-C$_6$ alkyl,
t) —NR$^a$SO$_2$—C$_3$-C$_6$ cycloalkyl,
u) —NR$^a$SO$_2$—C$_1$-C$_6$ alkyl,
v) —NR$^a$SO$_2$—NR$^a$R$^b$,
w) —CH$_2$NHC(=NH)NHR$^b$;
x) —NHC(=NH)NH$_2$;
y) —OR$^a$,
z) —O(CH$_2$)$_{0-6}$NR$^a$R$^b$;
aa) —O—C$_1$-C$_6$ hydroxyalkyl,
bb) —(CH$_2$)$_{0-1}$SO$_2$(CH$_2$)$_{0-2}$NR$^a$R$^b$,
cc) —SO$_2$(CH$_2$)$_{0-2}$OH,
dd) —CN,
ee) halogen,
ff) —CF$_3$,
gg) —CH$_2$NR$^a$(CH$_2$)$_{0-1}$—C$_3$-C$_6$cycloalkyl optionally substituted with —OH, NR$^a$R$^b$ or 2 F,
hh) —(CH$_2$)$_{0-1}$-AryB,
ii) —CH$_2$NR$^a$—C$_1$-C$_3$alkyl-AryB,
jj) —CH$_2$NR$^a$—CH(COOH)CH$_2$-AryB,
kk) —C$_0$-C$_2$alkyl-HetB,
ll) —CH(OH)-HetB,
mm) —(CH$_2$)$_{0-1}$NR$^a$(CH$_2$)$_{0-2}$-HetB,
nn) —C(=NH)NH-HetB;
oo) —O(CH$_2$)$_{0-2}$-HetB,
pp) —C(O)-HetB, and
qq) —C(O)NR$^a$(CH$_2$)$_{0-2}$-HetB; or
2) a 9- or 10-membered bicyclic ring with 0, 1, 2, 3 or 4 heteroatom ring atoms selected from N, O and S, wherein an N atom is optionally in the form of a quaternary amine and wherein the ring is optionally substituted with 1, 2 or 3 substituents independently selected from C$_1$-C$_6$ alkyl, C$_3$-C$_6$ cycloalkyl, C$_1$-C$_6$ alkoxy, C$_1$-C$_6$ hydroxyalkyl, C$_1$-C$_6$ aminoalkyl, —CF$_3$, —C(=NH)NH$_2$, —COOR$^a$, —(CH$_2$)$_{0-1}$C(O)NR$^a$R$^b$, —CN, —(CH$_2$)$_{0-3}$NR$^a$R$^b$, —NHCH$_2$CH$_2$N(CH$_3$)$_2$, —NH—C$_3$-C$_6$ cycloalkyl, —NHC(=NH)NH$_2$, —NH-HetB, —OR$^a$, —SO$_2$—C$_1$-C$_6$ alkyl, —SO$_2$-phenyl, halogen, and oxo, wherein the C$_3$-C$_6$ cycloalkyl is optionally substituted with —NH$_2$;
AryB is
1) a 5-6 membered monocyclic aromatic ring with 0, 1, 2, 3, or 4 ring atoms selected from N, O and S, optionally substituted with 1 or 2 substituents selected from C$_1$-C$_6$ alkyl, —CH$_2$NH$_2$, —CH$_2$OH, —CONH$_2$, —NH$_2$, —OH, —CH(OH)R$^e$, halogen, —CF$_3$, and pyrrolidinyl; or
2) a 9- or 10-membered bicyclic ring with 1, 2 or 3 N ring atoms optionally substituted with 1 or 2 substituents selected from C$_1$-C$_6$ alkyl, C$_1$-C$_6$ hydroxyalkyl, C$_1$-C$_6$ aminoalkyl, —CONH$_2$, —NH$_2$, —OH, —CH(OH)R$^e$, halogen, —CF$_3$, piperidinyl, pyrrolidinyl, and oxo;
AryC is
1) phenyl optionally substituted with —CONH$_2$;
2) a 5-6 membered monocyclic aromatic ring with 1 or 2 N ring atoms, optionally substituted with —CH$_3$ or —OH; or
3) a 9-membered bicyclic ring with 1 N ring atom optionally substituted with oxo;
AryD is a 5-membered monocyclic aromatic ring with 2 N ring atoms, optionally substituted with —CH$_3$;
HetA is
1) a 4-6-membered saturated or monounsaturated monocyclic ring with 1 or 2 heteroatom ring atoms independently selected from N, O and S, wherein an N atom is optionally in the form of a quaternary amine and wherein the ring is optionally substituted with 1 or 2 substituents independently selected from
a) C$_1$-C$_6$ alkyl,
b) —C$_1$-C$_6$ hydroxyalkyl,
c) C$_3$-C$_6$cycloalkyl optionally substituted with —NH$_2$,
d) —C(O)—C$_3$-C$_6$cycloalkyl optionally substituted with phenyl,
e) —(CH$_2$)$_{0-4}$NR$^a$R$^b$,
f) —C(=NH)NH$_2$;
g) —(CH$_2$)$_{0-1}$C(O)NR$^a$R$^b$,
h) —(CH$_2$)$_{0-2}$C(O)OR$^a$,
i) —(CH$_2$)$_{0-2}$SO$_2$—C$_1$-C$_6$ alkyl,
j) —CN,
k) —NHC(=NH)NH$_2$;
l) —OR$^a$,
m) F,
n) —CF$_3$,
o) —(CH$_2$)$_{0-1}$-AryB,
p) —O-AryB,
q) —C$_0$-C$_2$ alkyl-HetB, and
r) oxo; or
2) a 6-11-membered bicyclic ring with 1 to 3 heteroatom ring atoms selected from N and O, optionally substituted with —CH$_2$OH, —C(=NH)NH$_2$; —CH$_2$C$_3$-C$_6$cycloalkyl, —C(=O), —NH$_2$, or oxo, wherein the rings in the bicyclic ring are bridged, fused or spirocyclic, and wherein the C$_3$-C$_6$cycloalkyl is optionally substituted with —NH$_2$;
HetB is
1) a 4-7 membered saturated or monounsaturated monocyclic ring with 1 or 2 heteroatom ring atoms independently selected from N, O and S, wherein an N atom is optionally in the form of a quaternary amine and wherein the ring is optionally substituted with 1, 2 or 3 substituents independently selected from —CF$_3$, F, C$_1$-C$_6$ alkyl, C$_1$-C$_6$ hydroxyalkyl, C$_2$-C$_6$ aminoalkyl, C$_1$-C$_6$ haloalkyl, —CH$_2$CH$_2$N$^+$(CH$_3$)$_3$; —(CH$_2$)$_{0-1}$C$_3$-C$_6$ cycloalkyl, —OH, C$_1$-C$_6$ alkoxy, —C(O)OR$^a$, —C(O)NH$_2$, —CH(=NH), —C(=NH)NH$_2$, —CN, —C(OH)(CH$_3$)$_2$, —CH(OH)(CH$_3$), —(CH$_2$)$_{0-2}$NR$^a$R$^b$, —CH$_2$CHR$^f$—(CH$_2$)$_{0-2}$—NHR$^g$, —CH$_2$-AryD, —(CH$_2$)$_{0-2}$-HetD, oxo, —SO$_2$—C$_1$-C$_6$ alkyl, wherein the cycloalkyl is optionally substituted with —(CH$_2$)$_{0-2}$NHR$^a$; or
2) a 7-11-membered bicyclic ring with 1 or 2 N ring atoms optionally substituted with methyl, wherein the bicyclic ring is bridged, fused or spirocyclic;
HetC is a 5-6 membered saturated monocyclic ring with 1 or 2 heteroatom ring atoms independently selected from N, O and S, optionally substituted with 1 or 2 oxo substituents;
HetD is
1) a 4-6 membered saturated monocyclic ring with 1 or 2 heteroatom ring atoms independently selected from N, and O;

2) 7-9 membered bicyclic ring with 1 N heteroatom ring atom, wherein the bicyclic ring is bridged or spirocyclic;

$R^a$ is H or $C_1$-$C_6$ alkyl;

$R^b$ is H, —OH, $C_1$-$C_6$ alkyl, $C_1$-$C_6$ alkoxy, $C_2$-$C_6$ hydroxyalkyl, $C_2$-$C_6$ aminoalkyl, $C_2$-$C_6$ dihydroxyalkyl, $C_2$-$C_6$ diaminoalkyl, dimethylamino$C_2$-$C_6$alkyl, $C_2$-$C_6$ hydroxyaminoalkyl, —$(CH_2)_{0-1}$—$C_3$-$C_6$ cycloalkyl, —C(O)$C_1$-$C_6$ alkyl, or —$CH_2C(O)NHOH$; or $R^a$ and $R^b$ together with the atom(s) to which they are attached form a 3-7 membered cycloheteroalkyl ring with 0, 1 or 2 additional heteroatom ring atoms independently selected from N, O and S, wherein N is optionally substituted with $R^d$;

$R^d$ is H, $C_1$-$C_6$ alkyl, $C_3$-$C_6$ cycloalkyl, —C(O)—$C_1$-$C_6$ alkyl, —C(O)-AryC, —$SO_2$—$C_1$-$C_6$ alkyl, and —$SO_2$-AryC; and $R^e$ is $C_1$-$C_6$ alkyl, —$CF_3$ or —$CHF_2$;

$R^f$ is $C_1$-$C_6$ alkyl, —$CH_2OH$, —$(CH_2)_{1-4}NH_2$, —$(CH_2)_{1-3}$$CONH_2$, —$CH_2$-imidazole, benzyl; and $R^g$ is H or $C_1$-$C_6$ alkyl; or $R^f$ and $R^g$ together with the atom(s) to which they are attached form a 4-6 membered cycloheteroalkyl ring with 0, 1 or 2 additional heteroatom ring atoms independently selected from N, O and S.

2. The compound of claim 1, or a pharmaceutically acceptable salt thereof, wherein:

$X^2$ is N or $CR^B$;

$X^3$ is N or $CR^C$;

$X^4$ is N or $CR^D$;

wherein no more than 2 of $X^2$, $X^3$, and $X^4$ are N;

Z is tetrazolyl, wherein Z is linked to the six membered ring through a carbon to carbon bond;

$R^A$ is H, $C_1$-$C_6$ alkyl, —$(CH_2)_{0-3}$—$C_3$-$C_8$ cycloalkyl, —$CF_3$, $C_1$-$C_6$ alkoxy, —$COOR^a$, —CN, —$NR^aR^b$, —$(CH_2)_{0-3}$HetA, —$(CH_2)_{0-3}$-AryA, —$(CH_2)_{0-1}$—O-AryA, —$NR^a(CH_2)_{1-2}$—$C_3$-$C_8$ cycloalkyl, —$NR^a(CH_2)_{1-2}$-phenyl, —C≡C-pyridinyl, —C≡C—$CH_2$-HetC, or —C≡C—$CH_2$—O-HetC, wherein the $R^A$ $C_1$-$C_6$ alkyl or any $R^A$ $C_3$-$C_5$ cycloalkyl is optionally substituted with 1, 2, or 3 substituents independently selected from $C_1$-$C_6$ alkoxy, $C_3$-$C_7$ cycloalkyl, —OH, F, —$CF_3$, —CN, —$(CH_2)_{0-3}NR^aR^b$, —$CONR^aR^b$, —$NHCONR^aR^b$, —$NHSO_2$—$C_1$-$C_6$ alkyl, —$SO_2$—$C_1$-$C_6$alkyl, —$SO_2$—$C_3$-$C_6$cycloalkyl, —$SO_2NR^aR^b$, AryB, and HetB;

$R^B$ is H, $C_1$-$C_6$ alkyl, —OH, $C_1$-$C_6$ alkoxy, —CN, F, Cl, Br, or —$NR^aR^b$, wherein the $R^B$ $C_1$-$C_6$ alkyl is optionally be substituted with 1, 2 or 3 substituents selected from —OH, —F, —$NR^aR^b$, —$CF_3$, $C_1$-$C_6$ alkoxy, and —$CONR^aR^b$;

or $R^A$ and $R^B$ together with the atom(s) to which they are attached form a 5-7 membered fused ring containing 0, 1, or 2 heteroatoms independently selected from N, O and S, wherein N is optionally substituted with $R^d$;

$R^C$ is H, $C_1$-$C_6$ alkyl, F, Cl, —$CF_3$, —$COOCH_3$, —C(O)$NH_2$, or AryC;

$R^D$ is H, $C_1$-$C_6$ alkyl, $C_3$-$C_6$ cycloalkyl, —$CF_3$, F, Cl, or Br, wherein the $R^D$ $C_1$-$C_6$ alkyl or $R^D$ $C_3$-$C_6$ cycloalkyl is optionally substituted with 1, 2, or 3 substituents independently selected from $C_3$-$C_6$ cycloalkyl, —OH, F, —CN, —$(CH_2)_{0-3}NR^aR^b$, —$CF_3$, —$(CH_2)_{0-2}$HetB, —$(CH_2)_{0-2}$AryB, —$SO_2$—$C_1$-$C_6$alkyl, —$SO_2$—$C_3$-$C_6$cycloalkyl, —$SO_2NR^aR^b$, $C_1$-$C_6$ alkoxy, and —$(CH_2)_{0-4}CONR^aR^b$;

wherein when $R^A$, $R^B$, $R^C$ and $R^D$ are all present, then 1, 2 or 3 of $R^A$, $R^B$, $R^C$ and $R^D$ are H;

wherein when 1 or 2 of $X^2$, $X^3$, $X^4$ are N, then at least one of $R^A$, $R^B$, $R^C$, and $R^D$, if present, is not H;

AryA is an aromatic ring system selected from:

1) a 5-6 membered monocyclic ring with 0, 1, 2 or 3 heteroatom ring atoms independently selected from N, O and S, optionally substituted with 1, 2 or 3 substituents independently selected from:
   a) —$C_1$-$C_6$ alkyl,
   b) —$C_1$-$C_6$ hydroxyalkyl,
   c) —$C_3$-$C_6$ cycloalkyl optionally substituted with —OH or —$NR^aR^b$,
   d) —$C_3$-$C_6$ cycloalkenyl optionally substituted with —CN,
   e) —$(CH_2)_{0-6}NR^aR^b$,
   f) —CH(OH)$R^e$,
   g) —$CH_2OR^a$,
   h) —$(CH_2)_{0-1}C(O)NR^aR^b$,
   i) —$CH_2NR^a$—$C_2$-$C_4$alkyl-$NR^aR^b$,
   j) —$CH_2NHCH_2C(O)NR^aR^b$,
   k) —$(CH_2)_{0-2}C(O)OR^a$,
   l) —$CH_2NR^a$—$C_1$-$C_3$alkyl-C(O)$OR^a$,
   m) —$CH_2NH$—$CH[C(OH)CH_3][C(O)OR^a]$,
   n) —$CH_2NR^a$—$C_1$-$C_6$ hydroxyalkyl,
   o) —$(CH_2)_{0-2}SO_2$—$C_1$-$C_6$ alkyl,
   p) —$NR^aSO_2$—$C_1$-$C_6$ alkyl,
   q) —$OR^a$,
   r) —O$(CH_2)_{0-6}NR^aR^b$;
   s) —O—$C_1$-$C_6$ hydroxyalkyl,
   t) —$SO_2NR^aR^b$,
   u) —CN,
   v) halogen,
   w) —$CF_3$,
   x) —$CH_2NR^a(CH_2)_{0-1}$—$C_3$-$C_6$cycloalkyl optionally substituted with —OH, $NR^aR^b$ or 2 F,
   y) —$(CH_2)_{0-1}$-AryB,
   z) —$CH_2NR^a$—$C_1$-$C_3$alkyl-AryB,
   aa) —$CH_2NR^a$—CH(COOH)$CH_2$-AryB,
   bb) —$C_0$-$C_2$alkyl-HetB,
   cc) —$(CH_2)_{0-1}NR^a(CH_2)_{0-2}$-HetB,
   dd) —O$(CH_2)_{0-2}$-HetB,
   ee) —C(O)-HetB, and
   ff) —C(O)$NR^a(CH_2)_{0-2}$-HetB; or 2) a 9- or 10-membered bicyclic ring with 1, 2, 3 or 4 heteroatom ring atoms selected from N, O and S, optionally substituted with 1, 2 or 3 substituents independently selected from $C_1$-$C_6$ alkyl, $C_3$-$C_6$ cycloalkyl, $C_1$-$C_6$ alkoxy, $C_1$-$C_6$ hydroxyalkyl, $C_1$-$C_6$ aminoalkyl, —$CF_3$, —$COOR^a$, —$(CH_2)_{0-1}C(O)NR^aR^b$, —CN, —$(CH_2)_{0-3}NR^aR^b$, —$OR^a$, —$SO_2$—$C_1$-$C_6$ alkyl, —$SO_2$-phenyl, halogen, and oxo;

AryB is 1) a 5-6 membered monocyclic aromatic ring with 0, 1, 2, 3, or 4 ring atoms selected from N, O and S, optionally substituted with 1 or 2 substituents selected from $C_1$-$C_6$ alkyl, —$CH_2NH_2$, —$CONH_2$, —$NH_2$, —OH, —CH(OH)$R^e$, halogen, —$CF_3$, and pyrrolidinyl; or 2) a 9- or 10-membered bicyclic ring with 1, 2 or 3 N ring atoms optionally substituted with 1 or 2 substituents selected from $C_1$-$C_6$ alkyl, $C_1$-$C_6$ hydroxyalkyl, $C_1$-$C_6$ aminoalkyl, —CONH$_2$, —NH$_2$, —OH, —CH(OH)R$^e$, halogen, —CF$_3$, piperidinyl, pyrrolidinyl, and oxo;

AryC is
1) phenyl optionally substituted with —CONH$_2$;
2) a 5-6 membered monocyclic aromatic ring with 1 or 2 N ring atoms, optionally substituted with —CH$_3$ or —OH; or
3) a 9-membered bicyclic ring with 1 N ring atom optionally substituted with oxo;

HetA is
1) a 5-6-membered saturated or monounsaturated monocyclic ring with 1 or 2 heteroatom ring atoms independently selected from N, O and S, optionally substituted with 1 or 2 substituents independently selected from
   a) $C_1$-$C_6$ alkyl,
   b) —$C_1$-$C_6$ hydroxyalkyl,
   c) —C(O)—$C_3$-$C_6$cycloalkyl optionally substituted with phenyl,
   d) —(CH$_2$)$_{0-3}$NR$^a$R$^b$,
   e) —(CH$_2$)$_{0-1}$C(O)NR$^a$R$^b$,
   f) —(CH$_2$)$_{0-2}$C(O)OR$^a$,
   g) —(CH$_2$)$_{0-2}$SO$_2$—$C_1$-$C_6$ alkyl,
   h) —CN,
   i) —OR$^a$,
   j) F,
   k) —CF$_3$,
   l) —(CH$_2$)$_{0-1}$-AryB,
   m) —O-AryB,
   n) —C$_0$-C$_2$ alkyl-HetB, and
   o) oxo; or
2) a 10-11-membered spirocyclic ring with 2 or 3 N ring atoms optionally substituted with oxo;

HetB is
1) a 4-6 membered saturated or monounsaturated monocyclic ring with 1 or 2 heteroatom ring atoms independently selected from N, O and S, optionally substituted with 1, 2 or 3 substituents independently selected from —CF$_3$, F, $C_1$-$C_6$ alkyl, $C_1$-$C_6$ hydroxyalkyl, $C_3$-$C_6$ cycloalkyl, —OH, $C_1$-$C_6$ alkoxy, —C(O)OR$^a$, —C(O)NH$_2$, —C(=NH$_2$)NH$_2$, —CN, —C(OH)(CH$_3$)$_2$, —CH(OH)(CH$_3$), —(CH$_2$)$_{0-2}$NR$^a$R$^b$, —CH$_2$CHR$^f$—(CH$_2$)$_{0-2}$—NHR$^g$, and oxo; or
2) 8-methyl-8-azabicyclo[3.2.1]octane with the point of attachment being the 3-position of the bridged bicyclic ring;

HetC is a 5-6 membered saturated monocyclic ring with 1 or 2 heteroatom ring atoms independently selected from N, O and S, optionally substituted with 1 or 2 oxo substituents;

R$^a$ is H or $C_1$-$C_6$ alkyl;

R$^b$ is H, —OH, $C_1$-$C_6$ alkyl, $C_1$-$C_6$ alkoxy, $C_2$-$C_6$ hydroxyalkyl, $C_2$-$C_6$ aminoalkyl, $C_2$-$C_6$ dihydroxyalkyl, $C_2$-$C_6$ diaminoalkyl, $C_2$-$C_6$ hydroxyaminoalkyl, —(CH$_2$)$_{0-1}$—$C_3$-$C_6$ cycloalkyl, —C(O)$C_1$-$C_6$ alkyl, or —CH$_2$C(O)NHOH; or R$^a$ and R$^b$ together with the atom(s) to which they are attached form a 3-7 membered cycloheteroalkyl ring with 0, 1 or 2 additional heteroatom ring atoms independently selected from N, O and S, wherein N is optionally substituted with R$^d$;

R$^d$ is H, $C_1$-$C_6$ alkyl, $C_3$-$C_6$ cycloalkyl, —C(O)—$C_1$-$C_6$ alkyl, —C(O)-AryC, —SO$_2$—$C_1$-$C_6$ alkyl, and —SO$_2$-AryC; and R$^e$ is $C_1$-$C_6$ alkyl, —CF$_3$ or —CHF$_2$;

R$^f$ is $C_1$-$C_6$ alkyl, —CH$_2$OH, —(CH$_2$)$_{1-4}$NH$_2$, —(CH$_2$)$_{1-3}$CONH$_2$, —CH$_2$-imidazole, benzyl; and R$^g$ is H or $C_1$-$C_6$ alkyl; or R$^f$ and R$^g$ together with the atom(s) to which they are attached form a 4-6 membered cycloheteroalkyl ring with 0, 1 or 2 additional heteroatom ring atoms independently selected from N, O and S.

3. The compound of claim 1, or a pharmaceutically acceptable salt thereof,
wherein:
R$^A$ is H, $C_1$-$C_6$ alkyl, —(CH$_2$)$_{0-2}$—$C_3$-$C_8$ cycloalkyl, —CF$_3$, $C_1$-$C_6$ alkoxy, —COOR$^a$, —CN, —NR$^a$R$^b$, HetA, —(CH$_2$)$_{0-2}$-AryA, —(CH$_2$)$_{0-1}$—O-AryA, —NR$^a$(CH$_2$)$_{1-2}$—$C_3$-$C_8$ cycloalkyl, —NR$^a$(CH$_2$)$_{1-2}$-phenyl, —C≡C-pyridinyl, or —C≡C—CH$_2$-HetC; wherein the R$^A$ $C_1$-$C_6$ alkyl or any R$^A$ $C_3$-$C_8$ cycloalkyl is optionally substituted with —OH, —(CH$_2$)$_{0-2}$NR$^a$R$^b$, —NHSO$_2$—$C_1$-$C_6$ alkyl, AryB, or HetB;

R$^B$ is H, $C_1$-$C_6$ alkyl, —OH, $C_1$-$C_6$ alkoxy, —CN, F, or —NR$^a$R$^b$;

or R$^A$ and R$^B$ together with the atom(s) to which they are attached form a 5-6 membered fused aromatic ring containing 0, 1, or 2 heteroatoms independently selected from N, O and S, wherein N is optionally substituted with R$^d$;

R$^C$ is H, $C_1$-$C_6$ alkyl, F, Cl, —COOCH$_3$, —C(O)NH$_2$, or AryC;

R$^D$ is H, $C_1$-$C_6$ alkyl, —(CH$_2$)$_{0-1}$$C_3$-$C_6$ cycloalkyl, —CH$_2$-phenyl, —CH$_2$-azetidinyl, —(CH$_2$)$_{1-2}$-piperidinyl, or —CH$_2$-pyrrolidinyl, —CF$_3$, —CN, Cl, or Br, wherein the cycloalkyl is optionally substituted with —(CH$_2$)$_{0-1}$NH$_2$ and the piperidinyl is optionally substituted with fluoro;

AryA is an aromatic ring system selected from:
1) a 5-6 membered monocyclic ring with 0, 1, 2 or 3 heteroatom ring atoms independently selected from N, O and S, optionally substituted with 1 or 2 substituents independently selected from:
   a) —$C_1$-$C_6$ alkyl,
   b) —$C_1$-$C_6$ hydroxyalkyl,
   c) —$C_3$-$C_6$ cycloalkyl optionally substituted with —OH,
   d) —$C_3$-$C_6$ cycloalkenyl optionally substituted with —CN,
   e) —(CH$_2$)$_{0-6}$NR$^a$R$^b$,
   f) —CH$_2$NHCH=NH,
   g) —CH(OH)R$^e$,
   h) —CH$_2$OR$^a$,
   i) —(CH$_2$)$_{0-1}$C(O)NR$^a$R$^b$,
   j) —CH$_2$NR$^a$—$C_3$-$C_4$alkyl-NR$^a$R$^b$,
   k) —CH$_2$NHCH$_2$C(O)NR$^a$R$^b$,
   l) —(CH$_2$)$_{0-2}$C(O)OR$^a$,
   m) —CH$_2$NR$^a$—$C_1$-$C_3$alkyl-C(O)OR$^a$,
   n) —CH$_2$NH—CH[C(OH)CH$_3$][C(O)OR$^a$],
   o) —CH$_2$NR$^a$—$C_1$-$C_6$ hydroxyalkyl,
   p) —(CH$_2$)$_{0-2}$SO$_2$—$C_1$-$C_6$ alkyl,
   q) —NR$^a$SO$_2$—$C_1$-$C_6$ alkyl,
   r) —OR$^a$,
   s) —O(CH$_2$)$_{0-6}$NR$^a$R$^b$;
   t) —O—$C_1$-$C_6$ hydroxyalkyl,
   u) —SO$_2$NR$^a$R$^b$,
   v) —CN,
   w) halogen,
   x) —CH$_2$NR$^a$(CH$_2$)$_{0-1}$—$C_3$-$C_6$cycloalkyl optionally substituted with —OH, NR$^a$R$^b$ or 2 F,
   y) —(CH$_2$)$_{0-1}$-AryB,
   z) —CH$_2$NR$^a$—$C_1$-$C_3$alkyl-AryB, aa) —CH₂NRᵃ—CH(COOH)CH₂-AryB,
bb) —C₀-C₂alkyl-HetB,
cc) —(CH₂)₀₋₁NRᵃ(CH₂)₀₋₂-HetB,
dd) —O(CH₂)₀₋₂-HetB,
ee) —C(O)-HetB, and
ff) —C(O)NRᵃ(CH₂)₀₋₂-HetB; or 2) a 9- or 10-membered bicyclic ring with 1, 2 or 3 heteroatom ring atoms selected from N, O and S, optionally substituted with 1 or 2 substituents independently selected from C₁-C₆ alkyl, C₁-C₆ alkoxy, —NH₂, C₁-C₆ aminoalkyl, —CF₃, —COORᵃ, —CONH₂, —SO₂—C₁-C₆ alkyl, —SO₂-phenyl, —CN, Cl, and oxo;

AryB is
1) a 5-6 membered monocyclic aromatic ring with 0, 1, 2, 3, or 4 ring atoms selected from N, O and S, optionally substituted with C₁-C₆ alkyl, —CH₂NH₂, —NH₂, —CH(OH)Rᵉ, or pyrrolindinyl; or
2) a 9-membered bicyclic ring with 2 or 3 N ring atoms optionally substituted with CH₃;

AryC is
1) phenyl optionally substituted with —CONH₂,
2) a 5-6 membered monocyclic aromatic ring with 1 or 2 N ring atoms, optionally substituted with —CH₃ or —OH; or
3) a 9-membered bicyclic ring with 1 N ring atom optionally substituted with oxo;

HetA is
1) a 6-membered monounsaturated monocyclic ring with 1 heteroatom ring atom independently selected from N, O or S, optionally substituted with 1 or 2 substituents independently selected from C₁-C₆ alkyl, —CN, and oxo;
2) a 6-membered saturated monocyclic ring with 1 N ring atom, optionally substituted with 1 substituent selected from
 a) —C₁-C₆ hydroxyalkyl,
 b) —C(O)—C₃-C₆cycloalkyl,
 c) —(CH₂)₁₋₂NRᵃRᵃ,
 d) —(CH₂)₀₋₁C(O)NRᵃRᵃ,
 e) —(CH₂)₀₋₂C(O)ORᵃ,
 f) —(CH₂)₀₋₂SO₂—C₁-C₆ alkyl,
 g) —OH,
 h) —(CH₂)₀₋₁-AryB,
 i) —O-AryB, and
 j) —C₀-C₂ alkyl-HetB; or
3) a 10-11-membered spirocyclic ring with 2 or 3 N ring atoms optionally substituted with oxo;

HetB is
1) a 4-6 membered saturated or monounsaturated monocyclic ring with 1 or 2 heteroatom ring atoms independently selected from N, O and S, optionally substituted with 1, 2 or 3 substituents independently selected from —CF₃, F, C₁-C₆ alkyl, C₁-C₆ hydroxyalkyl, C₃-C₆ cycloalkyl, —OH, C₁-C₆ alkoxy, —C(O)ORᵃ, —C(O)NH₂, —C(=NH₂)NH₂, —CN, —C(OH)(CH₃)₂, —CH(OH)(CH₃), —NH₂, —N(CH₃)₂, and oxo; or
2) 8-methyl-8-azabicyclo[3.2.1]octane with the point of attachment being the 3-position of the bridged bicycle;

HetC is a 5-6 membered saturated monocyclic ring with 1 or 2 heteroatom ring atoms independently selected from N, O and S, optionally substituted with 1 or 2 oxo substituents;

Rᵃ is H or C₁-C₆ alkyl;
Rᵇ is H, —OH, C₁-C₆ alkyl, C₁-C₆ alkoxy, C₁-C₆ hydroxyalkyl, C₁-C₆ dihydroxyalkyl, C₃-C₆ cycloalkyl, —C(O)C₁-C₆ alkyl, —CH₂C(O)NHOH, or C₁-C₆ aminoalkyl; or
Rᵃ and Rᵇ together with the atom(s) to which they are attached form a 3-7 membered cycloheteroalkyl ring with 0, 1 or 2 additional heteroatom ring atoms independently selected from N, O and S, wherein N is optionally substituted with Rᵈ;
Rᵉ is —C₁-C₆ alkyl, —CF₃ or —CHF₂.

4. The compound of claim 1, or a pharmaceutically acceptable salt thereof, wherein R^A is H, C₁-C₆ alkyl, —(CH₂)₀₋₂—C₃-C₈ cycloalkyl, —CF₃, C₁-C₆ alkoxy, —COORᵃ, —CN, —NRᵃRᵇ, HetA, —(CH₂)₀₋₂-AryA, —CH₂—O-AryA, —NRᵃ(CH₂)₁₋₂—C₃-C₈ cycloalkyl, —NRᵃ(CH₂)₁₋₂-phenyl, —C≡C-pyridinyl, or —C≡C—CH₂-HetC; wherein the R^A cycloalkyl is optionally substituted with —OH, —(CH₂)₀₋₂NH₂, —NHSO₂—C₁-C₆ alkyl or HetB, or R^A and R^B together with the atom(s) to which they are attached form a 5-7 membered fused ring containing 0, 1, or 2 heteroatoms independently selected from N, O and S, wherein N is optionally substituted with Rᵈ.

5. The compound of claim 4, or a pharmaceutically acceptable salt thereof, wherein Formula I is

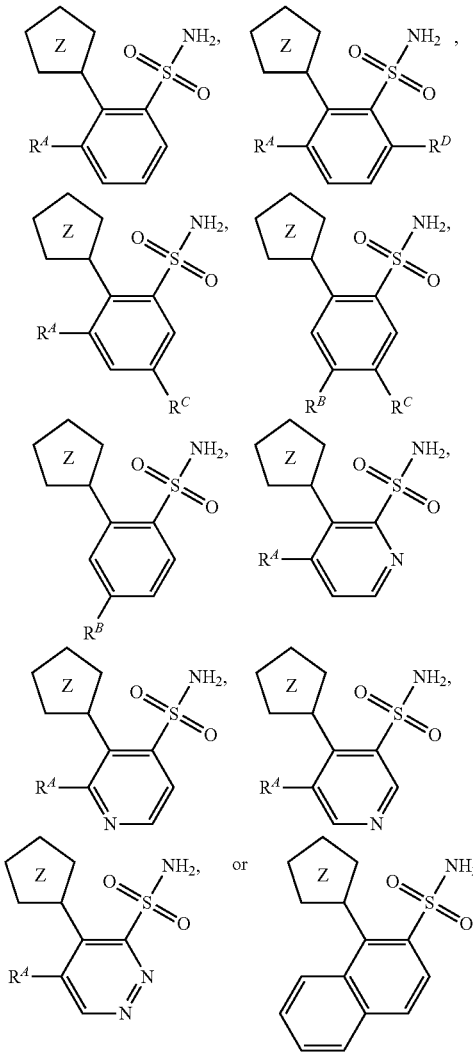

wherein $R^A$ is $C_1$-$C_6$ alkyl; —$(CH_2)_{0-2}$—$C_3$-$C_8$ cycloalkyl; —$CF_3$; $C_1$-$C_6$ alkoxy; —$COOR^a$; —CN; —$NR^aR^b$; HetA; —$(CH_2)_{0-2}$-AryA; —$CH_2$—O-AryA; —$NR^a(CH_2)_{1-2}$—$C_3$-$C_8$ cycloalkyl; —$NR^a(CH_2)_{1-2}$-phenyl; —C≡C-pyridinyl; or —C≡C—$CH_2$-HetC; wherein the $R^A$ cycloalkyl is optionally substituted with —$(CH_2)_{0-1}NR^aR^b$, AryB, or —OH;

$R^B$ is $C_1$-$C_6$ alkyl, —OH, $C_1$-$C_6$ alkoxy, —CN, F, or —$NR^aR^b$, $R^C$ is $C_1$-$C_6$ alkyl, Cl, —$COOCH_3$, —$C(O)NH_2$, or AryC; and $R^D$ is $C_1$-$C_6$ alkyl, —$(CH_2)_{0-1}C_3$-$C_8$ cycloalkyl, —$CH_2$-phenyl, —$CH_2$-azetidinyl, —$(CH_2)_{1-2}$-piperidinyl, or —$CH_2$-pyrrolidinyl, —$CF_3$, Cl, or Br, wherein the cycloalkyl is optionally substituted with —$(CH_2)_{0-1}NH_2$ and the piperidinyl is optionally substituted with fluoro.

6. The compound of claim 5, or a pharmaceutically acceptable salt thereof, wherein AryA is 1) phenyl optionally substituted with:
   a) —$C_1$-$C_6$ alkyl,
   b) —$C_1$-$C_2$ hydroxyalkyl,
   c) —$(CH_2)_{1-3}NR^aR^b$,
   d) —$CH_2NHCH=NH$;
   e) —$CH_2NHC(=NH)NH_2$;
   f) —$CH(OH)R^e$,
   g) —$CH_2OR^a$,
   h) —$CH_2NR^a$—$C_1$-$C_6$ hydroxyalkyl,
   i) —$(CH_2)_{0-1}C(O)NR^aR^b$,
   j) —$C(O)OR^a$,
   k) —$NHSO_2$—$C_1$-$C_6$ alkyl,
   l) —$OR^a$,
   m) —$OCH(CH_3)CH_2OH$,
   n) —$SO_2$—$C_1$-$C_6$ alkyl,
   o) —$SO_2NR^aR^b$,
   p) halogen,
   q) —CN,
   r) —$CH_2NR^a(CH_2)_{0-1}$—$C_3$-$C_6$cycloalkyl optionally substituted with —OH, $NR^aR^b$ or 2 F,
   s) AryB,
   t) —$CH_2NR^a$—$C_3$-$C_4$alkyl-$NR^aR^b$,
   u) —$CH_2NHCH_2C(O)NR^aR^b$,
   v) —$CH_2NR^a$—$C_1$-$C_3$ alkyl-$C(O)OR^a$,
   w) —$CH_2NH$—$CH[C(OH)CH_3][C(O)OR^a]$,
   x) —$CH_2NR^a$—$C_1$-$C_3$ alkyl-AryB,
   y) —$CH_2NR^a$—$CH(COOH)CH_2$-AryA,
   z) —$C_0$-$C_2$ alkyl-HetB,
   aa) —C(O)-HetB,
   bb) —$(CH_2)_{0-1}NR^a(CH_2)_{0-2}$-HetB,
   cc) —$C(O)NR^a(CH_2)_{0-2}$-HetB, or
   dd) —$O(CH2)_{0-2}$-HetB; or 2) dihydroindenyl substituted with —$NH_2$ or —$NHC(=NH)NH_2$.

7. The compound of claim 5, or a pharmaceutically acceptable salt thereof, wherein AryA is an aromatic ring system selected from:

a) a 5-6 membered monocyclic ring with 1 or 2 heteroatom ring atoms independently selected from N, O and S, optionally substituted with 1 or 2 substituents selected from $C_1$-$C_6$ alkyl; $C_1$-$C_6$ hydroxyalkyl; $C_1$-$C_6$ alkoxy; $C_1$-$C_6$ aminoalkyl; $C_3$-$C_6$ hydroxycycloalkyl; —$CH_2CH_2C(O)OCH_2CH_3$; —CN, —$(CH_2)_{0-2}SO_2CH_3$; —$NR^aR^b$, —$N(R^a)SO_2CH_3$; —OH; —$O(CH_2)_{0-6}NR^aR^b$; dioxolanyl substituted with —$CF_3$; halogen; —$(CH_2)_{0-1}$-AryB; —$C_0$-$C_2$alkyl-HetB; and —$(CH_2)_{0-1}NR^a(CH_2)_{0-2}$-HetB; or b) a 9- or 10-membered bicyclic ring with 1, 2 or 3 heteroatom ring atoms selected from N, S and O, optionally substituted with 1 or 2 substituents independently selected from $C_1$-$C_6$ alkyl, $C_1$-$C_6$ alkoxy, —$NR^aR^b$, $C_1$-$C_6$ aminoalkyl, —$CF_3$, —$C(=NH)NH_2$, —$COOR^a$, —$CONH_2$, —$SO_2$—$C_1$-$C_6$ alkyl, —$SO_2$-phenyl, —CN, Cl, and oxo.

8. The compound of claim 7, or a pharmaceutically acceptable salt thereof, wherein AryA is an aromatic ring system selected from:

a) a monocyclic ring selected from furanyl, imidazolyl, morpholinyl, pyrazinyl, pyrazolyl, pyridazinyl, pyridinyl; pyrimidinyl, thiazolyl, and thiophenyl, wherein the monocyclic ring is optionally substituted with 1 or 2 substituents selected from $C_1$-$C_6$ alkyl; $C_1$-$C_6$ hydroxyalkyl; $C_1$-$C_6$ alkoxy; $C_1$-$C_6$ aminoalkyl; $C_3$-$C_6$ hydroxycycloalkyl; —$CH_2CH_2C(O)OCH_2CH_3$; —CN; —$(CH_2)_{0-2}SO_2CH_3$; —$NR^aR^b$; —$N(R^a)SO_2CH_3$; —OH; —$O(CH_2)_{0-6}NR^aR^b$; dioxolanyl substituted with —$CF_3$; halogen; —$(CH_2)_{0-1}$-AryB; —$C_0$-$C_2$alkyl-HetB; and —$(CH_2)_{0-1}NR^a(CH_2)_{0-2}$-HetB; or b) a bicyclic ring selected from 1H-benzo[d]imidazolyl, benzodiimidazolyl, benzooxadiazolyl, benzo[d]thiazolyl, benzothiophenyl, benzotriazolyl, dihydrobenzimidazol, dihydrobenzodioxinyl, dihydrobenzooxazinyl, dihydrochromenyl, dihydroisoindolyl, dihydroindolyl, dihydroquinazolinyl, furopyridinyl, imidazopyridinyl, indazolyl, indolinyl, indolyl, isoindolinyl, isoquinolinyl, naphthyridinyl, pyrazolopyrazinyl, pyrazolopyridinyl, pyrrolopyrazinyl, pyrroloppyridinyl, quinolinyl, tetrahydroimidazopyridinyl, tetrahydropyrazolopyridinyl, tetrahydroquinolinyl, and triazolopyridinyl; wherein the bicyclic ring is optionally substituted with 1 or 2 substituents independently selected from $C_1$-$C_6$ alkyl, $C_1$-$C_6$ alkoxy, —$NR^aR^b$, $C_1$-$C_6$ aminoalkyl, —$CF_3$, —$COOR^a$, —$CONH_2$, —$SO_2$—$C_1$-$C_6$ alkyl, —$SO_2$-phenyl, —CN, Cl, and oxo.

9. The compound of claim 8, or a pharmaceutically acceptable salt thereof, wherein HetB is azabicyclo[3.2.1]octyl, azetidinyl, 1,1-dimethylazetidin-1-ium, 1,1-dimethylpiperidin-1-ium, dioxolanyl, morpholinyl, oxoimidazolidinyl, oxazolidinyl, oxopiperazinyl, oxopiperidinyl, oxopyrrolidinyl, oxazolidinyl, piperidinyl, piperazinyl, pyrazolyl, pyrrolidinyl, tetrahydrofuranyl, tetrahydropyranyl, or thiazolidinyl; wherein HetB is optionally substituted with 1, 2 or 3 substituents independently selected from —$CF_3$, F, $C_1$-$C_6$ alkyl, —$C_1$-$C_6$ hydroxyalkyl, $C_3$-$C_6$ cycloalkyl, —OH, $C_1$-$C_6$ alkoxy, —$C(O)OR^a$, —$C(O)NH_2$, —$CH(=NH)$, —$C(=NH_2)NH_2$, —CN, —$C(OH)(CH_3)_2$, —$CH(OH)(CH_3)$, —$NH_2$, —$N(CH_3)_2$, —$(CH_2)$-azetidinyl, and oxo; or HetC is dioxidothiomorpholinyl, morpholinyl, piperidinyl, or pyrrolidin-1-yl.

10. The compound of claim 1, or a pharmaceutically acceptable salt thereof, wherein Formula I is

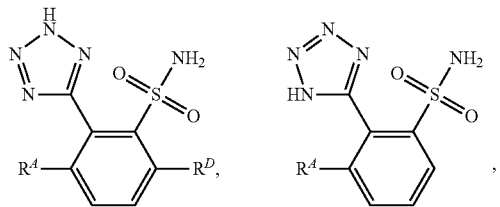

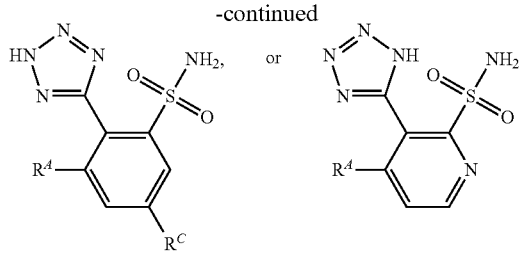

wherein
R^A is 1) —(CH$_2$)$_{0-2}$AryA optionally substituted with
  a) —C$_1$-C$_6$ alkyl,
  b) —C$_1$-C$_2$ hydroxyalkyl,
  c) —(CH$_2$)$_{0-3}$NR$^a$R$^b$,
  d) —C(=NH)NH$_2$
  e) —CH$_2$NHCH=NH;
  f) —CH$_2$NHC(=NH)NH$_2$;
  g) —(CH$_2$)$_{0-1}$C(O)NR$^a$R$^b$,
  h) —NHC(=NH)NH$_2$;
  i) —NHSO$_2$—C$_1$-C$_6$ alkyl,
  j) —OH,
  k) —SO$_2$NR$^a$R$^b$, or
  l) HetB, or
2) —(CH$_2$)$_{0-2}$ C$_3$-C$_6$-cycloalkyl, wherein the C$_3$-C$_6$ cycloalkyl optionally substituted with —OH or —(CH$_2$)$_{0-2}$NR$^a$R$^b$;
HetB is
1) a 4-6 membered saturated or monounsaturated monocyclic ring with 1 N ring atom, optionally substituted with 1 or 2 substituents selected from —CH(=NH), —C(=NH)NH$_2$, —NH$_2$, and —OH; or
2) a 4-6 membered saturated monocyclic ring with 1 N ring atom, in the form of a quarternary amine, wherein the N ring atom is substituted with 2 methyl;
R$^C$ is Cl;
R$^D$ is C$_1$-C$_6$ alkyl, C$_3$-C$_6$ cycloalkyl, —CF$_3$, Cl, Br, —CH$_2$-cyclohexyl-(CH$_2$)$_{0-1}$NH$_2$, —CH$_2$-azetidinyl, —(CH$_2$)$_{1-2}$-piperidinyl, or —CH$_2$-pyrrolidinyl, wherein the piperidinyl is optionally substituted with fluoro;
R$^a$ is H or CH$_3$; and
R$^b$ is H or CH$_3$.

11. The compound of claim 10, or a pharmaceutically acceptable salt thereof, wherein AryA is phenyl substituted with 1) —CH$_3$, 2) —CH$_2$CH$_2$CH$_3$, 3) —CH$_2$OH, 4) —CH$_2$NH$_2$, 5) —CH$_2$NHCH=NH, 6) —CH$_2$NHC(=NH)NH$_2$, 7) —CH$_2$CH$_2$NH$_2$, 8) —CH$_2$CH$_2$CH$_2$NH$_2$, 9) —C(O)NH$_2$, 10) —(CH$_2$)C(O)NH$_2$, 11) —NHSO$_2$CH$_3$, 12) —SO$_2$NH$_2$, 13) —SO$_2$NHCH$_3$, 14) dimethylazetidinium, 15) azetidinyl optionally substituted with —C(=NH)NH$_2$ or —OH, 16) piperidinyl optionally substituted with 1 or 2 substituents selected from —NH$_2$, 17) —C(=NH)NH$_2$, 18) —CH(=NH), 19) —CH-azetidinyl, or 20) pyrrolidinyl optionally substituted with —OH or 2,5-dihydro-1H-pyrrolyl.

12. The compound of claim 10, or a pharmaceutically acceptable salt thereof, wherein AryA is pyridinyl substituted with —NH$_2$.

13. The compound of claim 10, or a pharmaceutically acceptable salt thereof, wherein AryA is benzodimidazolyl substituted with —NH$_2$; benzothiophenyl; benzothiazolyl substituted with —NH$_2$ or —C(=NH)NH$_2$; dihydrobenzimidazol; dihydroindenyl substituted with —NH$_2$ or —NHC(=NH)NH$_2$; dihydroisoindolyl substituted with oxo; imidazopyridinyl; indazolyl optionally substituted with —NH$_2$; isoindolinyl optionally substituted with —CH(=NH)NH$_2$; pyrazolopyridinyl; pyrrolopyrazinyl; pyrrolopyridinyl; quinolinyl optionally substituted with —CH$_2$NH$_2$; or tetrahydroimidazopyridinyl.

14. The compound of claim 1 which is

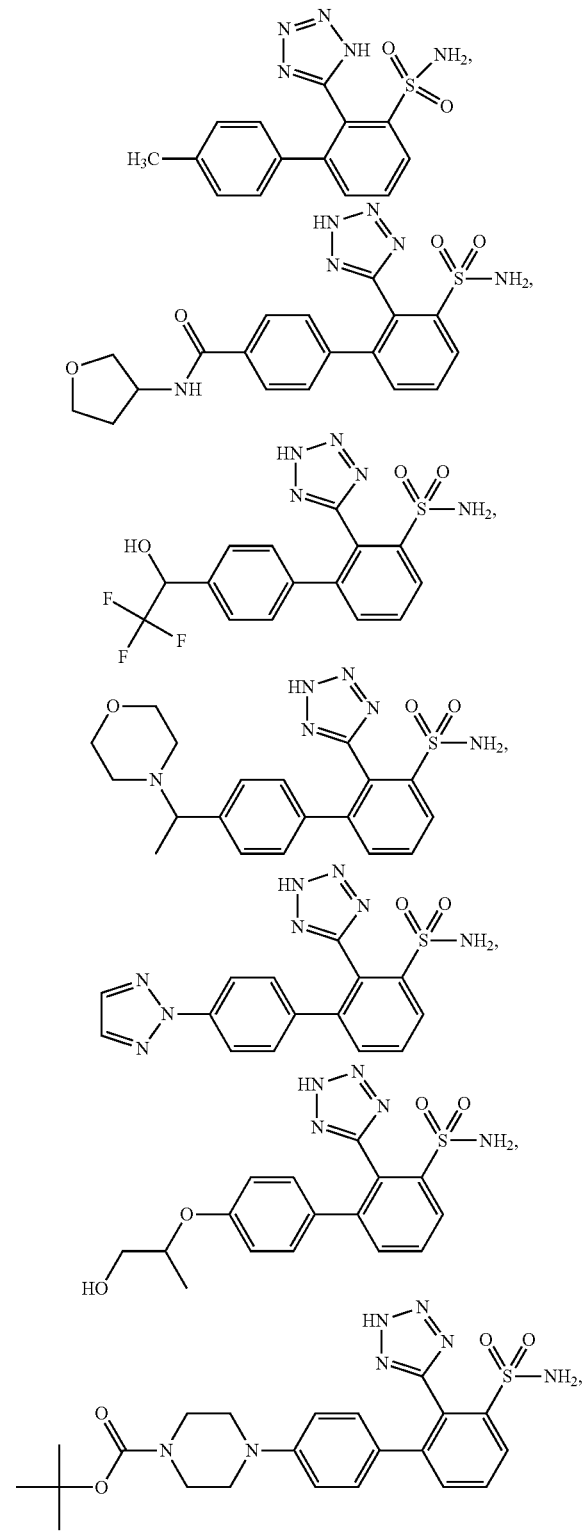

-continued
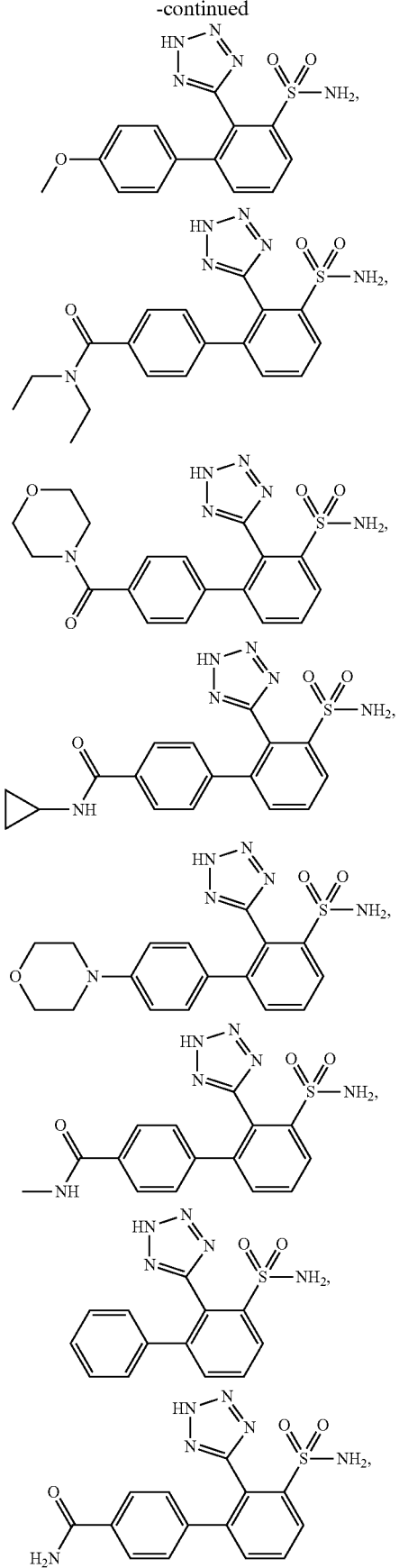
-continued
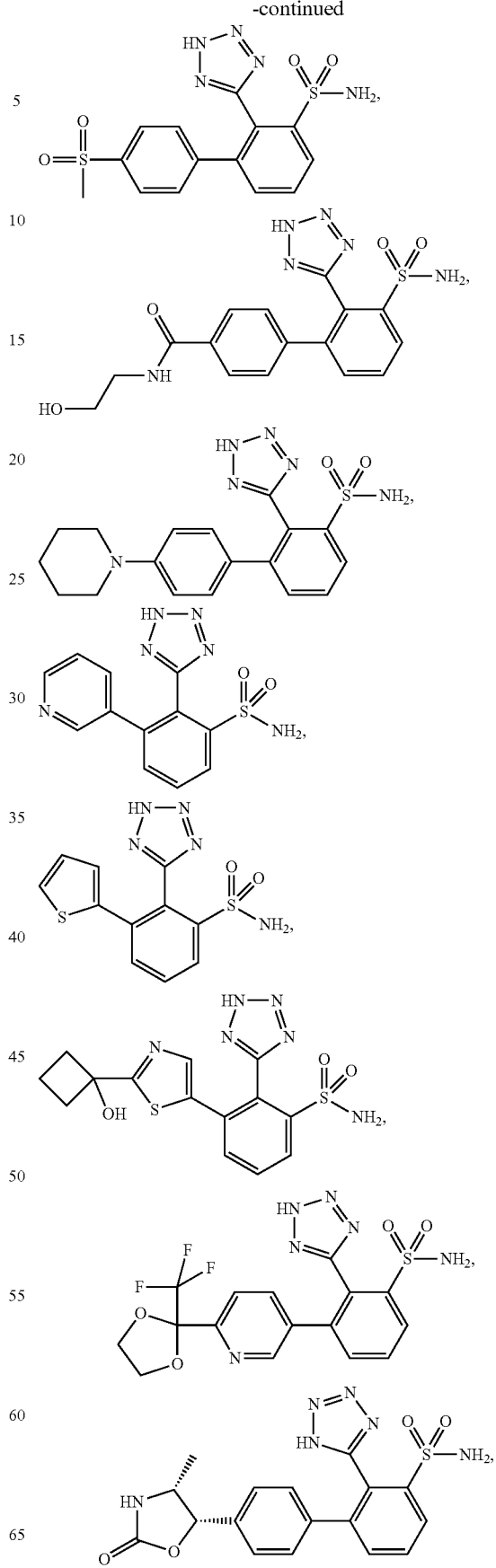

625
-continued
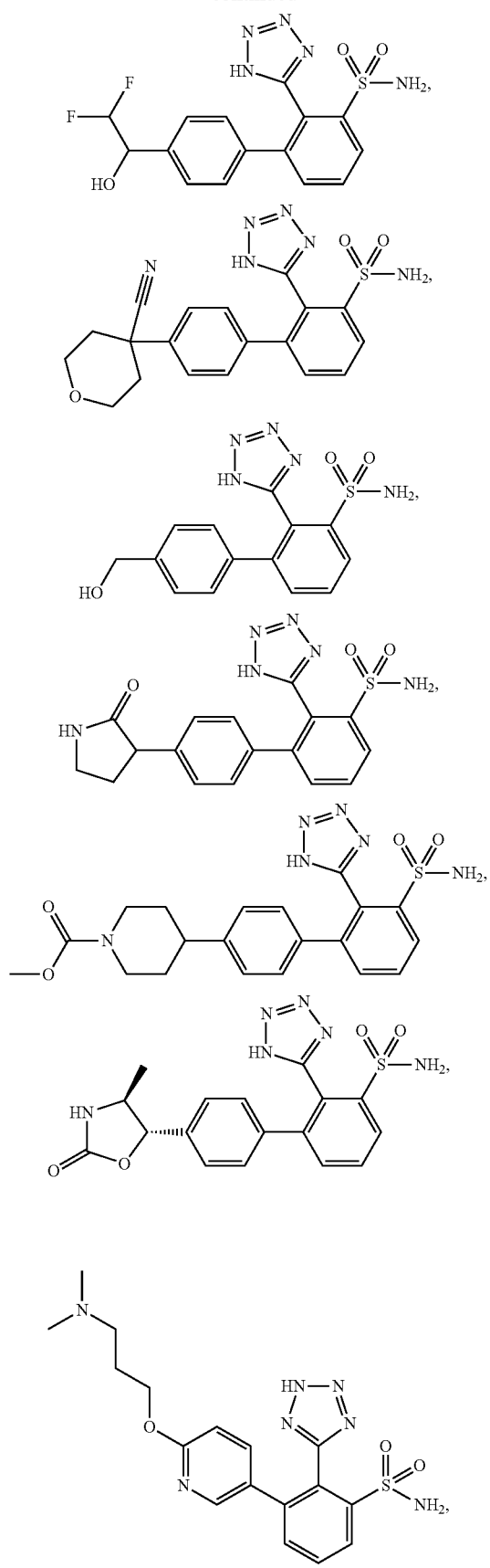
626
-continued
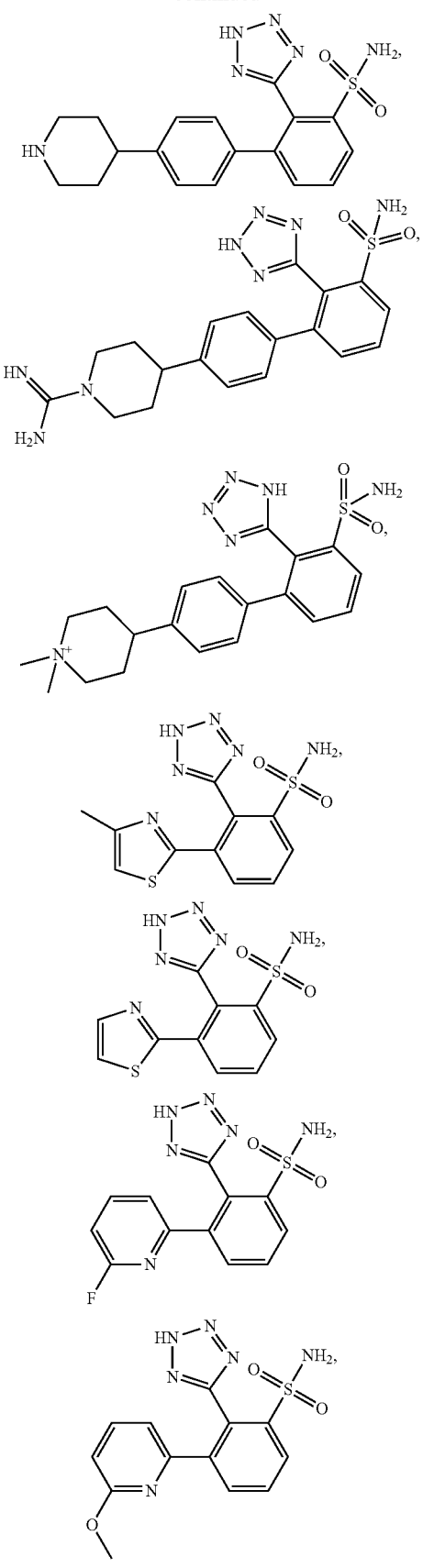

627
-continued
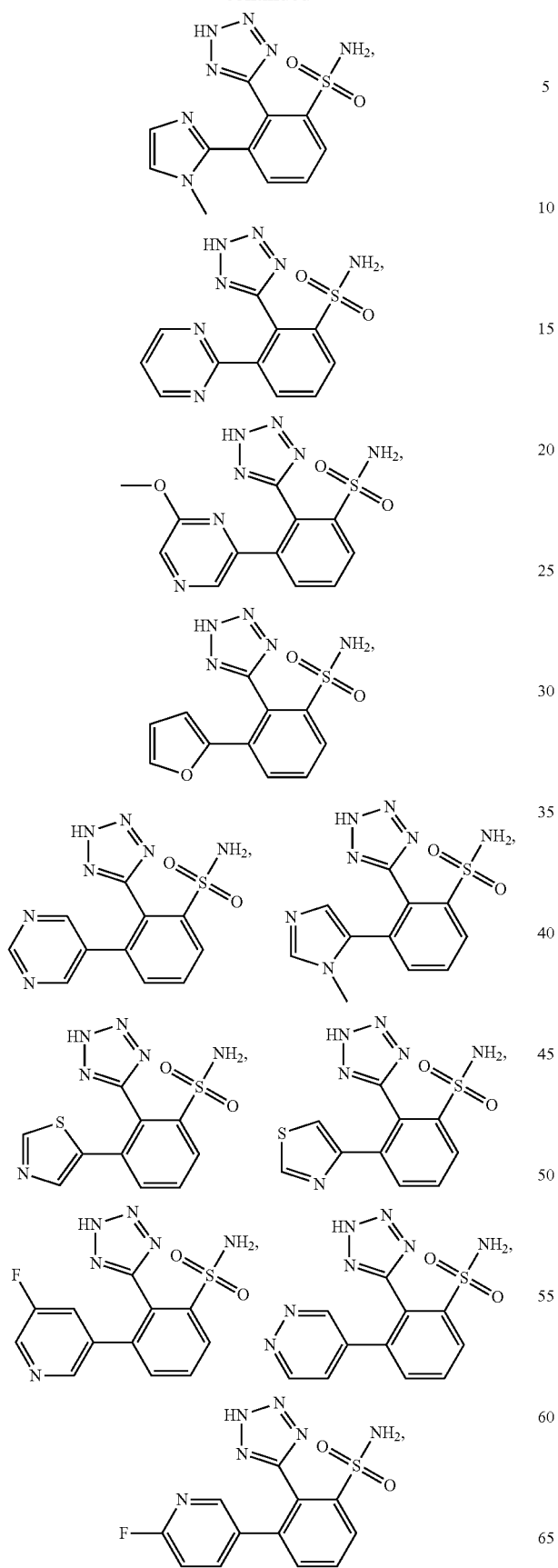
628
-continued
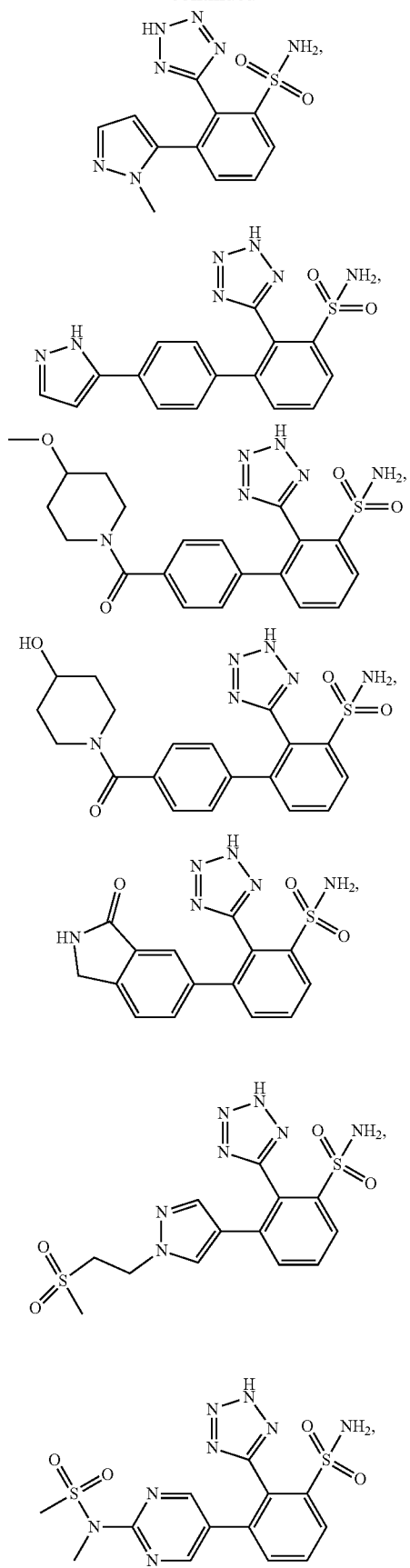

629
-continued
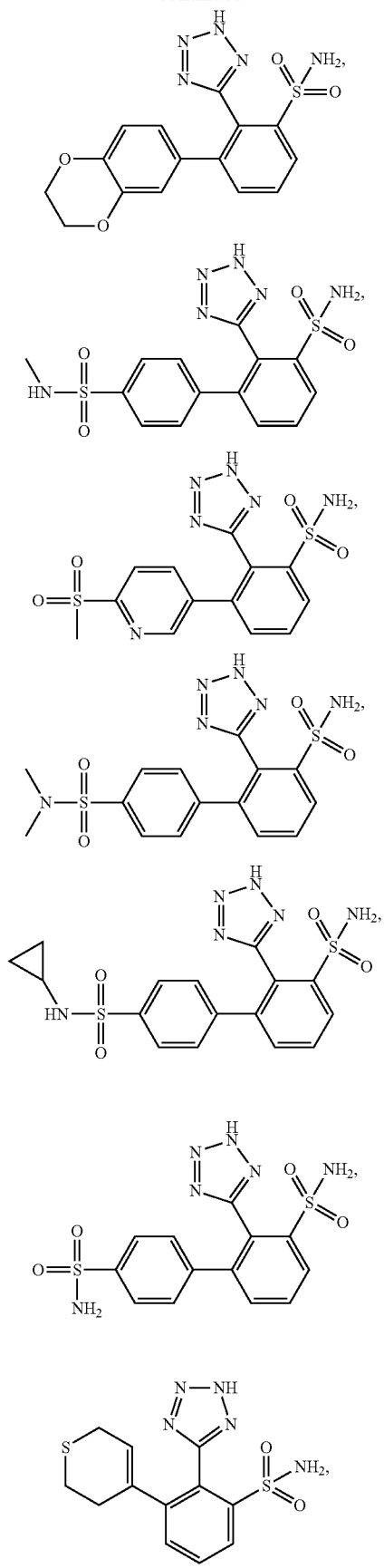
630
-continued
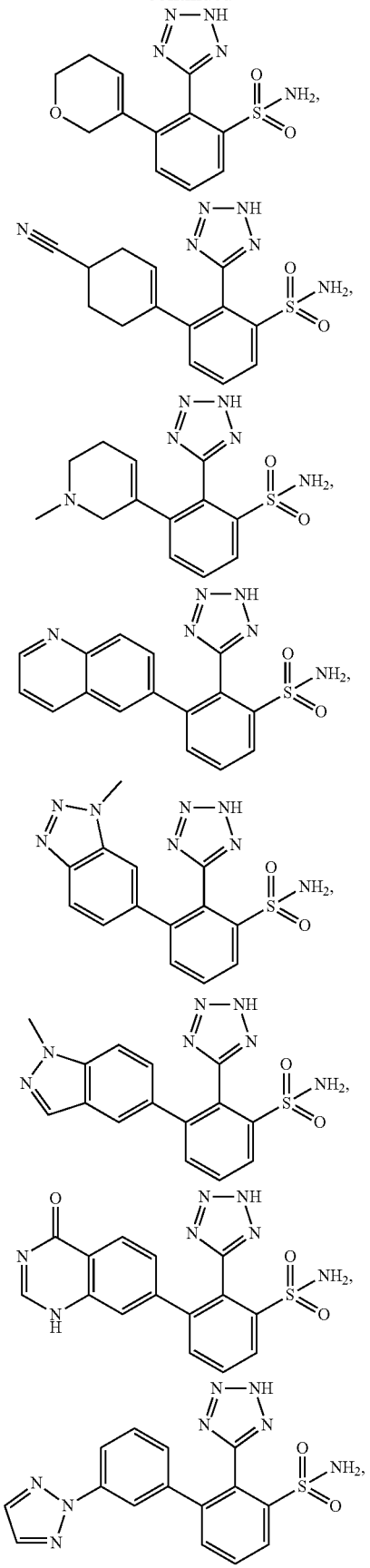

631
-continued
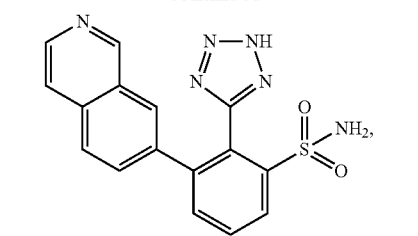
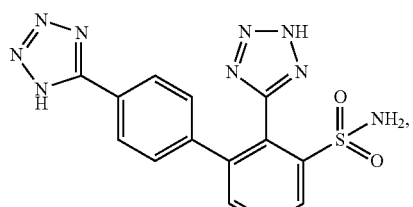
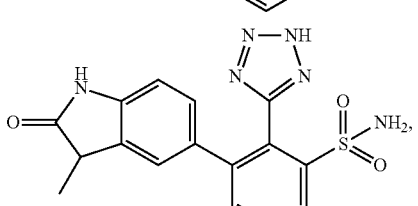
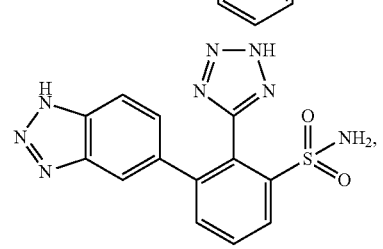
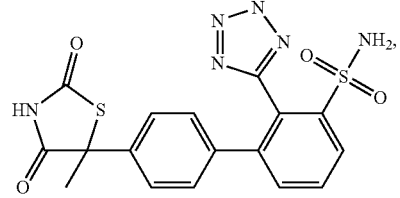
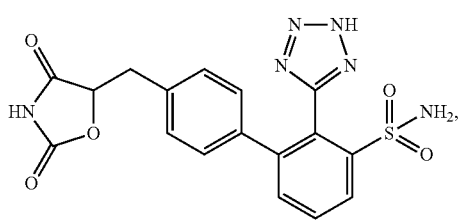
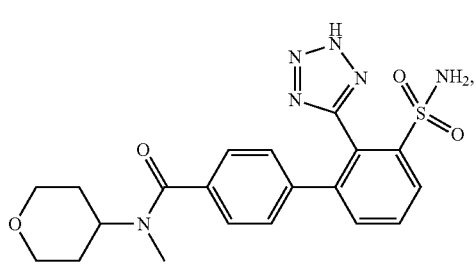
632
-continued
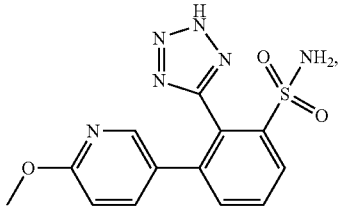
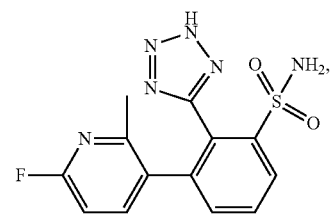
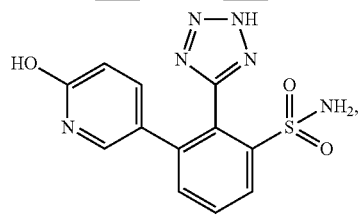
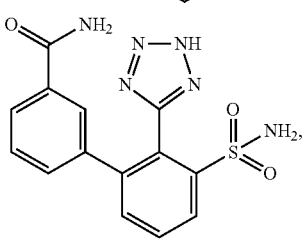
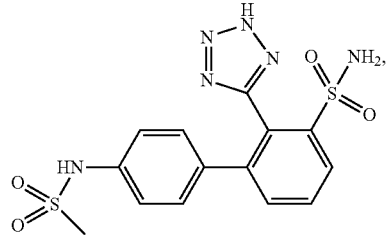
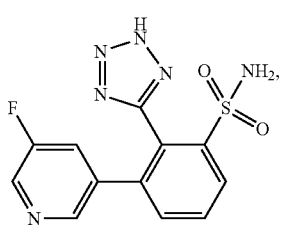
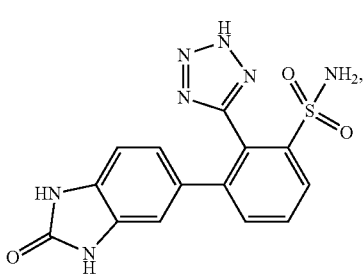

633
-continued
634
-continued
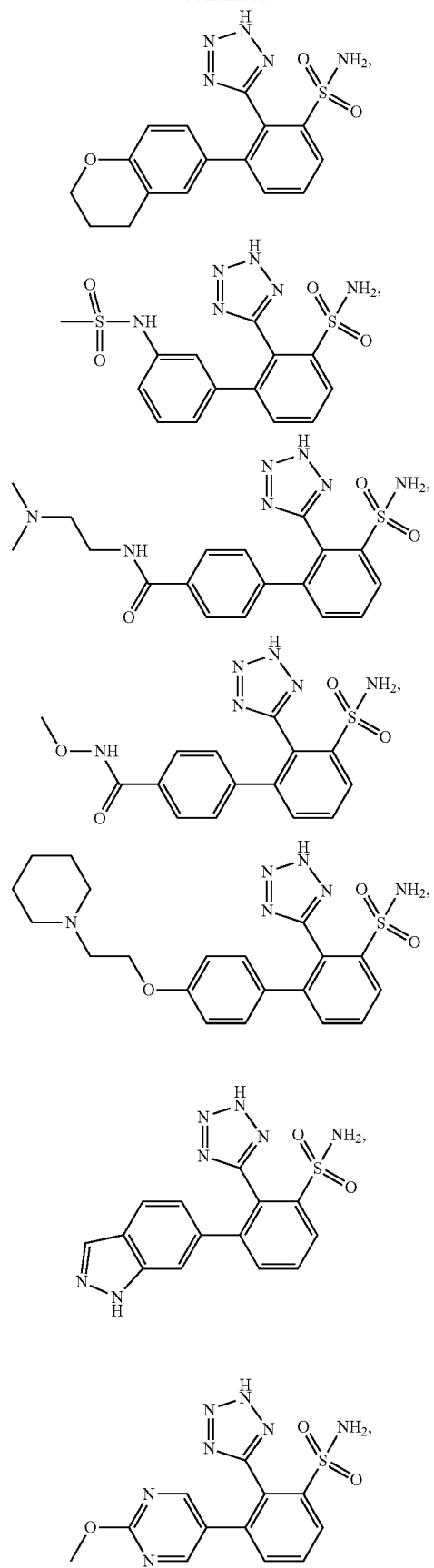
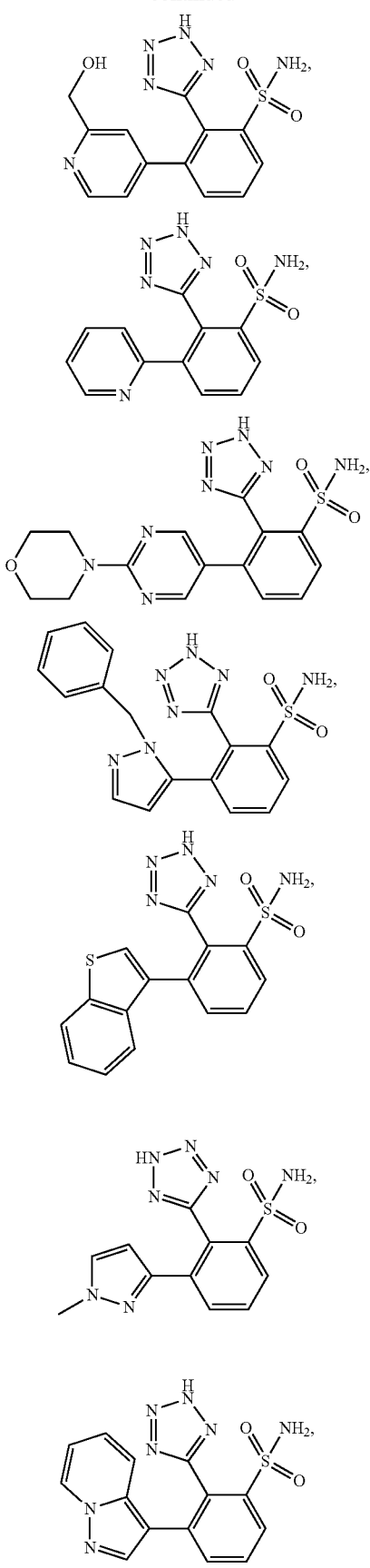

635
-continued
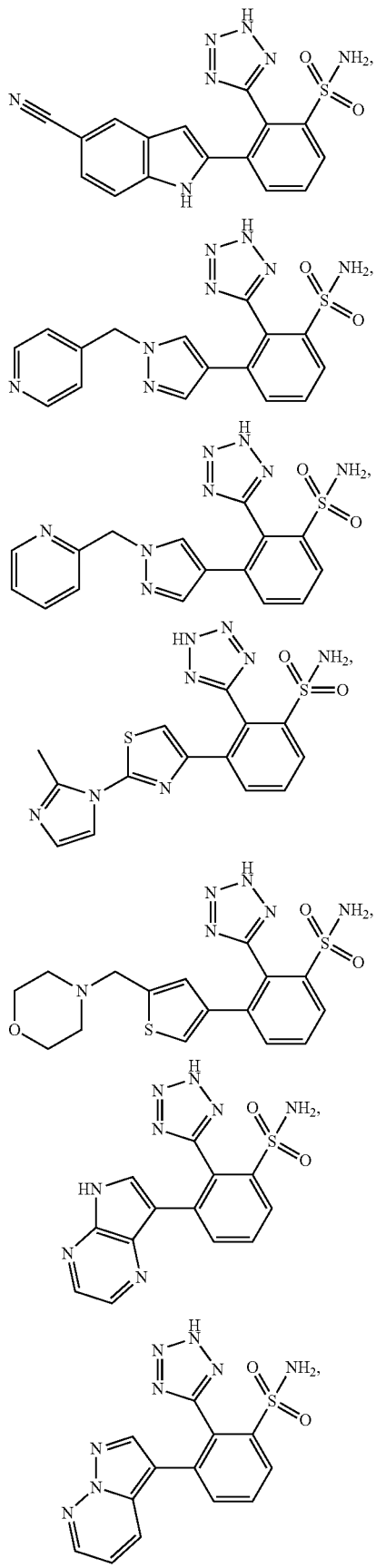
636
-continued
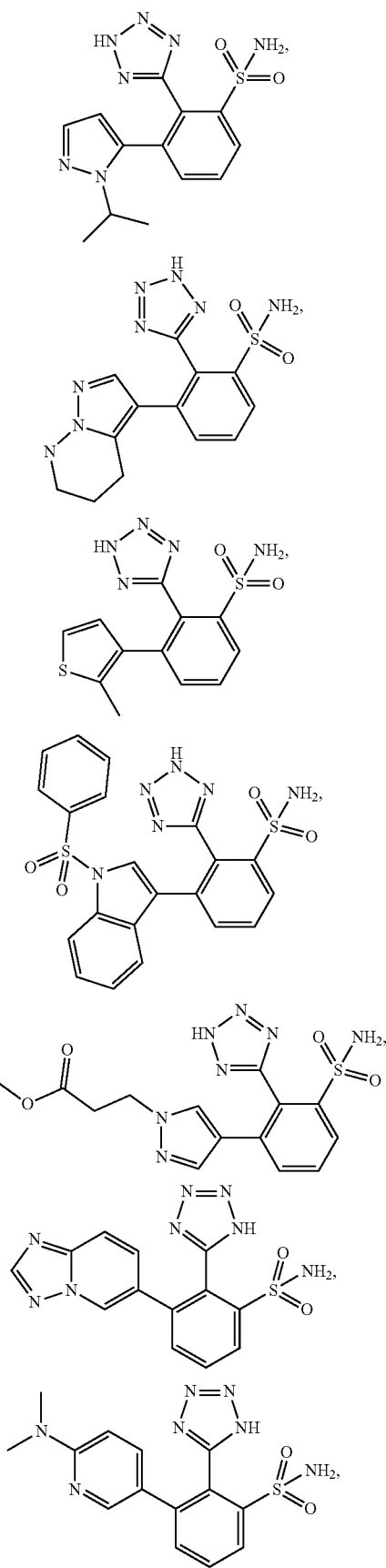

637
-continued
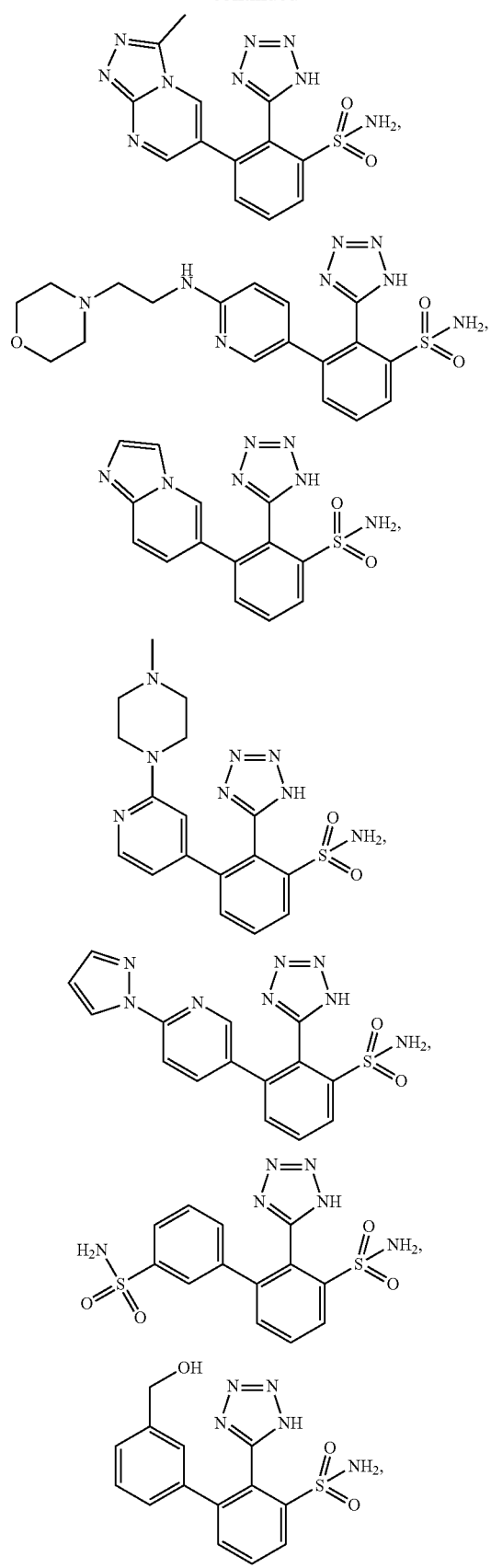
638
-continued
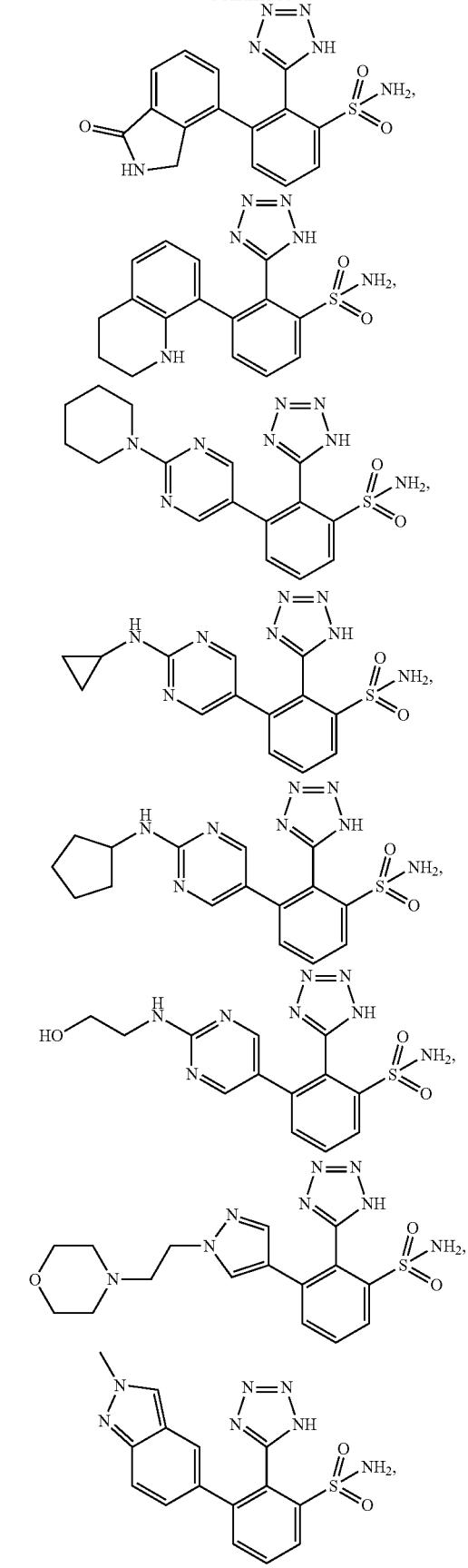

639
-continued
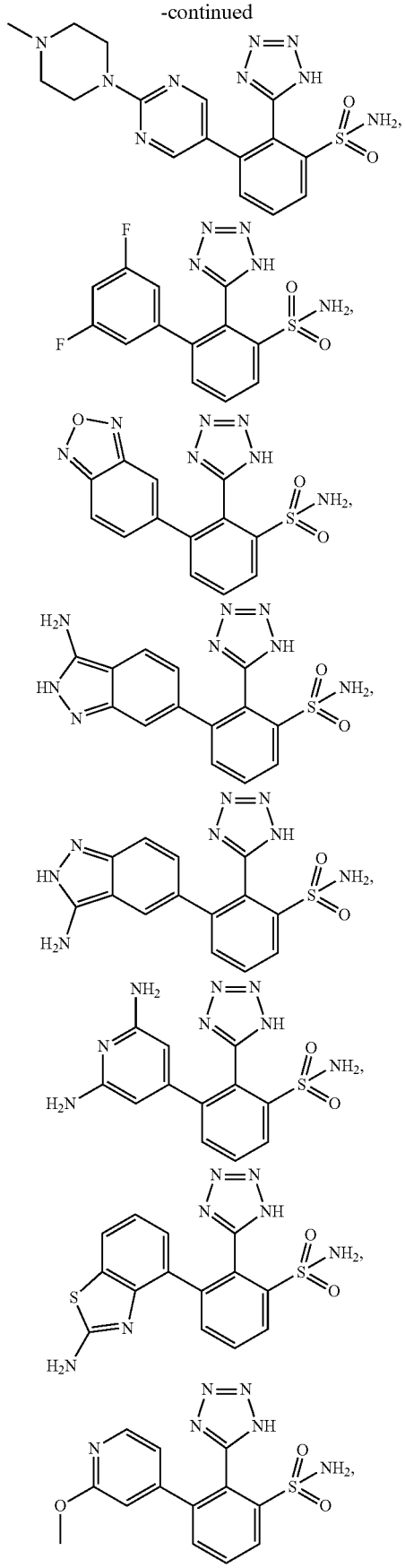
640
-continued
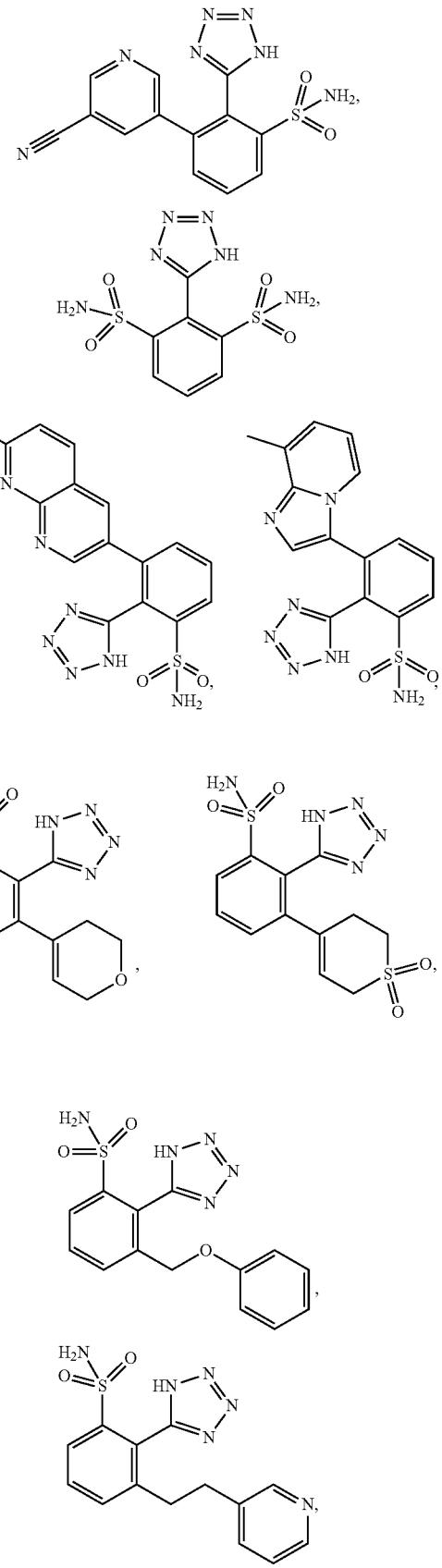

641
-continued
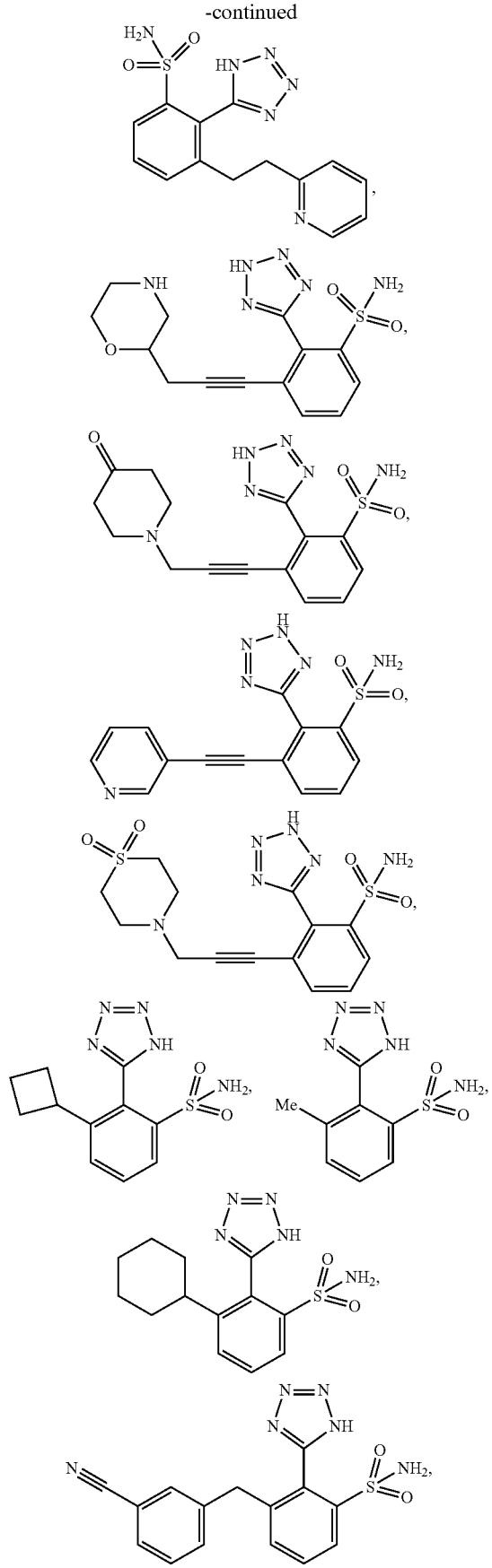
642
-continued
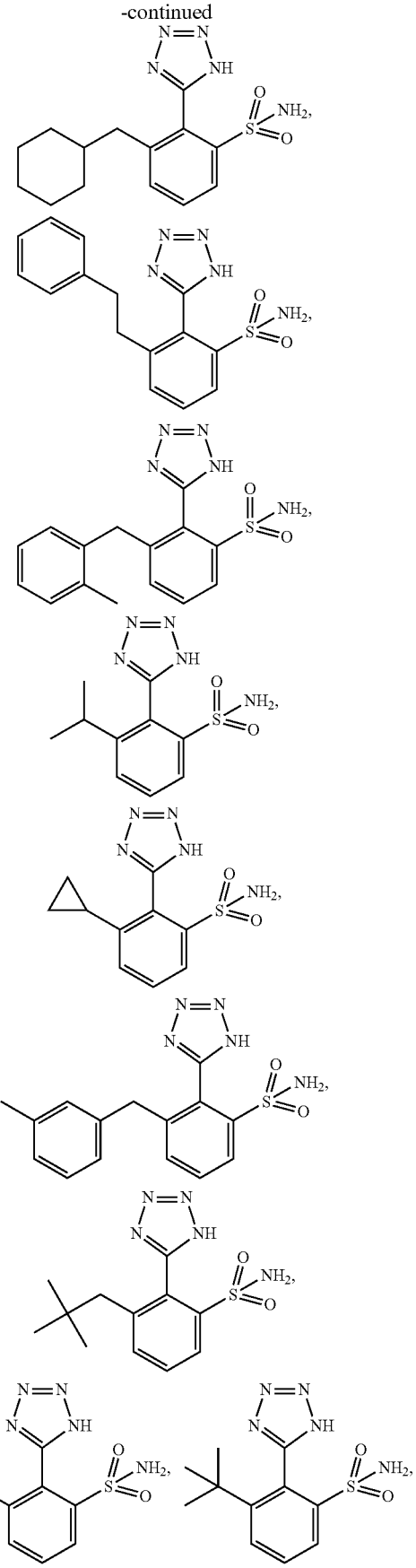

643
-continued
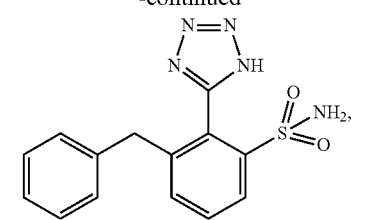
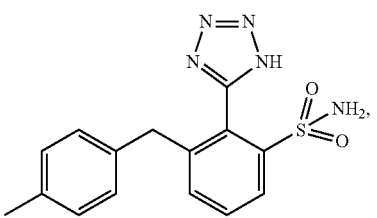
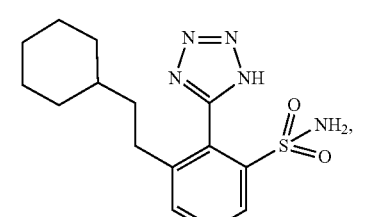
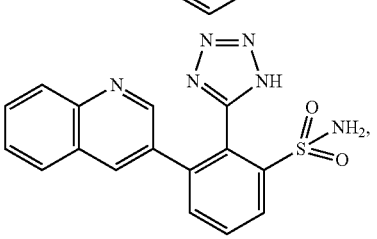
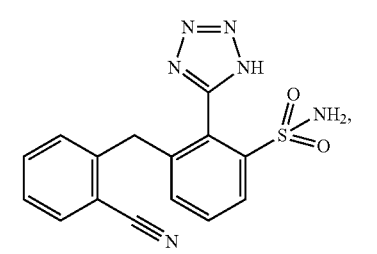
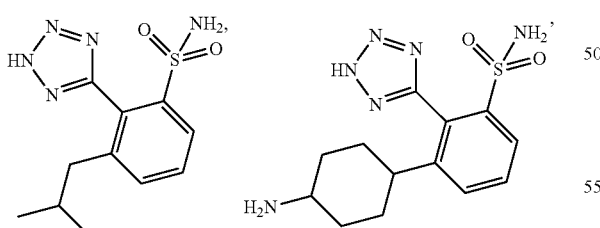
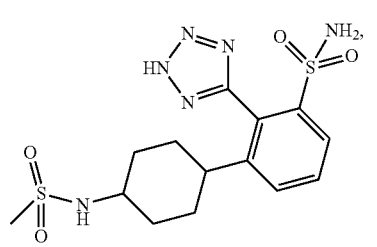
644
-continued
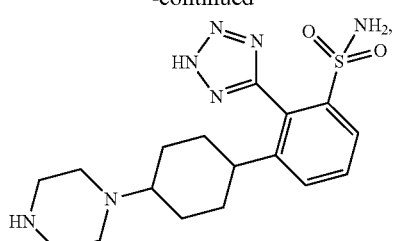
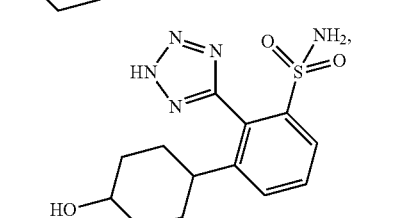
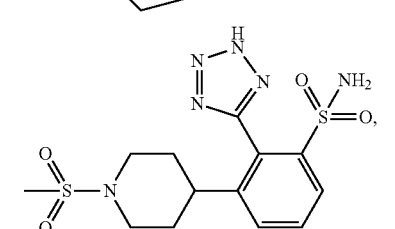
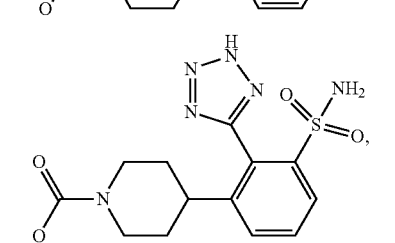
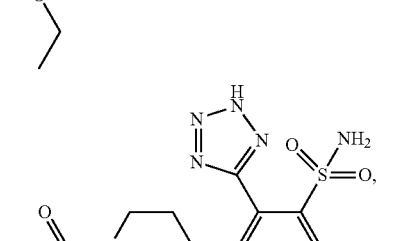
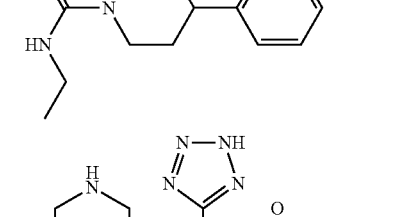
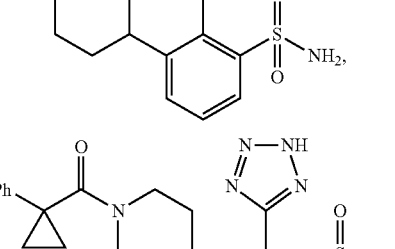

645
-continued
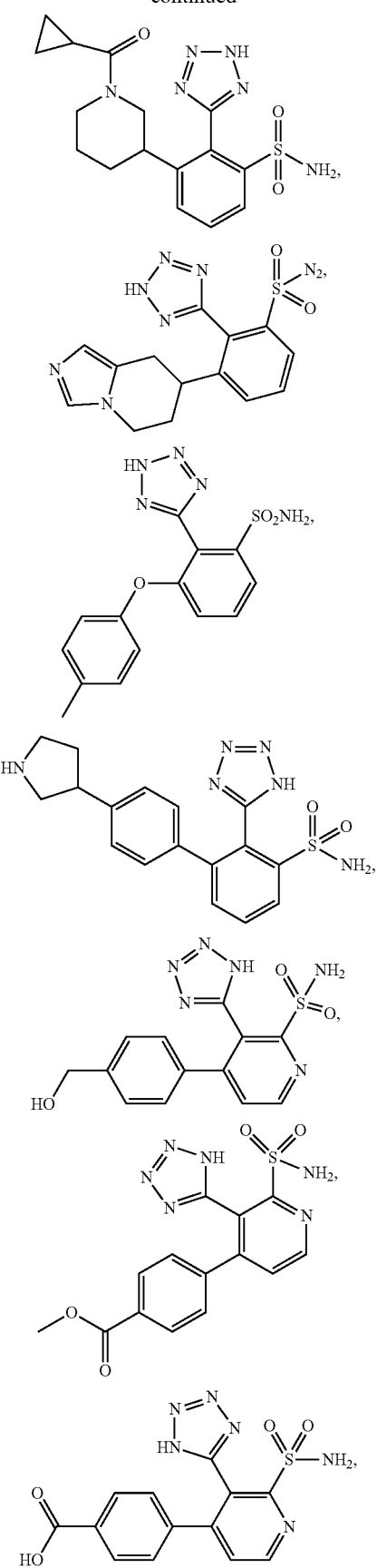
646
-continued
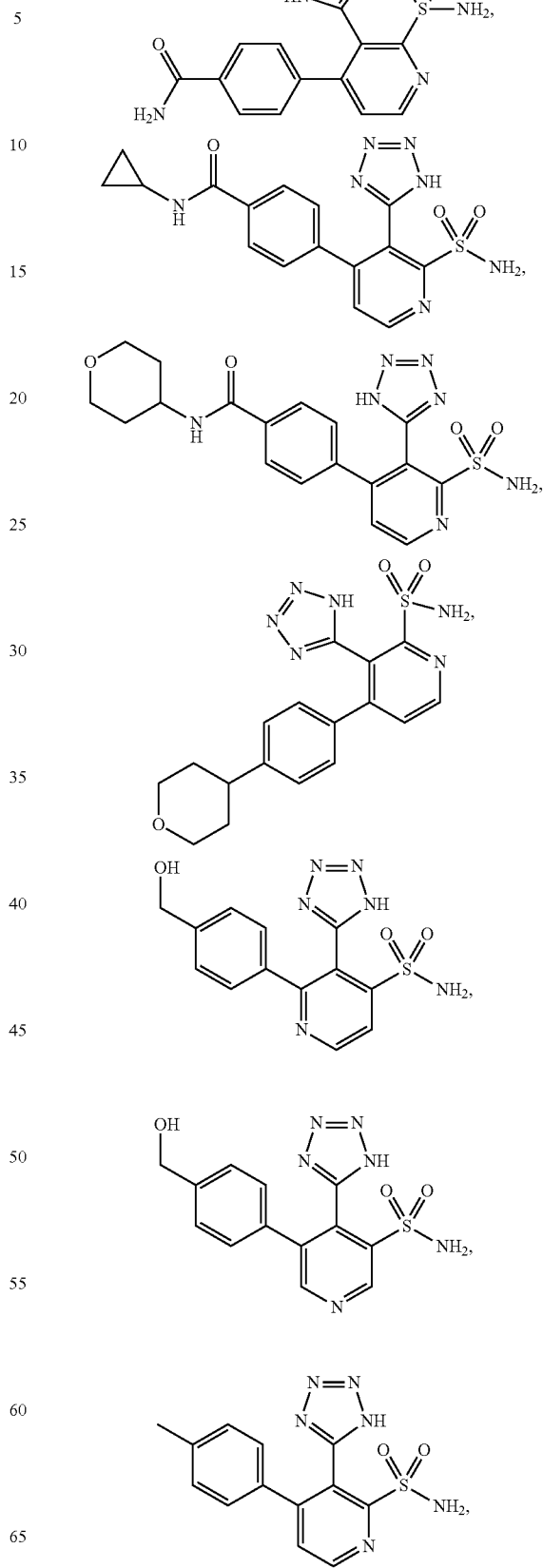

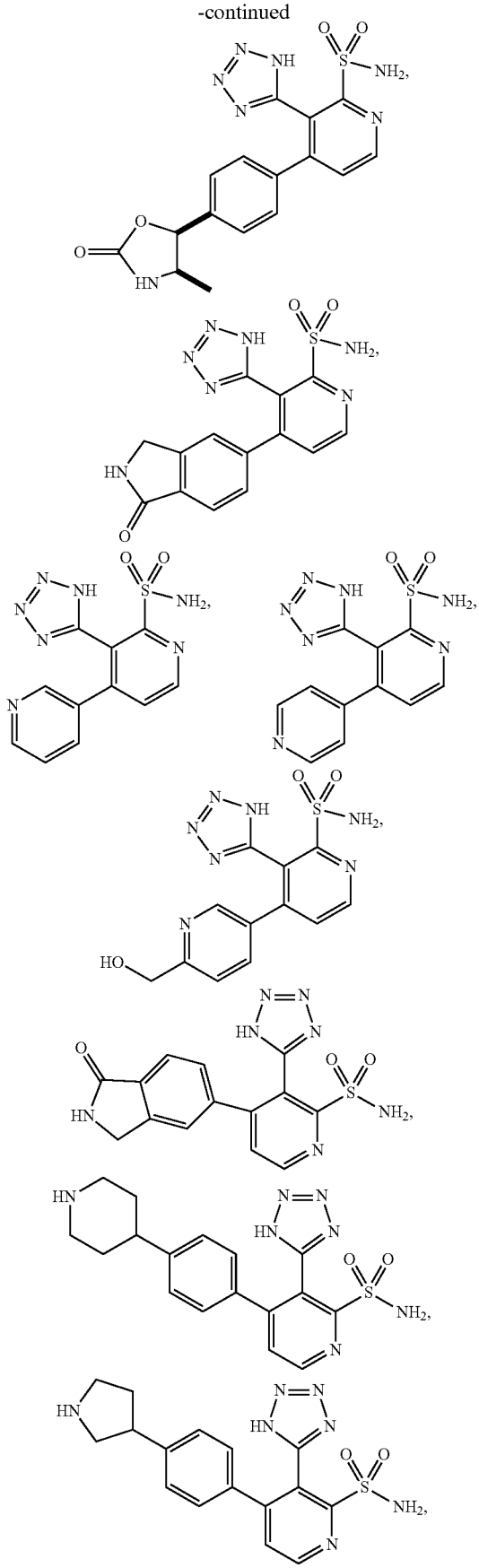
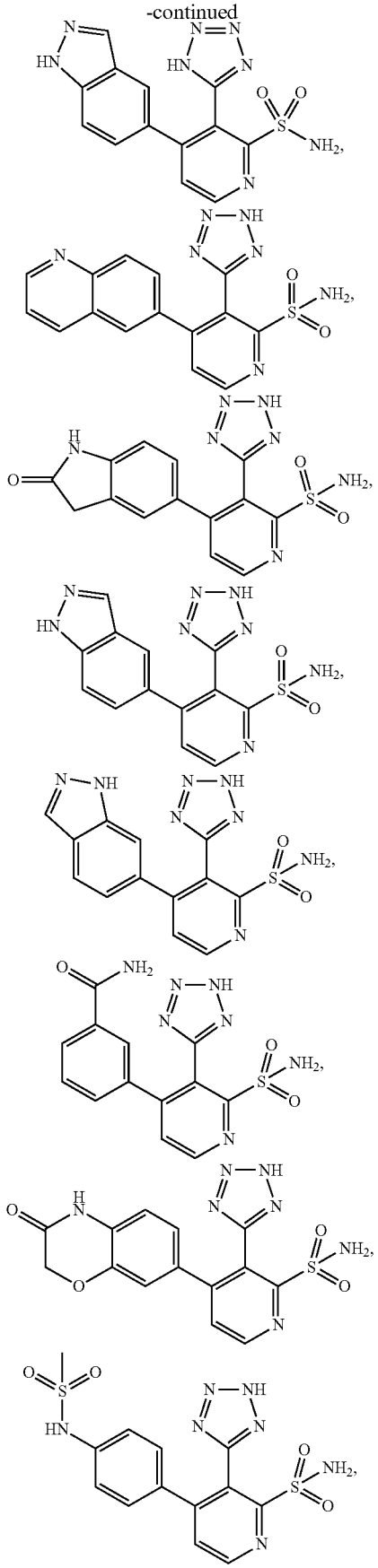

649
-continued
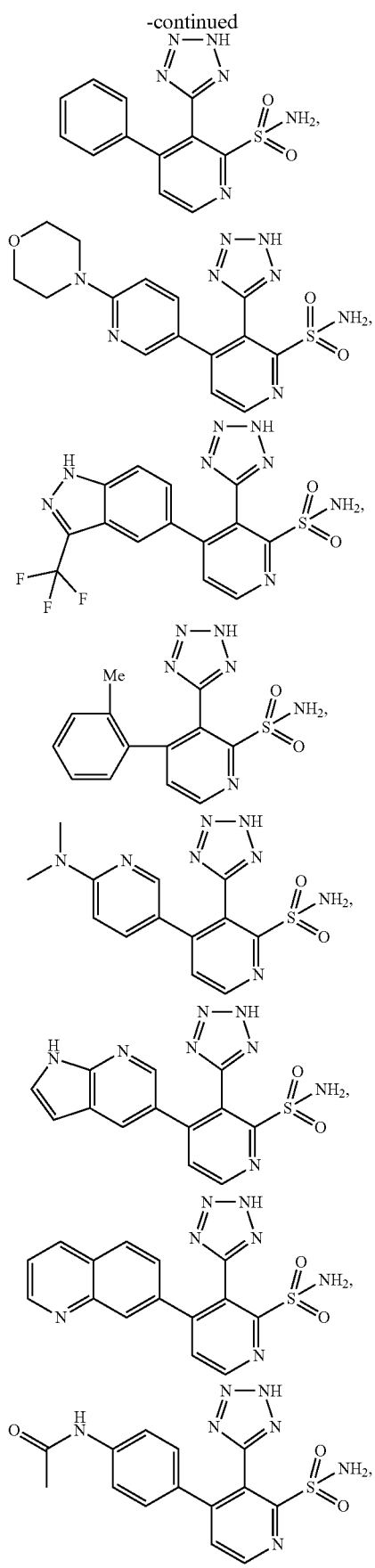
650
-continued
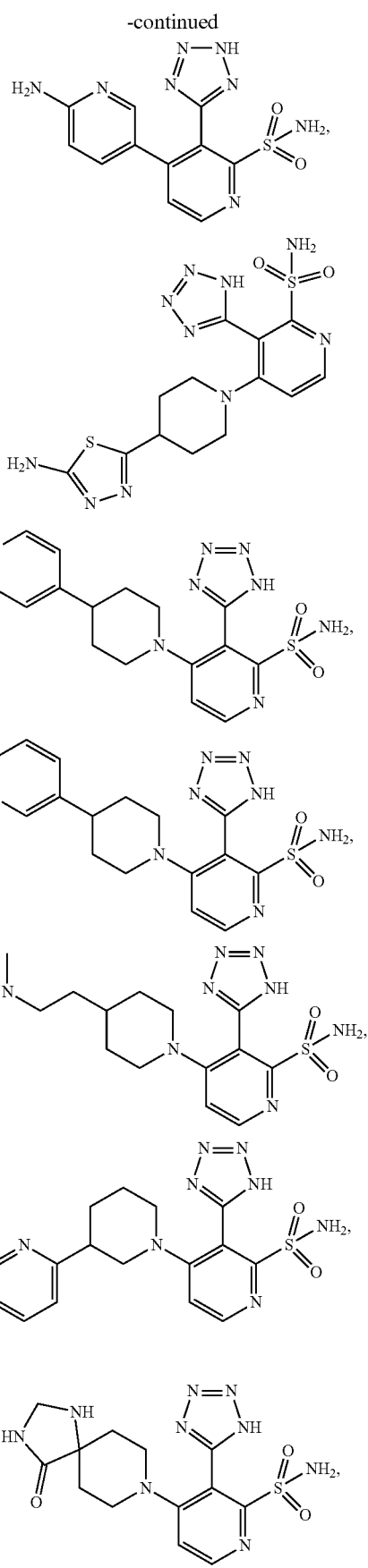

651
-continued
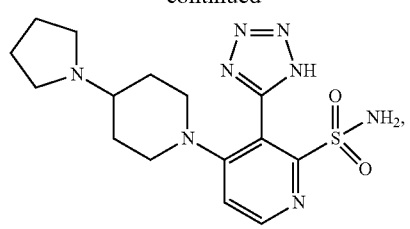
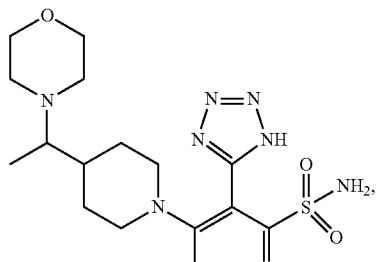
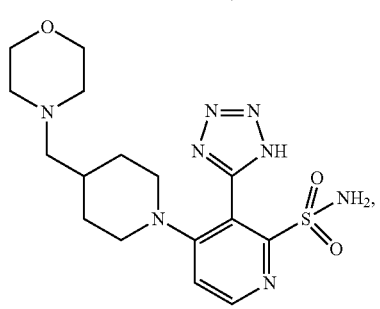
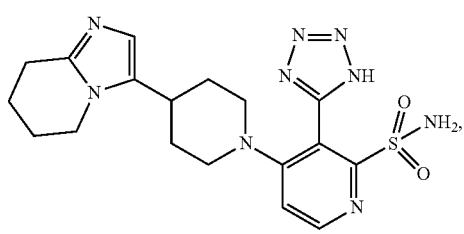
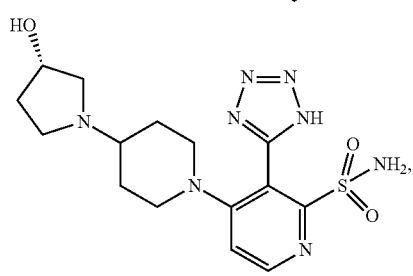
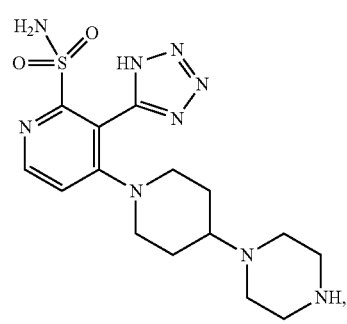
652
-continued
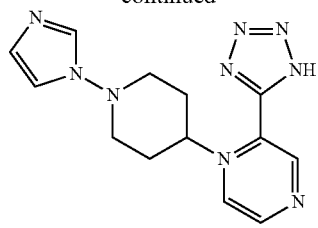
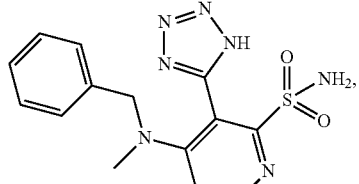
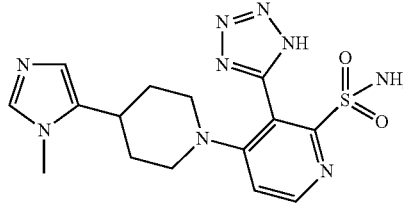
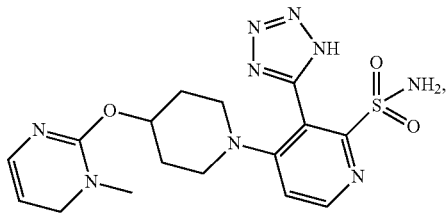
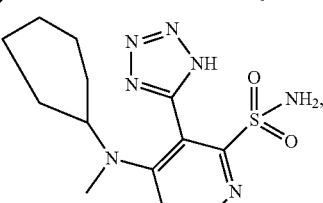
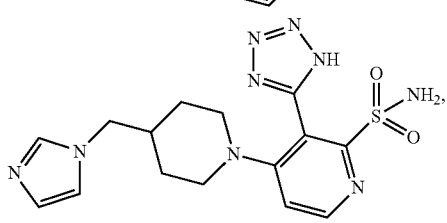
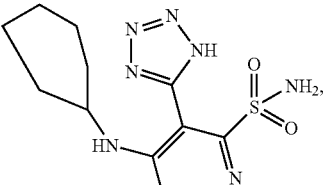

653
-continued
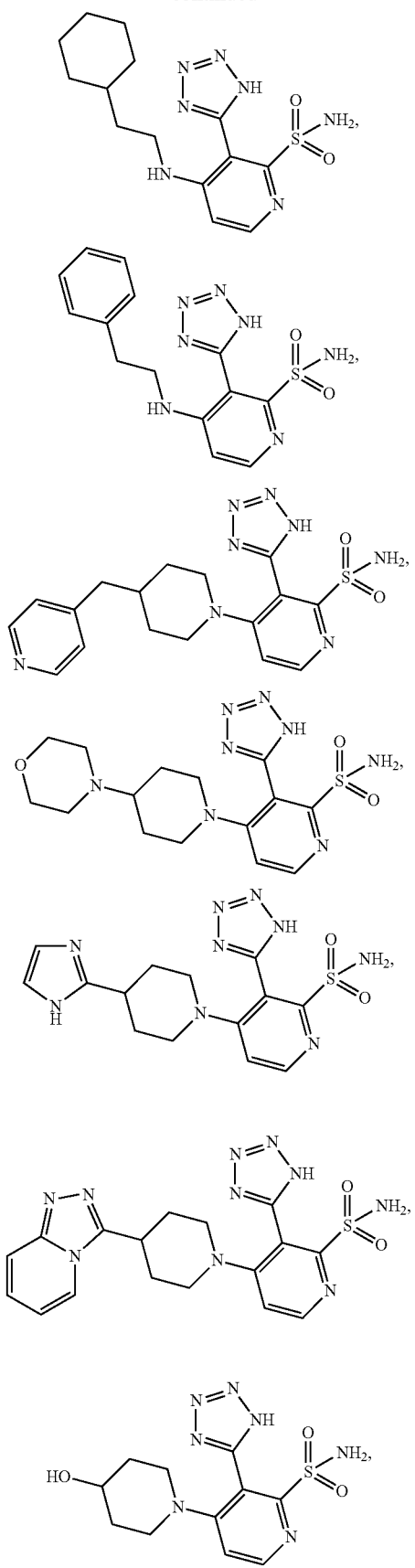
654
-continued
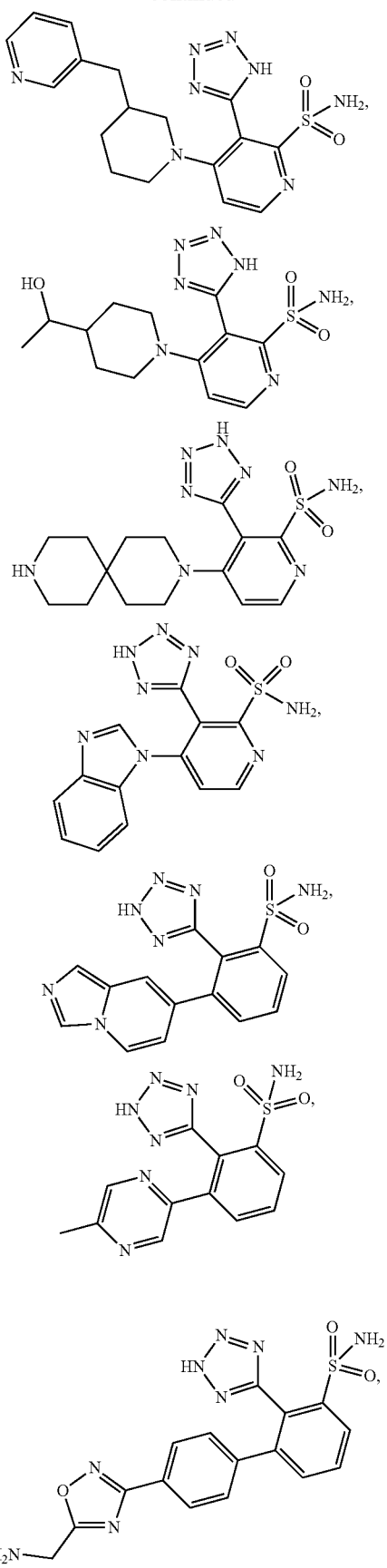

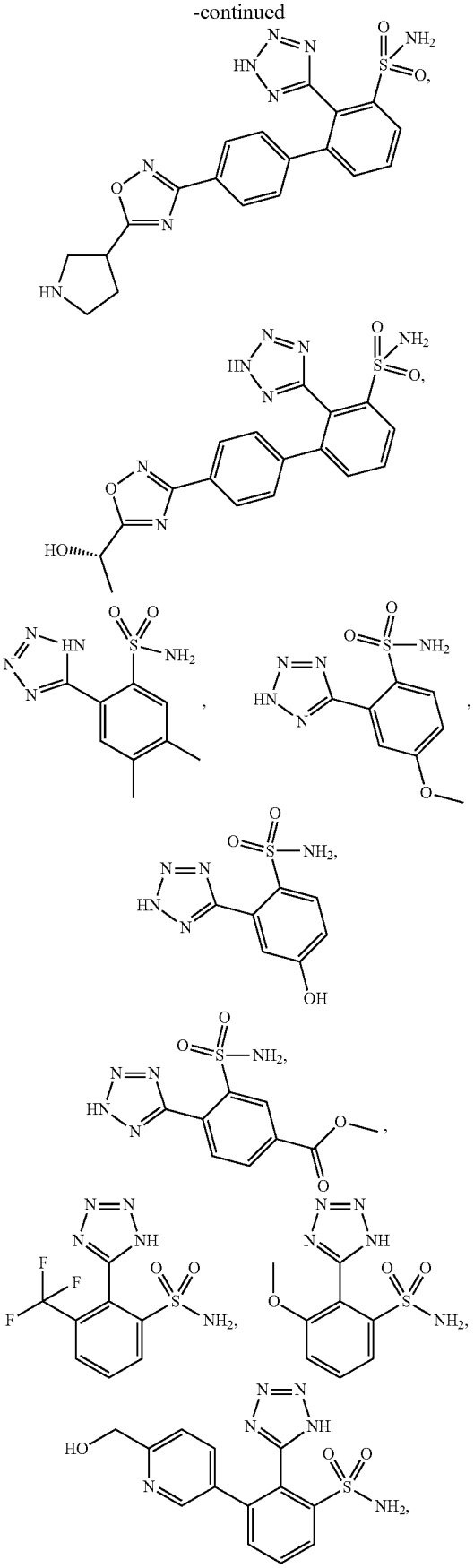
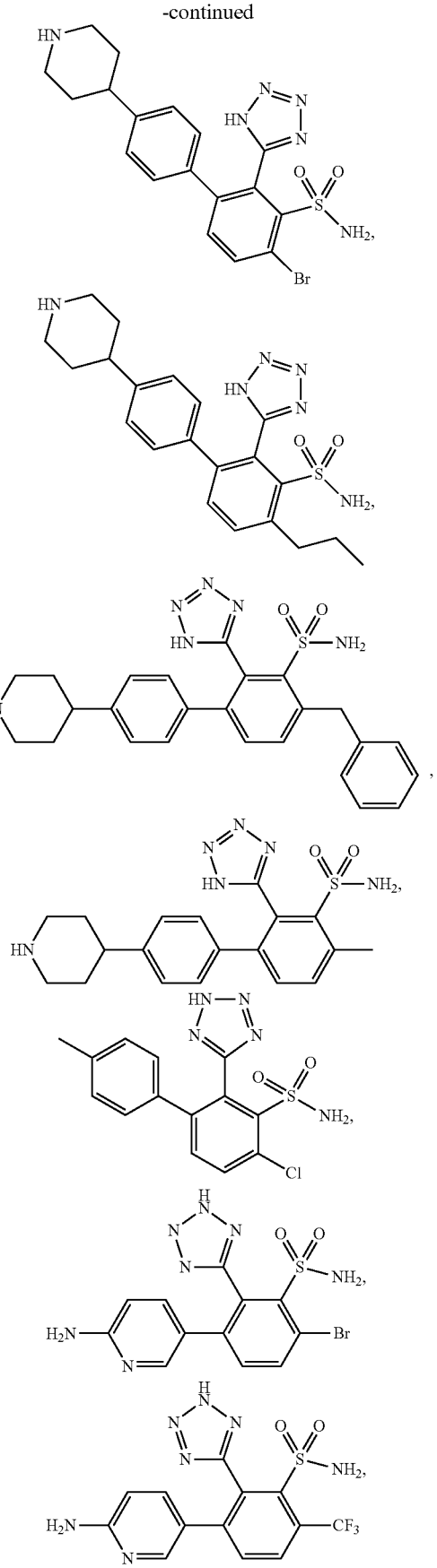

-continued
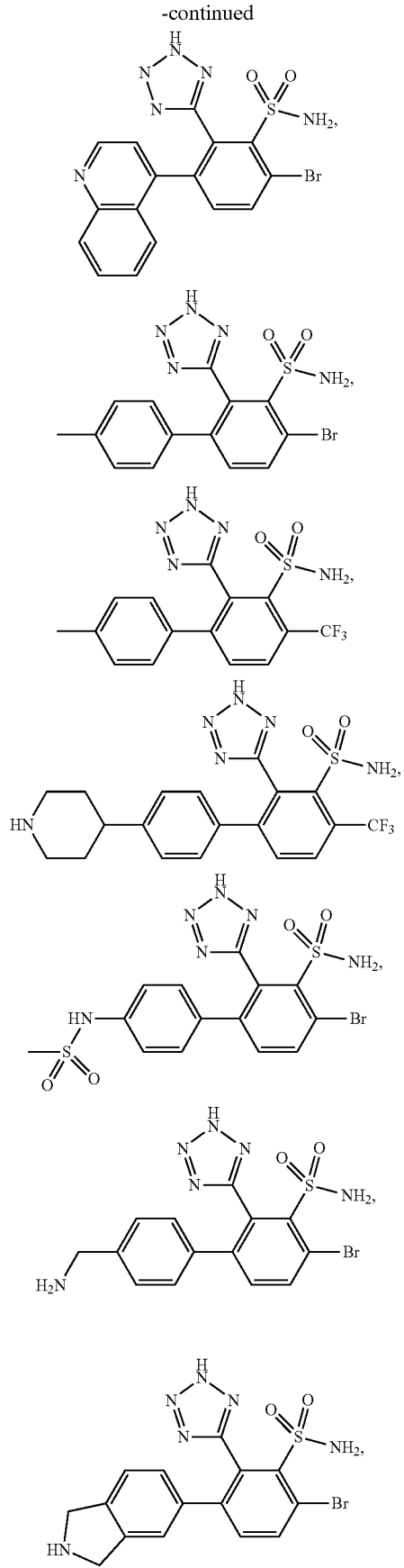
-continued
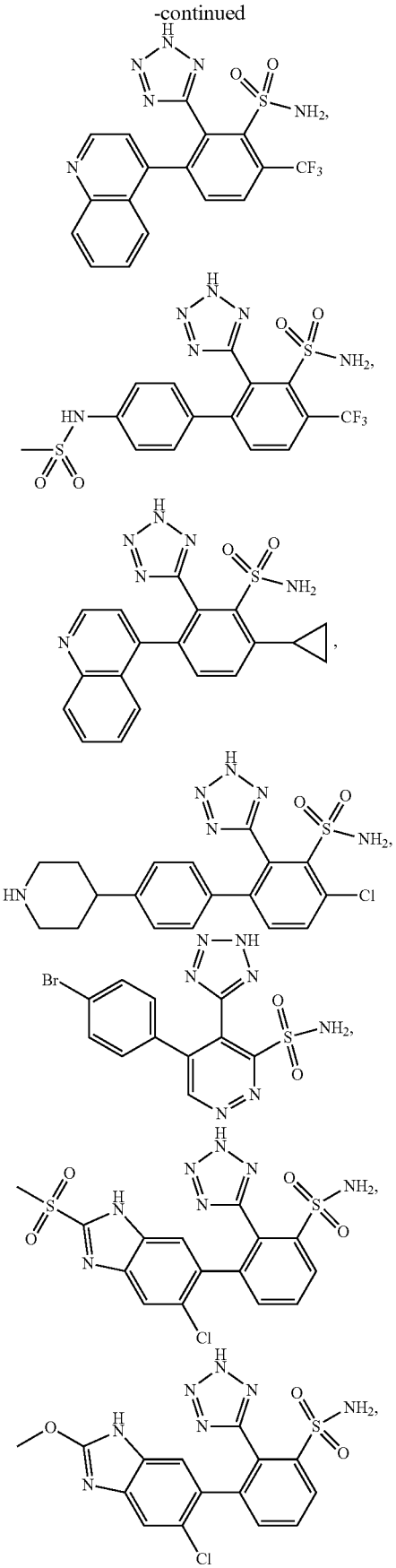

659
-continued
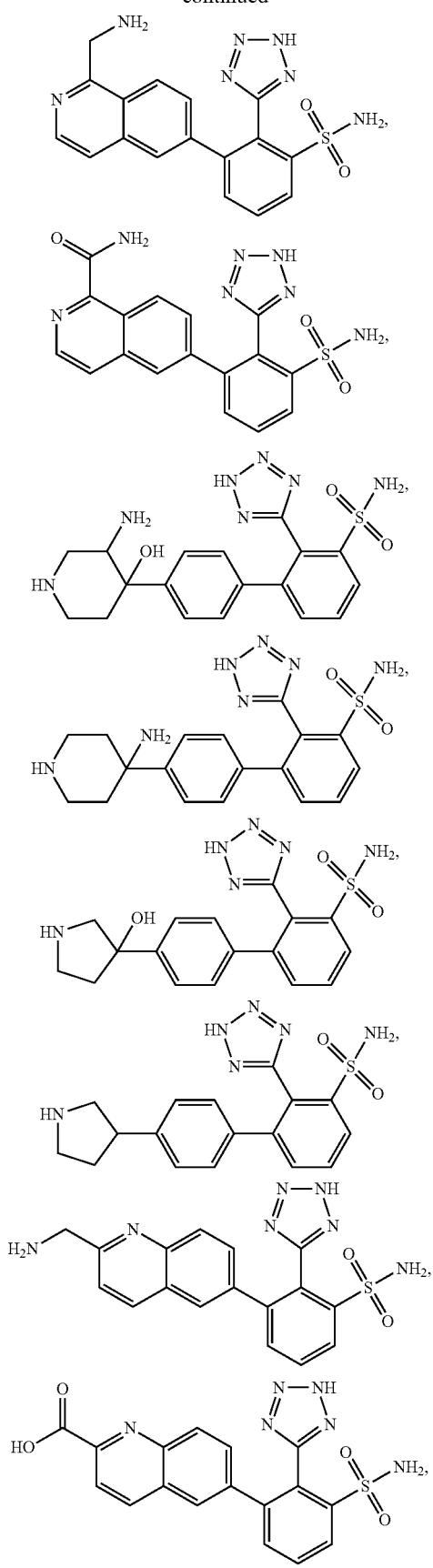
660
-continued
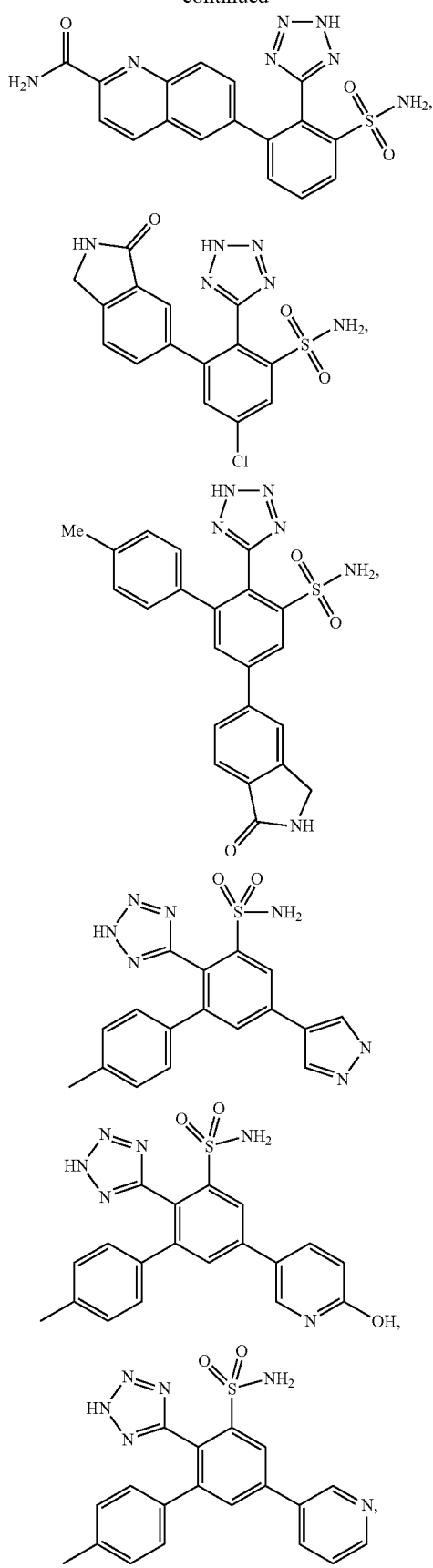

661
-continued
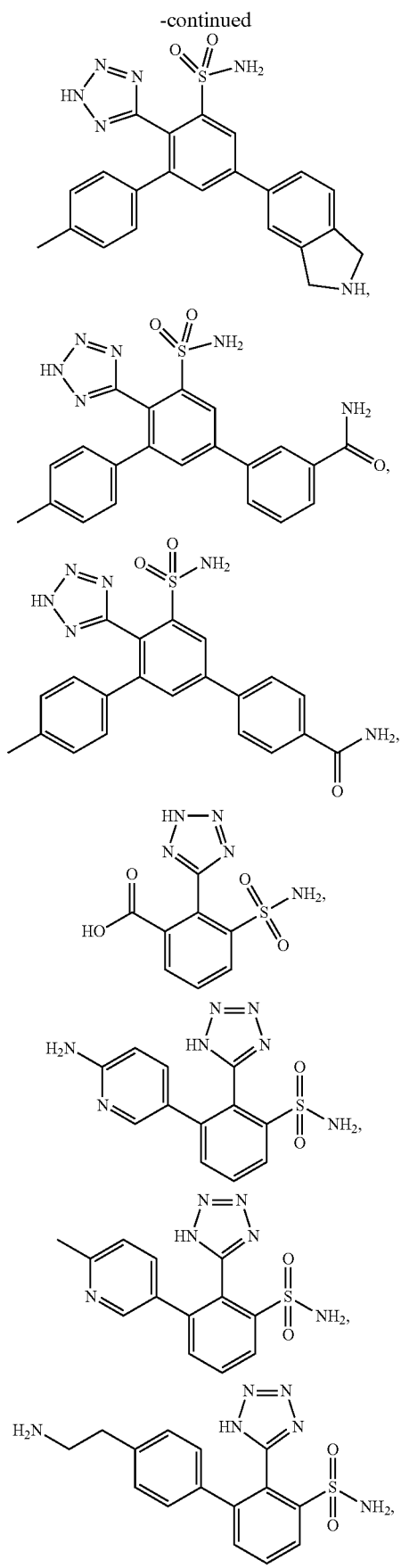
662
-continued
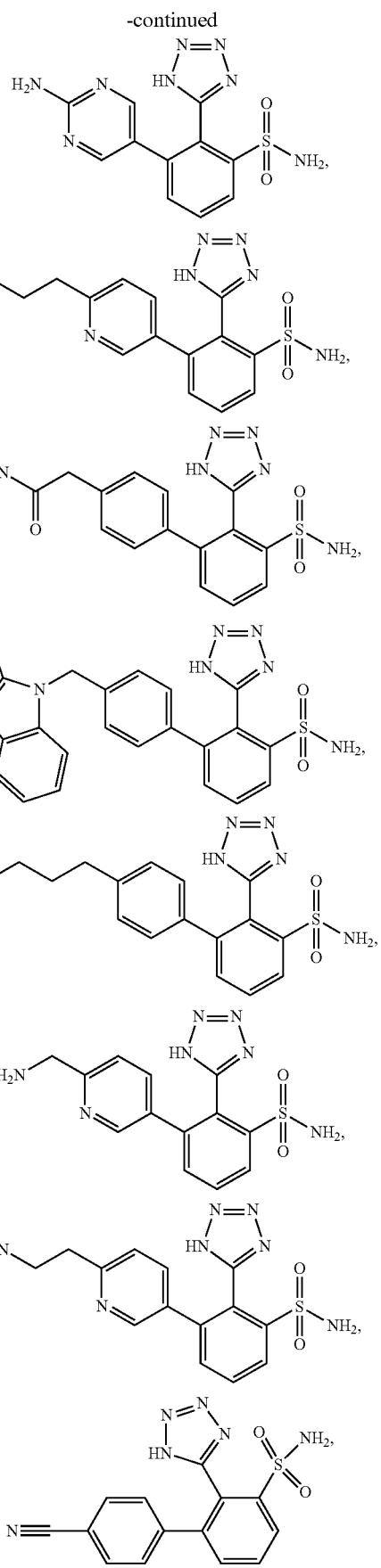

663
-continued
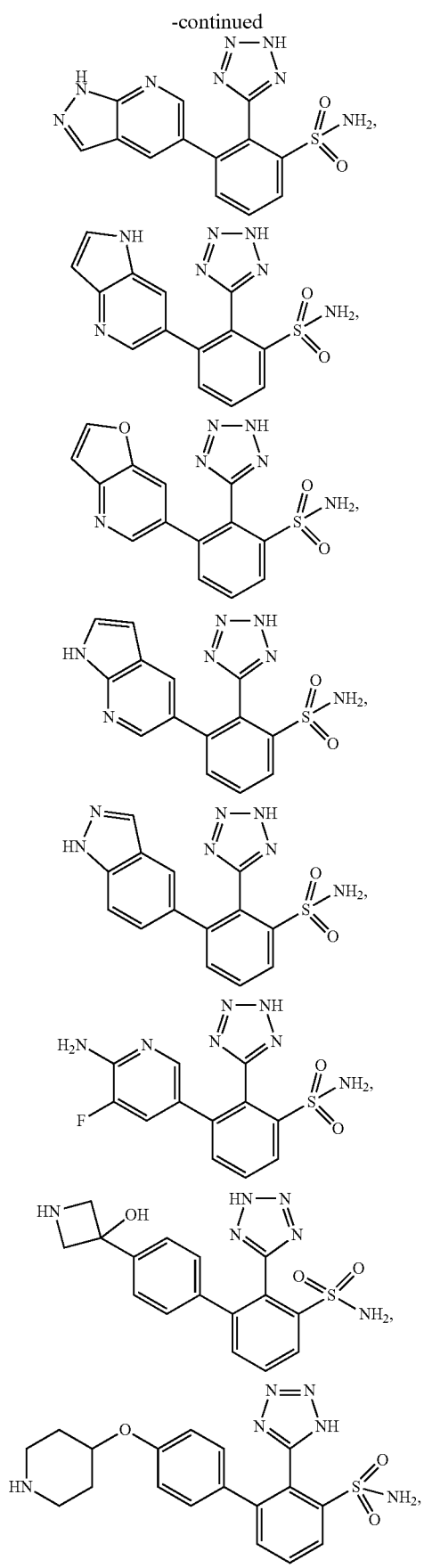
664
-continued
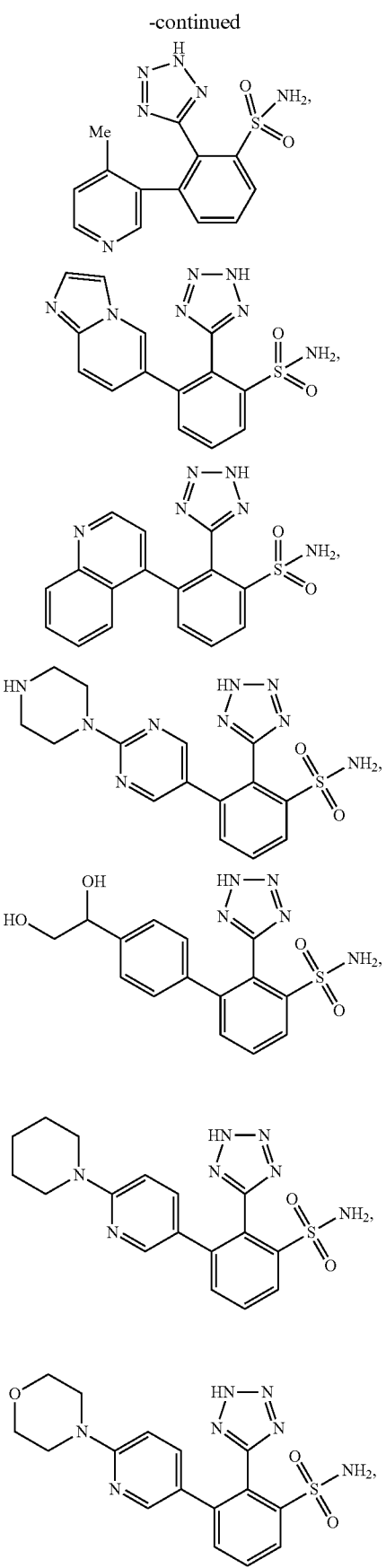

665
-continued
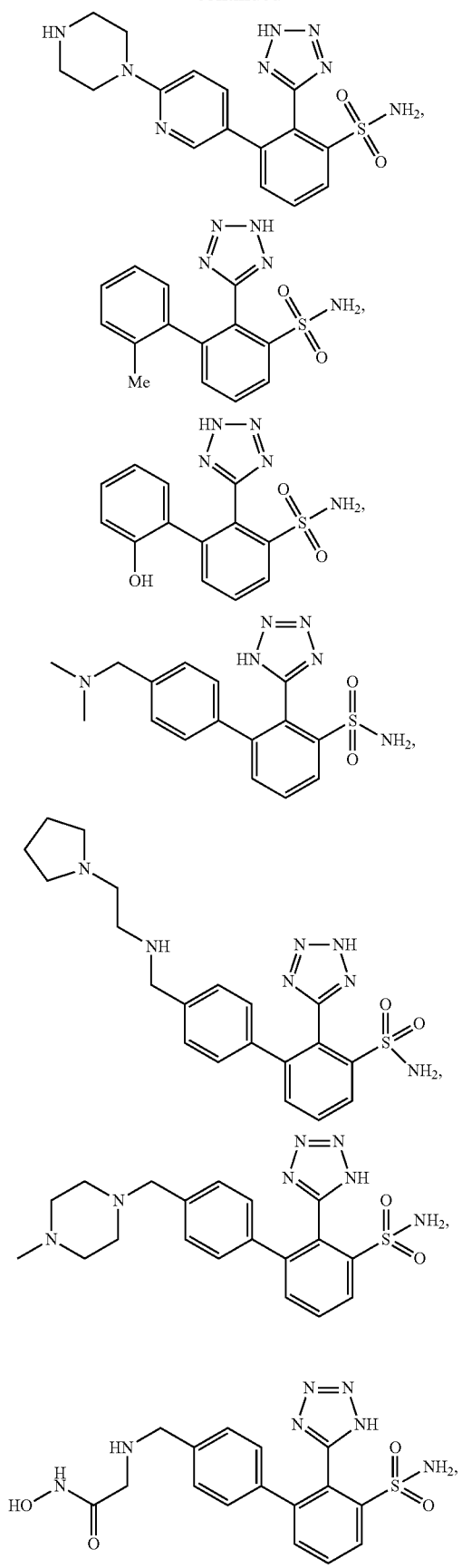
666
-continued
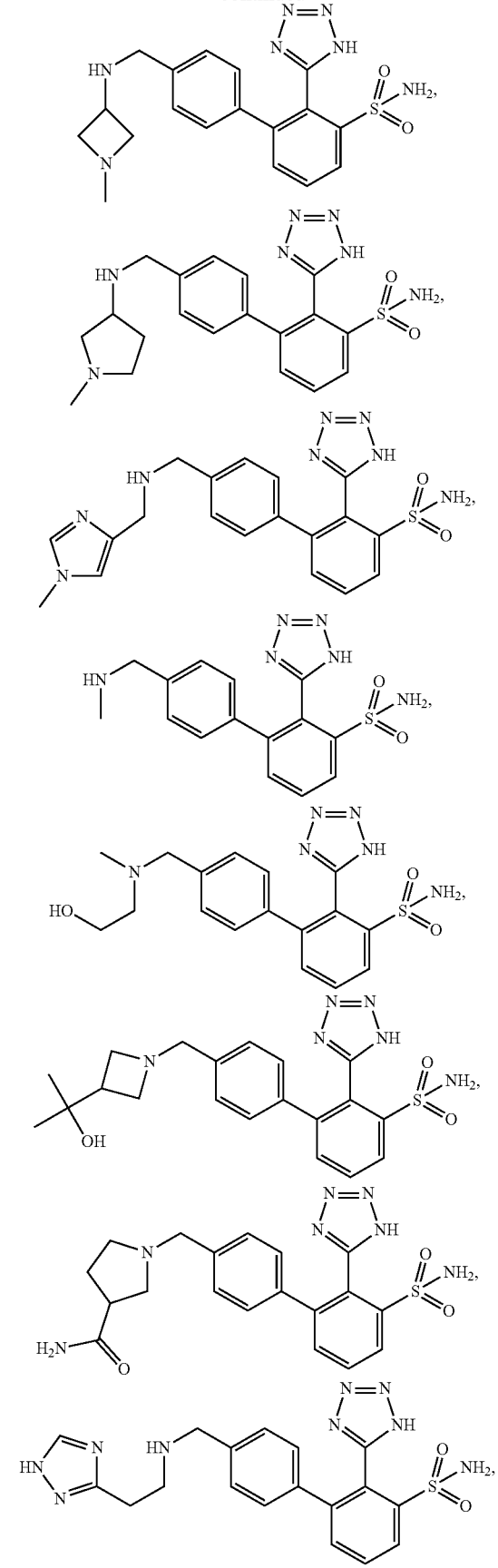

667
-continued
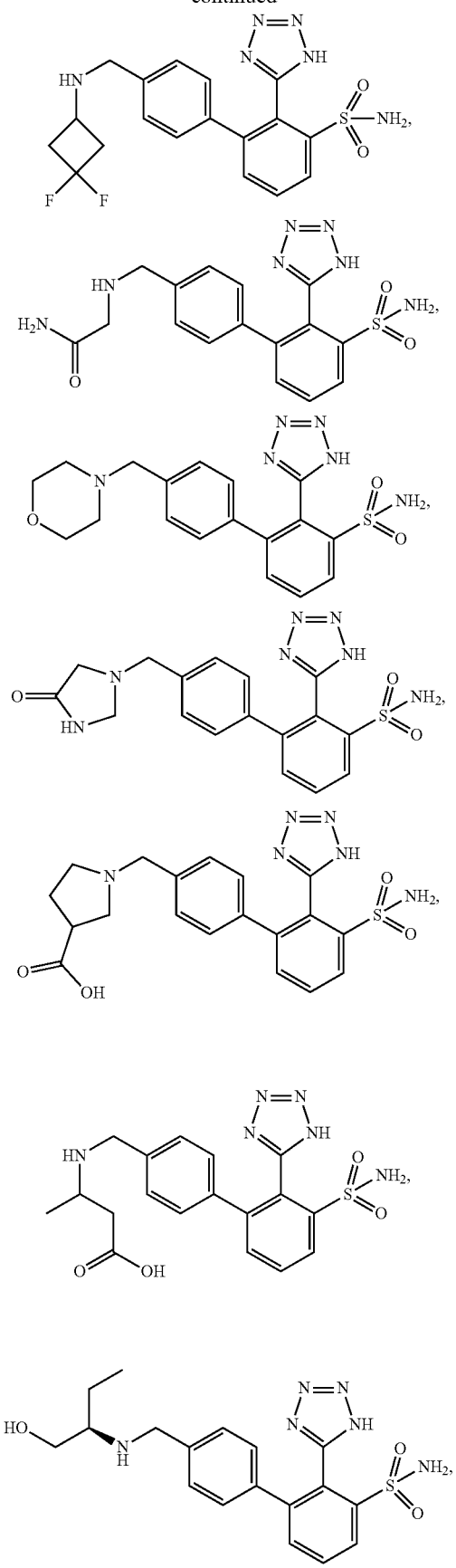
668
-continued
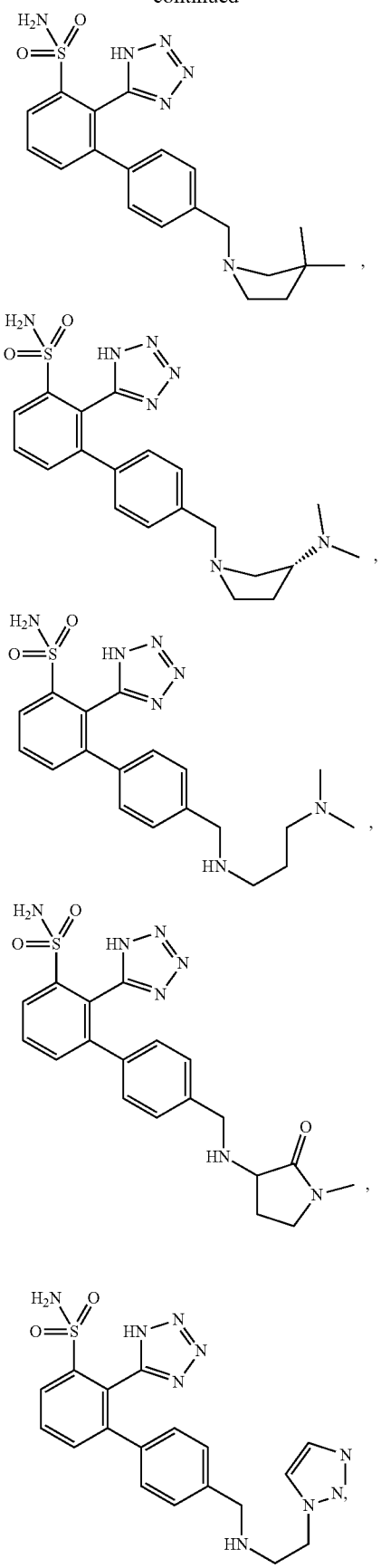

669
-continued
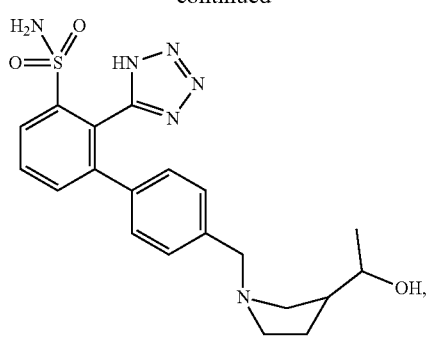
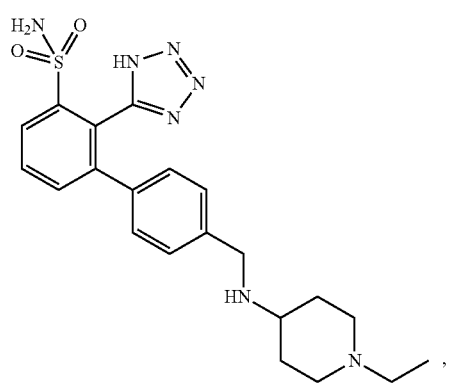
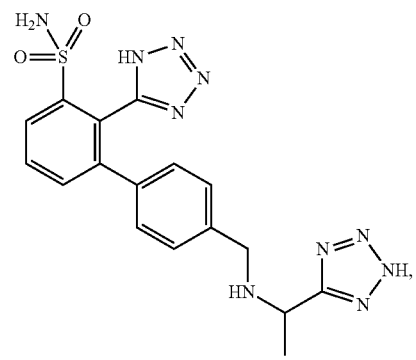
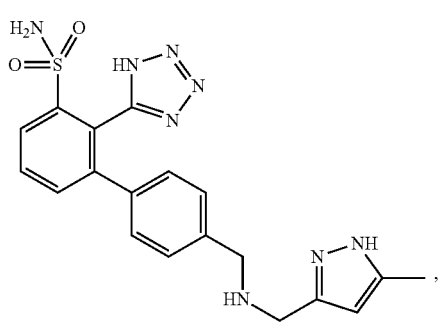
670
-continued
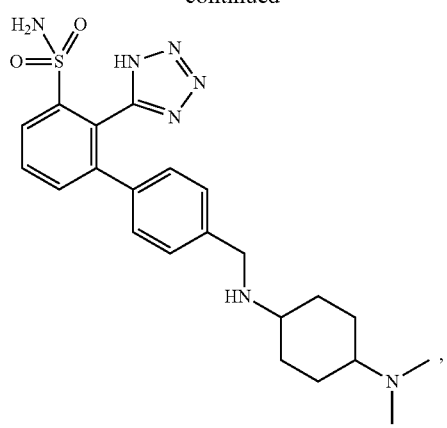
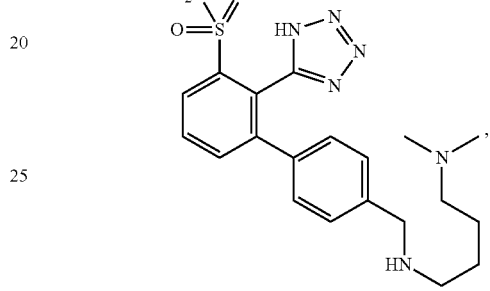
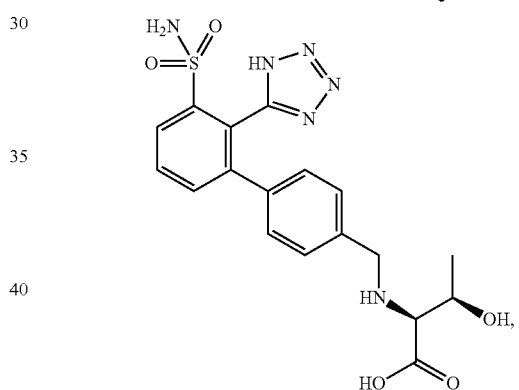
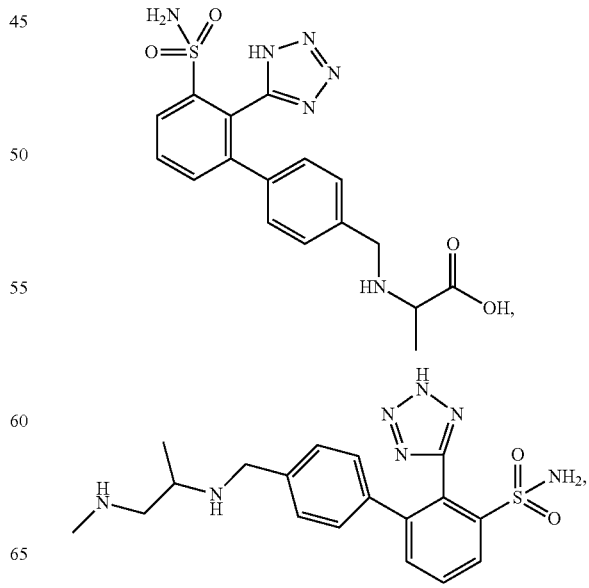

671
-continued
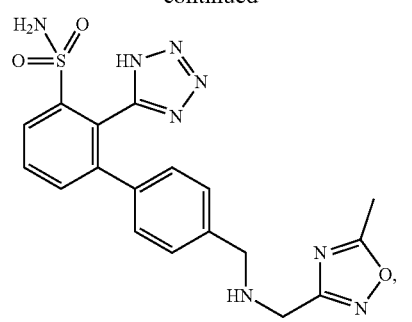
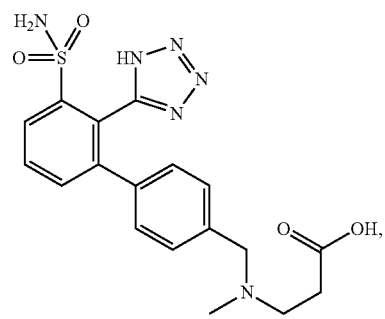
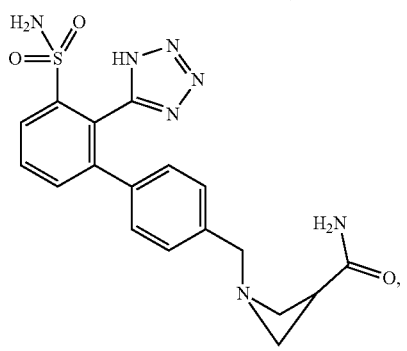
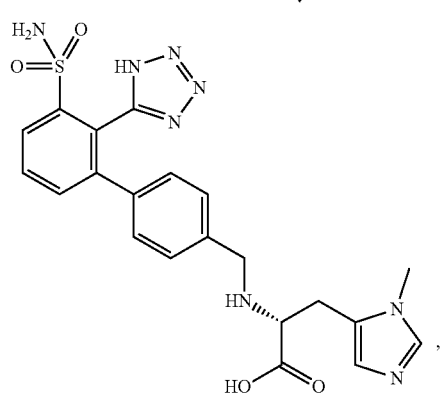
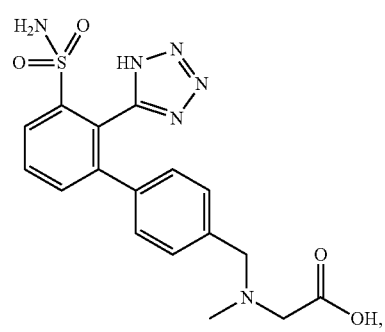
672
-continued
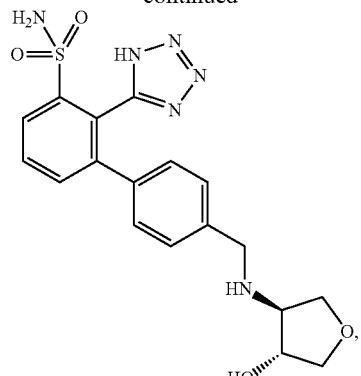
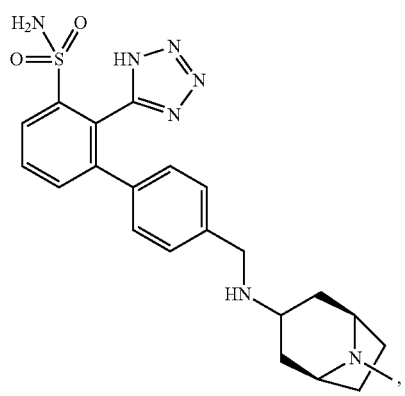
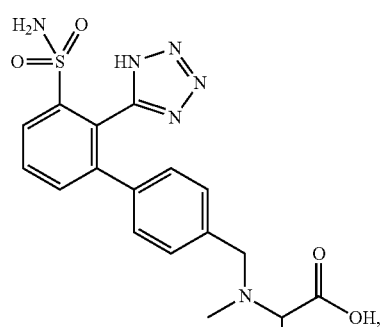
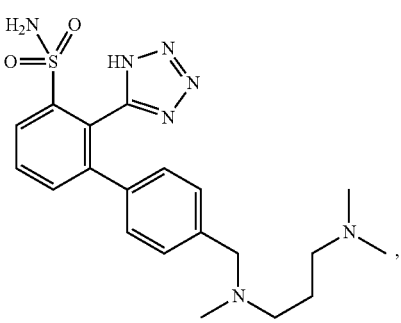

673
-continued
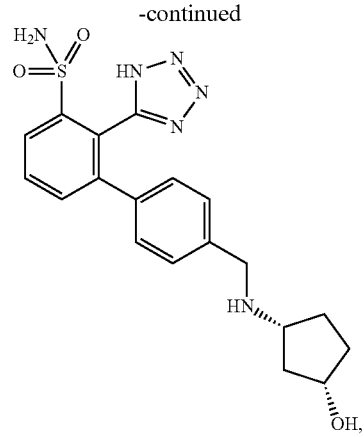
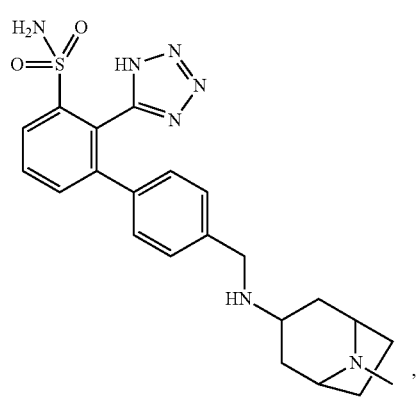
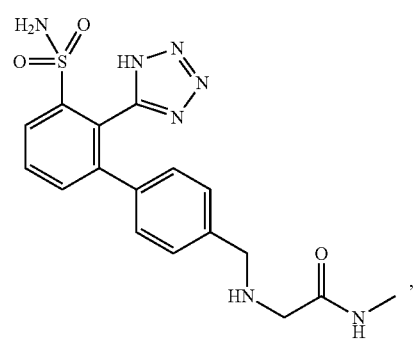
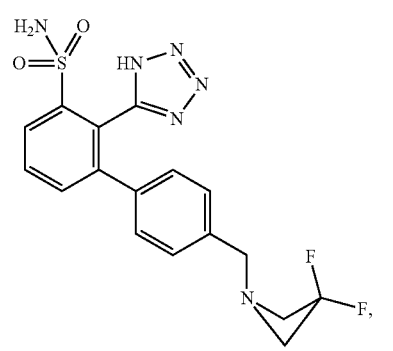
674
-continued
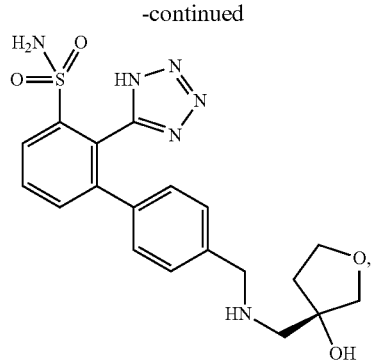
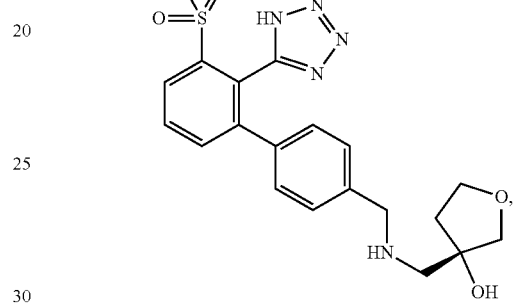
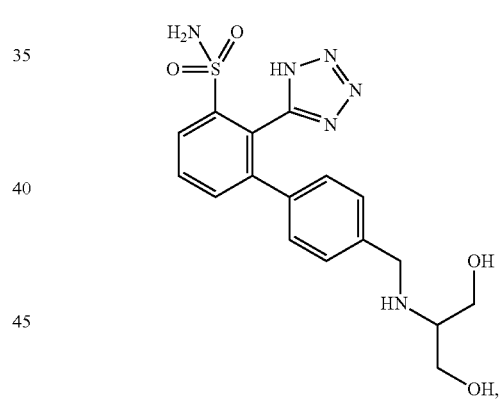
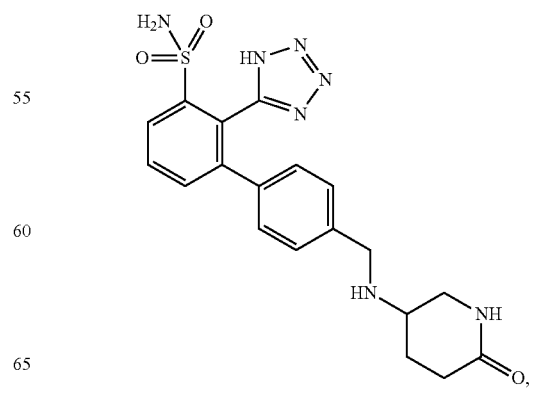

675
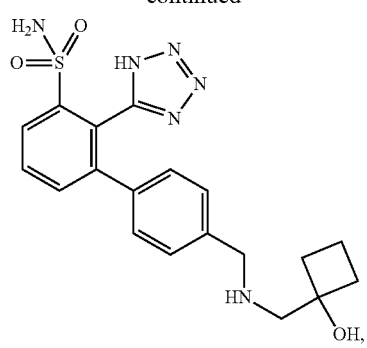
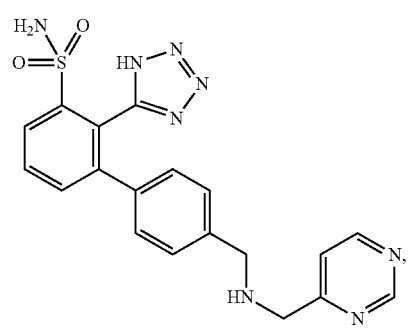
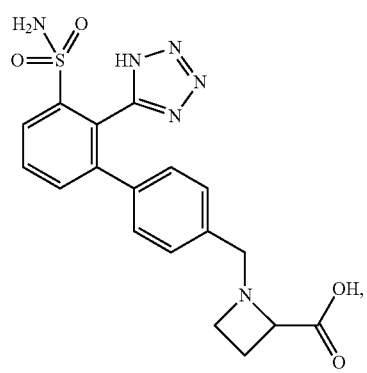
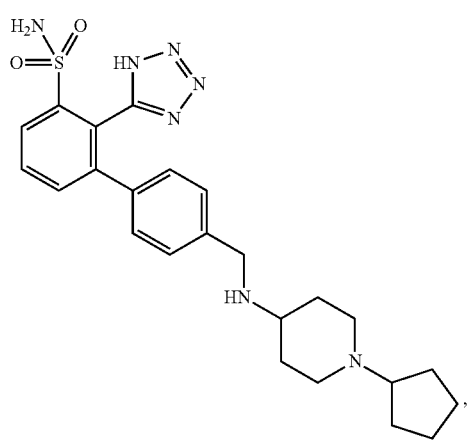
676
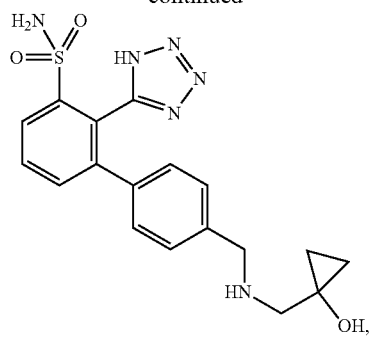
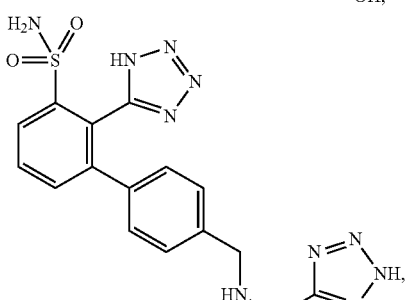
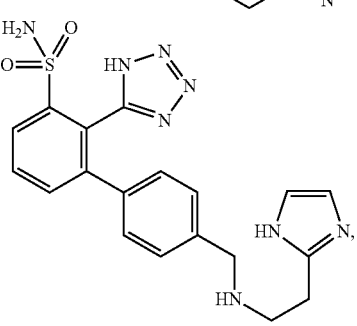
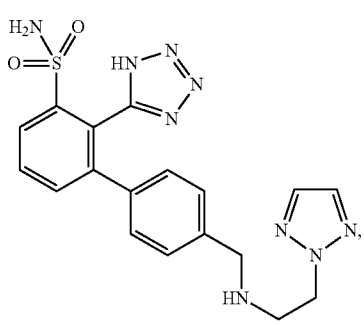
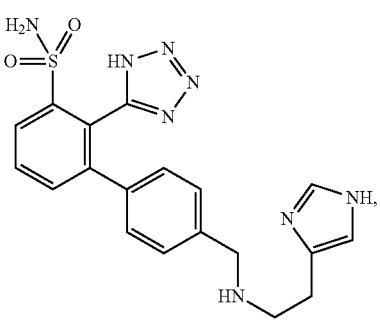

677
-continued
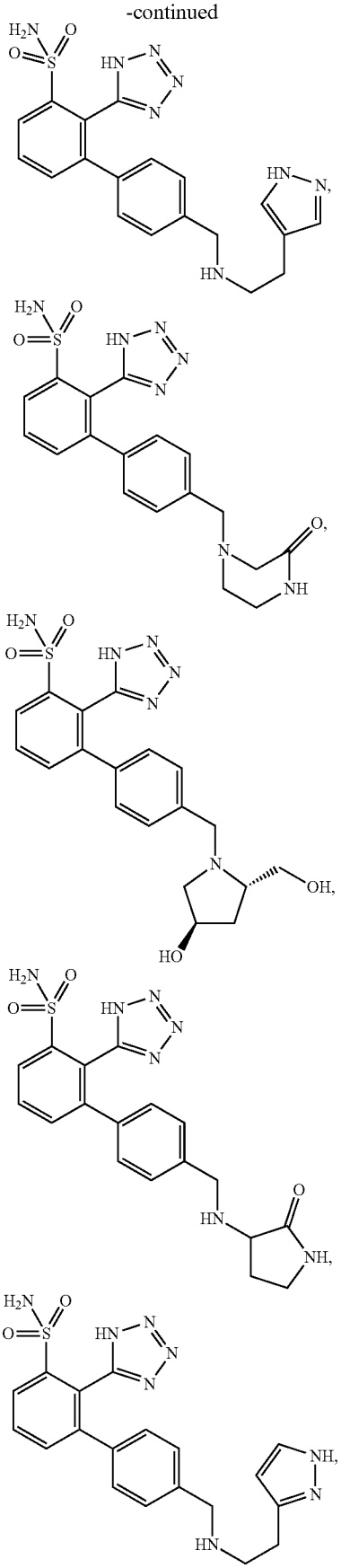
678
-continued
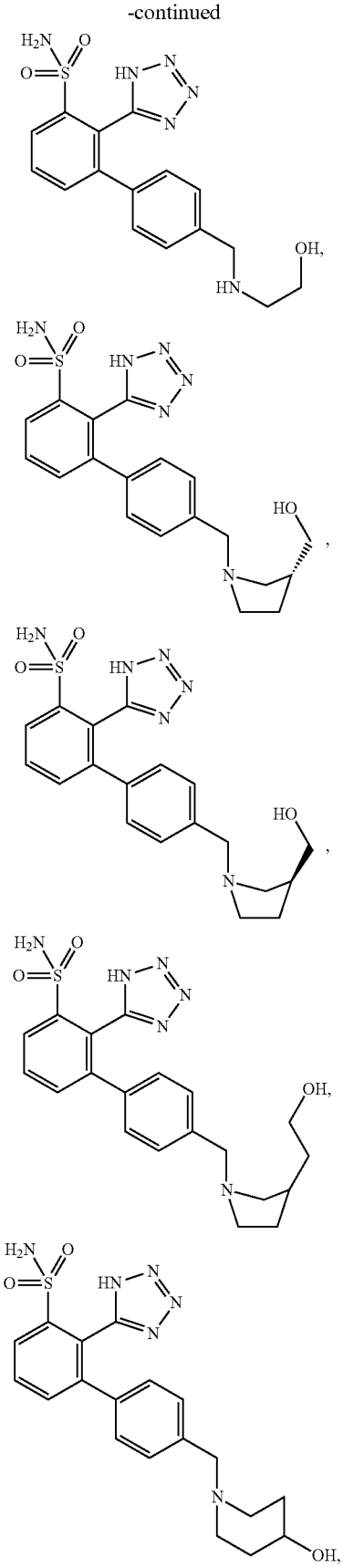

679
-continued
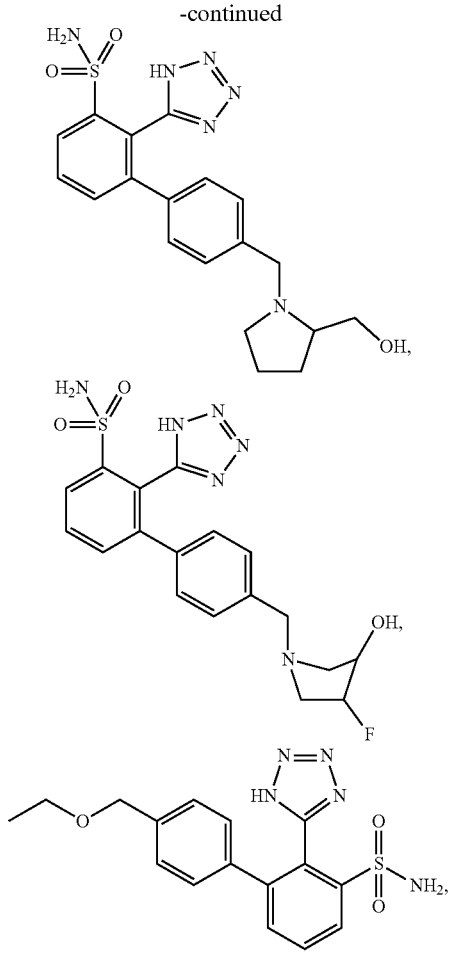
680
-continued
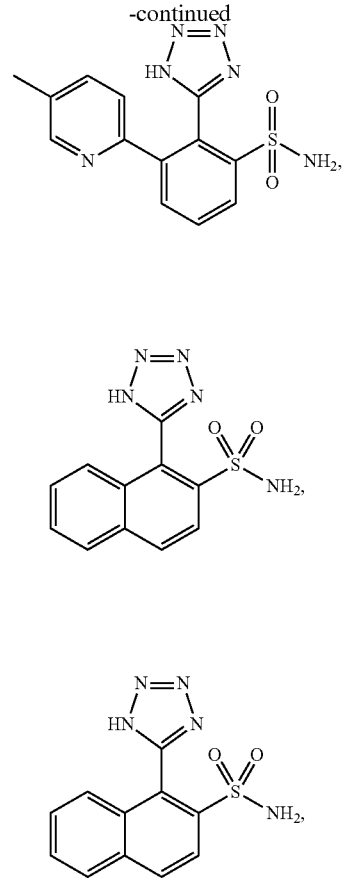
or a pharmaceutically acceptable salt thereof.
15. The compound of claim 1 which is
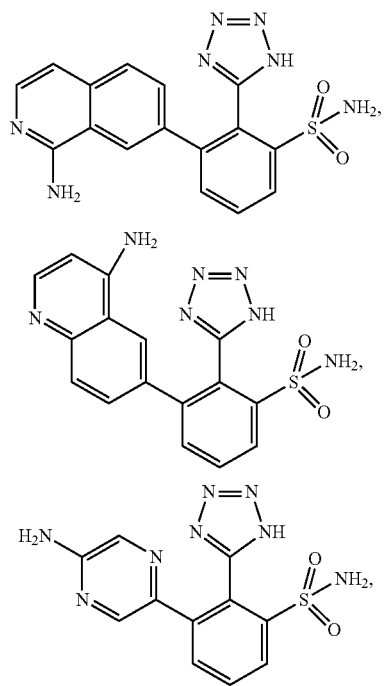

-continued
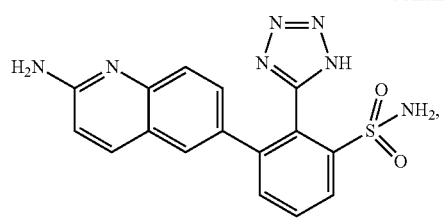
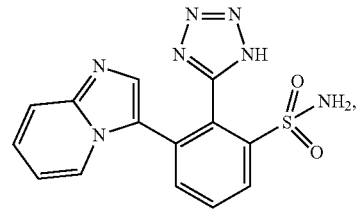
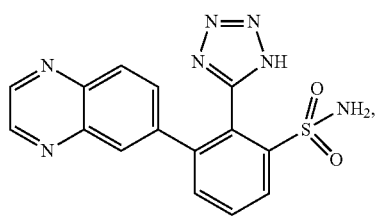
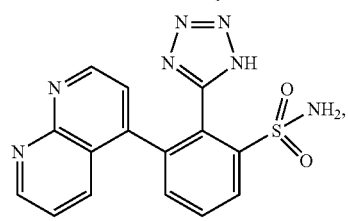
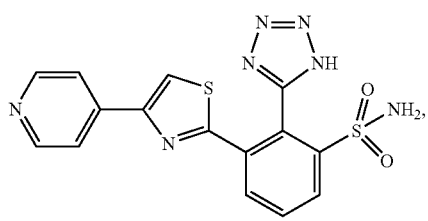
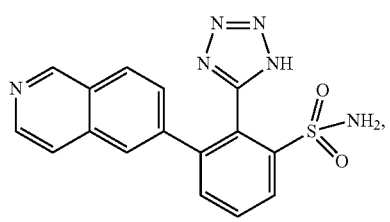
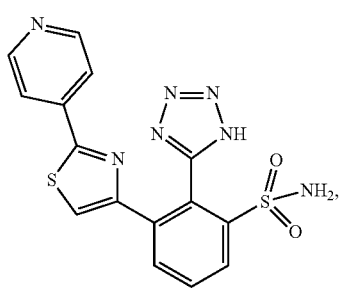

-continued
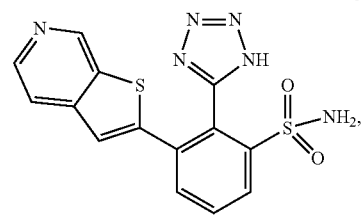
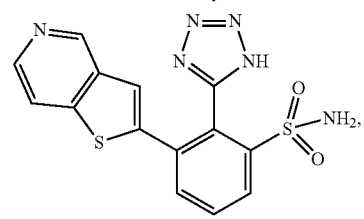
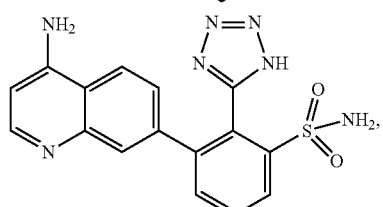
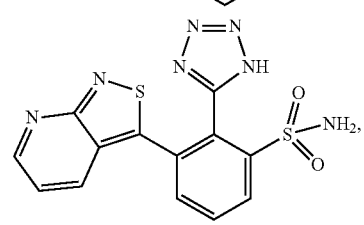
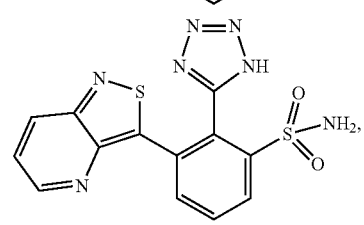
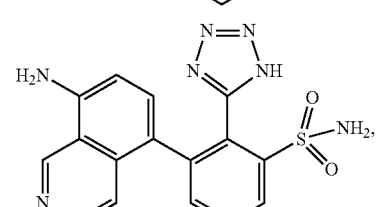
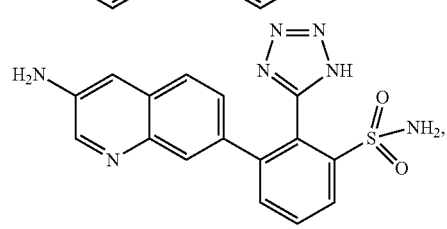
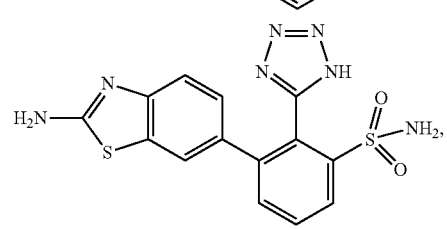

-continued
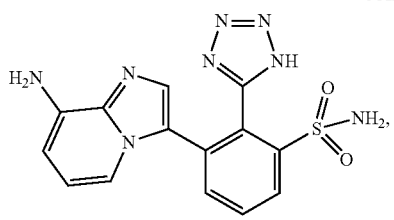
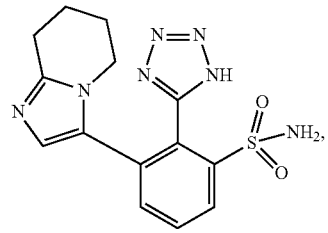
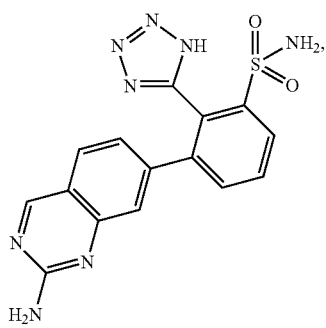
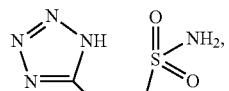
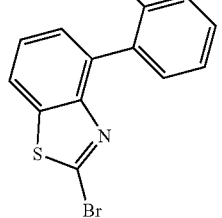
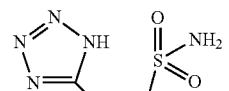
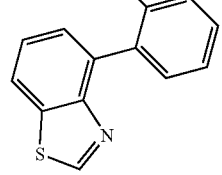
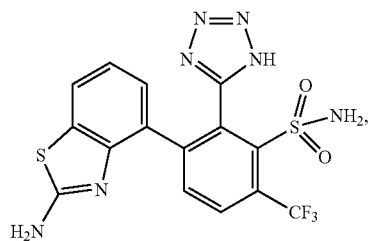

-continued
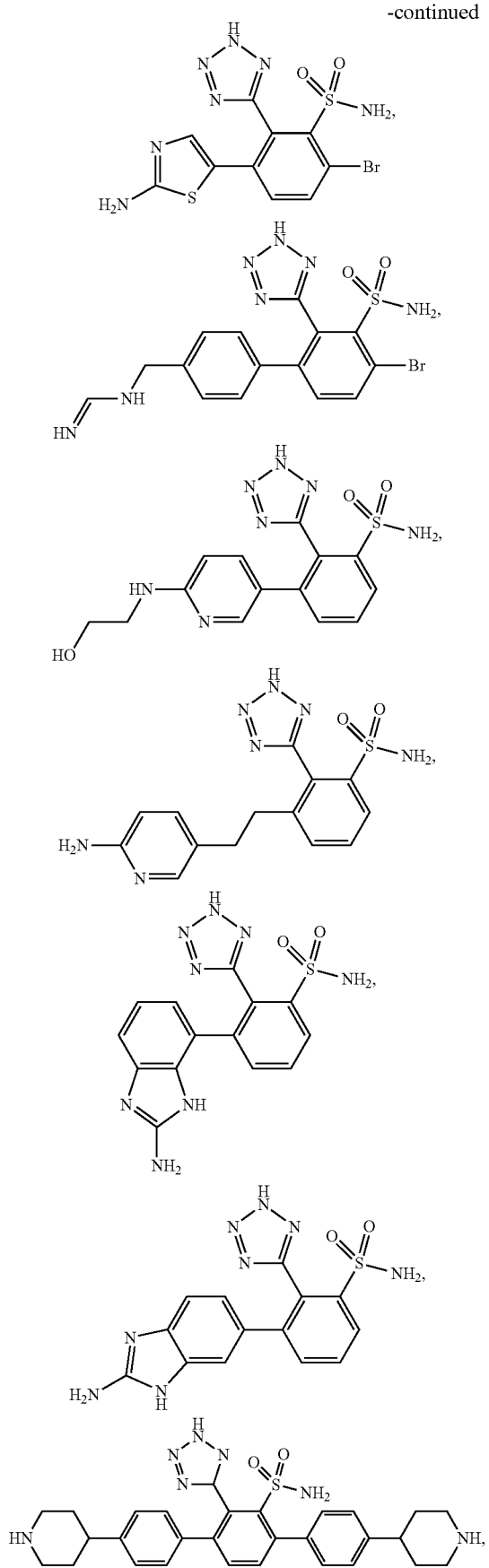

-continued
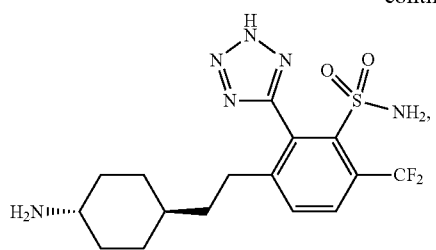
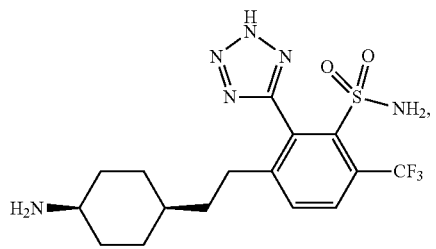
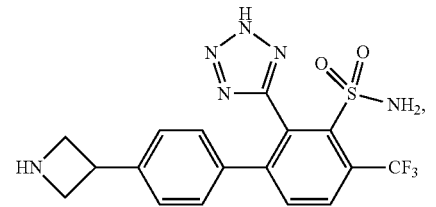
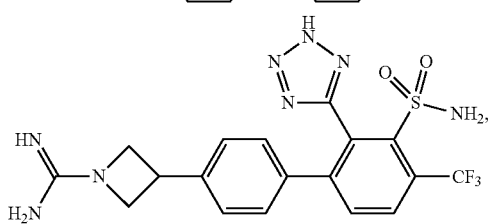
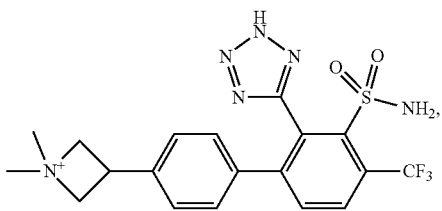
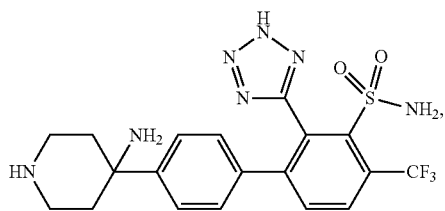
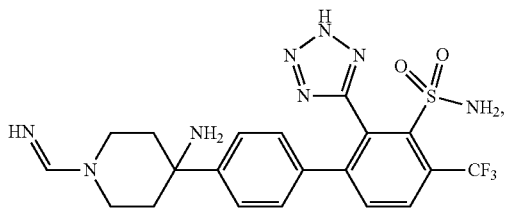

-continued
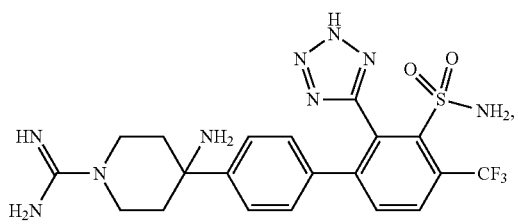
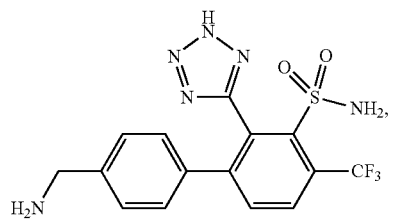
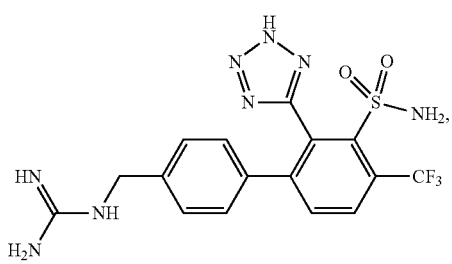
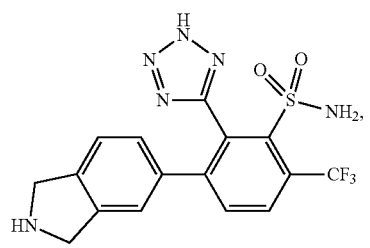
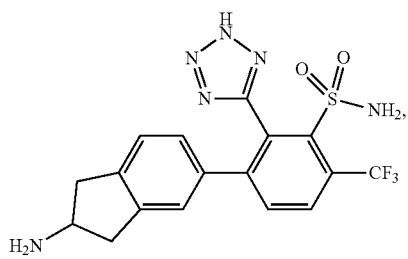
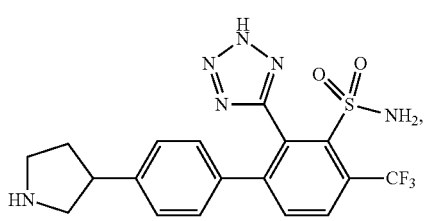
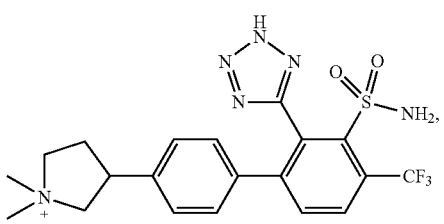

-continued
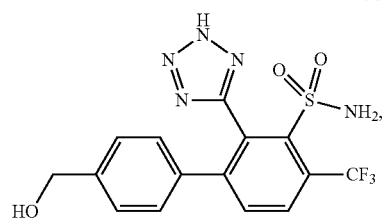
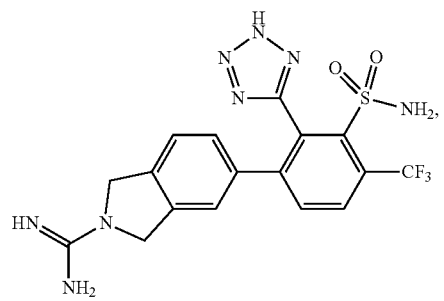
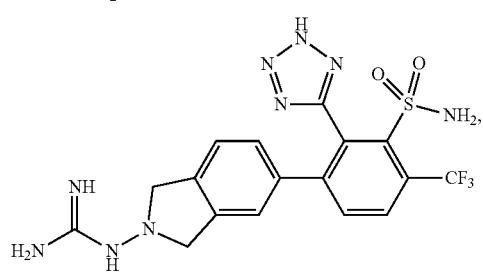
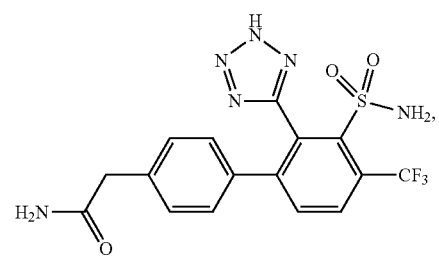
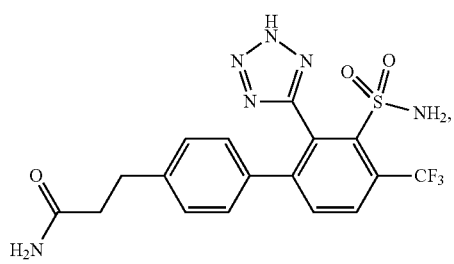
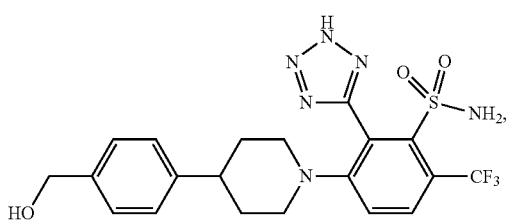

-continued
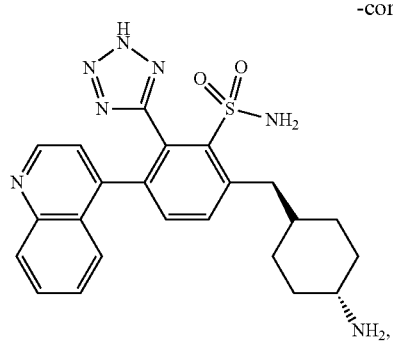
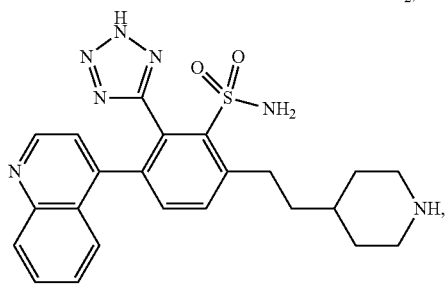
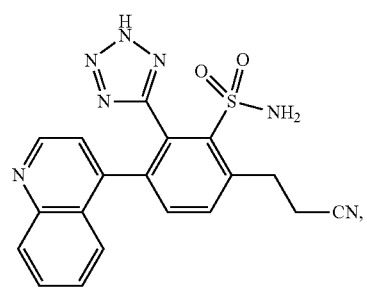
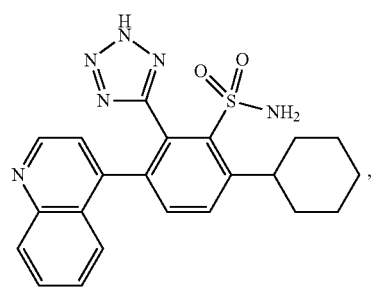
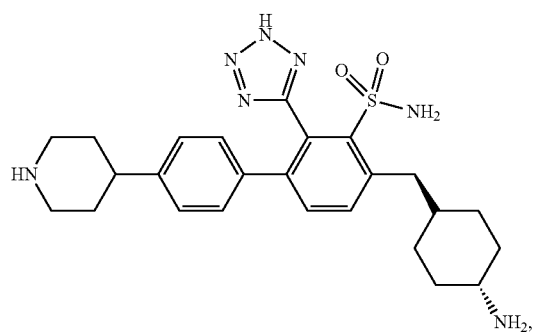

-continued
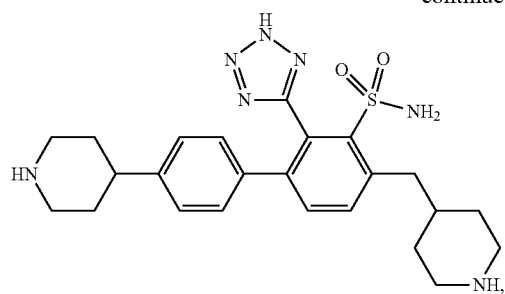
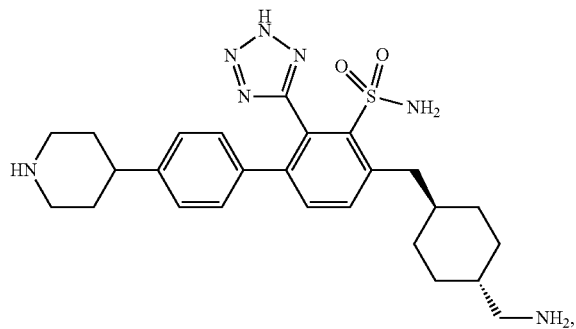
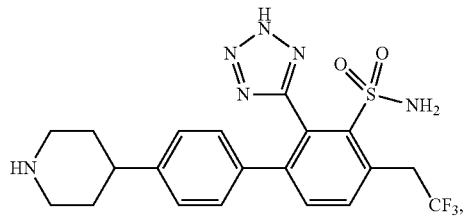
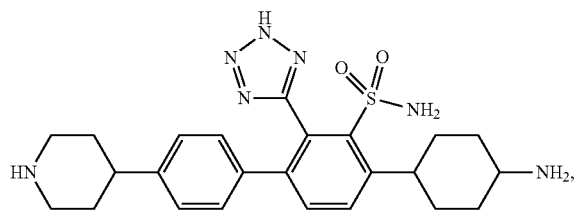
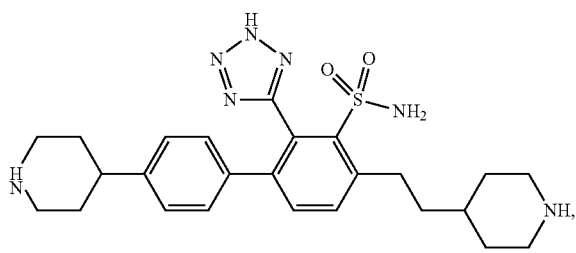
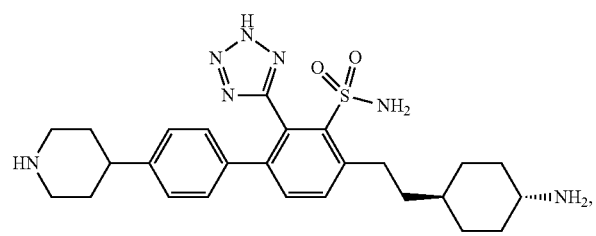

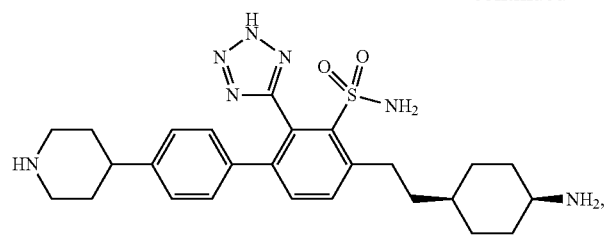
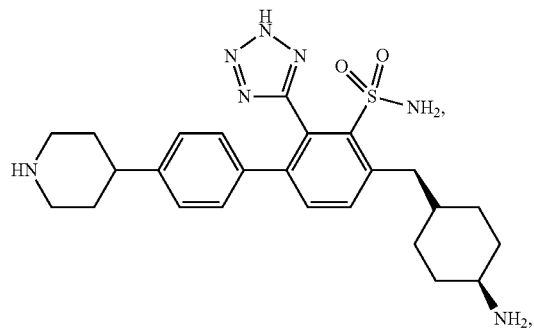
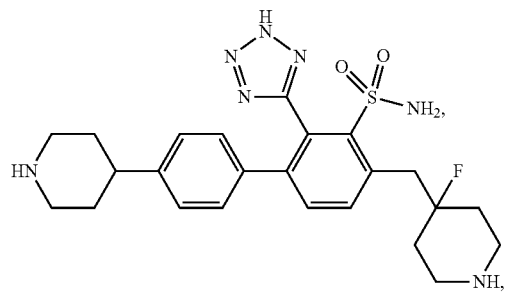
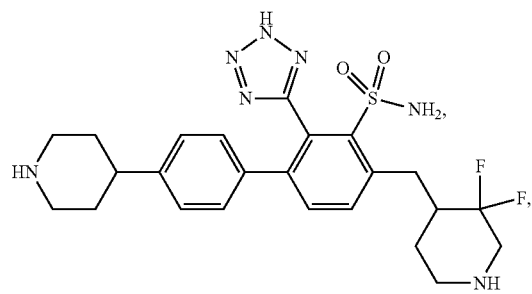
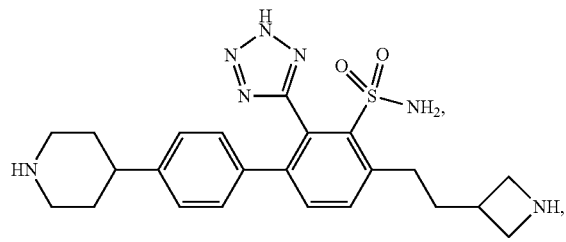
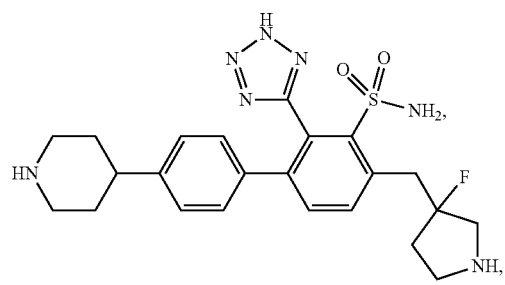

-continued
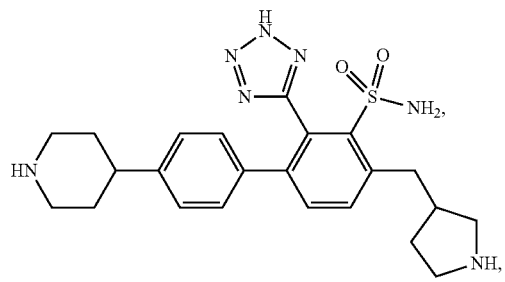
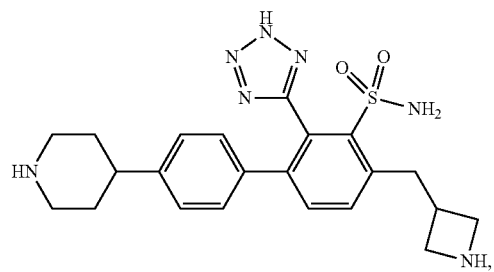
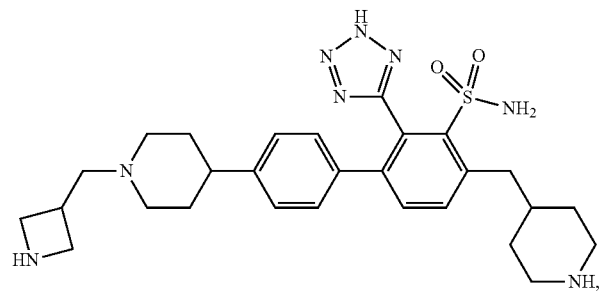
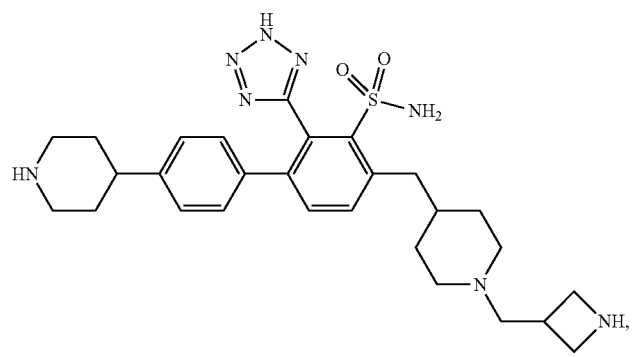
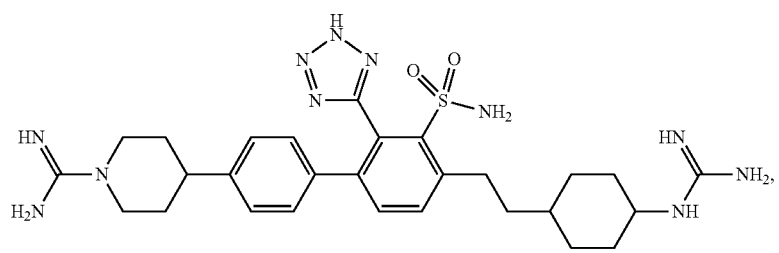
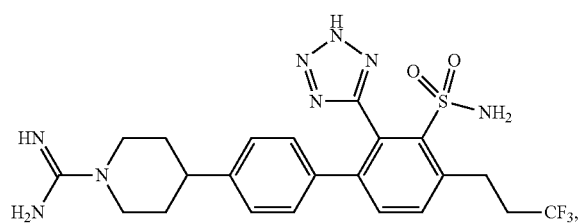

-continued
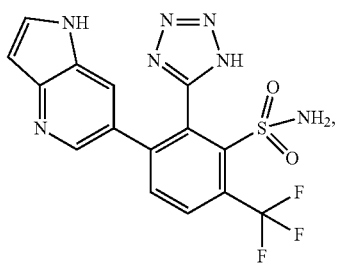
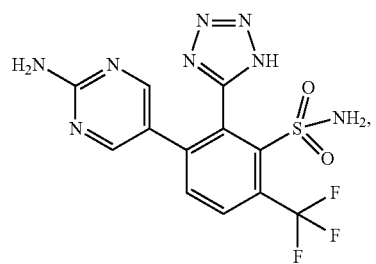
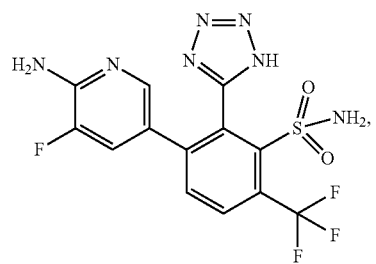
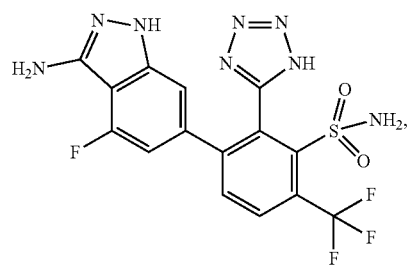
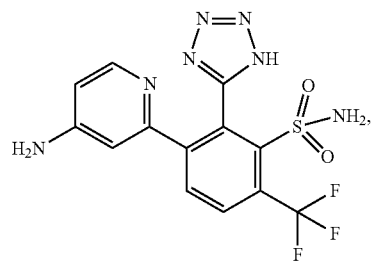
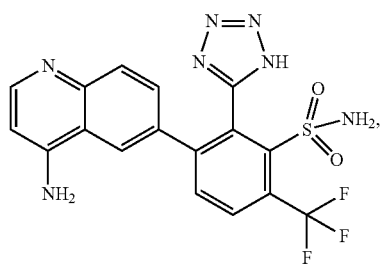

-continued
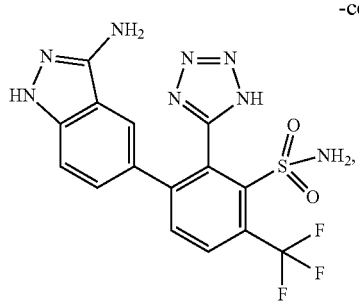
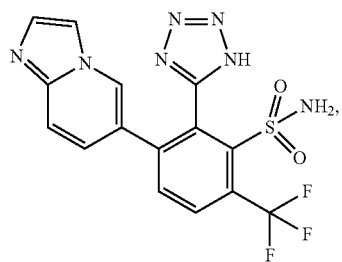
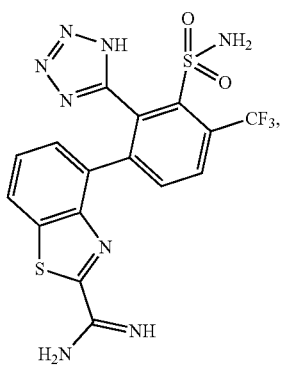
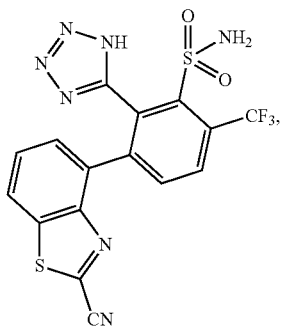
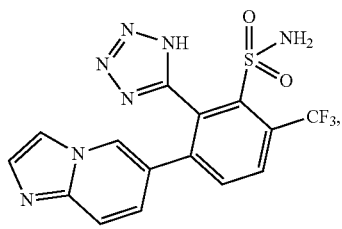

-continued
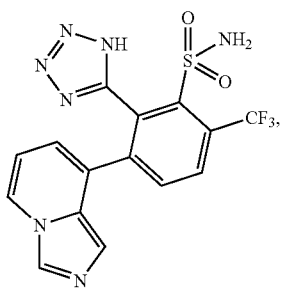
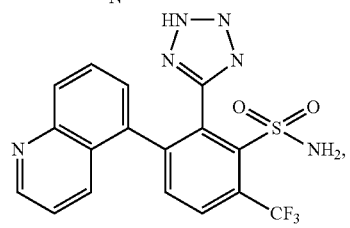
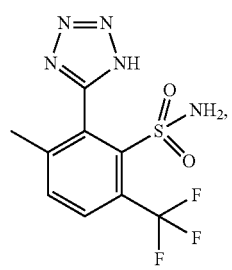
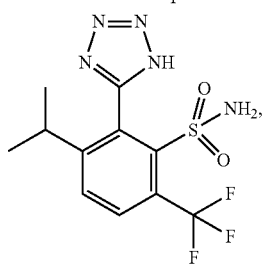
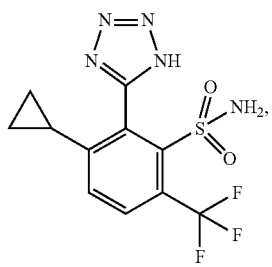
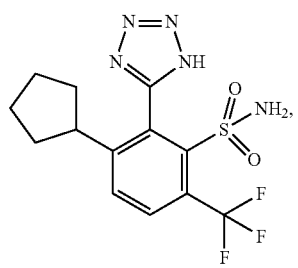

-continued
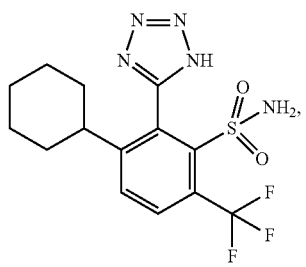
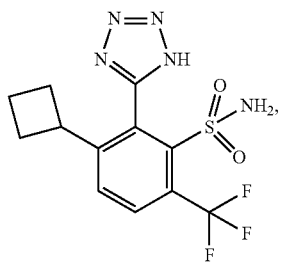
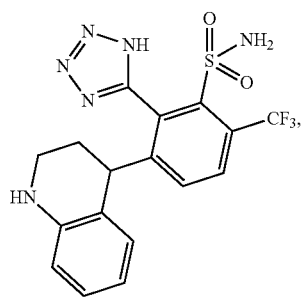
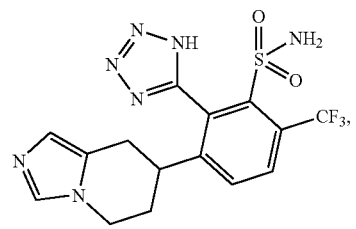
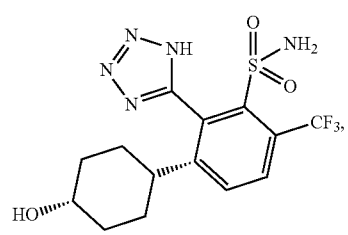
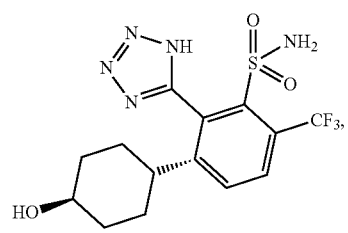

-continued
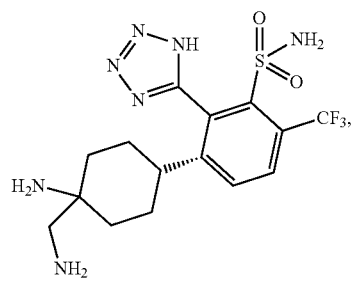
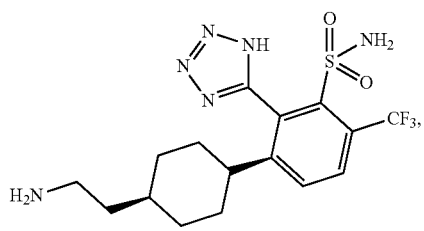
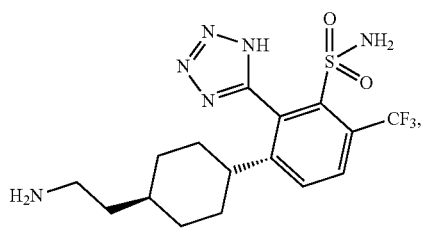
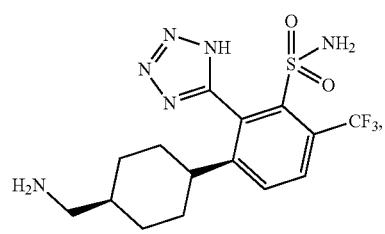
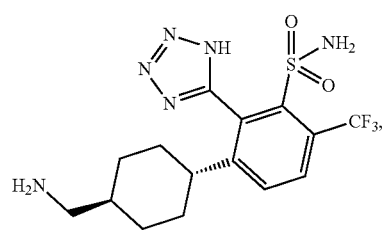
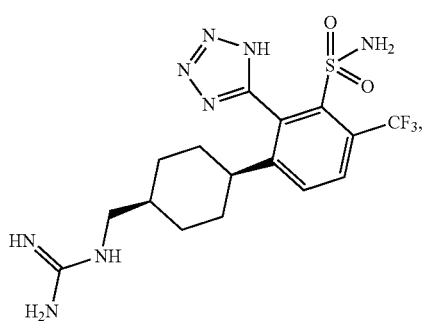

-continued
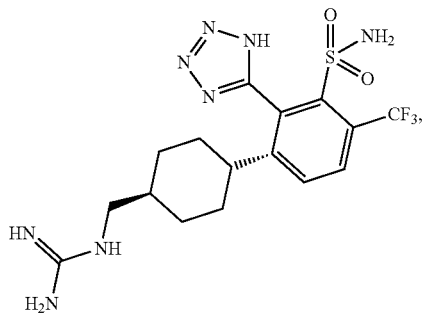
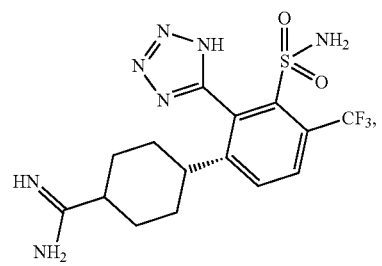
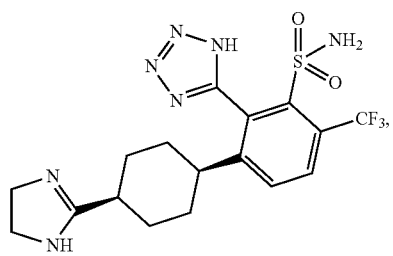
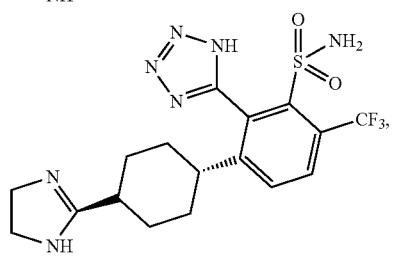
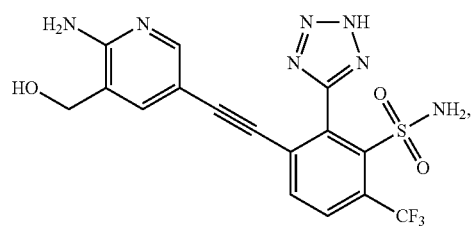
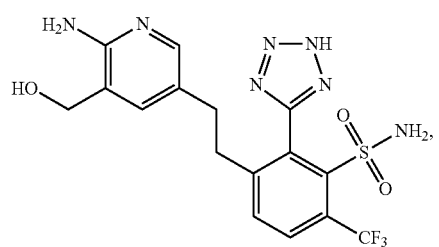

-continued
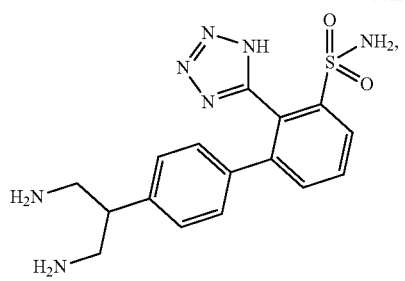
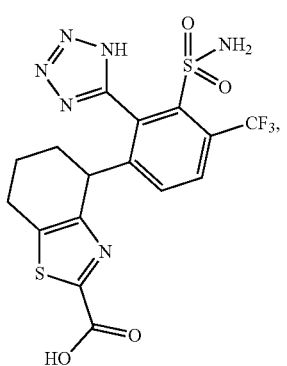
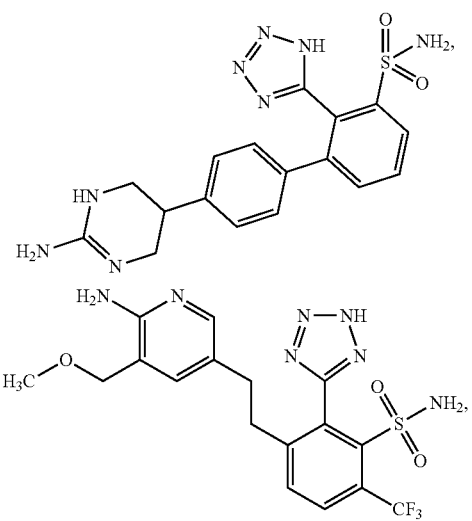
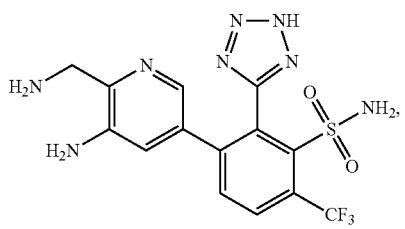
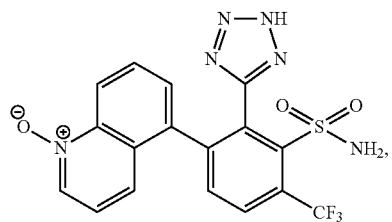

-continued
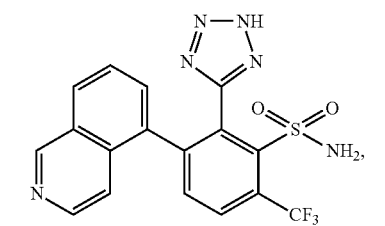
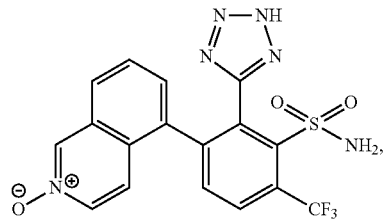
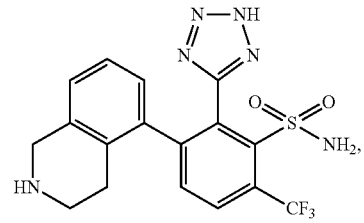
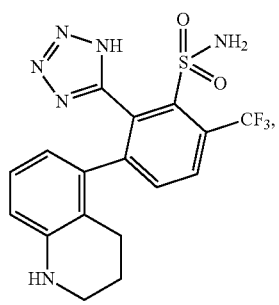
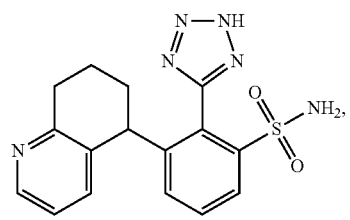
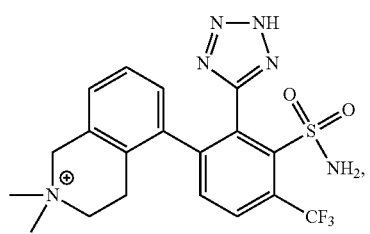
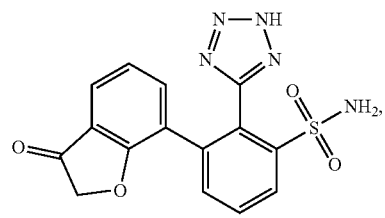

-continued
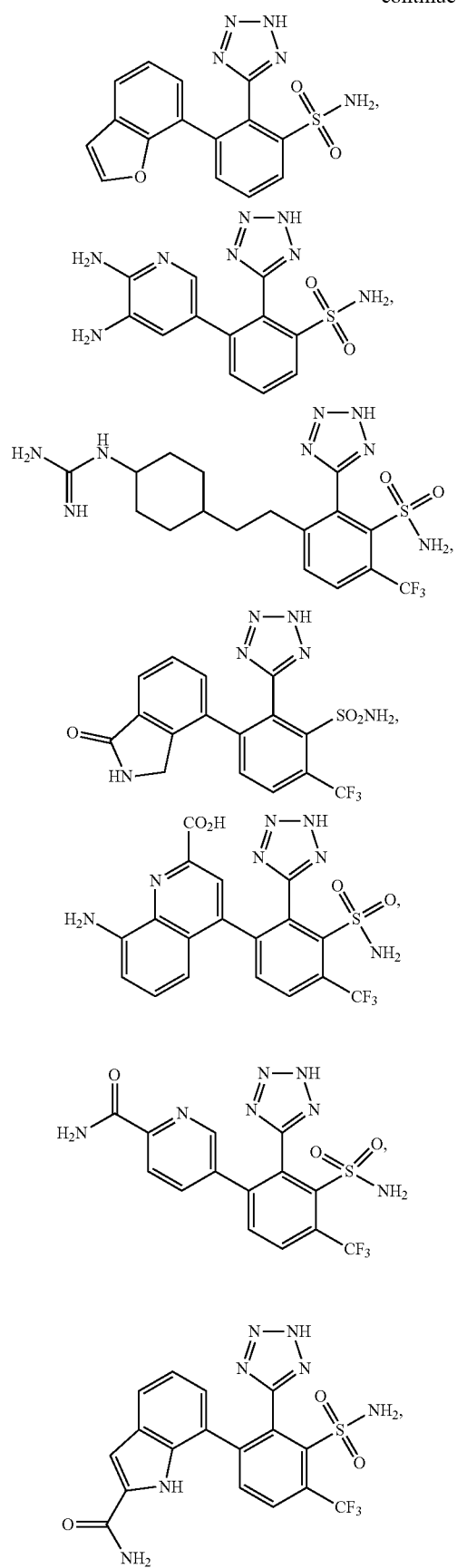

-continued
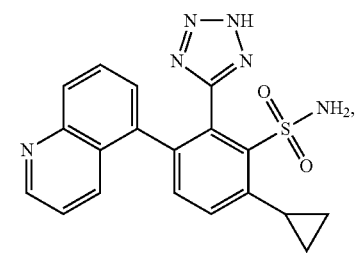
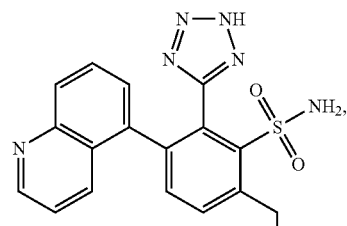
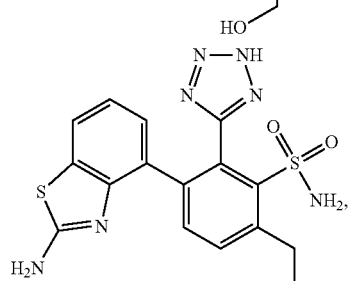
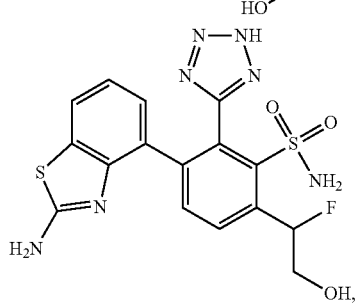
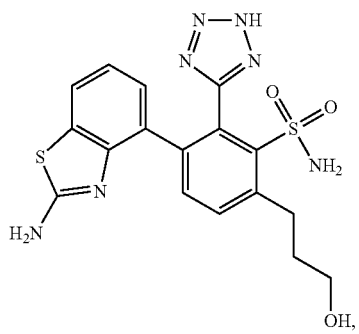
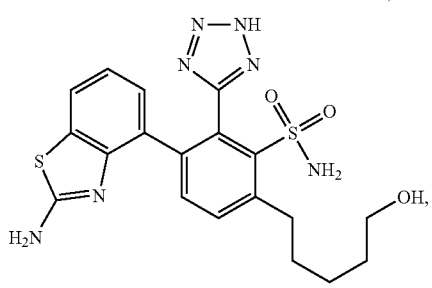

-continued
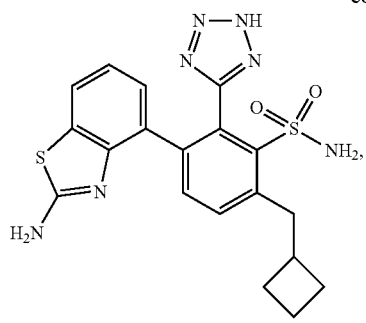
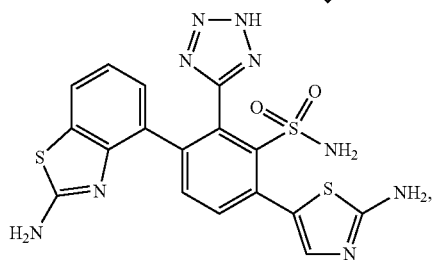
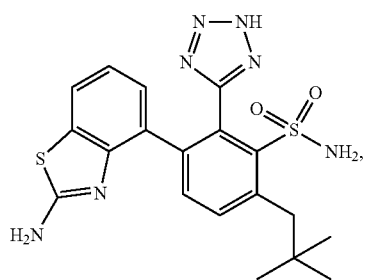
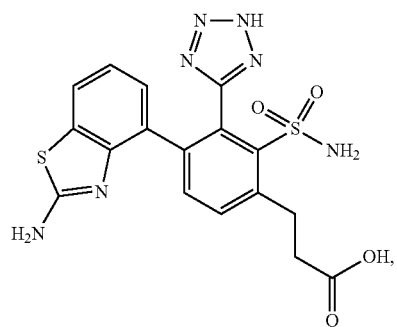
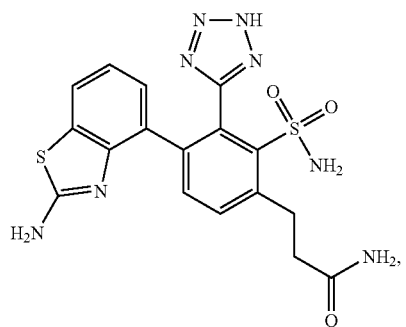

-continued
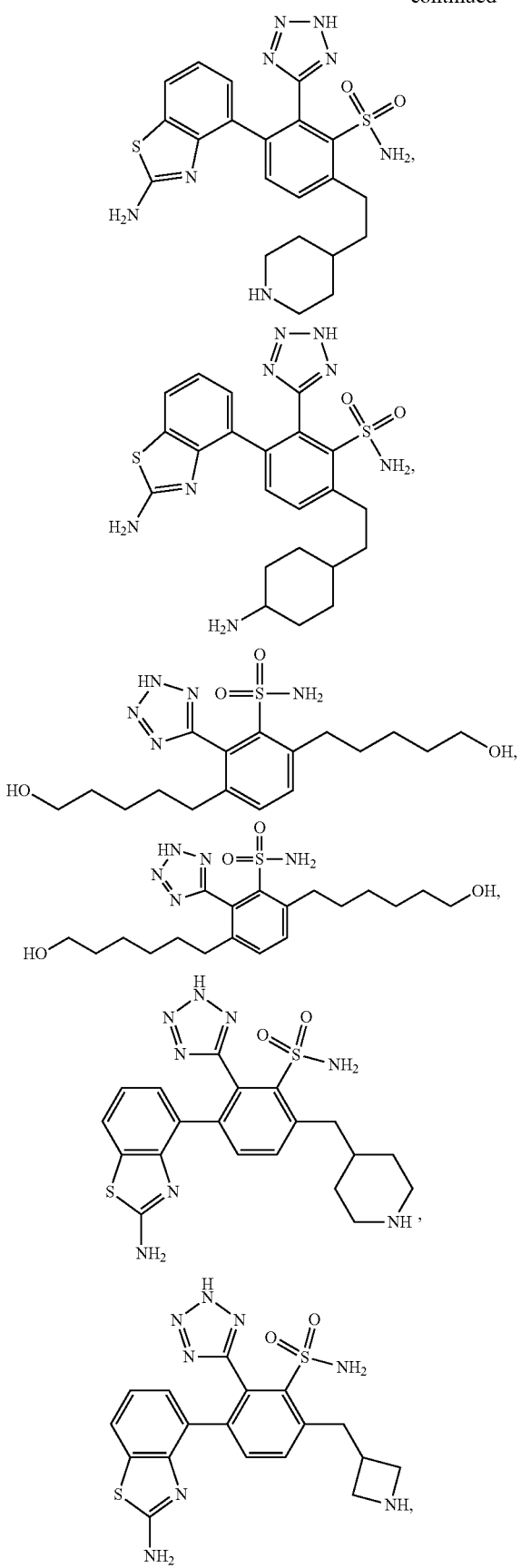

-continued
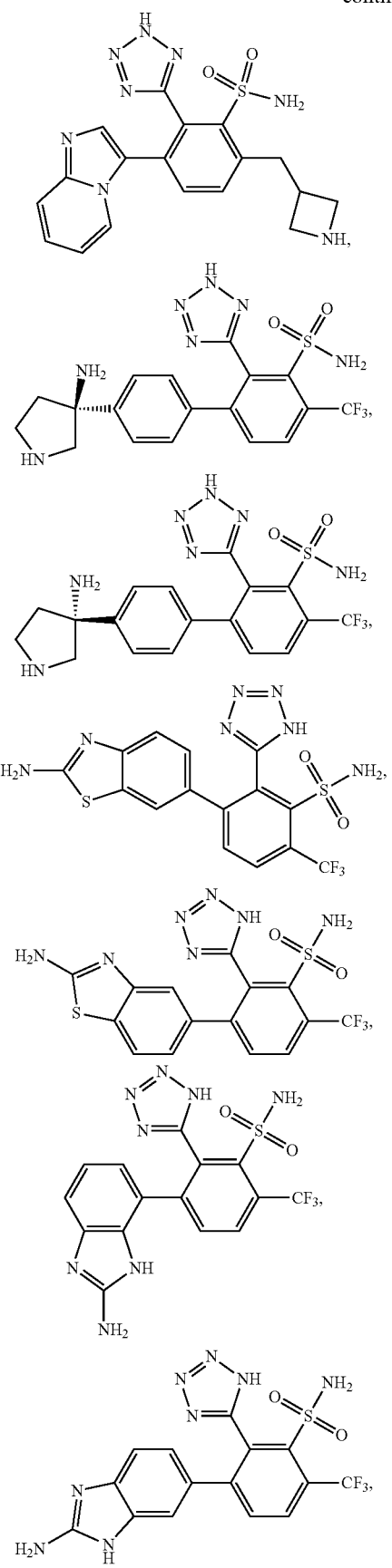

-continued
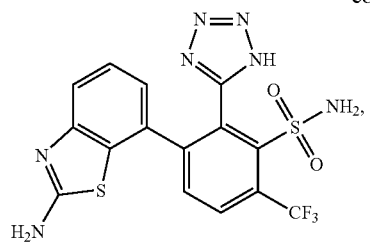
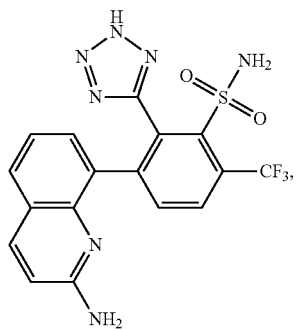
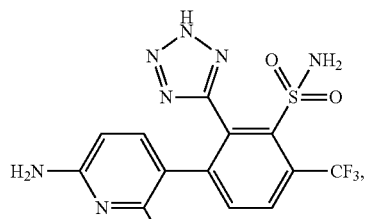
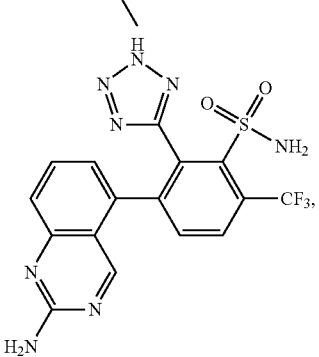
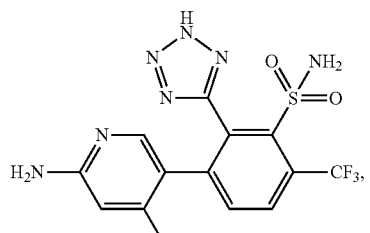
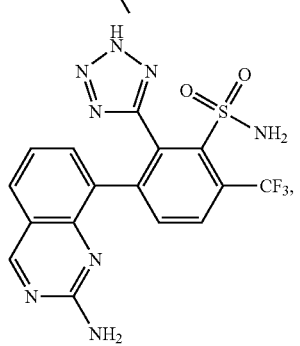

-continued
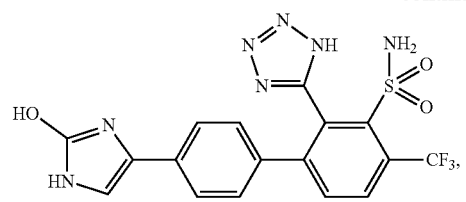
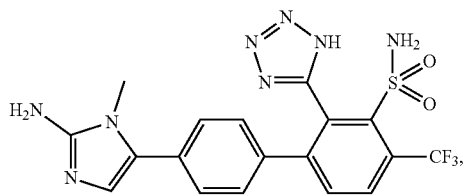
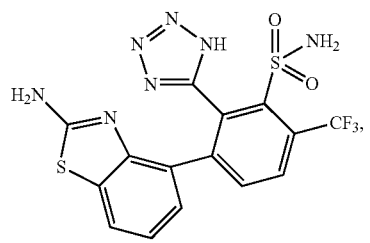
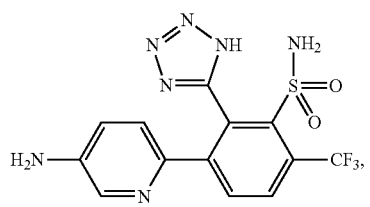
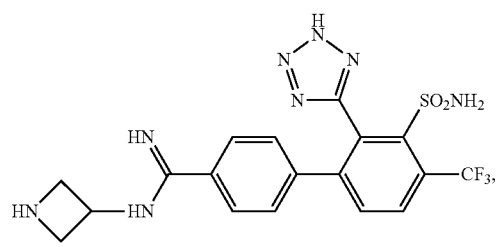
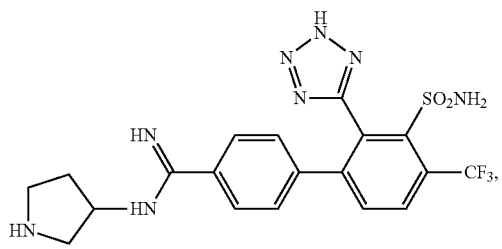
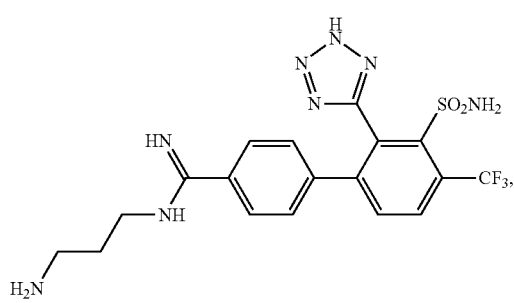

-continued
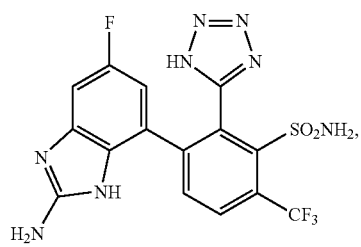
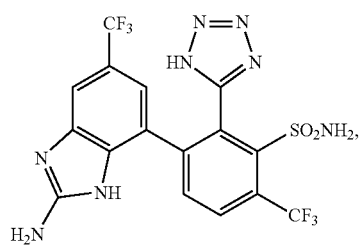
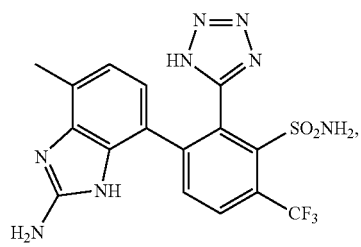
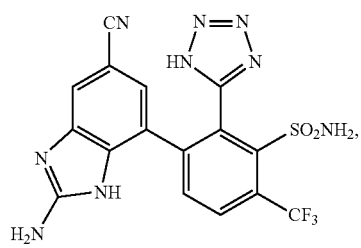
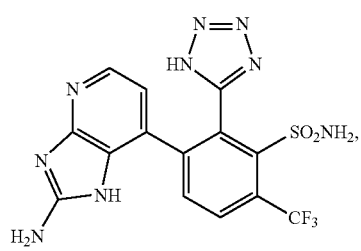
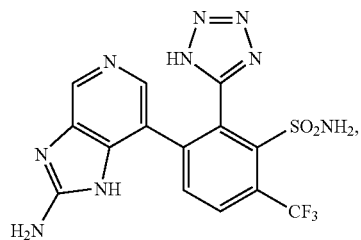

-continued
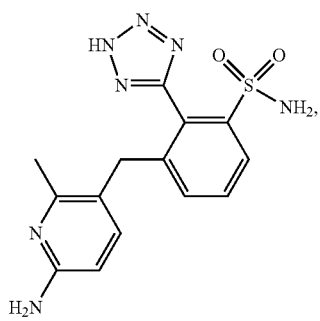
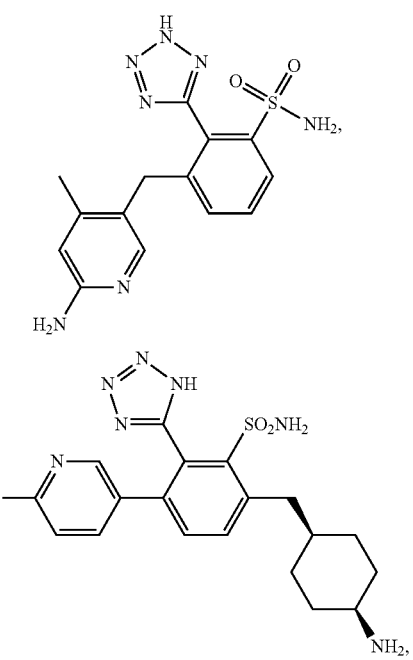
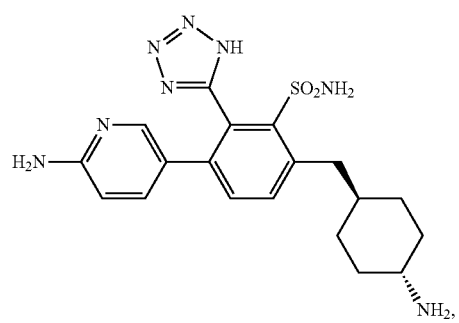
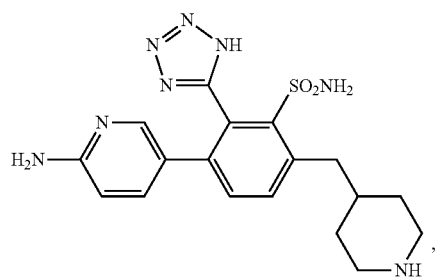

-continued
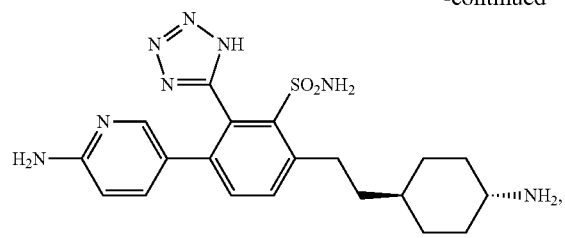
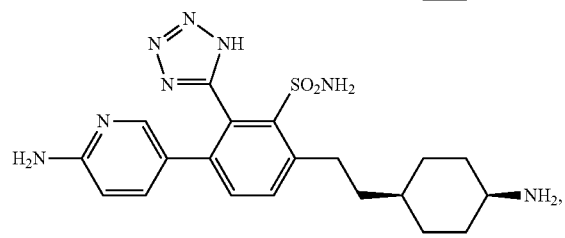
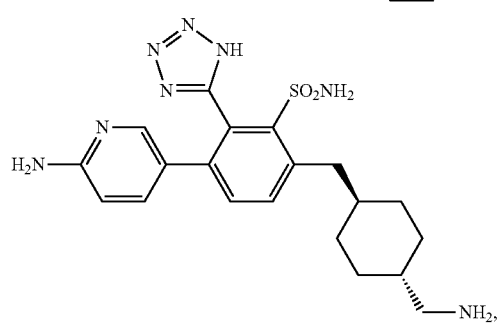
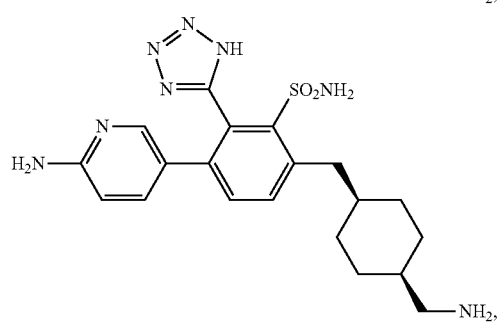
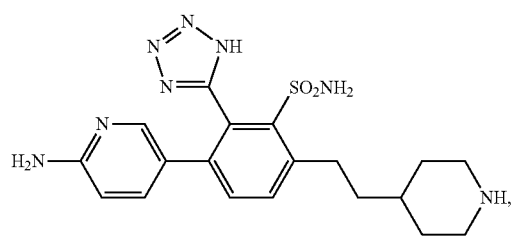
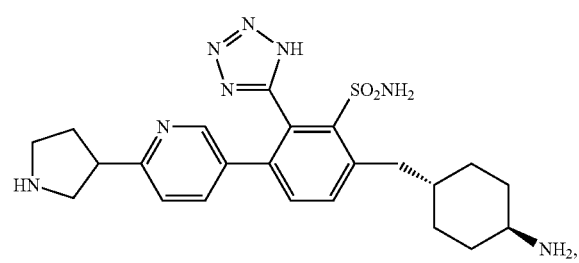

-continued
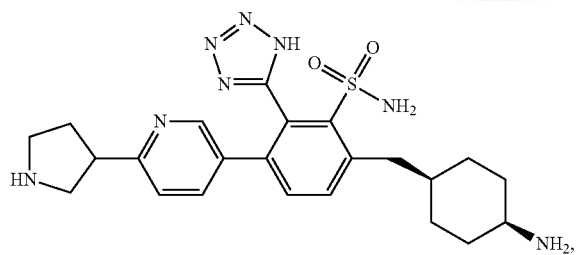
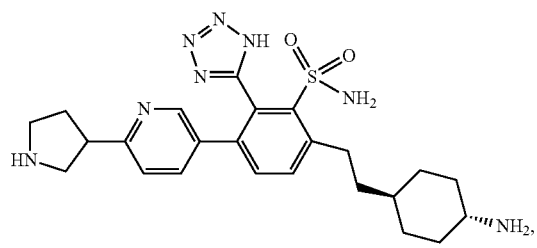
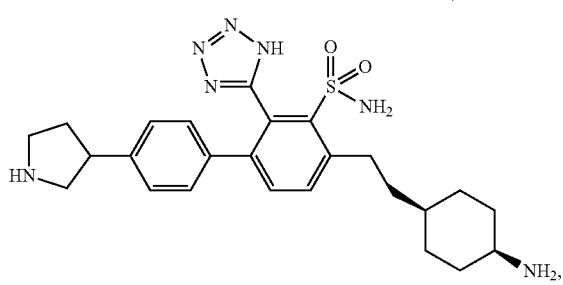
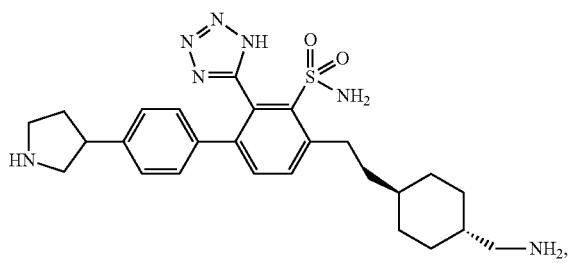
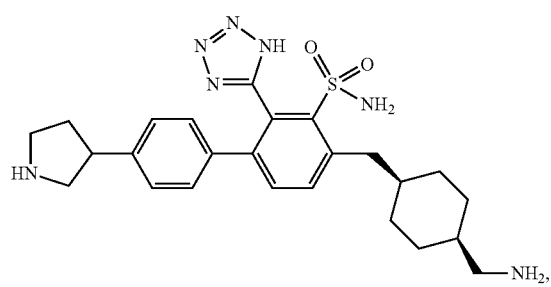
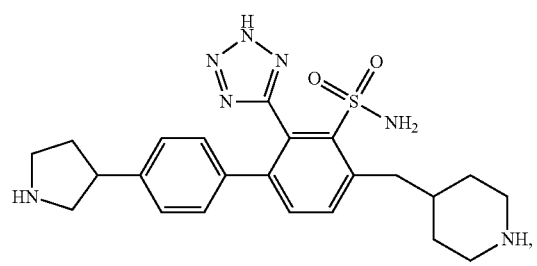

-continued
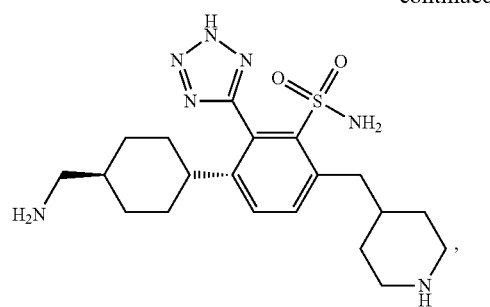
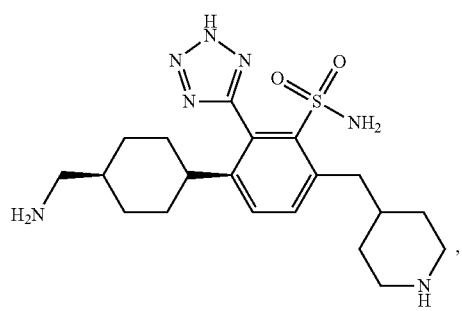
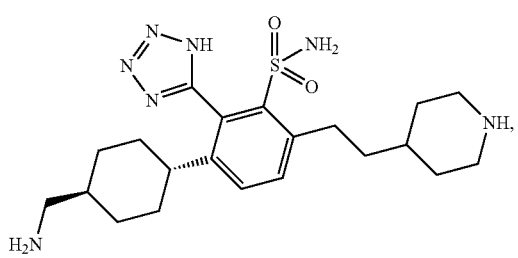
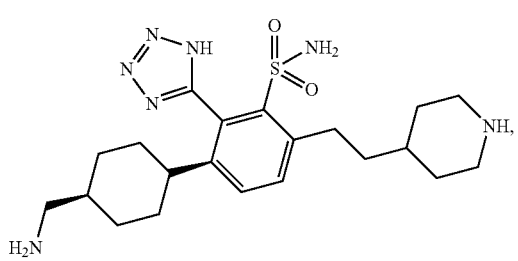
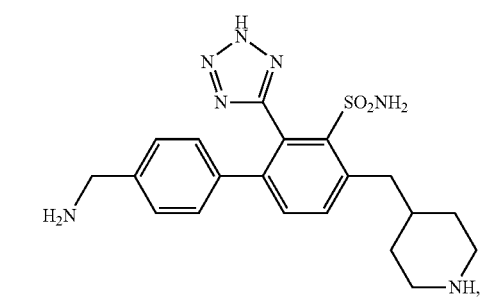
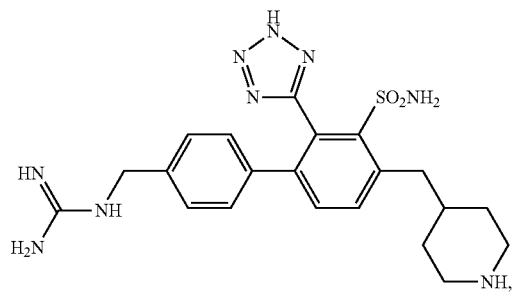

-continued
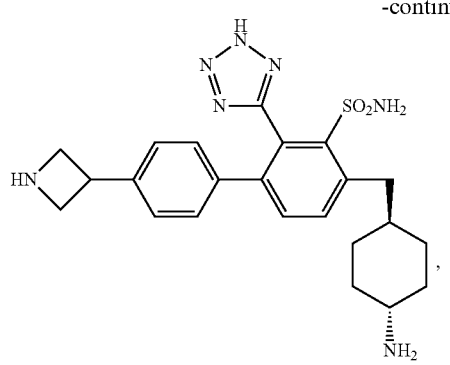
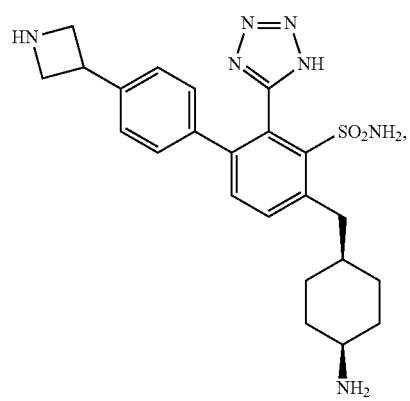
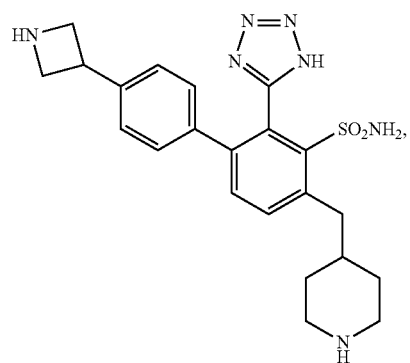
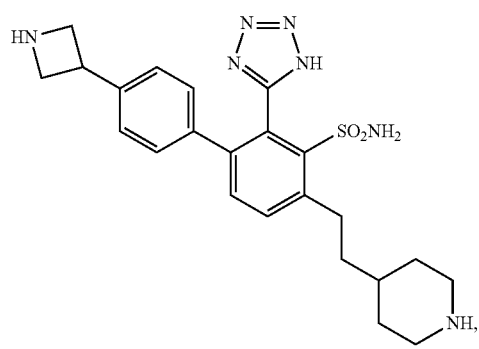

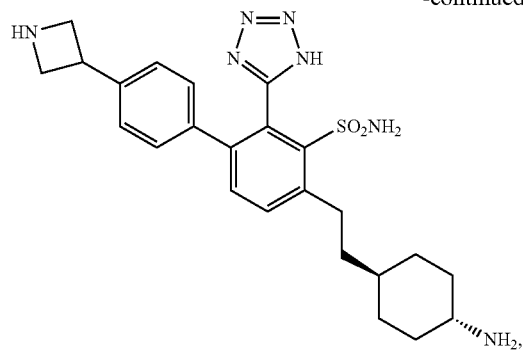
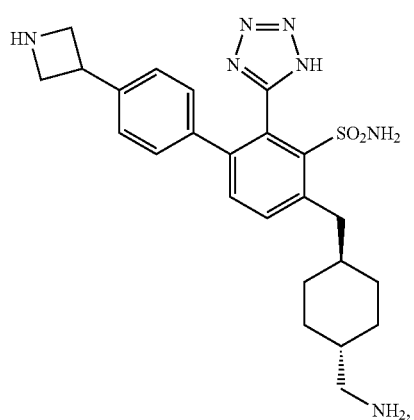
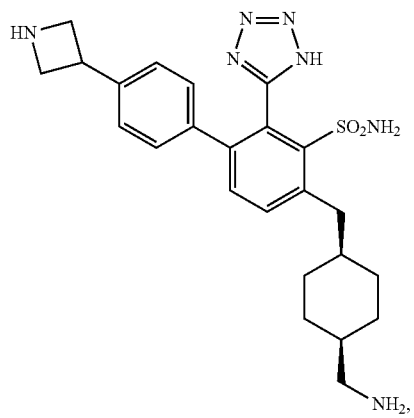
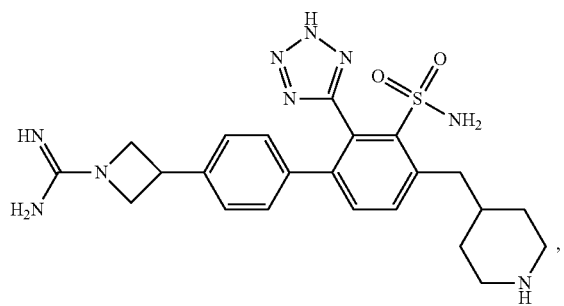

-continued
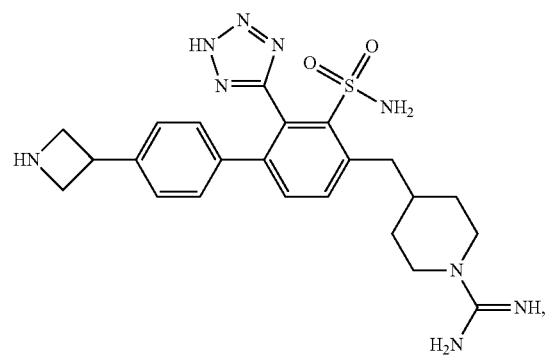
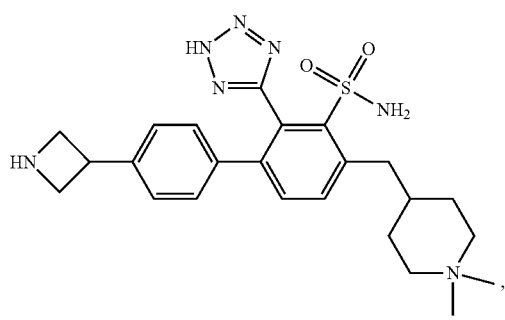
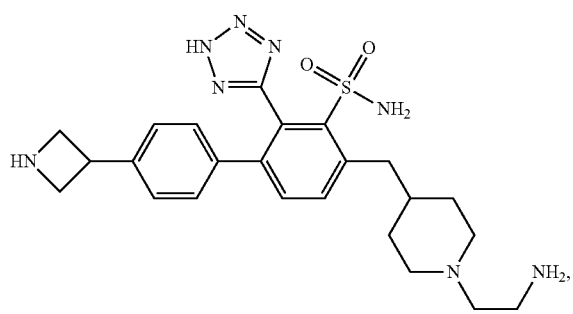
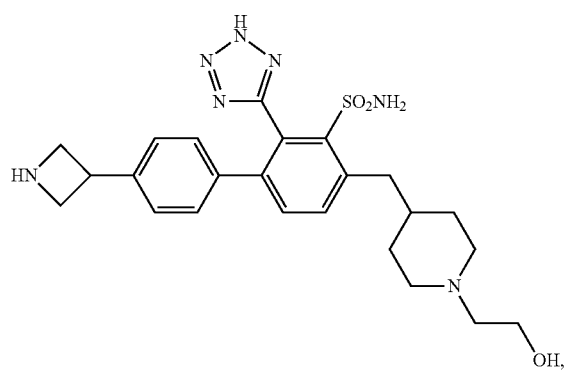
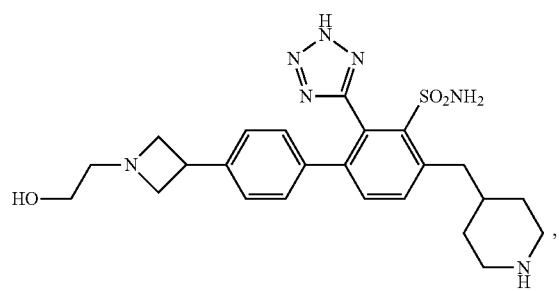

-continued
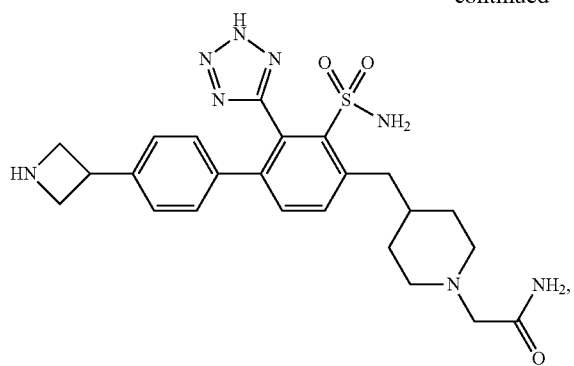
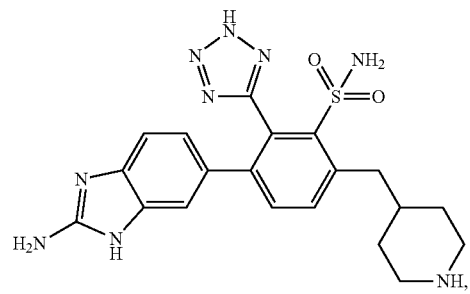
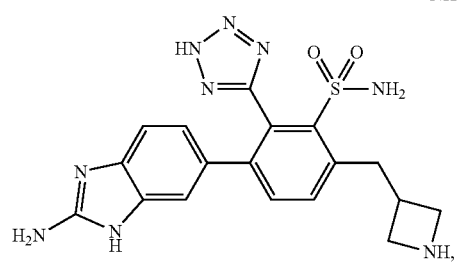
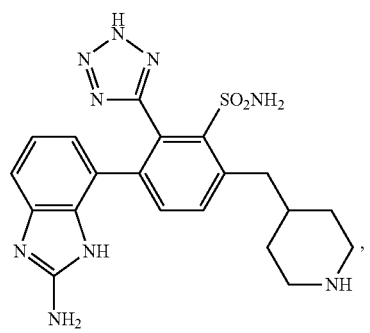
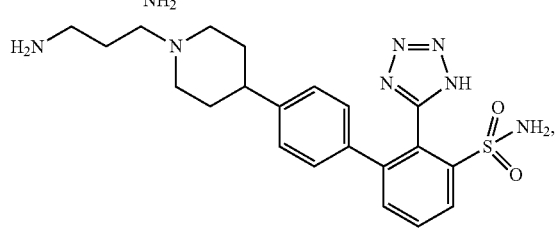
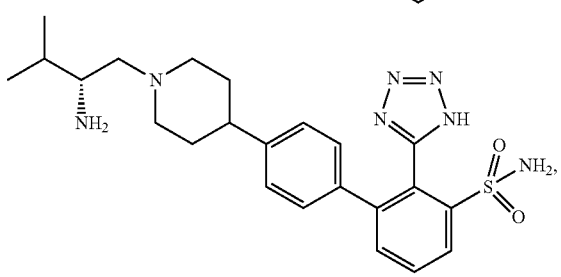

-continued
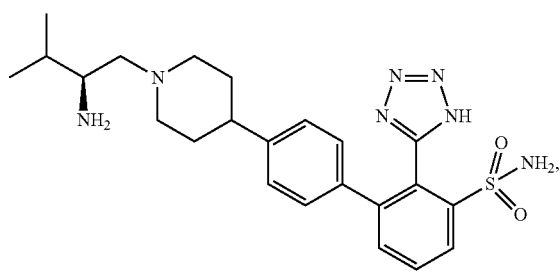
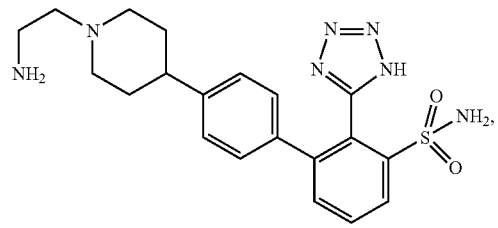
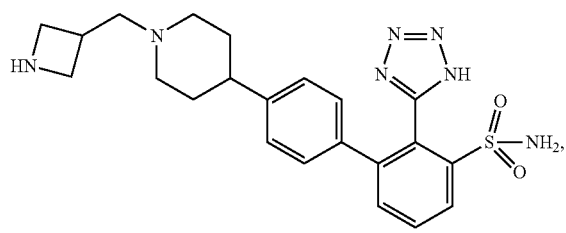
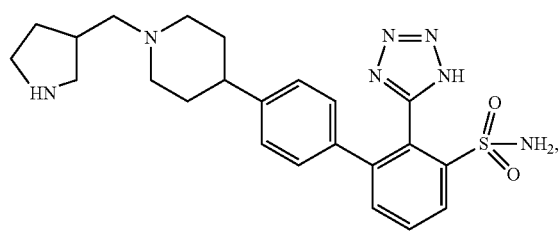
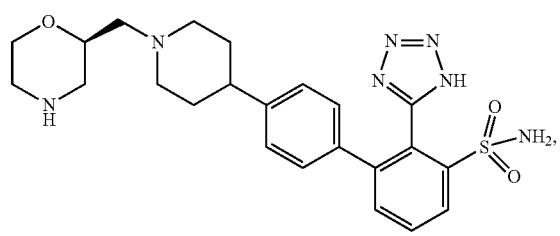
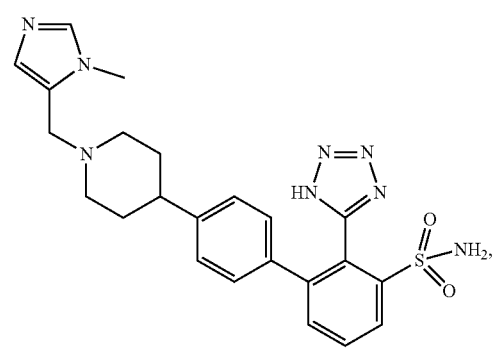

-continued
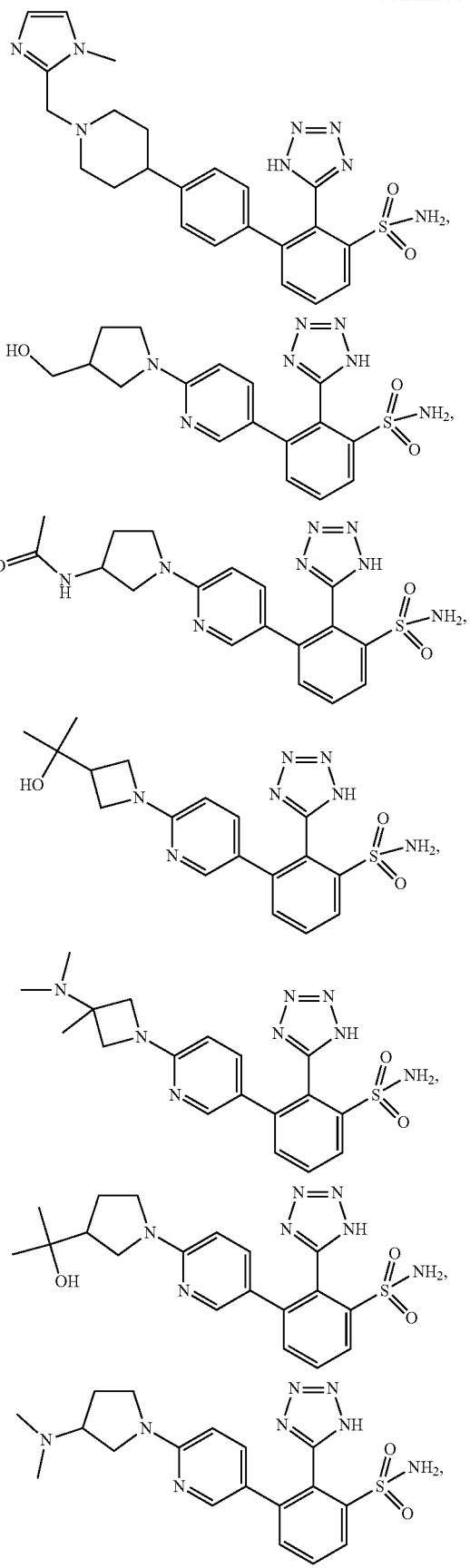

-continued
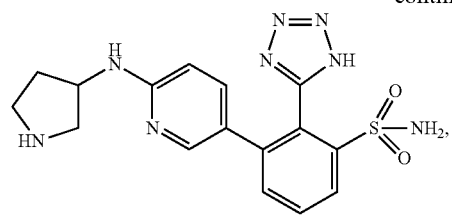
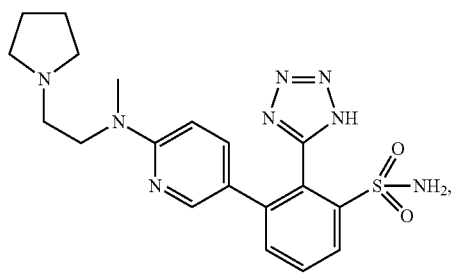
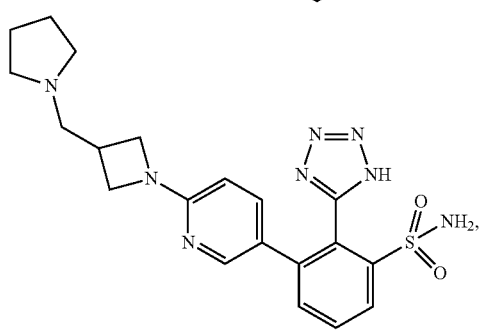
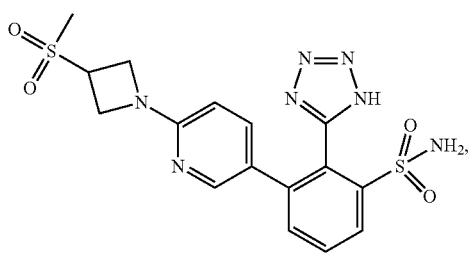
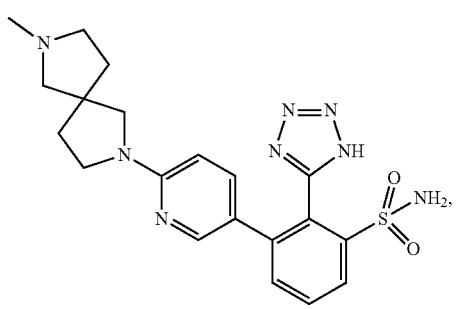
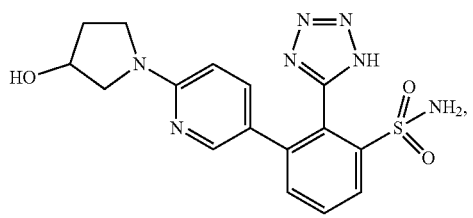

-continued
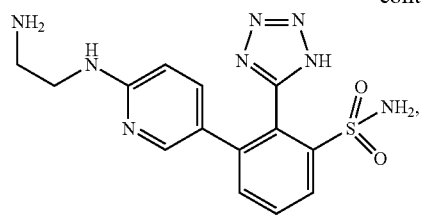
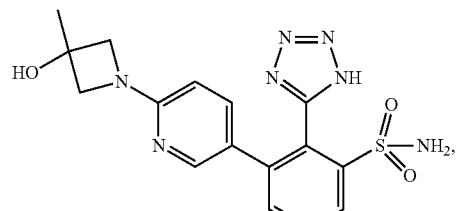
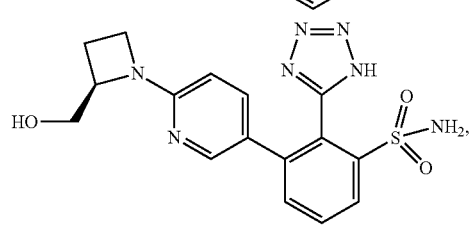
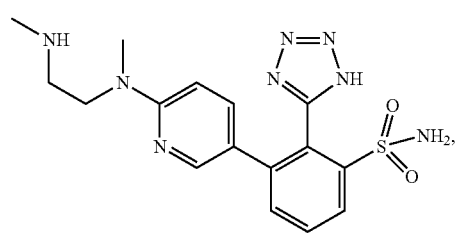
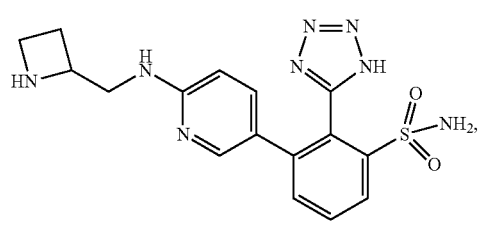
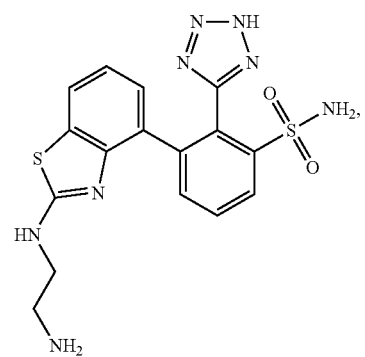

-continued
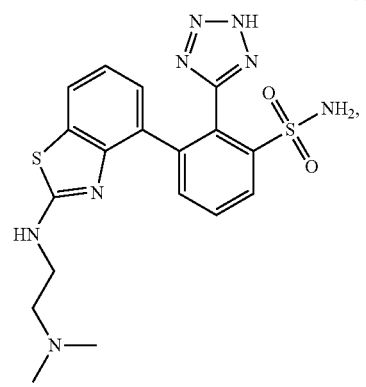
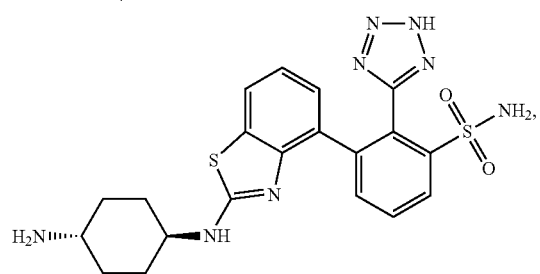
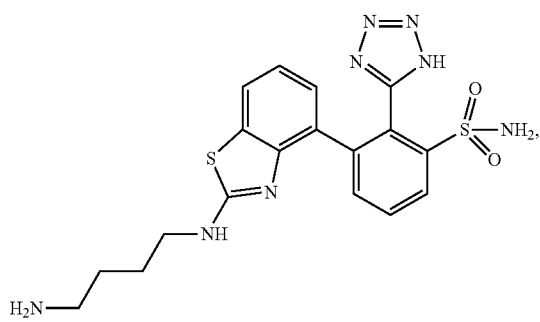
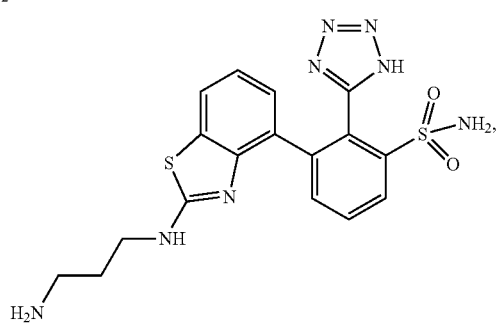
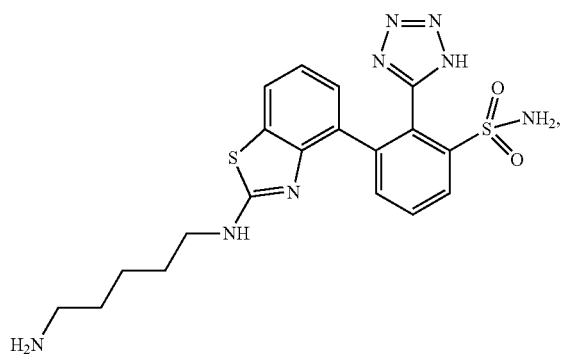

-continued
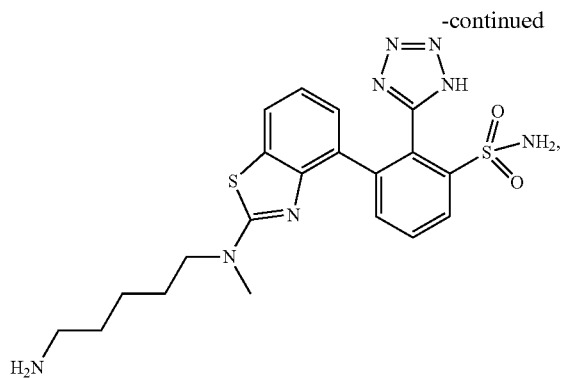
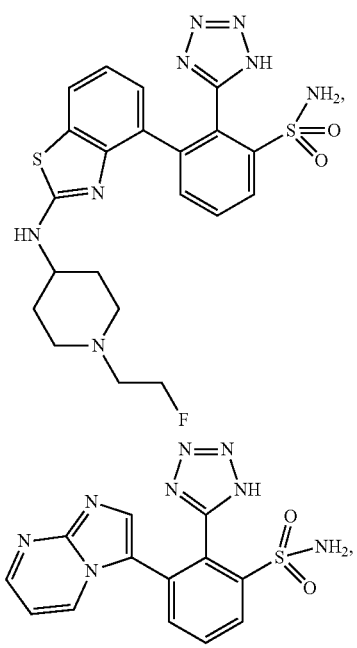
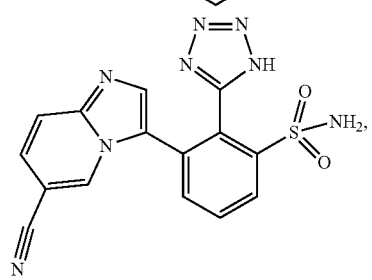
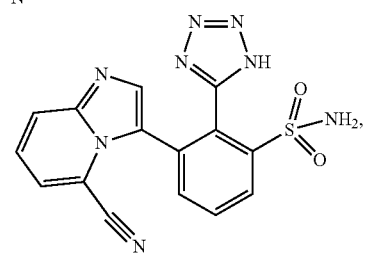
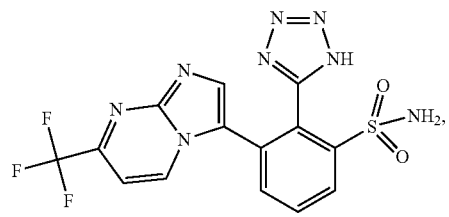

-continued
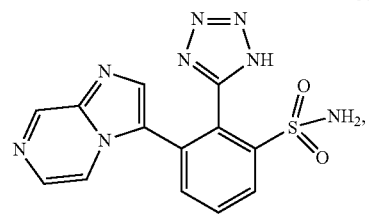
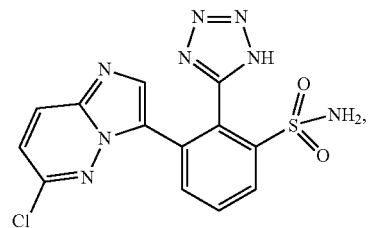
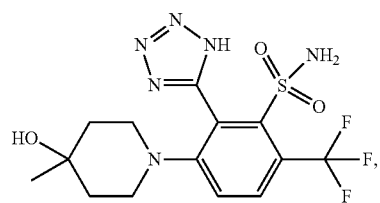
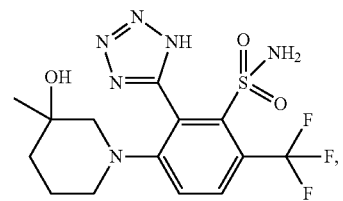
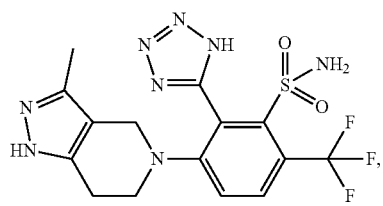
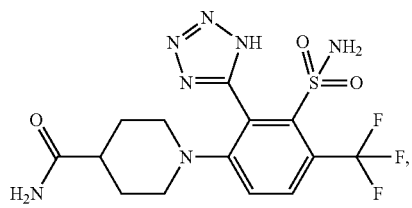
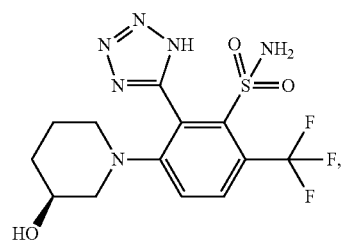
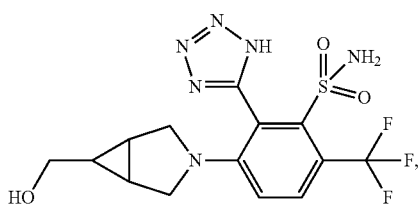

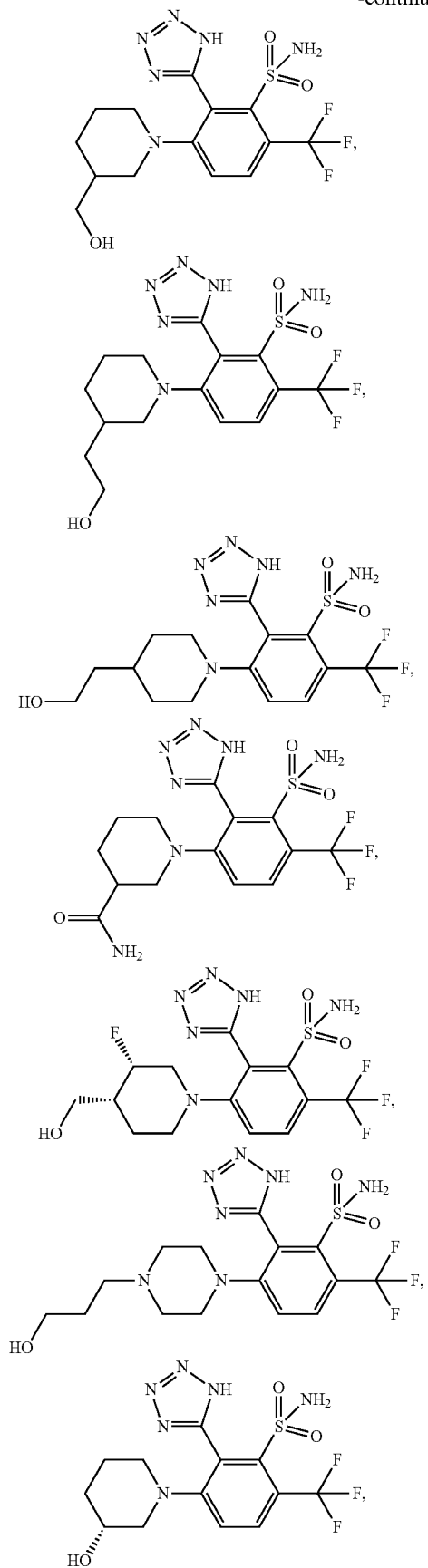

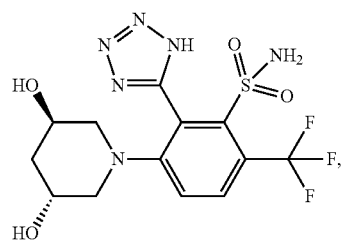
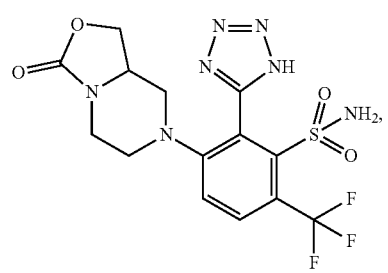
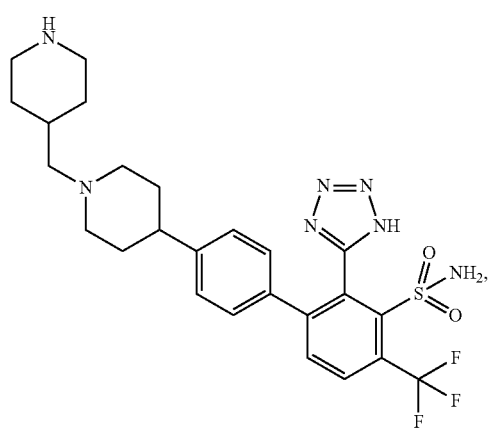
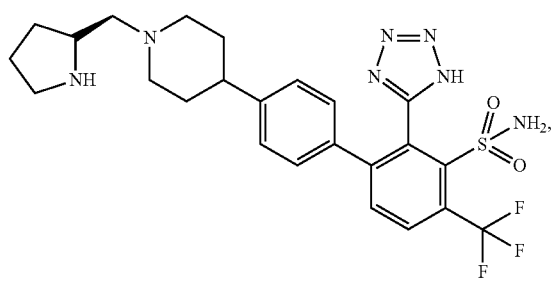
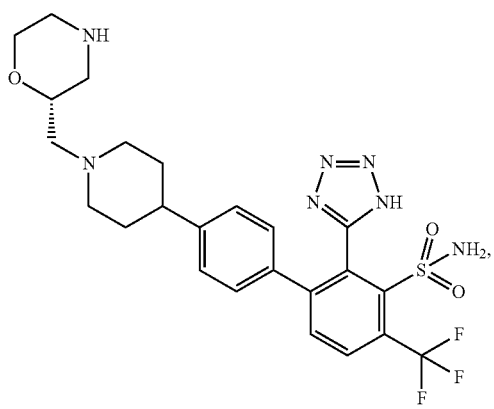

-continued
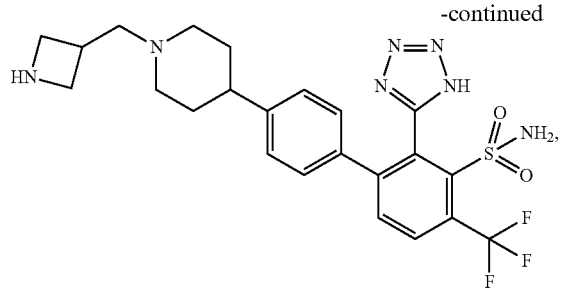
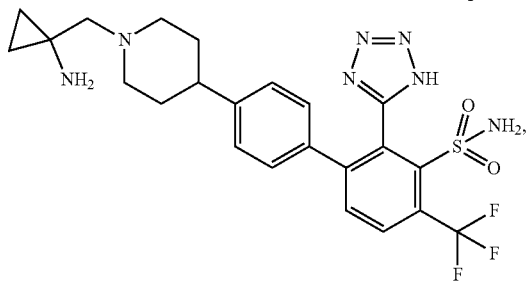
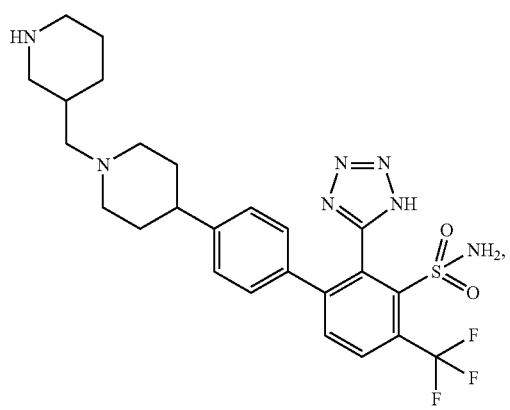
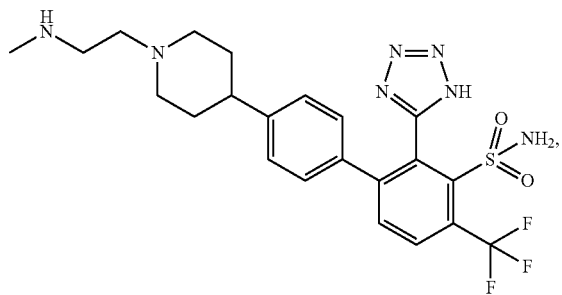
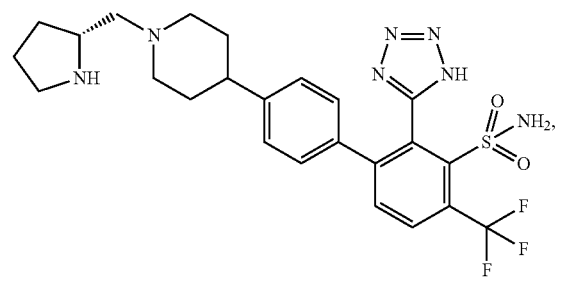

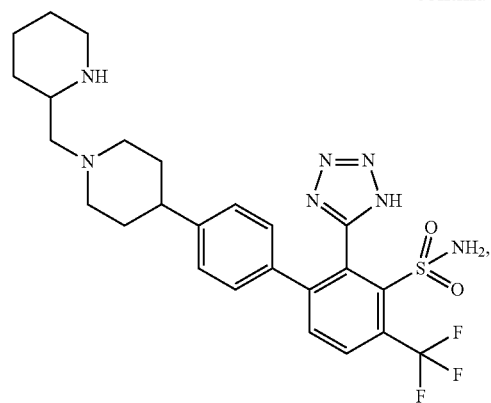
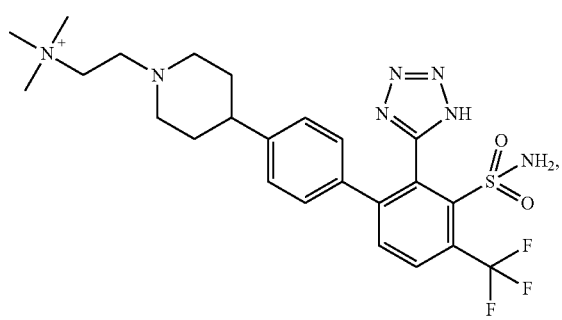
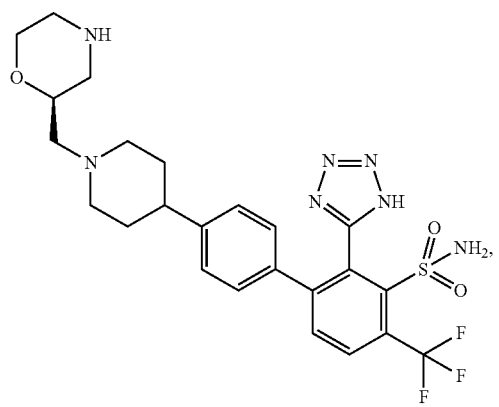
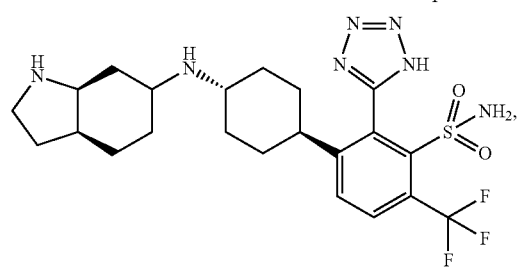
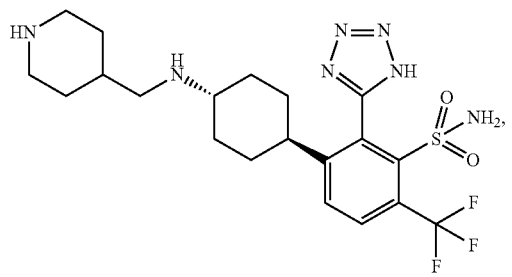

-continued
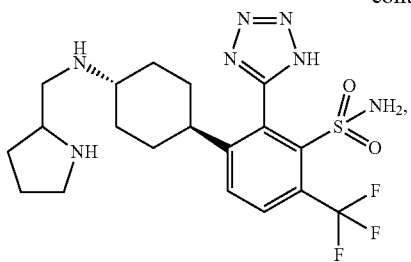
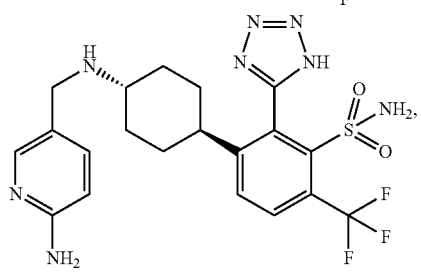
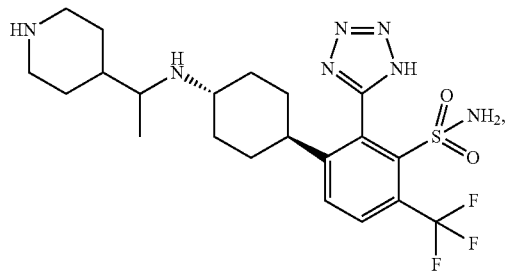
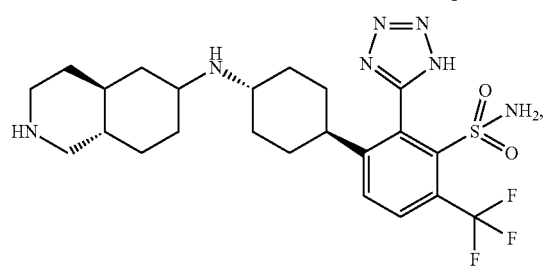
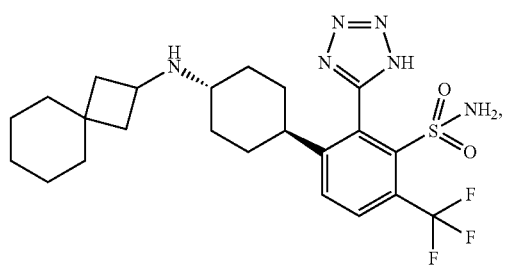
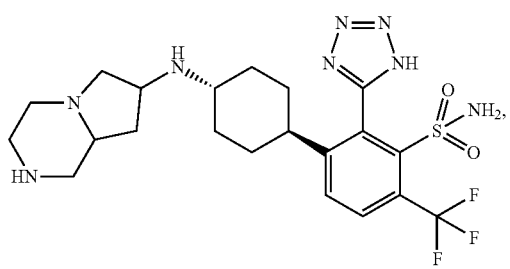

-continued
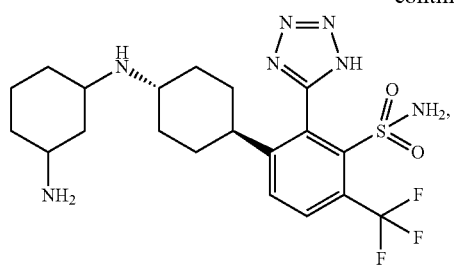
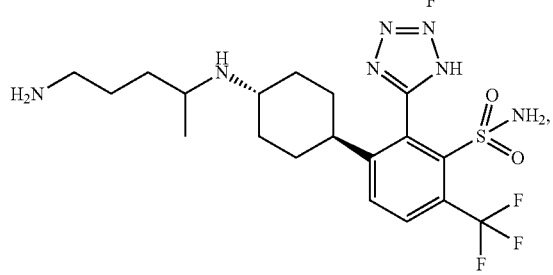
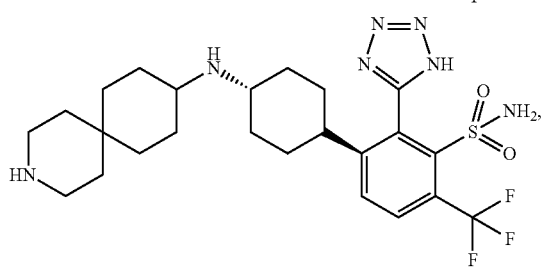
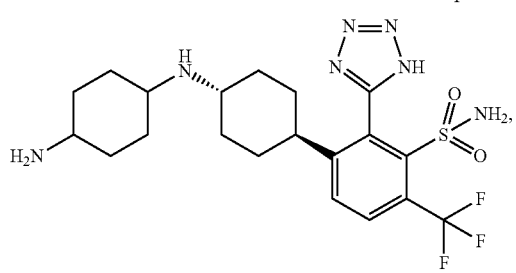
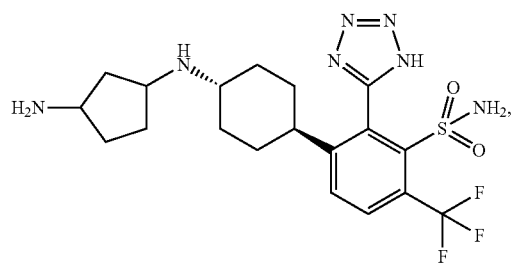
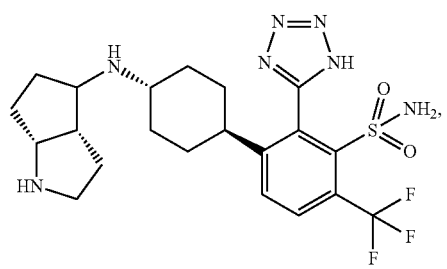

-continued
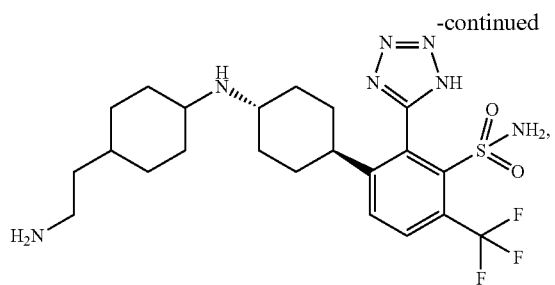
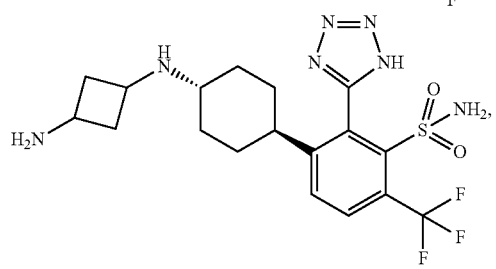
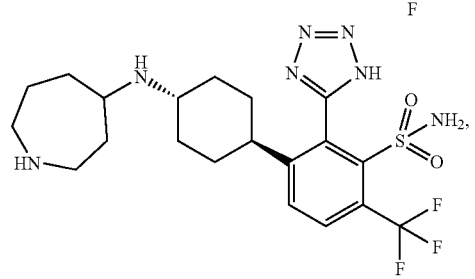
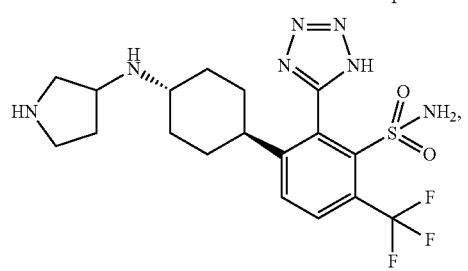
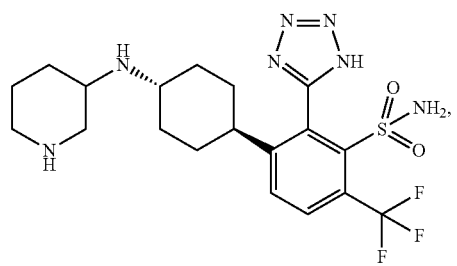
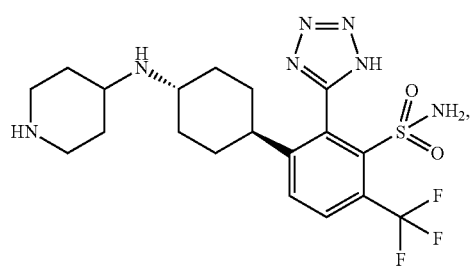

-continued
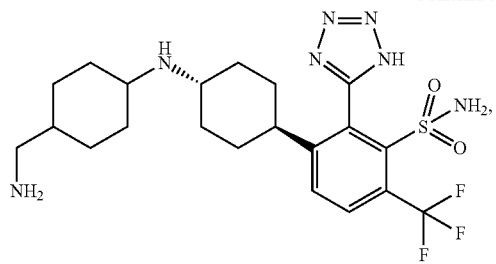
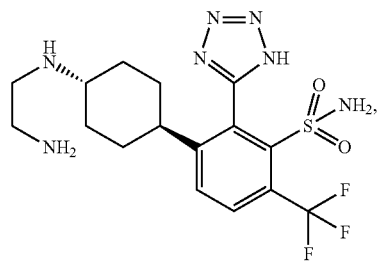
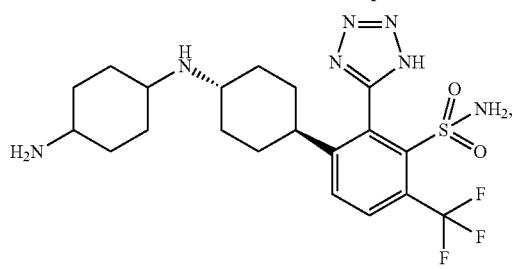
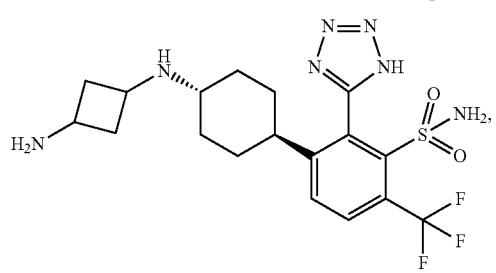
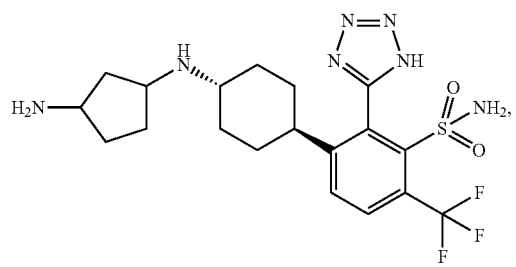
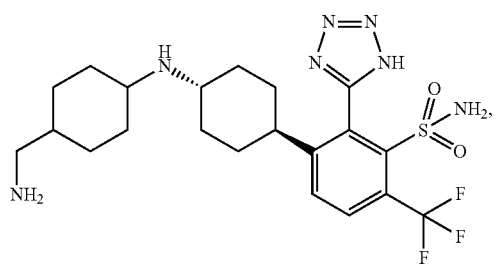

-continued
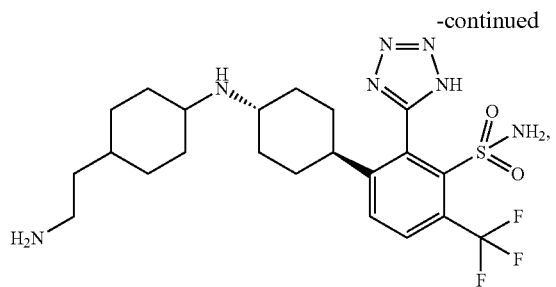
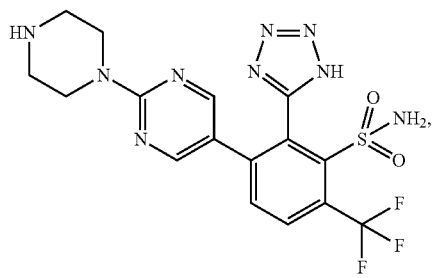
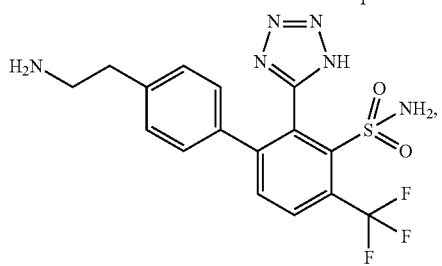
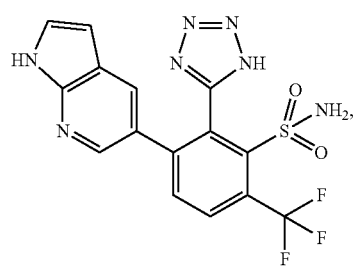
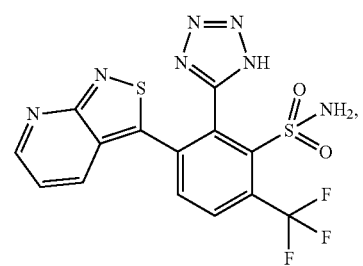
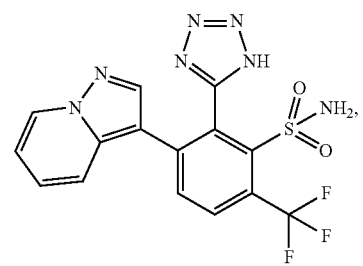

-continued
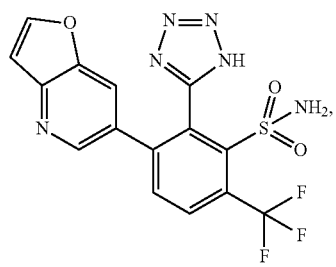
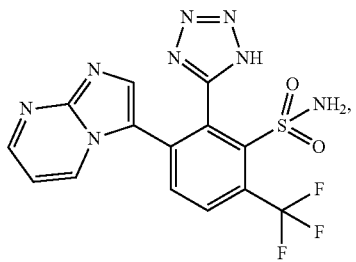
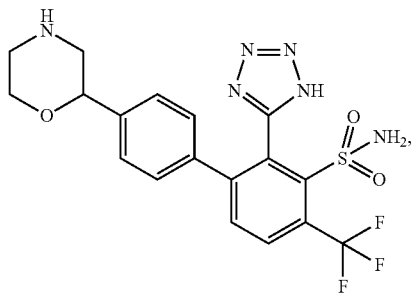
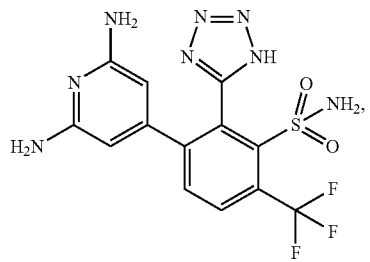
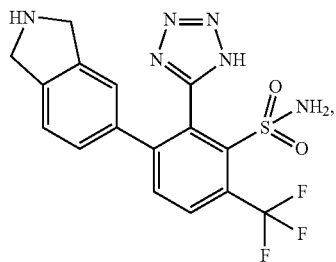
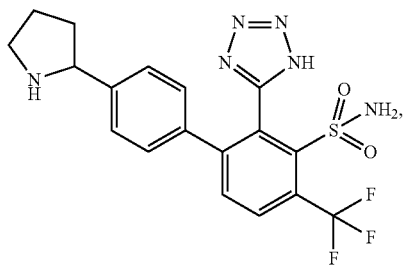

-continued
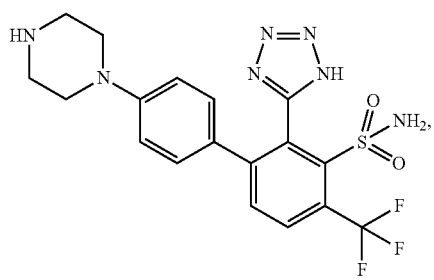
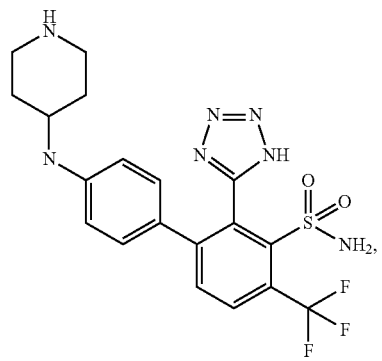
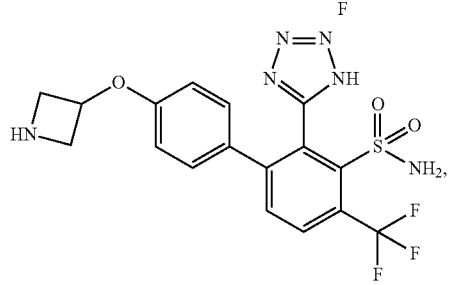
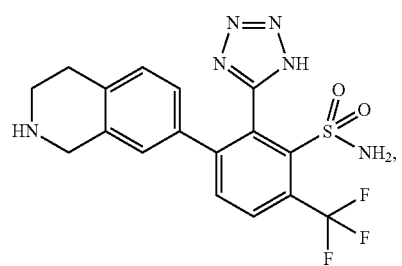
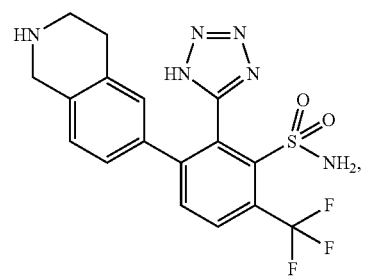
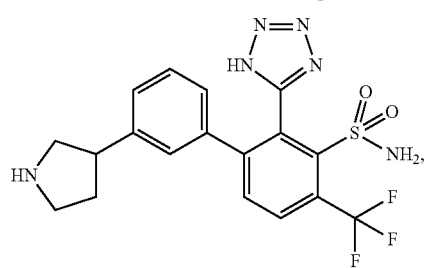

-continued
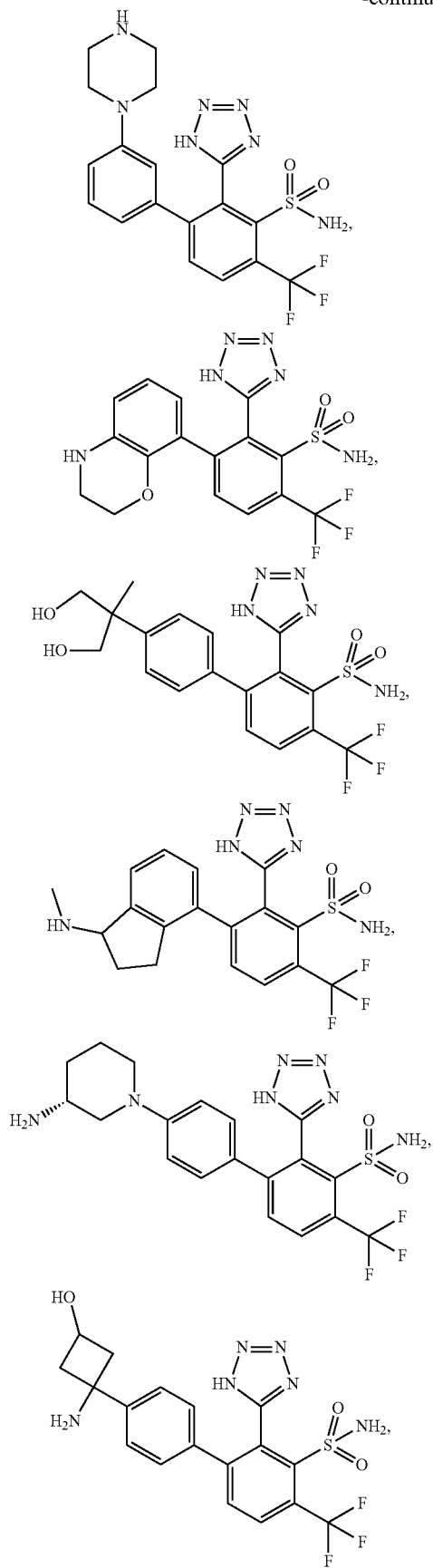

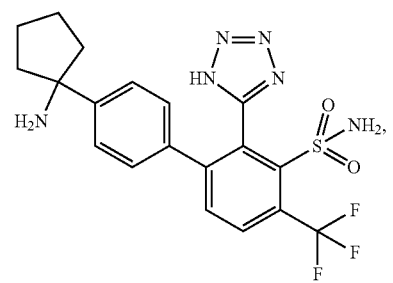
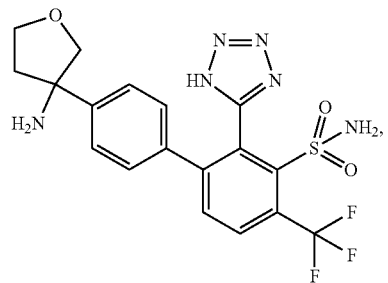
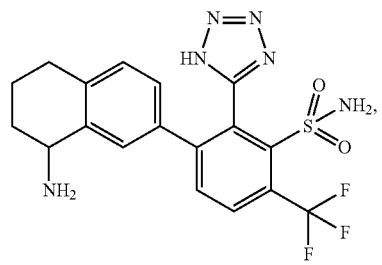
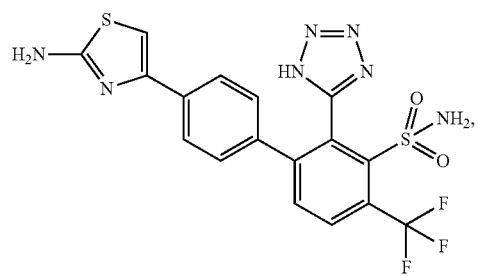
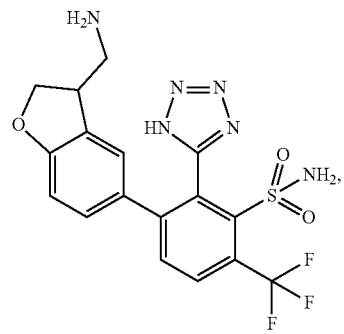
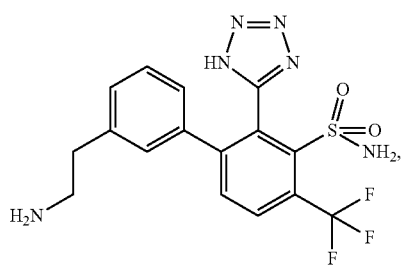

-continued
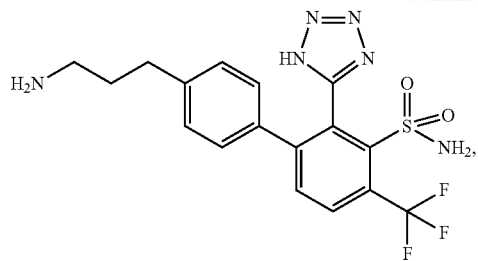
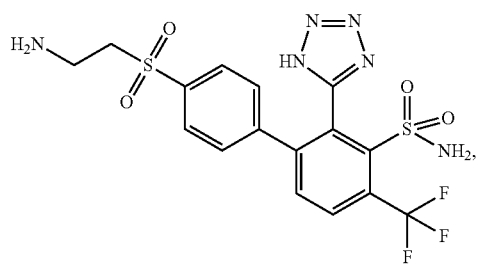
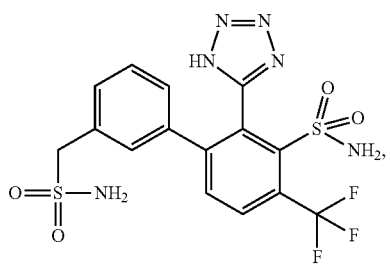
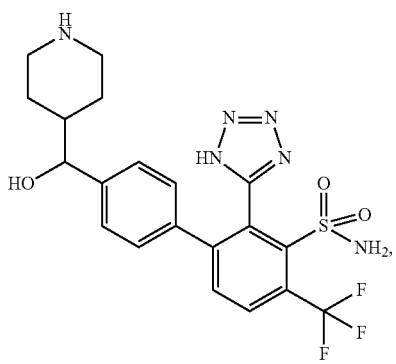
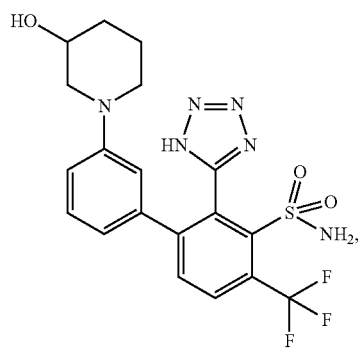

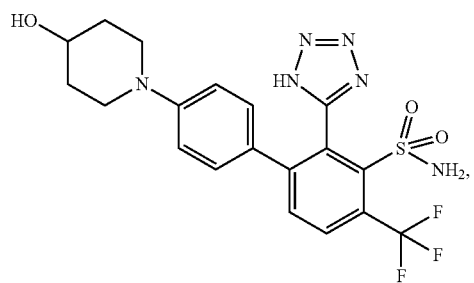
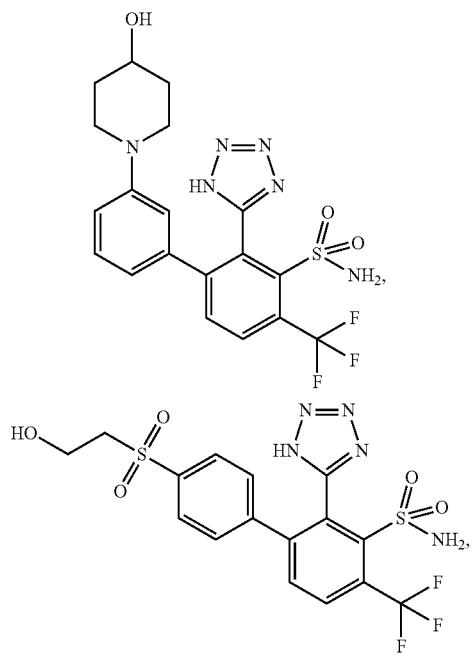
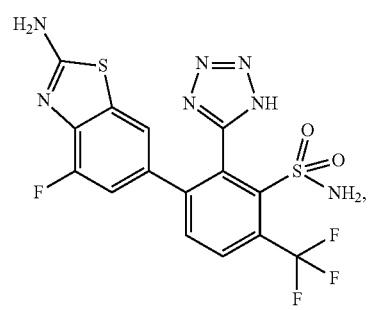
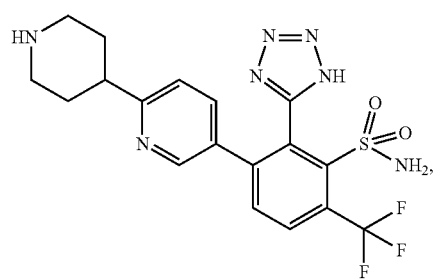

-continued
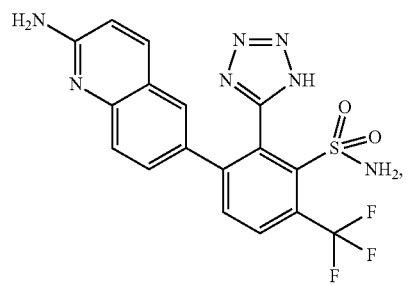
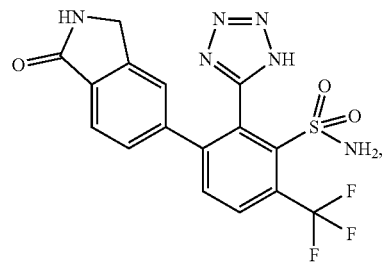
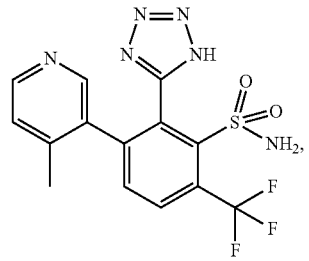
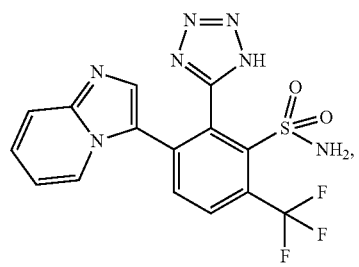
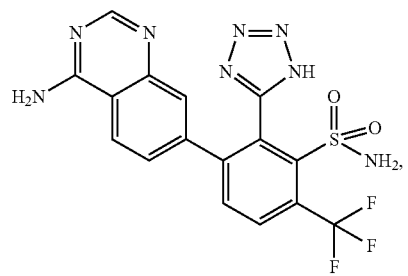
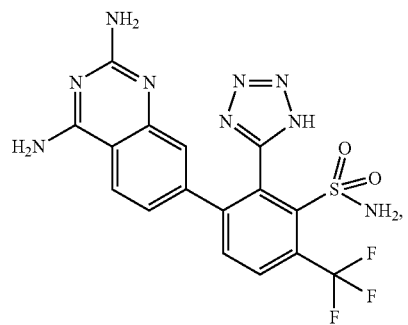

-continued
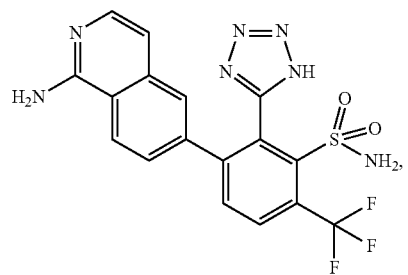
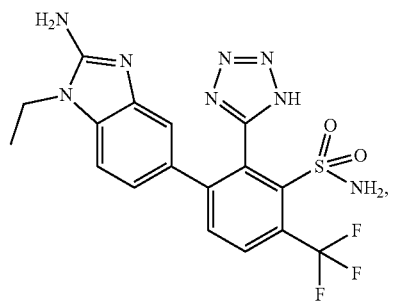
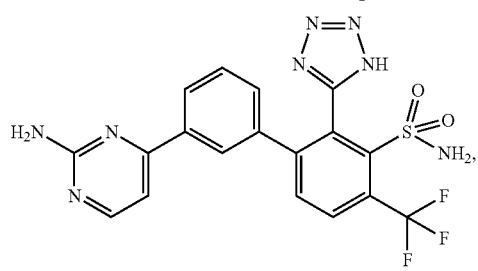
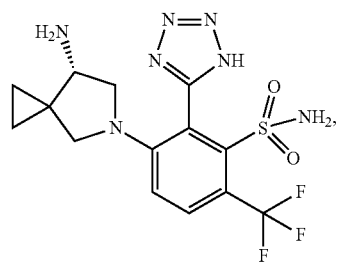
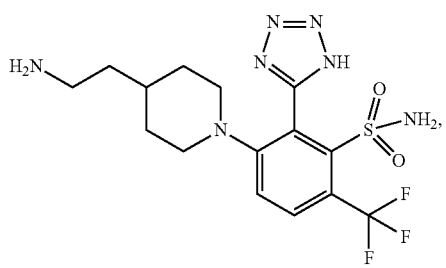
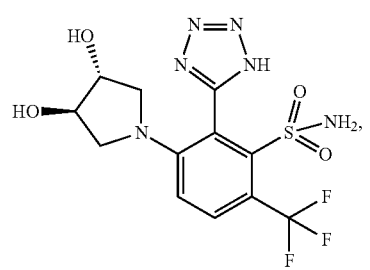

-continued
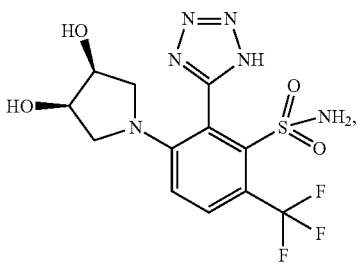
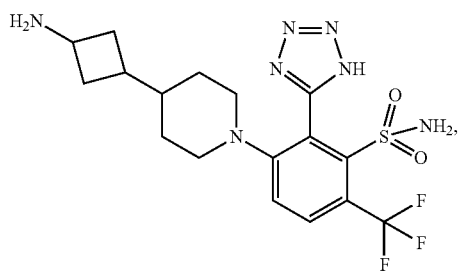
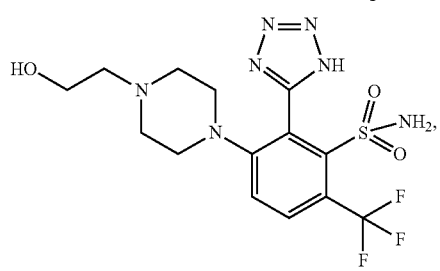
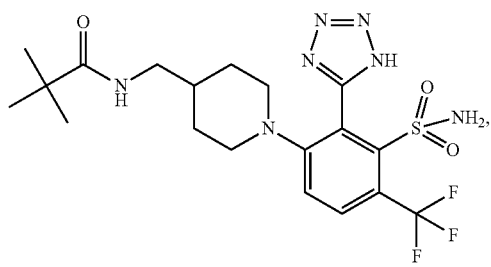
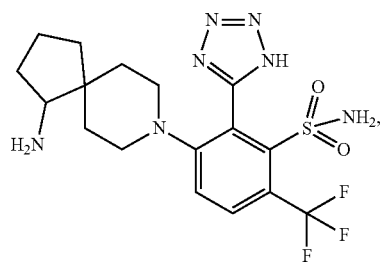
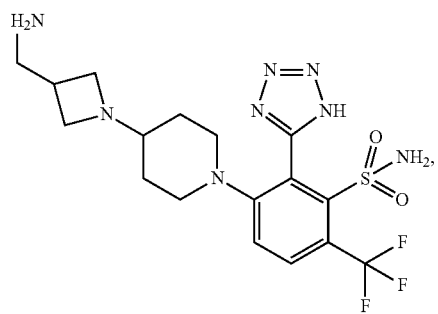

-continued
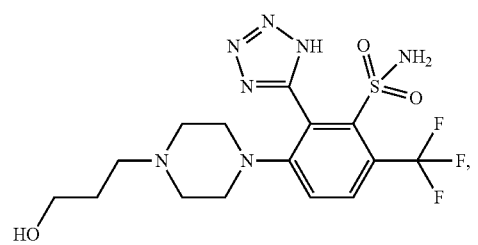
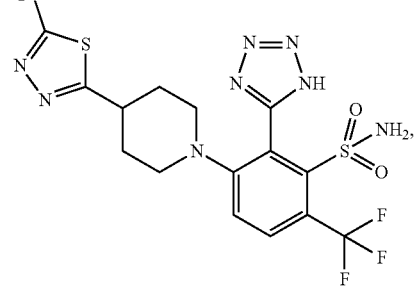
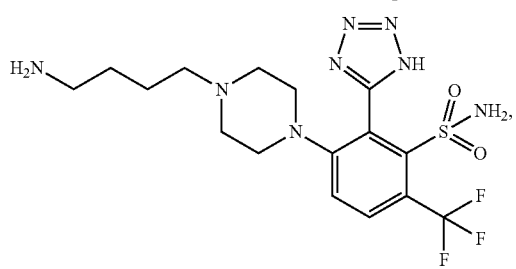
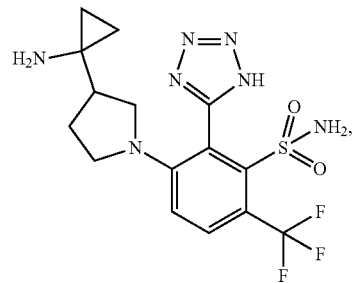
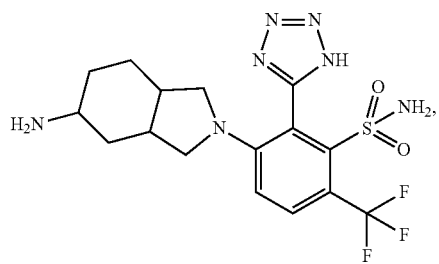
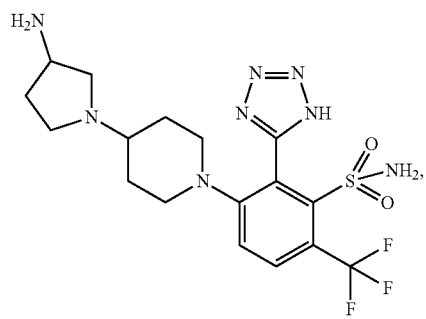

-continued
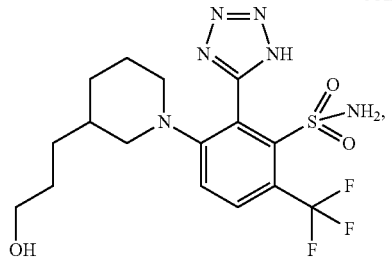
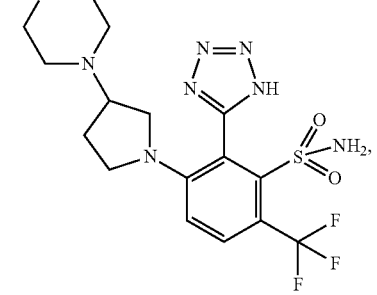
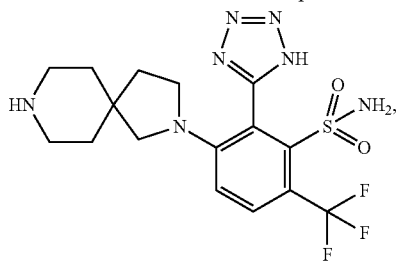
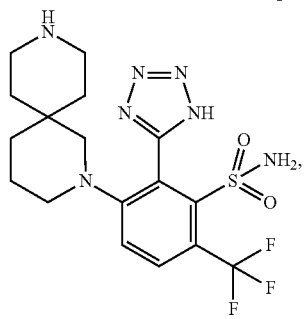
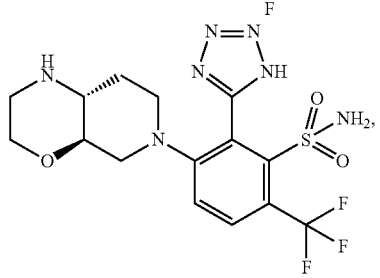
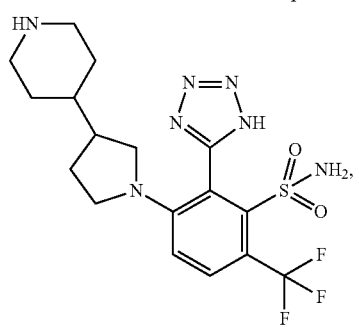

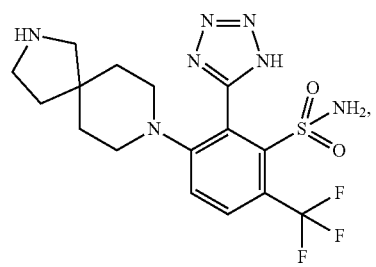
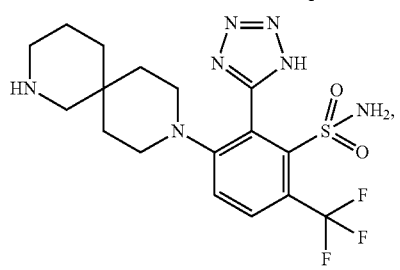
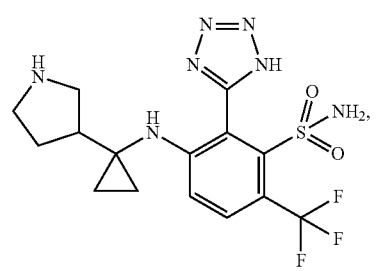
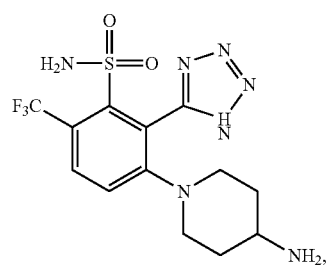
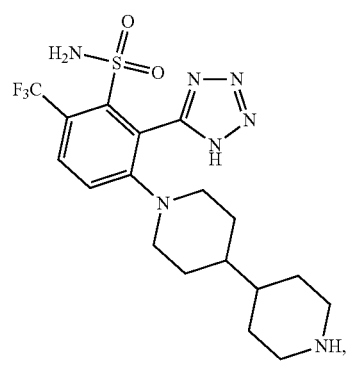

-continued
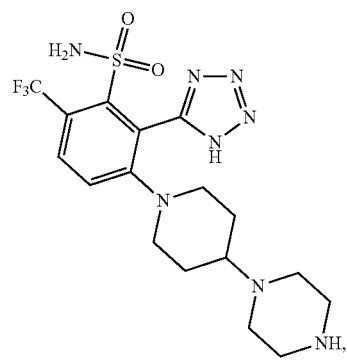
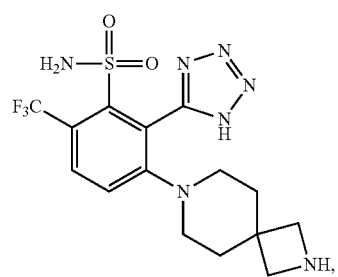
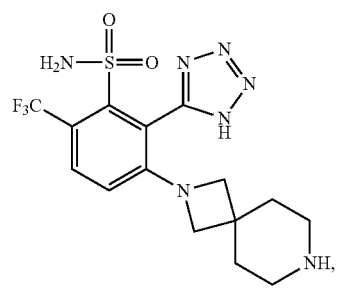
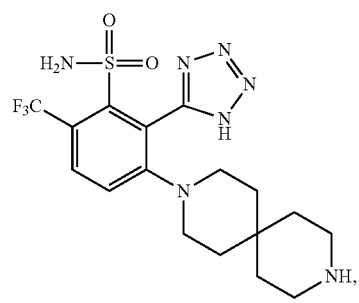
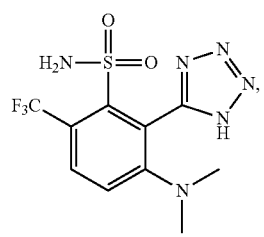

-continued
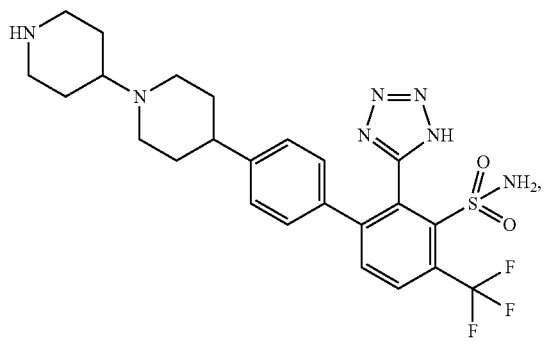
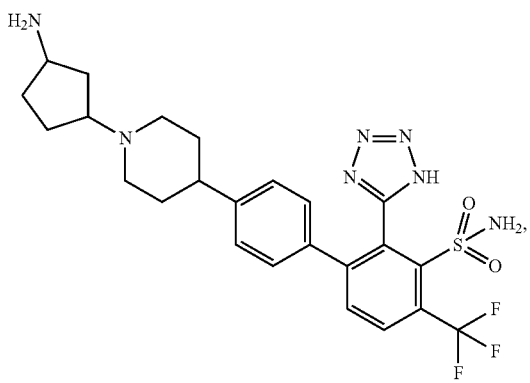
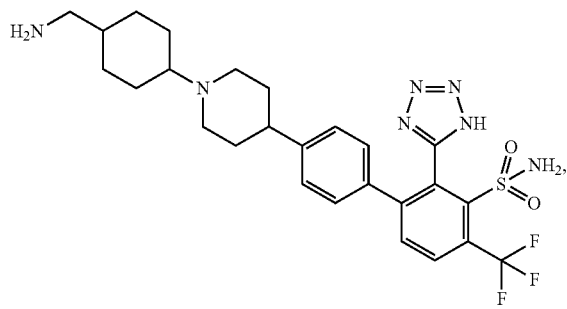
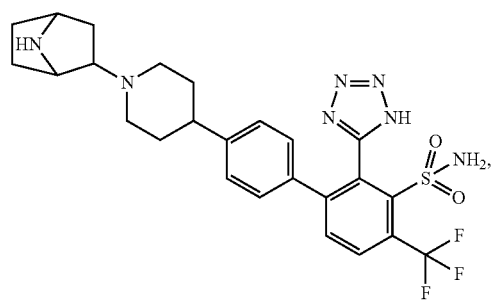
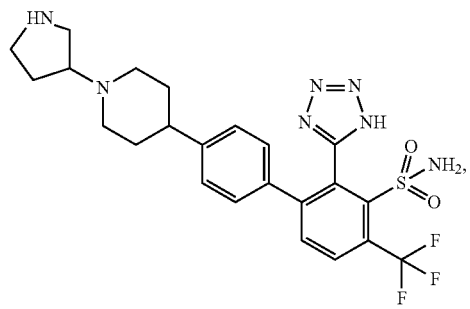

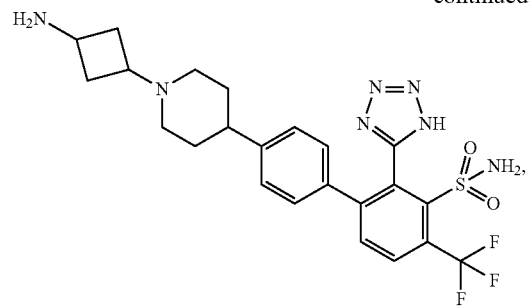
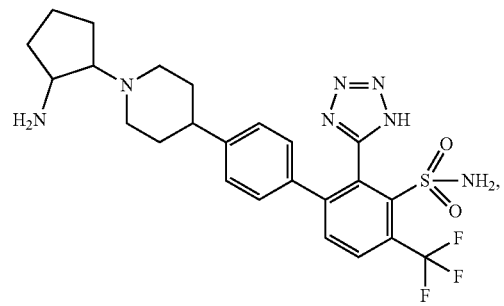
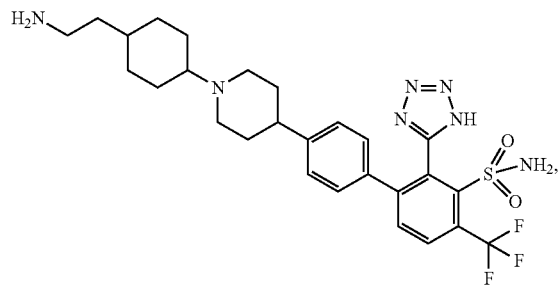
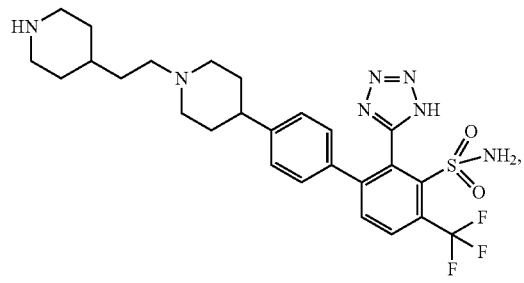
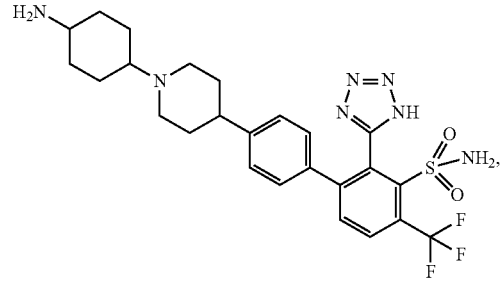
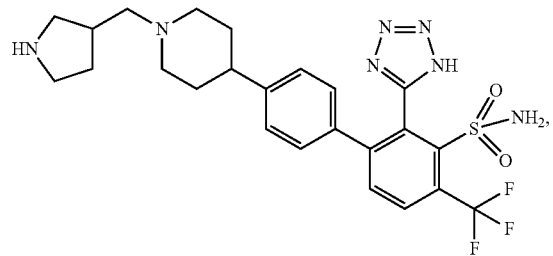

-continued
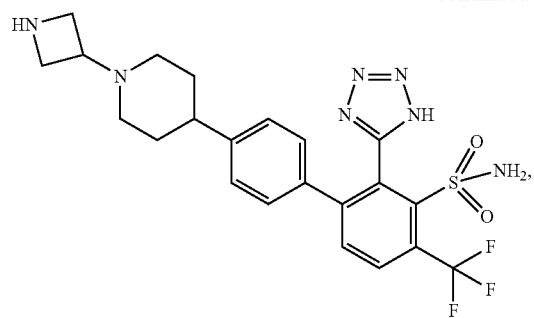
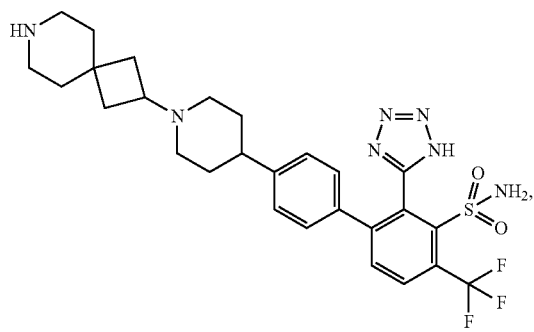
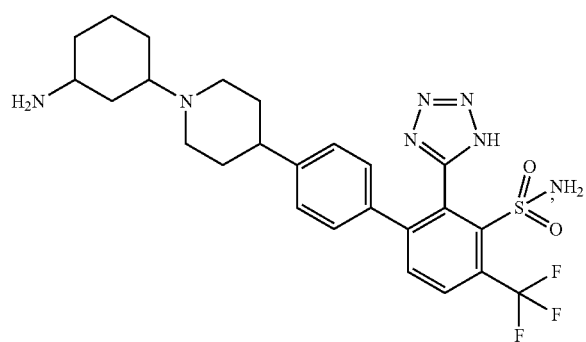
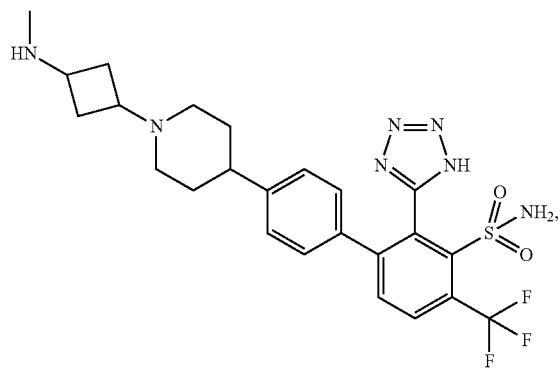
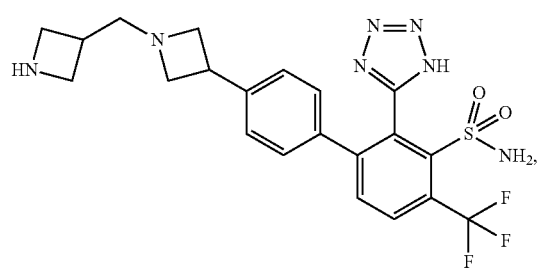

-continued
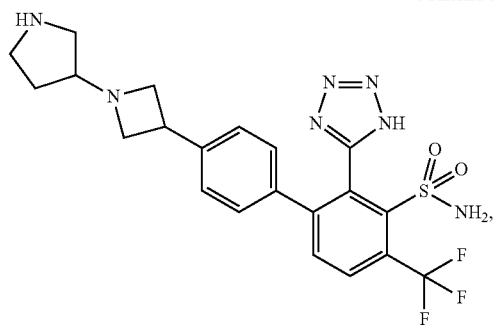
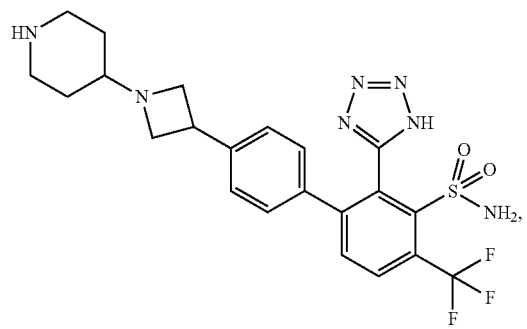
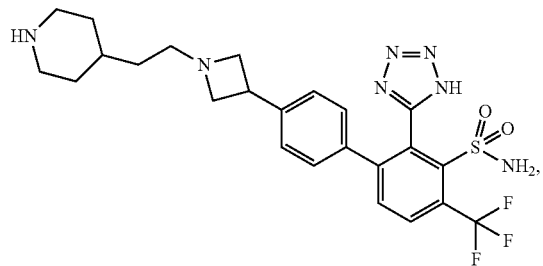
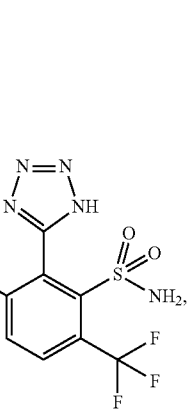
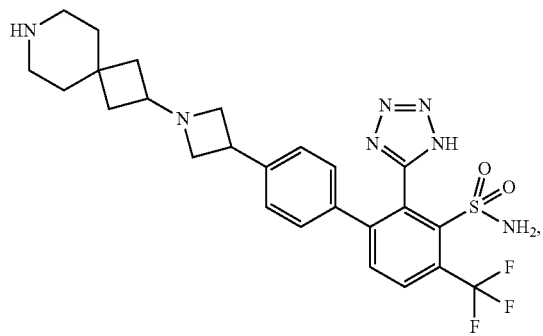

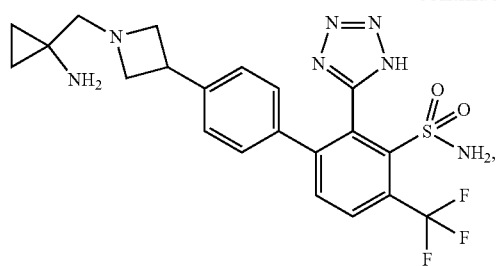
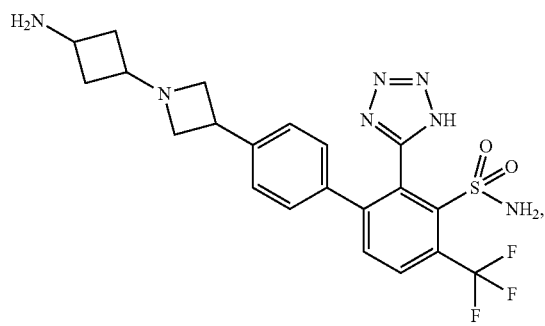
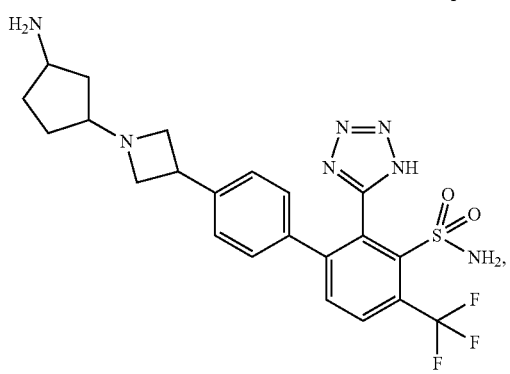
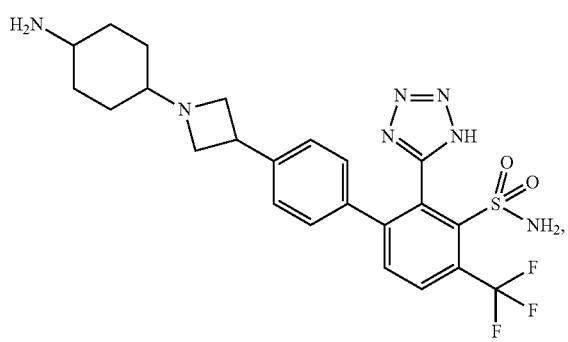
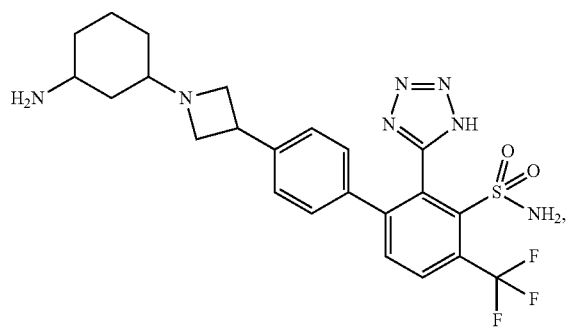

-continued
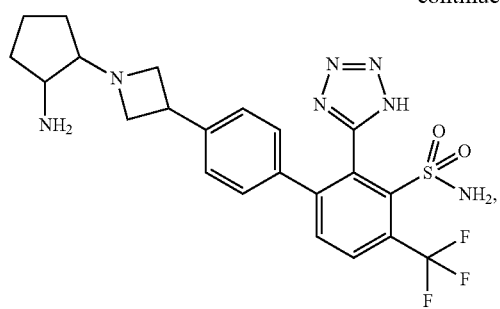
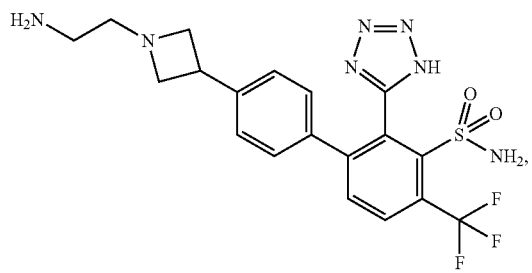
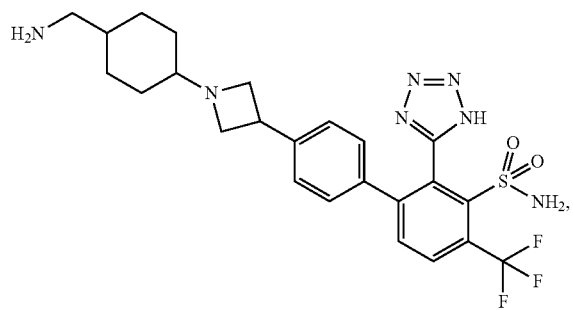
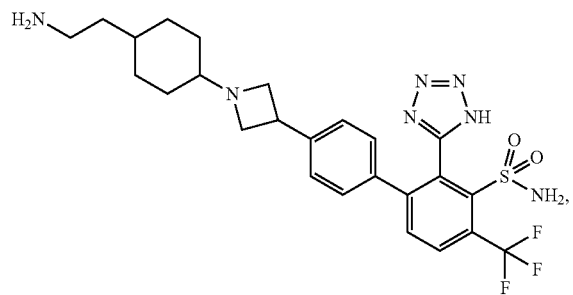
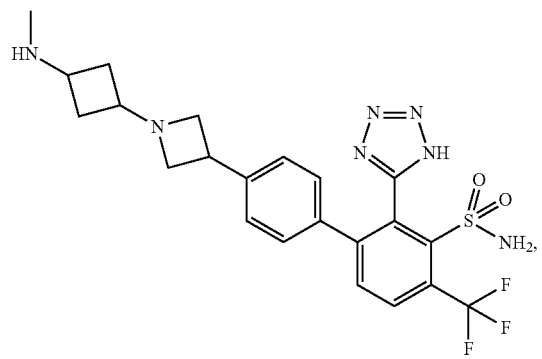

-continued
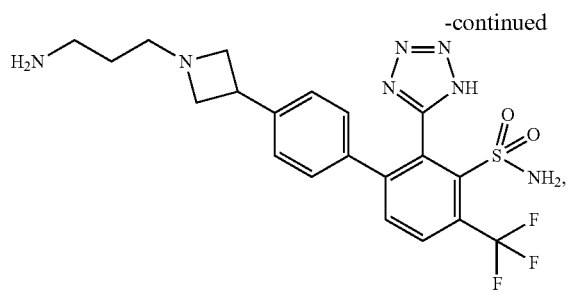
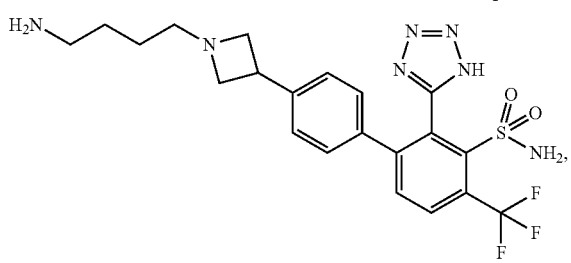
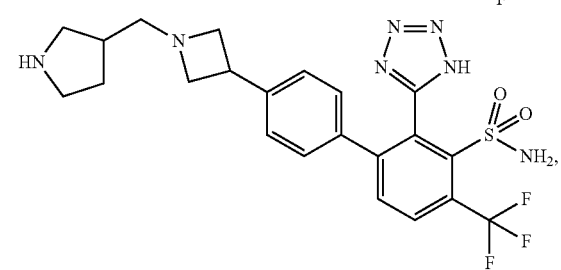
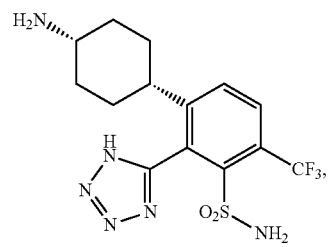
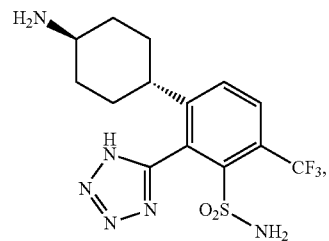
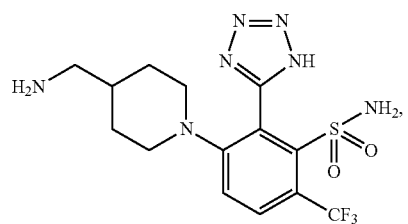

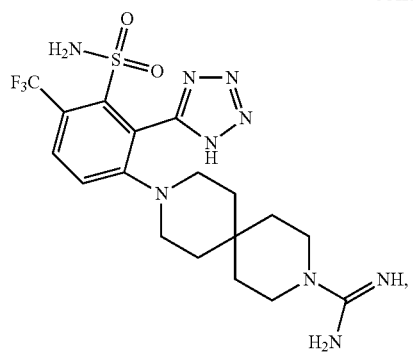
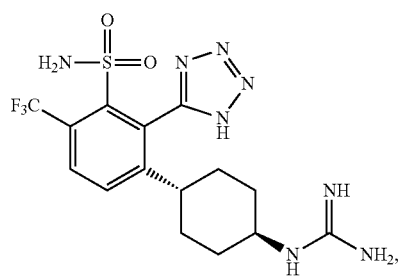
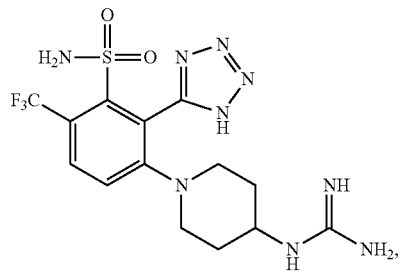
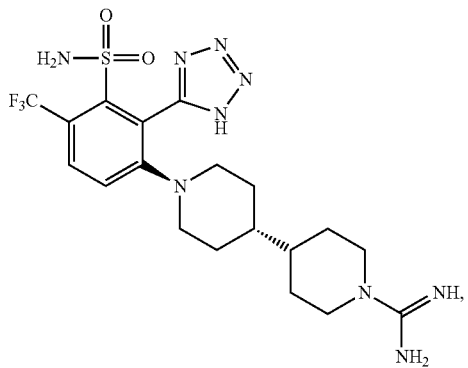
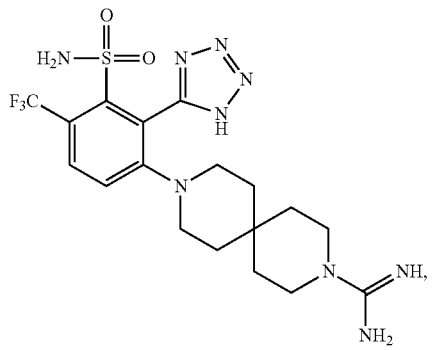

-continued
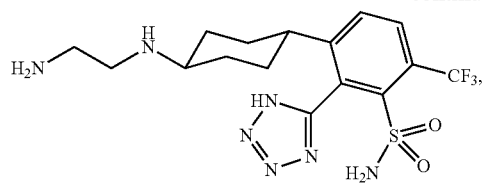
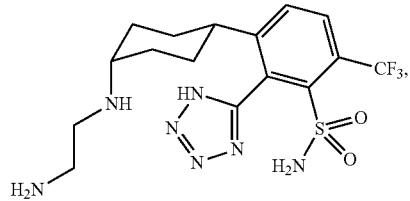
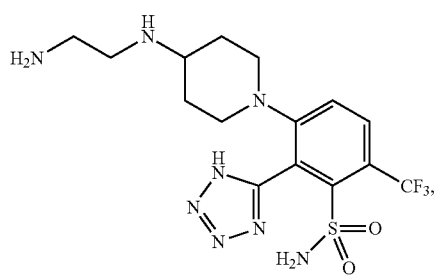
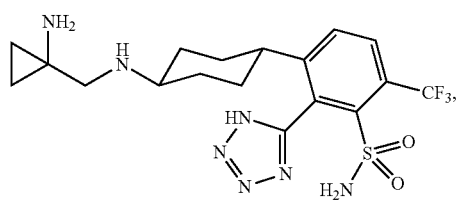
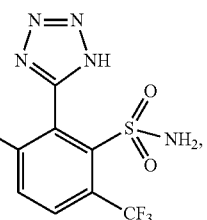
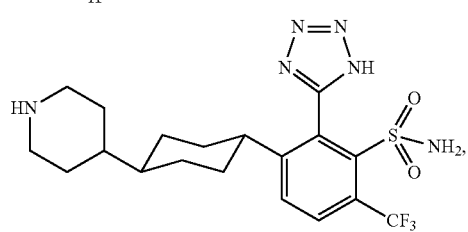
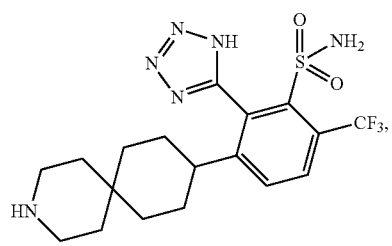

-continued
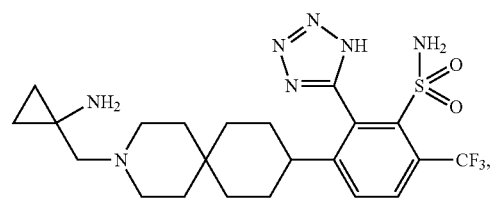
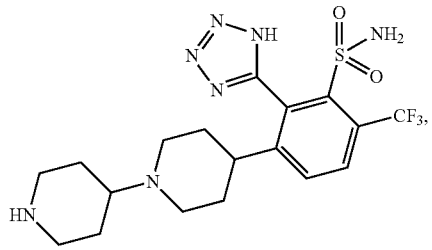
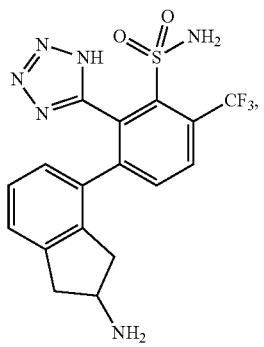
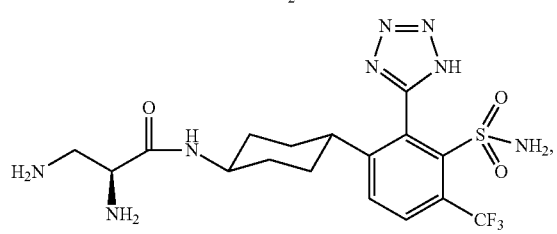
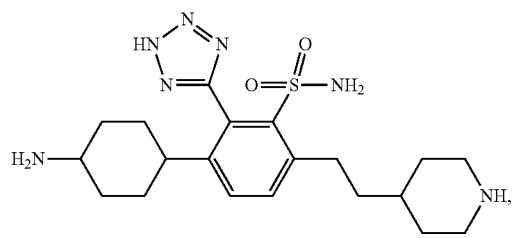
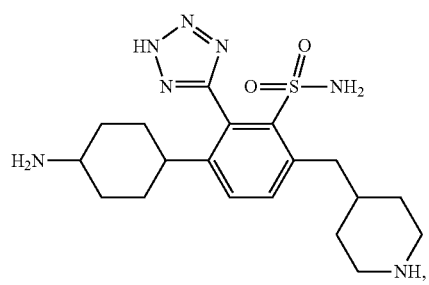

-continued
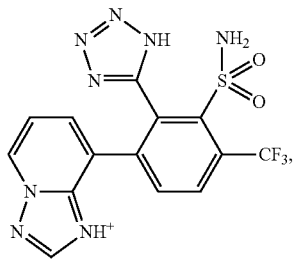
or a pharmaceutically acceptable salt thereof.
16. The compound of claim 1 which is
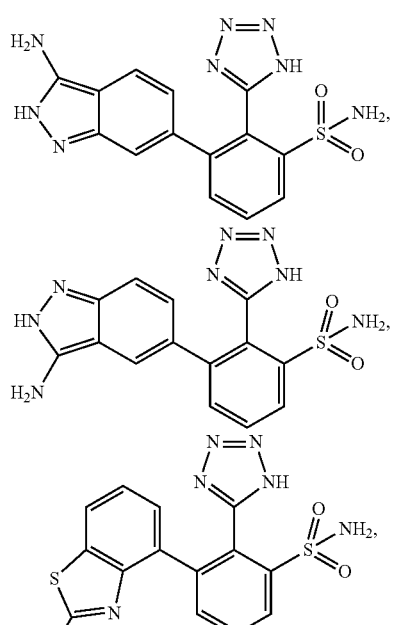
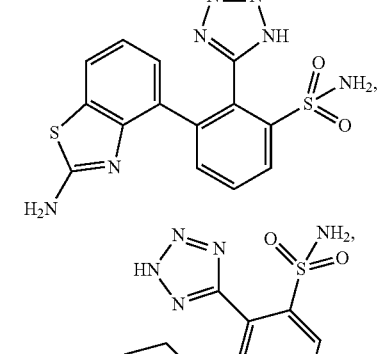
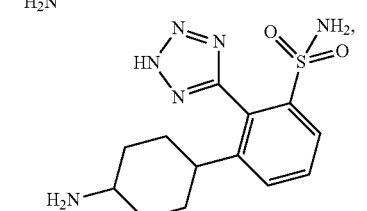
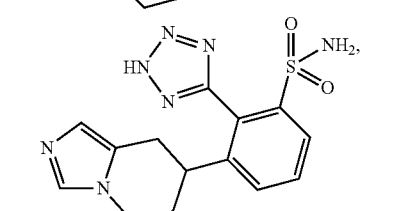
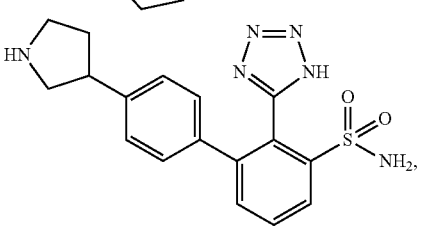
-continued
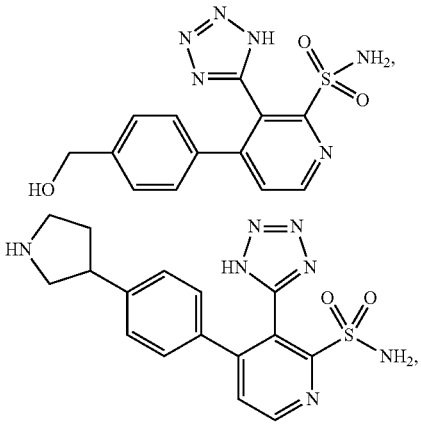
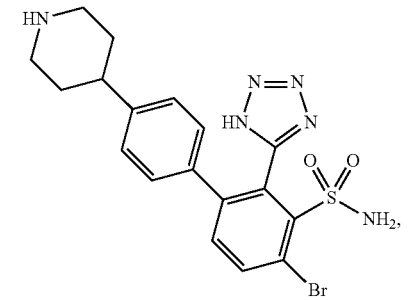
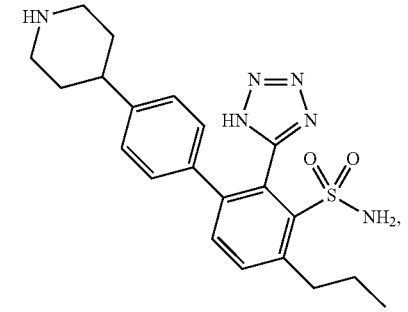
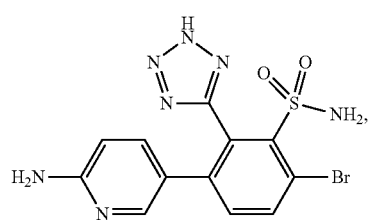

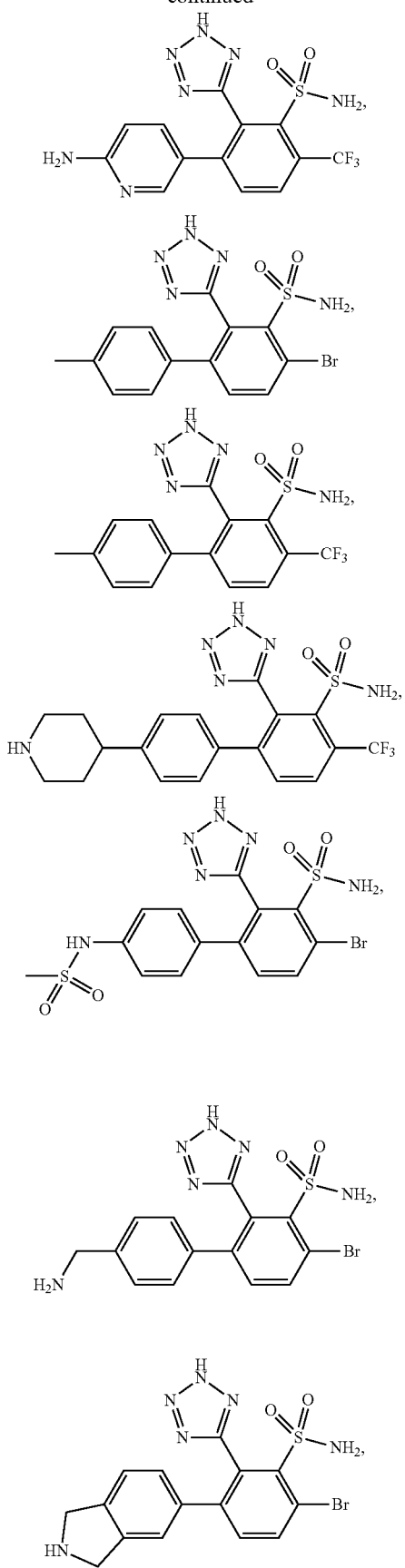
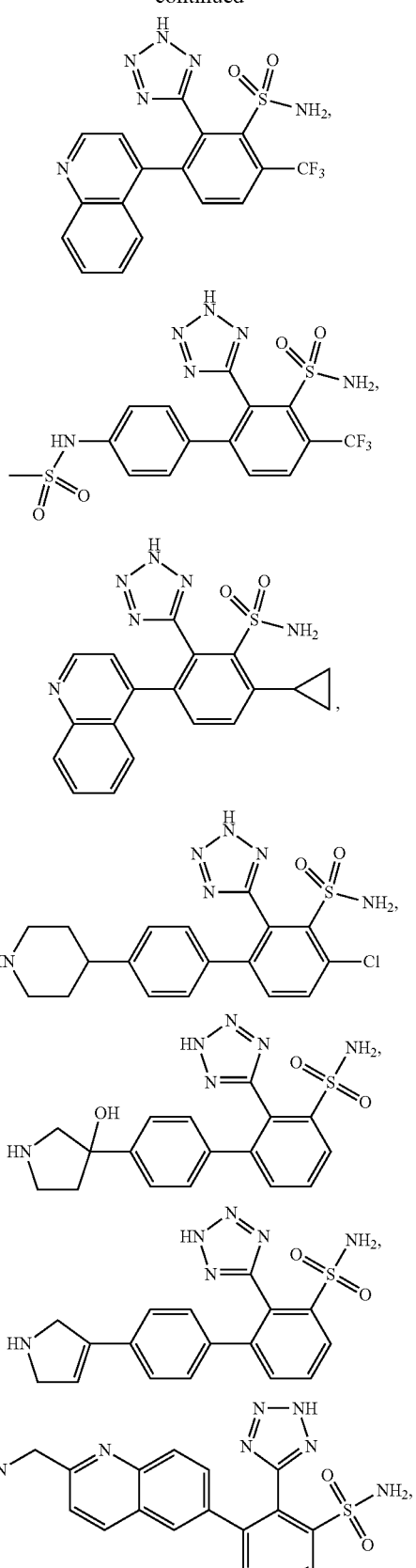

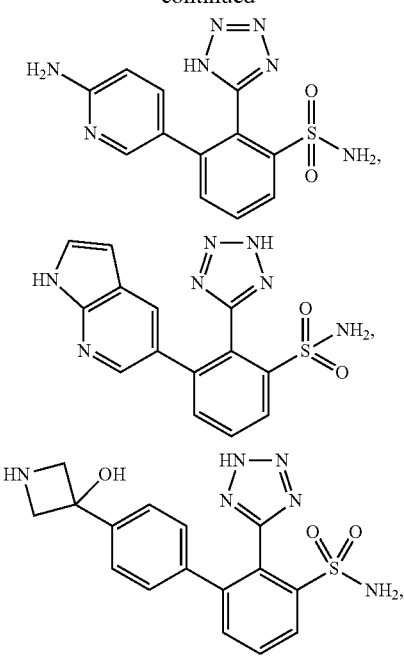
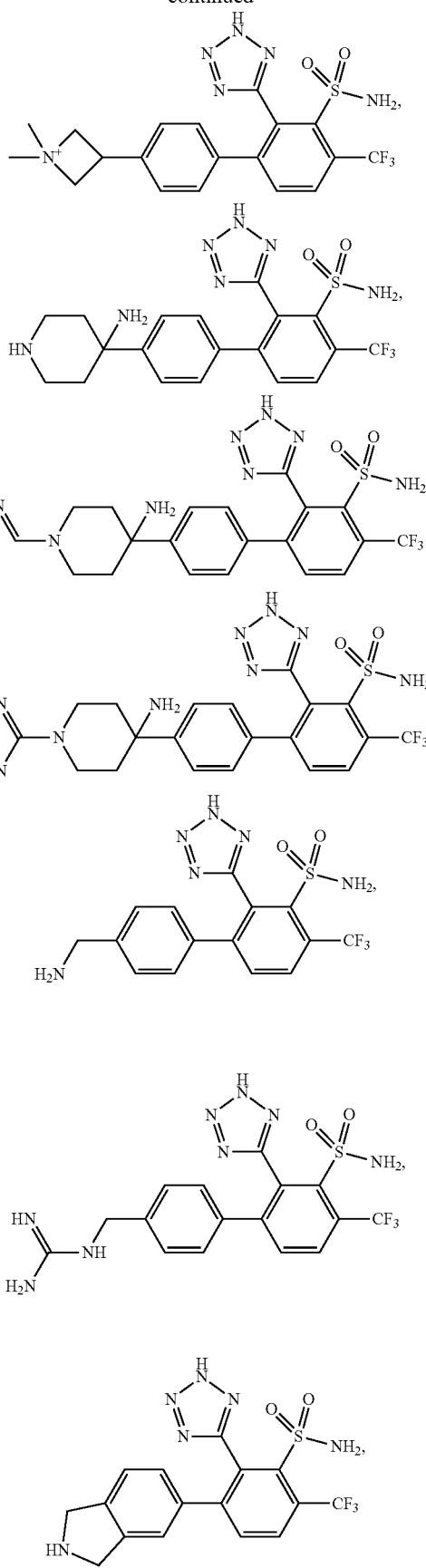
or a pharmaceutically acceptable salt thereof.
17. The compound of claim 1 which is
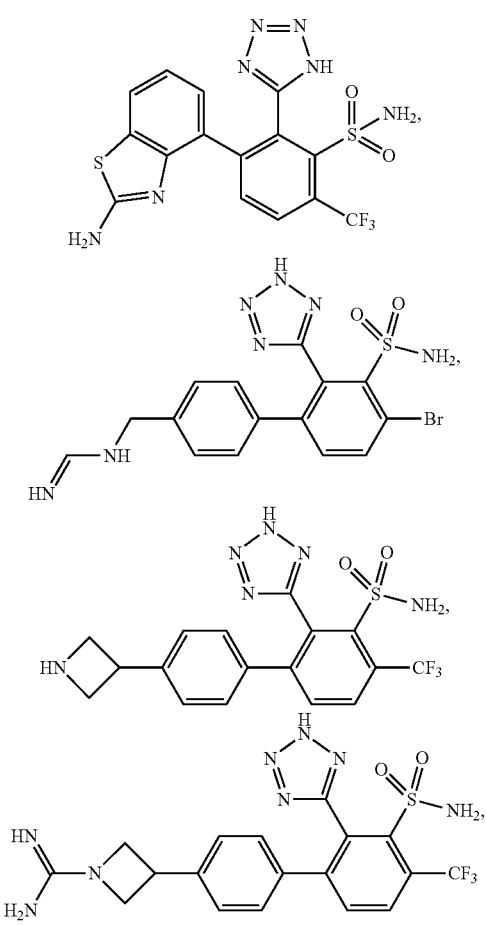

835
-continued
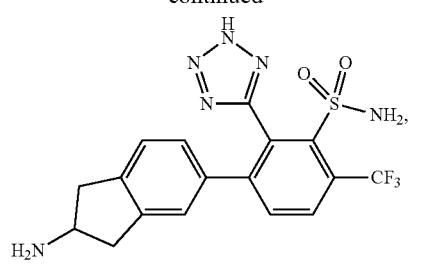
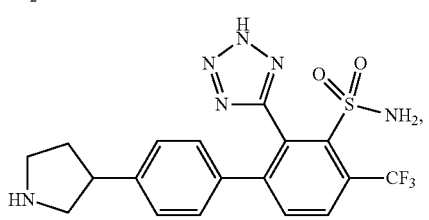
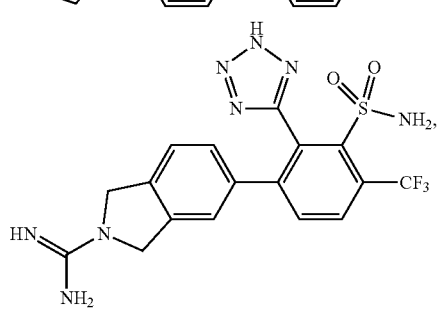
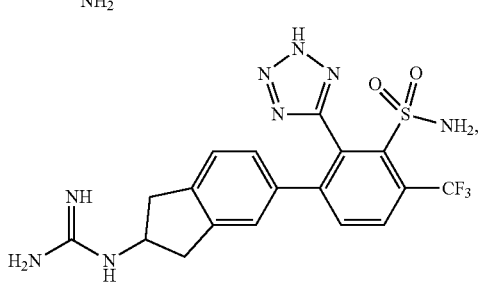
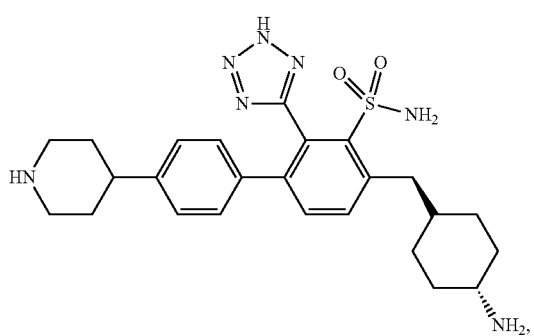
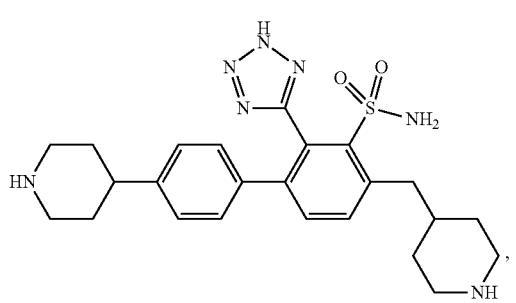
836
-continued
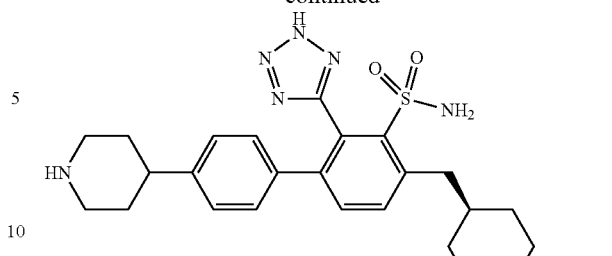
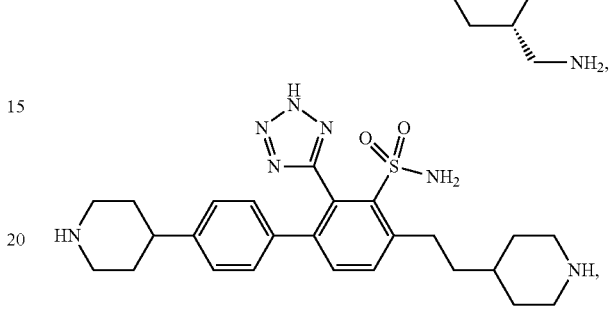
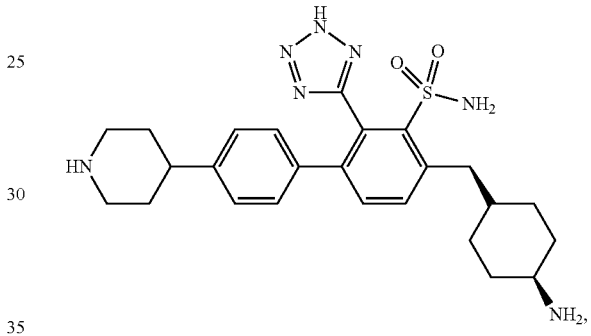
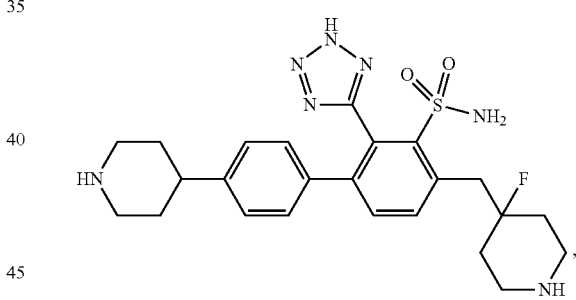
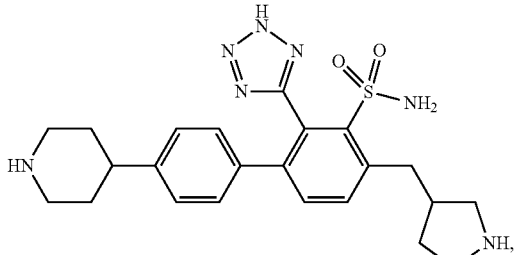
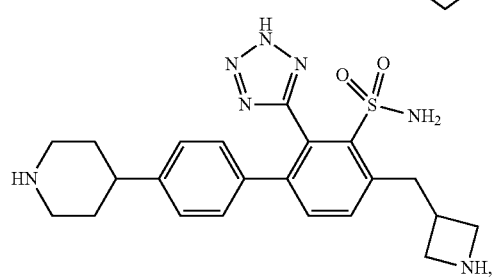

837
-continued
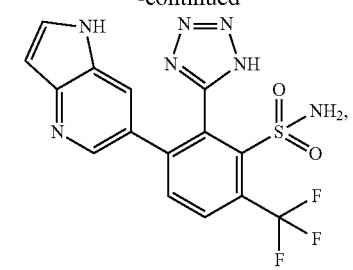
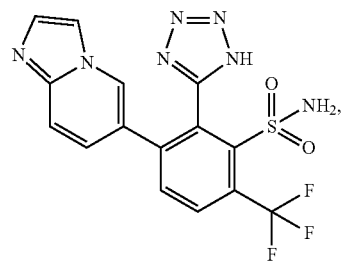
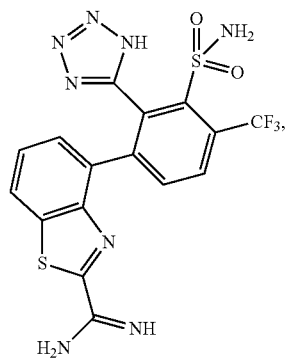
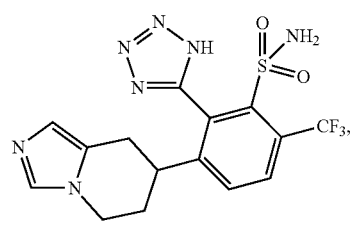
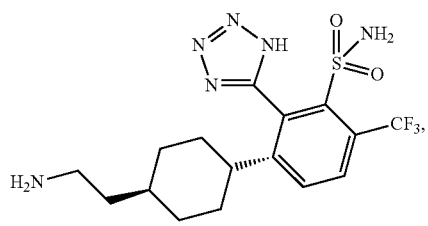
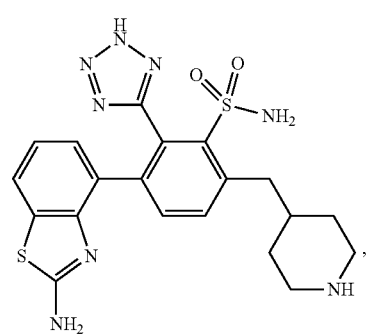
838
-continued
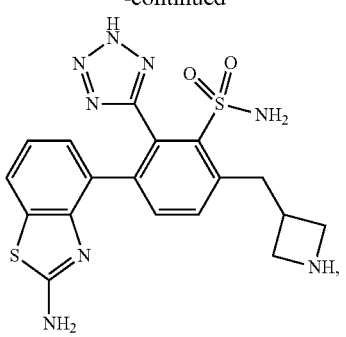
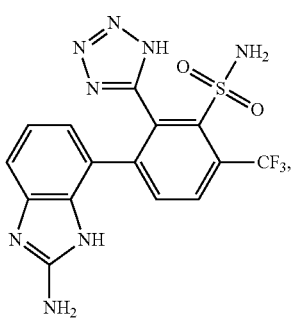
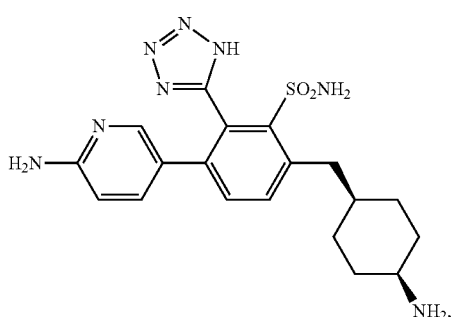
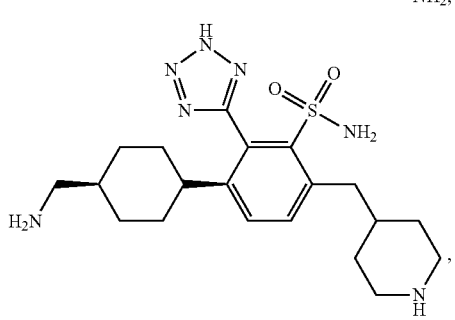
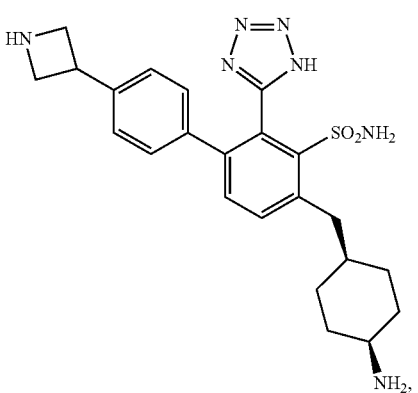

-continued

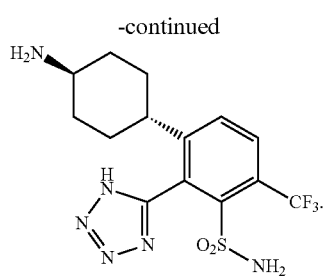

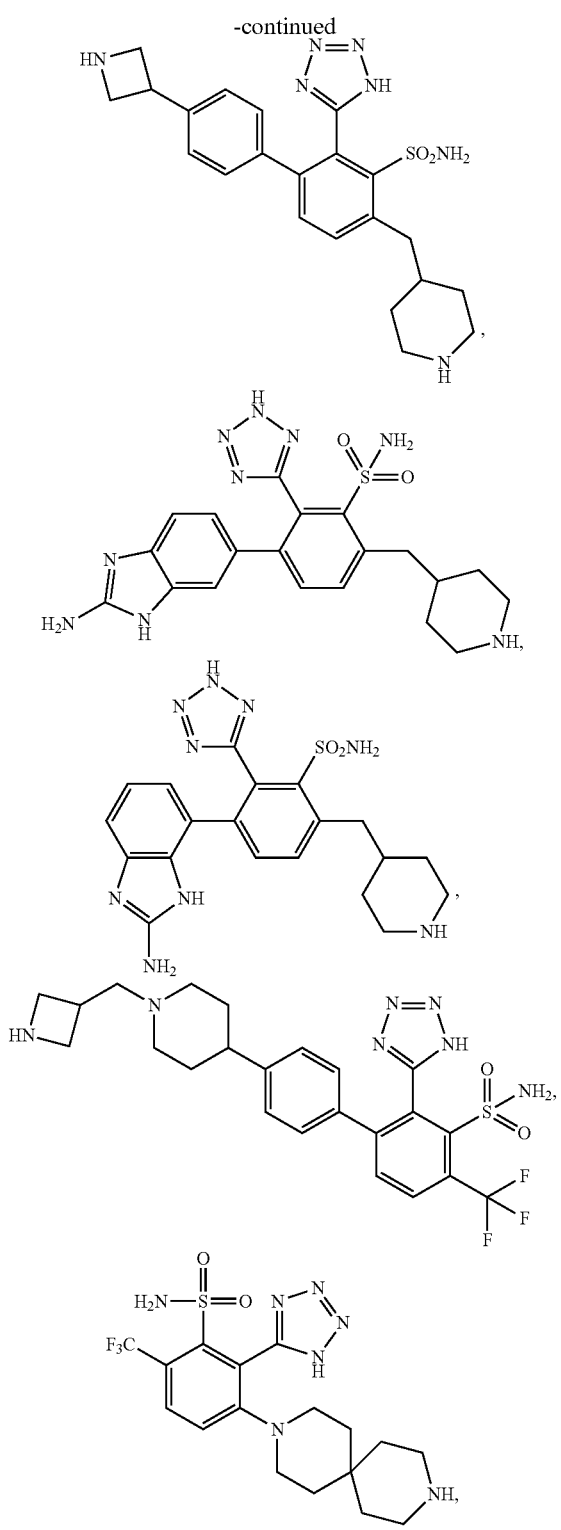

or a pharmaceutically acceptable salt thereof.

18. A pharmaceutical composition which comprises a compound according to claim 1, or a pharmaceutically acceptable salt thereof, and a pharmaceutically acceptable carrier.

19. A pharmaceutical composition according to claim 18, which further comprises an effective amount of a beta-lactam antibiotic.

20. The pharmaceutical composition according to claim 19, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidime.

21. The pharmaceutical composition according to claim 20, wherein the beta-lactam antibiotic is imipenem.

22. The pharmaceutical composition according to claim 21, further comprising cilastatin or a pharmaceutically acceptable salt thereof.

23. A method for inhibiting beta-lactamase in a subject which comprises administering to the subject an effective amount of a compound according to claim 1, or a pharmaceutically acceptable salt thereof, optionally in combination with a beta-lactam antibiotic.

24. A method for treating a bacterial infection which comprises administering to a subject in need of such treatment a therapeutically effective amount of a compound according to claim 1, or a pharmaceutically acceptable salt thereof, in combination with a beta-lactam antibiotic.

25. The method of claim 23, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, and ceftazidimem.

26. The method of claim 23, wherein the beta-lactam antibiotic is imipenem.

* * * * *